(12) United States Patent
Le Bourdonnec et al.

(10) Patent No.: US 12,180,221 B2
(45) Date of Patent: Dec. 31, 2024

(54) COMPOUNDS AND USES THEREOF

(71) Applicant: JANSSEN PHARMACEUTICA NV, Beerse (BE)

(72) Inventors: Bertrand Le Bourdonnec, Northborough, MA (US); Matthew Lucas, Lexington, MA (US); Kerem Ozboya, Cambridge, MA (US); Bhaumik Pandya, Bedford, MA (US); Parcharee Tivitmahaisoon, Boston, MA (US); Iwona Wrona, Sharon, MA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 121 days.

(21) Appl. No.: 17/028,778

(22) Filed: Sep. 22, 2020

(65) Prior Publication Data
US 2022/0298168 A1    Sep. 22, 2022

Related U.S. Application Data

(63) Continuation of application No. PCT/US2019/023737, filed on Mar. 22, 2019.

(60) Provisional application No. 62/647,308, filed on Mar. 23, 2018.

(51) Int. Cl.
| | |
|---|---|
| C07D 491/107 | (2006.01) |
| C07D 213/82 | (2006.01) |
| C07D 237/04 | (2006.01) |
| C07D 237/24 | (2006.01) |
| C07D 401/12 | (2006.01) |
| C07D 401/14 | (2006.01) |
| C07D 403/12 | (2006.01) |
| C07D 405/14 | (2006.01) |
| C07D 409/14 | (2006.01) |
| C07D 413/12 | (2006.01) |
| C07D 417/12 | (2006.01) |
| C07D 417/14 | (2006.01) |
| C07D 471/04 | (2006.01) |
| C07D 487/04 | (2006.01) |
| C07D 495/04 | (2006.01) |
| C07D 513/04 | (2006.01) |

(52) U.S. Cl.
CPC ....... *C07D 491/107* (2013.01); *C07D 213/82* (2013.01); *C07D 237/04* (2013.01); *C07D 237/24* (2013.01); *C07D 401/12* (2013.01); *C07D 401/14* (2013.01); *C07D 403/12* (2013.01); *C07D 405/14* (2013.01); *C07D 409/14* (2013.01); *C07D 413/12* (2013.01); *C07D 417/12* (2013.01); *C07D 417/14* (2013.01); *C07D 471/04* (2013.01); *C07D 487/04* (2013.01); *C07D 495/04* (2013.01); *C07D 513/04* (2013.01)

(58) Field of Classification Search
CPC .................................................. C07D 491/107
USPC ...................................................... 514/210.16
See application file for complete search history.

(56) References Cited

U.S. PATENT DOCUMENTS

| | | | |
|---|---|---|---|
| 4,782,071 A | 11/1988 | Butler et al. | |
| 5,780,472 A | 7/1998 | Cho et al. | |
| 6,727,247 B2 | 4/2004 | Flohr et al. | |
| 7,074,809 B2 | 7/2006 | Arora et al. | |
| 7,132,424 B2 | 11/2006 | Picard | |
| 7,381,749 B2 | 6/2008 | Malecha et al. | |
| 7,459,562 B2 | 12/2008 | Borzilleri et al. | |
| 7,767,677 B2 | 8/2010 | Kamboj et al. | |
| 7,790,408 B1 | 9/2010 | Ntambi et al. | |
| 8,063,224 B2 | 11/2011 | Lachance et al. | |
| 8,129,376 B2 | 3/2012 | Sundaresan et al. | |
| 8,207,147 B2 | 6/2012 | Fyfe et al. | |
| 8,207,199 B2 | 6/2012 | Aoki et al. | |
| 8,258,160 B2 | 9/2012 | Dales et al. | |
| 8,314,138 B2 | 11/2012 | Dales et al. | |
| 8,541,457 B2 | 9/2013 | Fu et al. | |
| 8,563,539 B2 | 10/2013 | Baldino et al. | |
| 8,673,917 B2 | 3/2014 | Zoller et al. | |
| 8,791,136 B2 | 7/2014 | Goff et al. | |
| 8,822,513 B2 | 9/2014 | Lu et al. | |
| 8,946,225 B2 | 2/2015 | Dupont-Passelaigue et al. | |
| 9,266,832 B2 | 2/2016 | Griffioen et al. | |
| 9,290,465 B2 | 3/2016 | Derryberry et al. | |
| 9,296,711 B2 | 3/2016 | Erickson et al. | |
| 10,941,134 B2 | 3/2021 | Goff et al. | |
| 10,973,810 B2 | 4/2021 | Vincent et al. | |
| 2002/0019389 A1 | 2/2002 | Kim et al. | |
| 2002/0133005 A1 | 9/2002 | Iino et al. | |
| 2004/0023973 A1 | 2/2004 | Nagato et al. | |

(Continued)

FOREIGN PATENT DOCUMENTS

| | | |
|---|---|---|
| CN | 1177352 | 3/1998 |
| CN | 1630650 | 6/2005 |

(Continued)

OTHER PUBLICATIONS

U.S. Appl. No. 16/751,803, Wrona et al.

(Continued)

*Primary Examiner* — Ana Z Muresan
(74) *Attorney, Agent, or Firm* — Wan Chieh Lee; Haug Partners LLP

(57) ABSTRACT

The present invention features compounds useful in the treatment of neurological disorders. The compounds of the invention, alone or in combination with other pharmaceutically active agents, can be used for treating or preventing neurological disorders.

20 Claims, No Drawings

(56) References Cited

U.S. PATENT DOCUMENTS

| | | |
|---|---|---|
| 2004/0097483 A1 | 5/2004 | Zeng et al. |
| 2004/0127521 A1 | 7/2004 | Cai et al. |
| 2004/0146872 A1 | 7/2004 | Winther et al. |
| 2005/0032859 A1 | 2/2005 | Chen |
| 2005/0119242 A1 | 6/2005 | DeLuca et al. |
| 2005/0256068 A1 | 11/2005 | McSwiggen et al. |
| 2006/0116382 A1 | 6/2006 | Yao et al. |
| 2006/0167044 A1 | 7/2006 | Arnaiz et al. |
| 2006/0270686 A1 | 11/2006 | Kelly et al. |
| 2007/0087363 A1 | 4/2007 | Bartel et al. |
| 2008/0015230 A1 | 1/2008 | Kamboj et al. |
| 2008/0021028 A1 | 1/2008 | Swinnen et al. |
| 2008/0132542 A1 | 6/2008 | Lachance et al. |
| 2008/0207587 A1 | 8/2008 | Kamboj et al. |
| 2008/0249100 A1 | 10/2008 | Chisholm et al. |
| 2008/0255130 A1 | 10/2008 | Koltun et al. |
| 2008/0255161 A1 | 10/2008 | Koltun et al. |
| 2008/0280891 A1 | 11/2008 | Kelly et al. |
| 2009/0098105 A1 | 4/2009 | Hopf et al. |
| 2009/0118296 A1 | 5/2009 | Black et al. |
| 2009/0149466 A1 | 6/2009 | Gillespie et al. |
| 2009/0163545 A1 | 6/2009 | Goldfarb |
| 2009/0170822 A1 | 7/2009 | DeLuca et al. |
| 2009/0170828 A1 | 7/2009 | Isabel et al. |
| 2009/0221597 A1 | 9/2009 | Ruah et al. |
| 2009/0239810 A1 | 9/2009 | Sundaresan et al. |
| 2009/0246137 A1 | 10/2009 | Hadida Ruah et al. |
| 2009/0253693 A1 | 10/2009 | Koltun et al. |
| 2009/0253738 A1 | 10/2009 | Koltun et al. |
| 2009/0325956 A1 | 12/2009 | Taniguchi et al. |
| 2010/0022486 A1 | 1/2010 | Bouillot et al. |
| 2010/0029722 A1 | 2/2010 | Dales et al. |
| 2010/0041696 A1 | 2/2010 | Daugan et al. |
| 2010/0160323 A1 | 6/2010 | Bischoff et al. |
| 2010/0210649 A1 | 8/2010 | Djaballah et al. |
| 2012/0010186 A1 | 1/2012 | Lachance et al. |
| 2012/0178678 A1 | 7/2012 | Dupont-Passelaigue et al. |
| 2012/0196844 A1 | 8/2012 | Alper et al. |
| 2012/0252850 A1 | 10/2012 | Milne et al. |
| 2012/0316182 A1 | 12/2012 | Whitten et al. |
| 2013/0011361 A1 | 1/2013 | Dales et al. |
| 2013/0225529 A1 | 8/2013 | Rigas |
| 2013/0317020 A1 | 11/2013 | Ruah et al. |
| 2014/0364393 A1 | 12/2014 | Yang et al. |
| 2015/0051206 A1 | 2/2015 | Loren et al. |
| 2015/0087673 A1 | 3/2015 | Hitoshi et al. |
| 2015/0246893 A1 | 9/2015 | Devaraj et al. |
| 2015/0252032 A1 | 9/2015 | Bolli et al. |
| 2016/0223559 A1 | 8/2016 | Devaraj et al. |
| 2016/0251336 A1 | 9/2016 | Yang et al. |
| 2016/0332989 A1 | 11/2016 | Wu et al. |
| 2017/0015654 A1 | 1/2017 | Imamura et al. |
| 2017/0174699 A1 | 6/2017 | Hadari et al. |
| 2017/0226086 A1 | 8/2017 | Li et al. |
| 2018/0015068 A1 | 1/2018 | Inoue et al. |
| 2018/0193325 A1 | 7/2018 | Vincent et al. |
| 2019/0302121 A1 | 10/2019 | Copland, III et al. |
| 2019/0330198 A1 | 10/2019 | Wrona et al. |
| 2020/0010462 A1 | 1/2020 | Lucas et al. |
| 2020/0262828 A1 | 8/2020 | Lucas et al. |
| 2021/0139471 A1 | 5/2021 | Wrona et al. |
| 2022/0040167 A1 | 2/2022 | Vincent et al. |

FOREIGN PATENT DOCUMENTS

| | | |
|---|---|---|
| CN | 101083994 | 12/2007 |
| CN | 101128435 | 2/2008 |
| CN | 101137363 | 3/2008 |
| CN | 101589039 | 11/2009 |
| CN | 101641347 | 2/2010 |
| CN | 101835776 | 9/2010 |
| CN | 103221408 | 7/2013 |
| CN | 103328482 | 9/2013 |
| CN | 103619825 | 3/2014 |
| CN | 103748087 | 4/2014 |
| CN | 104163794 | 11/2014 |
| EP | 1193255 A1 | 4/2002 |
| EP | 1737451 A2 | 1/2007 |
| EP | 2455080 | 5/2012 |
| EP | 2455081 | 5/2012 |
| EP | 2598483 | 6/2013 |
| EP | 2462121 | 2/2015 |
| EP | 2980077 A1 | 2/2016 |
| EP | 2990400 A1 | 3/2016 |
| EP | 3284738 A1 | 2/2018 |
| EP | 3381908 A1 | 10/2018 |
| JP | H11501021 | 1/1999 |
| JP | 2005-213233 A | 8/2005 |
| JP | 2008513514 | 5/2008 |
| JP | 2008525478 | 7/2008 |
| JP | 2008526796 | 7/2008 |
| JP | 2008539275 | 11/2008 |
| JP | 2008545760 | 12/2008 |
| JP | 2009-19013 A | 1/2009 |
| JP | 2009501733 | 3/2009 |
| JP | 2010-43052 A | 2/2010 |
| JP | 2010506859 | 3/2010 |
| JP | 2010510272 | 4/2010 |
| JP | 2010510993 | 4/2010 |
| JP | 2010513400 | 4/2010 |
| JP | 2010516714 | 5/2010 |
| JP | 2010535847 | 11/2010 |
| JP | 2011516420 | 5/2011 |
| JP | 2011529102 | 12/2011 |
| JP | 2012518603 | 8/2012 |
| JP | 2013537180 | 9/2013 |
| JP | 2014501274 | 1/2014 |
| JP | 2014509600 | 4/2014 |
| JP | 2014510708 | 5/2014 |
| JP | 2014513071 | 5/2014 |
| JP | 2014518240 | 7/2014 |
| KR | 10-2015-0014719 A | 2/2015 |
| KR | 10-2015-0015305 A | 2/2015 |
| KR | 20160020616 | 2/2016 |
| WO | WO-96/26937 A1 | 9/1996 |
| WO | WO-99/63979 A2 | 12/1999 |
| WO | WO-00/20414 A1 | 4/2000 |
| WO | WO-0114339 | 3/2001 |
| WO | WO-0105769 | 11/2001 |
| WO | WO-02/066470 A1 | 8/2002 |
| WO | WO-03/070885 A2 | 8/2003 |
| WO | WO-03/084948 A1 | 10/2003 |
| WO | WO-2004014892 | 2/2004 |
| WO | WO-2005/011654 A2 | 2/2005 |
| WO | WO-2005/011655 A2 | 2/2005 |
| WO | WO-2005/011656 A2 | 2/2005 |
| WO | WO-2005/011657 A2 | 2/2005 |
| WO | WO-2005/014607 A2 | 2/2005 |
| WO | WO-2005023833 | 3/2005 |
| WO | WO-2005026137 | 3/2005 |
| WO | WO-2006/014168 A1 | 2/2006 |
| WO | WO-2006/015621 A1 | 2/2006 |
| WO | WO-2006012325 | 2/2006 |
| WO | WO-2006/034279 A1 | 3/2006 |
| WO | WO-2006/034312 A1 | 3/2006 |
| WO | WO-2006/034315 A2 | 3/2006 |
| WO | WO-2006/034338 A1 | 3/2006 |
| WO | WO-2006/034341 A2 | 3/2006 |
| WO | WO-2006/034440 A2 | 3/2006 |
| WO | WO-2006/034441 A1 | 3/2006 |
| WO | WO-2006/034446 A2 | 3/2006 |
| WO | WO 2006022442 * | 3/2006 |
| WO | WO-2006/057902 A2 | 6/2006 |
| WO | WO-2006/067531 A1 | 6/2006 |
| WO | WO-2006/071730 A1 | 7/2006 |
| WO | WO-2006/072436 A1 | 7/2006 |
| WO | WO-2006074025 | 7/2006 |
| WO | WO-2006/086445 A2 | 8/2006 |
| WO | WO-2006/086447 A2 | 8/2006 |
| WO | WO-2006/125179 A1 | 11/2006 |
| WO | WO-2006/125181 A2 | 11/2006 |
| WO | WO-2006/125194 A2 | 11/2006 |
| WO | WO-2006116713 | 11/2006 |
| WO | WO-2006/130986 A1 | 12/2006 |

(56) References Cited

FOREIGN PATENT DOCUMENTS

| | | |
|---|---|---|
| WO | WO-2007/009236 A1 | 1/2007 |
| WO | WO-2007/044085 A2 | 4/2007 |
| WO | WO-2007/046868 A2 | 4/2007 |
| WO | WO-2007/056846 A1 | 5/2007 |
| WO | WO-2007/076055 A2 | 7/2007 |
| WO | WO-2007079180 | 7/2007 |
| WO | WO-2007/120702 A2 | 10/2007 |
| WO | WO-2007/130075 A1 | 11/2007 |
| WO | WO-2007/134457 A1 | 11/2007 |
| WO | WO-2007/136746 A2 | 11/2007 |
| WO | WO-2007/143597 A2 | 12/2007 |
| WO | WO-2007/143823 A1 | 12/2007 |
| WO | WO-2007/143824 A1 | 12/2007 |
| WO | WO-2008/003753 A1 | 1/2008 |
| WO | WO-2008008059 | 1/2008 |
| WO | WO-2008008852 A2 | 1/2008 |
| WO | WO-2008008854 A2 | 1/2008 |
| WO | WO-2008/017161 A1 | 2/2008 |
| WO | WO-2008/023720 A1 | 2/2008 |
| WO | WO-2008/024390 A2 | 2/2008 |
| WO | WO-2008017161 | 2/2008 |
| WO | WO-2008024139 | 2/2008 |
| WO | WO-2008/029266 A1 | 3/2008 |
| WO | WO-2008/036715 A1 | 3/2008 |
| WO | WO-2008/043087 A2 | 4/2008 |
| WO | WO-2008/044767 A1 | 4/2008 |
| WO | WO-2008/046226 A1 | 4/2008 |
| WO | WO-2008/056687 A1 | 5/2008 |
| WO | WO-2008/062276 A2 | 5/2008 |
| WO | WO-2008057280 | 5/2008 |
| WO | WO-2008061795 | 5/2008 |
| WO | WO-2008/064474 A1 | 6/2008 |
| WO | WO-2008/074824 A2 | 6/2008 |
| WO | WO-2008/074832 A2 | 6/2008 |
| WO | WO-2008/074833 A2 | 6/2008 |
| WO | WO-2008/074834 A2 | 6/2008 |
| WO | WO-2008/074835 A1 | 6/2008 |
| WO | WO-2008076356 | 6/2008 |
| WO | WO-2008/089580 A1 | 7/2008 |
| WO | WO-2008/096746 A1 | 8/2008 |
| WO | WO-2008/104524 A1 | 9/2008 |
| WO | WO-2008/116898 A1 | 10/2008 |
| WO | WO-2008/120744 A1 | 10/2008 |
| WO | WO-2008/120759 A1 | 10/2008 |
| WO | WO-2008/123469 A1 | 10/2008 |
| WO | WO-2008/127349 A2 | 10/2008 |
| WO | WO-2008/128335 A1 | 10/2008 |
| WO | WO-2008/139845 A1 | 11/2008 |
| WO | WO-2008/141455 A1 | 11/2008 |
| WO | WO-2008/157844 A1 | 12/2008 |
| WO | WO-2009/010560 A1 | 1/2009 |
| WO | WO-2009/012573 A1 | 1/2009 |
| WO | WO-2009/016216 A1 | 2/2009 |
| WO | WO-2009/019566 A1 | 2/2009 |
| WO | WO-2009/021990 A1 | 2/2009 |
| WO | WO-2009/037542 A2 | 3/2009 |
| WO | WO-2009/056556 A1 | 5/2009 |
| WO | WO-2009/060053 A1 | 5/2009 |
| WO | WO-2009/060054 A1 | 5/2009 |
| WO | WO-2009/070533 A1 | 6/2009 |
| WO | WO-2009/073973 A1 | 6/2009 |
| WO | WO-2009/103739 A1 | 8/2009 |
| WO | WO-2009/106991 A2 | 9/2009 |
| WO | WO-2009/117659 A1 | 9/2009 |
| WO | WO-2009/124259 A1 | 10/2009 |
| WO | WO-2009/129625 A1 | 10/2009 |
| WO | WO-2009123896 | 10/2009 |
| WO | WO-2009/150196 A1 | 12/2009 |
| WO | WO-2009/156484 A2 | 12/2009 |
| WO | WO-2010/006962 A1 | 1/2010 |
| WO | WO-2010/007482 A2 | 1/2010 |
| WO | WO-2010007966 | 1/2010 |
| WO | WO-2010/013037 A1 | 2/2010 |
| WO | WO-2010/022055 A2 | 2/2010 |
| WO | WO-2010/025553 A1 | 3/2010 |
| WO | WO-2010/035052 A1 | 4/2010 |
| WO | WO-2010/037225 A1 | 4/2010 |
| WO | WO-2010/039186 A2 | 4/2010 |
| WO | WO-2010/043052 A1 | 4/2010 |
| WO | WO-2010/045371 A1 | 4/2010 |
| WO | WO-2010/045374 A1 | 4/2010 |
| WO | WO-2010/048149 | 4/2010 |
| WO | WO-2010/056230 A1 | 5/2010 |
| WO | WO-2010057833 | 5/2010 |
| WO | WO-2010060996 | 6/2010 |
| WO | WO-2010/094120 A1 | 8/2010 |
| WO | WO-2010/094126 A1 | 8/2010 |
| WO | WO-2010/108268 A1 | 9/2010 |
| WO | WO-2010101964 | 9/2010 |
| WO | WO-2010/112520 A1 | 10/2010 |
| WO | WO-2011/011506 A1 | 1/2011 |
| WO | WO-2011/011508 A1 | 1/2011 |
| WO | WO-2011/011872 A1 | 2/2011 |
| WO | WO-2011/015629 | 2/2011 |
| WO | WO-2011/015629 A1 | 2/2011 |
| WO | WO-2011/025690 A1 | 3/2011 |
| WO | WO-2011/030312 A1 | 3/2011 |
| WO | WO-2011/039358 A1 | 4/2011 |
| WO | WO-2011/047481 A1 | 4/2011 |
| WO | WO-2011109059 | 9/2011 |
| WO | WO-2011/131593 A1 | 10/2011 |
| WO | WO-2011123681 | 10/2011 |
| WO | WO-2011157793 | 12/2011 |
| WO | WO-2012009134 | 1/2012 |
| WO | WO-2012/016133 | 2/2012 |
| WO | WO-2012016217 | 2/2012 |
| WO | WO-2012/035023 A1 | 3/2012 |
| WO | WO-2012/046681 A1 | 4/2012 |
| WO | WO-2012/066077 A1 | 5/2012 |
| WO | WO-2012/080729 A2 | 6/2012 |
| WO | WO-2012/082817 A1 | 6/2012 |
| WO | WO-2012/093809 A2 | 7/2012 |
| WO | WO-2012/123449 A1 | 9/2012 |
| WO | WO-2012/136492 A1 | 10/2012 |
| WO | WO-2012/169649 A1 | 12/2012 |
| WO | WO-2013/004642 A1 | 1/2013 |
| WO | WO-2013/026587 A1 | 2/2013 |
| WO | WO-2013/056148 A2 | 4/2013 |
| WO | WO-2013046136 | 4/2013 |
| WO | WO-2013070660 | 5/2013 |
| WO | WO-2013/085954 A1 | 6/2013 |
| WO | WO-2013/085957 A1 | 6/2013 |
| WO | WO-2013098373 A1 | 7/2013 |
| WO | WO-2013/134546 A1 | 9/2013 |
| WO | WO-2013/160811 A1 | 10/2013 |
| WO | WO-2013/175474 | 11/2013 |
| WO | WO-2013170072 | 11/2013 |
| WO | WO-2014003153 | 1/2014 |
| WO | WO-2014031928 | 2/2014 |
| WO | WO-2014/092104 A1 | 6/2014 |
| WO | WO-2014/116386 A1 | 7/2014 |
| WO | WO-2015048547 | 4/2015 |
| WO | WO-2015101293 | 7/2015 |
| WO | WO-2015113920 A1 | 8/2015 |
| WO | WO-2015/132610 A1 | 9/2015 |
| WO | WO-2015/137385 A1 | 9/2015 |
| WO | WO-2015/140130 A1 | 9/2015 |
| WO | WO-2016022626 | 2/2016 |
| WO | WO-2016022955 | 2/2016 |
| WO | WO-2016/040794 A1 | 3/2016 |
| WO | WO-2016/049586 A2 | 3/2016 |
| WO | WO-2016098005 | 6/2016 |
| WO | WO-2016/107603 A1 | 7/2016 |
| WO | WO-2017/066705 A1 | 4/2017 |
| WO | WO-2017/093263 A1 | 6/2017 |
| WO | WO-2017093263 | 6/2017 |
| WO | WO-2017112777 | 6/2017 |
| WO | WO-2017212425 | 12/2017 |
| WO | WO-2018026663 A1 | 2/2018 |
| WO | WO-2018/081167 A1 | 5/2018 |
| WO | WO-2018112077 | 6/2018 |
| WO | WO-2018129403 | 7/2018 |
| WO | WO-2018/161033 A1 | 9/2018 |
| WO | WO-2018160717 | 9/2018 |

(56) References Cited

FOREIGN PATENT DOCUMENTS

| WO | WO-2018195450 A1 | 10/2018 |
|---|---|---|
| WO | WO-2019018795 | 1/2019 |
| WO | WO-2019/084157 A1 | 5/2019 |
| WO | WO-2019123375 | 6/2019 |
| WO | WO-2019123378 | 6/2019 |
| WO | WO-2019140188 | 7/2019 |
| WO | WO-2019173394 | 9/2019 |
| WO | WO-2019183587 | 9/2019 |
| WO | WO-2019209948 | 10/2019 |
| WO | WO-2019209962 | 10/2019 |
| WO | WO-2020023657 | 1/2020 |
| WO | WO-2020132378 | 6/2020 |
| WO | WO-2020154571 | 7/2020 |
| WO | WO-2020198026 | 10/2020 |
| WO | WO-2021092240 | 5/2021 |
| WO | WO-2021092262 | 5/2021 |
| WO | WO-2021097240 | 5/2021 |
| WO | WO-2021139595 | 7/2021 |
| WO | WO-2021154571 | 8/2021 |

OTHER PUBLICATIONS

International Search Report and Written Opinion for International Patent Application No. PCT/US2019/023737, dated Jul. 5, 2019 (16 pages).
Berge et al., "Pharmaceutical salts," J Pharm Sci. 66(1):1-19 (1977).
Black et al., "Advances and limitations in the evaluation of analgesic combination therapy," Neurology. 65(12 Suppl 4):S3-6 (2005) (14 pages).
Bähler et al., "Heterologous modules for efficient and versatile PCR-based gene targeting in Schizosaccharomyces pombe," Yeast. 14(10):943-51 (1998).
Chung et al., "Identification and rescue of alpha-synuclein toxicity in Parkinson patient-drived neurons," available in PMC Nov. 22, 2014, published in final edited form as: Science. 342(6161):983-7 (2013) (12 pages).
Cingolani et al., "A program for annotating and predicting the effects of single nucleotide polymorphisms, SnpEff: SNPs in the genome of Drosophila melanogaster strain w1118; iso-2; iso-3," Fly(Austin). 6(2):80-92 (2012).
Cooper et al., "Alpha-synuclein blocks ER-Golgi traffic and Rabi rescues neuron loss in Parkinson's models," available in PMC Sep. 19, 2007, published in final edited form as: Science. 313(5785):324-8 (2006) (12 pages).
Dillon et al., "Development of a novel LC/MS method to quantitate cellular stearoyl-CoA desaturase activity," Anal Chim Acta. 627(1):99-104 (2008).
Friedrich et al., "Mechanism of amyloid plaque formation suggests an intracellular basis of Abeta pathogenicity," Proc Natl Acad Sci U.S.A. 107(5):1942-7 (2010).
Garrison et al., "Haplotype-based variant detection from short-read sequencing," <https://arxiv.org/pdf/1207.3907.pdf>, retrieved Apr. 23, 2018 (2012) (9 pages).
Gietz, "Yeast transformation by the LiAc/SS carrier DNA/PEG method," Methods Mol Biol. 1205:1-12 (2014).
Kamboh et al., "A novel mutation in the apolipoprotein E gene (APOE*4 Pittsburgh) is associated with the risk of late-onset Alzheimer's disease," Neurosci Lett. 263(2-3):129-32 (1999).
Larson et al., "Soluble α-synuclein is a novel modulator of Alzheimer's disease pathophysiology," Available in PMC Jan. 25, 2013, published in final edited form as: J Neurosci. 32(30):10253-66 (2012) (28 pages).
Li et al., "Fast and accurate long-read alignment with Burrows-Wheeler transform," Bioinformatics. 26(5):589-95 (2010).
Li et al., "Fast and accurate short read alignment with Burrows-Wheeler transform," Bioinformatics. 25(14):1754-60 (2009).
Li et al., "The sequence alignment/map format and SAMtools," Bioinformatics. 25(16):2078-9 (2009).

Longtine et al., "Additional modules for versatile and economical PCR-based gene deletion and modification in Saccharomyces cerevisiae," Yeast. 14(10):953-61 (1998).
Miyazaki et al., "The biosynthesis of hepatic cholesterol esters and triglycerides is impaired in mice with a disruption of the gene for stearoyl-CoA desaturase 1," J Biol Chem. 275(39):30132-8 (2000).
Piotrowski et al., "Plant-derived antifungal agent poacic acid targets beta-1,3-glucan," Proc Natl Acad Sci U S A. 112(12):E1490-7 (2015).
Shanklin et al., "Stearoyl-acyl-carrier-protein desaturase from higher plants is structurally unrelated to the animal and fungal homologs," Proc Natl Acad Sci U S A. 88(6):2510-4 (1991).
Simon et al., "Total ApoE and ApoE4 isoform assays in an Alzheimer's disease case-control study by targeted mass spectrometry (n=669): a pilot assay for methionine-containing proteotypic peptides," Mol Cell Proteomics. 11(11):1389-403 (2012).
Soulard et al., "Development of a high-throughput screening assay for stearoyl-CoA desaturase using rat liver microsomes, deuterium labeled stearoyl-CoA and mass spectrometry," Anal Chim Acta. 627(1):105-11 (2008).
Su et al., "Compounds from an unbiased chemical screen reverse both ER-to-Golgi trafficking defects and mitochondrial dysfunction in Parkinson's disease models," Dis Model Meeh. 3(3-4):194-208 (2010).
Suzuki et al., "Knocking out multi-gene redundancies via cycles of sexual assortment and fluorescence selection," available in PMC Aug. 1, 2011, published in final edited form as: Nat Methods. 8(2):159-64 (2011) (15 pages).
Tafesse et al., "Disruption of Sphingolipid Biosynthesis Blocks Phagocytosis of Candida albicans," PLoS Pathog. 11(10):e1005188 (2015) (27 pages).
Tindale et al., "Rare and common variants in the Apolipoprotein E gene in healthy oldest old," Neurobiol Aging. 35(3):727.e1-3 (2014) (3 pages).
Wang et al., "Characterization of HSCD5, a novel human stearoyl-CoA desaturase unique to primates," Biochem Biophys Res Commun. 332(3):735-42 (2005).
"List of neurological conditions and disorders," <https://en.wikipedia.org/wiki/List_of_neurological_conditions_and_disorders>, retrieved on Jun. 27, 2019 (12 pages).
Ponomarenko et al., "The Size of the Human Proteome: The Width and Depth," Int J Anal Chem. 2016:7426849 (2016) (6 pages).
Astarita et al., "Elevated stearoyl-CoA desaturase in brains of patients with Alzheimer's disease," PLoS One. 6(10):e24777 (2011) (9 pages).
Hamilton et al., "Aberrant Lipid Metabolism in the Forebrain Niche Suppresses Adult Neural Stem Cell Proliferation in an Animal Model of Alzheimer's Disease," Cell Stem Cell. 17(4):397-411 (2015) (16 pages).
Zhang et al., "Revisiting the Medical Management of Parkinson's Disease: Levodopa Versus Dopamine Agonist," Curr Neuropharmacol. 14(4):356-363 (2016).
Pankratz et al., "Presence of an APOE4 Allele Results in Significantly Earlier Onset of Parkinson's Disease and a Higher Risk With Dementia," Mov Disord. 21(1):45-49 (2006).
Verghese et al., "Roles of Apolipoprotein E in Alzheimer's disease and other neurological disorders," Lancet Neurol. 10(3):241-252 (2011).
Crews et al., "Role of Synucleins in Alzheimer's Disease," Neurotox Res. 16(3):306-317 (2009).
Horan et al., "Piperazinyl-oxadiazoles as selective sphingosine-1-phosphate receptor agonists," Bioorg Med Chem Lett. 24(20):4807-11 (2014) (5 pages).
Huestis et al., "The Vinyl Moiety as a Handle for regiocontrol in the Preparation of Unsymmetrical 2,3-Aliphatic-Substituted Indoles and Pyrroles," Angew Chem Int Ed Engl. 50(6):1338-41 (2011).
Jarvis et al., "A-803467, a potent and selective Nav1.8 sodium channel blocker, attenuates neuropathic and inflammatory pain in the rat," Proc Natl Acad Sci U.S.A. 104(20):8520-5 (2007).
Krasavin et al., "Antiproliferative 4-(1,2,4-oxadiazol-5-yl)piperidine-1-carboxamides, a new tubulin inhibitor chemotype," Bioorg Med Chem Lett. 24(18): 4477-4481 (2014) (5 pages).

(56) References Cited

OTHER PUBLICATIONS

Muraglia et al., "N-(2-alkylaminoethyl)-4-(1,2,4-oxadiazol-5-yl)piperazine-1-carboxamides as highly potent smoothened antagonists," Bioorg Med Chem Lett. 21(18): 5283-8 (2011) (6 pages).
Ontoria et al., "Identification of a series of 4-[3-(quinolin-2-yl)-1,2,4-oxadiazol-5-yl]piperazinyl ureas as potent smoothened antagonist hedgehog pathway inhibitors," 21(18): 5274-82 (2011) (9 pages).
PubChem Compound Summary for CID 126485826, dated Apr. 22, 2017 (6 pages).
PubChem Compound Summary for CID 127012056, dated Jun. 2, 2017 (12 pages).
PubChem Compound Summary for CID 127868748, dated Jun. 18, 2017 (9 pages).
PubChem Compound Summary for CID 15985883, "5-[5-[4-[(4-Chlorophenyl)methyl]piperidin-1-yl]-5-oxopentyl]-1H-pyridin-2-one," created Mar. 27, 2007, retrieved Mar. 25, 2020 (7 pages).
PubChem Compound Summary for CID 53003909, dated Jun. 21, 2011 (7 pages).
PubChem Compound Summary for CID 56980069, dated Jun. 13, 2012 (11 pages).
PubChem Compound Summary for CID 7059272, dated Jul. 29, 2006 (12 pages).
Tiwari et al., "Synthesis of 3-(5-bromo-2,3-dimethoxy-phenyl)-[1,2,4] oxadiazole analogues and their evaluation as anti-Parkinson's agents," Med Chem Res. 17:386-398 (2008) (12 pages).
Extended European Search Report for European Patent Application No. 19771620.2, dated Feb. 18, 2022 (17 pages).
Partial Supplementary European Search Report for International Patent Application No. PCT/US2019/023737, dated Nov. 18, 2021 (19 pages).
Berlin et al., 16(4) Bioorg. & Med. Chem. Letts., pp. 989-994 (2006).
Dai et al., "SCD1 Confes Temozolomide Resistance to Human Glioma Cells via Akt/GSK3β/β-Catenin Signaling Axis," Frontiers in Pharmacology, vol. 8, Art. 960 (2018).
Debenham et al., "Discovery of N-[Bis(4-methoxyphenyl)methyl]-4-hydroxy-2-(pyridazin-3-y1)pyrimidine-5-carboxamide (MK-8617), an Orally Active Pan-Inhibitor of Hypoxia-Inducible Factor Prolyl Hydroxylase1-3 (Hif PHD1-3) for the Treatment of Anemia," J. Med. Chem. 59, 11039-11049 (2016).
Fatutta Et Al: "Comportamento di alcune idrazidi di fronte a composti y-dicarbonilici. (*)", Gazzetta Chimica Italiana, Societa Chimica Italiana, IT, vol. 90, Jan. 1, 1960 (Jan. 1, 2960), pp. 1645-1657, XP009532381.
Goedert, M., "Parkinson's disease and other alpha-synucleinopathies," Clin Chem Lab Med. 39(4):308-12 (2001) (Abstract onlv).
Kumar et al., "Design and Synthesis of 3,5-Disubstituted-1,2,4-Oxadiazoles as Potent Inhibitors of Phosphodiesterase 4 B2" Chem Biol Drug Des. 79(5):810-8 (2012).
Maya S. Salnikova, Rational Development of Protein Formulations in Solid and Solution States.
Mikolaenko et al., "Alpha-synuclein lesions in normal aging, Parkinson disease, and Alzheimer disease: evidence from the Baltimore Longitudinal Study of Aging (BLSA)," J Neuropathol Exp Neurol. 64(2):156-62 (2005).
Ng Davis Et Al: "Reviewing editor",Jul. 20, 2016 (Jul. 20, 2016), pp. 1-33, XP055921015,Retrieved from the Internet: URL:https://www.ncbi.nlm.nih.gov/pmc/artic les/PMC4954757/pdf/elife-11878.pdf.
Oatman et al. "Mechanisms of stearoyl CoA desaturase inhibitor sensitivity and acquired resistance in cancer" Science Advances. Feb. 10, 2021 (Feb. 10, 2021) vol. 7, p. 1-19.
Shen et al., "Discovery of a Highly Potent, Selective, and Bioavailable Soluble Epoxide Hydrolase Inhibitor with Excellent Ex Vivo Target Engagement." J Med Chem. 52(16):5009-12 (2009).
Sinner et al., "StearoylCoA Desaturase-5: A novel regulator of neuronal cell proliferation and differentiation" PLoS One. 7(6):e39787 (2012) (12 pages).
Skedelj Veronika Et Al: "ATP-Binding Site of Bacterial Enzymes as a Target for Antibacterial Drug Design", Journal of Medicinal Chemistry, vol. 54, No. 4, Jan. 14, 2011 (Jan. 14, 2011), pp. 915-929, XP055922741.
Terry-Kantor et al., "Rapid Alpha-Synuclein Toxicity in a Neural Cell Model and Its Rescue by a Stearoyl-CoA Desaturase Inhibitor," Int. J. Mol. Sci., 21, 5193, 1-16 (Jul. 22. 2020).
Tesfay et al., "Steroyl-CoA Desaturase (SCD1) protects ovarian cancer cells from ferroptotic cell death," Cancer Res. 79(20): 5355-5366 (Oct. 15, 2019).
Zhang et al., "Opportunities and Challenges in Develping Stearoyl-Coenzyme A Desaturase-1 Inhibitors as Novel Therapeutics for Human Disease," J. Med. Chem., 57, 5039-5056 (2014).
Zhou, Youping, Zhong, et al. Inhibition of stearoyl-coenzyme A desaturase 1 ameliorates hepatic steatosis by inducing AMPK-mediated lipophagy. Aging, 12(8):7350-7362 (Apr. 23, 2020).
Database Registry Chemical Abstracts Service, Columbus, Ohio, Accession No. RN 276236-86-3, Entered STN: Jul. 11, 2000.
Database Registry Chemical Abstracts Service, RN 887202-53-1, entered STN: Jun. 8, 2006 (3 pages).
NCBI, Gene ID: 79966, "SCD5 stearoyl-CoA desaturase 5 [Homo sapiens (human)]," <https://web.archive.org/web/20150828032953/http://www.ncbi.nlm.nih.gov:80/gene/79966>, last modified Jul. 23, 2015 (5 pages).
PubChem Compound Summary for CID 71908265, retrieved from <https://pubchem.ncbi.nlm.nih.gov/compound/71908265>, created Nov. 29, 2013, retrieved Jan. 4, 2021 (8 pages).
Registry (STN) [online] and Feb. 29, 2012 CAS Registration No. 1358463-36-1 etc. (13 pages).
RN1266245-83-3, registry database compound, 2011.
Vincent et al. "Inhibiting Stearoyl-CoA Desaturase Ameliorates a-Synuclein Cytotoxicity," Cell Reports, 25: 2742-2754 (2018).
Madia Valentina Noemi et al., "Novel Benzazole Derivatives Endowed with Potent Antiheparanase Activity", Journal of Medicinal Chemistry, vol. 61, No. 15, Jul. 16, 2018 (Jul. 16, 2018), pp. 6918-6936, XP093025853, US.
Trivedi Prakruti et al., "Design, synthesis and biological screening of 2-aminobenzamides as selective HDAC3 inhibitors with promising anticancer effects", European Journal of Pharmaceutical Sciences, Elsevier Amsterdam, NL, vol. 124, Aug. 29, 2018 (Aug. 29, 2018), pp. 165-181, XP085483648.
Tang Qidong et al., "Discovery of novel 7-azaindole derivatives bearing dihydropyridazine moiety as c-Met kinase inhibitors", European Journal of Medicinal Chemistry, vol. 133, Jun. 1, 2017 (Jun. 1, 2017), pp. 97-106, XP093026184.
Wang Lin Xiao et al., "Discovery of novel pyrrolo-pyridine/pyrimidine derivatives bearing pyridazinone moiety as c-Met kinase inhibitors", European Journal of Medicinal Chemistry, vol. 141, Oct. 13, 2017 (Oct. 13, 2017), pp. 538-551, XP085259430.
Byrd Katherine M. et al., "Synthesis and Biological Evaluation of Stilbene Analogues as Hsp90 C-Terminal Inhibitors", Chemmedchem Communications, vol. 12, No. 24, Nov. 30, 2017 (Nov. 30, 2017), pp. 2022-2029, XP093025869.

\* cited by examiner

COMPOUNDS AND USES THEREOF

PRIORITY CLAIM

This application is continuation application under 35 U.S.C. § 120 of PCT Application No. PCT/US2019/023737, filed on Mar. 22, 2019, published on Sep. 26, 2019 under Publication Number WO2019/183587, which claims the benefit of priority under 35 U.S.C. § 119 of U.S. Provisional Application No. 62/647,308 filed on Mar. 23, 2018, the entireties of which are herein incorporated by reference.

BACKGROUND

An incomplete understanding of the molecular perturbations that cause disease, as well as a limited arsenal of robust model systems, has contributed to a failure to generate successful disease-modifying therapies against common and progressive neurological disorders, such as Parkinson's Disease (PD) and Alzheimer's Disease (AD). Progress is being made on many fronts to find agents that can arrest the progress of these disorders. However, the present therapies for most, if not all, of these diseases provide very little relief. Accordingly, a need exists to develop therapies that can alter the course of neurodegenerative diseases. More generally, a need exists for better methods and compositions for the treatment of neurodegenerative diseases in order to improve the quality of the lives of those afflicted by such diseases.

SUMMARY OF THE INVENTION

In an aspect, this disclosure features a compound having the structure of Formula I:

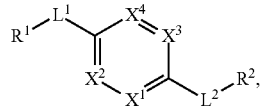

Formula I where $R^1$ is optionally substituted $C_1$-$C_6$ alkyl, optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl;

$L^1$ is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ alkynylene, optionally substituted $C_3$-$C_6$ carbocyclylene,

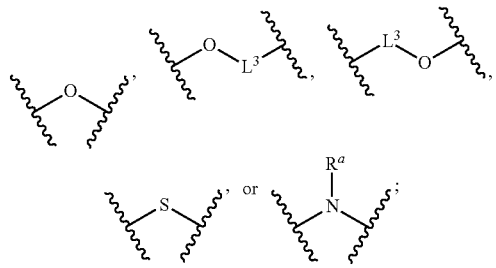

$R^a$ is H or optionally substituted $C_1$-$C_6$ alkyl;
$L^3$ is optionally substituted $C_2$-$C_9$ heterocyclylene;
each of $X^1$, $X^2$, $X^3$, and $X^4$ is, independently, N or CH;

$L^2$ is optionally substituted $C_1$-$C_6$ alkylene or optionally substituted $C_1$-$C_6$ heteroalkylene; and $R^2$ is optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, or a pharmaceutically acceptable salt thereof.

In some embodiments, $L^1$ is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ alkynylene, optionally substituted $C_3$-$C_6$ carbocyclylene,

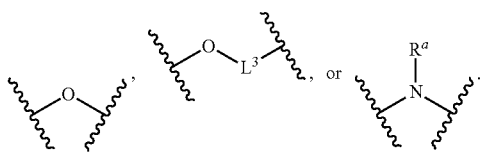

In some embodiments, $L^1$ is optionally substituted $C_1$-$C_6$ alkylene, optionally substituted $C_2$-$C_6$ alkenylene, or optionally substituted $C_2$-$C_6$ alkynylene.

In some embodiments, $L^1$ is

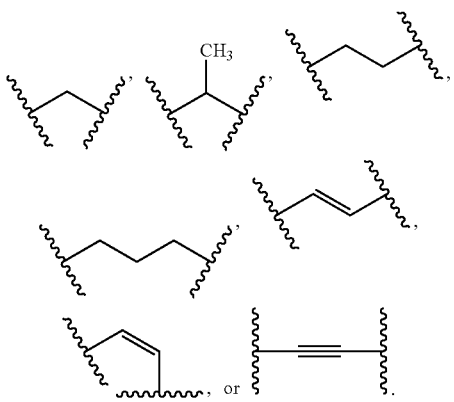

In some embodiments, $L^1$ is

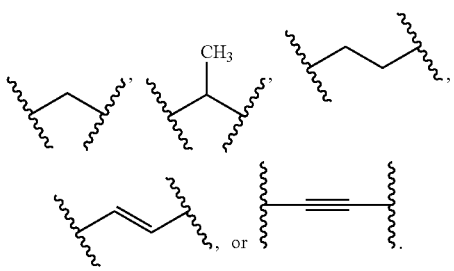

In some embodiments, $L^1$ is

In some embodiments, $L^1$ is optionally substituted $C_3$-$C_6$ carbocyclylene.

In some embodiments, $L^1$ is

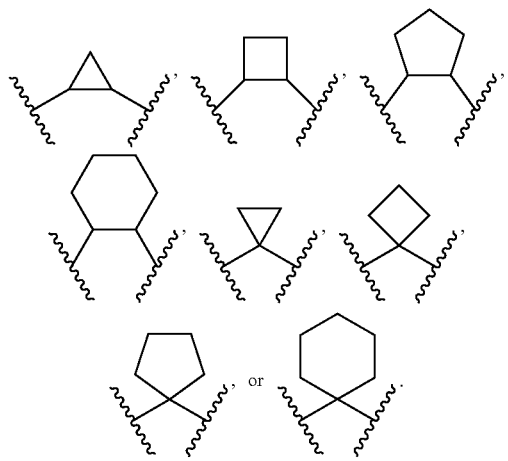

In some embodiments, $L^1$ is

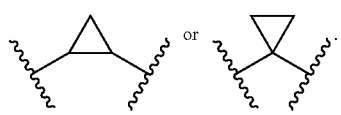 [SMILES: *C1CC1* ; *C1(*)CC1]

In some embodiments, $L^1$ is

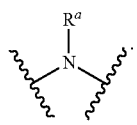

In some embodiments, $L^1$ is

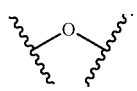 [SMILES: *O*]

In some embodiments, $L^1$ is

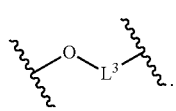

In some embodiments, $L^1$ is

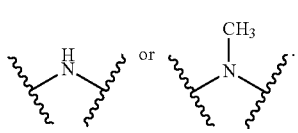

In some embodiments, $L^1$ is

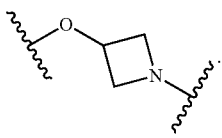 [SMILES: *OC1CN(*)C1]

In some embodiments, $L^1$ is optionally substituted $C_1$-$C_6$ heteroalkylene.

In some embodiments, $L^1$ is

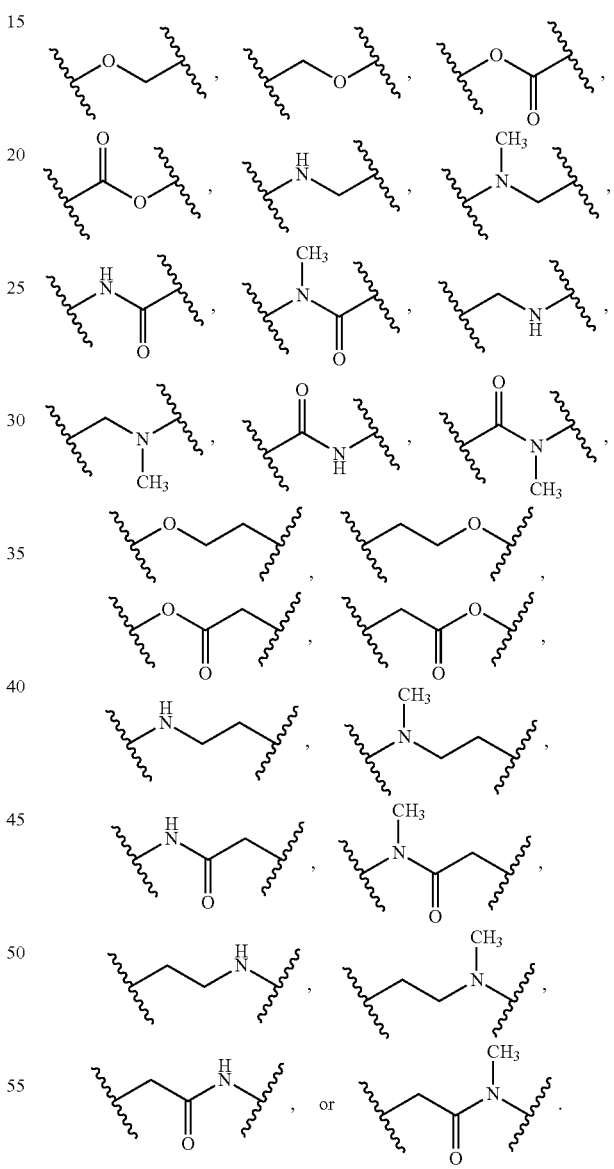

In some embodiments, $L^1$ is

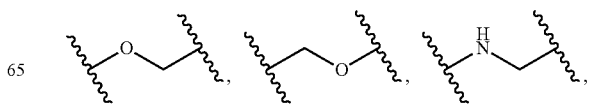

-continued

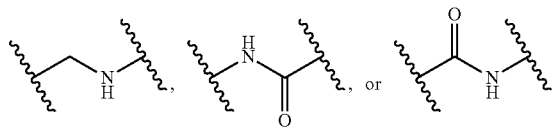

In some embodiments, L¹ is

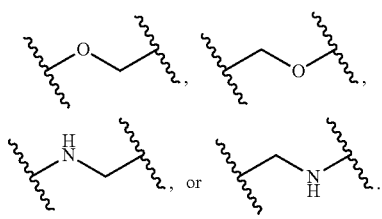

In some embodiments, L² is optionally substituted $C_1$-$C_6$ heteroalkyl.

In some embodiments, L² is

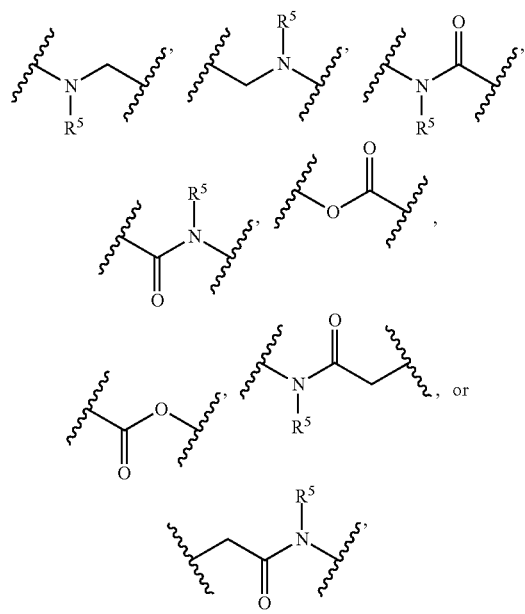

where R⁵ is H or optionally substituted $C_1$-$C_6$ alkyl.

In some embodiments, L² is

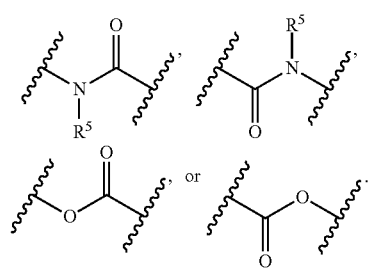

In some embodiments, L² is

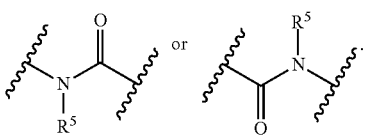

In some embodiments, R⁵ is H or $CH_3$. In some embodiments, R⁵ is H.

In some embodiments, X¹ is N. In some embodiments, X¹ is CH.

In some embodiments, X² is N. In some embodiments, X² is CH.

In some embodiments, X³ is N. In some embodiments, X³ is CH.

In some embodiments, X⁴ is N. In some embodiments, X⁴ is CH.

In some embodiments, at most two of X¹, X², X³, and X⁴ are N.

In some embodiments, the compound has the structure of Formula Ia:

Formula Ia

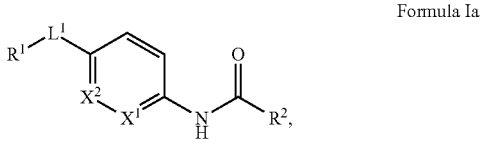

or a pharmaceutically acceptable salt thereof.

In some embodiments, the compound has the structure of Formula Ib:

Formula Ib

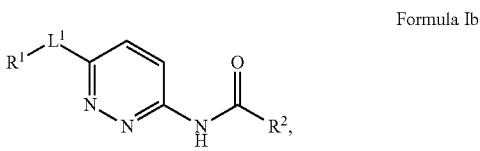

or a pharmaceutically acceptable salt thereof.

In some embodiments, the compound has the structure of Formula Ic:

Formula Ic

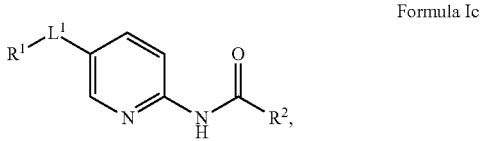

or a pharmaceutically acceptable salt thereof.

In some embodiments, the compound has the structure of Formula Id:

Formula Id

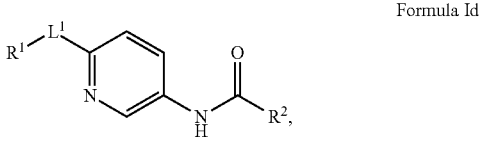

or a pharmaceutically acceptable salt thereof.

In some embodiments, the compound has the structure of Formula Ie:

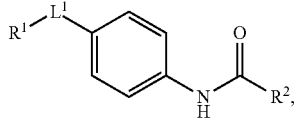

Formula Ie or a pharmaceutically acceptable salt thereof.

In some embodiments, $R^2$ is optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $R^2$ is optionally substituted $C_2$-$C_9$ heterocyclyl, optionally substituted $C_6$-$C_{10}$ aryl, or optionally substituted $C_2$-$C_9$ heteroaryl.

In some embodiments, $R^2$ is optionally substituted $C_2$-$C_9$ heterocyclyl or optionally substituted $C_2$-$C_9$ heteroaryl.

In some embodiments, $R^2$ is optionally substituted $C_2$-$C_9$ heterocyclyl.

In some embodiments, $R^2$ is optionally substituted $C_2$-$C_5$ heterocyclyl.

In some embodiments, $R^2$ is

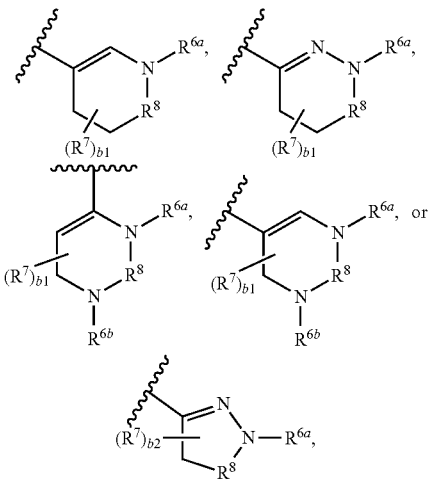

where b1 is 0, 1, 2, 3, or 4;
b2 is 0, 1, or 2;
$R^{6a}$ is H, optionally substituted $C_1$-$C_6$ alkyl, or optionally substituted $C_3$-$C_6$ carbocyclyl;
$R^{6b}$ is H, optionally substituted $C_1$-$C_6$ alkyl, or optionally substituted $C_3$-$C_6$ carbocyclyl;
each $R^7$ is, independently, halo or optionally substituted $C_1$-$C_6$ alkyl; and
$R^8$ is

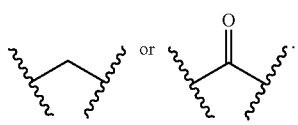

In some embodiments, $R^{6a}$ is H or optionally substituted $C_1$-$C_6$ alkyl.

In some embodiments, $R^{6a}$ is H,

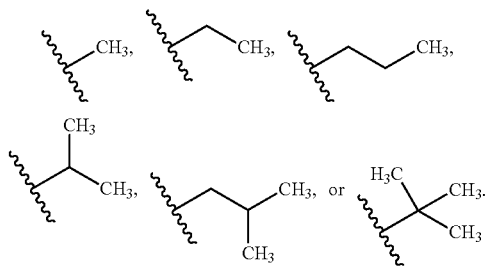

In some embodiments, $R^{6a}$ is H or

In some embodiments, $R^{6b}$ is H or optionally substituted $C_1$-$C_6$ alkyl.

In some embodiments, $R^{6b}$ is H,

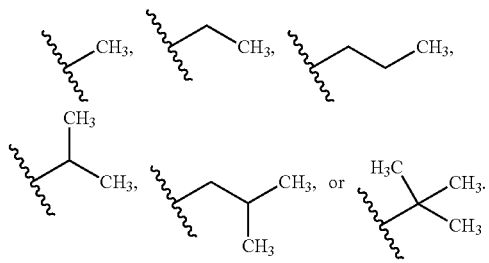

In some embodiments, $R^{6b}$ is H or

In some embodiments, $R^8$ is

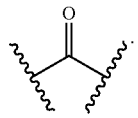

In some embodiments, each $R^7$ is, independently, F, Cl, Br, I,

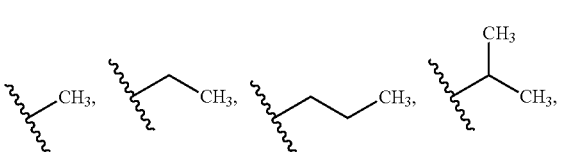

-continued

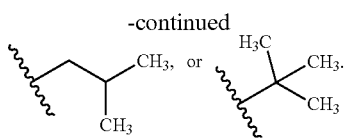

In some embodiments, each $R^7$ is, independently,

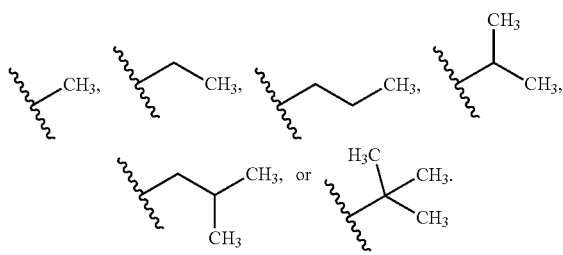

In some embodiments, b1 is 0 or 1. In some embodiments, b1 is 0. In some embodiments, b1 is 1.

In some embodiments, b2 is 0 or 1. In some embodiments, b2 is 0. In some embodiments, b2 is 1.

In some embodiments, $R^2$ is

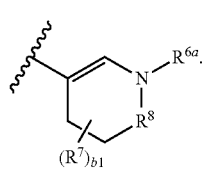

In some embodiments, $R^2$ is

In some embodiments,

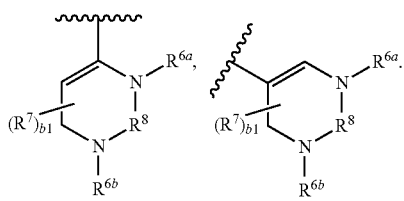

In some embodiments, $R^2$ is

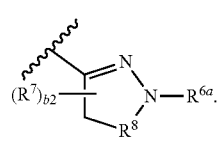

In some embodiments, $R^2$ is

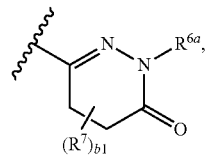

In some embodiments, $R^2$ is

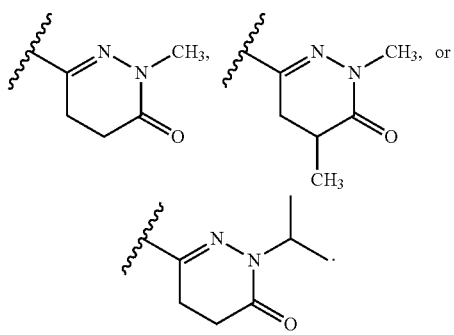

In some embodiments, $R^2$ is

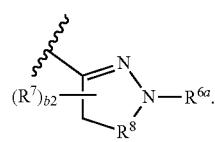

In some embodiments, $R^2$ is

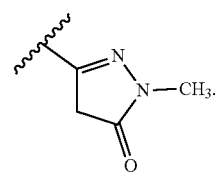 [SMILES: *C1=NN(C)C(=O)C1]

In some embodiments, $R^2$ is

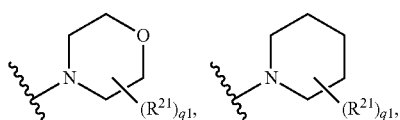
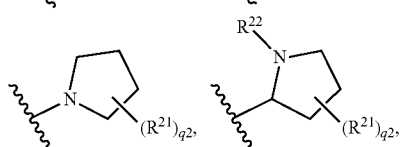
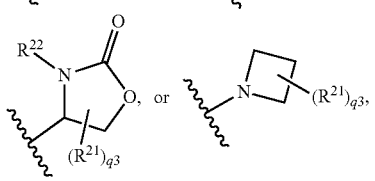

where
q1 is 0, 1, 2, 3, 4, 5, or 6;
q2 is 0, 1, 2, 3, or 4;
q3 is 0, 1, or 2;
each $R^{21}$ is, independently, hydroxyl, optionally substituted $C_1$-$C_6$ alkyl, or optionally substituted $C_1$-$C_6$ heteroalkyl; or two of the $R^{21}$ groups, taken together with the carbon atom to which each is attached, combine to form an optionally substituted $C_3$-$C_{10}$ carbocyclyl or optionally substituted $C_2$-$C_6$ heterocyclyl; and
$R^{22}$ is H or optionally substituted $C_1$-$C_6$ alkyl.

In some embodiments, each $R^{21}$ is, independently,

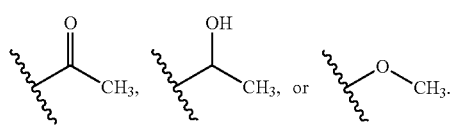

In some embodiments, $R^{22}$ is H or

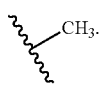

In some embodiments, $R^2$ is

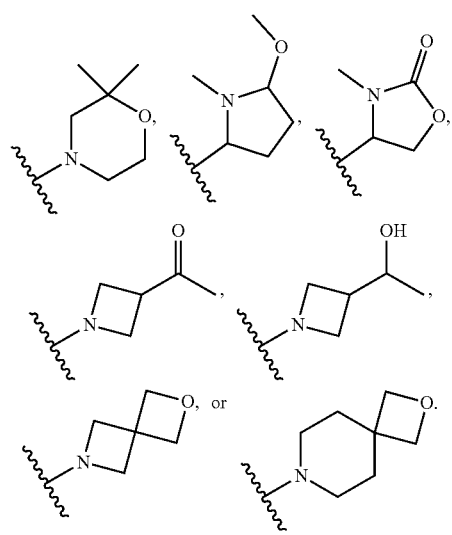

In some embodiments, $R^2$ is optionally substituted $C_2$-$C_9$ heteroaryl.

In some embodiments, $R^2$ is optionally substituted $C_2$-$C_5$ heteroaryl.

In some embodiments, $R^2$ is

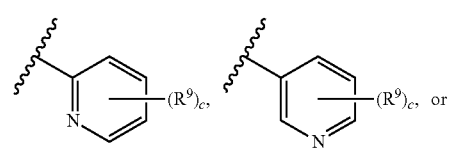

-continued where
c is 0, 1, 2, 3, or 4; and
each $R^9$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^9$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^9$ is, independently, F, Cl, Br, I, CN,

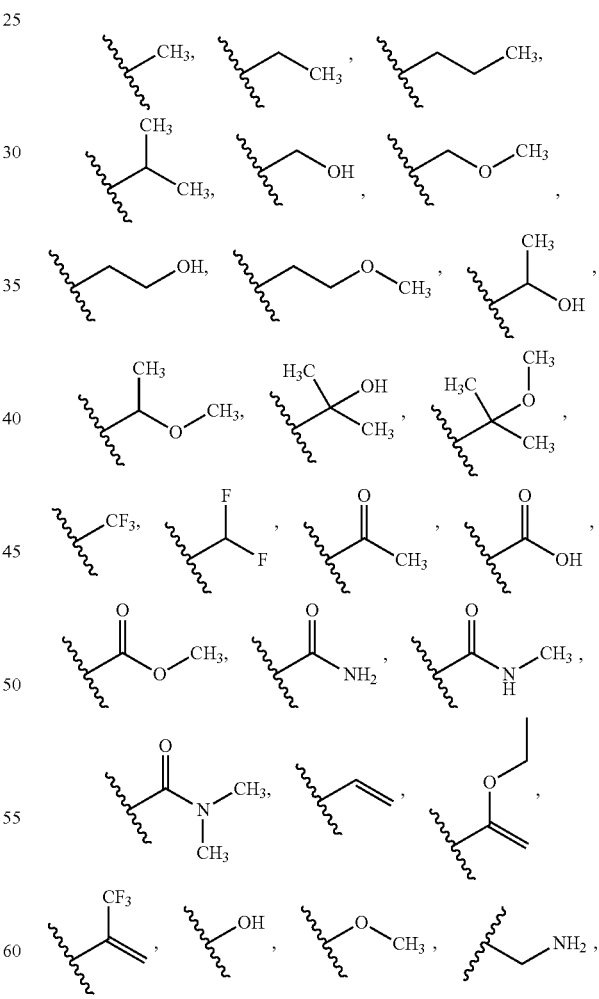

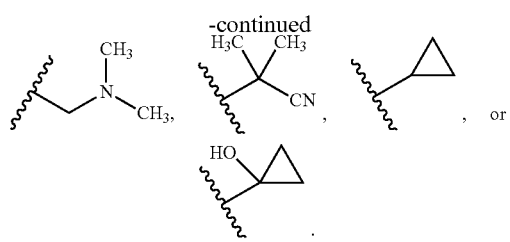
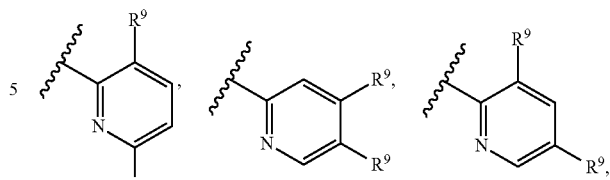
In some embodiments, c is 0, 1, or 2. In some embodiments, c is 0. In some embodiments, c is 1. In some embodiments, c is 2.
In some embodiments, $R^2$ is
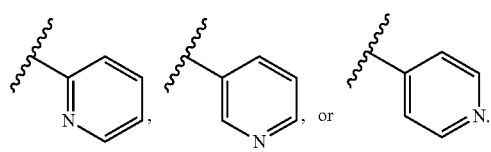
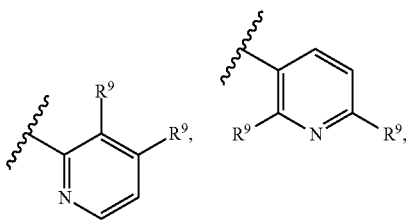
In some embodiments, $R^2$ is
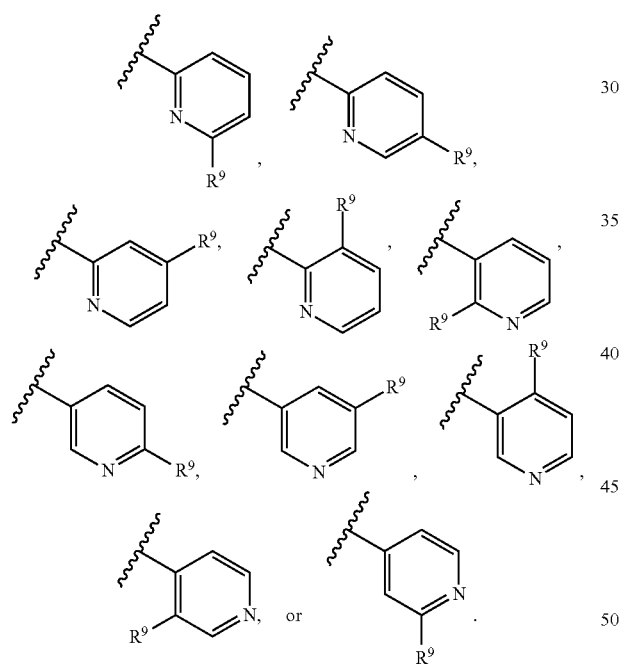
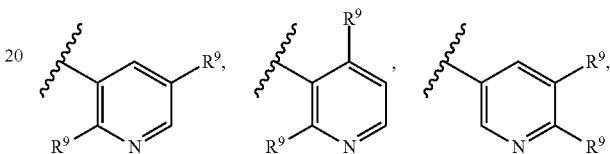
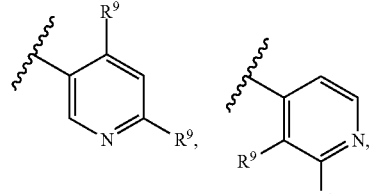
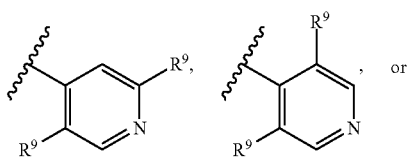
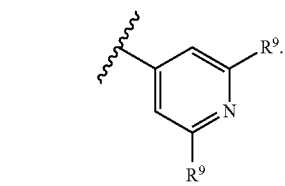
In some embodiments, $R^2$ is
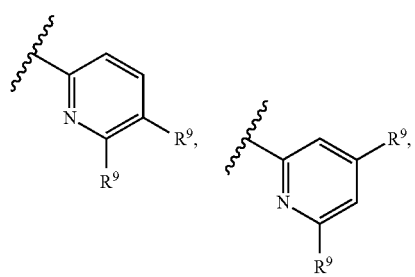
In some embodiments, $R^2$ is
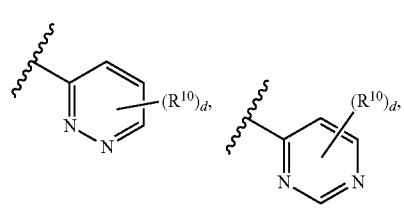
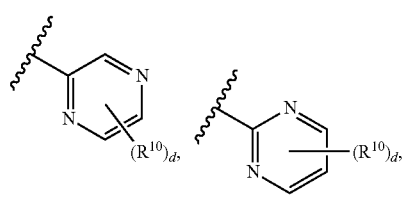

-continued

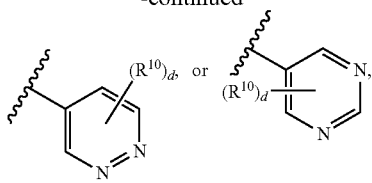

where d is 0, 1, 2, or 3; and each $R^{10}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{10}$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^{10}$ is, independently, F, Cl, Br, I, CN,

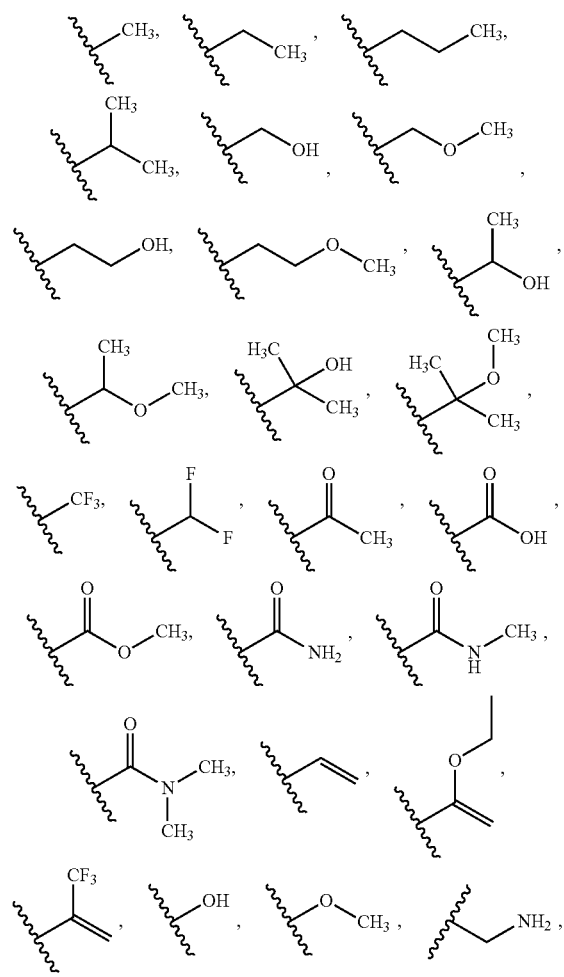

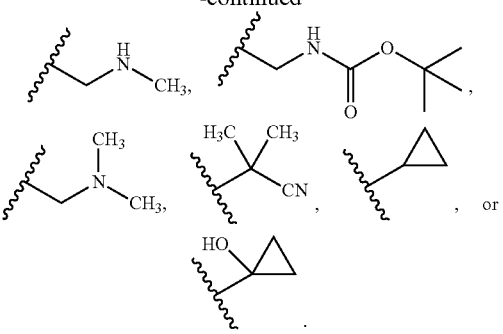

In some embodiments, d is 0, 1, or 2. In some embodiments, d is 0. In some embodiments, d is 1. In some embodiments, d is 2.

In some embodiments, $R^2$ is

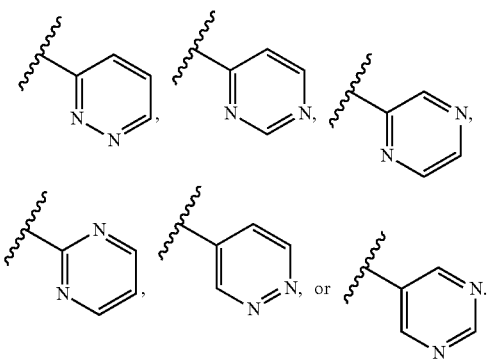

In some embodiments, $R^2$ is

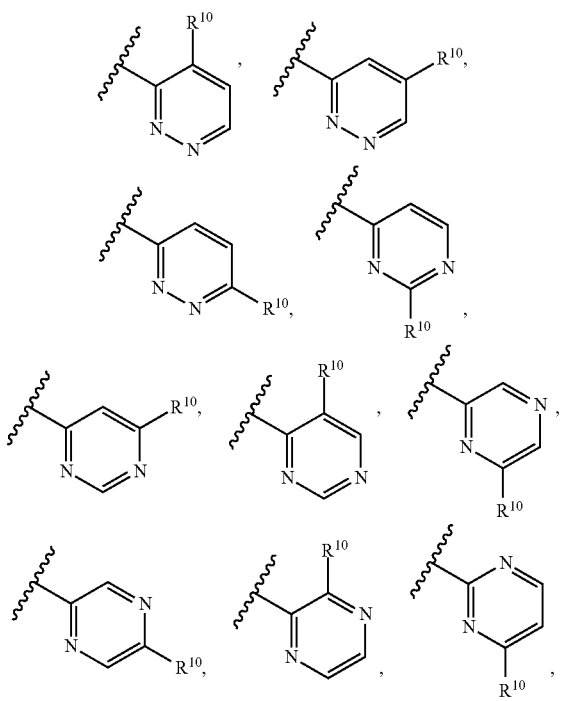

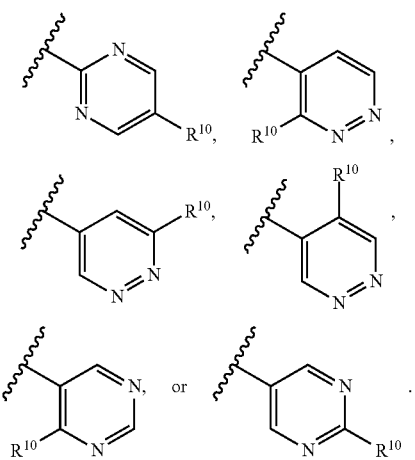
In some embodiments, $R^2$ is
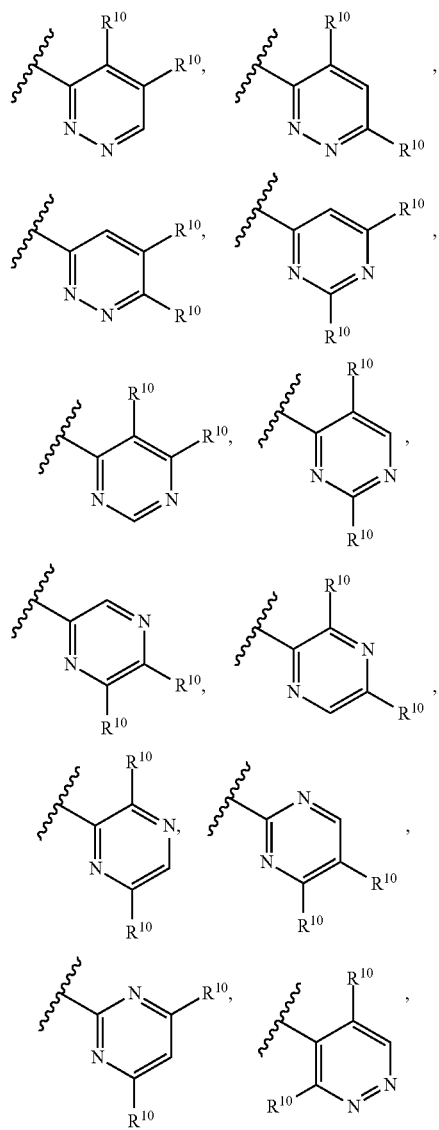
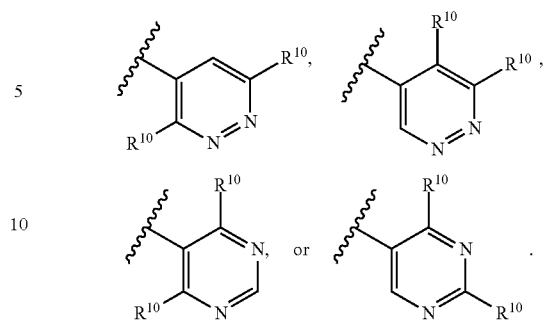
In some embodiments, $R^2$
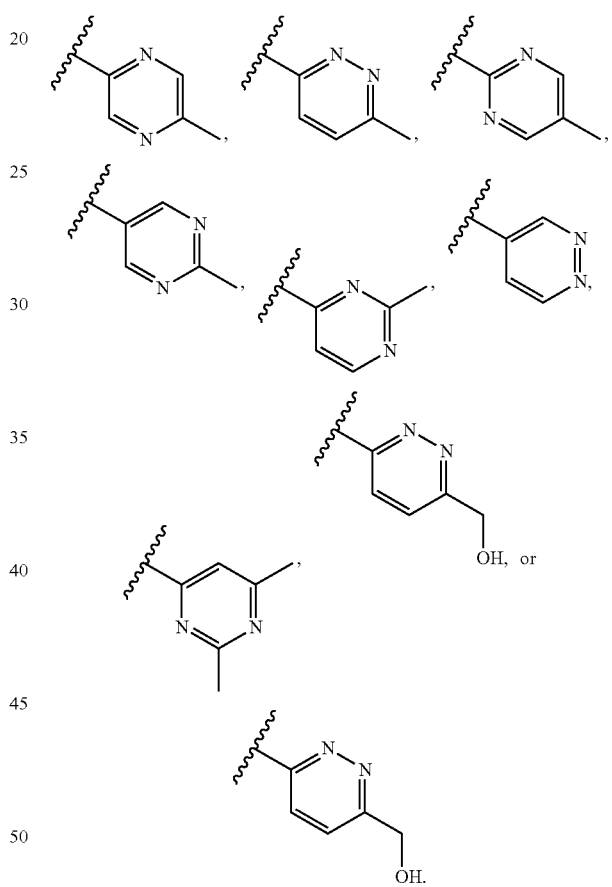
In some embodiments, $R^2$
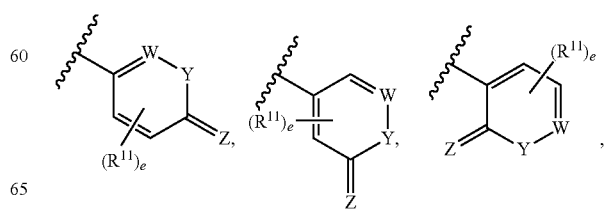

-continued

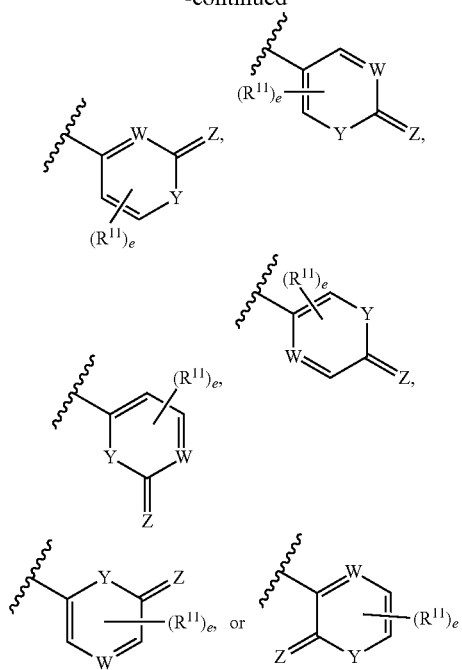

where e is 0, 1, or 2;

each $R^{11}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

W is CH or N;

Y is O, S, or $NR^{Y1}$;

$R^{Y1}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl;

Z is O, S, or $NR^{71}$; and $R^{Z1}$ is H or optionally substituted $C_1$-$C_6$ alkyl.

In some embodiments, each $R^{11}$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^{11}$ is, independently, F, Cl, Br, I, CN,

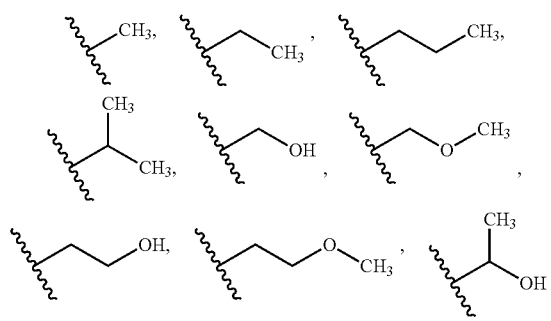

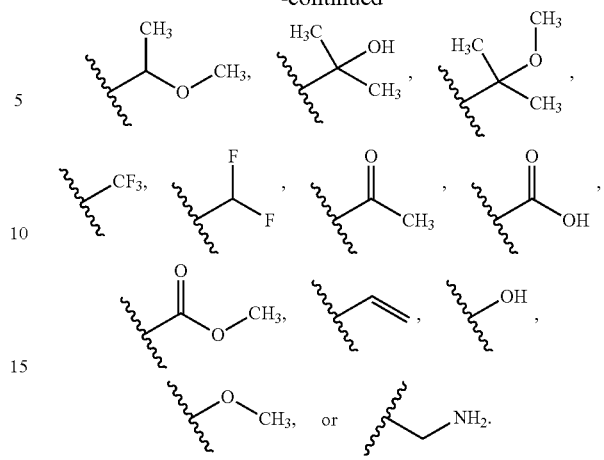

In some embodiments, W is CH. In some embodiments, W is N.

In some embodiments, Y is $NR^{Y1}$.

In some embodiments, $R^{Y1}$ is H, optionally substituted $C_1$-$C_6$ alkyl, or optionally substituted $C_3$-$C_{10}$ carbocyclyl.

In some embodiments, $R^{Y1}$ is H. In some embodiments, $R^{Y1}$ is optionally substituted $C_1$-$C_6$ alkyl.

In some embodiments, $R^{Y1}$ is

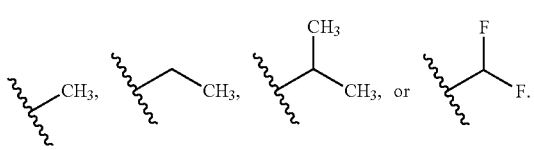

In some embodiments, $R^{Y1}$ is optionally substituted $C_3$-$C_{10}$ carbocyclyl.

In some embodiments, $R^{Y1}$ is optionally substituted $C_3$-$C_6$ carbocyclyl.

In some embodiments, $R^{Y1}$ is

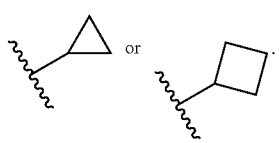

In some embodiments, Z is O.

In some embodiments, $R^2$ is

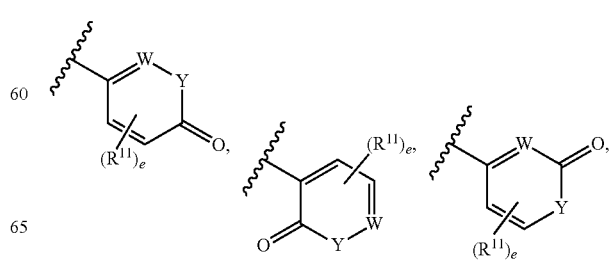

-continued
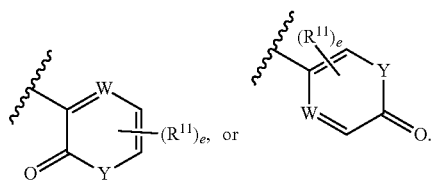
In some embodiments, e is 0 or 1. In some embodiments, e is 0. In some embodiments, e is 1.
In some embodiments, $R^2$ is
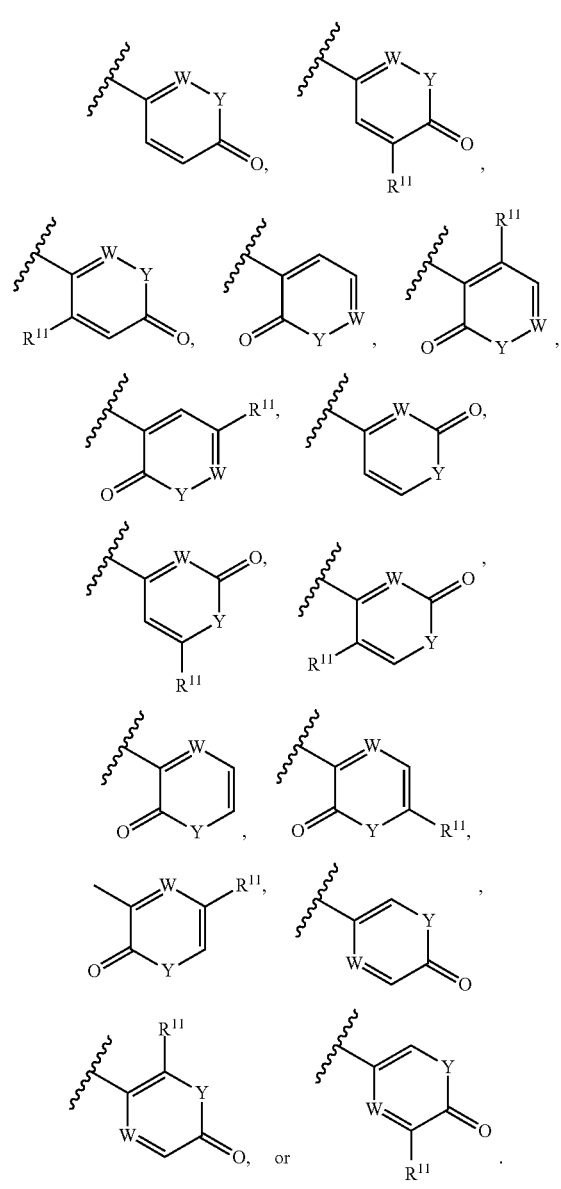
In some embodiments, $R^2$ is
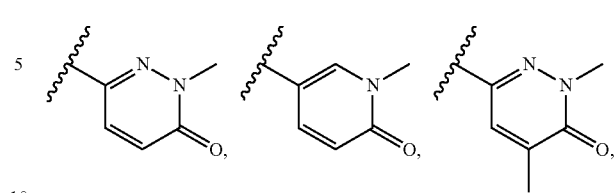
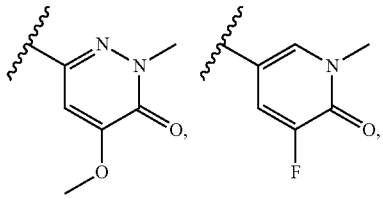
In some embodiments, $R^2$ is
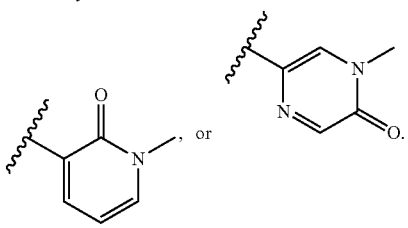
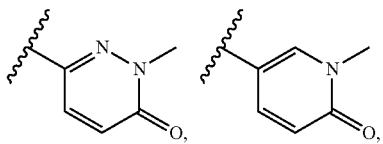
In some embodiments, $R^2$
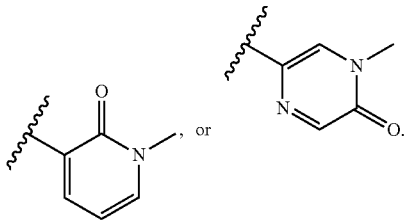
In some embodiments, $R^2$ is

where
$R^{12a}$ is H, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;

each of $Y^a$ and $Y^b$ is, independently, O, S, or $NR^{Y2}$;
$R^{Y2}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl;
$Z^a$ is O, S, or $NR^{Z2}$; and
$R^{Z2}$ is H or optionally substituted $C_1$-$C_6$ alkyl.

In some embodiments, $R^{12a}$ is H.
In some embodiments, $Z^a$ is O.
In some embodiments, $R^2$ is

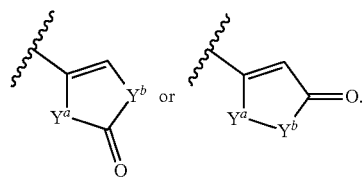

In some embodiments, each of $Y^a$ and $Y^b$ is $NR^{Y2}$.
In some embodiments, $R^{Y2}$ is H, optionally substituted $C_1$-$C_6$ alkyl, or optionally substituted $C_3$-$C_{10}$ carbocyclyl.
In some embodiments, $R^{Y2}$ is H,

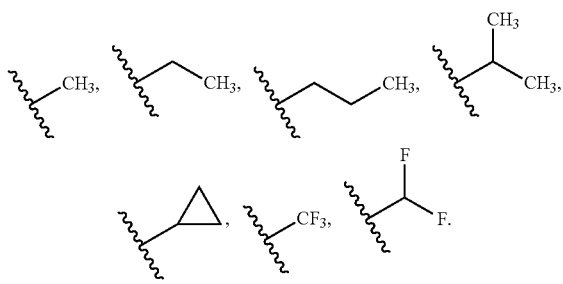

In some embodiments, $R^2$ is

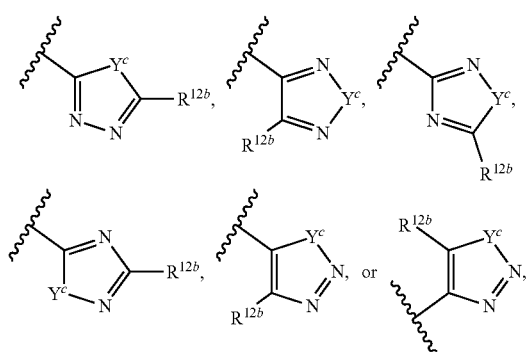

where
$R^{12b}$ is H, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; and $Y^c$ is O, S, or $NR^{Y3}$;
$R^{Y3}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl.

In some embodiments, $R^{12b}$ is H.
In some embodiments, $Y^c$ is $NR^{Y3}$.
In some embodiments, $R^{Y3}$ is H, optionally substituted $C_1$-$C_6$ alkyl, or optionally substituted $C_3$-$C_{10}$ carbocyclyl.
In some embodiments, $R^{Y3}$ is H,

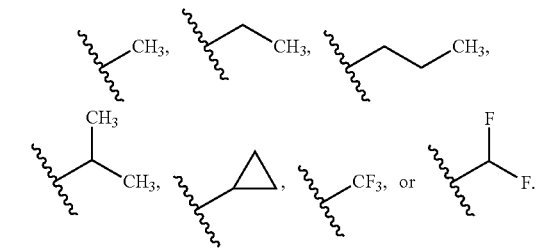

In some embodiments, $R^2$ is

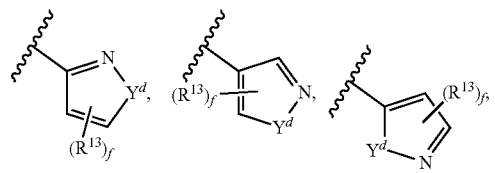
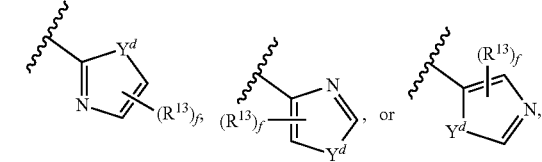

where
f is 0, 1, or 2;
each $R^{13}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; and $Y^d$ is O, S, or $NR^{Y4}$;
$R^{Y4}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl.

In some embodiments, each $R^{13}$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^{13}$ is, independently, halo, CN, or optionally substituted $C_1$-$C_6$ alkyl.

In some embodiments, f is 0 or 1. In some embodiments, f is 0. In some embodiments, f is 1.

In some embodiments, $Y^d$ is $NR^{Y4}$.

In some embodiments, $R^{Y4}$ is H, optionally substituted $C_1$-$C_6$ alkyl, or optionally substituted $C_3$-$C_{10}$ carbocyclyl.

In some embodiments, $R^{Y4}$ is H,

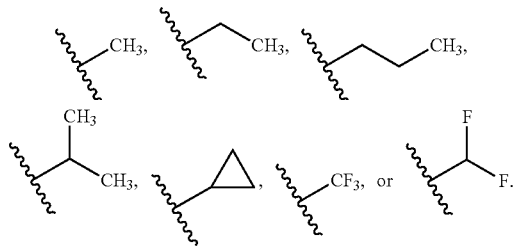

In some embodiments, $Y^d$ is O.
In some embodiments, $R^2$ is

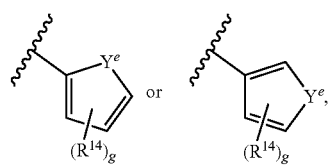

where
g is 0, 1, 2, 3, or 4;
each $R^{14}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$;
$Y^e$ is O, S, or $NR^{Y5}$; and
$R^{Y5}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_6$ heterocyclyl.

In some embodiments, $R^{14}$ is halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, $R^{14}$ is halo, CN, or optionally substituted $C_1$-$C_6$ alkyl.

In some embodiments, g is 0, 1, or 2. In some embodiments, g is 0. In some embodiments, g is 1. In some embodiments, g is 2.

In some embodiments, $Y^e$ is $NR^{Y5}$.

In some embodiments, $R^{Y5}$ is H, optionally substituted $C_1$-$C_6$ alkyl, or optionally substituted $C_3$-$C_{10}$ carbocyclyl.

In some embodiments, $R^{Y5}$ is

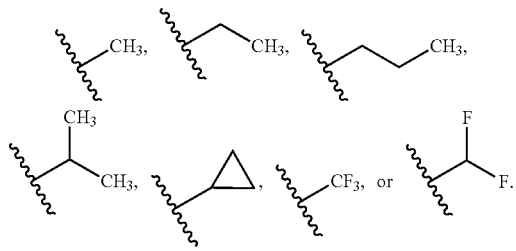

In some embodiments, $Y^e$ is O. In some embodiments, $Y^e$ is S.

In some embodiments, $R^2$ is

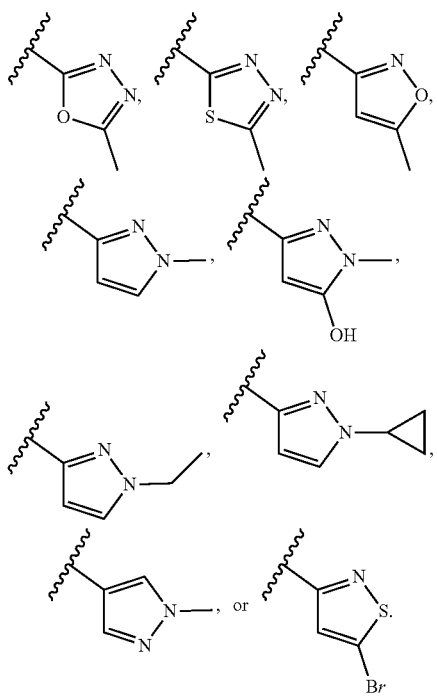

In some embodiments, $R^2$ is

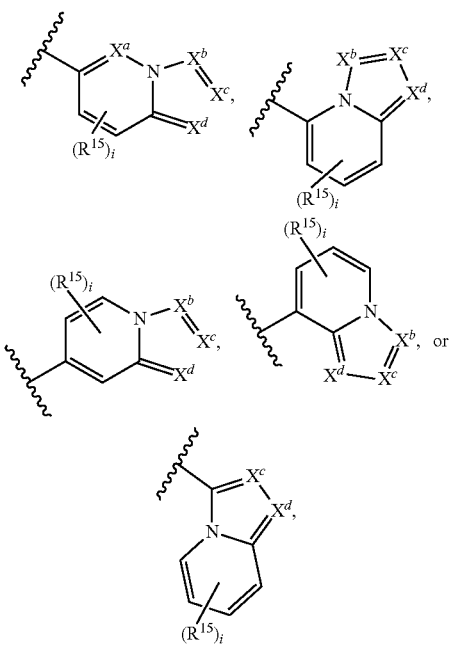

where
each of $X^a$, $X^b$, $X^c$, and $X^d$ is, independently, N or $CR^{17}$;
each $R^{17}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;

i is 0, 1, 2, or 3; and each $R^{15}$ is, independently, halo, CN, $NO_2$, optionally substituted $C_1$-$C_6$ alkyl, optionally substituted $C_2$-$C_9$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{15}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, i is 0 or 1. In some embodiments, i is 0. In some embodiments, i is 1.

In some embodiments, $R^2$ is

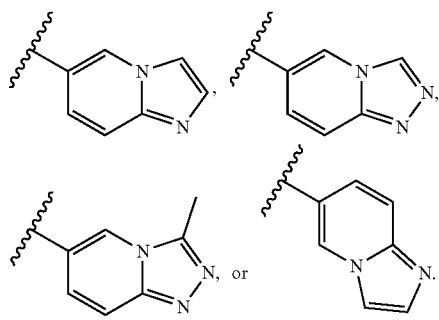

In some embodiments, $R^2$ is

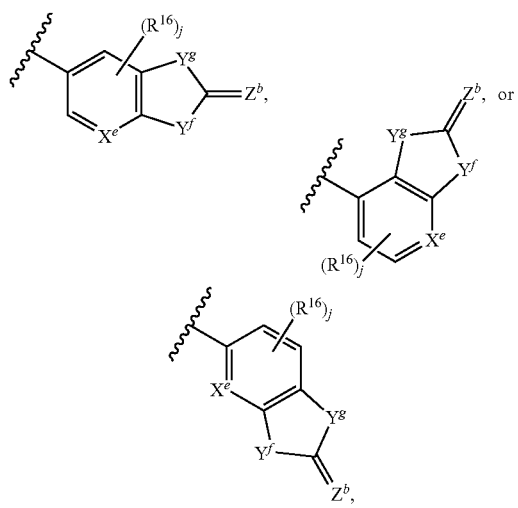

where $X^e$ is N or $CR^{18}$;

$R^{18}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;

j is 0, 1, or 2;

each $R^{16}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;

each of $Y^f$ and $Y^g$ is, independently, O, S, or $NR^{Y6}$;

$R^{Y6}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_6$ heterocyclyl;

$Z^b$ is O, S, or $NR^{Z3}$; and $R^{Z3}$ is H or optionally substituted $C_1$-$C_6$ alkyl.

In some embodiments, each $R^{16}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, j is 0 or 1. In some embodiments, j is 0. In some embodiments, j is 1.

In some embodiments, Z is O.

In some embodiments, $R^2$ is

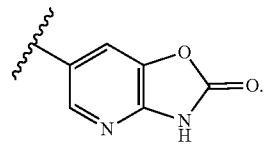 [SMILES: *c1cnc2[nH]c(=O)oc2c1]

In some embodiments, $R^2$ is

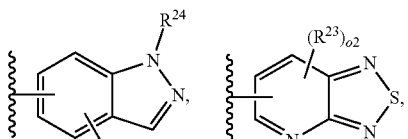

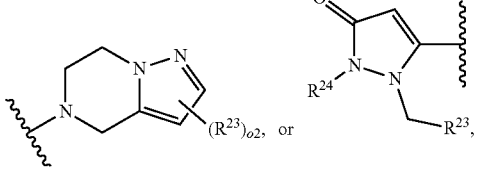

where o1 is 0, 1, 2, or 3;

o2 is 0, 1, or 2;

each $R^{23}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; and $R^{24}$ is H or optionally substituted $C_1$-$C_6$ alkyl.

In some embodiments, $R^2$ is

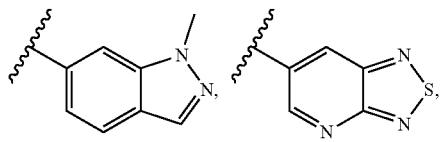

-continued

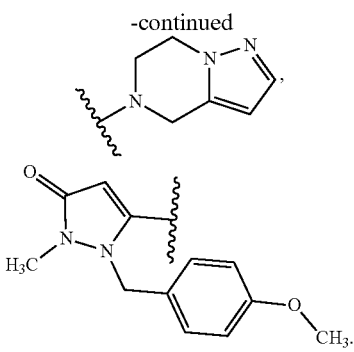

In some embodiments, $R^2$ is optionally substituted $C_6$-$C_{10}$ aryl.

In some embodiments, $R^2$ is

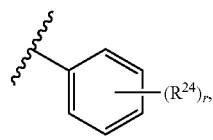

where r is 0, 1, 2, 3, or 4; and each $R^{24}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted sulfone, SH, OH, or $NH_2$.

In some embodiments, each $R^{24}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{24}$ is, independently, halo, CN, $NO_2$, optionally substituted $C_1$-$C_6$ alkyl, optionally substituted $C_1$-$C_6$ heteroalkyl, SH, OH, or $NH_2$.

In some embodiments, r is 0, 1, or 2. In some embodiments, r is 0. In some embodiments, r is 1.

In some embodiments, r is 2.

In some embodiments, $R^2$ is optionally substituted $C_1$-$C_6$ heteroalkyl.

In some embodiments, $R^2$ is

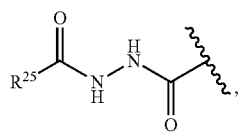

where $R^{25}$ is optionally substituted $C_1$-$C_6$ alkyl or optionally substituted $C_1$-$C_6$ heteroalkyl.

In some embodiments, $R^{25}$ is

In some embodiments, $R^1$ is optionally substituted $C_1$-$C_6$ alkyl.

In some embodiments, $R^1$ is

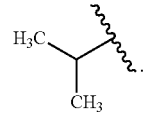

In some embodiments, $R^1$ is optionally substituted $C_6$-$C_{10}$ aryl.

In some embodiments, $R^1$ is

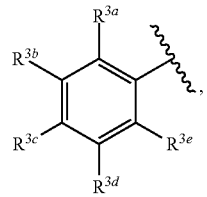

where each of $R^{3a}$, $R^{3b}$, $R^{3c}$, $R^{3d}$, and $R^{3e}$ is, independently, H, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; or $R^{3a}$ and $R^{3b}$, $R^{3b}$ and $R^{3c}$, $R^{3c}$ and $R^{3d}$, or $R^{3d}$ and $R^{3e}$, together with the atoms to which each is attached, combine to form optionally substituted $C_3$-$C_{10}$ carbocyclyl or optionally substituted $C_2$-$C_9$ heterocyclyl.

In some embodiments, each of $R^{3a}$, $R^{3b}$, $R^{3c}$, $R^{3d}$, and $R^{3e}$ is, independently, H, halo, CN, $NO_2$, optionally substituted $C_1$-$C_6$ alkyl, optionally substituted $C_1$-$C_6$ heteroalkyl, SH, OH, or $NH_2$.

In some embodiments, each of $R^{3a}$, $R^{3b}$, $R^{3c}$, $R^{3d}$, and $R^{3e}$ is, independently, H, F, Cl, Br, I, CN,

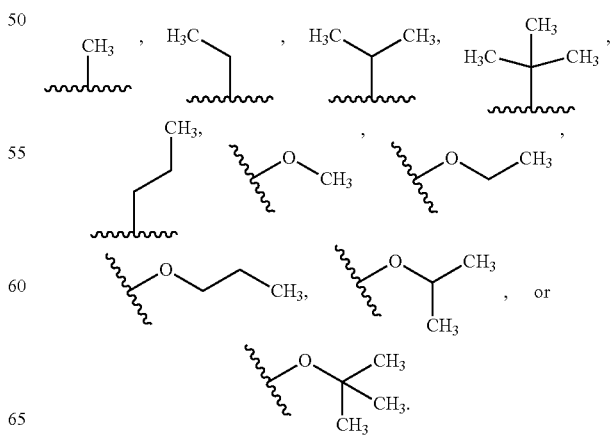

In some embodiments, $R^1$ is

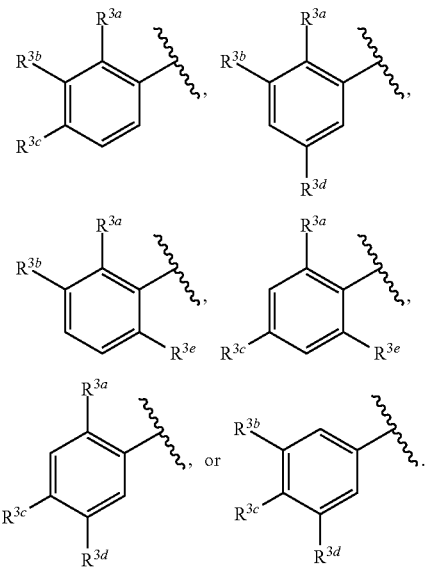

In some embodiments, $R^1$ is

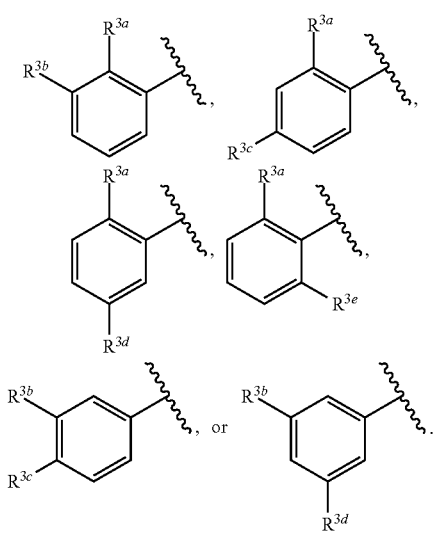

In some embodiments, $R^1$ is

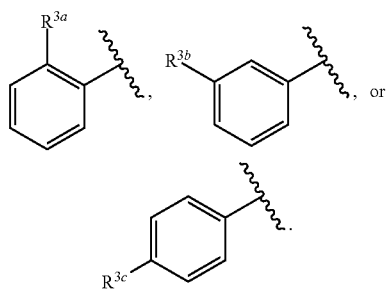

In some embodiments, $R^1$ is

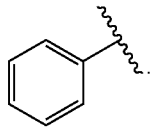

In some embodiments, $R^1$ is phenyl, 3-fluoro-phenyl, 4-fluoro-phenyl, 3-chloro-phenyl, 4-chloro-phenyl, 2-methoxy-phenyl, 3-methoxy-phenyl, 4-methoxy-phenyl, 3,4-di-fluoro-phenyl, 3,4-dichloro-phenyl, 3,5-di-fluoro-phenyl, 3,5-dichloro-phenyl, 3-chloro-4-fluoro-phenyl, 4-chloro-3-fluoro-phenyl, 3-chloro-4-nitrile-phenyl, 3-nitrile-4-fluoro-phenyl, 3-trifluoromethyl-phenyl, 4-trifluoromethyl-phenyl, 3-bromo-phenyl, 3-cyclopropyl-phenyl, 3-cyano-5-fluoro-phenyl, 3-chloro-5-fluoro-phenyl, 3-chloro-5-cyano-phenyl, 3-chloro-5-methoxy-phenyl, or 1,3-dihydroisobenzofuran.

In some embodiments, $R^1$ is optionally substituted $C_3$-$C_{10}$ carbocyclyl.

In some embodiments, $R^1$ is optionally substituted $C_3$-$C_{10}$ cycloalkyl.

In some embodiments, $R^1$ is

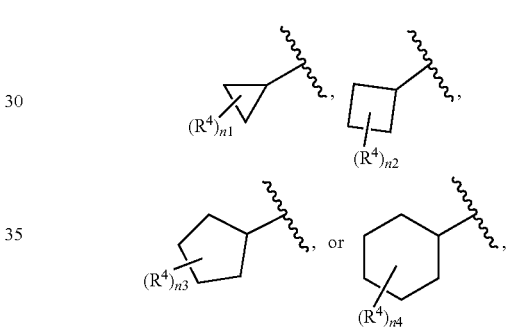

where
n1 is 0, 1, 2, or 3;
n2 is 0, 1, 2, 3, or 4;
n3 is 0, 1, 2, 3, 4, or 5;
n4 is 0, 1, 2, 3, 4, 5, or 6; and
each $R^4$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$.

In some embodiments, $R^1$ is

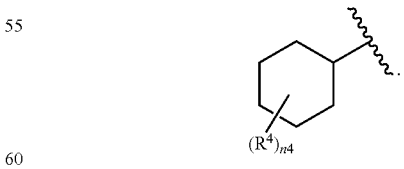

In some embodiments, each $R^4$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, each $R^4$ is, independently, F, Cl, Br, I, CN,

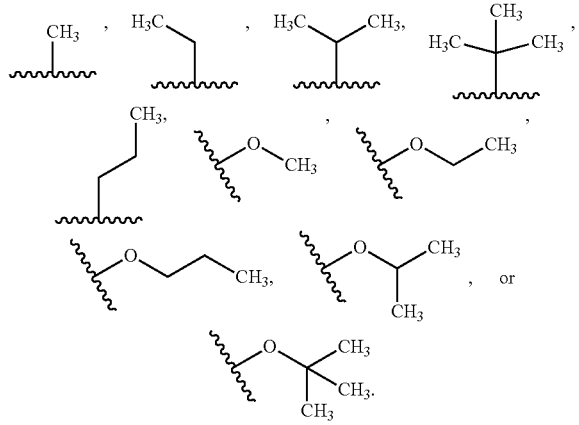

In some embodiments, $R^1$ is optionally substituted cycloalkenyl.

In some embodiments, $R^1$ is where
n5 is 0, 1, 2, 3, or 4;
n6 is 0, 1, 2, 3, 4, or 5; and
each $R^4$ is, independently, halo, CN, NO$_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_9$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or NH$_2$.

In some embodiments, $R^1$ is

In some embodiments, each $R^4$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or NH$_2$.

In some embodiments, each $R^4$ is, independently, F, Cl, Br, I, CN,

In some embodiments, $R^1$ is optionally substituted $C_2$-$C_6$ heteroaryl.

In some embodiments, $R^1$ is where k is 0, 1, 2, or 3;
each $R^{19}$ is, independently, halo, CN, NO$_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or NH$_2$;
$Y^h$ is O, S, or NR$^{Y7}$; and
$R^{Y7}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl.

In some embodiments, each $R^{19}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or NH$_2$.

In some embodiments, each $R^{19}$ is, independently, F, Cl, Br, I, CN, or

In some embodiments, $Y^h$ is S.

In some embodiments, k is 0 or 1. In some embodiments, k is 0. In some embodiments, k is 1.

In some embodiments, $R^1$ is

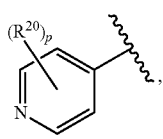

where p is 0, 1, 2, 3, or 4; and each $R^{20}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{20}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, each $R^{20}$ is, independently, F, Cl, Br, I, CN, or

In some embodiments, p is 0 or 1. In some embodiments, p is 0. In some embodiments, p is 1.

In some embodiments, $R^1$ is

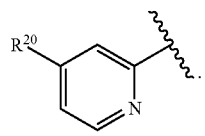

In some embodiments, $R^1$ is 5-chloropyridin-3-yl, 5-trifluoromethyl-pyridin-3-yl, 4-trifluoromethyl-pyridin-2-yl, 5-fluoropyridin-3-yl, or 5-fluoropyridin-3-yl.

In an aspect, the disclosure features a compound having the structure of Formula II:

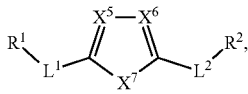

Formula II where $R^1$ is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl;

$L^1$ is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ alkynylene, optionally substituted $C_3$-$C_6$ carbocyclylene,

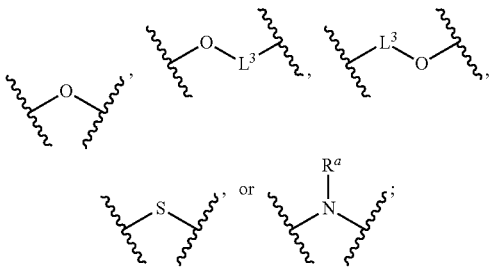

$R^a$ is H or optionally substituted $C_1$-$C_6$ alkyl;

$L^3$ is optionally substituted $C_2$-$C_9$ heterocyclylene;

each of $X^5$ and $X^6$ is, independently, N or CH;

$X^7$ is O, S, or $NR^b$;

$R^b$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl;

$L^2$ is optionally substituted $C_1$-$C_6$ alkylene or optionally substituted $C_1$-$C_6$ heteroalkylene; and $R^2$ is optionally substituted $C_1$-$C_6$ heteroalkyl, optionally substituted $C_3$-$C_{10}$ carbocyclyl, optionally substituted $C_2$-$C_6$ heterocyclyl, optionally substituted $C_6$-$C_{10}$ aryl, or optionally substituted $C_2$-$C_6$ heteroaryl, or a pharmaceutically acceptable salt thereof.

In some embodiments, $L^1$ is optionally substituted $C_1$-$C_6$ alkylene, optionally substituted $C_1$-$C_6$ heteroalkylene, optionally substituted $C_2$-$C_6$ alkenylene, optionally substituted $C_2$-$C_6$ alkynylene, optionally substituted $C_3$-$C_6$ carbocyclylene,

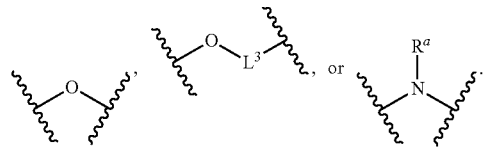

In some embodiments, $L^1$ is optionally substituted $C_1$-$C_6$ alkylene, optionally substituted $C_2$-$C_6$ alkenylene, or optionally substituted $C_2$-$C_6$ alkynylene.

In some embodiments, $L^1$ is

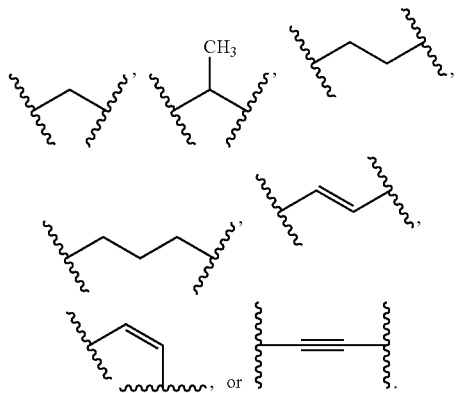

In some embodiments, $L^1$ is

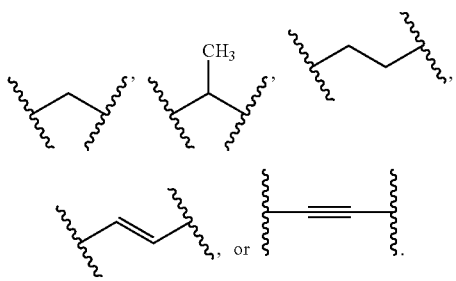

In some embodiments, $L^1$ is

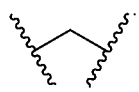

In some embodiments, $L^1$ is optionally substituted $C_3$-$C_6$ carbocyclylene.

In some embodiments, $L^1$ is

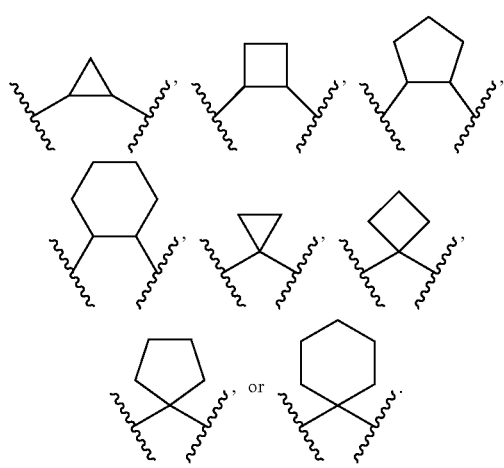

In some embodiments, $L^1$ is

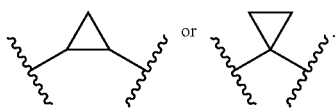 [SMILES: *C1CC1* ; *C1(*)CC1]

In some embodiments, $L^1$ is

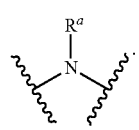

In some embodiments, $L^1$ is

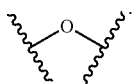 [SMILES: *O*]

In some embodiments, $L^1$ is

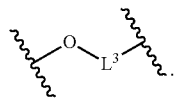

In some embodiments, $L^1$ is

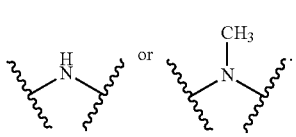

In some embodiments, $L^1$ is

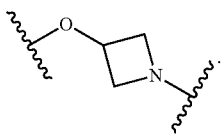 [SMILES: *OC1CN(*)C1]

In some embodiments, $L^1$ is optionally substituted $C_1$-$C_6$ heteroalkylene.

In some embodiments, $L^1$ is

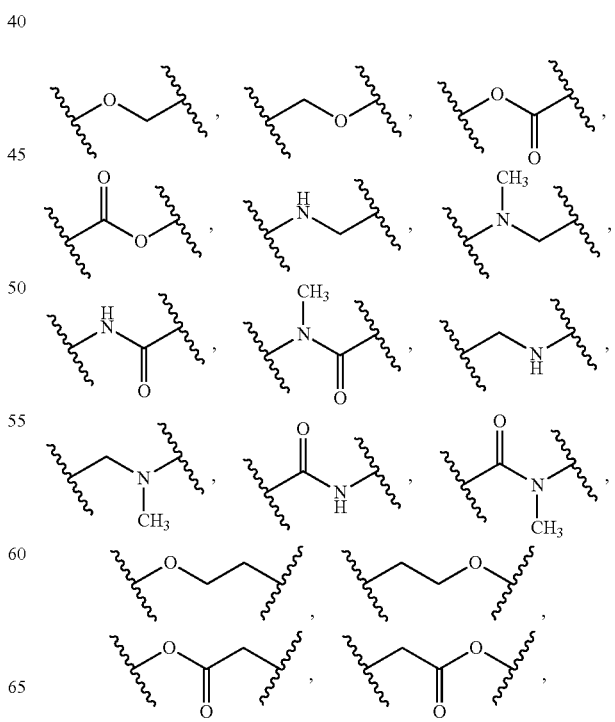

-continued

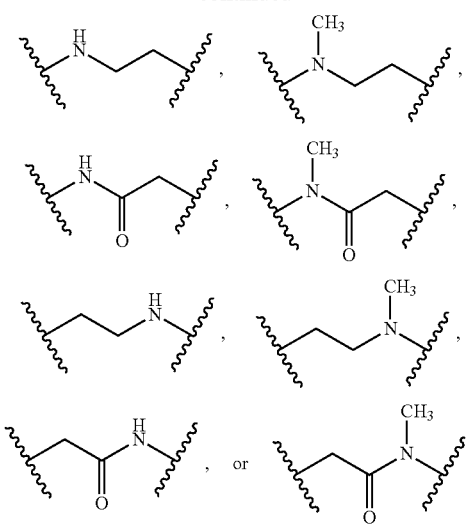

In some embodiments, $L^1$ is

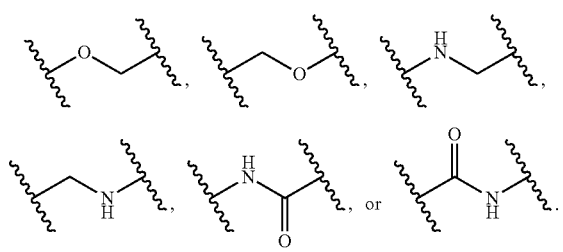

In some embodiments, $L^1$ is

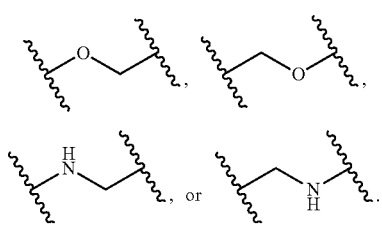

In some embodiments, $L^2$ is optionally substituted $C_1$-$C_6$ heteroalkyl.

In some embodiments, $L^2$ is

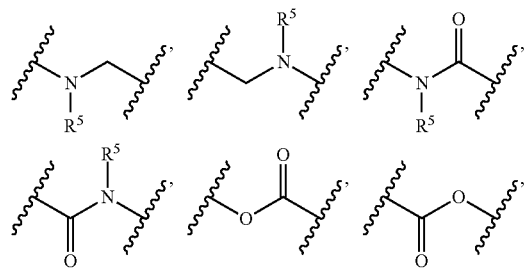

-continued

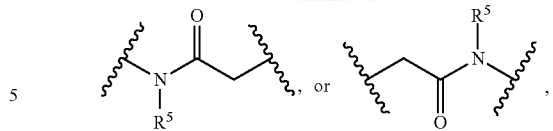

where $R^5$ is H or optionally substituted $C_1$-$C_6$ alkyl.

In some embodiments, $L^2$ is

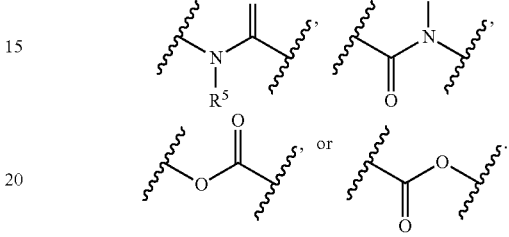

In some embodiments, $L^2$ is

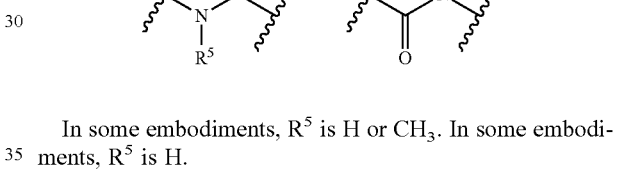

In some embodiments, $R^5$ is H or $CH_3$. In some embodiments, $R^5$ is H.

In some embodiments, $X^5$ is CH. In some embodiments, $X^5$ is N.

In some embodiments, $X^6$ is CH. In some embodiments, $X^6$ is N.

In some embodiments, $X^7$ is S.

In some embodiments, the compound has the structure of Formula IIa:

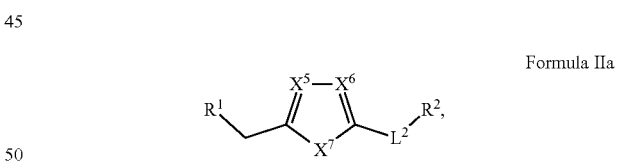

Formula IIa or a pharmaceutically acceptable salt thereof.

In some embodiments, $R^2$ is optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl.

In some embodiments, $R^2$ is optionally substituted $C_2$-$C_9$ heterocyclyl, optionally substituted $C_6$-$C_{10}$ aryl, or optionally substituted $C_2$-$C_9$ heteroaryl.

In some embodiments, $R^2$ is optionally substituted $C_2$-$C_9$ heterocyclyl or optionally substituted $C_2$-$C_9$ heteroaryl.

In some embodiments, $R^2$ is optionally substituted $C_2$-$C_9$ heterocyclyl.

In some embodiments, $R^2$ is optionally substituted $C_2$-$C_5$ heterocyclyl.

In some embodiments, $R^2$ is

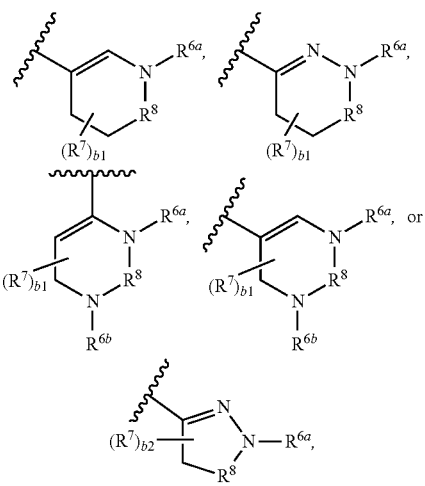

where b1 is 0, 1, 2, 3, or 4;
b2 is 0, 1, or 2;
$R^{6a}$ is H, optionally substituted $C_1$-$C_6$ alkyl, or optionally substituted $C_3$-$C_6$ carbocyclyl;
$R^{6b}$ is H, optionally substituted $C_1$-$C_6$ alkyl, or optionally substituted $C_3$-$C_6$ carbocyclyl;
each $R^7$ is, independently, halo or optionally substituted $C_1$-$C_6$ alkyl; and
$R^8$ is

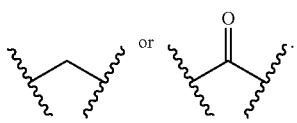

In some embodiments, $R^{6a}$ is H or optionally substituted $C_1$-$C_6$ alkyl.

In some embodiments, $R^{6a}$ is H,

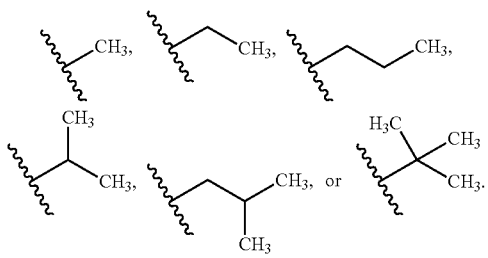

In some embodiments, $R^{6a}$ is H or

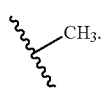

In some embodiments, $R^{6b}$ is H or optionally substituted $C_1$-$C_6$ alkyl.

In some embodiments, $R^{6b}$ is H,

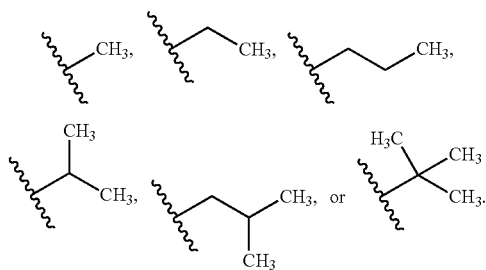

In some embodiments, $R^{6b}$ is H or

In some embodiments, $R^8$ is

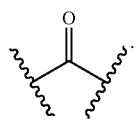 [SMILES: *C(*)=O]

In some embodiments, each $R^7$ is, independently, F, Cl, Br, I,

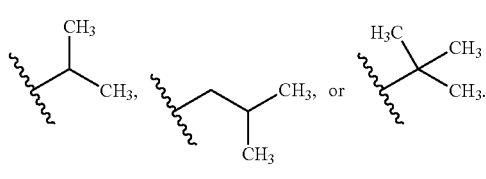

In some embodiments, each $R^7$ is, independently,

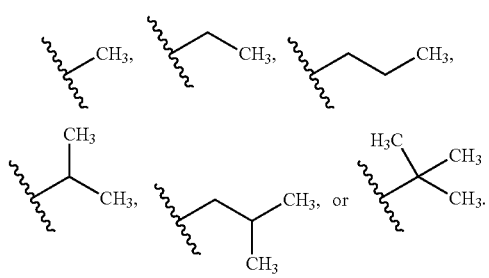

In some embodiments, b1 is 0 or 1. In some embodiments, b1 is 0. In some embodiments, b1 is 1.
In some embodiments, b2 is 0 or 1. In some embodiments, b2 is 0. In some embodiments, b2 is 1.

In some embodiments, $R^2$ is

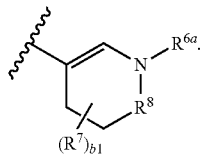

In some embodiments, $R^2$ is

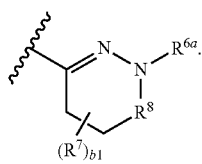

In some embodiments,

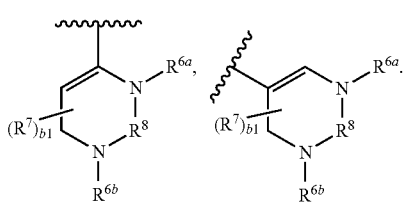

In some embodiments, $R^2$ is

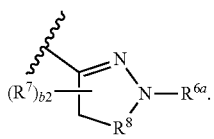

In some embodiments, $R^2$ is

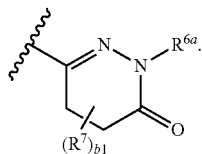

In some embodiments, $R^2$ is

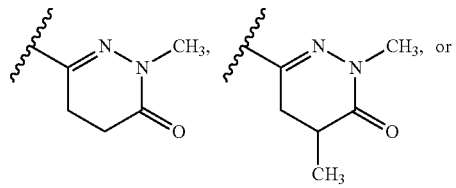

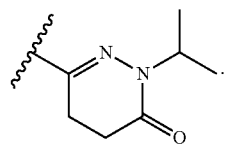

In some embodiments, $R^2$ is

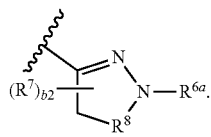

In some embodiments, $R^2$ is

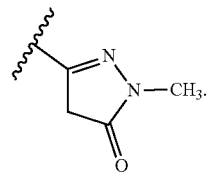 [SMILES: *C1=NN(C)C(=O)C1]

In some embodiments, $R^2$ is

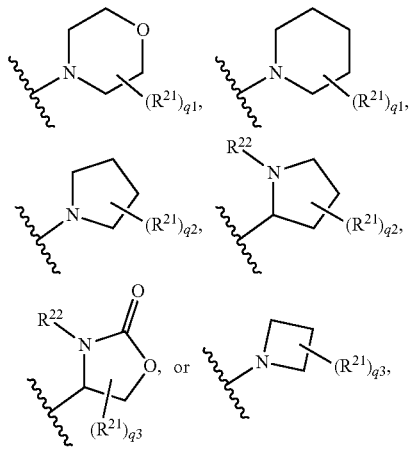

where q1 is 0, 1, 2, 3, 4, 5, or 6;

q2 is 0, 1, 2, 3, or 4;

q3 is 0, 1, or 2;

each $R^{21}$ is, independently, hydroxyl, optionally substituted $C_1$-$C_6$ alkyl, or optionally substituted $C_1$-$C_6$ heteroalkyl; or two of the $R^{21}$ groups, taken together with the carbon atom to which each is attached, combine to form an optionally substituted $C_3$-$C_{10}$ carbocyclyl or optionally substituted $C_2$-$C_9$ heterocyclyl; and $R^{22}$ is H or optionally substituted $C_1$-$C_6$ alkyl.

In some embodiments, each $R^{21}$ is, independently,

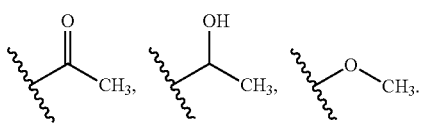

In some embodiments, $R^{22}$ is H or

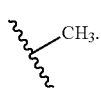

In some embodiments, $R^2$ is

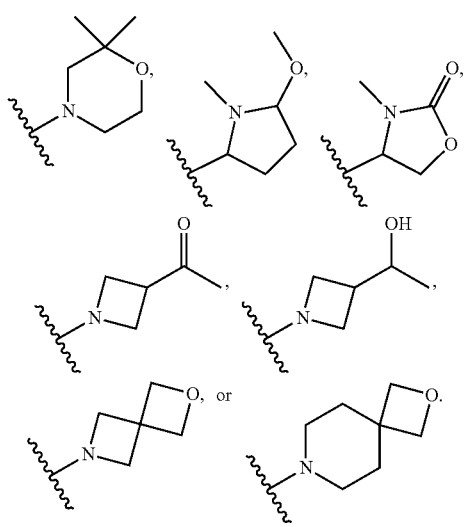

In some embodiments, $R^2$ is optionally substituted $C_2$-$C_9$ heteroaryl.

In some embodiments, $R^2$ is optionally substituted $C_2$-$C_5$ heteroaryl.

In some embodiments, $R^2$ is

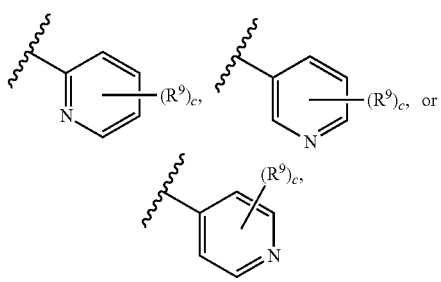

where
c is 0, 1, 2, 3, or 4; and
each $R^9$ is, independently, halo, CN, NO$_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_6$ heteroaryl, SH, OH, or NH$_2$.

In some embodiments, each $R^9$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or NH$_2$.

In some embodiments, each $R^9$ is, independently, F, Cl, Br, I, CN,

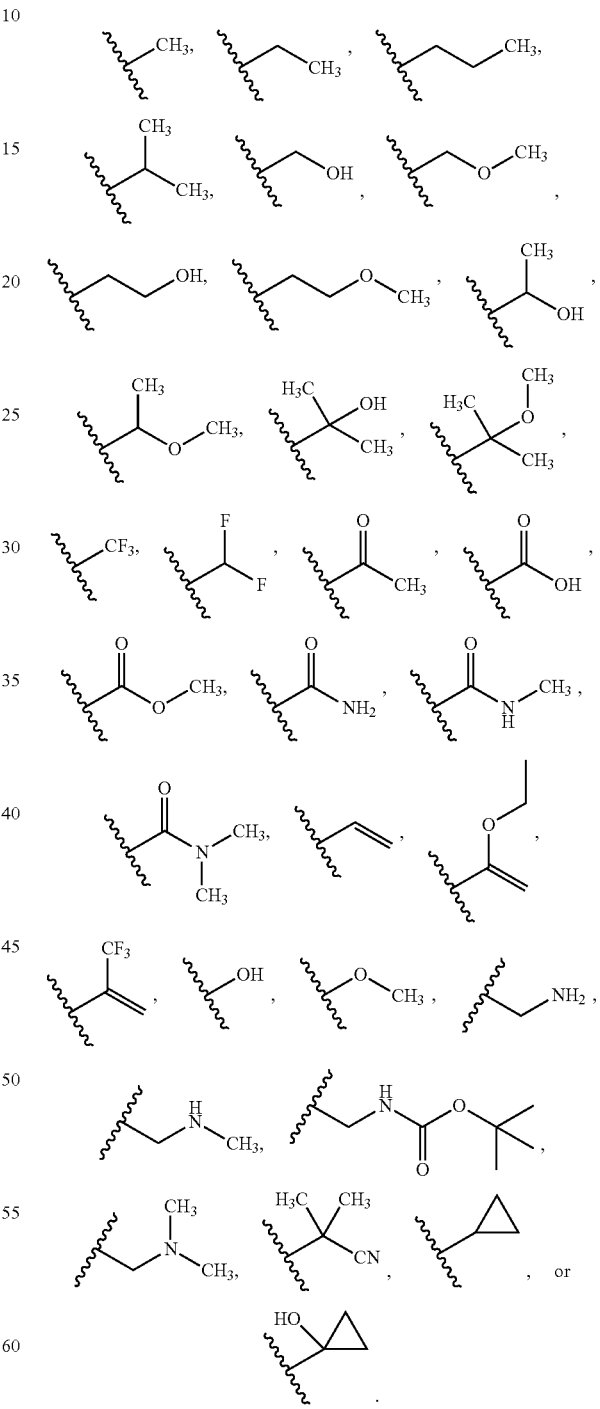

In some embodiments, c is 0, 1, or 2. In some embodiments, c is 0. In some embodiments, c is 1. In some embodiments, c is 2.

In some embodiments, $R^2$ is

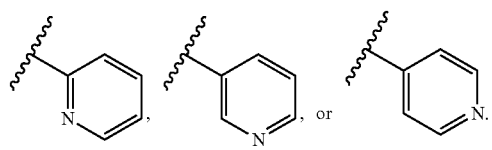

In some embodiments, $R^2$ is

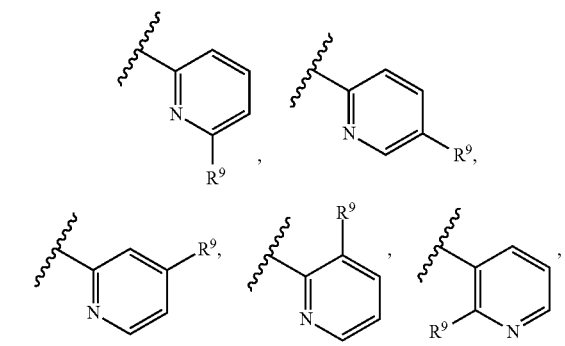

In some embodiments, $R^2$ is

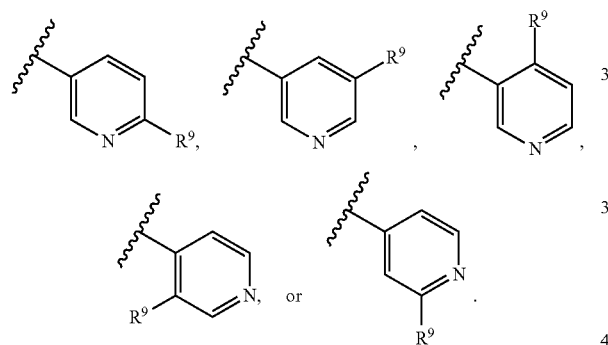

In some embodiments, $R^2$ is

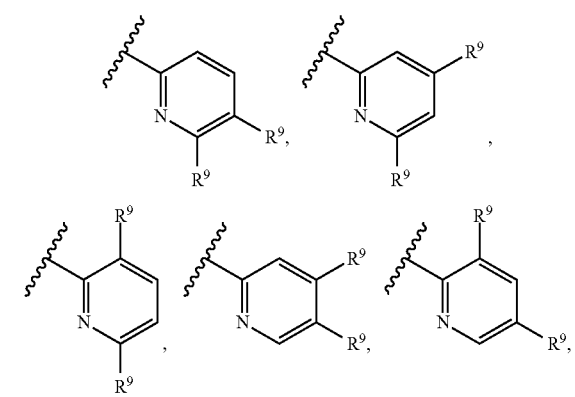

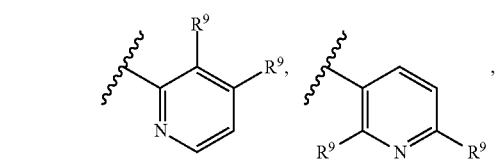

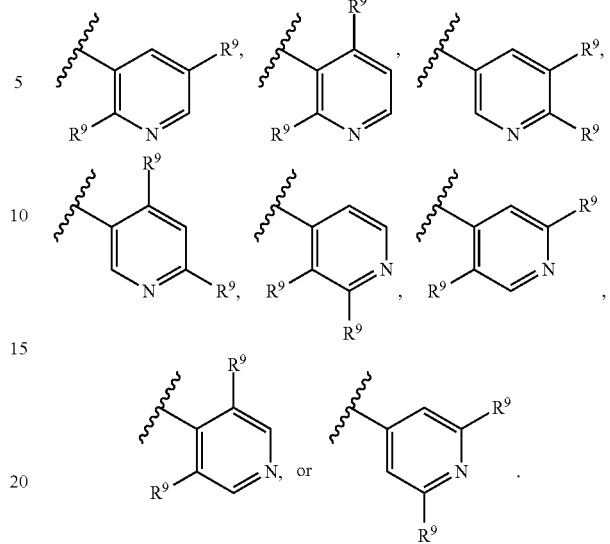

In some embodiments, $R^2$ is

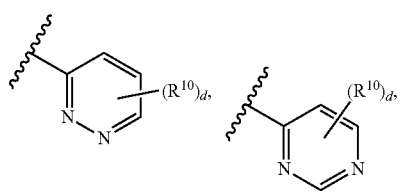

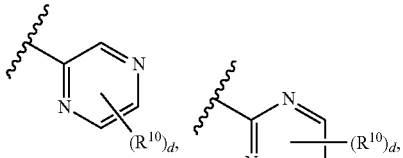

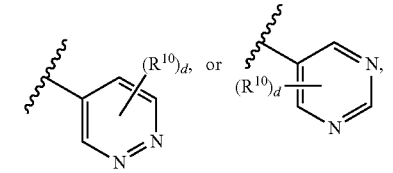

where d is 0, 1, 2, or 3; and each $R^{10}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{10}$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^{10}$ is, independently, F, Cl, Br, I, CN,

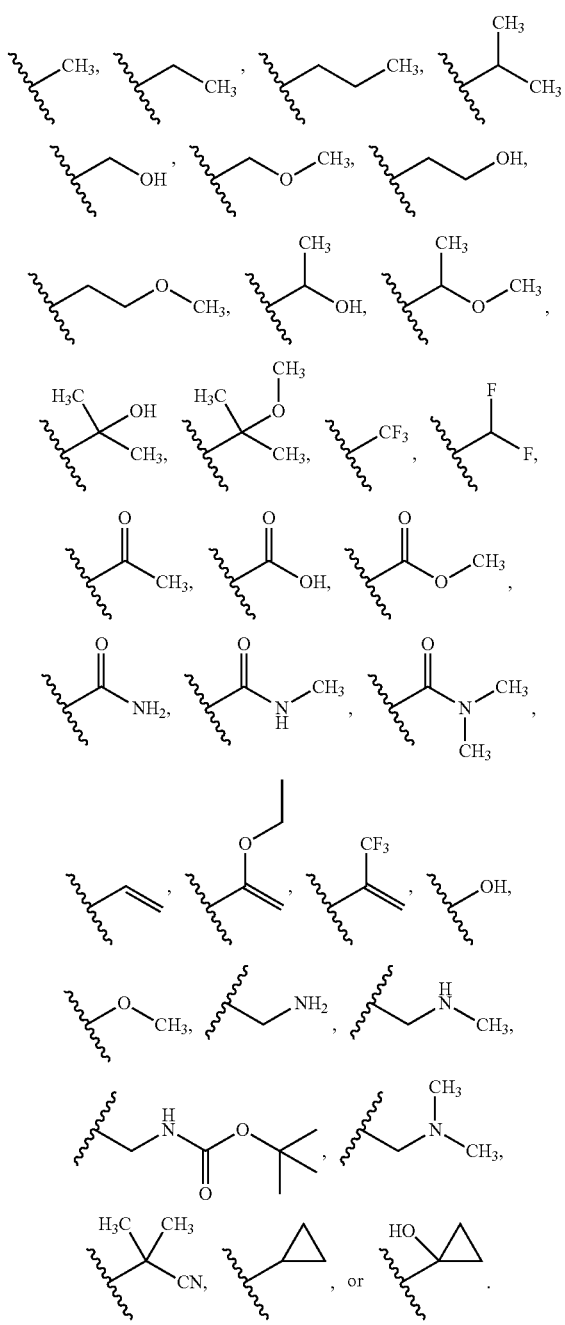
In some embodiments, d is 0, 1, or 2. In some embodiments, d is 0. In some embodiments, d is 1. In some embodiments, d is 2.
In some embodiments, $R^2$ is
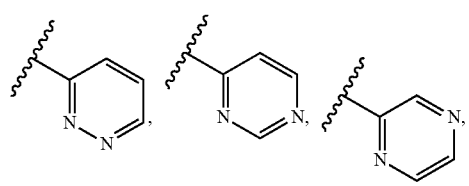
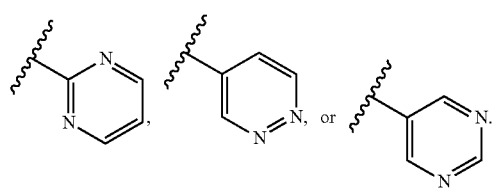
In some embodiments, $R^2$ is
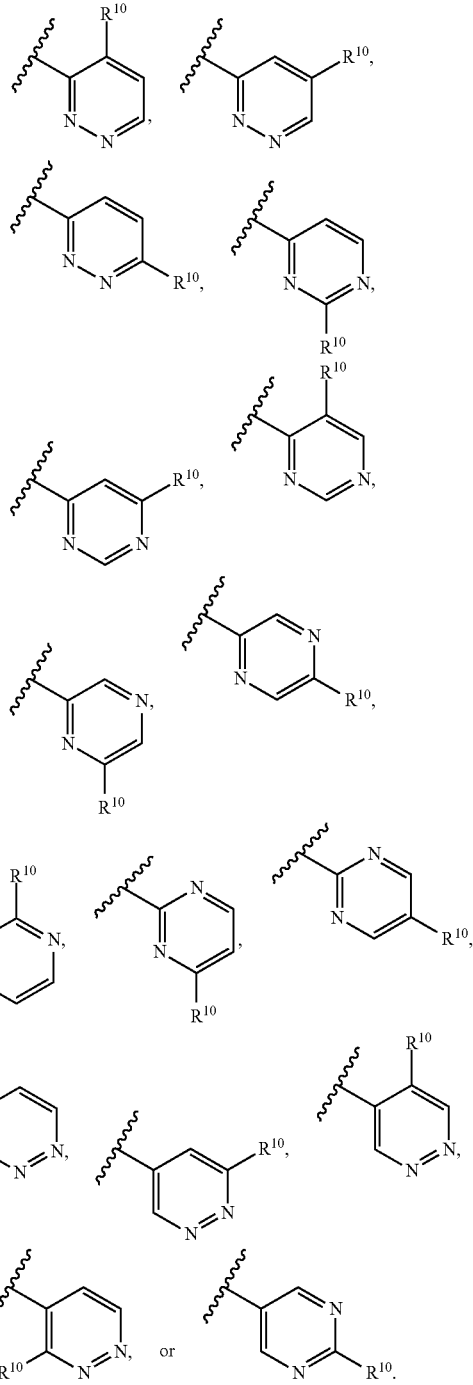

In some embodiments, $R^2$ is

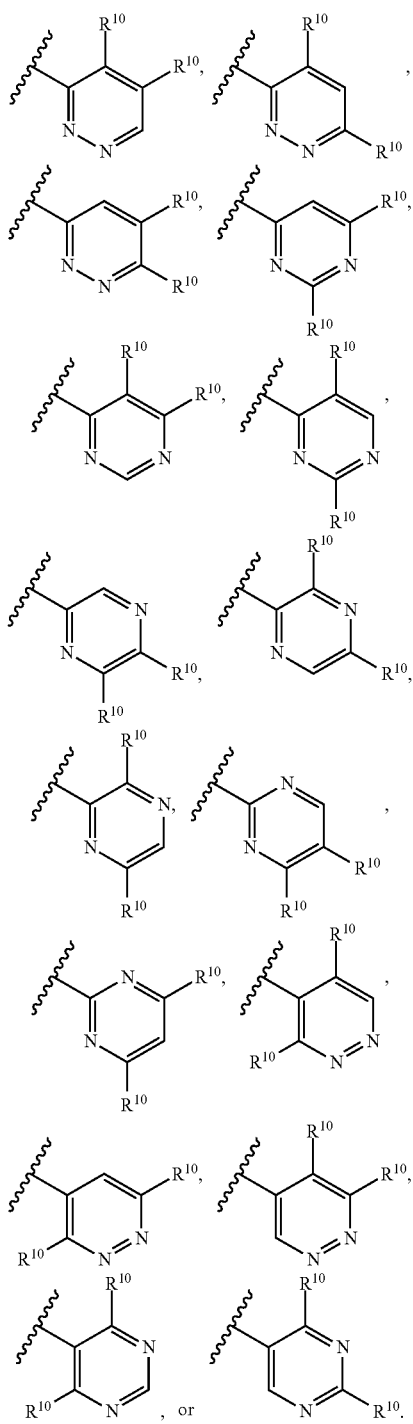

In some embodiments, $R^2$

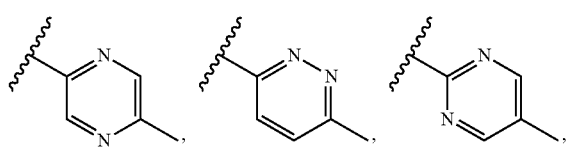

-continued

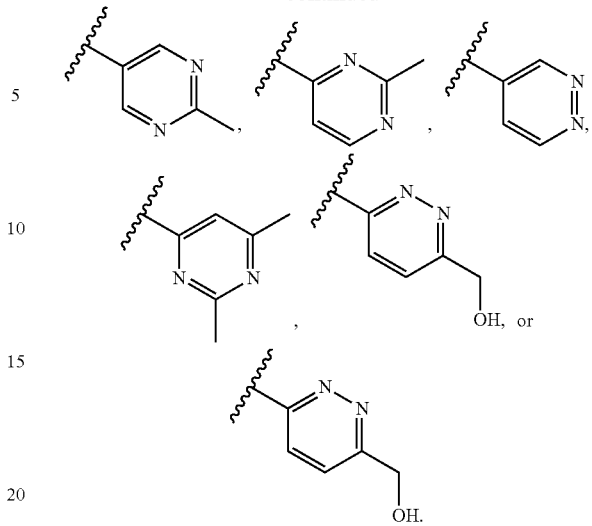

In some embodiments,

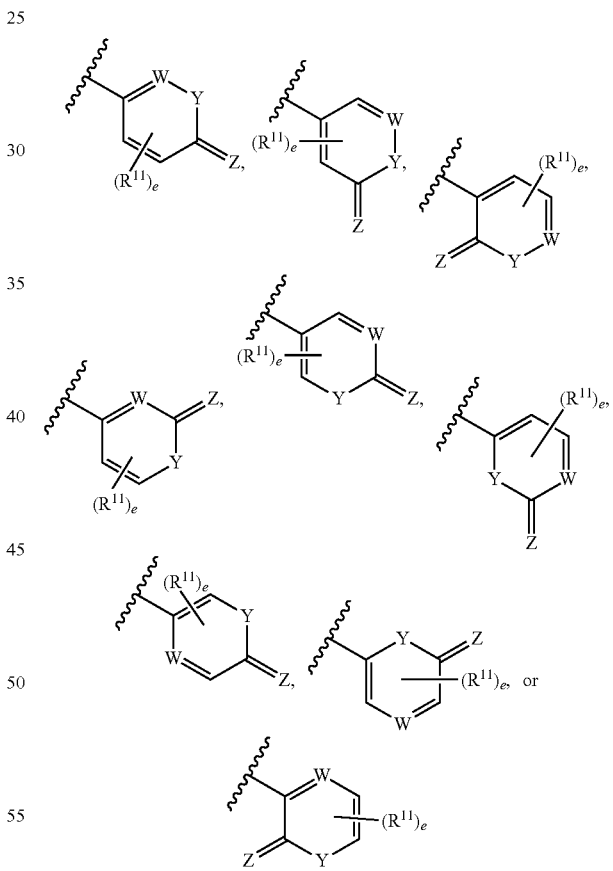

where
e is 0, 1, or 2;
each $R^{11}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

W is CH or N;

Y is O, S, or $NR^{Y1}$;

$R^{Y1}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl;

Z is O, S, or $NR^{71}$; and $R^{Z1}$ is H or optionally substituted $C_1$-$C_6$ alkyl.

In some embodiments, each $R^{11}$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^{11}$ is, independently, F, Cl, Br, I, CN,

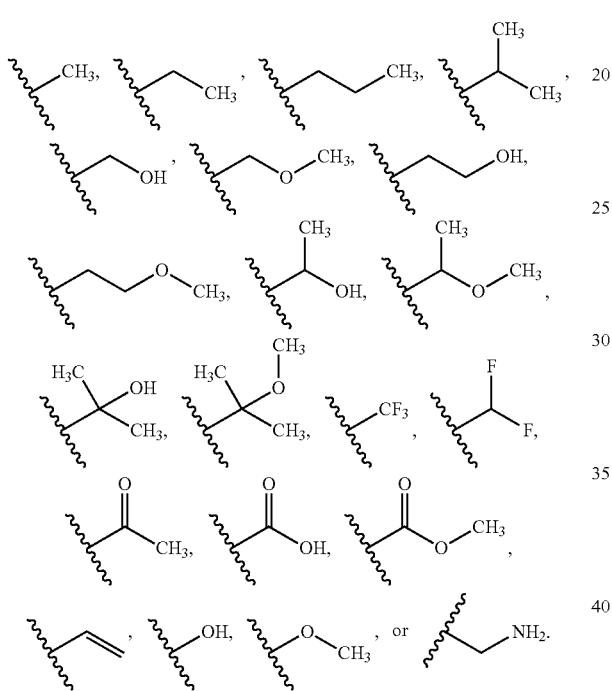

In some embodiments, W is CH. In some embodiments, W is N.

In some embodiments, Y is $NR^{Y1}$.

In some embodiments, $R^{Y1}$ is H, optionally substituted $C_1$-$C_6$ alkyl, or optionally substituted $C_3$-$C_{10}$ carbocyclyl.

In some embodiments, $R^{Y1}$ is H. In some embodiments, $R^{Y1}$ is optionally substituted $C_1$-$C_6$ alkyl.

In some embodiments, $R^{Y1}$ is

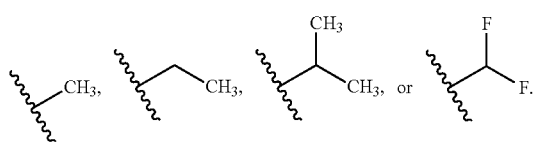

In some embodiments, $R^{Y1}$ is optionally substituted $C_3$-$C_{10}$ carbocyclyl.

In some embodiments, $R^{Y1}$ is optionally substituted $C_3$-$C_6$ carbocyclyl.

In some embodiments, $R^{Y1}$ is

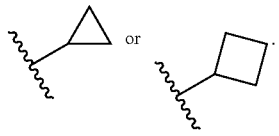

In some embodiments, Z is O.

In some embodiments, $R^2$ is

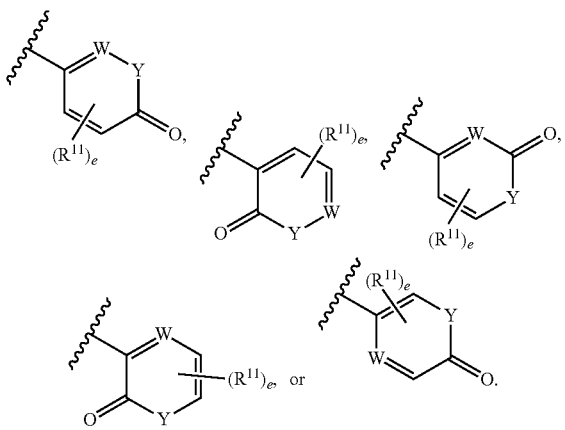

In some embodiments, e is 0 or 1. In some embodiments, e is 0. In some embodiments, e is 1.

In some embodiments, $R^2$ is

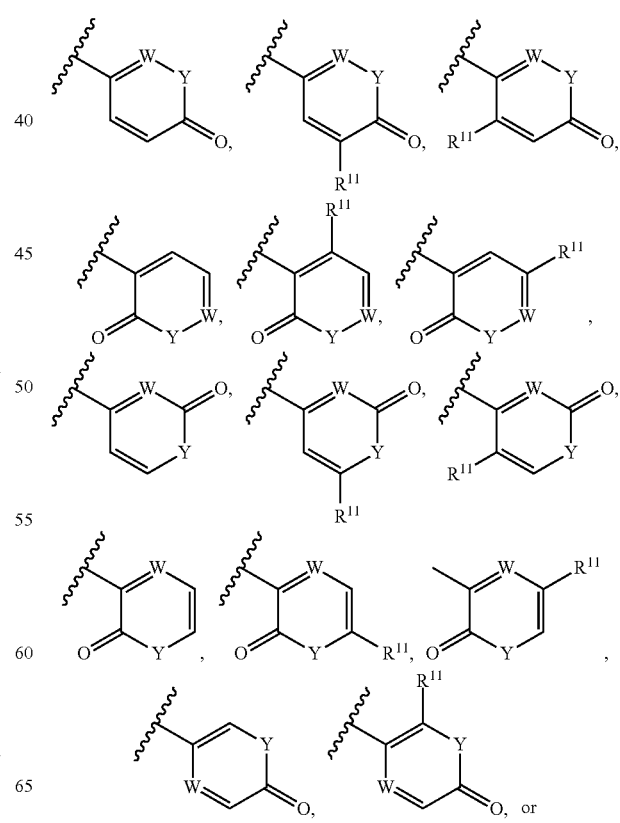

-continued

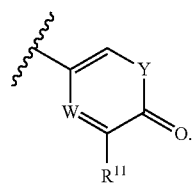

In some embodiments, $R^2$ is

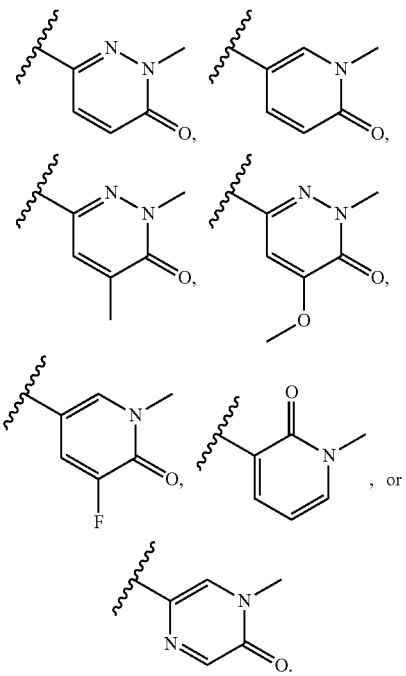

In some embodiments, $R^2$ is

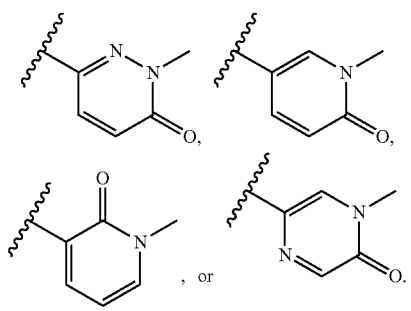

In some embodiments, $R^2$

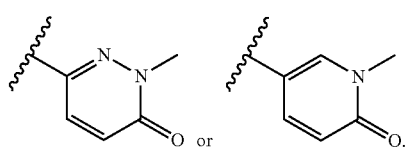

In some embodiments, $R^2$ is

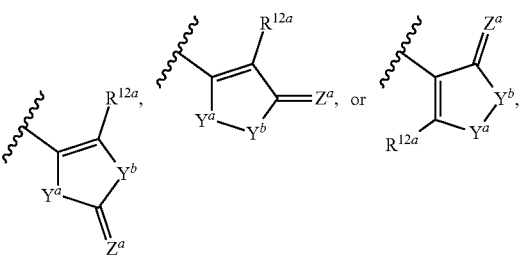

where $R^{12a}$ is H, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$;

each of $Y^a$ and $Y^b$ is, independently, O, S, or $NR^{Y2}$;

$R^{Y2}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_6$ heterocyclyl;

$Z^a$ is O, S, or $NR^{Z2}$; and $R^{Z2}$ is H or optionally substituted $C_1$-$C_6$ alkyl.

In some embodiments, $R^{12a}$ is H.

In some embodiments, $Z^a$ is O.

In some embodiments, $R^2$ is

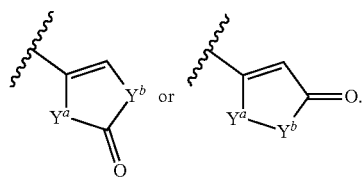

In some embodiments, each of $Y^a$ and $Y^b$ is $NR^{Y2}$.

In some embodiments, $R^{Y2}$ is H, optionally substituted $C_1$-$C_6$ alkyl, or optionally substituted $C_3$-$C_{10}$ carbocyclyl.

In some embodiments, $R^{Y2}$ is H,

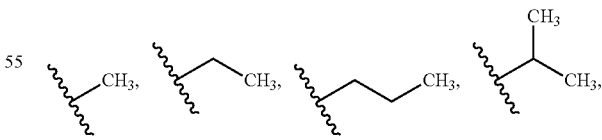

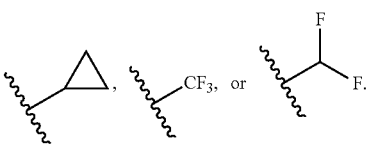

In some embodiments, $R^2$ is

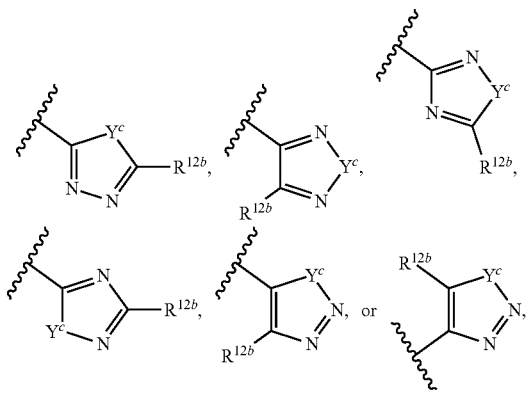

where $R^{12b}$ is H, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$; and $Y^c$ is O, S, or $NR^{Y3}$;

$R^{Y3}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_6$ heterocyclyl.

In some embodiments, $R^{12b}$ is H.
In some embodiments, $Y^c$ is $NR^{Y3}$.
In some embodiments, $R^{Y3}$ is H, optionally substituted $C_1$-$C_6$ alkyl, or optionally substituted $C_3$-$C_{10}$ carbocyclyl.
In some embodiments, $R^{Y3}$ is H,

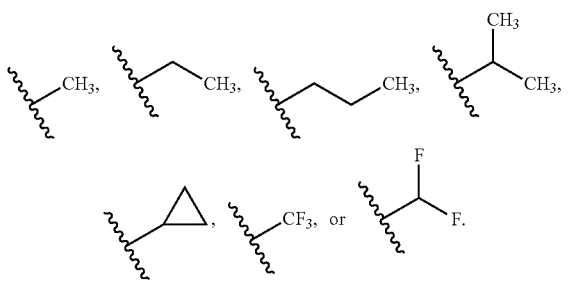

In some embodiments, $R^2$ is

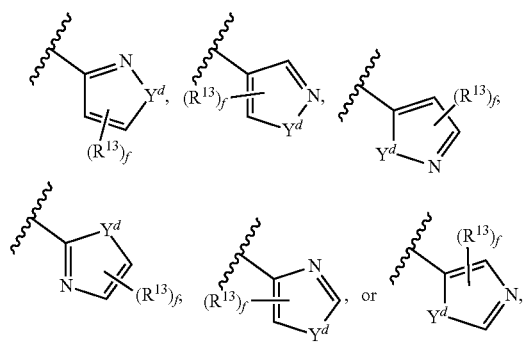

where f is 0, 1, or 2;

each $R^{13}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; and $Y^d$ is O, S, or $NR^{Y4}$;

$R^{Y4}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl.

In some embodiments, each $R^{13}$ is, independently, halo, CN, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, each $R^{13}$ is, independently, halo, CN, or optionally substituted $C_1$-$C_6$ alkyl.

In some embodiments, f is 0 or 1. In some embodiments, f is 0. In some embodiments, f is 1.

In some embodiments, $Y^d$ is $NR^{Y4}$.

In some embodiments, $R^{Y4}$ is H, optionally substituted $C_1$-$C_6$ alkyl, or optionally substituted $C_3$-$C_{10}$ carbocyclyl.

In some embodiments, $R^{Y4}$ is H,

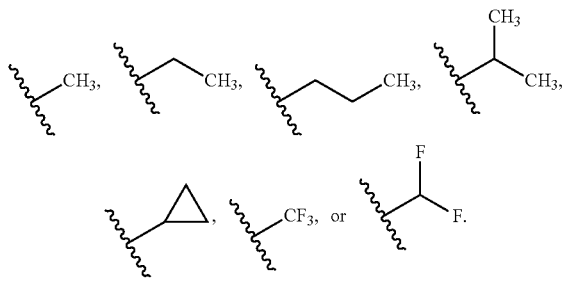

In some embodiments, $Y^d$ is O.
In some embodiments, $R^2$ is

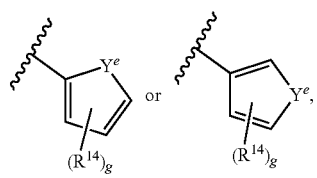

where g is 0, 1, 2, 3, or 4;

each $R^{14}$ is, independently, halo, CN, $NO_2$, optionally substituted $C_1$-$C_6$ alkyl, optionally substituted $C_2$-$C_6$ alkenyl, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;

$Y^e$ is O, S, or $NR^{Y5}$; and $R^{Y5}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl.

In some embodiments, $R^{14}$ is halo, CN, optionally substituted $C_1$-$C_6$ alkyl, optionally substituted $C_2$-$C_9$ alkene, optionally substituted $C_1$-$C_6$ heteroalkyl, optionally substituted $C_2$-$C_6$ heteroalkenyl, optionally substituted $C_3$-$C_{10}$ carbocyclyl, OH, or $NH_2$.

In some embodiments, $R^{14}$ is halo, CN, or optionally substituted $C_1$-$C_6$ alkyl.

In some embodiments, g is 0, 1, or 2. In some embodiments, g is 0. In some embodiments, g is 1. In some embodiments, g is 2.

In some embodiments, $Y^e$ is $NR^{Y5}$.

In some embodiments, $R^{Y5}$ is H, optionally substituted $C_1$-$C_6$ alkyl, or optionally substituted $C_3$-$C_{10}$ carbocyclyl.

In some embodiments, $R^{Y5}$ is

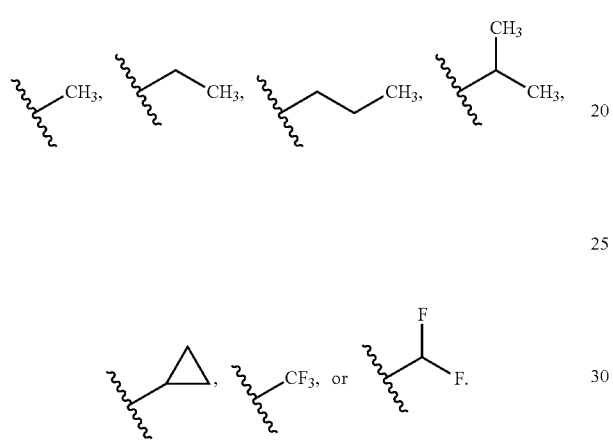

In some embodiments, $Y^e$ is O. In some embodiments, $Y^e$ is S.

In some embodiments, $R^2$ is

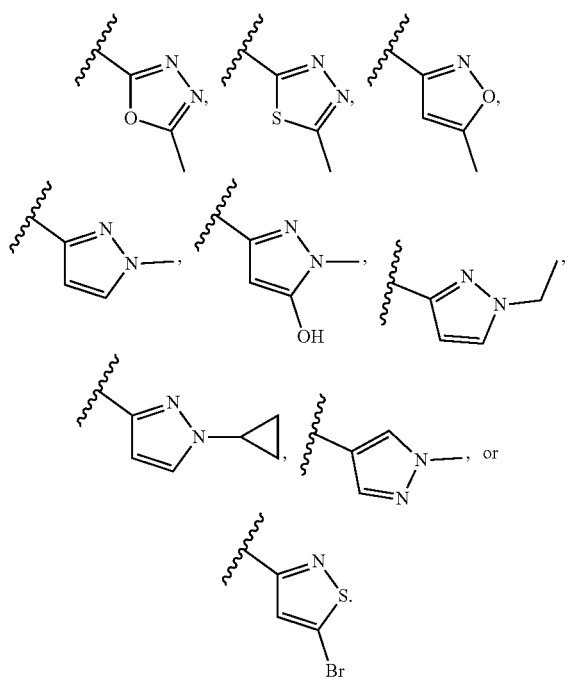

In some embodiments, $R^2$ is

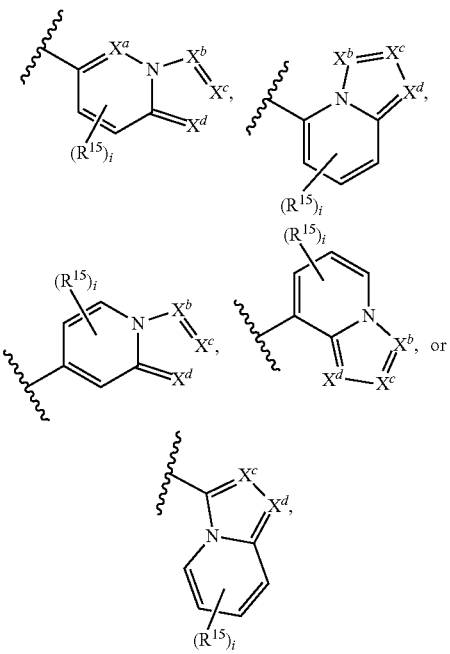

where
each of $X^a$, $X^b$, $X^c$, and $X^d$ is, independently, N or $CR^{17}$;
each $R^{17}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;
i is 0, 1, 2, or 3; and
each $R^{15}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$.

In some embodiments, each $R^{15}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, i is 0 or 1. In some embodiments, i is 0. In some embodiments, i is 1.

In some embodiments, $R^2$ is

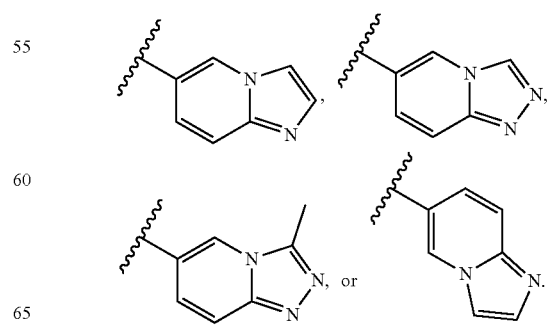

In some embodiments, $R^2$ is

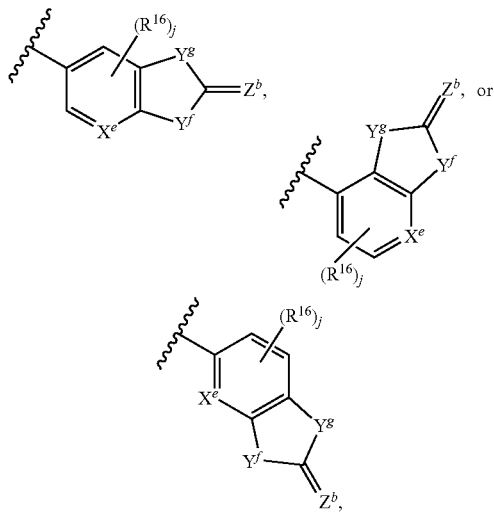

where $X^e$ is N or $CR^{18}$;

$R^{18}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$;

j is 0, 1, or 2;

each $R^{16}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_6$ heterocyclyl, optionally substituted $C_6$-$C_{10}$ aryl, optionally substituted $C_2$-$C_9$ heteroaryl, SH, OH, or $NH_2$;

each of $Y^f$ and $Y^g$ is, independently, O, S, or $NR^{Y6}$;

$R^{Y6}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_6$ heterocyclyl;

$Z^b$ is O, S, or $NR^{Z3}$; and $R^{Z3}$ is H or optionally substituted $C_1$-$C_6$ alkyl.

In some embodiments, each $R^{16}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, j is 0 or 1. In some embodiments, j is 0. In some embodiments, j is 1.

In some embodiments, Z is O.

In some embodiments, $R^2$ is

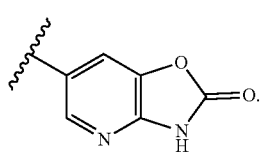 [SMILES: *c1cnc2[nH]c(=O)oc2c1]

In some embodiments, $R^2$ is

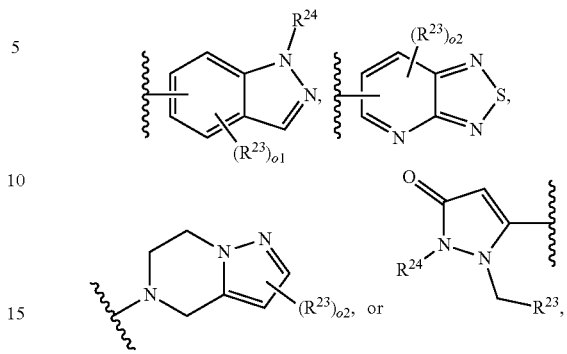

where o1 is 0, 1, 2, or 3;

o2 is 0, 1, or 2;

each $R^{23}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; and $R^{24}$ is H or optionally substituted $C_1$-$C_6$ alkyl.

In some embodiments, $R^2$ is

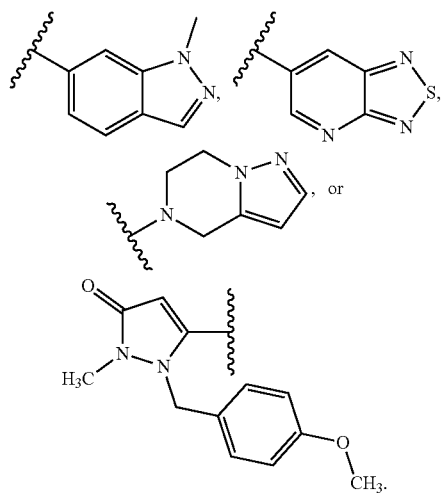

In some embodiments, $R^2$ is optionally substituted $C_6$-$C_{10}$ aryl.

In some embodiments, $R^2$ is

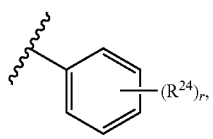

where r is 0, 1, 2, 3, or 4; and each $R^{24}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted sulfone, SH, OH, or $NH_2$.

In some embodiments, each $R^{24}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{24}$ is, independently, halo, CN, $NO_2$, optionally substituted $C_1$-$C_6$ alkyl, optionally substituted $C_1$-$C_6$ heteroalkyl, SH, OH, or $NH_2$.

In some embodiments, r is 0, 1, or 2. In some embodiments, r is 0. In some embodiments, r is 1.

In some embodiments, r is 2.

In some embodiments, $R^2$ is optionally substituted $C_1$-$C_6$ heteroalkyl.

In some embodiments, $R^2$ is

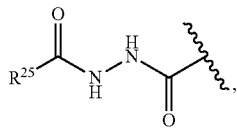

where $R^{25}$ is optionally substituted $C_1$-$C_6$ alkyl or optionally substituted $C_1$-$C_6$ heteroalkyl.

In some embodiments, $R^{25}$ is

In some embodiments, $R^1$ is optionally substituted $C_1$-$C_6$ alkyl.

In some embodiments, $R^1$ is

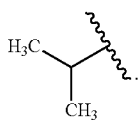

In some embodiments, $R^1$ is optionally substituted $C_6$-$C_{10}$ aryl.

In some embodiments, $R^1$ is

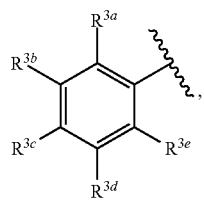

where
each of $R^{3a}$, $R^{3b}$, $R^{3c}$, $R^{3d}$, and $R^{3e}$ is, independently, H, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$; or $R^{3a}$ and $R^{3b}$, $R^{3b}$ and $R^{3c}$, $R^{3c}$ and $R^{3d}$, or $R^{3d}$ and $R^{3e}$, together with the atoms to which each is attached, combine to form optionally substituted $C_3$-$C_{10}$ carbocyclyl or optionally substituted $C_2$-$C_9$ heterocyclyl.

In some embodiments, each of $R^{3a}$, $R^{3b}$, $R^{3c}$, $R^{3d}$, and $R^{3e}$ is, independently, H, halo, CN, $NO_2$, optionally substituted $C_1$-$C_6$ alkyl, optionally substituted $C_1$-$C_6$ heteroalkyl, SH, OH, or $NH_2$.

In some embodiments, each of $R^{3a}$, $R^{3b}$, $R^{3c}$, $R^{3d}$, and $R^{3e}$ is, independently, H, F, Cl, Br, I, CN,

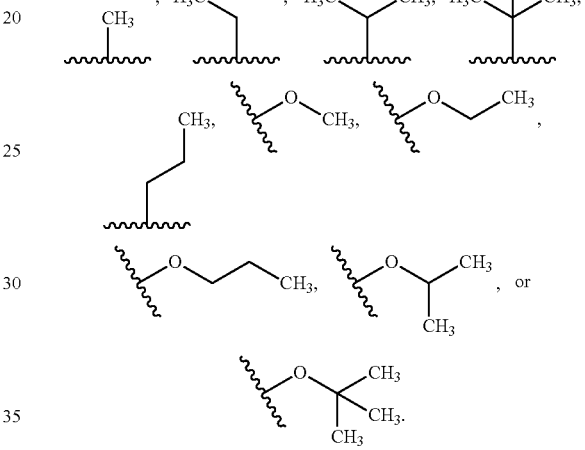

In some embodiments, $R^1$ is

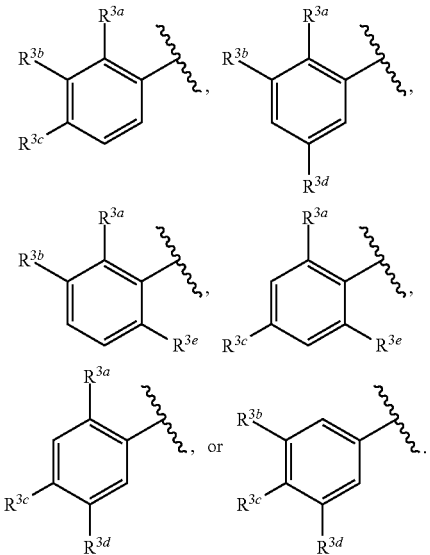

In some embodiments, $R^1$

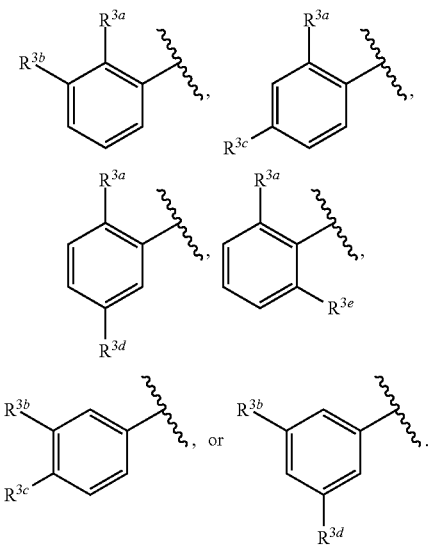

In some embodiments, $R^1$ is

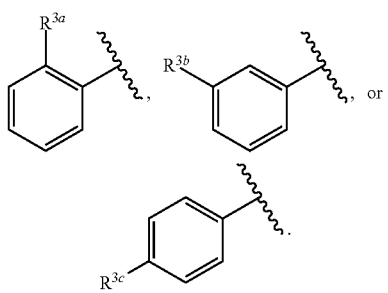

In some embodiments, $R^1$ is

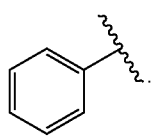 [SMILES: *c1ccccc1]

In some embodiments, $R^1$ is phenyl, 3-fluoro-phenyl, 4-fluoro-phenyl, 3-chloro-phenyl, 4-chloro-phenyl, 2-methoxy-phenyl, 3-methoxy-phenyl, 4-methoxy-phenyl, 3,4-di-fluoro-phenyl, 3,4-dichloro-phenyl, 3,5-di-fluoro-phenyl, 3,5-dichloro-phenyl, 3-chloro-4-fluoro-phenyl, 4-chloro-3-fluoro-phenyl, 3-chloro-4-nitrile-phenyl, 3-nitrile-4-fluoro-phenyl, 3-trifluoromethyl-phenyl, 4-trifluoromethyl-phenyl, 3-bromo-phenyl, 3-cyclopropyl-phenyl, 3-cyano-5-fluoro-phenyl, 3-chloro-5-fluoro-phenyl, 3-chloro-5-cyano-phenyl, 3-chloro-5-methoxy-phenyl, or 1,3-dihydroisobenzofuran.

In some embodiments, $R^1$ is optionally substituted $C_3$-$C_{10}$ carbocyclyl.

In some embodiments, $R^1$ is optionally substituted $C_3$-$C_{10}$ cycloalkyl.

In some embodiments, $R^1$ is

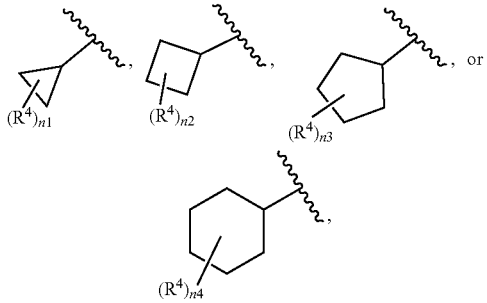

where
n1 is 0, 1, 2, or 3;
n2 is 0, 1, 2, 3, or 4;
n3 is 0, 1, 2, 3, 4, or 5;
n4 is 0, 1, 2, 3, 4, 5, or 6; and
each $R^4$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, $R^1$ is

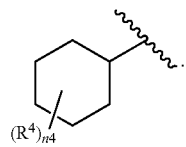

In some embodiments, each $R^4$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, each $R^4$ is, independently, F, Cl, Br, I, CN,

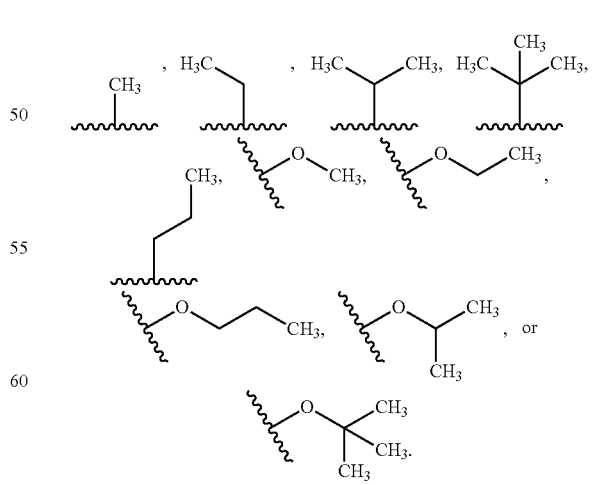

In some embodiments, $R^1$ is optionally substituted cycloalkenyl.

In some embodiments, R¹ is

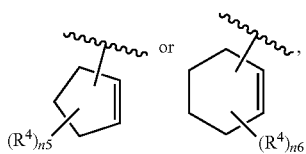

where
n5 is 0, 1, 2, 3, or 4;
n6 is 0, 1, 2, 3, 4, or 5; and
each $R^4$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, R¹ is

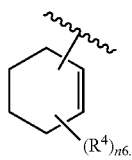

In some embodiments, each $R^4$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, each $R^4$ is, independently, F, Cl, Br, I, CN,

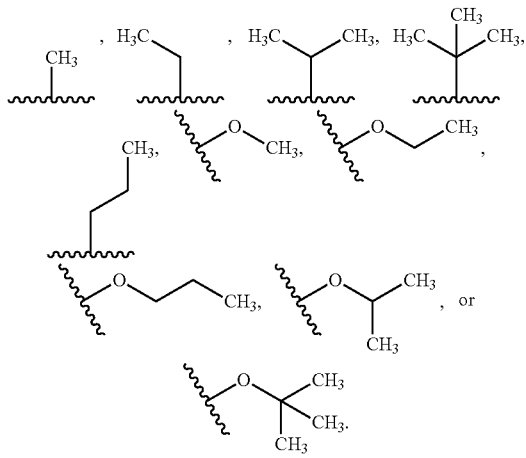

In some embodiments, R¹ is optionally substituted $C_2$-$C_6$ heteroaryl.

In some embodiments, R¹ is

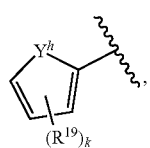

where k is 0, 1, 2, or 3;

each $R^{19}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$;

$Y^h$ is O, S, or $NR^{Y7}$; and $R^{Y7}$ is H, optionally substituted $C_1$-$C_6$ alkyl, optionally substituted $C_1$-$C_6$ heteroalkyl, optionally substituted $C_3$-$C_{10}$ carbocyclyl, or optionally substituted $C_2$-$C_9$ heterocyclyl.

In some embodiments, each $R^{19}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, each $R^{19}$ is, independently, F, Cl, Br, I, CN, or

In some embodiments, $Y^h$ is S.

In some embodiments, k is 0 or 1. In some embodiments, k is 0. In some embodiments, k is 1.

In some embodiments, R¹ is

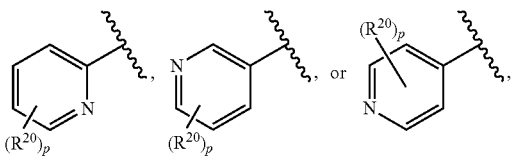

where p is 0, 1, 2, 3, or 4; and each $R^{20}$ is, independently, halo, CN, $NO_2$, optionally substituted $C_1$-$C_6$ alkyl, optionally substituted $C_2$-$C_6$ alkene, optionally substituted $C_1$-$C_6$ heteroalkyl, optionally substituted $C_2$-$C_6$ heteroalkenyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, SH, OH, or $NH_2$.

In some embodiments, each $R^{20}$ is, independently, halo, CN, optionally substituted $C_1$-$C_6$ alkyl, optionally substituted $C_2$-$C_6$ alkene, optionally substituted $C_1$-$C_6$ heteroalkyl, SH, OH, or $NH_2$.

In some embodiments, each $R^{20}$ is, independently, F, Cl, Br, I, CN, or

In some embodiments, p is 0 or 1. In some embodiments, p is 0. In some embodiments, p is 1.

In some embodiments, R[1] is

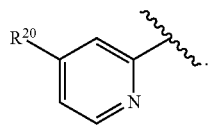

In some embodiments, R[1] is 5-chloropyridin-3-yl, 5-trifluoromethyl-pyridin-3-yl, 4-trifluoromethyl-pyridin-2-yl, 5-fluoropyridin-3-yl, or 5-fluoropyridin-3-yl.

In another aspect, this disclosure features a compound, or pharmaceutically acceptable salt thereof, having the structure of any one of compounds 1-683 in Table 1 and Table 2. In some embodiments, the compound is any one of compounds 1-475 in Table 1. In some embodiments, the compound is any one of compounds 476-683 in Table 2.

In some embodiments, the compound is any one of compounds 40, 41, 46, 48, 53, 56, 57, 59, 66, 74-76, 79, 89, 91, 94, 95, 99, 111-114, 116, 119, 121, 122, 125, 128, 131, 132, 134, 137, 140, 142, 144, 146, 148, 149, 150, 202, 207, 216, 236, 239, 242-244, 248, 290, 292, 311, 315, 316, 321, 328-331, 366, 371, and 375 in Table 1. In some embodiments, the compound is any one of compounds 56, 76, 91, 94, 111, 112, 114, 116, 119, 122, 125, 131, 132, 137, 144, 148, 150, 236, 242-244, 290, 315, 316, 321, and 375 in Table 1. In some embodiments, the compound is any one of compounds 484, 494-497, 500-503, 506, 526, 528, 532, 540, 542, 543, 547, 555, 556, 559, 562, 567, 571, 572, 575, 580, 603, 616, 626, 627, 642-644, 657, 661, 668, 676, and 679 in Table 2. In some embodiments, the compound is any one of compounds 494, 497, 501, 503, 532, 559, 567, 572, 580, 603, 657, and 668 in Table 2.

In some embodiments, the compound is any one of compounds 1-200, 238-305, 310-316, 318-321, 323-335, 337-339, 342, 344-346, 348, 349, 351, 352, 354-376, 379, 381-384, 387, 391-393, 396, 397, 401-403, 410-412, 415, 417, 418, 421, 423, 425-429, 433, 435-456, 458-460, 463, 467-472, 474, and 475 in Table 1 and 476-683 in Table 2. In some embodiments, the compound is any one of compounds 1-200, 238-305, 310-316, 318-321, 323-335, 337-339, 342, 344-346, 348, 349, 351, 352, 354-376, 379, 381-384, 387, 391-393, 396, 397, 401-403, 410-412, 415, 417, 418, 421, 423, 425-429, 433, 435-456, 458-460, 463, 467-472, 474, and 475 in Table 1. In some embodiments, the compound is any one of compounds 476-681 and 683 in Table 2. In some embodiments, the compound is any one of compounds 201-237, 317, 340, 341, 343, 345-347, 350, 353, 377, 378, 380, 385, 386, 388-390, 398-400, 404-409, 413, 414, 416, 419, 420, 422, 424, 430, 431, 461, 462, 464-466, and 473 in Table 1. In some embodiments, the compound is any one of compounds 305-309, 322, 336, 394, 432, 434, and 457 in Table 1. In some embodiments, the compound is any one of compounds 305-309 in Table 1.

As used herein, "CMPD" refers to "compound."

TABLE 1

Compounds of the Invention

| CMPD No. | Structure |
|---|---|
| 1 | 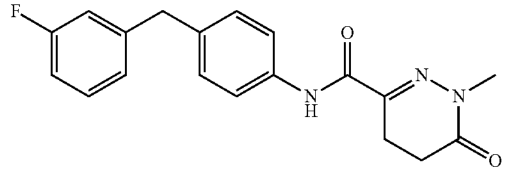 |
| 2 | 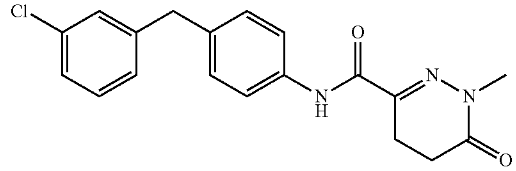 [SMILES: CN1N=C(C(=O)Nc2ccc(Cc3cccc(Cl)c3)cc2)CCC1=O] |
| 3 | 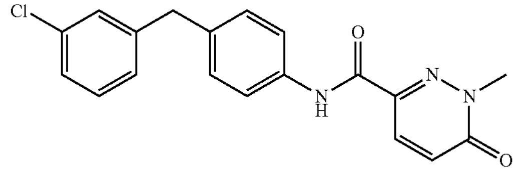 [SMILES: Cn1nc(C(=O)Nc2ccc(Cc3cccc(Cl)c3)cc2)ccc1=O] |
| 4 | 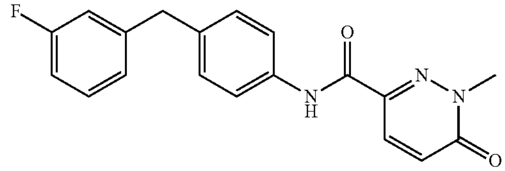 [SMILES: Cn1nc(C(=O)Nc2ccc(Cc3cccc(F)c3)cc2)ccc1=O] |

TABLE 1-continued

Compounds of the Invention

| CMPD No. | Structure |
|---|---|
| 5 | *[Structure: 3-fluorobenzyl-phenyl-NH-C(O)-1-methyl-6-oxo-1,6-dihydropyridine-3-carboxamide]* |
| 6 | *[Structure: 5-(3-fluorobenzyl)pyridin-2-yl-NH-C(O)-1-methyl-6-oxo-1,4,5,6-tetrahydropyridazine-3-carboxamide]* |
| 7 | *[Structure: 5-(3-chloro-4-fluorobenzyl)pyridin-2-yl-NH-C(O)-1-methyl-6-oxo-1,4,5,6-tetrahydropyridazine-3-carboxamide]* |
| 8 | *[Structure: 5-(3-cyanobenzyl)pyridin-2-yl-NH-C(O)-1-methyl-6-oxo-1,4,5,6-tetrahydropyridazine-3-carboxamide]* |
| 9 | *[Structure: 5-(4-trifluoromethylbenzyl)pyridin-2-yl-NH-C(O)-1-methyl-6-oxo-1,4,5,6-tetrahydropyridazine-3-carboxamide]* |
| 10 | *[Structure: 5-(3-cyano-4-fluorobenzyl)pyridin-2-yl-NH-C(O)-1-methyl-6-oxo-1,4,5,6-tetrahydropyridazine-3-carboxamide]* |
| 11 | *[Structure: 5-(4-chloro-3-fluorobenzyl)pyridin-2-yl-NH-C(O)-1-methyl-6-oxo-1,4,5,6-tetrahydropyridazine-3-carboxamide]* |
| 12 | *[Structure: 5-(4-chlorobenzyl)pyridin-2-yl-NH-C(O)-1-methyl-6-oxo-1,4,5,6-tetrahydropyridazine-3-carboxamide]* |

TABLE 1-continued
Compounds of the Invention
| CMPD No. | Structure |
|---|---|
| 13 | 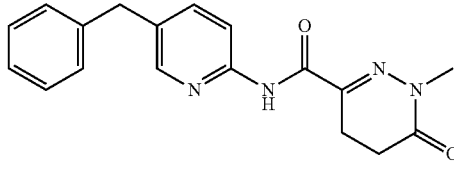 |
| 14 | 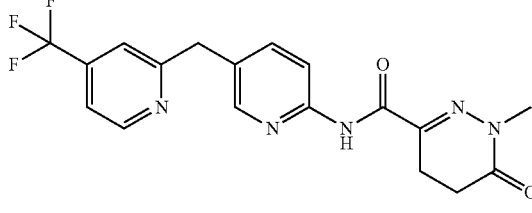 |
| 15 | 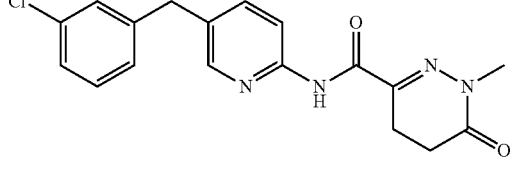 |
| 16 | 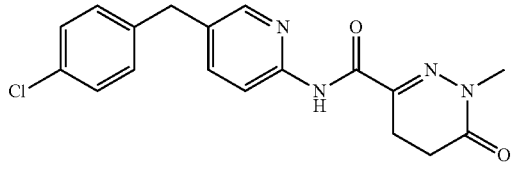 |
| 17 | 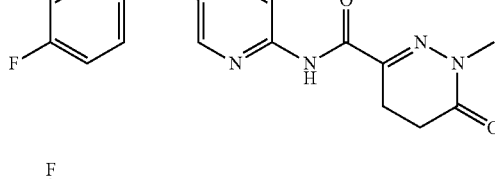 |
| 18 | 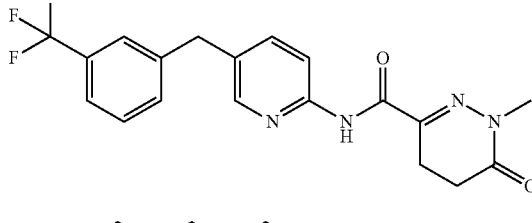 |
| 19 | 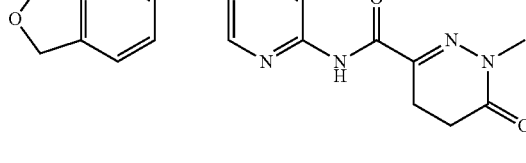 |
| 20 | 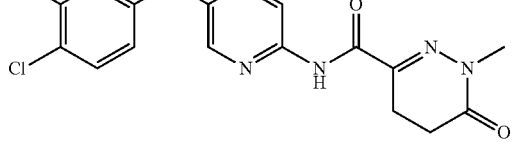 |

TABLE 1-continued
Compounds of the Invention
| CMPD No. | Structure |
|---|---|
| 21 | 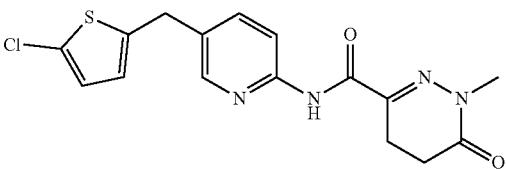 [SMILES: CN1N=C(C(=O)Nc2ccc(Cc3ccc(Cl)s3)cn2)CCC1=O] |
| 22 | 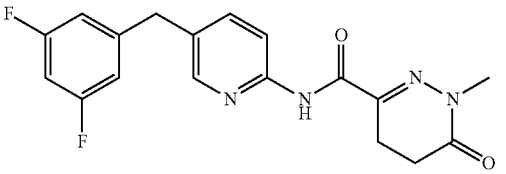 [SMILES: CN1N=C(C(=O)Nc2ccc(Cc3cc(F)cc(F)c3)cn2)CCC1=O] |
| 23 | 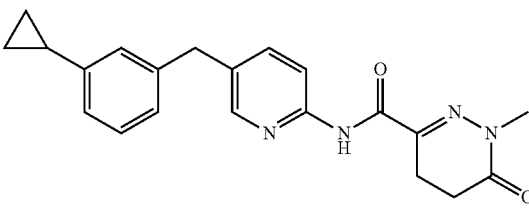 |
| 24 | 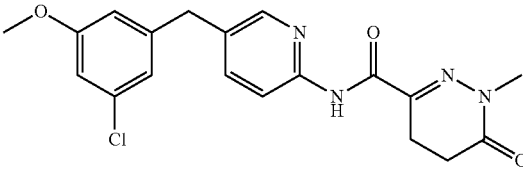 |
| 25 | 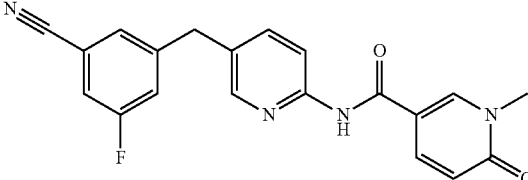 |
| 26 | 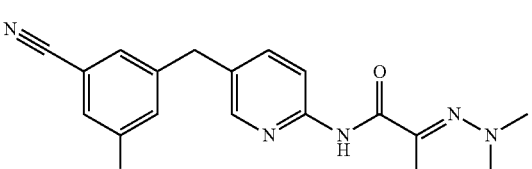 |
| 27 | 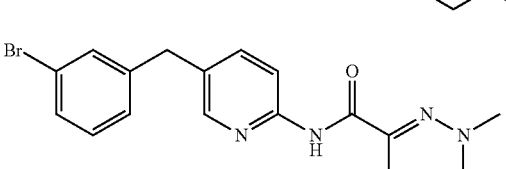 |
| 28 | 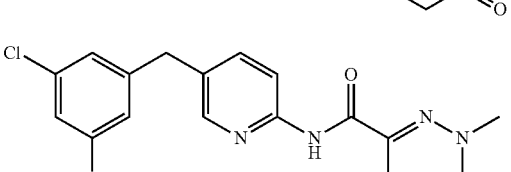 |

TABLE 1-continued

Compounds of the Invention

| CMPD No. | Structure |
|---|---|
| 29 | (3,4,5-trifluorobenzyl)pyridin-2-yl attached via NH-C(O) to 1-methyl-6-oxo-1,4,5,6-tetrahydropyridazin-3-yl |
| 30 | (3-methoxybenzyl)pyridin-2-yl attached via NH-C(O) to 1-methyl-6-oxo-1,4,5,6-tetrahydropyridazin-3-yl |
| 31 | (3,5-dichlorobenzyl)pyridin-2-yl attached via NH-C(O) to 1-methyl-6-oxo-1,4,5,6-tetrahydropyridazin-3-yl |
| 32 | (3-(difluoromethyl)benzyl)pyridin-2-yl attached via NH-C(O) to 1-methyl-6-oxo-1,4,5,6-tetrahydropyridazin-3-yl |
| 33 | (3-chloro-4-cyanobenzyl)pyridin-2-yl attached via NH-C(O) to 1-methyl-6-oxo-1,4,5,6-tetrahydropyridazin-3-yl |
| 34 | (cyclohex-1-en-1-ylmethyl)pyridin-2-yl attached via NH-C(O) to 1-methyl-6-oxo-1,4,5,6-tetrahydropyridazin-3-yl |
| 35 | (3,4-difluorobenzyl)pyridin-2-yl attached via NH-C(O) to 1-methyl-6-oxo-1,6-dihydropyridazin-3-yl |
| 36 | (4-chlorobenzyl)pyridin-2-yl attached via NH-C(O) to 1-methyl-6-oxo-1,6-dihydropyridazin-3-yl |

TABLE 1-continued

Compounds of the Invention

| CMPD No. | Structure |
|---|---|
| 37 | (3,5-difluorobenzyl)pyridine-pyridazinone amide |
| 38 | (cyclohexylmethyl)pyridine-pyridazinone amide |
| 39 | (4-(trifluoromethyl)benzyl)pyridine-pyridazinone amide |
| 40 | (3-chloro-5-fluorobenzyl)pyridine-pyridazinone amide |
| 41 | (3,4,5-trifluorobenzyl)pyridine-pyridazinone amide |
| 42 | (3-cyano-5-fluorobenzyl)pyridine-pyridazinone amide |
| 43 | (3-cyanobenzyl)pyridine-pyridazinone amide |
| 44 | (3-methoxybenzyl)pyridine-pyridazinone amide |

TABLE 1-continued

Compounds of the Invention

| CMPD No. | Structure |
|---|---|
| 45 | *3-fluorobenzyl-pyridin-2-yl N-(1-methyl-6-oxo-1,6-dihydropyridazine-3-carboxamide)* |
| 46 | *3-chloro-4-fluorobenzyl-pyridin-2-yl N-(1-methyl-6-oxo-1,6-dihydropyridazine-3-carboxamide)* |
| 47 | *3-chlorobenzyl-pyridin-2-yl N-(1-methyl-6-oxo-1,6-dihydropyridazine-3-carboxamide)* |
| 48 | *3-chlorobenzyl-pyridin-2-yl N-(1-methyl-6-oxo-1,6-dihydropyridine-3-carboxamide)* |
| 49 | *3-fluoro-4-methoxybenzyl-pyridin-2-yl N-(1-methyl-6-oxo-1,6-dihydropyridine-3-carboxamide)* |
| 50 | *3-chloro-5-methoxybenzyl-pyridin-2-yl N-(1-methyl-6-oxo-1,6-dihydropyridine-3-carboxamide)* |
| 51 | *3-chloro-5-cyanobenzyl-pyridin-2-yl N-(1-methyl-6-oxo-1,4,5,6-tetrahydropyridazine-3-carboxamide)* |
| 52 | *3-fluoro-5-methoxybenzyl-pyridin-2-yl N-(1-methyl-6-oxo-1,6-dihydropyridine-3-carboxamide)* |

TABLE 1-continued

Compounds of the Invention

| CMPD No. | Structure |
|---|---|
| 53 | 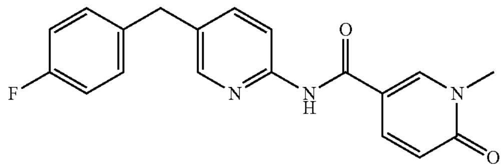 [SMILES: Cn1cc(C(=O)Nc2ccc(Cc3ccc(F)cc3)cn2)ccc1=O] |
| 54 | 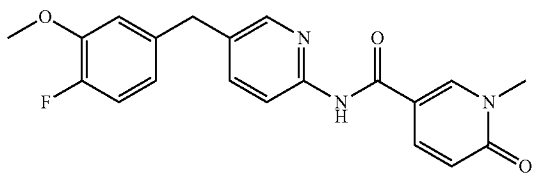 [SMILES: COc1cc(Cc2ccc(NC(=O)c3ccc(=O)n(C)c3)nc2)ccc1F] |
| 55 | 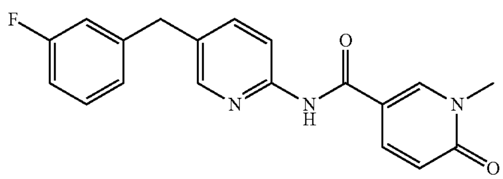 [SMILES: Cn1cc(C(=O)Nc2ccc(Cc3cccc(F)c3)cn2)ccc1=O] |
| 56 | 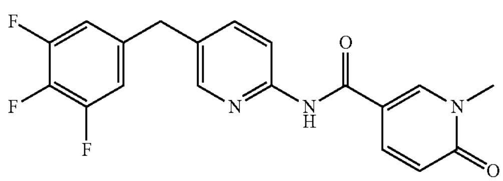 [SMILES: Cn1cc(C(=O)Nc2ccc(Cc3cc(F)c(F)c(F)c3)cn2)ccc1=O] |
| 57 | 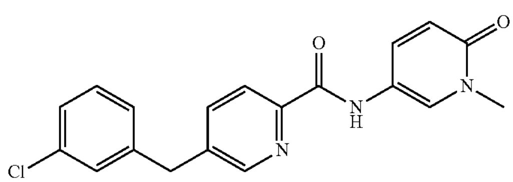 [SMILES: Cn1cc(NC(=O)c2ccc(Cc3cccc(Cl)c3)cn2)ccc1=O] |
| 58 | 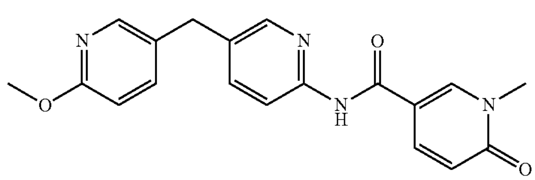 [SMILES: COc1ccc(Cc2ccc(NC(=O)c3ccc(=O)n(C)c3)nc2)cn1] |
| 59 | 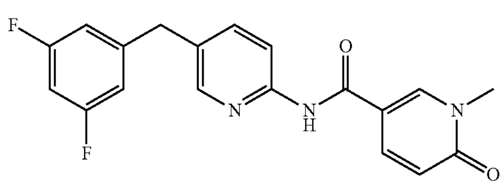 [SMILES: Cn1cc(C(=O)Nc2ccc(Cc3cc(F)cc(F)c3)cn2)ccc1=O] |
| 60 | 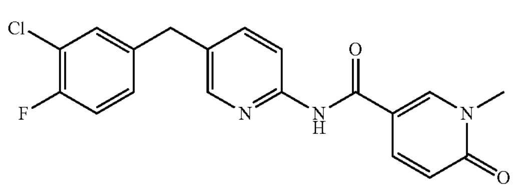 [SMILES: Cn1cc(C(=O)Nc2ccc(Cc3ccc(F)c(Cl)c3)cn2)ccc1=O] |

TABLE 1-continued

Compounds of the Invention

| CMPD No. | Structure |
|---|---|
| 61 | 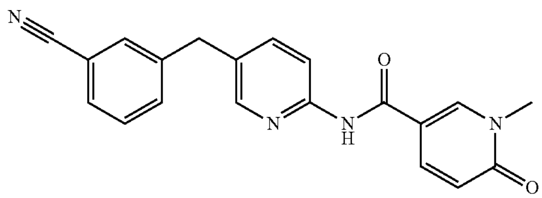 [SMILES: Cn1cc(C(=O)Nc2ccc(Cc3cccc(C#N)c3)cn2)ccc1=O] |
| 62 | 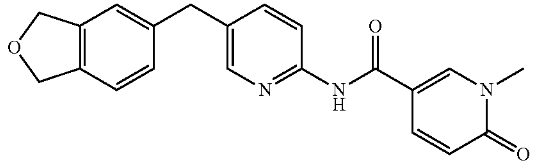 [SMILES: Cn1cc(C(=O)Nc2ccc(Cc3ccc4c(c3)COC4)cn2)ccc1=O] |
| 63 | 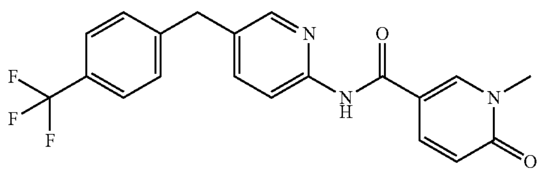 [SMILES: Cn1cc(C(=O)Nc2ccc(Cc3ccc(C(F)(F)F)cc3)cn2)ccc1=O] |
| 64 | 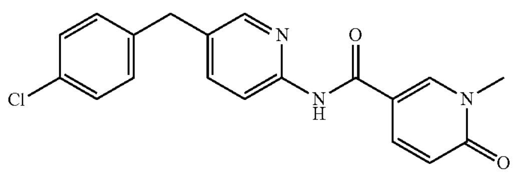 [SMILES: Cn1cc(C(=O)Nc2ccc(Cc3ccc(Cl)cc3)cn2)ccc1=O] |
| 65 | 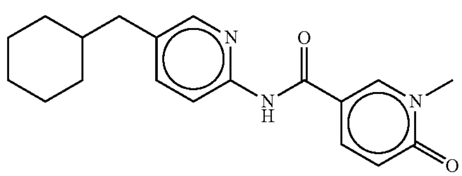 |
| 66 | 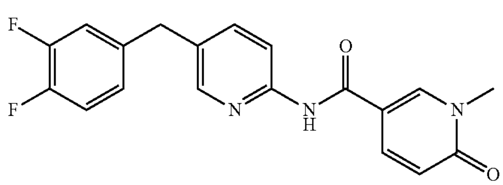 |
| 67 | 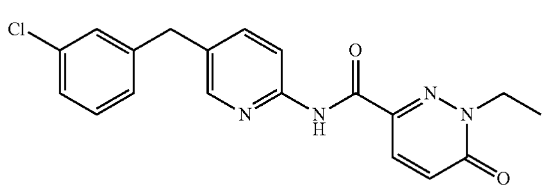 [SMILES: CCn1nc(C(=O)Nc2ccc(Cc3cccc(Cl)c3)cn2)ccc1=O] |
| 68 | 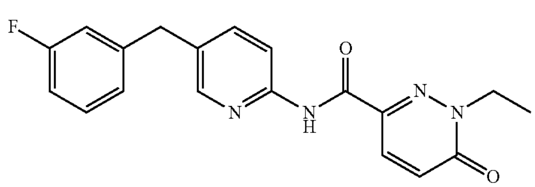 [SMILES: CCn1nc(C(=O)Nc2ccc(Cc3cccc(F)c3)cn2)ccc1=O] |

TABLE 1-continued

Compounds of the Invention

| CMPD No. | Structure |
|---|---|
| 69 | 3-cyano-5-fluorobenzyl-pyridin-2-yl-NH-C(O)-(1-ethyl-6-oxo-pyridazin-3-yl) |
| 70 | 3,4-dichlorobenzyl-pyridin-2-yl-NH-C(O)-(1-ethyl-6-oxo-pyridazin-3-yl) |
| 71 | 3-fluorobenzyl-pyridin-2-yl-NH-C(O)-(1-propyl-6-oxo-pyridazin-3-yl) |
| 72 | 3-fluorobenzyl-pyridin-2-yl-NH-C(O)-(1-isopropyl-6-oxo-pyridazin-3-yl) |
| 73 | 3-chlorobenzyl-pyridin-2-yl-NH-C(O)-(1-isopropyl-6-oxo-pyridazin-3-yl) |
| 74 | 3-fluoro-5-chlorobenzyl-pyridin-2-yl-NH-C(O)-(1-cyclopropyl-6-oxo-pyridazin-3-yl) |
| 75 | 3-fluorobenzyl-pyridin-2-yl-NH-C(O)-(1-cyclopropyl-6-oxo-pyridazin-3-yl) |
| 76 | 3-chloro-4-fluorobenzyl-pyridin-2-yl-NH-C(O)-(1-cyclopropyl-6-oxo-pyridazin-3-yl) |

TABLE 1-continued
Compounds of the Invention
| CMPD No. | Structure |
|---|---|
| 77 | 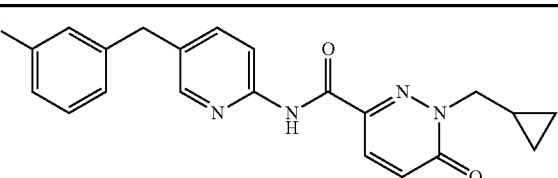 |
| 78 | 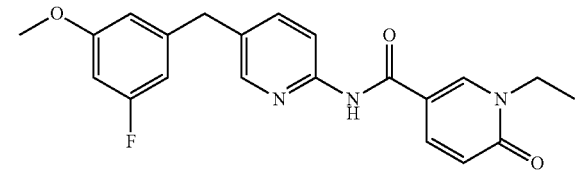 [SMILES: CCn1cc(C(=O)Nc2ccc(Cc3cc(F)cc(OC)c3)cn2)ccc1=O] |
| 79 | 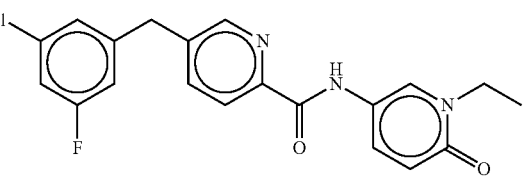 |
| 80 | 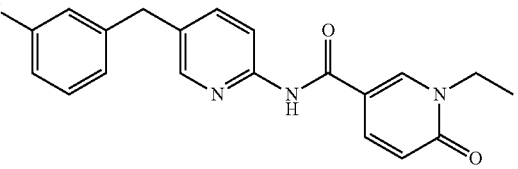 |
| 81 | 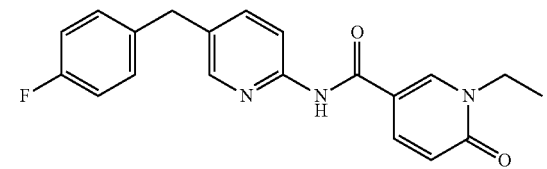 [SMILES: CCn1cc(C(=O)Nc2ccc(Cc3ccc(F)cc3)cn2)ccc1=O] |
| 82 | 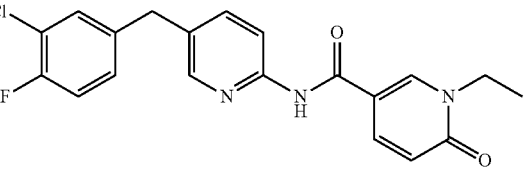 |
| 83 | 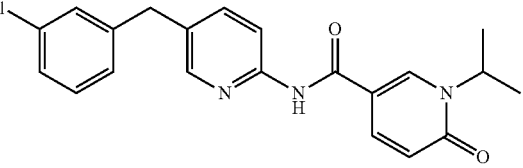 |
| 84 | 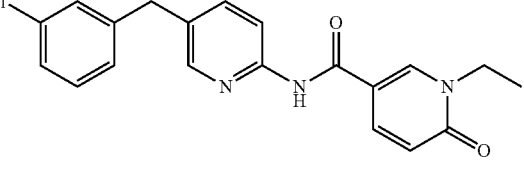 |

TABLE 1-continued
Compounds of the Invention
| CMPD No. | Structure |
|---|---|
| 85 | 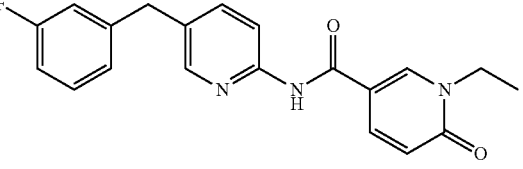 |
| 86 | 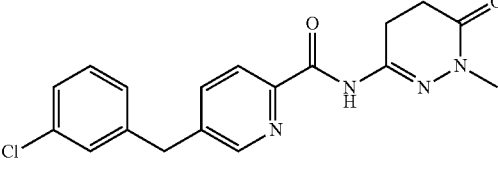 |
| 87 | 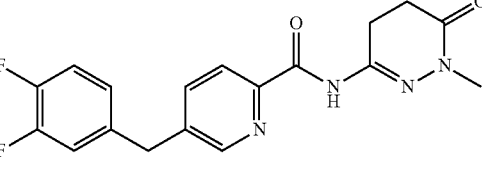 |
| 88 | 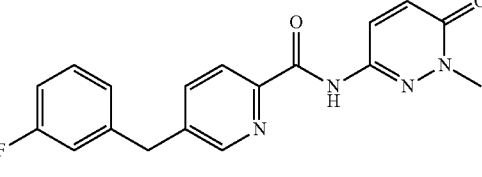 |
| 89 | 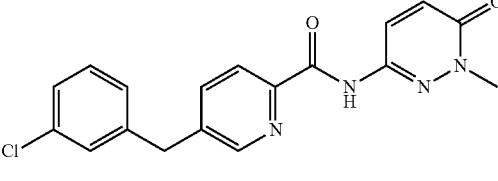 |
| 90 | 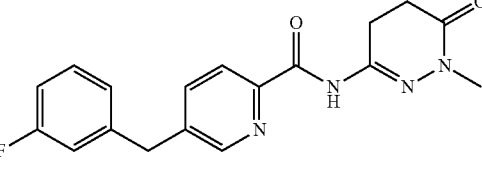 |
| 91 | 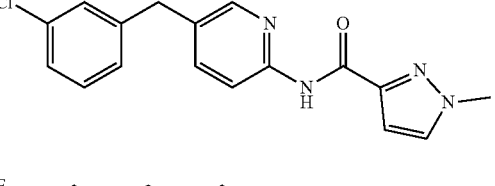 |
| 92 | 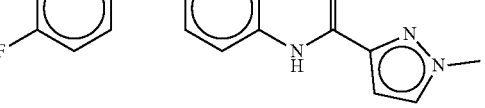 |

TABLE 1-continued

Compounds of the Invention

| CMPD No. | Structure |
|---|---|
| 93 | 4-fluorobenzyl-pyridine-2-yl N-(1-methyl-1H-pyrazol-3-yl)carboxamide |
| 94 | 3-chlorobenzyl-pyridine-2-yl N-(1-methyl-1H-pyrazol-4-yl)carboxamide |
| 95 | 3-fluorobenzyl-pyridine-2-yl N-(1-methyl-1H-pyrazol-3-yl)carboxamide |
| 96 | 3-cyano-5-fluorobenzyl-pyridine-2-yl N-(1-methyl-1H-pyrazol-3-yl)carboxamide |
| 97 | 3,5-difluorobenzyl-pyridine-2-yl N-(1-ethyl-1H-pyrazol-3-yl)carboxamide |
| 98 | 3,4-difluorobenzyl-pyridine-2-yl N-(1-ethyl-1H-pyrazol-3-yl)carboxamide |
| 99 | 3-chloro-5-fluorobenzyl-pyridine-2-yl N-(1-ethyl-1H-pyrazol-3-yl)carboxamide |
| 100 | 3-chlorobenzyl-pyridine-2-yl N-(1-ethyl-1H-pyrazol-3-yl)carboxamide |
| 101 | 3-fluorobenzyl-pyridine-2-yl N-(1-ethyl-1H-pyrazol-3-yl)carboxamide |

TABLE 1-continued

Compounds of the Invention

| CMPD No. | Structure |
|---|---|
| 102 | 4-fluorobenzyl-pyridine-2-yl carboxamide of 1-ethyl-pyrazole-3-carboxamide |
| 103 | 3-chlorobenzyl-pyridine-2-yl carboxamide of 5-methyl-1,3,4-thiadiazole-2-carboxamide |
| 104 | 3-chlorobenzyl-pyridine-2-yl carboxamide of 5-methyl-1,3,4-oxadiazole-2-carboxamide |
| 105 | 3-chlorobenzyl-pyridine-2-yl carboxamide of 1-methyl-5-oxo-4,5-dihydro-1H-pyrazole-3-carboxamide |
| 106 | 3-fluorobenzyl-pyridine-2-yl carboxamide of 5-hydroxy-1-methyl-1H-pyrazole-3-carboxamide |
| 107 | 3-fluorobenzyl-pyridine-2-yl carboxamide of 5-methylisoxazole-3-carboxamide |
| 108 | 3-chlorobenzyl-pyridine-2-yl carboxamide of 1-methyl-6-oxo-1,6-dihydropyrazine-2-carboxamide |
| 109 | 3-fluorobenzyl-pyridine-2-yl carboxamide of 2-methyl-3-oxo-2,3-dihydropyridazine-4-carboxamide |

TABLE 1-continued

Compounds of the Invention

| CMPD No. | Structure |
|---|---|
| 110 | (structure) |
| 111 | (structure) |
| 112 | (structure) |
| 113 | (structure) |
| 114 | (structure) |
| 115 | (structure) |
| 116 | (structure) |
| 117 | (structure) |

TABLE 1-continued

Compounds of the Invention

| CMPD No. | Structure |
|---|---|
| 118 | *(structure)* |
| 119 | *(structure)* |
| 120 | *(structure)* |
| 121 | *(structure)* |
| 122 | *(structure)* |
| 123 | *(structure)* |
| 124 | *(structure)* |
| 125 | *(structure)* |

TABLE 1-continued

Compounds of the Invention

| CMPD No. | Structure |
|---|---|
| 126 | 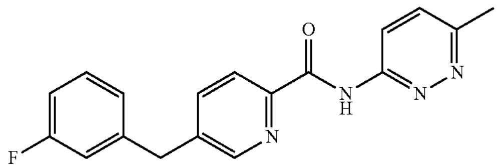 [SMILES: Cc1ccc(NC(=O)c2ccc(Cc3cccc(F)c3)cn2)nn1] |
| 127 | 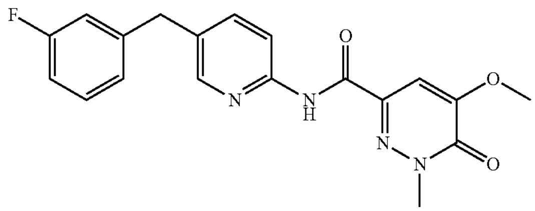 |
| 128 | 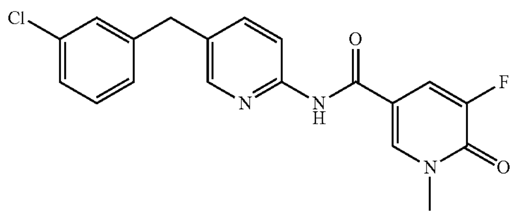 [SMILES: Cn1cc(C(=O)Nc2ccc(Cc3cccc(Cl)c3)cn2)cc(F)c1=O] |
| 129 | 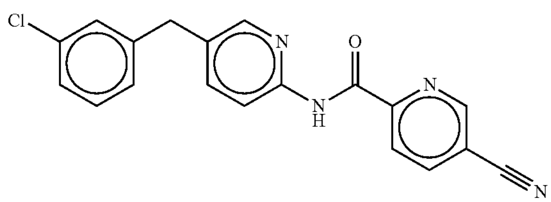 |
| 130 | 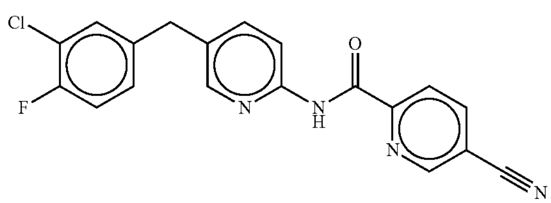 |
| 131 | 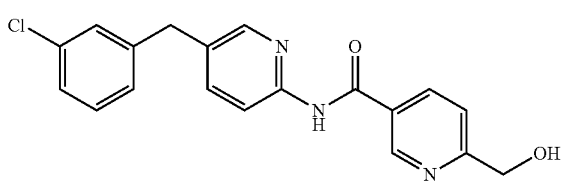 [SMILES: O=C(Nc1ccc(Cc2cccc(Cl)c2)cn1)c1ccc(CO)nc1] |
| 132 | 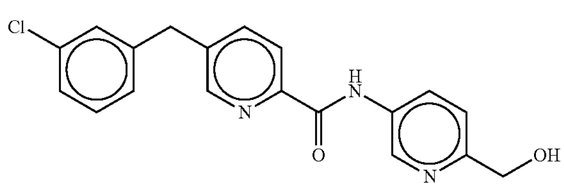 |

TABLE 1-continued

Compounds of the Invention

| CMPD No. | Structure |
|---|---|
| 133 | (structure) |
| 134 | (structure) |
| 135 | (structure) |
| 136 | (structure) |
| 137 | (structure) |
| 138 | (structure) |
| 139 | (structure) |
| 140 | (structure) |

TABLE 1-continued
Compounds of the Invention
| CMPD No. | Structure |
|---|---|
| 141 | 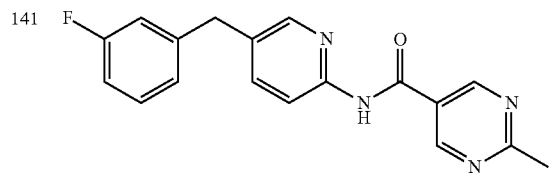 |
| 142 | 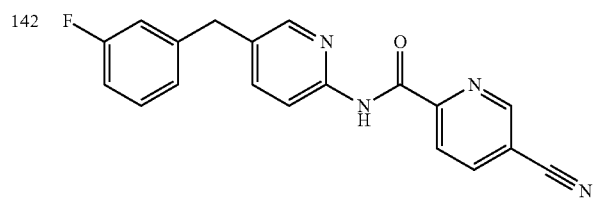 |
| 143 | 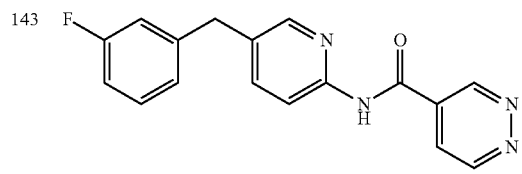 |
| 144 | 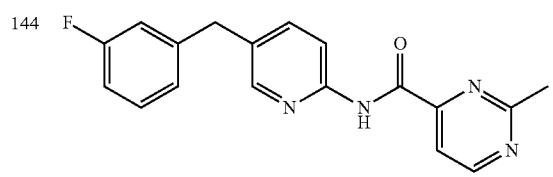 |
| 145 | 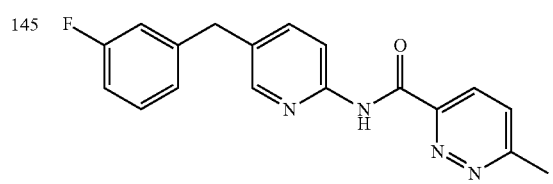 |
| 146 | 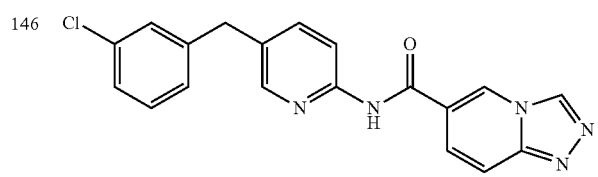 |
| 147 | 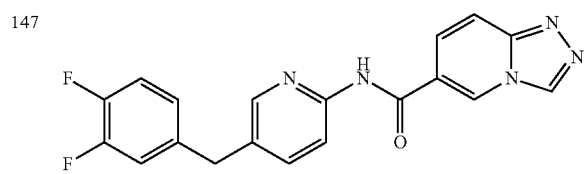 |
| 148 | 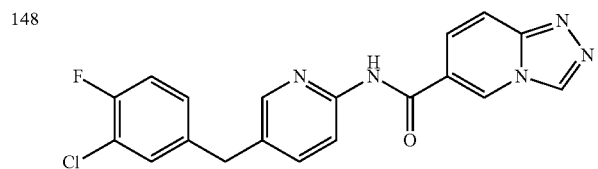 |

TABLE 1-continued

Compounds of the Invention

| CMPD No. | Structure |
|---|---|
| 149 | 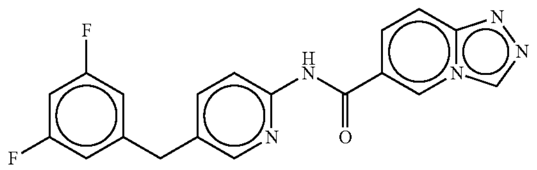 |
| 150 | 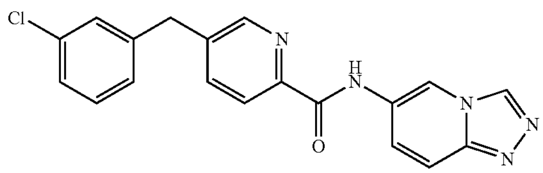 [SMILES: O=C(Nc1ccc2nncn2c1)c1ccc(Cc2cccc(Cl)c2)cn1] |
| 151 | 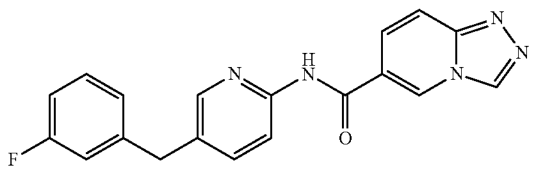 [SMILES: O=C(Nc1ccc(Cc2cccc(F)c2)cn1)c1ccc2nncn2c1] |
| 152 | 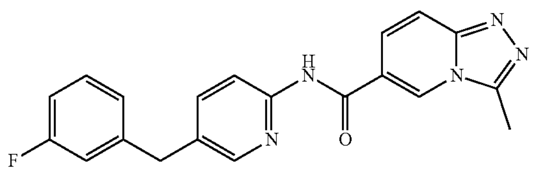 [SMILES: Cc1nnc2ccc(C(=O)Nc3ccc(Cc4cccc(F)c4)cn3)cn12] |
| 153 | 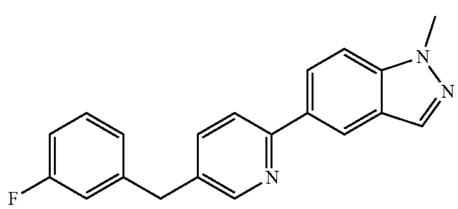 [SMILES: Cn1ncc2cc(-c3ccc(Cc4cccc(F)c4)cn3)ccc21] |
| 154 | 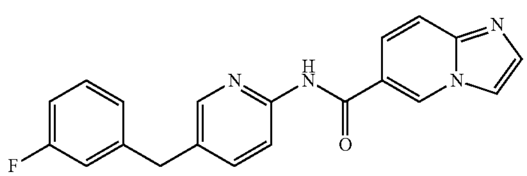 [SMILES: O=C(Nc1ccc(Cc2cccc(F)c2)cn1)c1ccc2nccn2c1] |
| 155 | 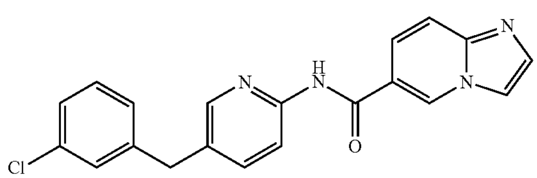 [SMILES: O=C(Nc1ccc(Cc2cccc(Cl)c2)cn1)c1ccc2nccn2c1] |
| 156 | 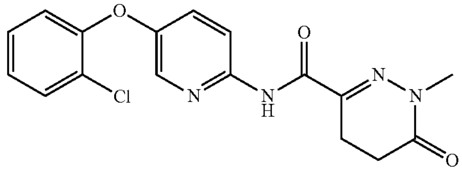 [SMILES: CN1N=C(C(=O)Nc2ccc(Oc3ccccc3Cl)cn2)CCC1=O] |

TABLE 1-continued
Compounds of the Invention
| CMPD No. | Structure |
|---|---|
| 157 | 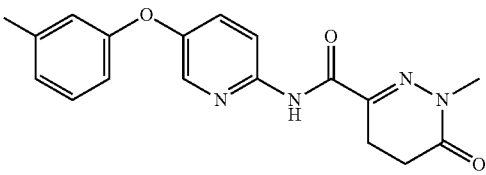 |
| 158 | 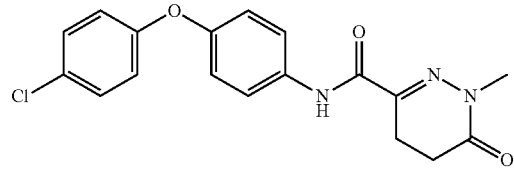 [SMILES: CN1N=C(C(=O)Nc2ccc(Oc3ccc(Cl)cc3)cc2)CCC1=O] |
| 159 | 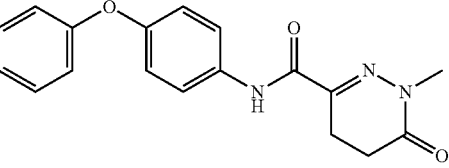 |
| 160 | 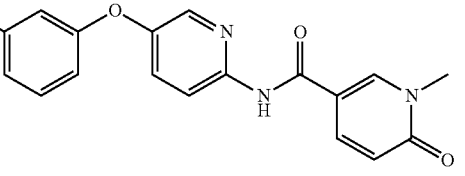 |
| 161 | 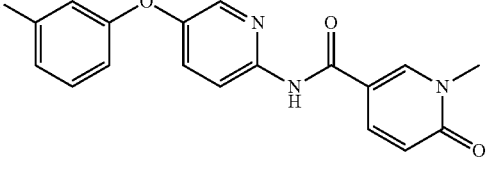 |
| 162 | 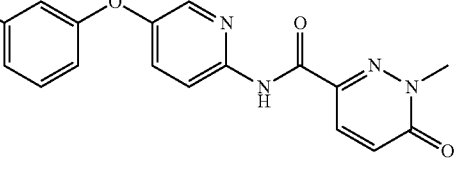 |
| 163 | 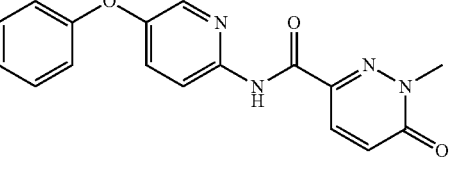 |
| 164 | 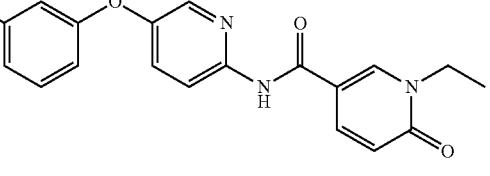 |

TABLE 1-continued
Compounds of the Invention
| CMPD No. | Structure |
|---|---|
| 165 | 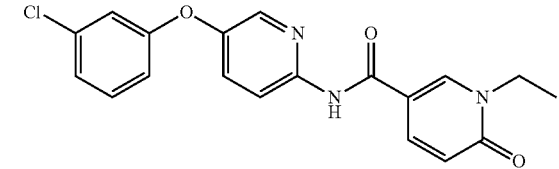 [SMILES: CCn1cc(C(=O)Nc2ccc(Oc3cccc(Cl)c3)cn2)ccc1=O] |
| 166 | 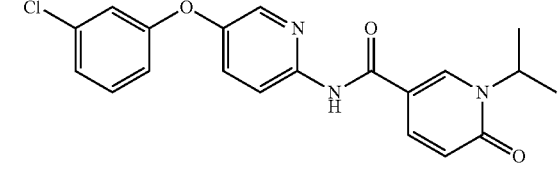 [SMILES: CC(C)n1cc(C(=O)Nc2ccc(Oc3cccc(Cl)c3)cn2)ccc1=O] |
| 167 | 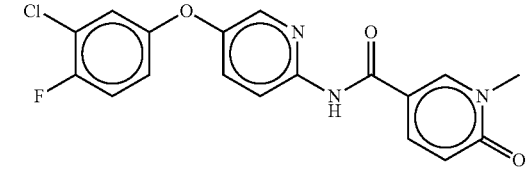 |
| 168 | 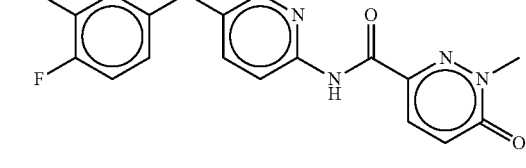 |
| 169 | 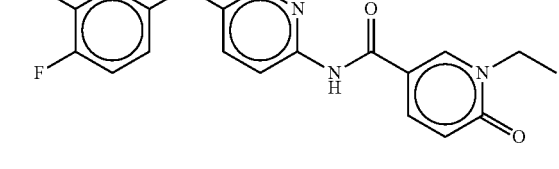 |
| 170 | 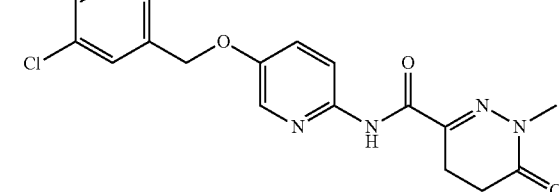 |
| 171 | 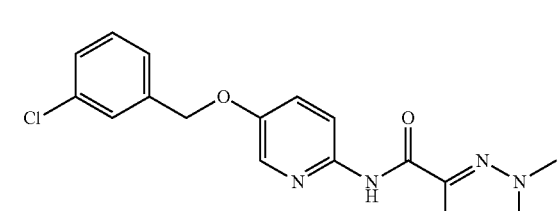 |

113
114
TABLE 1-continued
Compounds of the Invention
| CMPD No. | Structure |
|---|---|
| 172 | 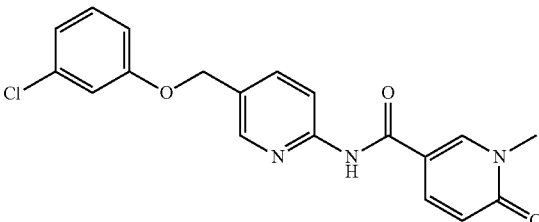 |
| 173 | 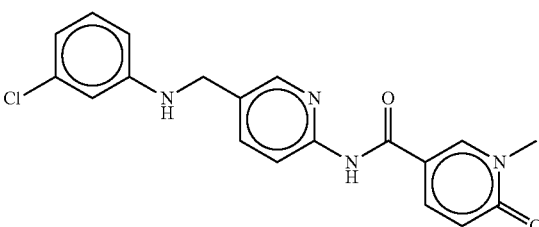 |
| 174 | 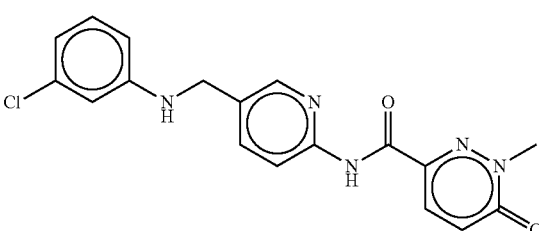 |
| 175 | 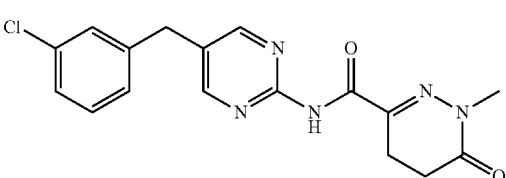 |
| 176 | 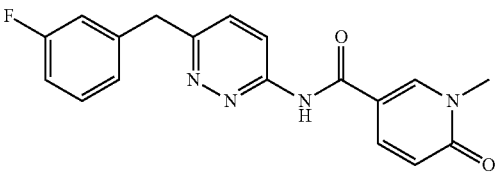 [SMILES: Cn1cc(C(=O)Nc2ccc(Cc3cccc(F)c3)nn2)ccc1=O] |
| 177 | 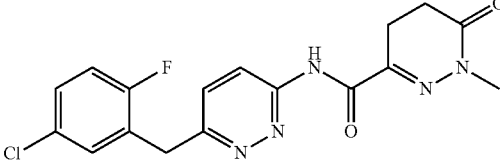 |
| 178 | 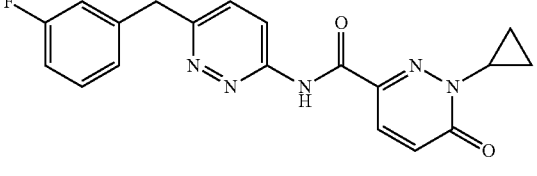 |

TABLE 1-continued

Compounds of the Invention

| CMPD No. | Structure |
|---|---|
| 179 | 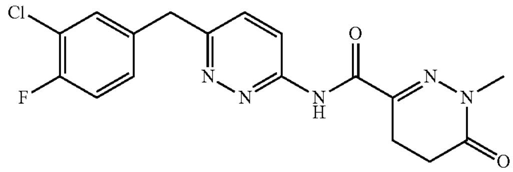 |
| 180 | 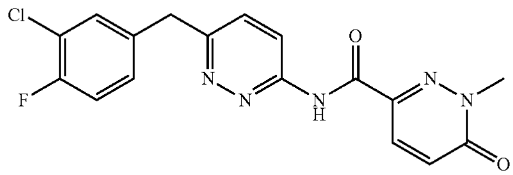 [SMILES: Cn1nc(C(=O)Nc2ccc(Cc3ccc(F)c(Cl)c3)nn2)ccc1=O] |
| 181 | 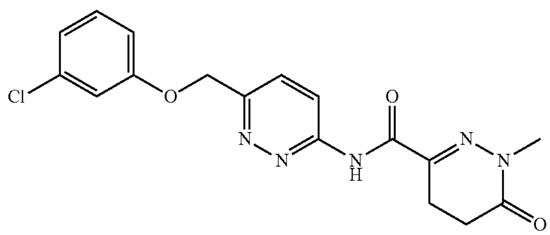 [SMILES: CN1N=C(C(=O)Nc2ccc(COc3cccc(Cl)c3)nn2)CCC1=O] |
| 182 | 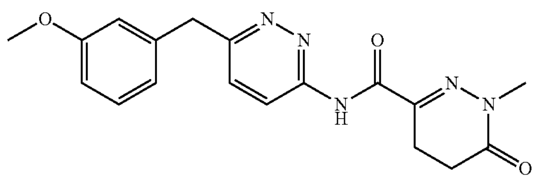 [SMILES: COc1cccc(Cc2ccc(NC(=O)C3=NN(C)C(=O)CC3)nn2)c1] |
| 183 | 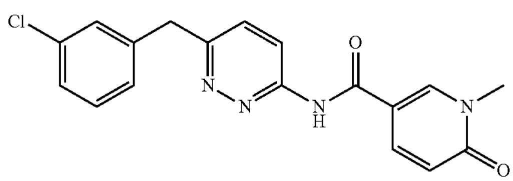 [SMILES: Cn1cc(C(=O)Nc2ccc(Cc3cccc(Cl)c3)nn2)ccc1=O] |
| 184 | 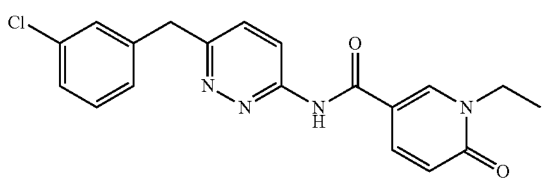 [SMILES: CCn1cc(C(=O)Nc2ccc(Cc3cccc(Cl)c3)nn2)ccc1=O] |
| 185 | 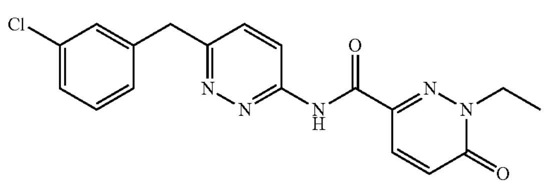 [SMILES: CCn1nc(C(=O)Nc2ccc(Cc3cccc(Cl)c3)nn2)ccc1=O] |
| 186 | 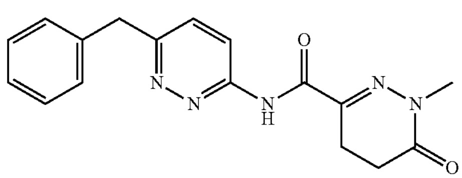 [SMILES: CN1N=C(C(=O)Nc2ccc(Cc3ccccc3)nn2)CCC1=O] |

TABLE 1-continued
Compounds of the Invention
| CMPD No. | Structure |
|---|---|
| 187 | 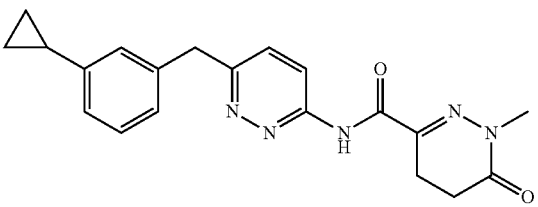 [SMILES: CN1N=C(C(=O)Nc2ccc(Cc3cccc(C4CC4)c3)nn2)CCC1=O] |
| 188 | 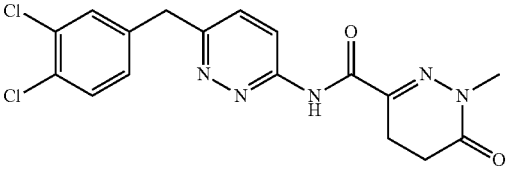 [SMILES: CN1N=C(C(=O)Nc2ccc(Cc3ccc(Cl)c(Cl)c3)nn2)CCC1=O] |
| 189 | 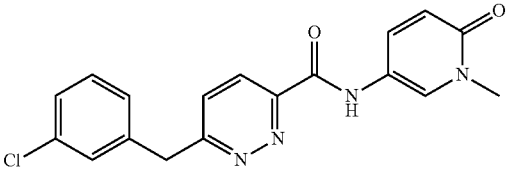 [SMILES: Cn1cc(NC(=O)c2ccc(Cc3cccc(Cl)c3)nn2)ccc1=O] |
| 190 | 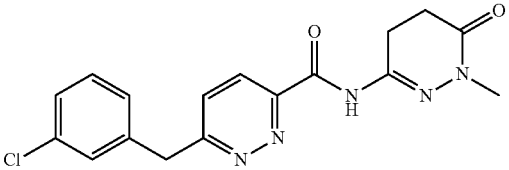 |
| 191 | 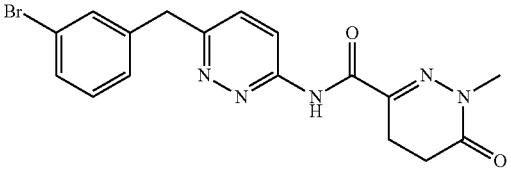 |
| 192 | 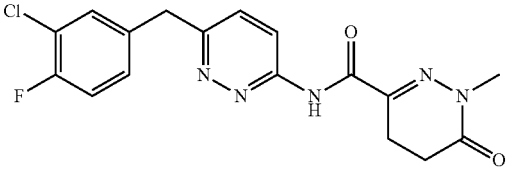 |
| 193 | 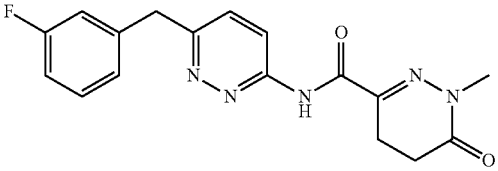 [SMILES: CN1N=C(C(=O)Nc2ccc(Cc3cccc(F)c3)nn2)CCC1=O] |
| 194 | 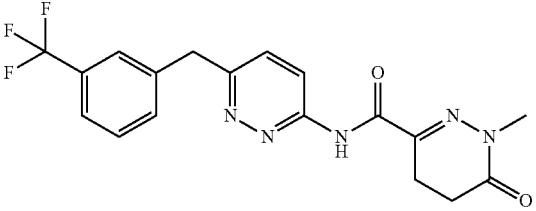 [SMILES: CN1N=C(C(=O)Nc2ccc(Cc3cccc(C(F)(F)F)c3)nn2)CCC1=O] |

TABLE 1-continued
Compounds of the Invention
| CMPD No. | Structure |
|---|---|
| 195 | 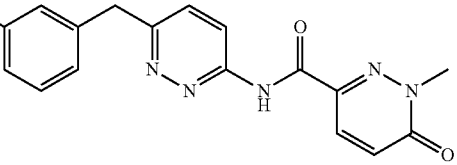 |
| 196 | 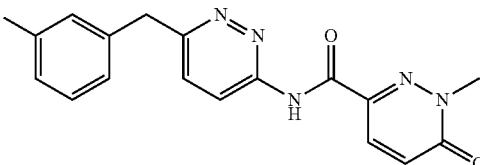 |
| 197 | 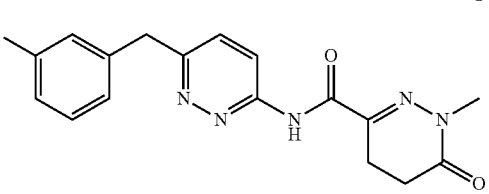 |
| 198 | 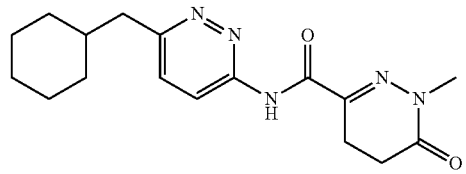 [SMILES: CN1N=C(C(=O)Nc2ccc(CC3CCCCC3)nn2)CCC1=O] |
| 199 | 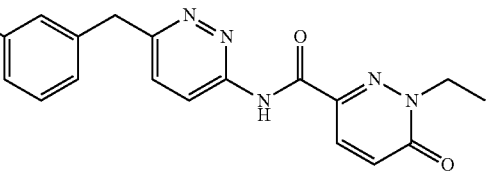 |
| 200 | 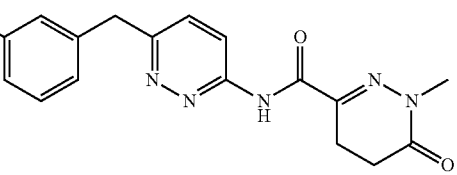 |
| 201 | 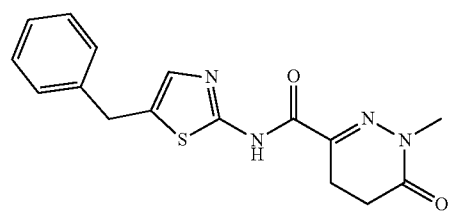 [SMILES: CN1N=C(C(=O)Nc2ncc(Cc3ccccc3)s2)CCC1=O] |
| 202 | 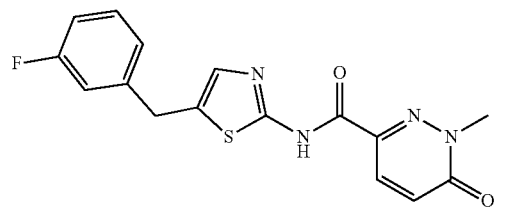 [SMILES: Cn1nc(C(=O)Nc2ncc(Cc3cccc(F)c3)s2)ccc1=O] |

TABLE 1-continued

Compounds of the Invention

| CMPD No. | Structure |
|---|---|
| 203 | 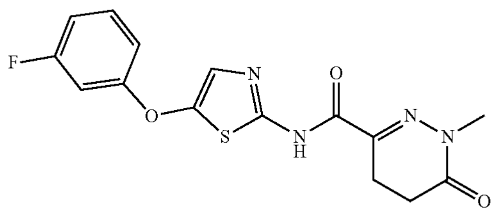 [SMILES: CN1N=C(C(=O)Nc2ncc(Oc3cccc(F)c3)s2)CCC1=O] |
| 204 | 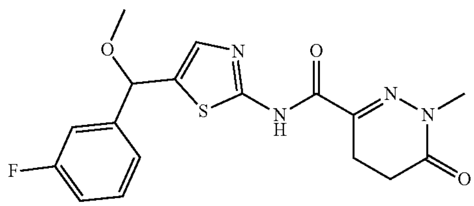 [SMILES: COC(c1cccc(F)c1)c1cnc(NC(=O)C2=NN(C)C(=O)CC2)s1] |
| 205 | 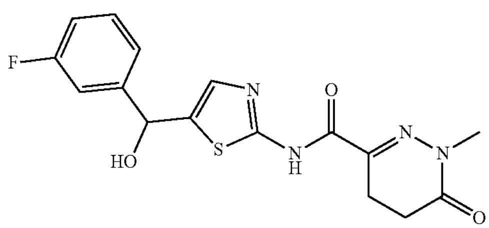 [SMILES: CN1N=C(C(=O)Nc2ncc(C(O)c3cccc(F)c3)s2)CCC1=O] |
| 206 | 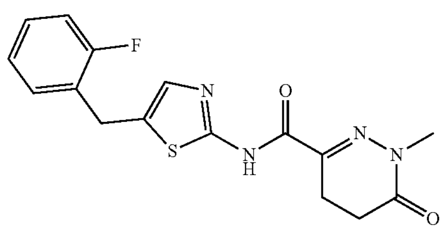 [SMILES: CN1N=C(C(=O)Nc2ncc(Cc3ccccc3F)s2)CCC1=O] |
| 207 | 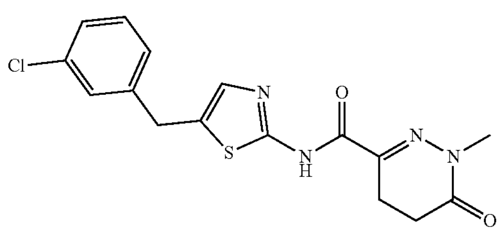 [SMILES: CN1N=C(C(=O)Nc2ncc(Cc3cccc(Cl)c3)s2)CCC1=O] |
| 208 | 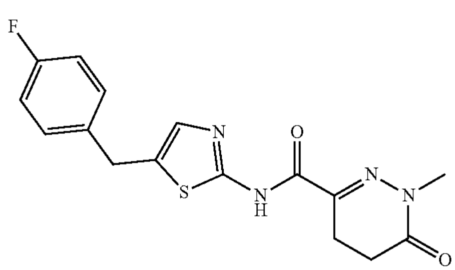 [SMILES: CN1N=C(C(=O)Nc2ncc(Cc3ccc(F)cc3)s2)CCC1=O] |

TABLE 1-continued
Compounds of the Invention
| CMPD No. | Structure |
|---|---|
| 209 | 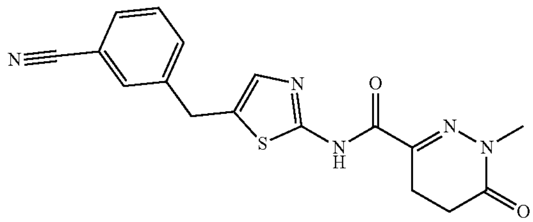 [SMILES: CN1N=C(C(=O)Nc2ncc(Cc3cccc(C#N)c3)s2)CCC1=O] |
| 210 | 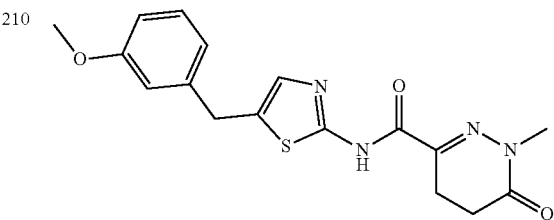 |
| 211 | 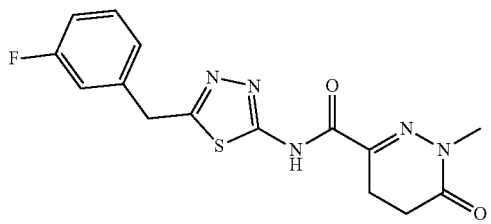 [SMILES: CN1N=C(C(=O)Nc2nnc(Cc3cccc(F)c3)s2)CCC1=O] |
| 212 | 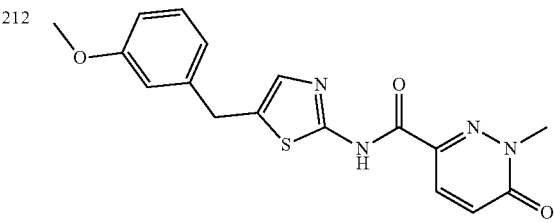 |
| 213 | 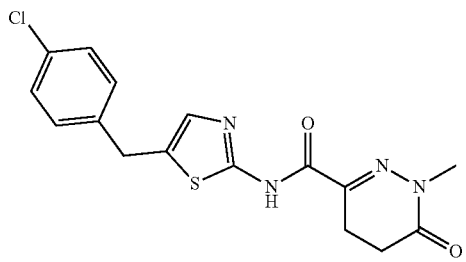 [SMILES: CN1N=C(C(=O)Nc2ncc(Cc3ccc(Cl)cc3)s2)CCC1=O] |
| 214 | 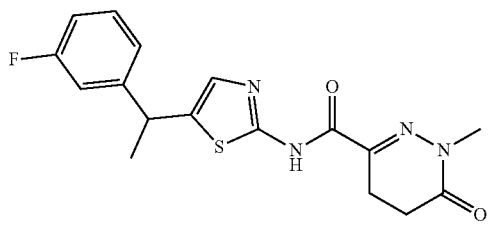 [SMILES: CC(c1cccc(F)c1)c1cnc(NC(=O)C2=NN(C)C(=O)CC2)s1] |

TABLE 1-continued
Compounds of the Invention
| CMPD No. | Structure |
|---|---|
| 215 | 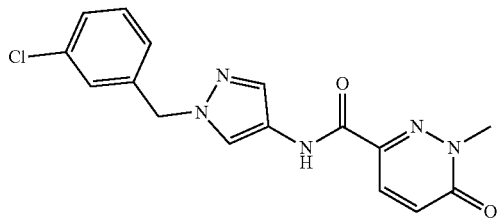 [SMILES: Cn1nc(C(=O)Nc2cnn(Cc3cccc(Cl)c3)c2)ccc1=O] |
| 216 | 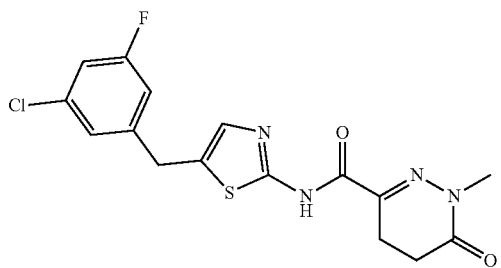 [SMILES: CN1N=C(C(=O)Nc2ncc(Cc3cc(F)cc(Cl)c3)s2)CCC1=O] |
| 217 | 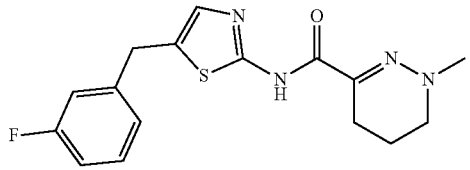 [SMILES: CN1CCCC(C(=O)Nc2ncc(Cc3cccc(F)c3)s2)=N1] |
| 218 | 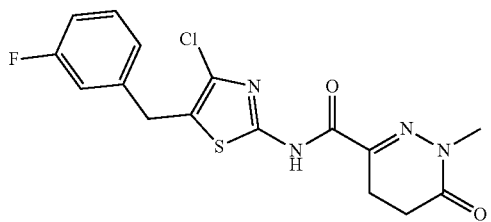 [SMILES: CN1N=C(C(=O)Nc2nc(Cl)c(Cc3cccc(F)c3)s2)CCC1=O] |
| 219 | 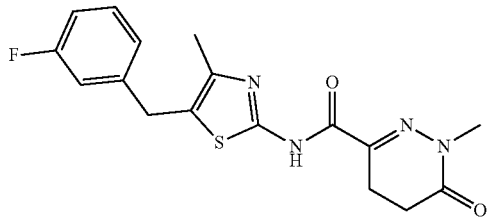 [SMILES: Cc1nc(NC(=O)C2=NN(C)C(=O)CC2)sc1Cc1cccc(F)c1] |
| 220 | 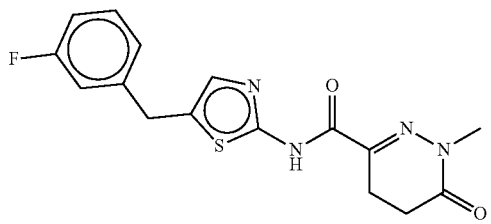 |

TABLE 1-continued
Compounds of the Invention
| CMPD No. | Structure |
|---|---|
| 221 | 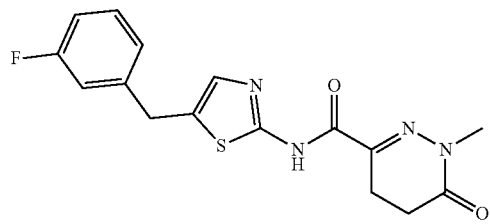 [SMILES: CN1N=C(C(=O)Nc2ncc(Cc3cccc(F)c3)s2)CCC1=O] |
| 222 | 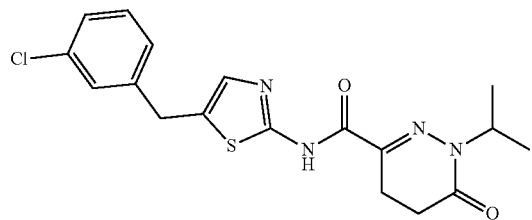 [SMILES: CC(C)N1N=C(C(=O)Nc2ncc(Cc3cccc(Cl)c3)s2)CCC1=O] |
| 223 | 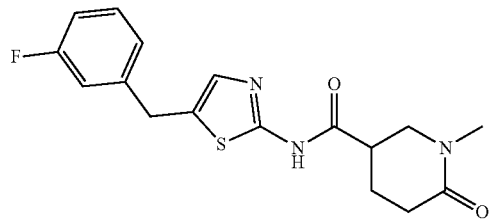 [SMILES: CN1CC(C(=O)Nc2ncc(Cc3cccc(F)c3)s2)CCC1=O] |
| 224 | 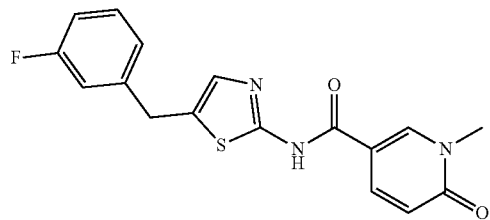 [SMILES: Cn1cc(C(=O)Nc2ncc(Cc3cccc(F)c3)s2)ccc1=O] |
| 225 | 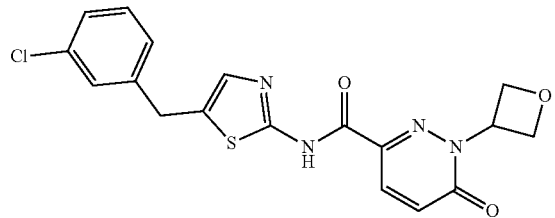 [SMILES: O=C(Nc1ncc(Cc2cccc(Cl)c2)s1)c1ccc(=O)n(C2COC2)n1] |
| 226 | 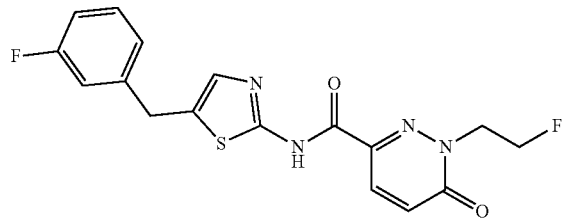 [SMILES: O=C(Nc1ncc(Cc2cccc(F)c2)s1)c1ccc(=O)n(CCF)n1] |

TABLE 1-continued
Compounds of the Invention
| CMPD No. | Structure |
|---|---|
| 227 | 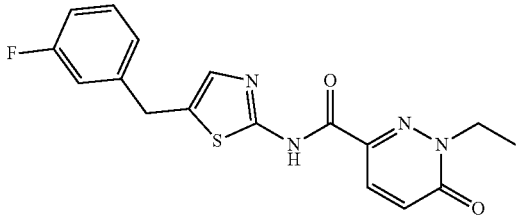 [SMILES: CCn1nc(C(=O)Nc2ncc(Cc3cccc(F)c3)s2)ccc1=O] |
| 228 | 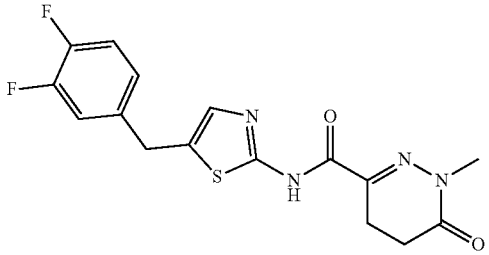 [SMILES: CN1N=C(C(=O)Nc2ncc(Cc3ccc(F)c(F)c3)s2)CCC1=O] |
| 229 | 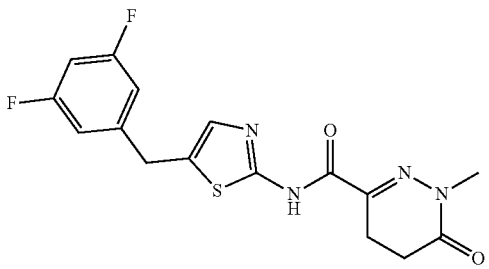 [SMILES: CN1N=C(C(=O)Nc2ncc(Cc3cc(F)cc(F)c3)s2)CCC1=O] |
| 230 | 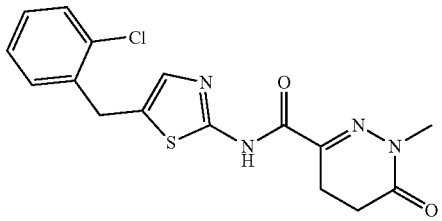 |
| 231 | 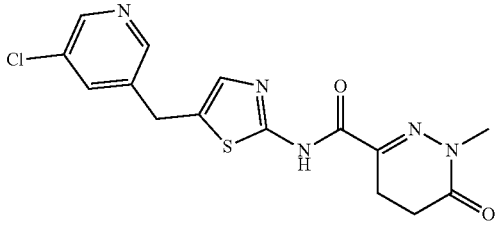 [SMILES: CN1N=C(C(=O)Nc2ncc(Cc3cncc(Cl)c3)s2)CCC1=O] |
| 232 | 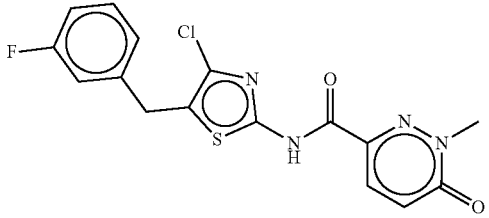 |

TABLE 1-continued

Compounds of the Invention

| CMPD No. | Structure |
|---|---|
| 233 | 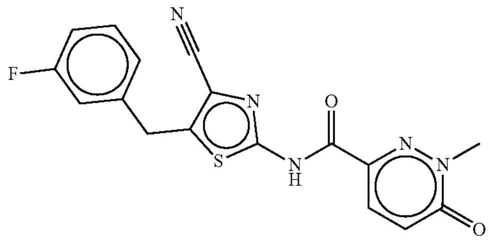 |
| 234 | 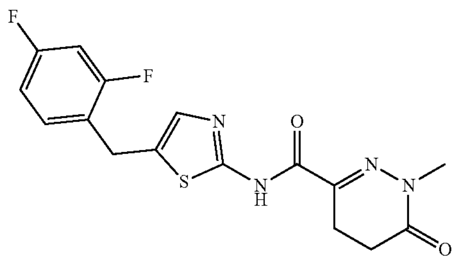 [SMILES: CN1N=C(C(=O)Nc2ncc(Cc3ccc(F)cc3F)s2)CCC1=O] |
| 235 | 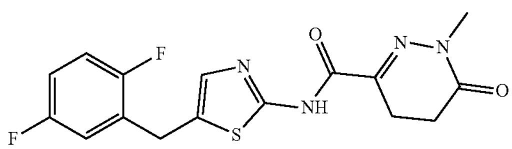 [SMILES: CN1N=C(C(=O)Nc2ncc(Cc3cc(F)ccc3F)s2)CCC1=O] |
| 236 | 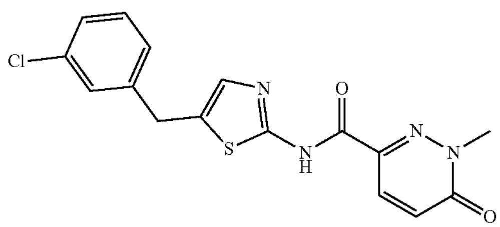 [SMILES: Cn1nc(C(=O)Nc2ncc(Cc3cccc(Cl)c3)s2)ccc1=O] |
| 237 | 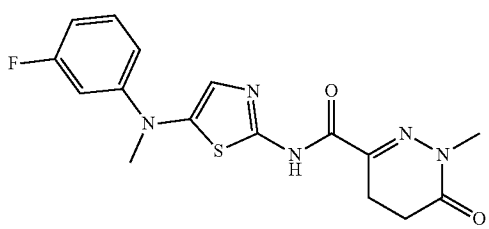 [SMILES: CN1N=C(C(=O)Nc2ncc(N(C)c3cccc(F)c3)s2)CCC1=O] |
| 238 | 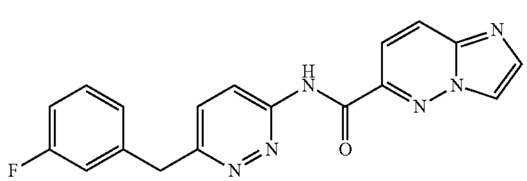 [SMILES: O=C(Nc1ccc(Cc2cccc(F)c2)nn1)c1ccc2nccn2n1] |
| 239 | 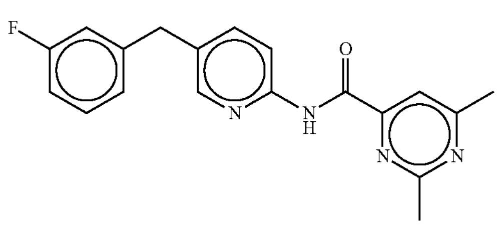 |

TABLE 1-continued

Compounds of the Invention

| CMPD No. | Structure |
|---|---|
| 240 | 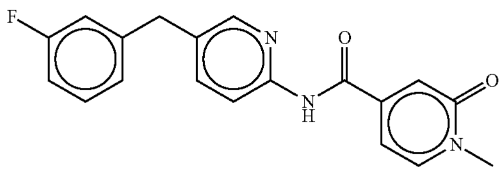 |
| 241 | 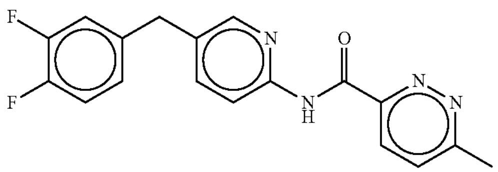 |
| 242 | 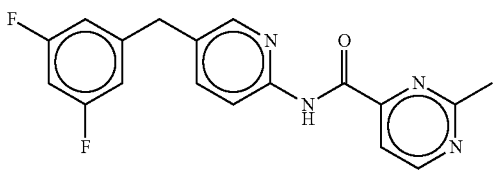 |
| 243 | 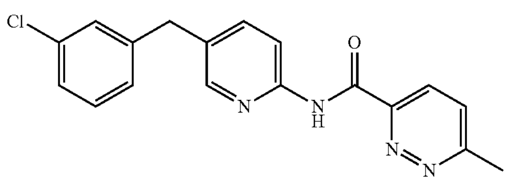 [SMILES: Cc1ccc(C(=O)Nc2ccc(Cc3cccc(Cl)c3)cn2)nn1] |
| 244 | 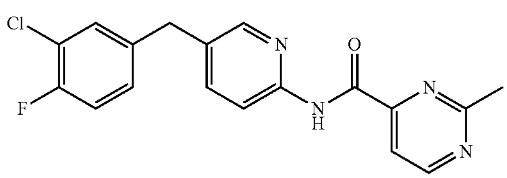 [SMILES: Cc1nccc(C(=O)Nc2ccc(Cc3ccc(F)c(Cl)c3)cn2)n1] |
| 245 | 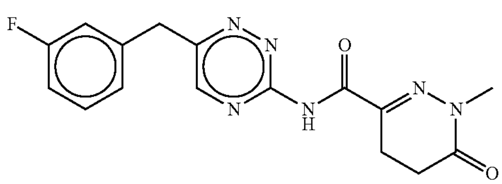 |
| 246 | 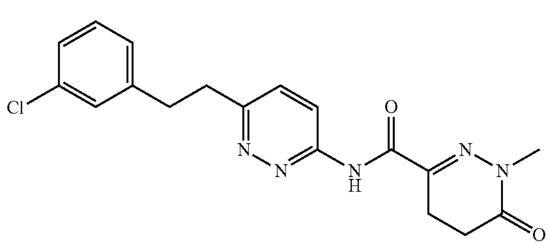 |
| 247 | 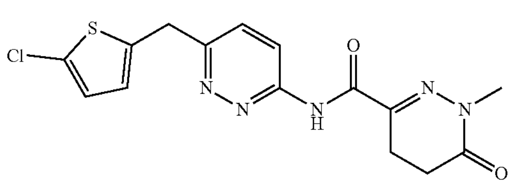 [SMILES: CN1N=C(C(=O)Nc2ccc(Cc3ccc(Cl)s3)nn2)CCC1=O] |

US 12,180,221 B2
135                                                                      136
TABLE 1-continued
Compounds of the Invention
| CMPD No. | Structure |
|---|---|
| 248 | 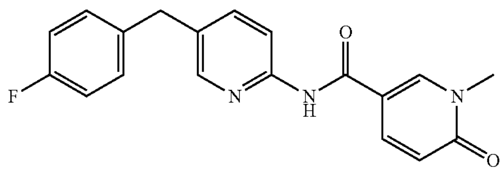 [SMILES: Cn1cc(C(=O)Nc2ccc(Cc3ccc(F)cc3)cn2)ccc1=O] |
| 249 | 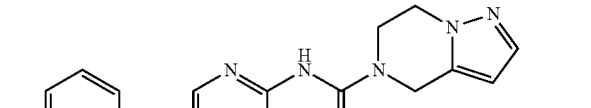 |
| 250 | 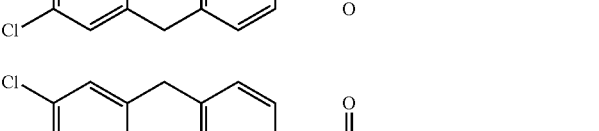 |
| 251 | 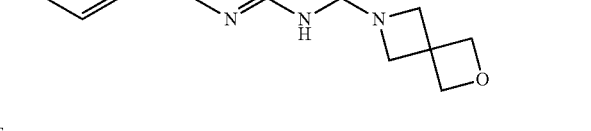 |
| 252 | 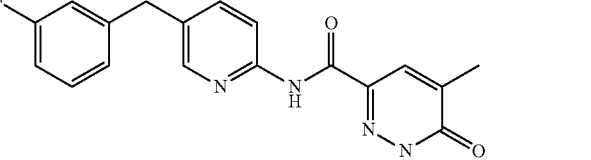 |
| 253 | 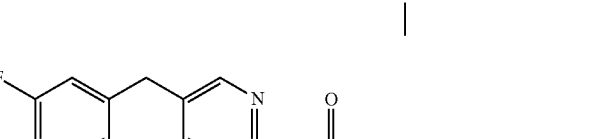 |
| 254 | 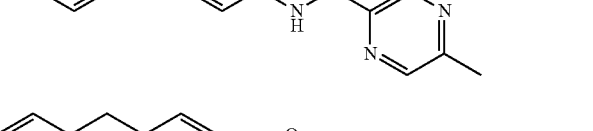 |
| 255 | 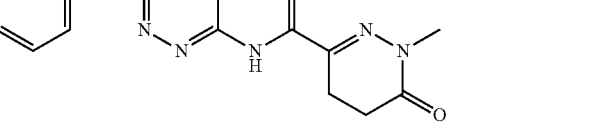 |

TABLE 1-continued

Compounds of the Invention

| CMPD No. | Structure |
|---|---|
| 256 | 3-chlorobenzyl-pyridine-carboxamide-N-cyclopropyl-pyridazinone |
| 257 | 3-chlorobenzyl-pyridazine-carboxamide-N-propyl-pyridazinone |
| 258 | 3-fluorobenzyl-pyridine-carboxamide-N-cyclopropyl-pyridinone |
| 259 | 3-chlorophenoxymethyl-pyridazine-carboxamide-N-methyl-pyridinone |
| 260 | 3-fluorophenoxymethyl-pyridine-carboxamide-N-methyl-dihydropyridazinone |
| 261 | 3-chlorophenoxymethyl-pyridine-carboxamide-N-methyl-dihydropyridazinone |
| 262 | 3-chlorophenoxymethyl-pyridine-carboxamide-N-methyl-pyridazinone |

TABLE 1-continued
Compounds of the Invention
| CMPD No. | Structure |
|---|---|
| 263 | 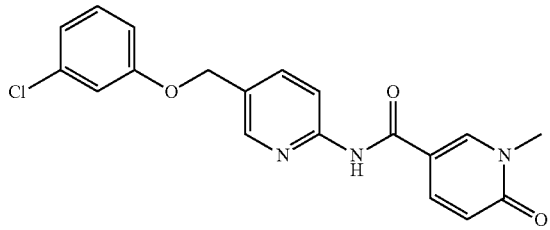 |
| 264 | 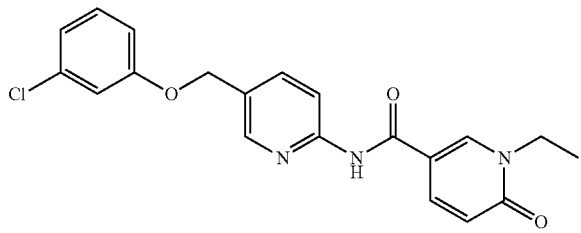 [SMILES: CCn1cc(C(=O)Nc2ccc(COc3cccc(Cl)c3)cn2)ccc1=O] |
| 265 | 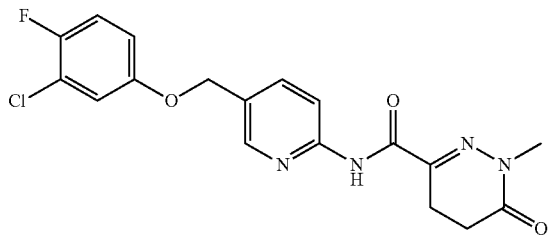 [SMILES: CN1N=C(C(=O)Nc2ccc(COc3ccc(F)c(Cl)c3)cn2)CCC1=O] |
| 266 | 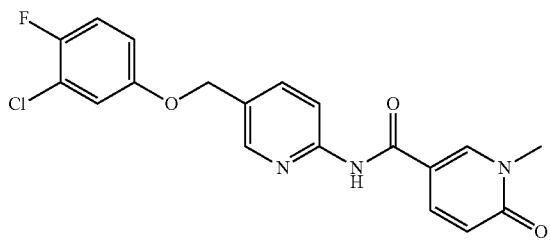 [SMILES: Cn1cc(C(=O)Nc2ccc(COc3ccc(F)c(Cl)c3)cn2)ccc1=O] |
| 267 | 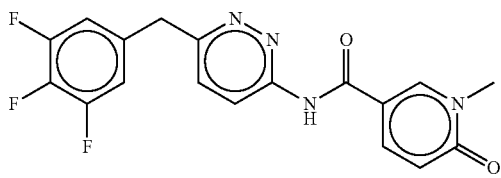 |
| 268 | 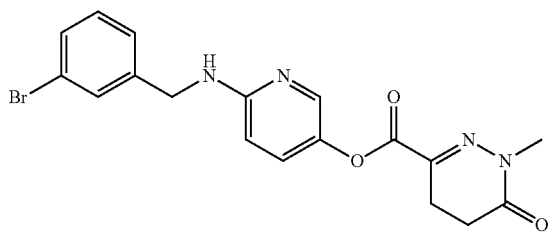 [SMILES: CN1N=C(C(=O)Oc2ccc(NCc3cccc(Br)c3)nc2)CCC1=O] |

TABLE 1-continued

Compounds of the Invention

| CMPD No. | Structure |
|---|---|
| 269 | 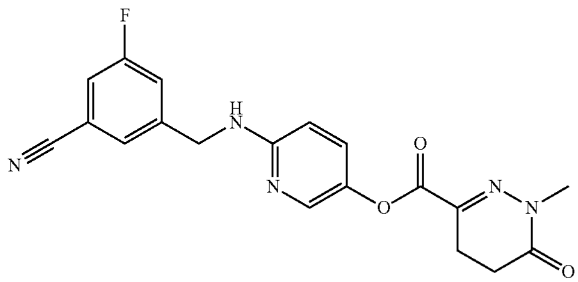 [SMILES: CN1N=C(C(=O)Oc2ccc(NCc3cc(F)cc(C#N)c3)nc2)CCC1=O] |
| 270 | 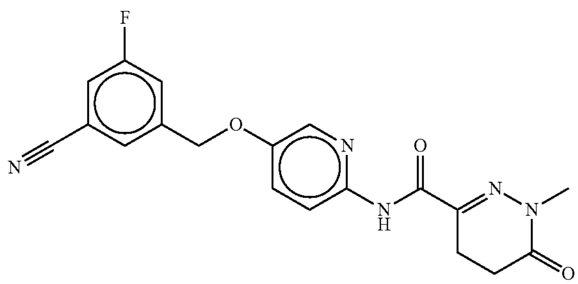 |
| 271 | 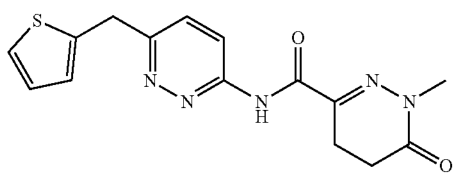 [SMILES: CN1N=C(C(=O)Nc2ccc(Cc3cccs3)nn2)CCC1=O] |
| 272 | 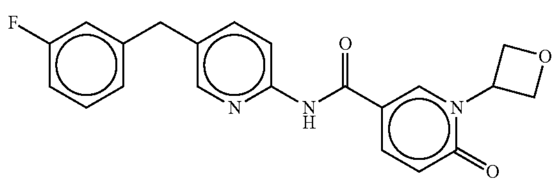 |
| 273 | 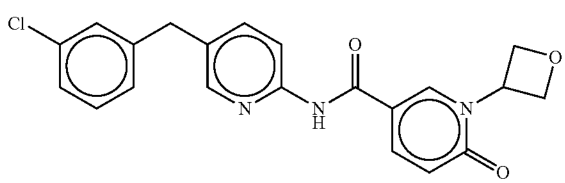 |
| 274 | 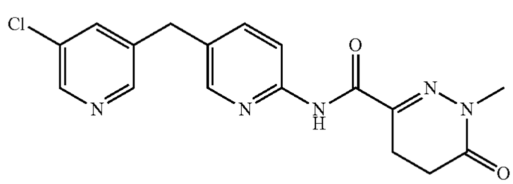 [SMILES: CN1N=C(C(=O)Nc2ccc(Cc3cncc(Cl)c3)cn2)CCC1=O] |
| 275 | 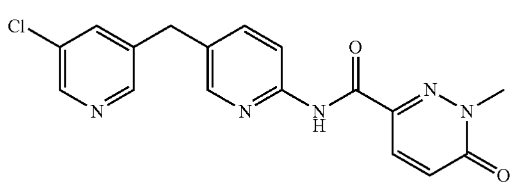 [SMILES: Cn1nc(C(=O)Nc2ccc(Cc3cncc(Cl)c3)cn2)ccc1=O] |

TABLE 1-continued

Compounds of the Invention

| CMPD No. | Structure |
|---|---|
| 276 | 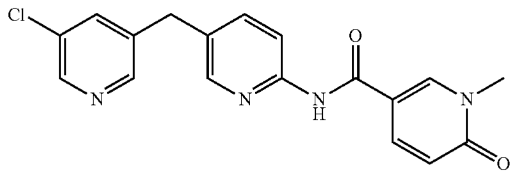 |
| 277 | 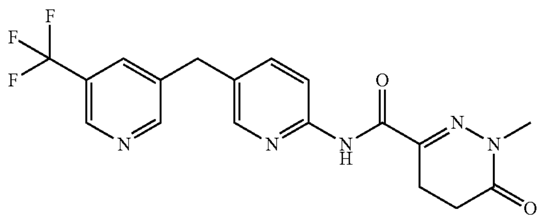 |
| 278 | 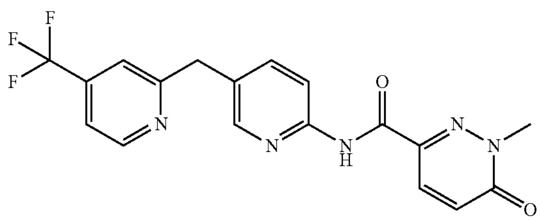 [SMILES: Cn1nc(C(=O)Nc2ccc(Cc3cc(C(F)(F)F)ccn3)cn2)ccc1=O] |
| 279 | 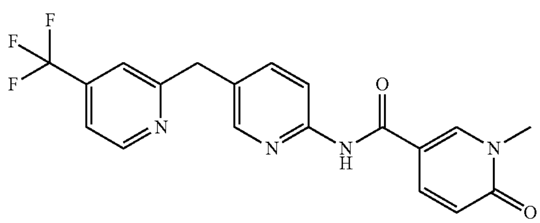 [SMILES: Cn1cc(C(=O)Nc2ccc(Cc3cc(C(F)(F)F)ccn3)cn2)ccc1=O] |
| 280 | 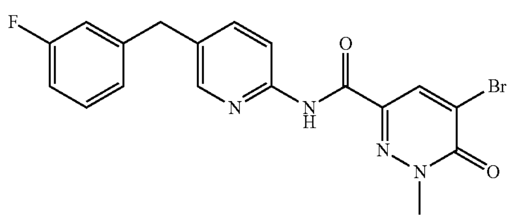 [SMILES: Cn1nc(C(=O)Nc2ccc(Cc3cccc(F)c3)cn2)cc(Br)c1=O] |
| 281 | 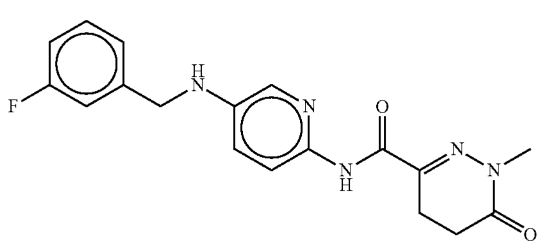 |
| 282 | 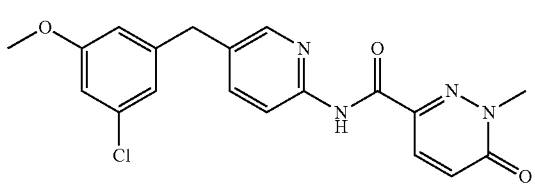 [SMILES: COc1cc(Cl)cc(Cc2ccc(NC(=O)c3ccc(=O)n(C)n3)nc2)c1] |

TABLE 1-continued
Compounds of the Invention
| CMPD No. | Structure |
|---|---|
| 283 | 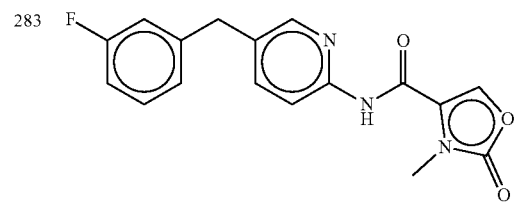 |
| 284 | 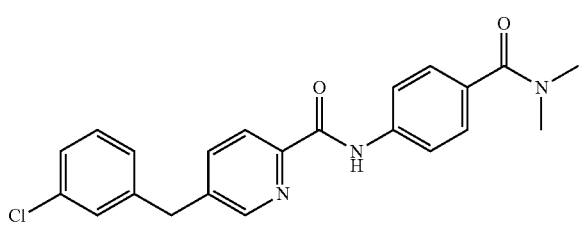 [SMILES: CN(C)C(=O)c1ccc(NC(=O)c2ccc(Cc3cccc(Cl)c3)cn2)cc1] |
| 285 | 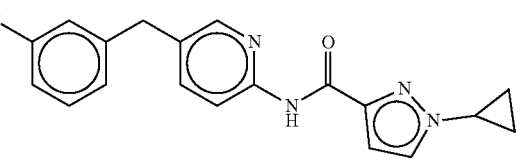 |
| 286 | 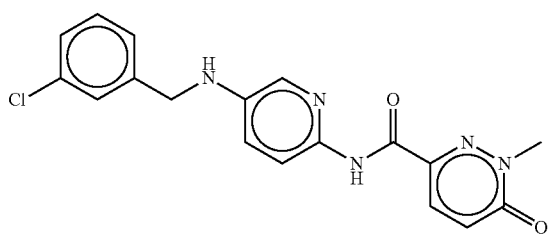 |
| 287 | 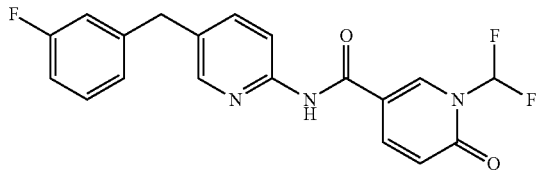 [SMILES: O=C(Nc1ccc(Cc2cccc(F)c2)cn1)c1ccc(=O)n(C(F)F)c1] |
| 288 | 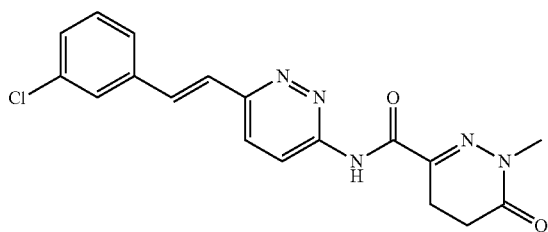 [SMILES: CN1N=C(C(=O)Nc2ccc(/C=C/c3cccc(Cl)c3)nn2)CCC1=O] |
| 289 | 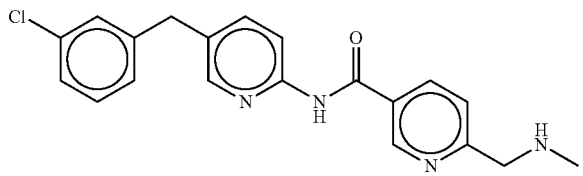 |

TABLE 1-continued
Compounds of the Invention
| CMPD No. | Structure |
|---|---|
| 290 | 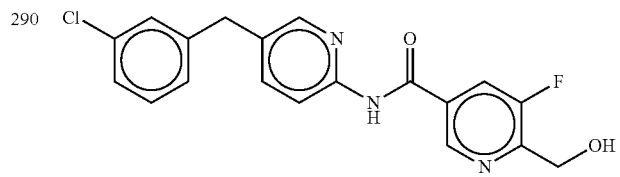 |
| 291 | 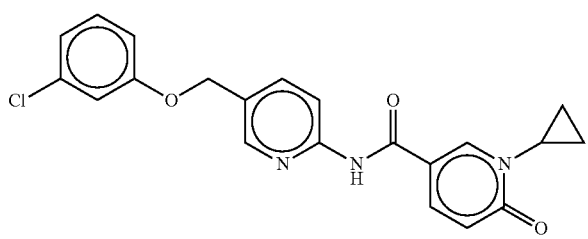 |
| 292 | 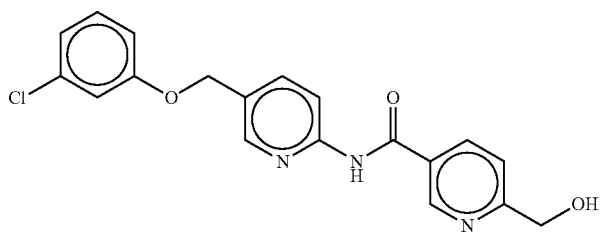 |
| 293 | 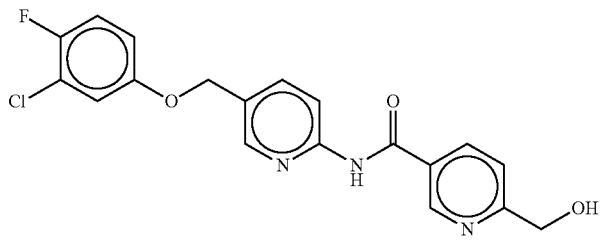 |
| 294 | 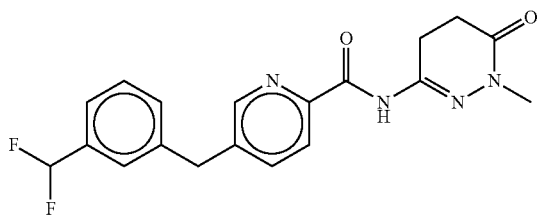 |
| 295 | 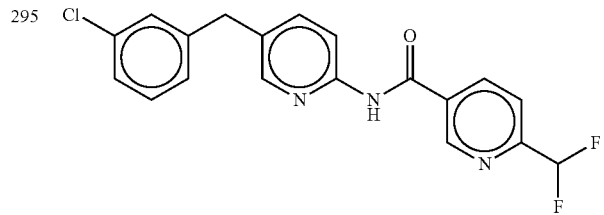 |

TABLE 1-continued
Compounds of the Invention
| CMPD No. | Structure |
|---|---|
| 296 | 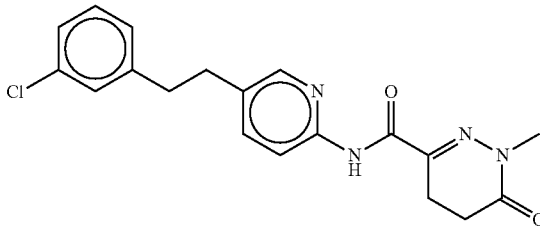 |
| 297 | 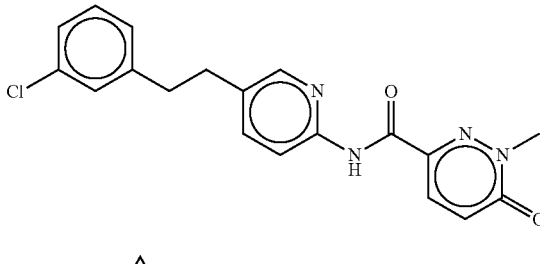 |
| 298 | 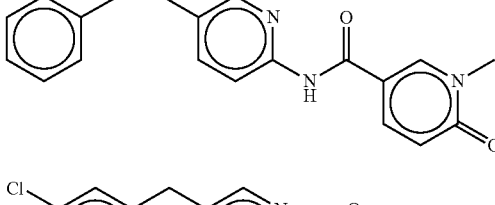 |
| 299 | 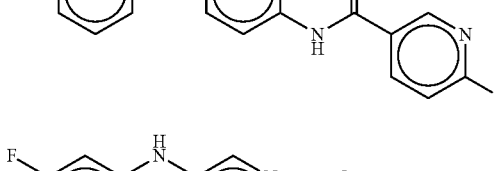 |
| 300 | 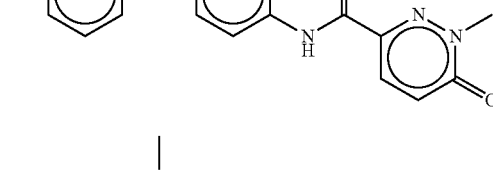 |
| 301 | 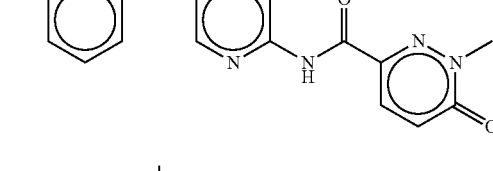 |
| 302 | 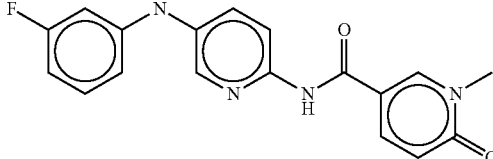 |

151

TABLE 1-continued

Compounds of the Invention

| CMPD No. | Structure |
|---|---|
| 303 | (3-chlorophenyl)amino-pyridin-2-yl-NH-C(O)-(1-cyclopropyl-6-oxo-pyridazin-3-yl) |
| 304 | (3-fluorophenyl)amino-pyridin-2-yl-NH-C(O)-(1-cyclopropyl-6-oxo-pyridazin-3-yl) |
| 305 | 4-(3-chlorophenoxy)piperidine-1-carboxamide-N-(1-methyl-6-oxo-pyridin-3-yl) |
| 306 | 4-(3-chlorophenoxy)piperidine-1-carboxylate-(1-methyl-6-oxo-pyridin-3-yl) |
| 307 | 4-(3-chlorophenoxy)piperidine-1-carboxylate-(1-methyl-6-oxo-pyridazin-3-yl) |
| 308 | 4-(3-chlorobenzyl)piperidine-1-carboxamide-N-(1-methyl-6-oxo-pyridin-3-yl) |
| 309 | 4-(3-chlorobenzyl)piperidine-1-carboxamide-N-(1-methyl-6-oxo-pyridazin-3-yl) |
| 310 | 5-(3,5-difluorobenzyl)pyridine-2-carboxamide-N-(1-methyl-6-oxo-pyridazin-3-yl) |

TABLE 1-continued

Compounds of the Invention

| CMPD No. | Structure |
|---|---|
| 311 | *(structure)* |
| 312 | *(structure)* |
| 313 | *(structure)* |
| 314 | *(structure)* |
| 315 | *(structure)* |
| 316 | *(structure)* |
| 317 | *(structure)* |
| 318 | *(structure)* |

TABLE 1-continued

Compounds of the Invention

| CMPD No. | Structure |
|---|---|
| 319 | 3-chlorobenzyl-pyridinyl-N-H-C(O)-pyridine(F)(Cl) |
| 320 | 3-chlorobenzyl-pyridinyl-N-H-C(O)-pyridinyl-C(=CH2)-OEt |
| 321 | cyclohexylmethyl-pyridinyl-N-H-C(O)-pyridinyl-CH2OH |
| 322 | 3-chlorobenzyl-cyclohexyl-NH-C(O)-NH-(1-methyl-6-oxo-pyridazinyl) |
| 323 | (4-F,3-Cl)-benzyl-pyridinyl-N-H-C(O)-(1-methyl-5-hydroxy-pyrazol-3-yl) |
| 324 | (3,4-diF)-benzyl-pyridinyl-N-H-C(O)-(1-methyl-5-hydroxy-pyrazol-3-yl) |
| 325 | (3,5-diF)-benzyl-pyridinyl-N-H-C(O)-(1-methyl-5-hydroxy-pyrazol-3-yl) |
| 326 | cyclohexylmethyl-pyridinyl-N-H-C(O)-(1-ethyl-6-oxo-pyridinyl) |

TABLE 1-continued
Compounds of the Invention
| CMPD No. | Structure |
|---|---|
| 327 | 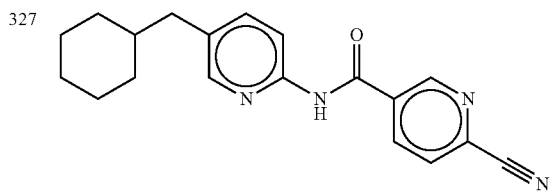 |
| 328 | 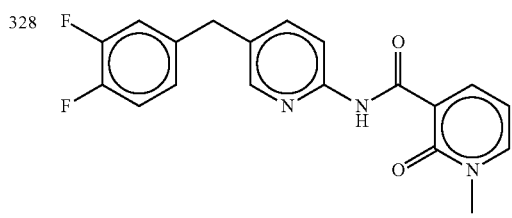 |
| 329 | 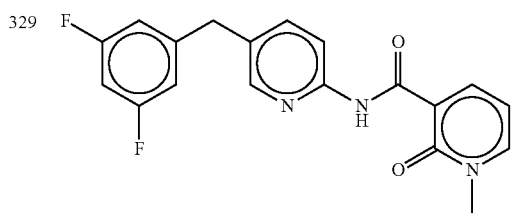 |
| 330 | 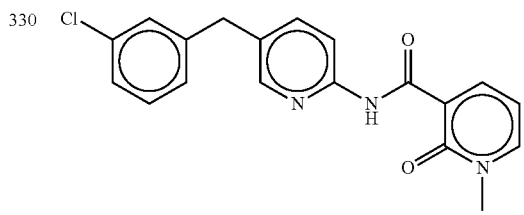 |
| 331 | 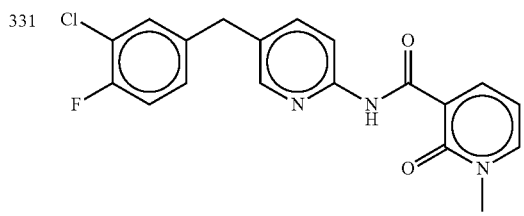 |
| 332 | 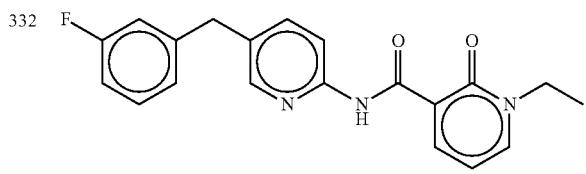 |
| 333 | 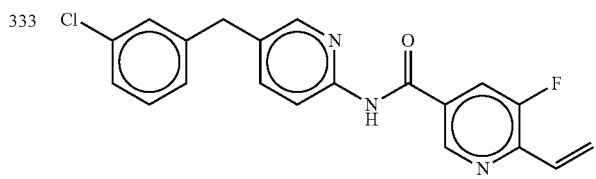 |

TABLE 1-continued
Compounds of the Invention
| CMPD No. | Structure |
|---|---|
| 334 | 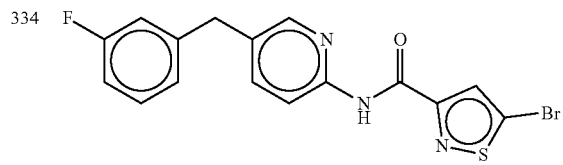 |
| 335 | 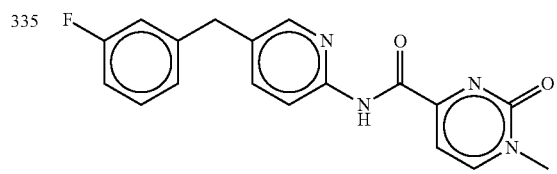 |
| 336 | 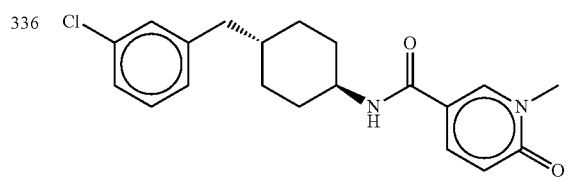 |
| 337 | 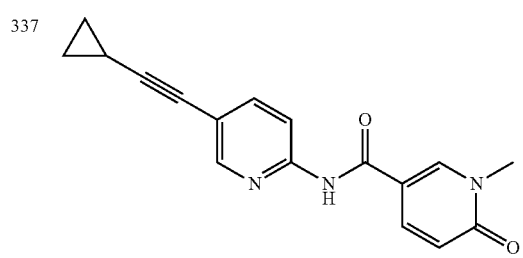 |
| 338 | 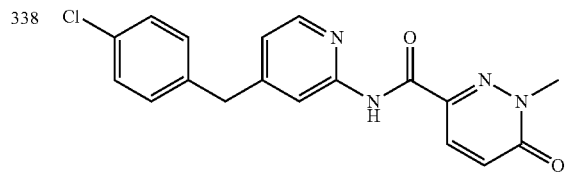 |
| 339 | 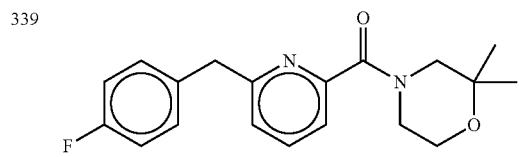 |
| 340 | 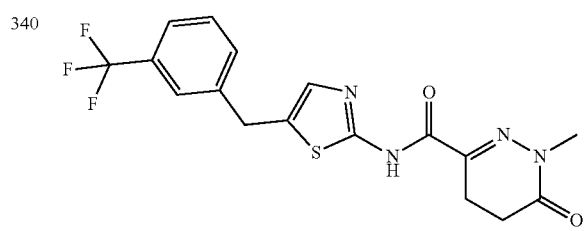 |

TABLE 1-continued
Compounds of the Invention
| CMPD No. | Structure |
|---|---|
| 341 | 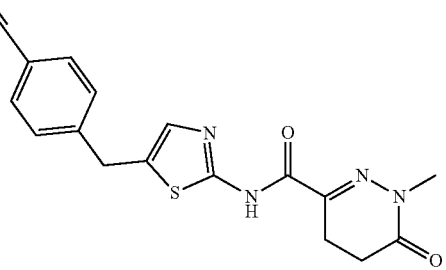 |
| 342 | 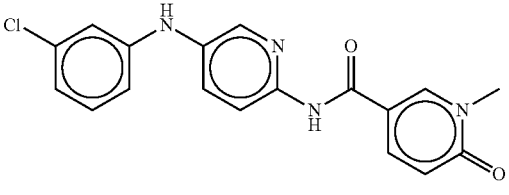 |
| 343 | 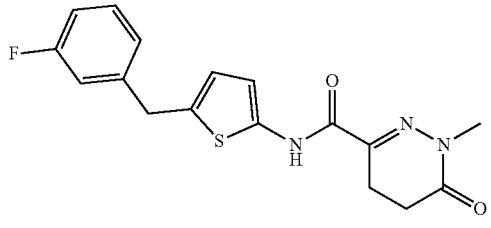 [SMILES: CN1N=C(C(=O)Nc2ccc(Cc3cccc(F)c3)s2)CCC1=O] |
| 344 | 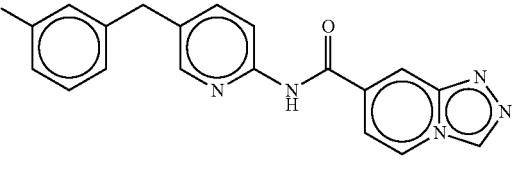 |
| 345 | 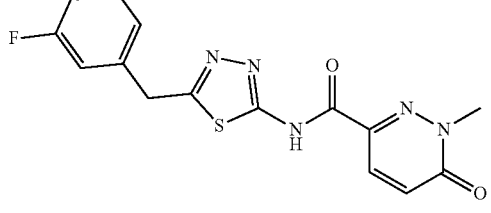 |
| 346 | 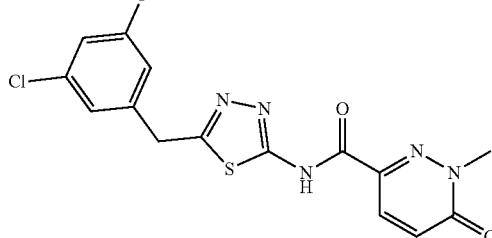 |

TABLE 1-continued
Compounds of the Invention
| CMPD No. | Structure |
|---|---|
| 347 | 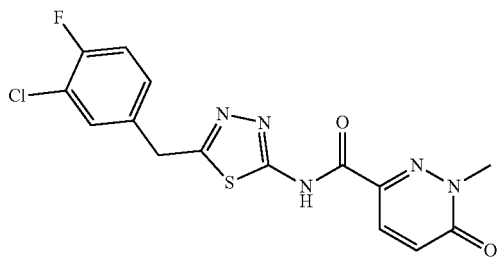 [SMILES: Cn1nc(C(=O)Nc2nnc(Cc3ccc(F)c(Cl)c3)s2)ccc1=O] |
| 348 | 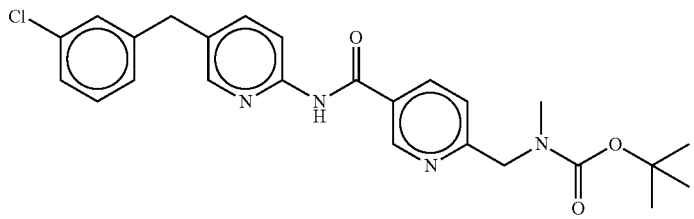 |
| 349 | 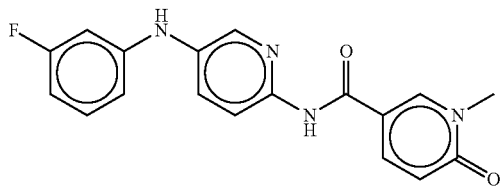 |
| 350 | 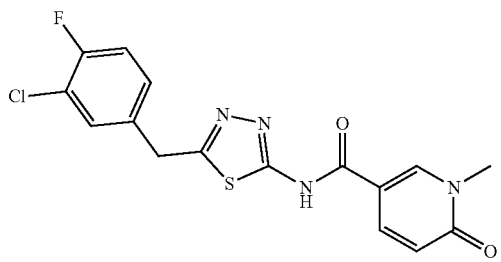 |
| 351 | 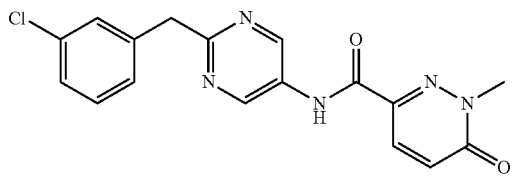 [SMILES: Cn1nc(C(=O)Nc2cnc(Cc3cccc(Cl)c3)nc2)ccc1=O] |
| 352 | 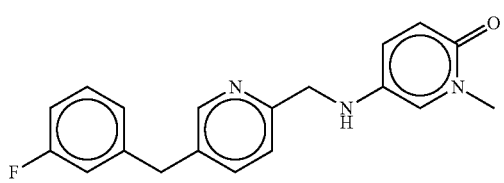 |

TABLE 1-continued
Compounds of the Invention
| CMPD No. | Structure |
|---|---|
| 353 | 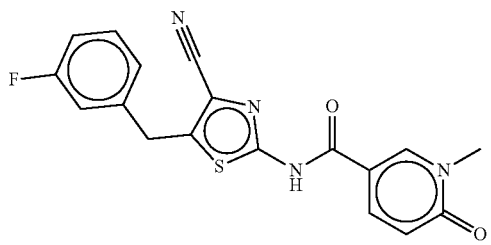 |
| 354 | 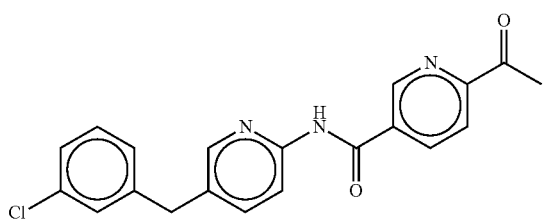 |
| 355 | 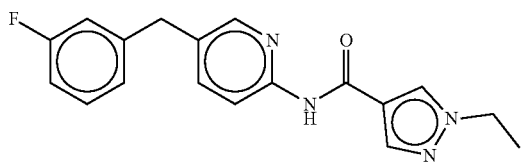 |
| 356 | 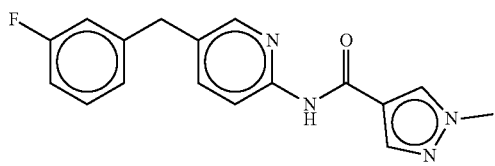 |
| 357 | 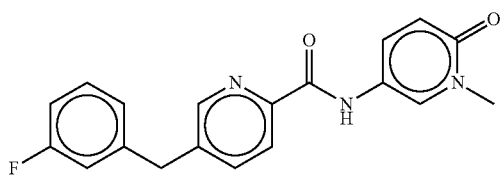 |
| 358 | 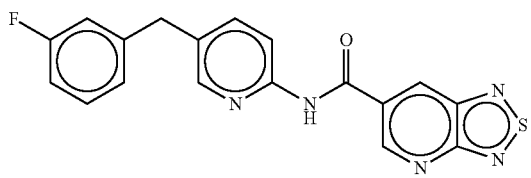 |
| 359 | 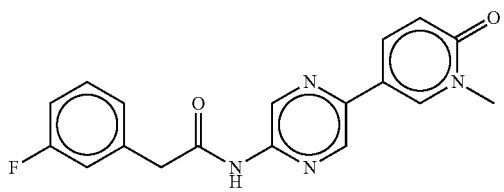 |

TABLE 1-continued
Compounds of the Invention
| CMPD No. | Structure |
|---|---|
| 360 | 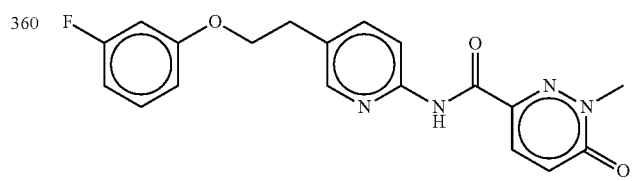 |
| 361 | 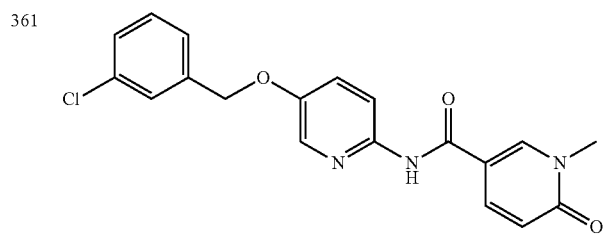 |
| 362 | 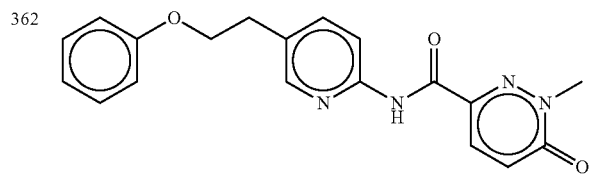 |
| 363 | 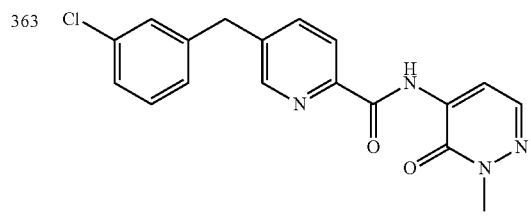 |
| 364 | 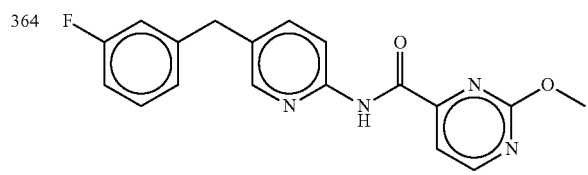 |
| 365 | 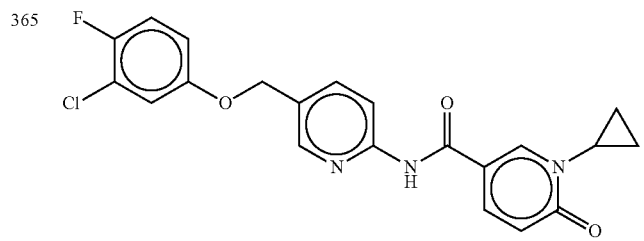 |
| 366 | 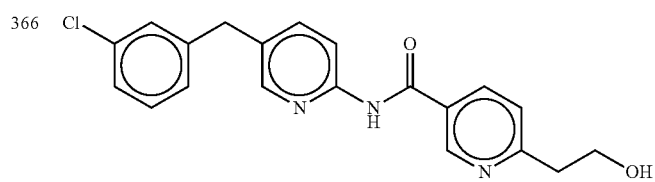 |

TABLE 1-continued
Compounds of the Invention
| CMPD No. | Structure |
|---|---|
| 367 | 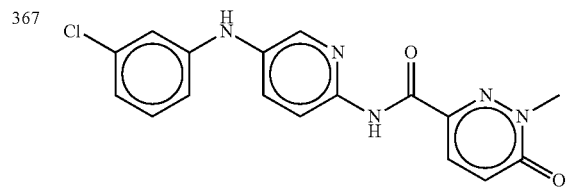 |
| 368 | 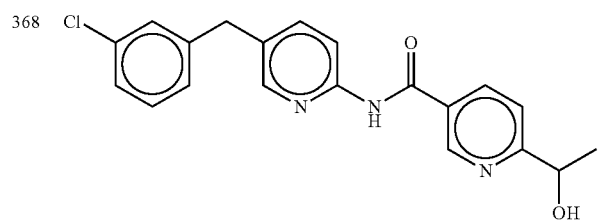 |
| 369 | 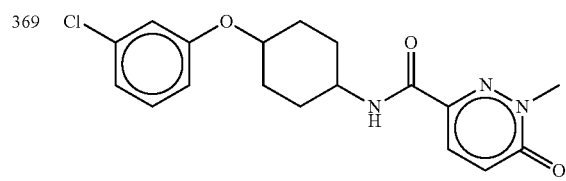 |
| 370 | 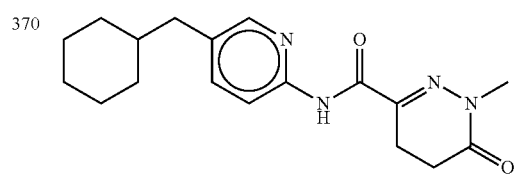 |
| 371 | 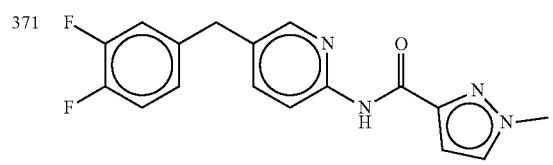 |
| 372 | 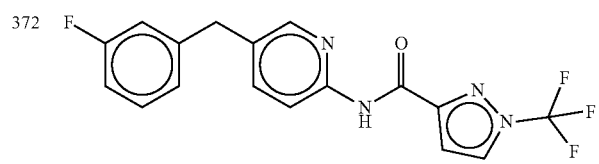 |
| 373 | 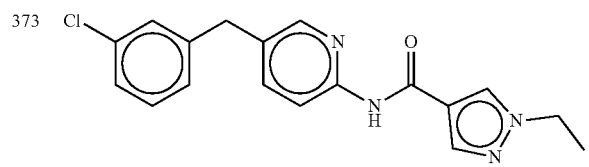 |
| 374 | 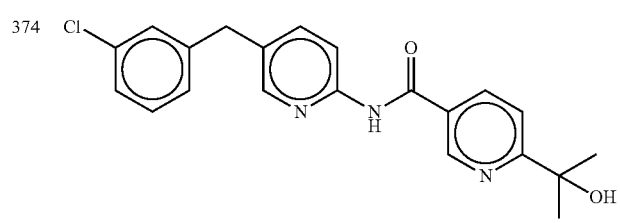 |

171
172
TABLE 1-continued
Compounds of the Invention
| CMPD No. | Structure |
|---|---|
| 375 | 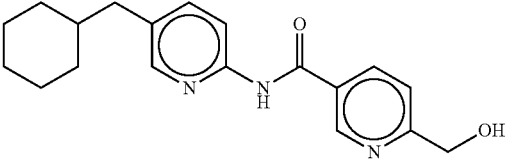 |
| 376 | 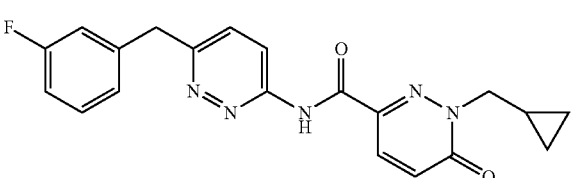 |
| 377 | 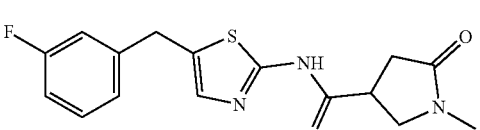 |
| 378 | 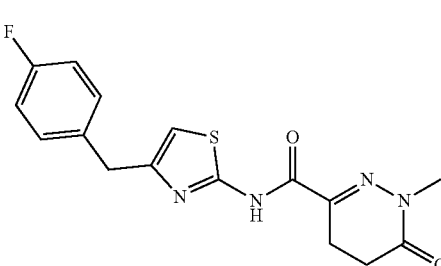 |
| 379 | 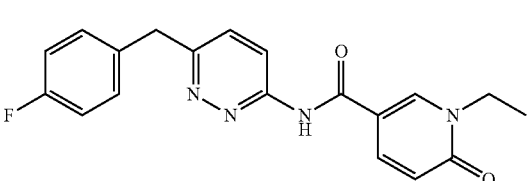 |
| 380 | 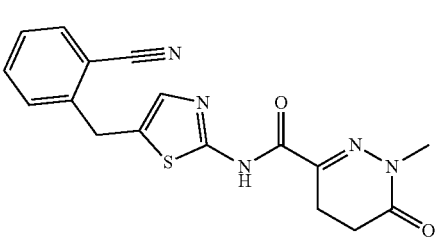 [SMILES: CN1N=C(C(=O)Nc2ncc(Cc3ccccc3C#N)s2)CCC1=O] |
| 381 | 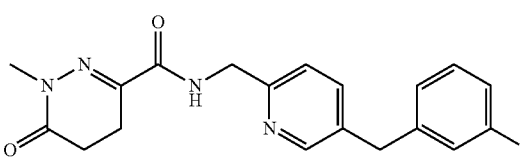 |
| 382 | 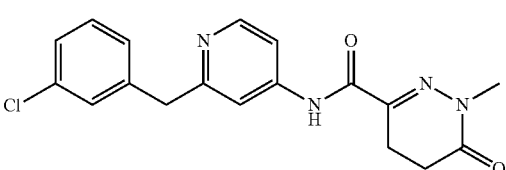 |

TABLE 1-continued

Compounds of the Invention

| CMPD No. | Structure |
|---|---|
| 383 | 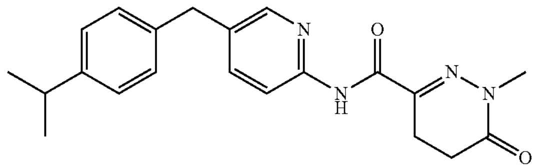 [SMILES: CC(C)c1ccc(Cc2ccc(NC(=O)C3=NN(C)C(=O)CC3)nc2)cc1] |
| 384 | 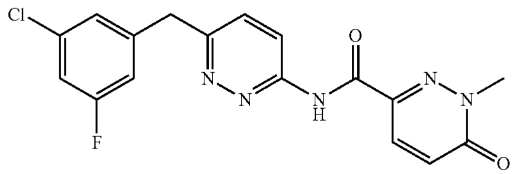 [SMILES: Cn1nc(C(=O)Nc2ccc(Cc3cc(F)cc(Cl)c3)nn2)ccc1=O] |
| 385 | 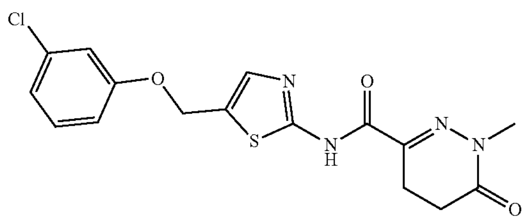 [SMILES: CN1N=C(C(=O)Nc2ncc(COc3cccc(Cl)c3)s2)CCC1=O] |
| 386 | 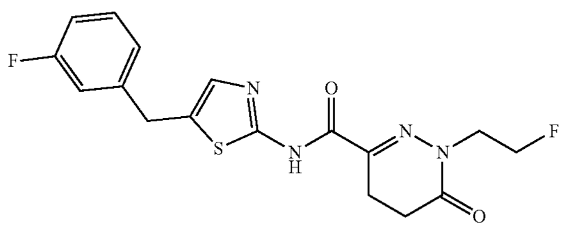 [SMILES: O=C(Nc1ncc(Cc2cccc(F)c2)s1)C1=NN(CCF)C(=O)CC1] |
| 387 | 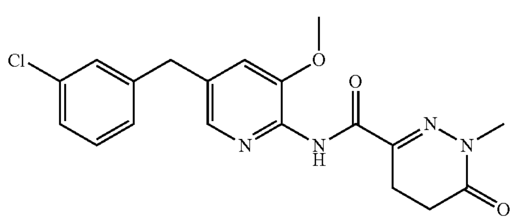 [SMILES: COc1cc(Cc2cccc(Cl)c2)cnc1NC(=O)C1=NN(C)C(=O)CC1] |
| 388 | 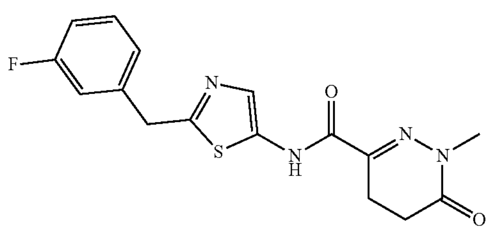 [SMILES: CN1N=C(C(=O)Nc2cnc(Cc3cccc(F)c3)s2)CCC1=O] |
| 389 | 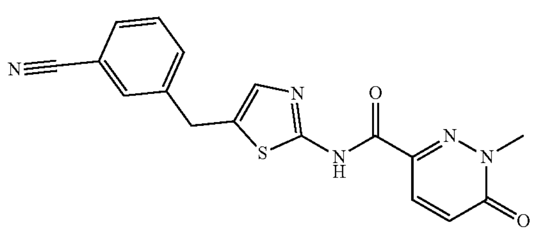 [SMILES: Cn1nc(C(=O)Nc2ncc(Cc3cccc(C#N)c3)s2)ccc1=O] |

TABLE 1-continued
Compounds of the Invention
| CMPD No. | Structure |
|---|---|
| 390 | 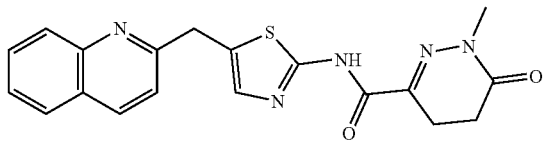 [SMILES: CN1N=C(C(=O)Nc2ncc(Cc3ccc4ccccc4n3)s2)CCC1=O] |
| 391 | 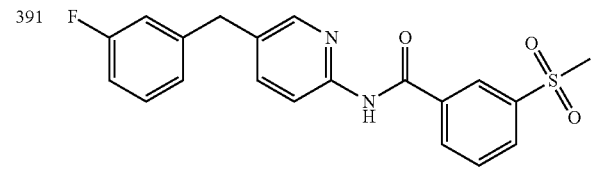 |
| 392 | 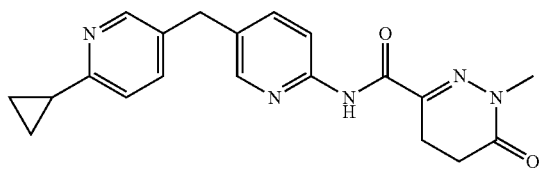 [SMILES: CN1N=C(C(=O)Nc2ccc(Cc3ccc(C4CC4)nc3)cn2)CCC1=O] |
| 393 | 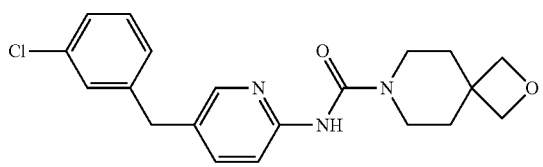 [SMILES: O=C(Nc1ccc(Cc2cccc(Cl)c2)cn1)N1CCC2(CC1)COC2] |
| 394 | 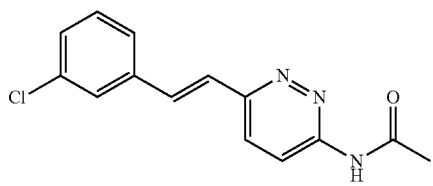 [SMILES: CC(=O)Nc1ccc(/C=C/c2cccc(Cl)c2)nn1] |
| 395 | 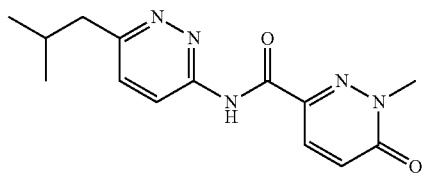 [SMILES: CC(C)Cc1ccc(NC(=O)c2ccc(=O)n(C)n2)nn1] |
| 396 | 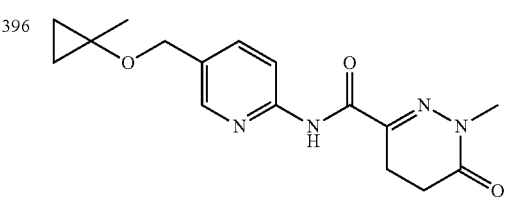 |
| 397 | 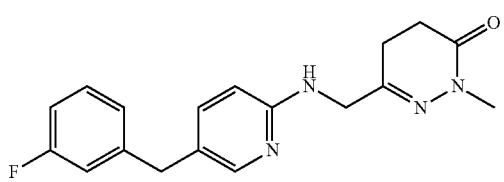 [SMILES: CN1N=C(CNc2ccc(Cc3cccc(F)c3)cn2)CCC1=O] |

TABLE 1-continued
Compounds of the Invention
| CMPD No. | Structure |
|---|---|
| 398 | 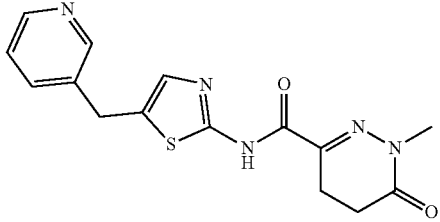 [SMILES: CN1N=C(C(=O)Nc2ncc(Cc3cccnc3)s2)CCC1=O] |
| 399 | 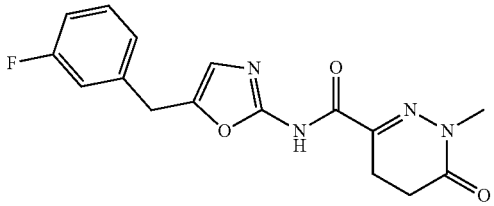 [SMILES: CN1N=C(C(=O)Nc2ncc(Cc3cccc(F)c3)o2)CCC1=O] |
| 400 | 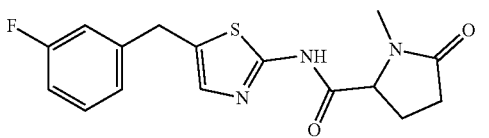 [SMILES: CN1C(=O)CCC1C(=O)Nc1ncc(Cc2cccc(F)c2)s1] |
| 401 | 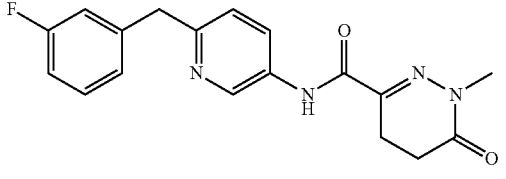 [SMILES: CN1N=C(C(=O)Nc2ccc(Cc3cccc(F)c3)nc2)CCC1=O] |
| 402 | 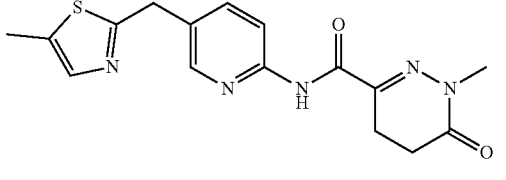 [SMILES: Cc1cnc(Cc2ccc(NC(=O)C3=NN(C)C(=O)CC3)nc2)s1] |
| 403 | 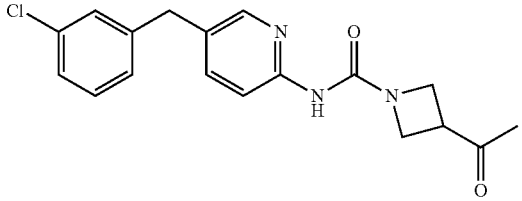 [SMILES: CC(=O)C1CN(C(=O)Nc2ccc(Cc3cccc(Cl)c3)cn2)C1] |
| 404 | 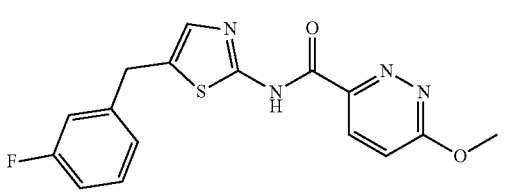 [SMILES: COc1ccc(C(=O)Nc2ncc(Cc3cccc(F)c3)s2)nn1] |

TABLE 1-continued

Compounds of the Invention

| CMPD No. | Structure |
|---|---|
| 405 | 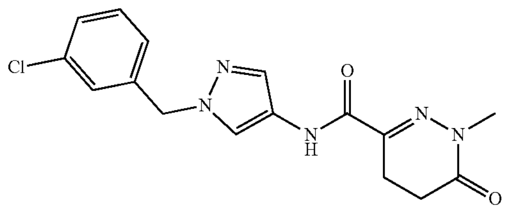 [SMILES: CN1N=C(C(=O)Nc2cnn(Cc3cccc(Cl)c3)c2)CCC1=O] |
| 406 | 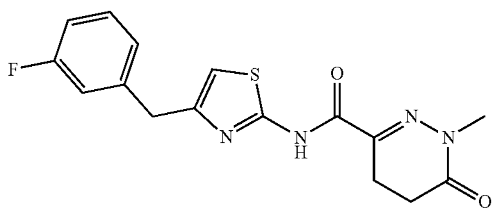 [SMILES: CN1N=C(C(=O)Nc2nc(Cc3cccc(F)c3)cs2)CCC1=O] |
| 407 | 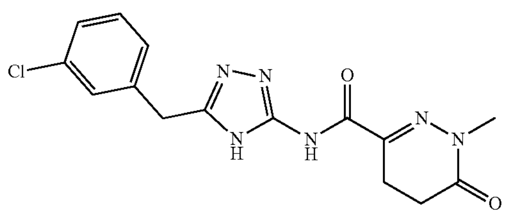 [SMILES: CN1N=C(C(=O)Nc2nnc(Cc3cccc(Cl)c3)[nH]2)CCC1=O] |
| 408 | 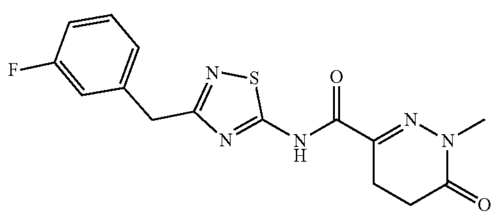 [SMILES: CN1N=C(C(=O)Nc2nc(Cc3cccc(F)c3)ns2)CCC1=O] |
| 409 | 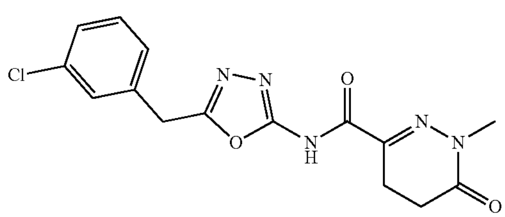 [SMILES: CN1N=C(C(=O)Nc2nnc(Cc3cccc(Cl)c3)o2)CCC1=O] |
| 410 | 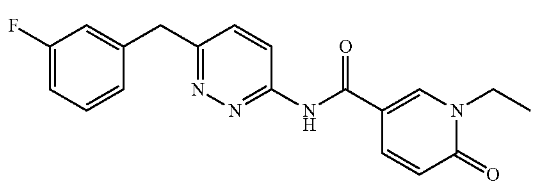 [SMILES: CCn1cc(C(=O)Nc2ccc(Cc3cccc(F)c3)nn2)ccc1=O] |
| 411 | 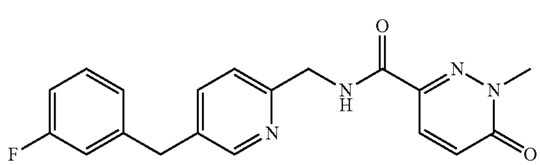 [SMILES: Cn1nc(C(=O)NCc2ccc(Cc3cccc(F)c3)cn2)ccc1=O] |

TABLE 1-continued

Compounds of the Invention

| CMPD No. | Structure |
|---|---|
| 412 | 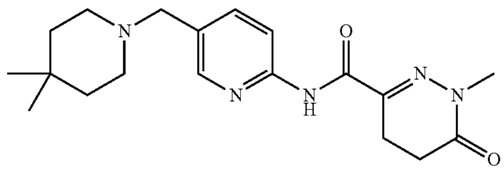 [SMILES: CN1N=C(C(=O)Nc2ccc(CN3CCC(C)(C)CC3)cn2)CCC1=O] |
| 413 | 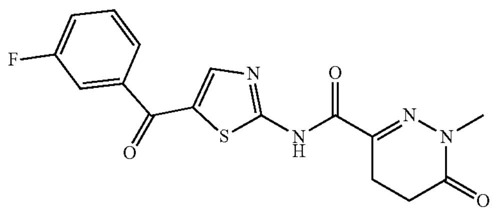 [SMILES: CN1N=C(C(=O)Nc2ncc(C(=O)c3cccc(F)c3)s2)CCC1=O] |
| 414 | 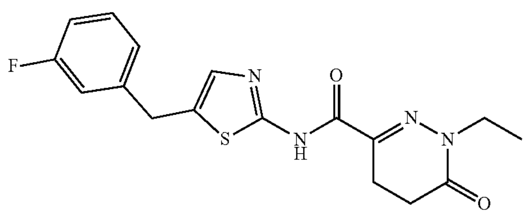 [SMILES: CCN1N=C(C(=O)Nc2ncc(Cc3cccc(F)c3)s2)CCC1=O] |
| 415 | 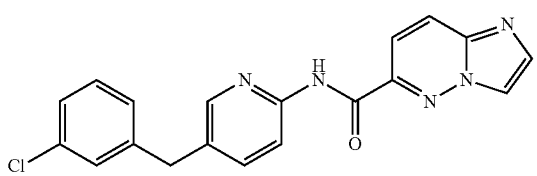 [SMILES: O=C(Nc1ccc(Cc2cccc(Cl)c2)cn1)c1ccc2nccn2n1] |
| 416 | 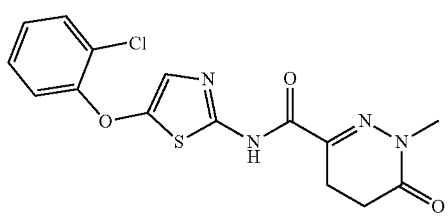 [SMILES: CN1N=C(C(=O)Nc2ncc(Oc3ccccc3Cl)s2)CCC1=O] |
| 417 | 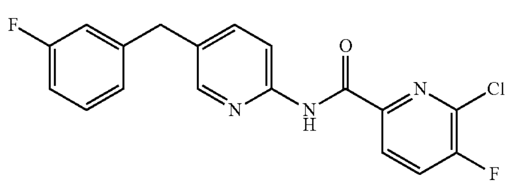 [SMILES: O=C(Nc1ccc(Cc2cccc(F)c2)cn1)c1ccc(F)c(Cl)n1] |
| 418 | 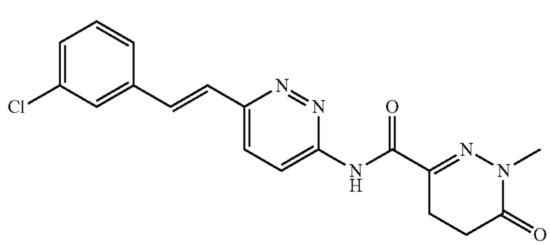 [SMILES: CN1N=C(C(=O)Nc2ccc(/C=C/c3cccc(Cl)c3)nn2)CCC1=O] |

TABLE 1-continued

Compounds of the Invention

| CMPD No. | Structure |
|---|---|
| 419 | 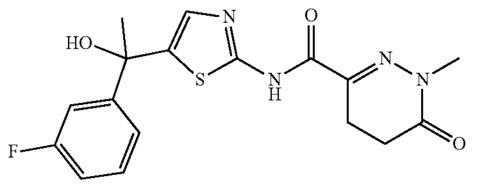 [SMILES: CN1N=C(C(=O)Nc2ncc(C(C)(O)c3cccc(F)c3)s2)CCC1=O] |
| 420 | 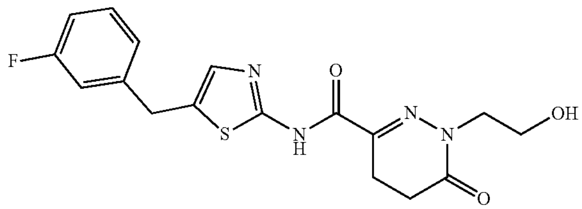 [SMILES: O=C(Nc1ncc(Cc2cccc(F)c2)s1)C1=NN(CCO)C(=O)CC1] |
| 421 | 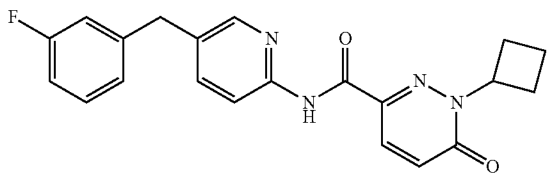 [SMILES: O=C(Nc1ccc(Cc2cccc(F)c2)cn1)c1ccc(=O)n(C2CCC2)n1] |
| 422 | 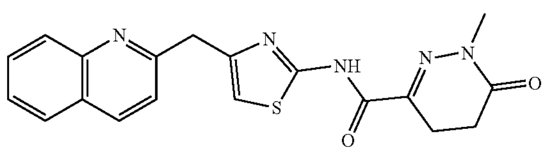 [SMILES: CN1N=C(C(=O)Nc2nc(Cc3ccc4ccccc4n3)cs2)CCC1=O] |
| 423 | 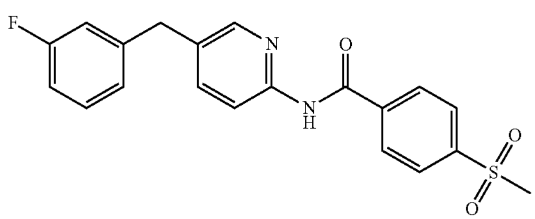 [SMILES: CS(=O)(=O)c1ccc(C(=O)Nc2ccc(Cc3cccc(F)c3)cn2)cc1] |
| 424 | 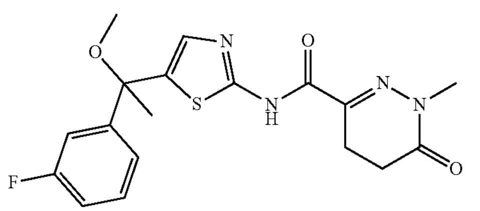 [SMILES: COC(C)(c1cccc(F)c1)c1cnc(NC(=O)C2=NN(C)C(=O)CC2)s1] |
| 425 | 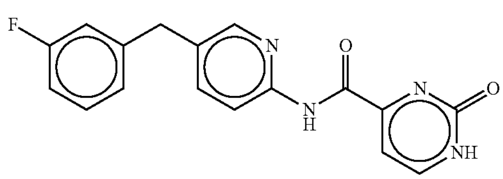 |
| 426 | 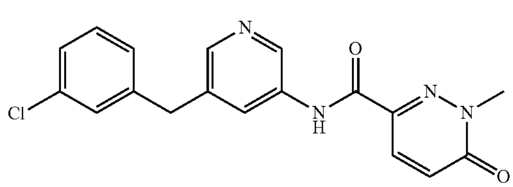 [SMILES: Cn1nc(C(=O)Nc2cncc(Cc3cccc(Cl)c3)c2)ccc1=O] |

TABLE 1-continued
Compounds of the Invention
| CMPD No. | Structure |
|---|---|
| 427 | 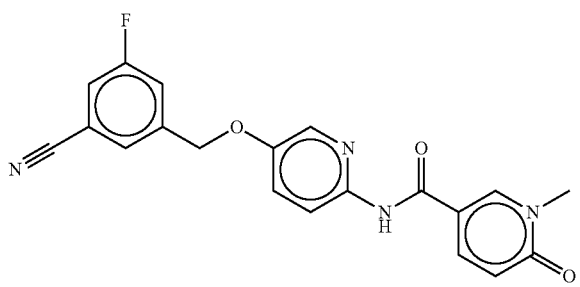 |
| 428 | 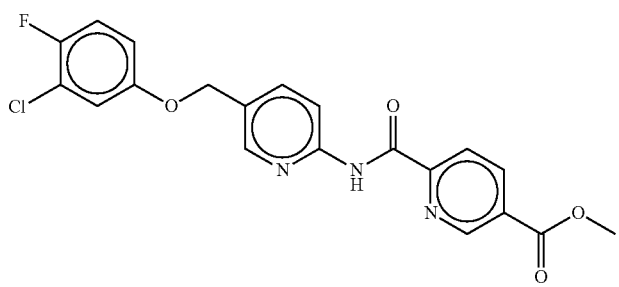 |
| 429 | 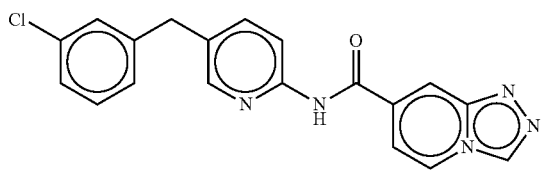 |
| 430 | 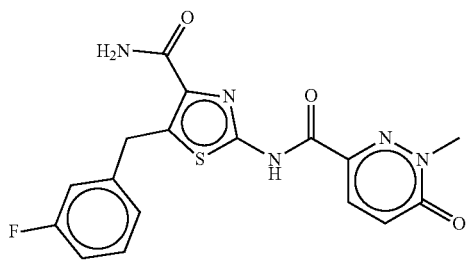 |
| 431 | 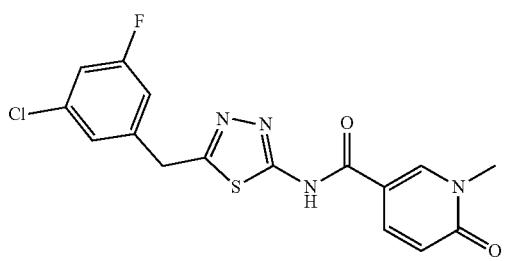 [SMILES: Cn1cc(C(=O)Nc2nnc(Cc3cc(F)cc(Cl)c3)s2)ccc1=O] |
| 432 | 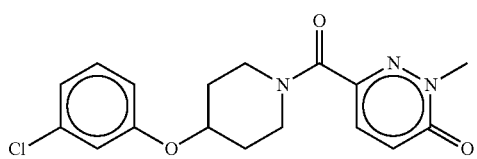 |

TABLE 1-continued

Compounds of the Invention

| CMPD No. | Structure |
|---|---|
| 433 | 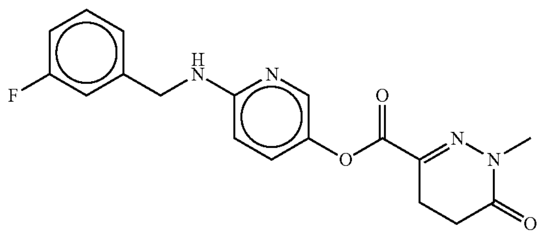 |
| 434 | 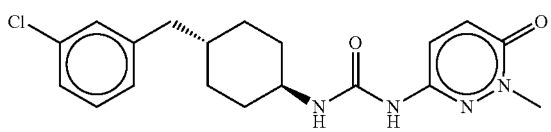 |
| 435 | 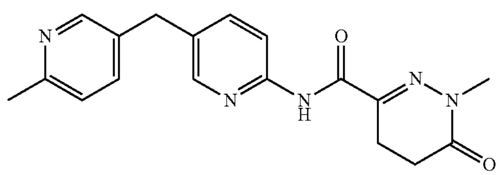 [SMILES: Cc1ccc(Cc2ccc(NC(=O)C3=NN(C)C(=O)CC3)nc2)cn1] |
| 436 | 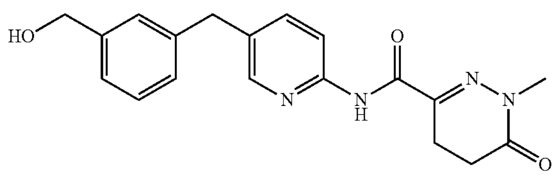 [SMILES: CN1N=C(C(=O)Nc2ccc(Cc3cccc(CO)c3)cn2)CCC1=O] |
| 437 | 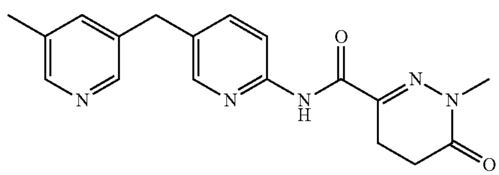 [SMILES: Cc1cncc(Cc2ccc(NC(=O)C3=NN(C)C(=O)CC3)nc2)c1] |
| 438 | 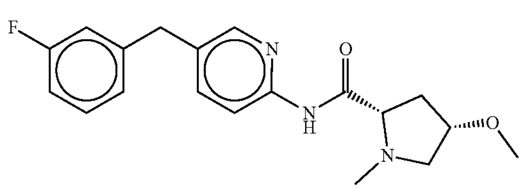 |
| 439 | 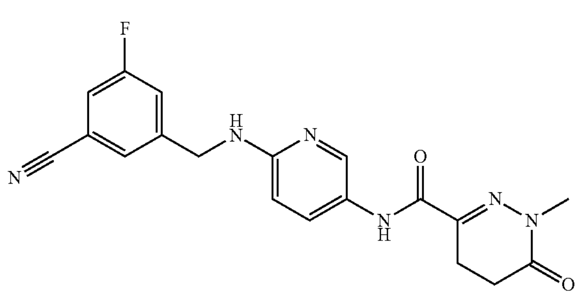 [SMILES: CN1N=C(C(=O)Nc2ccc(NCc3cc(F)cc(C#N)c3)nc2)CCC1=O] |

TABLE 1-continued
Compounds of the Invention
| CMPD No. | Structure |
|---|---|
| 440 | 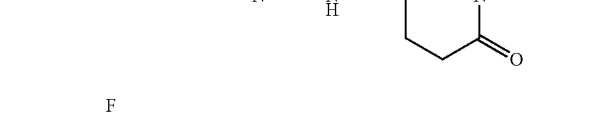 |
| 441 | 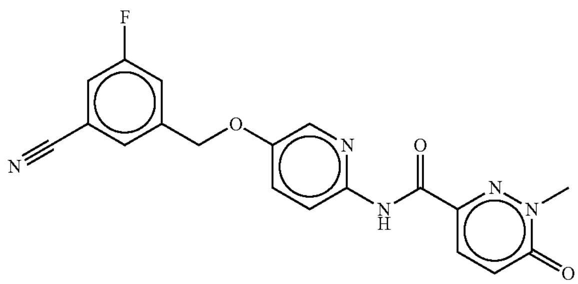 |
| 442 | 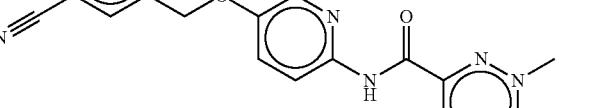 |
| 443 | 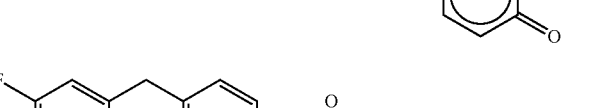 |
| 444 | 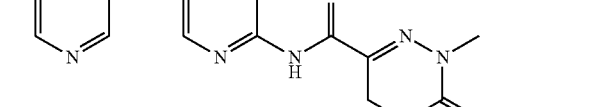 |
| 445 | 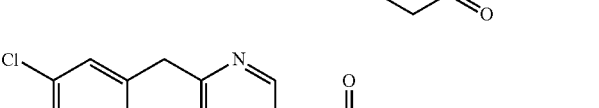 |
| 446 | 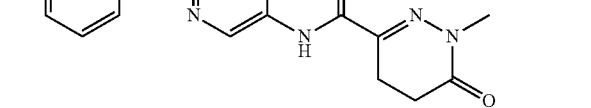 |

TABLE 1-continued

Compounds of the Invention

| CMPD No. | Structure |
|---|---|
| 447 | 3-fluorobenzyl-pyridine-carboxamide-(2S,4S)-4-methoxypyrrolidine |
| 448 | 5-(3-fluorobenzyl)-N-(5-fluoro-6-methylpyridine-2-carbonyl)pyridin-2-amine |
| 449 | 5-((6-methylpyridin-3-yl)methyl)-N-(1-methyl-6-oxo-1,6-dihydropyridine-3-carbonyl)pyridin-2-amine |
| 450 | 5-((5-methylpyridin-3-yl)methyl)-N-(1-methyl-6-oxo-1,6-dihydropyridine-3-carbonyl)pyridin-2-amine |
| 451 | 6-((5-(3-chlorobenzyl)pyridin-2-yl)carbamoyl)pyridazine-3-carboxylic acid |
| 452 | 5-((4-fluorophenoxy)methyl)-N-(1-methyl-6-oxo-1,6-dihydropyridine-3-carbonyl)pyridin-2-amine |
| 453 | 5-((5-fluoropyridin-3-yl)methyl)-N-(1-methyl-6-oxo-1,6-dihydropyridine-3-carbonyl)pyridin-2-amine |

TABLE 1-continued

Compounds of the Invention

| CMPD No. | Structure |
|---|---|
| 454 | 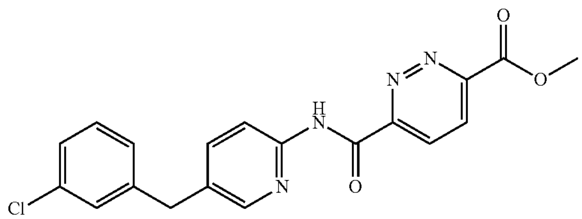 [SMILES: COC(=O)c1ccc(C(=O)Nc2ccc(Cc3cccc(Cl)c3)cn2)nn1] |
| 455 | 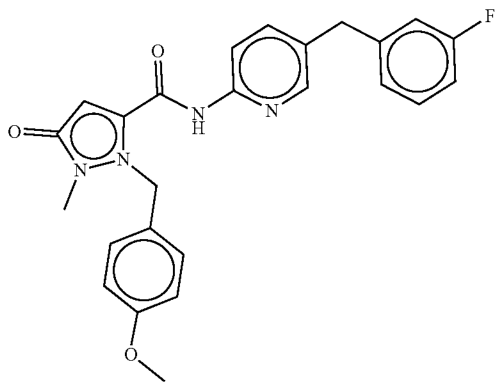 |
| 456 | 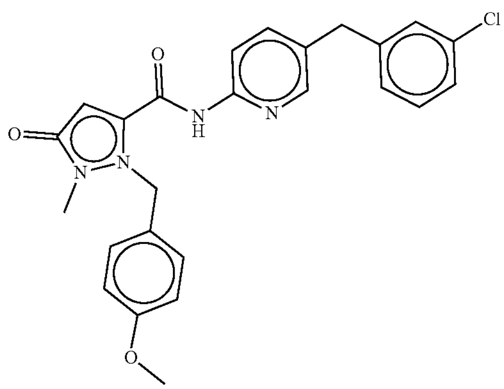 |
| 457 | 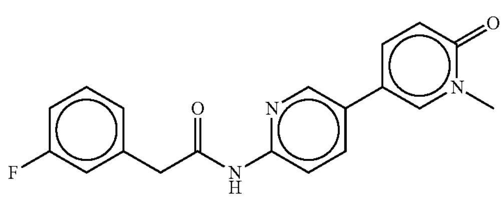 |
| 458 | 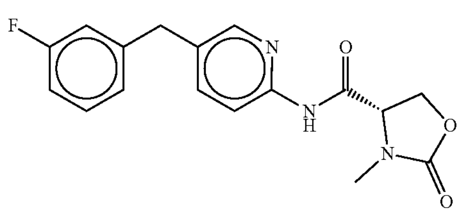 |

TABLE 1-continued

Compounds of the Invention

| CMPD No. | Structure |
|---|---|
| 459 | 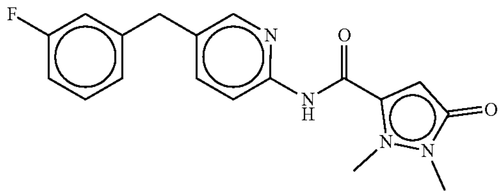 |
| 460 | 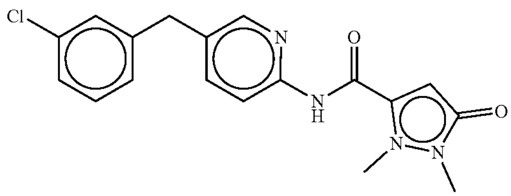 |
| 461 | 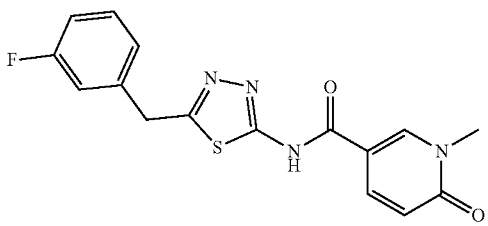 [SMILES: Cn1cc(C(=O)Nc2nnc(Cc3cccc(F)c3)s2)ccc1=O] |
| 462 | 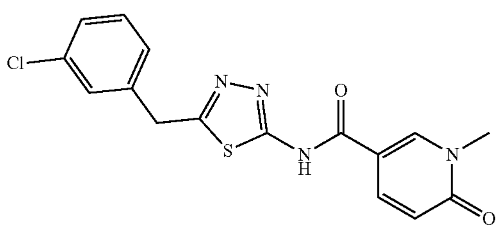 [SMILES: Cn1cc(C(=O)Nc2nnc(Cc3cccc(Cl)c3)s2)ccc1=O] |
| 463 | 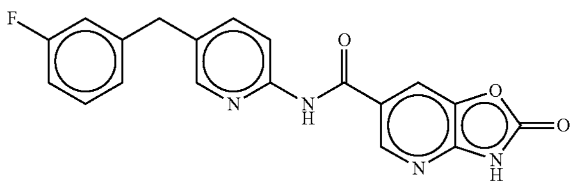 |
| 464 | 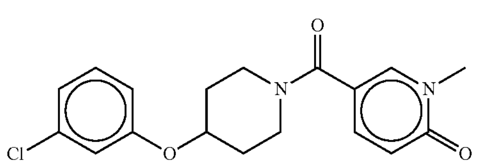 |
| 465 | 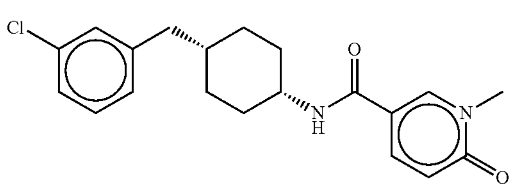 |

TABLE 1-continued
Compounds of the Invention
| CMPD No. | Structure |
|---|---|
| 466 | 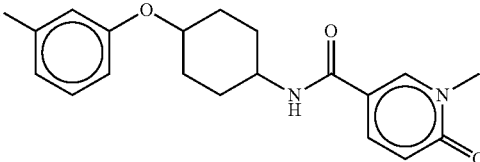 |
| 467 | 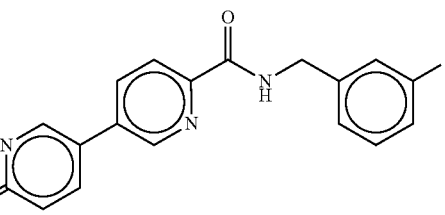 |
| 468 | 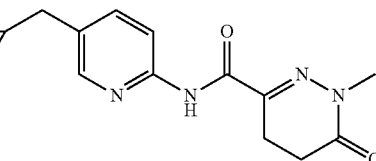 |
| 469 | 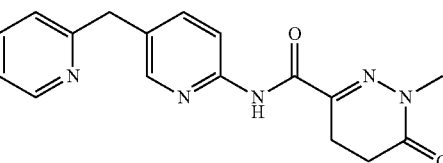 |
| 470 | 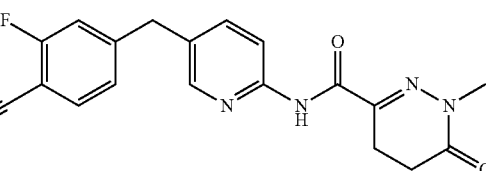 |
| 471 | 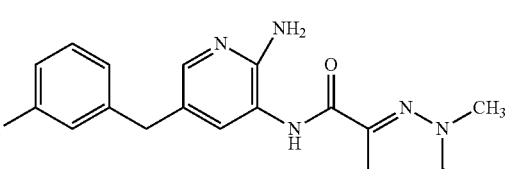 |
| 472 | 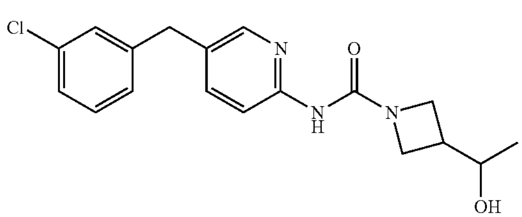 [SMILES: CC(O)C1CN(C(=O)Nc2ccc(Cc3cccc(Cl)c3)cn2)C1] |

TABLE 1-continued
Compounds of the Invention
| CMPD No. | Structure |
|---|---|
| 473 | 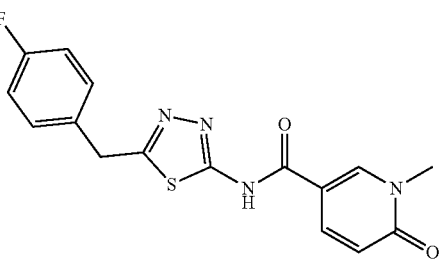 |
| 474 | 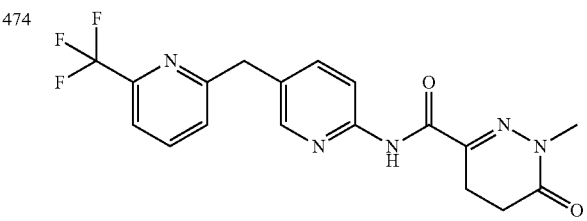 |
| 475 | 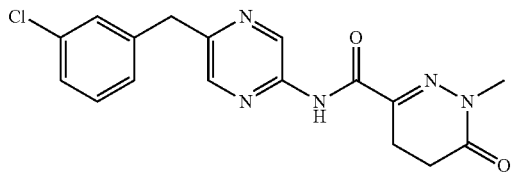 |
TABLE 2
Compounds of the Invention
| CMPD No. | Structure |
|---|---|
| 476 | 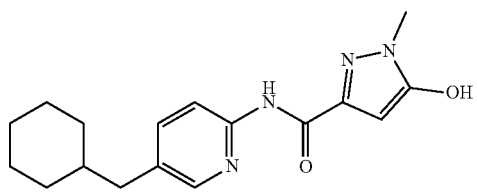 [SMILES: Cn1nc(C(=O)Nc2ccc(CC3CCCCC3)cn2)cc1O] |
| 477 | 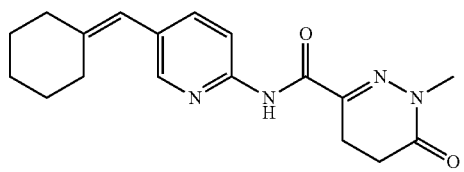 [SMILES: CN1N=C(C(=O)Nc2ccc(C=C3CCCCC3)cn2)CCC1=O] |
| 478 | 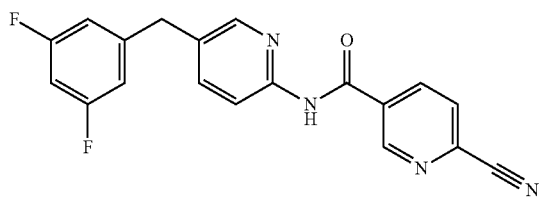 [SMILES: N#Cc1ccc(C(=O)Nc2ccc(Cc3cc(F)cc(F)c3)cn2)cn1] |

TABLE 2-continued

Compounds of the Invention

| CMPD No. | Structure |
|---|---|
| 479 | 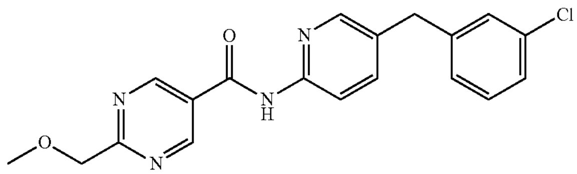 [SMILES: COCc1ncc(C(=O)Nc2ccc(Cc3cccc(Cl)c3)cn2)cn1] |
| 480 | 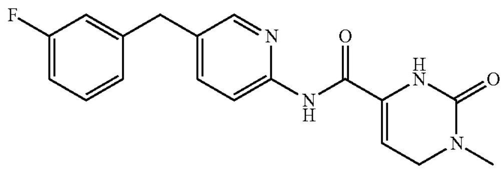 [SMILES: CN1CC=C(C(=O)Nc2ccc(Cc3cccc(F)c3)cn2)NC1=O] |
| 481 | 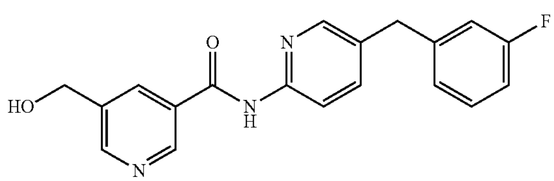 [SMILES: O=C(Nc1ccc(Cc2cccc(F)c2)cn1)c1cncc(CO)c1] |
| 482 | 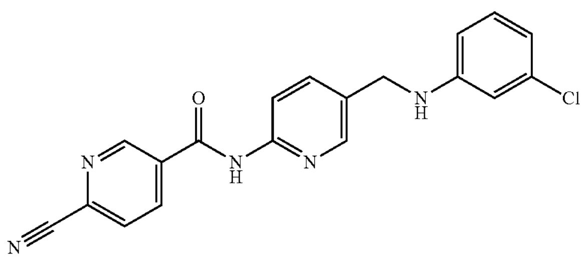 |
| 483 | 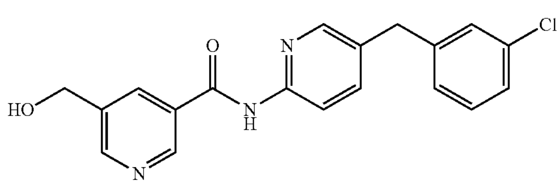 [SMILES: O=C(Nc1ccc(Cc2cccc(Cl)c2)cn1)c1cncc(CO)c1] |
| 484 | 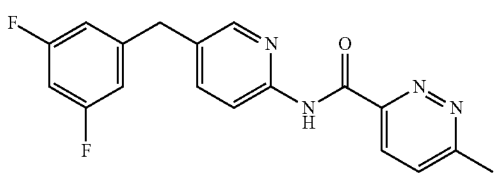 [SMILES: Cc1ccc(C(=O)Nc2ccc(Cc3cc(F)cc(F)c3)cn2)nn1] |
| 485 | 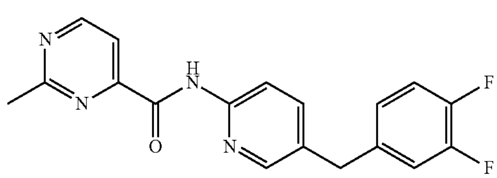 [SMILES: Cc1nccc(C(=O)Nc2ccc(Cc3ccc(F)c(F)c3)cn2)n1] |
| 486 | 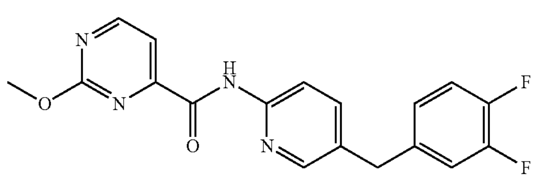 [SMILES: COc1nccc(C(=O)Nc2ccc(Cc3ccc(F)c(F)c3)cn2)n1] |

TABLE 2-continued

Compounds of the Invention

| CMPD No. | Structure |
|---|---|
| 487 | (3-chlorophenoxymethyl-pyridine-2-carboxamide linked to N-methyl-6-oxo-pyridin-3-yl) |
| 488 | (3-chloro-4-fluorophenoxymethyl-pyridine-2-carboxamide linked to N-methyl-6-oxo-pyridin-3-yl) |
| 489 | (1-ethyl-5-hydroxy-pyrazole-3-carboxamide linked to 5-(3-chlorobenzyl)pyridin-2-yl) |
| 490 | (5-bromopyrimidine-2-carboxamide linked to 5-(3-fluorobenzyl)pyridin-2-yl) |
| 491 | (6-(2-cyanopropan-2-yl)pyridine-3-carboxamide linked to 5-(3-chlorobenzyl)pyridin-2-yl) |
| 492 | (6-cyanopyridine-3-carboxamide linked to 5-((3-chlorophenoxy)methyl)pyridin-2-yl) |
| 493 | (5-(3,5-difluorobenzyl)pyridin-2-yl amide of 5-cyanopyridine-2-carboxamide) |

TABLE 2-continued
Compounds of the Invention
| CMPD No. | Structure |
|---|---|
| 494 | 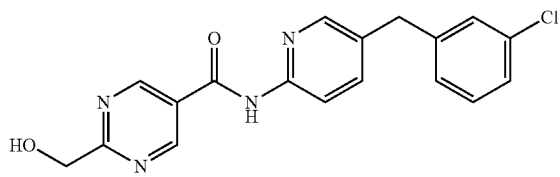 |
| 495 | 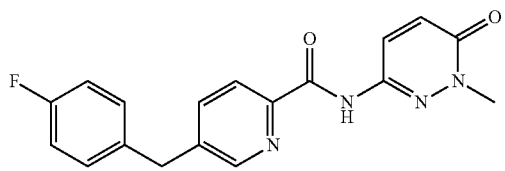 [SMILES: Cn1nc(NC(=O)c2ccc(Cc3ccc(F)cc3)cn2)ccc1=O] |
| 496 | 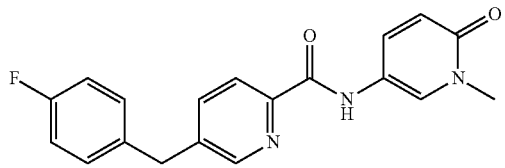 [SMILES: Cn1cc(NC(=O)c2ccc(Cc3ccc(F)cc3)cn2)ccc1=O] |
| 497 | 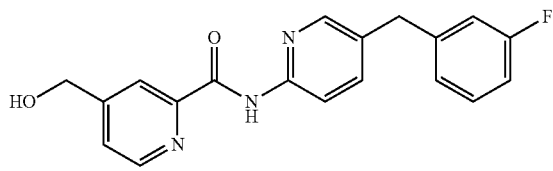 [SMILES: O=C(Nc1ccc(Cc2cccc(F)c2)cn1)c1cc(CO)ccn1] |
| 498 | 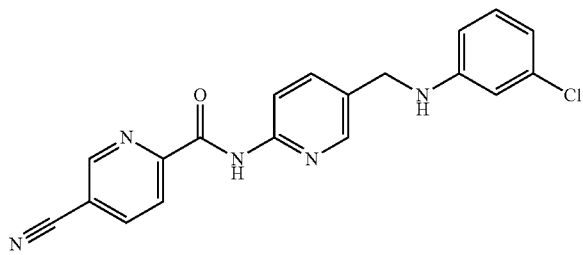 [SMILES: N#Cc1ccc(C(=O)Nc2ccc(CNc3cccc(Cl)c3)cn2)nc1] |
| 499 | 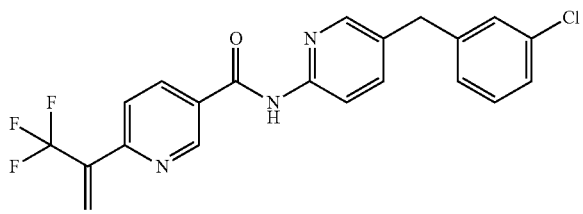 [SMILES: C=C(c1ccc(C(=O)Nc2ccc(Cc3cccc(Cl)c3)cn2)cn1)C(F)(F)F] |
| 500 | 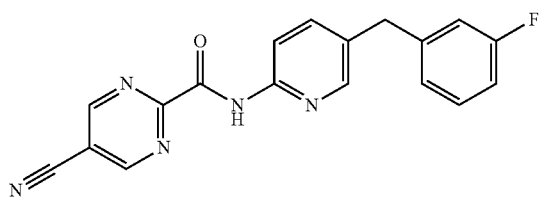 [SMILES: N#Cc1cnc(C(=O)Nc2ccc(Cc3cccc(F)c3)cn2)nc1] |

TABLE 2-continued
Compounds of the Invention
| CMPD No. | Structure |
|---|---|
| 501 | 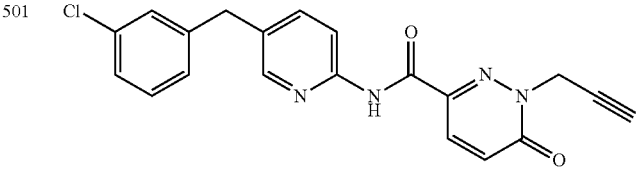 |
| 502 | 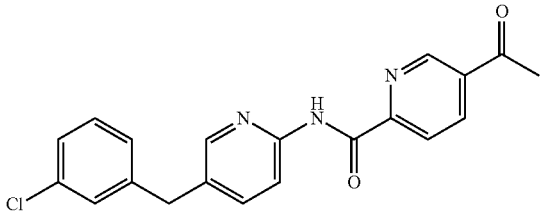 [SMILES: CC(=O)c1ccc(C(=O)Nc2ccc(Cc3cccc(Cl)c3)cn2)nc1] |
| 503 | 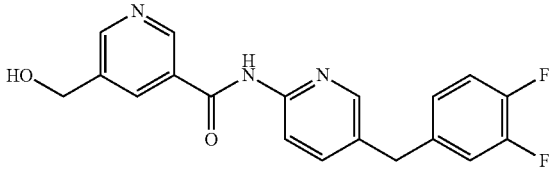 [SMILES: O=C(Nc1ccc(Cc2ccc(F)c(F)c2)cn1)c1cncc(CO)c1] |
| 504 | 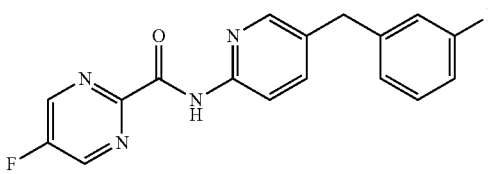 |
| 505 | 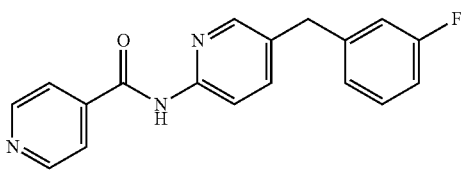 [SMILES: O=C(Nc1ccc(Cc2cccc(F)c2)cn1)c1ccncc1] |
| 506 | 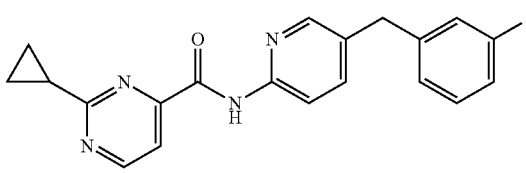 |
| 507 | 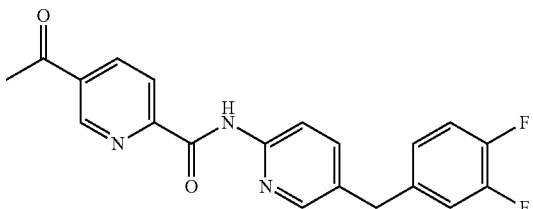 |
| 508 | 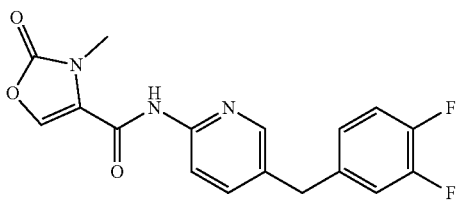 [SMILES: Cn1c(C(=O)Nc2ccc(Cc3ccc(F)c(F)c3)cn2)coc1=O] |

TABLE 2-continued
Compounds of the Invention
CMPD No. Structure
509 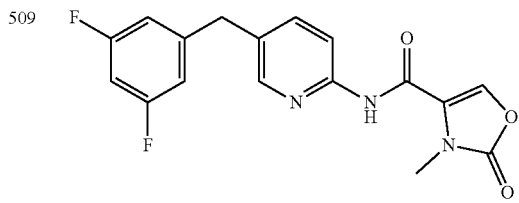
510 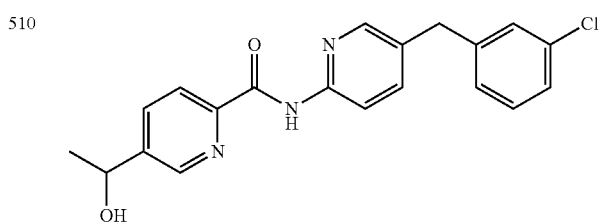
511 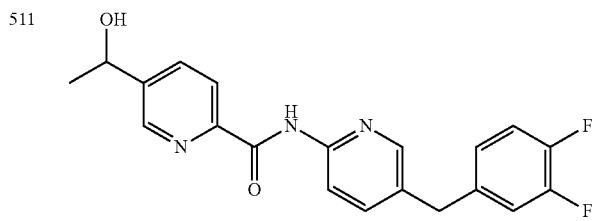
512 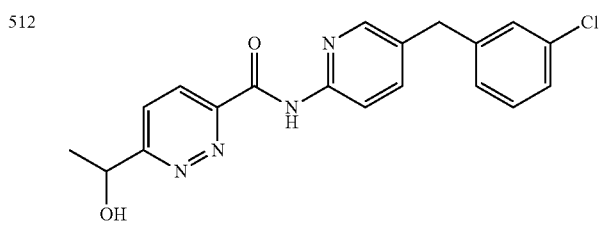
513 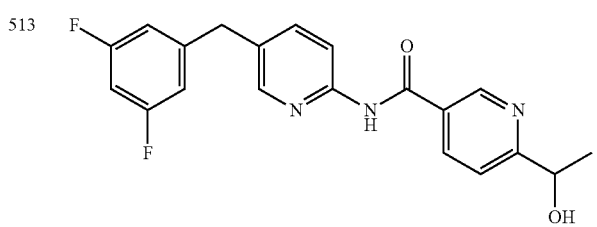
514 
515 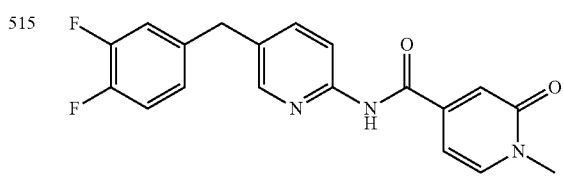

TABLE 2-continued
Compounds of the Invention
| CMPD No. | Structure |
|---|---|
| 516 | 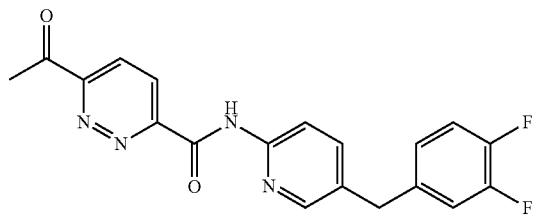 [SMILES: CC(=O)c1ccc(C(=O)Nc2ccc(Cc3ccc(F)c(F)c3)cn2)nn1] |
| 517 | 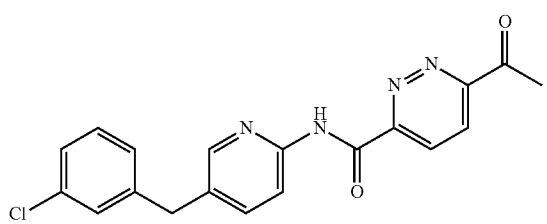 [SMILES: CC(=O)c1ccc(C(=O)Nc2ccc(Cc3cccc(Cl)c3)cn2)nn1] |
| 518 | 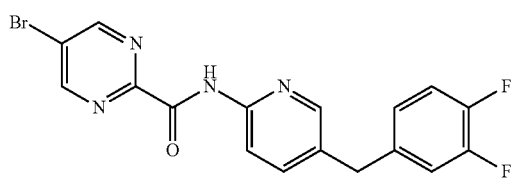 |
| 519 | 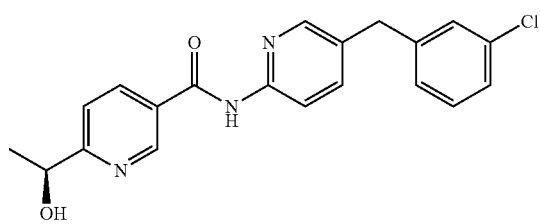 [SMILES: C[C@H](O)c1ccc(C(=O)Nc2ccc(Cc3cccc(Cl)c3)cn2)cn1] |
| 520 | 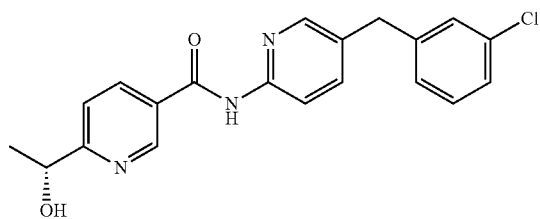 [SMILES: C[C@@H](O)c1ccc(C(=O)Nc2ccc(Cc3cccc(Cl)c3)cn2)cn1] |
| 521 | 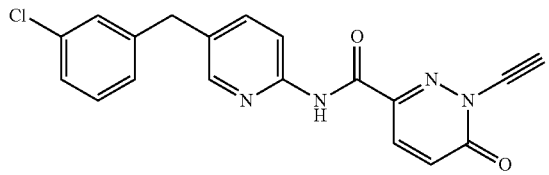 [SMILES: C#Cn1nc(C(=O)Nc2ccc(Cc3cccc(Cl)c3)cn2)ccc1=O] |
| 522 | 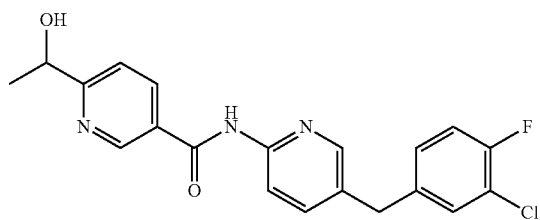 [SMILES: CC(O)c1ccc(C(=O)Nc2ccc(Cc3ccc(F)c(Cl)c3)cn2)cn1] |

TABLE 2-continued
Compounds of the Invention
| CMPD No. | Structure |
|---|---|
| 523 | 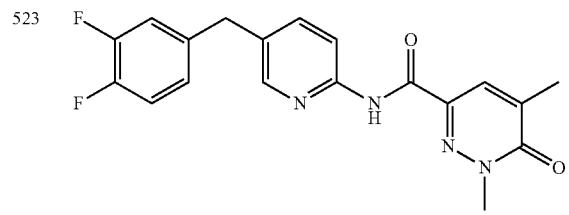 |
| 524 | 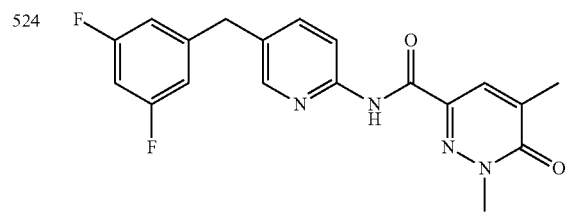 |
| 525 | 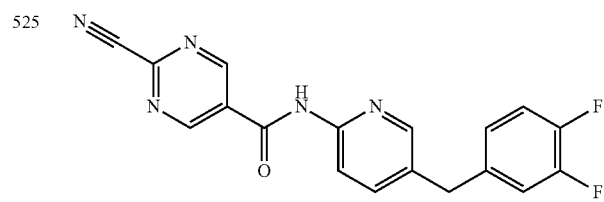 |
| 526 | 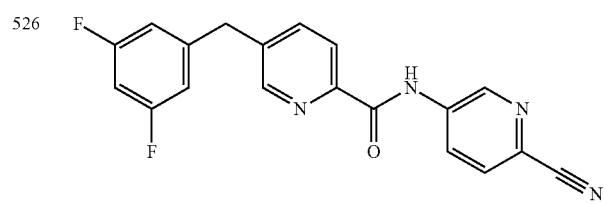 |
| 527 | 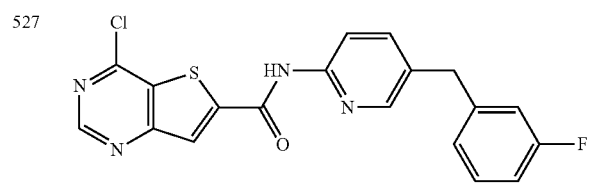 |
| 528 | 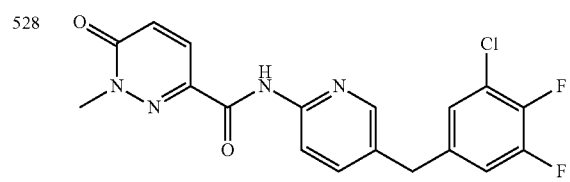 |
| 529 | 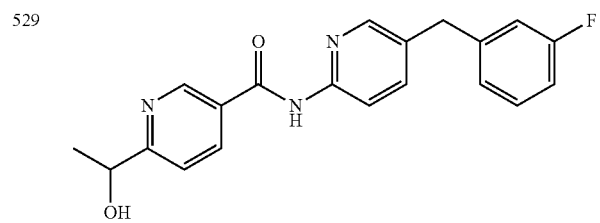 |

TABLE 2-continued
Compounds of the Invention
CMPD No. Structure
530
531
532
533
534
535
536
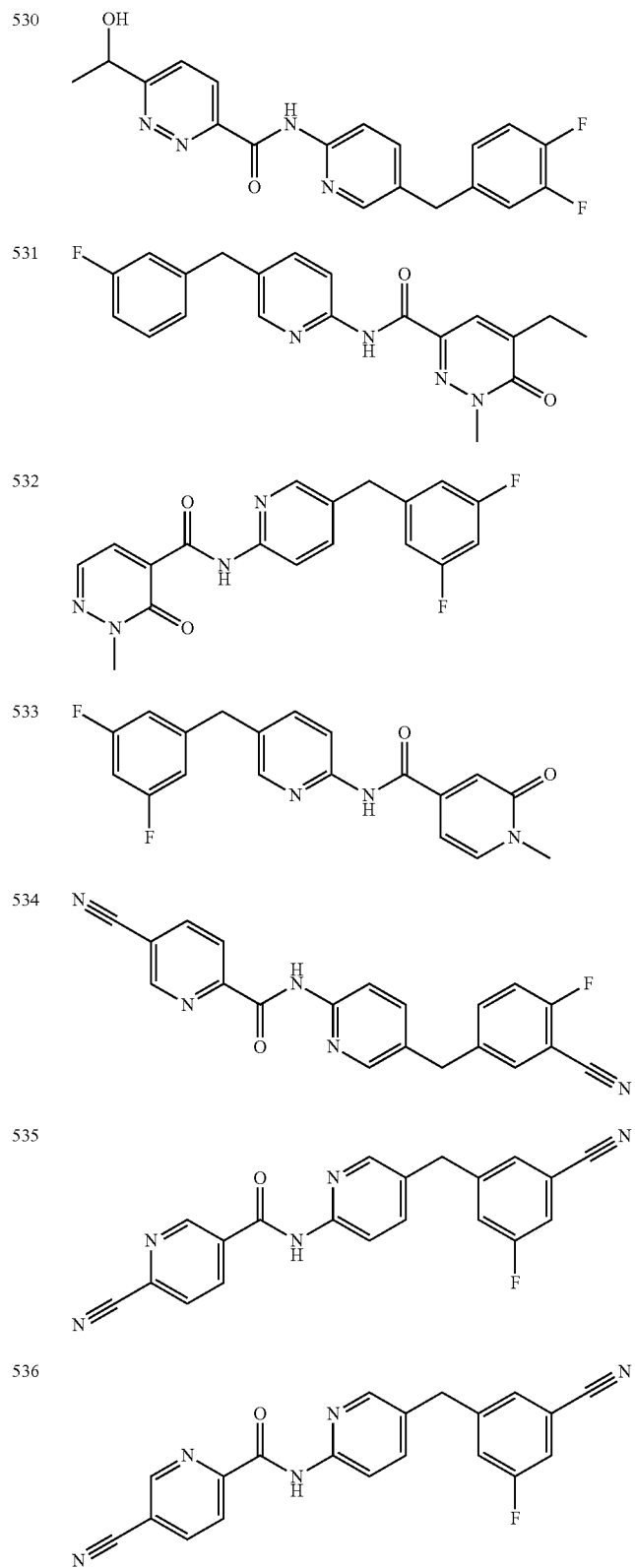

TABLE 2-continued
Compounds of the Invention
| CMPD No. | Structure |
|---|---|
| 537 | 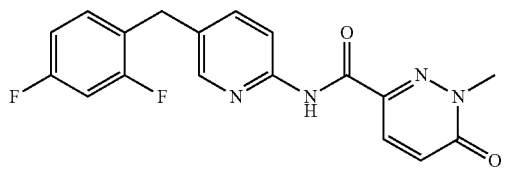 [SMILES: Cn1nc(C(=O)Nc2ccc(Cc3ccc(F)cc3F)cn2)ccc1=O] |
| 538 | 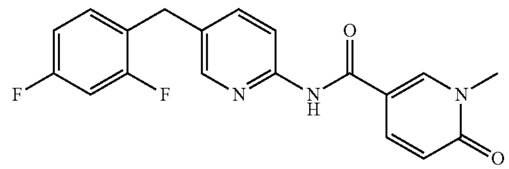 [SMILES: Cn1cc(C(=O)Nc2ccc(Cc3ccc(F)cc3F)cn2)ccc1=O] |
| 539 | 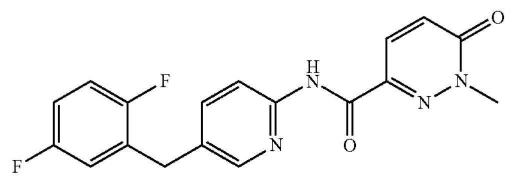 [SMILES: Cn1nc(C(=O)Nc2ccc(Cc3cc(F)ccc3F)cn2)ccc1=O] |
| 540 | 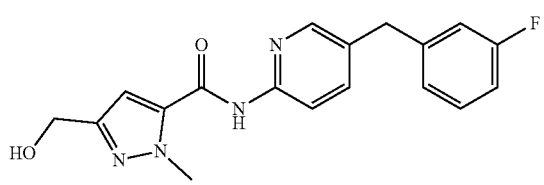 [SMILES: Cn1nc(CO)cc1C(=O)Nc1ccc(Cc2cccc(F)c2)cn1] |
| 541 | 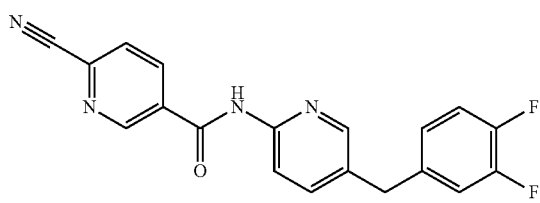 [SMILES: N#Cc1ccc(C(=O)Nc2ccc(Cc3ccc(F)c(F)c3)cn2)cn1] |
| 542 | 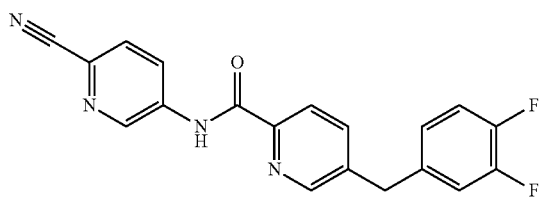 [SMILES: N#Cc1ccc(NC(=O)c2ccc(Cc3ccc(F)c(F)c3)cn2)cn1] |
| 543 | 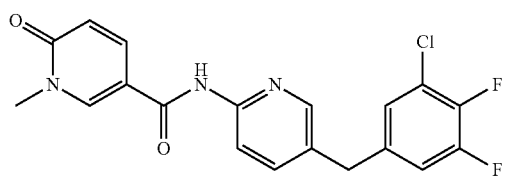 [SMILES: Cn1cc(C(=O)Nc2ccc(Cc3cc(F)c(F)c(Cl)c3)cn2)ccc1=O] |
| 544 | 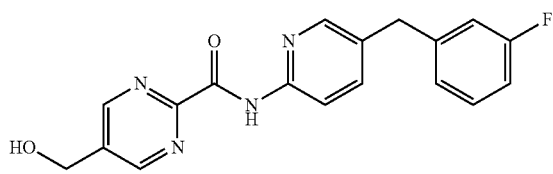 [SMILES: O=C(Nc1ccc(Cc2cccc(F)c2)cn1)c1ncc(CO)cn1] |

TABLE 2-continued
Compounds of the Invention
CMPD No. Structure
545 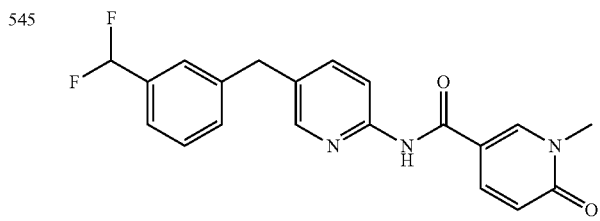
546 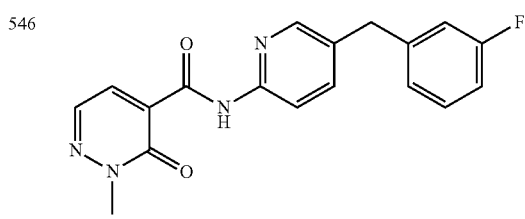
547 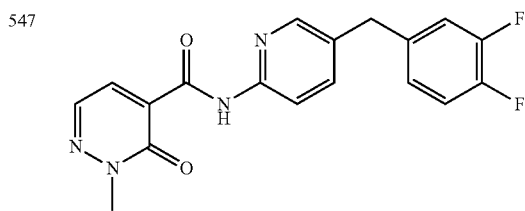
548 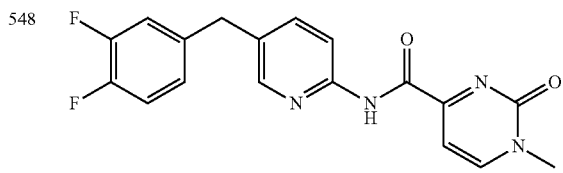
549 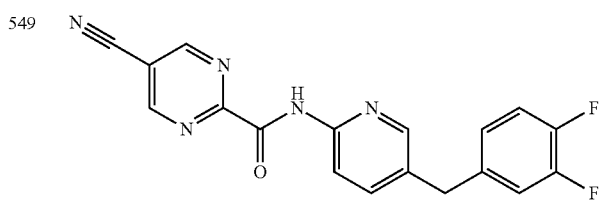
550 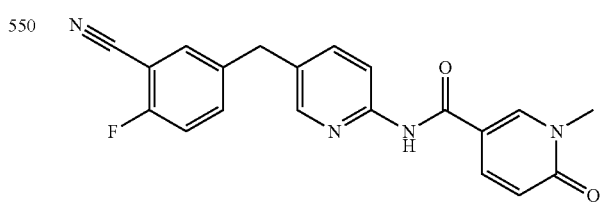
551 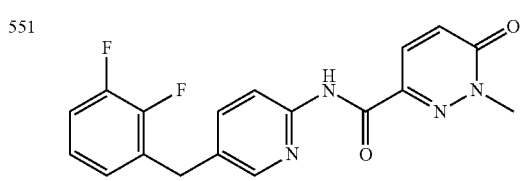

TABLE 2-continued
Compounds of the Invention
| CMPD No. | Structure |
|---|---|
| 552 | 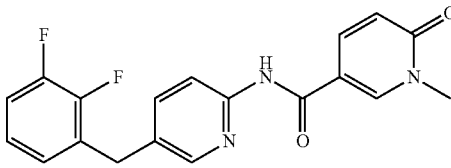 |
| 553 | 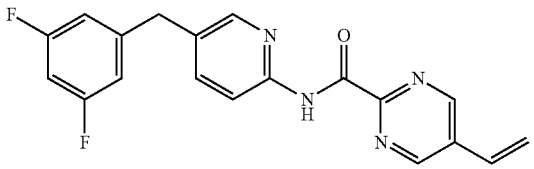 [SMILES: C=Cc1cnc(C(=O)Nc2ccc(Cc3cc(F)cc(F)c3)cn2)nc1] |
| 554 | 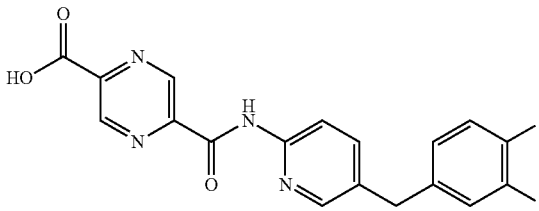 |
| 555 | 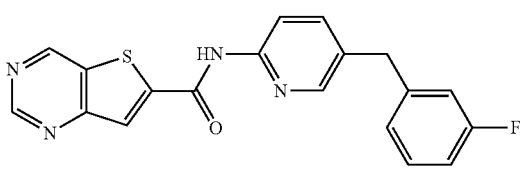 [SMILES: O=C(Nc1ccc(Cc2cccc(F)c2)cn1)c1cc2ncncc2s1] |
| 556 | 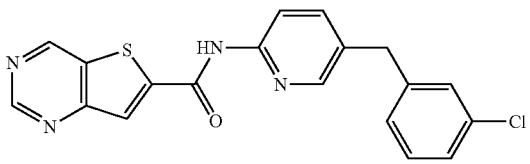 [SMILES: O=C(Nc1ccc(Cc2cccc(Cl)c2)cn1)c1cc2ncncc2s1] |
| 557 | 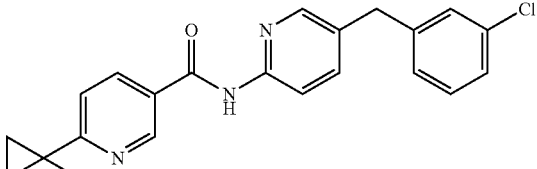 |
| 558 | 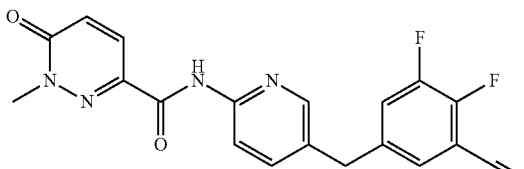 |
| 559 | 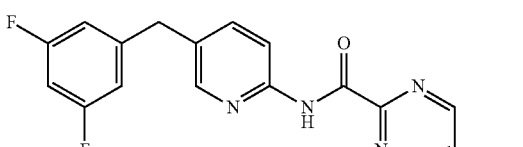 |

TABLE 2-continued
Compounds of the Invention
| CMPD No. | Structure |
|---|---|
| 560 | 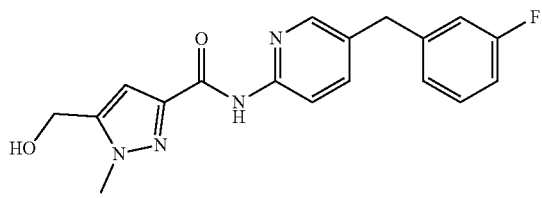 [SMILES: Cn1nc(C(=O)Nc2ccc(Cc3cccc(F)c3)cn2)cc1CO] |
| 561 | 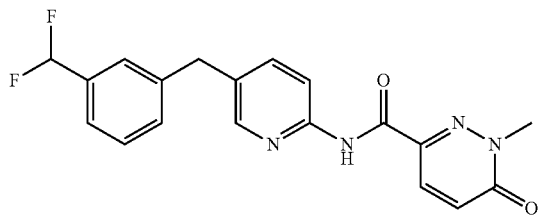 [SMILES: Cn1nc(C(=O)Nc2ccc(Cc3cccc(C(F)F)c3)cn2)ccc1=O] |
| 562 | 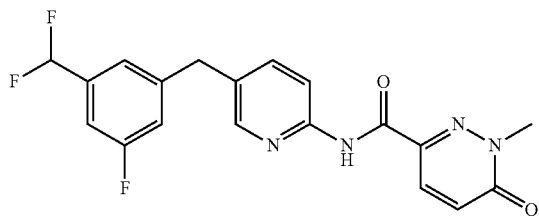 [SMILES: Cn1nc(C(=O)Nc2ccc(Cc3cc(F)cc(C(F)F)c3)cn2)ccc1=O] |
| 563 | 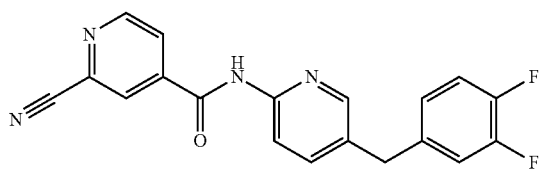 [SMILES: N#Cc1cc(C(=O)Nc2ccc(Cc3ccc(F)c(F)c3)cn2)ccn1] |
| 564 | 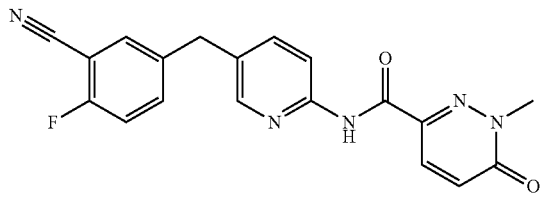 [SMILES: Cn1nc(C(=O)Nc2ccc(Cc3ccc(F)c(C#N)c3)cn2)ccc1=O] |
| 565 | 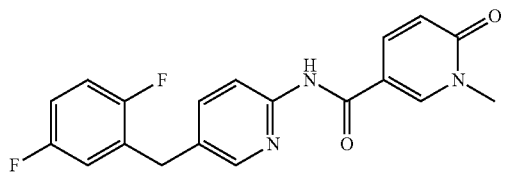 [SMILES: Cn1cc(C(=O)Nc2ccc(Cc3cc(F)ccc3F)cn2)ccc1=O] |
| 566 | 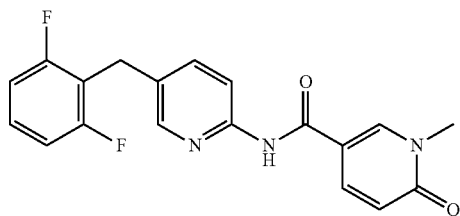 [SMILES: Cn1cc(C(=O)Nc2ccc(Cc3c(F)cccc3F)cn2)ccc1=O] |

TABLE 2-continued
Compounds of the Invention
| CMPD No. | Structure |
|---|---|
| 567 | 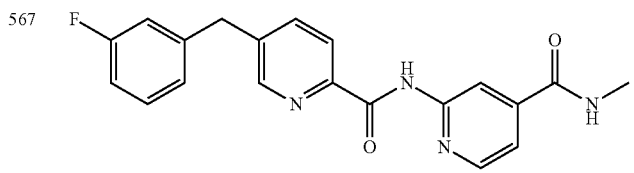 |
| 568 | 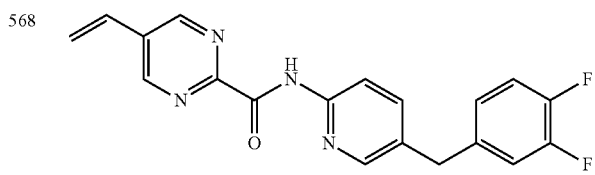 |
| 569 | 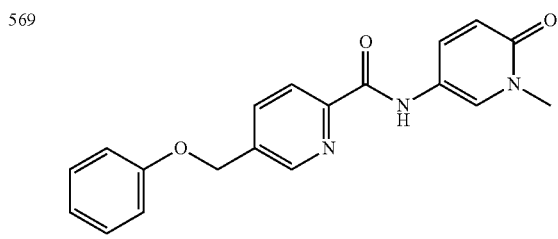 |
| 570 | 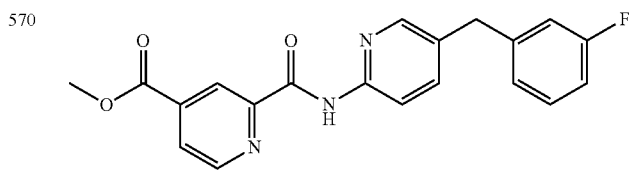 |
| 571 | 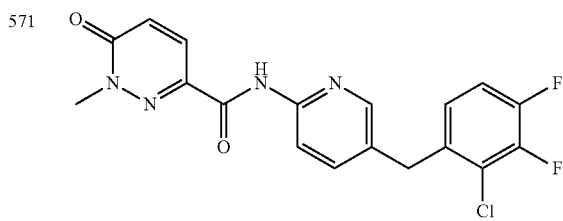 |
| 572 | 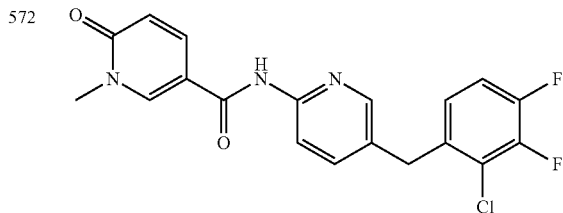 |
| 573 | 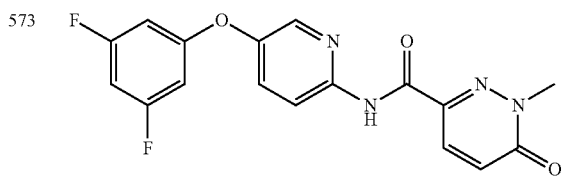 |

TABLE 2-continued

Compounds of the Invention

| CMPD No. | Structure |
|---|---|
| 574 | 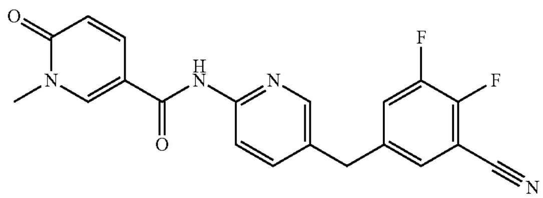 [SMILES: Cn1cc(C(=O)Nc2ccc(Cc3cc(F)c(F)c(C#N)c3)cn2)ccc1=O] |
| 575 | 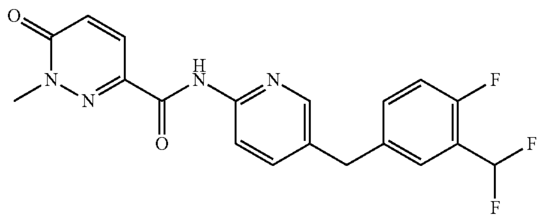 [SMILES: Cn1nc(C(=O)Nc2ccc(Cc3ccc(F)c(C(F)F)c3)cn2)ccc1=O] |
| 576 | 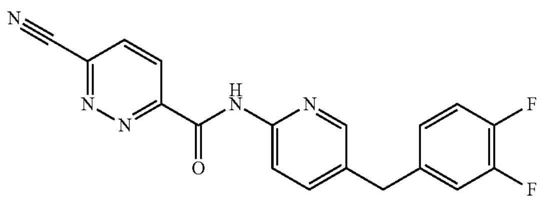 [SMILES: N#Cc1ccc(C(=O)Nc2ccc(Cc3ccc(F)c(F)c3)cn2)nn1] |
| 577 | 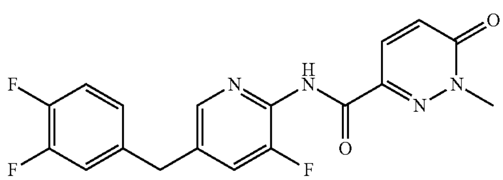 [SMILES: Cn1nc(C(=O)Nc2ncc(Cc3ccc(F)c(F)c3)cc2F)ccc1=O] |
| 578 | 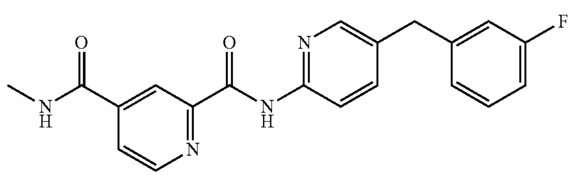 [SMILES: CNC(=O)c1ccnc(C(=O)Nc2ccc(Cc3cccc(F)c3)cn2)c1] |
| 579 | 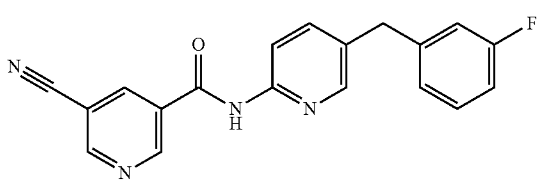 [SMILES: N#Cc1cncc(C(=O)Nc2ccc(Cc3cccc(F)c3)cn2)c1] |
| 580 | 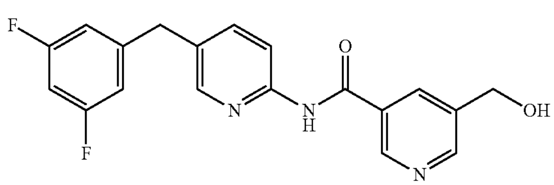 [SMILES: O=C(Nc1ccc(Cc2cc(F)cc(F)c2)cn1)c1cncc(CO)c1] |
| 581 | 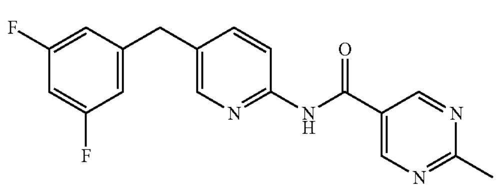 [SMILES: Cc1ncc(C(=O)Nc2ccc(Cc3cc(F)cc(F)c3)cn2)cn1] |

TABLE 2-continued
Compounds of the Invention
| CMPD No. | Structure |
|---|---|
| 582 | 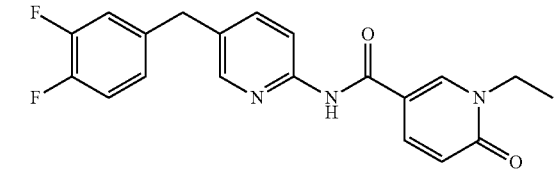 [SMILES: CCn1cc(C(=O)Nc2ccc(Cc3ccc(F)c(F)c3)cn2)ccc1=O] |
| 583 | 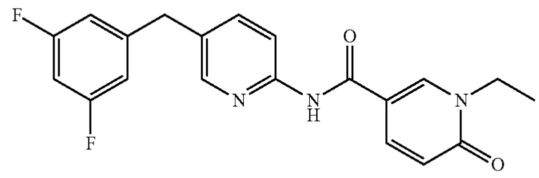 [SMILES: CCn1cc(C(=O)Nc2ccc(Cc3cc(F)cc(F)c3)cn2)ccc1=O] |
| 584 | 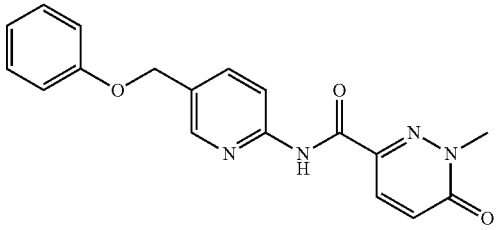 [SMILES: Cn1nc(C(=O)Nc2ccc(COc3ccccc3)cn2)ccc1=O] |
| 585 | 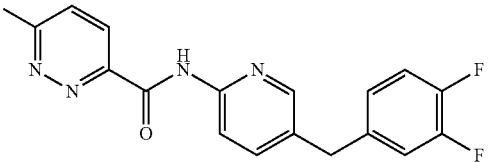 |
| 586 | 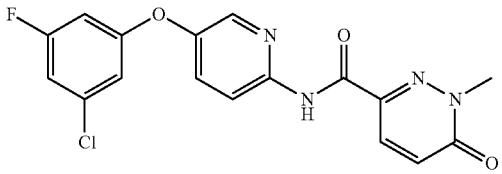 [SMILES: Cn1nc(C(=O)Nc2ccc(Oc3cc(F)cc(Cl)c3)cn2)ccc1=O] |
| 587 | 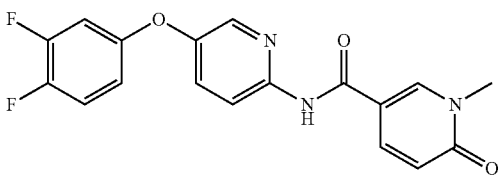 [SMILES: Cn1cc(C(=O)Nc2ccc(Oc3ccc(F)c(F)c3)cn2)ccc1=O] |
| 588 | 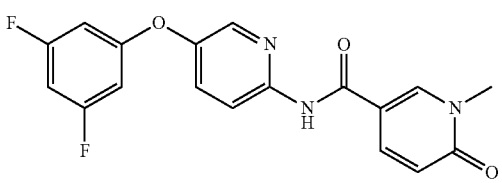 [SMILES: Cn1cc(C(=O)Nc2ccc(Oc3cc(F)cc(F)c3)cn2)ccc1=O] |
| 589 | 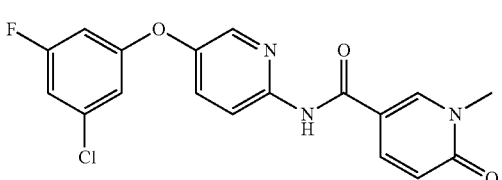 |

TABLE 2-continued
Compounds of the Invention
| CMPD No. | Structure |
|---|---|
| 590 | 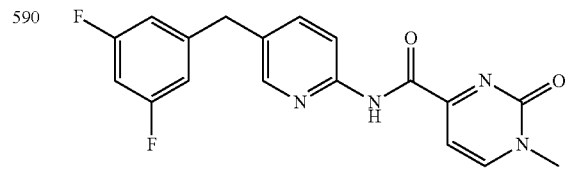 |
| 591 | 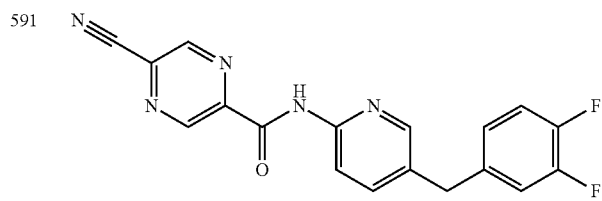 |
| 592 | 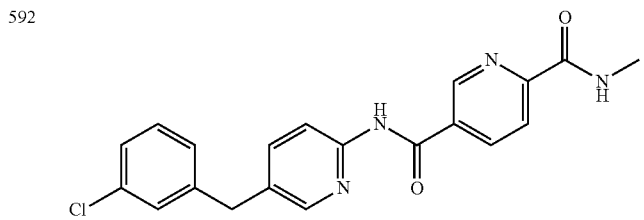 |
| 593 | 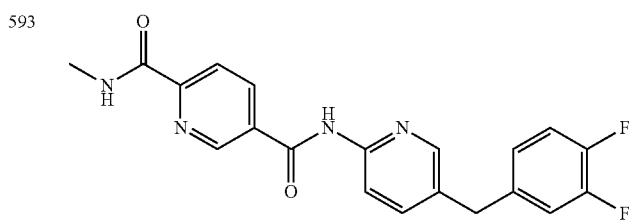 |
| 594 | 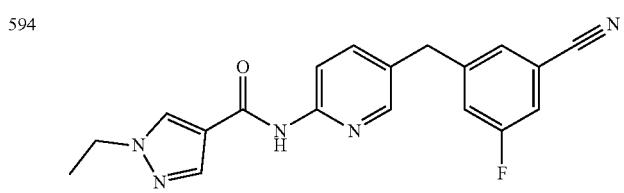 |
| 595 | 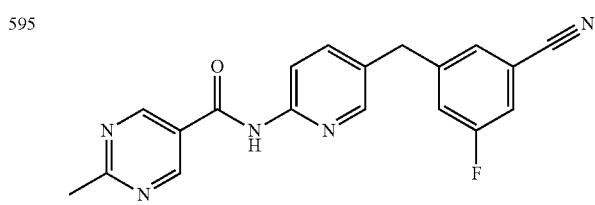 |
| 596 | 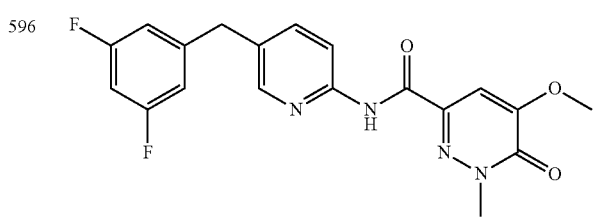 |

TABLE 2-continued
Compounds of the Invention
| CMPD No. | Structure |
|---|---|
| 597 | 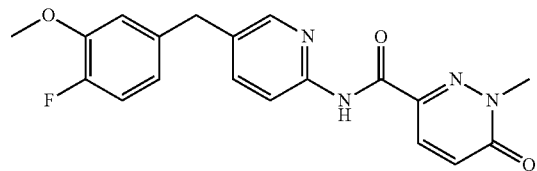 |
| 598 | 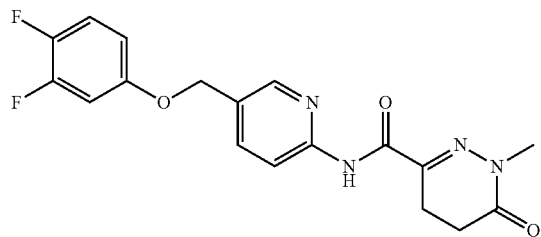 [SMILES: CN1N=C(C(=O)Nc2ccc(COc3ccc(F)c(F)c3)cn2)CCC1=O] |
| 599 | 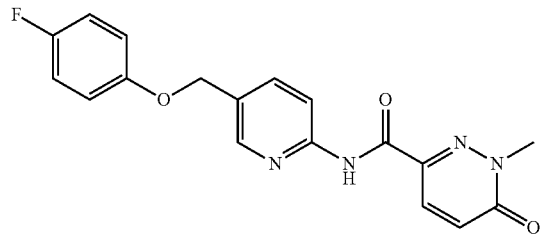 [SMILES: Cn1nc(C(=O)Nc2ccc(COc3ccc(F)cc3)cn2)ccc1=O] |
| 600 | 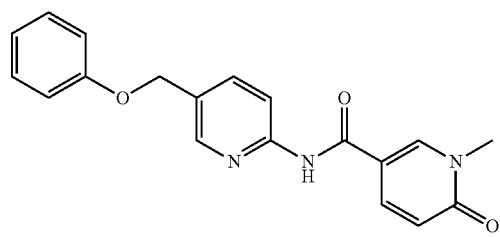 [SMILES: Cn1cc(C(=O)Nc2ccc(COc3ccccc3)cn2)ccc1=O] |
| 601 | 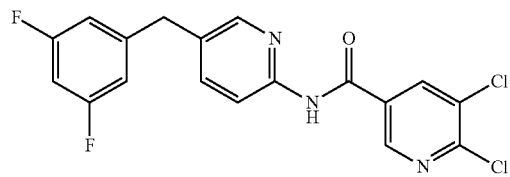 [SMILES: O=C(Nc1ccc(Cc2cc(F)cc(F)c2)cn1)c1cnc(Cl)c(Cl)c1] |
| 602 | 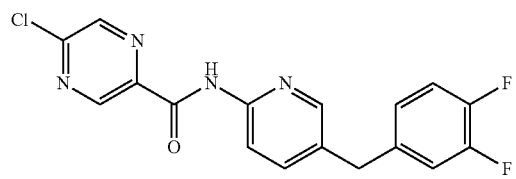 [SMILES: O=C(Nc1ccc(Cc2ccc(F)c(F)c2)cn1)c1cnc(Cl)cn1] |
| 603 | 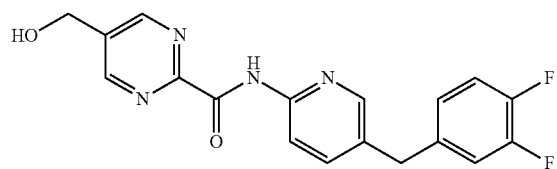 [SMILES: O=C(Nc1ccc(Cc2ccc(F)c(F)c2)cn1)c1ncc(CO)cn1] |

TABLE 2-continued
Compounds of the Invention
CMPD No. Structure
604
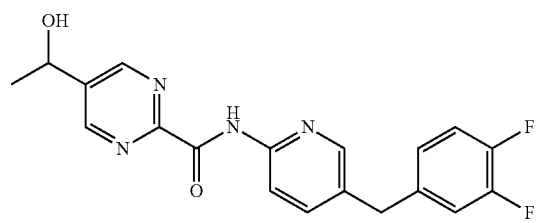
605
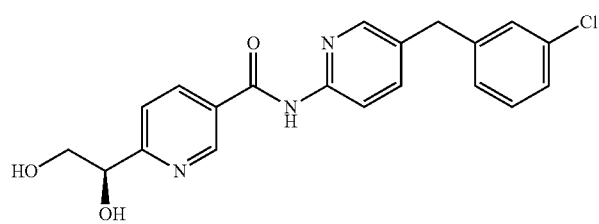 [SMILES: O=C(Nc1ccc(Cc2cccc(Cl)c2)cn1)c1ccc([C@@H](O)CO)nc1]
606
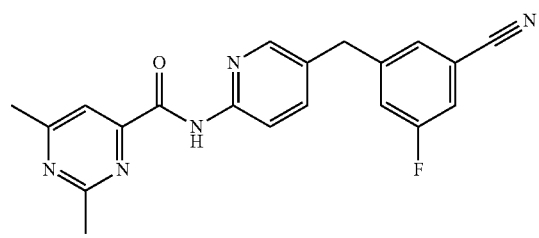 [SMILES: Cc1cc(C(=O)Nc2ccc(Cc3cc(F)cc(C#N)c3)cn2)nc(C)n1]
607
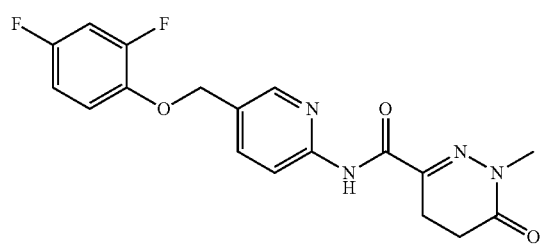 [SMILES: CN1N=C(C(=O)Nc2ccc(COc3ccc(F)cc3F)cn2)CCC1=O]
608
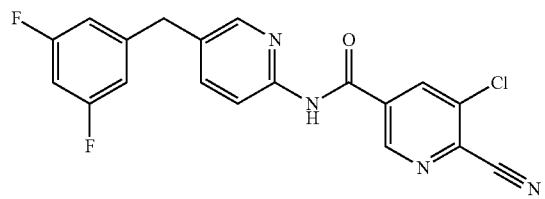 [SMILES: N#Cc1ncc(C(=O)Nc2ccc(Cc3cc(F)cc(F)c3)cn2)cc1Cl]
609
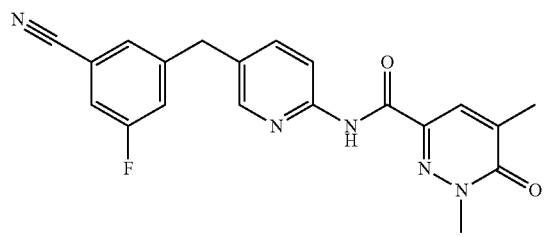 [SMILES: Cc1cc(C(=O)Nc2ccc(Cc3cc(F)cc(C#N)c3)cn2)nn(C)c1=O]

TABLE 2-continued
Compounds of the Invention
CMPD No. Structure
610 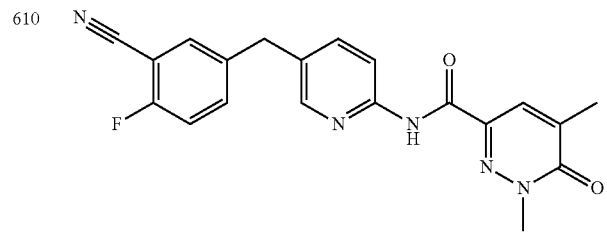
611 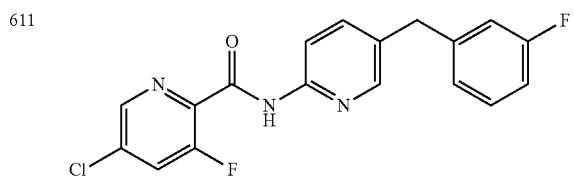
612 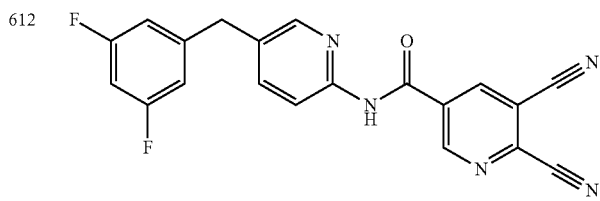
613 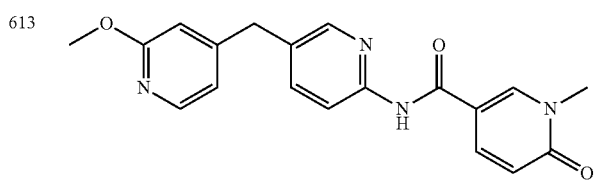
614 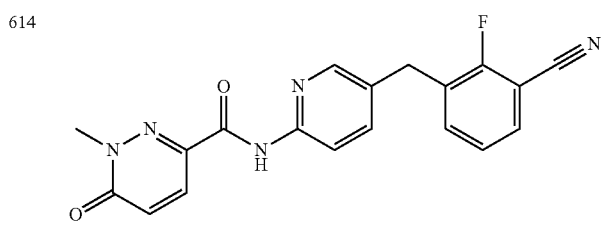
615 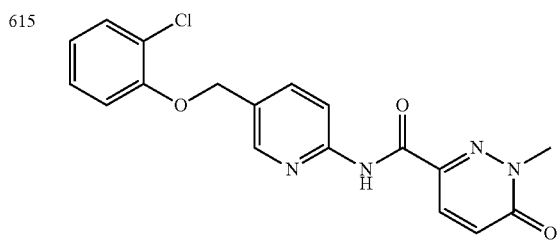
616 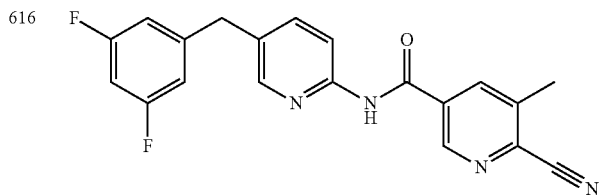

TABLE 2-continued
Compounds of the Invention
| CMPD No. | Structure |
|---|---|
| 617 | 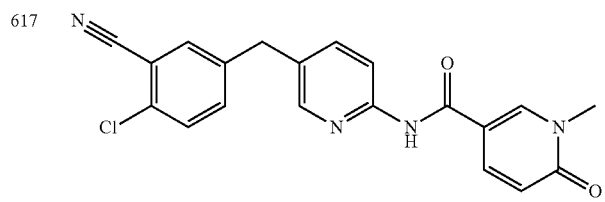 |
| 618 | 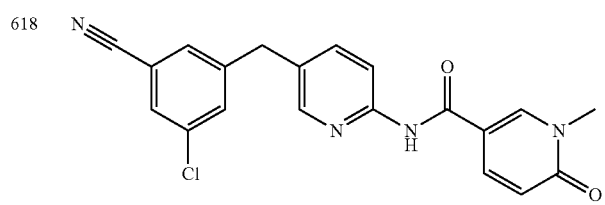 |
| 619 | 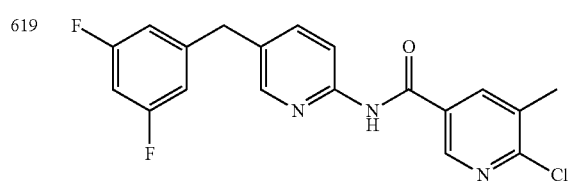 |
| 620 | 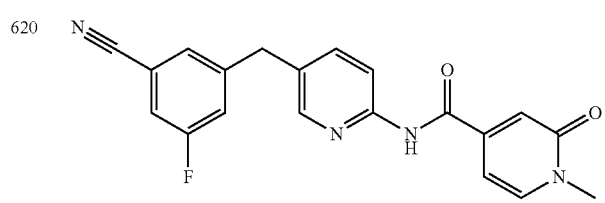 |
| 621 | 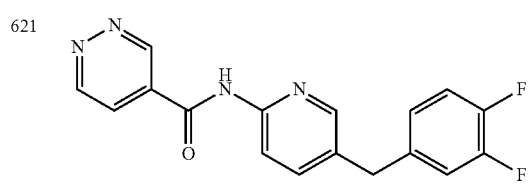 |
| 622 | 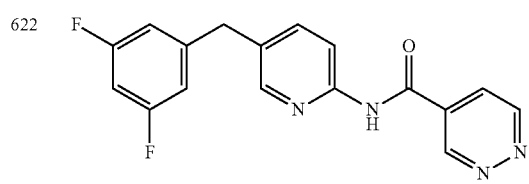 |
| 623 | 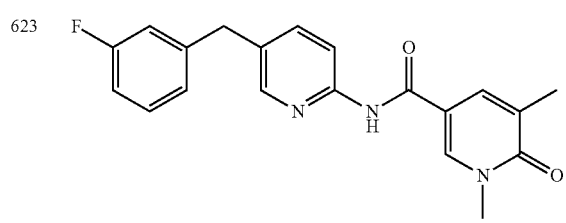 |

TABLE 2-continued
Compounds of the Invention
| CMPD No. | Structure |
|---|---|
| 624 | 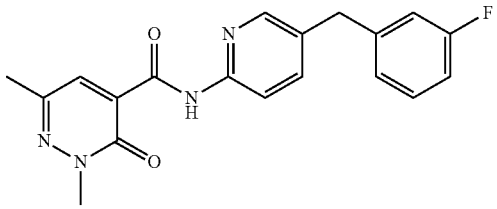 [SMILES: Cc1cc(C(=O)Nc2ccc(Cc3cccc(F)c3)cn2)c(=O)n(C)n1] |
| 625 | 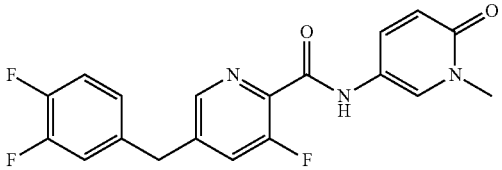 [SMILES: Cn1cc(NC(=O)c2ncc(Cc3ccc(F)c(F)c3)cc2F)ccc1=O] |
| 626 | 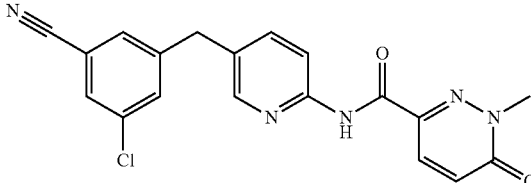 |
| 627 | 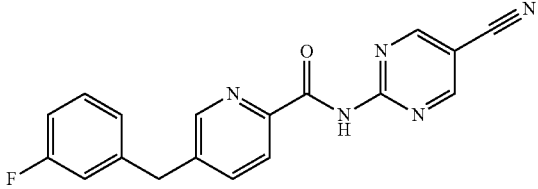 [SMILES: N#Cc1cnc(NC(=O)c2ccc(Cc3cccc(F)c3)cn2)nc1] |
| 628 | 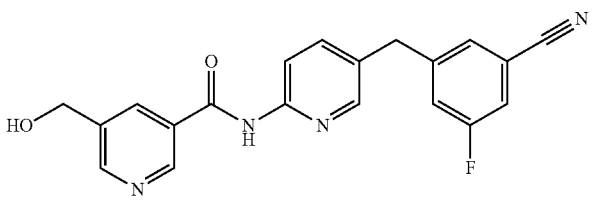 [SMILES: N#Cc1cc(F)cc(Cc2ccc(NC(=O)c3cncc(CO)c3)nc2)c1] |
| 629 | 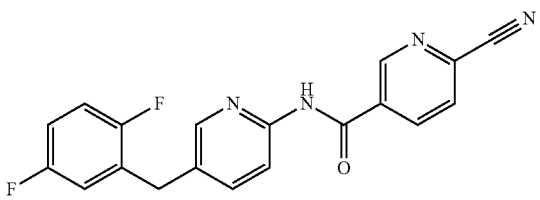 [SMILES: N#Cc1ccc(C(=O)Nc2ccc(Cc3cc(F)ccc3F)cn2)cn1] |
| 630 | 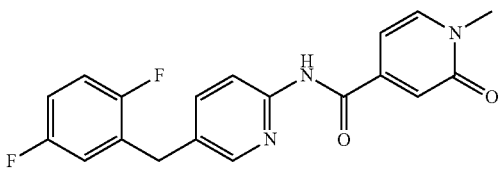 [SMILES: Cn1ccc(C(=O)Nc2ccc(Cc3cc(F)ccc3F)cn2)cc1=O] |

TABLE 2-continued
Compounds of the Invention
| CMPD No. | Structure |
|---|---|
| 631 | 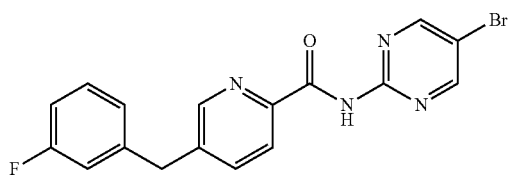 [SMILES: O=C(Nc1ncc(Br)cn1)c1ccc(Cc2cccc(F)c2)cn1] |
| 632 | 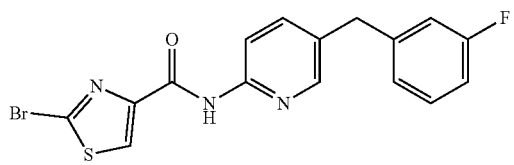 [SMILES: O=C(Nc1ccc(Cc2cccc(F)c2)cn1)c1csc(Br)n1] |
| 633 | 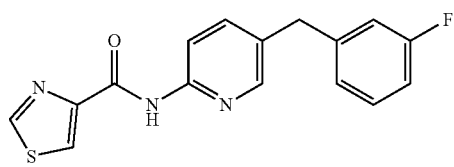 [SMILES: O=C(Nc1ccc(Cc2cccc(F)c2)cn1)c1cscn1] |
| 634 | 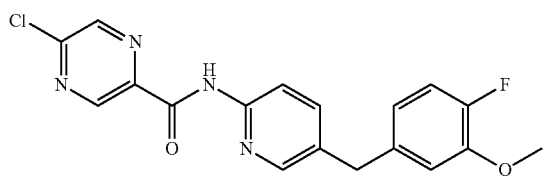 [SMILES: COc1cc(Cc2ccc(NC(=O)c3cnc(Cl)cn3)nc2)ccc1F] |
| 635 | 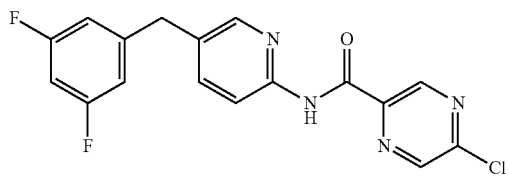 [SMILES: O=C(Nc1ccc(Cc2cc(F)cc(F)c2)cn1)c1cnc(Cl)cn1] |
| 636 | 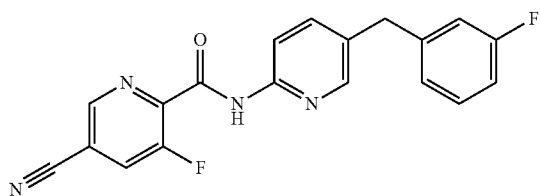 [SMILES: N#Cc1cnc(C(=O)Nc2ccc(Cc3cccc(F)c3)cn2)c(F)c1] |
| 637 | 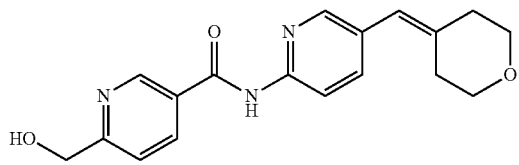 [SMILES: O=C(Nc1ccc(C=C2CCOCC2)cn1)c1ccc(CO)nc1] |
| 638 | 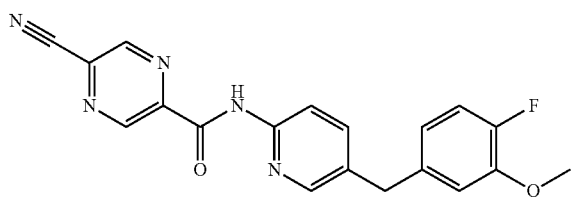 [SMILES: COc1cc(Cc2ccc(NC(=O)c3cnc(C#N)cn3)nc2)ccc1F] |

TABLE 2-continued
Compounds of the Invention
| CMPD No. | Structure |
|---|---|
| 639 | 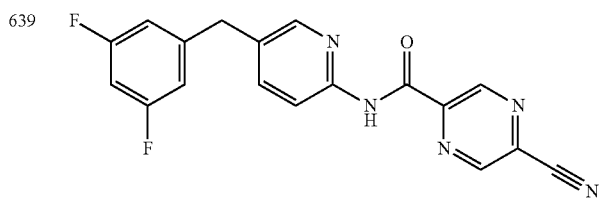 |
| 640 | 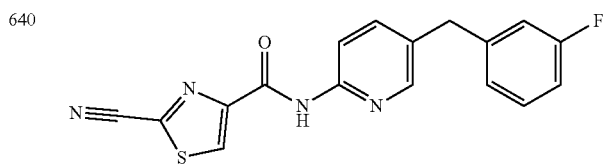 |
| 641 | 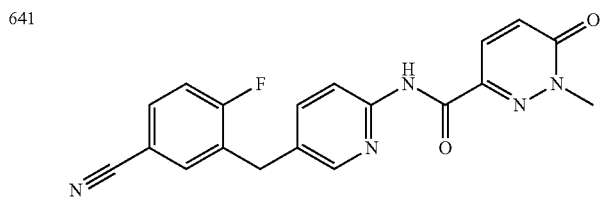 |
| 642 | 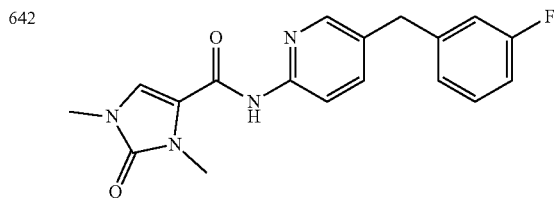 |
| 643 | 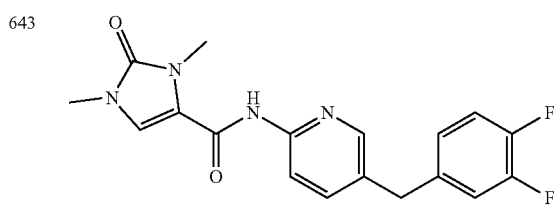 |
| 644 | 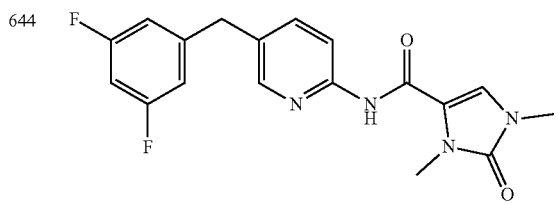 |
| 645 | 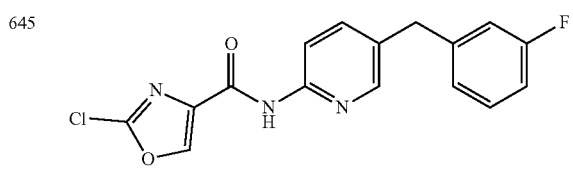 |

TABLE 2-continued
Compounds of the Invention
| CMPD No. | Structure |
|---|---|
| 646 | 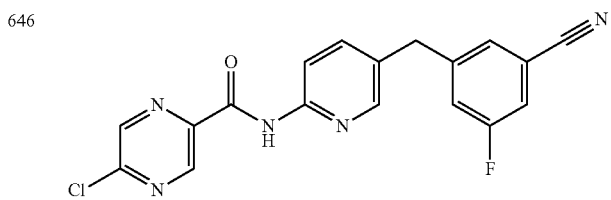 |
| 647 | 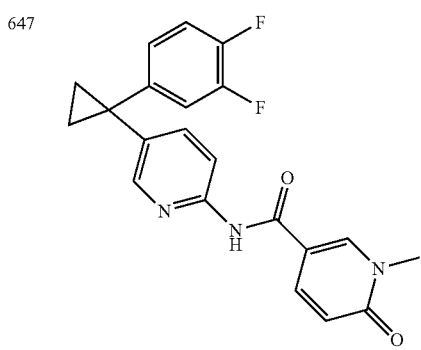 |
| 648 | 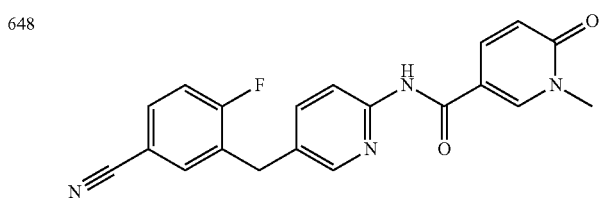 |
| 649 | 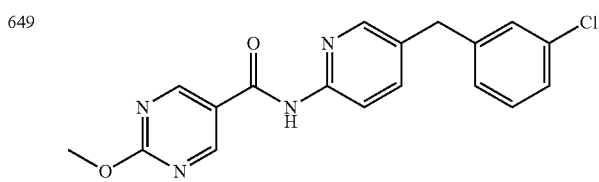 |
| 650 | 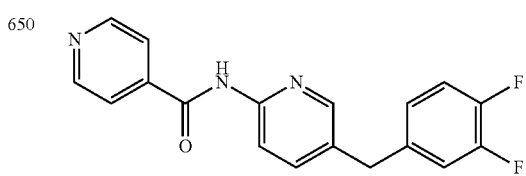 |
| 651 | 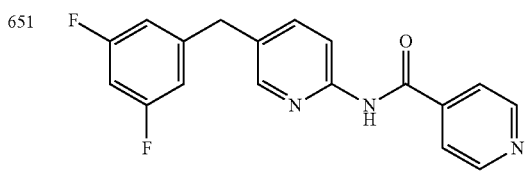 |
| 652 | 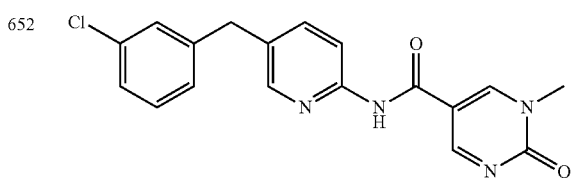 |

TABLE 2-continued
Compounds of the Invention
| CMPD No. | Structure |
|---|---|
| 653 | 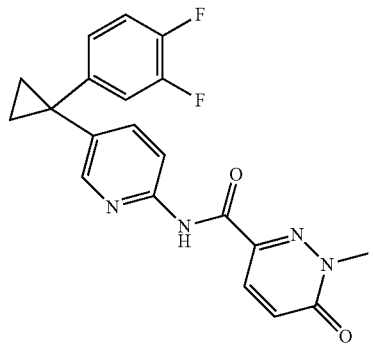 [SMILES: Cn1nc(C(=O)Nc2ccc(C3(c4ccc(F)c(F)c4)CC3)cn2)ccc1=O] |
| 654 | 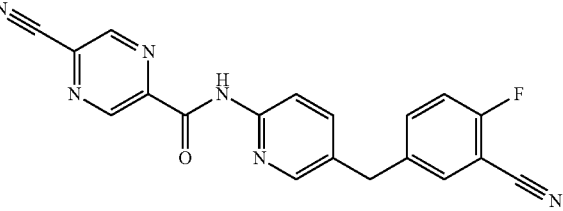 |
| 655 | 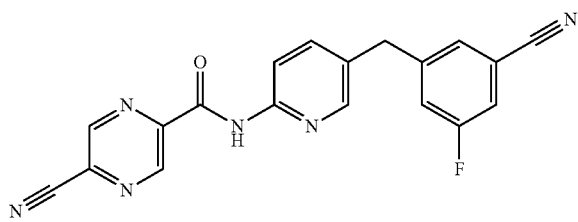 [SMILES: N#Cc1cc(F)cc(Cc2ccc(NC(=O)c3cnc(C#N)cn3)nc2)c1] |
| 656 | 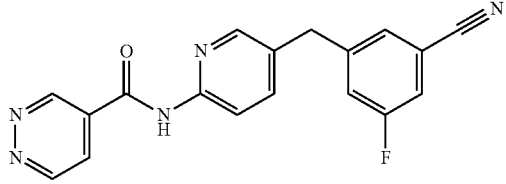 [SMILES: N#Cc1cc(F)cc(Cc2ccc(NC(=O)c3ccnnc3)nc2)c1] |
| 657 | 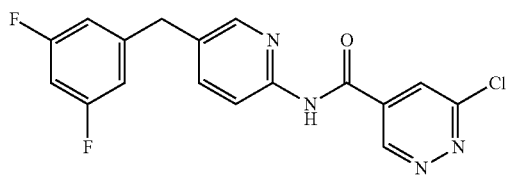 [SMILES: O=C(Nc1ccc(Cc2cc(F)cc(F)c2)cn1)c1cnnc(Cl)c1] |
| 658 | 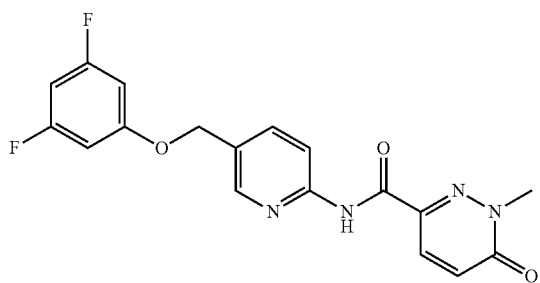 [SMILES: Cn1nc(C(=O)Nc2ccc(COc3cc(F)cc(F)c3)cn2)ccc1=O] |

TABLE 2-continued
Compounds of the Invention
| CMPD No. | Structure |
|---|---|
| 659 | 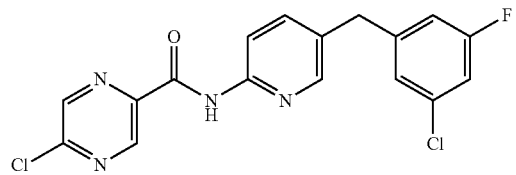 [SMILES: O=C(Nc1ccc(Cc2cc(F)cc(Cl)c2)cn1)c1cnc(Cl)cn1] |
| 660 | 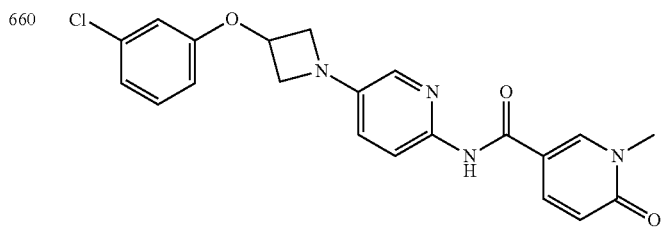 |
| 661 | 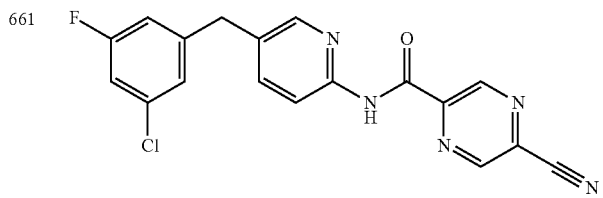 |
| 662 | 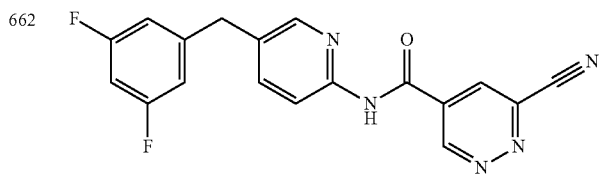 |
| 663 | 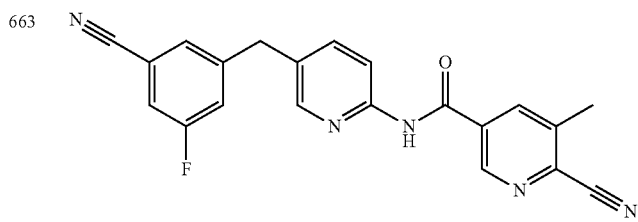 |
| 664 | 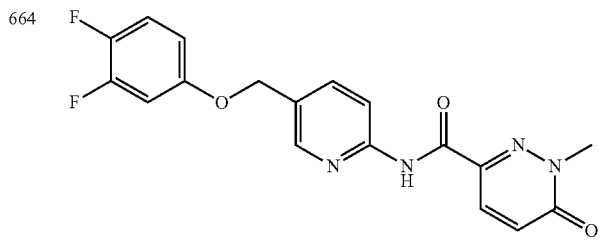 |
| 665 | 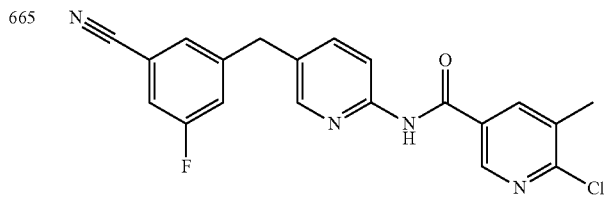 |

TABLE 2-continued
Compounds of the Invention
| CMPD No. | Structure |
|---|---|
| 666 | 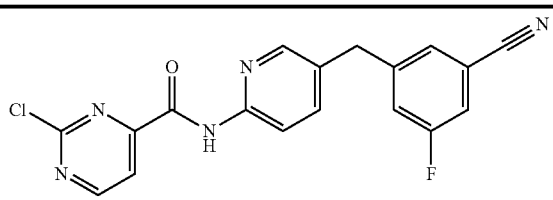 |
| 667 | 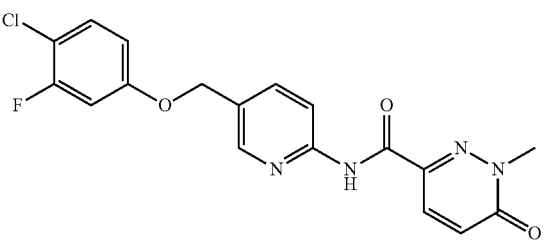 [SMILES: Cn1nc(C(=O)Nc2ccc(COc3ccc(Cl)c(F)c3)cn2)ccc1=O] |
| 668 | 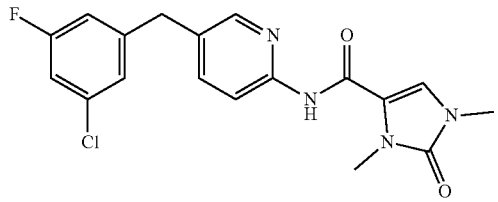 [SMILES: Cn1cc(C(=O)Nc2ccc(Cc3cc(F)cc(Cl)c3)cn2)n(C)c1=O] |
| 669 | 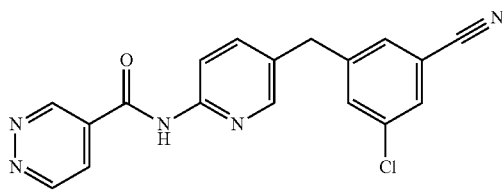 [SMILES: N#Cc1cc(Cl)cc(Cc2ccc(NC(=O)c3ccnnc3)nc2)c1] |
| 670 | 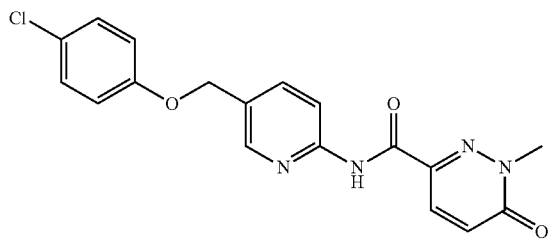 [SMILES: Cn1nc(C(=O)Nc2ccc(COc3ccc(Cl)cc3)cn2)ccc1=O] |
| 671 | 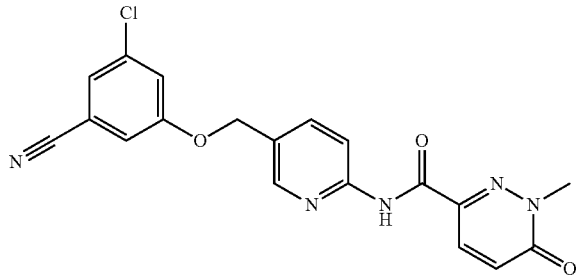 [SMILES: Cn1nc(C(=O)Nc2ccc(COc3cc(Cl)cc(C#N)c3)cn2)ccc1=O] |
| 672 | 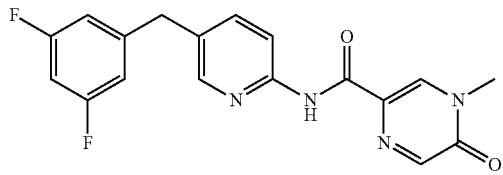 |

TABLE 2-continued
Compounds of the Invention
| CMPD No. | Structure |
|---|---|
| 673 | 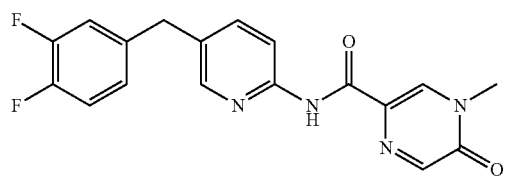 [SMILES: Cn1cc(C(=O)Nc2ccc(Cc3ccc(F)c(F)c3)cn2)ncc1=O] |
| 674 | 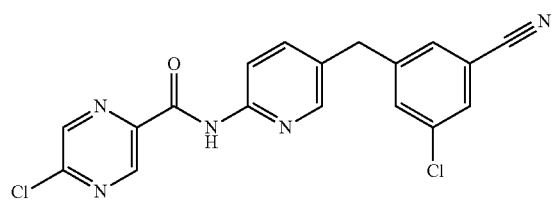 |
| 675 | 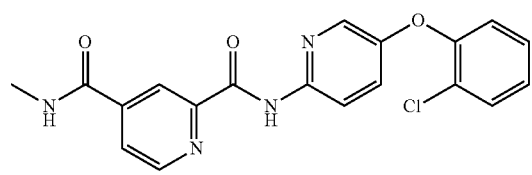 [SMILES: CNC(=O)c1ccnc(C(=O)Nc2ccc(Oc3ccccc3Cl)cn2)c1] |
| 676 | 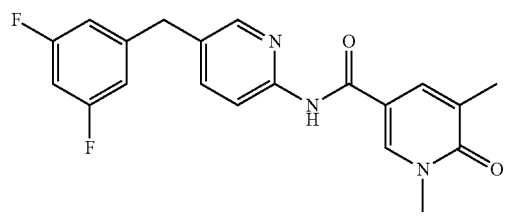 [SMILES: Cc1cc(C(=O)Nc2ccc(Cc3cc(F)cc(F)c3)cn2)cn(C)c1=O] |
| 677 | 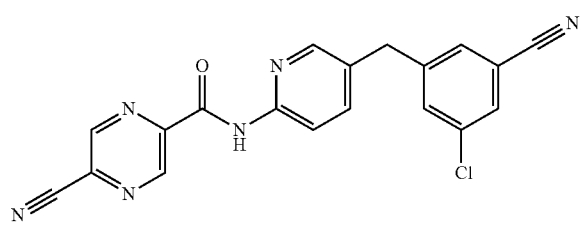 [SMILES: N#Cc1cc(Cl)cc(Cc2ccc(NC(=O)c3cnc(C#N)cn3)nc2)c1] |
| 678 | 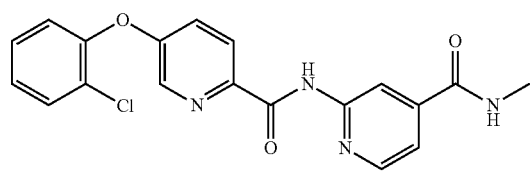 [SMILES: CNC(=O)c1ccnc(NC(=O)c2ccc(Oc3ccccc3Cl)cn2)c1] |
| 679 | 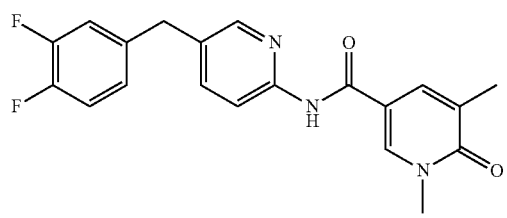 [SMILES: Cc1cc(C(=O)Nc2ccc(Cc3ccc(F)c(F)c3)cn2)cn(C)c1=O] |

TABLE 2-continued

Compounds of the Invention

| CMPD No. | Structure |
|---|---|
| 680 | 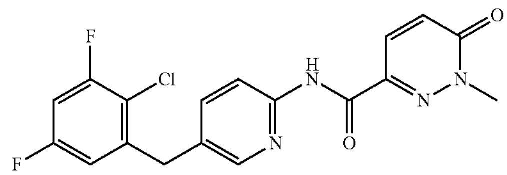 [SMILES: Cn1nc(C(=O)Nc2ccc(Cc3cc(F)cc(F)c3Cl)cn2)ccc1=O] |
| 681 | 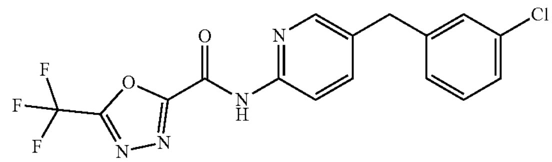 [SMILES: O=C(Nc1ccc(Cc2cccc(Cl)c2)cn1)c1nnc(C(F)(F)F)o1] |
| 682 | 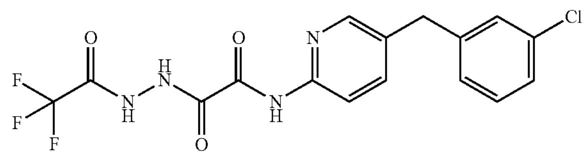 [SMILES: O=C(NNC(=O)C(F)(F)F)C(=O)Nc1ccc(Cc2cccc(Cl)c2)cn1] |
| 683 | 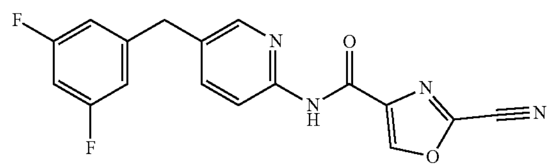 [SMILES: N#Cc1nc(C(=O)Nc2ccc(Cc3cc(F)cc(F)c3)cn2)co1] |

In an aspect, this disclosure features a pharmaceutical composition comprising a compound of any of the foregoing compounds, or pharmaceutically acceptable salt thereof, and a pharmaceutically acceptable excipient.

In some embodiments, the pharmaceutical composition includes a compound of Formula I or Formula II and a pharmaceutically acceptable excipient.

In an aspect, this disclosure features a method of treating a neurological disorder in a subject in need thereof, the method comprising administering an effective amount of any of the foregoing compounds or a pharmaceutical composition thereof.

In an aspect, this disclosure features a method of inhibiting toxicity in a cell related to a protein, the method comprising administering an effective amount of any of the foregoing compounds or a pharmaceutical composition thereof.

In some embodiments, the toxicity is α-synuclein-related toxicity. In some embodiments, the toxicity is ApoE4-related toxicity.

In some embodiments, the cell is a mammalian neural cell.

In an aspect, this disclosure features a method of treating a stearoyl-CoA desaturase (SCD)-associated disorder in a subject in need thereof, the method comprising administering an effective amount of any of the foregoing compounds, or pharmaceutically acceptable salts thereof, or a pharmaceutical composition thereof.

Non-limiting exemplary SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome.

In some embodiments, the SCD-associated disorder is a SCD1-associated disorder.

In some embodiments, the SCD-associated disorder is a SCD5-associated disorder.

In an aspect, this disclosure features a method of inhibiting SCD5, the method comprising contacting a cell with an effective amount of any of the foregoing compounds, or pharmaceutically acceptable salts thereof, or a pharmaceutical composition thereof.

In an aspect, this disclosure features a method of inhibiting SCD1, the method comprising contacting a cell with an effective amount of any of the foregoing compounds, or pharmaceutically acceptable salts thereof, or a pharmaceutical composition thereof.

Chemical Terms

It is to be understood that the terminology employed herein is for the purpose of describing particular embodiments and is not intended to be limiting.

Those skilled in the art will appreciate that certain compounds described herein can exist in one or more different isomeric (e.g., stereoisomers, geometric isomers, tautomers) and/or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion, e.g., the interconversion illustrated in the scheme below:

includes a plurality of positions at which substitutes are disclosed in groups or in ranges, unless otherwise indicated, the present disclosure is intended to cover individual compounds and groups of compounds (e.g., genera and subgenera) containing each and every individual subcombination of members at each position.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

The term "acyl," as used herein, represents a hydrogen or an alkyl group, as defined herein that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

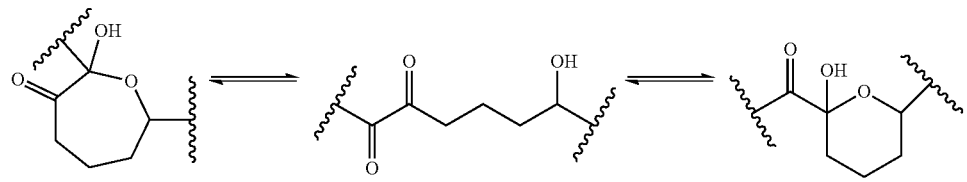

Those skilled in the art will appreciate that, in some embodiments, isotopes of compounds described herein may be prepared and/or utilized in accordance with the present invention. "Isotopes" refers to atoms having the same atomic number but different mass numbers resulting from a different number of neutrons in the nuclei. For example, isotopes of hydrogen include tritium and deuterium. In some embodiments, an isotopic substitution (e.g., substitution of hydrogen with deuterium) may alter the physiciochemical properties of the molecules, such as metabolism and/or the rate of racemization of a chiral center.

As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized in any form, including in any solid form. In some embodiments, such entities are utilized in a particular form, for example in a particular solid form.

In some embodiments, compounds described and/or depicted herein may be provided and/or utilized in salt form.

In certain embodiments, compounds described and/or depicted herein may be provided and/or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —N($R^{N1}$)$_2$, wherein each $R^{N1}$ is, independently, H, OH, NO$_2$, N($R^{N2}$)$_2$, SO$_2$O$R^{N2}$, SO$_2$$R^{N2}$, SO$R^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "cyano," as used herein, represents a CN group.

The terms "carbocyclyl," as used herein, refer to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "St," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition (e.g., a compound, a complex or a preparation that includes a compound or complex as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

As used herein, the term "animal" refers to any member of the animal kingdom. In some embodiments, "animal" refers to humans, at any stage of development. In some embodiments, "animal" refers to non-human animals, at any stage of development. In some embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the terms "approximately" and "about" are each intended to encompass normal statistical variation as would be understood by those of ordinary skill in the art as appropriate to the relevant context. In certain embodiments, the terms "approximately" or "about" each refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population).

In the practice of the methods of the present invention, an "effective amount" of any one of the compounds of the invention or a combination of any of the compounds of the invention or a pharmaceutically acceptable salt thereof, is administered via any of the usual and acceptable methods known in the art, either singly or in combination.

As used herein, the term "combination therapy" refers to those situations in which a subject is simultaneously exposed to two or more therapeutic agents. In some embodiments, two or more compounds may be administered simultaneously; in some embodiments, such compounds may be administered sequentially; in some embodiments, such compounds are administered in overlapping dosing regimens.

As used herein, the term "dosage form" refers to a physically discrete unit of an active compound (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Prop-*

*erties, Selection, and Use*, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

The term "pure" means substantially pure or free of unwanted components (e.g., other compounds and/or other components of a cell lysate), material defilement, admixture or imperfection.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "stearoyl-CoA desaturase (SCD)-associated disorder" refers to an undesired physiological condition, disorder, or disease that is associated with and/or mediated at least in part by an SCD protein. In some instances, SCD-associated disorders are associated with excess SCD levels and/or activity. SCDs introduce a double bond in the C9-C10 position of saturated fatty acids such as palmitoyl-CoA and stearoyl-CoA which are converted to palmitoleoyl-CoA and oleoyl-CoA, respectively. One SCD gene, SCD1, has been characterized in humans for which there are two isoforms, SCD1 and SCD5. An SCD-associated disorder may be associated with and/or mediated at least in part by SCD1 and/or SCD5. Exemplary SCD-associated disorders include SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome. Additional SCD-associated disorders are described herein or known in the art.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

A "therapeutic regimen" refers to a dosing regimen whose administration across a relevant population is correlated with a desired or beneficial therapeutic outcome.

The term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

DETAILED DESCRIPTION

The invention features compounds useful for the treatment of neurological disorders, e.g., by inhibiting α-synuclein toxicity in a cell such as a neural cell, or by inhibiting SCD5 and/or SCD1 in a cell such as a neural cell. Exemplary compounds described herein include compounds having a structure according to Formula I or Formula II:

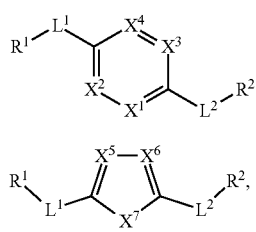

Formula I

Formula II or pharmaceutically acceptable salts thereof.

In some embodiments, the compound has the structure of any one of compounds 1-475 in Table 1. In some embodiments, the compound has the structure of any one of compounds 476-683 in Table 2.

Other embodiments, as well as exemplary methods for the synthesis or production of these compounds, are described herein.

Pharmaceutical Uses

The compounds described herein are useful in the methods of the invention and, while not bound by theory, are believed to exert their desirable effects through their ability to inhibit toxicity caused by protein aggregation, e.g., α-synuclein aggregation, in a cell.

Another aspect of the present invention relates to methods of treating and/or preventing neurological disorders such as neurodegenerative diseases in a subject in need thereof. The pathology of neurodegenerative disease may be characterized by the presence of inclusion bodies in brain tissue of affected patients.

In certain embodiments, neurological disorders that may be treated and/or prevented by the inventive methods include, but are not limited to, Alexander disease, Alper's disease, AD, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Ref sum's disease, Sandhoff disease, Schilder's disease, Steele-RichardsonOlszewski disease, tabes *dorsalis*, and Guillain-Barre Syndrome.

The compounds described herein are useful as inhibitors of stearoyl-CoA desaturase (SCD), including SCD1 and/or SCD5. SCD inhibitors are known in the art to be useful in methods of treating and/or preventing SCD-associated disorders. SCD-associated disorders are described, for example, in U.S. Pat. No. 8,148,378, and in International Patent Application Publication Nos. WO 2011/047481, WO 2010/112520, WO 2010/045374, WO 2010/028761; WO 2009150196, and WO 2009/106991. Accordingly, another aspect of the present invention relates to methods of treating and/or preventing an SCD-associated disorder in a subject in need thereof.

SCD-associated disorders include metabolic disorders (e.g., insulin resistance, diabetes mellitus (e.g., Type I diabetes, Type II diabetes, non-insulin-dependent diabetes mellitus, gestational diabetes, and diabetic complications (e.g., diabetic peripheral neuropathy, diabetic nephropathy diseases, diabetic retinopathy, diabetic macroangiopathy, vascular complications of diabetes, and diabetic arteriosclerosis)), hyperglycemia, metabolic syndrome, hyperinsulinanemia, glucose intolerance, impaired glucose tolerance, body weight disorders (e.g., obesity (e.g., abdominal obesity), overweight, cachexia, body mass index, and anorexia), lipid disorders (e.g., abnormal lipid levels (e.g., elevated lipid levels, for example, in plasma), dyslipidemia (e.g., diabetic dyslipidemia), mixed dyslipidemia, hyperlipidemia, hypertriglyceridemia, hypoalphalipoproteinemia, hyperbetalipoproteinemia, atherosclerosis, hypercholesterolemia (e.g., familial hypercholesterolemia), low HDL, high LDL, diseases related to accumulation of lipids in liver, familial histiocytic reticulosis, lipoprotein lipase deficiency, polyunsaturated fatty acid (PUFA) disorder, fatty acid desaturation index (e.g. the ratio of 18:1/18:0 fatty acids, or other fatty acids), and abnormal lipid metabolism disorders), disorders of abnormal plasma lipoprotein, disorders of pancreatic beta cell regeneration, fatty liver, nonalcoholic steatohepatitis (NASH), nonalcoholic fatty liver disease (NAFLD), hypertension, and microalbuminemia, leptin related diseases, hyperleptinaemia, appetite disorder, essential fatty acid deficiency, and adverse weight gain associated with a drug therapy).

Additional SCD-associated disorders include cancer, including solid tumors or hematological malignancies (e.g., esophageal cancer, pancreatic cancer, endometrial cancer, kidney cancer, hepatoma, thyroid cancer, gallbladder cancer, prostate cancer, leukemia (e.g., lymphomas and myelomas), ENT-related cancer, brain cancer, colon cancer, rectal cancer, colorectal cancer, ovarian cancer, uterine cancer, breast cancer, skin cancer, and prostate cancer), neoplasia, malignancy, metastases, tumors (benign or malignant), carcinogenesis, and hepatomas.

Further SCD-associated disorders include cardiovascular disease (e.g., heart disease, atherosclerosis, hypertension, lipidemia, dyslipidemia, elevated blood pressure, microalbuminemia, hyperuricaemia, hypercholesterolemia, hyperlipidemias, hypertriglyceridemias, arteriosclerosis, coronary artery disease, myocardial infarction, vascular complications of diabetes, and diabetic arteriosclerosis), inflammation, sinusitis, asthma, pancreatitis, osteoarthritis, rheumatoid arthritis, hepatitis (e.g., sexual hepatitis), meibomitis, cystic fibrosis, pre-menstrual syndrome, osteoporosis, thrombosis, cardiovascular risks, weight loss, angina, high blood pressure, ischemia, cardiac ischemia, reperfusion injury, angioplastic restenosis, infertility, liver disease (e.g., fatty liver, cirrhosis, nonalcoholic steatohepatitis, liver fibrosis, and hepatitis C related steatosis), kidney disease (e.g., tubulointerstitial fibrosis, kidney lipid accumulation, glomerular sclerosis, and proteinuria), osteoarthritis (e.g., osteoarthritis of the knee), gastro-esophageal disease, sleep apnea, secondary hyperparathyroidism of renal osteodystrophy, peripheral vascular disease, cerebrovascular disease (e.g., stroke, ischemic stroke and transient ischemic attack (TIA), and ischemic retinopathy), hyperandrogenism, malignant syndrome, extrapyramidal symptoms, hyperuricemia, hypercoagulability, syndrome X, cataract, polycystic ovary syndrome, breathing abnormalities, sleep-disordered breathing, low back pain, gout, gallstone disease, myopathies, lipid myopathies (e.g., carnitine palmitoyltransferase deficiency (CPT I or CPT II)), autoimmune diseases (e.g., lupus, host versus graft rejection, and rejection of organ transplants), asthma, inflammatory bowel diseases, nephropathy, retinopathy, erythrohepatic protoporphyria, iron overload disorders, and hereditary hemochromatosis.

Still further SCD-associated disorders include central nervous system (CNS) disorders, dementia, schizophrenia, mild cognitive impairment, Alzheimer's Disease, cerebral amyloid angiopathy, dementia associated with Down Syndrome, other neurodegenerative diseases, psychiatric disorders, eye diseases, immune disorders, multiple sclerosis, neuropathy, and depression.

Additional SCD-associated disorders include skin disorders (e.g., acne (e.g., acne vulgaris), psoriasis, hirsutism, rosacea, seborrheic skin, oily skin (syn seborrhea), seborrheic dermatitis, hyperseborrhea, eczema, keloid scar, skin ageing, diseases related to production or secretions from mucous membranes, wrinkles, lack of adequate skin firmness, lack of adequate dermal hydration, insufficient sebum secretion, oily hair, shiny skin, greasy-looking skin, greasy-looking hair, and other skin conditions caused by lipid imbalance).

An SCD-associated disorder can also include a disease or condition which is, or is related to, viral diseases or infections.

In some embodiments, the SCD-associated disorder is acne (e.g., acne vulgaris). In some embodiments, the SCD-associated disorder is diabetes (e.g., type II diabetes, including diabetes with inadequate glycemic control). In some embodiments, the SCD-associated disorder is nonalcoholic fatty liver disease (NAFLD). In some embodiments, the SCD-associated disorder is nonalcoholic steatohepatitis (NASH). In some embodiments, the SCD-associated disorder is cancer. In some embodiments, the SCD-associated disorder is obesity. In some embodiments, the SCD-associated disorder is metabolic syndrome (e.g., dyslipidemia, obesity, insulin resistance, hypertension, microalbuminemia, hyperuricaemia, and hypercoagulability), syndrome X, diabetes, insulin resistance, decreased glucose tolerance, non-insulin-dependent diabetes mellitus, Type II diabetes, Type I diabetes, diabetic complications, body weight disorders (e.g., obesity, overweight, cachexia, and anorexia), weight loss, body mass index, leptin related diseases, or a skin disorder (e.g., eczema, acne, psoriasis, and keloid scar). In some embodiments, the SCD-associated disorder is diabetes, metabolic syndrome, insulin resistance, obesity, a cardiovascular disorder, a CNS disorder, schizophrenia, or Alzheimer's disease.

Combination Formulations and Uses Thereof

The compounds of the invention can be combined with one or more therapeutic agents. In particular, the therapeutic agent can be one that treats or prophylactically treats any neurological disorder described herein.

Combination Therapies

A compound of the invention can be used alone or in combination with other agents that treat neurological disorders or symptoms associated therewith, or in combination with other types of treatment to treat, prevent, and/or reduce the risk of any neurological disorders. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

The synthesis of compounds of this invention can be synthesized according to one or more of the general schemes of 1-13 shown below. The variables recited in the general schemes below are as defined for Formulae I, II, III, and IV.

General Scheme 1

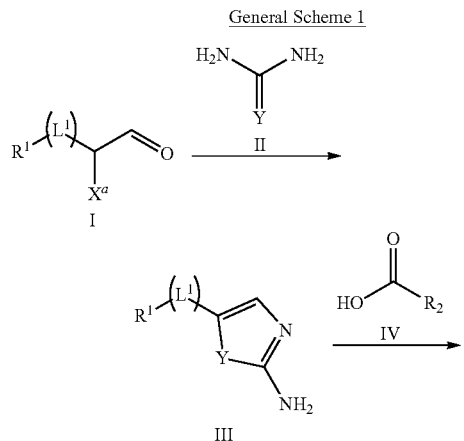

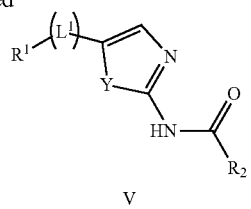

An appropriately substituted alpha-halo aldehyde I ($X^a$ is a halo, such as Cl or Br) can be condensed with urea or thiourea II to give appropriate 5-membered heterocycle III, where Y is either an O or S. This amine can be coupled with acid IV under a variety of conditions to provide the desired amide V.

General Scheme 2

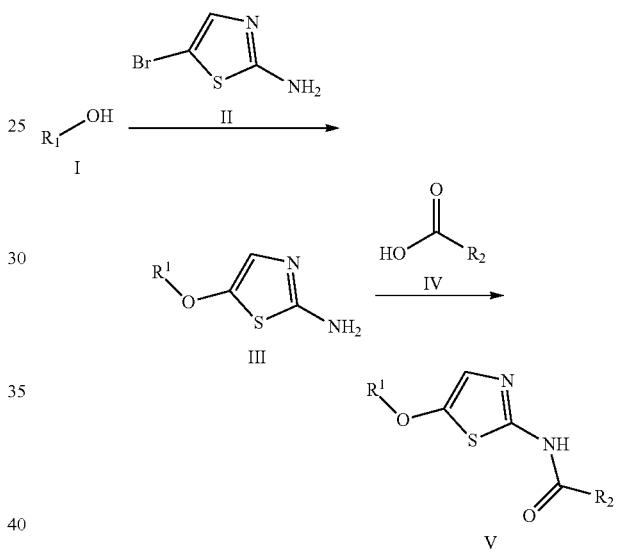

An appropriately substituted alcohol I can be reacted with a haloated heterocycle such as II under basic conditions (eg cesium carbonate) to give ether intermediate III. Coupling of amine 3 with acid IV affords the desired heterocyclic compound V.

General Scheme 3

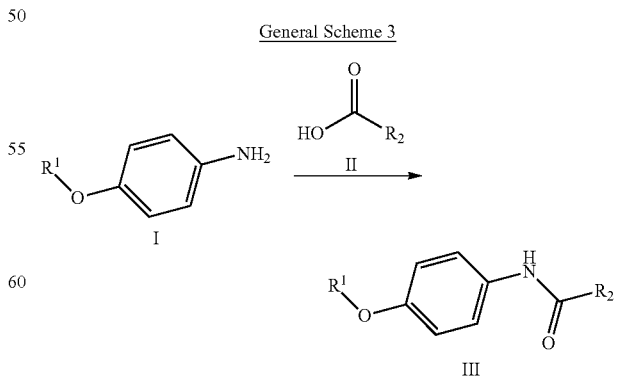

Coupling of amine I with acid II under a variety of coupling conditions affords the desired adduct III.

General Scheme 4

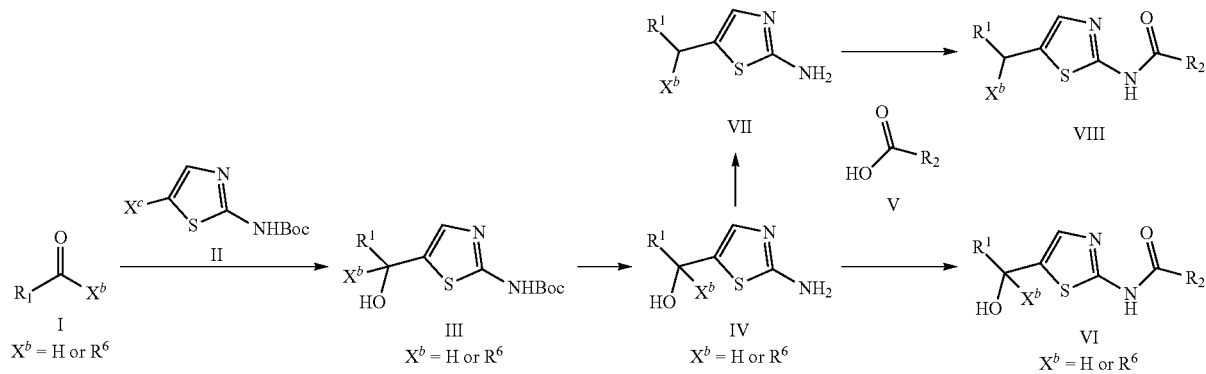

Appropriately substituted aldehyde or ketone I can be alkylated with heterocycle II (where $X^c$ is H or halide, usually bromide) under basic conditions (e.g. n-butyllithium) to give alcohol intermediate III. Deprotection of III under a variety of acidic conditions (e.g. trifluoroacetic acid) gives amine IV. Coupling of this amine IV to acid V under a variety of coupling conditions affords desired compound VI. Alternatively, deoxygenation of IV strong under acidic conditions gives intermediate VII which can be coupled with acid V under a variety of coupling conditions to give amide VIII.

General Scheme 5

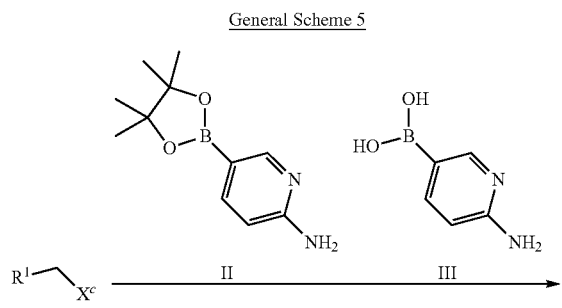

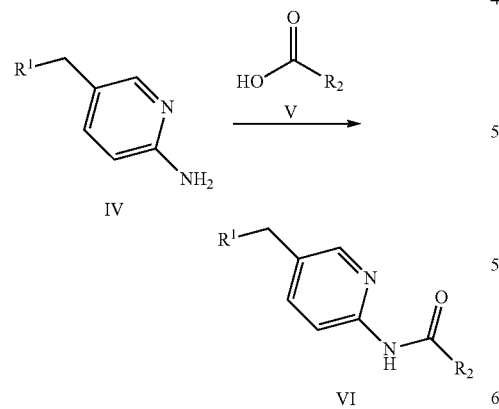

Appropriately substituted halide I can be reacted under metal catalysis conditions with appropriately substituted boronic ester II or acid III to give amine intermediate IV. Coupling of amine IV with appropriately substituted acid V under a variety of coupling conditions gives amide VI.

General Scheme 6

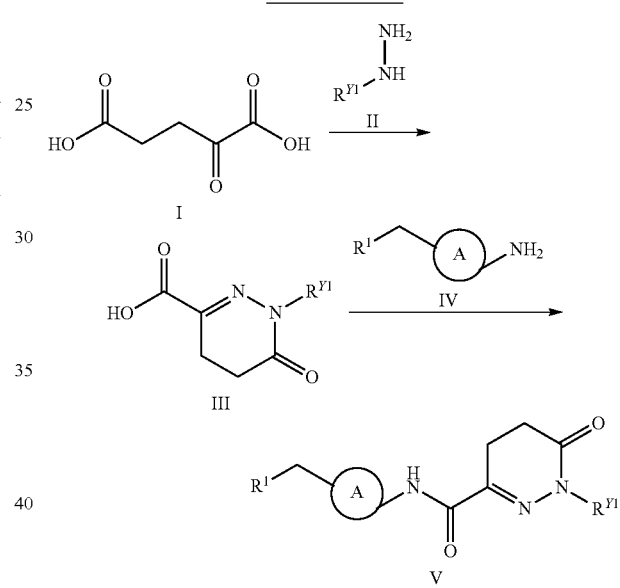

Condensation of di-acid I with appropriately substituted hydrazine II gives substituted acid III. Coupling with appropriately substituted amine IV under a variety of coupling conditions (e.g. HATU) gives amide V.

General Scheme 7

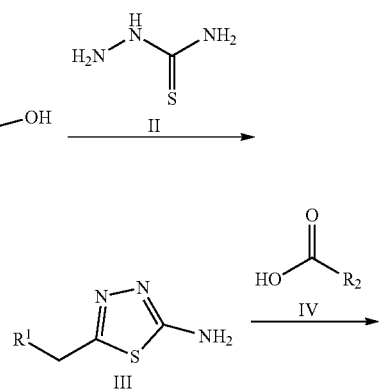

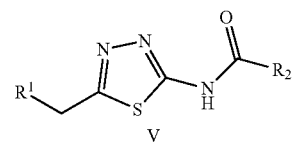

Condensation of appropriately substituted acid I with aminothiourea II gives appropriately substituted thiadiazole isomer III. Reaction of amine III with appropriately substituted acid IV under a variety of coupling conditions (e.g. HATU) yields amide V.

General Scheme 8

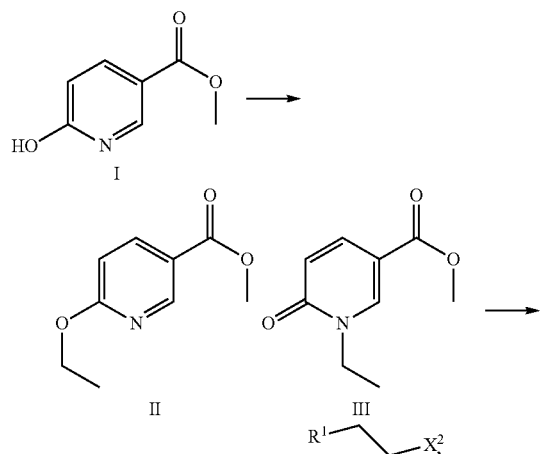

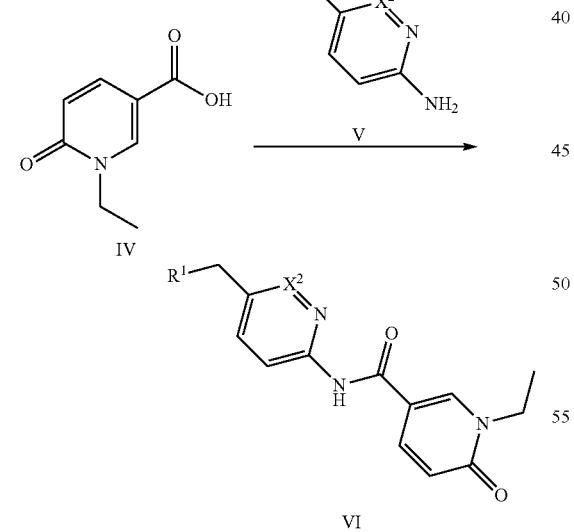

Pyridine I is alkylated with alkyl halide under basic conditions (e.g. potassium carbonate) to give two regioisomers II and III. The alkylated amide III is hydrolyzed under various conditions to give acid IV. Subsequent coupling with appropriately substituted amine V under various coupling conditions (e.g. HATU) affords amide VI.

General Scheme 9

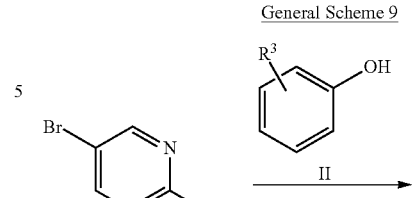

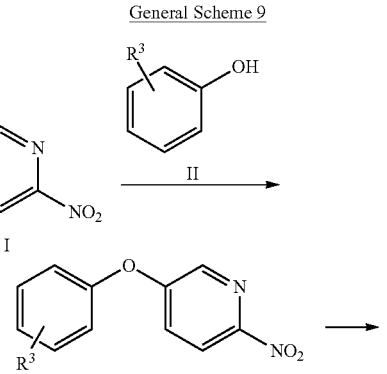

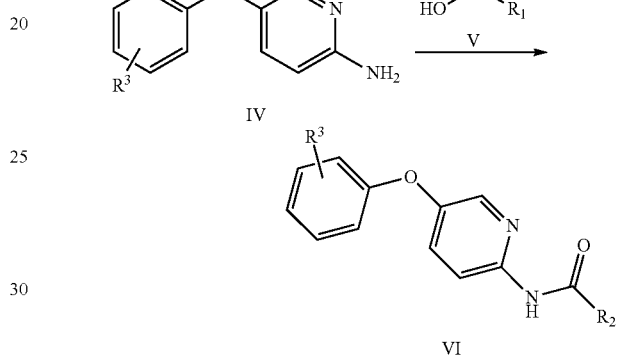

An appropriately substituted phenol II is alkylated under basic conditions with pyridine I to give ether III. Reduction of nitro group in presence of iron affords amine intermediate IV. Coupling of IV with appropriately substituted acid V under a variety of coupling conditions gives VI.

General Scheme 10

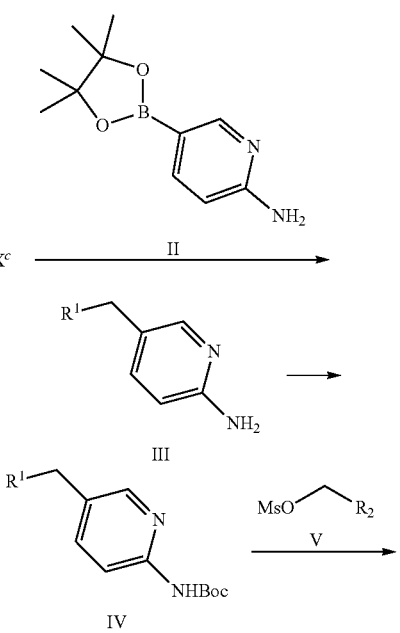

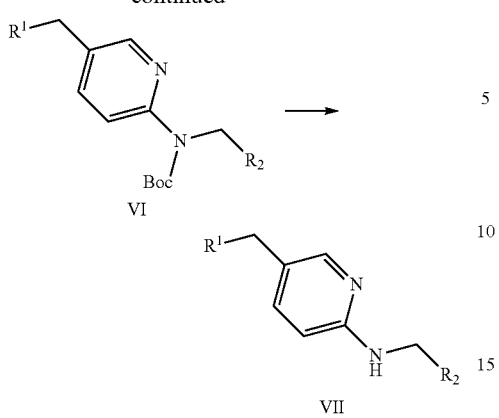

Appropriately substituted halide I can be reacted under metal catalysis conditions with appropriately substituted boronic ester II to give amine intermediate III. Protection of amine III with a carbamate group (e.g. Boc) under standard conditions affords amine intermediate IV. Displacement of mesylate V with amine IV affords product VI which can be deprotected under standard acidic conditions to give amine VII.

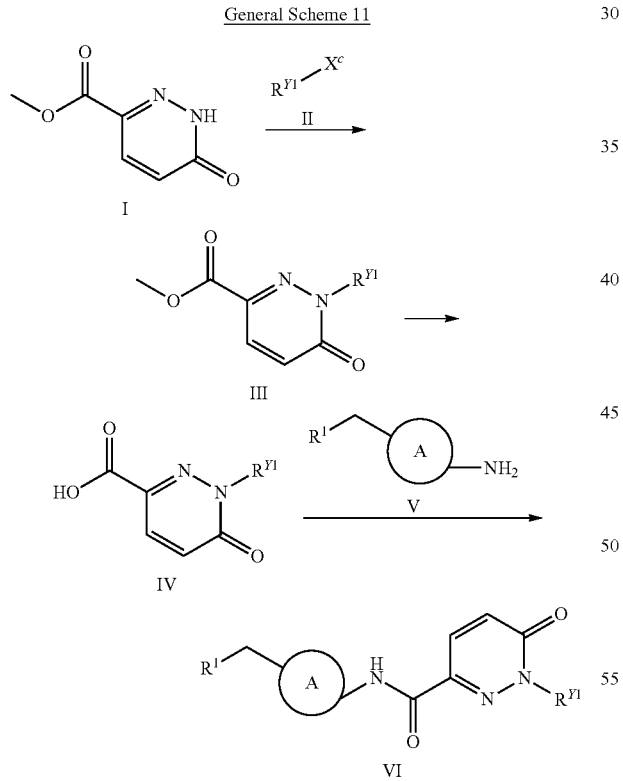

Ester I can be coupled with a variety of alkyl halides II (where $X^c$ is a halide, usually Br) to give alkylated pyridazinone III. Hydrolysis of ester under basic conditions (usually lithium hydroxide) gives acid intermediate IV. Coupling of acid IV with an appropriately substituted amine V under various peptide coupling conditions affords amide VI.

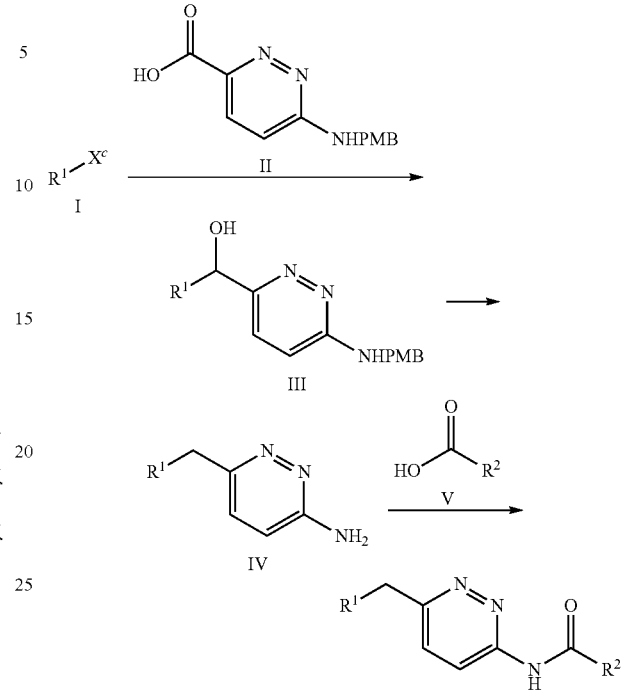

Appropriately substituted halide I (where $X^c$ is typically a bromine) is reacted with aldehyde II under basic conditions (e.g. n-butyllithium) to give alcohol III. Global deprotection of PMB and Boc groups affords amine IV which can reacted with appropriately substituted acid V under a variety of coupling conditions to give amide VI.

General Scheme 13

Appropriately substituted halide I (usually X is a bromide) is converted to zincate II. Coupling of dichloride III with zincate II under metal catalysis conditions affords chloride IV. Reaction of IV with appropriately substituted amide V under metal catalysis conditions gives amide VI.

Example 1. Preparation of N-(4-(3-fluorobenzyl)phenyl)-1-methyl-6-oxo-1,4,5,6-tetrahydropyridazine-3-carboxamide (1)

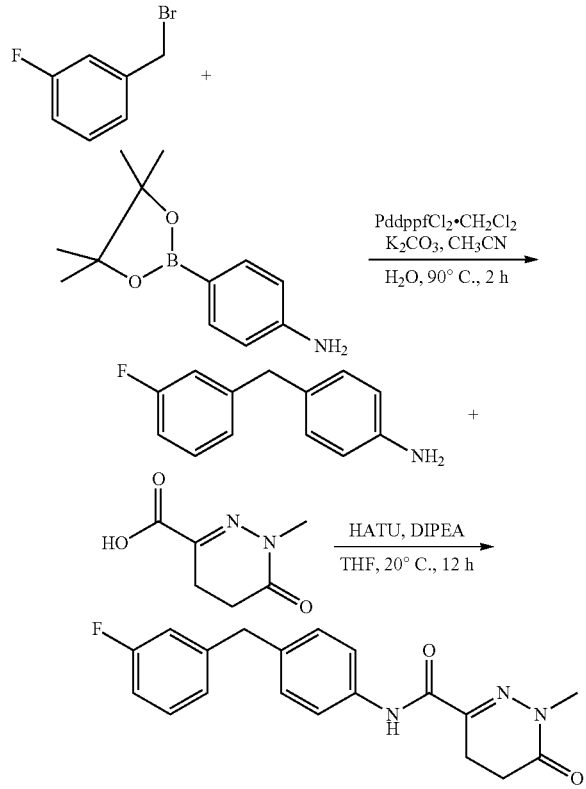

Step 1: Preparation of 4-(3-fluorobenzyl)aniline

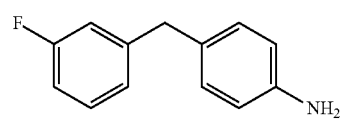 [SMILES: Nc1ccc(Cc2cccc(F)c2)cc1]

To a solution of 1-(bromomethyl)-3-fluorobenzene (2.0 g, 10.6 mmol), 4-(4,4,5,5-tetramethyl-1,3,2-dioxaborolan-2-yl)aniline (2.33 g, 10.4 mmol), potassium carbonate (2.93 g, 21.3 mmol) acetonitrile (60 mL) and water (10 mL) was added [1,1'-bis(diphenylphosphino)ferrocene]dichloropalladium(II)-dichloromethane (0.868 g, 1.06 mmol) under nitrogen. The mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then re-adjusted to pH=8-10 with aqueous sodium bicarbonate and extracted with dichloromethane (50 mL×2). The combined dichloromethane layers were dried over sodium sulfate, filtered and concentrated. Purification by column chromatography (silica gel, (petroleum ether/ethyl acetate=4/1) yields 4-(3-fluorobenzyl)aniline (0.800 g, 3.98 mmol, 38.3%) as a red oil. LCMS (ESI) m/z: 202.1 [M+H]+.

Step 2: Preparation of N-(4-(3-fluorobenzyl)phenyl)-1-methyl-6-oxo-1,4,5,6-tetrahydropyridazine-3-carboxamide

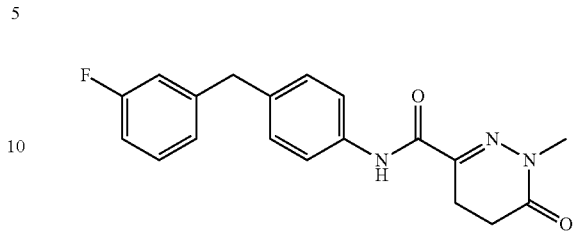

To a solution of 1-methyl-6-oxo-1,4,5,6-tetrahydropyridazine-3-carboxylic acid (0.100 g, 0.641 mmol), N,N-diisopropylethylamine (0.248 g, 1.92 mmol) in tetrahydrofuran (5 mL) at room temperature, was added [bis(dimethylamino)methylene]-1H-1,2,3-triazolo[4,5-b]pyridinium 3-oxid hexafluorophosphate (366 mg, 0.962 mmol). The reaction was stirred for 20 minutes before a solution of 4-(3-fluorobenzyl)aniline (0.129 g, 0.641 mmol) in tetrahydrofuran (1.0 mL) was added. The reaction mixture was stirred at 20° C. for 16 h. The volatiles were removed under reduced pressure and the crude material was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(3-fluorobenzyl)phenyl)-1-methyl-6-oxo-1,4,5,6-tetrahydropyridazine-3-carboxamide (0.0643 g, 0.192 mmol, 30%) as a white solid. $^1$H NMR (400 MHz, Dimethylsulfoxide-$d_6$) δ 9.95 (s, 1H), 7.66 (d, J=8.5 Hz, 1H), 7.33 (t, J=3.8 Hz, 1H), 7.21 (d, J=8.5 Hz, 2H), 6.99-7.08 (m, 3H), 3.92 (s, 2H), 3.36 (s, 3H), 2.82 (t, J=8.5 Hz, 1H), 2.48-2.50 (m, 2H); LCMS (ESI) m/z: 340.1 [M+H]+.

Example 2. Preparation of N-(4-(3-chlorobenzyl)phenyl)-1-methyl-6-oxo-1,4,5,6-tetrahydropyridazine-3-carboxamide (2)

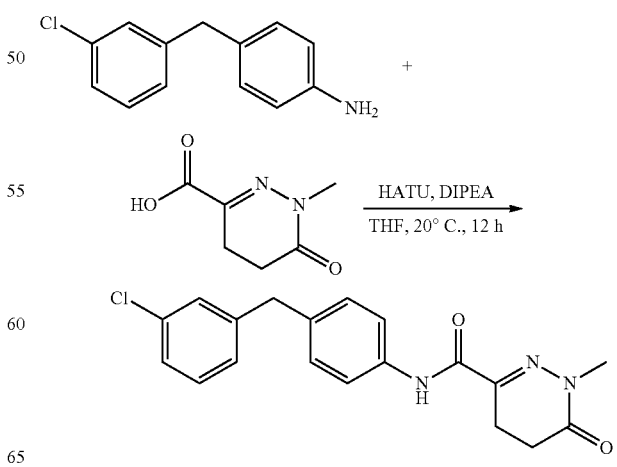

Step 1: Preparation of 4-(3-chlorobenzyl)aniline

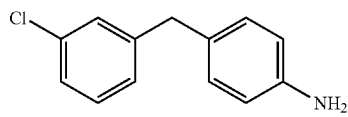 [SMILES: Nc1ccc(Cc2cccc(Cl)c2)cc1]

To a solution of 1-(bromomethyl)-3-chlorobenzene (2.0 g, 9.81 mmol), 4-(4,4,5,5-tetramethyl-1,3,2-dioxaborolan-2-yl)aniline (2.15 g, 9.81 mmol), potassium carbonate (2.71 g, 19.6 mmol) in acetonitrile (16 mL) and water (4 mL) was added 1,1'-bis(diphenylphosphino)ferrocene-palladium(II) dichloride dichloromethane (0.800 g, 0.981 mmol) under nitrogen. The mixture was heated to 90° C. and stirred for 2 h. The volatiles were removed under reduced pressure and the slurry was acidified to pH=1-3 with aqueous 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 4-(3-chlorobenzyl)aniline as a yellow oil (0.800 g, crude). LCMS (ESI) m/z: 239.1 [M+H]$^+$.

Step 2: Preparation of N-(4-(3-chlorobenzyl)phenyl)-1-methyl-6-oxo-1,4,5,6-tetrahydropyridazine-3-carboxamide

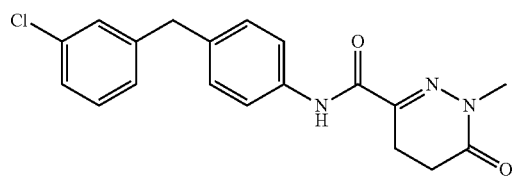 [SMILES: CN1N=C(C(=O)Nc2ccc(Cc3cccc(Cl)c3)cc2)CCC1=O]

At 20° C. 1-[bis(dimethylamino)methylene]-1H-1,2,3-triazolo[4,5-b]pyridinium 3-oxid hexafluorophosphate (0.366 g, 0.962 mmol) was added to mixture of 1-methyl-6-oxo-1,4,5,6-tetrahydropyridazine-3-carboxylic acid (0.100 g, 0.641 mmol), N,N-diisopropylethylamine (0.248 g, 1.92 mmol) and tetrahydrofuran (5 mL). The reaction was stirred for 20 minutes before a solution of 4-(3-chlorobenzyl)aniline (0.139 g, 0.641 mmol) in tetrahydrofuran (1.0 mL) was added. The reaction solution was stirred at 20° C. for 16 h. The volatiles were removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(3-chlorobenzyl)phenyl)-1-methyl-6-oxo-1,4,5,6-tetrahydropyridazine-3-carboxamide as a white solid (0.0812 g, 0.231 mmol, 36%). $^1$H NMR (400 MHz, Dimethylsulfoxide-d$_6$) δ 9.94 (s, 1H), 7.66 (d, J=8 Hz, 1H), 7.20-7.32 (m, 6H), 3.91 (s, 2H), 3.36 (s, 3H), 2.82 (t, J=8.7 Hz, 2H), 2.48-2.52 (m, 2H). LCMS (ESI) m/z: 356.1 [M+H]$^+$.

Example 3. Preparation of N-(4-(3-chlorobenzyl)phenyl)-1-methyl-6-oxo-1,6-dihydropyridazine-3-carboxamide (3)

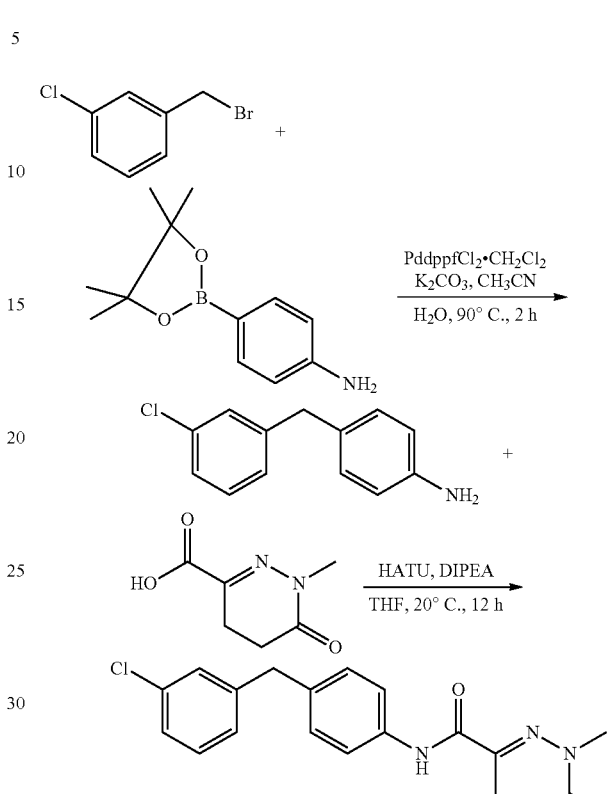

Step 1: Preparation of 4-(3-chlorobenzyl)aniline

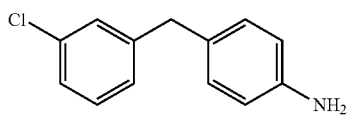 [SMILES: Nc1ccc(Cc2cccc(Cl)c2)cc1]

To a solution of 1-(bromomethyl)-3-chlorobenzene (2.0 g, 9.81 mmol), 4-(4,4,5,5-tetramethyl-1,3,2-dioxaborolan-2-yl)aniline (2.15 g, 9.81 mmol), potassium carbonate (2.71 g, 19.6 mmol) in acetonitrile (16 mL) and water (4 mL) was added 1,1'-bis(diphenylphosphino)ferrocene]dichloropalladium(II)dichloromethane complex (0.800 g, 0.981 mmol) under nitrogen. The mixture was heated to 90° C. and stirred for 2 h. The volatiles were removed under reduced pressure and the slurry was acidified to pH=1-3 with aqueous 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 4-(3-chlorobenzyl)aniline (0.800 g, crude) as a yellow oil. LCMS (ESI) m/z: 239.1 [M+H]$^+$.

Step 2: Preparation of 1-methyl-6-oxo-1,6-dihydropyridazine-3-carboxylic acid

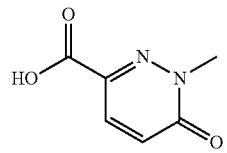

To a solution of methyl 1-methyl-6-oxo-1,6-dihydropyridazine-3-carboxylate (0.350 g, 2.08 mmol) in water (3 mL) was added sodium hydroxide (166 mg, 4.16 mmol). The reaction mixture was heated to 60° C. and stirred for 1 h. The volatiles were removed under reduced pressure to offer the crude 1-methyl-6-oxo-1,6-dihydropyridazine-3-carboxylic acid as a white solid (0.330 g, crude). LCMS (ESI) m/z: 155.1 [M+H]$^+$.

Step 3: Preparation of N-(4-(3-chlorobenzyl)phenyl)-1-methyl-6-oxo-1,6-dihydropyridazine-3-carboxamide

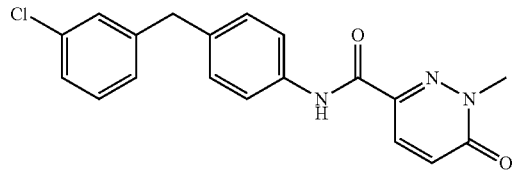 [SMILES: Cn1nc(C(=O)Nc2ccc(Cc3cccc(Cl)c3)cc2)ccc1=O]

To a solution of 1-methyl-6-oxo-1,6-dihydropyridazine-3-carboxylic acid (0.100 g, 0.649 mmol), N,N-diisopropylethylamine (0.252 g, 1.947 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.370 g, 0.974 mmol). The reaction was stirred for 20 minutes before a solution of 4-(3-chlorobenzyl)aniline (0.141 g, 0.649 mmol) in tetrahydrofuran (1.0 mL) was added. The reaction solution was stirred at 20° C. for 16 h. The volatiles were removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(3-chlorobenzyl)phenyl)-1-methyl-6-oxo-1,6-dihydropyridazine-3-carboxamide as a white solid (0.0899 g, 0.247 mmol, 38%). $^1$H NMR (400 MHz, Dimethylsulfoxide-d$_6$) δ 10.23 (s, 1H), 7.92 (d, J=10 Hz, 1H), 7.70 (d, J=8 Hz, 2H), 7.21-7.32 (m, 6H), 7.06 (d, J=9.5 Hz, 1H), 3.93 (s, 2H), 3.79 (s, 3H), 3.32 (s, 2H); LCMS (ESI) m/z: 354.1 [M+H]$^+$.

Example 4. Preparation of N-(4-(3-fluorobenzyl)phenyl)-1-methyl-6-oxo-1,6-dihydropyridazine-3-carboxamide (4)

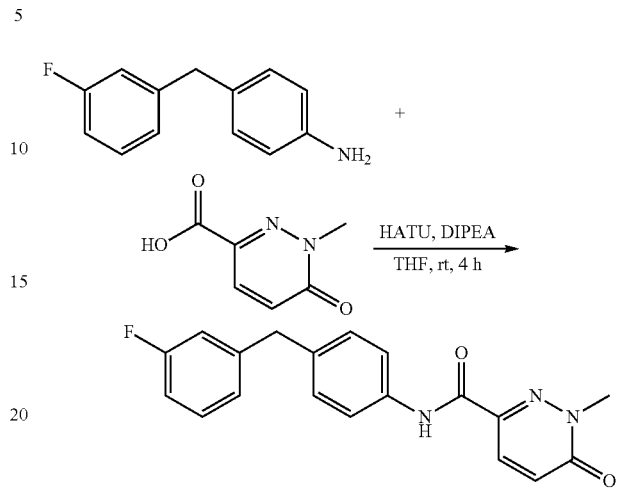

Step 1: Preparation of N-(4-(3-fluorobenzyl)phenyl)-1-methyl-6-oxo-1,6-dihydropyridazine-3-carboxamide

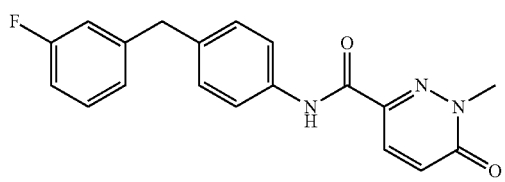 [SMILES: Cn1nc(C(=O)Nc2ccc(Cc3cccc(F)c3)cc2)ccc1=O]

To a solution of 1-methyl-6-oxo-1,6-dihydropyridazine-3-carboxylic acid (0.100 g, 0.649 mmol), N,N-diisopropylethylamine (0.252 g, 1.95 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.370 g, 0.974 mmol). The reaction was stirred for 20 minutes before a solution of 4-(3-fluorobenzyl)aniline (0.130 g, 0.649 mmol) in tetrahydrofuran (1.0 mL) was added. The solution was stirred at 20° C. for 16 h. The volatiles were removed under reduced pressure and the resulting slurry was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(3-fluorobenzyl)phenyl)-1-methyl-6-oxo-1,6-dihydropyridazine-3-carboxamide as a white solid (0.195 g, 0.571 mmol, 88%). $^1$H NMR (400 MHz, Dimethylsulfoxide-d$_6$) δ 10.23 (s, 1H), 7.92 (d, J=9 Hz, 1H), 7.70 (d, J=8.5 Hz, 2H), 7.33 (m, 1H), 7.24 (d, J=10.4 Hz, 2H), 7.01 (m, 4H), 3.94 (s, 2H), 3.79 (s, 3H); LCMS (ESI) m/z: 338.1 [M+H]$^+$.

Example 5. Preparation of N-(4-(3-fluorobenzyl)phenyl)-1-methyl-6-oxo-1,6-dihydropyridine-3-carboxamide (5)

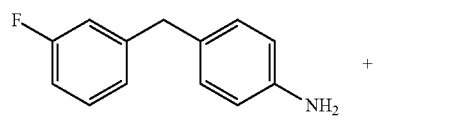

+

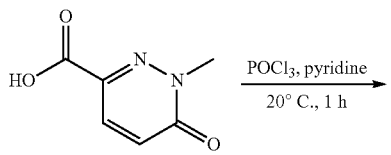

Step 1: Preparation of N-(4-(3-fluorobenzyl)phenyl)-1-methyl-6-oxo-1,6-dihydropyridine-3-carboxamide

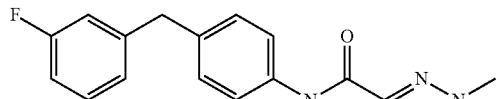

To a solution of 1-methyl-6-oxo-1,6-dihydropyridine-3-carboxylic acid (0.150 g, 0.98 mmol), 4-(3-fluorobenzyl)aniline (0.197 g, 0.98 mmol) in pyridine (5 mL) at 20° C. was added phosphorus(V) oxychloride (0.446 g, 2.94 mmol). The reaction mixture was stirred at room temperature for 1 h. Volatiles were removed under reduced pressure and the resulting solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(3-fluorobenzyl)phenyl)-1-methyl-6-oxo-1,6-dihydropyridine-3-carboxamide as a white solid (90.2 mg, 27%). $^1$H NMR (400 MHz, Dimethylsulfoxide-$d_6$) δ 9.92 (s, 1H), 8.49 (d, J=2.5 Hz, 1H), 7.95-7.97 (m, 1H), 7.61 (d, J=8.5 Hz, 2H), 7.31-7.48 (m, 1H), 7.21 (d, J=8.5 Hz, 2H), 6.99-7.06 (m, 3H), 6.45 (d, J=9 Hz, 1H), 3.93 (s, 2H), 3.51 (s, 3H); LCMS (ESI) m/z: 337.1 [M+H]$^+$.

Example 6. Preparation of N-(5-(3-fluorobenzyl)pyridin-2-yl)-1-methyl-6-oxo-1,4,5,6-tetrahydro-3-carboxamide (6)

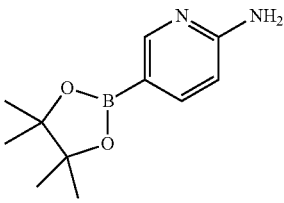

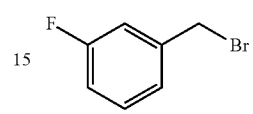

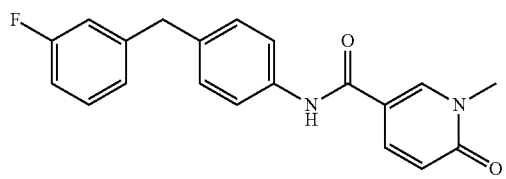 [SMILES: Cn1cc(C(=O)Nc2ccc(Cc3cccc(F)c3)cc2)ccc1=O]

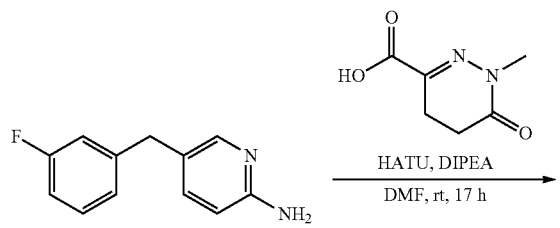

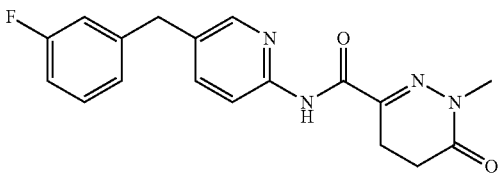

Step 1: Preparation of 5-(3-fluorobenzyl)pyridin-2-amine

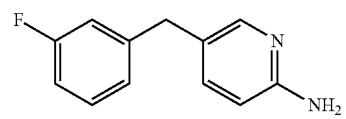

A mixture of 1-(bromomethyl)-3-fluorobenzene (0.400 g, 2.12 mmol), 5-(4,4,5,5-tetramethyl-1,3,2-dioxaborolan-2-yl)pyridin-2-amine (0.467 g, 2.12 mmol), [1,1'-bis(diphenylphosphino)ferrocene]dichloropalladium(II) (0.154 g, 0.21 mmol) and potassium carbonate (0.586 g, 4.24 mmol) in acetonitrile (40 mL) and water (10 mL) under nitrogen atmosphere was heated 80° C. for 3 h. The mixture was cooled to room temperature and concentrated under reduced pressure. The resulting residue was purified by column chromatography (silica gel, petroleum ether/ethyl acetate=1/1) to give 5-(3-fluorobenzyl)pyridin-2-amine (0.256 g, 1.27 mmol, 60%) as a yellow solid. LCMS (ESI) m/z: 203.2 [M+H]$^+$.

Step 2: Preparation of N-(5-(3-fluorobenzyl)pyridin-2-yl)-1-methyl-6-oxo-1,4,5,6-tetrahydropyridazine-3-carboxamide

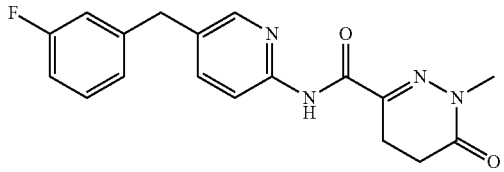 [SMILES: CN1N=C(C(=O)Nc2ccc(Cc3cccc(F)c3)cn2)CCC1=O]

The synthesis of N-(5-(3-fluorobenzyl)pyridin-2-yl)-1-methyl-6-oxo-1,4,5,6-tetrahydropyridazine-3-carboxamide followed synthetic procedure reported for Example 19 The crude sample was dissolved in minimal N,N-dimethylformamide and purified via prep-HPLC (Boston C18 21*250 mm 10 μM column; acetonitrile/0.01% aqueous trifluoroacetic acid) to give N-(5-(3-fluorobenzyl)pyridin-2-yl)-1-methyl-6-oxo-1,4,5,6-tetrahydropyridazine-3-carboxamide (0.0649 mg, 0.19 mmol, 45.4%) as a white solid. $^1$H NMR (500 MHz, Dimethylsulfoxide-$d_6$) δ 9.98 (s, 1H), 8.32 (d, J=2.0 Hz, 1H), 8.03 (d, J=8.5 Hz, 1H), 7.82 (dd, J=8.5 Hz 2.0 Hz, 1H), 7.37-7.33 (m, 1H), 7.13-7.11 (m, 2H), 7.06-7.02 (m, 1H), 3.99 (s, 2H), 3.36 (s, 3H), 2.85 (t, J=8.5 Hz, 2H), 2.53 (t, J=8.5 Hz, 2H); LCMS (ESI) m/z: 341.2 [M+H]$^+$.

Example 7. Preparation of N-(5-(4-chloro-3-fluorobenzyl)pyridin-2-yl)-1-methyl-6-oxo-1,4,5,6-tetrahydropyridazine-3-carboxamide (7)

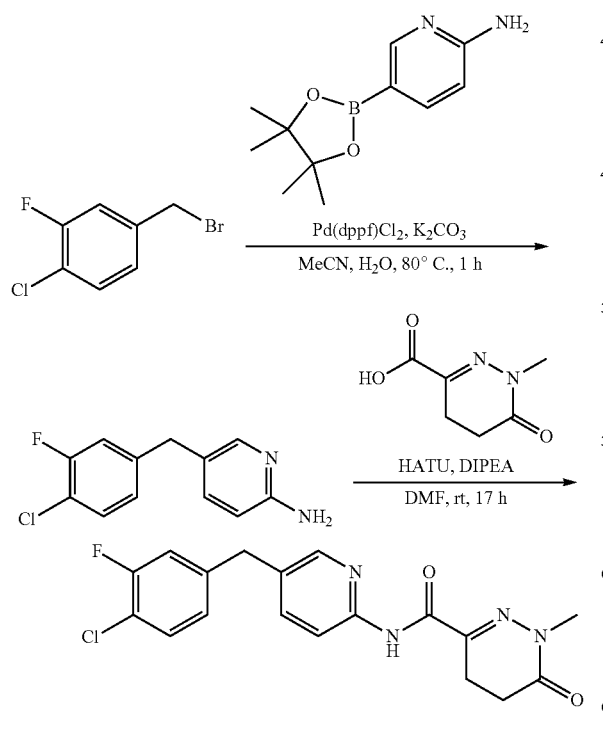

Step 1: Preparation of 5-(4-chloro-3-fluorobenzyl)pyridin-2-amine

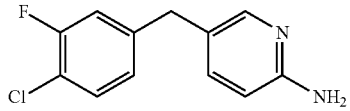 [SMILES: Nc1ccc(Cc2ccc(Cl)c(F)c2)cn1]

The synthesis of 5-(4-chloro-3-fluorobenzyl)pyridin-2-amine followed synthetic procedure reported for Example 6. The crude sample was dissolved in minimal N,N-dimethylformamide and purified via prep-HPLC (Boston C18 21*250 mm 10 μm column; acetonitrile/0.01% aqueous trifluoroacetic acid) to give 5-(4-chloro-3-fluorobenzyl)pyridin-2-amine (0.230 g, 0.97 mmol, 55%) as a yellow solid. LCMS (ESI) m/z: 237.1 [M+H]$^+$.

Step 2: Preparation of N-(5-(4-chloro-3-fluorobenzyl)pyridin-2-yl)-1-methyl-6-oxo-1,4,5,6-tetrahydropyridazine-3-carboxamide

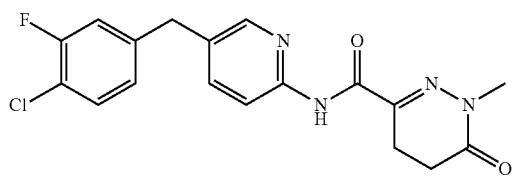 [SMILES: CN1N=C(C(=O)Nc2ccc(Cc3ccc(Cl)c(F)c3)cn2)CCC1=O]

The synthesis of N-(5-(4-chloro-3-fluorobenzyl)pyridin-2-yl)-1-methyl-6-oxo-1,4,5,6-tetrahydropyridazine-3-carboxamide followed synthetic procedure reported for Example 19. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(4-chloro-3-fluorobenzyl)pyridin-2-yl)-1-methyl-6-oxo-1,4,5,6-tetrahydropyridazine-3-carboxamide (0.0606 g, 0.16 mmol, 38.1%,) as a white solid. $^1$H NMR (500 MHz, Dimethylsulfoxide-$d_6$) δ 9.87 (s, 1H), 8.32 (d, J=2.0 Hz, 1H), 8.03 (d, J=8.5 Hz, 1H), 7.82 (dd, J=8.5 Hz 2.5 Hz, 1H), 7.52 (dd, J=7.5 Hz 2.0 Hz, 1H), 7.37-7.33 (m, 1H), 7.30-7.27 (m, 1H), 3.97 (s, 2H), 3.36 (s, 3H), 2.85 (t, J=8.5 Hz, 2H), 2.53 (t, J=8.5 Hz, 2H); LCMS (ESI) m/z: 375.1 [M+H]$^+$.

Example 8. Preparation of N-(5-(3-cyanobenzyl)pyridin-2-yl)-1-methyl-6-oxo-1,4,5,6-tetrahydropyridazine-3-carboxamide (8)

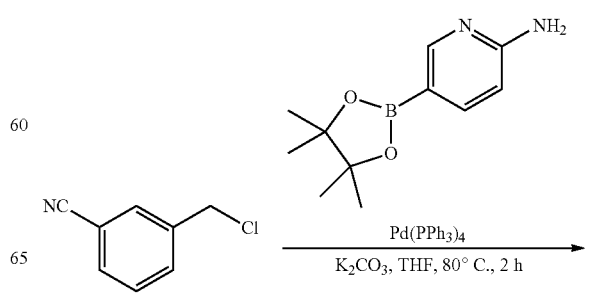

-continued

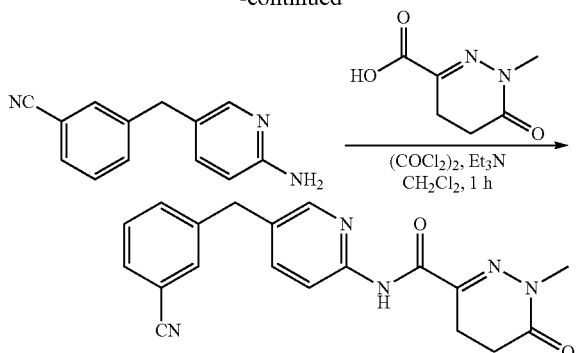

Step 1: Preparation of
3-((6-aminopyridin-3-yl)methyl)benzonitrile

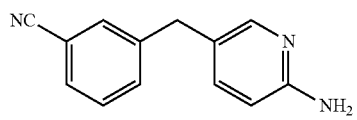 [SMILES: N#Cc1cccc(Cc2ccc(N)nc2)c1]

To a mixture of 3-(chloromethyl)benzonitrile (0.500 g, 3.31 mmol), 5-(4,4,5,5-tetramethyl-1,3,2-dioxaborolan-2-yl)pyridin-2-amine (0.948 g, 4.30 mmol) and potassium carbonate (0.913 g, 6.62 mmol) in tetrahydrofuran (8 mL) and water (2 mL) under nitrogen was added tetrakis(triphenylphosphine)palladium(0) (0.382 g, 0.331 mmol). Reaction was then heated to 80° C. and stirred for 2 h. The volatiles were removed under reduced pressure and the aqueous phase was adjusted to pH=1~3 with 1 N hydrogen chloride solution. The water layer was then extracted with ethyl acetate (50 mL) and discarded. The aqueous phase was then adjusted to pH=8-10 with aqueous sodium bicarbonate solution and extracted with dichloromethane (50 mL×2). The organic layers were dried over sodium sulfate, filtered and concentrated to yield 3-((6-aminopyridin-3-yl)methyl)benzonitrile (0.400 g, crude) as a yellow oil. LCMS (ESI) m/z: 210.2 [M+H]$^+$.

Step 2: Preparation of N-(5-(3-cyanobenzyl)pyridin-2-yl)-1-methyl-6-oxo-1,4,5,6-tetrahydropyridazine-3-carboxamide

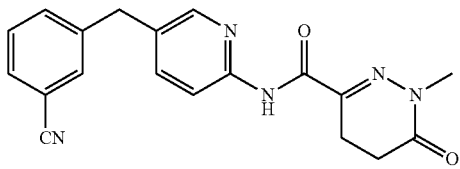 [SMILES: CN1N=C(C(=O)Nc2ccc(Cc3cccc(C#N)c3)cn2)CCC1=O]

To a solution of 1-methyl-6-oxo-1,4,5,6-tetrahydropyridazine-3-carboxylic acid (0.150 g, 0.961 mmol) in dichloromethane (2 mL) at 20° C. was added oxalyl chloride (1 mL). The reaction was stirred at room temperature for 0.5 h and concentrated in vacuo. The crude solid was dissolved in dichloromethane (4.0 mL) and added to a mixture of 3-((6-aminopyridin-3-yl)methyl)benzonitrile (0.201 g, 0.961 mmol), triethylamine (0.291 g, 2.883 mmol) in dichloromethane (5.0 mL) dropwise. The mixture was stirred for another 0.5 h and the solvent was removed under reduced pressure. The residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; the mobile phase acetonitrile/0.01% aqueous trifluoroacetic acid) to give N-(5-(3-cyanobenzyl)pyridin-2-yl)-1-methyl-6-oxo-1,4,5,6-tetrahydropyridazine-3-carboxamide (0.0162 g, 0.048 mmol, 5%) as a white solid. $^1$H NMR (400 MHz, Dimethylsulfoxide-d$_6$) δ 9.74 (s, 1H), 8.32-8.32 (d, J=1.2 Hz, 1H), 8.02-8.04 (d, J=6.8 Hz, 1H), 7.62-7.79 (m, 4H), 7.51-7.54 (t, J=6.2 Hz, 1H), 4.02 (s, 2H), 3.36 (s, 3H), 2.83-2.86 (t, J=6.8 Hz, 2H), 2.52-2.54 (m, 2H); LCMS (ESI) m/z: 348.1 [M+H]$^+$.

Example 9. Preparation of 1-methyl-6-oxo-N-(5-(4-(trifluoromethyl)benzyl)pyridin-2-yl)-1,4,5,6-tetrahydropyridazine-3-carboxamide (9)

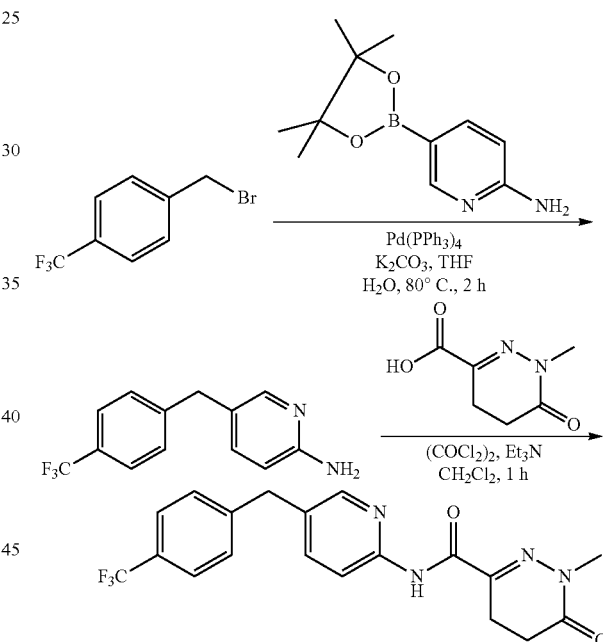

Step 1: Preparation of
5-(4-(trifluoromethyl)benzyl)pyridin-2-amine

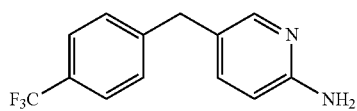

To a solution of 1-(bromomethyl)-4-(trifluoromethyl)benzene (0.500 g, 2.1 mmol), 5-(4,4,5,5-tetramethyl-1,3,2-dioxaborolan-2-yl)pyridin-2-amine (0.463 g, 2.1 mmol), potassium carbonate (0.579 g, 4.2 mmol) in tetrahydrofuran (8 mL) and water (2 mL) was added tetrakis(triphenylphosphine)palladium(0) (0.242 g, 0.21 mmol) under nitrogen.

The mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-(4-(trifluoromethyl)benzyl)pyridin-2-amine (0.310 g, crude) as a yellow oil. LCMS (ESI) m/z: 253.1 [M+H]$^+$.

Step 2: Preparation of 1-methyl-6-oxo-N-(5-(4-(trifluoromethyl)benzyl)pyridin-2-yl)-1,4,5,6-tetrahydropyridazine-3-carboxamide

To a solution of 1-methyl-6-oxo-1,4,5,6-tetrahydropyridazine-3-carboxylic acid (0.100 g, 0.641 mmol) in dichloromethane (2 mL) at 20° C. was added oxalyl chloride (1 mL). The reaction was stirred at 20° C. for 0.5 h and concentrated in vacuo. The crude solid was dissolved in dichloromethane (4 mL) and added to a mixture of 5-(4-(trifluoromethyl)benzyl)pyridin-2-amine (0.162 g, 0.641 mmol) and triethylamine (0.194 g, 1.92 mmol) in dichloromethane (5.0 mL) dropwise. The reaction was stirred at 20° C. for 20 minutes and was concentrated, in vacuo. The crude sample was purified by prep-TLC (petroleum ether/ethyl acetate=2:1) to afford 1-methyl-6-oxo-N-(5-(4-(trifluoromethyl)benzyl)pyridin-2-yl)-1,4,5,6-tetrahydropyridazine-3-carboxamide (0.0308 g, 0.0769 mmol, 12%) as a white solid. $^1$H NMR (400 MHz, Dimethylsulfoxide-d$_6$) δ 9.73 (s, 1H), 8.32 (d, J=2.0 Hz, 1H), 8.04 (d, J=6.8 Hz, 1H), 7.72-7.74 (m, 1H), 7.67 (d, J=6.4 Hz, 2H), 7.49 (d, J=6.8 Hz, 2H), 4.06 (s, 2H), 3.36 (s, 3H), 2.84 (t, J=7.0 Hz, 2H), 2.52-2.54 (m, 2H); LCMS (ESI) m/z: 391.0 [M+H]$^+$.

Example 10. Preparation of N-(5-(3-cyano-4-fluorobenzyl)pyridin-2-yl)-1-methyl-6-oxo-1,4,5,6-tetrahydropyridazine-3-carboxamide (10)

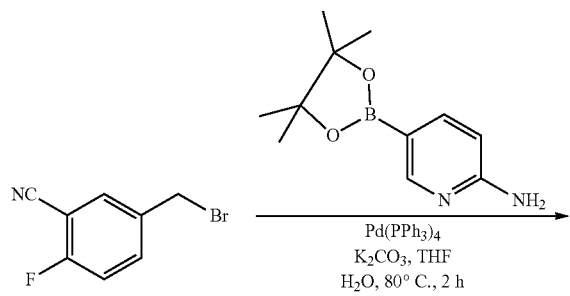

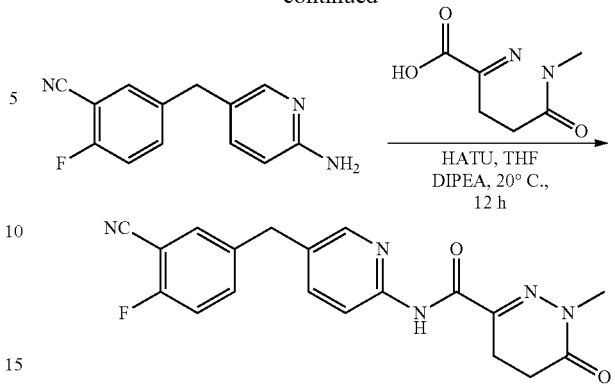

Step 1: Preparation of 5-((6-aminopyridin-3-yl)methyl)-2-fluorobenzonitrile

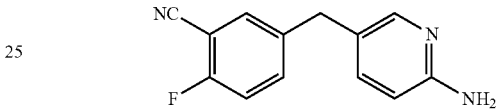

To a solution of 5-(bromomethyl)-2-fluorobenzonitrile (0.500 g, 2.35 mmol), 5-(4,4,5,5-tetramethyl-1,3,2-dioxaborolan-2-yl)pyridin-2-amine (0.517 g, 2.35 mmol), potassium carbonate (0.648 g, 4.70 mmol) in tetrahydrofuran (8 mL) and water (2 mL) was added tetrakis(triphenylphosphine)palladium(0) (0.271 g, 0.234 mmol) under nitrogen. The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-((6-aminopyridin-3-yl)methyl)-2-fluorobenzonitrile (430 mg, crude) as a yellow oil. LCMS (ESI) m/z 228.1 [M+H]$^+$.

Step 2: Preparation of N-(5-(3-cyano-4-fluorobenzyl)pyridin-2-yl)-1-methyl-6-oxo-1,4,5,6-tetrahydropyridazine-3-carboxamide

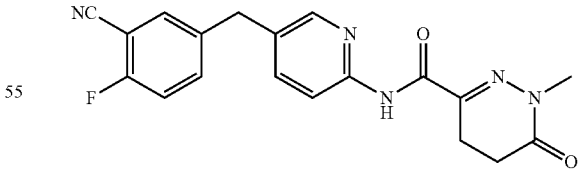

To a solution of 1-methyl-6-oxo-1,4,5,6-tetrahydropyridazine-3-carboxylic acid (0.150 g, 0.961 mmol), N,N-diisopropylethylamine (0.373 g, 2.88 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.548 g, 1.44 mmol). The reaction was stirred for 20 minutes before a solution of 5-((6-aminopyridin-3-yl)methyl)-2-fluorobenzonitrile (0.218 g, 0.961 mmol) in tetrahydrofuran (1.0 mL) was added. The solution was stirred at 20° C. for 16 h. The volatiles were removed under reduced pressure and the residue was added to a mixture of dichloromethane (50 mL) and water (50 mL). The organic layer was separated, dried over sodium sulfate, filtered and concentrated. Purification by prep-TLC (dichloromethane) afforded the desired product as a white solid (0.0672 g, 0.183 mmol, 19%). $^1$H NMR (400 MHz, Dimethylsulfoxide-d$_5$) δ 9.73 (s, 1H), 8.32 (s, 1H), 8.03 (d, J=7.2 Hz, 1H), 7.89 (d, J=4.4 Hz, 1H), 7.68-7.75 (m, 2H), 7.47 (t, J=7.2 Hz, 1H), 4.00 (s, 2H), 3.36 (s, 3H), 2.85 (t, J=6.6 Hz, 2H), 2.52-2.54 (m, 2H); LCMS (ESI) m/z: 366.1 [M+H]$^+$.

Example 11. Preparation of N-(5-(4-chloro-3-fluorobenzyl)pyridin-2-yl)-1-methyl-6-oxo-1,4,5,6-tetrahydropyridazine-3-carboxamide (11)

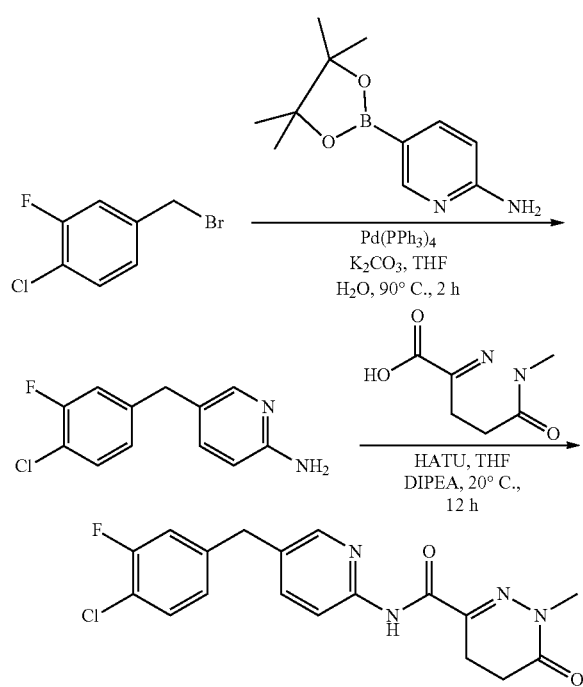

Step 1: Preparation of 5-(4-chloro-3-fluorobenzyl)pyridin-2-amine

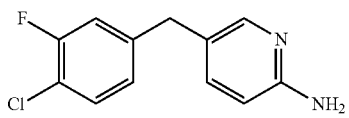

To a solution of 4-(bromomethyl)-1-chloro-2-fluorobenzene (0.500 g, 2.25 mmol), 5-(4,4,5,5-tetramethyl-1,3,2-dioxaborolan-2-yl)pyridin-2-amine (0.496 g, 2.25 mmol), potassium carbonate (0.621 g, 4.51 mmol) in tetrahydrofuran (8 mL) and water (2 mL) under nitrogen was added tetrakis(triphenylphosphine)palladium(0) (0.260 g, 0.225 mmol). The mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2).

The combined dichloromethane layers were dried over sodium sulfate, filtered and concentrated to give 5-(4-chloro-3-fluorobenzyl)pyridin-2-amine (0.250 g, crude) as a yellow oil. LCMS (ESI) m/z: 237.1 [M+H]$^+$. Used in the next step without further purification.

Step 2: Preparation of N-(5-(4-chloro-3-fluorobenzyl)pyridin-2-yl)-1-methyl-6-oxo-1,4,5,6-tetrahydropyridazine-3-carboxamide

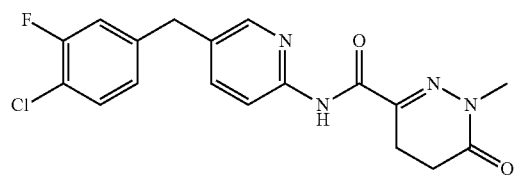 [SMILES: CN1N=C(C(=O)Nc2ccc(Cc3ccc(Cl)c(F)c3)cn2)CCC1=O]

To a mixture of 1-methyl-6-oxo-1,4,5,6-tetrahydropyridazine-3-carboxylic acid (0.150 g, 0.961 mmol), N,N-diisopropylethylamine (0.373 g, 2.88 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.548 g, 1.44 mmol). The mixture was stirred for 20 minutes before a solution of 5-(4-chloro-3-fluorobenzyl)pyridin-2-amine (0.227 g, 0.961 mmol) in tetrahydrofuran (1.0 mL) was added. The solution was stirred at 20° C. for 16 h. The volatiles were removed under reduced pressure and the residue was added to a mixture of dichloromethane (50 mL) and water (50 mL). The organic layer was separated, dried over sodium sulfate, filtered and concentrated. Purification by prep-TLC (dichloromethane) gives the desired product as a white solid (0.0515 g, 0.137 mmol, 14.3%). $^1$H NMR (400 MHz, Dimethylsulfoxide-d$_6$) δ 9.72 (s, 1H), 8.30-8.30 (d, J=1.2 Hz, 1H), 8.03 (d, J=6.8 Hz, 1H), 7.72-7.74 (m, 1H), 7.50-7.53 (t, J=6.6 Hz, 1H), 7.35-7.37 (m, 1H), 7.14 (d, J=6.4 Hz, 1H), 3.97 (s, 2H), 3.36 (s, 3H), 2.83 (t, J=10.8 Hz, 2H), 2.52-2.54 (m, 2H); LCMS (ESI) m/z: 375.1 [M+H]$^+$.

Example 12. Preparation of N-(5-(4-chlorobenzyl)pyridin-2-yl)-1-methyl-6-oxo-1,4,5,6-tetrahydropyridazine-3-carboxamide (12)

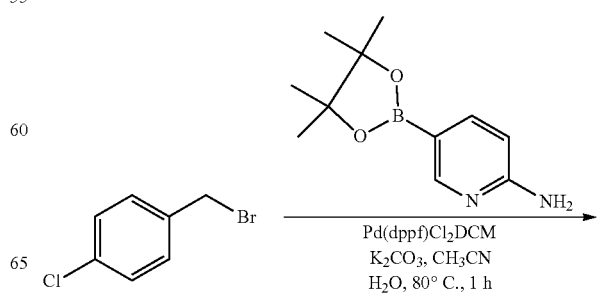

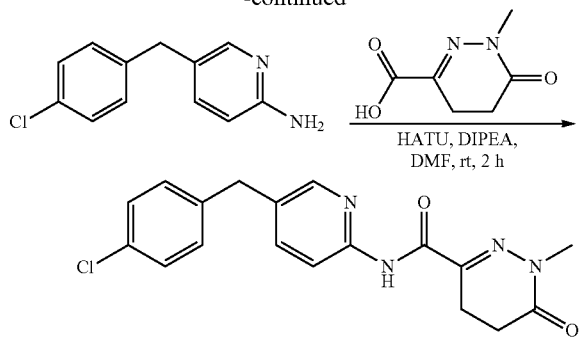

Step 1: Preparation of
5-(4-chlorobenzyl)pyridin-2-amine

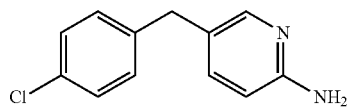

To a solution of 1-(bromomethyl)-4-chlorobenzene (0.410 g, 2 mmol), 5-(4,4,5,5-tetramethyl-1,3,2-dioxaborolan-2-yl)pyridin-2-amine (0.528 g, 2.4 mmol), potassium carbonate (0.552 g, 4 mmol) in acetonitrile (10 mL) and water (2.5 mL) was added [1,1'-bis(diphenylphosphino)ferrocene]dichloropalladium(II)dichloromethane (0.163 g, 0.2 mmol) under nitrogen. The reaction mixture was stirred at 80° C. for 1 h. The reaction mixture was filtered, and the filtrate was extracted with ethyl acetate (50 mL×2), washed with 1 N hydrogen chloride (10 mL×3). The aqueous phase was then neutralized to pH=7 with aqueous sodium bicarbonate solution and extracted with ethyl acetate (30 mL×2), washed with brine, dried with sodium sulfate, filtered and concentrated to give 5-(4-chlorobenzyl)pyridin-2-amine (250 mg, crude) as a yellow oil. LCMS (ESI) m/z: 218.9 [M+H]+. Used in the next step directly without additional purification.

Step 2: Preparation of N-(5-(4-chlorobenzyl)pyridin-2-yl)-1-methyl-6-oxo-1,4,5,6-tetrahydropyridazine-3-carboxamide

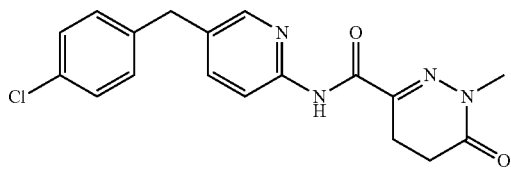 [SMILES: CN1N=C(C(=O)Nc2ccc(Cc3ccc(Cl)cc3)cn2)CCC1=O]

To a solution of 1-methyl-6-oxo-1,6-dihydropyridine-3-carboxylic acid (0.100 g, 0.65 mmol), 5-(4-chlorobenzyl)pyridin-2-amine (0.170 g, 0.78 mmol), 1-[bis(dimethylamino)methylene]-1H-1,2,3-triazolo[4,5-b]pyridinium 3-oxid hexafluorophosphate (0.371 g, 0.975 mmol) in N,N-dimethylformamide (4 mL) was added N,N-diisopropylethylamine (252 mg, 1.95 mmol). The reaction mixture was stirred at room temperature for 2 h. The reaction solution was added to ice water slowly and the precipitate was filtered. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(4-chlorobenzyl)pyridin-2-yl)-1-methyl-6-oxo-1,4,5,6-tetrahydropyridazine-3-carboxamide as a white solid (0.0613 g, 0.172 mmol 26.5%). $^1$H NMR (400 MHz, Dimethylsulfoxide-$d_6$) δ 9.87 (s, 1H), 8.29 (d, J=1.6 Hz, 1H), 8.02 (d, J=6.8 Hz, 1H), 7.75, 7.74 (dd, J=3.4, 3.4 Hz, 1H), 7.37 (t, J=3.2 Hz, 2H), 7.28 (d, J=5.6 Hz, 2H), 3.96 (s, 2H), 3.36 (s, 3H), 2.84 (t, J=6.8 Hz, 2H), 2.52 (t, J=6.8 Hz, 2H); LCMS (ESI) m/z: 357.1 [M+H]+.

Example 13. Preparation of N-(5-benzylpyridin-2-yl)-1-methyl-6-oxo-1,4,5,6-tetrahydropyridazine-3-carboxamide (13)

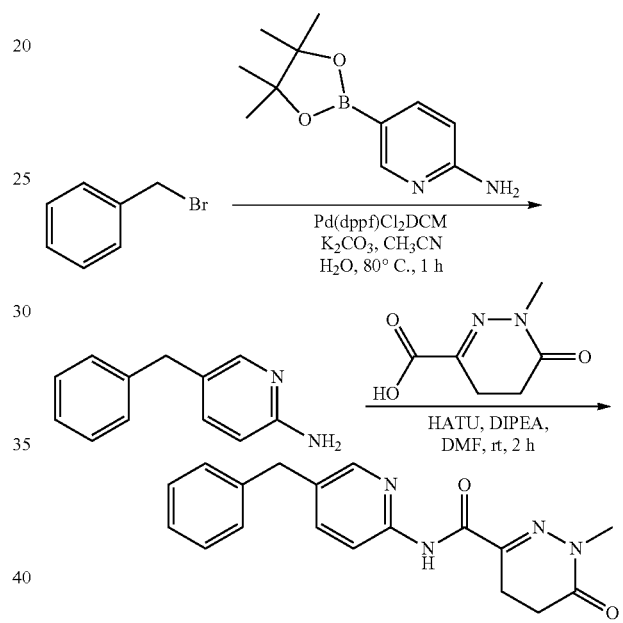

Step 1: Preparation of 5-benzylpyridin-2-amine

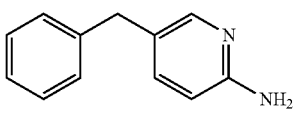

To a solution of benzyl bromide (0.471 g, 2.76 mmol), 5-(4,4,5,5-tetramethyl-1,3,2-dioxaborolan-2-yl)pyridin-2-amine (0.728 g, 3.31 mmol), potassium carbonate (0.762 g, 5.52 mmol) in acetonitrile (15 mL) and water (4 mL) at room temperature was added [1,1'-bis(diphenylphosphino)ferrocene]dichloropalladium(II)dichloromethane (0.225 g, 0.276 mmol) under nitrogen. The mixture was then stirred at 80° C. for 2 h. The reaction was filtered and the filtrate was extracted with ethyl acetate (50 mL×2) and washed with aqueous 1 N hydrogen chloride solution (10 mL×3). The aqueous phase was then neutralized to pH=7 with aqueous sodium bicarbonate solution and extracted with ethyl acetate (30 mL×2), washed with brine, dried with sodium sulfate, filtered and concentrated to give 5-benzylpyridin-2-amine as a yellow oil (0.200 g, crude); LCMS (ESI) m/z: 185.0 [M+H]+. Used in the next step directly without additional purification.

Step 2: Preparation of N-(5-benzylpyridin-2-yl)-1-methyl-6-oxo-1,4,5,6-tetrahydropyridazine-3-carboxamide

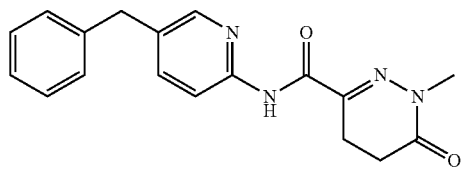 [SMILES: CN1N=C(C(=O)Nc2ccc(Cc3ccccc3)cn2)CCC1=O]

To a solution of 1-methyl-6-oxo-1,6-dihydropyridine-3-carboxylic acid (0.100 g, 0.65 mmol), 5-benzylpyridin-2-amine (0.144 g, 0.78 mmol), 1-[bis(dimethylamino)methylene]-1H-1,2,3-triazolo[4,5-b]pyridinium 3-oxid hexafluorophosphate (0.371 g, 0.975 mmol) in N,N-dimethylformamide (3 mL) was added N,N-diisopropylethylamine (0.251 g, 1.95 mmol). The reaction mixture was stirred at room temperature for 3 h. The reaction solution was poured into ice water slowly and the resulting precipitate was filtered. The crude solid was dissolved in minimal N,N-dimethylformamide and purified via prep-HPLC (Boston C18 21*250 mm 10 μm column; acetonitrile/0.01% aqueous trifluoroacetic acid) to give (0.0545 g, 0.169 mmol, 26%). 1H NMR (400 MHz, Dimethylsulfoxide-d6) δ 9.75 (s, 1H), 8.28 (d, J=1.6 Hz, 1H), 8.02 (d, J=8.4 Hz, 1H), 7.21, 7.01 (dd, J=4.2, 4.4 Hz, 1H), 7.32-7.28 (m, 2H), 7.26 (t, J=4.0 Hz, 2H), 7.22 (t, J=8.4 Hz, 1H), 3.95 (s, 2H), 3.35 (s, 3H), 2.84 (t, J=8.2 Hz, 2H), 2.52 (t, J=5.6 Hz, 2H); LCMS (ESI) m/z: 323.2. [M+H]+.

Example 14. Preparation of 1-methyl-6-oxo-N-(5-((4-(trifluoromethyl)pyridin-2-yl)methyl)pyridin-2-yl)-1,4,5,6-tetrahydropyridazine-3-carboxamide (14)

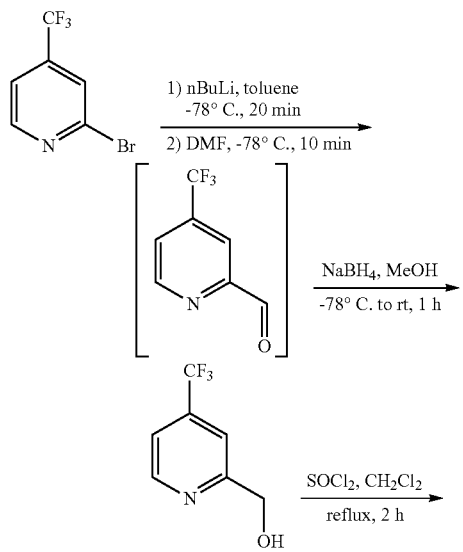

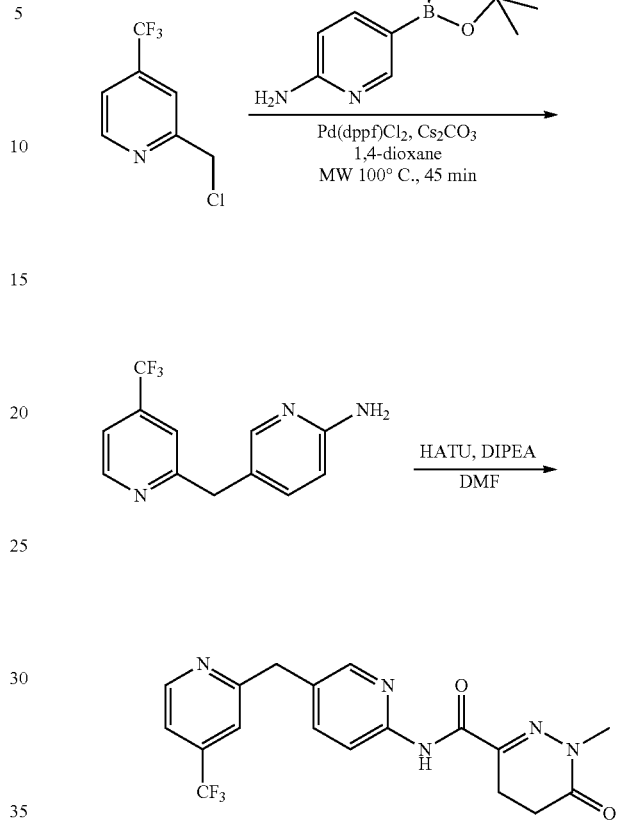

Step 1: Preparation of (4-(trifluoromethyl)pyridin-2-yl)methanol

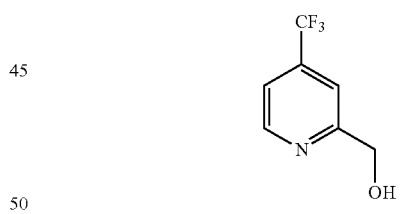

To a solution of 2-bromo-4-(trifluoromethyl)pyridine (1.5 g, 6.64 mmol) in dry toluene (20 mL), at −78° C., was added n-butyllithium (3.3 mL, 8.30 mmol, 2.5 M) dropwise under nitrogen. After the addition, the reaction was stirred at −78° C. for 10 minutes and N,N-dimethylformamide (0.77 mL, 9.95 mmol) was added dropwise at −78° C. and stirred for 10 minutes at −78° C. before sodium borohydride (0.5 g, 13.3 mmol) and methanol (3.75 mL) were added. The reaction was warmed to room temperature and stirred for 1 h. The reaction was quenched with aqueous ammonium chloride solution and extracted with ethyl acetate (30 mL×2). The combined organic phases were washed with brine (30 mL), dried over sodium sulfate, filtered and concentrated to give (4-(trifluoromethyl)pyridin-2-yl) methanol (1.1 g, 6.21 mmol, 94%) as a white solid. LCMS (ESI) 178.1 [M+H]+.

Step 2: Preparation of 2-(chloromethyl)-4-(trifluoromethyl)pyridine

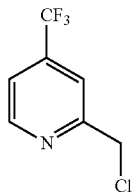

To a solution of (4-(trifluoromethyl)pyridin-2-yl)methanol (1.1 g, 6.21 mmol) in dichloromethane (25 mL) was added thionyl chloride (2 mL) dropwise at room temperature. The reaction was stirred at 60° C. for 2 h and was concentrated. The residue was diluted with dichloromethane/water (20 mL/20 mL), neutralized with aqueous sodium bicarbonate solution, and extracted with dichloromethane (20 mL×2). The combined organic phases were washed with brine (30 mL), dried over sodium sulfate, filtered and concentrated to provide 2-(chloromethyl)-4-(trifluoromethyl)pyridine (0.64 g, 3.28 mmol, 53%) as a yellow oil. $^1$H NMR (500 MHz, Chloroform-d) δ 8.78 (d, J=5 Hz, 1H), 7.75 (s, 1H), 7.50 (d, J=4.5 Hz, 1H), 4.77 (s, 2H); LCMS (ESI) m/z: 196.1 [M+H]$^+$.

Step 3: Preparation of 5-((4-(trifluoromethyl)pyridin-2-yl)methyl)pyridin-2-amine

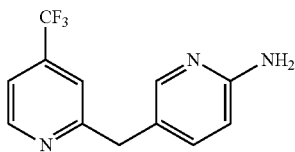 [SMILES: Nc1ccc(Cc2cc(C(F)(F)F)ccn2)cn1]

A mixture of 2-(chloromethyl)-4-(trifluoromethyl)pyridine (0.34 g, 1.74 mmol), 5-(4,4,5,5-tetramethyl-1,3,2-dioxaborolan-2-yl)pyridin-2-amine (0.46 g, 2.09 mmol), [1,1'-bis(diphenylphosphino)ferrocene]dichloropalladium(II) (0.13 g, 0.17 mmol) and cesium carbonate (1.1 g, 3.48 mmol) in 1,4-dioxane (12 mL) was stirred at 100° C. in a microwave for 45 minutes. The volatiles were removed under reduced pressure. The residue was diluted with ethyl acetate/water (20 mL/20 mL), extracted with ethyl acetate (30 mL×2). The combined organic phases were washed with brine (30 mL), dried over sodium sulfate, filtered and concentrated. The crude sample was purified by column chromatography (Biotage, 40 g silica gel, eluted with methanol/dichloromethane=1:8, containing 0.5% 7 N ammonia in methanol, in dichloromethane from 30% to 40%) to afford 5-((4-(trifluoromethyl)pyridin-2-yl)methyl)pyridin-2-amine (0.17 g, 0.67 mmol, 38.6%) as a yellow solid. LCMS (ESI) m/z: 254.1 [M+H]$^+$.

Step 4: Preparation of 1-methyl-6-oxo-N-(5-((4-(trifluoromethyl)pyridin-2-yl)methyl)pyridin-2-yl)-1,4,5,6-tetrahydropyridazine-3-carboxamide

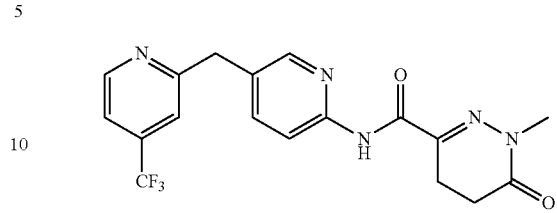

Followed the same procedure as for Example 213 using 5-((4-(trifluoromethyl)pyridin-2-yl)methyl)pyridin-2-amine (0.15 g, 0.59 mmol). The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give 1-methyl-6-oxo-N-(5-((4-(trifluoromethyl)pyridin-2-yl)methyl)pyridin-2-yl)-1,4,5,6-tetrahydropyridazine-3-carboxamide (0.090 g, 0.23 mmol, 39%) as a white solid. $^1$H NMR (500 MHz, Dimethylsulfoxide-d$_6$) δ 9.73 (s, 1H), 8.78 (d, J=5 Hz, 1H), 8.35 (d, J=2 Hz, 1H), 8.03 (d, J=8.5 Hz, 1H), 7.65-7.80 (m, 2H), 7.63 (d, J=4.5 Hz, 1H), 4.24 (s, 2H), 3.36 (s, 3H), 2.85 (t, J=8.5 Hz, 2H), 2.53 (t, J=8.5 Hz, 2H); LCMS (ESI) m/z: 392.1 [M+H]$^+$.

Example 15. Preparation of N-(5-(3-chlorobenzyl)pyridin-2-yl)-1-methyl-6-oxo-1,4,5,6-tetrahydropyridazine-3-carboxamide (15)

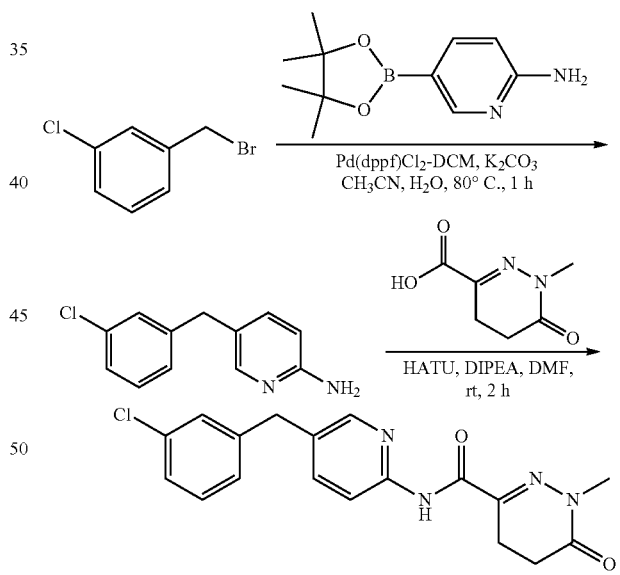

Step 1: Preparation of 5-(3-chlorobenzyl)pyridin-2-amine

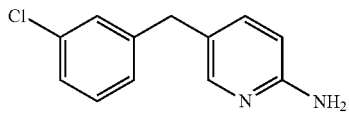 [SMILES: Nc1ccc(Cc2cccc(Cl)c2)cn1]

A mixture of 1-(bromomethyl)-3-chlorobenzene (0.157 g, 0.77 mmol), 5-(4,4,5,5-tetramethyl-1,3,2-dioxaborolan-2-yl)pyridin-2-amine (0.220 g, 1.00 mmol), [1,1'-bis(diphenylphosphino)ferrocene]dichloropalladium(II)-dichloromethane (0.063 g, 0.077 mmol) and potassium carbonate (0.213 g, 1.54 mmol) in acetonitrile (4.00 mL) and water (1.00 mL) under nitrogen atmosphere was heated to 80° C. for 1 h. The mixture was concentrated, under reduced pressure and the residue was purified by column chromatography (silica gel, petroleum ether/ethyl acetate=1/1) to yield 5-(3-chlorobenzyl)pyridin-2-amine (0.137 g, 0.63 mmol, 81.6%) as a pale-yellow solid. LCMS (ESI) m/z: 219.1 [M+H]$^+$.

Step 2: Preparation of N-(5-(3-chlorobenzyl)pyridin-2-yl)-1-methyl-6-oxo-1,4,5,6-tetrahydropyridazine-3-carboxamide

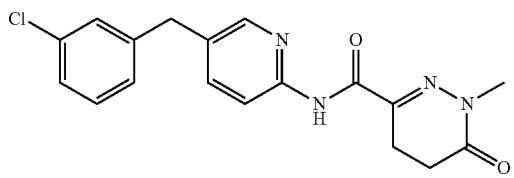

To a stirred solution of 5-(3-chlorobenzyl)pyridin-2-amine (0.130 g, 0.60 mmol), 1-methyl-6-oxo-1,4,5,6-tetrahydropyridazine-3-carboxylic acid (0.113 g, 0.72 mmol) and 1-[bis(dimethylamino)methylene]-1H-1,2,3-triazolo[4,5-b]pyridinium 3-oxid hexafluorophosphate (0.274 g, 0.72 mmol) in N,N-dimethylformamide (5.00 mL) was added N,N-diisopropylethylamine (0.232 g, 1.80 mmol). After addition, the reaction mixture was stirred at room temperature for 2 h. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give N-(5-(3-chlorobenzyl)pyridin-2-yl)-1-methyl-6-oxo-1,4,5,6-tetrahydropyridazine-3-carboxamide (0.040 g, 0.11 mmol, 18.7%) as a grey solid. $^1$H NMR (500 MHz, Dimethylsulfoxide-d$_6$) δ 9.71 (s, 1H), 8.30 (d, J=1.9 Hz, 1H), 8.03 (d, J=8.5 Hz, 1H), 7.73 (dd, J=8.5, 2.2 Hz, 1H), 7.40-7.07 (m, 4H), 3.96 (s, 2H), 3.36 (s, 3H), 2.85 (t, J=8.5 Hz, 2H), 2.53 (d, J=8.5 Hz, 2H); LCMS (ESI) m/z: 357.1. [M+H]$^+$.

Example 16. Preparation of N-(4-(3-chlorobenzyl)pyridin-2-yl)-1-methyl-6-oxo-1,4,5,6-tetrahydropyridazine-3-carboxamide (16)

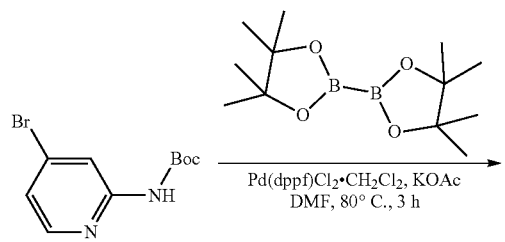

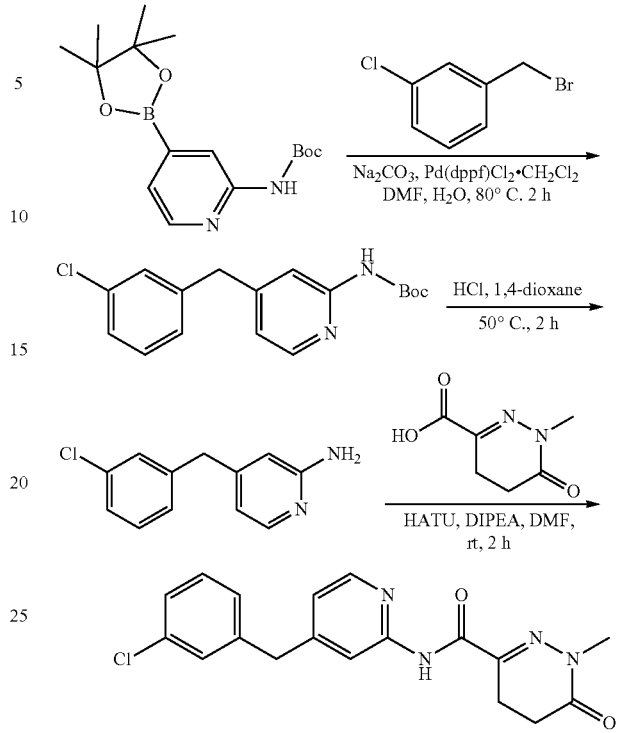

Step 1: Preparation of tert-butyl 4-(3-chlorobenzyl)pyridin-2-ylcarbamate

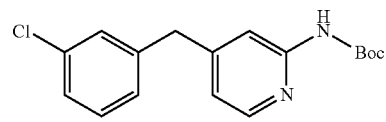 [SMILES: CC(C)(C)OC(=O)Nc1cc(Cc2cccc(Cl)c2)ccn1]

A mixture of tert-butyl 4-bromopyridin-2-ylcarbamate (0.301 g, 1.10 mmol), 4,4,4',4',5,5,5',5'-octamethyl-2,2'-bi(1,3,2-dioxaborolane) (0.309 g, 1.22 mmol), potassium acetate (0.356 g, 3.36 mmol) and [1,1'-bis(diphenylphosphino)ferrocene]dichloropalladium(II)-dichloromethane (0.048 g, 0.066 mmol) in dry N,N-dimethylformamide (7.5 mL) was stirred at 80° C. for 3 h under nitrogen. After being cooled to room temperature, 1-(bromomethyl)-3-chlorobenzene (0.150 g, 0.73 mmol, [1,1'-bis(diphenylphosphino)ferrocene]dichloropalladium(II)-dichloromethane (0.048 g, 0.066 mmol), sodium carbonate (0.0583 g, 5.5 mmol) and water (2.5 mL) were added. The mixture was stirred at 85° C. for 2 h under nitrogen atmosphere. The reaction was concentrated, under reduced pressure, and the residue was purified by column chromatography (silica gel, petroleum ether/ethyl acetate=1/1) to obtain tert-butyl 4-(3-chlorobenzyl)pyridin-2-ylcarbamate (0.036 g, 0.11 mmol, 10.3% for 2 steps) as a white solid. LCMS (ESI) m/z: 319.1 [M+H]$^+$.

Step 2: Preparation of 4-(3-chlorobenzyl)pyridin-2-ammonium chloride

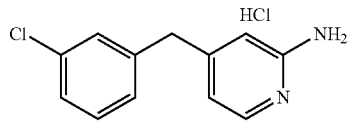 [SMILES: Cl ; Nc1cc(Cc2cccc(Cl)c2)ccn1]

A solution of tert-butyl 4-(3-chlorobenzyl)pyridin-2-yl-carbamate (0.036 g, 0.11 mmol) in hydrogen chloride (2 mL, 4 M in 1,4-dioxane) was stirred at 50° C. for 2 h. After being concentrated, compound 4-(3-chlorobenzyl)pyridin-2-ammonium chloride (0.027 g, 0.106 mmol, 96.4%) was obtained as a white solid which was used in next step without further purification. LCMS (ESI) for m/z: 219.1 [M+H]$^+$.

Step 3: Preparation of N-(4-(3-chlorobenzyl)pyridin-2-yl)-1-methyl-6-oxo-1,4,5,6-tetrahydropyridazine-3-carboxamide

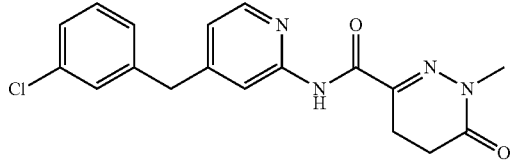

To a stirred solution of 4-(3-chlorobenzyl)pyridin-2-ammonium chloride (0.027 g, 0.106 mmol), 1-methyl-6-oxo-1,4,5,6-tetrahydropyridazine-3-carboxylic acid (0.020 g, 0.127 mmol) and 1-[bis(dimethylamino)methylene]-1H-1,2,3-triazolo[4,5-b]pyridinium 3-oxid hexafluorophosphate (0.048 g, 0.127 mmol) in N,N-dimethylformamide (1.50 mL) was added N,N-diisopropylethylamine (0.041 g, 0.318 mmol). After addition, the reaction mixture was stirred at room temperature for 2 h. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give N-(4-(3-chlorobenzyl)pyridin-2-yl)-1-methyl-6-oxo-1,4,5,6-tetrahydropyridazine-3-carboxamide (0.011 g, 0.03 mmol, 29.2%) as a white solid. $^1$H NMR (500 MHz, Dimethylsulfoxide-d$_6$) δ 9.77 (s, 1H), 8.27 (d, J=5.1 Hz, 1H), 7.99 (s, 1H), 7.36 (t, J=7.7 Hz, 2H), 7.33-7.27 (m, 1H), 7.24 (d, J=7.5 Hz, 1H), 7.10 (dd, J=5.1, 1.3 Hz, 1H), 4.03 (s, 2H), 2.84 (t, J=8.5 Hz, 2H), 2.65-2.38 (m, 5H); LCMS (ESI) m/z: 357.1 [M+H]$^+$.

Example 17. Preparation of N-(5-(4-fluorobenzyl)pyridin-2-yl)-1-methyl-6-oxo-1,4,5,6-tetrahydropyridazine-3-carboxamide (17)

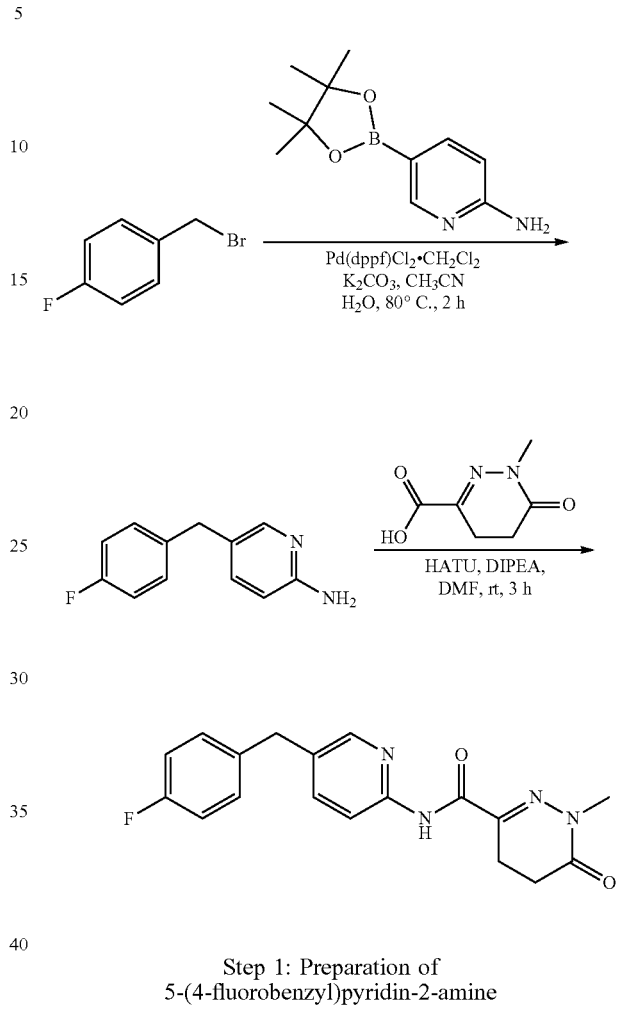

Step 1: Preparation of 5-(4-fluorobenzyl)pyridin-2-amine

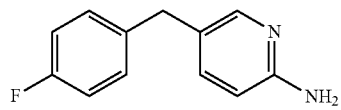 [SMILES: Nc1ccc(Cc2ccc(F)cc2)cn1]

To a mixture of 1-(bromomethyl)-4-fluorobenzene (0.378 g, 2 mmol), 5-(4,4,5,5-tetramethyl-1,3,2-dioxaborolan-2-yl)pyridin-2-amine (0.528 g, 2.4 mmol) and potassium carbonate (0.552 g, 4 mmol) in acetonitrile (10 mL) and water (2.5 mL) was added [1,1'-bis(diphenylphosphino)ferrocene]dichloropalladium(II)dichloromethane (0.163 g, 0.2 mmol) under nitrogen. The mixture was stirred at 80° C. for 2 h before it was filtered. The filtrate was extracted with ethyl acetate (50 mL×2) and washed with aqueous 1 N hydrogen chloride (10 mL×3). The aqueous phase was then neutralized with aqueous sodium bicarbonate solution and extracted with ethyl acetate (30 mL×2). Combined organic layers were washed with brine, dried over sodium sulfate, filtered and concentrated to give 5-(4-fluorobenzyl)pyridin-2-amine (0.250 g, crude) as a brown oil. LCMS (ESI) m/z: 203.0 [M+H]$^+$. Use in the next step without additional purification.

Step 2: Preparation of N-(5-(4-fluorobenzyl)pyridin-2-yl)-1-methyl-6-oxo-1,4,5,6-tetrahydropyridazine-3-carboxamide

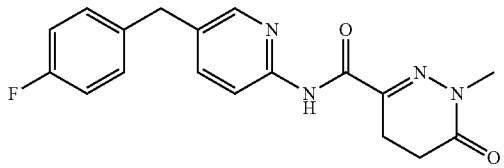 [SMILES: CN1N=C(C(=O)Nc2ccc(Cc3ccc(F)cc3)cn2)CCC1=O]

To a solution of 1-methyl-6-oxo-1,6-dihydropyridine-3-carboxylic acid (0.100 g, 0.65 mmol), 5-(4-fluorobenzyl)pyridin-2-amine (0.158 g, 0.78 mmol), 1-[bis(dimethylamino)methylene]-1H-1,2,3-triazolo[4,5-b]pyridinium 3-oxid hexafluorophosphate (0.371 g, 0.975 mol) in N,N-dimethylformamide (3 mL) was added N,N-diisopropylethylamine (0.251 g, 1.95 mmol). The reaction mixture was stirred at room temperature for 3 h. The reaction mixture was added to ice water slowly and resulting precipitate was filtered. The crude solid was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give N-(5-(4-fluorobenzyl)pyridin-2-yl)-1-methyl-6-oxo-1,4,5,6-tetrahydropyridazine-3-carboxamide (0.0777 g, 0.229 mmol, 35.2%) as a white solid. $^1$H NMR (400 MHz, Dimethylsulfoxide-$d_6$) δ 9.76 (s, 1H), 8.28 (d, J=2.0 Hz, 1H), 8.02 (d, J=8.4 Hz, 1H), 7.70 (dd, J=4.4, 4.2 Hz, 1H), 7.37-7.27 (m, 2H), 7.15-7.09 (m, 2H), 3.94 (s, 2H), 3.35 (s, 3H), 2.84 (t, J=8.6 Hz, 2H), 2.52 (t, J=8.5 Hz, 2H); LCMS (ESI) m/z: 341.2 [M+H]$^+$.

Example 18. Preparation of 1-methyl-6-oxo-N-(5-(3-(trifluoromethyl)benzyl)pyridin-2-yl)-1,4,5,6-tetrahydropyridazine-3-carboxamide (18)

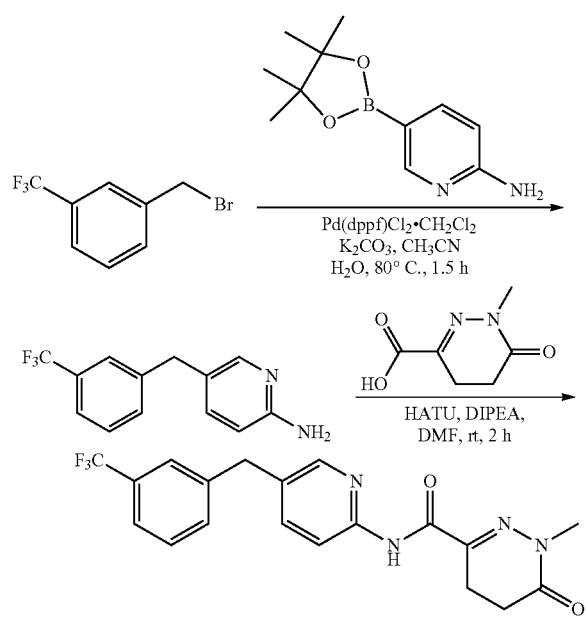

Step 1: Preparation of 5-(3-(trifluoromethyl)benzyl)pyridin-2-amine

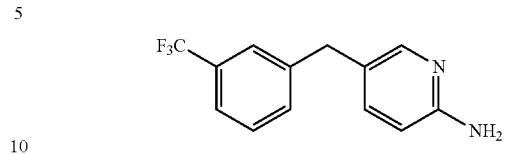

To a solution of 1-(bromomethyl)-3-(trifluoromethyl)benzene (0.406 g, 1.7 mmol), 5-(4,4,5,5-tetramethyl-1,3,2-dioxaborolan-2-yl)pyridin-2-amine (0.411 g, 1.87 mmol), potassium carbonate (0.469 g, 3.4 mmol) in acetonitrile (9 mL) and water (3 mL) at room temperature was added [1,1'-bis(diphenylphosphino)ferrocene]dichloropalladium(II)dichloromethane (0.139 g, 0.17 mmol) under nitrogen. The reaction mixture was stirred at 80° C. for 1.5 h. The reaction mixture was filtered and the filtrate was extracted with ethyl acetate (50 mL×2). The combined organic layers were washed with 1 N hydrogen chloride (30 mL×2). Aqueous layer was then neutralized with aqueous sodium bicarbonate solution and then extracted with ethyl acetate (50 mL×2). The combined organic layers were washed with brine, dried over sodium sulfate, filtered and concentrated to provide 5-(3-(trifluoromethyl)benzyl)pyridin-2-amine as an oil (0.230 g, crude); LCMS (ESI) m/z: 253.1 [M+H]$^+$. Used in the next step without additional purification.

Step 2: Preparation of 1-methyl-6-oxo-N-(5-(3-(trifluoromethyl)benzyl)pyridin-2-yl)-1,4,5,6-tetrahydropyridazine-3-carboxamide

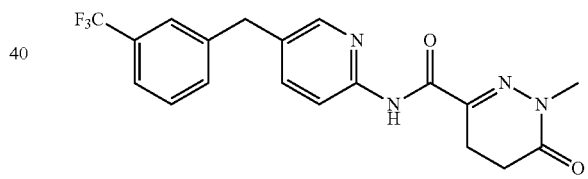

A solution of 1-methyl-6-oxo-1,6-dihydropyridine-3-carboxylic acid (0.100 g, 0.65 mmol), 5-(3-(trifluoromethyl)benzyl)pyridin-2-amine (0.144 g, 0.78 mmol), 1-[bis(dimethylamino)methylene]-1H-1,2,3-triazolo[4,5-b]pyridinium 3-oxid hexafluorophosphate (0.371 g, 0.975 mmol) and N,N-diisopropylethylamine (0.252 g, 1.95 mmol) in N,N-dimethylformamide (3 mL) was stirred at room temperature for 2 h. The reaction mixture was poured into ice water and the precipitate was filtered. The crude solid was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give 1-methyl-6-oxo-N-(5-(3-(trifluoromethyl)benzyl)pyridin-2-yl)-1,4,5,6-tetrahydropyridazine-3-carboxamide as a white solid (0.0665 g, 25.2%). $^1$H NMR (400 MHz, Dimethylsulfoxide-$d_6$) δ 9.80 (s, 1H), 8.33 (d, J 2.0 Hz, 1H), 8.03 (d, J=6.8 Hz, 1H), 7.7 (dd, J=3.4, 3.6 Hz, 1H), 7.65 (s, 1H), 7.59-7.54 (m, 3H), 4.07 (s, 2H), 3.35 (s, 3H), 2.84 (t, J=6.8 Hz, 2H), 2.52 (t, J=6.6 Hz, 2H); LCMS (ESI) m/z: 391.1. [M+H]$^+$.

Example 19. Preparation of N-(5-((1,3-dihydroisobenzofuran-5-yl)methyl)pyridin-2-yl)-1-methyl-6-oxo-1,4,5,6-tetrahydropyridazine-3-carboxamide (19)

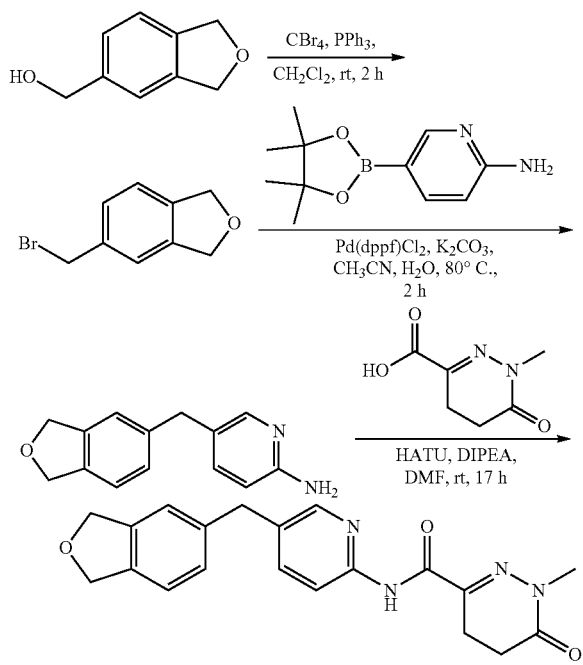

Step 1: Preparation of 5-(bromomethyl)-1,3-dihydroisobenzofuran

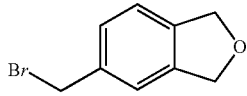

To a solution of (1,3-dihydroisobenzofuran-5-yl)methanol (0.900 g, 6 mmol) in dichloromethane (36 mL) was added carbon tetrabromide (2.78 g, 8.4 mmol) and triphenylphosphine (2.2 g, 8.4 mmol). The reaction mixture was stirred at room temperature for 2 h. Concentration and purification with column chromatography (silica gel, petroleum ether/ethyl acetate=4/1) affords 5-(bromomethyl)-1,3-dihydroisobenzofuran as a white solid (1.1 g, 86.6%); LCMS (ESI) for m/z: 215.1 [M+H]⁺. Used directly in the next step.

Step 2: Preparation of 5-((1,3-dihydroisobenzofuran-5-yl)methyl)pyridin-2-amine

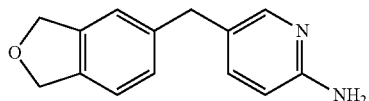

To a solution of 5-(bromomethyl)-1,3-dihydroisobenzofuran (0.530 g, 2.5 mmol), 5-(4,4,5,5-tetramethyl-1,3,2-dioxaborolan-2-yl)pyridin-2-amine (0.660 g, 3 mmol) and potassium carbonate (0.690 g, 5 mmol) at 80° C. in acetonitrile (12 mL) and water (3 mL) was added [1,1'-bis(diphenylphosphino)ferrocene]dichloropalladium(II)dichloromethane (0.204 g, 0.25 mmol). Reaction was stirred for 2 h at 80° C. before it was extracted with ethyl acetate (50 mL×2). Combined organic layers were washed with brine (50 mL), dried over sodium sulfate, filtered and concentrated.

Purification with column chromatography (silica gel, petroleum ether/ethyl acetate=1:2) affords 5-((1,3-dihydroisobenzofuran-5-yl)methyl)pyridin-2-amine (0.370 g, 1.64 mmol, 65.5%) as a white solid; LCMS (ESI) m/z: 227.1 [M+H]⁺.

Step 3: Preparation of N-(5-((1,3-dihydroisobenzofuran-5-yl)methyl)pyridin-2-yl)-1-methyl-6-oxo-1,4,5,6-tetrahydropyridazine-3-carboxamide

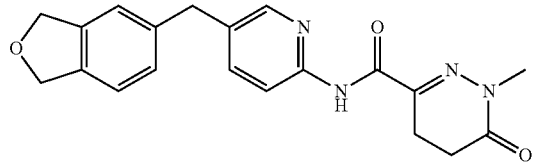 [SMILES: CN1N=C(C(=O)Nc2ccc(Cc3ccc4c(c3)COC4)cn2)CCC1=O]

A solution of 1-methyl-6-oxo-1,4,5,6-tetrahydropyridazine-3-carboxylic acid (0.100 g, 0.64 mmol), 5-((1,3-dihydroisobenzofuran-5-yl)methyl)pyridin-2-amine (0.159 g, 0.704 mmol), 1-[bis(dimethylamino)methylene]-1H-1,2,3-triazolo[4,5-b]pyridinium 3-oxid hexafluorophosphate (0.365 g, 0.96 mmol) and N,N-diisopropylethylamine (0.248 mg, 1.92 mmol) in N,N-dimethylformamide (3 mL) was stirred at room temperature for 17 h. Resulting precipitate was filtered and with washed with methanol and water followed by freeze drying to offer N-(5-((1,3-dihydroisobenzofuran-5-yl)methyl)pyridin-2-yl)-1-methyl-6-oxo-1,4,5,6-tetrahydropyridazine-3-carboxamide (0.0757 g, 0.208 mmol, 32.5%) as a white solid. ¹H NMR (500 MHz, Dimethylsulfoxide-d₆) δ9.70 (s, 1H), 8.2 (d, J=1.9 Hz, 1H), 8.01 (d, J=8.5 Hz, 1H), 7.70 (dd, J=8.5, 2.2 Hz, 1H), 7.23 (d, J=7.5 Hz, 1H), 7.17 (d, J=8.0 Hz, 2H), 4.95 (s, 4H), 3.96 (s, 2H), 3.36 (s, 3H), 2.84 (t, J=8.5 Hz, 2H), 2.52 (t, J=7.3 Hz, 2H); LCMS (ESI) m/z: 354.1 [M+H]⁺.

Example 20. Preparation of N-(5-(3,4-dichlorobenzyl)pyridin-2-yl)-1-methyl-6-oxo-1,4,5,6-tetrahydropyridazine-3-carboxamide (20)

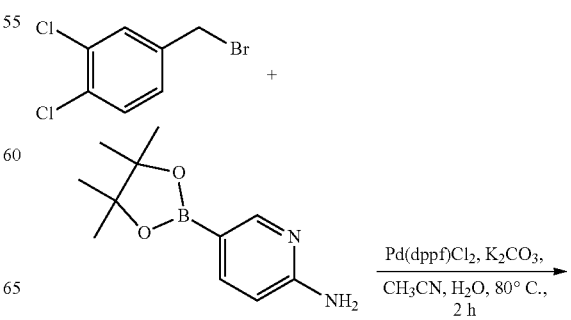

Step 1: Preparation of 5-(3,4-dichlorobenzyl)pyridin-2-amine

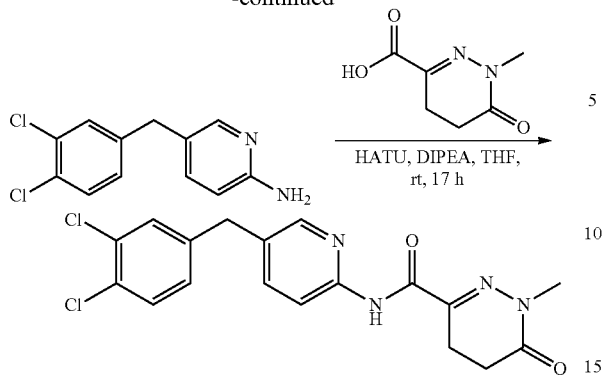

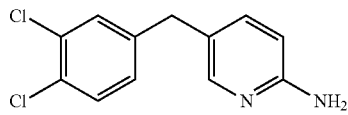 [SMILES: Nc1ccc(Cc2ccc(Cl)c(Cl)c2)cn1]

To a solution of 4-(bromomethyl)-1,2-dichlorobenzene (0.720 g, 3 mmol), 5-(4,4,5,5-tetramethyl-1,3,2-dioxaborolan-2-yl)pyridin-2-amine (0.726 mg, 3.3 mmol), potassium carbonate (0.828 mg, 6 mmol) in acetonitrile (15 mL) and water (4 mL) was added [1,1'-bis(diphenylphosphino)ferrocene]dichloropalladium(II)dichloromethane (0.245 mg, 0.3 mmol). Reaction mixture was stirred at 80° C. for 2 h. The reaction mixture was filtered, extracted with ethyl acetate (100 mL×2). The combined organics layers was washed with brine (100 mL), dried over sodium sulfate, filtered and concentrated to offer 5-(3,4-dichlorobenzyl)pyridin-2-amine as a brown oil (0.380 g, 1.5 mmol, 50%); LCMS (ESI) m/z: 253.0 [M+H]$^+$.

Step 2: Preparation of N-(5-(3,4-dichlorobenzyl)pyridin-2-yl)-1-methyl-6-oxo-1,4,5,6-tetrahydropyridazine-3-carboxamide

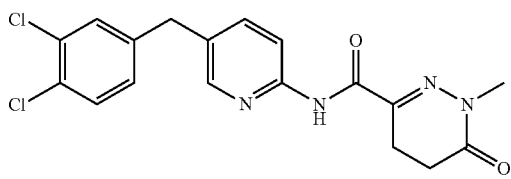

A solution of 1-methyl-6-oxo-1,4,5,6-tetrahydropyridazine-3-carboxylic acid (0.100 g, 0.64 mmol), 5-(3,4-dichlorobenzyl)pyridin-2-amine (0.178 g, 0.7 mmol), 1-[bis(dimethylamino)methylene]-1H-1,2,3-triazolo[4,5-b]pyridinium 3-oxid hexafluorophosphate (0.365 g, 0.96 mmol) and N,N-diisopropylethylamine (0.248 g, 1.92 mmol) in tetrahydrofuran (5 mL) was stirred at room temperature for 17 h. Volatiles were removed under reduced pressure. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to yield N-(5-(3,4-dichlorobenzyl)pyridin-2-yl)-1-methyl-6-oxo-1,4,5,6-tetrahydropyridazine-3-carboxamide (0.128 g, 0.326 mmol, 51%) as a white solid. $^1$H NMR (500 MHz, Dimethylsulfoxide-d$_6$) δ 9.82 (s, 1H), 8.31 (d, J=1.5 Hz, 1H), 8.04 (d, J=8.5 Hz, 1H), 7.77 (dd, J=8.5, 2.2 Hz, 1H), 7.56 (d, J=5.8 Hz, 2H), 7.26 (dd, J=8.3, 1.9 Hz, 1H), 3.96 (s, 2H), 3.36 (s, 3H), 2.84 (t, J=8.5 Hz, 2H), 2.52 (d, J=9.0 Hz, 2H); LCMS (ESI) m/z: 391.0 [M+H]$^+$.

Example 21. Preparation of N-(5-((5-chlorothiophen-2-yl)methyl)pyridin-2-yl)-1-methyl-6-oxo-1,4,5,6-tetrahydropyridazine-3-carboxamide (21)

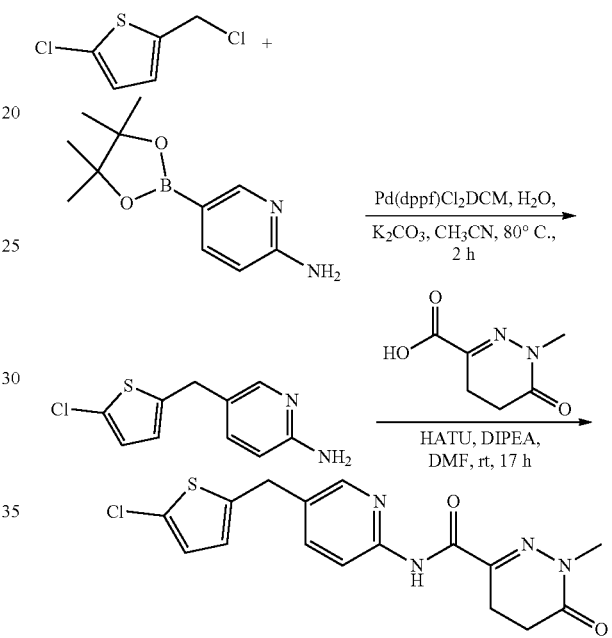

Step 1: Preparation of 5-((5-chlorothiophen-2-yl)methyl)pyridin-2-amine

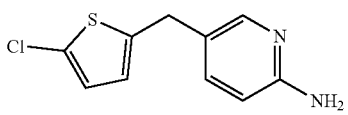 [SMILES: Nc1ccc(Cc2ccc(Cl)s2)cn1]

To a solution of 2-chloro-5-(chloromethyl)thiophene (0.830 g, 5 mmol), 5-(4,4,5,5-tetramethyl-1,3,2-dioxaborolan-2-yl)pyridin-2-amine (1.21 g, 5.5 mmol) and potassium carbonate (1.38 g, 10 mmol) in acetonitrile (24 mL) and water (6 mL) was added [1,1'-bis(diphenylphosphino)ferrocene]dichloropalladium(II)dichloromethane (0.408 g, 0.5 mmol). Reaction mixture was stirred at 80° C. for 2 h and then it was extracted with ethyl acetate (100 mL×2).

The combined organic layers were washed with brine (80 mL), dried over sodium sulfate, filtered and concentrated. The crude residue was purified by column chromatography (silica gel, petroleum ether/ethyl acetate=2/1) to give 5-((5-chlorothiophen-2-yl)methyl)pyridin-2-amine as a brown solid (0.600 g, 2.24 mmol, 44.8%); LCMS (ESI) m/z: 225.1 [M+H]$^+$.

Step 2: Preparation of N-(5-((5-chlorothiophen-2-yl)methyl)pyridin-2-yl)-1-methyl-6-oxo-1,4,5,6-tetrahydropyridazine-3-carboxamide

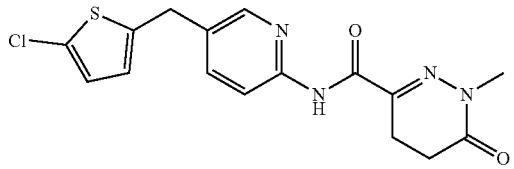 [SMILES: CN1N=C(C(=O)Nc2ccc(Cc3ccc(Cl)s3)cn2)CCC1=O]

A solution of 1-methyl-6-oxo-1,4,5,6-tetrahydropyridazine-3-carboxylic acid (0.173 g, 0.77 mmol), 5-((5-chlorothiophen-2-yl)methyl)pyridin-2-amine (0.100 g, 0.64 mmol), 1-[bis(dimethylamino)methylene]-1H-1,2,3-triazolo[4,5-b]pyridinium 3-oxid hexafluorophosphate (0.365 g, 0.96 mmol) and N,N-diisopropylethylamine (0.248 g, 1.92 mmol) in N,N-dimethylformamide (3 mL) was stirred at room temperature for 17 h. Volatiles were removed under reduced pressure. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to yield N-(5-((5-chlorothiophen-2-yl)methyl)pyridin-2-yl)-1-methyl-6-oxo-1,4,5,6-tetrahydropyridazine-3-carboxamide (0.0787 g, 0.218 mmol, 34%) as a white solid. $^1$H NMR (500 MHz, Dimethylsulfoxide-$d_6$) δ 9.79 (s, 1H), 8.30 (d, J=2.0 Hz, 1H), 8.06 (d, J=8.5 Hz, 1H), 7.76 (dd, J=8.5, 2.2 Hz, 1H), 6.96 (d, J=3.7 Hz, 1H), 6.81 (d, J=3.7 Hz, 1H), 4.12 (s, 2H), 3.36 (s, 3H), 2.85 (t, J=8.5 Hz, 2H), 2.52 (d, J=9.3 Hz, 2H); LCMS (ESI) m/z: 363.1 [M+H]$^+$.

Example 22. Preparation of N-(5-(3,5-difluorobenzyl)pyridin-2-yl)-1-methyl-6-oxo-1,4,5,6-tetrahydropyridazine-3-carboxamide (22)

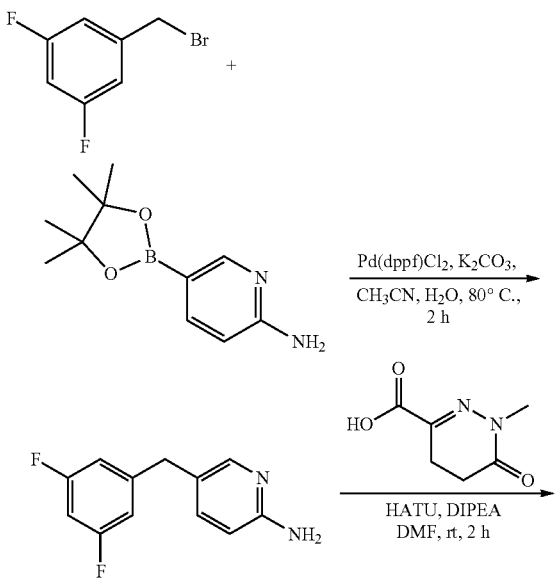

Step 1: Preparation of 5-(3,5-difluorobenzyl)pyridin-2-amine

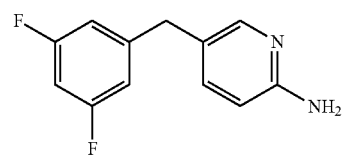 [SMILES: Nc1ccc(Cc2cc(F)cc(F)c2)cn1]

To a solution of 1-(bromomethyl)-3,5-difluorobenzene (1.0 g, 4.83 mmol), 5-(4,4,5,5-tetramethyl-1,3,2-dioxaborolan-2-yl)pyridin-2-amine (1.28 g, 5.8 mmol), potassium carbonate (1.33 g, 9.66 mmol) in acetonitrile (24 mL) and water (6 mL) at room temperature was added [1,1'-bis(diphenylphosphino)ferrocene]dichloropalladium(II)dichloromethane (0.394 g, 0.483 mmol). The reaction mixture was stirred at 80° C. for 2 h before it was extracted with ethyl acetate (50 mL×2). The combined organic layers were washed with brine (50 mL), dried over sodium sulfate, filtered and concentrated. Purification by column chromatography (silica gel, petroleum ether/ethyl acetate=1/1) gives -(3,5-difluorobenzyl)pyridin-2-amine (0.700 g, 3.19 mmol, 66%) as a brown oil. LCMS (ESI) m/z: 211.1 [M+H]$^+$.

Step 2: Preparation of N-(5-(3,5-difluorobenzyl)pyridin-2-yl)-1-methyl-6-oxo-1,4,5,6-tetrahydropyridazine-3-carboxamide

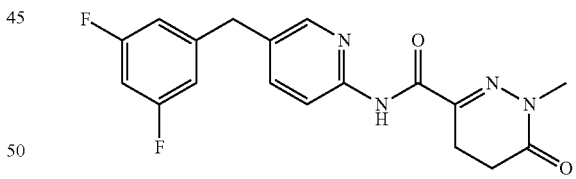

A solution of 1-methyl-6-oxo-1,4,5,6-tetrahydropyridazine-3-carboxylic acid (0.125 g, 0.8 mmol), 5-(3,5-difluorobenzyl)pyridin-2-amine (0.211 g, 0.96 mmol), 1-[bis(dimethylamino)methylene]-1H-1,2,3-triazolo[4,5-b]pyridinium 3-oxid hexafluorophosphate (0.456 g, 1.2 mol) and N,N-diisopropylethylamine (0.310 g, 2.4 mmol) in N,N-dimethylformamide (3.5 mL) was stirred at room temperature for 2 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,5-difluorobenzyl)pyridin-2-yl)-1-methyl-6-oxo-1,4,5,6-tetrahydropyridazine-3-carboxamide as a white solid (0.120 g, 0.336 mmol, 42%). $^1$H NMR (500 MHz, Dimethylsulfoxide-$d_6$) δ 9.72 (s, 1H), 8.32 (d, J=2.0 Hz, 1H), 8.03 (d, J=8.5 Hz, 1H), 7.75 (dd, J=8.5, 2.3 Hz, 1H), 7.08-7.02 (m, 3H), 3.97 (s, 2H), 3.36 (s, 3H), 2.85 (t, J=8.5 Hz, 2H), 2.52 (d, J=9.0 Hz, 2H); LCMS (ESI) m/z: 359.0 [M+H]⁺.

Example 23. Preparation of N-(5-(3-cyclopropylbenzyl)pyridin-2-yl)-1-methyl-6-oxo-1,4,5,6-tetrahydropyridazine-3-carboxamide (23)

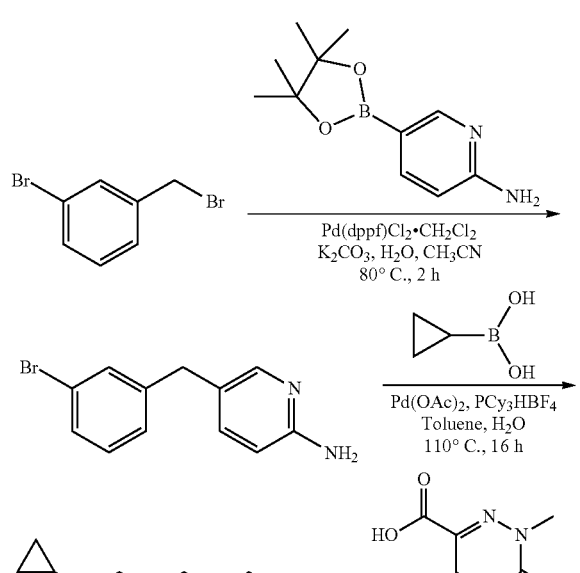

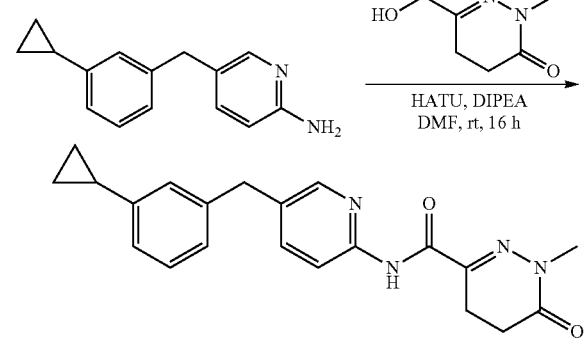

Step 1: Preparation of 5-(3-bromobenzyl)pyridin-2-amine

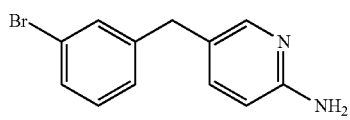 [SMILES: Nc1ccc(Cc2cccc(Br)c2)cn1]

A mixture of 1-bromo-3-(bromomethyl)benzene(2.2 g, 8.87 mmol), 5-(4,4,5,5-tetramethyl-1,3,2-dioxaborolan-2-yl)pyridin-2-amine (2.2 g, 10.0 mmol), [1,1'-bis(diphenylphosphino)ferrocene]dichloropalladium(II)-dichloromethane complex (0.361 g, 0.44 mmol), potassium carbonate (2.45 g, 17.7 mmol), acetonitrile (80 mL) and water (16 mL) was stirred at 80° C. under nitrogen for 2 h. The mixture was poured into water, extracted with ethyl acetate (150 mL×2). The combined organic phase was concentrated. The residue was purified by column chromatography (silica gel, petroleum ether/ethyl acetate=1/1) to afford compound 5-(3-bromobenzyl)pyridin-2-amine (1.6 g, 6.10 mmol, 68.8%) as a light-yellow oil. LCMS (ESI) m/z: 263.0/265.0 [M+H]⁺.

Step 2: Preparation of 5-(3-cyclopropylbenzyl)pyridin-2-amine

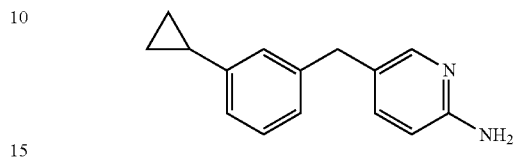

A mixture of 5-(3-bromobenzyl)pyridin-2-amine (0.800 g, 3.05 mmol), cyclopropylboronic acid (0.787 g, 9.15 mmol), palladium(II) acetate (0.067 g, 0.3 mmol), tricyclohexylphosphine tetrafluoroborate (0.220 g, 0.6 mmol), potassium phosphate (1.3 g, 6.1 mmol) in toluene (60 mL) and water (15 mL) was stirred at 110° C. under nitrogen for 16 h. The mixture was poured into water and extracted with ethyl acetate (150 mL×2). The combined organic phases were concentrated. The crude residue was purified by column chromatography (silica gel, petroleum ether/ethyl acetate=1/2) to afford 5-(3-cyclopropylbenzyl)pyridin-2-amine (0.350 g, 0.156 mmol, 51%) as a grey solid. LCMS (ESI) m/z: 225.2 [M+H]⁺.

Step 3: Preparation of N-(5-(3-cyclopropylbenzyl)pyridin-2-yl)-1-methyl-6-oxo-1,4,5,6-tetrahydropyridazine-3-carboxamide

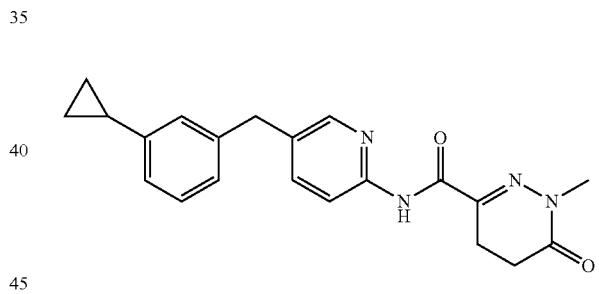

A mixture of 1-methyl-6-oxo-1,4,5,6-tetrahydropyridazine-3-carboxylic acid (0.208 g, 1.33 mmol), 5-(3-cyclopropylbenzyl)pyridin-2-amine (0.298 g, 1.33 mmol), 1-[bis(dimethylamino)methylene]-1H-1,2,3-triazolo[4,5-b]pyridinium 3-oxid hexafluorophosphate (0.760 g, 2.0 mmol), N,N-diisopropylethylamine (0.516 g, 3.99 mmol) in N,N-dimethylformamide (6 mL) was stirred at room temperature 16 h. The mixture was poured into water and extracted with ethyl acetate (80 mL×3). The combined organic phases were concentrated. The residue was purified by column chromatography (silica gel, petroleum ether/ethyl acetate=3/1) to afford N-(5-(3-cyclopropylbenzyl)pyridin-2-yl)-1-methyl-6-oxo-1,4,5,6-tetrahydropyridazine-3-carboxamide (0.134 g, 0.371 mmol, 27.9%) as a white solid. ¹H NMR (500 MHz, Dimethylsulfoxide-$d_6$) δ. 9.69 (s, 1H), 8.27 (d, J=2.0 Hz, 1H), 8.02 (d, J=8.5 Hz, 1H), 7.69 (dd, J=2.0, 8.5 Hz, 1H), 7.16 (t, J=8.0 Hz, 1H), 6.99 (m, 2H), 6.88 (d, J=7.5 Hz, 1H), 3.89 (s, 2H), 3.36 (s, 3H), 2.85 (t, J=8.5 Hz, 2H), 2.52 (t, J=8.5 Hz, 2H), 1.89-1.84 (m, 1H), 0.93-0.90 (m, 2H), 0.65-0.62 (m, 2H); LCMS (ESI) m/z: 363.2 [M+H]⁺.

Example 24. Preparation of N-(5-(3-chloro-5-methoxybenzyl)pyridin-2-yl)-1-methyl-6-oxo-1,4,5,6-tetrahydropyridazine-3-carboxamide (24)

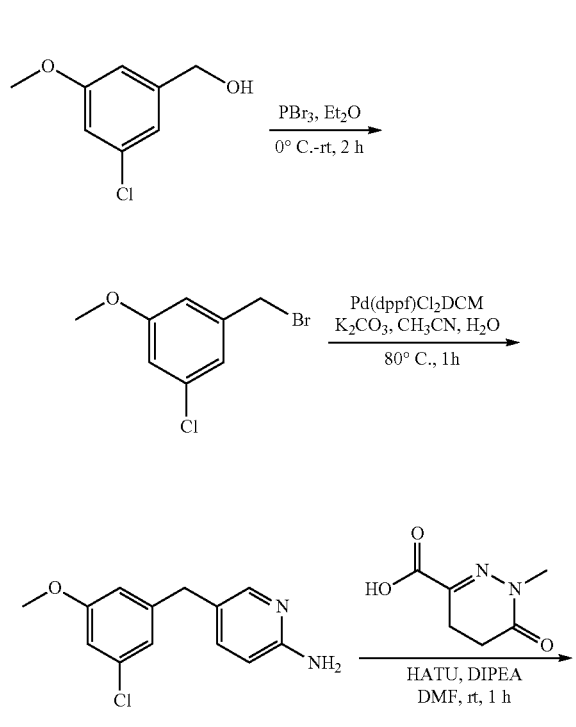

Step 1: Preparation of 1-(bromomethyl)-3-chloro-5-methoxybenzene

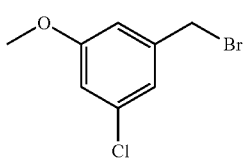

To a solution of (3-chloro-5-methoxyphenyl)methanol (2.0 g, 11.6 mmol) in diethyl ether (20 mL) at 0° C. was added phosphorus tribromide (0.5 mL). The reaction mixture was stirred at 0° C. for 2 h. Reaction was poured into saturated aqueous sodium bicarbonate (150 mL) and extracted with ethyl acetate (200 mL×2). The combined organic phases were dried over sodium sulfate, filtered and concentrated to afford 1-(bromomethyl)-3-chloro-5-methoxybenzene (2.15 g, 9.16 mmol, 79%) as a light-yellow solid. Used in the next step directly without additional purification.

Step 2: Preparation of 5-(3-chloro-5-methoxybenzyl)pyridin-2-amine

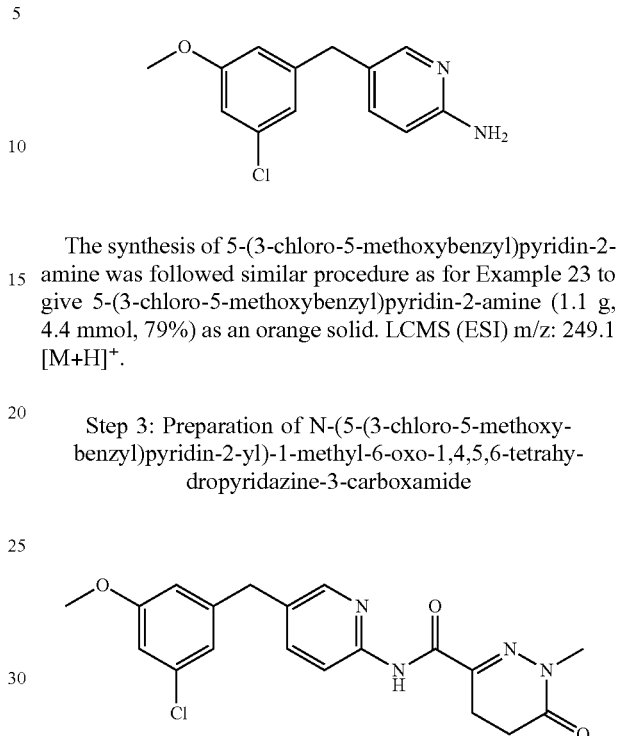

The synthesis of 5-(3-chloro-5-methoxybenzyl)pyridin-2-amine was followed similar procedure as for Example 23 to give 5-(3-chloro-5-methoxybenzyl)pyridin-2-amine (1.1 g, 4.4 mmol, 79%) as an orange solid. LCMS (ESI) m/z: 249.1 [M+H]$^+$.

Step 3: Preparation of N-(5-(3-chloro-5-methoxybenzyl)pyridin-2-yl)-1-methyl-6-oxo-1,4,5,6-tetrahydropyridazine-3-carboxamide A solution of 5-(3-chloro-5-methoxybenzyl)pyridin-2-amine (0.300 mg, 1.2 mmol), 1-methyl-6-oxo-1,4,5,6-tetrahydropyridazine-3-carboxylic acid (0.188 g, 1.2 mmol), 1-[bis(dimethylamino)methylene]-1H-1,2,3-triazolo[4,5-b]pyridinium 3-oxid hexafluorophosphate (0.684 g, 1.8 mmol), N,N-diisopropylethylamine (0.465 g, 3.6 mmol) in N,N-dimethylformamide (10 mL) was stirred at room temperature for 1 h. The mixture was poured into water. The formed precipitate was filtered, washed with ethyl acetate (25 mL) and dried in vacuo to afford N-(5-(3-chloro-5-methoxybenzyl)pyridin-2-yl)-1-methyl-6-oxo-1,4,5,6-tetrahydropyridazine-3-carboxamide (0.0638 g, 0.165 mmol, 13.7%) as an off-white solid. $^1$H NMR (500 MHz, Dimethylsulfoxide-d$_6$) δ. 9.72 (s, 1H), 8.31 (d, J=1.5 Hz, 1H), 9.03 (d, J=8.5 Hz, 1H), 7.74 (dd, J=2.0, 8.5 Hz, 1H), 6.90-6.84 (m, 3H), 3.91 (s, 2H), 3.75 (s, 3H), 3.36 (s, 3H), 2.85 (t, J=8.5 Hz, 2H), 2.52 (t, J=8.5 Hz, 2H); LCMS (ESI) m/z: 387.1 [M+H]$^+$.

Example 25. Preparation of N-(5-(3-cyano-5-fluorobenzyl)pyridin-2-yl)-1-methyl-6-oxo-1,6-dihydropyridine-3-carboxamide (25)

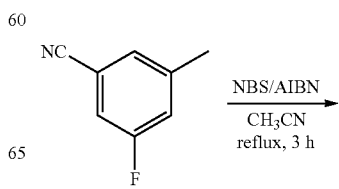

-continued

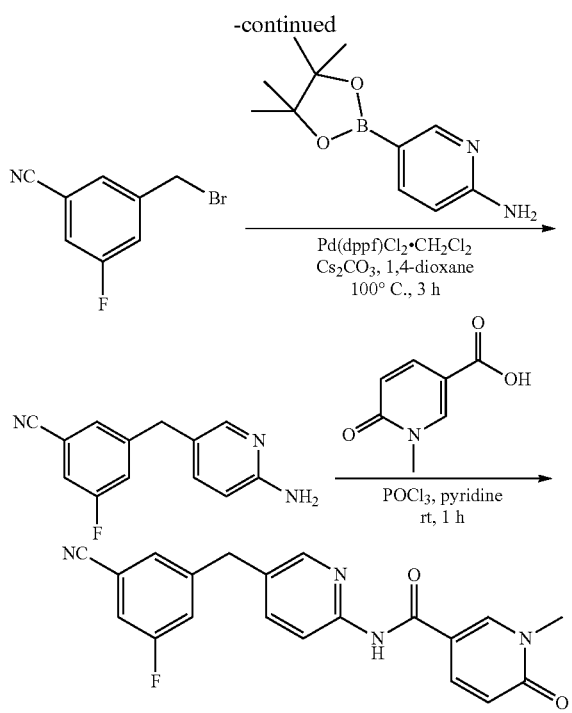

Step 1: Preparation of 3-(bromomethyl)-5-fluorobenzonitrile

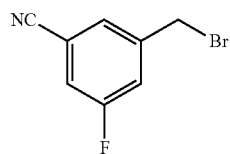 [SMILES: N#Cc1cc(F)cc(CBr)c1]

A mixture of 3-fluoro-5-methylbenzonitrile (2.0 g, 14.8 mmol), N-bromosuccinimide (2.85 g, 16.3 mmol), 2,2'-azobis(2-methylpropionitrile) (242 mg, 1.48 mmol) in acetonitrile (20 mL) was stirred at reflux for 3 h. The mixture was concentrated. The reside was purified by column chromatography (silica gel, petroleum ether/ethyl acetate=10/1) to afford 3-(bromomethyl)-5-fluorobenzonitrile (1.55 g, 6.96 mmol, 47%) as a light-yellow oil. $^1$H NMR (500 MHz, Chloroform-d) δ 7.51 (s, 1H), 7.40 (dt, J=2.0, 9.0 Hz, 1H), 7.33 (dt, J=1.5, 8.0 Hz, 1H), 4.45 (s, 2H).

Step 2: Preparation of 3-((6-aminopyridin-3-yl)methyl)-5-fluorobenzonitrile

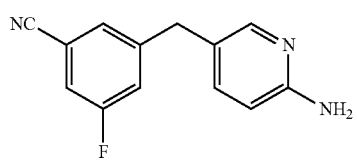 [SMILES: N#Cc1cc(F)cc(Cc2ccc(N)nc2)c1]

A mixture of 3-(bromomethyl)-5-fluorobenzonitrile (1.0 g, 4.68 mmol), 5-(4,4,5,5-tetramethyl-1,3,2-dioxaborolan-2-yl)pyridin-2-amine (1.03 g, 4.68 mmol), [1,1'-bis(diphenylphosphino)ferrocene]dichloropalladium(II)-dichloromethane complex (0.380 g, 0.468 mmol), cesium carbonate (3.04 g, 9.36 mmol) in 1,4-dioxane (40 mL) was stirred at 100° C. for 3 h. The mixture was concentrated, and the crude material was purified by column chromatography (silica gel, petroleum ether/ethyl acetate=1/1) to afford 3-((6-aminopyridin-3-yl)methyl)-5-fluorobenzonitrile (0.720 g, 3.14 mmol, 67%) as a brown oil. LCMS (ESI) m/z: 228.1 [M+H]$^+$.

Step 3: Preparation of N-(5-(3-cyano-5-fluorobenzyl)pyridin-2-yl)-1-methyl-6-oxo-1,6-dihydropyridine-3-carboxamide

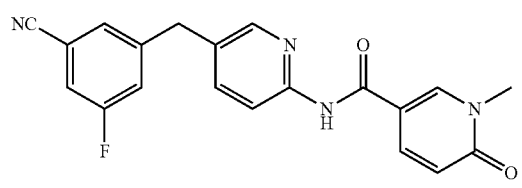 [SMILES: Cn1cc(C(=O)Nc2ccc(Cc3cc(F)cc(C#N)c3)cn2)ccc1=O]

To a solution of 3-((6-aminopyridin-3-yl)methyl)-5-fluorobenzonitrile (0.350 g, 1.54 mmol), 1-methyl-6-oxo-1,6-dihydropyridine-3-carboxylic acid (0.170 g, 1.11 mmol) in pyridine (10 mL) at 0° C. was added phosphorus(V) oxychloride (0.4 mL) dropwise. The reaction mixture was stirred at room temperature for 2 h. The mixture was poured into crushed ice and extracted with ethyl acetate (100 mL×2). The combined organic phases were concentrated. The residue was purified by column chromatography (silica gel, 10% methanol in ethyl acetate) and the obtained solid was washed with methanol (4 mL). The gray solid (0.070 g) was dissolved in minimal N,N-dimethylformamide and purified by prep-HPLC (Boston C18 21*250 mm 10 µM column. The mobile phase was acetonitrile/10 mM ammonium acetate aqueous solution) to give N-(5-(3-cyano-5-fluorobenzyl)pyridin-2-yl)-1-methyl-6-oxo-1,6-dihydropyridine-3 carboxamide (0.019 g, 0.052 mmol, 3.4%) as a white solid. $^1$H NMR (500 MHz, Dimethylsulfoxide-d$_6$) δ. 10.55 (s, 1H), 8.67 (d, J=2.5 Hz, 1H), 8.35 (d, J=2.0 Hz, 1H), 8.06 (d, J=8.0 Hz, 1H), 7.98 (dd, J=3.0, 9.5 Hz, 1H), 7.75-7.68 (m, 3H), 7.58 (d, J=9.5 Hz, 1H), 6.43 (d, J=9.5 Hz, 1H), 4.03 (s, 2H), 3.50 (s, 3H); LCMS (ESI) m/z: 363.1 [M+H]$^+$.

Example 26. Preparation of N-(5-(3-cyano-5-fluorobenzyl)pyridin-2-yl)-1-methyl-6-oxo-1,4,5,6-tetrahydropyridazine-3-carboxamide (26)

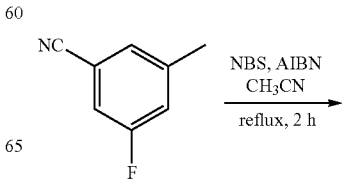

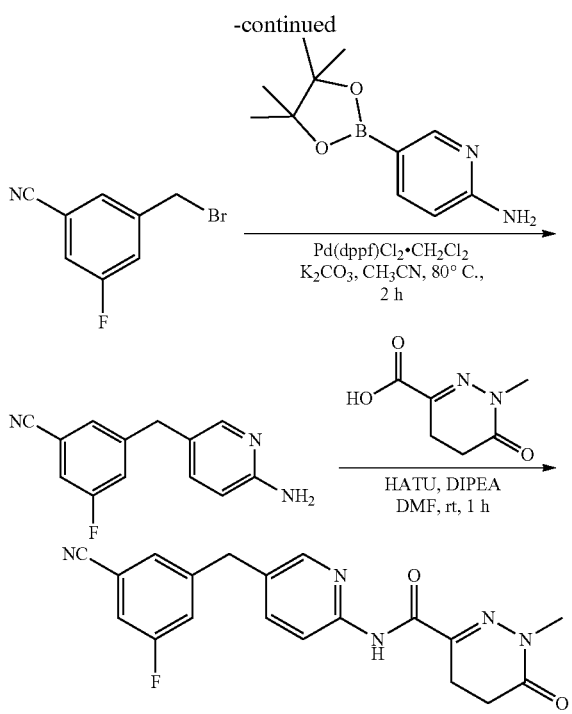

Step 1: Preparation of 3-(bromomethyl)-5-fluorobenzonitrile

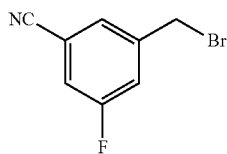 [SMILES: N#Cc1cc(F)cc(CBr)c1]

A mixture of 3-fluoro-5-methylbenzonitrile (2.0 g, 14.8 mmol), N-bromosuccinimide (2.85 g, 16.3 mmol), 2,2′-azobis(2-methylpropionitrile) (0.242 g, 1.48 mmol) in acetonitrile (20 mL) was stirred at reflux for 3 h. The mixture was concentrated. The crude sample was purified by column chromatography (silica gel, petroleum ether/ethyl acetate=10/1) to give 3-(bromomethyl)-5-fluorobenzonitrile (1.55 g, 6.96 mmol, 47%) as a light-yellow oil. $^1$H NMR (500 MHz, Chloroform-d) δ. 7.51 (s, 1H), 7.40 (dt, J=2.0, 9.0 Hz, 1H), 7.33 (dt, J=1.5, 8.0 Hz, 1H), 4.45 (s, 2H).

Step 2: Preparation of 3-((6-aminopyridin-3-yl)methyl)-5-fluorobenzonitrile

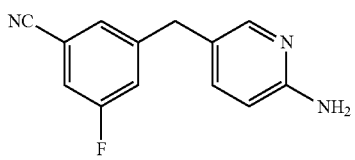 [SMILES: N#Cc1cc(F)cc(Cc2ccc(N)nc2)c1]

A mixture of 3-(bromomethyl)-5-fluorobenzonitrile (1.0 g, 4.68 mmol), 5-(4,4,5,5-tetramethyl-1,3,2-dioxaborolan-2-yl)pyridin-2-amine (1.03 g, 4.68 mmol), [1,1′-bis(diphenylphosphino)ferrocene]dichloropalladium(II)-dichloromethane complex (0.380 g, 0.468 mmol), cesium carbonate (3.04 g, 9.36 mmol) in 1,4-dioxane (40 mL) was stirred at 100° C. under nitrogen for 3 h. The mixture was concentrated. The residue was purified by column chromatography (silica gel, petroleum ether/ethyl acetate=1/1) to afford compound 3-((6-aminopyridin-3-yl)methyl)-5-fluorobenzonitrile (0.720 g, 0.314 mmol, 67%) as a brown oil. LCMS (ESI) m/z: 228.1 [M+H]$^+$.

Step 3: Preparation of N-(5-(3-cyano-5-fluorobenzyl)pyridin-2-yl)-1-methyl-6-oxo-1,4,5,6-tetrahydropyridazine-3-carboxamide

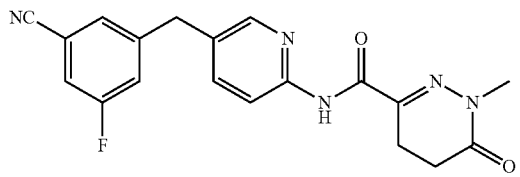 [SMILES: CN1N=C(C(=O)Nc2ccc(Cc3cc(F)cc(C#N)c3)cn2)CCC1=O]

A mixture of 1-methyl-6-oxo-1,4,5,6-tetrahydropyridazine-3-carboxylic acid (0.210 g, 1.34 mmol), 3-((6-aminopyridin-3-yl)methyl)-5-fluorobenzonitrile (0.300 g, 1.32 mmol), 1-[bis(dimethylamino)methylene]-1H-1,2,3-triazolo[4,5-b]pyridinium 3-oxid hexafluorophosphate (0.750 g, 1.97 mmol), N,N-diisopropylethylamine (0.510 g, 3.95 mmol) in N,N-dimethylformamide (5 mL) was stirred at room temperature for 1 h. The mixture was poured into water and extracted with ethyl acetate (80 mL×2). The combined organic phases were concentrated. The residue was purified by column chromatography (silica gel, petroleum ether/ethyl acetate=1/1) to afford 130 mg of a white solid. This sample was dissolved in minimal N,N-dimethylformamide and purified via prep-HPLC (Boston C18 21*250 mm 10 μm column; acetonitrile/0.01% aqueous trifluoroacetic acid) to yield N-(5-(3-cyano-5-fluorobenzyl)pyridin-2-yl)-1-methyl-6-oxo-1,4,5,6-tetrahydropyridazine-3-carboxamide (0.0755 g, 0.206 mmol, 13.4%) as a white solid. $^1$H NMR (500 MHz, Dimethylsulfoxide-d$_6$) δ. 9.73 (s, 1H), 8.34 (d, J=1.5 Hz, 1H), 8.04 (d, J=8.5 Hz, 1H), 7.77 (dd, J=1.5, 8.5 Hz, 1H), 7.71-6.68 (m, 2H), 7.57 (d, J=9.5 Hz, 1H), 4.03 (s, 2H), 3.35 (s, 3H), 2.85 (t, J=8.5 Hz, 2H), 2.52 (t, J=8.5 Hz, 2H); LCMS (ESI) m/z: 366.1 [M+H]$^+$.

Example 27. Preparation of N-(5-(3-bromobenzyl)pyridin-2-yl)-1-methyl-6-oxo-1,4,5,6-tetrahydropyridazine-3-carboxamide (27)

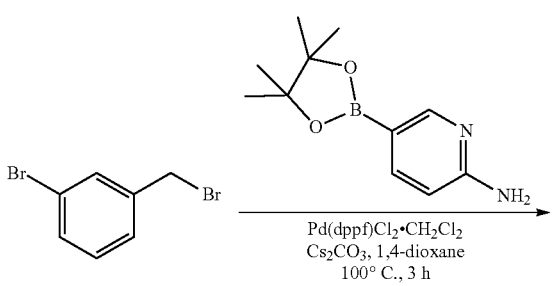

-continued

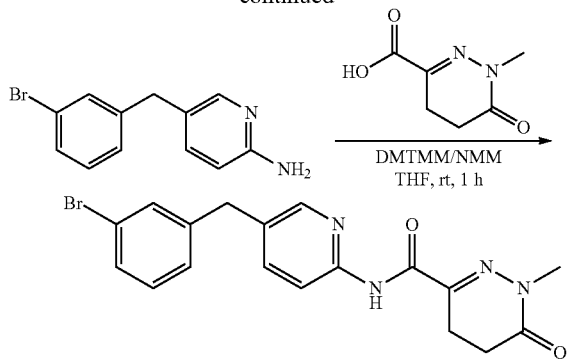

Step 1: Preparation of 5-(3-bromobenzyl)pyridin-2-amine

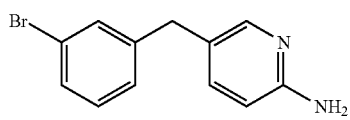

The synthesis of 5-(3-bromobenzyl)pyridin-2-amine was following similar procedures as Example 25. Compound 5-(3-bromobenzyl)pyridin-2-amine (0.500 g, 1.9 mmol, 37%) was obtained as a brown oil. LCMS (ESI) m/z: 263.0/265.0 [M+H]$^+$.

Step 2: Preparation of N-(5-(3-bromobenzyl)pyridin-2-yl)-1-methyl-6-oxo-1,4,5,6-tetrahydropyridazine-3-carboxamide

A mixture of 1-methyl-6-oxo-1,4,5,6-tetrahydropyridazine-3-carboxylic acid (0.200 g, 1.28 mmol) 5-(3-bromobenzyl)pyridin-2-amine (0.400 g, 1.52 mmol), 4-(4,6-dimethoxy-1,3,5-triazin-2-yl)-4-methylmorpholinium chloride (0.447 g, 1.52 mmol), 4-methylmorpholine (0.460 g, 4.56 mmol) in tetrahydrofuran (8 mL) was stirred at room temperature for 1 h. The mixture was poured into water and extracted with ethyl acetate (150 mL×2). The combined organic phases were concentrated. The residue was purified by column chromatography (silica gel, petroleum ether/ethyl acetate=1/1) and then 100 mg was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(3-bromobenzyl)pyridin-2-yl)-1-methyl-6-oxo-1,4,5,6-tetrahydropyridazine-3-carboxamide (0.0347 g, 0.086 mmol, 5.7%) as a white solid. $^1$H NMR (500 MHz, Dimethylsulfoxide-d$_6$) δ. 9.72 (s, 1H), 8.31 (d, J=2.5 Hz, 1H), 8.03 (d, J=8.5 Hz, 1H), 7.73 (dd, J=2.0, 8.5 Hz, 1H), 7.49 (s, 1H), 7.42-7.40 (m, 1H), 7.28-7.27 (m, 2H), 3.96 (s, 2H), 3.36 (s, 3H), 2.85 (t, J=8.5 Hz, 2H), 2.52 (t, J=8.5 Hz, 2H); LCMS (ESI) m/z: 401.0/403.0 [M+H]$^+$.

Example 28. Preparation of N-(5-(3-chloro-5-fluorobenzyl)pyridin-2-yl)-1-methyl-6-oxo-1,4,5,6-tetrahydropyridazine-3-carboxamide (28)

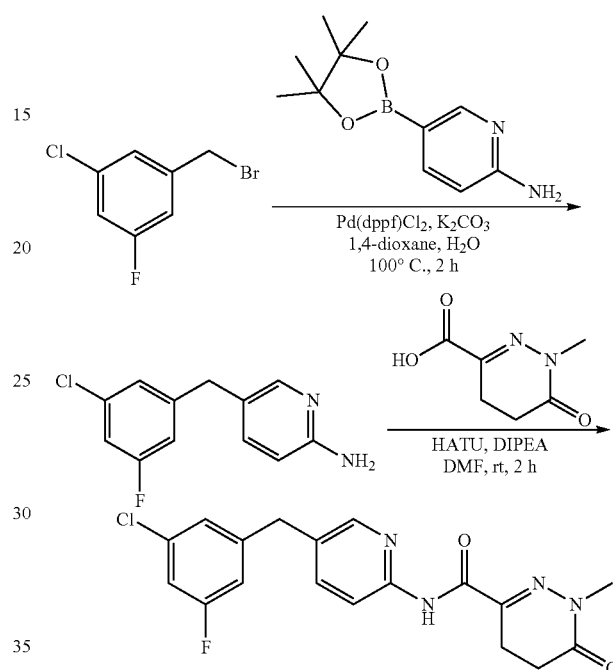

Step 1: Preparation of 5-(3-chloro-5-fluorobenzyl)pyridin-2-amine

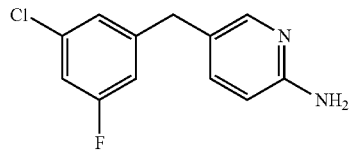 [SMILES: Nc1ccc(Cc2cc(F)cc(Cl)c2)cn1]

To a solution of 1-(bromomethyl)-3-chloro-5-fluorobenzene (3.0 g, 13.4 mmol) and 5-(4,4,5,5-tetramethyl-1,3-dioxolan-2-yl)pyridin-2-amine (3.54 g, 16.1 mmol), potassium carbonate (3.71 g, 26.8 mmol) in 1,4-dioxane (72 mL) and water (24 mL) was added [1,1'-bis(diphenylphosphino)ferrocene]dichloropalladium(II) (1.10 g, 1.34 mmol) under nitrogen. The mixture was stirred at 100° C. for 3 h. Reaction was quenched with water (200 mL) and the mixture was extracted with ethyl acetate (150 mL×3). The combined organic layers were dried with sodium sulfate, filtered and concentrated. The crude material was purified by column chromatography (petroleum ether/ethyl acetate from 100/0 to 60/100) to give 5-(3-chloro-5-fluorobenzyl)pyridin-2-amine (2.5 g, 10.6 mmol, 79%) as a yellow oil. LCMS (ESI) m/z: 237.1 [M+H]+:

Step 2: Preparation of N-(5-(3-chloro-5-fluorobenzyl)pyridin-2-yl)-1-methyl-6-oxo-1,4,5,6-tetrahydropyridazine-3-carboxamide

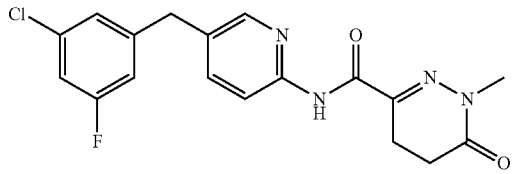

To a solution of 5-(3-chloro-5-fluorobenzyl)pyridin-2-amine (2.3 g, 9.72 mmol), 1-methyl-6-oxo-1,4,5,6-tetrahydropyridazine-3-carboxylic acid (2.28 g, 14.6 mmol) and 1-[bis(dimethylamino)methylene]-1H-1,2,3-triazolo[4,5-b]pyridinium 3-oxid hexafluorophosphate (7.39 g, 19.4 mmol) in N,N-dimethylformamide (30 mL) at 0° C. was added N,N-diisopropylethylamine (5.02 g, 38.9 mmol) dropwise under nitrogen. The mixture was stirred at room temperature for 2 h before it was poured into water and filtered to obtain a crude product. The crude residue was recrystallized from ethanol (220 mL) to obtain N-(5-(3-chloro-5-fluorobenzyl)pyridin-2-yl)-1-methyl-6-oxo-1,4,5,6-tetrahydropyridazine-3-carboxamide (2.2 g, 5.93 mmol, 61%) as a white solid. $^1$H NMR (400 MHz, Dimethylsulfoxide-$d_6$) δ 9.73 (s, 1H), 8.36-8.33 (m, 1H), 8.04 (d, J=8.5 Hz, 1H), 7.77 (dd, $J_1$=2.4 Hz, $J_2$=8.5 Hz 1H), 7.24-7.28 (m, 2H), 7.17 (d, J=10.0 Hz, 1H), 3.98 (s, 2H), 3.36 (s, 3H), 2.85 (t, J=8.5 Hz, 2H), 2.54-2.51 (m, 2H); LCMS (ESI) m/z: 375.1 [M+H]$^+$.

Example 29. Preparation of 1-methyl-6-oxo-N-(5-(3,4,5-trifluorobenzyl)pyridin-2-yl)-1,4,5,6-tetrahydropyridazine-3-carboxamide (29)

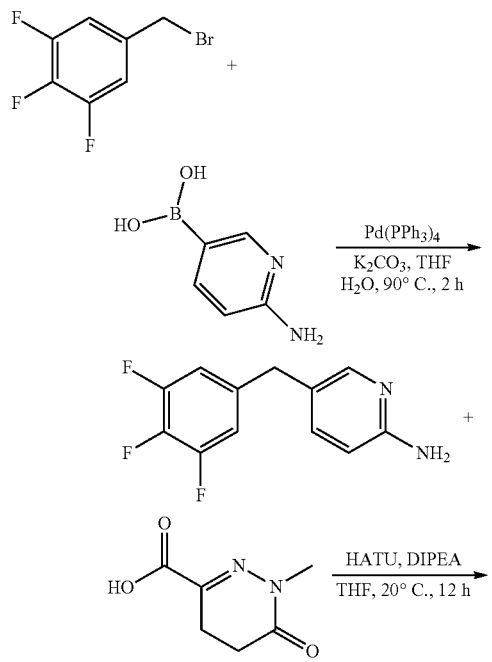

-continued

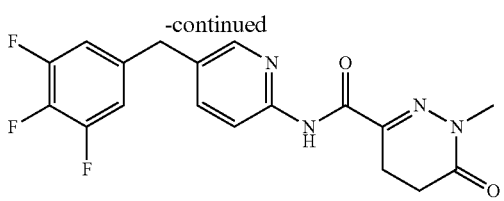

Step 1: Preparation of 5-(3,4,5-trifluorobenzyl)pyridin-2-amine

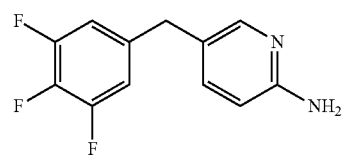 [SMILES: Nc1ccc(Cc2cc(F)c(F)c(F)c2)cn1]

To a solution of 5-(bromomethyl)-1,2,3-trifluorobenzene (1.0 g, 4.47 mmol), 6-aminopyridin-3-ylboronic acid (0.617 g, 4.47 mmol), potassium carbonate (1.23 g, 8.94 mmol) in tetrahydrofuran (12 mL) and water (3 mL) was added tetrakis(triphenylphosphine)palladium(0) (0.516 g, 0.447 mmol) under nitrogen. The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give as a yellow oil (0.300 g, crude); LCMS (ESI) m/z: 239.1 [M+H]$^+$.

Step 2: Preparation of 1-methyl-6-oxo-N-(5-(3,4,5-trifluorobenzyl)pyridin-2-yl)-1,4,5,6-tetrahydropyridazine-3-carboxamide

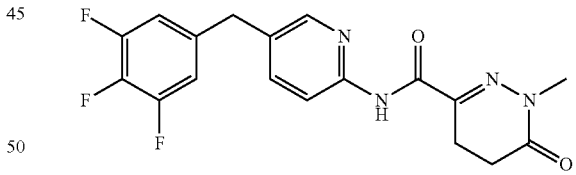

To a solution of 1-methyl-6-oxo-1,4,5,6-tetrahydropyridazine-3-carboxylic acid (0.100 g, 0.641 mmol), N,N-diisopropylethylamine (0.248 g, 1.92 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.366 g, 0.962 mmol). The reaction was stirred for 20 minutes before a solution of 5-(3,4,5-trifluorobenzyl)pyridin-2-amine (0.153 g, 0.641 mmol) in tetrahydrofuran (1.0 mL) was added. The reaction mixture was stirred at 20° C. for 16 h. The volatiles were removed under reduced pressure and the crude residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep- HPLC (Boston C18 21*250 mm 10 μm column; acetonitrile/ 0.01% aqueous trifluoroacetic acid) to give 1-methyl-6-oxo-N-(5-(3,4,5-trifluorobenzyl)pyridin-2-yl)-1,4,5,6-tetrahydropyridazine-3-carboxamide as a white solid (0.126 g, 0.333 mmol, 52%). $^1$H NMR (400 MHz, Dimethylsulfoxide-$d_6$) δ 9.75 (s, 1H), 8.32 (d, J=2.5 Hz, 1H), 8.03 (d, J=8.5 Hz, 1H), 7.74-7.77 (m, 1H), 7.26-7.30 (m, 2H), 3.95 (s, 2H), 3.36 (s, 3H), 2.85 (t, J=8.5 Hz, 2H), 2.52 (t, J=8.5 Hz, 2H); LCMS (ESI) m/z: 377.0 [M+H]$^+$.

Example 30. Preparation of N-(5-(3-methoxybenzyl)pyridin-2-yl)-1-methyl-6-oxo-1,4,5,6-tetrahydropyridazine-3-carboxamide (30)

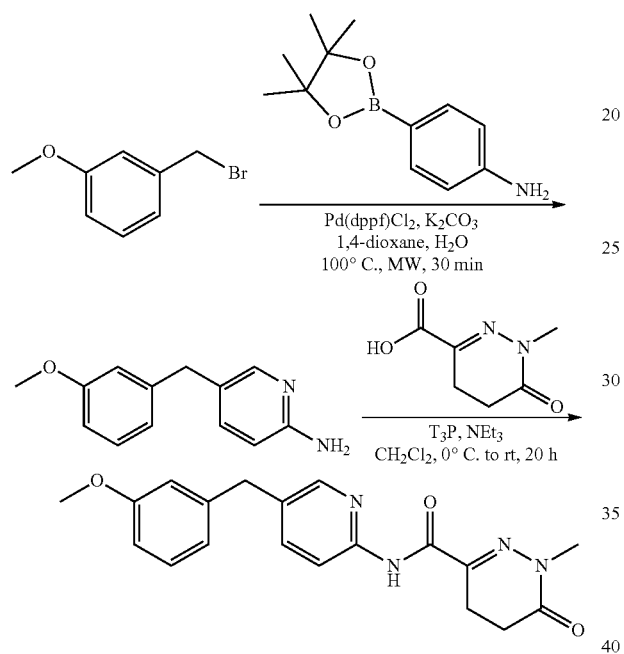

Step 1: Preparation of 5-(3-methoxybenzyl)pyridin-2-amine

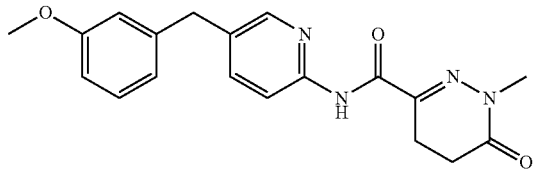

To a solution of 1-(bromomethyl)-3-methoxybenzene (0.362 g, 1.8 mmol) and 5-(4,4,5,5-tetramethyl-1,3-dioxolan-2-yl)pyridin-2-amine (0.480 g, 2.16 mmol) and potassium carbonate (0.498 g, 3.6 mmol) in 1,4-dioxane (9 mL) and water (3 mL) was added [1,1'-bis(diphenylphosphino)ferrocene]dichloropalladium(II) (132 mg, 0.18 mmol) under nitrogen. The reaction mixture was stirred in the microwave at 100° C. for 30 minutes. After the reaction was completed, water (50 mL) was added, the mixture was extracted with ethyl acetate (80 mL×3). The organic layers were dried with sodium sulfate, filtered and concentrated. The crude product was purified by silica gel column (petroleum ether/ethyl acetate from 1/1 to 0/1) to give 5-(3-methoxybenzyl)pyridin-2-amine (0.285 g, 1.33 mmol, 74%) as a brown solid. LCMS (ESI) m/z: 215.1 [M+H]$^+$.

Step 2: Preparation of N-(5-(3-methoxybenzyl)pyridin-2-yl)-1-methyl-6-oxo-1,4,5,6-tetrahydropyridazine-3-carboxamide To a solution of 5-(3-methoxybenzyl)pyridin-2-amine (0.086 g, 0.4 mmol), 1-methyl-6-oxo-1,4,5,6-tetrahydropyridazine-3-carboxylic acid (0.063 g, 0.4 mmol) and triethylamine (0.404 g, 4 mmol) in dichloromethane (30 mL) at 0° C. was added propylphosphonic anhydride (1.27 g, 2 mmol) slowly under nitrogen. Reaction was diluted with dichloromethane (50 mL) and washed with water (30 mL×2). The organic layer was dried over sodium sulfate, filtered and concentrated. The crude product was purified by prep-TLC (dichloromethane: 7 N ammonia in methanol=30/1) to give N-(5-(3-methoxybenzyl)pyridin-2-yl)-1-methyl-6-oxo-1,4,5,6-tetrahydropyridazine-3-carboxamide (0.0857 g, 0.244 mmol, 61%) as a white solid. $^1$H NMR (400 MHz, Dimethylsulfoxide-$d_6$) δ 9.70 (s, 1H), 8.28-8.29 (m, 1H), 8.02 (d, J=8.4 Hz, 1H), 7.71 (dd, $J_1$=2.0 Hz, $J_2$=8.4 Hz 1H), 7.22 (t, J=9.2 Hz, 1H), 6.76-6.84 (m, 3H), 3.91 (s, 2H), 3.73 (s, 3H), 3.36 (s, 3H), 2.85 (t, J=8.4 Hz, 2H), 2.50-2.55 (m, 2H); LCMS (ESI) m/z: 353.1 [M+H]$^+$.

Example 31. Preparation of N-(5-(3-methoxybenzyl)pyridin-2-yl)-1-methyl-6-oxo-1,4,5,6-tetrahydropyridazine-3-carboxamide (31)

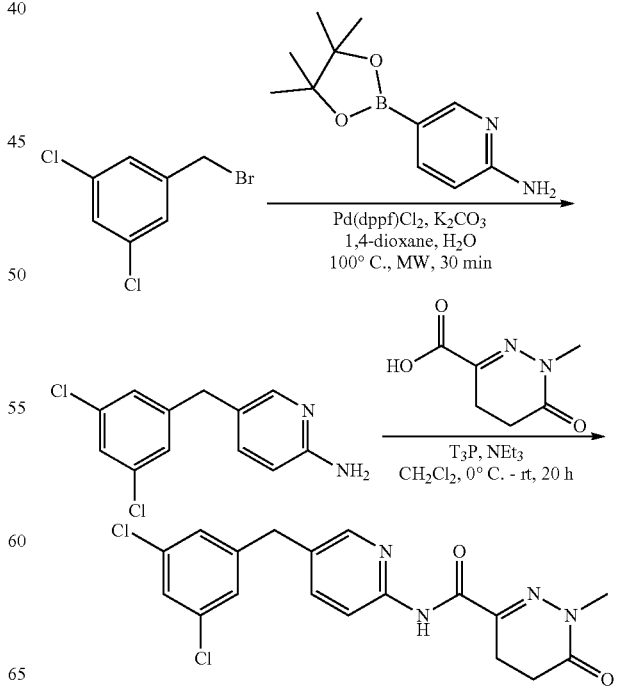

Step 1: Preparation of N-(5-(3-methoxybenzyl)pyridin-2-yl)-1-methyl-6-oxo-1,4,5,6-tetrahydropyridazine-3-carboxamide 5-(3,5-dichlorobenzyl)pyridin-2-amine

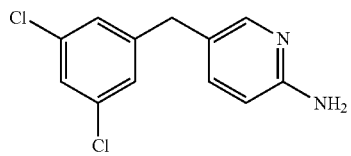 [SMILES: Nc1ccc(Cc2cc(Cl)cc(Cl)c2)cn1]

To a solution of 1-(bromomethyl)-3,5-dichlorobenzene (0.480 g, 2.0 mmol), 5-(4,4,5,5-tetramethyl-1,3-dioxolan-2-yl)pyridin-2-amine (0.534 g, 2.4 mmol) and potassium carbonate (0.553 g, 4.0 mmol) in 1,4-dioxane (9 mL) and water (3 mL) was added [1,1'-bis(diphenylphosphino)ferrocene]dichloropalladium(II) (0.147 g, 0.2 mmol) under nitrogen. The reaction mixture was stirred in the microwave at 100° C. for 0.5 h. Water (50 mL) was added and the mixture was extracted with ethyl acetate (80 mL×3). The combined organic layers were dried with sodium sulfate, filtered and concentrated. Purification by column chromatography (silica gel, petroleum ether/ethyl acetate from 1/1 to 1/2) gives N-(5-(3-methoxybenzyl)pyridin-2-yl)-1-methyl-6-oxo-1,4,5,6-tetrahydropyridazine-3-carboxamide 5-(3,5-dichlorobenzyl)pyridin-2-amine (0.458 g, 1.8 mmol, 90%) as a brown solid. LCMS (ESI) m/z: 253.0 [M+H]$^+$.

Step 2: Preparation of N-(5-(3-methoxybenzyl)pyridin-2-yl)-1-methyl-6-oxo-1,4,5,6-tetrahydropyridazine-3-carboxamide

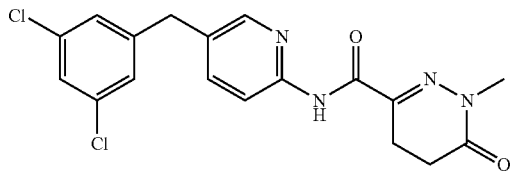 [SMILES: CN1N=C(C(=O)Nc2ccc(Cc3cc(Cl)cc(Cl)c3)cn2)CCC1=O]

To a solution of 5-(3,5-dichlorobenzyl)pyridin-2-amine (0.076 g, 0.3 mmol), 1-methyl-6-oxo-1,4,5,6-tetrahydropyridazine-3-carboxylic acid (0.047 g, 0.3 mmol) and triethylamine (0.303 g, 3 mmol) in dichloromethane (15 mL) at 0° C. was added propylphosphonic anhydride (0.955 g, 1.5 mmol) under nitrogen. Reaction was diluted with dichloromethane (50 mL) and washed with water (30 mL×2). The organic layer was dried with sodium sulfate, filtered and concentrated. Purification by prep-TLC (dichloromethane: 7 N ammonia in methanol=30/1) gives N-(5-(3-methoxybenzyl)pyridin-2-yl)-1-methyl-6-oxo-1,4,5,6-tetrahydropyridazine-3-carboxamide as a white solid (0.0547 g, 0.141 mmol, 47%). $^1$H NMR (400 MHz, Dimethylsulfoxide-$d_6$) δ 9.73 (s, 1H), 8.33 (s, 1H), 8.04 (d, J=8.8 Hz, 1H), 7.76 (dd, $J_1$=1.6 Hz, $J_2$=8.4 Hz, 1H), 7.46 (s, 1H), 7.38 (s, 2H), 3.97 (s, 2H), 3.36 (s, 3H), 2.85 (t, J=8.4 Hz, 2H), 2.51-2.55 (m, 2H); LCMS (ESI) m/z: 390.9 [M+H]$^+$.

Example 32. Preparation of N-(5-(3-(difluoromethyl)benzyl)pyridin-2-yl)-1-methyl-6-oxo-1,4,5,6-tetrahydropyridazine-3-carboxamide (32)

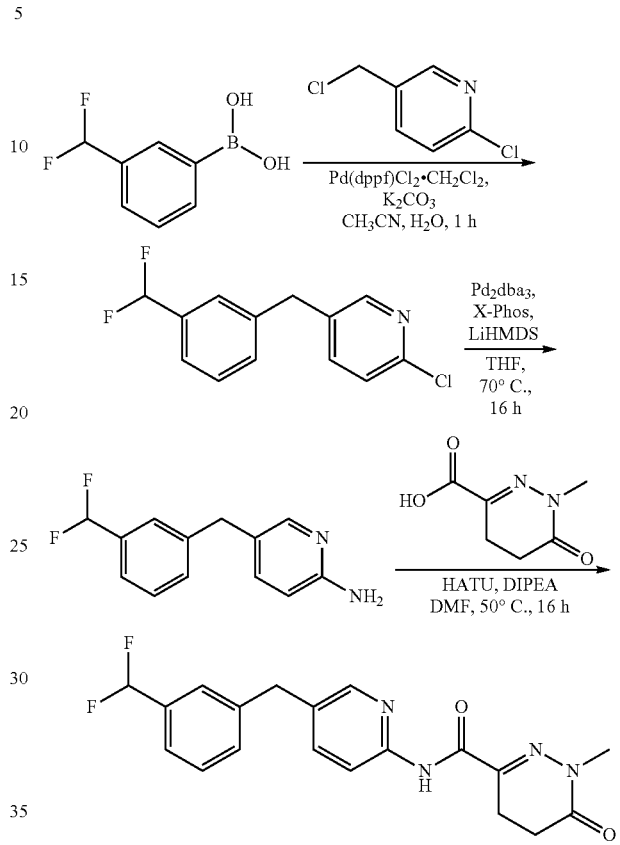

Step 1: Preparation of 2-chloro-5-(3-(difluoromethyl)benzyl)pyridine

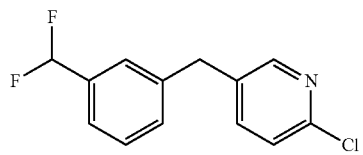 [SMILES: FC(F)c1cccc(Cc2ccc(Cl)nc2)c1]

To a solution of (3-(difluoromethyl)phenyl)boronic acid (0.405 g, 2.5 mmol) and 2-chloro-5-(chloromethyl)pyridine (0.430 g, 2.5 mmol) and potassium carbonate (0.691 g, 5 mmol) in acetonitrile (70 mL) and water (10 mL) was added [1,1'-bis(diphenylphosphino)ferrocene]dichloropalladium (II) dichloromethane (0.204 g, 0.25 mmol) under argon. The mixture was stirred at 50° C. for 1 h. Volatiles were removed under reduced pressure and water (50 mL) was added. The aqueous layer was extracted with ethyl acetate (80 mL×3), dried with sodium sulfate, filtered and concentrated. The crude material was purified by column chromatography (silica gel, petroleum ether/ethyl acetate=12/1) to give 2-chloro-5-(3-(difluoromethyl)benzyl)pyridine (0.397 g, 1.45 mmol, 58%) as a colorless oil. LCMS (ESI) m/z: 254.1 [M+H]$^+$.

Step 2: Preparation of 5-(3-(difluoromethyl)benzyl)pyridin-2-amine

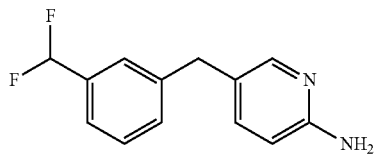 [SMILES: Nc1ccc(Cc2cccc(C(F)F)c2)cn1]

To a solution of 2-chloro-5-(3-(difluoromethyl)benzyl)pyridine (0.319 g, 1.26 mmol) in tetrahydrofuran (40 mL) was added sequentially tris(dibenzylideneacetone)dipalladium(0) (0.115 g, 0.126 mmol) and X-Phos (0.120 g, 0.252 mmol) followed by lithium bis(trimethylsilyl)amide (3.8 mL, 3.8 mmol). Reaction vessel was heated to 70° C. and stirred for 1 h before it was quenched with water and extracted with dichloromethane (50 mL×3). The combined organic layers were dried with sodium sulfate, filtered and concentrated. The crude product was purified by column chromatography (silica gel, dichloromethane/ammonia in methanol (7 N)=40/1) to give 5-(3-(difluoromethyl)benzyl)pyridin-2-amine (0.410 g, 0.781 mmol, 62%) as a yellow oil. (LCMS (ESI) 235.2 [M+H]$^+$.

Step 3: Preparation of N-(5-(3-(difluoromethyl)benzyl)pyridin-2-yl)-1-methyl-6-oxo-1,4,5,6-tetrahydropyridazine-3-carboxamide

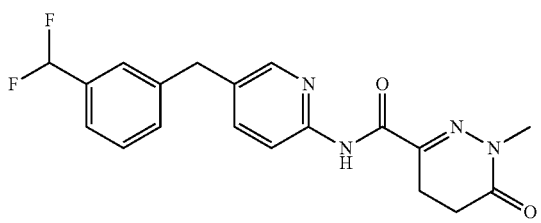 [SMILES: CN1N=C(C(=O)Nc2ccc(Cc3cccc(C(F)F)c3)cn2)CCC1=O]

To a solution of 1-methyl-6-oxo-1,4,5,6-tetrahydropyridazine-3-carboxylic acid (0.125 g, 0.8 mmol) and 1-[bis(dimethylamino)methylene]-1H-1,2,3-triazolo[4,5-b]pyridinium 3-oxid hexafluorophosphate (0.228 g, 0.6 mmol) in N,N-dimethylformamide (15 mL) at room temperature was added N,N-diisopropylethylamine (0.155 g, 1.2 mmol) under nitrogen. The mixture was stirred at room temperature for 30 minutes before 5-(3-(difluoromethyl)benzyl)pyridin-2-amine (0.188 g, 0.4 mmol) was added. The reaction mixture was stirred at 50° C. for 16 h. Reaction mixture was cooled to room temperature and diluted with ethyl acetate (100 mL). The combined organic layers were washed with brine (30 mL×3), dried with sodium sulfate, filtered and concentrated. The crude sample was dissolved in minimal N,N-dimethylformamide and purified via prep-HPLC (Boston C18 21*250 mm 10 µm column; acetonitrile/0.01% aqueous trifluoroacetic acid) to give N-(5-(3-(difluoromethyl)benzyl)pyridin-2-yl)-1-methyl-6-oxo-1,4,5,6-tetrahydropyridazine-3-carboxamide as a white solid (0.102 g, 0.22 mmol, 55%). $^1$H NMR (500 MHz, Dimethylsulfoxide-d$_6$) δ 9.73 (s, 1H), 8.31 (d, J=2 Hz, 1H), 8.04 (d, J=8.5 Hz, 1H), 7.73 (dd, J$_1$=2.0 Hz, J$_2$=7 Hz, 1H), 7.41-7.47 (m, 4H), 7.00 (t, J=56 Hz, 1H), 4.03 (s, 2H), 3.362 (s, 3H), 2.85 (t, J=8.5 Hz, 2H), 2.51-2.54 (m, 2H); LCMS (ESI) m/z: 373.1 [M+H]$^+$.

Example 33. Preparation of N-(5-(3-chloro-4-cyanobenzyl)pyridin-2-yl)-1-methyl-6-oxo-1,4,5,6-tetrahydropyridazine-3-carboxamide (33)

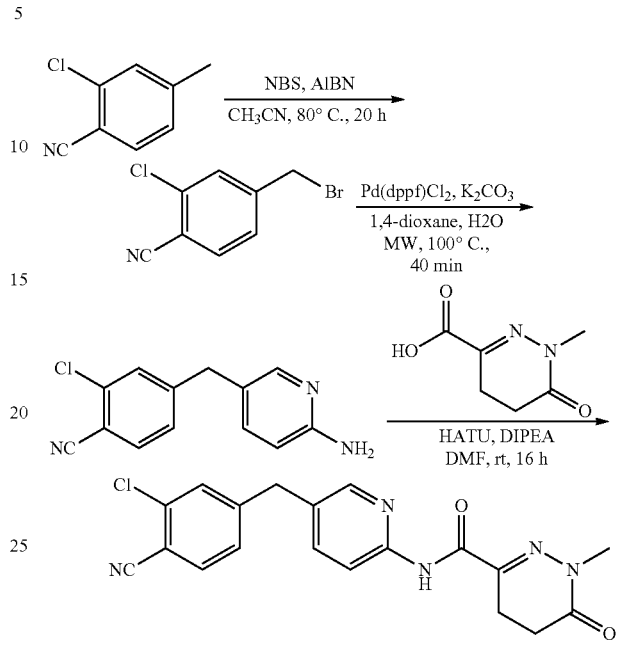

Step 1: Preparation of 4-(bromomethyl)-2-chlorobenzonitrile

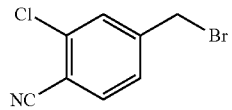

To a solution of 2-chloro-4-methylbenzonitrile (1.06 g, 7 mmol) and N-bromosuccinimide (1.37 g, 7.7 mmol) in acetonitrile (70 mL) was added 2,2-azobis(2-methylpropionitrile (0.230 g, 1.4 mmol) under argon. The mixture was stirred at 80° C. for 20 h. The reaction mixture was filtered and washed with ethyl acetate (80 mL). The filtrate was concentrated, and the resulting crude material was purified by column chromatography (silica gel, petroleum ether/ethyl acetate=10/1) to give 4-(bromomethyl)-2-chlorobenzonitrile as a light-yellow solid (0.661 g, 2.87 mmol, 41%). $^1$H NMR (400 MHz, Chloroform-d) δ 7.67-7.69 (m, 1H), 7.57-7.58 (m, 1H), 7.41 (dd, J$_1$=1.5 Hz, J$_2$=8.0 Hz, 1H), 4.454 (s, 2H).

Step 2: Preparation of 4-((6-aminopyridin-3-yl)methyl)-2-chlorobenzonitrile

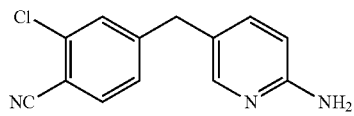 [SMILES: N#Cc1ccc(Cc2ccc(N)nc2)cc1Cl]

To a solution of 4-(bromomethyl)-2-chlorobenzonitrile (0.461 g, 2 mmol) and 5-(4,4,5,5-tetramethyl-1,3-dioxolan- 2-yl)pyridin-2-amine (0.534 g, 2.4 mmol) and potassium carbonate (0.563 g, 4 mmol) in 1,4-dioxane (9 mL) and water (3 mL) was added [1,1'-bis(diphenylphosphino)ferrocene]dichloropalladium(II) (0.147 g, 0.2 mmol) under nitrogen. The reaction mixture was stirred at 100° C. for 40 min in the microwave. Reaction was diluted with water (50 mL) and the aqueous layer was extracted with ethyl acetate (80 mL×3). The combined organic layers were dried with sodium sulfate, filtered and concentrated. The crude residue was purified by column chromatography (silica gel, petroleum ether/ethyl acetate from 1:1 to 0:1) to give 4-((6-aminopyridin-3-yl)methyl)-2-chlorobenzonitrile as a yellow solid (0.263 g, 1.08 mmol, 54%). LCMS (ESI) m/z: 244.1 [M+H]$^+$.

Step 3: Preparation of N-(5-(3-chloro-4-cyanobenzyl)pyridin-2-yl)-1-methyl-6-oxo-1,4,5,6-tetrahydropyridazine-3-carboxamide

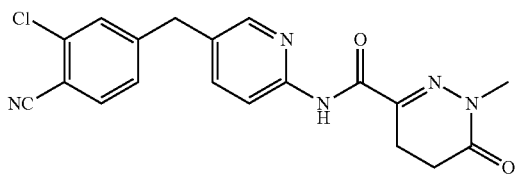 [SMILES: CN1N=C(C(=O)Nc2ccc(Cc3ccc(C#N)c(Cl)c3)cn2)CCC1=O]

To a solution of 1-methyl-6-oxo-1,4,5,6-tetrahydropyridazine-3-carboxylic acid (0.052 g, 0.33 mmol) and 1-[bis(dimethylamino)methylene]-1H-1,2,3-triazolo[4,5-b]pyridinium 3-oxid hexafluorophosphate (0.171 g, 0.45 mmol) in N,N-dimethylformamide (3 mL) was added N,N-diisopropylethylamine (0.116 g, 0.9 mmol) at room temperature under nitrogen. The mixture was stirred at room temperature for 30 minutes before 4-((6-aminopyridin-3-yl)methyl)-2-chlorobenzonitrile (0.073 g, 0.3 mmol) was added. The reaction mixture was stirred at room temperature for 16 h. The reaction mixture was diluted with ethyl acetate (80 mL) and washed with brine (40 mL×3). The combined organic layers were dried with sodium sulfate, filtered and concentrated. The crude material was purified by Prep-TLC (dichloromethane: ammonia in methanol (7 N)=40/1) to give N-(5-(3-chloro-4-cyanobenzyl)pyridin-2-yl)-1-methyl-6-oxo-1,4,5,6-tetrahydropyridazine-3-carboxamide as a white solid (0.0736 g, 0.106 mmol, 32%). $^1$H NMR (400 MHz, Dimethylsulfoxide-d$_6$) δ 9.75 (s, 1H), 8.34 (d, J=1.5 Hz, 1H), 8.04 (d, J=8.5 Hz, 1H), 7.92 (d, J=8.0 Hz, 1H), 7.76 (dd, J$_1$=2.0 Hz, J$_2$=8.5 Hz, 1H), 7.72 (s, 1H), 7.46 (d, J=8.0 Hz, 1H), 4.07 (s, 2H), 3.36 (s, 3H), 2.85 (t, J=8.0 Hz, 2H), 2.51-2.54 (m, 2H); LCMS (ESI) m/z: 382.1 [M+H]$^+$.

Example 34. Preparation of N-(5-(cyclohexenylmethyl)pyridin-2-yl)-1-methyl-6-oxo-1,4,5,6-tetrahydropyridazine-3-carboxamide (34)

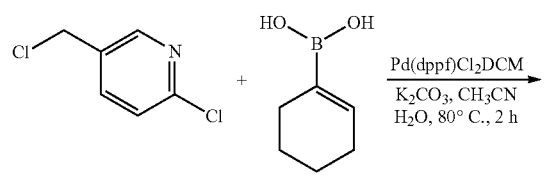

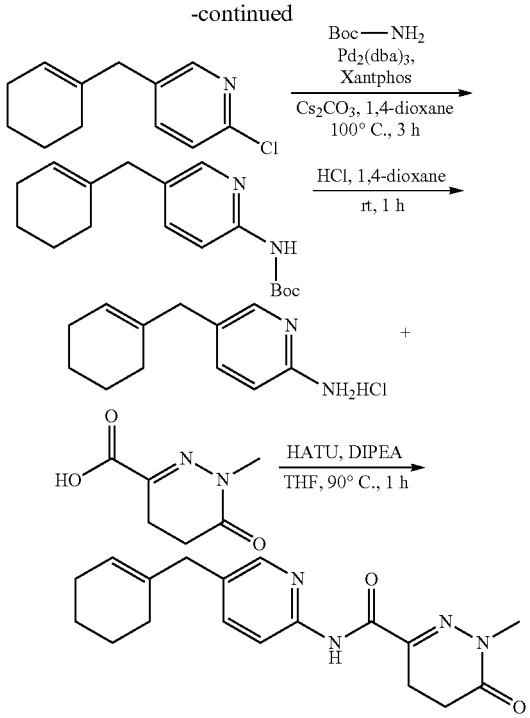

Step 1: Preparation of 2-chloro-5-(cyclohexenylmethyl)pyridine

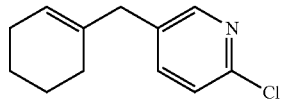 [SMILES: Clc1ccc(CC2=CCCCC2)cn1]

To a solution of 2-chloro-5-(chloromethyl)pyridine (6.38 g, 39.65 mmol), cyclohexenylboronic acid (5 g, 39.65 mmol) and potassium carbonate (11 g, 79.3 mmol) in water (30 mL) and acetonitrile (120 mL) was added [1,1'-bis(diphenylphosphino)ferrocene]palladium(II) dichloride dichloromethane adduct (3.23 g, 3.97 mmol) under nitrogen. The reaction mixture was heated to 50° C. and stirred for 1 h before volatiles were removed under reduced pressure. The aqueous layer was extracted with dichloromethane (50 mL). The combined organic layers were collected, dried over sodium sulfate, filtered and concentrated. The residue was purified by column chromatography (silica gel, petroleum ether/ethyl acetate=10/1) to offer 2-chloro-5-(cyclohexenylmethyl)pyridine (5.3 g, 25.6 mmol, 65%) as a white solid. LCMS (ESI) m/z: 208.1 [M+H]$^+$.

Step 2: Preparation of tert-butyl 5-(cyclohexenylmethyl)pyridin-2-ylcarbamate

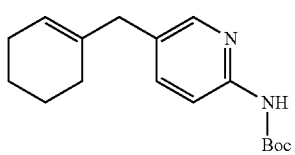 [SMILES: CC(C)(C)OC(=O)Nc1ccc(CC2=CCCCC2)cn1]

To a solution of 2-chloro-5-(cyclohexenylmethyl)pyridine (0.9 g, 4.35 mmol), tert-butyl carbamate (509 mg, 4.35 mmol), XantPhos (377 mg, 0.653 mmol) and cesium carbonate (2.83 g, 8.7 mmol) in 1,4-dioxane (10 mL) was added tris(dibenzylideneacetone)dipalladium(0) (401 mg, 0.435 mmol) under nitrogen. The reaction mixture was heated to 100° C. and stirred for 3 h. The solid was filtered and the filtrate was concentrated, and purified by column chromatography (silica gel, petroleum ether/ethyl acetate=10/1) to offer tert-butyl 5-(cyclohexenylmethyl)pyridin-2-ylcarbamate (0.6 g, 2.08 mmol, 48%) as a white solid. LCMS (ESI) m/z: 289.1 [M+H]$^+$.

Step 3: Preparation of 5-(cyclohexenylmethyl)pyridin-2-ammonium chloride

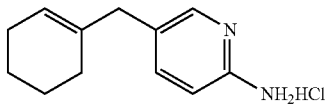

A solution of tert-butyl 5-(cyclohexenylmethyl)pyridin-2-ylcarbamate (0.3 g, 1.04 mmol) in hydrochloric acid/1,4-dioxane (5 mL) was heated to 60° C. and stirred for 1 h. The volatiles were removed under the reduced pressure to give 5-(cyclohexenylmethyl)pyridin-2-amine as it's hydrochloride salt (0.2 g, 0.9 mmol, 86%, crude) as a white solid which was used in the next step without purification. LCMS (ESI) m/z: 189.1 [M+H]$^+$.

Step 4: Preparation of N-(5-(cyclohexenylmethyl)pyridin-2-yl)-1-methyl-6-oxo-1,4,5,6-tetrahydropyridazine-3-carboxamide

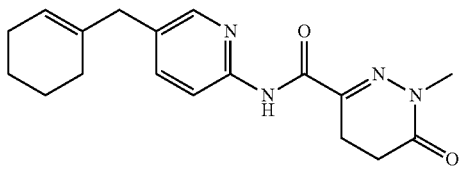 [SMILES: CN1N=C(C(=O)Nc2ccc(CC3=CCCCC3)cn2)CCC1=O]

To a solution of 1-methyl-6-oxo-1,4,5,6-tetrahydropyridazine-3-carboxylic acid (100 mg, 0.641 mmol) and diisopropylethylamine (249 mg, 1.923 mmol) in tetrahydrofuran (5 mL) at 20° C. was added 1-[bis(dimethylamino)methylene]-1H-1,2,3-triazolo[4,5-b]pyridinium 3-oxid hexafluorophosphate (366 mg, 0.962 mmol). The reaction mixture was stirred for 20 minutes before a solution of 5-(cyclohexenylmethyl)pyridin-2-ammonium chloride (144 mg, 0.641 mmol) in tetrahydrofuran (1.0 mL) was added. The reaction solution was heated to 90° C. and stirred for 1 h. The volatiles were removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(cyclohexenylmethyl)pyridin-2-yl)-1-methyl-6-oxo-1,4,5,6-tetrahydropyridazine-3-carboxamide (13.6 mg, 0.042 mmol, 6%) as a white solid. $^1$H NMR (400 MHz, Dimethylsulfoxide-d$_6$) δ 9.70 (s, 1H), 8.16 (d, J=4.0 Hz, 1H), 8.03 (d, J=8.0 Hz, 1H), 7.64 (q, J=4.0 Hz, 1H), 5.44 (s, 1H), 3.36 (s, 3H), 3.21 (s, 2H), 2.86 (t, J=10.0 Hz, 2H), 2.53-2.55 (m, 2H), 1.97 (s, 2H), 1.82 (s, 2H), 1.48-1.54 (m, 4H); LCMS (ESI) m/z: 327.1 [M+H]$^+$.

Example 35. Preparation of N-(5-(3,4-difluorobenzyl)pyridin-2-yl)-1-methyl-6-oxo-1,6-dihydropyridazine-3-carboxamide (35)

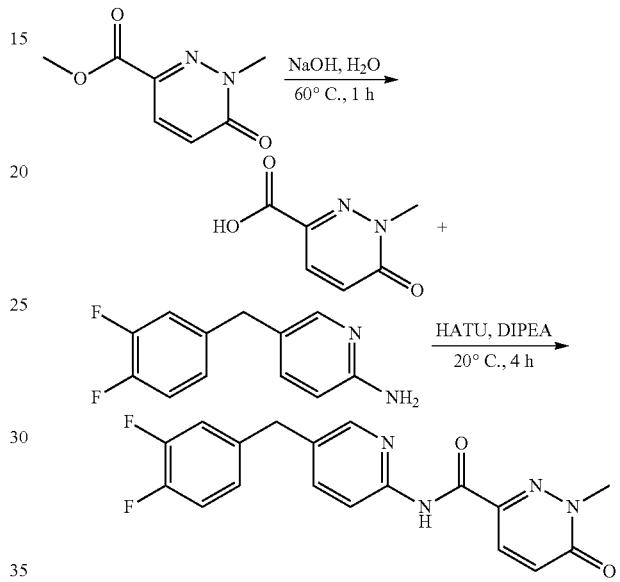

Step 1: Preparation of 5-(3,4-difluorobenzyl)pyridin-2-amine

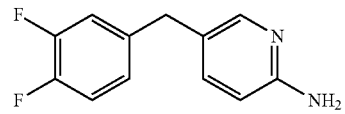 [SMILES: Nc1ccc(Cc2ccc(F)c(F)c2)cn1]

To a solution of 4-(bromomethyl)-1,2-difluorobenzene (2.0 g, 9.71 mmol), 5-(4,4,5,5-tetramethyl-1,3,2-dioxaborolan-2-yl)pyridin-2-amine (2.14 g, 9.71 mmol) and potassium carbonate (2.7 g, 19.42 mmol) in tetrahydrofuran (20 mL) and water (5 mL) was added tetrakis(triphenylphosphine)palladium(0) (1.12 g, 0.971 mmol) under nitrogen. The reaction mixture was heated to 90° C. and stirred for 2 h. The volatiles were removed under reduced pressure and the aqueous layer was adjusted to pH=1 with ~1 N hydrochloric acid. The aqueous layer was extracted with ethyl acetate (50 mL) before aqueous sodium bicarbonate added to adjust the pH=8=10. The aqueous layer was extracted with dichloromethane (50 mL×2). The combined dichloromethane layers were collected, dried over sodium sulfate, filtered and concentrated. The crude sample was purified by column chromatography (silica gel, dichloromethane/methanol=20/1) to offer 5-(3,4-difluorobenzyl)pyridin-2-amine as a yellow oil (800 mg, 3.64 mmol, 37%); LCMS (ESI) m/z: 221.1 [M+H]$^+$.

Step 2: Preparation of 1-methyl-6-oxo-1,6-dihydropyridazine-3-carboxylic acid

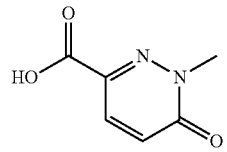

To a solution of methyl 1-methyl-6-oxo-1,6-dihydropyridazine-3-carboxylate (0.150 g, 0.892 mmol) in water (3 mL) was added sodium hydroxide (71 mg, 1.785 mmol). The reaction mixture was heated to 60° C. and stirred for 1 h. The reaction solution was treated with 1 N hydrochloric acid to adjust the pH value to 3=5 before all volatiles were removed to yield 1-methyl-6-oxo-1,6-dihydropyridazine-3-carboxylic acid as a white solid (110 mg, crude); LCMS (ESI) m/z: 155.1 [M+H]$^+$.

Step 3: Preparation of N-(5-(3,4-difluorobenzyl)pyridin-2-yl)-1-methyl-6-oxo-1,6-dihydropyridazine-3-carboxamide

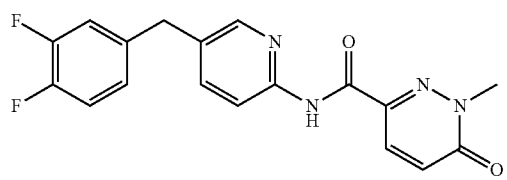 [SMILES: Cn1nc(C(=O)Nc2ccc(Cc3ccc(F)c(F)c3)cn2)ccc1=O]

To a solution of 1-methyl-6-oxo-1,6-dihydropyridazine-3-carboxylic acid (100 mg, 0.649 mmol) and diisopropylethylamine (252 mg, 1.947 mmol) in tetrahydrofuran (4 mL) at 20° C. was added 1-[bis(dimethylamino)methylene]-1H-1,2,3-triazolo[4,5-b]pyridinium 3-oxid hexafluorophosphate (370 mg, 0.974 mmol). The reaction mixture was stirred for 20 minutes before a solution of 5-(3,4-difluorobenzyl)pyridin-2-amine (143 mg, 0.649 mmol) in tetrahydrofuran (1.0 mL) was added. The reaction solution was stirred at 20° C. for 4 h. The volatiles were removed under reduced pressure and the residue was added to a mixture of dichloromethane (50 mL) and water (50 mL). The organic layer was collected, dried over sodium sulfate, filtered and concentrated. The crude sample was purified by column chromatography (silica gel, dichloromethane/methanol=20/1) to offer N-(5-(3,4-difluorobenzyl)pyridin-2-yl)-1-methyl-6-oxo-1,6-dihydropyridazine-3-carboxamide (130.3 mg, 0.36 mmol, 55%) as a white solid. $^1$H NMR (400 MHz, trifluoroacetic acid-d) δ 8.75-8.84 (m, 3H), 8.30 (d, J=7.2 Hz, 1H), 7.95 (d, J=7.6 Hz, 1H), 7.65-7.67 (m, 1H), 7.47-7.52 (m, 2H), 4.64 (s, 2H), 4.54 (s, 3H); LCMS (ESI) m/z: 357.1 [M+H]$^+$.

Example 36. Preparation of N-(5-(4-chlorobenzyl)pyridin-2-yl)-1-methyl-6-oxo-1,6-dihydropyridazine-3-carboxamide (36)

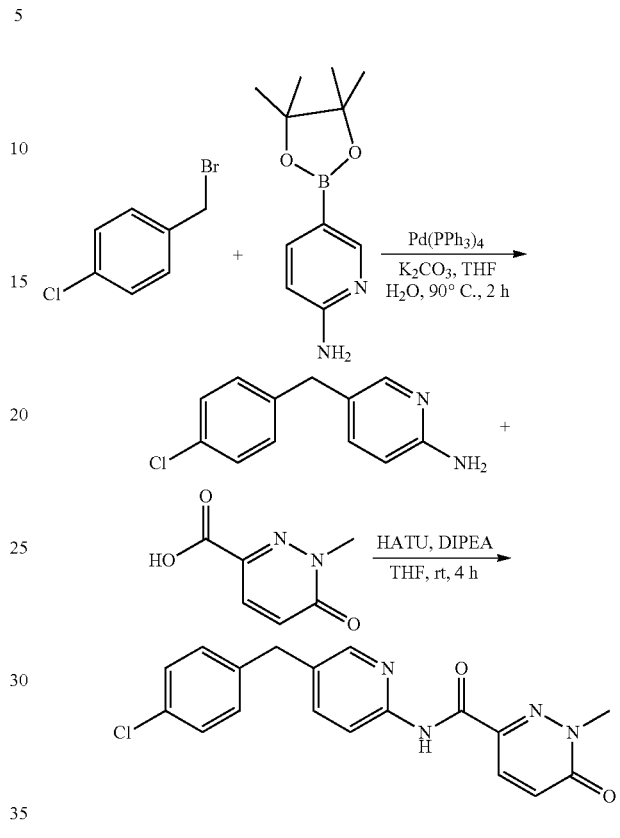

Step 1: Preparation of 5-(4-chlorobenzyl)pyridin-2-amine

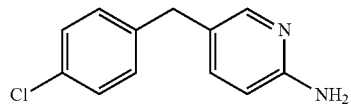 [SMILES: Nc1ccc(Cc2ccc(Cl)cc2)cn1]

To a solution of 1-(bromomethyl)-4-chlorobenzene (1.0 g, 4.90 mmol), 5-(4,4,5,5-tetramethyl-1,3,2-dioxaborolan-2-yl)pyridin-2-amine (1.08 g, 4.90 mmol), potassium carbonate (1.35 g, 9.80 mmol), in tetrahydrofuran (12 mL) and water (3 mL) was added tetrakis(triphenylphosphine)palladium(0) (0.566 g, 0.49 mmol) under nitrogen. The reaction mixture was heated to 90° C. and stirred for 2 h. The volatiles were removed under reduced pressure and the aqueous phase was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated. The crude material was purified by column chromatography (silica gel, petroleum ether/ethyl acetate=1/1) to offer 5-(4-chlorobenzyl)pyridin-2-amine (0.55 g, 2.52 mmol, 51%) as a yellow solid. LCMS (ESI) m/z: 219.1 [M+H]$^+$.

Step 2: Preparation of N-(6-(3-chlorobenzyl)pyridazin-3-yl)-6-oxo-1-propyl-1,6-dihydropyridazine-3-carboxamide

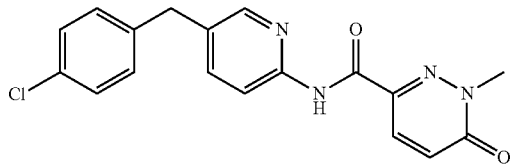 [SMILES: Cn1nc(C(=O)Nc2ccc(Cc3ccc(Cl)cc3)cn2)ccc1=O]

To a solution of 1-methyl-6-oxo-1,6-dihydropyridazine-3-carboxylic acid (0.100 g, 0.649 mmol), diisopropylethylamine (0.168 g, 1.298 mmol) in tetrahydrofuran (5 mL) at 20° C., was added 1-[bis(dimethylamino)methylene]-1H-1,2,3-triazolo[4,5-b]pyridinium 3-oxid hexafluorophosphate (370 mg, 0.974 mmol). The reaction mixture was stirred for 20 minutes before a solution of 5-(4-chlorobenzyl)pyridin-2-amine (0.142 g, 0.649 mmol) in tetrahydrofuran (1.0 mL) was added. The reaction solution was stirred at 20° C. for 4 h. The volatiles were removed under the reduced pressure and the crude residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to offer N-(5-(4-chlorobenzyl)pyridin-2-yl)-1-methyl-6-oxo-1,6-dihydropyridazine-3-carboxamide (94.2 mg, 0.27 mmol, 41%) as a white solid. $^1$H NMR (400 MHz, Dimethylsulfoxide-$d_6$) δ 10.11 (s, 1H), 8.31 (s, 1H), 8.07-8.09 (d, J=8.4 Hz, 1H), 7.93-7.95 (d, J=9.6 Hz, 1H), 7.71-7.73 (d, J=8.4 Hz, 1H), 7.28-7.37 (m, 4H), 7.06-7.08 (d, J=9.6 Hz, 1H), 3.96 (s, 2H), 3.78 (s, 3H); LCMS (ESI) m/z: 355.1 [M+H]$^+$.

Example 37. Preparation of N-(5-(3,5-difluorobenzyl)pyridin-2-yl)-1-methyl-6-oxo-1,6-dihydropyridazine-3-carboxamide (37)

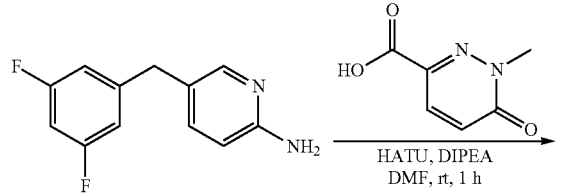

Step 1: Preparation of N-(5-(3,5-difluorobenzyl)pyridin-2-yl)-1-methyl-6-oxo-1,6-dihydropyridazine-3-carboxamide

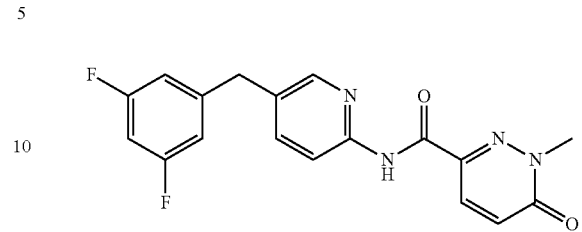

A mixture of 5-(3,5-difluorobenzyl)pyridin-2-amine (200 mg, 0.9 mmol), 1-methyl-6-oxo-1,6-dihydropyridazine-3-carboxylic acid (139 mg, 0.9 mmol), 2-(7-azabenzotriazol-1-yl)-N,N,N',N'-tetramethyluronium hexafluorophosphate (513 mg, 1.35 mmol) and N,N-diisopropylethylamine (349 mg, 2.7 mmol) in N,N-dimethylformamide (8 mL) was stirred at room temperature for 1 h. The mixture was poured into water. The formed precipitate was collected by filtration and the obtained solid was washed with methanol (20 mL) to give N-(5-(3,5-difluorobenzyl)pyridin-2-yl)-1-methyl-6-oxo-1,6-dihydropyridazine-3-carboxamide (0.134 g, 0.38 mmol, 42%) as a grey solid. $^1$H NMR (500 MHz, Dimethylsulfoxide-$d_6$) δ 10.12 (s, 1H), 8.34 (d, J=2.0 Hz, 1H), 8.07 (d, J=10.5 Hz, 1H), 7.93 (d, J=12.5 Hz, 1H), 7.76 (dd, J=10.5, 3.0 Hz, 1H), 7.08-7.02 (m, 4H), 3.97 (s, 2H), 3.77 (s, 3H); LCMS (ESI) m/z: 357.1 [M+H]$^+$.

Example 38. Preparation of N-(5-(cyclohexylmethyl)pyridin-2-yl)-1-methyl-6-oxo-1,6-dihydropyridazine-3-carboxamide (38)

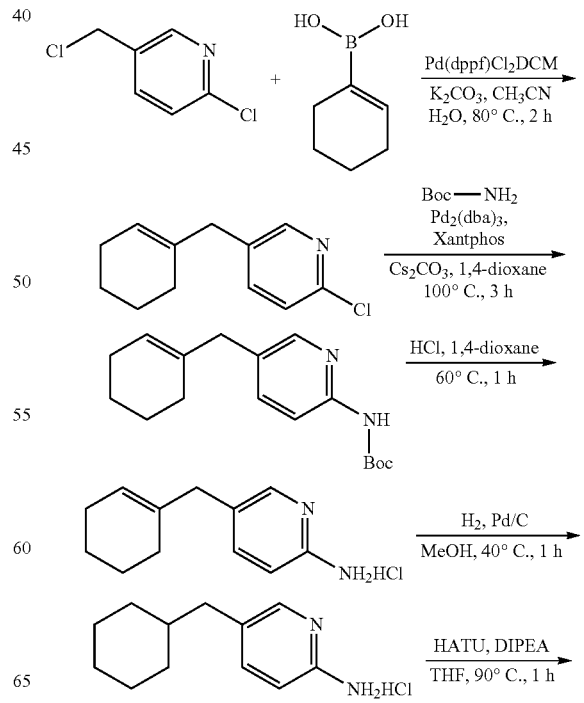

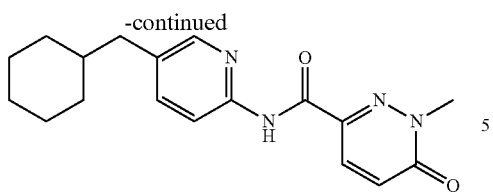

Step 1: Preparation of 2-chloro-5-(cyclohexenylmethyl)pyridine

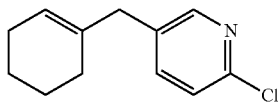 [SMILES: Clc1ccc(CC2=CCCCC2)cn1]

To a solution of 2-chloro-5-(chloromethyl)pyridine (6.38 g, 39.7 mmol), cyclohexenylboronic acid (5 g, 39.7 mmol) and potassium carbonate (11 g, 79.3 mmol) in water (30 mL) and acetonitrile (120 mL) was added [1,1'-bis(diphenylphosphino)ferrocene]palladium(II) dichloride dichloromethane adduct (3.23 g, 3.97 mmol) under nitrogen. The reaction mixture was heated to 50° C. and stirred for 1 h before volatiles were removed under reduced pressure. The aqueous layer was extracted with dichloromethane (50 mL×2). The combined organic layers were collected, dried over sodium sulfate, filtered and concentrated. The crude product was purified by column chromatography (silica gel, petroleum ether/ethyl acetate=10/1) to offer 2-chloro-5-(cyclohexenylmethyl)pyridine (5.3 g, 25.6 mmol, 65%) as a white solid. LCMS (ESI) m/z: 208.1 [M+H]+.

Step 2: Preparation of tert-butyl 5-(cyclohexenylmethyl)pyridin-2-ylcarbamate

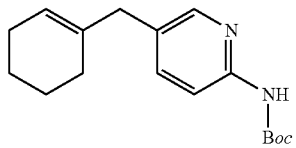 [SMILES: CC(C)(C)OC(=O)Nc1ccc(CC2=CCCCC2)cn1]

To a solution of 2-chloro-5-(cyclohexenylmethyl)pyridine (5.2 g, 25.1 mmol), tert-butyl carbamate (2.94 g, 25.1 mmol), XantPhos (2.2 g, 3.77 mmol) and cesium carbonate (16.4 g, 50.2 mmol) in 1,4-dioxane (60 mL) was added tris(dibenzylideneacetone)dipalladium(0) (2.3 g, 2.51 mmol) under nitrogen. The reaction mixture was heated to 100° C. and stirred for 3 h. The solid was filtered and the filtrate was concentrated, and purified by column chromatography (silica gel, petroleum ether/ethyl acetate=10/1) to offer tert-butyl 5-(cyclohexenylmethyl)pyridin-2-ylcarbamate (2.4 g, 8.32 mmol, 33%) as a white solid. LCMS (ESI) m/z: 289.1 [M+H]+.

Step 3: Preparation of 5-(cyclohexenylmethyl)pyridin-2-ammonium chloride

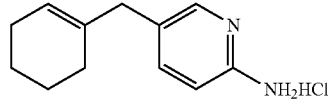

A solution of tert-butyl 5-(cyclohexenylmethyl)pyridin-2-ylcarbamate (2.4 g, 8.32 mmol) in hydrochloric acid in 1,4-dioxane (20 mL) was heated to 60° C. and stirred for 1 h. The volatiles were removed under reduced pressure to offer 5-(cyclohexenylmethyl)pyridin-2-ammonium chloride (1.5 g, 6.69 mmol, 80%, crude) as a white solid which was used in the next step without further purification. LCMS (ESI) m/z: 189.1 [M+H]+.

Step 4: Preparation of 5-(cyclohexylmethyl)pyridin-2-ammonium chloride

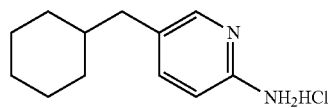

To a solution of 5-(cyclohexenylmethyl)pyridin-2-ammonium chloride (1.5 g, 6.69 mmol) in methanol (10 mL) was added palladium on activated carbon (450 mg) under nitrogen. Reaction mixture was heated to 40° C. under hydrogen and stirred for 12 h. The solid was filtered off and the filtrate was concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give 5-(cyclohexylmethyl)pyridin-2-amine as the hydrochloride salt (0.400 g, 1.77 mmol, 26%, crude) as a brown solid. LCMS (ESI) m/z: 191.3 [M+H]+.

Step 5: Preparation of N-(5-(cyclohexylmethyl)pyridin-2-yl)-1-methyl-6-oxo-1,6-dihydropyridazine-3-carboxamide

To a solution of 1-methyl-6-oxo-1,6-dihydropyridazine-3-carboxylic acid (69 mg, 0.446 mmol) and diisopropylethylamine (173 mg, 1.34 mmol) in tetrahydrofuran (4 mL) at 20° C. was added 1-[bis(dimethylamino)methylene]-1H-1,2,3-triazolo[4,5-b]pyridinium 3-oxid hexafluorophosphate (254 mg, 0.669 mmol). The reaction mixture was stirred for 20 minutes before a solution of 5-(cyclohexylmethyl)pyridin-2-ammonium chloride (100 mg, 0.446 mmol) in tetrahydrofuran (1.0 mL) was added. The reaction solution was heated to 90° C. and stirred for 1 h. The volatiles were removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(cyclohexylmethyl)pyridin-2-yl)-1-methyl-6-oxo-1,6-dihydropyridazine-3-carboxamide (35.8 mg, 0.11 mmol, 25%) as a white solid. ¹H NMR (400 MHz, Dimethylsulfoxide-d₆) δ 10.08 (s, 1H), 8.18 (d, J=4.0 Hz, 1H), 8.07 (d, J=8.0 Hz, 1H), 7.96 (d, J=8.0 Hz, 1H), 7.68 (q, J=4.0 Hz, 1H), 7.08 (d, J=8.0 Hz, 1H), 3.79 (s, 3H), 2.46-2.48 (m, 2H), 1.59-1.67 (m, 5H), 1.48-1.51 (m, 1H), 1.10-1.23 (m, 3H), 0.88-0.97 (m, 2H); LCMS (ESI) m/z: 327.1 [M+H]⁺.

Example 39. Preparation of 1-methyl-6-oxo-N-(5-(4-(trifluoromethyl)benzyl)pyridin-2-yl)-1,6-dihydropyridazine-3-carboxamide (39)

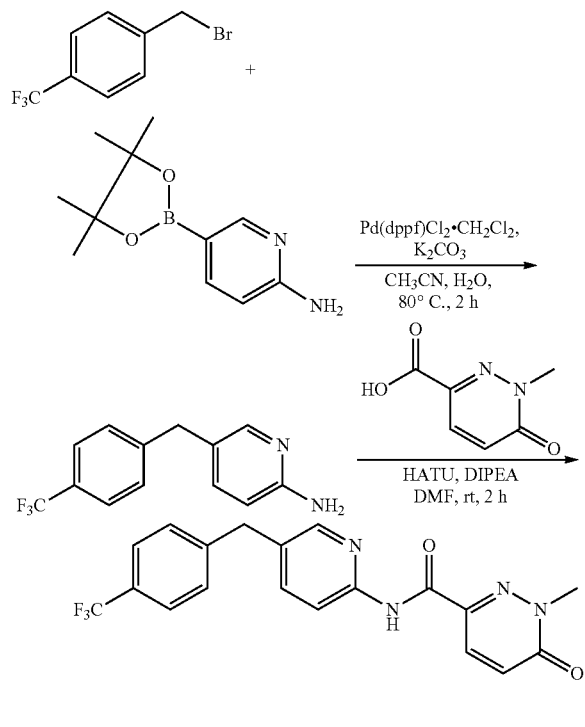

Step 1: Preparation of 5-(4-(trifluoromethyl)benzyl)pyridin-2-amine

To a solution of 1-(bromomethyl)-4-(trifluoromethyl)benzene (1.6 g, 6.7 mmol), 5-(4,4,5,5-tetramethyl-1,3,2-dioxaborolan-2-yl)pyridin-2-amine (1.77 g, 8 mmol) and potassium carbonate (1.85 g, 13.4 mmol) in acetonitrile (32 mL) and water (8 mL) was added 1,1'-bis(diphenylphosphino)ferrocene-palladium(II)dichloride dichloromethane complex (0.147 g, 0.67 mmol) under argon. The reaction mixture was stirred at 80° C. for 2 h. The reaction solution was extracted with ethyl acetate (50 mL×2). The combined organic layers were washed with brine (50 mL), dried over sodium sulfate, filtered and concentrated. The crude residue was purified by column chromatography (silica gel, dichloromethane/methanol=100/1) to give 5-(4-(trifluoromethyl)benzyl)pyridin-2-amine (1.2 g, 4.8 mmol, 71%) as a color oil. LCMS (ESI) m/z: 253.1 [M+H]⁺.

Step 2: Preparation of 1-methyl-6-oxo-N-(5-(4-(trifluoromethyl)benzyl)pyridin-2-yl)-1,6-dihydropyridazine-3-carboxamide

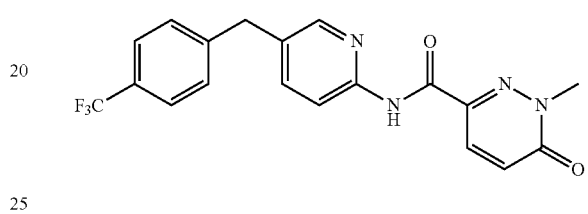

A solution of 5-(4-(trifluoromethyl)benzyl)pyridin-2-amine (0.194 g, 0.77 mmol), 1-methyl-6-oxo-1,6-dihydropyridazine-3-carboxylic acid (0.154 g, 0.64 mmol), 2-(7-azabenzotriazol-1-yl)-N,N,N',N'-tetramethyluronium hexafluorophosphate (0.365 g, 0.96 mmol) and ethyldiisopropylamine (0.248 g, 1.92 mmol) in N,N-dimethylformamide (3.5 mL) was stirred at room temperature for 2 h. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give 1-methyl-6-oxo-N-(5-(4-(trifluoromethyl)benzyl)pyridin-2-yl)-1,6-dihydropyridazine-3-carboxamide (0.0912 g, 0.24 mmol, 37.2%) as a white solid. ¹H NMR (500 MHz, Dimethylsulfoxide-d₆) δ 10.15 (s, 1H), 8.35 (d, J=2.5 Hz, 1H), 8.09 (d, J=8.5 Hz, 1H), 7.94 (d, J=9.1 Hz, 1H), 7.76 (dd, J=8.5, 2.0 Hz, 1H), 7.67 (d, J=8.5 Hz, 2H), 7.49 (d, J=8.0 Hz, 2H), 7.07 (d, J=9.5 Hz, 1H), 4.07 (s, 2H), 3.76 (s, 3H); LCMS (ESI) m/z: 389.0 [M+H]⁺.

Example 40. Preparation of N-(5-(3-chloro-5-fluorobenzyl)pyridin-2-yl)-1-methyl-6-oxo-1,6-dihydropyridazine-3-carboxamide (40)

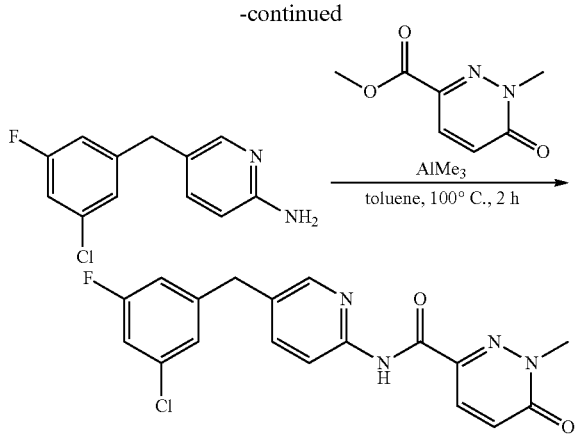

Step 1: Preparation of
5-(3-chloro-5-fluorobenzyl)pyridin-2-amine

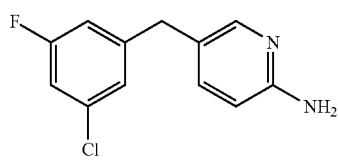

To a solution of 1-(bromomethyl)-3-chloro-5-fluorobenzene (2.23 g, 10 mmol), 5-(4,4,5,5-tetramethyl-1,3-dioxolan-2-yl)pyridin-2-amine (2.67 g, 12 mmol) and potassium carbonate (2.76 g, 20 mmol) in 1,4-dioxane (45 mL) and water (15 mL) was added [1,1'-bis(diphenylphosphino)ferrocene]dichloropalladium(II) (0.732 g, 1.0 mmol) under nitrogen. The reaction mixture was stirred at 100° C. for 2 h. The volatiles were concentrated and water (50 mL) was added. The aqueous layer was extracted with ethyl acetate (80 mL×3). The combined organic layers were dried over sodium sulfate, filtered and concentrated. The crude product was purified by column chromatography (silica gel, petroleum ether/ethyl acetate from 1:1 to 0:1) to give 5-(3-chloro-5-fluorobenzyl)pyridin-2-amine (1.9 g, 8.1 mmol, 81%) as a brown solid. LCMS (ESI) m/z: 237.1 [M+H]⁺.

Step 2: Preparation of N-(5-(3-chloro-5-fluorobenzyl)pyridin-2-yl)-1-methyl-6-oxo-1,6-dihydropyridazine-3-carboxamide

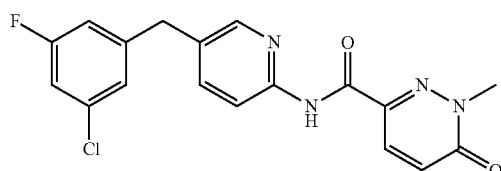

To a solution of 5-(3-chloro-5-fluorobenzyl)pyridin-2-amine (0.285 g, 1.2 mmol) in toluene (5 mL) at room temperature was added trimethylaluminum (0.6 mL, 1.2 mmol, 2 M in toluene) slowly under argon. The reaction mixture was stirred at room temperature for 1 h before methyl 1-methyl-6-oxo-1,6-dihydropyridazine-3-carboxy-late (0.168 g, 1.0 mmol) in toluene (5 mL) was added. The resulting solution was heated to 100° C. and stirred for 2 h. The reaction mixture was quenched with methanol and aqueous 2 N hydrochloric acid. The volatiles were removed under pressure and water (20 mL) was added. The aqueous layer was extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-(3-chloro-5-fluorobenzyl)pyridin-2-yl)-1-methyl-6-oxo-1,6-dihydropyridazine-3-carboxamide (0.151 g, 0.41 mmol, 41%) as a white solid. ¹H NMR (400 MHz, Dimethylsulfoxide-d₆) δ 10.13 (s, 1H), 8.35 (d, J=2.0 Hz, 1H), 8.08 (d, J=8.8 Hz, 1H), 7.94 (d, J=10.0 Hz, 1H), 7.77 (dd, J₁=2.0 Hz, J₂=8.4 Hz, 1H), 7.24-7.28 (m, 2H), 7.15-7.18 (m, 1H), 7.06 (d, J=10.0 Hz, 1H), 3.98 (s, 2H), 3.78 (s, 3H); LCMS (ESI) m/z: 373.1 [M+H]⁺.

Example 41. Preparation of 1-methyl-6-oxo-N-(5-(3,4,5-trifluorobenzyl)pyridin-2-yl)-1,6-dihydro-pyridazine-3-carboxamide (41)

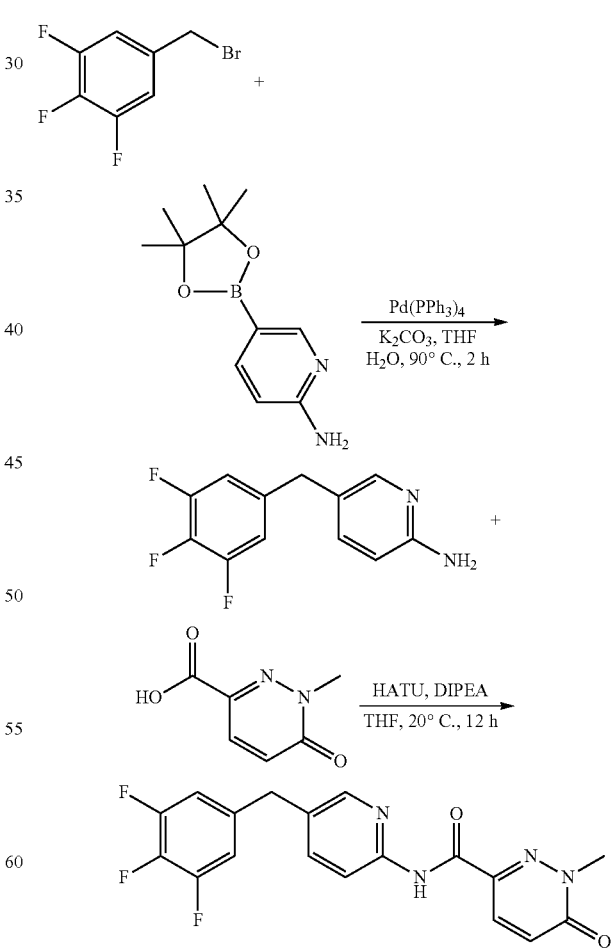

Step 1: Preparation of 5-(3,4,5-trifluorobenzyl)pyridin-2-amine

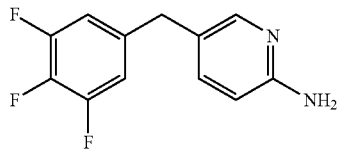 [SMILES: Nc1ccc(Cc2cc(F)c(F)c(F)c2)cn1]

To a solution of 5-(bromomethyl)-1,2,3-trifluorobenzene (1.0 g, 4.47 mmol), 5-(4,4,5,5-tetramethyl-1,3,2-dioxaborolan-2-yl)pyridin-2-amine (0.983 g, 4.47 mmol), potassium carbonate (1.23 g, 8.94 mmol) in tetrahydrofuran (16 mL) and water (4 mL) under nitrogen was added tetrakis(triphenylphosphine)palladium(0) (0.516 g, 0.447 mmol). The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-(3,4,5-trifluorobenzyl)pyridin-2-amine (0.750 g, crude) as a yellow oil. LCMS (ESI) m/z: 239.1 [M+H]$^+$. Used in the next step without further purification.

Step 2: Preparation of 1-methyl-6-oxo-1,6-dihydropyridazine-3-carboxylic acid

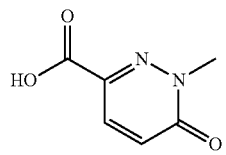

To a solution of methyl 1-methyl-6-oxo-1,6-dihydropyridazine-3-carboxylate (0.200 g, 1.19 mmol) in water (2 mL) was added sodium hydroxide (0.095 g, 2.38 mmol). The reaction was heated to 60° C. and stirred for 1 h. The aqueous layer was adjusted to pH=3=5 with aqueous 1 N hydrogen chloride. Solution mixture was concentrated, down to dryness to afford 1-methyl-6-oxo-1,6-dihydropyridazine-3-carboxylic acid as a white solid (0.130 g, crude); LCMS (ESI) m/z: 155.1 [M+H]$^+$.

Step 3: Preparation of 1-methyl-6-oxo-N-(5-(3,4,5-trifluorobenzyl)pyridin-2-yl)-1,6-dihydropyridazine-3-carboxamide

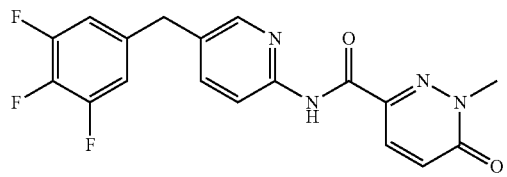 [SMILES: Cn1nc(C(=O)Nc2ccc(Cc3cc(F)c(F)c(F)c3)cn2)ccc1=O]

To a solution of 1-methyl-6-oxo-1,6-dihydropyridazine-3-carboxylic acid (0.100 g, 0.649 mmol), N,N-diisopropylethylamine (0.252 g, 1.95 mmol) in tetrahydrofuran (4 mL) at 20° C. was added 1-[bis(dimethylamino)methylene]-1H-1,2,3-triazolo[4,5-b]pyridinium 3-oxid hexafluorophosphate (0.370 g, 0.974 mmol). The reaction was stirred for 20 minutes before a solution of 5-(3,4,5-trifluorobenzyl)pyridin-2-amine (0.154 g, 0.649 mmol) in tetrahydrofuran(1.0 mL) was added. The solution was stirred at 20° C. 16 h and the volatiles were removed under reduced pressure. The crude residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 1-methyl-6-oxo-N-(5-(3,4,5-trifluorobenzyl)pyridin-2-yl)-1,6-dihydropyridazine-3-carboxamide as a white solid (0.064 g, 0.169 mmol, 26%). $^1$H NMR (400 MHz, Dimethylsulfoxide-d$_5$) δ 10.13 (s, 1H), 8.35 (s, 1H), 8.08 (d, J=6 Hz, 1H), 7.95 (d, J=7.5 Hz, 1H), 7.76-7.79 (m, 1H), 7.27-7.31 (m, 2H), 7.06-7.09 (d, J=12 Hz, 1H), 3.96 (s, 2H), 3.79 (s, 3H); LCMS (ESI) m/z: 375.1 [M+H]$^+$.

Example 42. Preparation of N-(5-(3-cyano-5-fluorobenzyl)pyridin-2-yl)-1-methyl-6-oxo-1,6-dihydropyridine-3-carboxamide (42)

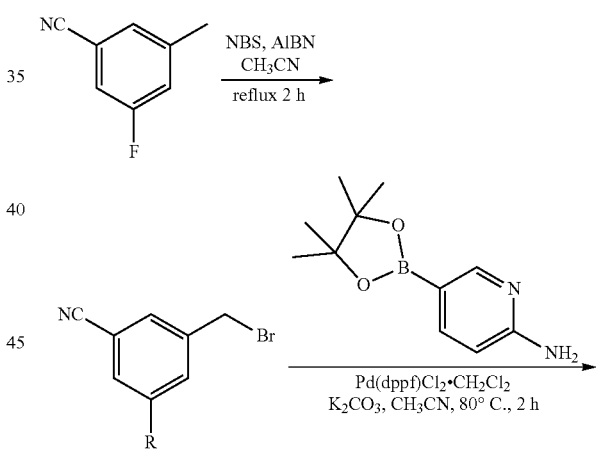

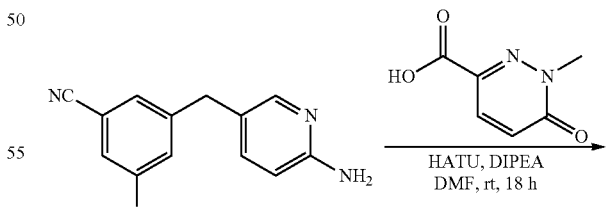

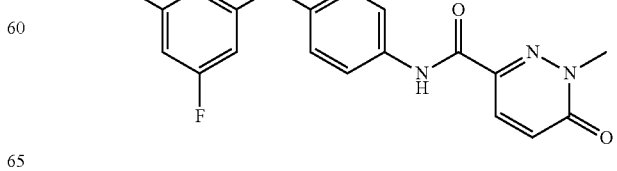

Step 1: Preparation of 3-(bromomethyl)-5-fluorobenzonitrile

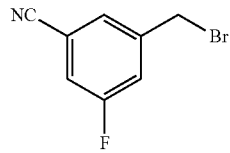 [SMILES: N#Cc1cc(F)cc(CBr)c1]

The synthesis of 3-(bromomethyl)-5-fluorobenzonitrile followed similar procedures as for Example 25. Compound 3-(bromomethyl)-5-fluorobenzonitrile (17.0 g, 79.4 mmol, 107%) was obtained as a colorless oil. ¹H NMR (500 MHz, Chloroform-d) δ 7.51 (s, 1H), 7.38 (dt, J=2.5, 11.0 Hz, 1H), 7.32 (dt, J=1.5, 10.0 Hz, 1H), 4.45 (s, 2H).

Step 2: Preparation of 3-((6-aminopyridin-3-yl)methyl)-5-fluorobenzonitrile

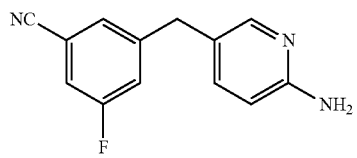 [SMILES: N#Cc1cc(F)cc(Cc2ccc(N)nc2)c1]

The synthesis of 3-((6-aminopyridin-3-yl)methyl)-5-fluorobenzonitrile was followed with similar procedures as for Example 23. Compound 3-((6-aminopyridin-3-yl)methyl)-5-fluorobenzonitrile (0.800 g, 3.50 mmol, 50%) was obtained as a light-yellow oil. LCMS (ESI) for m/z: 228.1 [M+H]⁺.

Step 3: Preparation of N-(5-(3-cyano-5-fluorobenzyl)pyridin-2-yl)-1-methyl-6-oxo-1,6-dihydropyridine-3-carboxamide

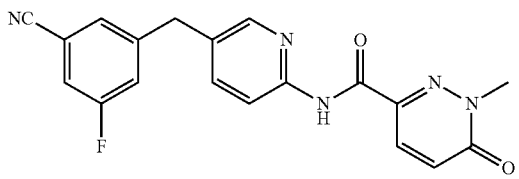 [SMILES: Cn1nc(C(=O)Nc2ccc(Cc3cc(F)cc(C#N)c3)cn2)ccc1=O]

A mixture of 1-methyl-6-oxo-1,6-dihydropyridazine-3-carboxylic acid (0.203 g, 1.32 mmol), 3-((6-aminopyridin-3-yl)methyl)-5-fluorobenzonitrile (0.300 g, 1.32 mmol), 1-[bis(dimethylamino)methylene]-1H-1,2,3-triazolo[4,5-b]pyridinium 3-oxid hexafluorophosphate (0.752 g, 1.98 mmol), N,N-diisopropylethylamine (0.511 g, 3.96 mmol) in N,N-dimethylformamide (10 mL) was stirred at room temperature for 2 h. The mixture was poured into water. The formed precipitate was collected by filtration and washed with methanol (25 mL) to afford N-(5-(3-cyano-5-fluorobenzyl)pyridin-2-yl)-1-methyl-6-oxo-1,6-dihydropyridazine-3-carboxamide (0.198 g, 0.545 mmol, 41%) as an off-white solid. ¹H NMR (500 MHz, Trifluoroacetic acid-d) δ. 8.91-8.88 (m, 2H), 8.78 (d, J=9.5 Hz, 1H), 8.39 (d, J=4.0 Hz, 1H), 7.99-7.94 (m, 3H), 7.86 (d, J=8.5 Hz, 1H), 4.80 (s, 2H), 4.57 (s, 3H); LCMS (ESI) m/z: 364.0 [M+H]⁺.

Example 43. Preparation of N-(5-(3-cyanobenzyl)pyridin-2-yl)-1-methyl-6-oxo-1,6-dihydropyridazine-3-carboxamide (43)

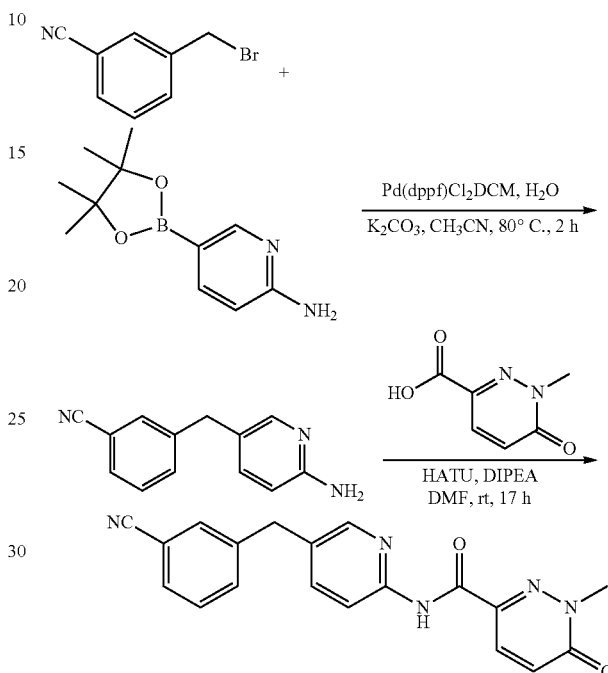

Step 1: Preparation of 3-((6-aminopyridin-3-yl)methyl)benzonitrile

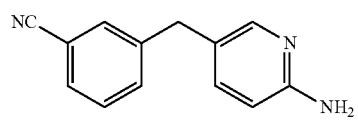

To a solution of 3-(bromomethyl)benzonitrile (0.980 g, 5 mmol), 5-(4,4,5,5-tetramethyl-1,3,2-dioxaborolan-2-yl)pyridin-2-amine (1.21 g, 5.5 mmol), potassium carbonate (1.38 g, 10 mmol) in acetonitrile (24 mL) and water (6 mL) was added [1,1'-bis(diphenylphosphino)ferrocene]dichloropalladium(II)dichloromethane (0.408 g, 0.5 mmol). Reaction was stirred at 80° C. for 2 h. The reaction mixture was extracted with ethyl acetate (50 mL×2), washed with brine (50 mL), dried over sodium sulfate, filtered and concentrated. The residue was purified by column chromatography (silica gel, (dichloromethane: methanol=13/1) to give 3-((6-aminopyridin-3-yl)methyl)benzonitrile (0.900 g, 4.31 mmol, 86.1%) as a brown liquid. LCMS (ESI) m/z: 210.1 [M+H]⁺.

Step 2: Preparation of N-(5-(3-cyanobenzyl)pyridin-2-yl)-1-methyl-6-oxo-1,6-dihydropyridazine-3-carboxamide

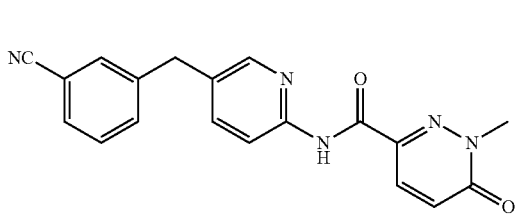 [SMILES: Cn1nc(C(=O)Nc2ccc(Cc3cccc(C#N)c3)cn2)ccc1=O]

A solution of 1-methyl-6-oxo-1,6-dihydropyridazine-3-carboxylic acid (0.100 g, 0.65 mmol), 3-((6-aminopyridin-3-yl)methyl)benzonitrile (0.163 g, 0.78 mmol), 1-[bis(dimethylamino)methylene]-1H-1,2,3-triazolo[4,5-b]pyridinium 3-oxid hexafluorophosphate (0.371 g, 0.975 mol) and N,N-diisopropylethylamine (0.252 g, 1.95 mmol) in N,N-dimethylformamide (3 mL) was stirred at room temperature for 17 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-cyanobenzyl)pyridin-2-yl)-1-methyl-6-oxo-1,6-dihydropyridazine-3-carboxamide (0.0738 g, 0.174 mmol, 26.7%) as a white solid. $^1$H NMR (400 MHz, Dimethylsulfoxide-$d_6$) δ 10.10 (s, 1H), 8.36 (d, J=2.0 Hz, 1H), 8.09 (d, J=8.5 Hz, 1H), 7.95 (d, J=9.7 Hz, 1H), 7.78-7.73 (m, 2H), 7.70 (d, J=7.6 Hz, 1H), 7.63 (d, J=7.9 Hz, 1H), 7.53 (t, J=7.7 Hz, 1H), 7.08 (d, J=9.7 Hz, 1H), 4.03 (s, 2H), 3.78 (s, 3H); LCMS (ESI) m/z: 346.1 [M+H]$^+$.

Example 44. Preparation of N-(5-(3-methoxybenzyl)pyridin-2-yl)-1-methyl-6-oxo-1,6-dihydropyridazine-3-carboxamide (44)

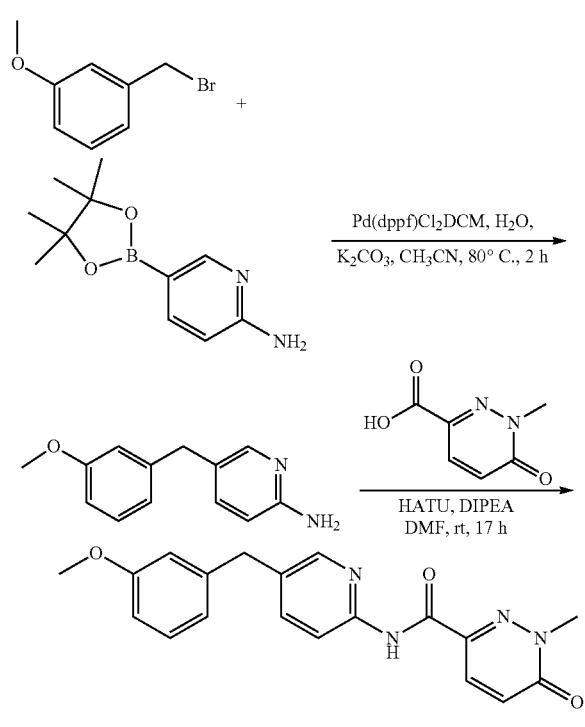

Step 1: Preparation of 5-(3-methoxybenzyl)pyridin-2-amine

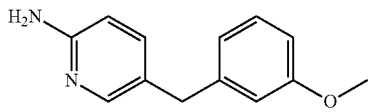 [SMILES: COc1cccc(Cc2ccc(N)nc2)c1]

To a solution of 1-(bromomethyl)-3-methoxybenzene (1.00 g, 5.00 mmol), 5-(4,4,5,5-tetramethyl-1,3,2-dioxaborolan-2-yl)pyridin-2-amine (1.21 g, 5.50 mmol), potassium carbonate (1.38 g, 10.0 mmol) in acetonitrile (24 mL) and water (6 mL) at room temperature was added [1,1'-bis(diphenylphosphino)ferrocene]dichloropalladium(II)dichloromethane (0.408 g, 0.500 mmol). Reaction was stirred at 80° C. for 2 h. The reaction mixture was extracted with ethyl acetate (50 mL×2), washed with brine (50 mL), dried over sodium sulfate, filtered and concentrated. The residue was purified by column chromatography (silica gel, (dichloromethane/methanol=13/1) to yield 5-(3-methoxybenzyl)pyridin-2-amine as a brown liquid (0.740 g, 3.46 mmol, 69.2%). LCMS (ESI) m/z: 215.1 [M+H]$^+$.

Step 2: Preparation of N-(5-(3-methoxybenzyl)pyridin-2-yl)-1-methyl-6-oxo-1,6-dihydropyridazine-3-carboxamide

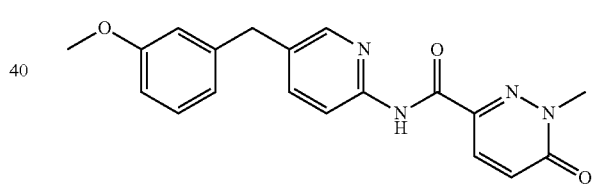

A solution of 1-methyl-6-oxo-1,6-dihydropyridazine-3-carboxylic acid (0.100 g, 0.65 mmol), 5-(3-methoxybenzyl)pyridin-2-amine (0.167 g, 0.78 mmol), 1-[bis(dimethylamino)methylene]-1H-1,2,3-triazolo[4,5-b]pyridinium 3-oxid hexafluorophosphate (0.371 g, 0.975 mmol) and N,N-diisopropylethylamine (0.252 g, 1.95 mmol) in N,N-dimethylformamide (3 mL) was stirred at room temperature for 2 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-methoxybenzyl)pyridin-2-yl)-1-methyl-6-oxo-1,6-dihydropyridazine-3-carboxamide (0.0787 g, 0.221 mmol, 34%) as a white solid. $^1$H NMR (500 MHz, Dimethylsulfoxide-$d_6$) δ 8.31 (s, 1H), 8.07 (d, J=8.4 Hz, 1H), 7.94 (d, J=9.7 Hz, 1H), 7.73 (d, J=8.4 Hz, 1H), 7.22 (t, J=7.8 Hz, 1H), 7.07 (d, J=9.7 Hz, 1H), 6.84-6.77 (m, 3H), 3.93 (s, 2H), 3.78 (s, 3H), 3.72 (s, 3H); LCMS (ESI) for m/z: 351.1[M+H]$^+$.

Example 45. Preparation of N-(5-(3-fluorobenzyl)pyridin-2-yl)-1-methyl-6-oxo-1,6-dihydropyridazine-3-carboxamide (45)

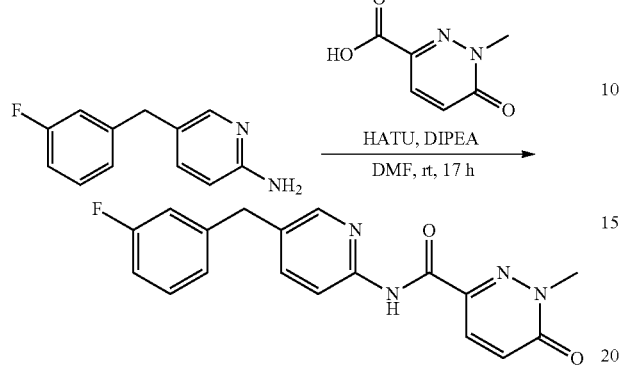

Step 1: Preparation of N-(5-(3-fluorobenzyl)pyridin-2-yl)-1-methyl-6-oxo-1,6-dihydropyridazine-3-carboxamide

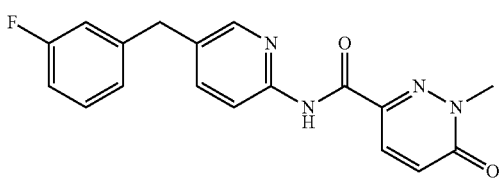 [SMILES: Cn1nc(C(=O)Nc2ccc(Cc3cccc(F)c3)cn2)ccc1=O]

The synthesis of N-(5-(3-fluorobenzyl)pyridin-2-yl)-1-methyl-6-oxo-1,6-dihydropyridazine-3-carboxamide followed synthetic procedure reported for Example 43. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-fluorobenzyl)pyridin-2-yl)-1-methyl-6-oxo-1,6-dihydropyridazine-3-carboxamide (0.0206 g, 0.06 mmol, 14.3%) as a white solid. $^1$H NMR (500 MHz, Dimethylsulfoxide-$d_6$) δ 10.21 (s, 1H), 8.34 (d, J=2.0 Hz, 1H), 8.08 (d, J=8.5 Hz, 1H), 7.95 (d, J=9.0 Hz, 1H), 7.78 (dd, J=8.5 Hz 2.0 Hz, 1H), 7.38-7.33 (m, 1H), 7.14-7.02 (m, 3H), 3.99 (s, 2H), 3.79 (s, 3H); LCMS (ESI) m/z: 339.1 [M+H]$^+$.

Example 46. Preparation of N-(5-(3-chloro-4-fluorobenzyl)pyridin-2-yl)-1-methyl-6-oxo-1,6-dihydropyridazine-3-carboxamide (46)

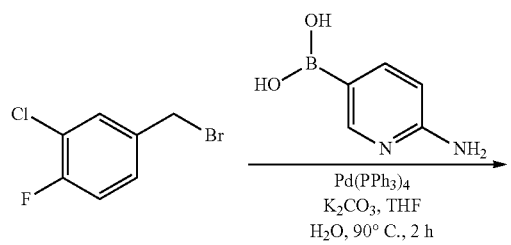

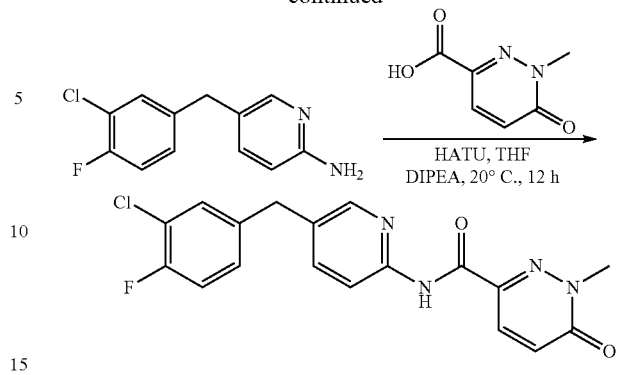

Step 1: Preparation of 5-(3-chloro-4-fluorobenzyl)pyridin-2-amine

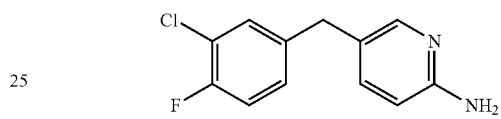

To a solution of 4-(bromomethyl)-1-chloro-2-fluorobenzene (0.500 g, 2.25 mmol), 6-aminopyridin-3-ylboronic acid (0.311 g, 2.25 mmol), potassium carbonate (0.621 g, 4.51 mmol) in tetrahydrofuran (8 mL) and water (2 mL) was added tetrakis(triphenylphosphine)palladium(0) (0.260 g, 0.225 mmol) under nitrogen. The mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-(3-chloro-4-fluorobenzyl)pyridin-2-amine as a yellow oil (0.300 g, crude); LCMS (ESI) m/z: 237.1 [M+H]$^+$. Used in the next step without additional purification.

Step 2: Preparation of 1-methyl-6-oxo-1,6-dihydropyridazine-3-carboxylic acid

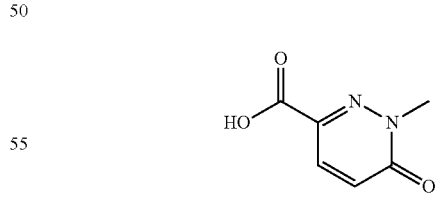

To a solution of methyl 1-methyl-6-oxo-1,6-dihydropyridazine-3-carboxylate (0.200 g, 1.19 mmol) in water (1.5 mL) was added sodium hydroxide (0.095 g, 2.38 mmol). The reaction was heated to 60° C. and stirred for 1 h. The aqueous layer was then adjusted to pH=8-10 with aqueous sodium bicarbonate and all volatiles were removed to afford 1-methyl-6-oxo-1,6-dihydropyridazine-3-carboxylic acid (0.130 g, crude) as a white solid. LCMS (ESI) m/z: 155.1 [M+H]$^+$. Used in the next step without further purification.

Step 3: Preparation of N-(5-(3-chloro-4-fluorobenzyl)pyridin-2-yl)-1-methyl-6-oxo-1,6-dihydropyridazine-3-carboxamide

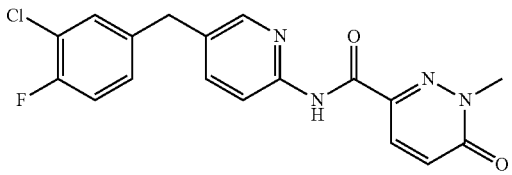

To a solution of 1-methyl-6-oxo-1,6-dihydropyridazine-3-carboxylic acid (0.130 g, 0.844 mmol), N,N-diisopropylethylamine (0.327 g, 2.53 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.481 g, 1.23 mmol). The reaction was stirred for 20 minutes before a solution of 5-(3-chloro-4-fluorobenzyl)pyridin-2-amine (0.199 g, 0.844 mmol) in tetrahydrofuran (1.0 mL) was added. The reaction mixture was stirred at 20° C. for 16 h. The volatiles were removed under reduced pressure and the residue was added to a mixture of dichloromethane (50 mL) and water (50 mL). The organic layer was separated, dried over sodium sulfate, filtered and concentrated. Purification by prep-HPLC gives N-(5-(3-chloro-4-fluorobenzyl)pyridin-2-yl)-1-methyl-6-oxo-1,6-dihydropyridazine-3-carboxamide as a white solid (0.0262 g, 0.070 mmol, 8.3%). $^1$H NMR (400 MHz, Dimethylsulfoxide-$d_6$) δ 10.14 (s, 1H), 8.34 (d, J=1.6 Hz, 1H), 8.08 (d, J=6.8 Hz, 1H), 7.95 (d, J=7.6 Hz, 1H), 7.75-7.77 (m, 1H), 7.52-7.54 (m, 1H), 7.33-7.35 (m, 2H), 7.08 (d, J=8.0 Hz, 1H), 3.97 (s, 2H), 3.79 (s, 3H); LCMS (ESI) m/z: 373.0 [M+H]$^+$.

Example 47. Preparation of N-(5-(3-chlorobenzyl)pyridin-2-yl)-1-methyl-6-oxo-1,6-dihydropyridazine-3-carboxamide (47)

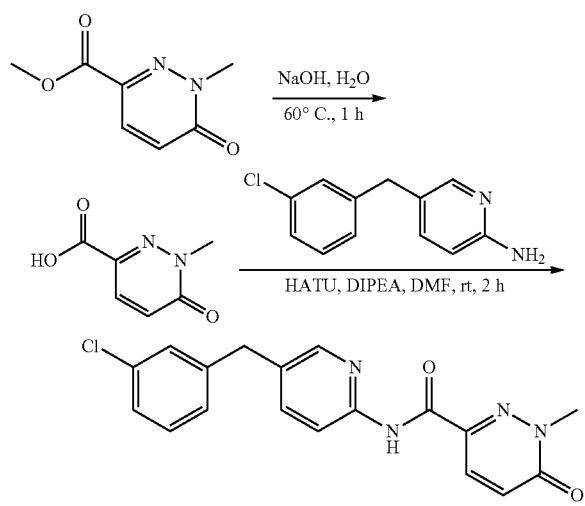

Step 1: Preparation of 1-methyl-6-oxo-1,6-dihydropyridazine-3-carboxylic acid

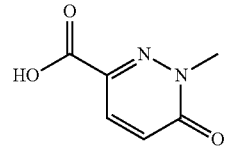

To a solution of methyl 1-methyl-6-oxo-1,6-dihydropyridazine-3-carboxylate (0.100 g, 0.60 mmol) in water (1.2 mL) was added sodium hydroxide (0.048 g, 1.20 mmol). The mixture was stirred at 60° C. for 1 h. After being cooled to room temperature, hydrogen chloride (1 N, 1.2 mL) was added and the aqueous phase was extracted with ethyl acetate (20 mL×5). The combined organic layers were washed with brine (20 mL), dried with sodium sulfate, filtered and concentrated to afford 1-methyl-6-oxo-1,6-dihydropyridazine-3-carboxylic acid (0.045 g, 0.29 mmol, 48.7%) as a white solid. LCMS (ESI) m/z: 155.1 [M+H]$^+$. Used in the next step directly without additional purification.

Step 2: Preparation of N-(5-(3-chlorobenzyl)pyridin-2-yl)-1-methyl-6-oxo-1,6-dihydropyridazine-3-carboxamide

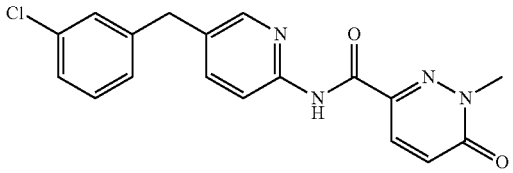 [SMILES: Cn1nc(C(=O)Nc2ccc(Cc3cccc(Cl)c3)cn2)ccc1=O]

To a stirred solution of 5-(3-chlorobenzyl)pyridin-2-amine (0.076 g, 0.35 mmol), 1-methyl-6-oxo-1,6-dihydropyridazine-3-carboxylic acid (0.045 g, 0.29 mmol) and 1-[bis(dimethylamino)methylene]-1H-1,2,3-triazolo[4,5-b]pyridinium 3-oxid hexafluorophosphate (0.133 g, 0.35 mmol) in N,N-dimethylformamide (2.00 mL) was added N,N-diisopropylethylamine (0.112 g, 0.87 mmol). After addition, the reaction mixture was stirred at room temperature for 2 h. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give N-(5-(3-chlorobenzyl)pyridin-2-yl)-1-methyl-6-oxo-1,6-dihydropyridazine-3-carboxamide (0.010 g, 0.028 mmol, 9.74%) as a white solid. $^1$H NMR (500 MHz, Dimethylsulfoxide-$d_6$) δ 10.15 (s, 1H), 8.34 (d, J=1.7 Hz, 1H), 8.09 (d, J=8.5 Hz, 1H), 7.95 (d, J=9.7 Hz, 1H), 7.76 (dd, J=8.5, 2.1 Hz, 1H), 7.44-7.31 (m, 2H), 7.26 (dd, J=16.1, 7.9 Hz, 2H), 7.08 (d, J=9.7 Hz, 1H), 3.98 (s, 2H), 3.79 (s, 3H); LCMS (ESI) m/z: 355.0 [M+H]$^+$.

Example 48. Preparation of N-(5-(3-chlorobenzyl)pyridin-2-yl)-1-methyl-6-oxo-1,6-dihydropyridine-3-carboxamide (48)

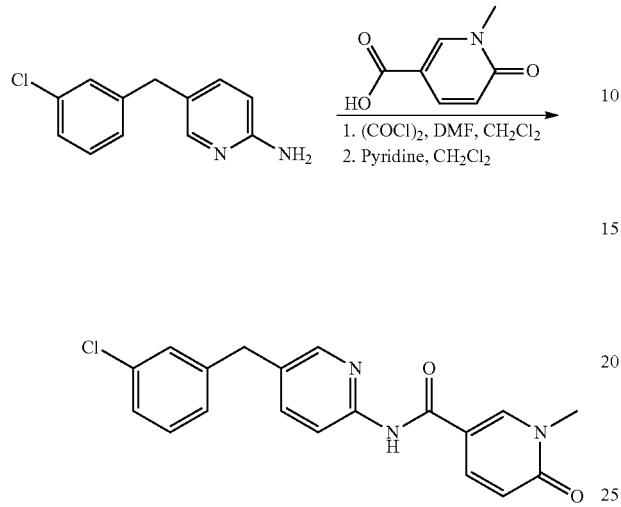

Step 1: Preparation of N-(5-(3-chlorobenzyl)pyridin-2-yl)-1-methyl-6-oxo-1,6-dihydropyridine-3-carboxamide

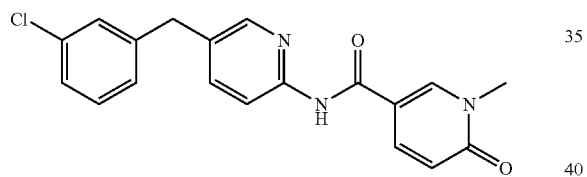

To a solution of 1-methyl-6-oxo-1,6-dihydropyridine-3-carboxylic acid (0.153 g, 1 mmol) in dichloromethane (30 mL) at 0° C. was added N,N-dimethylformamide (2 drops) and oxalyl chloride (0.635 g, 5 mmol) dropwise. Reaction was warmed to room temperature over 2 h before it was concentrated. The crude solid was dissolved in dichloromethane (5 mL) and added to a solution of 5-(3-chlorobenzyl)pyridin-2-amine (0.262 g, 1.2 mmol) in pyridine (6 mL) at 0° C. Reaction mixture was warmed to room temperature over 2 h. Reaction was poured into ice water and extracted with ethyl acetate (50 mL×2). The combined organic layers were washed with brine (60 mL), dried over sodium sulfate, filtered and concentrated. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to yield N-(5-(3-chlorobenzyl)pyridin-2-yl)-1-methyl-6-oxo-1,6-dihydropyridine-3-carboxamide as a white solid (0.046 g, 0.13 mmol, 13%). $^1$H NMR (400 MHz, Dimethylsulfoxide-$d_6$) δ 10.59 (s, 1H), 8.67 (d, J=2.6 Hz, 1H), 8.31 (d, J=2.1 Hz, 1H), 8.04 (d, J=8.8 Hz, 1H), 7.98 (dd, J=4.8 Hz, 4.8 Hz, 1H), 7.72 (dd, J=8.6, 2.3 Hz, 1H), 7.35 (t, J=6.0 Hz, 2H), 7.28-7.23 (m, 2H), 6.43 (d, J=9.5 Hz, 1H), 3.97 (s, 2H), 3.50 (s, 3H); LCMS (ESI) m/z: 354.1 [M+H]$^+$.

Example 49. Preparation of N-(5-(3-fluoro-4-methoxybenzyl)pyridin-2-yl)-1-methyl-6-oxo-1,6-dihydropyridine-3-carboxamide (49)

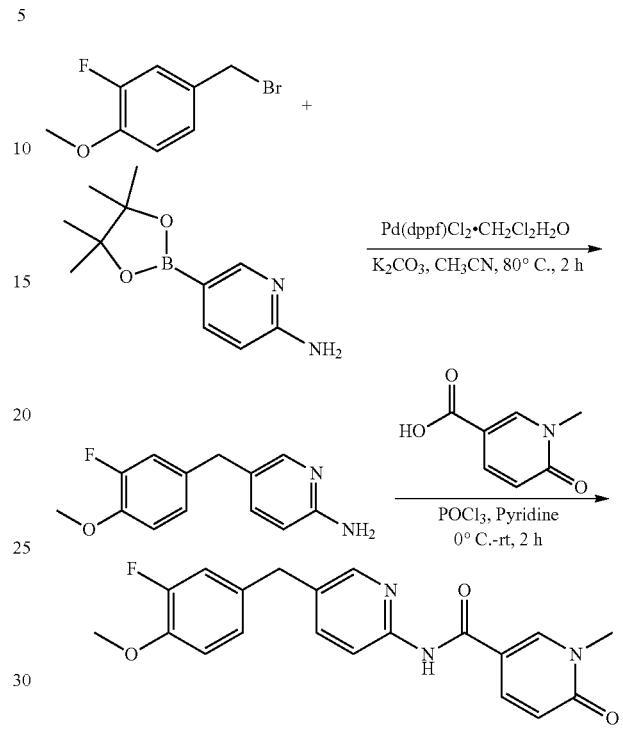

Step 1: Preparation of 5-(3-fluoro-4-methoxybenzyl)pyridin-2-amine

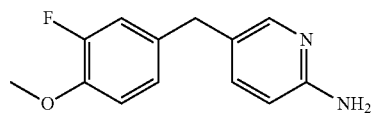 [SMILES: COc1ccc(Cc2ccc(N)nc2)cc1F]

To a solution of 4-(bromomethyl)-2-fluoro-1-methoxybenzene (0.767 g, 3.50 mmol), 5-(4,4,5,5-tetramethyl-1,3,2-dioxaborolan-2-yl)pyridin-2-amine (0.847 g, 3.68 mmol), potassium carbonate (0.966 g, 7.00 mmol) in acetonitrile (17 mL) and water (4.2 mL) was added [1,1'-bis(diphenylphosphino)ferrocene]dichloropalladium(II)dichloromethane (0.286 g, 0.35 mmol). Reaction mixture was stirred at 80° C. for 3 h before it was filtered and extracted with ethyl acetate (80 mL×2). The combined organic layers were washed with brine (80 mL), dried over sodium sulfate, filtered and concentrated. The residue was purified by column chromatography (silica gel, petroleum ether/ethyl acetate=2/3) to give 5-(3-fluoro-4-methoxybenzyl)pyridin-2-amine as a brown oil (0.380 g, 1.27 mmol, 36.4%); LCMS (ESI) m/z: 233.2 [M+H]$^+$.

Step 2: Preparation of N-(5-(3-fluoro-4-methoxy-benzyl)pyridin-2-yl)-1-methyl-6-oxo-1,6-dihydro-pyridine-3-carboxamide

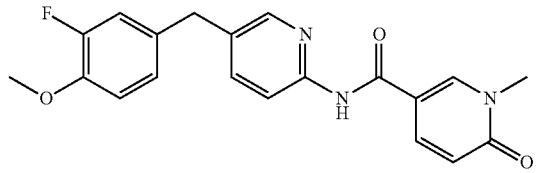

To a solution of 1-methyl-6-oxo-1,6-dihydropyridine-3-carboxylic acid (0.086 g, 0.56 mmol) and 5-(3-fluoro-4-methoxybenzyl)pyridin-2-amine (0.130 g, 0.56 mmol) in pyridine (4.3 mL) at 0° C. was added phosphorus(V) oxychloride (0.257 g, 1.68 mmol). The reaction mixture was warmed to room temperature over 2 h. The reaction mixture was poured into ice water and extracted with ethyl acetate (30 mL×2). The combined organic layers were washed with brine (30 mL), dried over sodium sulfate, filtered and concentrated. The crude sample was dissolved in minimal N,N-dimethylformamide and purified via prep-HPLC (Boston C18 21*250 mm 10 µm column; acetonitrile/0.01% aqueous trifluoroacetic acid) to give N-(5-(3-fluoro-4-methoxybenzyl)pyridin-2-yl)-1-methyl-6-oxo-1,6-dihydro-pyridine-3-carboxamide (0.0058 g, 0.0123 mmol, 2.2%) as a white solid. $^1$H NMR (400 MHz, Dimethylsulfoxide-$d_5$) δ 10.52 (s, 1H), 8.66 (d, J=2.6 Hz, 1H), 8.27 (d, J=2.1 Hz, 1H), 8.04 (d, J=8.5 Hz, 1H), 7.98 (dd, J=9.5, 2.6 Hz, 1H), 7.66 (dd, J=8.6, 2.3 Hz, 1H), 7.14-7.07 (m, 2H), 7.02 (d, J=8.5 Hz, 1H), 6.43 (d, J=9.5 Hz, 1H), 3.88 (s, 2H), 3.79 (s, 3H), 3.50 (s, 3H); LCMS (ESI) m/z: 368.2 [M+H]$^+$.

Example 50. Preparation of N-(5-(3-chloro-5-methoxybenzyl)pyridin-2-yl)-1-methyl-6-oxo-1,6-dihydropyridine-3-carboxamide (50)

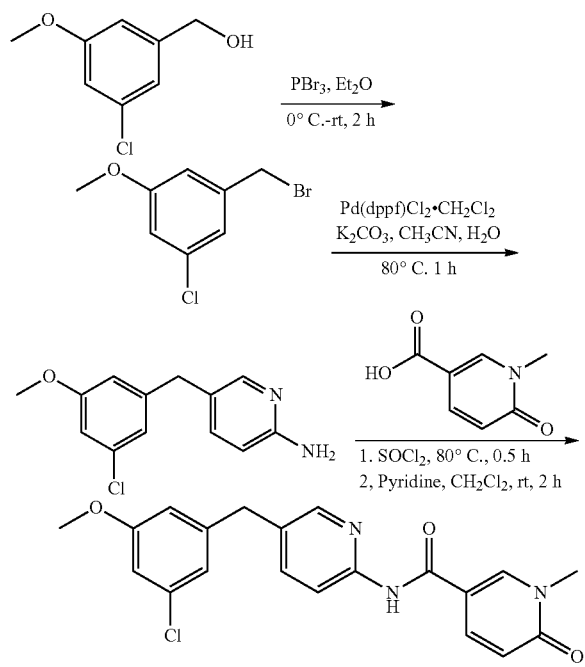

Step 1: Preparation of 1-(bromomethyl)-3-chloro-5-methoxybenzene

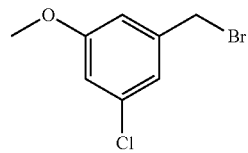

To a solution of (3-chloro-5-methoxyphenyl)methanol (2.0 g, 11.6 mmol) in diethyl ether (20 mL) at 0° C. was added phosphorus tribromide (0.5 mL). The mixture was stirred for 2 h at 0° C. Reaction mixture was poured into saturated aqueous sodium bicarbonate solution (150 mL) and extracted with ethyl acetate (200 mL×2). The combined organic phases were dried over sodium sulfate, filtered and concentrated to afford 1-(bromomethyl)-3-chloro-5-methoxybenzene (2.15 g, 9.16 mmol, 79%) as a light-yellow solid. Used in the next step directly without additional purification.

Step 2: Preparation of 5-(3-chloro-5-methoxybenzyl)pyridin-2-amine

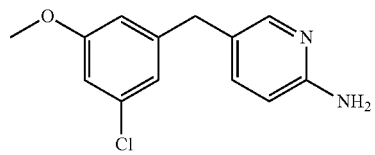

The synthesis of 5-(3-chloro-5-methoxybenzyl)pyridin-2-amine was following a similar procedure as for Example 23 to yield 5-(3-chloro-5-methoxybenzyl)pyridin-2-amine (1.1 g, 4.40 mmol, 79%) as an orange solid. LCMS (ESI) m/z: 249.1 [M+H]$^+$.

Step 3: Preparation of N-(5-(3-chloro-5-methoxy-benzyl)pyridin-2-yl)-1-methyl-6-oxo-1,6-dihydro-pyridine-3-carboxamide

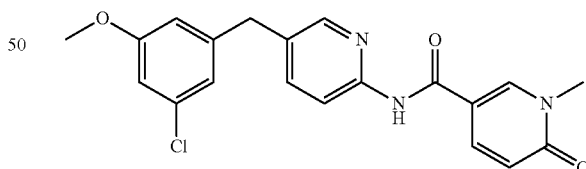

A solution of 1-methyl-6-oxo-1,6-dihydropyridine-3-carboxylic acid (0.200 g, 1.3 mmol) in thionyl chloride (15 mL) was stirred at 80° C. for 1 h. Once the suspension went clear volatiles were removed under reduced pressure. The crude residue was dissolved in dichloromethane (5 mL) and added slowly to a solution of 5-(3-chloro-5-methoxybenzyl)pyridin-2-amine (0.248 g, 1.0 mmol) and pyridine (0.240 g, 3.0 mmol) in dichloromethane (5 mL) at 0° C. The resulting mixture was stirred at room temperature for another 2 h. The mixture was poured into water and extracted with dichloromethane (50 mL×2). The combined organic phases were concentrated. The residue was purified by column chromatography (silica gel, 10% methanol in ethyl acetate) to afford 250 mg of brown oil, The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(3-chloro-5-methoxybenzyl)pyridin-2-yl)-1-methyl-6-oxo-1,6-dihydropyridine-3-carboxamide (0.148 g, 0.386 mmol, 38.6%) as a white solid. $^1$H NMR (500 MHz, Dimethylsulfoxide-d$_6$) δ. 10.59 (s, 1H), 8.67 (d, J=2.5 Hz, 1H), 8.32 (d, J=2.0 Hz, 1H), 8.04 (d, J=8.5 Hz, 1H), 7.98 (dd, J=3.0, 9.5 Hz, 1H), 7.73 (dd, J=2.5, 8.5 Hz, 1H), 6.90-6.84 (m, 3H), 6.43 (d, J=9.5 Hz, 1H), 3.92 (s, 2H), 3.75 (s, 3H), 3.50 (s, 3H); LCMS (ESI) m/z: 384.1 [M+H]$^+$.

Example 51. Preparation of N-(5-(3-chloro-5-cyanobenzyl)pyridin-2-yl)-1-methyl-6-oxo-1,4,5,6-tetrahydropyridazine-3-carboxamide (51)

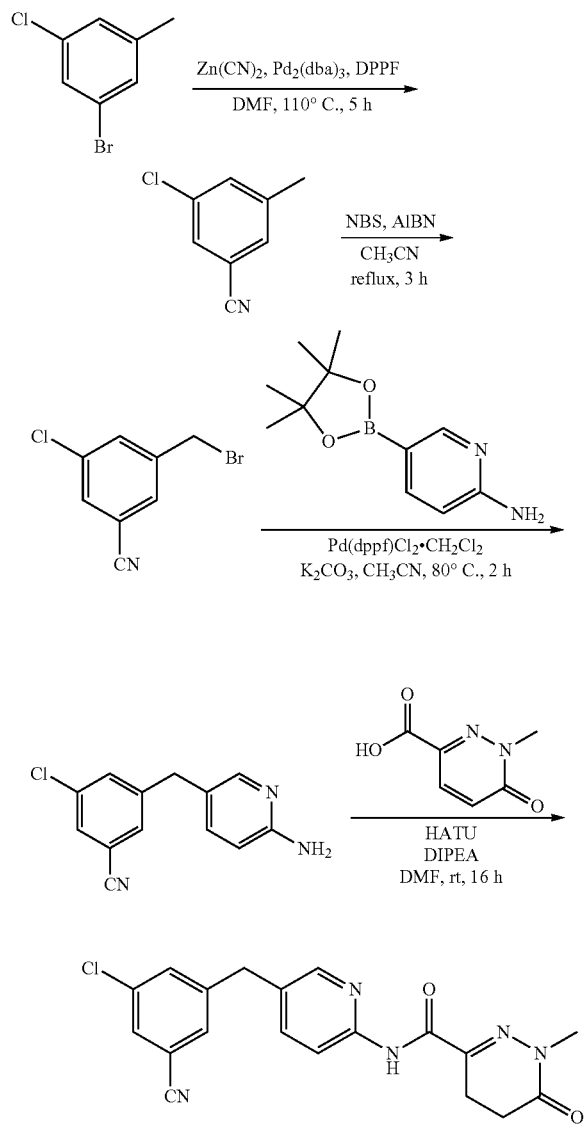

Step 1: Preparation of 3-chloro-5-methylbenzonitrile

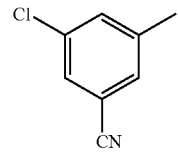

A mixture of 1-bromo-3-chloro-5-methylbenzene (2.0 g, 10.0 mmol), zinc cyanide (0.700 g, 6.0 mmol), 1,1'-ferrocenediyl-bis(diphenylphosphine) (1.1 g, 2.0 mmol), tris(dibenzylideneacetone)dipalladium(0) (0.900 g, 1.0 mmol) in N,N-dimethylformamide (15 mL) was stirred at 110° C. under nitrogen for 5 h. The reaction was poured into water and the aqueous layer was extracted with ethyl acetate (200 mL×2). The combined organic phases were concentrated. The residue was purified by column chromatography (silica gel, petroleum ether/ethyl acetate=60/1) to afford 3-chloro-5-methylbenzonitrile (1.4 g, 9.2 mmol, 92%) as a yellow solid. $^1$H NMR (500 MHz, Chloroform-d) δ. 7.46 (s, 1H), 7.42 (s, 1H), 7.37 (m, 1H), 2.40 (s, 3H).

Step 2: Preparation of 3-(bromomethyl)-5-chlorobenzonitrile

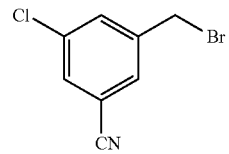 [SMILES: N#Cc1cc(Cl)cc(CBr)c1]

The synthesis of 3-(bromomethyl)-5-chlorobenzonitrile was following a similar procedure to Example 25. Product 3-(bromomethyl)-5-chlorobenzonitrile (0.800 g, 3.47 mmol, 48%) was obtained as a yellow solid. $^1$H NMR (500 MHz, Chloroform-d) δ. 7.64 (m, 1H), 7.59 (m, 2H), 4.44 (s, 2H).

Step 3: Preparation of 3-((6-aminopyridin-3-yl)methyl)-5-chlorobenzonitrile

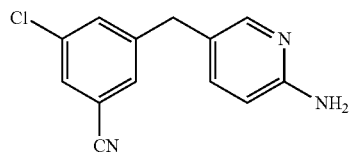 [SMILES: N#Cc1cc(Cl)cc(Cc2ccc(N)nc2)c1]

The synthesis of 3-((6-aminopyridin-3-yl)methyl)-5-chlorobenzonitrile was followed similar procedure to Example 23. Product 3-((6-aminopyridin-3-yl)methyl)-5-chlorobenzonitrile (0.190 g, 56% purity; 260 mg, 79% purity) was obtained as a yellow oil. LCMS (ESI) m/z: 244.1 [M+H]$^+$.

Step 4: Preparation of N-(5-(3-chloro-5-cyanobenzyl)pyridin-2-yl)-1-methyl-6-oxo-1,4,5,6-tetrahydropyridazine-3-carboxamide

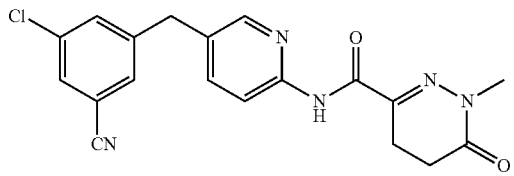 [SMILES: CN1N=C(C(=O)Nc2ccc(Cc3cc(Cl)cc(C#N)c3)cn2)CCC1=O]

A solution of 3-((6-aminopyridin-3-yl)methyl)-5-chlorobenzonitrile (0.190 g (56% purity), 0.43 mmol), 1-methyl-6-oxo-1,4,5,6-tetrahydropyridazine-3-carboxylic acid (0.122 g, 0.78 mmol), 1-[bis(dimethylamino)methylene]-1H-1,2,3-triazolo[4,5-b]pyridinium 3-oxid hexafluorophosphate (0.445 g, 1.17 mmol), N,N-diisopropylethylamine (0.302 g, 2.34 mmol) in N,N-dimethylformamide (5 mL) was stirred at room temperature 16 h. The mixture was poured into water. The formed precipitate was collected by filtration and purified by chiral prep-HPLC to afford compound N-(5-(3-chloro-5-cyanobenzyl)pyridin-2-yl)-1-methyl-6-oxo-1,4,5,6-tetrahydropyridazine-3-carboxamide (0.0794 g, 0.208 mmol, 45%) as a white solid. $^1$H NMR (500 MHz, Dimethylsulfoxide-$d_6$) δ. 9.73 (s, 1H), 8.35 (d, J=2.0 Hz, 1H), 8.04 (d, J=8.5 Hz, 1H), 7.89 (s, 1H), 7.80-7.76 (m, 3H), 4.02 (s, 2H), 3.36 (s, 3H), 2.85 (t, J=8.5 Hz, 2H), 2.52 (t, J=8.5 Hz, 2H); LCMS (ESI) m/z: 382.0 [M+H]$^+$.

Example 52. Preparation of N-(5-(3-fluoro-5-methoxybenzyl)pyridin-2-yl)-1-methyl-6-oxo-1,6-dihydropyridine-3-carboxamide (52)

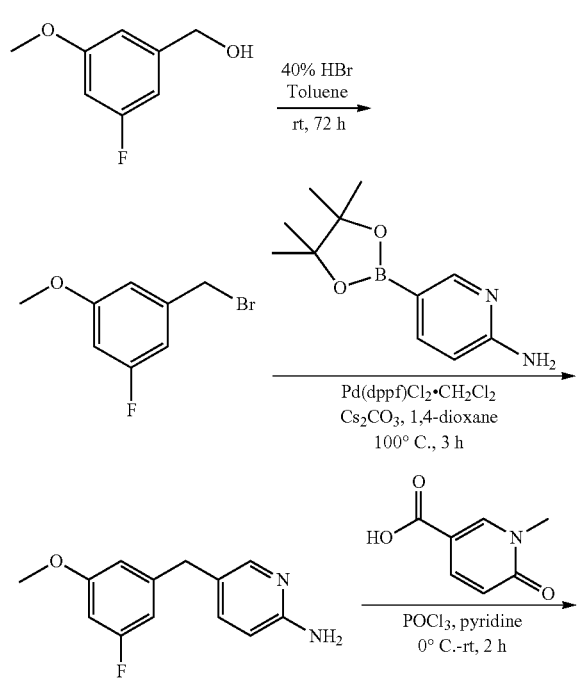

Step 1: Preparation of 1-(bromomethyl)-3-fluoro-5-methoxybenzene

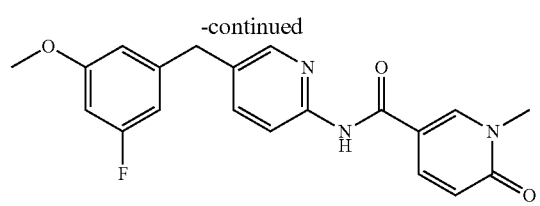

A solution of (3-fluoro-5-methoxyphenyl)methanol (1.5 g, 6.88 mmol), 40% hydrogen bromide (6 mL) and toluene (10 mL) was stirred at room temperature for 3 days. The reaction mixture was poured into water and extracted with ethyl acetate (160 mL×3). The combined organic phases were concentrated. The crude residue was purified by column chromatography (silica gel, petroleum ether/ethyl acetate=16/1) to afford 1-(bromomethyl)-3-fluoro-5-methoxybenzene (1.7 g, 5.57 mmol, 81%) as a light-yellow oil. $^1$H NMR (500 MHz, Chloroform-d) δ 6.74-6.71 (m, 2H), 6.58-6.55 (m, 1H), 4.42 (s, 2H), 3.82 (s, 3H).

Step 2: Preparation of 5-(3-fluoro-5-methoxybenzyl)pyridin-2-amine

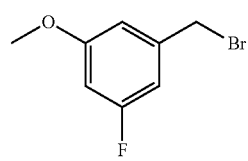

The synthesis of 5-(3-fluoro-5-methoxybenzyl)pyridin-2-amine was following similar procedure to Example 25. Product 5-(3-fluoro-5-methoxybenzyl)pyridin-2-amine (0.600 g, 2.57 mmol, 70%) was obtained as a brown oil. LCMS (ESI) m/z: 233.1 [M+H]$^+$.

Step 3: Preparation of N-(5-(3-fluoro-5-methoxybenzyl)pyridin-2-yl)-1-methyl-6-oxo-1,6-dihydropyridine-3-carboxamide

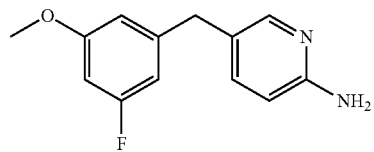

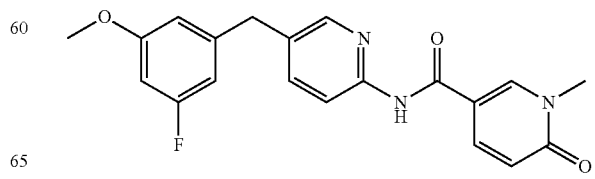

The synthesis of N-(5-(3-fluoro-5-methoxybenzyl)pyridin-2-yl)-1-methyl-6-oxo-1,6-dihydropyridine-3-carboxamide was following a similar procedure for Example 25. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(3-fluoro-5-methoxybenzyl)pyridin-2-yl)-1-methyl-6-oxo-1,6-dihydropyridine-3-carboxamide (0.0704 g, 0.191 mmol, 12.8%) as a white solid. $^1$H NMR (500 MHz, Dimethylsulfoxide-$d_6$) δ 10.60 (s, 1H), 8.67 (s, 1H), 8.31 (d, J=2.5 Hz, 1H), 8.04-7.97 (m, 2H), 7.73 (d, J=8.0 Hz, 1H), 6.71-6.68 (m, 3H), 6.43 (d, J=9.5 Hz, 1H), 3.92 (s, 2H), 3.74 (s, 3H), 3.50 (s, 3H); LCMS (ESI) m/z: 368.2 [M+H]$^+$.

Example 53. Preparation of N-(5-(4-fluorobenzyl)pyridin-2-yl)-1-methyl-6-oxo-1,6-dihydropyridine-3-carboxamide (53)

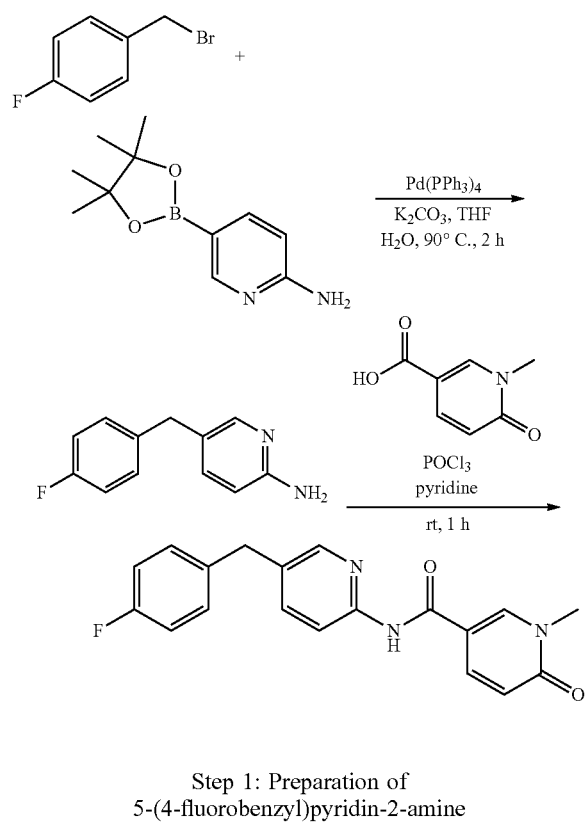

Step 1: Preparation of 5-(4-fluorobenzyl)pyridin-2-amine

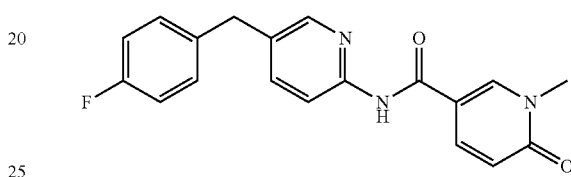

To a solution of 1-(bromomethyl)-4-fluorobenzene (3.0 g, 16.0 mmol), 5-(4,4,5,5-tetramethyl-1,3,2-dioxaborolan-2-yl)pyridin-2-amine (3.51 g, 16.0 mmol), potassium carbonate (4.4 g, 31.9 mmol) in tetrahydrofuran (48 mL) and water (12 mL) was added tetrakis(triphenylphosphine)palladium (0) (1.84 g, 1.60 mmol) under nitrogen. The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated. Purification by column chromatography (silica gel, petroleum ether/ethyl acetate=1/1) affords 5-(4-fluorobenzyl)pyridin-2-amine (1.8 g, 8.96 mmol, 56%) as a yellow solid. LCMS (ESI) m/z: 203.1 [M+H]$^+$.

Step 2: Preparation of N-(5-(4-fluorobenzyl)pyridin-2-yl)-1-methyl-6-oxo-1,6-dihydropyridine-3-carboxamide

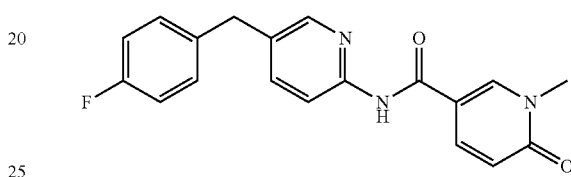

To a solution of 1-methyl-6-oxo-1,6-dihydropyridine-3-carboxylic acid (0.200 g, 1.31 mmol), 5-(4-fluorobenzyl)pyridin-2-amine (0.264 g, 1.31 mmol) in pyridine (8 mL) at 20° C. was added phosphorus(V) oxychloride (0.595 g, 3.921 mmol). The reaction mixture was stirred at room temperature for 3 h. The solvent was removed under reduced pressure and the crude solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(4-fluorobenzyl)pyridin-2-yl)-1-methyl-6-oxo-1,6-dihydropyridine-3-carboxamide as a light-yellow solid (0.170 g, 0.503 mmol, 38.4%). $^1$H NMR (400 MHz, Dimethylsulfoxide-$d_6$) δ 10.62 (s, 1H), 8.67 (s, 1H), 8.29 (s, 1H), 8.02 (d, J=8 Hz, 1H), 7.98 (d, J=9.5 Hz, 1H), 7.71 (d, J=8.5 Hz, 1H), 7.30 (t, J=6 Hz, 2H), 7.12 (t, J=8.3 Hz, 2H), 6.44 (t, J=9.5 Hz, 2H), 3.95 (s, 2H), 3.50 (s, 3H); LCMS (ESI) m/z: 338.1 [M+H]$^+$.

Example 54. Preparation of N-(5-(4-fluoro-3-methoxybenzyl)pyridin-2-yl)-1-methyl-6-oxo-1,6-dihydropyridine-3-carboxamide (54)

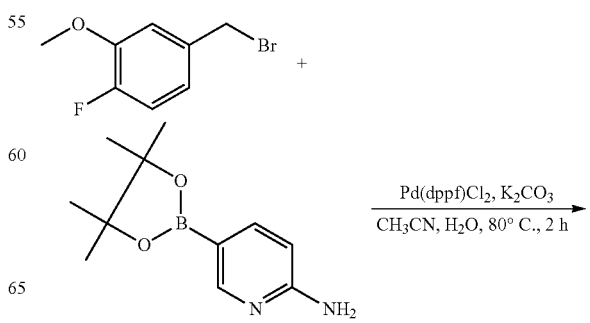

367

-continued

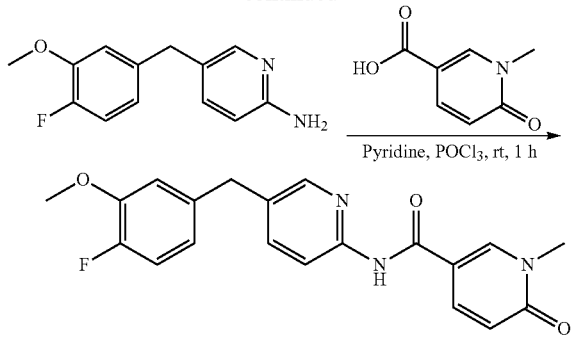

Step 1: Preparation of 5-(4-fluoro-3-methoxybenzyl)pyridin-2-amine

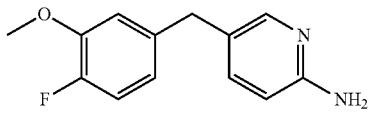 [SMILES: COc1cc(Cc2ccc(N)nc2)ccc1F]

A mixture of 4-(bromomethyl)-1-fluoro-2-methoxybenzene (0.5 g, 2.29 mmol), 5-(4,4,5,5-tetramethyl-1,3,2-dioxaborolan-2-yl)pyridin-2-amine (0.56 g, 2.52 mmol), potassium carbonate (0.63 g, 4.59 mmol) and [1,1'-bis(diphenylphosphino)ferrocene]dichloropalladium(II) (0.19 g, 0.23 mmol) in acetonitrile (20.0 mL) and water (5.00 mL) was stirred at 80° C. under nitrogen atmosphere for 2 h. The reaction mixture was cooled down to room temperature and filtered. The filtrate was concentrated, under reduced pressure and the residue was purified by column chromatography (silica gel, petroleum ether/ethyl acetate=1/1) to give 5-(4-fluoro-3-methoxybenzyl)pyridin-2-amine (0.30 g, 1.29 mmol, 56.3%) as a yellow solid. LCMS (ESI) m/z: 233.1 [M+H]+.

368

Step 2: Preparation of N-(5-(4-fluoro-3-methoxybenzyl)pyridin-2-yl)-1-methyl-6-oxo-1,6-dihydropyridine-3-carboxamide

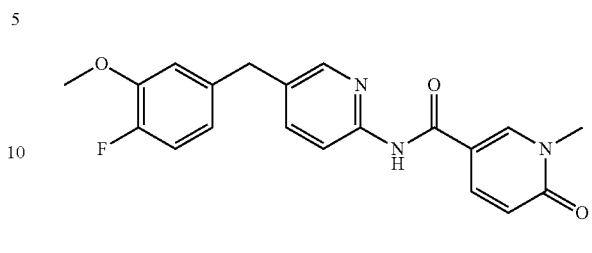

To a solution of 5-(4-fluoro-3-methoxybenzyl)pyridin-2-amine (0.20 g, 0.86 mmol), 1-methyl-6-oxo-1,6-dihydropyridine-3-carboxylic acid (0.15 g, 0.95 mmol) in pyridine (4.0 mL) was added phosphorus(V) oxychloride (0.0681 g, 0.86 mmol) at 0 dropwise. The reaction mixture was warmed to room temperature and stirred for 1 h. The reaction mixture was quenched with water (20 mL) and the aqueous layer was extracted with ethyl acetate (20 mL). The combined organic layers were washed with water (10 mL×2) and brine (10 mL×2), dried over anhydrous sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(4-fluoro-3-methoxybenzyl)pyridin-2-yl)-1-methyl-6-oxo-1,6-dihydropyridine-3-carboxamide (0.0324 g, 0.09 mmol, 10.5%) as a white solid. $^1$H NMR (500 MHz, Dimethylsulfoxide-d$_6$) δ 10.55 (s, 1H), 8.66 (d, J=2.6 Hz, 1H), 8.30 (d, J=2.6 Hz, 1H), 8.07-7.92 (m, 2H), 7.70 (dd, J=8.6, 2.3 Hz, 1H), 7.17-7.02 (m, 2H), 6.83-6.71 (m, 1H), 6.43 (d, J=9.5 Hz, 1H), 3.92 (s, 2H), 3.82 (s, 3H), 3.50 (s, 3H); LCMS (ESI) m/z: 368.2 [M+H]+.

Example 55. Preparation of N-(5-(2-fluorobenzyl)pyridin-2-yl)-1-methyl-6-oxo-1,6-dihydropyridine-3-carboxamide (55)

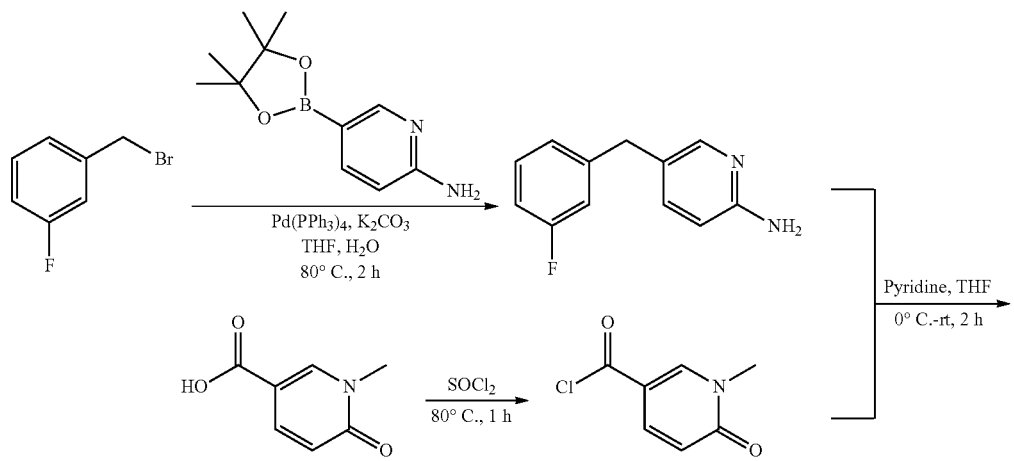

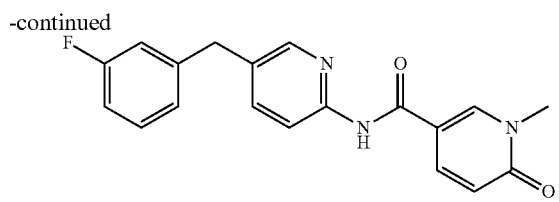

Step 1: Preparation of 5-(3-Fluorobenzyl)pyridin-2-amine

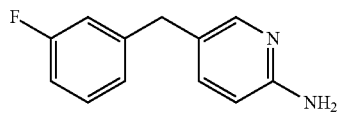

To a solution of 5-(4,4,5,5-tetramethyl-1,3,2-dioxaborolan-2-yl)pyridin-2-amine (5.0 g, 22.72 mmol) in tetrahydrofuran (75 mL) and water (19 mL) at room temperature was added 1-(bromomethyl)-3-fluorobenzene (4.30 g, 22.7 mmol), tetrakis(triphenylphosphine)palladium(0) (2.63 g, 2.27 mmol) and potassium carbonate (6.27 g, 45.4 mmol) under nitrogen. The reaction mixture was stirred at 80° C. for 2 h, then cooled to room temperature and diluted with water (100 mL). Volatiles were removed under reduced pressure. Aqueous layer was acidified to pH=2-3 with 4 N hydrogen chloride and extracted with ethyl acetate (80 mL×2). The aqueous layer was then adjusted to pH=9-10 with aqueous sodium carbonate and extracted with dichloromethane (80 mL×2). The combined dichloromethane layers were dried over sodium sulfate, filtered and concentrated to give 5-(3-fluorobenzyl)pyridin-2-amine (4.4 g, 21.8 mmol, 95.7%) as a pale yellow solid. LCMS (ESI) m/z: 203.2 [M+H]+.

Step 2: Preparation of N-(5-(3-fluorobenzyl)pyridin-2-yl)-1-methyl-6-oxo-1,6-dihydropyridine-3-carboxamide

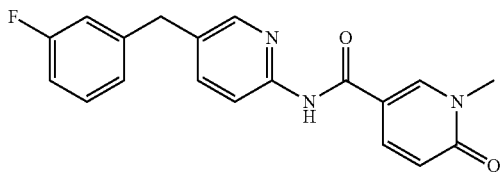

A suspension of 1-methyl-6-oxo-1,6-dihydropyridine-3-carboxylic acid (6.00 g, 39.2 mmol) in thionyl chloride (30 mL) was heated to 80° C. for 1 h. After being concentrated and dried in vacuo, the residue was dissolved in dry tetrahydrofuran (60 mL). This solution was added dropwise to a mixture of 5-(3-fluorobenzyl)pyridin-2-amine (6.00 g, 30.2 mmol) and pyridine (7.20 mL, 90.5 mmol) in dry tetrahydrofuran (60 mL) at 0° C. over 15 minutes. The reaction mixture was warmed to room temperature and stirred for 2 h. The white solid precipitate was collected by filtration and the filter cake was washed with ethanol (60 mL) and tert-butyl methyl ether (60 mL). The filtrate was concentrated, and the resulting solid was washed with ethanol (60 mL) and tert-butyl methyl ether (60 mL). Combined solids were dried in vacuo to give crude N-(5-(3-fluorobenzyl)pyridin-2-yl)-1-methyl-6-oxo-1,6-dihydropyridine-3-carboxamide (7.3 g). The crude material (7.3 g) was dissolved in ethanol (1.10 L) at 80° C. After being filtered, the filtrate was concentrated, to about 300 mL and cooled down to room temperature. The solid was collected by filtration and the filter cake was washed with ethanol (50 mL) and tert-butyl methyl ether (50 mL). The white solid was dried in vacuo to obtain N-(5-(3-fluorobenzyl)pyridin-2-yl)-1-methyl-6-oxo-1,6-dihydropyridine-3-carboxamide (5.05 g, 15.0 mmol, 49.7%). $^1$H NMR (500 MHz, Dimethylsulfoxide-d$_6$) δ 11.47 (s, 1H), 8.91 (d, J=2.4 Hz, 1H), 8.36 (d, J=1.8 Hz, 1H), 8.12 (d, J=8.7 Hz, 1H), 8.06-7.94 (m, 2H), 7.42-7.28 (m, 1H), 7.14 (t, J=8.6 Hz, 2H), 7.05 (dd, J=9.0, 2.0 Hz, 1H), 6.47 (d, J=9.6 Hz, 1H), 4.04 (s, 2H), 3.52 (s, 3H); LCMS (ESI) m/z: 338.0 [M+H]+.

Example 56. Preparation of 1-methyl-6-oxo-N-(5-(3,4,5-trifluorobenzyl)pyridin-2-yl)-1,6-dihydropyridine-3-carboxamide (56)

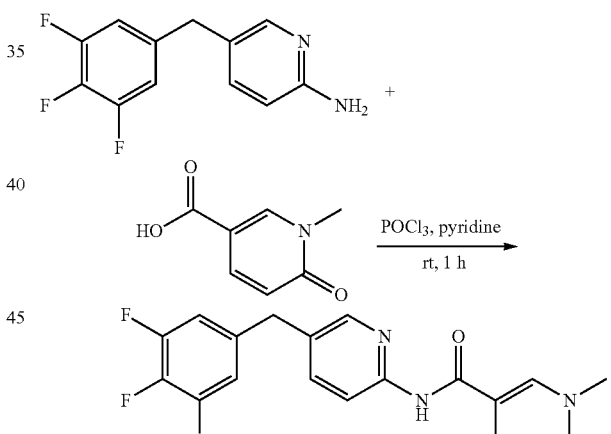

Step 1: Preparation of 1-methyl-6-oxo-N-(5-(3,4,5-trifluorobenzyl)pyridin-2-yl)-1,6-dihydropyridine-3-carboxamide

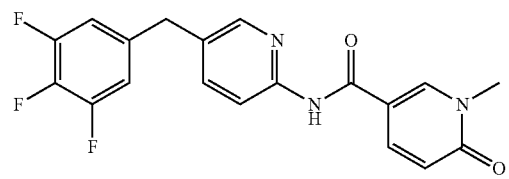 [SMILES: Cn1cc(C(=O)Nc2ccc(Cc3cc(F)c(F)c(F)c3)cn2)ccc1=O]

To a solution of 1-methyl-6-oxo-1,6-dihydropyridine-3-carboxylic acid (0.100 g, 0.653 mmol), 5-(3,4,5-trifluorobenzyl)pyridin-2-amine (0.155 g, 0.653 mmol) in pyridine (4 mL) at 20° C. was added phosphorus(V) oxychloride (0.297 g, 1.96 mmol). The reaction mixture was stirred at room temperature for 1 h. The solvent was removed under reduced pressure and the solid was dissolved in dichloromethane (10.0 mL). The resulting solution was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 1-methyl-6-oxo-N-(5-(3,4,5-trifluorobenzyl)pyridin-2-yl)-1,6-dihydropyridine-3-carboxamide as a light-yellow solid (0.0286 g, mmol, 0.078 mmol, 12%). $^1$H NMR (400 MHz, Dimethylsulfoxide-$d_6$) δ 10.56 (s, 1H), 8.67 (d, J=2.5 Hz, 1H), 8.32 (d, J=2 Hz, 1H), 7.97-8.06 (m, 2H), 7.71-7.73 (m, 1H), 7.27-7.30 (m, 2H), 6.42-6.44 (d, J=10 Hz, 1H), 3.95 (s, 2H), 3.50 (s, 3H). LCMS (ESI) m/z: 374.0 [M+H]$^+$.

Example 57. Preparation of 5-(3-chlorobenzyl)-N-(1-methyl-6-oxo-1,6-dihydropyridin-3-yl)picolinamide (57)

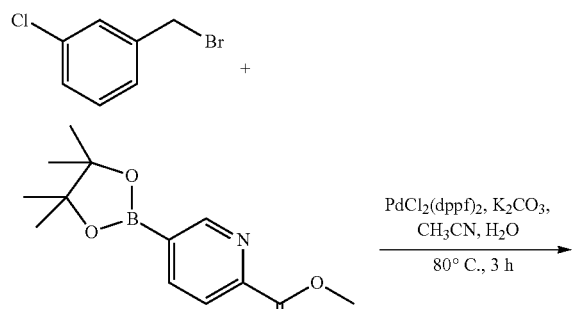

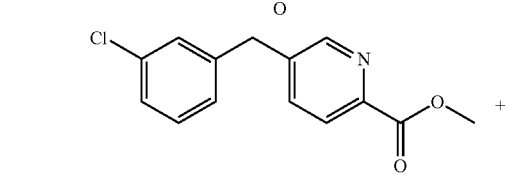

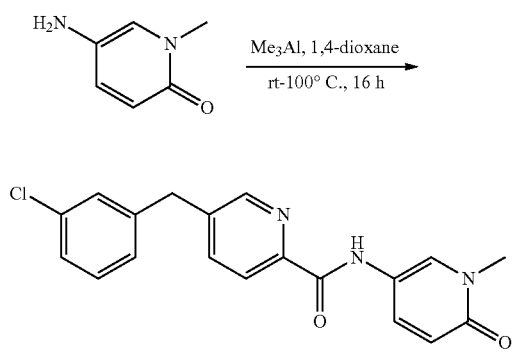

Step 1: Preparation of methyl 5-(3-chlorobenzyl)picolinate

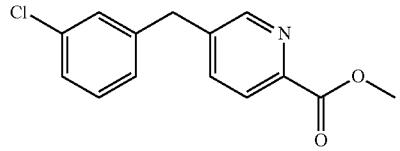 [SMILES: COC(=O)c1ccc(Cc2cccc(Cl)c2)cn1]

To a solution of 1-(bromomethyl)-3-chlorobenzene (1.56 g, 7.60 mmol) in acetonitrile (80.0 mL) and water (20 mL) at room temperature, was added potassium carbonate (2.10 g, 15.2 mmol), [1,1'-bis(diphenylphosphino)ferrocene]dichloropalladium(II) (0.434 g, 0.532 mmol) and methyl 5-(4,4,5,5-tetramethyl-1,3,2-dioxaborolan-2-yl)picolinate (2.0 g, 7.60 mmol) under nitrogen. The reaction mixture was stirred at 80° C. for 3 h, cooled to room temperature and diluted with water (200 mL). The aqueous layer was extracted with ethyl acetate (80 mL×3). The combined organic layers were dried over sodium sulfate, filtered and concentrated. The crude residue was purified by column chromatography (silica gel, ethyl acetate/petroleum ether=⅓) to afford methyl 5-(3-chlorobenzyl)picolinate (1.3 g, 4.97 mmol, 65.4%) as a brown oil. LCMS (ESI) m/z: 262.1 [M+H]$^+$.

Step 2: Preparation of (5-(3-chlorobenzyl)-N-(1-methyl-6-oxo-1,6-dihydropyridin-3-yl)picolinamide

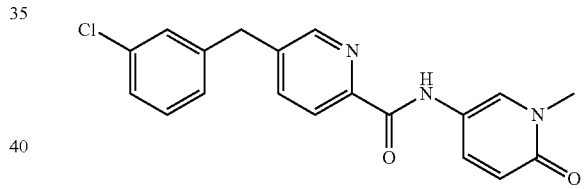

To a solution of 5-amino-1-methylpyridin-2(1H)-one (0.200 g, 1.66 mmol) in anhydrous 1,4-dioxane (8 mL) was added trimethylaluminum (0.81 mL, 1.62 mmol, 2 Min toluene) under nitrogen. The reaction mixture was stirred at room temperature for 1 h before methyl 5-(3-chlorobenzyl)picolinate (0.106 g, 0.404 mmol) in 1,4-dioxane (3.0 mL) was added and stirred at 100° C. for 16 h. The mixture was cooled to room temperature and quenched with water (100 mL). The aqueous layer was extracted with ethyl acetate (50 mL×3). The combined organic layers were washed with brine, dried over sodium sulfate, filtered and concentrated. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give (5-(3-chlorobenzyl)-N-(1-methyl-6-oxo-1,6-dihydropyridin-3-yl)picolinamide (0.101 g, 0.285 mmol, 70.5%) as a white solid. $^1$H NMR (500 MHz, Dimethylsulfoxide-$d_6$) δ 10.47 (s, 1H), 8.67 (s, 1H), 8.34 (d, J=2.5 Hz, 1H), 8.04 (d, J=8.5 Hz, 1H), 7.90 (dd, J=8.0, 2.0 Hz, 1H), 7.77 (dd, J=9.5, 3.0 Hz, 1H), 7.40 (s, 1H), 7.35 (t, J=7.5 Hz, 1H), 7.30-7.27 (m, 2H), 6.42 (d, J=9.0 Hz, 1H), 4.12 (s, 2H), 3.44 (s, 3H); LCMS (ESI) m/z: 354.1 [M+H]$^+$.

Example 58. Preparation of N-(5-((6-methoxypyridin-3-yl)methyl)pyridin-2-yl)-1-methyl-6-oxo-1,6-dihydropyridine-3-carboxamide (58)

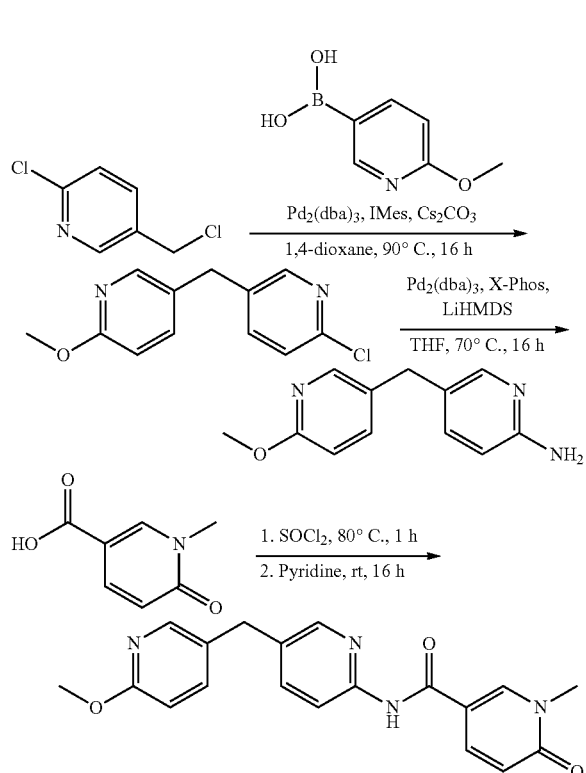

Step 1: Preparation of 2-chloro-5-((6-methoxypyridin-3-yl)methyl)pyridine

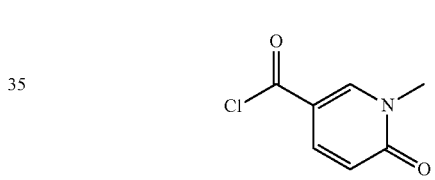

A mixture of 2-chloro-5-(chloromethyl)pyridine (1 g, 6.21 mmol), 6-methoxypyridin-3-ylboronic acid (1.12 g, 7.45 mmol), tris(dibenzylideneacetone)dipalladium(0) (0.28 g, 0.31 mmol), 1,3-bis(2,4,6-trimethylphenyl)imidazolium chloride (0.21 g, 0.62 mmol) and cesium carbonate (4 g, 12.42 mmol) in 1,4-dioxane (50 mL) was evacuated and refilled with argon (3×) and stirred at 90° C. for 16 h. The reaction was cooled down, diluted with ethyl acetate (30 mL), filtered through a pad of silica gel and concentrated. The residue was purified by Combi-Flash (Biotage, 40 g silica gel, eluted with ethyl acetate in petroleum ether from 20% to 30%) to give 2-chloro-5-((6-methoxypyridin-3-yl)methyl)pyridine (0.85 g, 3.63 mmol, 58.6%) as a yellow oil. LCMS (ESI) m/z: 235.1 [M+H]⁺.

Step 2: Preparation of 5-((6-methoxypyridin-3-yl)methyl)pyridin-2-amine

A solution of 2-chloro-5-((6-methoxypyridin-3-yl)methyl)pyridine (0.5 g, 2.13 mmol) in dry-tetrahydrofuran (20 mL) was evacuated and refilled with nitrogen (2×) and was charged with tris(dibenzylideneacetone)dipalladium(0) (0.19 g, 0.21 mmol), X-Phos (0.2 g, 0.42 mmol) and 1 M lithium bis(trimethylsilyl)amide tetrahydrofuran solution (6.4 mL, 6.4 mmol). The mixture was again evacuated and refilled with nitrogen (2×) and stirred at 70° C. for 16 h. The volatiles were concentrated and the crude residue was purified by Combi-Flash (Biotage, 40 g silica gel, eluted with methanol/dichloromethane=1/10, containing 0.5% 7 N ammonia in methanol, in from 30% to 40%) to give 5-((6-methoxypyridin-3-yl)methyl)pyridin-2-amine (0.22 g, 1.02 mmol, 48%) as a yellow oil. LCMS (ESI) m/z: 216.2 [M+H]⁺.

Step 3: Preparation of 1-methyl-6-oxo-1,6-dihydropyridine-3-carbonyl chloride A mixture of 1-methyl-6-oxo-1,6-dihydropyridine-3-carboxylic acid (0.6 g, 3.92 mmol) and thionyl chloride (5 mL) was stirred at 80° C. for 1 h. The reaction mixture was concentrated, to afford 1-methyl-6-oxo-1,6-dihydropyridine-3-carbonyl chloride (0.6 g, crude) as a white solid. Used directly in next step without further purification.

Step 4: Preparation of N-(5-((6-methoxypyridin-3-yl)methyl)pyridin-2-yl)-1-methyl-6-oxo-1,6-dihydropyridine-3-carboxamide

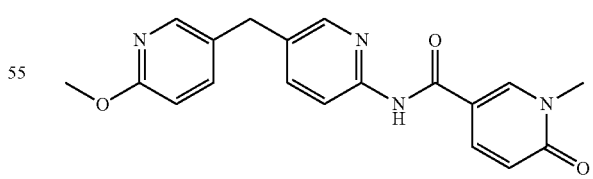

To a solution of 5-((6-methoxypyridin-3-yl)methyl)pyridin-2-amine (0.17 g, 0.79 mmol) in tetrahydrofuran (20 mL) at 0° C. was added pyridine (0.2 mL, 2.37 mmol) followed by 1-methyl-6-oxo-1,6-dihydropyridine-3-carbonyl chloride (0.2 g, 1.19 mmol) in small portions. The reaction mixture was stirred at room temperature for 16 h. Another portion of 1-methyl-6-oxo-1,6-dihydropyridine-3-carbonyl chloride (0.1 g, 0.79 mmol) was added and the reaction was stirred at 30° C. for 5 h. The reaction mixture was diluted with water (20 mL) and extracted with ethyl acetate (30 mL×3). The combined organic layers were dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-((6-methoxypyridin-3-yl)methyl)pyridin-2-yl)-1-methyl-6-oxo-1,6-dihydropyridine-3-carboxamide (0.088 g, 0.25 mmol, 32%) as a white solid. $^1$H NMR (400 MHz, Dimethylsulfoxide-d$_6$) δ 10.50 (s, 1H), 8.65 (d, 1H, J=2.8 Hz), 8.27 (d, 1H, J=2 Hz), 8.10 (d, 1H, J=2 Hz), 8.04 (d, 1H, J=8.8 Hz), 7.97 (dd, 1H, J=2.8 Hz, 9.6 Hz), 7.65 (dd, 1H, J=2.4 Hz, 8.4 Hz), 7.56 (dd, 1H, J=2.4 Hz, 8.4 Hz), 6.75 (d, 1H, J=8.4 Hz), 6.42 (d, 1H, J=9.6 Hz), 3.88 (s, 2H), 3.00 (s, 3H), 3.48 (s, 3H); LCMS (ESI) m/z: 351.1 [M+H]$^+$.

Example 59. Preparation of N-(5-(3,5-difluorobenzyl)pyridin-2-yl)-1-methyl-6-oxo-1,6-dihydropyridine-3-carboxamide (59)

borolan-2-yl)pyridin-2-amine (12.2 g, 55.26 mmol) in 1,4-dioxane (240 mL) was added a solution of potassium carbonate (13.9 g, 100 mmol) in water (80 mL). The reaction mixture was degassed with nitrogen for 1 minute before 1,1'-bis(diphenylphosphino)ferrocene-palladium(II) dichloride dichloromethane complex (2.04 g, 2.50 mmol) was added and the mixture was degassed with nitrogen for 1 minute. The reaction mixture was stirred at 90° C. for 2 h and was concentrated and diluted with water (250 mL). The aqueous layer was extracted with ethyl acetate (300 mL×3). The combined organic layers were dried over sodium sulfate, filtered and concentrated. The residue was purified by column chromatography (silica gel, ethyl acetate then dichloromethane:ethyl acetate=2:1) to afford compound 5-(3,5-difluorobenzyl)pyridin-2-amine (8.02 g, 36.4 mmol, 72%) as a pale yellow solid. The pale yellow solid (4.6 g) was re-purified by column chromatography (silica gel, dichloromethane: ammonia in methanol (7 N)=20/1) to afford 5-(3,5-difluorobenzyl)pyridin-2-amine (4.4 g, 20 mmol, 95%) as a pale yellow solid. LCMS (ESI) m/z: 221.1 [M+H]$^+$.

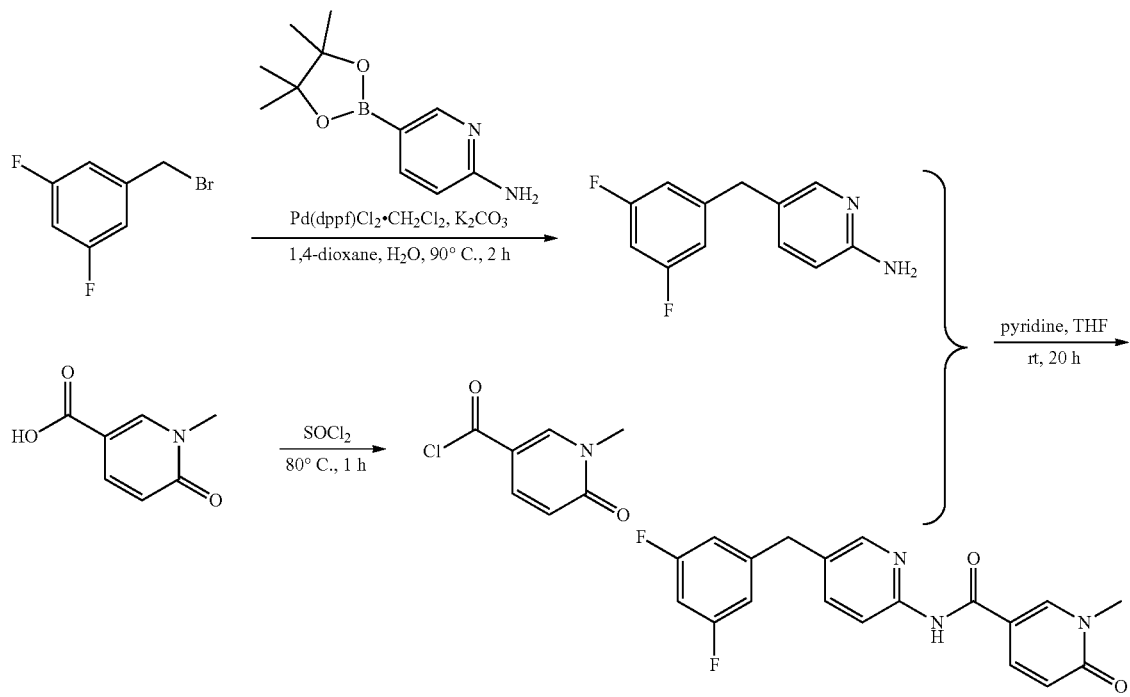

Step 1: Preparation of 5-(3,5-difluorobenzyl)pyridin-2-amine

Step 2: Preparation of N-(5-(3,5-difluorobenzyl)pyridin-2-yl)-1-methyl-6-oxo-1,6-dihydropyridine-3-carboxamide

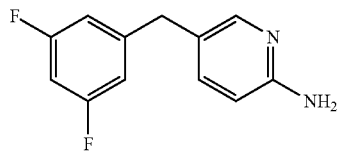 [SMILES: Nc1ccc(Cc2cc(F)cc(F)c2)cn1]

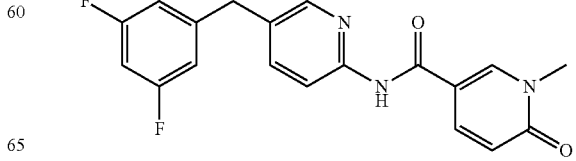

To a solution of 1-(bromomethyl)-3,5-difluorobenzene (10.4 g, 50.2 mmol) and 5-(4,4,5,5-tetramethyl-1,3,2-dioxa- A suspension of 1-methyl-6-oxo-1,6-dihydropyridine-3-carboxylic acid (4.0 g, 26 mmol) in thionyl chloride (40 mL) was heated to 80° C. for 1 h. After being concentrated and dried in vacuo, the residue was dissolved in dry tetrahydrofuran (100 mL) and added to a mixture of 5-(3,5-difluorobenzyl)pyridin-2-amine (4.4 g, 20 mmol) and pyridine (8.0 g, 100 mmol) in dry tetrahydrofuran (50 mL) at room temperature over 1 h. The reaction mixture was stirred at room temperature for 20 h. The yellow solid precipitated out of the reaction solution and was collected by filtration. The filter cake was washed with ethanol (50 mL) and tert-butyl methyl ether (50 mL). The filtrate was concentrated, and the residue was washed with ethanol (20 mL) and tert-butyl methyl ether (20 mL). Combined both solids and dried in vacuo to give crude N-(5-(3,5-difluorobenzyl)pyridin-2-yl)-1-methyl-6-oxo-1,6-dihydropyridine-3-carboxamide (4.1 g) which was dissolved in ethanol (500 mL) at 110° C. After being filtered, the filtrate was cooled to room temperature. The solid was collected by filtration and the cake was washed with ethanol (50 mL) and tert-butyl methyl ether (50 mL). The off-white solid was slurring in water for 3 h before filtered and dried over vacuo to give N-(5-(3,5-difluorobenzyl)pyridin-2-yl)-1-methyl-6-oxo-1,6-dihydropyridine-3-carboxamide (2.9 g, 8.17 mmol, 41%) as an off-white solid. $^1$H NMR (400 MHz, Dimethylsulfoxide-$d_6$) δ 10.55 (s, 1H), 8.66 (d, J=2.4 Hz, 1H), 8.31 (d, J=1.6 Hz, 1H), 8.05 (d, J=8.8 Hz, 1H), 7.97 (dd, $J_1$=2.4 Hz, $J_2$=9.6 Hz, 1H), 7.71 (dd, $J_1$=2.4 Hz, $J_2$=8.8 Hz, 1H), 7.02-7.08 (m, 3H), 6.42 (d, J=9.6 Hz, 1H), 3.96 (s, 2H), 3.49 (s, 3H); LCMS (ESI) m/z: 356.0 [M+H]$^+$.

Example 60. Preparation of N-(5-(3-chloro-4-fluorobenzyl)pyridin-2-yl)-1-methyl-6-oxo-1,6-dihydropyridine-3-carboxamide (60)

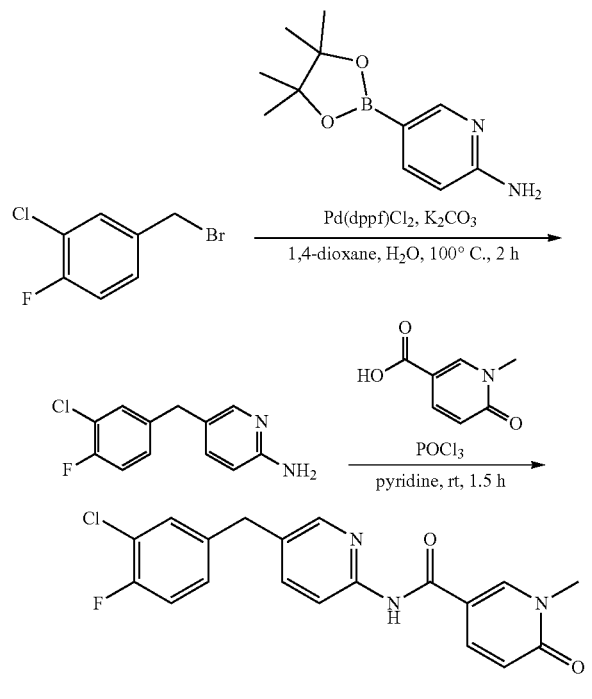

Step 1: Preparation of 5-(3-chloro-4-fluorobenzyl)pyridin-2-amine

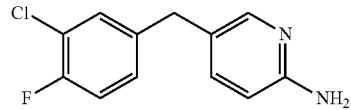 [SMILES: Nc1ccc(Cc2ccc(F)c(Cl)c2)cn1]

To a solution of 4-(bromomethyl)-2-chloro-1-fluorobenzene (1.12 g, 5 mmol), 5-(4,4,5,5-tetramethyl-1,3-dioxolan-2-yl)pyridin-2-amine (1.34 g, 6 mmol) and potassium carbonate (1.38 g, 10 mmol) in 1,4-dioxane (30 mL) and water (10 mL) was added [1,1'-bis(diphenylphosphino)ferrocene]dichloropalladium(II) (0.366 g, 0.5 mmol) under nitrogen. The reaction mixture was stirred at 100° C. for 2 h. The reaction mixture was concentrated, and water (50 mL) was added. The aqueous phase was extracted with ethyl acetate (80 mL×3). The combined organic layers were dried over sodium sulfate, filtered and concentrated. The crude product was purified by column chromatography (silica gel, petroleum ether/ethyl acetate from 1/1-0/1) to give 5-(3-chloro-4-fluorobenzyl)pyridin-2-amine (870 mg, 74%) as a yellow solid. LCMS (ESI) m/z: 237.1 [M+H]$^+$.

Step 2: Preparation of N-(5-(3-chloro-4-fluorobenzyl)pyridin-2-yl)-1-methyl-6-oxo-1,6-dihydropyridine-3-carboxamide

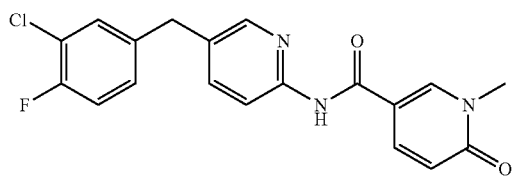 [SMILES: Cn1cc(C(=O)Nc2ccc(Cc3ccc(F)c(Cl)c3)cn2)ccc1=O]

To a solution of 5-(3-chloro-4-fluorobenzyl)pyridin-2-amine (0.142 g, 0.6 mmol) and 1-methyl-6-oxo-1,6-dihydropyridine-3-carboxylic acid (0.092 g, 0.6 mmol) in pyridine (4 mL) at room temperature was added phosphorus oxychloride (0.276 g, 1.8 mmol) slowly under argon. The reaction mixture was stirred at room temperature for 1.5 h. The reaction mixture was concentrated, and water (30 mL) was added. The aqueous layer was extracted with dichloromethane (30 mL×2). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-(3-chloro-4-fluorobenzyl)pyridin-2-yl)-1-methyl-6-oxo-1,6-dihydropyridine-3-carboxamide (14.3 mg, 0.04 mmol, 6.5%) as a white solid. $^1$H NMR (400 MHz, Dimethylsulfoxide-$d_6$) δ 10.53 (s, 1H), 8.65 (d, J=2.8 Hz, 1H), 8.30 (d, J=2.0 Hz, 1H), 8.05 (d, J=8.8 Hz, 1H), 7.96 (dd, $J_1$=2.8 Hz, $J_2$=9.6 Hz, 1H), 7.68 (dd, $J_1$=2.4 Hz, $J_2$=8.4 Hz, 1H), 7.51 (dd, $J_1$=2.0 Hz, $J_2$=6.8 Hz, 1H), 7.32-7.36 (m, 1H), 7.25-7.29 (m, 1H), 6.42 (d, J=9.2 Hz, 1H), 3.94 (s, 2H), 3.48 (s, 3H); LCMS (ESI) m/z: 372.0 [M+H]$^+$.

Example 61. Preparation of N-(5-(3-cyanobenzyl)pyridin-2-yl)-1-methyl-6-oxo-1,6-dihydropyridine-3-carboxamide (61)

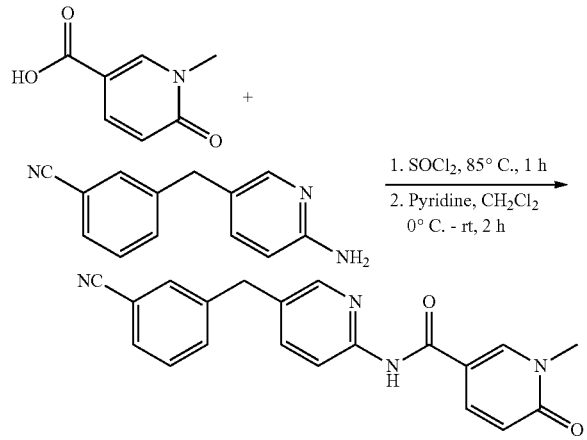

Step 1: Preparation of N-(5-(3-cyanobenzyl)pyridin-2-yl)-1-methyl-6-oxo-1,6-dihydropyridine-3-carboxamide

A suspension of 1-methyl-6-oxo-1,6-dihydropyridine-3-carboxylic acid (0.184 g, 1.2 mmol) in thionyl chloride (4 mL) was stirred at 85° C. for 1 h. The reaction mixture was concentrated, dissolved in dichloromethane (6 mL) and added to a solution of 3-((6-aminopyridin-3-yl)methyl)benzonitrile (0.209 g, 1 mmol) in pyridine (6 mL) at 0° C. The reaction mixture was stirred at 0° C.~room temperature for 2 h and was poured into ice water. The aqueous layer was extracted with dichloromethane (20 mL×2). The combined organic layers washed with brine (20 mL) were dried over sodium sulfate, filtered and concentrated. The crude sample was dissolved in minimal N,N-dimethylformamide and purified via prep-HPLC (Boston C18 21*250 mm 10 urn column. The mobile phase was acetonitrile/0.01% aqueous trifluoroacetic acid) to give N-(5-(3-cyanobenzyl)pyridin-2-yl)-1-methyl-6-oxo-1,6-dihydropyridine-3-carboxamide (0.159 g, 0.46 mmol, 46%) as a white solid. $^1$H NMR (500 MHz, Dimethylsulfoxide-$d_6$) δ 10.61 (s, 1H), 8.67 (d, J=3.0 Hz, 1H), 8.33 (d, J=2.0 Hz, 1H), 8.04 (d, J=8.5 Hz, 1H), 7.98 (dd, J=9.5, 2.5 Hz, 1H), 7.78 (s, 1H), 7.74 (dd, J=8.5, 2.5 Hz, 1H), 7.69 (d, J=7.5 Hz, 1H), 7.63 (d, J=8.5 Hz, 1H), 7.52 (t, J=7.5 Hz, 1H), 6.43 (d, J=9.5 Hz, 1H), 4.02 (s, 2H), 3.50 (s, 3H); LCMS (ESI) m/z: 345.1 [M+H]$^+$.

Example 62. Preparation of N-(5-((1,3-dihydroisobenzofuran-5-yl)methyl)pyridin-2-yl)-1-methyl-6-oxo-1,6-dihydropyridine-3-carboxamide (62)

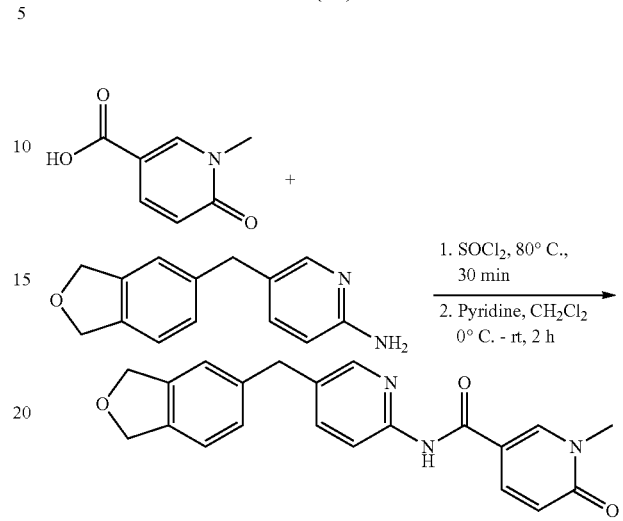

Step 1: Preparation of N-(5-((1,3-dihydroisobenzofuran-5-yl)methyl)pyridin-2-yl)-1-methyl-6-oxo-1,6-dihydropyridine-3-carboxamide

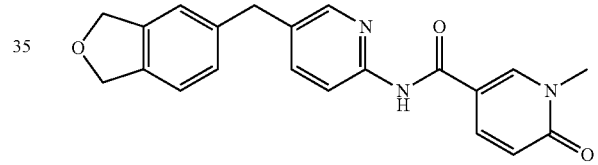

A suspension of 1-methyl-6-oxo-1,6-dihydropyridine-3-carboxylic acid (0.081 g, 0.531 mmol) in thionyl chloride (3 mL) was stirred at 80° C. for 0.5 h under nitrogen. The reaction mixture was concentrated, dissolved in dichloromethane (3 mL) and added to a solution of 5-((1,3-dihydroisobenzofuran-5-yl)methyl)pyridin-2-amine (0.100 g, 0.442 mmol) in pyridine (3 mL) at 0° C. The reaction mixture was then stirred at 0° C.~room temperature for 2 h. The reaction solution was poured into ice water and extracted with dichloromethane (20 mL×2). The combined organic layers were washed with brine (20 mL), dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-((1,3-dihydroisobenzofuran-5-yl)methyl)pyridin-2-yl)-1-methyl-6-oxo-1,6-dihydropyridine-3-carboxamide (0.0885 g, 0.245 mmol, 55.3%) as a white solid. $^1$H NMR (400 MHz, Dimethylsulfoxide-$d_6$) δ 10.61 (s, 1H), 8.66 (d, J=2.8 Hz, 1H), 8.29 (d, J=1.6 Hz, 1H), 8.01 (d, J=8.4 Hz, 1H), 7.97 (dd, J=9.6, 2.8 Hz, 1H), 7.70 (dd, J=8.8, 2.4 Hz, 1H), 7.23 (d, J=8.4 Hz, 1H), 7.17 (d, J=6.8 Hz, 2H), 6.43 (d, J=9.6 Hz, 1H), 4.95 (s, 4H), 3.97 (s, 2H), 3.50 (s, 3H); LCMS (ESI) m/z: 362.1 [M+H]$^+$.

Example 63. Preparation of 1-methyl-6-oxo-N-(5-(4-(trifluoromethyl)benzyl)pyridin-2-yl)-1,6-dihydropyridine-3-carboxamide (63)

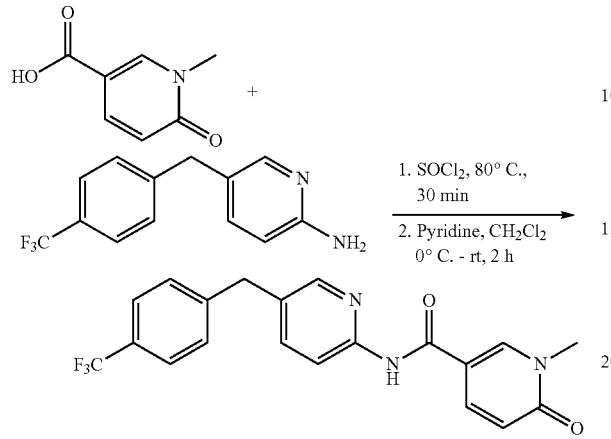

Step 1: Preparation of 1-methyl-6-oxo-N-(5-(4-(trifluoromethyl)benzyl)pyridin-2-yl)-1,6-dihydropyridine-3-carboxamide

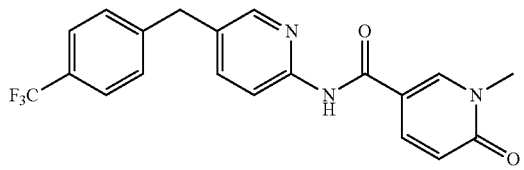 [SMILES: Cn1cc(C(=O)Nc2ccc(Cc3ccc(C(F)(F)F)cc3)cn2)ccc1=O]

A suspension of 1-methyl-6-oxo-1,6-dihydropyridine-3-carboxylic acid (0.184 g, 1.2 mmol) in thionyl chloride (4 mL) was stirred at 80° C. for 0.5 h under nitrogen. The reaction mixture was concentrated, dissolved in dichloromethane (6 mL) and added to a solution of 5-(4-(trifluoromethyl)benzyl)pyridin-2-amine (0.252 g, 1 mmol) in pyridine (6 mL) at 0° C. The reaction mixture was stirred at room temperature for 2 h and was poured into ice water. The aqueous layer was extracted with dichloromethane (20 mL×2). The combined organic layers were washed with brine (20 mL), dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give 1-methyl-6-oxo-N-(5-(4-(trifluoromethyl)benzyl)pyridin-2-yl)-1,6-dihydropyridine-3-carboxamide (0.1955 g, 0.51 mmol, 50.5%) as a white solid. $^1$H NMR (400 MHz, Dimethylsulfoxide-$d_6$) δ 10.60 (s, 1H), 8.67 (d, J=2.4 Hz, 1H), 8.32 (d, J=2.0 Hz, 1H), 8.04 (d, J=8.8 Hz, 1H), 7.97 (dd, J=9.6, 2.8 Hz, 1H), 7.72 (dd, J=8.8, 2.8 Hz, 1H), 7.67 (d, J=8.4 Hz, 2H), 7.49 (d, J=8.0 Hz, 2H), 6.43 (d, J=9.6 Hz, 1H), 4.07 (s, 2H), 3.50 (s, 3H); LCMS (ESI) m/z: 388.1 [M+H]$^+$.

Example 64. Preparation of N-(5-(4-chlorobenzyl)pyridin-2-yl)-1-methyl-6-oxo-1,6-dihydropyridine-3-carboxamide (64)

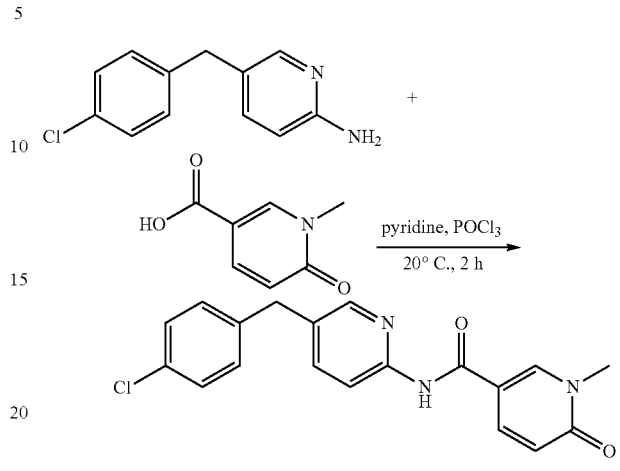

Step 1: Preparation of N-(5-(4-chlorobenzyl)pyridin-2-yl)-1-methyl-6-oxo-1,6-dihydropyridine-3-carboxamide

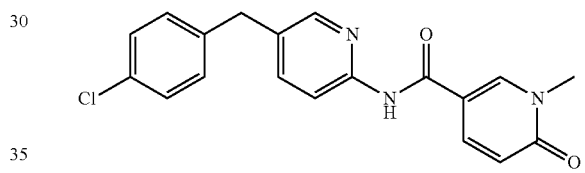

To a solution of 1-methyl-6-oxo-1,6-dihydropyridine-3-carboxylic acid (0.100 g, 0.653 mmol), 5-(4-chlorobenzyl)pyridin-2-amine (0.142 g, 0.653 mmol) in pyridine (4 mL) at 20° C. was added phosphorus oxychloride (0.297 g, 1.96 mmol). The reaction mixture was stirred at 20° C. for 2 h. The volatiles were removed under reduced pressure. The crude solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to offer N-(5-(4-chlorobenzyl)pyridin-2-yl)-1-methyl-6-oxo-1,6-dihydropyridine-3-carboxamide (29.6 mg, 0.084 mmol, 13%) as a white solid. $^1$H NMR (400 MHz, Dimethylsulfoxide-$d_6$) δ 10.55 (s, 1H), 8.66-8.67 (d, J=2.4 Hz, 1H), 8.28 (s, 1H), 7.96-8.05 (m, 2H), 7.66-7.69 (q, J=3.6 Hz, 1H), 7.27-7.38 (m, 4H), 6.42-6.44 (d, J=9.6 Hz, 1H), 3.95 (s, 2H), 3.50 (s, 3H); LCMS (ESI) m/z: 354.1 [M+H]$^+$.

Example 65. Preparation of N-(5-(cyclohexylmethyl)pyridin-2-yl)-1-methyl-6-oxo-1,6-dihydropyridine-3-carboxamide (65)

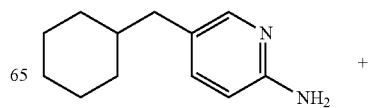

383

-continued

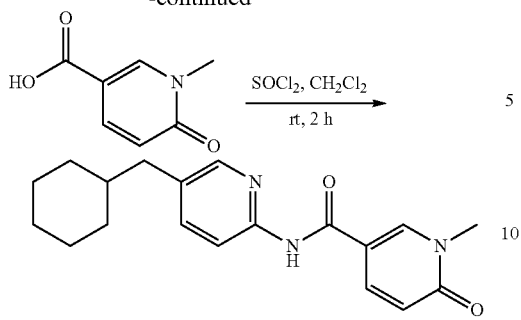

Step 1: Preparation of N-(5-(cyclohexylmethyl)
pyridin-2-yl)-1-methyl-6-oxo-1,6-dihydropyridine-3-
carboxamide

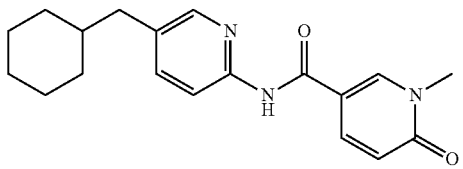 [SMILES: Cn1cc(C(=O)Nc2ccc(CC3CCCCC3)cn2)ccc1=O]

To a solution of 1-methyl-6-oxo-1,6-dihydropyridine-3-carboxylic acid (80 mg, 0.526 mmol) in dichloromethane (5 mL) at 20° C. was added thionyl chloride (5 mL). The reaction mixture was heated to 90° C. and refluxed for 0.5 h. The volatiles were removed under reduced pressure and the solid was dissolved in dichloromethane (2 mL) and was added to a solution of 5-(cyclohexylmethyl)pyridin-2-amine (50 mg, 0.263 mmol) and pyridine (62 mg, 0.789 mmol) in dichloromethane (5 mL). The reaction solution was stirred at 20° C. for 2 h. The reaction mixture was portioned between dichloromethane (50 mL) and water (50 mL). The organic layer was collected, dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(cyclohexylmethyl)pyridin-2-yl)-1-methyl-6-oxo-1,6-dihydropyridine-3-carboxamide (25.6 mg, 0.079 mmol, 30%) as a white solid. $^1$H NMR (400 MHz, Dimethylsulfoxide-$d_6$) δ 10.56 (s, 1H), 8.68 (d, J=4.0 Hz, 1H), 8.16 (s, 2H), 8.02 (t, J=8.0 Hz, 1H), 7.64-7.67 (m, 1H), 6.44 (d, J=8.0 Hz, 1H), 3.50 (s, 3H), 2.46 (d, J=8.0 Hz, 2H), 1.59-1.67 (m, 5H), 1.49-1.51 (m, 1H), 1.10-1.29 (m, 3H), 0.88-0.96 (m, 2H); LCMS (ESI) m/z: 326.2 [M+H]$^+$.

Example 66. Preparation of N-(5-(3,4-difluoroben-zyl)pyridin-2-yl)-1-methyl-6-oxo-1,6-dihydropyri-dine-3-carboxamide (66)

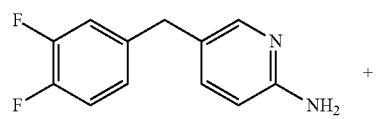

+

384

-continued

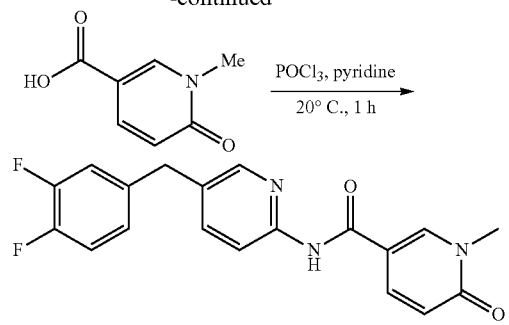

Step 1: Preparation of N-(5-(3,4-difluorobenzyl)
pyridin-2-yl)-1-methyl-6-oxo-1,6-dihydropyridine-3-
carboxamide

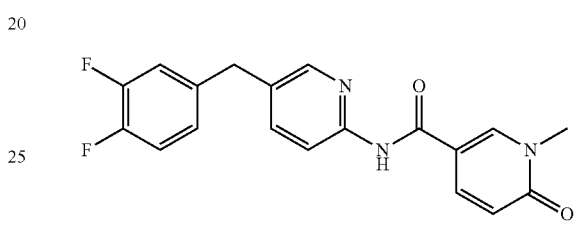

To a solution of 1-methyl-6-oxo-1,6-dihydropyridine-3-carboxylic acid (100 mg, 0.653 mmol) and 5-(3,4-difluorobenzyl)pyridin-2-amine (144 mg, 0.653 mmol) in pyridine (4 mL) at 20° C., was added phosphorus oxychloride (297 mg, 1.96 mmol). The reaction mixture was stirred at 20° C. for 4 h. The volatiles were removed under reduced pressure, and the resulting crude solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,4-difluorobenzyl)pyridin-2-yl)-1-methyl-6-oxo-1,6-dihydropyridine-3-carboxamide (39.8 mg, 0.11 mmol, 17%) as a light-yellow solid. $^1$H NMR (400 MHz, Dimethylsulfoxide-$d_6$) δ 10.56 (s, 1H), 8.67 (d, J=2.0 Hz, 1H), 8.30 (s, 1H), 8.05 (d, J=8.4 Hz, 1H), 7.99 (d, J=2.8 Hz, 1H), 7.69-7.72 (m, 1H), 7.33-7.40 (m, 2H), 7.10-7.13 (m, 1H), 6.43 (d, J=9.6 Hz, 1H), 3.95 (s, 2H), 3.50 (s, 3H); LCMS (ESI) m/z: 356.0 [M+H]$^+$.

Example 67. Preparation of N-(5-(3-chlorobenzyl)
pyridin-2-yl)-1-ethyl-6-oxo-1,6-dihydropyridazine-
3-carboxamide (67)

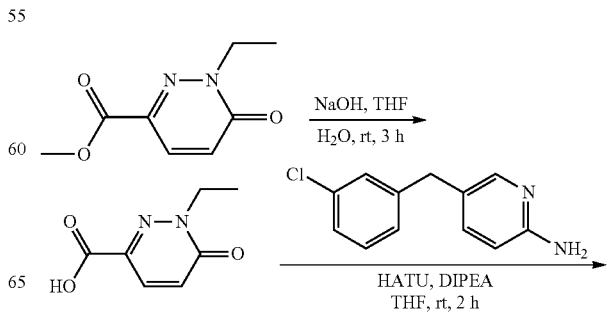

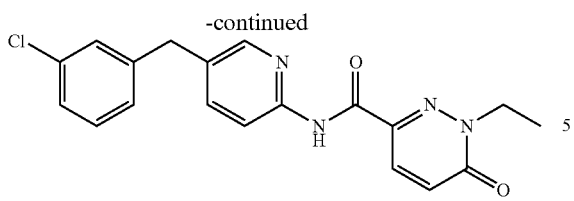

Step 1: Preparation of 1-ethyl-6-oxo-1,6-dihydropyridazine-3-carboxylic acid

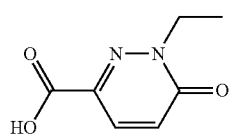

To a solution of methyl 1-ethyl-6-oxo-1,6-dihydropyridazine-3-carboxylate (0.637 g, 3.5 mmol) in tetrahydrofuran (5 mL) and water (1.5 mL) was added sodium hydroxide (0.280 g, 7 mmol). The reaction mixture was stirred at room temperature for 3 h before it was neutralized to pH=6 with aqueous 1 N hydrogen chloride. The mixture was concentrated, to 1-ethyl-6-oxo-1,6-dihydropyridazine-3-carboxylic acid as a white solid (0.900 g, crude); LCMS (ESI) m/z: 169.1 [M+H]$^+$. Used in the next step without additional purification.

Step 2: Preparation of N-(5-(3-chlorobenzyl)pyridin-2-yl)-1-ethyl-6-oxo-1,6-dihydropyridazine-3-carboxamide

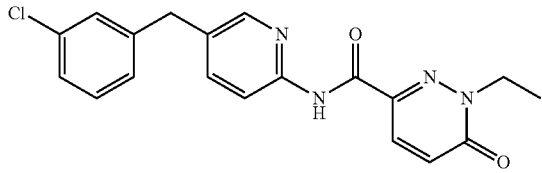 [SMILES: CCn1nc(C(=O)Nc2ccc(Cc3cccc(Cl)c3)cn2)ccc1=O]

A solution of 1-ethyl-6-oxo-1,6-dihydropyridazine-3-carboxylic acid (0.100 g, 0.6 mmol), 5-(3-chlorobenzyl)pyridin-2-amine (0.157 g, 0.75 mmol), 1-[bis(dimethylamino)methylene]-1H-1,2,3-triazolo[4,5-b]pyridinium 3-oxid hexafluorophosphate (0.342 g, 0.9 mmol) and N,N-diisopropylethylamine (0.232 mg, 1.8 mmol) in tetrahydrofuran (4 mL) was stirred at room temperature for 2 h. Volatiles were removed under reduced pressure. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to yield N-(5-(3-chlorobenzyl)pyridin-2-yl)-1-ethyl-6-oxo-1,6-dihydropyridazine-3-carboxamide as a white solid (0.050 g, 0.136 mmol, 22.6%). $^1$H NMR (400 MHz, Dimethylsulfoxide-d$_5$) δ 10.23 (s, 1H), 8.35 (d, J=2.0 Hz, 1H), 8.08 (d, J=8.4 Hz, 1H), 7.93 (d, J=4.8 Hz, 1H), 7.78 (dd, J=4.2, 4.0 Hz, 1H), 7.36-7.32 (m, 2H), 7.28-7.23 (m, 2H), 7.07 (d, J=9.2 Hz, 1H), 4.24-4.18 (m, 2H), 3.99 (s, 2H), 1.35 (t, J=7.2 Hz, 3H); LCMS (ESI) 369.1 [M+H]$^+$.

Example 68. Preparation of 1-ethyl-N-(5-(3-fluorobenzyl)pyridin-2-yl)-6-oxo-1,6-dihydropyridazine-3-carboxamide (68)

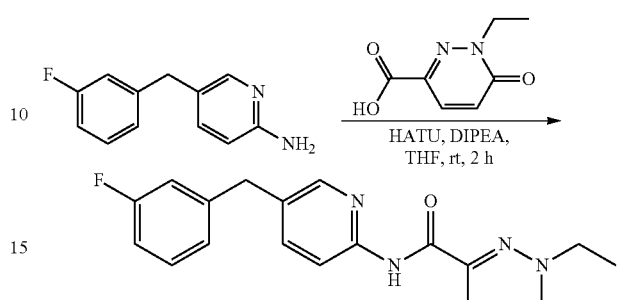

Step 1: Preparation of 1-ethyl-N-(5-(3-fluorobenzyl)pyridin-2-yl)-6-oxo-1,6-dihydropyridazine-3-carboxamide

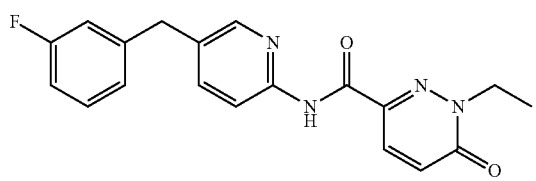 [SMILES: CCn1nc(C(=O)Nc2ccc(Cc3cccc(F)c3)cn2)ccc1=O]

A solution of 1-ethyl-6-oxo-1,6-dihydropyridazine-3-carboxylic acid (120 mg, 0.71 mmol), 5-(3-fluorobenzyl)pyridin-2-amine (162 mg, 0.86 mmol), 1-[bis(dimethylamino)methylene]-1H-1,2,3-triazolo[4,5-b]pyridinium 3-oxid hexafluorophosphate (405 mg, 1.065 mol) and N-N,N-diisopropylethylamine (275 mg, 2.13 mmol) in tetrahydrofuran (4 mL) was stirred at room temperature for 2 h. Volatiles were removed under reduced pressure. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to yield 1-ethyl-N-(5-(3-fluorobenzyl)pyridin-2-yl)-6-oxo-1,6-dihydropyridazine-3-carboxamide as a white solid (0.0973 g, 0.275 mmol, 38.8%). $^1$H NMR (400 MHz, Dimethylsulfoxide-d$_6$) δ 10.21 (s, 1H), 8.34 (d, J=2.0 Hz, 1H), 8.08 (d, J=8.8 Hz, 1H), 7.93 (d, J=10.0 Hz, 1H), 7.77 (dd, J=4.2, 4.2 Hz, 1H), 7.37-7.32 (m, 1H), 7.13-7.01 (m, 4H), 4.23-4.18 (m, 2H), 3.99 (s, 2H), 1.34 (t, J=7.2 Hz, 3H); LCMS (ESI) m/z: 353.1 [M+H]$^+$.

Example 69. Preparation of N-(5-(3-cyano-5-fluorobenzyl)pyridin-2-yl)-1-ethyl-6-oxo-1,6-dihydropyridazine-3-carboxamide (69)

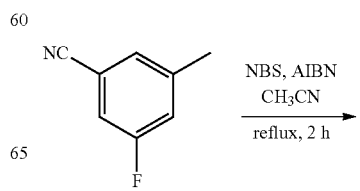

-continued

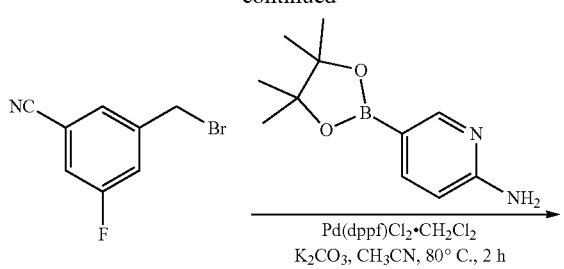

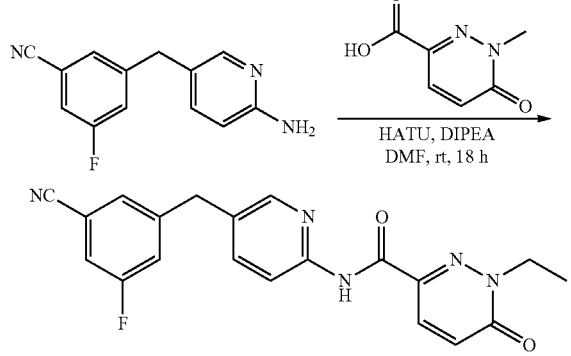

Step 1: Preparation of 3-(bromomethyl)-5-fluorobenzonitrile

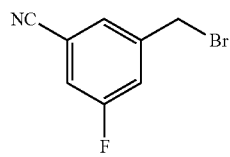

The synthesis of 3-(bromomethyl)-5-fluorobenzonitrile was followed using similar procedure to Example 25. Product 3-(bromomethyl)-5-fluorobenzonitrile (17.0 g, 79.4 mmol, 107%) was obtained as a colorless oil. $^1$H NMR (500 MHz, Chloroform-d) δ 7.51 (s, 1H), 7.38 (dt, J=2.5, 11.0 Hz, 1H), 7.32 (dt, J=1.5, 10.0 Hz, 1H), 4.45 (s, 2H).

Step 2: Preparation of 3-((6-aminopyridin-3-yl)methyl)-5-fluorobenzonitrile

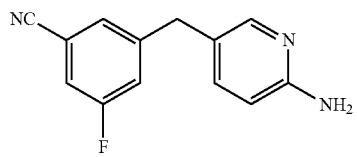 [SMILES: N#Cc1cc(F)cc(Cc2ccc(N)nc2)c1]

The synthesis of 3-((6-aminopyridin-3-yl)methyl)-5-fluorobenzonitrile was following similar procedures to Example 23. Product 3-((6-aminopyridin-3-yl)methyl)-5-fluorobenzonitrile (800 mg, 3.5 mmol, 50%) was obtained as a light-yellow oil. LCMS (ESI) m/z: 228.1 [M+H]$^+$.

Step 3: Preparation of N-(5-(3-cyano-5-fluorobenzyl)pyridin-2-yl)-1-ethyl-6-oxo-1,6-dihydropyridazine-3-carboxamide

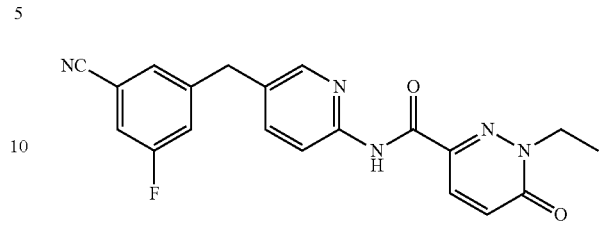

The synthesis of N-(5-(3-cyano-5-fluorobenzyl)pyridin-2-yl)-1-ethyl-6-oxo-1,6-dihydropyridazine-3-carboxamide followed similar procedures as for Example 42. Compound N-(5-(3-cyano-5-fluorobenzyl)pyridin-2-yl)-1-ethyl-6-oxo-1,6-dihydropyridazine-3-carboxamide (0.180 g, 0.478 mmol, 43.4%) was obtained as an off-white solid. $^1$H NMR (500 MHz, Dimethylsulfoxide-d$_6$) δ 10.19 (s, 1H), 8.38 (d, J=2.0 Hz, 1H), 8.09 (d, J=9.0 Hz, 1H), 7.94 (d, J=9.5 Hz, 1H), 7.80 (dd, J=2.5, 9.0 Hz, 1H), 7.72-7.69 (m, 2H), 7.58 (d, J=10.0 Hz, 1H), 7.07 (d, J=9.5 Hz, 1H), 4.20 (q, J=7.0 Hz, 2H), 4.05 (s, 2H), 1.35 (t, J=7.0 Hz, 3H); LCMS (ESI) m/z: 378.1 [M+H]$^+$.

Example 70. Preparation of N-(5-(3,4-dichlorobenzyl)pyridin-2-yl)-1-ethyl-6-oxo-1,6-dihydropyridazine-3-carboxamide (70)

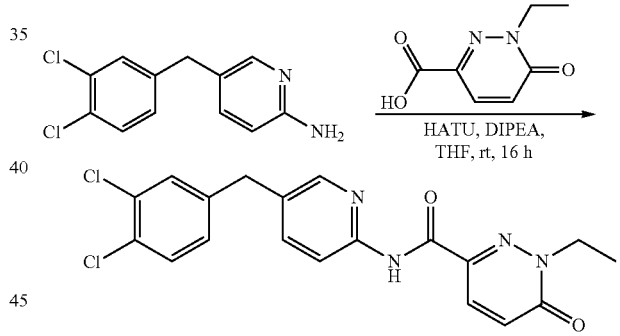

Step 1: Preparation of N-(5-(3,4-dichlorobenzyl)pyridin-2-yl)-1-ethyl-6-oxo-1,6-dihydropyridazine-3-carboxamide

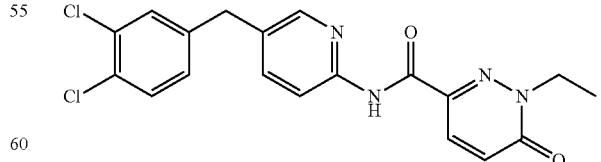

A solution of 1-ethyl-6-oxo-1,6-dihydropyridazine-3-carboxylic acid (0.127 g, 0.75 mmol), 5-(3,4-dichlorobenzyl)pyridin-2-amine (0.230 g, 0.90 mmol), 1-[bis(dimethylamino)methylene]-1H-1,2,3-triazolo[4,5-b]pyridinium 3-oxid hexafluorophosphate (0.427 g, 1.125 mmol) and N,N-diisopropylethylamine (0.290 g, 2.25 mmol) in tetrahydrofuran (4 mL) was stirred at room temperature for 16 h. Then the reaction mixture was concentrated, and the crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,4-dichlorobenzyl)pyridin-2-yl)-1-ethyl-6-oxo-1,6-dihydropyridazine-3-carboxamide as a white solid (0.0679 g, 0.141 18.8%). $^1$H NMR (500 MHz, Dimethylsulfoxide-$d_6$) δ 10.20 (s, 1H), 8.35 (d, J=2.0 Hz, 1H), 8.09 (d, J=8.5 Hz, 1H), 7.94 (d, J=9.7 Hz, 1H), 7.76 (dd, J=8.5, 2.3 Hz, 1H), 7.57 (t, J=5.4 Hz, 2H), 7.27 (dd, J=8.3, 2.0 Hz, 1H), 7.07 (d, J=9.7 Hz, 1H), 4.21 (t, J=7.2 Hz, 2H), 3.99 (s, 2H), 1.34 (t, J=7.2 Hz, 3H); LCMS (ESI) m/z: 403.0 [M+H]$^+$.

Example 71. Preparation of N-(5-(3-fluorobenzyl)pyridin-2-yl)-6-oxo-1-propyl-1,6-dihydropyridazine-3-carboxamide (71)

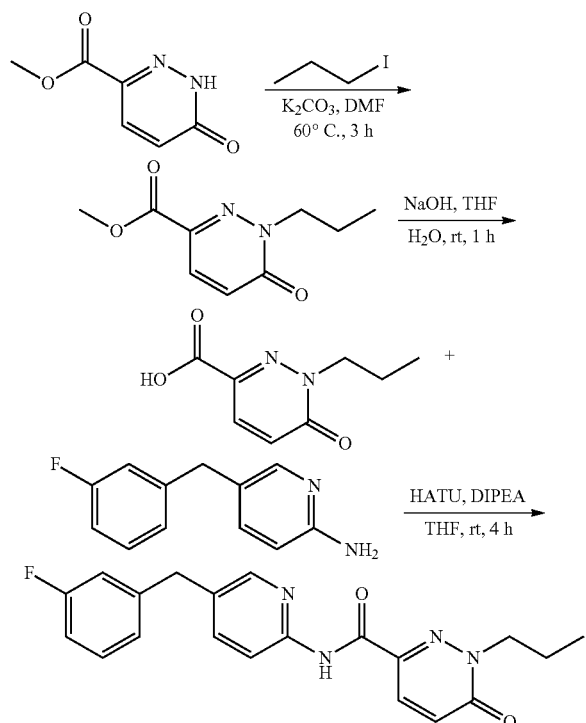

Step 1: Preparation of methyl 6-oxo-1-propyl-1,6-dihydropyridazine-3-carboxylate

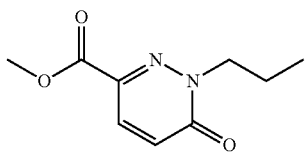

To a solution of methyl 6-oxo-1,6-dihydropyridazine-3-carboxylate (1.0 g, 6.49 mmol), potassium carbonate (2.68 g, 19.5 mmol) in N,N-dimethylformamide (15.0 mL) was added 1-iodopropane (1.65 g, 9.74 mmol). The reaction mixture was heated to 60° C. and stirred for 3 h. The reaction solution was dissolved in ethyl acetate (50 mL) and washed with water (50 mL), dried over sodium sulfate, filtered and concentrated. The crude material was purified by column chromatography (silica gel, petroleumether/ethyl acetate=1/1) to afford methyl 6-oxo-1-propyl-1,6-dihydropyridazine-3-carboxylate (0.700 g, 3.57 mmol, 55%) as a white solid. LCMS (ESI) m/z: 197.2 [M+H]$^+$.

Step 2: Preparation of 6-oxo-1-propyl-1,6-dihydropyridazine-3-carboxylic acid

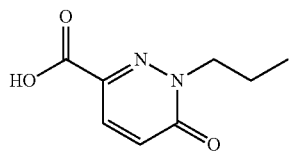

Sodium hydroxide (81.6 mg, 2.04 mmol) was added to a mixture of methyl 6-oxo-1-propyl-1,6-dihydropyridazine-3-carboxylate (200 mg, 1.02 mmol), tetrahydrofuran (4 mL) and water (2 mL) before the reaction was heated to 60° C. and stirred for 1 h. 1 N hydrochloric acid was added to adjust the pH value to 3-5 before all the solvent was removed to offer crude 6-oxo-1-propyl-1,6-dihydropyridazine-3-carboxylic acid (200 mg, crude).

Step 3: Preparation of N-(5-(3-fluorobenzyl)pyridin-2-yl)-6-oxo-1-propyl-1,6-dihydropyridazine-3-carboxamide

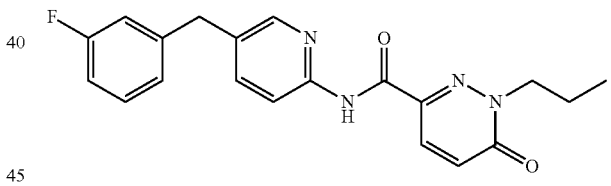

To a mixture of 6-oxo-1-propyl-1,6-dihydropyridazine-3-carboxylic acid (0.120 g, 0.659 mmol), diisopropylethylamine (0.255 g, 1.977 mmol) and tetrahydrofuran (5 mL) at 20° C. was added 1-[bis(dimethylamino)methylene]-1H-1,2,3-triazolo[4,5-b]pyridinium 3-oxid hexafluorophosphate (0.376 g, 0.659 mmol). The reaction solution was stirred for 20 minutes before a solution of 6-(3-chlorobenzyl)pyridazin-3-amine (0.144 g, 0.659 mmol) in tetrahydrofuran (1.0 mL) was added. The reaction solution was stirred at 20° C. for 16 h. The solvent was removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to offer N-(5-(3-fluorobenzyl)pyridin-2-yl)-6-oxo-1-propyl-1,6-dihydropyridazine-3-carboxamide (178.0 mg, 0.49 mmol, 74%) as a white solid. $^1$H NMR (400 MHz, Dimethylsulfoxide-$d_6$) δ 10.16 (s, 1H), 8.34 (s, 1H), 8.08-8.10 (d, J=8.4 Hz, 1H), 7.92-7.95 (d, J=9.6 Hz, 1H), 7.75-7.78 (m, 1H), 7.32-7.36 (m, 1H), 7.04-7.14 (m, 4H), 4.12-4.16 (t, J=7.2 Hz, 2H), 3.99 (s, 2H), 1.78-1.84 (q, J=7.4 Hz, 2H), 0.90-0.94 (t, J=7.4 Hz, 3H); LCMS (ESI) m/z: 367.1 [M+H]⁺.

Example 72. Preparation of N-(5-(3-fluorobenzyl)pyridin-2-yl)-1-isopropyl-6-oxo-1,6-dihydropyridazine-3-carboxamide (72)

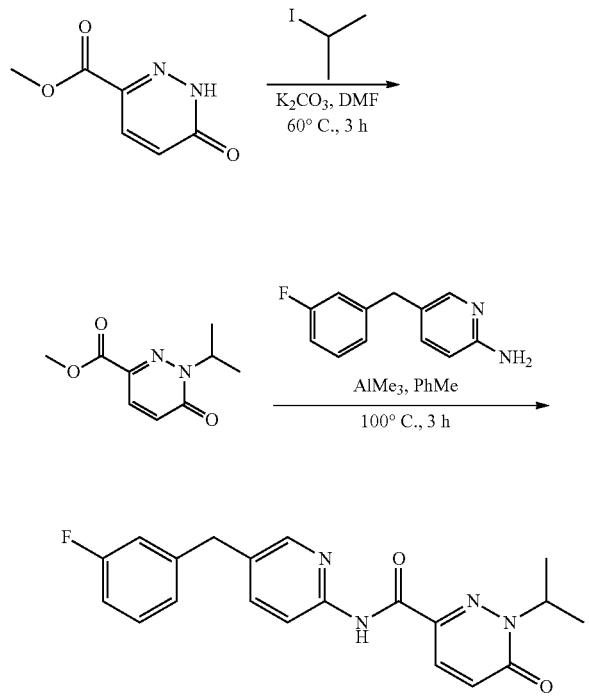

Step 1: Preparation of methyl 1-isopropyl-6-oxo-1,6-dihydropyridazine-3-carboxylate

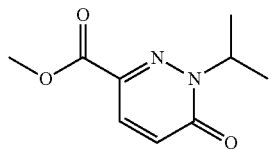

To a solution of methyl 6-oxo-1,6-dihydropyridazine-3-carboxylate (1.0 g, 6.49 mmol) and potassium carbonate (2.68 g, 19.47 mmol) in N,N-dimethylformamide (15.0 mL) at room temperate was added 2-iodopropane (1.65 g, 9.74 mmol). The reaction mixture was heated to 60° C. and stirred for 1 h. The reaction mixture was dissolved in ethyl acetate (50 mL) and washed with water (50 mL), dried over sodium sulfate, filtered and concentrated. The crude product was purified by column chromatography (silica gel, petroleum ether/ethyl acetate=1/1) to offer methyl 1-isopropyl-6-oxo-1,6-dihydropyridazine-3-carboxylate as a white solid (0.500 g, 2.55 mmol, 39%) as a white solid. LCMS (ESI) m/z: 197.1 [M+H]⁺.

Step 2: Preparation of N-(5-(3-fluorobenzyl)pyridin-2-yl)-1-isopropyl-6-oxo-1,6-dihydropyridazine-3-carboxamide

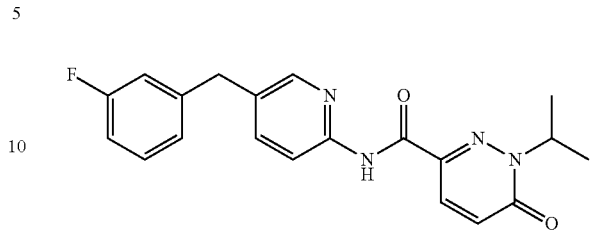

To a solution of 5-(3-fluorobenzyl)pyridin-2-amine (0.206 g, 1.02 mmol) in toluene (10 mL) at 20° C. was added trimethylaluminum (0.5 mL, 1.02 mmol, 2 M in toluene) under argon. The reaction mixture was stirred at 20° C. for 1 h before a solution of methyl 1-isopropyl-6-oxo-1,6-dihydropyridazine-3-carboxylate (0.100 g, 0.51 mmol) in toluene (5 mL) was added. The reaction solution was stirred at 100° C. for 2 h. The solvent was removed under reduced pressure and the residue was treated with a mixture of 1 N hydrochloric acid (5 mL) and methanol (20 mL). The volatiles were removed under reduced pressure and the crude product was dissolved in dichloromethane (50 mL) and water (50 mL). The organic layer was separated, dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to offer N-(5-(3-fluorobenzyl)pyridin-2-yl)-1-isopropyl-6-oxo-1,6-dihydropyridazine-3-carboxamide (0.0832 g, 0.23 mmol, 45%) as a white solid. ¹H NMR (400 MHz, Dimethylsulfoxide-d₆) δ 10.12 (s, 1H), 8.35 (s, 1H), 8.07-8.09 (d, J=8.4 Hz, 1H), 7.91-7.94 (d, J=9.6 Hz, 1H), 7.74-7.77 (m, 1H), 7.32-7.38 (m, 1H), 7.01-7.13 (m, 4H), 5.15-5.19 (t, J=6.6 Hz, 1H), 3.99 (s, 2H), 1.38-1.40 (d, J=6.4 Hz, 6H); LCMS (ESI) m/z: 367.1 [M+H]⁺.

Example 73. Preparation of N-(5-(3-chlorobenzyl)pyridin-2-yl)-1-isopropyl-6-oxo-1,6-dihydropyridazine-3-carboxamide (73)

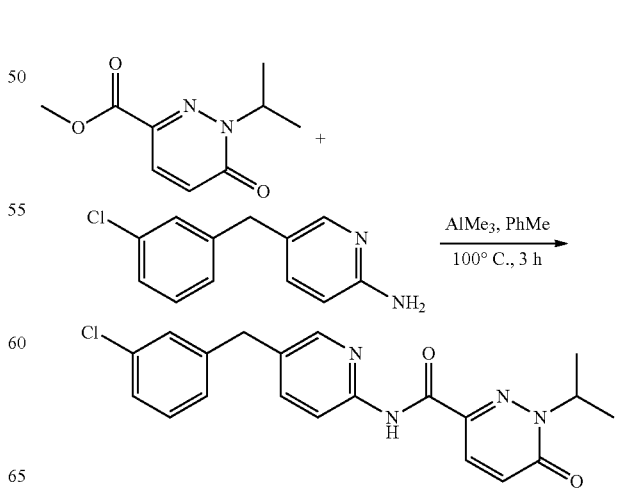

393

Step 1: Preparation of N-(5-(3-chlorobenzyl)pyridin-2-yl)-1-isopropyl-6-oxo-1,6-dihydropyridazine-3-carboxamide

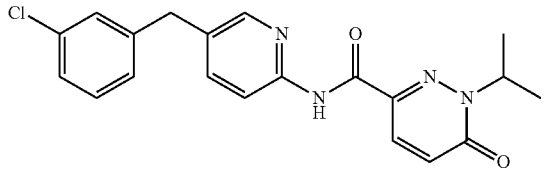 [SMILES: CC(C)n1nc(C(=O)Nc2ccc(Cc3cccc(Cl)c3)cn2)ccc1=O]

To a solution of 5-(3-chlorobenzyl)pyridin-2-amine (0.222 g, 1.02 mmol) in toluene (15 mL) at 20° C. was added trimethylaluminum (0.5 mL, 1.02 mmol, 2 M in toluene) under argon. The reaction mixture was stirred at 20° C. for 1 h before a solution of methyl 1-isopropyl-6-oxo-1,6-dihydropyridazine-3-carboxylate (0.100 g, 0.51 mmol) in toluene (15 mL) was added. The reaction solution was stirred at 100° C. for 2 h. The volatiles were removed under reduced pressure and the residue was quenched with water (50 mL) and extracted with dichloromethane (50 mL). The organic layer was dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to offer N-(5-(3-chlorobenzyl)pyridin-2-yl)-1-isopropyl-6-oxo-1,6-dihydropyridazine-3-carboxamide (107.8 mg, 0.28 mmol, 55%) as a white solid. $^1$H NMR (400 MHz, Dimethylsulfoxide-d$_6$) δ 10.11 (s, 1H), 8.36 (s, 1H), 8.07-8.09 (d, J=8.0 Hz, 1H), 7.92-7.94 (d, J=9.6 Hz, 1H), 7.75-7.77 (d, J=8.0 Hz, 1H), 7.23-7.35 (m, 4H), 7.05-7.07 (d, J=9.6 Hz, 1H), 5.16-5.19 (t, J=6.6 Hz, 1H), 3.99 (s, 2H), 1.39-1.40 (d, J=6.8 Hz, 6H); LCMS (ESI) m/z: 383.1 [M+H]$^+$.

Example 74. Preparation of N-(5-(3-chloro-5-fluorobenzyl)pyridin-2-yl)-1-cyclopropyl-6-oxo-1,6-dihydropyridazine-3-carboxamide (74)

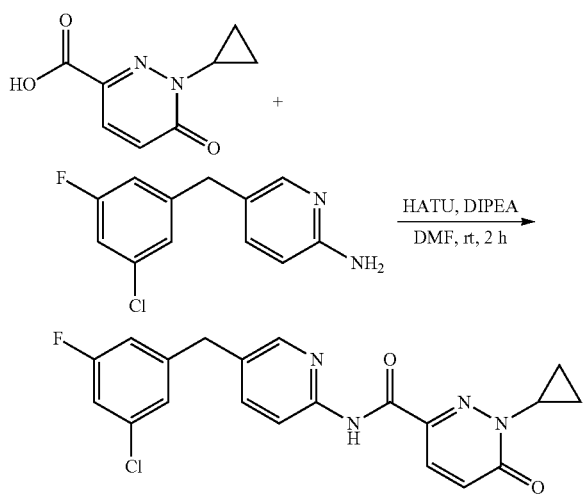

394

Step 1: Preparation of N-(5-(3-chloro-5-fluorobenzyl)pyridin-2-yl)-1-cyclopropyl-6-oxo-1,6-dihydropyridazine-3-carboxamide

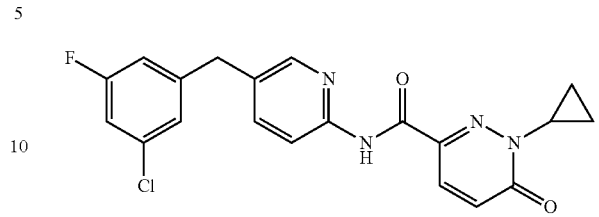

A solution of 1-cyclopropyl-6-oxo-1,6-dihydropyridazine-3-carboxylic acid (0.126 g, 0.7 mmol), 5-(3-chloro-5-fluorobenzyl)pyridin-2-amine (0.198 g, 0.84 mmol), 1-[bis(dimethylamino)methylene]-1H-1,2,3-triazolo[4,5-b]pyridinium 3-oxid hexafluorophosphate (0.400 g, 1.05 mmol) and N,N-diisopropylethylamine (0.271 g, 2.1 mmol) in N,N-dimethylformamide (3.5 mL) was stirred at room temperature for 2 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chloro-5-fluorobenzyl)pyridin-2-yl)-1-cyclopropyl-6-oxo-1,6-dihydropyridazine-3-carboxamide (0.104 g, 0.262 mmol, 37.4%) as a white solid. $^1$H NMR (500 MHz, Dimethylsulfoxide-d$_6$) δ 10.12 (s, 1H), 8.37 (d, J=2.0 Hz, 1H), 8.06 (d, J=8.5 Hz, 1H), 7.91 (d, J=9.7 Hz, 1H), 7.78 (dd, J=8.5, 2.3 Hz, 1H), 7.30-7.22 (m, 2H), 7.17 (d, J=9.5 Hz, 1H), 7.06 (d, J=9.7 Hz, 1H), 4.10-4.06 (m, 1H), 4.00 (s, 2H), 1.28-1.24 (m, 2H), 1.04-1.00 (m, 2H); LCMS (ESI) m/z: 399.1 [M+H]$^+$.

Example 75. Preparation of 1-cyclopropyl-N-(5-(3-fluorobenzyl)pyridin-2-yl)-6-oxo-1,6-dihydropyridazine-3-carboxamide (75)

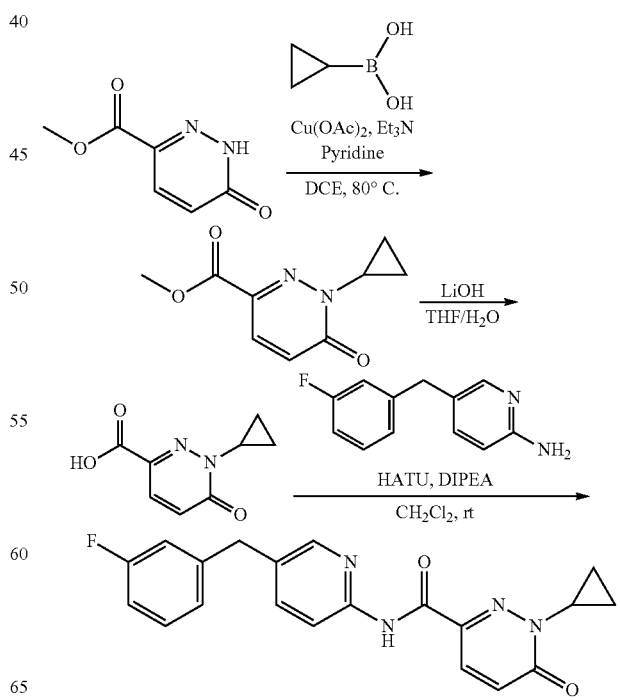

Step 1: Preparation of methyl 1-cyclopropyl-6-oxo-1,6-dihydropyridazine-3-carboxylate

Combined methyl 6-oxo-1,6-dihydropyridazine-3-carboxylate (0.400 g, 2.59 mmol) with cyclopropylboronic acid (0.444 g, 5.18 mmol) and copper(II) acetate (0.940 g, 5.18 mmol) and suspended in 1,2-dichloroethane (8.63 mL). Added triethylamine (1.43 mL, 10.3 mmol) and pyridine (1.04 mL, 12.9 mmol). The reaction was degassed by cycling with vacuum and nitrogen gas for 3 cycles. Stirred for 16 h at 80° C. Cooled to room temperature and quenched with saturated aqueous ammonium chloride (15 mL). Extracted with dichloromethane (10 mL×3). The combined organic layers were dried over sodium sulfate, filtered, and concentrated. Purified reaction by column chromatography (eluting with 0-100% ethyl acetate/hexanes through 40 g of silica gel) to give methyl 1-cyclopropyl-6-oxo-1,6-dihydropyridazine-3-carboxylate as a yellow solid (155 mg, 0.798 mmol, 31%). $^1$H NMR (300 MHz, Chloroform-d) δ 7.99 (d, J=9.7 Hz, 1H), 7.10 (d, J=9.7 Hz, 1H), 4.43-4.26 (m, 1H), 4.11 (s, 3H), 1.49-1.19 (m, 4H).

Step 2: Preparation of 1-cyclopropyl-6-oxo-1,6-dihydropyridazine-3-carboxylic acid

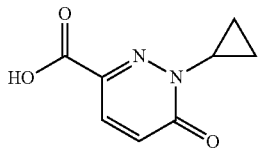 [SMILES: O=C(O)c1ccc(=O)n(C2CC2)n1]

Dissolved methyl 1-cyclopropyl-6-oxo-1,6-dihydropyridazine-3-carboxylate (0.135 g, 0.6951 mmol) in tetrahydrofuran (2.0 mL) and added lithium hydroxide hydrate (0.087 g, 2.08 mmol) and water (0.5 mL). Stirred at room temperature 16 h. Monitored reaction by LC/MS. Upon completion, quenched with 10% aqueous hydrochloric acid (7 mL) until acidic (pH ~3). Extracted with ethyl acetate (15 mL). Washed with brine (10 mL), then dried over sodium sulfate, filtered, and concentrated to give 1-cyclopropyl-6-oxo-1,6-dihydropyridazine-3-carboxylic acid, as a beige solid (80 mg, 0.444 mmol, 64%). $^1$H NMR (300 MHz, Chloroform-d) δ 7.90 (d, J=9.7 Hz, 1H), 7.03 (d, J=9.7 Hz, 1H), 4.24-4.08 (m, 1H), 1.26-1.09 (m, 4H).

Step 3: Preparation of 1-cyclopropyl-N-{5-[(3-fluorophenyl)methyl]pyridin-2-yl}-6-oxo-1,6-dihydropyridazine-3-carboxamide

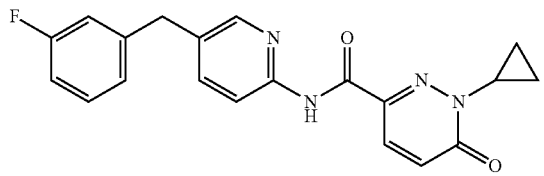 [SMILES: O=C(Nc1ccc(Cc2cccc(F)c2)cn1)c1ccc(=O)n(C2CC2)n1]

Combined 5-[(3-fluorophenyl)methyl]pyridin-2-amine (0.076 g, 0.3758 mmol) with 1-cyclopropyl-6-oxo-1,6-dihydropyridazine-3-carboxylic acid (0.068 g, 0.3758 mmol) and 1-[Bis(dimethylamino)methylene]-1H-1,2,3-triazolo[4,5-b]pyridinium 3-oxid hexafluorophosphate (0.121 g, 0.3758 mmol) in a 25 mL round bottom flask. Suspended in dichloromethane (4 mL) and added ethylbis(propan-2-yl)amine (98.1 µL, 0.5637 mmol). Stirred 16 h at room temperature. Concentrated reaction to remove solvent. Purified reaction by column chromatography (eluting with 0-100% ethyl acetate/hexanes through 24 g of silica gel) to give 1-cyclopropyl-N-{5-[(3-fluorophenyl)methyl]pyridin-2-yl}-6-oxo-1,6-dihydropyridazine-3-carboxamide (48 mg, 0.132 mmol, 35%) as a white solid. $^1$H NMR (300 MHz, Chloroform-d) δ 9.27 (s, 1H), 8.30-8.20 (m, 2H), 8.03 (d, J=9.7 Hz, 1H), 7.57 (dd, J=8.6, 2.5 Hz, 1H), 7.30 (d, J=2.0 Hz, 1H), 7.14-6.85 (m, 4H), 4.20-4.04 (m, 1H), 3.99 (s, 2H), 1.27-1.10 (m, 4H); LCMS (ESI) m/z: 365.5 [M+H]$^+$.

Example 76. Preparation of N-(5-(3-chloro-4-fluorobenzyl)pyridin-2-yl)-1-cyclopropyl-6-oxo-1,6-dihydropyridazine-3-carboxamide (76)

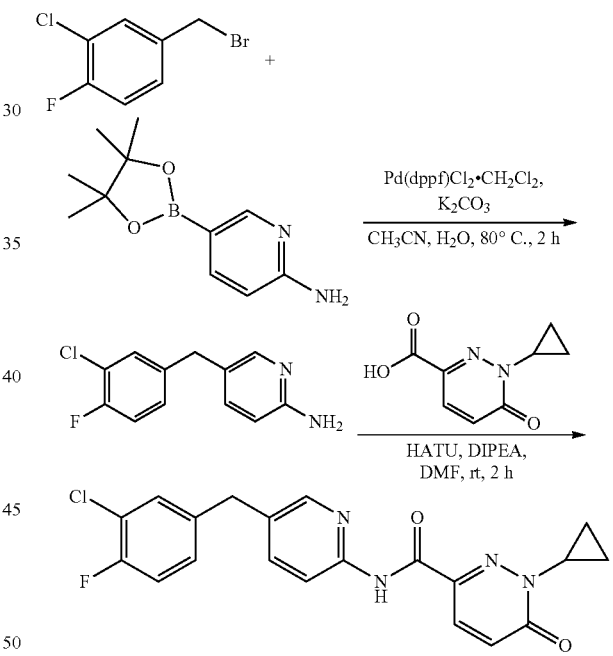

Step 1: Preparation of 5-(3-chloro-4-fluorobenzyl)pyridin-2-amine

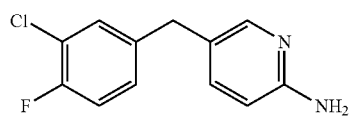 [SMILES: Nc1ccc(Cc2ccc(F)c(Cl)c2)cn1]

To a solution of 4-(bromomethyl)-2-chloro-1-fluorobenzene (1.12 g, 5 mmol), 5-(4,4,5,5-tetramethyl-1,3,2-dioxaborolan-2-yl)pyridin-2-amine (1.32 g, 6 mmol) and potassium carbonate (1.38 g, 10 mmol) in acetonitrile (24 mL)

and water (6 mL) at room temperature was added 1,1'-bis(diphenylphosphino)ferrocene-palladium(II)dichloride dichloromethane complex (0.408 g, 0.5 mmol) under argon. The reaction mixture was stirred at 80° C. for 2 h. The reaction mixture was extracted with ethyl acetate (50 mL×2). The combined organic layers were washed with brine (50 mL), dried over sodium sulfate, filtered and concentrated. The crude residue was purified by column chromatography (silica gel, petroleum ether/ethyl acetate=2/3) to give 5-(3-chloro-4-fluorobenzyl)pyridin-2-amine (0.8 g, 3.4 mmol, 67.8%) as a brown solid. LCMS (ESI) m/z: 237.1 [M+H]$^+$.

Step 2: Preparation of N-(5-(3-chloro-4-fluorobenzyl)pyridin-2-yl)-1-cyclopropyl-6-oxo-1,6-dihydropyridazine-3-carboxamide

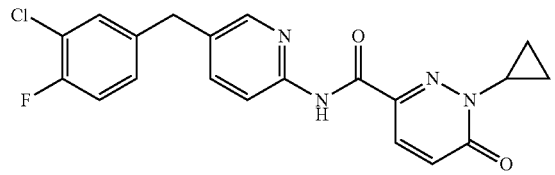 [SMILES: O=C(Nc1ccc(Cc2ccc(F)c(Cl)c2)cn1)c1ccc(=O)n(C2CC2)n1]

A solution of 5-(3-chloro-4-fluorobenzyl)pyridin-2-amine (0.198 g, 0.84 mmol), 1-cyclopropyl-6-oxo-1,6-dihydropyridazine-3-carboxylic acid (0.126 g, 0.7 mmol), 2-(7-azabenzotriazol-1-yl)-N,N,N',N'-tetramethyluronium hexafluorophosphate (400 mg, 1.05 mmol) and ethyldiisopropylamine (271 mg, 2.1 mmol) in N,N-dimethylformamide (3.5 mL) was stirred at room temperature for 2 h. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chloro-4-fluorobenzyl)pyridin-2-yl)-1-cyclopropyl-6-oxo-1,6-dihydropyridazine-3-carboxamide (71.4 mg, 0.18 mmol, 25.7%) as a white solid. $^1$H NMR (500 MHz, Dimethyl-sulfoxide-d$_5$) δ 10.11 (s, 1H), 8.35 (d, J=2.0 Hz, 1H), 8.05 (d, J=8.5 Hz, 1H), 7.90 (d, J=10.0 Hz, 1H), 7.74 (dd, J=8.5, 2.5 Hz, 1H), 7.51 (dd, J=7.5, 2.0 Hz, 1H), 7.35 (t, J=8.8 Hz, 1H), 7.29-7.26 (m, 1H), 7.06 (d, J=10.0 Hz, 1H), 4.10-4.07 (m, 1H), 3.97 (s, 2H), 1.28-1.23 (m, 2H), 1.04-1.00 (m, 2H); LCMS (ESI) m/z: 399.0 [M+H]$^+$.

Example 77. Preparation of 1-(cyclopropylmethyl)-N-(5-(3-fluorobenzyl)pyridin-2-yl)-6-oxo-1,6-dihydropyridazine-3-carboxamide (77)

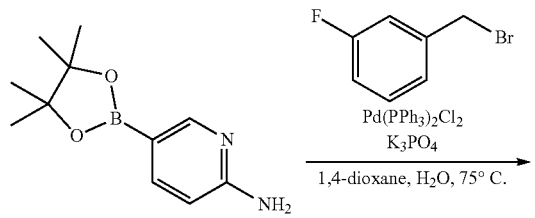

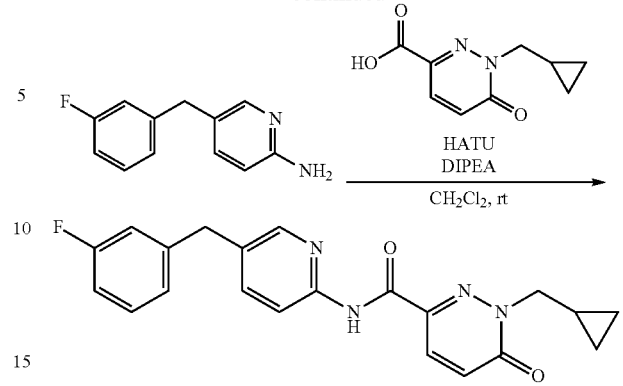

Step 1: Preparation of 5-[(3-fluorophenyl)methyl]pyridin-2-amine

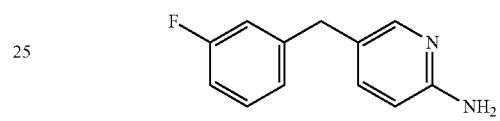

In a 40 mL reaction vial, combined 5-(4,4,5,5-tetramethyl-1,3,2-dioxaborolan-2-yl)pyridin-2-amine (0.500 g, 2.27 mmol), tripotassium phosphate (0.721 g, 3.40 mmol) and bis(triphenylphosphine)palladium(II) dichloride (0.080 g, 0.1135 mmol). Added tetrahydrofuran (3.0 mL) and water (1.0 mL) and added 1-(bromomethyl)-3-fluorobenzene (278 μL, 2.27 mmol). The reaction was degassed by cycling with vacuum and nitrogen gas for 3 cycles. The reaction was heated at 75° C. for 16 h. Cooled the reaction to room temperature and diluted with ethyl acetate (15 mL). Washed the organic layer with water (10 mL), then brine (10 mL). The combined organic layers were dried over sodium sulfate, filtered, and concentrated. Purified reaction by column chromatography (eluting with 0-100% ethyl acetate/hexanes through 24 g of silica gel) to give 5-[(3-fluorophenyl)methyl]pyridin-2-amine (33 mg, 0.163 mmol, 7%) as a yellow oil. $^1$H NMR (300 MHz, Chloroform-d) δ 8.31-8.17 (m, 2H), 8.04 (d, J=9.7 Hz, 1H), 7.04 (d, J=9.7 Hz, 1H), 7.02-6.87 (m, 2H), 3.99 (s, 2H).

Step 2: Preparation of 1-(cyclopropylmethyl)-N-{5-[(3-fluorophenyl)methyl]pyridin-2-yl}-6-oxo-1,6-dihydropyridazine-3-carboxamide

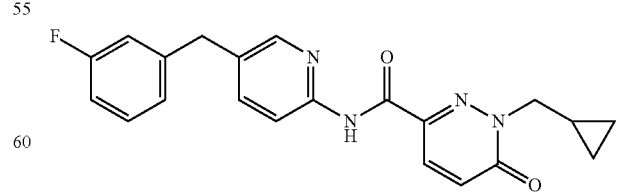

Dissolved 5-[(3-fluorophenyl)methyl]pyridin-2-amine (0.033 g, 0.1631 mmol) in methylene chloride (2.0 mL) and added 1-(cyclopropylmethyl)-6-oxo-1,6-dihydropyridazine-3-carboxylic acid (0.032 g, 0.1631 mmol), [bis(dimethylamino)methylidene]({3H-[1,2,3]triazolo[4,5-b]pyridin-3-yl})oxidanium; tetrafluoroboranuide (0.053 mg, 0.1631 mmol) and ethylbis(propan-2-yl)amine (42.5 µL, 0.2446 mmol). Stirred at room temperature 16 h. Directly purified reaction by column chromatography (eluting with 0-100% ethyl acetate/hexanes through 12 g of silica gel) to give 1-(cyclopropylmethyl)-N-{5-[(3-fluorophenyl)methyl]pyridin-2-yl}-6-oxo-1,6-dihydropyridazine-3-carboxamide (29 mg, 0.077 mmol, 47%) as a white solid. $^1$H NMR (300 MHz, Chloroform-d) δ 8.38-8.21 (m, 2H), 8.06 (d, J=9.7 Hz, 1H), 7.63-7.50 (m, 1H), 7.28 (s, 2H), 7.05 (d, J=9.7 Hz, 1H), 6.97 (t, J=8.1 Hz, 3H), 4.13 (d, J=7.3 Hz, 2H), 3.99 (s, 2H), 1.43 (t, J=8.0 Hz, 1H), 0.61 (d, J=7.7 Hz, 2H), 0.50 (d, J 5.1 Hz, 2H); LCMS (ESI) m/z: 379.3 [M+H]$^+$.

Example 78. Preparation of 1-ethyl-N-(5-(3-fluoro-5-methoxybenzyl)pyridin-2-yl)-6-oxo-1,6-dihydropyridine-3-carboxamide (78)

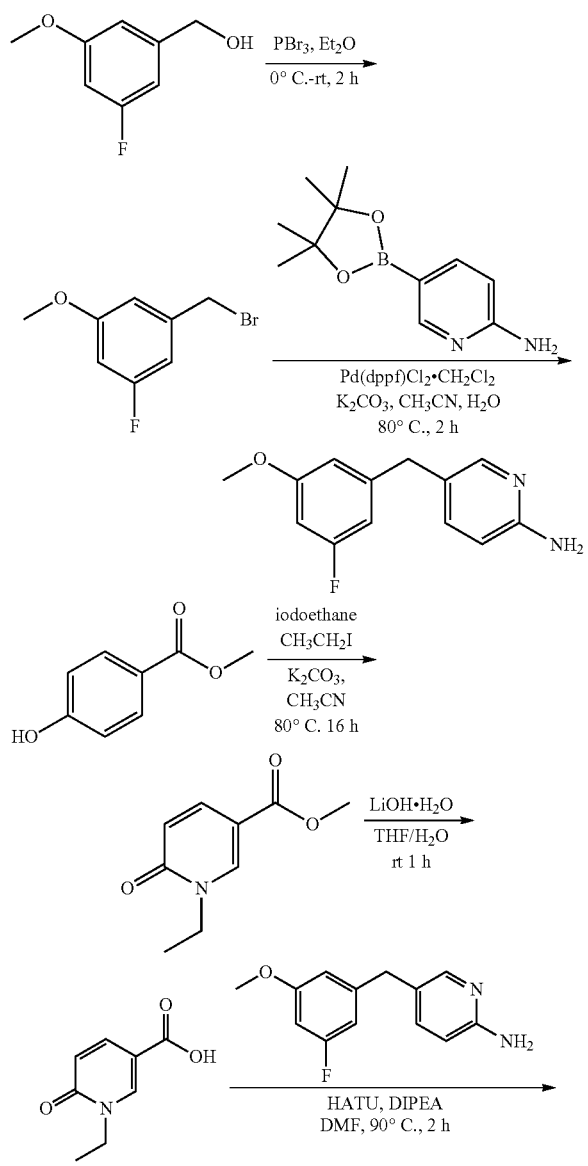

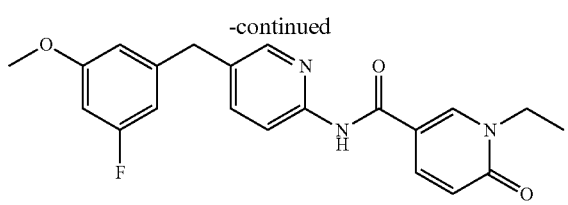

Step 1: Preparation of 1-(bromomethyl)-3-fluoro-5-methoxybenzene

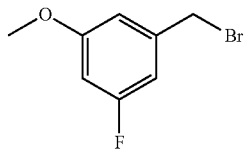

To a solution of (3-fluoro-5-methoxyphenyl)methanol (2.0 g, 12.8 mmol) in ethyl ether (30 mL) at 0° C. was added phosphorus tribromide (1.0 mL) slowly. The reaction mixture was stirred at room temperature for 2 h. The mixture was quenched with saturated aqueous sodium bicarbonate (150 mL). The aqueous layer was extracted with ethyl acetate (200 mL×2). The combined organic phases were dried over sodium sulfate, filtered and concentrated to afford 1-(bromomethyl)-3-fluoro-5-methoxybenzene (1.5 g, 6.88 mmol, 53%, crude) as a light-yellow oil. Used in the next step directly without additional purification.

Step 2: Preparation of 5-(3-fluoro-5-methoxybenzyl)pyridin-2-amine

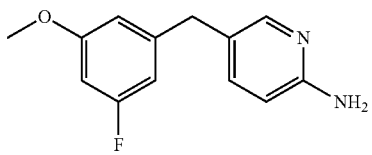

To a stirred solution of 1-(bromomethyl)-3-fluoro-5-methoxybenzene (1.5 g, 6.88 mmol), 5-(4,4,5,5-tetramethyl-1,3,2-dioxaborolan-2-yl)pyridin-2-amine (1.51 g, 6.88 mmol) in acetonitrile (60 mL) was added a solution of potassium carbonate (1.9 g, 13.76 mmol) in water (20 mL), followed by the addition of 1,1'-bis(diphenylphosphino)ferrocene-palladium(II)dichloride dichloromethane complex (280 mg, 0.34 mmol) under nitrogen. The mixture was stirred at 80° C. for 2 h. The reaction solution was poured into water and extracted with ethyl acetate (150 mL×2). The combined organic phases were concentrated and the crude residue was purified by column chromatography (silica gel, petroleum ether/ethyl acetate=1/2) to give 5-(3-fluoro-5-methoxybenzyl)pyridin-2-amine (0.9 g, 3.88 mmol, 56%) as a red oil. LCMS (ESI) m/z: 233.2 [M+H]$^+$.

Step 3: Preparation of methyl 1-ethyl-6-oxo-1,6-dihydropyridine-3-carboxylate

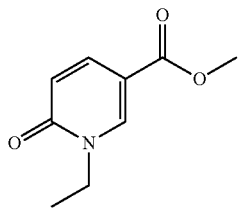

A mixture of methyl 6-hydroxynicotinate (10.0 g, 65.3 mmol), iodoethane (10.1 g, 65.3 mmol), potassium carbonate (18.0 g, 130.6 mmol) in acetonitrile (400 mL) was stirred at 80° C. for 16 h. The precipitate was filtered off and the filtrate was concentrated. The crude residue was purified by column chromatography (silica gel, petroleum ether/ethyl acetate=4/1 to 1/1) to give methyl 1-ethyl-6-oxo-1,6-dihydropyridine-3-carboxylate (8.7 g, 48.1 mmol, 73%) as a light-yellow solid. $^1$H NMR (500 MHz, Chloroform-d) δ 8.19 (d, J=2.5 Hz, 1H), 7.82 (dd, J=9.5, 2.0 Hz, 1H), 6.52 (d, J=9.0 Hz, 1H), 4.03 (q, J=7.0 Hz, 2H), 3.86 (s, 3H), 1.39 (t, J=7.0 Hz, 3H); LCMS (ESI) m/z: 182.1 [M+H]$^+$.

Step 4: Preparation of 1-ethyl-6-oxo-1,6-dihydropyridine-3-carboxylic acid

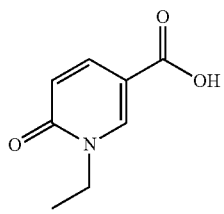

A mixture of methyl 1-ethyl-6-oxo-1,6-dihydropyridine-3-carboxylate (5.4 g, 29.8 mmol), lithium hydroxide hydrate (6.26 g, 149.1 mmol) in tetrahydrofuran (100 mL) and water (30 mL) was stirred at room temperature for 2 h. The mixture was acidified to pH 1-2 with dilute hydrogen chloride acid and extracted with ethyl acetate/tetrahydrofuran (200 mL/50 mL×3). The combined organic phases were dried over sodium sulfate, filtered and concentrated to afford 1-ethyl-6-oxo-1,6-dihydropyridine-3-carboxylic acid (4.7 g, 28.14 mmol, 94%) as an off-white solid. LCMS (ESI) m/z: 168.1 [M+H]$^+$. Used in the next step directly without additional purification.

Step 5: Preparation of 1-ethyl-N-(5-(3-fluoro-5-methoxybenzyl)pyridin-2-yl)-6-oxo-1,6-dihydropyridine-3-carboxamide

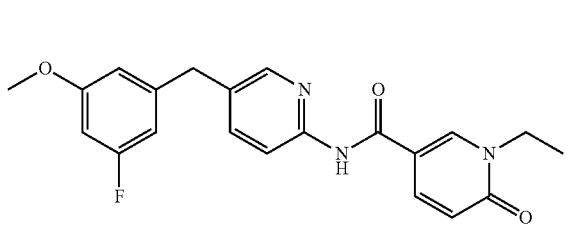 [SMILES: CCn1cc(C(=O)Nc2ccc(Cc3cc(F)cc(OC)c3)cn2)ccc1=O]

A mixture of 5-(3-fluoro-5-methoxybenzyl)pyridin-2-amine(232 mg, 1.0 mmol), 1-ethyl-6-oxo-1,6-dihydropyridine-3-carboxylic acid (167 mg, 1.0 mmol), 2-(7-azabenzotriazol-1-yl)-N,N,N',N'-tetramethyluronium hexafluorophosphate (570 mg, 1.5 mmol), N,N-diisopropylethyl amine (390 mg, 3.0 mmol) in N,N-dimethylformamide (8 mL) was stirred at room temperature for 0.5 h and at 90° C. for 2 h. The mixture was poured into water and extracted with ethyl acetate (200 mL×3). The combined organic phases were concentrated. The crude residue was purified first by column chromatography (silica gel, petroleum ether/ethyl acetate=1/1) and second by prep-HPLC (Boston C18 21*250 mm 10 μm column. The mobile phase was acetonitrile/10 mM ammonium acetate aqueous solution) to give 1-ethyl-N-(5-(3-fluoro-5-methoxybenzyl)pyridin-2-yl)-6-oxo-1,6-dihydropyridine-3-carboxamide (0.0594 g, 0.16 mmol, 16%) as a white solid. $^1$H NMR (500 MHz, Dimethylsulfoxide-d$_6$) δ 10.61 (s, 1H), 8.64 (d, J=2.5 Hz, 1H), 8.31 (d, J=2.0 Hz, 1H), 8.06 (d, J=8.5 Hz, 1H), 7.94 (dd, J=9.0, 2.5 Hz, 1H), 7.70 (dd, J=9.0, 2.5 Hz, 1H), 6.71-6.65 (m, 3H), 6.43 (d, J=9.5 Hz, 1H), 3.97 (q, J=7.0 Hz, 2H), 3.91 (s, 2H), 3.74 (s, 3H), 1.28 (t, J=7.0 Hz, 3H); LCMS (ESI) m/z: 382.1 [M+H]$^+$.

Example 79. Preparation of 5-(3-Chloro-5-fluorobenzyl)-N-(1-ethyl-6-oxo-1,6-dihydropyridin-3-yl)picolinamide (79)

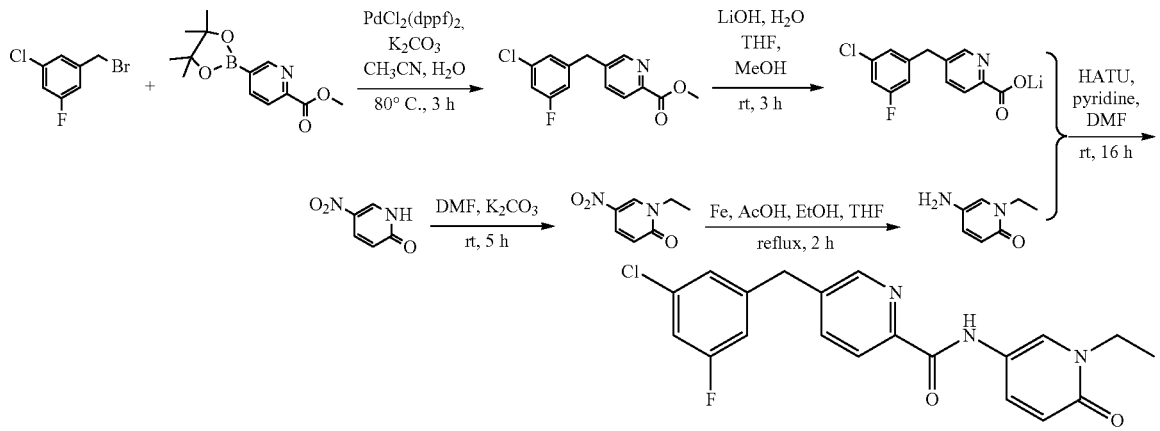

Step 1: Preparation of methyl 5-(3-chloro-5-fluorobenzyl)picolinate

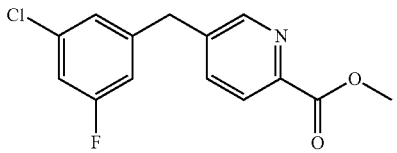 [SMILES: COC(=O)c1ccc(Cc2cc(F)cc(Cl)c2)cn1]

To a solution of methyl 5-(4,4,5,5-tetramethyl-1,3,2-dioxaborolan-2-yl)picolinate (1.0 g, 3.8 mmol) in acetonitrile (20 mL) and water (5 mL) at room temperature was added potassium carbonate (1.05 g, 7.6 mmol), 1,1'-bis(diphenylphosphino)ferrocene palladium(II)dichloride (0.310 g, 0.38 mmol) and 1-(bromomethyl)-3-chloro-5-fluorobenzene (0.850 g, 3.8 mmol) under nitrogen. The reaction mixture was stirred at 80° C. for 3 h. The reaction solution was cooled to room temperature and diluted with water (200 mL) The aqueous layer was extracted with ethyl acetate (100 mL×3). The combined organic layers were washed with brine (100 mL), dried over anhydrous sodium sulfate, filtered and concentrated. The crude product was purified by column chromatography (silica gel, petroleum ether/ethyl acetate=3/1) to give methyl 5-(3-chloro-5-fluorobenzyl)picolinate (0.550 g, 1.97 mmol, 52%) as a yellow solid. LCMS (ESI) m/z: 280.0 [M+H]+.

Step 2: Preparation of Lithium 5-(3-chloro-5-fluorobenzyl)picolinate

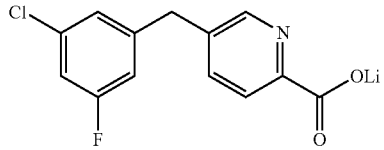

To a solution of methyl 5-(3-chloro-5-fluorobenzyl)picolinate (0.550 g, 1.97 mmol) in a mixture of tetrahydrofuran (2.0 mL), methanol (2.0 mL) and water (1.0 mL) at room temperature was added lithium hydroxide (0.083 g, 1.97 mmol). The reaction mixture was stirred at room temperature for 3 h before it was concentrated, to afford lithium 5-(3-chloro-5-fluorobenzyl)picolinate (0.610 g, 1.97 mmol, crude) as a white solid. LCMS (ESI) m/z: 266.1 [M+H]+. Used in the next step directly without additional purification.

Step 3: Preparation of 1-ethyl-5-nitropyridin-2(1H)-one

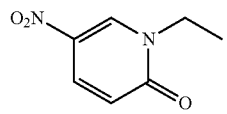

To a solution of 5-nitropyridin-2(1H)-one (3.0 g, 21.41 mmol) in N,N-dimethylformamide (60 mL) at room temperature was added potassium carbonate (5.91 g, 42.8 mmol) and iodoethane (4.35 g, 27.8 mmol). The reaction mixture was stirred at room temperature for 5 h before it was diluted with water (200 mL). The aqueous phase was extracted with ethyl acetate (100 mL×3). The combined organic layers were washed with brine (100 mL), dried over anhydrous sodium sulfate, filtered and concentrated. The crude sample was purified by column chromatography (petroleum ether/ethyl acetate=2/1) to give 1-ethyl-5-nitropyridin-2(1H)-one (2.3 g, 13.7 mmol, 64%) as a yellow solid. LCMS (ESI) m/z: 169.1 [M+H]+.

Step 4: Preparation of 5-amino-1-ethylpyridin-2(1H)-one

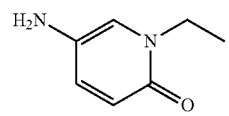

To a solution of 1-ethyl-5-nitropyridin-2(1H)-one (1.0 g, 5.95 mmol) in ethanol (15 mL) and tetrahydrofuran (15 mL) at room temperature was added acetic acid (5.0 mL) and iron (1.67 g, 29.8 mmol). The reaction mixture was refluxed for 2 h before it was cooled to room temperature and concentrated to give a residue. The residue was treated with aqueous saturated sodium carbonate solution (10 mL) and extracted with ethanol (80 mL×3). The combined organic layers were dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 5-amino-1-ethylpyridin-2(1H)-one (0.320 g, 2.31 mmol, 39%) as a colorless oil. LCMS (ESI) m/z: 139.1 [M+H]+.

Step 5: Preparation of 5-(3-chloro-5-fluorobenzyl)-N-(1-ethyl-6-oxo-1,6-dihydropyridin-3-yl)picolinamide

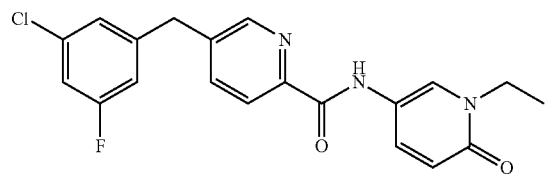 [SMILES: CCn1cc(NC(=O)c2ccc(Cc3cc(F)cc(Cl)c3)cn2)ccc1=O]

To a solution of lithium 5-(3-chloro-5-fluorobenzyl)picolinate (0.200 g, 0.74 mmol) in N,N-dimethylformamide (6 mL) at room temperature was added 5-amino-1-ethylpyridin-2(1H)-one (0.129 g, 0.74 mmol), 2-(7-aza-1H-benzotriazole-1-yl)-1,1,3,3-tetramethyluronium hexafluorophosphate (0.364 g, 0.96 mmol) and pyridine (0.291 g, 3.68 mmol). The reaction mixture was stirred at room temperature for 16 h. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to afford 5-(3-chloro-5-fluorobenzyl)-N-(1-ethyl-6-oxo-1,6-dihydropyridin-3-yl)picolinamide (0.065 g, 0.17 mmol, 23%) as a white solid. $^1$H NMR (400 MHz, Dimethylsulfoxide-d$_6$) δ 10.49 (s, 1H), 8.70 (s, 1H), 8.33 (d, J=2.4 Hz, 1H), 8.04 (d, J=8.0 Hz, 1H), 7.92 (dd, J$_1$=1.6 Hz, J$_2$=8.0 Hz, 1H), 7.77

(dd, $J_1$=2.8 Hz, $J_2$=10.0 Hz, 1H), 7.30 (d, J=4.8 Hz, 2H), 7.22 (d, J=9.2 Hz, 1H), 6.41 (d, J=9.6 Hz, 1H), 4.13 (s, 2H) 3.92 (q, J=7.2 Hz, 2H), 1.22 (t, J=7.2 Hz, 4H); LCMS (ESI) m/z: 386.1 [M+H]$^+$.

Example 80. Preparation of 1-ethyl-N-(5-(3-fluorobenzyl)pyridin-2-yl)-6-oxo-1,6-dihydropyridine-3-carboxamide (80)

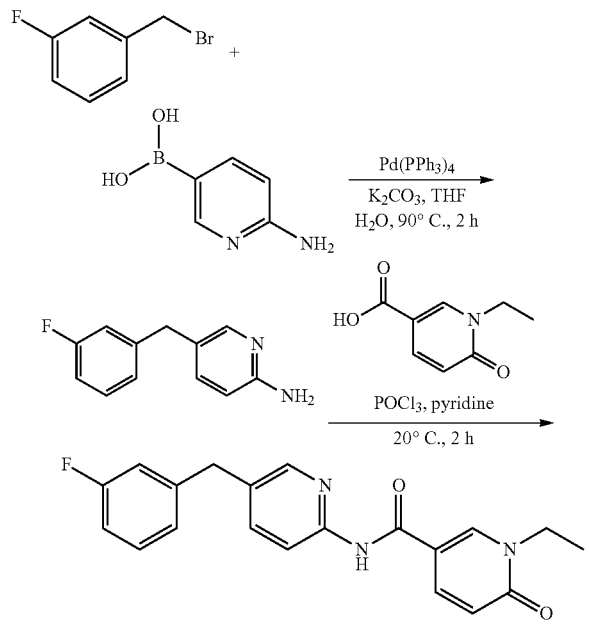

Step 1: Preparation of 5-(3-fluorobenzyl)pyridin-2-amine

To a solution of 1-(bromomethyl)-3-fluorobenzene (1.0 g, 5.32 mmol), 6-aminopyridin-3-ylboronic acid (0.734 g, 5.32 mmol), potassium carbonate (1.47 g, 10.6 mmol) in tetrahydrofuran (12 mL) and water (3 mL) under nitrogen was added tetrakis(triphenylphosphine)palladium(0) (0.614 g, 0.532 mmol). The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-(3-fluorobenzyl)pyridin-2-amine as a yellow oil (0.55 g); LCMS (ESI) m/z: 203.1 [M+H]$^+$.

Step 2: Preparation of 1-ethyl-N-(5-(3-fluorobenzyl)pyridin-2-yl)-6-oxo-1,6-dihydropyridine-3-carboxamide

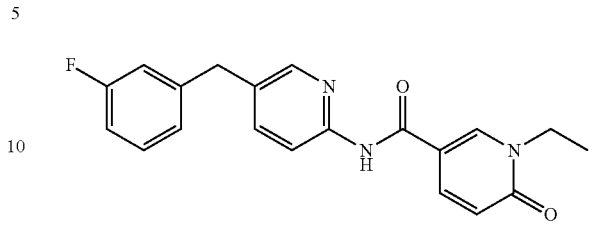

To a solution of 1-ethyl-6-oxo-1,6-dihydropyridine-3-carboxylic acid (0.150 g, 0.899 mmol), 5-(3-fluorobenzyl)pyridin-2-amine (0.181 g, 0.899 mmol) in pyridine (4 mL) at 20° C. was added phosphorus(V) oxychloride (0.410 g, 2.70 mmol). The reaction mixture was stirred at room temperature for 3 h. The solvent was removed under reduced pressure. The resulting solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 1-ethyl-N-(5-(3-fluorobenzyl)pyridin-2-yl)-6-oxo-1,6-dihydropyridine-3-carboxamide (0.0750 g, 0.216 mmol, 24%) as a light-yellow solid. $^1$H NMR (400 MHz, Dimethylsulfoxide-d$_6$) δ 10.65 (s, 1H), 8.64 (d, J=2.5 Hz, 1H), 8.31 (d, J=2.5 Hz, 1H), 8.05 (d, J=8.5 Hz, 1H), 7.93-7.95 (m, 1H), 7.70-7.73 (m, 1H), 7.35 (d, J=6.5 Hz, 1H), 7.04-7.13 (m, 3H), 6.43 (d, J=9.5 Hz, 1H), 3.95-3.99 (m, 4H), 1.27 (t, J=7.2 Hz, 3H); LCMS (ESI) m/z: 352.1 [M+H]$^+$.

Example 81. Preparation of 1-ethyl-N-(5-(4-fluorobenzyl)pyridin-2-yl)-6-oxo-1,6-dihydropyridine-3-carboxamide (81)

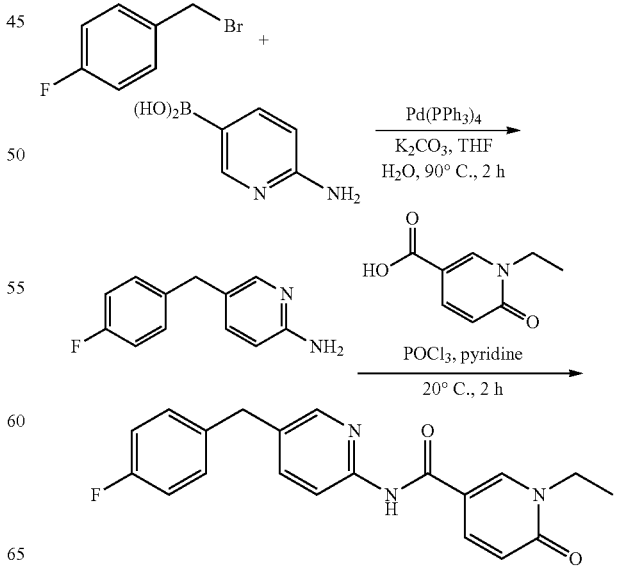

Step 1: Preparation of 5-(4-fluorobenzyl)pyridin-2-amine

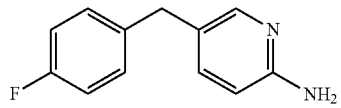 [SMILES: Nc1ccc(Cc2ccc(F)cc2)cn1]

To a solution of 1-(bromomethyl)-4-fluorobenzene (1.0 g, 5.32 mmol), 6-aminopyridin-3-ylboronic acid (0.735 g, 5.32 mmol), potassium carbonate (1.47 g, 10.6 mmol) in tetrahydrofuran (12 mL) and water (3 mL) under nitrogen was added tetrakis(triphenylphosphine)palladium(0) (0.614 g, 0.532 mmol). The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-(4-fluorobenzyl)pyridin-2-amine (0.35 g, crude) as a yellow oil. LCMS (ESI) m/z: 203.1 [M+H]$^+$. Used in the next step without further purification.

Step 2: Preparation of 1-ethyl-N-(5-(4-fluorobenzyl)pyridin-2-yl)-6-oxo-1,6-dihydropyridine-3-carboxamide

To a solution of 1-ethyl-6-oxo-1,6-dihydropyridine-3-carboxylic acid (0.150 g, 0.899 mmol), 5-(3-fluorobenzyl)pyridin-2-amine (0.181 g, 0.899 mmol) in pyridine (4 mL) at 20° C. was added, phosphorus(V) oxychloride (410 mg, 2.697 mmol). The reaction mixture was stirred at room temperature for 3 h. Volatiles were removed under reduced pressure and the solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 1-ethyl-N-(5-(4-fluorobenzyl)pyridin-2-yl)-6-oxo-1,6-dihydropyridine-3-carboxamide as a light-yellow solid (0.0340 g, 0.099 mmol, 11%). $^1$H NMR (400 MHz, Dimethylsulfoxide-d$_6$) δ 10.59 (s, 1H), 8.64 (d, J=2.5 Hz, 1H), 8.28 (d, J=2 Hz, 1H), 8.05 (d, J=8.5 Hz, 1H), 7.93-7.95 (m, 1H), 7.65-7.67 (m, 1H), 7.28-7.31 (m, 2H), 7.11-7.15 (m, 2H), 6.42 (d, J=9.5 Hz, 1H), 3.94-3.99 (m, 4H), 1.27 (t, J=7.0 Hz, 3H); LCMS (ESI) m/z: 352.1 [M+H]$^+$.

Example 82. Preparation of N-(5-(3-chloro-4-fluorobenzyl)pyridin-2-yl)-1-ethyl-6-oxo-1,6-dihydropyridine-3-carboxamide (82)

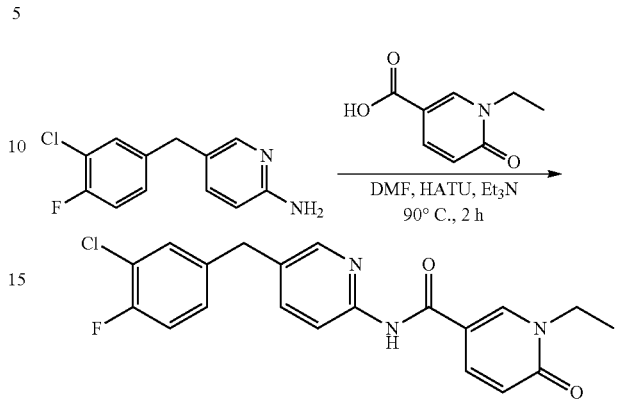

Step 1: Preparation of N-(5-(3-chloro-4-fluorobenzyl)pyridin-2-yl)-1-ethyl-6-oxo-1,6-dihydropyridine-3-carboxamide

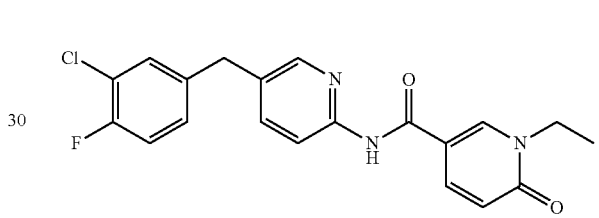

To a solution of 5-(3-chloro-4-fluorobenzyl)pyridin-2-amine (0.2 g, 0.85 mmol), 1-ethyl-6-oxo-1,6-dihydropyridine-3-carboxylic acid (0.17 g, 1.02 mmol) and 1-[bis(dimethylamino)methylene]-1H-1,2,3-triazolo[4,5-b]pyridinium 3-oxid hexafluorophosphate (0.39 g, 1.02 mmol) in N,N-dimethylformamide (3 mL) was added triethylamine (0.26 g, 2.53 mmol). The mixture was stirred at 90° C. for 2 h and then cooled to room temperature. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chloro-4-fluorobenzyl)pyridin-2-yl)-1-ethyl-6-oxo-1,6-dihydropyridine-3-carboxamide (0.0733 g, 0.19 mmol, 22.4%) as a white solid. $^1$H NMR (500 MHz, Dimethylsulfoxide-d$_6$) δ 10.68 (s, 1H), 8.64 (d, J=2.6 Hz, 1H), 8.32 (d, J=2.6 Hz, 1H), 8.04 (d, J=8.5 Hz, 1H), 7.94 (dd, J=8.5, 2.6 Hz, 1H), 7.73 (dd, J=8.5, 2.6 Hz, 1H), 7.52 (dd, J=7.2, 2.1 Hz, 1H), 7.40-7.23 (m, 2H), 6.43 (d, J=9.5 Hz, 1H), 4.03-3.90 (m, 4H), 1.28 (t, J=7.1 Hz, 3H); LCMS (ESI) m/z: 386.0 [M+H]$^+$.

Example 83. Preparation of N-(5-(3-chlorobenzyl)pyridin-2-yl)-1-isopropyl-6-oxo-1,6-dihydropyridine-3-carboxamide (83)

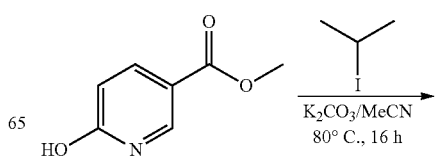

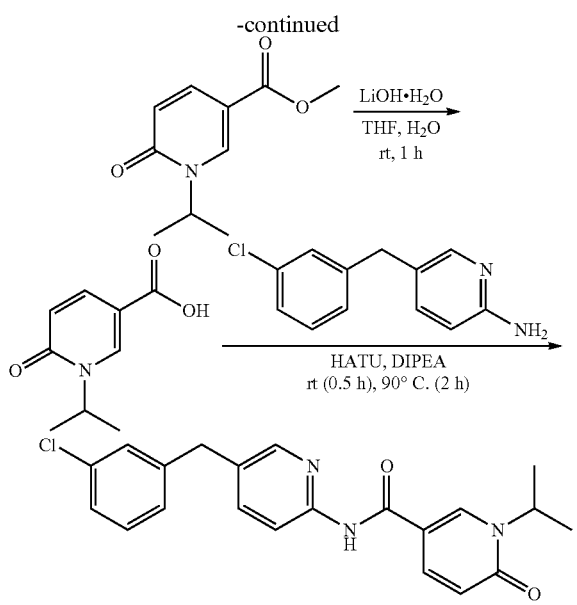

Step 1: Preparation of methyl 1-isopropyl-6-oxo-1,6-dihydropyridine-3-carboxylate

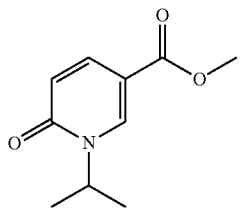

A mixture of methyl 6-hydroxynicotinate (10.0 g, 65.3 mmol), 2-iodopropane (11.1 g, 65.3 mmol), potassium carbonate (18.0 g, 130.6 mmol) in acetonitrile (450 mL) was stirred at 80° C. for 16 h. The precipitate was filtered and the filtrate was concentrated. The crude residue was purified by column chromatography (silica gel, petroleum ether/ethyl acetate=4/1 to 1/1) to give methyl 1-isopropyl-6-oxo-1,6-dihydropyridine-3-carboxylate (6.5 g, 33.3 mmol, 51%) as a white solid. $^1$H NMR (500 MHz, Chloroform-d) δ 8.23 (d, J=3.0 Hz, 1H), 7.82 (dd, J=9.0, 3.0 Hz, 1H), 6.54 (d, J=9.0 Hz, 1H), 5.28-5.23 (m, 1H), 3.88 (s, 3H), 1.41 (d, J=6.5 Hz, 6H); LCMS (ESI) m/z: 196.2 [M+H]$^+$.

Step 2: Preparation of 1-isopropyl-6-oxo-1,6-dihydropyridine-3-carboxylic acid

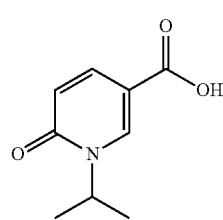

A mixture of methyl 1-isopropyl-6-oxo-1,6-dihydropyridine-3-carboxylate (4.0 g, 20.5 mmol), lithium hydroxide hydrate (4.3 g, 102.5 mmol) in tetrahydrofuran (100 mL) and water (25 mL) was stirred at room temperature for 2 h. The reaction solution was acidified to pH 1-2 with dilute hydrochloric acid and the aqueous layer was extracted with ethyl acetate/tetrahydrofuran (200 mL/50 mL×3). The combined organic phases were dried over sodium sulfate, filtered and concentrated to afford 1-isopropyl-6-oxo-1,6-dihydropyridine-3-carboxylic acid (3.5 g, 19.3 mmol, 94.3%) as an off-white solid. LCMS (ESI) m/z: 182.2 [M+H]$^+$. Used in the next step directly without additional purification.

Step 3: Preparation of N-(5-(3-chlorobenzyl)pyridin-2-yl)-1-isopropyl-6-oxo-1,6-dihydropyridine-3-carboxamide

A mixture of 5-(3-chlorobenzyl)pyridin-2-amine (218 mg, 1.0 mmol), 1-isopropyl-6-oxo-1,6-dihydropyridine-3-carboxylic acid (181 mg, 1.0 mmol), 2-(7-azabenzotriazol-1-yl)-N,N,N',N'-tetramethyluronium hexafluorophosphate (570 mg, 1.5 mmol), N-N,N-diisopropylethyl amine (390 mg, 3.0 mmol) in N,N-dimethylformamide (10 mL) was stirred at room temperature for 0.5 h and at 90° C. for 2 h. The mixture was poured into water and the aqueous layer was extracted with ethyl acetate (150 mL×2). The combined organic phases were concentrated. The crude residue was purified by column chromatography (silica gel, petroleum ether/ethyl acetate=1/1) and prep-HPLC (the crude sample was dissolved in minimal N-N,N-dimethylformamide and loaded onto Boston C18 21*250 mm 10 μm column. The mobile phase was acetonitrile/10 mM ammonium acetate aqueous solution) to afford N-(5-(3-chlorobenzyl)pyridin-2-yl)-1-isopropyl-6-oxo-1,6-dihydropyridine-3-carboxamide (0.056 g, 0.15 mmol, 14.6%) as a white solid. $^1$H NMR (500 MHz, Dimethylsulfoxide-d$_6$) δ 10.83 (s, 1H), 8.58 (d, J=2.5 Hz, 1H), 8.32 (d, J=2.0 Hz, 1H), 8.07 (d, J=8.0 Hz, 1H), 7.92 (dd, J=9.0, 2.5 Hz, 1H), 7.69 (dd, J=9.0, 2.5 Hz, 1H), 7.36-7.33 (m, 2H), 7.28-7.23 (m, 2H), 6.44 (d, J=9.5 Hz, 1H), 5.09-5.03 (m, 1H), 3.97 (s, 2H), 1.37 (d, J=7.0 Hz, 6H); LCMS (ESI) m/z: 382.1 [M+H]$^+$.

Example 84. Preparation of N-(5-(3-chlorobenzyl)pyridin-2-yl)-1-ethyl-6-oxo-1,6-dihydropyridine-3-carboxamide (84)

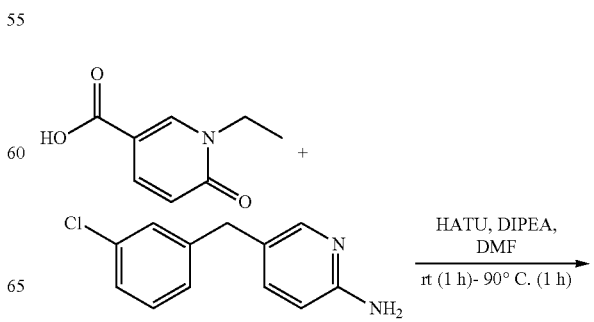

411

-continued

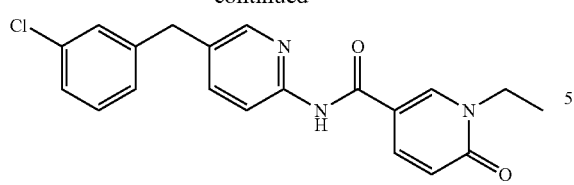

Step 1: Preparation of N-(5-(3-chlorobenzyl)pyridin-2-yl)-1-ethyl-6-oxo-1,6-dihydropyridine-3-carboxamide

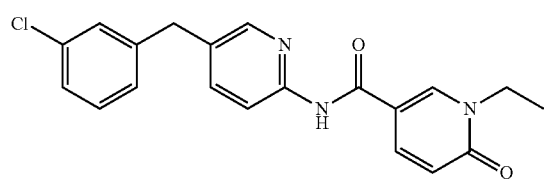 [SMILES: CCn1cc(C(=O)Nc2ccc(Cc3cccc(Cl)c3)cn2)ccc1=O]

A solution of 1-ethyl-6-oxo-1,6-dihydropyridine-3-carboxylic acid (0.100 g, 0.60 mmol), 5-(3-chlorobenzyl)pyridin-2-amine (0.157 g, 0.72 mmol), 1-[bis(dimethylamino)methylene]-1H-1,2,3-triazolo[4,5-b]pyridinium 3-oxid hexafluorophosphate (0.342 g, 0.9 mmol) and N,N-diisopropylethylamine (0.232 g, 1.8 mmol) in N,N-dimethylformamide (3 mL) was stirred at 90° C. for 1 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chlorobenzyl)pyridin-2-yl)-1-ethyl-6-oxo-1,6-dihydropyridine-3-carboxamide a white solid (0.056 g, 0.153 mmol, 25.5%). $^1$H NMR (500 MHz, Dimethylsulfoxide-$d_6$) δ 10.70 (s, 1H), 8.65 (d, J=2.5 Hz, 1H), 8.32 (d, J=1.8 Hz, 1H), 8.05 (d, J=8.5 Hz, 1H), 7.95 (dd, J=9.5, 2.5 Hz, 1H), 7.73 (dd, J=8.6, 2.1 Hz, 1H), 7.34-7.32 (m, 2H), 7.28-7.23 (m, 2H), 6.44 (d, J=9.5 Hz, 1H), 3.99-3.95 (m, 4H), 1.28 (t, J=7.1 Hz, 3H); LCMS (ESI) m/z: 368.0 [M+H]$^+$.

Example 85. Preparation of 1-ethyl-N-(5-(3-fluorobenzyl)pyridin-2-yl)-6-oxo-1,6-dihydropyridine-3-carboxamide (85)

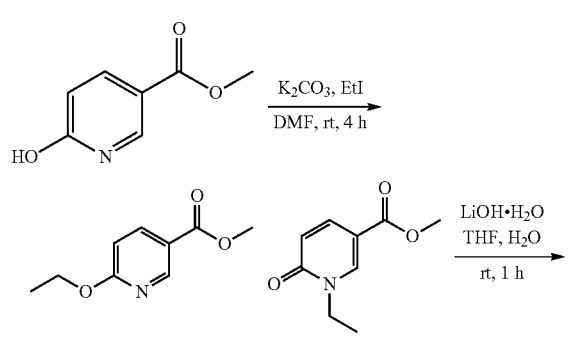

412

-continued

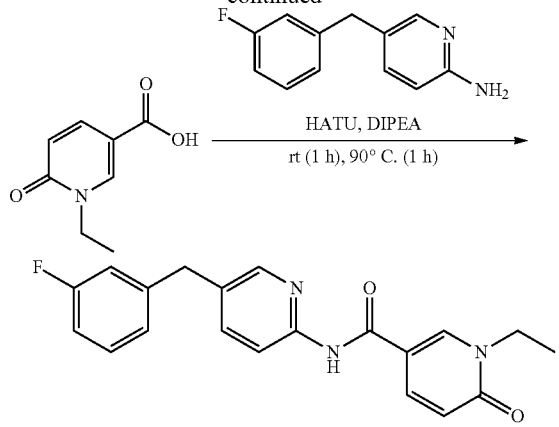

Step 1: Preparation of methyl 1-ethyl-6-oxo-1,6-dihydropyridine-3-carboxylate

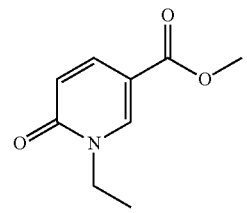

A mixture of methyl 6-hydroxynicotinate (15.3 g, 100 mmol), potassium carbonate (27.6 g, 200 mmol) in N,N-dimethylformamide (150 mL) was stirred at room temperature for 10 minutes, before iodoethane (17.2 g, 110 mmol) was added. The reaction mixture was stirred at room temperature for another 4 h and quenched with water (500 mL) and extracted with ethyl acetate (400 mL×3). The combined organic phases were washed with brine, dried over sodium sulfate, filtered and concentrated. The reside was purified by column chromatography (silica gel, petroleum ether/ethyl acetate=9/1 to 1/1) to afford methyl 1-ethyl-6-oxo-1,6-dihydropyridine-3-carboxylate (6.0 g, contained residual N,N-dimethylformamide) as an orange oil. $^1$H NMR (500 MHz, Chloroform-d) δ 8.22 (d, J=3.0 Hz, 1H), 7.83 (dd, J=12.0, 3.5 Hz, 1H), 6.52 (d, J=12.0 Hz, 1H), 4.04 (q, J=9.0 Hz, 2H), 3.86 (s, 3H), 1.38 (t, J=9.0 Hz, 3H); LCMS (ESI) 182.1 [M+H]$^+$.

Step 2: Preparation of 1-ethyl-6-oxo-1,6-dihydropyridine-3-carboxylic acid

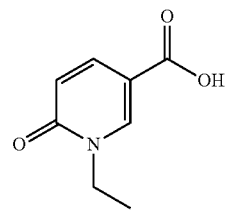

A mixture of methyl 1-ethyl-6-oxo-1,6-dihydropyridine-3-carboxylate (5.8 g, 32.0 mmol), lithium hydroxide (6.72 g, 160.0 mmol) in tetrahydrofuran (60 mL) and water (15 mL) was stirred at room temperature for 2 h. The organics were removed under reduced pressure. The water phase was acidified to pH=1-2 with dilute aqueous hydrogen chloride and extracted with 2-methylfuran (200 mL×3). The combined organic phases were dried over sodium sulfate, filtered and concentrated to afford 1-ethyl-6-oxo-1,6-dihydropyridine-3-carboxylic acid (2.8 g, 52.3%) as a light-yellow solid. $^1$H NMR (500 MHz, Dimethylsulfoxide-d$_6$) δ 12.80 (bs, 1H), 8.47 (d, J=2.5 Hz, 1H), 7.77 (dd, J=9.5, 2.5 Hz, 1H), 6.40 (d, J=9.5 Hz, 1H), 3.99 (q, J=7.0 Hz, 2H), 1.23 (d, J=7.0 Hz, 3H); LCMS (ESI) m/z: 168.1 [M+H]$^+$.

Step 3: Preparation of 1-ethyl-N-(5-(3-fluorobenzyl) pyridin-2-yl)-6-oxo-1,6-dihydropyridine-3-carboxamide

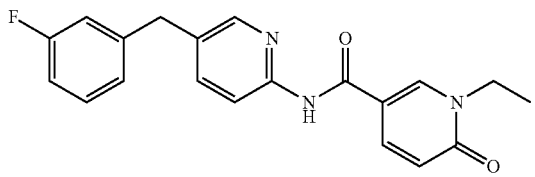 [SMILES: CCn1cc(C(=O)Nc2ccc(Cc3cccc(F)c3)cn2)ccc1=O]

A mixture of 1-ethyl-6-oxo-1,6-dihydropyridine-3-carboxylic acid (0.098 g, 0.59 mmol), 5-(3-fluorobenzyl)pyridin-2-amine (0.120 g, 0.59 mmol), 1-[bis(dimethylamino)methylene]-1H-1,2,3-triazolo[4,5-b]pyridinium 3-oxid hexafluorophosphate (0.342 g, 0.900 mmol) and N,N-diisopropylethylamine (0.155 g, 1.2 mmol) in N,N-dimethylformamide (3 mL) was stirred at room temperature for 1 h and then at 90° C. for 1 h. The mixture was poured into water and extracted with ethyl acetate (50 mL×3). The combined organic phases were concentrated. The residue was purified by column chromatography (silica gel, petroleum ether/ethyl acetate=1/4) and then by prep-HPLC twice (first by: sample was dissolved in minimal N,N-dimethylformamide and purified via prep-HPLC (Boston C18 21*250 mm 10 μm column; acetonitrile/0.01% aqueous trifluoroacetic acid). Second by: sample was dissolved in minimal N,N-dimethylformamide and purified by prep-HPLC (Boston C18 21*250 mm 10 μm column. The mobile phase was acetonitrile/10 mM ammonium acetate aqueous solution) to afford compound 1-ethyl-N-(5-(3-fluorobenzyl)pyridin-2-yl)-6-oxo-1,6-dihydropyridine-3-carboxamide (0.0179 g, 0.0507 mmol, 8.6%) as a grey solid. $^1$H NMR (500 MHz, Dimethylsulfoxide-d$_6$) δ 10.65 (s, 1H), 8.65 (d, J=2.5 Hz, 1H), 8.31 (d, J=2.5 Hz, 1H), 8.05 (d, J=8.5 Hz, 1H), 7.94 (dd, J=9.5, 3.0 Hz, 1H), 7.71 (dd, J=8.5, 2.0 Hz, 1H), 7.35 (dd, J=14.0, 8.5 Hz, 1H), 7.13-7.10 (m, 2H), 7.04 (td, J=8.5, 2.0 Hz, 1H), 6.43 (d, J=9.5 Hz, 1H), 3.99-3.95 (m, 4H), 1.28 (t, J=7.5 Hz, 3H); LCMS (ESI) m/z: 352.2 [M+H]$^+$.

Example 86. Preparation of 5-(3-Chlorobenzyl)-N-(1-methyl-6-oxo-1,4,5,6-tetrahydropyridazin-3-yl) picolinamide (86)

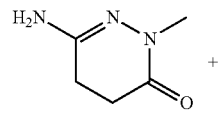 +

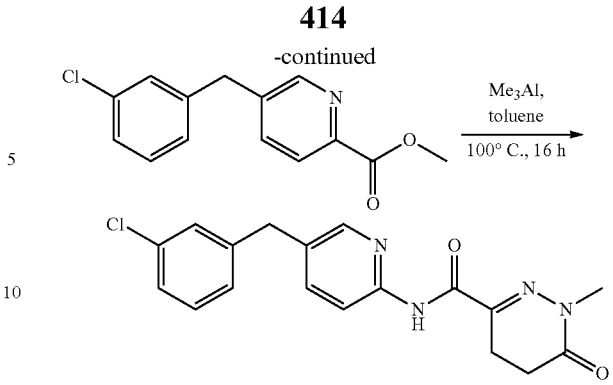

Step 1: Preparation of 5-(3-Chlorobenzyl)-N-(1-methyl-6-oxo-1,4,5,6-tetrahydropyridazin-3-yl)picolinamide

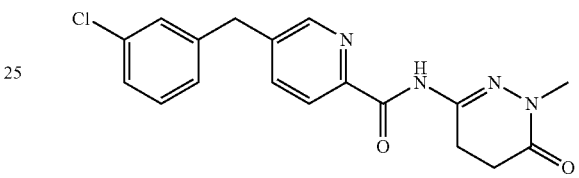

To a solution of 6-amino-2-methyl-4,5-dihydropyridazin-3(2H)-one (0.127 g, 1.0 mmol) in anhydrous toluene (8 mL) at room temperature was added trimethylaluminum (0.50 mL, 1.0 mmol, 2 Min toluene) under nitrogen. The reaction mixture was stirred at room temperature for 1 h before methyl 5-(3-chlorobenzyl)picolinate (0.130 g, 0.50 mmol) was added. Reaction mixture was stirred at 100° C. for 16 h. Reaction solution was cooled to room temperature and quenched with water (100 mL). The aqueous layer was extracted with ethyl acetate (50 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give 5-(3-chlorobenzyl)-N-(1-methyl-6-oxo-1,4,5,6-tetrahydropyridazin-3-yl)picolinamide (35.0 mg, 0.1 mmol, 20%) as a white solid. $^1$H NMR (500 MHz, Dimethylsulfoxide-d$_6$) δ 10.15 (s, 1H), 8.66 (d, J=1.5 Hz, 1H), 8.05 (d, J=8.0 Hz, 1H), 7.92 (dd, J$_1$=2.0 Hz, J$_2$=8.0 Hz, 1H), 7.40 (s, 1H), 7.37-7.33 (m, 1H), 7.30-7.26 (m, 2H), 4.12 (s, 2H), 3.21 (t, J=8.0 Hz, 2H), 3.17 (s, 3H), 2.48 (t, J=8.0 Hz, 2H); LCMS (ESI) m/z: 357.1 [M+H]$^+$.

Example 87. Preparation of 5-(3,4-Difluorobenzyl)-N-(1-methyl-6-oxo-1,4,5,6-tetrahydropyridazin-3-yl) picolinamide (87)

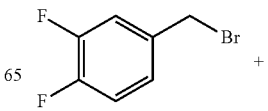 +

-continued

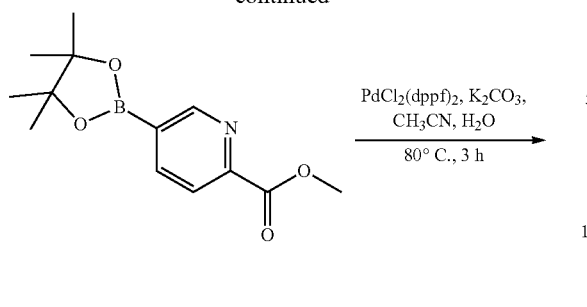

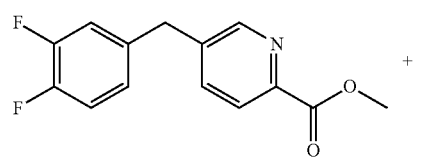

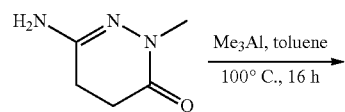

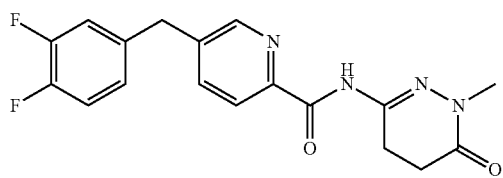

Step 1: Preparation of methyl 5-(3,4-difluorobenzyl)picolinate

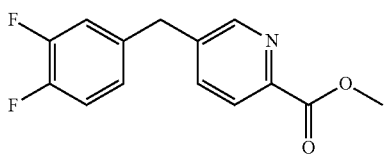 [SMILES: COC(=O)c1ccc(Cc2ccc(F)c(F)c2)cn1]

To a solution of methyl 5-(4,4,5,5-tetramethyl-1,3,2-dioxaborolan-2-yl)picolinate (1.0 g, 3.8 mmol) in acetonitrile (20 mL) and water (5 mL) at room temperature was added potassium carbonate (1.04 g, 7.6 mmol), 1,1'-bis(diphenylphosphino)ferrocene palladium(II)dichloride (0.310 g, 0.38 mmol) and 4-(bromomethyl)-1,2-difluorobenzene (0.787 g, 3.8 mmol) under nitrogen. The reaction mixture was stirred at 80° C. for 3 h. The reaction solution was cooled to room temperature and diluted with water (200 mL). The aqueous layer was extracted with ethyl acetate (80 mL×3). The combined organic layers were washed with brine (100 mL), dried over anhydrous sodium sulfate, filtered and concentrated. The crude sample was purified by column chromatography (silica gel, petroleum ether/ethyl acetate=3/1) to give methyl 5-(3,4-difluorobenzyl)picolinate (0.610 g, 2.31 mmol, 61%) as a yellow solid. LCMS (ESI) m/z: 264.1 [M+H]$^+$.

Step 2: Preparation of 5-(3,4-difluorobenzyl)-N-(1-methyl-6-oxo-1,4,5,6-tetrahydropyridazin-3-yl)picolinamide

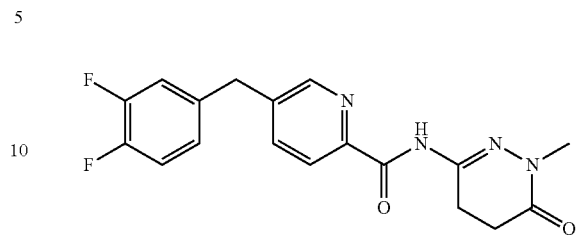

To a solution of 6-amino-2-methyl-4,5-dihydropyridazin-3(2H)-one (0.204 g, 1.6 mmol) in anhydrous toluene (12 mL) at room temperature was added trimethylaluminum (0.8 mL, 1.6 mmol, 2 Min toluene) under nitrogen. The reaction mixture was stirred at room temperature for 1 h before methyl 5-(3-fluorobenzyl)picolinate (0.210 g, 0.80 mmol) was added. The reaction mixture was stirred at 100° C. for 16 h. The reaction solution was cooled to room temperature and diluted with water (200 mL). The aqueous layer was extracted with ethyl acetate (50 mL×3). The combined organic layers were washed with brine (100 mL), dried over anhydrous sodium sulfate, filtered and concentrated. The crude sample was dissolved in minimal N,N-dimethylformamide and purified via prep-HPLC Boston C18 21*250 mm 10 μm column. The mobile phase was acetonitrile/10 mM ammonium acetate aqueous solution) to give 5-(3,4-difluorobenzyl)-N-(1-methyl-6-oxo-1,4,5,6-tetrahydropyridazin-3-yl)picolinamide (32 mg, 0.09 mmol, 11%) as a white solid. $^1$H NMR (500 MHz, Dimethylsulfoxide-d$_6$) δ 10.17 (s, 1H), 8.65 (d, J=1.5 Hz, 1H), 8.04 (d, J=8.0 Hz, 1H), 7.92 (dd, J$_1$=2.0 Hz, J$_2$=8.5 Hz, 1H), 7.44-7.35 (m, 2H), 7.16-7.14 (m, 1H), 4.10 (s, 2H) 3.21 (t, J=7.5 Hz, 2H), 3.17 (s, 3H), 2.48 (t, J=8.0 Hz, 2H); LCMS (ESI) m/z: 359.1 [M+H]$^+$.

Example 88. Preparation of 5-(3-Fluorobenzyl)-N-(1-methyl-6-oxo-1,6-dihydropyridazin-3-yl)picolinamide (88)

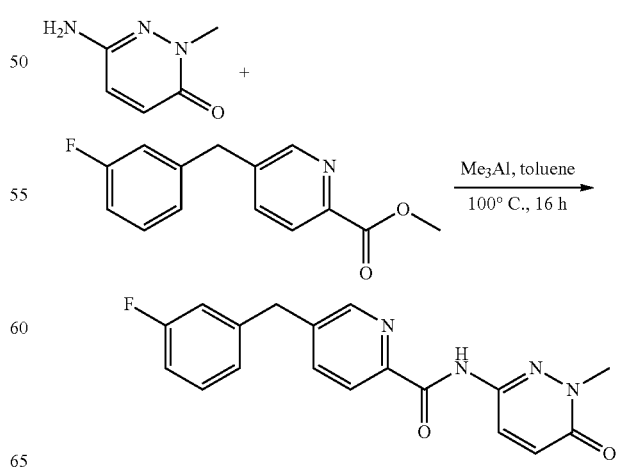

Step 1: Preparation of 5-(3-fluorobenzyl)-N-(1-methyl-6-oxo-1,6-dihydropyridazin-3-yl)picolinamide

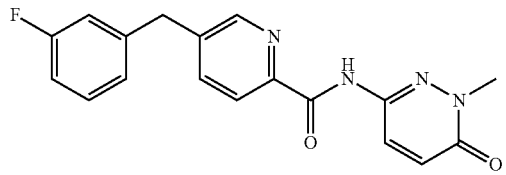 [SMILES: Cn1nc(NC(=O)c2ccc(Cc3cccc(F)c3)cn2)ccc1=O]

To a solution of 6-amino-2-methylpyridazin-3(2H)-one (0.133 g, 1.06 mmol) in anhydrous toluene (8 mL) at room temperature was added trimethylaluminum (0.53 mL, 1.0 mmol, 2 M in toluene) under nitrogen. The reaction mixture was stirred at room temperature for 1 h before methyl 5-(3-fluorobenzyl)picolinate (0.130 g, 0.53 mmol) was added and stirred at 100° C. for 16 h. The reaction solution was cooled to room temperature and quenched with water (100 mL). The aqueous layer was extracted with ethyl acetate (50 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give 5-(3-fluorobenzyl)-N-(1-methyl-6-oxo-1,6-dihydropyridazin-3-yl)picolinamide (0.087 g, 0.26 mmol, 49%) as a white solid. $^1$H NMR (500 MHz, Dimethylsulfoxide-$d_6$) δ 10.37 (s, 1H), 8.68 (d, J=1.0 Hz, 1H), 8.09-8.06 (m, 2H), 7.93 (dd, $J_1$=2.0 Hz, $J_2$=8.0 Hz, 1H), 7.39-7.34 (m, 1H), 7.19-7.08 (m, 2H), 7.07-7.04 (m, 2H), 4.13 (s, 2H), 3.61 (s, 3H); LCMS (ESI) m/z: 339.1 [M+H]$^+$.

Step 1: Preparation of 5-(3-chlorobenzyl)-N-(1-methyl-6-oxo-1,6-dihydropyridazin-3-yl)picolinamide

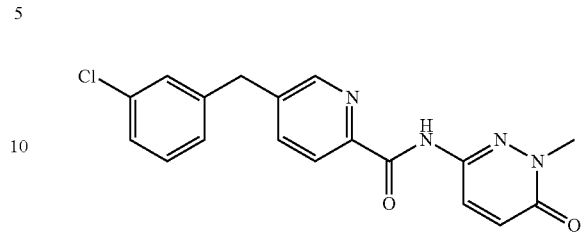

To a solution of 6-amino-2-methylpyridazin-3(2H)-one (0.125 g, 1.0 mmol) in anhydrous toluene (8 mL) at room temperature was added trimethylaluminum (0.5 mL, 1.0 mmol, 2 M in toluene) under nitrogen. The reaction mixture was stirred at room temperature for 1 h before methyl 5-(3-fluorobenzyl)picolinate (0.130 g, 0.50 mmol) was added and stirred at 100° C. for 16 h. The reaction mixture was cooled to room temperature and quenched with water (100 mL). The aqueous layer was extracted with ethyl acetate (50 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give 5-(3-chlorobenzyl)-N-(1-methyl-6-oxo-1,6-dihydropyridazin-3-yl)picolinamide (0.050 g, 0.14 mmol, 28%) as a white solid. $^1$H NMR (500 MHz, Dimethylsulfoxide-$d_6$) δ 10.03 (s, 1H), 8.69 (d, J=1.5 Hz, 1H), 8.09-8.06 (m, 2H), 7.93 (dd, $J_1$=2.0 Hz, $J_2$=8.0 Hz, 1H), 7.41 (s, 1H), 7.35 (t, J=8.0 Hz, 1H), 7.30-7.27 (m, 2H), 7.05 (d, J=10.0 Hz, 1H), 4.13 (s, 2H), 3.61 (s, 3H). LCMS (ESI) m/z: 355.0 [M+H]$^+$.

Example 89. Preparation of 5-(3-Chlorobenzyl)-N-(1-methyl-6-oxo-1,6-dihydropyridazin-3-yl)picolinamide (89)

Example 90. Preparation of 5-(3-Fluorobenzyl)-N-(1-methyl-6-oxo-1,4,5,6-tetrahydropyridazin-3-yl)picolinamide (90)

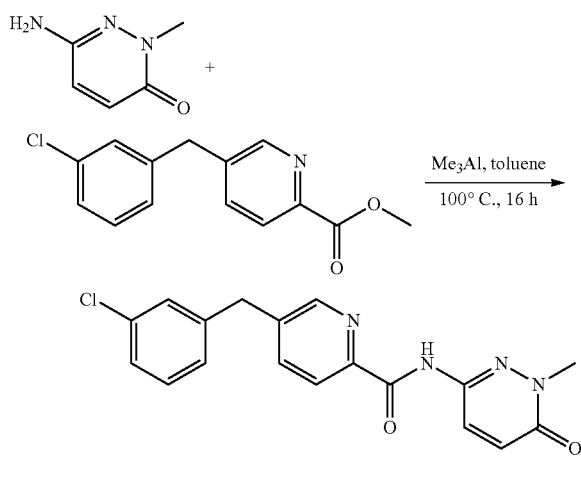

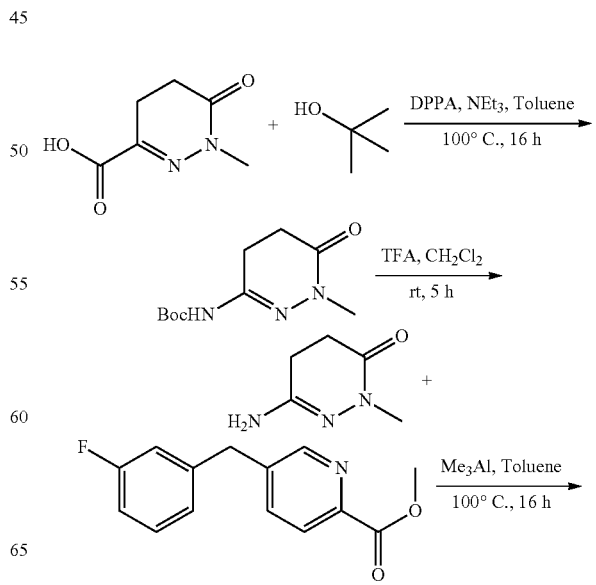

-continued

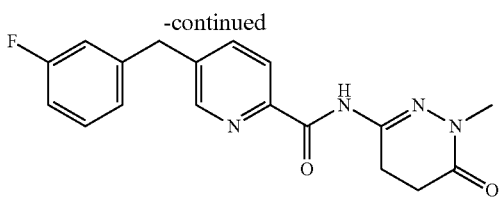

Step 1: Preparation of tert-butyl (1-methyl-6-oxo-1,4,5,6-tetrahydropyridazin-3-yl)carbamate

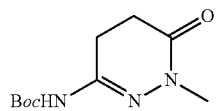

To a solution of 1-methyl-6-oxo-1,4,5,6-tetrahydropyridazine-3-carboxylic acid (6.0 g, 38.4 mmol) in toluene (150 mL) at room temperature was added sequentially 2-methylpropan-2-ol (28.5 g, 384 mmol), diphenyl phosphoryl azide (12.7 g, 46.1 mmol) and triethylamine (4.3 g, 42.3 mmol). The reaction mixture was stirred at 100° C. for 16 h, cooled to room temperature and concentrated. Purification over column chromatography (silica gel, petroleum ether/ethyl acetate=3/1) affords tert-butyl (1-methyl-6-oxo-1,4,5,6-tetrahydropyridazin-3-yl)carbamate (6.1 g, 26.8 mmol, 69.9%) as a white solid. LCMS (ESI) m/z: 228.1 [M+H]$^+$.

Step 2: Preparation of 6-amino-2-methyl-4,5-dihydropyridazin-3(2H)-one

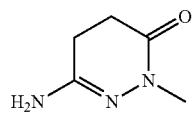

To a solution of tert-butyl (1-methyl-6-oxo-1,4,5,6-tetrahydropyridazin-3-yl)carbamate (0.500 g, 2.20 mmol) in dichloromethane (10 mL) at room temperature was added trifluoroacetic acid (10 mL). The reaction mixture was stirred at room temperature for 5 h. The mixture was concentrated, and the residue was diluted with water (200 mL) and extracted with dichloromethane (50 mL×3). The combined organic layers were washed with brine, dried over sodium sulfate, filtered and concentrated to afford 6-amino-2-methyl-4,5-dihydropyridazin-3(2H)-one (0.200 g, 1.57 mmol, 71.4%) as a white solid. LCMS (ESI) m/z: 128.1 [M+H]$^+$.

Step 3: Preparation of 5-(3-fluorobenzyl)-N-(1-methyl-6-oxo-1,4,5,6-tetrahydropyridazin-3-yl)picolinamide

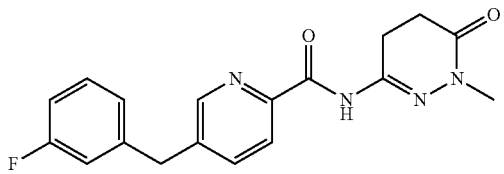 [SMILES: CN1N=C(NC(=O)c2ccc(Cc3cccc(F)c3)cn2)CCC1=O]

To a solution of 6-amino-2-methyl-4,5-dihydropyridazin-3(2H)-one (0.166 g, 1.3 mmol) in anhydrous toluene (15 mL) at 0° C. was added trimethylaluminum (0.65 mL, 2 M in toluene) under nitrogen. The mixture was stirred at room temperature for 2 h before methyl 5-(3-fluorobenzyl)picolinate (0.245 g, 1.0 mmol) was added. Reaction was stirred at 100° C. for 16 h. The reaction mixture was quenched with ice water (30 mL) and extracted with ethyl acetate (50 mL×3). The combined organic layer was washed with brine (100 mL), dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 5-(3-fluorobenzyl)-N-(1-methyl-6-oxo-1,4,5,6-tetrahydropyridazin-3-yl)picolinamide (0.170 g, 0.50 mmol, 50.0%) as a white solid. $^1$H NMR (500 MHz, Dimethylsulfoxide-d$_6$) δ 10.17 (s, 1H), 8.66 (s, 1H), 8.05 (d, J=8.0 Hz, 1H), 7.93 (dd, J=8.0, 1.8 Hz, 1H), 7.38-7.34 (m, 1H), 7.18-7.13 (m, 2H), 7.07-7.04 (m, 1H), 4.13 (s, 2H), 3.21 (t, J=8.2 Hz, 2H), 3.17 (s, 3H), 2.48 (d, J=8.2 Hz, 2H); LCMS (ESI) m/z: 341.1 [M+H]$^+$.

Example 91. Preparation of N-(5-(3-chlorobenzyl)pyridin-2-yl)-1-methyl-1H-pyrazole-3-carboxamide (91)

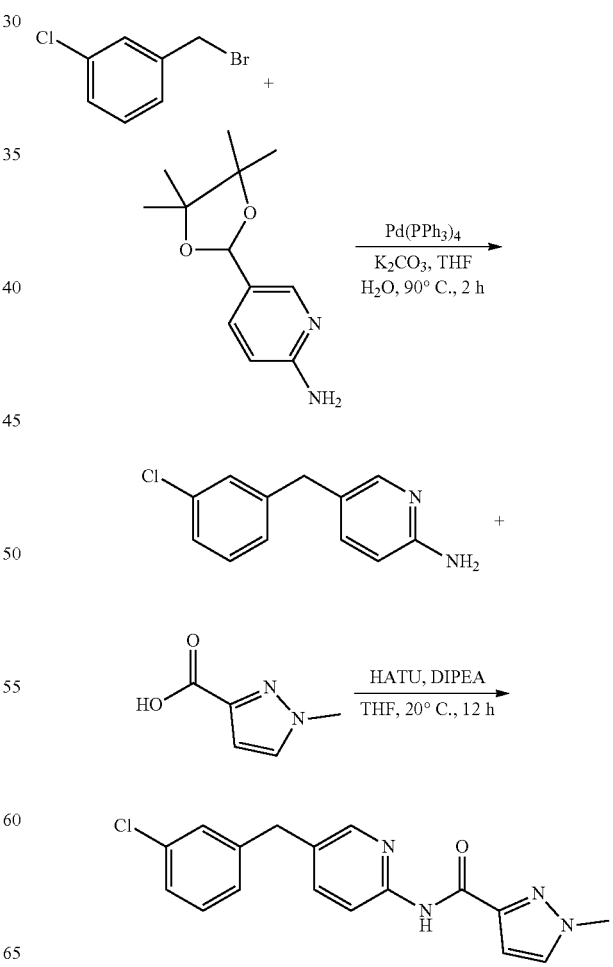

421

Step 1: Preparation of 5-(3-chlorobenzyl)pyridin-2-amine

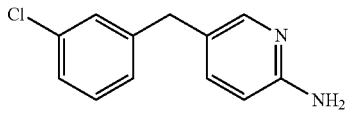

To a solution of 1-(bromomethyl)-3-chlorobenzene (10.0 g, 49.0 mmol), 5-(4,4,5,5-tetramethyl-1,3,2-dioxaborolan-2-yl)pyridin-2-amine (10.8 g, 49.0 mmol), potassium carbonate (13.5 g, 98.1 mmol) in tetrahydrofuran (40 mL) and water (10 mL) was added tetrakis(triphenylphosphine)palladium(0) (5.65 g, 4.9 mmol) under nitrogen. The reaction mixture was heated to 90° C. and stirred for 2 h. The volatiles were removed under reduced pressure. Aqueous layer was acidified to pH=1-3 with 1 N hydrogen chloride and extracted with ethyl acetate (50 mL). The aqueous layer was then adjusted to pH=8-10 with aqueous sodium bicarbonate and extracted with dichloromethane (50 mL×2). The combined dichloromethane layers were dried over sodium sulfate, filtered and concentrated to give 5-(3-chlorobenzyl)pyridin-2-amine as a yellow oil (8.0 g, crude); LCMS (ESI) m/z: 219.1 [M+H]$^+$.

Step 2: Preparation of N-(5-(3-chlorobenzyl)pyridin-2-yl)-1-methyl-1H-pyrazole-3-carboxamide

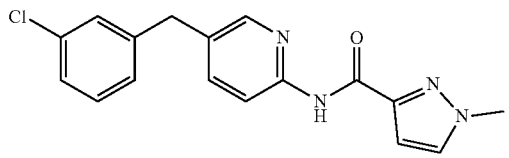 [SMILES: Cn1ccc(C(=O)Nc2ccc(Cc3cccc(Cl)c3)cn2)n1]

To a solution of 1-methyl-1H-pyrazole-3-carboxylic acid (0.100 g, 0.793 mmol), N,N-diisopropylethylamine (0.307 g, 2.38 mmol) in tetrahydrofuran (4 mL) at 20° C. was added 1-[bis(dimethylamino)methylene]-1H-1,2,3-triazolo[4,5-b]pyridinium 3-oxid hexafluorophosphate (0.452 g, 1.19 mmol). The reaction was stirred for 20 minutes before a solution of 5-(3-chlorobenzyl)pyridin-2-amine (0.173 g, 0.793 mmol) in tetrahydrofuran (1.0 mL) was added. The solution was stirred at 20° C. for 16 h. The volatiles were removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chlorobenzyl)pyridin-2-yl)-1-methyl-1H-pyrazole-3-carboxamide (0.0927 g, 0.285 mmol, 36%) as a white solid. $^1$H NMR (400 MHz, Dimethylsulfoxide-d$_6$) δ 9.51 (s, 1H), 8.29 (s, 1H), 8.10 (d, J=10.5 Hz, 1H), 7.88 (d, J=2.5 Hz, 1H), 7.71-7.74 (m, 1H), 7.23-7.35 (m, 4H), 6.84 (d, J=2.5 Hz, 1H), 3.96 (s, 5H); LCMS (ESI) m/z: 327.1 [M+H]$^+$.

422

Example 92. Preparation of N-(5-(3,4-difluorobenzyl)pyridin-2-yl)-1-methyl-1H-pyrazole-3-carboxamide (92)

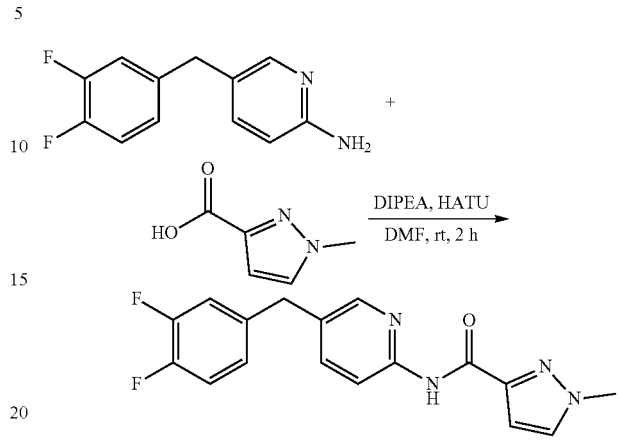

Step 1: Preparation of N-(5-(3,4-difluorobenzyl)pyridin-2-yl)-1-methyl-1H-pyrazole-3-carboxamide

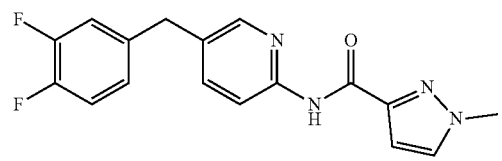 [SMILES: Cn1ccc(C(=O)Nc2ccc(Cc3ccc(F)c(F)c3)cn2)n1]

A mixture of 5-(3,4-difluorobenzyl)pyridin-2-amine (0.100 g, 0.45 mmol), 1-methyl-1H-pyrazole-3-carboxylic acid (0.048 g, 0.38 mmol), 1-[bis(dimethylamino)methylene]-1H-1,2,3-triazolo[4,5-b]pyridinium 3-oxid hexafluorophosphate (0.173 g, 0.45 mmol) and N,N-diisopropylethylamine (0.147 g, 1.14 mmol) in anhydrous N,N-dimethylformamide (4.00 mL) was stirred at 20° C. for 2 h. The reaction mixture was extracted with ethyl acetate (20 mL×2). The combined organic layers were washed with water (50 mL), brine (50 mL), dried over anhydrous sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,4-difluorobenzyl)pyridin-2-yl)-1-methyl-1H-pyrazole-3-carboxamide (0.0258 g, 0.08 mmol, 21%) as a white solid. [M+H]$^+$. $^1$H NMR (400 MHz, Dimethylsulfoxide-d$_6$) δ 10.03 (s, 1H), 8.32 (d, J=1.5 Hz, 1H), 8.09 (d, J=8.6 Hz, 1H), 7.88 (dd, J=24.1, 5.4 Hz, 1H), 7.56-7.23 (m, 2H), 7.23-7.01 (m, 1H), 6.87 (d, J=2.3 Hz, 1H), 4.14-3.77 (m, 5H); LCMS (ESI) m/z: 329.1

Example 93. Preparation of N-(5-(4-fluorobenzyl)pyridin-2-yl)-1-methyl-1H-pyrazole-3-carboxamide (93)

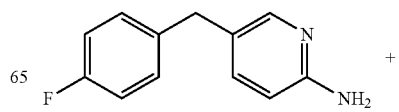

423
-continued

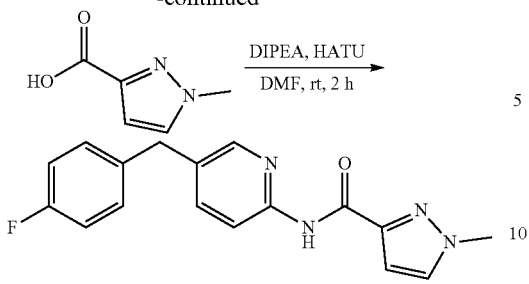

Step 1: Preparation of N-(5-(4-fluorobenzyl)pyridin-2-yl)-1-methyl-1H-pyrazole-3-carboxamide

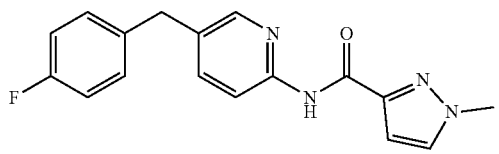 [SMILES: Cn1ccc(C(=O)Nc2ccc(Cc3ccc(F)cc3)cn2)n1]

A mixture of 5-(4-fluorobenzyl)pyridin-2-amine (0.100 g, 0.50 mmol), 1-methyl-1H-pyrazole-3-carboxylic acid (0.069 g, 0.55 mmol), 1-[bis(dimethylamino)methylene]-1H-1,2,3-triazolo[4,5-b]pyridinium 3-oxid hexafluorophosphate (0.232 g, 0.61 mmol) and N,N-diisopropylethylamine (213 mg, 1.65 mmol) in anhydrous N,N-dimethylformamide (4.00 mL) was stirred at 20° C. for 2 h. The reaction was diluted with water and extracted with ethyl acetate (20 mL×2). The combined organic layers were washed with water (50 mL) and brine (50 mL), dried over anhydrous sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(4-fluorobenzyl)pyridin-2-yl)-1-methyl-1H-pyrazole-3-carboxamide (0.0437 g, 0.14 mmol, 28%) as a white solid. $^1$H NMR (400 MHz, Dimethylsulfoxide-$d_6$) δ 9.50 (s, 1H), 8.26 (d, J=2.1 Hz, 1H), 8.09 (d, J=8.5 Hz, 1H), 7.88 (d, J=2.3 Hz, 1H), 7.69 (dd, J=8.5, 2.3 Hz, 1H), 7.30 (dd, J=8.5, 5.6 Hz, 2H), 7.22-7.04 (m, 2H), 6.84 (d, J=2.3 Hz, 1H), 4.10-3.73 (m, 5H); LCMS (ESI) m/z: 311.1 [M+H]$^+$.

Example 94. Preparation of N-(5-(3-chlorobenzyl)pyridin-2-yl)-1-methyl-1H-pyrazole-4-carboxamide (94)

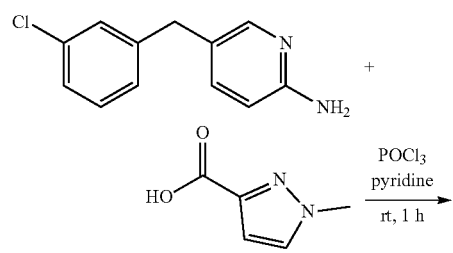

424
-continued

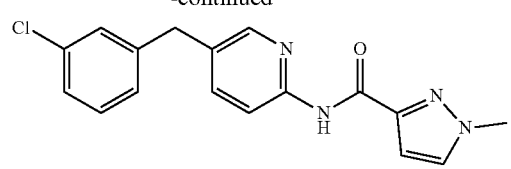

Step 1: Preparation of N-(5-(3-chlorobenzyl)pyridin-2-yl)-1-methyl-1H-pyrazole-4-carboxamide

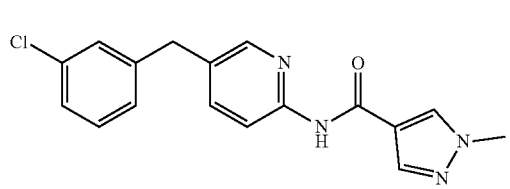 [SMILES: Cn1cc(C(=O)Nc2ccc(Cc3cccc(Cl)c3)cn2)cn1]

To a solution of 1-methyl-1H-pyrazole-4-carboxylic acid (0.100 g, 0.793 mmol), 5-(3-chlorobenzyl)pyridin-2-amine (0.173 g, 0.793 mmol) in pyridine (4 mL) at 20° C. was added phosphorus oxychloride (0.361 g, 2.38 mmol). The reaction mixture was stirred at room temperature for 1 h. The volatiles were removed under reduced pressure and the solid was dissolved in dichloromethane (10.0 mL). The resulting solution was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column. The mobile was acetonitrile/0.01% aqueous trifluoroacetic acid) to offer N-(5-(3-chlorobenzyl)pyridin-2-yl)-1-methyl-1H-pyrazole-4-carboxamide (0.0504 g, 0.15 mmol, 19%) as a white solid. $^1$H NMR (400 MHz, Dimethylsulfoxide-$d_6$) δ 10.53 (s, 1H), 8.42 (s, 1H), 8.29-8.29 (d, J=2.5 Hz, 1H), 8.12 (s, 1H), 8.06-8.08 (d, J=9.0 Hz, 1H), 7.69-7.72 (q, J=3.6 Hz, 1H), 7.23-7.35 (m, 4H), 3.96 (s, 2H), 3.88 (s, 3H); LCMS (ESI) m/z: 327.1 [M+H]$^+$.

Example 95. Preparation of 5-(3-fluorobenzyl)-N-(1-methyl-1H-pyrazol-3-yl)picolinamide (95)

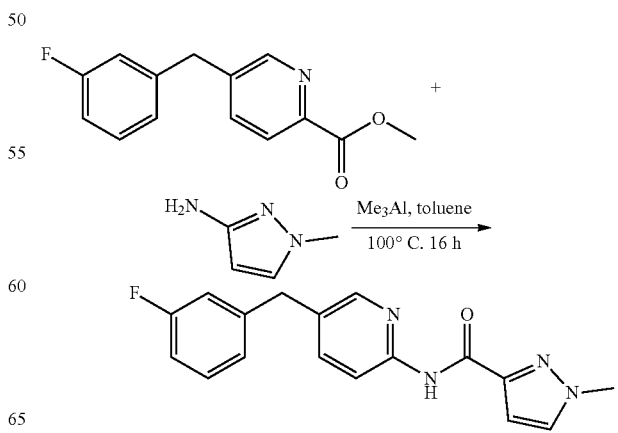

Step 1: Preparation of 5-(3-fluorobenzyl)-N-(1-methyl-1H-pyrazol-3-yl)picolinamide

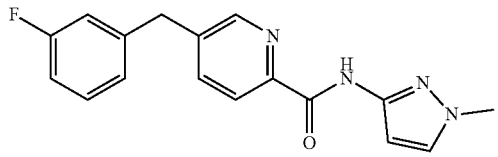 [SMILES: Cn1ccc(NC(=O)c2ccc(Cc3cccc(F)c3)cn2)n1]

To a solution of 1-methyl-1H-pyrazol-3-amine (0.159 g, 1.63 mmol) in anhydrous toluene (12 mL) at room temperature was added trimethylaluminum (0.82 mL, 1.63 mmol, 2 M in toluene) under nitrogen. The reaction mixture was stirred at room temperature for 1 h before methyl 5-(3-fluorobenzyl)picolinate (0.200 g, 0.82 mmol) was added and stirred at 100° C. for 16 h. The reaction mixture was cooled to room temperature diluted with water (200 mL). The aqueous phase was extracted with ethyl acetate (50 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give 5-(3-fluorobenzyl)-N-(1-methyl-1H-pyrazol-3-yl)picolinamide (95.0 mg, 0.31 mmol, 37%) as a white solid. $^1$H NMR (500 MHz, Dimethylsulfoxide-$d_6$) δ 10.33 (s, 1H), 8.65 (d, J=2.0 Hz, 1H), 8.06 (d, J=8.0 Hz, 1H), 7.91 (dd, $J_1$=2.5 Hz, $J_2$=8.5 Hz, 1H), 7.64 (d, J=2.0 Hz, 1H), 7.38-7.34 (m, 1H), 7.19-7.14 (m, 2H), 7.07-7.02 (m, 1H), 6.60 (d, J=2.0 Hz, 1H), 4.11 (s, 2H), 3.77 (s, 3H); LCMS (ESI) m/z: 311.1 [M+H]$^+$.

Example 96. Preparation of N-(5-(3-cyano-5-fluorobenzyl)pyridin-2-yl)-1-methyl-1H-pyrazole-3-carboxamide (96)

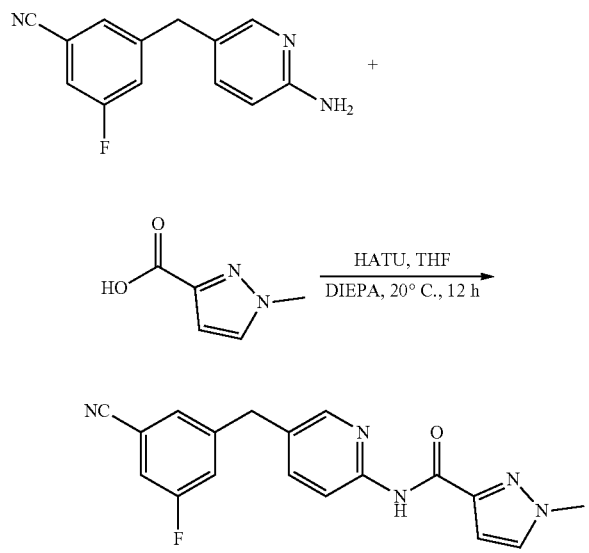

Step 1: Preparation of N-(5-(3-cyano-5-fluorobenzyl)pyridin-2-yl)-1-methyl-1H-pyrazole-3-carboxamide

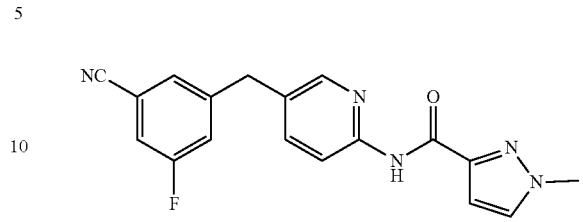

To a solution of 1-methyl-1H-pyrazole-3-carboxylic acid (50 mg, 0.397 mmol) and diisopropylethylamine (154 mg, 1.19 mmol) in tetrahydrofuran (4.0 mL) at 20° C. was added 1-[bis(dimethylamino)methylene]-1H-1,2,3-triazolo[4,5-b]pyridinium 3-oxid hexafluorophosphate (226 mg, 0.595 mmol). The reaction mixture was stirred for 20 minutes before a solution of 3-((6-aminopyridin-3-yl)methyl)-5-fluorobenzonitrile (90 mg, 0.397 mmol) in tetrahydrofuran (1.0 mL) was added. The reaction solution was stirred at 20° C. for 16 h. The volatiles were removed under reduced pressure and the crude residue was added to a mixture of dichloromethane (50 mL) and water (50 mL). The combined organic layers were collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-cyano-5-fluorobenzyl)pyridin-2-yl)-1-methyl-1H-pyrazole-3-carboxamide as a white solid (29.3 mg, 0.087 mmol, 22%). $^1$H NMR (400 MHz, Dimethylsulfoxide-$d_6$) δ 10.48 (s, 1H), 8.41 (s, 1H), 8.32 (d, J=1.8 Hz, 1H), 8.10 (d, J=8.9 Hz, 2H), 7.77-7.66 (m, 2H), 7.57 (d, J=9.4 Hz, 1H), 4.02 (s, 2H), 3.87 (s, 2H); LCMS (ESI) m/z: 336.1 [M+H]$^+$.

Example 97. Preparation of N-(5-(3,5-difluorobenzyl)pyridin-2-yl)-1-ethyl-1H-pyrazole-3-carboxamide (97)

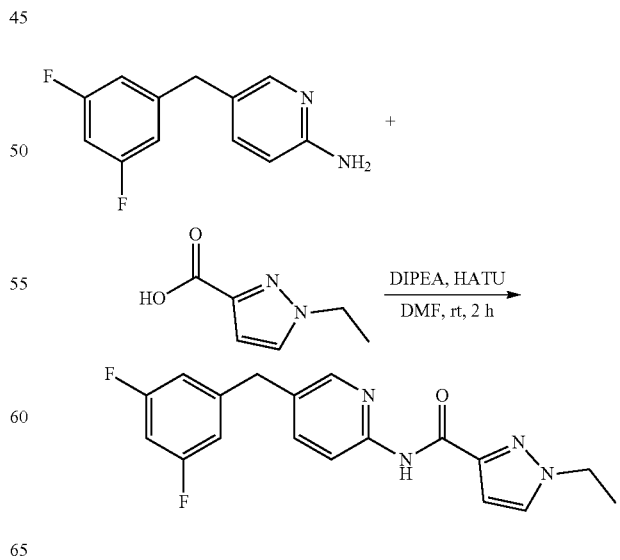

Step 1: Preparation of N-(5-(3,5-difluorobenzyl)pyridin-2-yl)-1-ethyl-1H-pyrazole-3-carboxamide

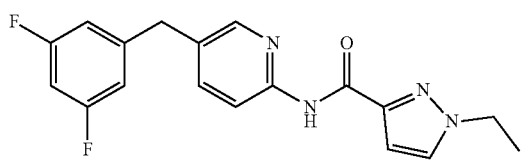

A mixture of 5-(3,5-difluorobenzyl)pyridin-2-amine (0.100 g, 0.45 mmol), 1-ethyl-1H-pyrazole-3-carboxylic acid (0.053 g, 0.38 mmol), 1-[bis(dimethylamino)methylene]-1H-1,2,3-triazolo[4,5-b]pyridinium 3-oxid hexafluorophosphate (0.173 g, 0.45 mmol) and N,N-diisopropylethylamine (0.147 g, 1.14 mmol) in anhydrous N,N-dimethylformamide (4.00 mL) was stirred at 20° C. for 2 h. The reaction solution was extracted with ethyl acetate (20 mL×20). The combined organic layers were washed with water (50 mL) and brine (50 mL) were dried over anhydrous sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,5-difluorobenzyl)pyridin-2-yl)-1-ethyl-1H-pyrazole-3-carboxamide (0.0304 g, 0.09 mmol, 23%) as a white solid. $^1$H NMR (400 MHz, Dimethylsulfoxide-d$_6$) δ 9.68 (s, 1H), 8.32 (d, J=1.8 Hz, 1H), 8.10 (d, J=8.5 Hz, 1H), 7.94 (s, 1H), 7.79 (dd, J=8.5, 2.2 Hz, 1H), 7.13-6.95 (m, 3H), 6.85 (d, J=2.3 Hz, 1H), 4.26 (q, J=7.3 Hz, 2H), 3.98 (s, 2H), 1.44 (t, J=7.3 Hz, 3H); LCMS (ESI) m/z: 343.1 [M+H]$^+$.

Example 98. Preparation of N-(5-(3,4-difluorobenzyl)pyridin-2-yl)-1-ethyl-1H-pyrazole-3-carboxamide (98)

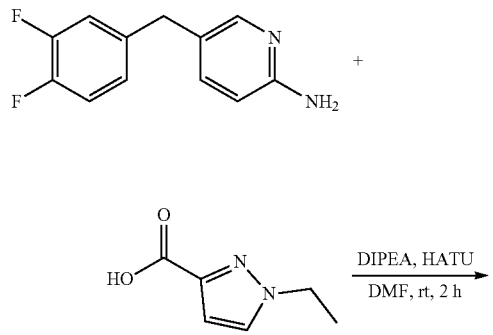

Step 1: Preparation of N-(5-(3,4-difluorobenzyl)pyridin-2-yl)-1-ethyl-1H-pyrazole-3-carboxamide

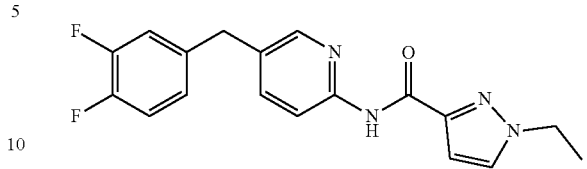

A mixture of 5-(3,4-difluorobenzyl)pyridin-2-amine (0.100 g, 0.45 mmol), 1-ethyl-1H-pyrazole-3-carboxylic acid (0.053 g, 0.38 mmol), 1-[bis(dimethylamino)methylene]-1H-1,2,3-triazolo[4,5-b]pyridinium 3-oxid hexafluorophosphate (0.173 g, 0.45 mmol) and N,N-diisopropylethylamine (0.147 g, 1.14 mmol) in anhydrous N,N-dimethylformamide (4.00 mL) was stirred at 20° C. for 2 h. The reaction was extracted with ethyl acetate (20 mL×2). The combined organic layers were washed with water (50 mL) and brine (50 mL), dried over anhydrous sodium sulfate, filtered and concentrated in vacuo The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,4-difluorobenzyl)pyridin-2-yl)-1-ethyl-1H-pyrazole-3-carboxamide (28.7 mg, 0.08 mmol, 22%) as a white solid. $^1$H NMR (400 MHz, Dimethylsulfoxide-d$_6$) δ 10.00 (s, 1H), 8.32 (d, J=1.7 Hz, 1H), 8.09 (d, J=8.6 Hz, 1H), 7.96 (d, J=2.3 Hz, 1H), 7.85 (dd, J=8.6, 1.9 Hz, 1H), 7.38 (ddd, J=17.0, 9.3, 5.4 Hz, 2H), 7.21-7.06 (m, 1H), 6.87 (d, J=2.3 Hz, 1H), 4.27 (q, J=7.3 Hz, 2H), 3.98 (s, 2H), 1.62-1.23 (m, 3H); LCMS (ESI) m/z: 343.2 [M+H]$^+$.

Example 99. Preparation N-(5-(3-chloro-5-fluorobenzyl)pyridin-2-yl)-1-ethyl-1H-pyrazole-3-carboxamide (99)

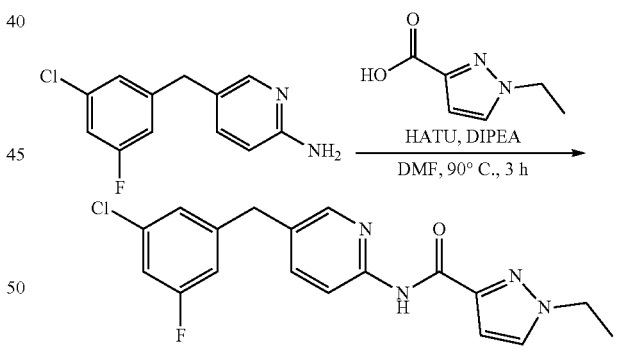

Step 1: Preparation of N-(5-(3-chloro-5-fluorobenzyl)pyridin-2-yl)-1-ethyl-1H-pyrazole-3-carboxamide

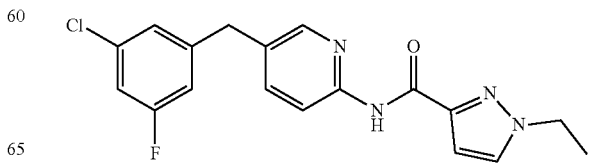

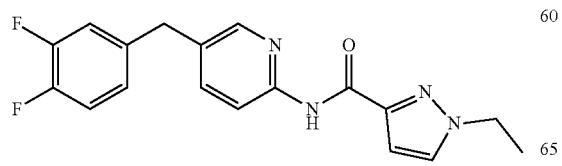

To a solution of 5-(3-chloro-5-fluorobenzyl)pyridin-2-amine (0.189 g, 0.8 mmol), 1-ethyl-1H-pyrazole-3-carboxylic acid (0.168 g, 1.2 mmol) and N,N-diisopropylethylamine (0.310 g, 2.4 mmol) in N,N-dimethylformamide (5 mL) at room temperature was added 1-[bis(dimethylamino)methylene]-1H-1,2,3-triazolo[4,5-b]pyridinium 3-oxid hexafluorophosphate (0.456 g, 1.2 mmol under nitrogen. The reaction mixture was stirred at 90° C. for 3 h. The reaction mixture was diluted with ethyl acetate (80 mL) and washed with brine (30 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-(3-chloro-5-fluorobenzyl)pyridin-2-yl)-1-ethyl-1H-pyrazole-3-carboxamide (44.7 mg, 0.13 mmol, 26%) as a pale white solid. $^1$H NMR (500 MHz, Dimethylsulfoxide-$d_6$) δ 9.55 (s, 1H), 8.32 (s, 1H), 8.11 (d, J=8.5 Hz, 1H), 7.94 (d, J=2.0 Hz, 1H), 7.76 (dd, $J_1$=1.5 Hz, $J_2$=8.0 Hz, 1H), 7.25-7.28 (m, 2H), 7.17 (d, J=9.5 Hz, 1H), 6.85 (d, J=2.0 Hz, 1H), 4.25 (dd, $J_1$=7.0 Hz, $J_2$=14.5 Hz, 2H), 3.97 (s, 2H), 1.43 (t, J=7.0 Hz, 3H); LCMS (ESI) m/z: 359.1 [M+H]$^+$.

Example 100. Preparation N-(5-(3-chlorobenzyl)pyridin-2-yl)-1-ethyl-1H-pyrazole-3-carboxamide (100)

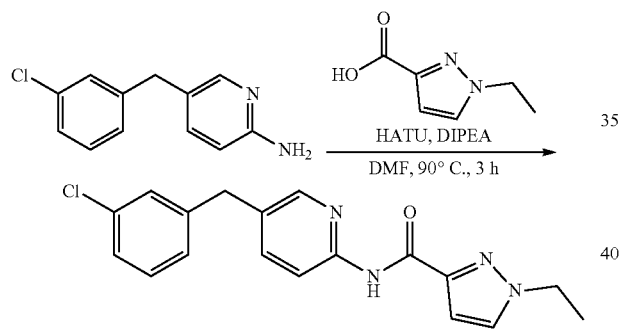

Step 1: Preparation of N-(5-(3-chlorobenzyl)pyridin-2-yl)-1-ethyl-1H-pyrazole-3-carboxamide

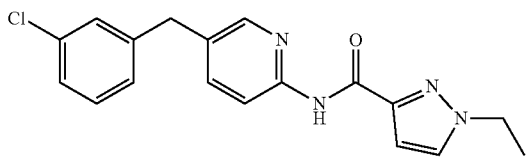 [SMILES: CCn1ccc(C(=O)Nc2ccc(Cc3cccc(Cl)c3)cn2)n1]

To a solution of 5-(3-chlorobenzyl)pyridin-2-amine (0.110 g, 0.5 mmol), 1-ethyl-1H-pyrazole-3-carboxylic acid (0.105 g, 0.75 mmol) and N,N-diisopropylethylamine (0.194 g, 1.5 mmol) in N,N-dimethylformamide (3 mL) at room temperature was added 1-[bis(dimethylamino) methylene]-1H-1,2,3-triazolo[4,5-b]pyridinium 3-oxid hexafluorophosphate (0.285 g, 0.75 mmol) under nitrogen. The reaction mixture was stirred at 90° C. for 3 h before it was diluted with ethyl acetate (80 mL) and washed with brine (30 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-(3-chlorobenzyl)pyridin-2-yl)-1-ethyl-1H-pyrazole-3-carboxamide (44.7 mg, 0.13 mmol, 26%) as a white solid. $^1$H NMR (500 MHz, Dimethylsulfoxide-$d_6$) δ 9.54 (s, 1H), 8.30 (d, J=2.0 Hz, 1H), 8.10 (d, J=8.5 Hz, 1H), 7.94 (d, J=2.0 Hz, 1H), 7.73 (dd, $J_1$=3.0 Hz, $J_2$=8.5 Hz, 1H), 7.33-7.36 (m, 2H), 7.24-7.29 (m, 2H), 6.85 (d, J=2.5 Hz, 1H), 4.25 (dd, $J_1$=7.5 Hz, $J_2$=14.5 Hz, 2H), 3.97 (s, 2H), 1.44 (t, J=7.0 Hz, 3H); LCMS (ESI) m/z: 341.1 [M+H]$^+$.

Example 101. Preparation of 1-ethyl-N-(5-(3-fluorobenzyl)pyridin-2-yl)-1H-pyrazole-3-carboxamide (101)

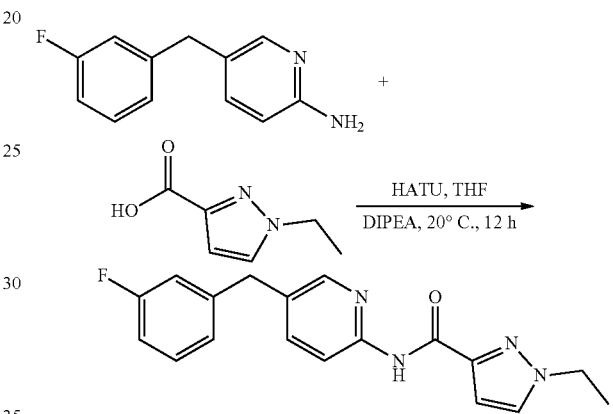

Step 1: Preparation of 1-ethyl-N-(5-(3-fluorobenzyl)pyridin-2-yl)-1H-pyrazole-3-carboxamide

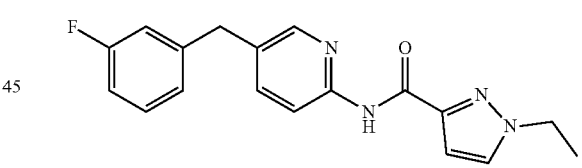

To a solution of 1-ethyl-1H-pyrazole-3-carboxylic acid (111 mg, 0.793 mmol) and diisopropylethylamine (307 mg, 2.379 mmol) in tetrahydrofuran (4.0 mL) at 20° C. was added 1-[bis(dimethylamino)methylene]-1H-1,2,3-triazolo[4,5-b]pyridinium 3-oxid hexafluorophosphate (452 mg, 1.19 mmol). The reaction mixture was stirred for 20 minutes before a solution of 5-(3-fluorobenzyl)pyridin-2-amine (160 mg, 0.793 mmol) in tetrahydrofuran (1.0 mL) was added. The solution mixture was stirred at 20° C. for 16 h. The volatiles were removed under reduced pressure and the residue was added to a mixture of dichloromethane (50 mL) and water (50 mL). The combined organic layers were collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give 1-ethyl-N-(5-(3-fluorobenzyl)pyridin-2-yl)-1H-pyrazole-3-carboxamide (43.0 mg, 0.132 mmol, 16.7%) as a white solid. ¹H NMR (400 MHz, Dimethylsulfoxide-d₆) δ 9.51 (s, 1H), 8.27 (d, J=2.0 Hz, 1H), 8.08 (d, J=8.5 Hz, 1H), 7.92 (d, J=2.3 Hz, 1H), 7.71-7.70 (dd, J=8.5, 2.2 Hz, 1H), 7.33-7.30 (dd, J=14.3, 8.0 Hz, 1H), 7.10-7.08 (t, J=7.0 Hz, 2H), 7.02-7.01 (dd, J=11.9, 5.3 Hz, 1H), 6.82 (d, J=2.3 Hz, 1H), 4.23-4.21 (q, J=7.3 Hz, 2H), 3.95 (s, 2H), 1.41-1.40 (t, J=7.3 Hz, 3H); LCMS (ESI) m/z: 325.1 [M+H]⁺.

Example 102. Preparation of N-(5-(3-fluorobenzyl)pyridin-2-yl)-5-methylpyrimidine-2-carboxamide (102)

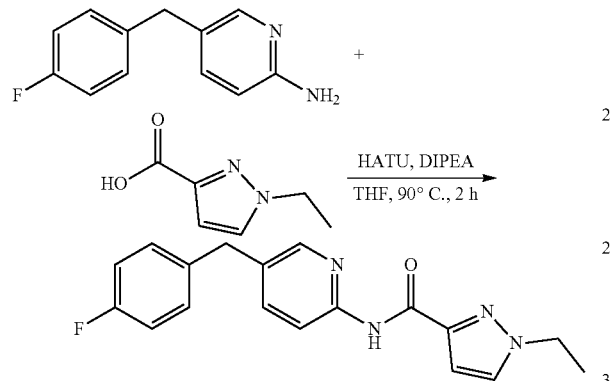

Step 1: Preparation of 1-ethyl-N-(5-(4-fluorobenzyl)pyridin-2-yl)-1H-pyrazole-3-carboxamide

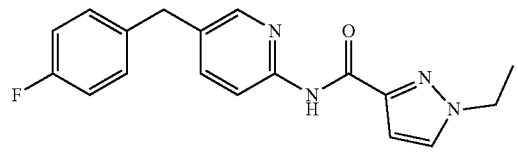 [SMILES: CCn1ccc(C(=O)Nc2ccc(Cc3ccc(F)cc3)cn2)n1]

To solution of 1-ethyl-1H-pyrazole-3-carboxylic acid (104 mg, 0.742 mmol) and diisopropylethylamine (288 mg, 2.226 mmol) in tetrahydrofuran (4 mL) at 20° C. was added 1-[bis(dimethylamino)methylene]-1H-1,2,3-triazolo[4,5-b]pyridinium 3-oxid hexafluorophosphate (423 mg, 1.113 mmol). The reaction mixture was stirred for 20 minutes before a solution of 5-(4-fluorobenzyl)pyridin-2-amine (150 mg, 0.742 mmol) in tetrahydrofuran (1.0 mL) was added. The reaction solution was heated to 90° C. and stirred for 2 h. The volatiles were removed under the reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give 1-ethyl-N-(5-(4-fluorobenzyl)pyridin-2-yl)-1H-pyrazole-3-carboxamide (89.9 mg, 0.28 mmol, 37%) as a white solid. ¹H NMR (400 MHz, Dimethylsulfoxide-d₆) δ 9.51 (s, 1H), 8.27 (d, J=4.0 Hz, 1H), 8.09 (d, J=8.0 Hz, 1H), 7.94 (d, J=4.0 Hz, 1H), 7.70 (q, J=2.6 Hz, 1H), 7.30 (q, J=2.6 Hz, 2H), 7.13 (t, J=10.0 Hz, 2H), 6.84 (s, 1H), 4.25 (q, J=8.0 Hz, 1H), 3.94 (s, 2H), 1.43 (t, J=8.0 Hz, 3H); LCMS (ESI) m/z: 325.1 [M+H]⁺.

Example 103. Preparation of N-(5-(3-chlorobenzyl)pyridin-2-yl)-5-methyl-1,3,4-thiadiazole-2-carboxamide (103)

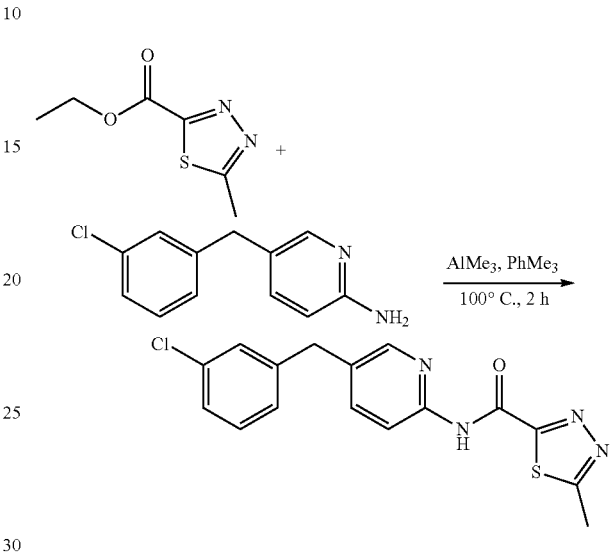

Step 1: Preparation of N-(5-(3-chlorobenzyl)pyridin-2-yl)-5-methyl-1,3,4-thiadiazole-2-carboxamide

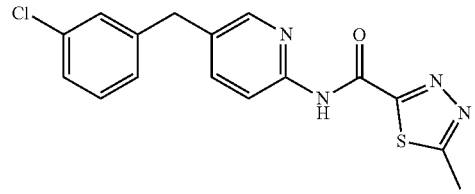

To a solution of 5-(3-chlorobenzyl)pyridin-2-amine (0.253 g, 1.16 mmol) in toluene (10 mL) at 20° C. was added trimethylaluminum (0.58 mL, 1.16 mmol, 2 M in toluene) under argon. The reaction mixture was stirred at 20° C. for 1 h before a solution of ethyl 5-methyl-1,3,4-thiadiazole-2-carboxylate (0.100 g, 0.581 mmol) in toluene (15 mL) was added. The reaction solution was stirred at 100° C. for 2 h. The volatiles were removed under reduced pressure and reaction was diluted with water (50 mL) and dichloromethane (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column. The mobile was acetonitrile/0.01% aqueous trifluoroacetic acid) to offer N-(5-(3-chlorobenzyl)pyridin-2-yl)-5-methyl-1,3,4-thiadiazole-2-carboxamide (0.0731 g, 0.21 mmol, 37%) as a white solid. ¹H NMR (400 MHz, Dimethylsulfoxide-d₆) δ 10.66 (s, 1H), 8.37 (s, 1H), 7.96-7.98 (d, J=8.8 Hz, 1H), 7.75-7.78 (m, 1H), 7.24-7.36 (m, 4H), 3.99 (s, 2H), 2.83 (s, 3H); LCMS (ESI) m/z: 345.1 [M+H]⁺.

Example 104. Preparation of N-(5-(3-chlorobenzyl)pyridin-2-yl)-1-isopropyl-6-oxo-1,6-dihydropyridazine-3-carboxamide (104)

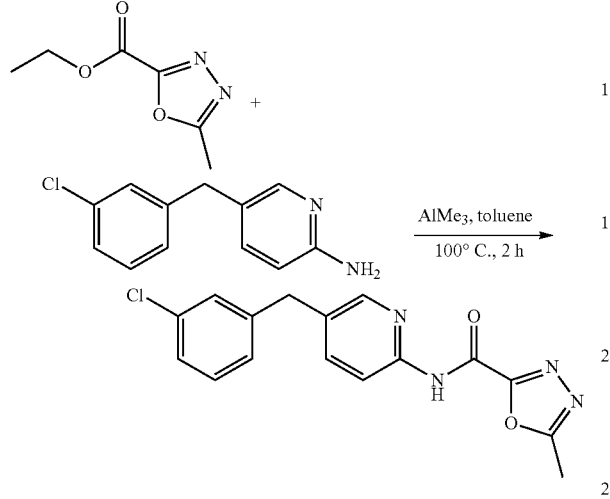

Step 1: Preparation of N-(5-(3-chlorobenzyl)pyridin-2-yl)-5-methyl-1,3,4-oxadiazole-2-carboxamide

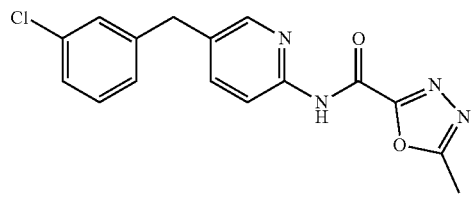 [SMILES: Cc1nnc(C(=O)Nc2ccc(Cc3cccc(Cl)c3)cn2)o1]

To a solution of 5-(3-chlorobenzyl)pyridin-2-amine (0.279 g, 1.28 mmol) in toluene (10 mL) at 20° C. was added trimethylaluminum (0.64 mL, 1.02 mmol, 2 M in toluene) under argon. The reaction mixture was stirred at 20° C. for 1 h before a solution of ethyl 5-methyl-1,3,4-oxadiazole-2-carboxylate (100 mg, 0.641 mmol) in toluene (15 mL) was added. The reaction solution was stirred at 100° C. for 1 h. The volatiles were removed under reduced pressure and the residue was quenched with water (50 mL) and extracted with dichloromethane (50 mL). The organic layer was dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to offer N-(5-(3-chlorobenzyl)pyridin-2-yl)-5-methyl-1,3,4-oxadiazole-2-carboxamide (0.109 g, 0.33 mmol, 51%) as a white solid. $^1$H NMR (400 MHz, Dimethylsulfoxide-$d_6$) δ 11.05 (s, 1H), 8.37 (s, 1H), 7.93-7.95 (d, J=8.4 Hz, 1H), 7.75-7.78 (m, 1H), 7.23-7.36 (m, 4H), 3.99 (s, 2H), 2.62 (s, 3H); LCMS (ESI) m/z: 329.0 [M+H]$^+$.

Example 105. Preparation of N-(5-(3-chlorobenzyl)pyridin-2-yl)-1-methyl-5-oxo-4,5-dihydro-1H-pyrazole-3-carboxamide (105)

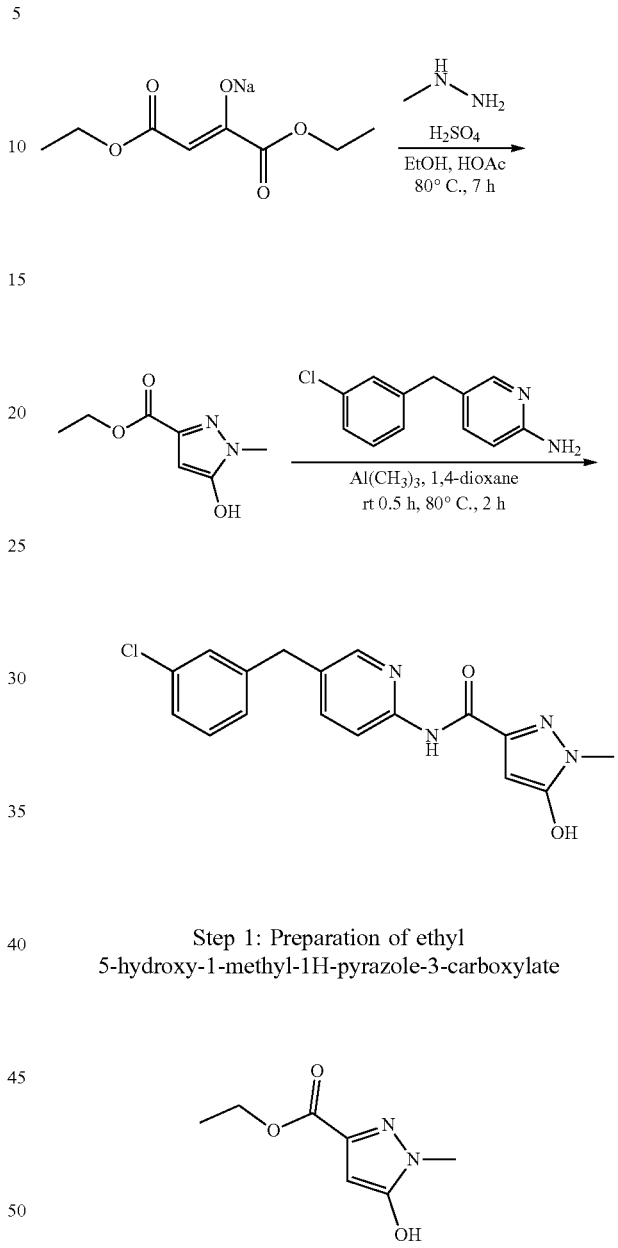

Step 1: Preparation of ethyl 5-hydroxy-1-methyl-1H-pyrazole-3-carboxylate

A mixture of methylhydrazine sulfate (7.2 g, 50.0 mmol), diethyl oxalacetate sodium salt (10.5 g, 50.0 mmol) in acetic acid (50 mL) and ethanol (100 mL) was stirred at 80° C. for 7 h. Ethanol was removed under reduced pressure and the residue was poured into water. The aqueous layers were extracted with ethyl acetate (200 mL×3). The combined organic layers were dried over sodium sulfate, filtered and concentrated. The crude material was purified by column chromatography (silica gel, petroleum ether/ethyl acetate=1/1) to give ethyl 5-hydroxy-1-methyl-1H-pyrazole-3-carboxylate (5.20 g, 30.6 mmol, 61%) as a light-yellow solid. $^1$H NMR (500 MHz, Dimethylsulfoxide-$d_6$) δ 11.40 (s, 1H), 5.76 (s, 1H), 4.20 (q, J=7.0 Hz, 2H), 3.59 (s, 3H), 1.25 (t, J=7.0 Hz, 3H); LCMS (ESI) m/z: 171.1 [M+H]$^+$.

Step 2: Preparation of N-(5-(3-chlorobenzyl)pyridin-2-yl)-5-hydroxy-1-methyl-1H-pyrazole-3-carboxamide

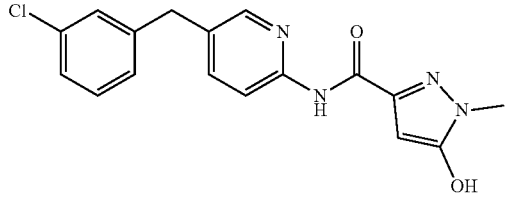

To a stirred solution of 5-(3-chlorobenzyl)pyridin-2-amine (218 mg, 1.0 mmol) in 1,4-dioxane (5 mL) under nitrogen at room temperature was added trimethylaluminum (2 M in toluene, 1.0 mL). The reaction mixture was stirred for 0.5 h before ethyl 5-hydroxy-1-methyl-1H-pyrazole-3-carboxylate (170 mg, 1.0 mmol) in 1,4-dioxane (5 mL) was added. The reaction solution was stirred at 80° C. for 2 h. The mixture was quenched with water and pH was adjusted to 1-2 with dilute hydrochloric acid. The solution mixture was concentrated, and the crude residue was purified by prep-HPLC×2 (Boston C18 21*250 mm 10 μm column. The mobile phase was acetonitrile/10 mM ammonium acetate aqueous solution) to afford N-(5-(3-chlorobenzyl)pyridin-2-yl)-5-hydroxy-1-methyl-1H-pyrazole-3-carboxamide (0.0164 g, 0.05 mmol, 4.8%) as an off-white solid. $^1$H NMR (500 MHz, Dimethylsulfoxide-d$_6$) δ 9.23 (s, 1H), 8.24 (d, J=2.0 Hz, 1H), 8.08 (d, J=8.5 Hz, 1H), 7.68 (dd, J=8.5, 2.0 Hz, 1H), 7.35 (d, J=2.0 Hz, 1H), 7.32 (d, J=8.0 Hz, 1H), 7.27-7.22 (m, 2H), 5.45 (s, 1H), 3.94 (s, 2H), 3.50 (s, 3H); LCMS (ESI) m/z: 343.1/345.1 [M+H]$^+$.

Example 106. Preparation of N-(5-(3-fluorobenzyl)pyridin-2-yl)-5-hydroxy-1-methyl-1H-pyrazole-3-carboxamide (106)

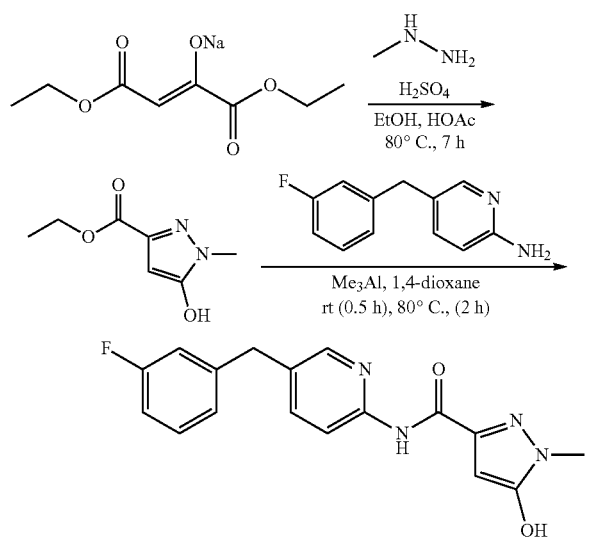

Step 1: Preparation of ethyl 5-hydroxy-1-methyl-1H-pyrazole-3-carboxylate

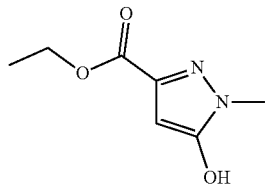

A mixture of methylhydrazine sulfate (7.2 g, 50.0 mmol), diethyl oxalacetate sodium salt (10.5 g, 50.0 mmol) in acetic acid (50 mL) and ethanol (100 mL) was stirred at 80° C. for 7 h. Ethanol was removed under reduced pressure and the residue was poured into water. The aqueous layer was extracted with ethyl acetate (200 mL×3). The combined organic layers were dried over sodium sulfate, filtered and concentrated. The crude residue was purified by column chromatography (silica gel, petroleum ether/ethyl acetate=1/1) to give ethyl 5-hydroxy-1-methyl-1H-pyrazole-3-carboxylate (5.20 g, 30.6 mmol, 61%) as a light-yellow solid. $^1$H NMR (500 MHz, Dimethylsulfoxide-d$_6$) δ 11.40 (s, 1H), 5.76 (s, 1H), 4.20 (q, J=7.0 Hz, 2H), 3.59 (s, 3H), 1.25 (t, J=7.0 Hz, 3H); LCMS (ESI) m/z: 171.1 [M+H]$^+$.

Step 2: Preparation of N-(5-(3-fluorobenzyl)pyridin-2-yl)-5-hydroxy-1-methyl-1H-pyrazole-3-carboxamide

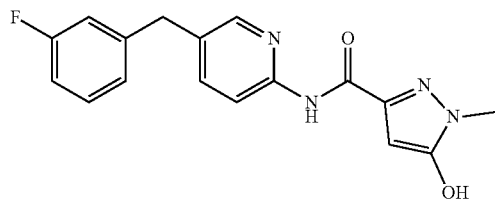 [SMILES: Cn1nc(C(=O)Nc2ccc(Cc3cccc(F)c3)cn2)cc1O]

To a stirred solution of 5-(3-fluorobenzyl)pyridin-2-amine (202 mg, 1.0 mmol) in 1,4-dioxane (5 mL) at room temperature under nitrogen was added trimethylaluminum (1.0 mL, 2 M in toluene) dropwise. The reaction mixture was stirred for 0.5 h, before ethyl 5-hydroxy-1-methyl-1H-pyrazole-3-carboxylate(170 mg, 1.0 mmol) in 1,4-dioxane (5 mL) was added. The reaction solution was stirred at 80° C. for 2 h. The reaction mixture was quenched with water and pH was adjusted to ~1-2 with dilute hydrochloric acid and concentrated to dryness. The crude residue was purified by prep-HPLC×2 (the crude sample was dissolved in minimal N,N-dimethylformamide and loaded onto Boston C18 21*250 mm 10 μm column. The mobile phase was acetonitrile/10 mM ammonium acetate aqueous solution) to afford N-(5-(3-chlorobenzyl)pyridin-2-yl)-5-hydroxy-1-methyl-1H-pyrazole-3-carboxamide (0.052 g, 0.16 mmol, 16%) as an off-white solid. $^1$H NMR (500 MHz, Dimethylsulfoxide-d$_6$) δ 9.26 (s, 1H), 8.25 (d, J=2.5 Hz, 1H), 8.07 (d, J=8.5 Hz, 1H), 7.69 (dd, J=8.5, 2.5 Hz, 1H), 7.36-7.31 (m, 1H), 7.12-7.09 (m, 2H), 7.03 (td, J=8.5, 2.0 Hz, 1H), 5.61 (s, 1H), 3.95 (s, 2H), 3.56 (s, 3H); LCMS (ESI) m/z: 327.1 [M+H]$^+$.

437

Example 107. Preparation of N-(5-(3-fluorobenzyl)pyridin-2-yl)-5-methyl isoxazole-3-carboxamide (107)

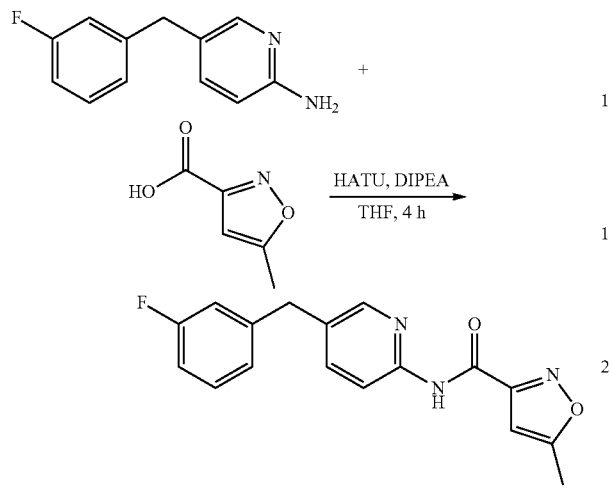

Step 1: Preparation of N-(5-(3-fluorobenzyl)pyridin-2-yl)-1-methyl-2-oxo-1,2-dihydropyridine-3-carboxamide

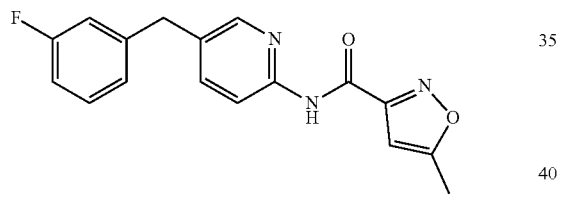

To a solution of 5-methylisoxazole-3-carboxylic acid (100 mg, 0.787 mmol) and diisopropylethylamine (305 mg, 2.36 mmol) in tetrahydrofuran (5 mL) at 20° C. was added 1-[bis(dimethylamino)methylene]-1H-1,2,3-triazolo[4,5-b]pyridinium 3-oxid hexafluorophosphate (449 mg, 1.18 mmol). The reaction mixture was stirred for 20 minutes before a solution of 5-(3-fluorobenzyl)pyridin-2-amine (159 mg, 0.787 mmol) in tetrahydrofuran (1.0 mL) was added. The reaction solution was stirred at 20° C. for 4 h. The volatiles were removed under reduced pressure and the residue was added to a mixture of dichloromethane (50 mL) and water (50 mL). The combined organic layers were dried over sodium sulfate, filtered and concentrated. The residue was purified by HPLC (the crude sample was dissolved in minimal N,N-dimethylformamide and loaded onto Boston C18 21*250 mm 10 μm column. The mobile phase was acetonitrile/10 mM ammonium acetate aqueous solution) to give to offer N-(5-(3-fluorobenzyl)pyridin-2-yl)-5-methylisoxazole-3-carboxamide (42.8 mg, 0.14 mmol, 17%) as a white solid. $^1$H NMR (400 MHz, Dimethylsulfoxide-$d_6$) δ 10.57 (s, 1H), 8.34 (s, 1H), 8.02 (d, J=12.0 Hz, 1H), 7.75 (q, J=5.2 Hz, 1H), 7.35 (q, J=8.0 Hz, 1H), 7.01-7.14 (m, 3H), 6.74 (s, 1H), 3.99 (s, 2H), 3.45 (s, 3H); LCMS (ESI) m/z: 312.1 [M+H]$^+$.

438

Example 108. Preparation of N-(5-(3-chlorobenzyl)pyridin-2-yl)-4-methyl-5-oxo-4,5-dihydropyrazine-2-carboxamide (108)

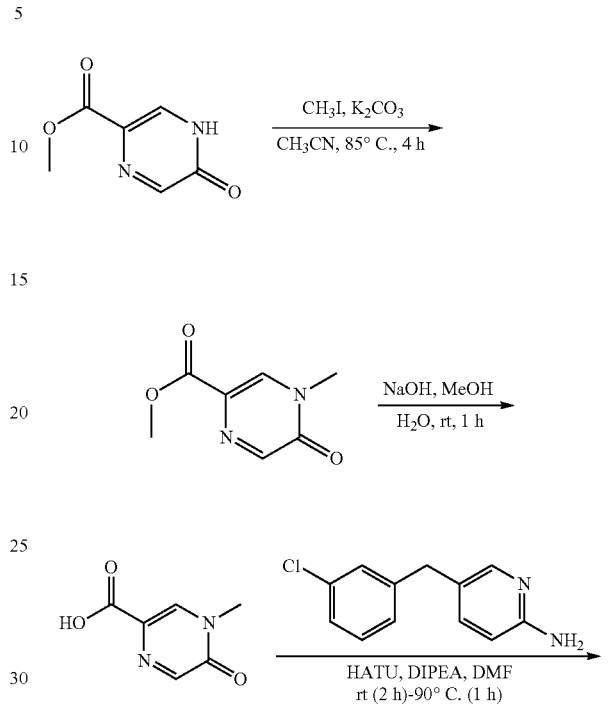

Step 1: Preparation of methyl 4-methyl-5-oxo-4,5-dihydropyrazine-2-carboxylate

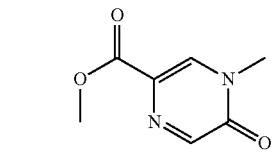

A solution of methyl 5-oxo-4,5-dihydropyrazine-2-carboxylate (1.00 g, 6.5 mmol), iodomethane (0.767 g, 5.4 mmol) and potassium carbonate (1.49 g, 10.8 mmol) in acetonitrile (27 mL) was stirred at 85° C. for 4 h. The reaction mixture was extracted with ethyl acetate (50 mL×2). The combined organic layers were washed with brine (50 mL), dried over sodium sulfate, filtered and concentrated. Purification by column chromatography (silica gel, petroleum ether/ethyl acetate=1/1) gives methyl 4-methyl-5-oxo-4,5-dihydropyrazine-2-carboxylate (0.480 g, 2.97 mmol, 45.7%) as a white solid. LCMS (ESI) m/z: 169.1 [M+H]$^+$.

Step 2: Preparation of 4-methyl-5-oxo-4,5-dihydropyrazine-2-carboxylic acid

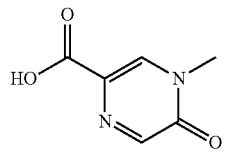

To a solution of methyl 4-methyl-5-oxo-4,5-dihydropyrazine-2-carboxylate (0.430 g, 2.56 mmol) in methanol (9 mL) and water (3 mL) was added sodium hydroxide (0.205 g, 5.12 mmol). The reaction mixture was stirred at room temperature for 1 h before aqueous 1 N hydrogen chloride was added and the pH was adjusted to 6. Concentration under reduced pressure gives 4-methyl-5-oxo-4,5-dihydropyrazine-2-carboxylic acid (0.660 g, crude) as a white solid. LCMS (ESI) m/z: 155.1 [M+H]+.

Step 3: Preparation of N-(5-(3-chlorobenzyl)pyridin-2-yl)-4-methyl-5-oxo-4,5-dihydropyrazine-2-carboxamide

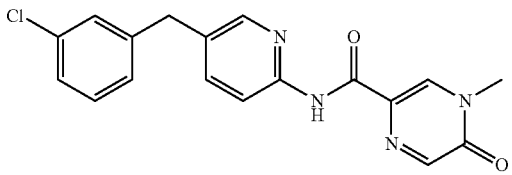

A solution of 4-methyl-5-oxo-4,5-dihydropyrazine-2-carboxylic acid (0.154 g, 1.0 mmol), 5-(3-chlorobenzyl)pyridin-2-amine (0.260 g, 1.2 mmol), 1-[bis(dimethylamino)methylene]-1H-1,2,3-triazolo[4,5-b]pyridinium 3-oxid hexafluorophosphate (0.570 g, 1.5 mmol) and N,N-diisopropylethylamine (0.387 g, 3 mmol) in N,N-dimethylformamide (4 mL) was stirred at room temperature for 2 h and then at 90° C. for 1 h. The reaction mixture was cooled to room temperature and the resulting precipitate was filtered and washed with water. Freeze drying yields N-(5-(3-chlorobenzyl)pyridin-2-yl)-4-methyl-5-oxo-4,5-dihydropyrazine-2-carboxamide (0.0756 g, 0.214 mmol, 21.4%) as a white solid. $^1$H NMR (500 MHz, Dimethylsulfoxide-d$_6$) δ 9.78 (s, 1H), 8.61 (s, 1H), 8.30 (d, J=1.5 Hz, 1H), 8.13 (d, J=8.5 Hz, 1H), 8.04 (s, 1H), 7.75 (dd, J=8.4, 2.0 Hz, 1H), 7.35-7.32 (m, 2H), 7.28-7.23 (m, 2H), 3.97 (s, 2H), 3.55 (s, 3H); LCMS (ESI) m/z: 355.1 [M+H]+.

Example 109. Preparation of 5-(3-fluorobenzyl)-N-(2-methyl-3-oxo-2,3-dihydropyridazin-4-yl)picolinamide (109)

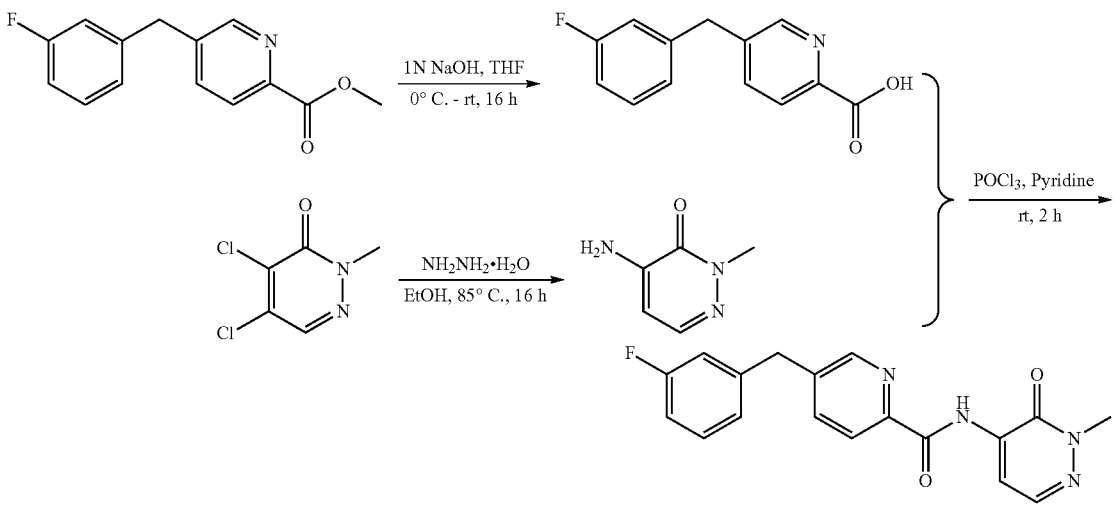

Step 1: Preparation of 5-(3-fluorobenzyl)picolinic acid

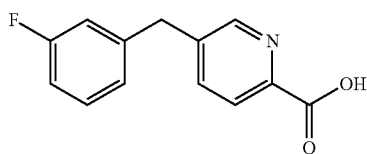 [SMILES: O=C(O)c1ccc(Cc2cccc(F)c2)cn1]

To a solution of methyl 5-(3-fluorobenzyl)picolinate (0.5 g, 2.04 mmol) in tetrahydrofuran (6 mL), at 0° C. was added aqueous sodium hydroxide solution (10 mL, 10 mmol, 1 M) dropwise. The reaction mixture was stirred at room temperature for 16 h before it was diluted with ethyl acetate/water (20 mL/20 mL) mixture and separated. The aqueous layer was acidified with 1 M hydrochloric acid aqueous solution (pH 2-3) and extracted with ethyl acetate (20 mL×2). The combined organic extracts were washed with brine (20 mL), dried over sodium sulfate, filtered and concentrated to give 5-(3-fluorobenzyl)picolinic acid (0.41 g, 1.77 mmol, 87%) as a white solid. LCMS (ESI) m/z: 232.1 [M+H]+.

Step 2: Preparation of 4-amino-2-methylpyridazin-3(2H)-one

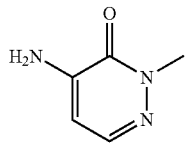

To a solution of 4,5-dichloro-2-methylpyridazin-3(2H)-one (1.5 g, 8.38 mmol) in ethanol (55 mL) at 85° C. was added hydrazine hydrate (4.2 g, 83.8 mmol). The reaction mixture was stirred for 16 h. The volatiles were removed and the crude residue was purified by Combi-Flash (Biotage, 40 g silica gel, eluted with ethyl acetate in petroleum ether from 40% to 60%) to give 4-amino-2-methylpyridazin-3(2H)-one (0.63 g, 5.04 mmol, 60.2%) as a yellow solid. LCMS (ESI) m/z: 126.2 [M+H]$^+$.

Step 3: Preparation of 5-(3-fluorobenzyl)-N-(2-methyl-3-oxo-2,3-dihydropyridazin-4-yl)picolinamide

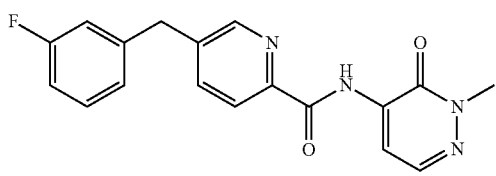 [SMILES: Cn1nccc(NC(=O)c2ccc(Cc3cccc(F)c3)cn2)c1=O]

To a mixture of 5-(3-fluorobenzyl)picolinic acid (0.2 g, 0.86 mmol) and 4-amino-2-methylpyridazin-3(2H)-one (0.1 g, 0.86 mmol) in dry pyridine (8 mL) was added phosphorus oxychloride (0.24 mL, 2.60 mmol) dropwise. The reaction mixture was stirred at room temperature for 2 h. The volatiles were removed and the crude residue was diluted with dichloromethane/water (20 mL/20 mL) mixture and extracted with dichloromethane (20 mL×2) twice. The combined organic layers were dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give 5-(3-fluorobenzyl)-N-(2-methyl-3-oxo-2,3-dihydropyridazin-4-yl)picolinamide (0.095 g, 0.28 mmol, 32%) as a white solid. $^1$H NMR (500 MHz, trifluoroacetic acid-d) δ 9.42 (s, 1H), 9.31 (d, 1H, J=8.5 Hz), 9.13 (d, 1H, J=8 Hz), 9.08 (d, 1H, J=5 Hz), 8.80 (d, 1H, J=5 Hz), 7.87-7.96 (m, 1H), 7.52-7.61 (m, 2H), 7.46 (d, 1H, J=9 Hz), 4.89 (s, 2H), 4.60 (s, 3H); LCMS (ESI) m/z: 339.1 [M+H]$^+$.

Example 110. Preparation of N-(5-(3-chlorobenzyl)pyridin-2-yl)-4-methoxy-2-(methoxymethyl)pyrimidine-5-carboxamide (110)

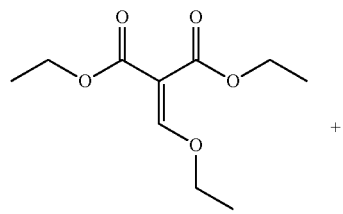

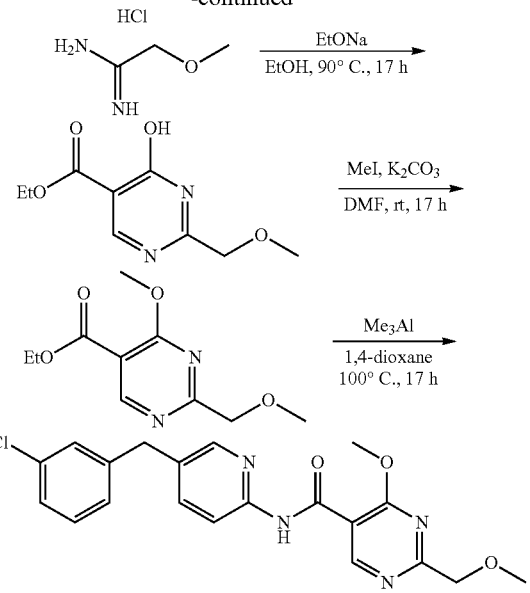

Step 1: Preparation of ethyl 4-hydroxy-2-(methoxymethyl)pyrimidine-5-carboxylate

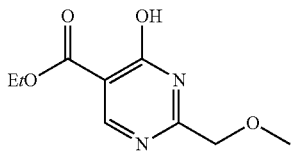

A mixture of diethyl 2-(ethoxymethylene)malonate (5 g, 23.2 mmol), 2-methoxyacetimidamide hydrochloride (2.88 g, 23.2 mmol) and sodium ethoxide (3.15 g, 46.3 mmol) in anhydrous ethanol (200 mL) was stirred at 90° C. for 17 h. The reaction mixture was concentrated, to give ethyl 4-hydroxy-2-(methoxymethyl)pyrimidine-5-carboxylate (4 g, 18.8 mmol, 81%) as a white solid. LCMS (ESI) m/z: 213.1 [M+H]$^+$.

Step 2: Preparation of ethyl 4-methoxy-2-(methoxymethyl)pyrimidine-5-carboxylate

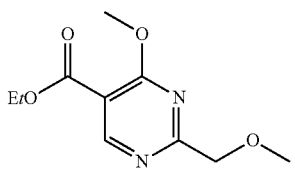 [SMILES: CCOC(=O)c1cnc(COC)nc1OC]

A mixture of ethyl 4-hydroxy-2-(methoxymethyl)pyrimidine-5-carboxylate (1.6 g, 7.55 mmol), iodomethane (1.61 g, 11.32 mmol) and potassium carbonate (2.08 g, 15.1 mmol) in anhydrous N,N-dimethylformamide (30 mL) was stirred at 20° C. for 17 h. The reaction mixture was diluted with water and extracted with ethyl acetate (100 mL×2). The combined organic layers were washed with water (200 mL) and brine (200 mL), dried over anhydrous sodium sulfate, Step 3: Preparation of N-(5-(3-chlorobenzyl)pyridin-2-yl)-4-methoxy-2-(methoxymethyl)pyrimidine-5-carboxamide

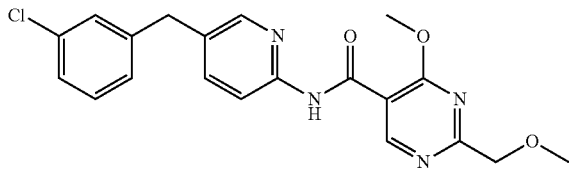 [SMILES: COCc1ncc(C(=O)Nc2ccc(Cc3cccc(Cl)c3)cn2)c(OC)n1]

To a mixture of 5-(3-chlorobenzyl)pyridin-2-amine (0.194 g, 0.88 mmol) in dry 1,4-dioxane (2 mL) was added trimethylaluminum (0.44 mL, 0.88 mmol, 2 M in toluene). The mixture was stirred at 20° C. for 0.5 h before a solution of ethyl 4-methoxy-2-(methoxymethyl)pyrimidine-5-carboxylate (0.050 g, 0.22 mmol) in dry 1,4-dioxane (2 mL) was added. The reaction mixture and stirred at 100° C. for 17 h. The reaction solution was extracted with ethyl acetate (20 mL×2). The combined organic layers were washed with water (50 mL) and brine (50 mL) dried over anhydrous sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chlorobenzyl)pyridin-2-yl)-4-methoxy-2-(methoxymethyl)pyrimidine-5-carboxamide (2.0 mg, 0.005 mmol, 2.2%) as a white solid. $^1$H NMR (500 MHz, Dimethylsulfoxide-$d_6$) δ 11.68 (s, 1H), 8.80 (s, 1H), 8.31 (d, J=1.8 Hz, 1H), 8.18 (d, J=8.5 Hz, 1H), 7.73 (dd, J=8.5, 2.2 Hz, 1H), 7.42-7.17 (m, 4H), 4.63 (s, 2H), 3.98 (s, 2H), 3.58 (s, 3H), 3.39 (s, 3H); LCMS (ESI) m/z: 399.1 [M+H]$^+$.

Example 111. Preparation of N-(5-(3-chloro-5-fluorobenzyl)pyridin-2-yl)-6-(hydroxymethyl)nicotinamide (111)

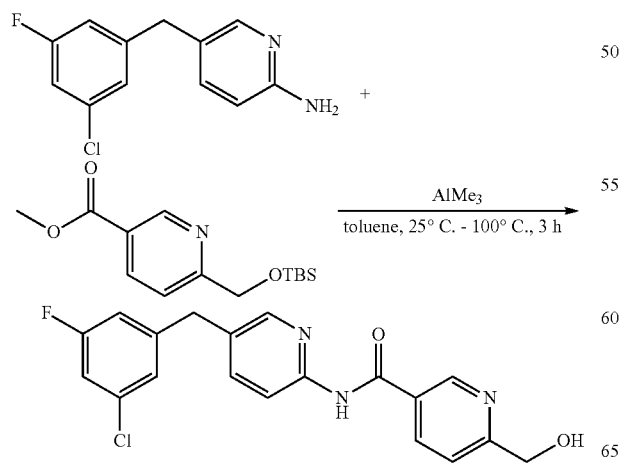

Step 1: Preparation of N-(5-(3-chloro-5-fluorobenzyl)pyridin-2-yl)-6 (hydroxymethyl)nicotinamide

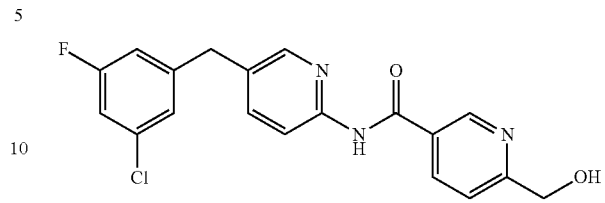

To a solution of 5-(3-chloro-5-fluorobenzyl)pyridin-2-amine (0.227 g, 0.96 mmol) in toluene (5 mL at room temperature) was added trimethylaluminum (0.5 mL, 1.0 mmol, 2 M in toluene) slowly under argon. The reaction mixture was stirred at room temperature for 1 h before methyl 6-((tert-butyldimethylsilyloxy)methyl)nicotinate (0.225 g, 0.8 mmol) in toluene (5 mL) was added. The resulting mixture was heated to 100° C. and stirred for 3 h. Reaction was quenched with methanol and aqueous 2 N hydrochloric acid. The volatiles were removed in vacuo. Water (20 mL) was added and the mixture was extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chloro-5-fluorobenzyl)pyridin-2-yl)-6-(hydroxymethyl)nicotinamide (0.113 g, 0.30 mmol, 38%) as a white solid. $^1$H NMR (400 MHz, Dimethylsulfoxide-$d_6$) δ 11.11 (s, 1H), 9.07 (s, 1H), 8.41 (dd, $J_1$=2.0 Hz, $J_2$=8.4 Hz, 1H), 8.36 (d, J=2.0 Hz, 1H), 8.11 (d, J=11.0 Hz, 1H), 7.77 (dd, $J_1$=2.4 Hz, $J_2$=8.4 Hz, 1H), 7.63 (d, J=8.0 Hz, 1H), 7.24-7.28 (m, 2H), 7.16 (d, J=9.6 Hz, 1H), 4.66 (s, 2H), 3.99 (s, 2H); LCMS (ESI) m/z: 372.1 [M+H]$^+$.

Example 112. Preparation of N-(5-(3-chloro-4-fluorobenzyl)pyridin-2-yl)-6-(hydroxymethyl)nicotinamide (112)

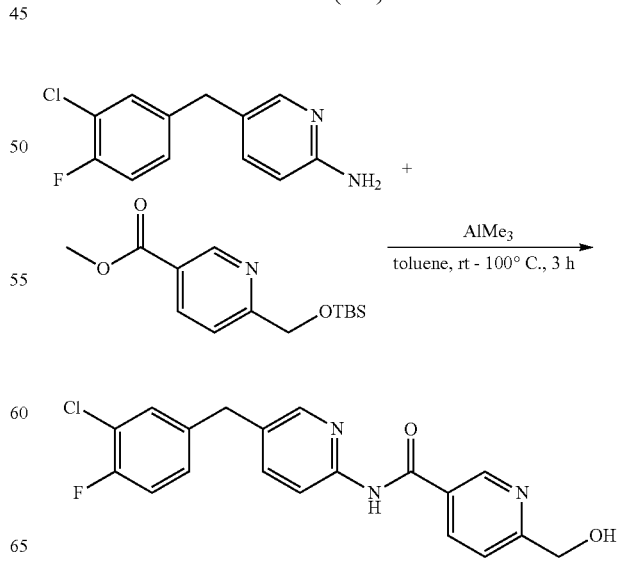

Step 1: Preparation of N-(5-(3-chloro-4-fluorobenzyl)pyridin-2-yl)-6 (hydroxymethyl)nicotinamide

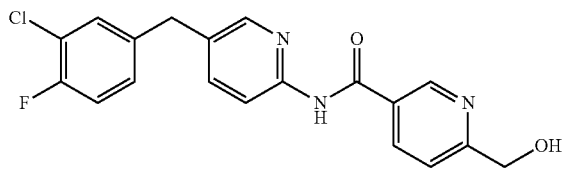 [SMILES: O=C(Nc1ccc(Cc2ccc(F)c(Cl)c2)cn1)c1ccc(CO)nc1]

To a solution of methyl 5-(3-chloro-4-fluorobenzyl)pyridin-2-amine (0.227 g, 0.96 mmol) in toluene (5 mL) at room temperature was added trimethylaluminum (0.5 mL, 1.0 mmol, 2 M in toluene) slowly under argon. The reaction mixture was stirred at room temperature for 1 h before methyl 6-((tert-butyldimethylsilyloxy)methyl)nicotinate (0.225 g, 0.8 mmol) in toluene (5 mL) was added. The resulting mixture was heated to 100° C. and stirred for 3 h. Reaction was cooled to room temperature and quenched with methanol and aqueous 2 N hydrochloric acid. The volatiles were concentrated in vacuo and water (20 mL) was added. The aqueous layer were extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chloro-4-fluorobenzyl)pyridin-2-yl)-6-(hydroxymethyl)nicotinamide (0.159 g, 0.42 mmol, 53%) as a light-yellow solid. $^1$H NMR (500 MHz, Dimethylsulfoxide-$d_6$) δ 11.15 (s, 1H), 9.09 (d, J=1.5 Hz, 1H), 8.45 (dd, $J_1$=2.0 Hz, $J_2$=8.0 Hz, 1H), 8.36 (d, J=1.5 Hz, 1H), 8.11 (d, J=8.5 Hz, 1H), 7.77 (dd, $J_1$=2.0 Hz, $J_2$=8.5 Hz, 1H), 7.67 (d, J=8.5 Hz, 1H), 7.53 (dd, $J_1$=2.0 Hz, $J_2$=7.5 Hz, 1H), 7.36 (t, J=9.0 Hz, 1H), 7.28-7.31 (m, 1H), 4.69 (s, 2H), 3.98 (s, 2H); LCMS (ESI) m/z: 372.1 [M+H]$^+$.

Example 113. Preparation of N-(5-(3-cyano-4-fluorobenzyl)pyridin-2-yl)-2-methylpyrimidine-4-carboxamide (113)

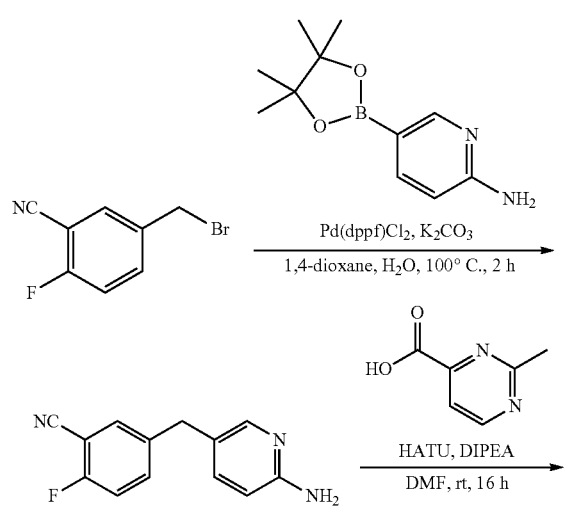

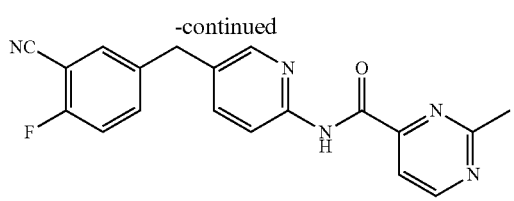

Step 1: Preparation of 5-((6-aminopyridin-3-yl)methyl)-2-fluorobenzonitrile

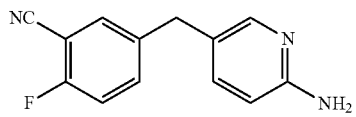 [SMILES: N#Cc1cc(Cc2ccc(N)nc2)ccc1F]

To a solution of 5-(bromomethyl)-2-fluorobenzonitrile (1.07 g, 5 mmol) and 5-(4,4,5,5-tetramethyl-1,3-dioxolan-2-yl)pyridin-2-amine (1.34 g, 6 mmol) and potassium carbonate (1.38 g, 10 mmol) in 1,4-dioxane (30 mL) and water (10 mL) was added [1,1'-bis(diphenylphosphino)ferrocene] palladium(II) dichloride (0.366 g, 0.5 mmol) under argon. The reaction mixture was stirred at 100° C. for 2 h. The volatiles were concentrated and water (50 mL) was added. The aqueous layer was extracted with ethyl acetate (80 mL×3). The combined organic layers were dried over sodium sulfate, filtered and concentrated. The crude product was purified by column chromatography (silica gel, petroleum ether/ethyl acetate from 1/1 to 0/1) to give 5-((6-aminopyridin-3-yl)methyl)-2-fluorobenzonitrile (1.01 g, 4.4 mmol, 89%) as a yellow solid. LCMS (ESI) m/z: 228.1 [M+H]$^+$.

Step 2: Preparation of N-(5-(3-cyano-4-fluorobenzyl)pyridin-2-yl)-2-methylpyrimidine-4-carboxamide

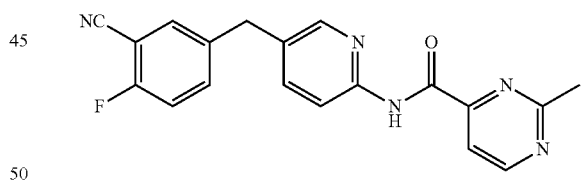

To a solution of 5-((6-aminopyridin-3-yl)methyl)-2-fluorobenzonitrile (0.227 mg, 1.0 mmol), 2-methylpyrimidine-4-carboxylic acid (276 mg, 2.0 mmol) and N,N-diisopropylethylamine (388 mg, 3.0 mmol) in N,N-dimethylformamide (10 mL) at room temperature was added 1-[bis(dimethylamino) methylene]-1H-1,2,3-triazolo[4,5-b]pyridinium 3-oxid hexafluorophosphate (0.570 g, 1.5 mmol) under nitrogen. The reaction mixture was stirred at room temperature for 16 h. The reaction mixture was diluted with ethyl acetate (100 mL) and washed with brine (30 mL×3). The combined organic layers were dried over sodium sulfate, filtered and concentrated. The crude sample was dissolved in minimal N,N-dimethylformamide and purified via prep-HPLC (Boston C18 21*250 mm 1011M column. The mobile phase was acetonitrile/10 mM ammonium acetate aqueous solution) to give N-(5-(3-cyano-4-fluorobenzyl)pyridin-2- yl)-2-methylpyrimidine-4-carboxamide (0.133 g, 0.38 mmol, 38%) as a white solid. ¹H NMR (400 MHz, Dimethylsulfoxide-d₆) δ 10.37 (s, 1H), 9.03 (d, J=5.2 Hz, 1H), 8.36 (d, J=1.6 Hz, 1H), 8.17 (d, J=8.4 Hz, 1H), 7.94 (d, J=4.8 Hz, 1H), 7.88 (dd, J₁=2.0 Hz, J₂=7.6 Hz, 1H), 7.79 (dd, =2.0 Hz, J₂=8.4 Hz, 1H), 7.68-7.72 (m, 1H), 7.46 (t, J=8.8 Hz, 1H), 4.02 (s, 2H), 2.77 (s, 3H); LCMS (ESI) m/z: 348.1 [M+H]⁺.

Example 114. Preparation N-(5-(3-chlorobenzyl)pyridin-2-yl)-2-methylpyrimidine-4-carboxamide (114)

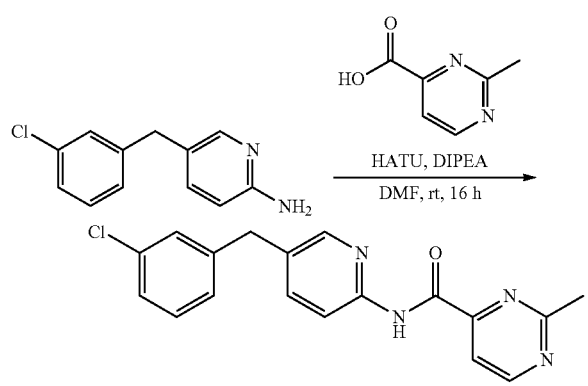

Step 1: Preparation of N-(5-(3-chlorobenzyl)pyridin-2-yl)-2-methylpyrimidine-4-carboxamide

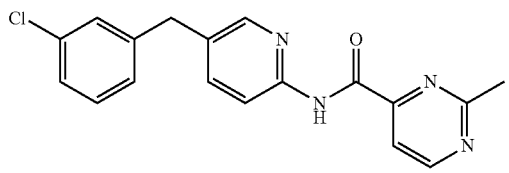 [SMILES: Cc1nccc(C(=O)Nc2ccc(Cc3cccc(Cl)c3)cn2)n1]

To a solution of 5-(3-chlorobenzyl)pyridin-2-amine (0.132 g, 0.6 mmol), 2-methylpyrimidine-4-carboxylic acid (0.166 g, 1.2 mmol) and N,N-diisopropylethylamine (0.233 g, 1.8 mmol) in N,N-dimethylformamide (10 mL) at room temperature was added 1-[bis(dimethylamino)methylene]-1H-1,2,3-triazolo[4,5-b]pyridinium 3-oxid hexafluorophosphate (0.342 g, 0.9 mmol) under nitrogen. The reaction mixture was stirred at room temperature for 16 h. The reaction mixture was, the mixture was diluted with ethyl acetate (100 mL) and washed with brine (30 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-(3-chlorobenzyl)pyridin-2-yl)-2-methylpyrimidine-4-carboxamide (0.0496 g, 0.15 mmol, 24%) as a yellow solid. ¹H NMR (500 MHz, Dimethylsulfoxide-d₆) δ 10.39 (s, 1H), 9.05 (d, J=5.0 Hz, 1H), 8.37 (d, J=2.0 Hz, 1H), 8.19 (d, J=9.0 Hz, 1H), 7.97 (d, J=5.0 Hz, 1H), 7.81 (dd, J₁=2.5 Hz, J₂=8.5 Hz, 1H), 7.33-7.37 (m, 2H), 7.25-7.29 (m, 2H), 4.00 (s, 2H), 2.79 (s, 3H); LCMS (ESI) m/z: 339.1 [M+H]⁺.

Example 115. Preparation of 5-(3-Fluorobenzyl)-N-(2-methylpyrimidin-4-yl)picolinamide (115)

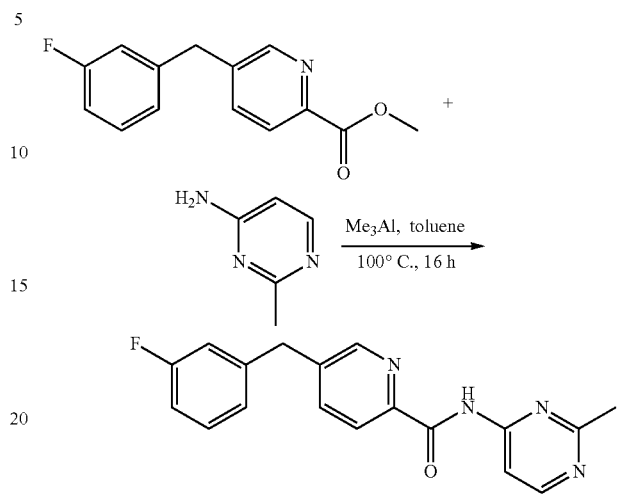

Step 1: Preparation of 5-(3-fluorobenzyl)-N-(2-methylpyrimidin-4-yl)picolinamide

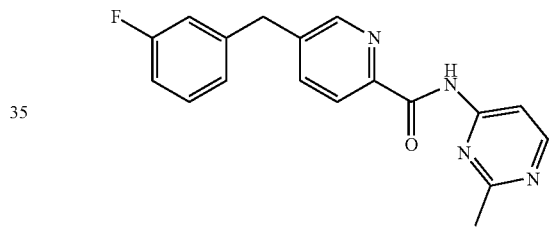

To a solution of 2-methylpyrimidin-4-amine (0.178 g, 1.63 mmol) in anhydrous toluene (12 mL) at room temperature was added trimethylaluminum (0.81 mL, 1.63 mmol, 2 M in toluene). The reaction mixture was stirred at room temperature for 1 h before methyl 5-(3-fluorobenzyl)picolinate (0.200 g, 0.82 mmol) was added. The reaction mixture was stirred at 100° C. for 16 h. The reaction solution was cooled to room temperature and diluted with water (200 mL). The aqueous layer was extracted with ethyl acetate (80 mL×3). The combined organic layers were washed with brine (100 mL), dried over anhydrous sodium sulfate, filtered and concentrated. The crude sample was dissolved in minimal N,N-dimethylformamide and purified via prep-HPLC Boston C18 21*250 mm 10 μm column. The mobile phase was acetonitrile/10 mM ammonium acetate aqueous solution) to give 5-(3-fluorobenzyl)-N-(2-methylpyrimidin-4-yl)picolinamide (0.099 g, 0.31 mmol, 37%) as a white solid. ¹H NMR (400 MHz, Dimethylsulfoxide-d₆) δ 10.43 (s, 1H), 8.72 (d, J=1.6 Hz, 1H), 8.66 (d, J=1.6 Hz, 1H), 8.14 (d, J=8.0 Hz, 1H), 8.04 (d, J=2.0 Hz, 1H), 7.97 (dd, J₁=2.0 Hz, J₂=8.0 Hz, 1H), 7.40-7.35 (m, 1H), 7.20-7.15 (m, 2H), 7.09-7.04 (m, 1H), 4.15 (s, 2H), 2.56 (s, 3H); LCMS (ESI) m/z: 323.0 [M+H]⁺.

Example 116. Preparation of N-(5-(4-fluorobenzyl)pyridin-2-yl)-6-(hydroxymethyl)nicotinamide (116)

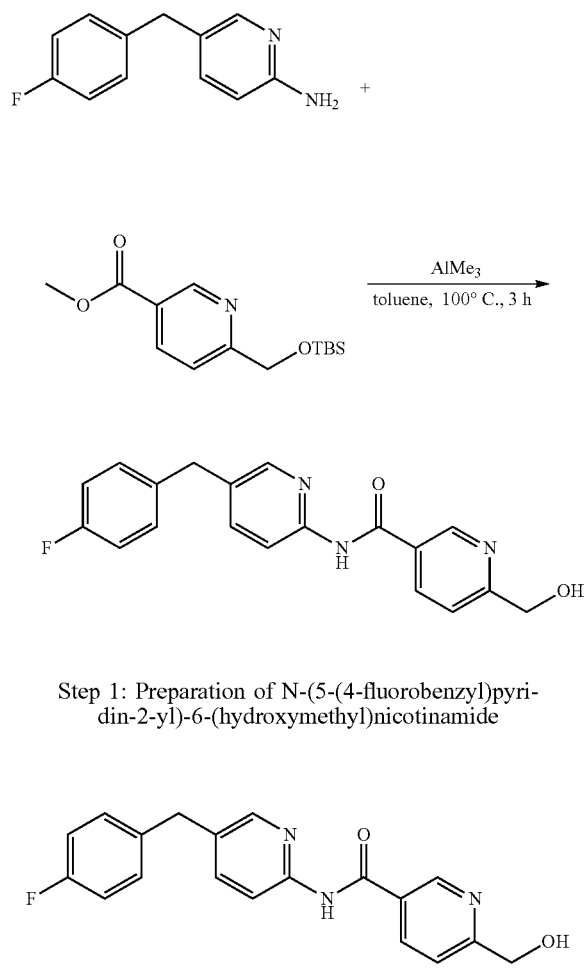

Step 1: Preparation of N-(5-(4-fluorobenzyl)pyridin-2-yl)-6-(hydroxymethyl)nicotinamide To a solution of 5-(4-fluorobenzyl)pyridin-2-amine (0.194 g, 0.96 mmol) in toluene (5 mL) at room temperature was added trimethylaluminum (0.5 mL, 1.0 mmol, 2 M in toluene) slowly under argon. The reaction mixture was stirred at room temperature for 1 h before methyl 6-((tert-butyldimethylsilyloxy)methyl)nicotinate (0.225 g, 0.8 mmol) in toluene (5 mL) was added. The resulting solution was heated to 100° C. and stirred for 3 h. The reaction mixture was quenched with methanol and aqueous 2 N hydrochloric acid. The volatiles were removed in vacuo and water (20 mL) was added. The aqueous layer was extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(4-fluorobenzyl)pyridin-2-yl)-6-(hydroxymethyl)nicotinamide (176.2 mg, 0.52 mmol, 65%) as a yellow solid. $^1$H NMR (400 MHz, Dimethylsulfoxide-$d_6$) δ 11.12 (s, 1H), 9.07 (s, 1H), 8.44 (dd, $J_1$=2.0 Hz, $J_2$=8.0 Hz, 1H), 8.32 (d, J=2.0 Hz, 1H), 8.09 (d, J=8.8 Hz, 1H), 7.72 (dd, $J_1$=2.0 Hz, $J_2$=8.4 Hz, 1H), 7.65 (d, J=8.0 Hz, 1H), 7.28-7.31 (m, 2H), 7.10-7.15 (m, 2H), 4.67 (s, 2H), 3.96 (s, 2H); LCMS (ESI) m/z: 338.0 [M+H]$^+$.

Example 117. Preparation of 5-fluoro-N-(5-(3-fluorobenzyl)pyridin-2-yl)-1-methyl-6-oxo-1,6-dihydropyridine-3-carboxamide (117)

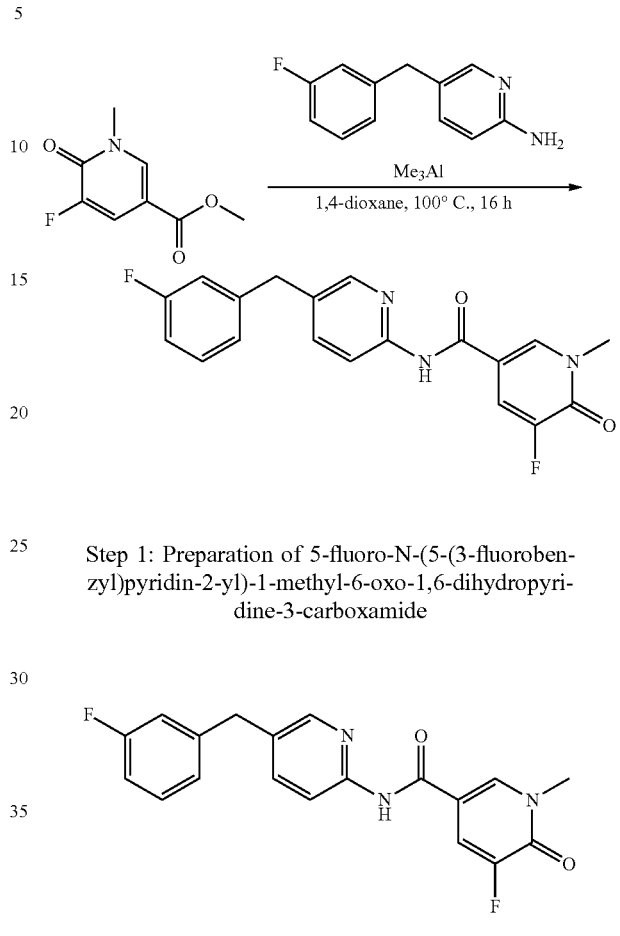

Step 1: Preparation of 5-fluoro-N-(5-(3-fluorobenzyl)pyridin-2-yl)-1-methyl-6-oxo-1,6-dihydropyridine-3-carboxamide To a solution of 5-(3-fluorobenzyl)pyridin-2-amine (300 mg, 1.48 mmol) in 1,4-dioxane (6 mL) was added trimethylaluminum (0.72 mL, 1.44 mmol, 2 M in toluene) slowly at room temperature under argon. The mixture was stirred at room temperature for 30 minutes before methyl 5-fluoro-1-methyl-6-oxo-1,6-dihydropyridine-3-carboxylate (67 mg, 0.36 mmol) in 1,4-dioxane (2 mL) was added. The resulting mixture was heated to 100° C. and stirred for 16 h. The reaction solution was cooled to room temperature and was quenched with hydrochloric acid (0.5 N, 25 mL) and ethyl acetate (50 mL). The organic was washed with hydrochloric acid (0.5 N, 25 mL×2), and brine (25 mL), dried over sodium sulfate, filtered and concentrated. The residue was purified by column chromatography (silica gel, ethyl acetate/petroleum ether=2/1). The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give 5-fluoro-N-(5-(3-fluorobenzyl)pyridin-2-yl)-1-methyl-6-oxo-1,6-dihydropyridine-3-carboxamide (70 mg, 0.20 mmol, 54.8%) as a white solid. $^1$H NMR (500 MHz, Dimethylsulfoxide-$d_6$) δ 10.66 (s, 1H), 8.57 (s, 1H), 8.32 (d, J=1.8 Hz, 1H), 8.04 (d, J=8.5 Hz, 1H), 7.96 (dd, J=11.0, 2.2 Hz, 1H), 7.73 (dd, J=8.6, 2.2 Hz, 1H), 7.35 (d, J=6.4 Hz, 1H), 7.21-7.08 (m, 2H), 7.04 (s, 1H), 3.98 (s, 2H), 3.58 (s, 3H); LCMS (ESI) m/z: 356.0 [M+H]$^+$.

451

Example 118. Preparation of N-(5-(3-fluorobenzyl)pyridin-2-yl)-1,5-dimethyl-6-oxo-1,4,5,6-tetrahydropyridazine-3-carboxamide (118)

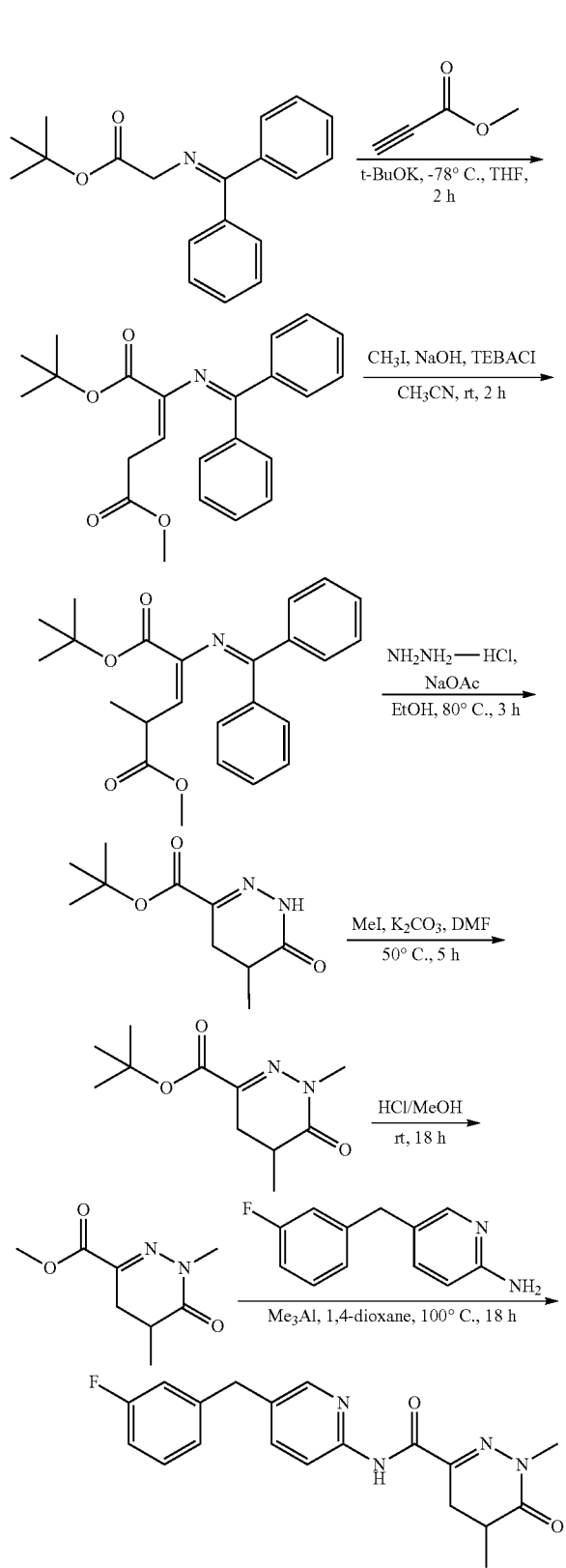

452

Step 1: Preparation of (E)-1-tert-butyl 5-methyl 2-(diphenylmethyleneamino)pent-2-enedioate

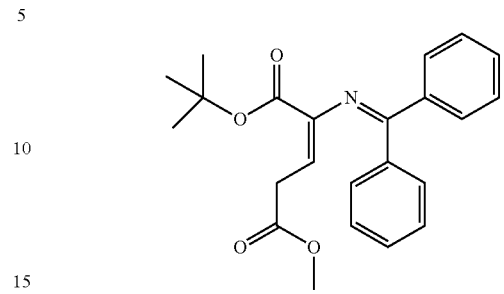

To a solution of tert-butyl 2-(diphenylmethyleneamino) acetate (5.00 g, 16.9 mmol) in tetrahydrofuran (100 mL) at −78° C. was added potassium tert-butoxide (2.10 g, 18.7 mmol). The reaction mixture was stirred for 10 minutes before methyl propiolate (1.57 g, 18.7 mmol) was added under nitrogen. The reaction mixture was stirred for 2 h before it was warmed to room temperature and diluted with ice-water (100 mL). The aqueous phases were extracted with ethyl acetate (200 mL×3). The combined organic layers were washed with water (200 mL×3) and brine (200 mL×3), dried over sodium sulfate, filtered and concentrated in vacuo. The residue was purified by column chromatography (silica gel, petroleum ether/ethyl acetate=20/1) to offer (E)-1-tert-butyl 5-methyl 2-(diphenylmethyleneamino)pent-2-enedioate (4.90 g, 12.93 mmol, 76%) as a yellow oil. LCMS (ESI) m/z: 380.2 [M+H]$^+$.

Step 2: Preparation of (E)-1-tert-butyl 5-methyl 2-(diphenylmethyleneamino)-4-methylpent-2-enedioate

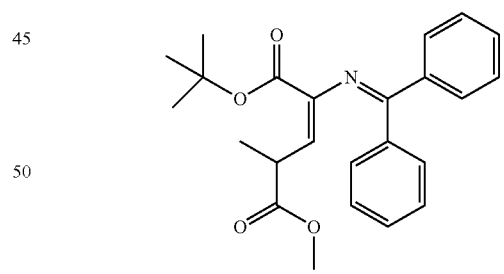

To a solution of (E)-1-tert-butyl 5-methyl 2-(diphenylmethyleneamino)pent-2-enedioate (3.00 g, 7.92 mmol) in acetonitrile (75 mL) at room temperature was added sequentially sodium hydroxide (0.38 g, 9.50 mmol), triethylbenzyl ammonium chloride (0.22 g, 0.95 mmol) and iodomethane (1.35 g, 9.50 mmol). The reaction mixture was stirred at this temperature for 2 h before it was filtered. The filtrate was concentrated, and the residue was purified by column chromatography (silica gel, petroleum ether/ethyl acetate=50/1) to offer (E)-1-tert-butyl 5-methyl 2-(diphenylmethyleneamino)-4-methylpent-2-enedioate (1.2 g, 3.05 mmol, 38.5%) as a yellow oil. LCMS (ESI) m/z: 394.1 [M+H]$^+$.

Step 3: Preparation of tert-butyl 5-methyl-6-oxo-1,4,5,6-tetrahydropyridazine-3-carboxylate

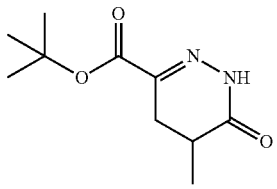

To a solution of (E)-1-tert-butyl 5-methyl 2-(diphenylmethyleneamino)-4-methylpent-2-enedioate (2.64 g, 6.72 mmol) in ethanol (350 mL) at room temperature was added hydrazine monohydrochloride (1.83 g, 26.87 mmol) and sodium acetate (2.20 g, 26.87 mmol). The reaction mixture was stirred at 80° C. for 3 h. The reaction mixture was cooled to room temperature and concentrated. The residue was purified by column chromatography (silica gel, petroleum ether/ethyl acetate=6/1) to offer tert-butyl 5-methyl-6-oxo-1,4,5,6-tetrahydropyridazine-3-carboxylate (1.00 g, 4.72 mmol, 70.2%) as a white solid. LCMS (ESI) m/z: 213.3 [M+H]+.

Step 4: Preparation of tert-butyl 1,5-dimethyl-6-oxo-1,4,5,6-tetrahydropyridazine-3-carboxylate

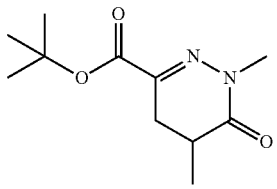 [SMILES: CC1CC(C(=O)OC(C)(C)C)=NN(C)C1=O]

A mixture of tert-butyl 5-methyl-6-oxo 1,4,5,6-tetrahydropyridazine-3-carboxylate (462 mg, 2.18 mmol), iodomethane (618 mg, 4.36 mmol) and potassium carbonate (903 mg, 6.54 mmol) in N,N-dimethylformamide (10 mL) was stirred at 50° C. for 5 h. The reaction mixture was cooled to room temperature and it was diluted with ethyl acetate (100 mL). The combined organic layers were washed with water (50 mL) and brine (50 mL), dried over sodium sulfate, filtered and concentrated to afford tert-butyl 1,5-dimethyl-6-oxo-1,4,5,6-tetrahydropyridazine-3-carboxylate (478 mg, 2.12 mmol, crude) as a pale-yellow solid. LCMS (ESI) m/z: 227.2 [M+H]+.

Step 5: Preparation of methyl 1,5-dimethyl-6-oxo-1,4,5,6-tetrahydropyridazine-3-carboxylate

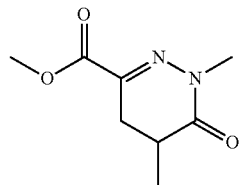

A solution of tert-butyl 1,5-dimethyl-6-oxo-1,4,5,6-tetrahydropyridazine-3-carboxylate (478 mg, 2.12 mmol) in hydrochloric acid (3 M in methanol, 20 mL) was stirred room temperature for 18 h. The reaction mixture was concentrated, and the residue was purified by column chromatography (silica gel, ethyl acetate/petroleum ether=1/1) to offer 1,5-dimethyl-6-oxo-1,4,5,6-tetrahydropyridazine-3-carboxylate (258 mg, 1.40 mmol, 64.3%) as a pale-yellow solid. LCMS (ESI) m/z: 185.2 [M+H]+.

Step 6: Preparation of N-(5-(3-fluorobenzyl)pyridin-2-yl)-1,5-dimethyl-6-oxo-1,4,5,6-tetrahydropyridazine-3-carboxamide

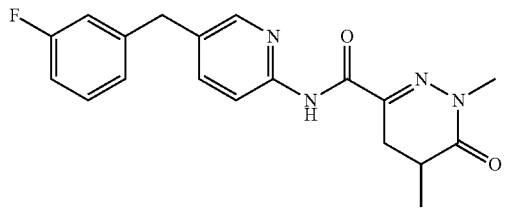 [SMILES: CC1CC(C(=O)Nc2ccc(Cc3cccc(F)c3)cn2)=NN(C)C1=O]

To a solution of 5-(3-fluorobenzyl)pyridin-2-amine (152 mg, 0.75 mmol) in 1,4-dioxane (4 mL) was added trimethylaluminum (0.38 mL, 0.75 mmol, 2 M in toluene) slowly at room temperature under argon. The mixture was stirred at room temperature for 30 minutes before methyl-1,5-dimethyl-6-oxo-1,4,5,6-tetrahydropyridazine-3-carboxylate (92 mg, 0.5 mmol) in 1,4-dioxane (1 mL) was added. The resulting mixture was heated to 100° C. and stirred for 18 h. The reaction mixture was cooled to room temperature, the mixture was quenched with aqueous hydrochloric acid (0.5 N, 25 mL) and ethyl acetate (50 mL). The combined organic layers were washed with hydrochloric acid (0.5 N, 25 mL×2), and brine (25 mL), dried over sodium sulfate, filtered and concentrated. The residue was first purified by column chromatography (silica gel, ethyl acetate/petroleum ether=2/1) and by prep-HPLC (Sunfire prep C18 10 μm OBD 19*250 mm; mobile phase: [water (0.05% trifluoroacetic acid)-acetonitrile]; B %: 60%-88%, 15 minutes) to offer N-(5-(3-fluorobenzyl)pyridin-2-yl)-1,5-dimethyl-6-oxo-1,4,5,6-tetrahydropyridazine-3-carboxamide (11 mg, 0.031 mmol, 6.21%) as a white solid. 1H NMR (500 MHz, Dimethylsulfoxide-d6) δ 9.76 (s, 1H), 8.30 (d, J=2.0 Hz, 1H), 8.03 (d, J=8.5 Hz, 1H), 7.74 (dd, J=8.5, 2.2 Hz, 1H), 7.42-7.26 (m, 1H), 7.12 (dd, J=10.5, 4.3 Hz, 2H), 7.04 (d, J=2.3 Hz, 1H), 3.97 (s, 2H), 3.37 (s, 3H), 3.08 (dd, J=17.3, 6.9 Hz, 1H), 2.59 (d, J=6.6 Hz, 1H), 2.49-2.39 (m, 1H), 1.13 (d, J=6.9 Hz, 3H); LCMS (ESI) m/z: 355.1 [M+H]+.

Example 119. Preparation of N-(5-(3-fluorobenzyl)pyridin-2-yl)-6-(hydroxymethyl)nicotinamide (119)

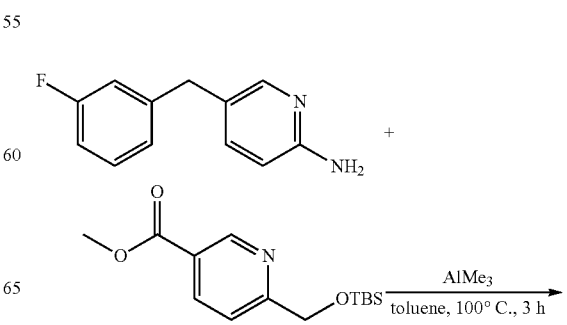

-continued

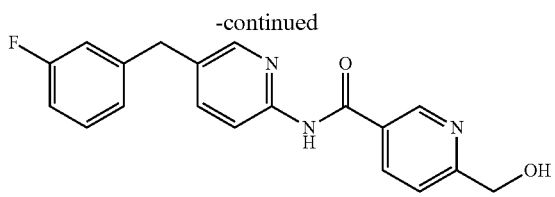

Step 1: Preparation of N-(5-(3-fluorobenzyl)pyridin-2-yl)-6-(hydroxymethyl)nicotinamide

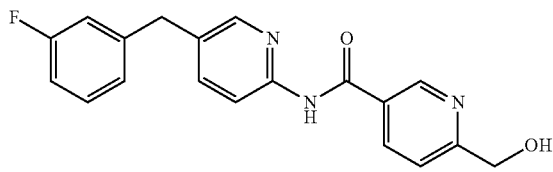 [SMILES: O=C(Nc1ccc(Cc2cccc(F)c2)cn1)c1ccc(CO)nc1]

To a solution of methyl 5-(3-fluorobenzyl)pyridin-2-amine (0.194 g, 0.96 mmol) in toluene (5 mL) at room temperature was added trimethylaluminum (0.5 mL, 1.0 mmol, 2 M in toluene) slowly under argon. The reaction mixture was stirred at room temperature for 1 h before methyl 6-((tert-butyldimethylsilyloxy)methyl)nicotinate (0.225 g, 0.8 mmol) in toluene (5 mL) was added. The reaction solution was heated to 100° C. and stirred for 3 h. The reaction mixture was cooled to room temperature and quenched with methanol and aqueous 2 N hydrochloric acid and the solvent was removed in vacuo. Water (20 mL) was added and the mixture was extracted with dichloromethane (50 mL×3). The combined organic layers were dried over sodium sulfate, filtered and concentrated. The crude sample was dissolved in minimal N-N,N-dimethylformamide and purified via prep-HPLC (Boston C18 21*250 mm 10 μm column. The mobile phase was acetonitrile/0.01% aqueous trifluoroacetic acid) to give N-(5-(3-fluorobenzyl)pyridin-2-yl)-6-(hydroxymethyl)nicotinamide (76 mg, 0.23 mmol, 28%) as a colorless oil. $^1$H NMR (400 MHz, Dimethylsulfoxide-d$_6$) δ 11.24 (s, 1H), 9.11 (s, 1H), 8.52 (dd, J$_1$=1.6 Hz, J$_2$=8.0 Hz, 1H), 8.35 (d, J=2.0 Hz, 1H), 8.09 (d, J=8.4 Hz, 1H), 7.77 (dd, J$_1$=2.4 Hz, J$_2$=8.4 Hz, 1H), 7.72 (d, J=8.4 Hz, 1H), 7.34 (dd, J$_1$=8.0 Hz, J$_2$=14.4 Hz, 1H), 7.10-7.13 (m, 2H), 7.00-7.05 (m, 1H), 4.72 (s, 2H), 3.99 (s, 2H); LCMS (ESI) m/z: 338.0 [M+H]$^+$.

Example 120. Preparation of N-(5-(3-chlorobenzyl)pyridin-2-yl)-6-cyanonicotinamide (120)

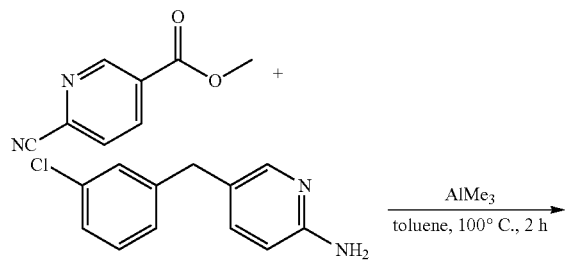

-continued

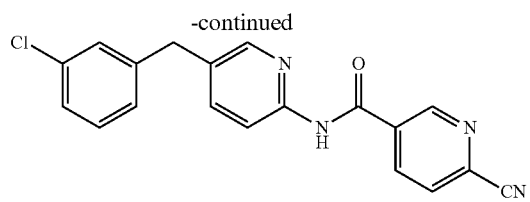

Step 1: Preparation of N-(5-(3-chlorobenzyl)pyridin-2-yl)-6-cyanonicotinamide

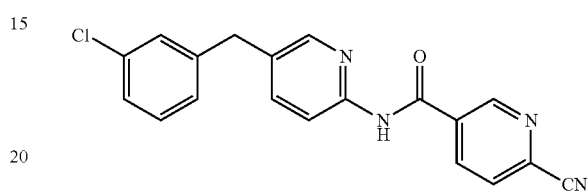

To a solution of methyl 5-(3-chlorobenzyl)pyridin-2-amine (0.262 g, 1.2 mmol) in toluene (7 mL) was added trimethylaluminum (0.6 mL, 1.2 mmol, 2 M in toluene) at room temperature under argon. The reaction mixture was stirred at room temperature for 1 h before a solution of methyl 6-cyanonicotinate (0.162 g, 1 mmol) in toluene (2 mL) was added. Reaction mixture was stirred at 100° C. for 2 h under argon. The reaction solution was cooled to room temperature and quenched with methanol (5 mL) and 1 N hydrochloric acid aqueous (5 mL). The volatiles were concentrated, and the aqueous phase was extracted with dichloromethane (100 mL×2). The combined organic layers were washed with brine (100 mL), dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chlorobenzyl)pyridin-2-yl)-6-cyanonicotinamide (70 mg, 0.20 mmol, 20.8%) as a white solid. $^1$H NMR (500 MHz, Dimethylsulfoxide-d$_6$) δ 11.33 (s, 1H), 9.22 (d, J=1.3 Hz, 1H), 8.53 (dd, J=4.3, 2.5 Hz, 1H), 8.36 (d, J=2.0 Hz, 1H), 8.20 (d, J=8.0 Hz, 1H), 8.12 (d, J=8.5 Hz, 1H), 7.75 (dd, J=4.3, 2.5 Hz, 1H), 7.35-7.32 (m, 2H), 7.28-7.23 (m, 2H), 3.99 (s, 2H); LCMS (ESI) m/z: 349.0 [M+H]$^+$.

Example 121. Preparation of 6-(aminomethyl)-N-(5-(3-chlorobenzyl)pyridin-2-yl)nicotinamide 2,2,2-trifluoroacetate (121)

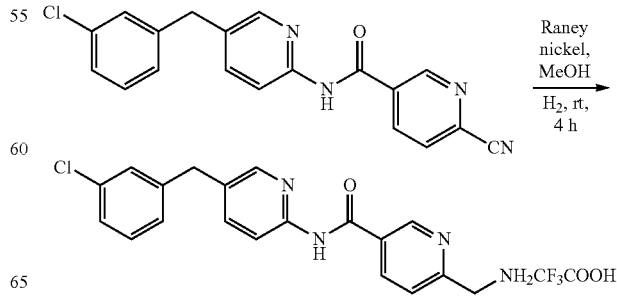

Step 1: Preparation of 6-(aminomethyl)-N-(5-(3-chlorobenzyl)pyridin-2-yl)nicotinamide trifluoroacetic acid

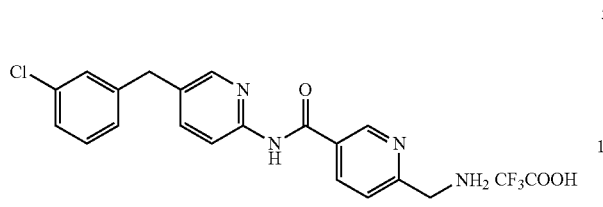

To a solution of N-(5-(3-chlorobenzyl)pyridin-2-yl)-6-cyanonicotinamide (0.174 g, 0.5 mmol) in methanol (20 mL) at room temperature under hydrogen was added Raney nickel (0.200 g). The reaction mixture was stirred at room temperature for 4 h. The reaction mixture was filtered and the filtrate was concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give 6-(aminomethyl)-N-(5-(3-chlorobenzyl)pyridin-2-yl)nicotinamide trifluoroacetic acid (36.7 mg, 0.10 mmol, 20.9%) as a white solid. $^1$H NMR (400 MHz, Dimethylsulfoxide-d$_6$) δ 11.18 (s, 1H), 9.18 (d, J=2.0 Hz, 1H), 8.43-8.36 (m, 5H), 8.13 (d, J=8.4 Hz, 1H), 7.75 (dd, J=8.8, 2.0 Hz, 1H), 7.61 (d, J=8.0 Hz, 1H), 7.37-7.33 (m, 2H), 7.29-7.24 (m, 2H), 4.33-4.29 (m, 2H), 3.99 (s, 2H); LCMS (ESI) m/z: 353.0 [M+H]$^+$.

Example 122. Preparation of N-(5-(3-chlorobenzyl)pyridin-2-yl)-6-(hydroxymethyl)pyridazine-3-carboxamide (122)

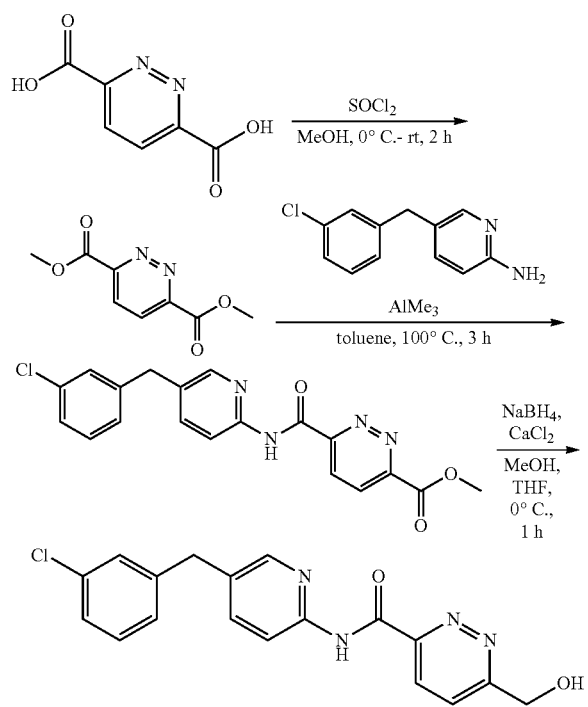

Step 1: Preparation of dimethyl pyridazine-3,6-dicarboxylate

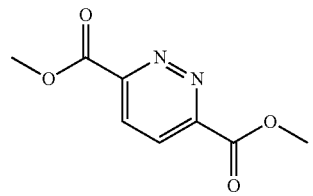

To a solution of pyridazine-3,6-dicarboxylic acid (2.52 g, 15 mmol) in methanol (125 mL) was added thionyl chloride (7.14 g, 6.0 mmol) dropwise at 0° C. under nitrogen. The reaction mixture was warmed to room temperature and stirred for 2 h. The volatiles were concentrated and water (50 mL) was added. The aqueous layer was extracted with ethyl acetate (80 mL×3). The combined organic layers were dried over sodium sulfate, filtered and concentrated. The crude product was purified by column chromatography (silica gel, dichloromethane/methanol=20/1) to give dimethyl pyridazine-3,6-dicarboxylate (1.12 g, 5.7 mmol, 38%) as a yellow solid. LCMS (ESI) m/z: 197.1 [M+H]$^+$.

Step 2: Preparation of methyl 6-(5-(3-chlorobenzyl)pyridin-2-ylcarbamoyl)pyridazine-3-carboxylate

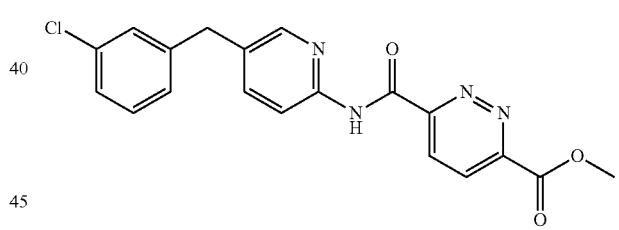

To a solution of 5-(3-chlorobenzyl)pyridin-2-amine (0.218 g, 1.0 mmol) in toluene (5 mL) at room temperature was added trimethylaluminum (0.5 mL, 1.0 mmol, 2 M in toluene) slowly under argon. The reaction mixture was stirred at room temperature for 1 h before dimethyl pyridazine-3,6-dicarboxylate (0.196 g, 1.0 mmol) in toluene (5 mL) was added and the resulting mixture was heated to 100° C. and stirred for 3 h. Reaction vessel was cooled to room temperature and reaction was quenched with methanol and aqueous 2 N hydrochloric acid. The volatiles were removed in vacuo and water (20 mL) was added to the residue. The aqueous layer was extracted with dichloromethane (50 mL×3). The combined organic layers were dried over sodium sulfate, filtered and concentrated. The crude material was purified by column chromatography (silica gel, petroleum ether/ethyl acetate from 1/1 to 0/1) to give methyl 6-(5-(3-chlorobenzyl)pyridin-2-ylcarbamoyl)pyridazine-3-carboxylate (0.150 g, 0.39 mmol, 39%) as a white solid. LCMS (ESI) m/z: 383.2 [M+H]$^+$.

Step 3: Preparation of N-(5-(3-chlorobenzyl)pyridin-2-yl)-6-(hydroxymethyl)pyridazine-3-carboxamide

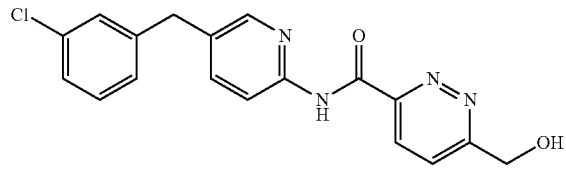 [SMILES: O=C(Nc1ccc(Cc2cccc(Cl)c2)cn1)c1ccc(CO)nn1]

To a solution of methyl 6-(5-(3-chlorobenzyl)pyridin-2-ylcarbamoyl)pyridazine-3-carboxylate (0.148 g, 0.39 mmol) and calcium chloride (0.173 g, 1.56 mmol) in methanol (20 mL) and tetrahydrofuran (10 mL) at 0° C. was added sodium borohydride (0.072 g, 1.94 mmol) slowly under nitrogen. The reaction mixture was stirred at 0° C. for 1 h before it was quenched with water. The aqueous layer was extracted with dichloromethane (50 mL×2). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chlorobenzyl)pyridin-2-yl)-6-(hydroxymethyl)pyridazine-3-carboxamide (0.0628 g, 0.18 mmol, 46%) as a white solid. $^1$H NMR (500 MHz, Dimethylsulfoxide-d$_6$) δ 8.37-8.38 (m, 2H), 8.19 (d, J=8.5 Hz, 1H), 8.01 (d, J=8.0 Hz, 1H), 7.81 (dd, J$_1$=2.5 Hz, J$_2$=8.5 Hz, 1H), 7.33-7.38 (m, 2H), 7.25-7.29 (m, 2H), 5.86 (s, 1H), 4.91 (s, 2H), 4.00 (s, 2H); LCMS (ESI) m/z: 355.1 [M+H]$^+$.

Example 123. Preparation of N-(5-(3-chlorobenzyl)-4-methylpyridin-2-yl)-1-methyl-6-oxo-1,4,5,6-tetrahydropyridazine-3-carboxamide (123)

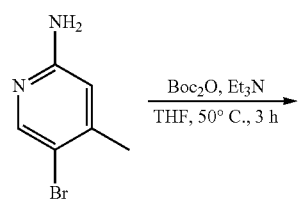

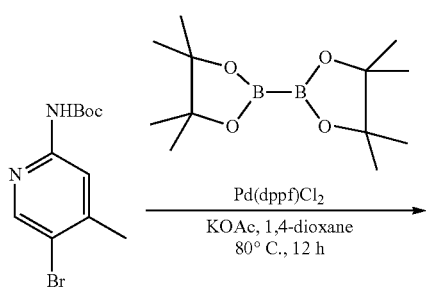

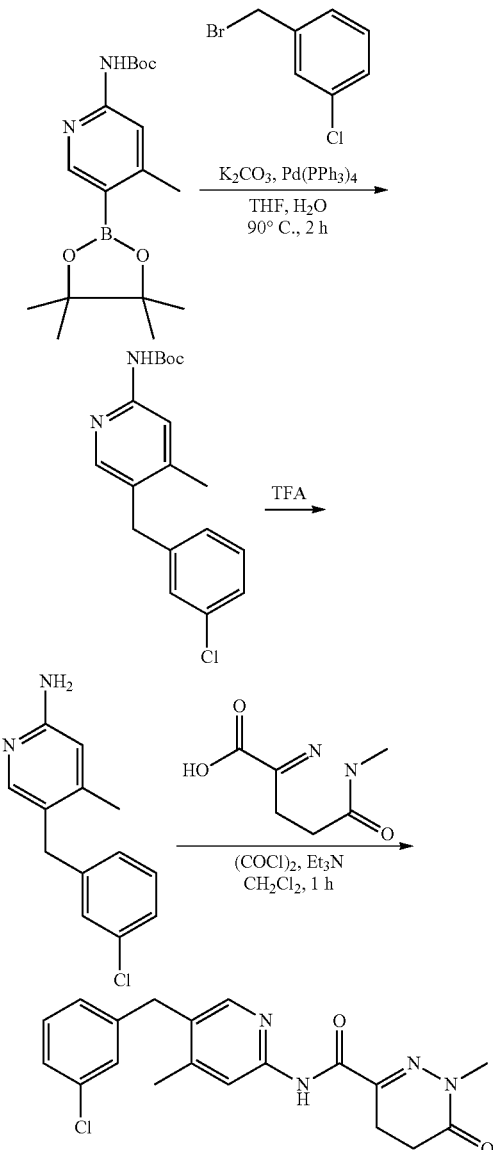

Step 1: Preparation of tert-butyl 5-bromo-4-methylpyridin-2-ylcarbamate

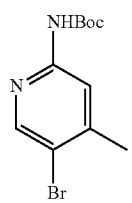

To a solution of 5-bromo-4-methylpyridin-2-amine (5.0 g, 27.0 mmol) and triethylamine (5.44 g, 53.8 mmol) in tetrahydrofuran (30 mL) was added di-tert-butyl dicarbonate (5.86 g, 27.0 mmol) slowly. Reaction was stirred at 60° C. for 2 h. The precipitated solid was filtered and collected to give tert-butyl 5-bromo-4-methylpyridin-2-ylcarbamate (4.2 g, 14.6 mmol, 54%) as a light-yellow solid. LCMS (ESI) m/z: 289.0 [M+H]⁺.

Step 2: Preparation of tert-butyl 4-methyl-5-(4,4,5,5-tetramethyl-1,3,2-dioxaborolan-2-yl)pyridin-2-ylcarbamate

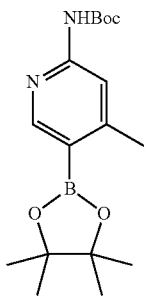

To a solution of tert-butyl 5-bromo-4-methylpyridin-2-ylcarbamate (1.5 g, 5.24 mmol), 4,4,4',4',5,5,5',5'-octamethyl-2,2'-bi(1,3,2-dioxaborolane) (1.6 g, 6.29 mmol) and potassium acetate (1.03 g, 10.5 mmol) in 1,4-dioxane (8.0 mL) was added [1,1'-bis(diphenylphosphino)ferrocene]dichloropalladium(II) (0.081 g, 0.10 mmol) under nitrogen. The reaction was heated to 80° C. and stirred for 12 h. The volatiles were removed under reduced pressure and the residue was added to a mixture of dichloromethane (100 mL) and water (100 mL). The organic layer was collected, dried over sodium sulfate, filtered and purified by column chromatography (silica gel, petroleum ether/ethyl acetate=4/1) to give tert-butyl 4-methyl-5-(4,4,5,5-tetramethyl-1,3,2-dioxaborolan-2-yl)pyridin-2-ylcarbamate (0.150 g, 0.472 mmol, 9%) as a white solid. LCMS (ESI) m/z: 335.2 [M+H]⁺.

Step 3: Preparation of tert-butyl 5-(3-chlorobenzyl)-4-methylpyridin-2-ylcarbamate

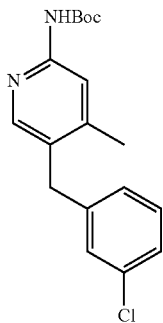 [SMILES: Cc1cc(NC(=O)OC(C)(C)C)ncc1Cc1cccc(Cl)c1]

To a solution of tert-butyl 4-methyl-5-(4,4,5,5-tetramethyl-1,3,2-dioxaborolan-2-yl)pyridin-2-ylcarbamate (0.140 g, 0.419 mmol), 1-(bromomethyl)-3-chlorobenzene (0.103 g, 0.503 mmol), potassium carbonate (0.116 g, 0.838 mmol) in tetrahydrofuran (4 mL) and water(2 mL) was added tetrakis(triphenylphosphine)palladium(0) (0.034 g, 0.04 mmol) under nitrogen. The mixture was then heated to 80° C. and stirred for 2 h. The volatiles were removed under reduced pressure and the resulting residue was diluted with ethyl acetate (100 mL), washed with water (100 mL), brine (100 mL), dried over sodium sulfate, filtered and concentrated. Purification by column chromatography (silica gel, petroleum ether/ethyl acetate=10/1) affords tert-butyl 5-(3-chlorobenzyl)-4-methylpyridin-2-ylcarbamates (0.120 g, 0.360 mmol, 86%) as a white solid. LCMS (ESI) m/z: 333.1 [M+H]⁺.

Step 4: Preparation of 5-(3-chlorobenzyl)-4-methylpyridin-2-amine

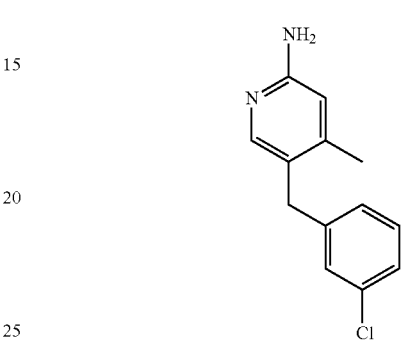

Trifluoroacetic acid (1.0 mL) was slowly added to tert-butyl 5-(3-chlorobenzyl)-4-methylpyridin-2-ylcarbamate (0.070 mg, 0.211 mmol). Reaction mixture was stirred at 20° C. for 0.5 h before trifluoroacetic acid was removed under reduced pressure. The residue was dissolved in dichloromethane (50 mL) and washed with water (50 mL), sodium bicarbonate aqueous (50 mL) and brine (50 mL), dried over sodium sulfate, filtered and concentrated under reduced pressure to yield 5-(3-chlorobenzyl)-4-methylpyridin-2-amine (0.050 g, crude) as a yellow solid. Used directly in the next step. LCMS (ESI) m/z: 233.1 [M+H]⁺.

Step 5: Preparation of N-(5-(3-chlorobenzyl)-4-methylpyridin-2-yl)-1-methyl-6-oxo-1,4,5,6-tetrahydropyridazine-3-carboxamide

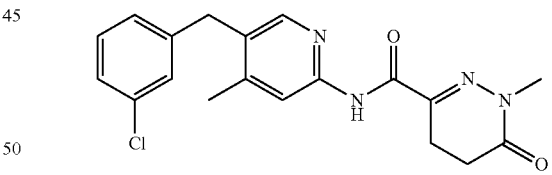

To a solution of 1-methyl-6-oxo-1,4,5,6-tetrahydropyridazine-3-carboxylic acid (0.034 g, 0.215 mmol) in dichloromethane (2 mL) at 20° C. was added oxalyl chloride (1 mL). The reaction was stirred at 0° C. for 0.5 h and concentrated in vacuo. The crude residue was dissolved in dichloromethane (2 mL) and added to a mixture of 5-(3-chlorobenzyl)-4-methylpyridin-2-amine (0.050 g, 0.215 mmol) and triethylamine (0.065 g, 0.645 mmol) in dichloromethane (3.0 mL) dropwise. The reaction was stirred for another 0.5 h and volatiles were removed under reduced pressure. The residue was added to a mixture of dichloromethane (50 mL) and water (50 mL) and the organic layer was collected, dried over sodium sulfate, filtered and concentrated. The crude sample was dissolved in minimal N,N-dimethylformamide and purified via prep-HPLC (Boston C18 21*250 mm 10 μm column; the mobile phase acetonitrile/0.01% aqueous trifluoroacetic acid) to give N-(5-(3-chlorobenzyl)-4-methylpyridin-2-yl)-1-methyl-6-oxo-1,4,5,6-tetrahydropyridazine-3-carboxamide (0.0515 g, 0.138 mmol, 64%) as a white solid. ¹H NMR (400 MHz, Dimethylsulfoxide-d₆) δ 9.88 (s, 1H), 8.19 (s, 1H), 7.95 (s, 1H), 7.32-7.35 (m, 1H), 7.13-7.29 (m, 3H), 4.02 (s, 2H), 3.37 (s, 3H), 2.84-2.87 (t, J=6.8 Hz, 2H), 2.52-2.55 (m, 2H), 2.23 (s, 3H); LCMS (ESI) m/z: 371.1 [M+H]⁺.

Example 124. Preparation of N-(5-(3-chlorobenzyl)-3-fluoropyridin-2-yl)-1-methyl-6-oxo-1,4,5,6-tetrahydropyridazine-3-carboxamide (124)

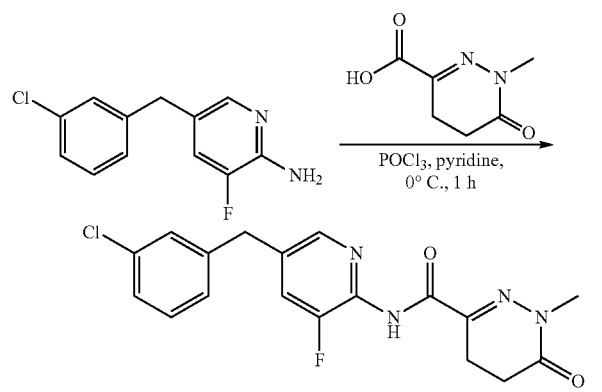

Step 1: Preparation of N-(5-(3-chlorobenzyl)-3-fluoropyridin-2-yl)-1-methyl-6-oxo-1,4,5,6-tetrahydropyridazine-3-carboxamide

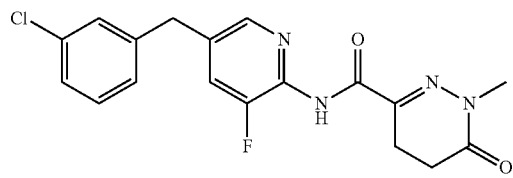 [SMILES: CN1N=C(C(=O)Nc2ncc(Cc3cccc(Cl)c3)cc2F)CCC1=O]

To an ice-cooled solution of 5-(3-chlorobenzyl)-3-fluoropyridin-2-amine (0.100 g, 0.42 mmol) and 1-methyl-6-oxo-1,4,5,6-tetrahydropyridazine-3-carboxylic acid (0.066 mg, 0.42 mmol) in dry pyridine (5.00 mL) was added phosphorus(V) oxychloride (0.193 g, 1.27 mmol) dropwise. The mixture was stirred at 0° C. for 1 h. The mixture was diluted with ethyl acetate (50 mL) and washed with aqueous saturated sodium bicarbonate solution (25 mL) and brine (25 mL). The organic layer was dried with sodium sulfate, filtered and concentrated. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give N-(5-(3-chlorobenzyl)-3-fluoropyridin-2-yl)-1-methyl-6-oxo-1,4,5,6-tetrahydropyridazine-3-carboxamide (0.060 g, 0.16 mmol, 38.2) as a white solid. ¹H NMR (500 MHz, Dimethylsulfoxide-d₆) δ 10.25 (s, 1H), 8.27 (s, 1H), 7.75 (dd, J=10.6, 1.5 Hz, 1H), 7.42 (s, 1H), 7.34 (d, J=7.6 Hz, 1H), 7.29 (d, J=8.0 Hz, 2H), 4.03 (s, 2H), 3.34 (s, 3H), 2.81 (t, J=8.5 Hz, 2H), 2.57-2.51 (m, 2H); LCMS (ESI) m/z: 375.1 [M+H]⁺.

Example 125. Preparation of 5-(3-Fluorobenzyl)-N-(6-(hydroxymethyl)pyridin-3-yl)picolinamide (125)

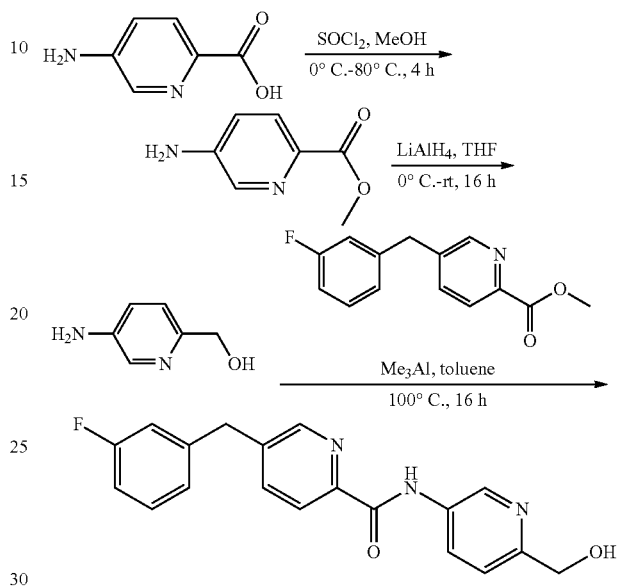

Step 1: Preparation of methyl 5-aminopicolinate

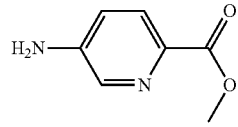

Thionyl chloride (12.9 g, 109 mmol) was added to methanol (60 mL) at 0° C. The reaction mixture was stirred at 0° C. for 1 h before 5-aminopicolinic acid (3.0 g, 21.7 mmol) was added. The reaction solution was refluxed for 4 h. The reaction solution was cooled to room temperature and concentrated. The crude residue was dissolved in water (100 mL) and treated with saturated aqueous of sodium bicarbonate (30 mL). The aqueous layer was extracted with ethyl acetate (100 mL×3). The combined organic layers were washed with brine (100 mL), dried over anhydrous sodium sulfate, filtered and concentrated to give methyl 5-aminopicolinate (2.6 g, 17.1 mmol, 78%) as a yellow oil. LCMS (ESI) m/z: 153.0 [M+H]⁺. Used in the next step directly without additional purification.

Step 2: Preparation of (5-aminopyridin-2-yl)methanol

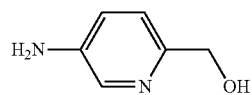

To a solution of methyl 5-aminopicolinate (1.0 g, 6.57 mmol) in anhydrous tetrahydrofuran (20 mL) was added lithium aluminum hydride (499 mg, 13.14 mmol) at 0° C. The reaction mixture was stirred at room temperature for 16 h before it was quenched with water (150 mL). The aqueous layer was extracted with 2-methyltetrahydrofuran (80 mL×3). The combined organic layers were dried over anhydrous sodium sulfate, filtered and concentrated to afford methyl (5-aminopyridin-2-yl)methanol (0.750 g, 17.1 mmol, 92%) as a yellow oil. LCMS (ESI) m/z: 125.1 [M+H]$^+$.

Step 3: Preparation of 5-(3-fluorobenzyl)-N-(6-(hydroxymethyl)pyridin-3-yl)picolinamide

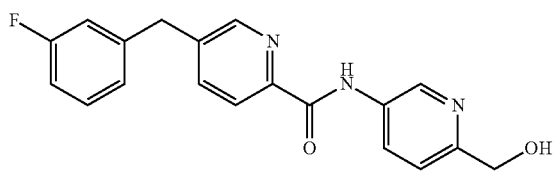 [SMILES: O=C(Nc1ccc(CO)nc1)c1ccc(Cc2cccc(F)c2)cn1]

To a solution of (5-aminopyridin-2-yl)methanol (0.248 g, 2.0 mmol) in anhydrous toluene (15 mL) at room temperature was added trimethylaluminum (1.0 mL, 2.0 mmol, 2 M in toluene) under nitrogen. The reaction mixture was stirred at room temperature for 1 h before methyl 5-(3-fluorobenzyl)picolinate (0.245 g, 1.0 mmol) was added and stirred at 100° C. for 16 h. The reaction mixture was cooled to room temperature and diluted with water (200 mL). The aqueous layer was extracted with ethyl acetate (80 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 µm column. The mobile phase was acetonitrile/10 mM ammonium acetate aqueous solution) to give 5-(3-fluorobenzyl)-N-(6-(hydroxymethyl)pyridin-3-yl)picolinamide (38 mg, 0.11 mmol, 11%) as a white solid. $^1$H NMR (500 MHz, Dimethylsulfoxide-d$_6$) δ 11.21 (s, 1H), 9.18 (s, 1H), 8.73 (d, J=1.0 Hz, 1H), 8.61 (dd, J$_1$=2.0 Hz, J$_2$=8.5 Hz, 1H), 8.12 (d, J=8.5 Hz, 1H), 7.94 (dd, J$_1$=2.0 Hz, J$_2$=8.0 Hz, 1H), 7.74 (d, J=8.5 Hz, 1H), 7.39-7.35 (m, 1H), 7.18-7.14 (m, 2H), 7.08-7.04 (m, 1H), 4.70 (s, 2H), 4.15 (s, 2H); LCMS (ESI) m/z: 338.1 [M+H]$^+$.

Example 126. Preparation of 5-(3-Fluorobenzyl)-N-(6-methylpyridazin-3-yl)picolinamide (126)

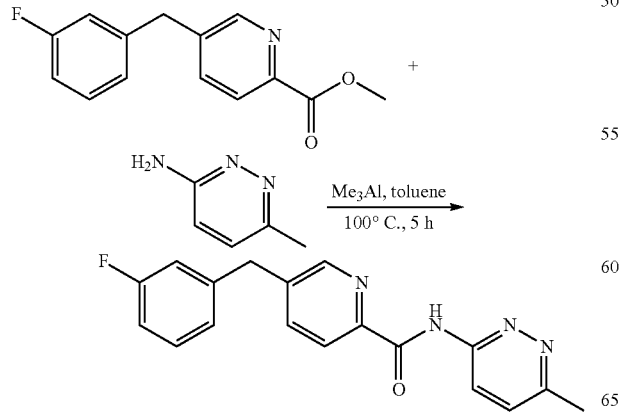

Step 1: Preparation of 5-(3-fluorobenzyl)-N-(6-methylpyridazin-3-yl)picolinamide

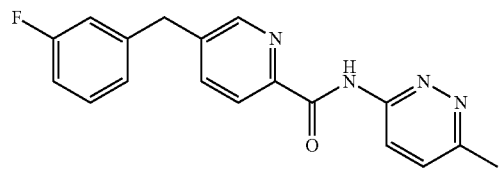 [SMILES: Cc1ccc(NC(=O)c2ccc(Cc3cccc(F)c3)cn2)nn1]

At room temperature to a solution of 6-methylpyridazin-3-amine (178.0 mg, 1.63 mmol) in anhydrous toluene (10 mL) was added trimethylaluminum (0.82 mL, 1.63 mmol, 2 M in toluene) under nitrogen. The reaction mixture was stirred at room temperature for 1 h before methyl 5-(3-fluorobenzyl)picolinate (0.200 g, 0.82 mmol) was added. The reaction mixture was stirred at 100° C. for 5 h. The reaction mixture was cooled to room temperature then diluted with water (200 mL) and extracted with ethyl acetate (80 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 µm column. The mobile phase was acetonitrile/10 mM ammonium acetate aqueous solution) to give 5-(3-fluorobenzyl)-N-(6-methylpyridazin-3-yl)picolinamide (0.062 g, 0.19 mmol, 23%) as a white solid. $^1$H NMR (500 MHz, Dimethylsulfoxide-d$_6$) δ 10.79 (s, 1H), 8.74 (d, J=2.0 Hz, 1H), 8.39 (d, J=9.5 Hz, 1H), 8.14 (d, J=7.5 Hz, 1H), 7.97 (dd, J$_1$=2.0 Hz, J$_2$=8.5 Hz, 1H), 7.68 (d, J=9.0 Hz, 1H), 7.39-7.35 (m, 1H), 7.20-7.15 (m, 2H), 7.08-7.04 (m, 1H), 4.15 (s, 2H), 2.60 (s, 3H); LCMS (ESI) m/z: 323.1 [M+H]$^+$.

Example 127. Preparation of N-(5-(3-chlorobenzyl)pyridin-2-yl)-6-(hydroxymethyl)nicotinamide (127)

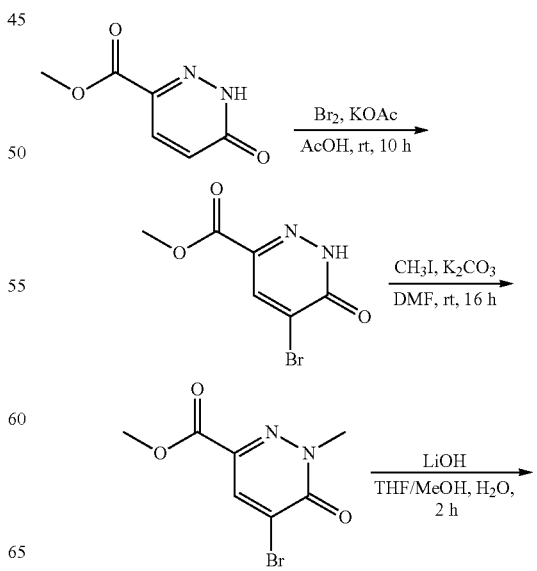

Step 1: Preparation of methyl 5-bromo-6-oxo-1,6-dihydropyridazine-3-carboxylate

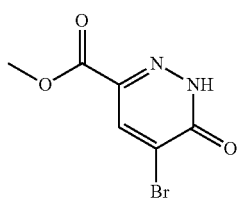

To a solution of methyl 6-oxo-1,6-dihydropyridazine-3-carboxylate (9.0 g, 58.4 mmol) in acetic acid (100 mL) at room temperature was added potassium acetate (17.2 g, 175 mmol) and bromine (18.66 g, 117 mmol). The resulting solution was stirred for 6 h at 80° C. The reaction mixture was quenched with aqueous sodium bisulfate solution (100 mL, 3 mol/L). The aqueous layer was extracted with ethyl acetate (100 mL×3). The combined organic layers were washed with brine, dried over sodium sulfate, filtered and concentrated to yield methyl 5-bromo-6-oxo-1,6-dihydro-pyridazine-3-car-boxylate (11.1 g, 47.9 mmol, 82%, crude) as a light-yellow solid. LCMS (ESI) m/z: 233.0 [M+H]$^+$. Used in the next step directly without additional purification.

Step 2: Preparation of methyl 5-bromo-1-methyl-6-oxo-1,6-dihydropyridazine-3-carboxylate

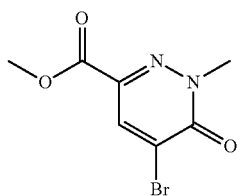

To a solution of methyl 6-oxo-1,6-dihydropyridazine-3-carboxylate (2.0 g, 8.58 mmol), potassium carbonate (2.38 g, 17.16 mmol) in N,N'-dimethylformamide (10.0 mL) was added 1-iodomethane (0.73 g, 5.15 mmol). The reaction mixture was stirred at room temperature for 3 h. The solution was dissolved in the ethyl acetate (50 mL). The combined organic layers were separated, washed with water (50 mL), dried over sodium sulfate, filtered and concentrated. The crude sample was purified by column chromatography (silica gel, petroleum ether/ethyl acetate=1/1) to offer methyl 5-bromo-1-methyl-6-oxo-1,6-dihydropyridazine-3-carboxylate (1.60 g, 6.50 mmol, 76.2%) as a white solid. LCMS (ESI) m/z: 247.0 [M+H]$^+$.

Step 3: Preparation of 5-methoxy-1-methyl-6-oxo-1,6-dihydropyridazine-3-carboxylic acid

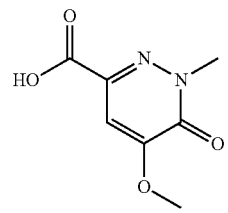

To a solution of methyl 5-bromo-1-methyl-6-oxo-1,6-dihydropyridazine-3-carboxylate (300 mg, 1.22 mmol) in methanol (4.0 mL), tetrahydrofuran (4.0 mL) and water (1.0 mL) mixture was added lithium hydroxide hydrate (102 mg, 2.44 mmol). The reaction solution was stirred at room temperature for 1 h before 1 N aqueous hydrochloric acid was added to adjust the pH value to 3-5. The volatiles were removed to give 5-methoxy-1-methyl-6-oxo-1,6-dihydro-pyridazine-3-carboxylic acid (200 mg, 1.09 mmol, 89%, crude) as a white solid. $^1$H NMR (400 MHz, Dimethyl-sulfoxide-d$_6$) δ 13.66 (s, 1H), 8.26 (s, 1H), 3.88 (s, 3H), 3.78 (s, 3H); LCMS (ESI) m/z: 185.1 [M+H]$^+$. Used in the next step directly without additional purification.

Step 4: Preparation of N-(5-(3-fluorobenzyl)pyridin-2-yl)-5-methoxy-1-methyl-6-oxo-1,6-dihydropyridazine-3-carboxamide

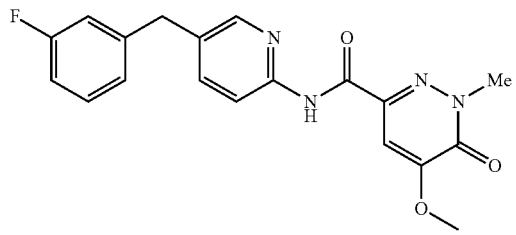 [SMILES: COc1cc(C(=O)Nc2ccc(Cc3cccc(F)c3)cn2)nn(C)c1=O]

To a solution of 5-methoxy-1-methyl-6-oxo-1,6-dihydro-pyridazine-3-carboxylic acid (121 mg, 0.659 mmol) and diisopropylethylamine (255 mg, 1.98 mmol) in tetrahydro-furan (5.0 mL) at 20° C. was added 1-[bis(dimethylamino)methylene]-1H-1,2,3-triazolo[4,5-b]pyridinium 3-oxid hexafluorophosphate (376 mg, 0.659 mmol). The reaction solution was stirred for 20 minutes before a solution of 5-(3-fluorobenzyl)pyridin-2-amine (144 mg, 0.659 mmol) in tetrahydrofuran (1.0 mL) was added. The reaction mixture was stirred at 20° C. for 16 h. The volatiles were removed under reduced pressure and the crude material was added to a mixture of dichloromethane (50 mL) and water (50 mL). The combined organic layers were collected, dried over sodium sulfate, filtered and concentrated. The crude sample was dissolved in minimal N,N-dimethylformamide and puri-

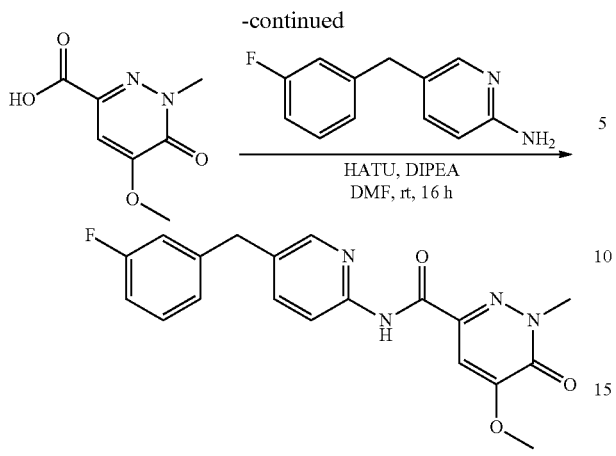

fied via prep-HPLC (Boston C18 21*250 mm 10 μm column; acetonitrile/0.01% aqueous trifluoroacetic acid) to give N-(5-(3-fluorobenzyl)pyridin-2-yl)-6-oxo-1-propyl-1,6-dihydropyridazine-3-carboxamide (43.0 mg, 0.117 mmol, 22%) as a white solid. $^1$H NMR (500 MHz, Dimethylsulfoxide-d$_6$) δ 10.05 (s, 1H), 8.33 (d, J=2.0 Hz, 1H), 8.09 (d, J=8.5 Hz, 1H), 7.75 (dd, J=8.5, 2.3 Hz, 1H), 7.34 (dd, J=14.3, 8.0 Hz, 1H), 7.26 (s, 1H), 7.11 (t, J=7.7 Hz, 2H), 7.04 (t, J=7.4 Hz, 1H), 3.99 (s, 2H), 3.93 (s, 3H), 3.78 (s, 3H); LCMS (ESI) m/z: 369.1 [M+H]$^+$.

Example 128. Preparation of N-(5-(3-chlorobenzyl)pyridin-2-yl)-5-fluoro-1-methyl-6-oxo-1,6-dihydropyridine-3-carboxamide (128)

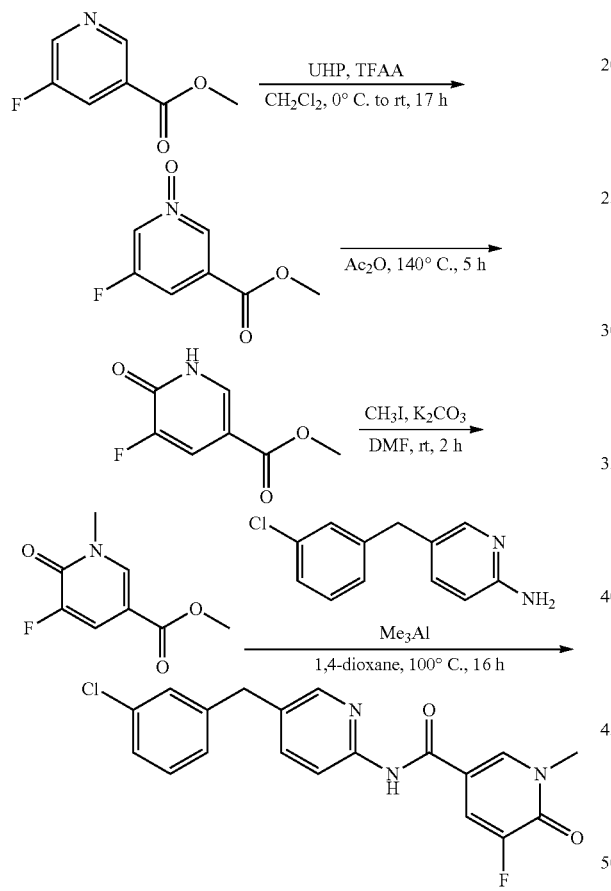

Step 1: Preparation of 3-fluoro-5-(methoxycarbonyl)pyridine 1-oxide

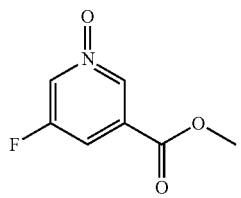

To a solution of methyl 5-fluoronicotinate (3.54 g, 22.8 mmol) and urea hydrogen peroxide (4.64 g, 47.88 mmol) in dichloromethane (50 mL) at 0° C. was added trifluoroacetic anhydride (6.4 mL, 118 mmol) dropwise under nitrogen. The reaction mixture was stirred at room temperature for 17 h. The reaction vessel was cooled to 0° C. and saturated aqueous sodium bisulfate was added. The aqueous layer extracted with dichloromethane (100 mL×3). The combined organic layers were washed with saturated aqueous sodium bisulfate (50 mL), dried over sodium sulfate, filtered and concentrated to give 3-fluoro-5-(methoxycarbonyl)pyridine 1-oxide as a light-yellow solid (3.78 g, 22.1 mmol, 97%); LCMS (ESI) m/z: 172.1 [M+H]$^+$.

Step 2: Preparation of methyl 5-fluoro-6-oxo-1,6-dihydropyridine-3-carboxylate

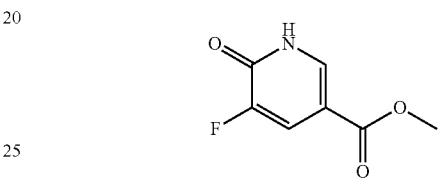

3-fluoro-5-(methoxycarbonyl)pyridine1-oxide (2.5 g, 14.6 mmol) in acetic anhydride (75 mL) was stirred at 140° C. for 5 h under nitrogen. The reaction was cooled to room temperature and was concentrated. The residue was heated to 50° C. for 15 minutes and concentrated. The crude brown solid was suspended in dichloromethane and filtered, the product was then dried in vacuo to give methyl 5-fluoro-6-oxo-1,6-dihydropyridine-3-carboxylate as a yellow solid (880 mg, 5.15 mmol, 35%); LCMS (ESI) m/z: 172.1 [M+H]$^+$.

Step 3: Preparation of methyl 5-fluoro-1-methyl-6-oxo-1,6-dihydropyridine-3-carboxylate

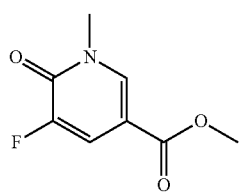

To a solution of methyl 5-fluoro-6-oxo-1,6-dihydropyridine-3-carboxylate (838 mg, 4.9 mmol) and potassium carbonate (1.36 g, 9.8 mmol) in N,N-dimethylformamide (20 mL) was added iodomethane (1.04 g, 7.35 mmol) at room temperature under nitrogen. The mixture was stirred at room temperature for 2 h. The volatiles were removed in vacuo and the crude product was purified by column chromatography (silica gel, petroleum ether/ethyl acetate=1/1) to give methyl 5-fluoro-1-methyl-6-oxo-1,6-dihydropyridine-3-carboxylate as a yellow solid (830 mg, 4.5 mmol, 91%); LCMS (ESI) m/z: 186.1 [M+H]$^+$.

Step 4: Preparation of N-(5-(3-chlorobenzyl)pyridin-2-yl)-5-fluoro-1-methyl-6-oxo-1,6-dihydropyridine-3-carboxamide

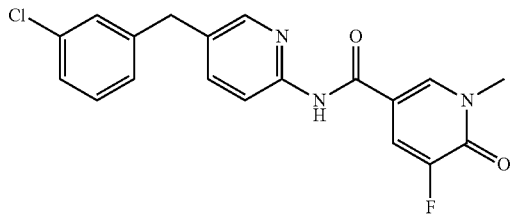 [SMILES: Cn1cc(C(=O)Nc2ccc(Cc3cccc(Cl)c3)cn2)cc(F)c1=O]

To a solution of 5-(3-chlorobenzyl)pyridin-2-amine (323 mg, 1.48 mmol) in 1,4-dioxane (6 mL) at room temperature was added trimethylaluminum (0.72 mL, 1.44 mmol, 2 M in toluene) slowly under argon. The mixture was stirred at room temperature for 30 minutes before methyl 5-fluoro-1-methyl-6-oxo-1,6-dihydropyridine-3-carboxylate (67 mg, 0.36 mmol) in 1,4-dioxane (2 mL) was added. The resulting solution was heated to 100° C. and stirred for 16 h. The reaction mixture was cooled to room temperature and was quenched with hydrochloric acid (0.5 N, 25 mL) and ethyl acetate (50 mL). The combined organic layers were washed with hydrochloric acid (0.5 N, 25 mL×2) and brine (25 mL), dried over sodium sulfate, filtered and concentrated. The residue was purified first by column chromatography (silica gel, ethyl acetate/petroleum ether=2/1) and by prep-HPLC (Sunfire prep C18 10 μm OBD 19*250 mm; mobile phase: [water (0.05% trifluoroacetic acid)-acetonitrile]; B %: 60%-88%, 15 minutes) to offer N-(5-(3-chlorobenzyl)pyridin-2-yl)-5-fluoro-1-methyl-6-oxo-1,6-dihydropyridine-3-carboxamide (70 mg, 0.19 mmol, 52.4%) as a white solid. $^1$H NMR (500 MHz, Dimethylsulfoxide-$d_6$) δ 10.66 (s, 1H), 8.57 (d, J=1.7 Hz, 1H), 8.33 (d, J=2.0 Hz, 1H), 8.05 (d, J=8.5 Hz, 1H), 7.96 (dd, J=11.0, 2.3 Hz, 1H), 7.73 (dd, J=8.6, 2.3 Hz, 1H), 7.37-7.31 (m, 2H), 7.30-7.18 (m, 2H), 3.97 (s, 2H), 3.58 (s, 3H); LCMS (ESI) m/z: 372.0 [M+H]$^+$.

Example 129. Preparation of N-(5-(3-chlorobenzyl)pyridin-2-yl)-5-cyanopicolinamide (129)

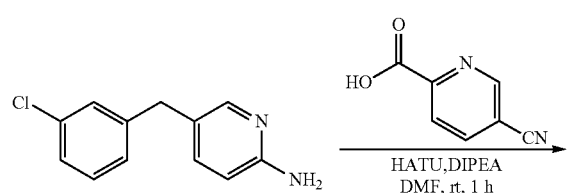

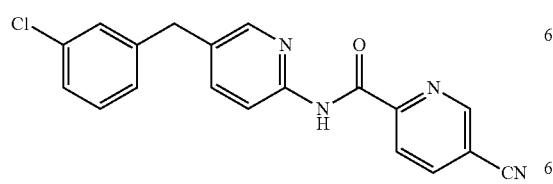

Step 1: Preparation of N-(5-(3-chlorobenzyl)pyridin-2-yl)-5-cyanopicolinamide

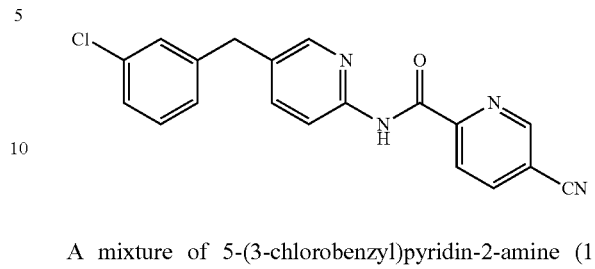

A mixture of 5-(3-chlorobenzyl)pyridin-2-amine (109 mg, 0.5 mmol), 5-cyanopicolinic acid (74 mg, 0.5 mmol), 2-(7-azabenzotriazol-1-yl)-N,N,N',N'-tetramethyluronium hexafluorophosphate (285 mg, 0.75 mmol), N,N-diisopropylethylamine (194 mg, 1.5 mmol) in N,N-dimethylformamide (4 mL) was stirred at room temperature for 1 h. The mixture was poured into water and the formed precipitate was collected by filtration. The obtained solid was washed with methanol (20 mL) to afford N-(5-(3-chlorobenzyl)pyridin-2-yl)-5-cyanopicolinamide (0.144 g, 0.41 mmol, 82%) as a grey solid. $^1$H NMR (500 MHz, Dimethylsulfoxide-$d_6$) δ 10.39 (s, 1H), 9.21 (d, J=1.5 Hz, 1H), 8.61 (dd, J=8.0, 1.5 Hz, 1H), 8.36 (d, J=1.0 Hz, 1H), 8.32 (d, J=8.0 Hz, 1H), 8.18 (d, J=8.0 Hz, 1H), 7.79 (dd, J=8.5, 2.0 Hz, 1H), 7.36-7.32 (m, 2H), 7.28-7.24 (m, 2H), 3.99 (s, 2H); LCMS (ESI) m/z: 349.1 [M+H]$^+$.

Example 130. Preparation of N-(5-(3-chloro-4-fluorobenzyl)pyridin-2-yl)-5-cyanopicolinamide (130)

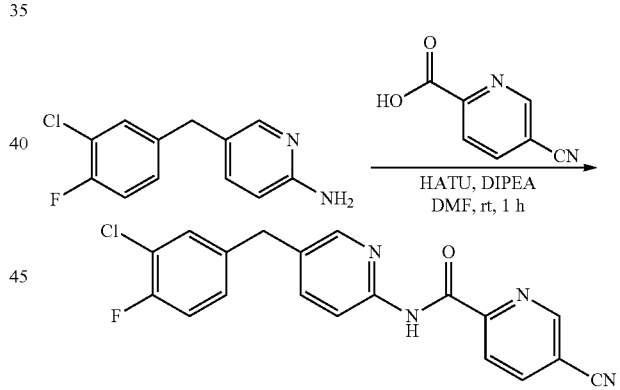

Step 1: Preparation of N-(5-(3-chloro-4-fluorobenzyl)pyridin-2-yl)-5-cyanopicolinamide

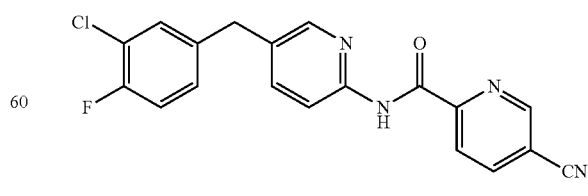

A mixture of 5-(3-chloro-4-fluorobenzyl)pyridin-2-amine (118 mg, 0.5 mmol), 5-cyanopicolinic acid (74 mg, 0.5 mmol), 2-(7-azabenzotriazol-1-yl)-N,N,N',N'-tetramethyluronium hexafluorophosphate (285 mg, 0.75 mmol) and N,N-diisopropylethylamine (194 mg, 1.5 mmol) in N,N-dimethylformamide (4 mL) was stirred at room temperature for 1 h. The mixture was purified directly by prep-HPLC (Boston C18 21*250 mm 10 μm column. The mobile phase was acetonitrile/10 mM ammonium acetate aqueous solution) to afford N-(5-(3-chloro-4-fluorobenzyl)pyridin-2-yl)-5-cyanopicolinamide (0.0514 g, 0.14 mmol, 28%) as a grey solid. $^1$H NMR (400 MHz, Dimethylsulfoxide-d$_6$) δ 10.41 (s, 1H), 9.22 (d, J=1.2 Hz, 1H), 8.62 (dd, J=8.0, 2.0 Hz, 1H), 8.37 (d, J=1.6 Hz, 1H), 8.32 (d, J=8.0 Hz, 1H), 8.18 (d, J=8.4 Hz, 1H), 7.80 (dd, J=8.4, 2.0 Hz, 1H), 7.54 (dd, J=7.6, 2.0 Hz, 1H), 7.38-7.28 (m, 2H), 3.98 (s, 2H); LCMS (ESI) m/z: 367.0 [M+H]$^+$.

Example 131. Preparation of N-(5-(3-chlorobenzyl)pyridin-2-yl)-6-(hydroxymethyl)nicotinamide (131)

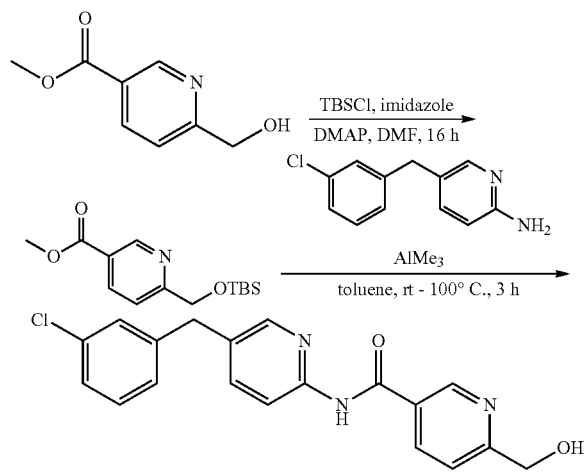

Step 1: Preparation of methyl 6-((tert-butyldimethylsilyloxy)methyl)nicotinate

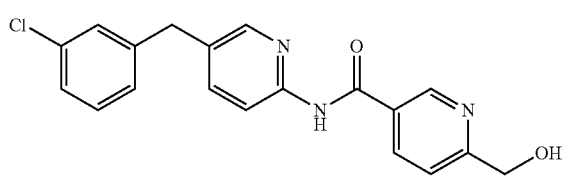 [SMILES: O=C(Nc1ccc(Cc2cccc(Cl)c2)cn1)c1ccc(CO)nc1]

To a solution of methyl 6-(hydroxymethyl)nicotinate (2 g, 12 mmol), imidazole (2.44 g, 36 mmol) and 4-dimethylaminepyridine (0.020 g, 0.16 mmol) in dry N,N-dimethylformamide (30 mL) was added dimethyl-tert-butylchlorosilane (2.17 g, 14.4 mmol) under argon. The reaction mixture was stirred at room temperature for 16 h and diluted with ethyl acetate (150 mL). The organic layer was washed with brine (50 mL×3). The combined organic layers were dried over sodium sulfate, filtered and concentrated. The crude sample was purified by column chromatography (silica gel, petroleum ether/ethyl acetate=10/1) to give methyl 6-((tert-butyldimethylsilyloxy)methyl)nicotinate (3.37 g, 1.19 mmol, 99%) as a colorless oil. LCMS (ESI) m/z: 282.1 [M+H]$^+$.

Step 2: Preparation of N-(5-(3-chlorobenzyl)pyridin-2-yl)-6-(hydroxymethyl)nicotinamide To a solution of methyl 5-(3-chlorobenzyl)pyridin-2-amine (0.218 g, 1.0 mmol) in toluene (10 mL) at room temperature was added trimethylaluminum (0.5 mL, 1.0 mmol, 2 M in toluene) slowly under argon. The reaction mixture was stirred at room temperature for 30 minutes before methyl 6-((tert-butyldimethylsilyloxy)methyl)nicotinate (0.141 g, 0.5 mmol) in toluene (2 mL) was added. The reaction vessel was heated to 100° C. and stirred for 3 h. Reaction was cooled to room temperature and quenched by addition of methanol and aqueous 2 N hydrochloric acid. The volatiles were removed in vacuo and water (20 mL) was added to the slurry mixture. The aqueous phase was extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chlorobenzyl)pyridin-2-yl)-6-(hydroxymethyl)nicotinamide (39.3 mg, 0.11 mmol, 22%) as a white solid. $^1$H NMR (500 MHz, Dimethylsulfoxide-d$_6$) δ 11.08 (s, 1H), 9.07 (d, J=2.0 Hz, 1H), 8.42 (dd, J$_1$=2.5 Hz, J$_2$ 8.5 Hz, 1H), 8.35 (d, J=2.0 Hz, 1H), 8.12 (d, J=8.5 Hz, 1H), 7.75 (dd, J$_1$=2.5 Hz, J$_2$ 8.5 Hz, 1H), 7.64 (d, J=8.0 Hz, 1H), 7.34-7.37 (m, 2H), 7.25-7.29 (m, 2H), 4.67 (s, 2H), 3.99 (s, 2H); LCMS (ESI) m/z: 354.1 [M+H]$^+$.

Example 132. Preparation of 5-(3-Chlorobenzyl)-N-(6-(hydroxymethyl)pyridin-3-yl)picolinamide (132)

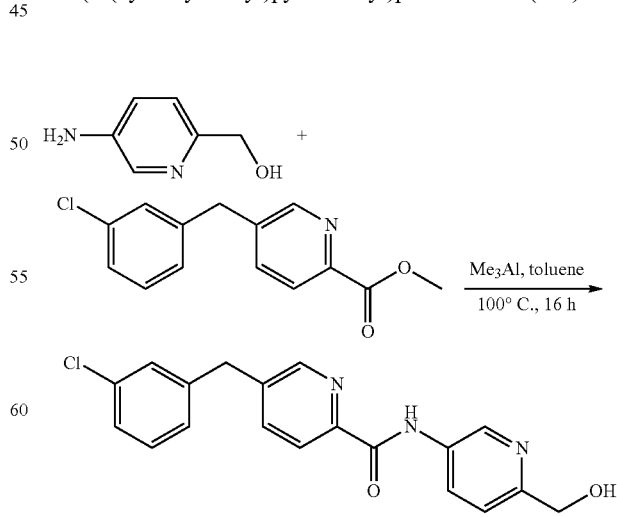

475

Step 1: Preparation of 5-(3-Chlorobenzyl)-N-(6-(hydroxymethyl)pyridin-3-yl)picolinamide

To a solution of (5-aminopyridin-2-yl)methanol (0.249 g, 2.0 mmol) in anhydrous toluene (15 mL) at room temperature was added trimethylaluminum (1.0 mL, 2.0 mmol, 2 M in toluene) under nitrogen. The reaction mixture was stirred at room temperature for 1 h before methyl 5-(3-chlorobenzyl)picolinate (0.261 g, 1.0 mmol) was added. The reaction mixture was stirred at 100° C. for 16 h. The reaction solution was cooled to room temperature and diluted with water (200 mL). The aqueous layer was extracted with ethyl acetate (80 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give 5-(3-chlorobenzyl)-N-(6-(hydroxymethyl)pyridin-3-yl)picolinamide (0.047 g, 0.13 mmol, 13%) as a white solid. $^1$H NMR (500 MHz, Dimethylsulfoxide-d$_6$) δ 10.83 (s, 1H), 8.96 (s, 1H), 8.72 (s, 1H), 8.29 (d, J=7.5 Hz, 1H), 8.10 (d, J=7.5 Hz, 1H), 7.92 (d, J=7.5 Hz, 1H), 7.45-7.41 (m, 2H), 7.37-7.27 (m, 3H), 5.38 (t, J=6.0 Hz, 1H), 4.54 (d, J=5.0 Hz, 2H), 4.14 (s, 2H); LCMS (ESI) m/z: 354.1 [M+H]$^+$.

Example 133. Preparation of 4-cyano-N-(5-(3-fluorobenzyl)pyridin-2-yl)benzamide (133)

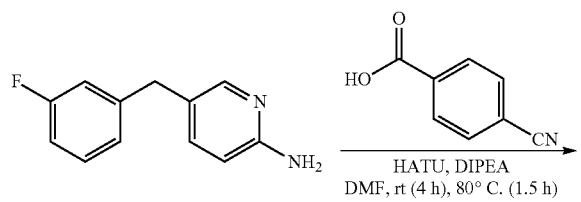

476

Step 1: Preparation of 4-cyano-N-(5-(3-fluorobenzyl)pyridin-2-yl)benzamide

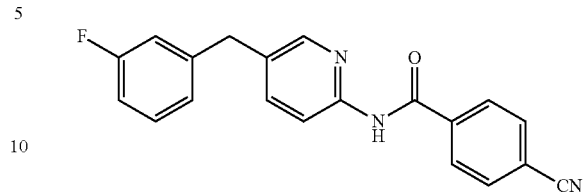

A mixture of 5-(3-fluorobenzyl)pyridin-2-amine (80 mg, 0.4 mmol), 4-cyanobenzoic acid (59 mg, 0.5 mmol), 2-(7-azabenzotriazol-1-yl)-N,N,N',N'-tetramethyluronium hexafluorophosphate (228 mg, 0.6 mmol) and diisopropylethylamine (155 mg, 1.2 mmol) in N,N-dimethylformamide (4 mL) was stirred at room temperature for 4 h and at 80° C. for 1.5 h. The mixture was purified directly by prep-HPLC (Boston C18 21*250 mm 10 μm column. The mobile phase was acetonitrile/10 mM ammonium acetate aqueous solution) to afford 4-cyano-N-(5-(3-fluorobenzyl)pyridin-2-yl)benzamide (0.0565 g, 0.17 mmol, 42.5%) as a grey solid. $^1$H NMR (500 MHz, Dimethylsulfoxide-d$_6$) δ 11.09 (s, 1H), 9.35 (d, J=1.5 Hz, 1H), 8.14-8.10 (m, 3H), 7.99 (d, J=8.0 Hz, 2H), 7.74 (dd, J=8.5, 2.0 Hz, 1H), 7.35 (dd, J=9.0, 2.5 Hz, 1H), 7.14-7.11 (m, 2H), 7.06-7.02 (m, 1H), 3.99 (s, 2H); LCMS (ESI) m/z: 332.1 [M+H]$^+$.

Example 134. Preparation of N-(5-(3-cyano-5-fluorobenzyl)pyridin-2-yl)-2-methylpyrimidine-4-carboxamide (134)

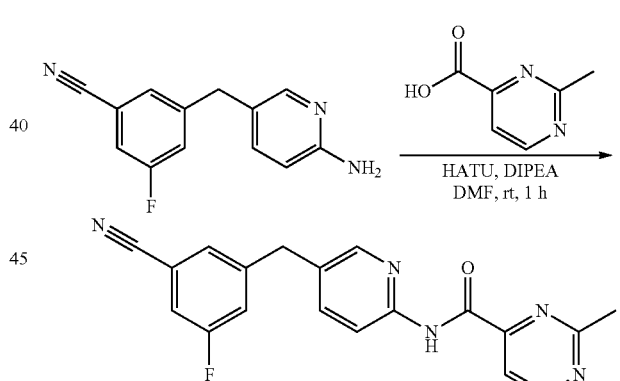

Step 1: Preparation of N-(5-(3-cyano-5-fluorobenzyl)pyridin-2-yl)-2-methylpyrimidine-4-carboxamide

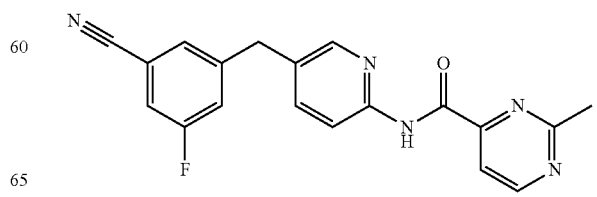

A mixture of 3-((6-aminopyridin-3-yl)methyl)-5-fluorobenzonitrile (227 mg, 1.0 mmol), 2-methylpyrimidine-4-carboxylic acid (138 mg, 1.0 mmol), 2-(7-azabenzotriazol-1-yl)-N,N,N',N'-tetramethyluronium hexafluorophosphate (570 mg, 1.5 mmol) and diisopropylethylamine (390 mg, 3.0 mmol) in N,N-dimethylformamide (4 mL) was stirred at room temperature for 1 h. The mixture was poured into water. The formed precipitate was collected by filtration and the obtained solid was washed with methanol (15 mL) to afford N-(5-(3-cyano-5-fluorobenzyl)pyridin-2-yl)-2-methylpyrimidine-4-carboxamide (0.228 g, 0.66 mmol, 66%) as a grey solid. $^1$H NMR (500 MHz, Dimethylsulfoxide-$d_6$) δ 10.40 (s, 1H), 9.05 (d, J=5.0 Hz, 1H), 8.40 (d, J=2.0 Hz, 1H), 8.19 (d, J=8.5 Hz, 1H), 7.96 (d, J=5.5 Hz, 1H), 7.84 (dd, J=8.5, 2.5 Hz, 1H), 7.72-7.70 (m, 2H), 7.60 (d, J=5.5 Hz, 1H), 4.06 (s, 2H), 2.78 (s, 3H); LCMS (ESI) m/z: 348.1 [M+H]$^+$.

Example 135. Preparation of 5-cyano-N-(5-(3-fluorobenzyl)pyridin-2-yl)picolinamide (135)

Step 1: Preparation of 5-cyano-N-(5-(3-fluorobenzyl)pyridin-2-yl)picolinamide

A mixture of 5-(3-fluorobenzyl)pyridin-2-amine (80 mg, 0.4 mmol), 5-cyanopicolinic acid (74 mg, 0.5 mmol), 2-(7-azabenzotriazol-1-yl)-N,N,N',N'-tetramethyluronium hexafluorophosphate (228 mg, 0.6 mmol) and diisopropylethylamine (155 mg, 1.2 mmol) in N,N-dimethylformamide (4 mL) was stirred at room temperature 1 h. The mixture was purified directly by prep-HPLC (Boston C18 21*250 mm 10 μm column. The mobile phase was acetonitrile/10 mM ammonium acetate aqueous solution) to afford 5-cyano-N-(5-(3-fluorobenzyl)pyridin-2-yl)picolinamide (0.0317 g, 0.095 mmol, 23.8%) as an off-white solid. $^1$H NMR (400 MHz, Dimethylsulfoxide-$d_6$) δ 10.34 (bs, 1H), 9.22 (d, J=1.2 Hz, 1H), 8.62 (dd, J=8.4, 2.0 Hz, 1H), 8.36 (d, J=1.6 Hz, 1H), 8.32 (d, J=8.4 Hz, 1H), 8.18 (d, J=8.4 Hz, 1H), 7.80 (dd, J=8.4, 2.4 Hz, 1H), 7.38-7.32 (m, 1H), 7.15-7.11 (m, 2H), 7.04 (td, dd, J=8.8, 2.0 Hz, 1H), 4.00 (s, 2H); LCMS (ESI) m/z: 333.1 [M+H]$^+$.

Example 136. Preparation of N-(5-(3-chlorobenzyl)pyridin-2-yl)-6-(methoxymethyl)nicotinamide (136)

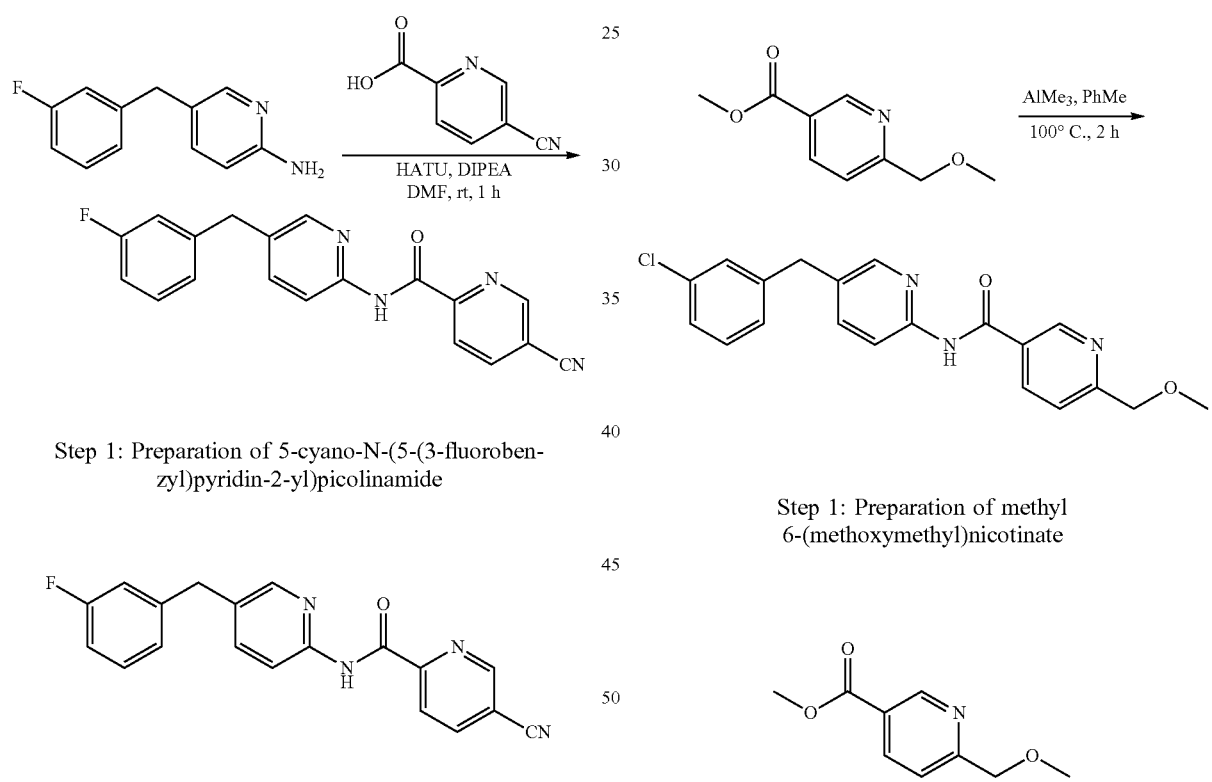

Step 1: Preparation of methyl 6-(methoxymethyl)nicotinate

To a solution of methyl 6-(hydroxymethyl)nicotinate (500 mg, 2.99 mmol) in dichloromethane (5 mL) at 20° C. was added thionyl chloride (529 mg, 4.49 mmol). The residue was stirred for 1 h before solvent was removed under reduced pressure. The crude material was dissolved in methanol (15 mL) and sodium methoxide (1 mL) was added. The reaction solution was stirred at 75° C. for 1 h. The volatiles were removed under reduced pressure and the crude product was purified by column chromatography (petroleum ether/ethyl acetate=4/1) to offer methyl 6-(methoxymethyl)nicotinate (250 mg, 1.38 mmol, 46%) as a yellow solid. LCMS (ESI) m/z: 182.1 [M+H]$^+$.

Step 2: Preparation of N-(5-(3-chlorobenzyl)pyridin-2-yl)-6-(methoxymethyl)nicotinamide

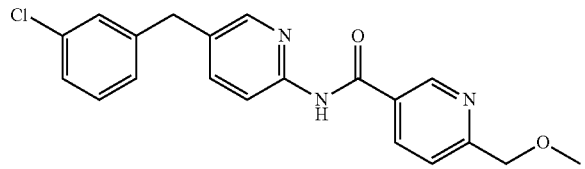 [SMILES: COCc1ccc(C(=O)Nc2ccc(Cc3cccc(Cl)c3)cn2)cn1]

To a solution of 5-(3-chlorobenzyl)pyridin-2-amine (300 mg, 1.376 mmol) in toluene (10 mL) at 20° C. was added trimethylaluminum (0.7 mL, 1.376 mmol, 2 M in toluene) under argon. The reaction mixture was stirred at 20° C. for 1 h before a solution of methyl 6-(methoxymethyl)nicotinate (125 mg, 0.688 mmol) in toluene (2 mL) was added. The reaction solution was stirred at 90° C. for 2 h. The volatiles were removed under reduced pressure and the residue was quenched with water (50 mL). The aqueous layer was extracted with dichloromethane (50 mL×2). The combined organic layers were dried over sodium sulfate, filtered and concentrated. The crude sample was purified by prep-HPLC (dissolved in minimal N,N-dimethylformamide and loaded onto Boston C18 21*250 mm 10 μm column; eluted with acetonitrile/0.01% aqueous trifluoroacetic acid) to give N-(5-(3-chlorobenzyl)pyridin-2-yl)-6-(methoxymethyl)nicotinamide (35.5 mg, 0.097 mmol, 14%) as a light-yellow solid. $^1$H NMR (400 MHz, Dimethylsulfoxide-d$_6$) δ 11.05 (s, 1H), 9.08 (s, 1H), 8.35-8.37 (m, 2H), 8.13 (d, J=12.0 Hz, 1H), 7.72-7.75 (m, 1H), 7.53 (d, J=8.0 Hz, 1H), 7.24-7.36 (m, 4H), 4.58 (s, 2H), 3.98 (s, 2H), 3.40 (s, 3H); LCMS (ESI) m/z: 368.0 [M+H]$^+$.

Example 137. Preparation of N-(5-(3-chlorobenzyl)pyridin-2-yl)-5-(hydroxymethyl)picolinamide (137)

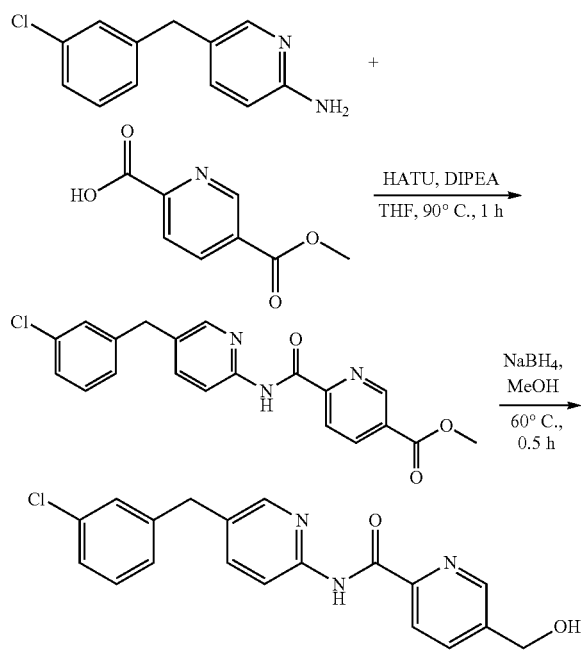

Step 1: Preparation of methyl 6-(5-(3-chlorobenzyl)pyridin-2-ylcarbamoyl)nicotinate

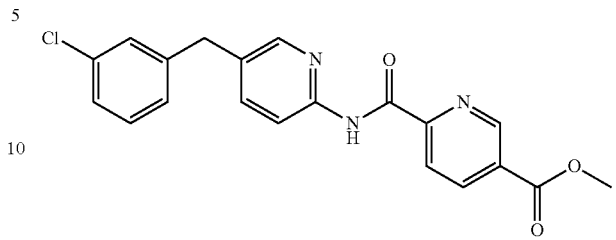

To a mixture of 5-(methoxycarbonyl)picolinic acid (300 mg, 1.657 mmol) and diisopropylethylamine (643 mg, 4.971 mmol) in tetrahydrofuran (10 mL) at 20° C. was added 1-[bis(dimethylamino)methylene]-1H-1,2,3-triazolo[4,5-b]pyridinium 3-oxid hexafluorophosphate (945 mg, 2.486 mmol). The reaction solution was stirred for 20 minutes before a solution of 5-(3-chlorobenzyl)pyridin-2-amine (300 mg, 1.657 mmol) in tetrahydrofuran (1.0 mL) was added. The reaction vessel was heated to 90° C. and stirred for 2 h. The volatiles were removed under reduced pressure and the residue was added to a mixture of dichloromethane (50 mL) and water (50 mL). The organic layer was separated, dried over sodium sulfate, filtered and concentrated. The crude product was purified by column chromatography (silica gel, dichloromethane/methanol=20/1) to offer methyl 6-(5-(3-chlorobenzyl)pyridin-2-ylcarbamoyl)nicotinate (410 mg, 1.08 mmol, 65%) as a white solid. LCMS (ESI) m/z: 382.0 [M+H]$^+$.

Step 2: Preparation of N-(5-(3-chlorobenzyl)pyridin-2-yl)-5-(hydroxymethyl)picolinamide

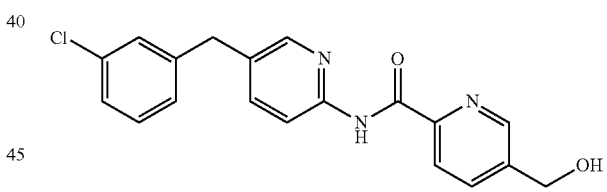

To a solution of methyl 6-(5-(3-chlorobenzyl)pyridin-2-ylcarbamoyl)nicotinate (200 mg, 0.525 mmol) in methanol (15 mL) was added sodium borohydride (100 mg, 2.624 mmol). The reaction mixture was heated to 60° C. for 1 h. The reaction solution was quenched with aqueous sodium bicarbonate (10 mL). The aqueous layer was extracted with dichloromethane (50 mL×2). The combined organic layers were collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chlorobenzyl)pyridin-2-yl)-5-(hydroxymethyl)picolinamide (58.1 mg, 0.16 mmol, 31%) as a white solid. $^1$H NMR (400 MHz, Dimethylsulfoxide-d$_6$) δ 10.39 (s, 1H), 8.68 (s, 1H), 8.34 (s, 1H), 8.20 (q, J=6.6 Hz, 1H), 8.02 (d, J=8.0 Hz, 1H), 7.78 (d, J=8.0 Hz, 1H), 7.32-7.37 (m, 4H), 5.55 (t, J=4.0 Hz, 1H), 4.68 (d, J=4.0 Hz, 2H), 3.98 (s, 2H); LCMS (ESI) m/z: 354.1 [M+H]$^+$.

Example 138. Preparation of N-(5-(3-chloro-4-fluorobenzyl)pyridin-2-yl)-5-methylpyrazine-2-carboxamide (138)

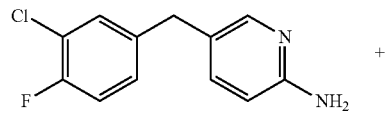

+

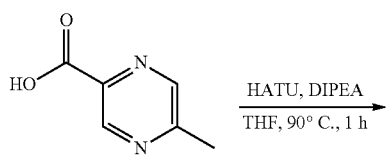

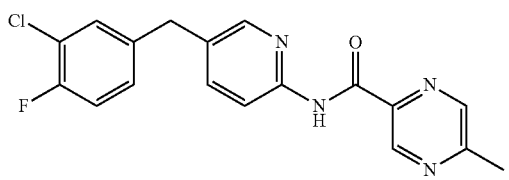 [SMILES: Cc1cnc(C(=O)Nc2ccc(Cc3ccc(F)c(Cl)c3)cn2)cn1]

Step 1: Preparation of N-(5-(3-chloro-4-fluorobenzyl)pyridin-2-yl)-5-methylpyrazine-2-carboxamide

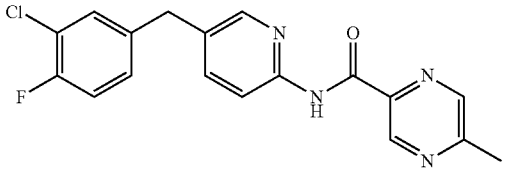

To a solution of 5-methylpyrazine-2-carboxylic acid (100 mg, 0.635 mmol) and diisopropylethylamine (246 mg, 1.905 mmol) in tetrahydrofuran (4 mL) at 20° C. was added 1-[bis(dimethylamino)methylene]-1H-1,2,3-triazolo[4,5-b]pyridinium 3-oxid hexafluorophosphate (362 mg, 0.953 mmol). The reaction mixture was stirred for 20 minutes before a solution of 5-(3-chloro-4-fluorobenzyl)pyridin-2-amine (150 mg, 0.635 mmol) in tetrahydrofuran (1.0 mL) was added. The reaction solution was heated to 90° C. and stirred for 1 h. The volatiles were removed under reduced pressure and the residue was added to a mixture of dichloromethane (50 mL) and water (50 mL). The organic layer was collected, dried over sodium sulfate, filtered and concentrated. The crude material was purified by column chromatography (silica gel, dichloromethane/methanol=20/1) to offer N-(5-(3-chloro-4-fluorobenzyl)pyridin-2-yl)-5-methylpyrazine-2-carboxamide (120.0 mg, 0.34 mmol, 54%) as a white solid. $^1$H NMR (400 MHz, Dimethylsulfoxide-$d_6$) δ 10.23 (s, 1H), 9.19 (s, 1H), 8.71 (s, 1H), 8.35 (s, 1H), 8.17 (d, J=8.0 Hz, 1H), 7.79 (q, J=2.6 Hz, 1H), 7.53 (q, J=2.6 Hz, 1H), 7.29-7.37 (m, 2H), 3.98 (s, 2H), 2.64 (s, 3H); LCMS (ESI) m/z: 357.1 [M+H]$^+$.

Example 139. Preparation of N-(5-(3-fluorobenzyl)pyridin-2-yl)-5-methylpyrimidine-2-carboxamide (139)

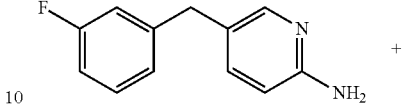

+

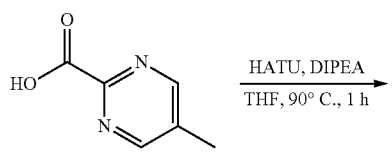

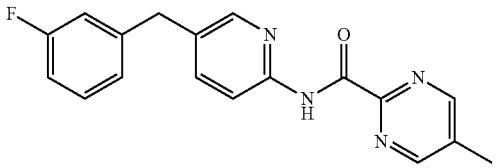 [SMILES: Cc1cnc(C(=O)Nc2ccc(Cc3cccc(F)c3)cn2)nc1]

Step 1: Preparation of N-(5-(3-fluorobenzyl)pyridin-2-yl)-5-methylpyrimidine-2-carboxamide

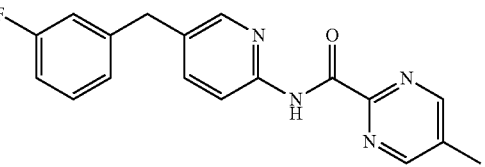

To a solution of 5-methylpyrimidine-2-carboxylic acid (102 mg, 0.742 mmol) and diisopropylethylamine (288 mg, 2.226 mmol) in tetrahydrofuran (4 mL) at 20° C. was added 1-[bis(dimethylamino)methylene]-1H-1,2,3-triazolo[4,5-b]pyridinium 3-oxid hexafluorophosphate (423 mg, 1.113 mmol). The reaction mixture was stirred for 20 minutes before a solution of 5-(3-fluorobenzyl)pyridin-2-amine (150 mg, 0.742 mmol) in tetrahydrofuran (1.0 mL) was added. The reaction solution was heated to 90° C. and stirred for 1 h. The volatiles were removed under reduced pressure and the residue was added to a mixture of dichloromethane (50 mL) and water (50 mL). The organic layer was collected, dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-(3-fluorobenzyl)pyridin-2-yl)-5-methylpyrimidine-2-carboxamide (150 mg, 0.47 mmol, 63%) as a white solid. $^1$H NMR (400 MHz, Dimethylsulfoxide-$d_6$) δ 10.44 (s, 1H), 8.90 (s, 2H), 8.34 (s, 1H), 8.19 (d, J=8.0 Hz, 1H), 7.79 (q, J=2.6 Hz, 1H), 7.34 (q, J=2.6 Hz, 1H), 7.01-7.14 (m, 3H), 3.99 (s, 2H), 2.40 (s, 3H); LCMS (ESI) m/z: 323.0 [M+H]$^+$.

Example 140. Preparation of N-(5-(3-fluorobenzyl) pyridin-2-yl)-1-methyl-2-oxo-1,2-dihydropyridine-3-carboxamide (140)

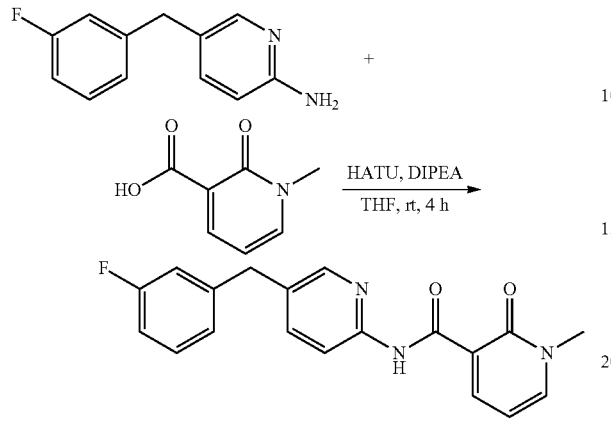

Step 1: Preparation of N-(5-(3-fluorobenzyl)pyridin-2-yl)-1-methyl-2-oxo-1,2-dihydropyridine-3-carboxamide

To a mixture of 1-methyl-2-oxo-1,2-dihydropyridine-3-carboxylic acid (100 mg, 0.653 mmol), and diisopropylethylamine (253 mg, 1.959 mmol) in tetrahydrofuran (5 mL) at 20° C. was added 1-[bis(dimethylamino)methylene]-1H-1,2,3-triazolo[4,5-b]pyridinium 3-oxid hexafluorophosphate (372 mg, 0.98 mmol). The reaction solution was stirred for 20 minutes before a solution of 5-(3-fluorobenzyl)pyridin-2-amine (132 mg, 0.653 mmol) in tetrahydrofuran (1.0 mL) was added. The reaction mixture was stirred at 20° C. for 4 h. The volatiles were removed under reduced pressure and the residue was added to a mixture of dichloromethane (50 mL) and water (50 mL). The organic layer was collected, dried over sodium sulfate, filtered and concentrated. The residue was purified by column chromatography (silica gel, dichloromethane/methanol=20/1) to offer N-(5-(3-fluorobenzyl)pyridin-2-yl)-1-methyl-2-oxo-1,2-dihydropyridine-3-carboxamide (89.6 mg, 0.27 mmol, 41%) as a white solid. $^1$H NMR (400 MHz, Dimethylsulfoxide-$d_6$) δ 12.48 (s, 1H), 8.45-8.47 (m, 1H), 8.29 (s, 1H), 8.21 (s, 1H), 8.17-8.19 (m, 1H), 7.69-7.72 (m, 1H), 7.35 (q, J=6.6 Hz, 1H), 7.10-7.13 (m, 2H), 7.03 (t, J=8.0 Hz, 1H), 6.60 (t, J=8.0 Hz, 1H), 3.96 (s, 2H), 3.63 (s, 3H); LCMS (ESI) m/z: 338.0 [M+H]$^+$.

Example 141. Preparation of N-(5-(3-fluorobenzyl) pyridin-2-yl)-2-methylpyrimidine-5-carboxamide (141)

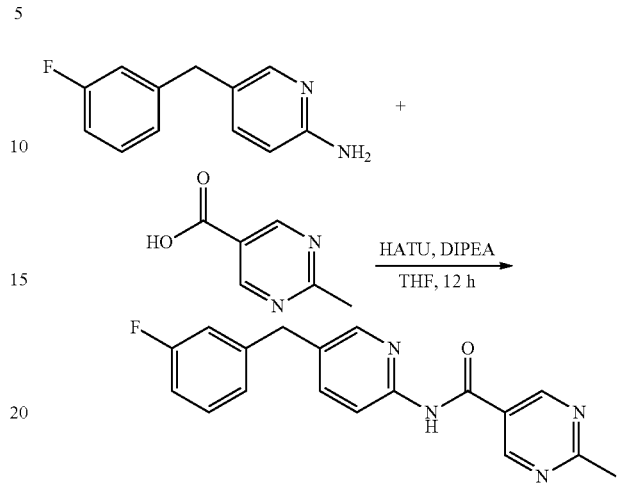

Step 1: Preparation of N-(5-(3-fluorobenzyl)pyridin-2-yl)-2-methylpyrimidine-5-carboxamide

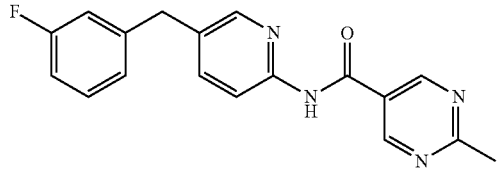 [SMILES: Cc1ncc(C(=O)Nc2ccc(Cc3cccc(F)c3)cn2)cn1]

To a solution of 2-methylpyrimidine-5-carboxylic acid (100 mg, 0.724 mmol) and diisopropylethylamine (281 mg, 2.17 mmol) in tetrahydrofuran (4 mL) at 20° C. was added 1-[bis(dimethylamino)methylene]-1H-1,2,3-triazolo[4,5-b]pyridinium 3-oxid hexafluorophosphate (413 mg, 1.09 mmol). The reaction mixture was stirred for 20 minutes before a solution of 5-(3-fluorobenzyl)pyridin-2-amine (146 mg, 0.724 mmol) in tetrahydrofuran (1.0 mL) was added. The reaction solution was heated to 90° C. and stirred at 90° C. for 1 h. The volatiles were removed under reduced pressure and the residue was added to a mixture of dichloromethane (50 mL) and water (50 mL). The organic layer was collected, dried over sodium sulfate, filtered and concentrated. The residue was purified by column chromatography (silica gel, dichloromethane/methanol=20/1) to offer N-(5-(3-fluorobenzyl)pyridin-2-yl)-2-methylpyrimidine-5-carboxamide (93.1 mg, 0.29 mmol, 40%) as a white solid. $^1$H NMR (400 MHz, Dimethylsulfoxide-$d_6$) δ 11.19 (s, 1H), 9.18 (s, 2H), 8.34 (d, J=2.0 Hz, 1H), 8.12 (d, J=8.8 Hz, 1H), 7.73-7.76 (m, 1H), 7.33-7.38 (m, 1H), 7.02-7.14 (m, 3H), 3.99 (s, 2H), 2.70 (s, 3H); LCMS (ESI) m/z: 323.1 [M+H]$^+$.

Example 142. Preparation of 5-cyano-N-(5-(3-fluorobenzyl)pyridin-2-yl)picolinamide (142)

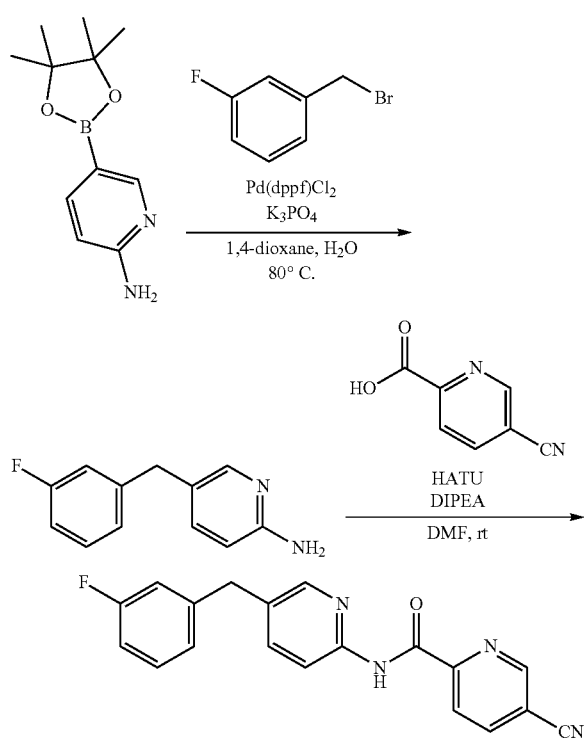

Step 1: Preparation of 5-[(3-fluorophenyl)methyl]pyridin-2-amine

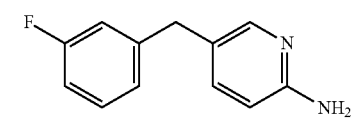

In a 40 mL reaction vial, combined 5-(4,4,5,5-tetramethyl-1,3,2-dioxaborolan-2-yl)pyridin-2-amine (1 g, 4.54 mmol), tripotassium phosphate (0.963 g, 4.54 mmol) and [1,1'-bis(diphenylphosphino)ferrocene]dichloropalladium (II) (0.165 g, 0.227 mmol). $R^{6a}$ gents were suspended in 1,4-dioxane (6 mL) and water (2 mL) and 1-(bromomethyl)-3-fluorobenzene (556 μL, 4.54 mmol) was added. The reaction was degassed by cycling with vacuum and nitrogen for 3 cycles. The reaction was stirred at 80° C. for 16 h. After cooling to room temperature, the reaction was diluted with ethyl acetate (15 mL) and washed with water (10 mL) and brine (10 mL). The combined organic layers were dried over sodium sulfate, filtered, and concentrated. Purified reaction by column chromatography (eluting with 0-100% ethyl acetate/hexanes through 12 g of silica gel) to give 5-[(3-fluorophenyl)methyl]pyridin-2-amine (90 mg, 0.445 mmol, 10%) as a brown oil. $^1$H NMR (300 MHz, Chloroform-d) δ 8.01-7.94 (m, 1H), 7.31-7.19 (m, 2H), 7.07-6.83 (m, 3H), 6.47 (dd, J=8.4, 0.8 Hz, 1H), 4.36 (s, 2H), 3.84 (s, 2H).

Step 2: Preparation of 5-cyano-N-{5-[(3-fluorophenyl)methyl]pyridin-2-yl}pyridine-2-carboxamide

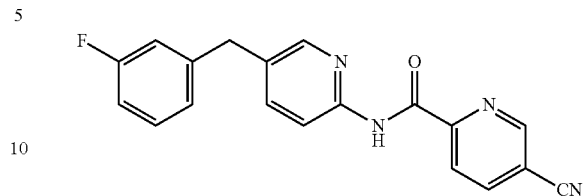

In a 25 mL round bottom flask, combined 5-[(3-fluorophenyl)methyl]pyridin-2-amine (90 mg, 0.445 mmol) with 5-cyanopyridine-2-carboxylic acid (0.065 g, 0.445 mmol) and 1-[(dimethylamino)(dimethyliminiumyl)methyl]-3-oxo-1H,2H,3H-3λ$^5$-[1,2,3]triazolo[5,4-b]pyridin-3-ylium-2-ide; hexafluoro-λ$^5$-phosphanuide (0.169 g, 0.445 mmol). $R^{6a}$ gents were suspended in N,N'-dimethylformamide (2 mL) and ethylbis(propan-2-yl)amine (116 μL, 0.6675 mmol) was added. Reaction mixture was stirred at room temperature 16 h. Diluted with ethyl acetate (20 mL) and washed with water (10 mL×3) and with brine (15 mL). The combined organic layers were dried over sodium sulfate, filtered, and concentrated. Purified reaction by column chromatography (eluting with 0-100% ethyl acetate/hexanes through 24 g of silica gel) to give 5-cyano-N-{5-[(3-fluorophenyl)methyl]pyridin-2-yl}pyridine-2-carboxamide (41 mg, 0.123 mmol, 28%) a white solid. $^1$H NMR (300 MHz, Chloroform-d) δ 10.36 (s, 1H), 8.94 (dd, J=2.0, 0.9 Hz, 1H), 8.44 (dd, J=8.1, 0.9 Hz, 1H), 8.39-8.31 (m, 1H), 8.29-8.15 (m, 2H), 7.60 (dd, J=8.4, 2.4 Hz, 1H), 7.38-7.24 (m, 1H), 7.12-6.84 (m, 3H), 3.99 (s, 2H); LCMS (ESI) m/z: 333.4 [M+H]$^+$.

Example 143. Preparation of N-(5-(3-fluorobenzyl)pyridin-2-yl)pyridazine-4-carboxamide (143)

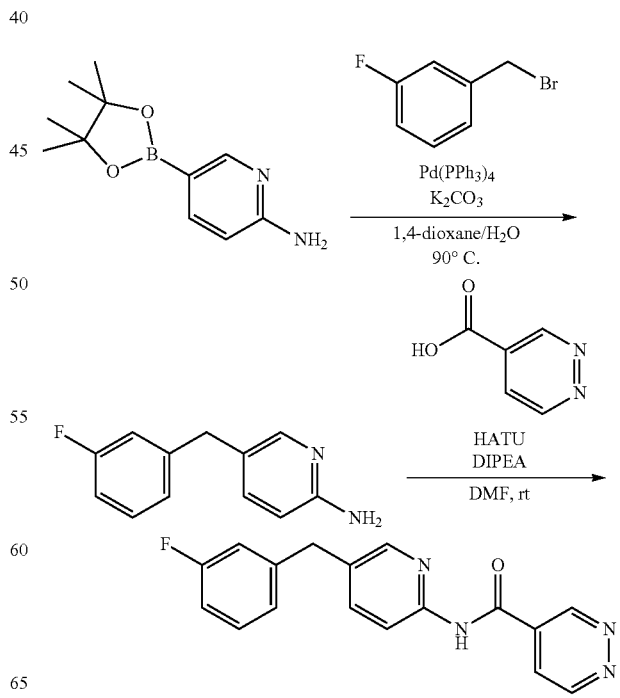

487

Step 1: Preparation of 5-[(3-fluorophenyl)methyl]pyridin-2-amine

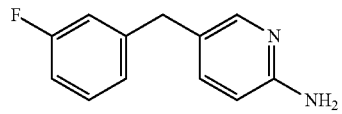 [SMILES: Nc1ccc(Cc2cccc(F)c2)cn1]

In a 40 mL reaction vial, combined 5-(4,4,5,5-tetramethyl-1,3,2-dioxaborolan-2-yl)pyridin-2-amine (0.5 g, 2.27 mmol), dipotassium carbonate (0.627 g, 4.54 mmol) and tetrakis(triphenylphosphane) palladium (0.131 g, 0.1135 mmol) and added a stir bar. Added 1,4-dioxane (6 mL) and water (2 mL) and 1-(bromomethyl)-3-fluorobenzene (278 µL, 2.27 mmol). The reaction was degassed by cycling with vacuum and nitrogen for 3 cycles. The reaction was stirred at 90° C. for 16 h. Diluted with ethyl acetate (15 mL) and washed with water (10 mL), then brine (10 mL). The combined organic layers were dried over sodium sulfate, filtered, and concentrated. Purified reaction by column chromatography (eluting with 0-100% ethyl acetate/hexanes through 24 g of silica gel) to give 5-[(3-fluorophenyl)methyl]pyridin-2-amine (203 mg, 1.00 mmol, 44%) as an orange solid. $^1$H NMR (300 MHz, Chloroform-d) δ 7.96 (dd, J=2.4, 0.8 Hz, 1H), 7.75-7.60 (m, 1H), 7.60-7.43 (m, 1H), 7.41-7.13 (m, 2H), 7.04-6.79 (m, 3H), 6.47 (dd, J=8.4, 0.8 Hz, 1H), 4.37 (s, 2H), 3.84 (s, 2H).

Step 2: Preparation of N-{5-[(3-fluorophenyl)methyl]pyridin-2-yl}pyridazine-4-carboxamide

Combined pyridazine-4-carboxylic acid (0.061 g, 0.4943 mmol) and 1-[bis(dimethylamino)methanidyl]-3-oxo-1H,2H,3H-3λ$^5$-[1,2,3]triazolo[5,4-b]pyridine-1,4-diium-3-ylium-2-ide, hexafluoro-λ$^5$-phosphanuide (0.188 g, 0.4943 mmol) in a 40 mL reaction vial and added a solution of 5-[(3-fluorophenyl)methyl]pyridin-2-amine (0.100 g, 0.4944 mmol) in 4 mL of N,N-N,N'-dimethylformamide. Added ethylbis(propan-2-yl)amine (129 µL, 0.7416 mmol), then stirred at room temperature 16 h. Diluted with ethyl acetate (15 mL), then washed with water (3×10 mL), then once with brine (10 mL). The combined organic layers were dried over sodium sulfate, filtered, and concentrated. Purified reaction by column chromatography (eluting with 0-100% ethyl acetate/hexanes through 12 g of silica gel) to give N-{5-[(3-fluorophenyl)methyl]pyridin-2-yl}pyridazine-4-carboxamide (24 mg, 0.078 mmol, 16%) as a white solid. $^1$H NMR (300 MHz, Chloroform-d) δ 9.72 (dd, J=2.4, 1.2 Hz, 1H), 9.46 (dd, J=5.3, 1.2 Hz, 1H), 8.45-8.30 (m, 1H), 8.15 (s, 1H), 8.14-7.97 (m, 1H), 7.75-7.61 (m, 1H), 7.60-7.41 (m, 1H), 7.28 (d, J=5.5 Hz, 2H), 7.04-6.91 (m, 1H), 6.87 (d, J=9.7 Hz, 1H), 4.00 (s, 2H); LCMS (ESI) m/z: 309.3 [M+H]$^+$.

488

Example 144. Preparation of N-(5-(3-fluorobenzyl)pyridin-2-yl)-2-methylpyrimidine-4-carboxamide (144)

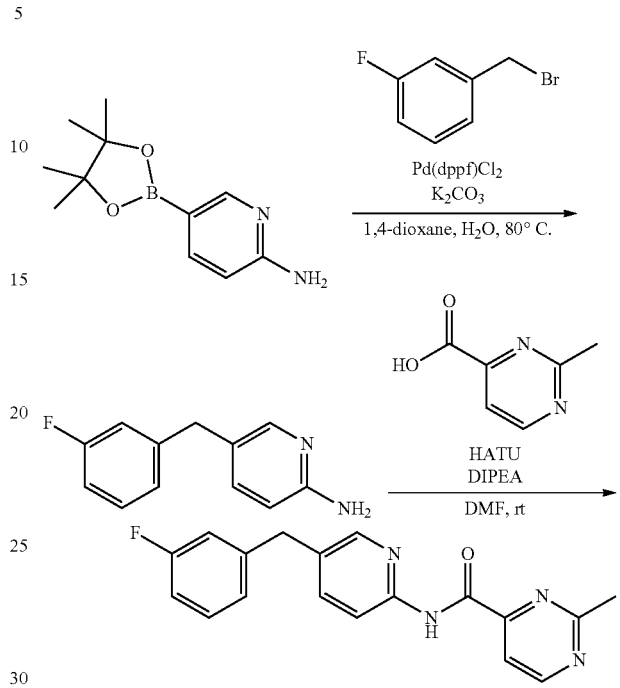

Step 1: Preparation of 5-[(3-fluorophenyl)methyl]pyridin-2-amine

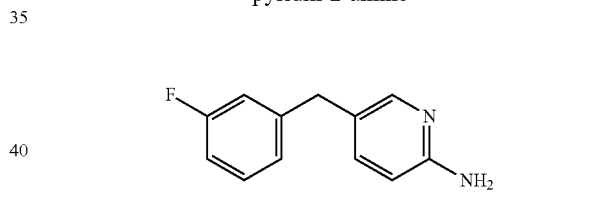

In a 40 mL reaction vial, combined 5-(4,4,5,5-tetramethyl-1,3,2-dioxaborolan-2-yl)pyridin-2-amine (0.500 g, 2.27 mmol), dipotassium carbonate (0.375 g, 2.72 mmol) and λ$^2$-iron(2+) bis((cyclopenta-2,4-diyn-1-yl)diphenyl-λ$^4$-phosphane) palladium dichloride (0.082 g, 0.1135 mmol). Added 1,4-dioxane (6 mL) and water (2 mL) and added 1-(bromomethyl)-3-fluorobenzene (278 µL, 2.27 mmol). The reaction was degassed by cycling with vacuum and nitrogen gas for 3 cycles. Stirred the reaction at 80° C. for 16 h. Cooled to room temperature and diluted with ethyl acetate (15 mL), then washed with water (10 mL), then brine (10 mL). The combined organic layers were dried over sodium sulfate, filtered, and concentrated. Purified reaction by column chromatography (eluting with 0-100% ethyl acetate/hexanes through 24 g of silica gel) to give 5-[(3-fluorophenyl)methyl]pyridin-2-amine as a brown solid (131 mg, 0.648 mmol, 28%). $^1$H NMR (300 MHz, Chloroform-d) δ 8.02-7.94 (m, 1H), 7.33-7.18 (m, 2H), 7.06-6.80 (m, 3H), 6.47 (dd, J=8.4, 0.9 Hz, 1H), 4.36 (s, 2H), 3.84 (s, 2H).

Step 2: Preparation of N-{5-[(3-fluorophenyl)methyl]pyridin-2-yl}-2-methylpyrimidine-4-carboxamide

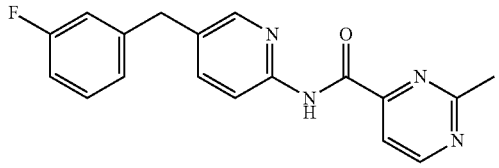 [SMILES: Cc1nccc(C(=O)Nc2ccc(Cc3cccc(F)c3)cn2)n1]

In a 40 mL reaction vial, combined 5-[(3-fluorophenyl)methyl]pyridin-2-amine (0.131 g, 0.6477 mmol) with 2-methylpyrimidine-4-carboxylic acid (0.089 g, 0.6477 mmol) and [bis(dimethylamino)methylidene]({3H-[1,2,3]triazolo[4,5-b]pyridin-3-yl}oxidanium; tetrafluoroboranuide (0.208 g, 0.6477 mmol). Dissolved in N,N'-dimethylformamide (3 mL) and added ethylbis(propan-2-yl)amine (168 µL, 0.9715 mmol). Stirred for 16 h at room temperature. Diluted with ethyl acetate (15 mL) and washed 3 times with water (10 mL), then once with brine (10 mL). The combined organic layers were dried over sodium sulfate, filtered, and concentrated. Purified reaction by column chromatography (eluting with 0-100% ethyl acetate/hexanes through 24 g of silica gel) to give N-{5-[(3-fluorophenyl)methyl]pyridin-2-yl}-2-methylpyrimidine-4-carboxamide as a white solid (88 mg, 0.273 mmol, 42%). $^1$H NMR (300 MHz, Chloroform-d) δ 8.95 (d, J=5.0 Hz, 1H), 8.41-8.32 (m, 1H), 8.27 (dd, J=2.4, 0.8 Hz, 1H), 8.01 (m, 1H), 7.66-7.52 (m, 1H), 7.28 (s, 2H), 7.05-6.84 (m, 2H), 4.00 (s, 2H), 2.85 (s, 3H); LCMS (ESI) m/z: 323.4 [M+H]$^+$.

Example 145. Preparation of N-(5-(3-fluorobenzyl)pyridin-2-yl)-6-methylpyridazine-3-carboxamide (145)

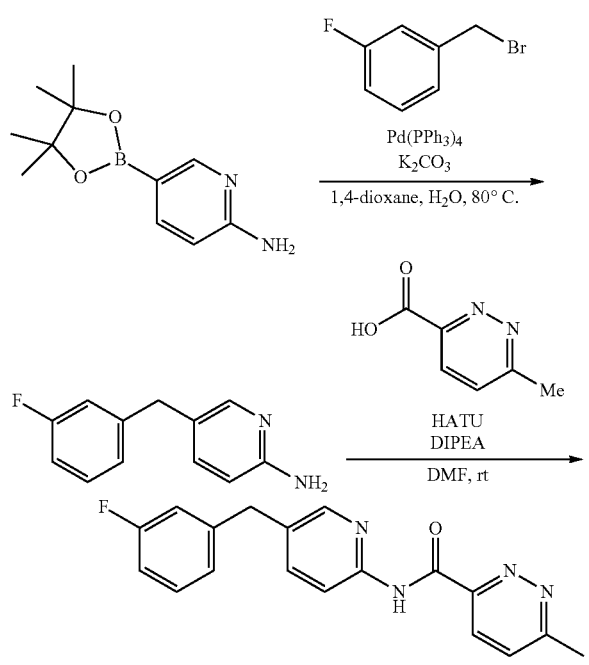

Step 1: Preparation of 5-[(3-fluorophenyl)methyl]pyridin-2-amine

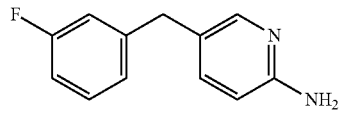 [SMILES: Nc1ccc(Cc2cccc(F)c2)cn1]

In a 40 mL reaction vial, combined 5-(4,4,5,5-tetramethyl-1,3,2-dioxaborolan-2-yl)pyridin-2-amine (0.500 g, 2.27 mmol), dipotassium carbonate (0.375 mg, 2.72 mmol) and tetrakis(triphenylphosphane) palladium (0.052 g, 0.0454 mmol). Added 1,4-dioxane (6.0 mL) and water (2.0 mL) and added 1-(bromomethyl)-3-fluorobenzene (278 µL, 2.27 mmol). The reaction was degassed by cycling with vacuum and nitrogen gas for 3 cycles. Stirred at 80° C. for 16 h. Diluted with ethyl acetate (15 mL) and washed with water (10 mL), then brine (10 mL). The combined organic layers were dried over sodium sulfate, filtered, and concentrated. Purified reaction by column chromatography (eluting with 0-100% ethyl acetate/hexanes through 24 g of silica gel) to give 5-[(3-fluorophenyl)methyl]pyridin-2-amine as a brown solid (102 mg, 0.504 mmol, 22%). $^1$H NMR (300 MHz, Chloroform-d) δ 7.81 (s, 1H), 7.34 (d, J=16.4 Hz, 2H), 7.11-6.78 (m, 3H), 6.64 (s, 1H), 3.85 (s, 2H).

Step 2: Preparation of N-{5-[(3-fluorophenyl)methyl]pyridin-2-yl}-6-methylpyridazine-3-carboxamide

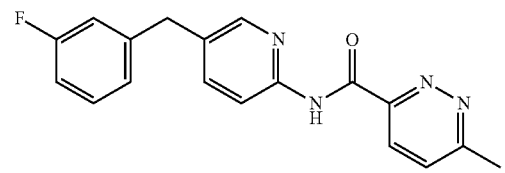 [SMILES: Cc1ccc(C(=O)Nc2ccc(Cc3cccc(F)c3)cn2)nn1]

In a 25 mL round bottom flask, combined 5-[(3-fluorophenyl)methyl]pyridin-2-amine (0.102 g, 0.504 mmol) with 6-methylpyridazine-3-carboxylic acid (0.070 g, 0.504 mmol) and 1-[Bis(dimethylamino)methylene]-1H-1,2,3-triazolo[4,5-b]pyridinium 3-oxid hexafluorophosphate (0.162 g, 0.504 mmol). Dissolved in 3.0 mL N,N'-dimethylformamide and added N,N-diisopropylethylamine (131 µL, 0.756 mmol). Stirred at room temperature 16 h. Diluted with ethyl acetate (15 mL) and washed 3 times with water (10 mL), then once with brine (15 mL). The combined organic layers were dried over sodium sulfate, filtered, and concentrated. Purified reaction by column chromatography (eluting with 0-100% ethyl acetate/hexanes through 24 g of silica gel) to give N-{5-[(3-fluorophenyl)methyl]pyridin-2-yl}-6-methylpyridazine-3-carboxamide as a white solid (71 mg, 0.220 mmol, 44%). $^1$H NMR (300 MHz, Chloroform-d) δ 10.54 (s, 1H), 8.39-8.20 (m, 3H), 7.63-7.51 (m, 2H), 7.30 (s, 1H), 6.96 (dd, J=18.6, 7.2 Hz, 3H), 3.99 (s, 2H), 2.86 (s, 3H); LCMS (ESI) m/z: 323.4 [M+H]$^+$.

Example 146. Preparation of N-(5-(3-chlorobenzyl)pyridin-2-yl)-[1,2,4]triazolo[4,3-a]pyridine-6-carboxamide (146)

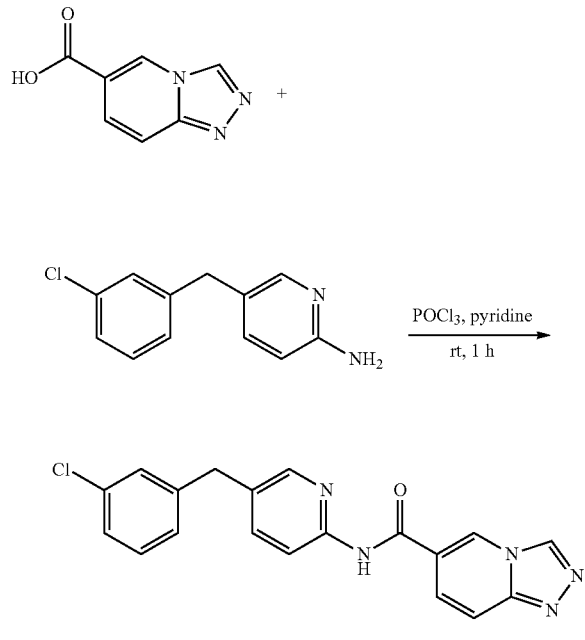

Step 1: Preparation of N-(5-(3-chlorobenzyl)pyridin-2-yl)-[1,2,4]triazolo[4,3-a]pyridine-6-carboxamide

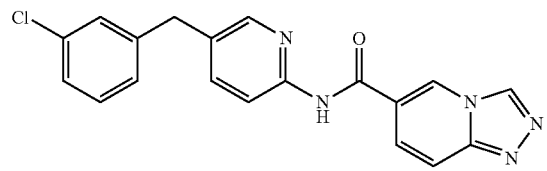 [SMILES: O=C(Nc1ccc(Cc2cccc(Cl)c2)cn1)c1ccc2nncn2c1]

To a solution of [1,2,4]triazolo[4,3-a]pyridine-6-carboxylic acid (100 mg, 0.613 mmol) and 5-(3-chlorobenzyl)pyridin-2-amine (134 mg, 0.613 mmol) in pyridine (4 mL) at 20° C. was added phosphorus oxychloride (279 mg, 1.839 mmol). The reaction mixture was stirred at room temperature for 1 h before solvent was removed under reduced pressure. The resulting solid was dissolved in dichloromethane (10.0 mL) and added to a mixture of dichloromethane (50 mL) and water (50 mL). The combined organic layers were collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chlorobenzyl)pyridin-2-yl)-[1,2,4]triazolo[4,3-a]pyridine-6-carboxamide (34.0 mg, 0.09 mmol, 15%) as a yellow solid. $^1$H NMR (400 MHz, Dimethylsulfoxide-$d_6$) δ 11.03 (s, 1H), 9.38 (s, 1H), 9.30 (s, 1H), 8.33 (d, J=2.0 Hz, 1H), 8.09 (d, J=8.4 Hz, 1H), 7.83 (s, 2H), 7.72-7.74 (m, 1H), 7.22-7.35 (m, 4H), 3.97 (s, 2H); LCMS (ESI) m/z: 364.0 [M+H]$^+$.

Example 147. Preparation of N-(5-(3,4-difluorobenzyl)pyridin-2-yl)-[1,2,4]triazolo[4,3-a]pyridine-6-carboxamide (147)

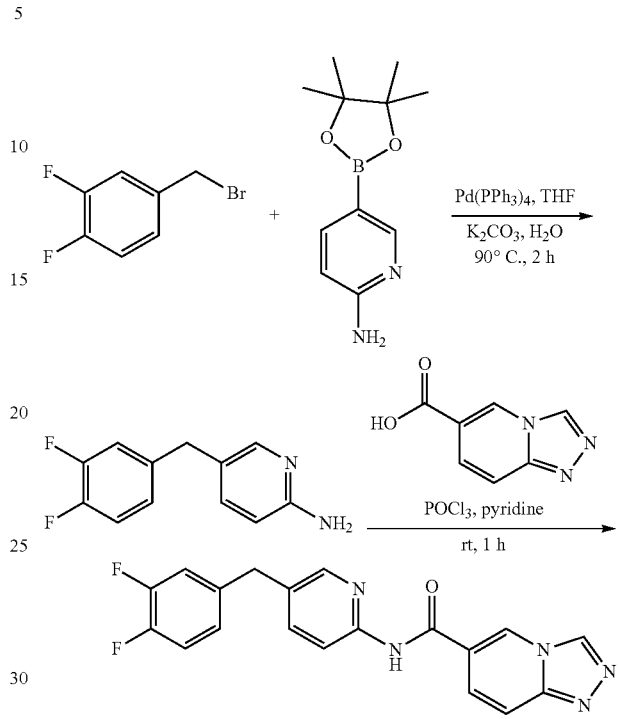

Step 1: Preparation of 5-(3,4-difluorobenzyl)pyridin-2-amine

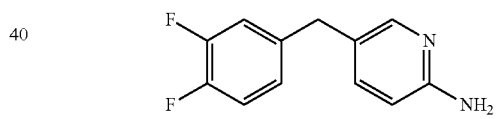

To a solution of 4-(bromomethyl)-1,2-difluorobenzene (2.0 g, 9.71 mmol), 5-(4,4,5,5-tetramethyl-1,3,2-dioxaborolan-2-yl)pyridin-2-amine (2.14 g, 9.71 mmol) and potassium carbonate (2.7 g, 19.42 mmol) in tetrahydrofuran (20 mL) and water (5 mL) was added tetrakis(triphenylphosphine)palladium(0) (1.12 g, 0.971 mmol) under nitrogen. The reaction mixture was heated to 90° C. and stirred for 2 h. The volatiles were removed under reduced pressure. The aqueous layer was treated with 1 N hydrochloric acid to adjust the pH value to 1-3. The aqueous layer was extracted with ethyl acetate (50 mL) before aqueous sodium bicarbonate was added to adjust the pH value to 8-10. The aqueous layer was extracted with dichloromethane (50 mL×2). The combined organic layers were collected, dried over sodium sulfate, filtered and concentrated. The crude material was purified by column chromatography (silica gel, dichloromethane/methanol=20/1) to offer 5-(3,4-difluorobenzyl)pyridin-2-amine as a yellow oil (800 mg, 3.64 mmol, 37%); LCMS (ESI) m/z: 221.1 [M+H]$^+$.

Step 2: Preparation of N-(5-(3,4-difluorobenzyl)pyridin-2-yl)-[1,2,4]triazolo[4,3-a]pyridine-6-carboxamide

To a solution of [1,2,4]triazolo[4,3-a]pyridine-6-carboxylic acid (100 mg, 0.613 mmol) and 5-(3,4-difluorobenzyl)pyridin-2-amine (135 mg, 0.613 mmol) in pyridine (4 mL) at 20° C. was added phosphorus oxychloride (279 mg, 1.839 mmol). The reaction mixture was stirred at room temperature for 2 h. The volatiles were removed under reduced pressure and the solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,4-difluorobenzyl)pyridin-2-yl)-[1,2,4]triazolo[4,3-a]pyridine-6-carboxamide (23.7 mg, 0.06 mmol, 10%) as a light-yellow solid. $^1$H NMR (400 MHz, Dimethylsulfoxide-$d_6$) δ 11.12 (s, 1H), 9.46 (s, 1H), 9.38 (s, 1H), 8.41 (d, J=2.4 Hz, 1H), 8.17 (d, J=8.4 Hz, 1H), 7.91 (s, 2H), 7.80-7.82 (m, 1H), 7.40-7.48 (m, 2H), 7.18-7.22 (m, 1H), 4.03 (s, 2H); LCMS (ESI) m/z: 366.1 [M+H]$^+$.

Example 148. Preparation of N-(5-(3-chloro-4-fluorobenzyl)pyridin-2-yl)-[1,2,4]triazolo[4,3-a]pyridine-6-carboxamide (148)

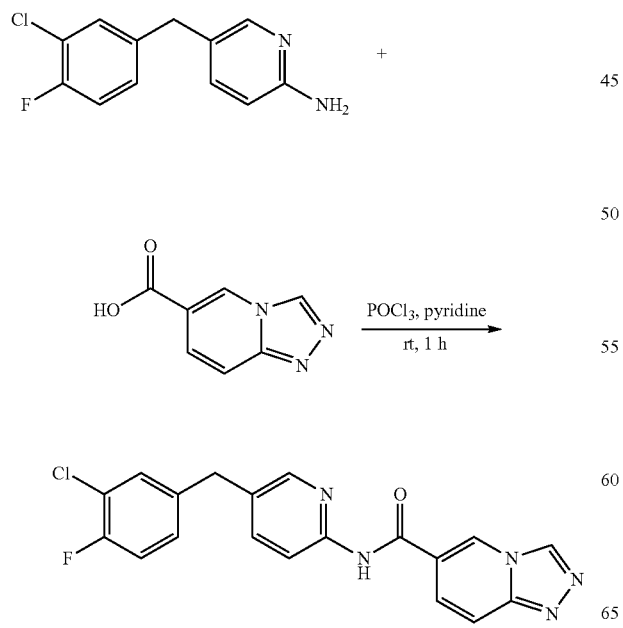

Step 1: Preparation of N-(5-(3-chloro-4-fluorobenzyl)pyridin-2-yl)-[1,2,4]triazolo[4,3-a]pyridine-6-carboxamide

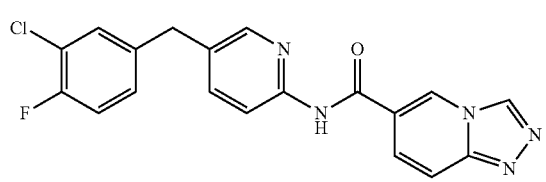 [SMILES: O=C(Nc1ccc(Cc2ccc(F)c(Cl)c2)cn1)c1ccc2nncn2c1]

To a solution of [1,2,4]triazolo[4,3-a]pyridine-6-carboxylic acid (100 mg, 0.613 mmol) and 5-(3-chloro-4-fluorobenzyl)pyridin-2-amine (135 mg, 0.613 mmol) in pyridine (4 mL) at 20° C. was added phosphorus oxychloride (279 mg, 1.84 mmol). The reaction mixture was stirred at room temperature for 2 h. The volatiles were removed under reduced pressure and the solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chloro-4-fluorobenzyl)pyridin-2-yl)-[1,2,4]triazolo[4,3-a]pyridine-6-carboxamide (21.8 mg, 0.06 mmol, 9%) as a light-yellow solid. $^1$H NMR (400 MHz, Dimethylsulfoxide-$d_6$) δ 11.03 (s, 1H), 9.38 (s, 1H), 9.30 (s, 1H), 8.33 (d, J=2.0 Hz, 1H), 8.09 (d, J=8.4 Hz, 1H), 7.83 (s, 2H), 7.72-7.74 (m, 1H), 7.50-7.54 (m, 1H), 7.26-7.36 (m, 2H), 3.96 (s, 2H); LCMS (ESI) m/z: 382.0 [M+H]$^+$.

Example 149. Preparation of N-(5-(3,5-difluorobenzyl)pyridin-2-yl)-[1,2,4]triazolo[4,3-a]pyridine-6-carboxamide (149)

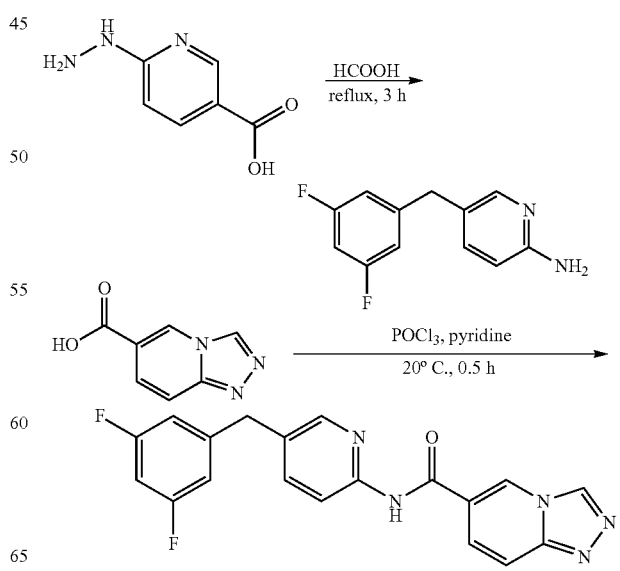

Step 1: Preparation of [1,2,4]triazolo[4,3-a]pyridine-6-carboxylic acid

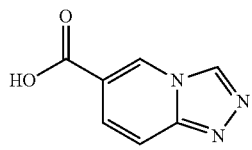 [SMILES: O=C(O)c1ccc2nncn2c1]

A solution of 6-hydrazinylnicotinic acid (1.0 g, 6.53 mmol) in formic acid (10 mL) was heated to 100° C. and refluxed for 3 h. The volatiles were removed to offer [1,2,4]triazolo[4,3-a]pyridine-6-carboxylic acid (1.0 g, 6.13 mmol, 94%, crude) as a white solid which was used in the next step without further purification. LCMS (ESI) m/z: 164.1 [M+H]$^+$.

Step 2: Preparation of N-(5-(3,5-difluorobenzyl)pyridin-2-yl)-[1,2,4]triazolo[4,3-a]pyridine-6-carboxamide

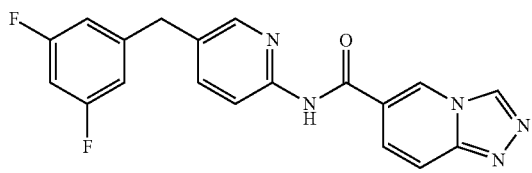 [SMILES: O=C(Nc1ccc(Cc2cc(F)cc(F)c2)cn1)c1ccc2nncn2c1]

To a solution of 1-methyl-1H-pyrazole-4-carboxylic acid (100 mg, 0.613 mmol), 5-(3,5-difluorobenzyl)pyridin-2-amine (135 mg, 0.613 mmol) in pyridine (5 mL) at 20° C. was added, phosphorus oxychloride (279 mg, 1.839 mmol). The reaction mixture was stirred at 20° C. for 1 h. The volatiles were removed under reduced pressure and the solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,5-difluorobenzyl)pyridin-2-yl)-[1,2,4]triazolo[4,3-a]pyridine-6-carboxamide (23.6 mg, 0.064 mmol, 10%) as a light-yellow solid. $^1$H NMR (400 MHz, Dimethylsulfoxide-d$_6$) δ 11.07 (s, 1H), 9.40 (s, 1H), 9.32 (s, 1H), 8.37 (s, 1H), 8.11 (d, J=8.0 Hz, 1H), 7.85 (s, 2H), 7.78 (q, J=4.0 Hz, 1H), 7.04-7.10 (m, 3H), 4.00 (s, 2H); LCMS (ESI) m/z: 366.1 [M+H]$^+$.

Example 150. Preparation of N-([1,2,4]triazolo[4,3-a]pyridin-6-yl)-5-(3-chlorobenzyl)picolinamide trifluoroacetic acid (150 TFA)

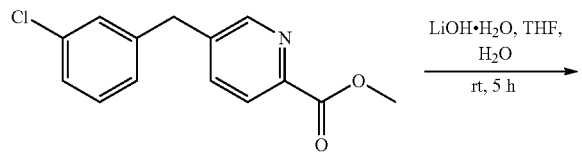

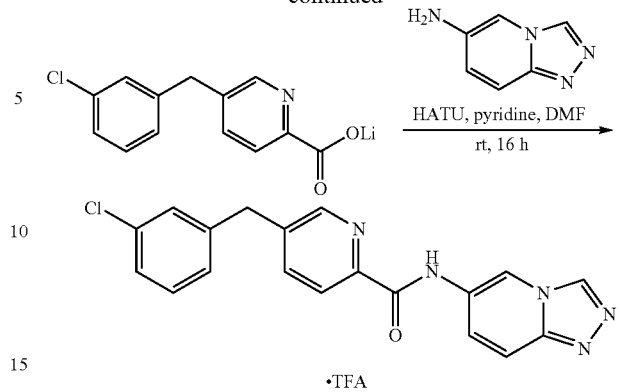

Step 1: Preparation of Lithium 5-(3-chlorobenzyl)picolinate

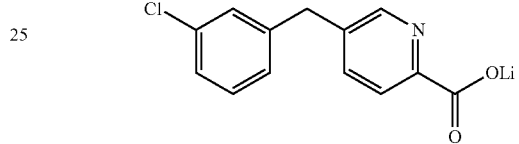

To a solution of methyl 5-(3-chlorobenzyl)picolinate (0.300 g, 1.15 mmol) in tetrahydrofuran (10 mL) and water (1.0 mL) at room temperature was added lithium hydroxide monohydrate (51.0 mg, 1.21 mmol). The reaction mixture was stirred at room temperature for 5 h. The volatiles were removed to reveal lithium 5-(3-chlorobenzyl)picolinate (0.365 g, 1.15 mmol, crude) as a white solid. LCMS (ESI) m/z: 248.1 [M+H]$^+$.

Step 2: Preparation of 5-(3-chlorobenzyl)-N-(6-(hydroxymethyl)pyridin-3-yl)picolinamide trifluoroacetate

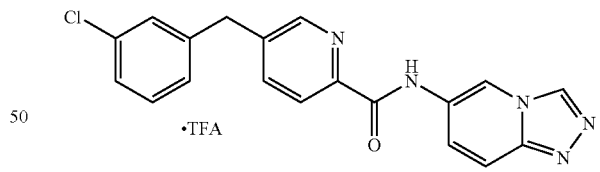

To a solution of lithium 5-(3-chlorobenzyl)picolinate (0.300 g, 1.18 mmol) in N,N-dimethylformamide (6 mL) at room temperature was added [1,2,4]triazolo[4,3-a]pyridin-6-amine (0.174 g, 1.30 mmol), 2-(7-aza-1H-benzotriazole-1-yl)-1,1,3,3-tetramethyluronium hexafluorophosphate (0.673 g, 1.77 mmol) and N,N-diisopropylethylamine (0.762 g, 5.9 mmol). The reaction mixture was stirred at room temperature for 16 h. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to afford 5-(3-chlorobenzyl)-N-(6-(hydroxymethyl)pyridin-3-yl)picolinamide trifluoroacetate (0.102 g, 0.21 mmol, 18%) as a white solid. $^1$H NMR (400 MHz, Dimethylsulfoxide-d₆) δ 11.09 (s, 1H), 9.62 (s, 1H), 9.48 (s, 1H), 8.75 (s, 1H), 8.12 (d, J=8.0 Hz, 1H), 8.02-7.92 (m, 3H), 7.42 (s, 1H), 7.38-7.27 (m, 3H), 4.15 (s, 2H); LCMS (ESI) m/z: 364.0 [M+H]$^+$.

Example 151. Preparation of N-(5-(3-fluorobenzyl)pyridin-2-yl)-[1,2,4]triazolo[4,3-a]pyridine-6-carboxamide (151)

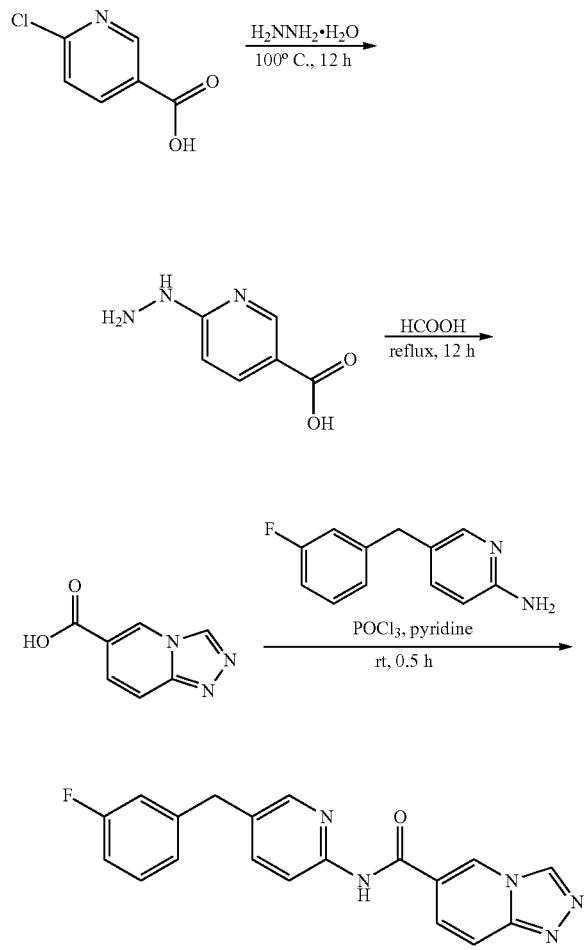

Step 1: Preparation of 6-hydrazinylnicotinic acid

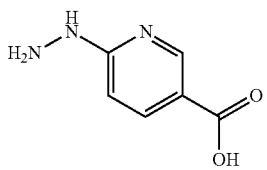 [SMILES: NNc1ccc(C(=O)O)cn1]

Hydrazine hydrate (8 mL) was added to 6-chloronicotinic acid (3.0 g, 19.1 mmol). The reaction mixture was heated to 100° C. and stirred 16 h. The volatiles were removed under reduced pressure and ethanol (50 mL) was added. The resulting precipitate was filtered and collected to give 6-hydrazinylnicotinic acid (2.8 g, crude) as a white solid. Used directly in the next step without further purification. LCMS (ESI) m/z: 154.1 [M+H]$^+$.

Step 2: Preparation of [1,2,4]triazolo[4,3-a]pyridine-6-carboxylic acid

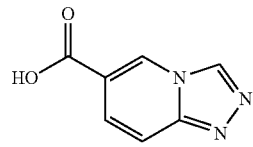 [SMILES: O=C(O)c1ccc2nncn2c1]

A solution of 6-hydrazinylnicotinic acid (1.0 g, 6.53 mmol) in formic acid (13 mL) was heated to 105° C. and stirred 16 h. The solution was cooled to room temperature and volatiles were removed to offer [1,2,4]triazolo[4,3-a]pyridine-6-carboxylic acid (1.1 g, crude) as a white solid. LCMS (ESI) m/z: 164.1. [M+H]$^+$. Used in the next step without further purification.

Step 3: Preparation of N-(5-(3-fluorobenzyl)pyridin-2-yl)-[1,2,4]triazolo[4,3-a]pyridine-6-carboxamide

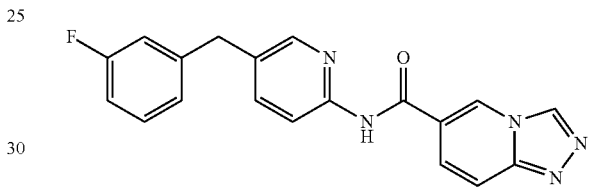

To a solution of [1,2,4]triazolo[4,3-a]pyridine-6-carboxylic acid (0.100 g, 0.613 mmol), 5-(3-fluorobenzyl)pyridin-2-amine (0.124 g, 0.613 mmol) and pyridine (5 mL) at 20° C. was added phosphorus(V) oxychloride (0.279 g, 1.84 mmol). The reaction mixture was stirred at room temperature for 1 h. The solvent was removed under reduced pressure. The crude solid was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 column; acetonitrile/0.01% aqueous trifluoroacetic acid) to give N-(5-(3-fluorobenzyl)pyridin-2-yl)-[1,2,4]triazolo[4,3-a]pyridine-6-carboxamide light-yellow solid (0.0281 g, 0.0797 mmol, 13%). $^1$H NMR (400 MHz, Dimethylsulfoxide-d₆) δ 11.06 (s, 1H), 9.41 (s, 1H), 9.33 (s, 1H), 8.35 (d, J=2 Hz, 1H), 8.10 (d, J=8.5 Hz, 1H), 7.86 (d, J=1.5 Hz, 2H), 7.74-7.76 (m, 1H), 7.34-7.38 (m, 1H), 7.06-7.14 (m, 2H), 7.02-7.05 (m, 1H), 4.0 (s, 2H). LCMS (ESI) m/z: 348.1 [M+H]$^+$.

Example 152. Preparation of N-(5-(3-fluorobenzyl)pyridin-2-yl)-3-methyl-[1,2,4]triazolo[4,3-a]pyridine-6-carboxamide (152)

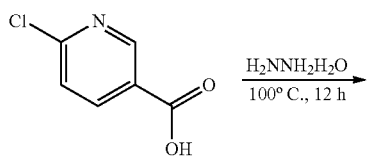

-continued

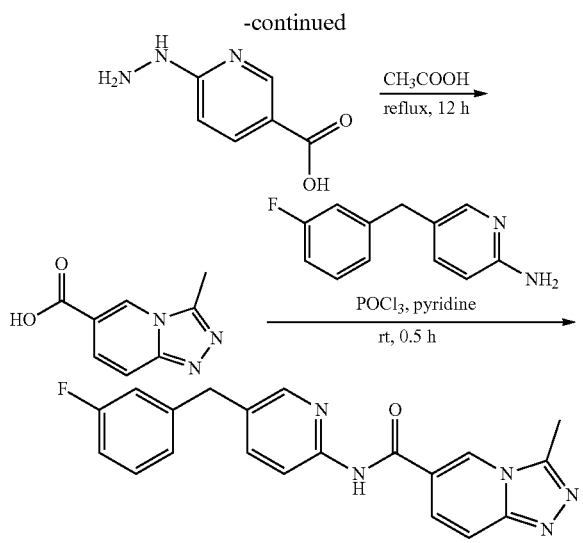

Step 1: Preparation of 6-hydrazinylnicotinic acid

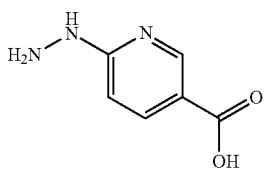 [SMILES: NNc1ccc(C(=O)O)cn1]

A solution of hydrazine hydrate (8 mL) and 6-chloronicotinic acid (3.0 g, 19.1 mmol) was heated to 100° C. and stirred 16 h. The volatiles were removed under reduced pressure. The crude material was treated with ethanol (50 mL) to precipitate solid. Filtration affords crude 6-hydrazinylnicotinic acid (2.8 g, crude) as a white solid. LCMS (ESI) m/z: 154.1 [M+H]+. Used in the next step without further purification.

Step 2: Preparation of 3-methyl-[1,2,4]triazolo[4,3-a]pyridine-6-carboxylic acid

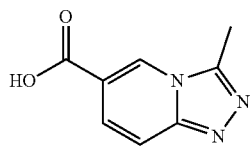

A solution of 6-hydrazinylnicotinic acid (1.0 g, 6.53 mmol) in acetic acid (13 mL) was heated to 120° C. and stirred 16 h. The solution was cooled to room temperature. The solid was filtered and collected to offer 3-methyl-[1,2,4]triazolo[4,3-a]pyridine-6-carboxylic acid as a white solid (0.48 g, crude). LCMS (ESI) m/z: 178.1 [M+H]±. Used in the next step without further purification.

Step 3: Preparation of N-(5-(3-fluorobenzyl)pyridin-2-yl)-3-methyl-[1,2,4]triazolo[4,3-a]pyridine-6-carboxamide

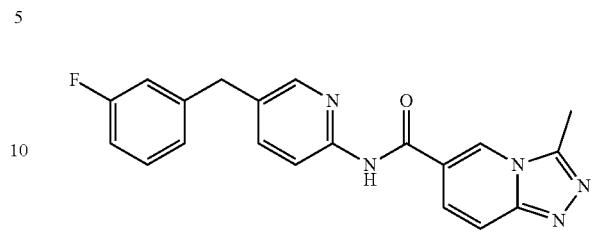

To a solution of 3-methyl-[1,2,4]triazolo[4,3-a]pyridine-6-carboxylic acid (0.100 g, 0.565 mmol), 5-(3-fluorobenzyl)pyridin-2-amine (0.114 g, 0.565 mmol) in pyridine (4 mL) at 20° C. was added phosphorus(V) oxychloride (0.257 g, 1.70 mmol). The reaction mixture was stirred at room temperature for 1 h and volatiles were removed under reduced pressure. The resulting crude material was dissolved in dichloromethane (10.0 mL) and added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-fluorobenzyl)pyridin-2-yl)-3-methyl-[1,2,4]triazolo[4,3-a]pyridine-6-carboxamide as a light red solid (0.067 g, 0.186 mmol, 33%). $^1$H NMR (400 MHz, Dimethylsulfoxide-d$_6$) δ 11.08 (s, 1H), 9.29 (s, 1H), 8.36 (d, J=2.0 Hz, 1H), 8.14 (d, J=8.5 Hz, 1H), 7.74-7.88 (m, 3H), 7.34-7.38 (m, 1H), 7.03-7.14 (m, 3H), 4.00 (s, 2H), 2.78 (s, 3H); LCMS (ESI) m/z: 362.1 [M+H]+.

Example 153. Preparation of 5-(5-(3-fluorobenzyl)pyridin-2-yl)-1-methyl-1H-indazole (153)

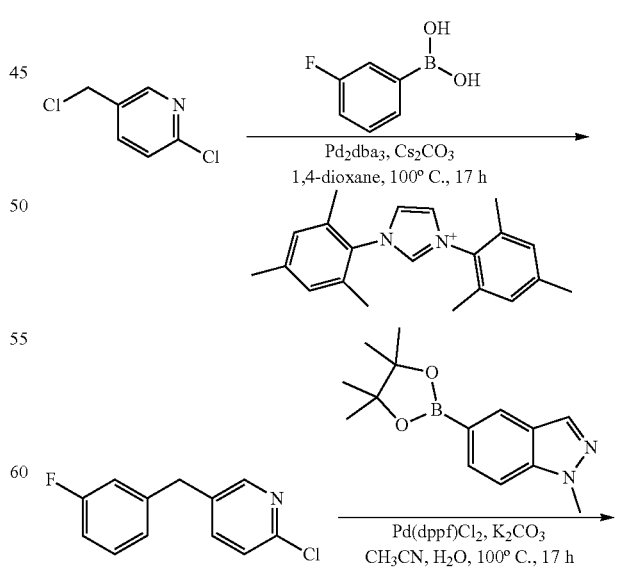

501

-continued

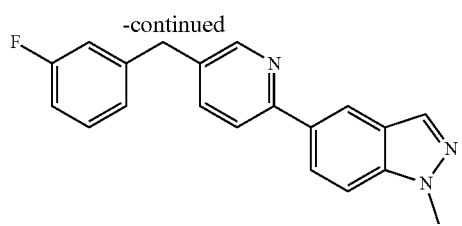

Step 1: Preparation of
2-chloro-5-(3-fluorobenzyl)pyridine

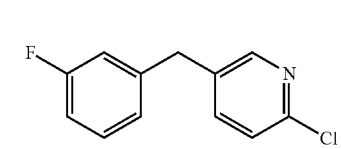 [SMILES: Fc1cccc(Cc2ccc(Cl)nc2)c1]

A mixture of 2-chloro-5-(chloromethyl)pyridine (1.0 g, 6.17 mmol), 3-fluorophenylboronic acid (1.30 g, 9.26 mmol), tris(dibenzylideneacetone)dipalladium(0) (0.16 g, 0.31 mmol), 1,3-dimesityl-1H-imidazol-3-ium chloride (0.10 g, 0.31 mmol) and cesium carbonate (4.0 g, 12.3 mmol) in 1,4-dioxane (30.0 mL) was stirred under nitrogen atmosphere at 100° C. for 17 h. The reaction mixture was cooled down to room temperature and filtered. The filtrate was concentrated, under reduced pressure and the crude solid was purified by column chromatography (silica gel, petroleum ether/ethyl acetate=1/1) to afford 2-chloro-5-(3-fluorobenzyl)pyridine (0.85 g, 3.85 mmol, 62.0%) as a yellow solid. LCMS (ESI) m/z: 222.1 [M+H]⁺.

Step 2: Preparation of 5-(5-(3-fluorobenzyl)pyridin-2-yl)-1-methyl-1H-indazole

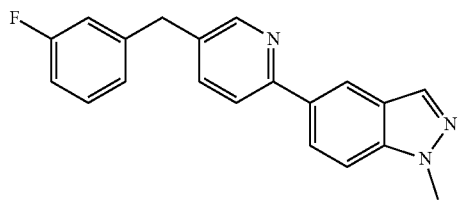 [SMILES: Cn1ncc2cc(-c3ccc(Cc4cccc(F)c4)cn3)ccc21]

A mixture of 2-chloro-5-(3-fluorobenzyl)pyridine (0.2 g, 0.90 mmol), 1-methyl-5-(4,4,5,5-tetramethyl-1,3,2-dioxaborolan-2-yl)-1H-indazole (0.26 g, 0.99 mmol), potassium carbonate (0.25 g, 1.81 mmol) and [1,1'-bis(diphenylphosphino)ferrocene]dichloropalladium(II) (0.074 g, 0.09 mmol) in acetonitrile (8.0 mL) and water (2.0 mL) under nitrogen atmosphere was stirred at 80° C. for 2 h. The reaction mixture was cooled down to room temperature and filtered. The filtrate was concentrated, under reduced pressure. The crude sample was dissolved in minimal N-N,N-dimethylformamide and purified via prep-HPLC (Boston C18 21*250 mm 10 µm column; acetonitrile/0.01% aqueous trifluoroacetic acid) to give 5-(5-(3-fluorobenzyl)pyridin-2-yl)-1-methyl-1H-indazole (0.0655 g, 0.21 mmol, 23.3%) as a white solid. ¹H NMR (500 MHz, Dimethylsulfoxide-d₆) δ 8.63 (s, 1H), 8.45 (s, 1H), 8.14 (d, J=9.8 Hz, 2H), 7.99 (d, J=9.8 Hz, 1H), 7.84-7.68 (m, 2H), 7.37 (dd, J=14.3, 7.9 Hz, 1H), 7.21-7.00 (m, 3H), 4.08 (s, 3H) 4.05 (s, 2H); LCMS (ESI) m/z: 318.1 [M+H]⁺.

502

Example 154. Preparation of N-(5-(3-fluorobenzyl)pyridin-2-yl)imidazo[1,2-a]pyridine-6-carboxamide (154)

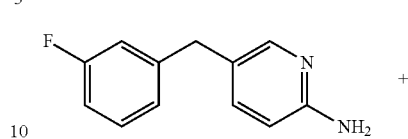

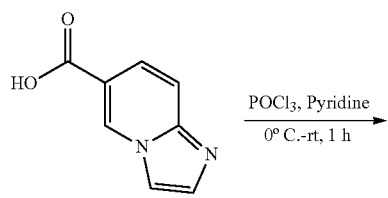

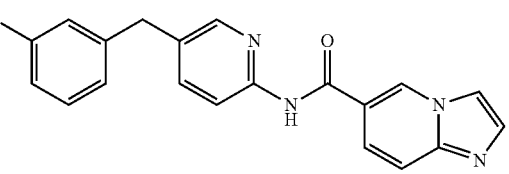

Step 1: Preparation of N-(5-(3-fluorobenzyl)pyridin-2-yl)imidazo[1,2-a]pyridine-6-carboxamide

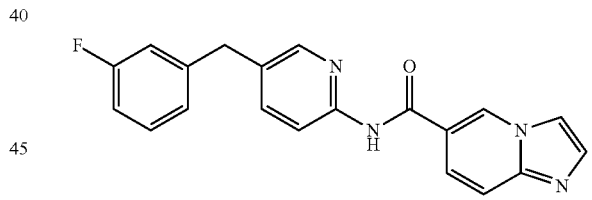

To a solution of imidazo[1,2-a]pyridine-6-carboxylic acid (0.151 g, 0.75 mmol) and 5-(3-fluorobenzyl)pyridin-2-amine (0.120 g, 0.75 mmol) in pyridine (4 mL) at 0° C. was added phosphorus(V) oxychloride (1.5 mL). Reaction was stirred at room temperature for 1 h. The reaction mixture was poured into ice water and extracted with ethyl acetate (100 mL×2). Combined organic layers were washed with brine (50 mL), dried over sodium sulfate, filtered and concentrated. The crude sample was dissolved in minimal N,N-dimethylformamide and purified via prep-HPLC (Boston C18 21*250 mm 10 µm column; acetonitrile/0.01% aqueous trifluoroacetic acid) to give N-(5-(3-fluorobenzyl)pyridin-2-yl)imidazo[1,2-a]pyridine-6-carboxamide (0.0314 g, 0.0908 mmol, 12.1%) as a yellow solid. ¹H NMR (500 MHz, Dimethylsulfoxide-d₆) δ 11.27 (s, 1H), 9.58 (s, 1H), 8.43 (d, J=1.7 Hz, 1H), 8.36 (d, J=9.7 Hz, 2H), 8.24 (d, J=1.7 Hz, 1H), 8.13 (d, J=8.5 Hz, 1H), 8.03 (d, J=9.4 Hz, 1H), 7.78 (dd, J=8.5, 2.2 Hz, 1H), 7.38-7.34 (m, 1H), 7.185-7.12 (m, 2H), 7.07-7.03 (m, 1H), 4.01 (s, 2H); LCMS (ESI) m/z: 347.1 [M+H]⁺.

503

Example 155. Preparation of N-(5-(3-chlorobenzyl)pyridin-2-yl)imidazo[1,2-a]pyridine-6-carboxamide (155)

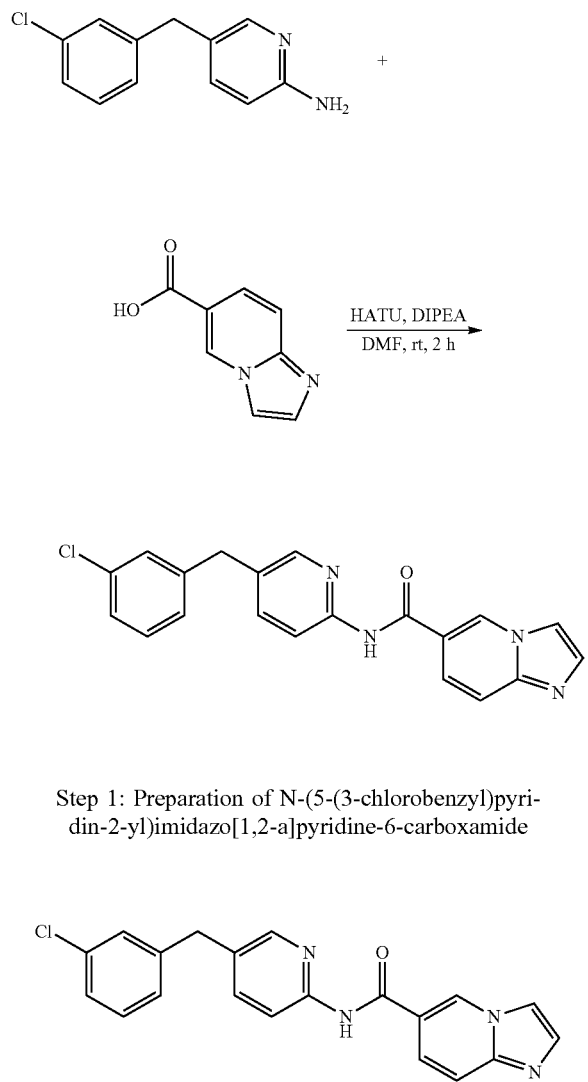

Step 1: Preparation of N-(5-(3-chlorobenzyl)pyridin-2-yl)imidazo[1,2-a]pyridine-6-carboxamide A solution of imidazo[1,2-a]pyridine-6-carboxylic acid (0.100 g, 0.62 mmol), 5-(3-chlorobenzyl)pyridin-2-amine (0.161 g, 0.74 mmol), 1-[bis(dimethylamino)methylene]-1H-1,2,3-triazolo[4,5-b]pyridinium 3-oxid hexafluorophosphate (0.353 g, 0.93 mmol) and N-N,N-diisopropylethylamine (0.240 g, 1.86 mmol) in N,N-dimethylformamide (3 mL) was stirred at room temperature for 2 h. The crude sample was dissolved in minimal N,N-dimethylformamide and purified via prep-HPLC (Boston C18 21*250 mm 10 µm column; acetonitrile/0.01% aqueous trifluoroacetic acid) to give N-(5-(3-chlorobenzyl)pyridin-2-yl)imidazo[1,2-a]pyridine-6-carboxamide (0.048 g, 0.112 mmol, 18.0%) as a faint yellow solid. $^1$H NMR (500 MHz, Dimethylsulfoxide-$d_6$) δ 11.26 (s, 1H), 9.57 (s, 1H), 8.41 (d, J=1.8 Hz, 1H), 8.37 (d, J=2.5 Hz, 1H), 8.34 (dd, J=4.8, 4.8 Hz, 1H), 8.22 (d, J 2.0 Hz, 1H), 8.12 (d, J=8.5 Hz, 1H), 8.02 (d, J=9.4 Hz, 1H), 7.77 (dd, J=8.5, 2.3 Hz, 1H), 7.36-7.33 (m, 2H), 7.29-7.25 (m, 2H), 4.00 (s, 2H); LCMS (ESI) m/z: 363.0 [M+H]$^+$.

504

Example 156. Preparation of N-(5-(2-chlorophenoxy)pyridin-2-yl)-1-methyl-6-oxo-1,4,5,6-tetrahydropyridazine-3-carboxamide (156)

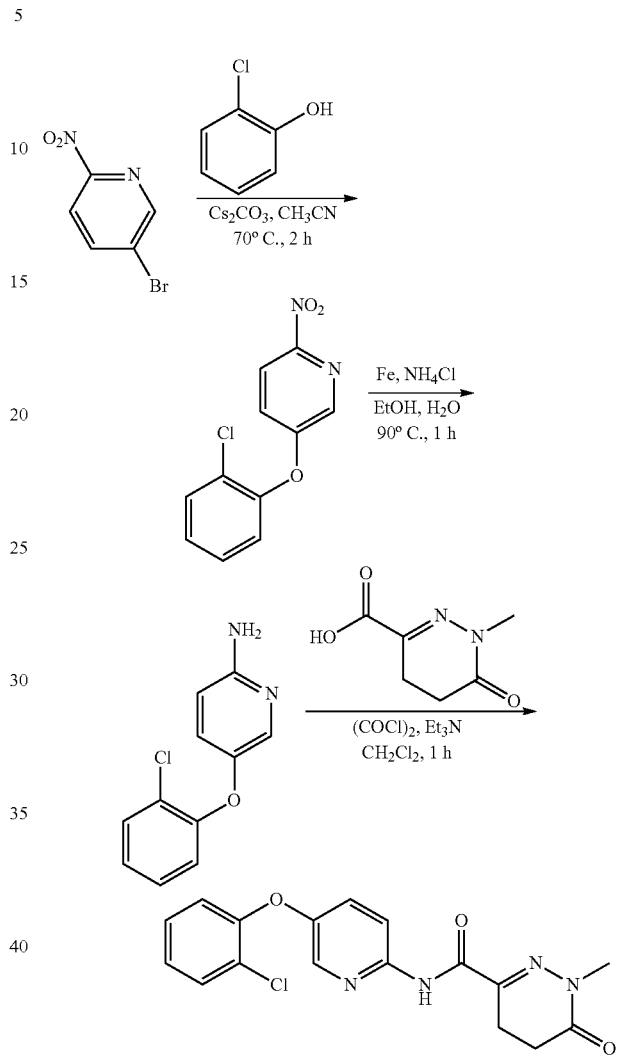

Step 1: Preparation of 5-(2-chlorophenoxy)-2-nitropyridine

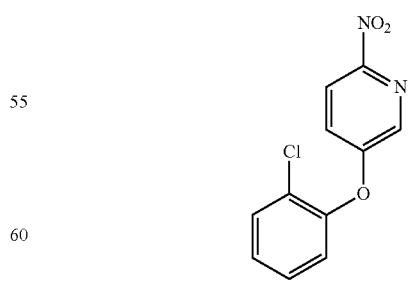

To a solution of 5-bromo-2-nitropyridine (1.0 g, 4.95 mmol), cesium carbonate (4.84 g, 14.9 mmol) in acetonitrile (10 mL) at 70° C. was added 2-chlorophenol (0.824 g, 6.44 mmol) dropwise. The mixture was stirred at 70° C. for 2 h.

The volatiles were removed under reduced pressure and the crude material was diluted with water (100 mL). The aqueous phase was extracted with dichloromethane (100 mL). The organic layer was dried over sodium sulfate, filtered and concentrated to give 5-(2-chlorophenoxy)-2-nitropyridine (1.10 g, crude) as a white oil. LCMS (ESI) m/z: 251.1 [M+H]$^+$. Used directly in the next step.

Step 2: Preparation of 5-(2-chlorophenoxy)pyridin-2-amine

To a mixture of 5-(2-chlorophenoxy)-2-nitropyridine (1.1 g, 4.4 mmol), ammonium chloride (0.466 g, 8.8 mmol) in ethanol (15 mL) and water (5 mL) was added iron powder (0.738 g, 13.2 mmol). Reaction mixture was heated to 90° C. and stirred for 1 h before it was filtered to remove iron powder. The filtrate was concentrated, under reduced pressure and dichloromethane (50 mL) was added to the residue. The resulting precipitate was filtered and the organic layer was concentrated. Purification via column chromatography (silica gel, petroleum ether/ethyl acetate=4/1) affords 5-(2-chlorophenoxy)pyridin-2-amine (0.500 g, 2.29 mmol, 52%) as a red oil. LCMS (ESI) m/z: 221.2 [M+H]$^+$.

Step 3: Preparation of N-(5-(2-chlorophenoxy)pyridin-2-yl)-1-methyl-6-oxo-1,4,5,6-tetrahydropyridazine-3-carboxamide

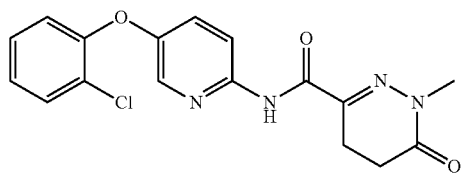 [SMILES: CN1N=C(C(=O)Nc2ccc(Oc3ccccc3Cl)cn2)CCC1=O]

To a solution of 1-methyl-6-oxo-1,4,5,6-tetrahydropyridazine-3-carboxylic acid (0.150 g, 0.961 mmol) in dichloromethane (2 mL) at 20° C. was added oxalyl chloride (2 mL). The reaction was stirred at 0° C. for 0.5 h and concentrated in vacuo. The crude solid was dissolved in dichloromethane (2 mL) and added to a mixture of 5-(2-chlorophenoxy)pyridin-2-amine (0.275 g, 1.25 mmol) and triethylamine (0.291 g, 2.88 mmol) in dichloromethane (5.0 mL) dropwise. The reaction was stirred at 0° C. for 20 minutes and was concentrated, in vacuo. The crude residue was purified via column chromatography (silica gel, petroleum ether/ethyl acetate=1/1) to yield N-(5-(2-chlorophenoxy)pyridin-2-yl)-1-methyl-6-oxo-1,4,5,6-tetrahydropyridazine-3-carboxamide as a white solid (0.0275 g, 0.0769 mmol, 8%). $^1$H NMR (400 MHz, Dimethylsulfoxide-d$_6$) δ 9.85 (s, 1H), 8.11-8.16 (m, 2H), 7.52-7.63 (m, 1H), 7.38 (s, 1H), 7.14-7.24 (m, 2H), 3.36 (s, 3H), 2.86 (s, 2H), 2.51-2.53 (m, 2H); LCMS (ESI) m/z: 359.1 [M+H]$^+$.

Example 157. Preparation of N-(5-(3-chlorophenoxy)pyridin-2-yl)-1-methyl-6-oxo-1,4,5,6-tetrahydropyridazine-3-carboxamide (1571

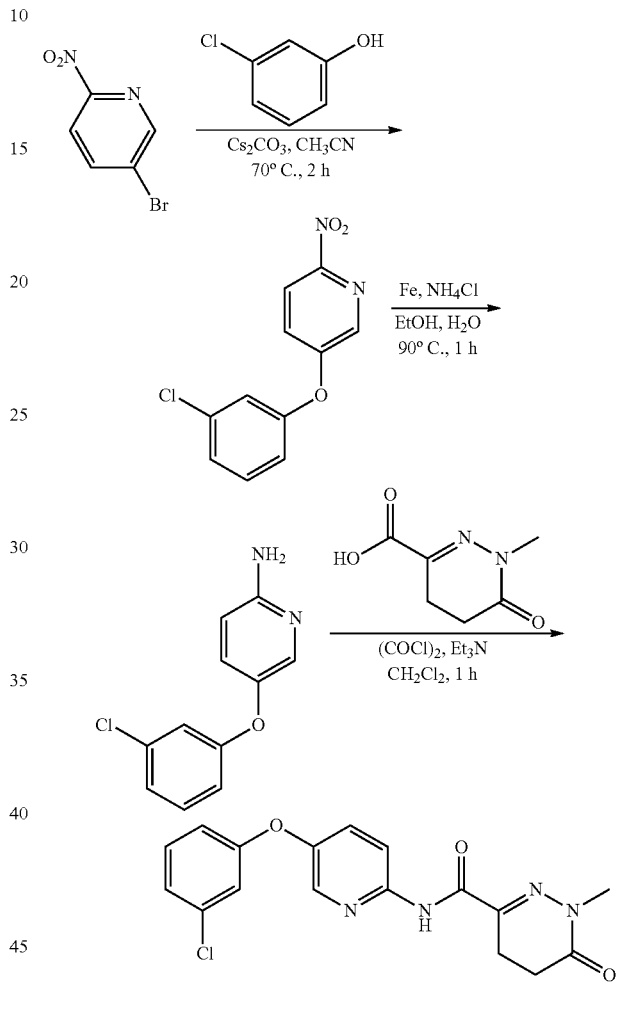

Step 1: Preparation of 5-(3-chlorophenoxy)-2-nitropyridine

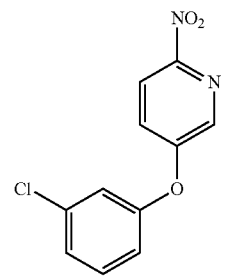 [SMILES: O=[N+]([O-])c1ccc(Oc2cccc(Cl)c2)cn1]

To a solution of 5-bromo-2-nitropyridine (1.0 g, 4.95 mmol), cesium carbonate (4.84 g, 14.9 mmol) in acetonitrile (10 mL) at 70° C. was added 3-chlorophenol (0.825 g, 6.44 mmol) dropwise. The mixture was stirred at 70° C. for 2 h. The solvent was removed under reduced pressure and the crude material was portioned with water (100 mL) and dichloromethane (100 mL). The organic layer was dried over sodium sulfate, filtered and concentrated to give 5-(3-chlorophenoxy)-2-nitropyridine (1.0 g, crude) as a white oil. LCMS (ESI) m/z: 251.1 [M+H]+. Used directly in the next step.

Step 2: Preparation of 5-(3-chlorophenoxy)pyridin-2-amine

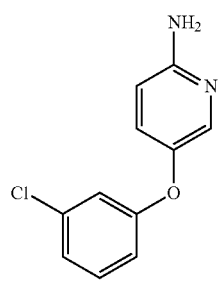

To a mixture of 5-(3-chlorophenoxy)-2-nitropyridine (1.0 g, 4.0 mmol), ammonium chloride (0.424 g, 8.0 mmol) in ethanol (15 mL) and water (5 mL) at 90° C. was added iron powder (0.671 g, 12 mmol). Reaction mixture was stir at 90° C. for 1 h. Reaction was filtered and the filtrate was concentrated, under reduced pressure. The crude material was treated with dichloromethane (50 mL) and the resulting percipiate was filtered off. The organic layer was then concentrated and purified by column chromatography (silica gel, petroleum ether/ethyl acetate=4/1) to afford 5-(3-chlorophenoxy)pyridin-2-amine (0.400 g, 1.8 mmol, 45%) as a green solid. LCMS (ESI) m/z: 221.1 [M+H]+.

Step 3: Preparation of N-(5-(3-chlorophenoxy)pyridin-2-yl)-1-methyl-6-oxo-1,4,5,6-tetrahydropyridazine-3-carboxamide

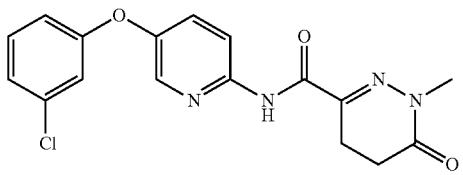 [SMILES: CN1N=C(C(=O)Nc2ccc(Oc3cccc(Cl)c3)cn2)CCC1=O]

To a solution of 1-methyl-6-oxo-1,4,5,6-tetrahydropyridazine-3-carboxylic acid (0.150 g, 0.961 mmol) in dichloromethane (2 mL) at 20° C. was added oxalyl chloride (2 mL). The reaction was stirred at 20° C. for 0.5 h and concentrated in vacuo. The crude solid was dissolved in dichloromethane (4 mL) and added to a mixture of 5-(3-chlorophenoxy)pyridin-2-amine (0.275 g, 1.25 mmol) and triethylamine (0.291 g, 2.88 mmol) in dichloromethane (5.0 mL) dropwise. The reaction was stirred at 20° C. for 20 minutes and was concentrated in vacuo. The crude sample was purified by prep-TLC (silica gel, petroleum ether/ethyl acetate=1/1) to yield N-(5-(3-chlorophenoxy)pyridin-2-yl)-1-methyl-6-oxo-1,4,5,6-tetrahydropyridazine-3-carboxamide (0.0119 g, 0.0336 mmol, 3.5%) as a white solid. 1H NMR (400 MHz, Dimethylsulfoxide-d6) δ 9.88 (s, 1H), 8.24 (d, J=2.4 Hz, 1H), 8.15 (d, J=7.6 Hz, 1H), 7.65-7.67 (m, 1H), 7.41-7.44 (m, 1H), 7.22-7.23 (m, 1H), 7.13 (s, 1H), 7.00-7.02 (m, 1H), 3.37 (s, 3H), 2.87 (t, J=6.8 Hz, 2H), 2.54 (d, J=6.4 Hz, 2H); LCMS (ESI) m/z: 359.1 [M+H]+.

Example 158. Preparation of N-(4-(4-chlorophenoxy)phenyl)-1-methyl-6-oxo-1,4,5,6-tetrahydropyridazine-3-carboxamide (158)

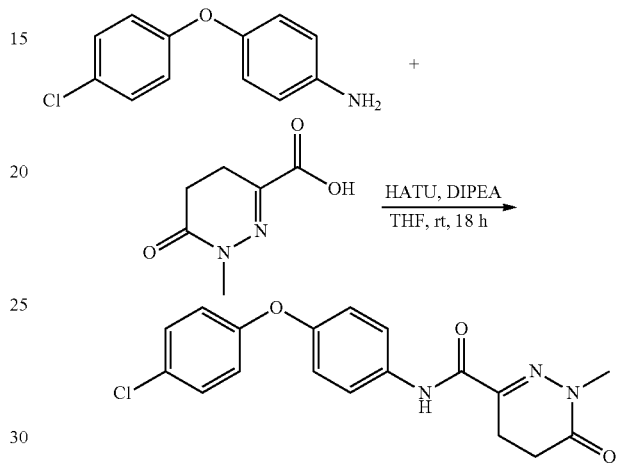

Step 1: Preparation of N-(4-(4-chlorophenoxy)phenyl)-1-methyl-6-oxo-1,4,5,6-tetrahydropyridazine-3-carboxamide

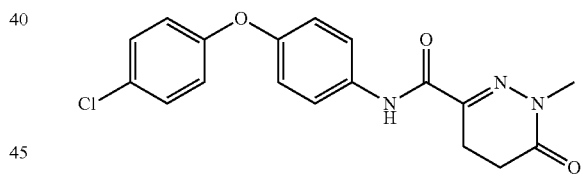

To a mixture of 4-(4-chlorophenoxy)aniline (0.100 g, 0.457 mmol) and 1-methyl-6-oxo-1,4,5,6-tetrahydropyridazine-3-carboxylic acid (0.072 mg, 0.457 mmol) in tetrahydrofuran (2 mL) was added 1-[bis(dimethylamino)methylene]-1H-1,2,3-triazolo[4,5-b]pyridinium 3-oxid hexafluorophosphate (0.208 g, 0.548 mmol) and N,N-diisopropylethylamine (0.118 g, 0.914 mmol). The reaction was stirred at room temperature 16 h. Mixture was combined with another batch (0.1 g) and diluted with water (20 mL). The aqueous layer was extracted with ethyl acetate (10 mL×3). The combined organic layers were washed with brine (10 mL), dried over sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(4-chlorophenoxy)phenyl)-1-methyl-6-oxo-1,4,5,6-tetrahydropyridazine-3-carboxamide (122.2 mg, 0.342 mmol, 68%,) as a light-yellow solid. 1H NMR (500 MHz, Chloroform-d) δ 8.75 (s, 1H), 7.62 (dd, J=7.0, 2.0 Hz, 2H), 7.30 (td, J=6.5, 2.5 Hz, 2H), 7.06-6.99 (m, 2H), 6.96 (dd, J=6.0, 4.0 Hz, 2H), 3.49 (s, 3H), 3.01 (t, J=8.5 Hz, 2H), 2.61 (t, J=8.5 Hz, 2H); LCMS (ESI) m/z: 358.0 [M+H]$^+$.

Example 159. Preparation of N-(4-(3-chlorophenoxy)phenyl)-1-methyl-6-oxo-1,4,5,6-tetrahydropyridazine-3-carboxamide (159)

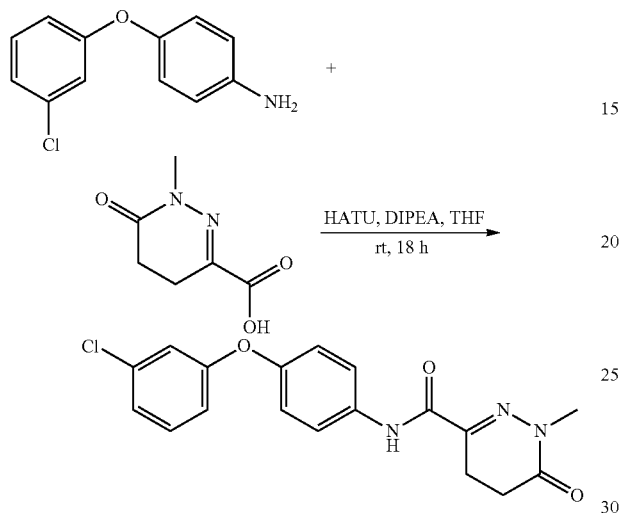

Step 1: Preparation of N-(4-(3-chlorophenoxy)phenyl)-1-methyl-6-oxo-1,4,5,6-tetrahydropyridazine-3-carboxamide

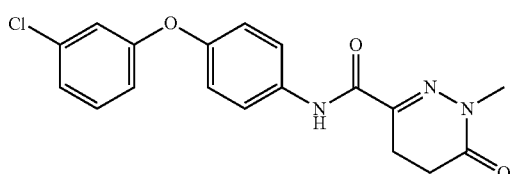

To a mixture of 4-(3-chlorophenoxy)aniline (0.100 g, 0.457 mmol) and 1-methyl-6-oxo-1,4,5,6-tetrahydropyridazine-3-carboxylic acid (0.072 g, 0.457 mmol) in tetrahydrofuran (2 mL) was added 1-[bis(dimethylamino)methylene]-1H-1,2,3-triazolo[4,5-b]pyridinium 3-oxid hexafluorophosphate (0.208 g, 0.548 mmol) and N,N-diisopropylethylamine (0.118 g, 0.914 mmol). The reaction was stirred at room temperature 16 h. Mixture was combined with another batch (0.100 g) and diluted with water (20 mL). The aqueous layer was extracted with ethyl acetate (10 mL×3). The combined organic layers were washed with brine (10 mL), dried over sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-(3-chlorophenoxy)phenyl)-1-methyl-6-oxo-1,4,5,6-tetrahydropyridazine-3-carboxamide (0.125 g, 0.350 mmol, 70%) as a light-yellow solid. $^1$H NMR (500 MHz, Dimethylsulfoxide-d$_6$) δ 10.10 (s, 1H), 7.84-7.76 (m, 2H), 7.40 (t, J=8.0 Hz, 1H), 7.18 (ddd, J=8.0, 2.0, 0.5 Hz, 1H), 7.12-7.05 (m, 2H), 7.02 (t, J=2.0 Hz, 1H), 6.95 (ddd, J=8.0, 2.5, 0.5 Hz, 1H), 3.38 (s, 3H), 2.85 (t, J=8.5 Hz, 2H), 2.56-2.50 (m, 2H); LCMS (ESI) m/z: 358.1 [M+H]$^+$.

Example 160. Preparation of N-[5-(3-fluorophenoxy)pyridin-2-yl]-1-methyl-6-oxo-1,6-dihydropyridine-3-carboxamide (160)

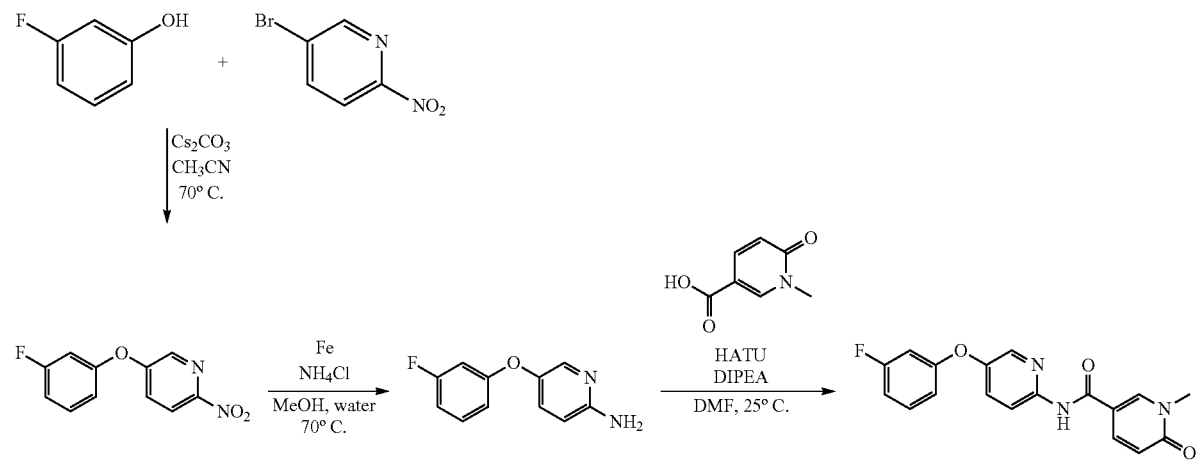

Step 1: Preparation of 5-(3-fluorophenoxy)-2-nitropyridine

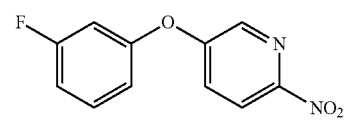

To a sealed tube was added 3-fluorophenol (0.551 g, 4.92 mmol), 5-bromo-2-nitropyridine (1.0 g, 4.92 mmol), and cesium carbonate (2.40 g, 7.37 mmol) and suspended in acetonitrile (10 mL). Reaction was heated to 70° C. for 2 h.

Reaction was cooled to room temperature and concentrated. The crude product was purified over silica gel (ISCO, 40 g, 0-15% ethyl acetate/hexanes, over 25 minutes) to give 5-(3-fluorophenoxy)-2-nitropyridine (644 mg, 2.74 mmol, 56%) as a yellow solid. ¹H NMR (300 MHz, Chloroform-d) δ 8.37 (d, J=2.8 Hz, 1H), 8.29 (d, J=8.9 Hz, 1H), 7.53-7.35 (m, 2H), 7.03 (tdd, J=8.3, 2.4, 0.9 Hz, 1H), 6.97-6.78 (m, 2H); LCMS (ESI) m/z: 235.1 [M+H]⁺.

Step 2: Preparation of
5-(3-fluorophenoxy)pyridin-2-amine

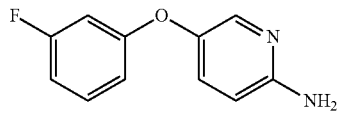

To a hot solution of 5-(3-fluorophenoxy)-2-nitropyridine (0.300 g, 1.28 mmol) and ammonium chloride (0.273 g, 5.12 mmol) in methanol (3.45 mL) and water (0.86 mL) at 70° C. was added iron (0.285 g, 5.12 mmol) in one portion. The reaction was stir heated at 70° C. for 16 h, after which the reaction was cooled to room temperature and diluted with saturated solution of sodium bicarbonate (40 mL). The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2).

The combined organic layers were dried over magnesium sulfate, filtered and concentrated to give the 5-(3-fluorophenoxy)pyridin-2-amine (0.261 g, 1.27 mmol, 100%) as a crude red solid. The crude material is used without further purification.

Step 3: Preparation of N-[5-(3-fluorophenoxy)pyridin-2-yl]-1-methyl-6-oxo-1,6-dihydropyridine-3-carboxamide

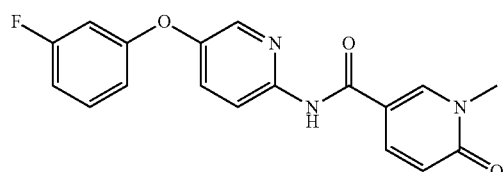

To a solution of 1-methyl-6-oxo-1,6-dihydropyridine-3-carboxylic acid (0.050 g, 0.327 mmol), 5-(3-fluorophenoxy)pyridin-2-amine (0.0666 g, 0.327 mmol) and [bis(dimethylamino)methylidene]({3H-[1,2,3]triazolo[4,5-b]pyridin-3-yl})oxidanium; hexafluoro-λ⁵-phosphanuide (0.124 g, 0.327 mmol) in tetrahydrofuran (1.1 mL) at room temperature was added diisopropylethylamine (0.113 mL, 0.653 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-fluorophenoxy)pyridin-2-yl]-1-methyl-6-oxo-1,6-dihydropyridine-3-carboxamide (27.7 mg, 0.0817 mmol, 21%) as a yellow solid. ¹H NMR (300 MHz, Dimethylsulfoxide-d₆) δ 10.67 (s, 1H), 8.68 (d, J=2.7 Hz, 1H), 8.31-8.12 (m, 2H), 8.00 (dd, J=9.6, 2.7 Hz, 1H), 7.64 (dd, J=9.1, 3.0 Hz, 1H), 7.43 (td, J=8.3, 6.9 Hz, 1H), 7.05-6.82 (m, 3H), 6.44 (d, J=9.5 Hz, 1H); LCMS (ESI) m/z: 340.3 [M+H]⁺.

Example 161. Preparation of N-[5-(3-chlorophenoxy)pyridin-2-yl]-1-methyl-6-oxo-1,6-dihydropyridine-3-carboxamide (161)

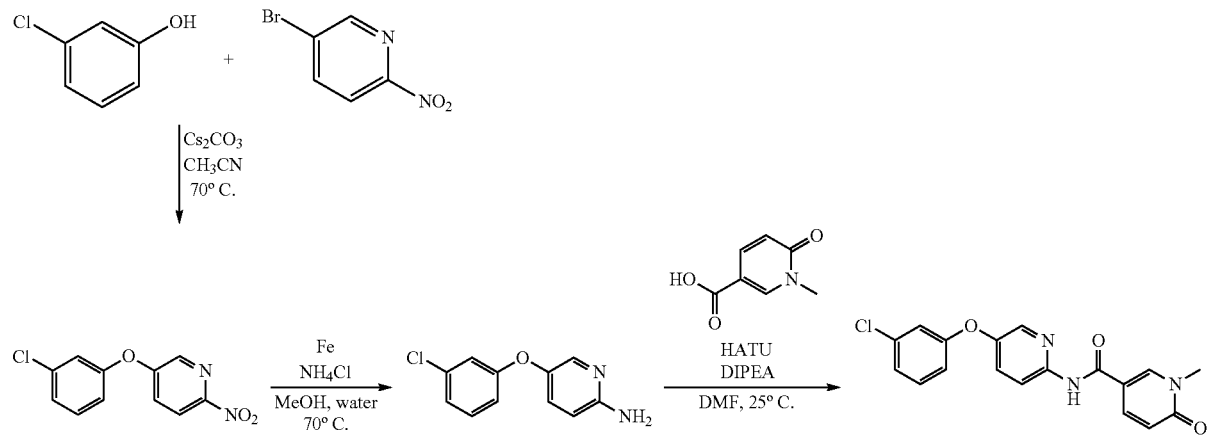

Step 1: Preparation of
5-(3-chlorophenoxy)-2-nitropyridine

A sealed tube was charged with 3-chlorophenol (0.632 g, 4.92 mmol), 5-bromo-2-nitropyridine (1.0 g, 4.92 mmol), cesium carbonate (2.40 g, 7.37 mmol) and acetonitrile (9.84 mL). Reaction was heated to 70° C. for 2 h. Reaction was cooled to room temperature and concentrated. The crude product was purified over silica gel chromatography (ISCO, 40 g, 0-15% ethyl acetate/hexanes, over 25 minutes) to give 5-(3-chlorophenoxy)-2-nitropyridine (0.807 g, 3.21 mmol, 65%) as a white solid. $^1$H NMR (300 MHz, Chloroform-d) δ 8.36 (d, J=2.8 Hz, 1H), 8.29 (d, J=8.9 Hz, 1H), 7.53-7.38 (m, 2H), 7.38-7.22 (m, 1H), 7.15 (t, J=2.1 Hz, 1H), 7.03 (ddd, J=8.2, 2.4, 1.0 Hz, 1H); LCMS (ESI) m/z: 251.0 [M+H]$^+$.

Step 2: Preparation of 5-(3-chlorophenoxy)pyridin-2-amine

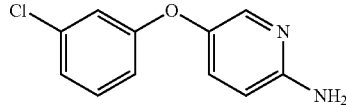

To a heated 70° C. solution of 5-(3-chlorophenoxy)-2-nitropyridine (0.300 g, 1.19 mmol) and ammonium chloride (0.254 g, 4.76 mmol) in a 4:1 mixture of methanol (3.2 mL) and water (0.80 mL) was added iron (0.265 g, 4.76 mmol) in one portion. The reaction was stir at 70° C. for 16 h, after which the reaction was cooled to room temperature and saturated bicarbonate (8 mL) was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chlorophenoxy)pyridin-2-amine (0.254 g, 1.15 mmol) as a crude a brown oil. $^1$H NMR (300 MHz, Chloroform-d) δ 7.93 (dd, J=2.9, 0.7 Hz, 1H), 7.31-7.12 (m, 2H), 7.03 (ddd, J=8.0, 2.0, 0.9 Hz, 1H), 6.91 (t, J=2.2 Hz, 1H), 6.89-6.79 (m, 1H), 6.55 (dd, J=8.8, 0.7 Hz, 1H), 4.45 (s, 2H); LCMS (ESI) m/z: 221.2 [M+H]$^+$. Used without further purification in the next step.

Step 3: Preparation of N-[5-(3-chlorophenoxy)pyridin-2-yl]-1-methyl-6-oxo-1,6-dihydropyridine-3-carboxamide

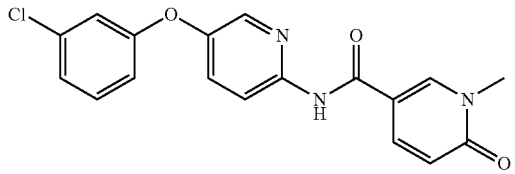

To a solution of 1-methyl-6-oxo-1,6-dihydropyridine-3-carboxylic acid (0.050 g, 0.327 mmol), 5-(3-chlorophenoxy)pyridin-2-amine (0.072 g, 0.327 mmol) and [bis(dimethylamino)methylidene]({3H-[1,2,3]triazolo[4,5-b]pyridin-3-yl})oxidanium; hexafluoro-λ$^5$-phosphanuide (0.124 g, 0.327 mmol) in tetrahydrofuran (1.1 mL) at room temperature was added diisopropylethylamine (0.113 mL, 0.653 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel via column chromatography (ISCO, 12 g, eluting with 0-80% ethyl acetate/hexanes for 20 minutes) to afford N-[5-(3-chlorophenoxy)pyridin-2-yl]-1-methyl-6-oxo-1,6-dihydropyridine-3-carboxamide (24.0 mg, 0.0675 mmol, 20.6%) as a yellow solid. $^1$H NMR (300 MHz, Dimethylsulfoxide-d$_5$) δ 10.68 (s, 1H), 8.68 (d, J=2.7 Hz, 1H), 8.25 (d, J=3.0 Hz, 1H), 8.19 (d, J=9.0 Hz, 1H), 7.99 (dd, J=9.5, 2.7 Hz, 1H), 7.64 (dd, J=9.1, 2.9 Hz, 1H), 7.42 (t, J=8.2 Hz, 1H), 7.21 (ddd, J=8.0, 2.0, 0.9 Hz, 1H), 7.12 (t, J=2.2 Hz, 1H), 7.00 (ddd, J=8.3, 2.4, 1.0 Hz, 1H), 6.44 (d, J=9.5 Hz, 1H); LCMS (ESI) m/z: 356. [M+H]$^+$.

Example 162. Preparation of N-[5-(3-fluorophenoxy)pyridin-2-yl]-1-methyl-6-oxo-1,6-dihydropyridazine-3-carboxamide (162)

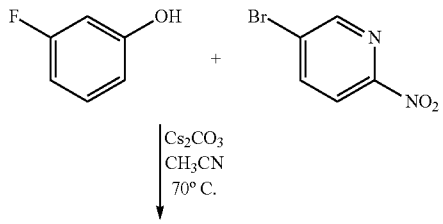

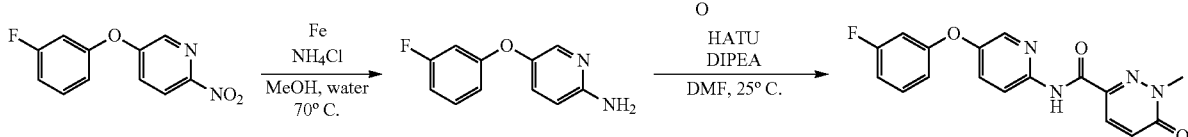

Step 1: Preparation of 5-(3-fluorophenoxy)-2-nitropyridine

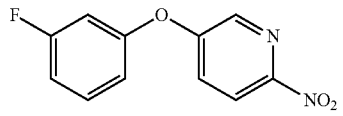 [SMILES: O=[N+]([O-])c1ccc(Oc2cccc(F)c2)cn1]

To a sealed tube was added 3-fluorophenol (0.551 g, 4.92 mmol), 5-bromo-2-nitropyridine (1.0 g, 4.92 mmol), and cesium carbonate (2.40 g, 7.37 mmol) and suspended in acetonitrile (10 mL). Reaction was heated to 70° C. for 2 h. Reaction was cooled to room temperature and concentrated. The crude product was purified over silica gel chromatography (ISCO, 40 g, 0-15% ethyl acetate/hexanes, over 25 minutes) to give 5-(3-fluorophenoxy)-2-nitropyridine (0.644 g, 2.74 mmol, 56%) as a yellow solid. $^1$H NMR (300 MHz, Chloroform-d) δ 8.37 (d, J=2.8 Hz, 1H), 8.29 (d, J=8.9 Hz, 1H), 7.53-7.35 (m, 2H), 7.03 (tdd, J=8.3, 2.4, 0.9 Hz, 1H), 6.97-6.78 (m, 2H); LCMS (ESI) m/z: 235.1 [M+H]$^+$.

Step 2: Preparation of 5-(3-fluorophenoxy)pyridin-2-amine

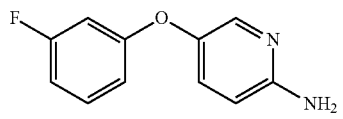

To a hot solution of 5-(3-fluorophenoxy)-2-nitropyridine (0.300 g, 1.28 mmol) and ammonium chloride (0.273 g, 5.12 mmol) in methanol (3.45 mL) and water (0.864 mL) at 70° C. was added iron (0.285 g, 5.12 mmol) in one portion. The reaction was stir heated at 70° C. for 16 h, after which the reaction was cool to room temperature and diluted with saturated solution of sodium bicarbonate (40 mL). The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The combined organic layers were dried over magnesium sulfate, filtered and concentrated to give the 5-(3-fluorophenoxy)pyridin-2-amine (0.261 g, 1.27 mmol, 100%) as a crude red solid. Used directly in the step without further purification.

Step 3: Preparation of N-[5-(3-fluorophenoxy)pyridin-2-yl]-1-methyl-6-oxo-1,6-dihydropyridazine-3-carboxamide

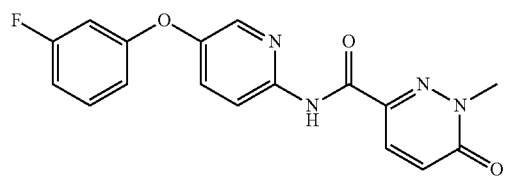

To a solution of 1-methyl-6-oxo-1,6-dihydropyridazine-3-carboxylic acid (0.050 g, 0.324 mmol), 5-(3-fluorophenoxy)pyridin-2-amine (0.0662 g, 0.324 mmol) and [bis(dimethylamino)methylidene]({3H-[1,2,3]triazolo[4,5-b]pyridin-3-yl})oxidanium; hexafluoro-λ$^5$-phosphanuide (0.123 g, 0.3244 mmol) in tetrahydrofuran (1.1 mL) at room temperature was added diisopropylethylamine (0.112 mL, 0.649 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-fluorophenoxy)pyridin-2-yl]-1-methyl-6-oxo-1,6-dihydropyridazine-3-carboxamide (59.8 mg, 0.176 mmol, 54.3%) as a yellow solid. $^1$H NMR (300 MHz, Chloroform-d) δ 9.49 (s, 1H), 8.36 (dt, J=9.1, 0.7 Hz, 1H), 8.18 (dt, J=2.9, 0.7 Hz, 1H), 8.08 (d, J=9.9 Hz, 1H), 7.48 (dd, J=9.0, 2.9 Hz, 1H), 7.39-7.28 (m, 1H), 7.07 (dt, J=9.6, 0.7 Hz, 1H), 6.93-6.67 (m, 3H), 3.91 (d, J=0.5 Hz, 3H); LCMS (ESI) m/z: 341.4 [M+H]$^+$.

Example 163. Preparation of N-[5-(3-chlorophenoxy)pyridin-2-yl]-1-methyl-6-oxo-1,6-dihydropyridazine-3-carboxamide (163)

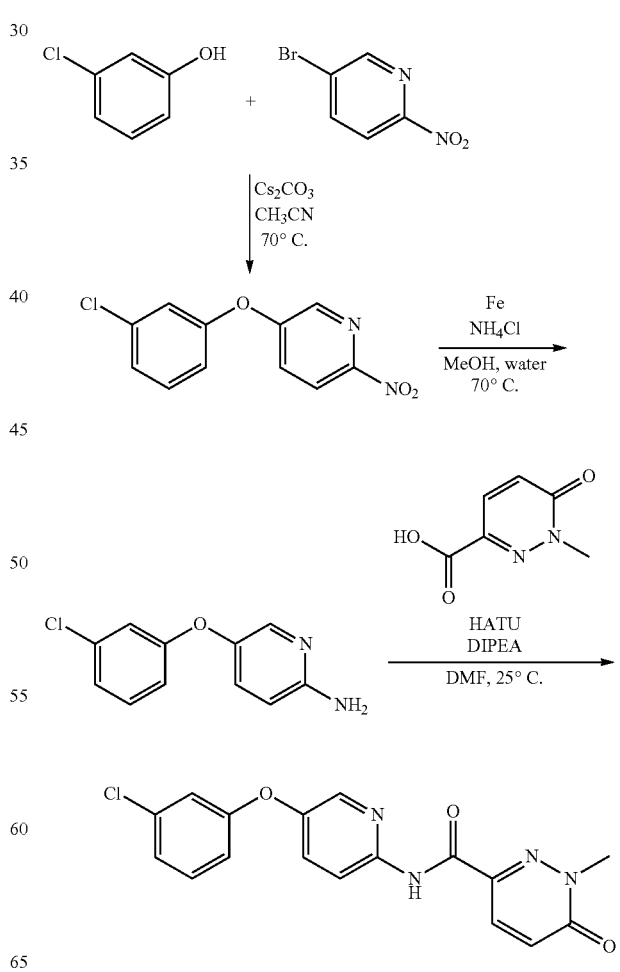

Step 1: Preparation of 5-(3-chlorophenoxy)-2-nitropyridine

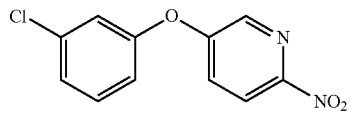

To a sealed tube was added 3-chlorophenol (0.632 g, 4.92 mmol), 5-bromo-2-nitropyridine (1.0 g, 4.92 mmol), and cesium carbonate (2.40 g, 7.37 mmol) and suspended in acetonitrile (9.84 mL). Reaction was heated to 70° C. for 2 h. Reaction was cooled to room temperature and concentrated. The crude product was purified over silica gel chromatography (ISCO, 40 g, 0-15% ethyl acetate/hexanes, over 25 minutes) to give 5-(3-chlorophenoxy)-2-nitropyridine (0.807 g, 3.21 mmol, 65%) as a white solid. $^1$H NMR (300 MHz, Chloroform-d) δ 8.36 (d, J=2.8 Hz, 1H), 8.29 (d, J=8.9 Hz, 1H), 7.53-7.38 (m, 2H), 7.38-7.22 (m, 1H), 7.15 (t, J=2.1 Hz, 1H), 7.03 (ddd, J=8.2, 2.4, 1.0 Hz, 1H); LCMS (ESI) m/z: 251.0 [M+H]$^+$.

Step 2: Preparation of 5-(3-chlorophenoxy)pyridin-2-amine

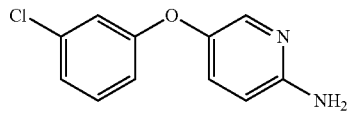 [SMILES: O=[N+]([O-])c1ccc(Oc2cccc(Cl)c2)cn1]

To a heated 70° C. solution of 5-(3-chlorophenoxy)-2-nitropyridine (0.300 g, 1.19 mmol) and ammonium chloride (0.254 g, 4.76 mmol) in a 4:1 mixture of methanol (3.21 mL) and water (0.80 mL) was added iron (0.265 g, 4.76 mmol) in one portion. The reaction was stir at 70° C. for 16 h, after which the reaction was cool to room temperature and 8 mL of saturated bicarbonate was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chlorophenoxy)pyridin-2-amine (0.254 g, 1.15 mmol) as a crude a brown oil. $^1$H NMR (300 MHz, Chloroform-d) δ 7.93 (dd, J=2.9, 0.7 Hz, 1H), 7.31-7.12 (m, 2H), 7.03 (ddd, J=8.0, 2.0, 0.9 Hz, 1H), 6.91 (t, J=2.2 Hz, 1H), 6.89-6.79 (m, 1H), 6.55 (dd, J=8.8, 0.7 Hz, 1H), 4.45 (s, 2H); LCMS (ESI) m/z: 221.2 [M+H]$^+$. The crude material is used without further purification in the next step.

Step 3: Preparation of N-[5-(3-chlorophenoxy)pyridin-2-yl]-1-methyl-6-oxo-1,6-dihydropyridazine-3-carboxamide

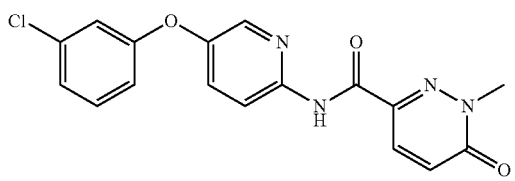 [SMILES: Cn1nc(C(=O)Nc2ccc(Oc3cccc(Cl)c3)cn2)ccc1=O]

To a solution of 1-methyl-6-oxo-1,6-dihydropyridazine-3-carboxylic acid (0.050 g, 0.3244 mmol), 5-(3-chlorophenoxy)pyridin-2-amine (0.0712 g, 0.324 mmol) and [bis(dimethylamino)methylidene]({3H-[1,2,3]triazolo[4,5-b]pyridin-3-yl})oxidanium; hexafluoro-λ$^5$-phosphanuide (0.123 g, 0.324 mmol) in tetrahydrofuran (1.1 mL) at room temperature was added diisopropylethylamine (0.112 mL, 0.649 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-chlorophenoxy)pyridin-2-yl]-1-methyl-6-oxo-1,6-dihydropyridazine-3-carboxamide (85.4 mg, 0.239 mmol, 77%) as a yellow solid. $^1$H NMR (300 MHz, Chloroform-d) δ 9.52 (s, 1H), 8.37 (d, J=9.0 Hz, 1H), 8.17 (dd, J=2.9, 0.7 Hz, 1H), 8.08 (d, J=9.7 Hz, 1H), 7.48 (dd, J=9.0, 2.9 Hz, 1H), 7.31 (d, J=8.2 Hz, 1H), 7.18-6.83 (m, 4H), 3.91 (s, 3H); LCMS (ESI) m/z: 357.5 [M+H]$^+$.

Example 164. Preparation of 1-ethyl-N-[5-(3-fluorophenoxy)pyridin-2-yl]-6-oxo-1,6-dihydropyridine-3-carboxamide (164)

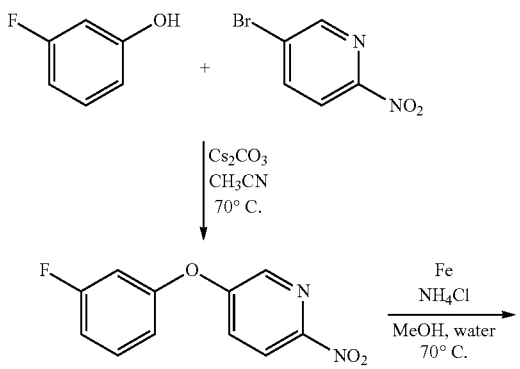

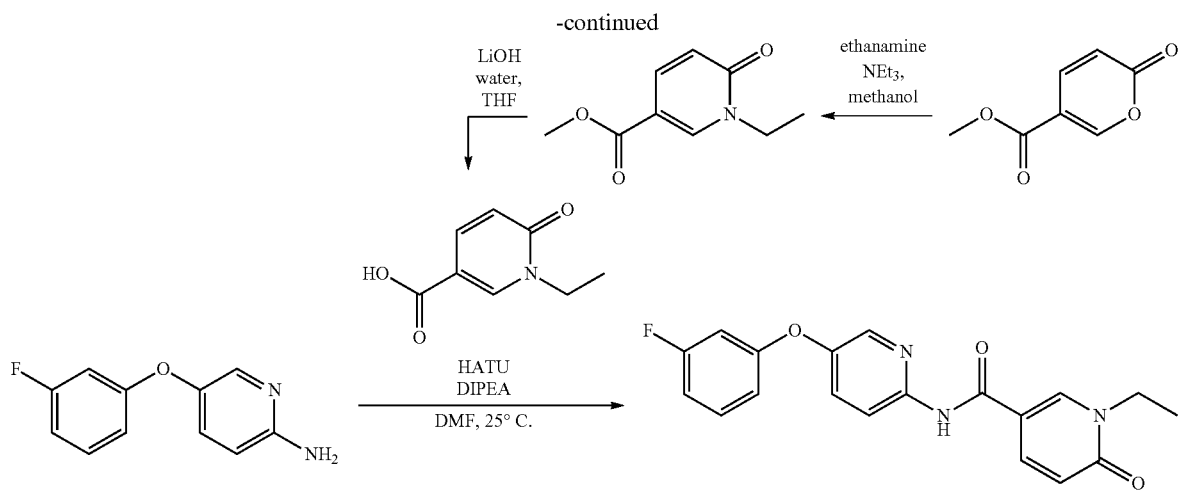

Step 1: Preparation of 5-(3-fluorophenoxy)-2-nitropyridine

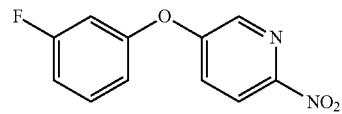

To a sealed tube was added 3-fluorophenol (0.551 g, 4.92 mmol), 5-bromo-2-nitropyridine (1.0 g, 4.92 mmol), and cesium carbonate (2.40 g, 7.37 mmol) and suspended in acetonitrile (10 mL). Reaction was heated to 70° C. for 2 h. Reaction was cooled to room temperature and concentrated. The crude product was purified over silica gel chromatography (ISCO, 40 g, 0-15% ethyl acetate/hexanes, over 25 minutes) to give 5-(3-fluorophenoxy)-2-nitropyridine (0.644 g, 2.74 mmol, 56%) as a yellow solid. $^1$H NMR (300 MHz, Chloroform-d) δ 8.37 (d, J=2.8 Hz, 1H), 8.29 (d, J=8.9 Hz, 1H), 7.53-7.35 (m, 2H), 7.03 (tdd, J=8.3, 2.4, 0.9 Hz, 1H), 6.97-6.78 (m, 2H); LCMS (ESI) m/z: 235.1 [M+H]$^+$.

Step 2: Preparation of 5-(3-fluorophenoxy)pyridin-2-amine

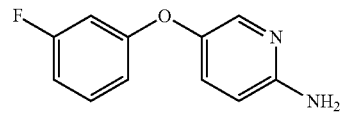 [SMILES: O=[N+]([O-])c1ccc(Oc2cccc(F)c2)cn1]

To a hot solution of 5-(3-fluorophenoxy)-2-nitropyridine (0.300 g, 1.28 mmol) and ammonium chloride (0.273 g, 5.12 mmol) in methanol (3.45 mL) and water (0.864 mL) at 70° C. was added iron (0.285 g, 5.12 mmol) in one portion. The reaction was stir heated at 70° C. for 16 h, after which the reaction was cool to room temperature and diluted with saturated solution of sodium bicarbonate (40 mL) was added. The reaction mixture volume was diluted with ethyl acetate (50 mL) and filtered through a pad of Celite®. The pad was washed with ethyl acetate (20 mL×3) and the aqueous layer was extracted with ethyl acetate (50 mL×2). The combined organic layers were dried over magnesium sulfate, filtered and concentrated to give the 5-(3-fluorophenoxy)pyridin-2-amine (0.261 g, 1.27 mmol, 100%) as a crude red solid. The crude material is used without further purification.

Step 3: Preparation of methyl 1-ethyl-6-oxo-1,6-dihydropyridine-3-carboxylate

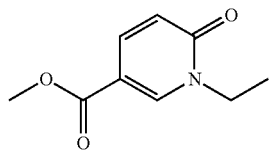

A solution of methyl 2-oxo-2H-pyran-5-carboxylate (0.500 g, 3.24 mmol) was added. in methanol (10.8 mL) at room temperature was treated with ethanamine(2.02 mL, 4.05 mmol) and triethylamine (0.796 mL, 5.67 mmol). Reaction mixture stirred for 1 h before it was concentrated, and purified by silica gel chromatography (ISCO, ethyl acetate/hexanes, 3:1, over 20 minutes) to give methyl 1-ethyl-6-oxo-1,6-dihydropyridine-3-carboxylate (0.380 g, 2.09 mmol, 64% as a brown oil. $^1$H NMR (300 MHz, Chloroform-d) δ 8.20 (dd, J=2.5, 0.6 Hz, 1H), 7.84 (dd, J=9.5, 2.5 Hz, 1H), 6.58-6.46 (m, 1H), 4.05 (q, J=7.2 Hz, 2H), 3.87 (s, 3H), 1.40 (t, J=7.2 Hz, 3H); LCMS (ESI) m/z: 182.2 [M+H]$^+$.

Step 4: Preparation of 1-ethyl-6-oxo-1,6-dihydropyridine-3-carboxylic acid

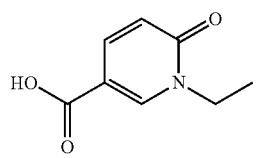

To a solution of methyl 1-ethyl-6-oxo-1,6-dihydropyridine-3-carboxylate (0.180 g, 0.9934 mmol) in tetrahydrofuran (3.31 mL) and water (0.83 mL) at 25° C. was added lithium hydrate hydroxide (0.0625 g, 1.49 mmol) in one portion. The reaction mixture was stirred at room temperature 3 h before it was evaporated to dryness, diluted with water (15 mL) and adjusted to pH=2 with 1N hydrogen chloride solution. The reaction mixture was extracted with ethyl acetate (20 mL×3). The combined organic layers were dried over magnesium sulfate, filtered and concentrated in vacou to give 1-ethyl-6-oxo-1,6-dihydropyridine-3-carboxylic acid (0.066 g, 0.407 mmol, 40.9%) as a yellow solid. $^1$H NMR (300 MHz, Dimethylsulfoxide-$d_6$) δ 12.80 (s, 1H), 8.46 (d, J=2.6 Hz, 1H), 7.77 (dt, J=9.5, 1.8 Hz, 1H), 6.39 (d, J=9.5 Hz, 1H), 3.98 (q, J=7.1 Hz, 2H), 1.20 (q, J=6.7 Hz, 4H); LCMS (ESI) m/z: 168.2 [M+H]$^+$. Used in the next step without further purification.

Step 5: Preparation of 1-ethyl-N-[5-(3-fluorophenoxy)pyridin-2-yl]-6-oxo-1,6-dihydropyridine-3-carboxamide

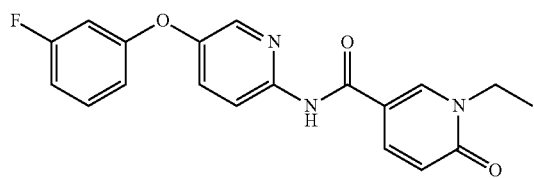 [SMILES: CCn1cc(C(=O)Nc2ccc(Oc3cccc(F)c3)cn2)ccc1=O]

To a solution of 1-ethyl-6-oxo-1,6-dihydropyridine-3-carboxylic acid (0.050 g, 0.2991 mmol), 5-(3-fluorophenoxy)pyridin-2-amine (0.061 g, 0.299 mmol) and [bis(dimethylamino)methylidene]({3H-[1,2,3]triazolo[4,5-b]pyridin-3-yl})oxidanium; hexafluoro-λ$^5$-phosphanuide (0.113 g, 0.2991 mmol) in tetrahydrofuran (1 mL) at room temperature was added N,N-diisopropylethylamine (0.1 mL, 0.5982 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford 1-ethyl-N-[5-(3-fluorophenoxy)pyridin-2-yl]-6-oxo-1,6-dihydropyridine-3-carboxamide (32.6 mg, 0.0924 mmol, 31%). $^1$H NMR (300 MHz, Chloroform-d) δ 8.32 (dd, J=9.0, 0.7 Hz, 1H), 8.24 (d, J=2.5 Hz, 2H), 8.13 (dd, J=2.9, 0.7 Hz, 1H), 7.74 (dd, J=9.6, 2.7 Hz, 1H), 7.47 (dd, J=9.0, 2.9 Hz, 1H), 7.36-7.28 (m, 1H), 6.92-6.67 (m, 3H), 6.63 (d, J=9.5 Hz, 1H), 4.10 (q, J=7.2 Hz, 2H), 1.44 (t, J=7.2 Hz, 3H); LCMS (ESI) m/z: 354.4 [M+H]$^+$.

Example 165. Preparation of N-[5-(3-chlorophenoxy)pyridin-2-yl]-1-ethyl-6-oxo-1,6-dihydropyridine-3-carboxamide (165)

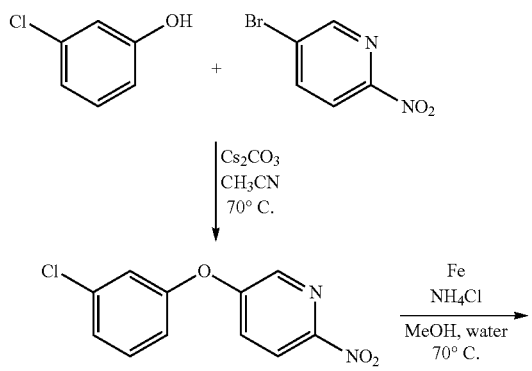

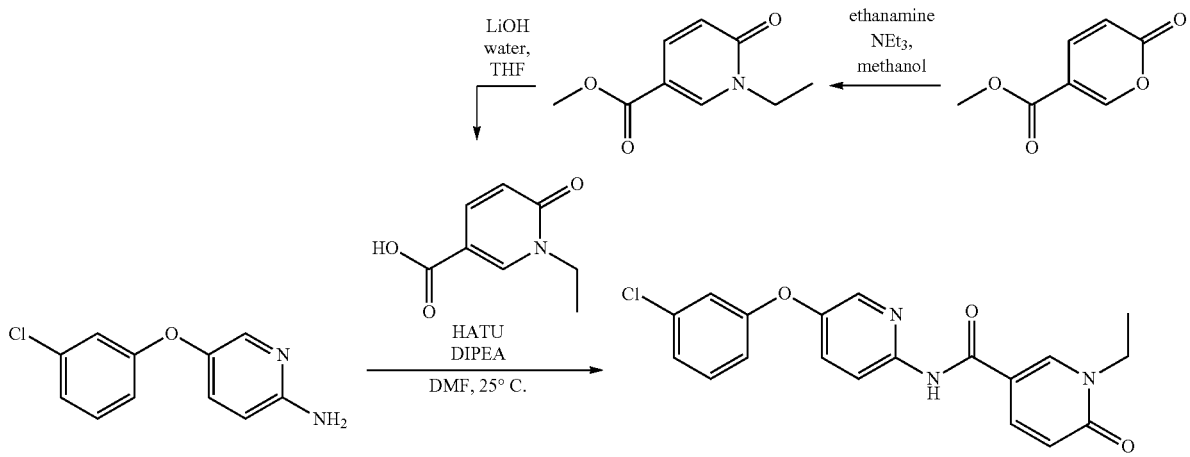

Step 1: Preparation of 5-(3-chlorophenoxy)-2-nitropyridine

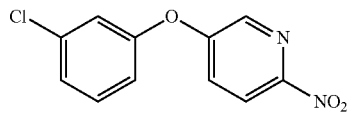 [SMILES: O=[N+]([O-])c1ccc(Oc2cccc(Cl)c2)cn1]

To a sealed tube was added 3-chlorophenol (0.632 g, 4.92 mmol), 5-bromo-2-nitropyridine (1.0 g, 4.92 mmol), and cesium carbonate (2.40 g, 7.37 mmol) and suspended in acetonitrile (9.84 mL). Reaction was heated to 70° C. for 2 h. Reaction was cooled to room temperature and concentrated. The crude product was purified over silica gel (ISCO, 40 g, 0-15% ethyl acetate/hexanes, over 25 minutes) to give 5-(3-chlorophenoxy)-2-nitropyridine (0.807 g, 3.21 mmol, 65%) as a white solid. $^1$H NMR (300 MHz, Chloroform-d) δ 8.36 (d, J=2.8 Hz, 1H), 8.29 (d, J=8.9 Hz, 1H), 7.53-7.38 (m, 2H), 7.38-7.22 (m, 1H), 7.15 (t, J=2.1 Hz, 1H), 7.03 (ddd, J=8.2, 2.4, 1.0 Hz, 1H); LCMS (ESI) m/z: 251.0 [M+H]$^+$.

Step 2: Preparation of 5-(3-chlorophenoxy)pyridin-2-amine

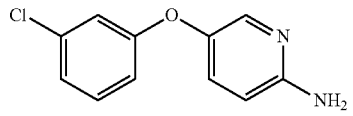

To a heated 70° C. solution of 5-(3-chlorophenoxy)-2-nitropyridine (0.300 g, 1.19 mmol) and ammonium chloride (0.254 g, 4.76 mmol) in a 4:1 mixture of methanol (3.21 mL) and water (0.80 mL) was added iron (0.265 g, 4.76 mmol) in one portion. The reaction was stir at 70° C. for 16 h, after which the reaction was cool to room temperature and 8 mL of saturated bicarbonate was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chlorophenoxy)pyridin-2-amine (0.254 g, 1.15 mmol) as a crude a brown oil. The crude material is used without further purification in the next step. $^1$H NMR (300 MHz, Chloroform-d) δ 7.93 (dd, J=2.9, 0.7 Hz, 1H), 7.31-7.12 (m, 2H), 7.03 (ddd, J=8.0, 2.0, 0.9 Hz, 1H), 6.91 (t, J=2.2 Hz, 1H), 6.89-6.79 (m, 1H), 6.55 (dd, J=8.8, 0.7 Hz, 1H), 4.45 (s, 2H); LCMS (ESI) m/z: 221.2 [M+H]$^+$.

Step 3: Preparation of methyl 1-ethyl-6-oxo-1,6-dihydropyridine-3-carboxylate

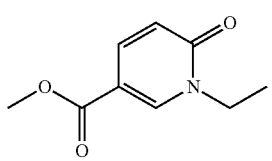

A solution of methyl 2-oxo-2H-pyran-5-carboxylate (0.500 g, 3.24 mmol) in methanol (10.8 mL) at room temperature was treated with ethanamine (2.0 mL, 4.05 mmol) and triethylamine (0.796 mL, 5.67 mmol). Reaction mixture stirred for 1 h before it was concentrated, and purified by silica gel chromatography (ISCO, ethyl acetate/hexanes, 3:1, over 20 minutes) to give methyl 1-ethyl-6-oxo-1,6-dihydropyridine-3-carboxylate (380 mg, 2.09 mmol, 64%) as a brown oil. $^1$H NMR (300 MHz, Chloroform-d) δ 8.20 (dd, J=2.5, 0.6 Hz, 1H), 7.84 (dd, J=9.5, 2.5 Hz, 1H), 6.58-6.46 (m, 1H), 4.05 (q, J=7.2 Hz, 2H), 3.87 (s, 3H), 1.40 (t, J=7.2 Hz, 3H); LCMS (ESI) m/z: 182.2 [M+H]$^+$.

Step 4: Preparation of 1-ethyl-6-oxo-1,6-dihydropyridine-3-carboxylic acid

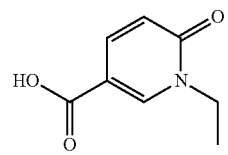

To a solution of methyl 1-ethyl-6-oxo-1,6-dihydropyridine-3-carboxylate (0.180 g, 0.9934 mmol) in tetrahydrofuran (3.31 mL) and water (0.83 mL) at 25° C. was added lithium hydroxide hydrate (62.5 mg, 1.49 mmol) in one portion. The reaction mixture was stirred at room temperature for 3 h before it was evaporated to dryness, diluted with water (15 mL) and adjusted to pH=2 with 1N hydrogen chloride solution. The reaction mixture was extracted with ethyl acetate (20 mL×3). The combined organic layers were dried over magnesium sulfate, filtered and concentrated in vacou to give 1-ethyl-6-oxo-1,6-dihydropyridine-3-carboxylic acid (0.066 g, 0.407 mmol, 40.9%) as a yellow solid. $^1$H NMR (300 MHz, Dimethylsulfoxide-d$_6$) δ 12.80 (s, 1H), 8.46 (d, J=2.6 Hz, 1H), 7.77 (dt, J=9.5, 1.8 Hz, 1H), 6.39 (d, J=9.5 Hz, 1H), 3.98 (q, J=7.1 Hz, 2H), 1.20 (q, J=6.7 Hz, 4H); LCMS (ESI) m/z: 168.2 [M+H]$^+$. Used in the next step without further purification.

Step 5: Preparation of N-[5-(3-chlorophenoxy)pyridin-2-yl]-1-ethyl-6-oxo-1,6-dihydropyridine-3-carboxamide

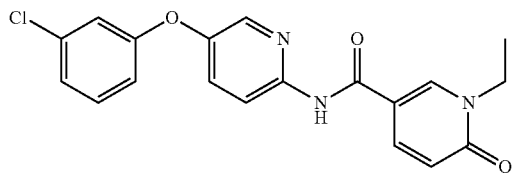

To a solution of 1-ethyl-6-oxo-1,6-dihydropyridine-3-carboxylic acid (0.050 g, 0.2991 mmol), 5-(3-chlorophenoxy)pyridin-2-amine (0.066 g, 0.299 mmol) and [bis(dimethylamino)methylidene]({3H-[1,2,3]triazolo[4,5-b]pyridin-3-yl})oxidanium; hexafluoro-λ$^5$-phosphanuide (0.113 g, 0.299 mmol) in tetrahydrofuran (1.0 mL) at room temperature was added diisopropylethylamine (0.10 mL, 0.598 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-chlorophenoxy)pyridin-2-yl]-1-ethyl-6-oxo-1,6-dihydropyridine-3-carboxamide (39.6 mg, 0.107 mmol, 36%). $^1$H NMR (300 MHz, Chloroform-d) δ 8.33 (d, J=9.1 Hz, 1H), 8.24 (d, J=2.7 Hz, 2H), 8.13 (d, J=2.8 Hz, 1H), 7.73 (dd, J=9.6, 2.8 Hz, 1H), 7.46 (dd, J=9.1, 2.9 Hz, 1H), 7.30 (t, J=8.2 Hz, 2H), 7.13 (d, J=8.6 Hz, 1H), 7.00 (t, J=2.2 Hz, 1H), 6.91 (dd, J=8.4, 2.1 Hz, 1H), 6.63 (d, J=9.5 Hz, 1H), 4.10 (q, J=7.3 Hz, 2H), 1.44 (t, J=7.2 Hz, 3H); LCMS (ESI) m/z: 370.4 [M+H]$^+$.

Example 166. Preparation of N-[5-(3-chlorophenoxy)pyridin-2-yl]-6-oxo-1-(propan-2-yl)-1,6-dihydropyridine-3-carboxamide (166)

acetonitrile (9.84 mL). Reaction was heated to 70° C. for 2 h. Reaction was cooled to room temperature and concentrated. The crude product was purified over silica gel (ISCO, 40 g, 0-15% ethyl acetate/hexanes, over 25 minutes) to give 5-(3-chlorophenoxy)-2-nitropyridine (0.807 g, 3.21 mmol, 65%) as a white solid. $^1$H NMR (300 MHz, Chloroform-d) δ 8.36 (d, J=2.8 Hz, 1H), 8.29 (d, J=8.9 Hz, 1H), 7.53-7.38 (m, 2H), 7.38-7.22 (m, 1H), 7.15 (t, J=2.1 Hz, 1H), 7.03 (ddd, J=8.2, 2.4, 1.0 Hz, 1H); LCMS (ESI) m/z: 251. [M+H]$^+$.

Step 2: Preparation of 5-(3-chlorophenoxy)pyridin-2-amine

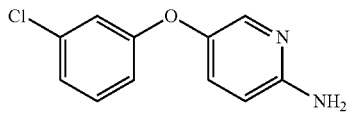

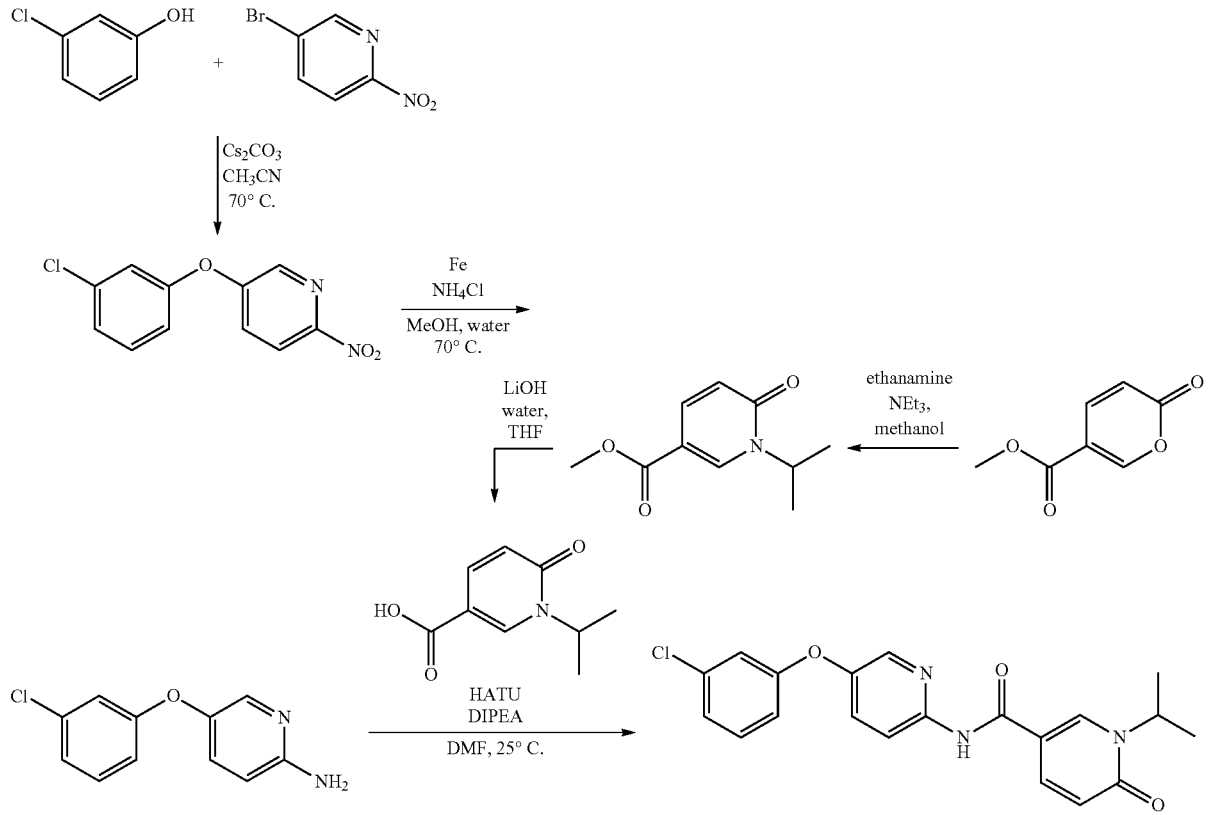

Step 1: Preparation of 5-(3-chlorophenoxy)-2-nitropyridine

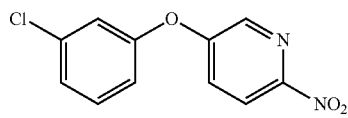 [SMILES: O=[N+]([O-])c1ccc(Oc2cccc(Cl)c2)cn1]

To a sealed tube was added 3-chlorophenol (0.632 g, 4.92 mmol), 5-bromo-2-nitropyridine (1.0 g, 4.92 mmol), and cesium carbonate (2.40 g, 7.37 mmol) and suspended in To a heated 70° C. solution of 5-(3-chlorophenoxy)-2-nitropyridine (0.300 g, 1.19 mmol) and ammonium chloride (0.254 g, 4.76 mmol) in a 4:1 mixture of methanol (3.2 mL) and water (0.80 mL) was added iron (0.265 g, 4.76 mmol) in one portion. The reaction was stir at 70° C. for 16 h, after which the reaction was cool to room temperature and 8 mL of saturated bicarbonate was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chlorophenoxy)pyridin-2-amine (0.254 g, 1.15 mmol) as a crude a brown oil. The crude material is used without further purification in the next step. ¹H NMR (300 MHz, Chloroform-d) δ 7.93 (dd, J=2.9, 0.7 Hz, 1H), 7.31-7.12 (m, 2H), 7.03 (ddd, J=8.0, 2.0, 0.9 Hz, 1H), 6.91 (t, J=2.2 Hz, 1H), 6.89-6.79 (m, 1H), 6.55 (dd, J=8.8, 0.7 Hz, 1H), 4.45 (s, 2H); LCMS (ESI) m/z: 221.2 [M+H]⁺.

Step 3: Preparation of methyl 6-oxo-1-(propan-2-yl)-1,6-dihydropyridine-3-carboxylate

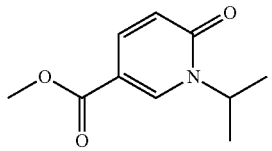

A solution of methyl 2-oxo-2H-pyran-5-carboxylate (0.500 g, 3.24 mmol) in methanol (10.8 mL) at room temperature was treated with propan-2-amine (239 mg, 4.05 mmol) and triethylamine (0.80 mL, 5.67 mmol). Reaction mixture stirred for 1 h before it was concentrated, and purified by silica gel chromatography (ISCO, 12 g, ethyl acetate/hexanes, 3:1, over 20 minutes) to give methyl 6-oxo-1-(propan-2-yl)-1,6-dihydropyridine-3-carboxylate (85.9 mg, 0.441 mmol, 13%) as a brown solid. ¹H NMR (300 MHz, Dimethylsulfoxide-d₆) δ 8.34 (dd, J=2.6, 0.6 Hz, 1H), 7.77 (dd, J=9.5, 2.6 Hz, 1H), 6.44 (dd, J=9.5, 0.5 Hz, 1H), 4.99 (hept, J=6.8 Hz, 1H), 3.79 (s, 3H), 1.33 (d, J=6.8 Hz, 6H); LCMS (ESI) m/z: 196.2 [M+H]⁺.

Step 4: Preparation of 6-oxo-1-(propan-2-yl)-1,6-dihydropyridine-3-carboxylic acid

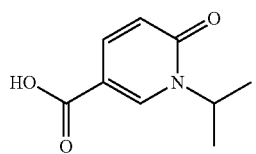

To a solution of methyl 6-oxo-1-(propan-2-yl)-1,6-dihydropyridine-3-carboxylate (0.086 g, 0.440 mmol) in tetrahydrofuran (1.5 mL) and water (0.366 mL) at 25° C. was added lithium hydroxide hydrate (27.6 mg, 0.66 mmol) in one portion. The reaction mixture was stirred at room temperature 3 h before it was evaporated to dryness, diluted with water (15 mL) and adjusted to pH 2 with 1N hydrogen chloride solution. The reaction mixture was extracted with ethyl acetate (20 mL×3). The combined organic layers were dried over magnesium sulfate, filtered and concentrated in vacou to give 6-oxo-1-(propan-2-yl)-1,6-dihydropyridine-3-carboxylic acid (0.064 g, 0.353 mmol, 80.3%) as a yellow solid. Use as is in the next step.

Step 5: Preparation of N-[5-(3-chlorophenoxy)pyridin-2-yl]-6-oxo-1-(propan-2-yl)-1,6-dihydropyridine-3-carboxamide

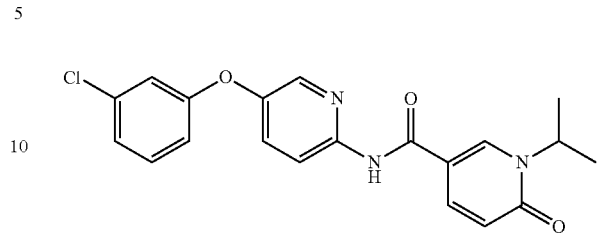

To a solution of 6-oxo-1-(propan-2-yl)-1,6-dihydropyridine-3-carboxylic acid (0.0402 g, 0.222 mmol), 5-(3-chlorophenoxy)pyridin-2-amine (0.049 g, 0.2220 mmol) and [bis(dimethylamino)methylidene]({3H-[1,2,3]triazolo[4,5-b]pyridin-3-yl})oxidanium; hexafluoro-λ⁵-phosphanuide (0.0844 g, 0.222 mmol) in tetrahydrofuran (740 µL) at room temperature was added N,N-diisopropylethylamine (77.2 µL, 0.444 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-chlorophenoxy)pyridin-2-yl]-6-oxo-1-(propan-2-yl)-1,6-dihydropyridine-3-carboxamide (14 0.7 mg, 0.0383 mmol, 17%) as a white solid. ¹H NMR (300 MHz, Chloroform-d) δ 8.36-8.18 (m, 3H), 8.13 (d, J=2.9 Hz, 1H), 7.70 (dd, J=9.6, 2.7 Hz, 1H), 7.46 (dd, J=9.0, 3.0 Hz, 1H), 7.31 (d, J=8.1 Hz, 1H), 7.13 (d, J=8.0 Hz, 1H), 7.00 (t, J=2.1 Hz, 1H), 6.98-6.88 (m, 1H), 6.63 (d, J=9.5 Hz, 1H), 5.33-5.25 (m, 1H), 1.45 (d, J=6.8 Hz, 6H); LCMS (ESI) m/z: 384.4 [M+H]⁺.

Example 167. Preparation of N-[5-(3-chloro-4-fluorophenoxy)pyridin-2-yl]-1-methyl-6-oxo-1,6-dihydropyridine-3-carboxamide (167)

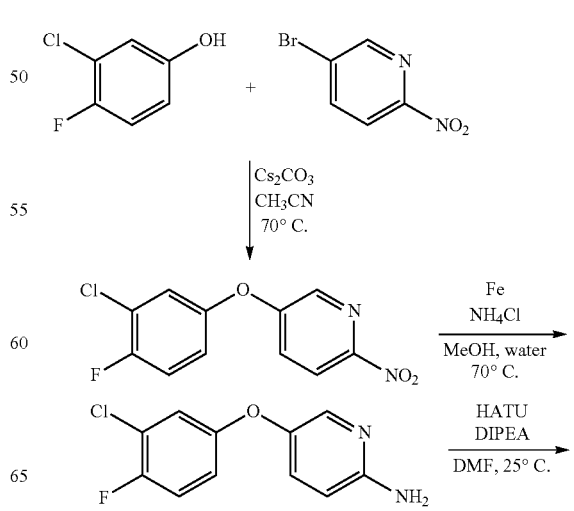

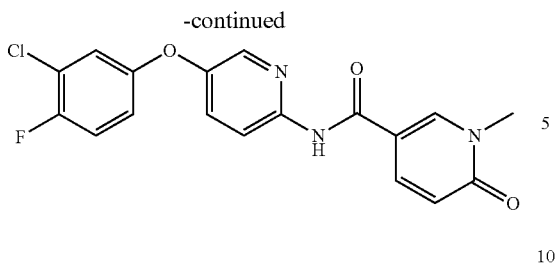

Step 1: Preparation of give 5-(4-chloro-3-fluorophenoxy)-2-nitropyridine

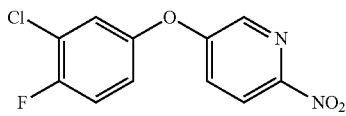

To a sealed tube was added 4-chloro-3-fluorophenol (0.597 m, 4.08 mmol), 5-bromo-2-nitropyridine (0.830 g, 4.08 mmol), and cesium carbonate (1.99 g, 6.12 mmol) and suspended in acetonitrile (10 mL). Reaction was heated to 70° C. for 2 h. Reaction was cooled to room temperature and concentrated. The crude product was purified over silica gel (ISCO, 40 g, 0-15% ethyl acetate/hexanes, over 25 minutes) to give 5-(4-chloro-3-fluorophenoxy)-2-nitropyridine (0.760 g, 2.82 mmol, 69.7%) as a yellow solid. $^1$H NMR (300 MHz, Methanol-d$_4$) δ 8.44-8.18 (m, 2H), 7.47 (ddt, J=8.9, 2.8, 1.0 Hz, 1H), 7.26 (s, 2H), 7.16-6.97 (m, 1H); LCMS (ESI) m/z: 269.2 [M+H]$^+$.

Step 2: Preparation of 5-(3-chloro-4-fluorophenoxy)pyridin-2-amine

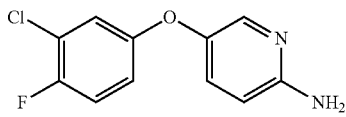 [SMILES: O=[N+]([O-])c1ccc(Oc2ccc(F)c(Cl)c2)cn1]

To a heated 70° C. solution of 5-(3-chloro-4-fluorophenoxy)-2-nitropyridine (0.760 g, 2.82 mmol) and ammonium chloride (0.599 m, 11.2 mmol) in a 4:1 mixture of methanol (7.62 mL) and water (1.90 mL) was added iron (625 mg, 11.2 mmol) in one portion. The reaction was stir at 70° C. for 16 h, after which the reaction was cool to room temperature and 8 mL of saturated bicarbonate was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chloro-4-fluorophenoxy)pyridin-2-amine (0.254 g, 1.06 mmol, 37.7%) as a crude a brown oil. The crude material is used without further purification in the next step. $^1$H NMR (300 MHz, Chloroform-d) δ 7.91 (d, J=2.9 Hz, 1H), 7.19 (dd, J=8.8, 2.9 Hz, 1H), 7.08 (t, J=8.8 Hz, 1H), 6.96 (dd, J=6.0, 3.0 Hz, 1H), 6.82 (ddd, J=9.0, 3.8, 3.0 Hz, 1H), 6.55 (d, J=8.8 Hz, 1H), 4.44 (s, 2H).

Step 3: Preparation of N-[5-(3-chloro-4-fluorophenoxy)pyridin-2-yl]-1-methyl-6-oxo-1,6-dihydropyridine-3-carboxamide

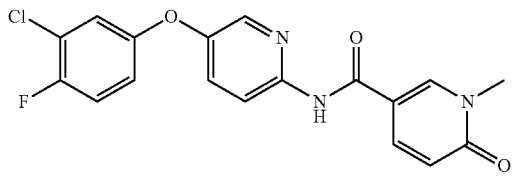

To a solution of 1-methyl-6-oxo-1,6-dihydropyridine-3-carboxylic acid (0.050 g, 0.327 mmol), 5-(3-chloro-4-fluorophenoxy)pyridin-2-amine (0.0779 g, 0.327 mmol) and [bis(dimethylamino)methylidene]({3H-[1,2,3]triazolo[4,5-b]pyridin-3-yl})oxidanium; hexafluoro-λ$^5$-phosphanuide (0.124 g, 0.327 mmol) in tetrahydrofuran (1.1 mL) at room temperature was added N,N-diisopropylethylamine (0.113 mL, 0.653 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-chloro-4-fluorophenoxy)pyridin-2-yl]-1-methyl-6-oxo-1,6-dihydropyridine-3-carboxamide 70.8 mg, 0.189 mmol, 58%) as a white solid. $^1$H NMR (300 MHz, Dimethylsulfoxide-d$_6$) to 10.66 (s, 1H), 8.67 (d, J=2.7 Hz, 1H), 8.29-8.12 (m, 2H), 7.99 (dd, J=9.5, 2.7 Hz, 1H), 7.60 (dd, J=9.1, 3.1 Hz, 1H), 7.45 (t, J=9.0 Hz, 1H), 7.36 (dd, J=6.2, 3.0 Hz, 1H), 7.09 (dt, J=9.0, 3.5 Hz, 1H), 6.44 (d, J=9.5 Hz, 1H); LCMS (ESI) m/z: 374.4 [M+H]$^+$.

Example 168. Preparation of N-[5-(3-chloro-4-fluorophenoxy)pyridin-2-yl]-1-methyl-6-oxo-1,6-dihydropyridazine-3-carboxamide (168)

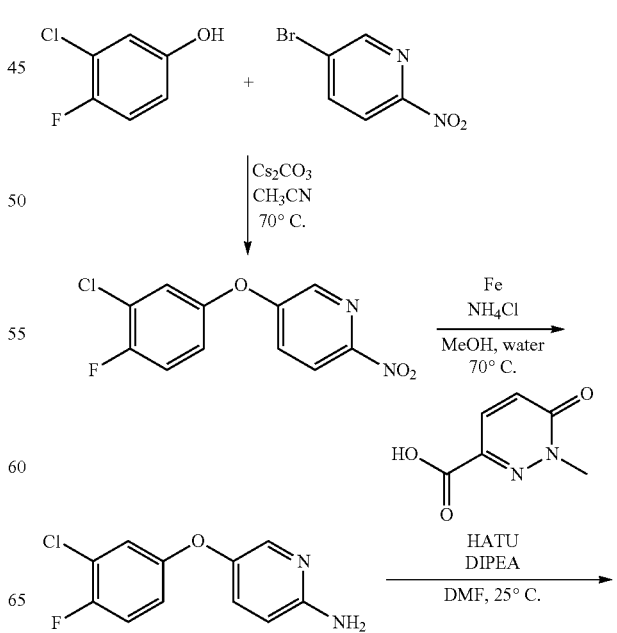

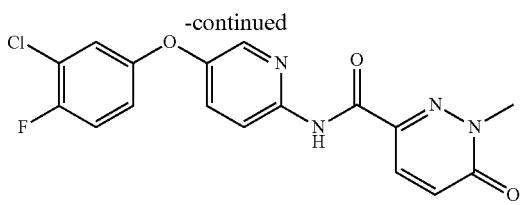

Step 1: Preparation of give 5-(4-chloro-3-fluorophenoxy)-2-nitropyridine

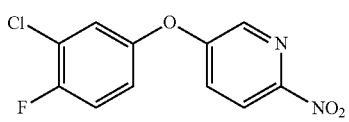

To a sealed tube was added 4-chloro-3-fluorophenol (0.597 g, 4.08 mmol), 5-bromo-2-nitropyridine (0.830 g, 4.08 mmol) and cesium carbonate (1.99 g, 6.12 mmol) and suspended in acetonitrile (10 mL). Reaction was heated to 70° C. for 2 h. Reaction was cooled to room temperature and concentrated. The crude product was purified over silica gel chromatography (ISCO, 40 g, 0-15% ethyl acetate/hexanes, over 25 minutes) to give 5-(4-chloro-3-fluorophenoxy)-2-nitropyridine (0.760 g, 2.82 mmol, 69.7%) as a yellow solid. $^1$H NMR (300 MHz, Methanol-$d_4$) δ 8.44-8.18 (m, 2H), 7.47 (ddt, J=8.9, 2.8, 1.0 Hz, 1H), 7.26 (s, 2H), 7.16-6.97 (m, 1H); LCMS (ESI) m/z: 269.2 [M+H]$^+$.

Step 2: Preparation of 5-(3-chloro-4-fluorophenoxy)pyridin-2-amine

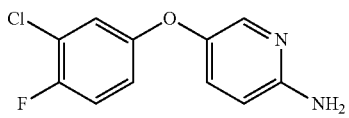

To a heated 70° C. solution of 5-(3-chloro-4-fluorophenoxy)-2-nitropyridine (0.760 g, 2.82 mmol) and ammonium chloride (0.599 g, 11.2 mmol) in a 4:1 mixture of methanol (7.62 mL) and water (1.90 mL) was added iron (0.625 g, 11.2 mmol) in one portion. The reaction was stir at 70° C. for 16 h, after which the reaction was cool to room temperature and 8 mL of saturated bicarbonate was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chloro-4-fluorophenoxy)pyridin-2-amine (0.254 g, 1.06 mmol, 37.7%) as a crude a brown oil. The crude material is used without further purification in the next step. $^1$H NMR (300 MHz, Chloroform-d) δ 7.91 (d, J=2.9 Hz, 1H), 7.19 (dd, J=8.8, 2.9 Hz, 1H), 7.08 (t, J=8.8 Hz, 1H), 6.96 (dd, J=6.0, 3.0 Hz, 1H), 6.82 (ddd, J=9.0, 3.8, 3.0 Hz, 1H), 6.55 (d, J=8.8 Hz, 1H), 4.44 (s, 2H).

Step 3: Preparation of N-[5-(3-chloro-4-fluorophenoxy)pyridin-2-yl]-1-methyl-6-oxo-1,6-dihydropyridazine-3-carboxamide

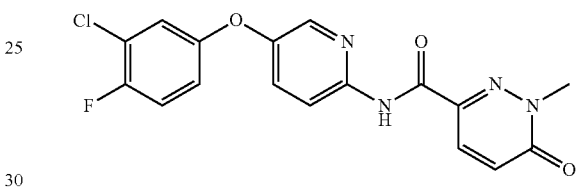

To a solution of 1-methyl-6-oxo-1,6-dihydropyridazine-3-carboxylic acid (0.050 g, 0.324 mmol), 5-(3-chloro-4-fluorophenoxy)pyridin-2-amine (0.0774 g, 0.324 mmol) and [bis(dimethylamino)methylidene]({3H-[1,2,3]triazolo[4,5-b]pyridin-3-yl})oxidanium; hexafluoro-$\lambda^5$-phosphanuide (0.123 g, 0.324 mmol) in tetrahydrofuran (1.1 mL) at room temperature was added diisopropylethylamine (0.112 mL, 0.649 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-chloro-4-fluorophenoxy)pyridin-2-yl]-1-methyl-6-oxo-1,6-dihydropyridazine-3-carboxamide (47.5 mg, 0.127 mmol, 39.2%). $^1$H NMR (300 MHz, Chloroform-d) δ 9.48 (s, 1H), 8.36 (dd, J=9.0, 0.7 Hz, 1H), 8.15 (dd, J=2.9, 0.7 Hz, 1H), 8.08 (d, J=9.7 Hz, 1H), 7.43 (dd, J=9.0, 2.9 Hz, 1H), 7.14 (d, J=8.6 Hz, 1H), 7.11-7.03 (m, 2H), 6.92 (ddd, J=9.0, 3.8, 3.0 Hz, 1H), 3.91 (s, 4H); LCMS (ESI) m/z: 375.4 [M+H]$^+$.

Example 169. Preparation of N-[5-(3-chloro-4-fluorophenoxy)pyridin-2-yl]-1-ethyl-6-oxo-1,6-dihydropyridine-3-carboxamide (169)

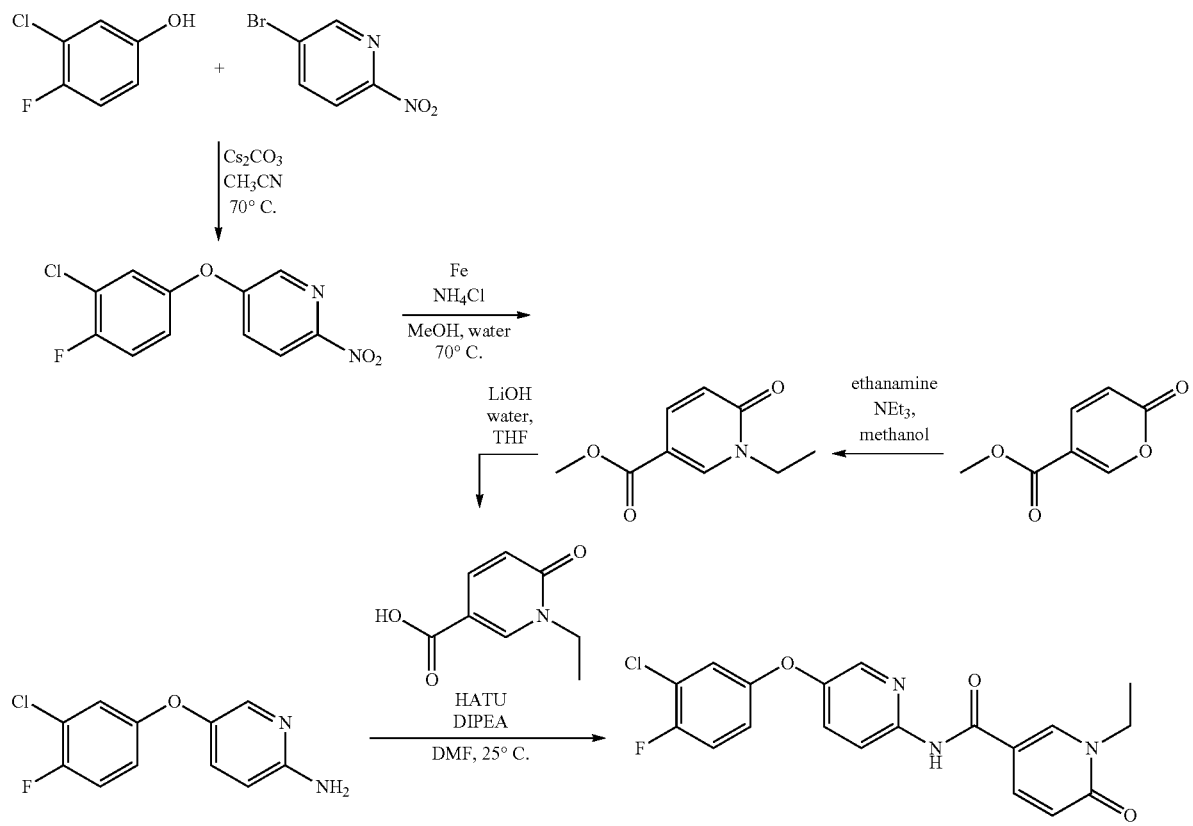

Step 1: Preparation of give 5-(4-chloro-3-fluorophenoxy)-2-nitropyridine

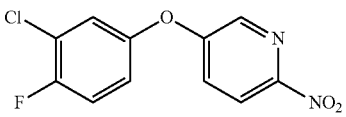

To a sealed tube was added 4-chloro-3-fluorophenol (0.597 g, 4.08 mmol), 5-bromo-2-nitropyridine (0.830 g, 4.08 mmol), and cesium carbonate (1.99 g, 6.12 mmol) and suspended in acetonitrile (10 mL). Reaction was heated to 70° C. for 2 h. Reaction was cooled to room temperature and concentrated. The crude product was purified over silica gel chromatography (ISCO, 40 g, 0-15% ethyl acetate/hexanes, over 25 minutes) to give 5-(4-chloro-3-fluorophenoxy)-2-nitropyridine (0.760 g, 2.82 mmol, 69.7%) as a yellow solid. $^{1}$H NMR (300 MHz, Methanol-$d_4$) δ 8.44-8.18 (m, 2H), 7.47 (ddt, J=8.9, 2.8, 1.0 Hz, 1H), 7.26 (s, 2H), 7.16-6.97 (m, 1H); LCMS (ESI) m/z: 269.2 [M+H]$^{+}$.

Step 2: Preparation of 5-(3-chloro-4-fluorophenoxy)pyridin-2-amine

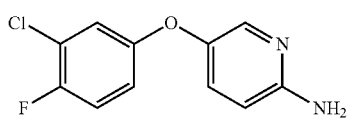

To a heated 70° C. solution of 5-(3-chloro-4-fluorophenoxy)-2-nitropyridine (0.760 g, 2.82 mmol) and ammonium chloride (0.599 g, 11.2 mmol) in a 4:1 mixture of methanol (7.62 mL) and water (1.90 mL) was added iron (0.625 g, 11.2 mmol) in one portion. The reaction was stirred at 70° C. for 16 h, after which the reaction was cooled to room temperature and 8 mL of saturated bicarbonate was added. The reaction mixture volume was diluted with ethyl acetate (50 mL) and filtered through a pad of Celite® and washed with ethyl acetate (20 mL×3). Layers were separated and the aqueous layer was extracted with ethyl acetate (50 mL×2). The organic layer was dried over magnesium sulfate, filtered and concentrated to give 5-(3-chloro-4-fluorophenoxy)pyridin-2-amine (0.254 g, 1.06 mmol, 37.7%) as a crude a brown oil. The crude material is used without further purification in the next step. $^{1}$H NMR (300 MHz, Chloroform-d) δ 7.91 (d, J=2.9 Hz, 1H), 7.19 (dd, J=8.8, 2.9 Hz, 1H), 7.08 (t, J=8.8

Hz, 1H), 6.96 (dd, J=6.0, 3.0 Hz, 1H), 6.82 (ddd, J=9.0, 3.8, 3.0 Hz, 1H), 6.55 (d, J=8.8 Hz, 1H), 4.44 (s, 2H).

Step 3: Preparation of methyl 1-ethyl-6-oxo-1,6-dihydropyridine-3-carboxylate

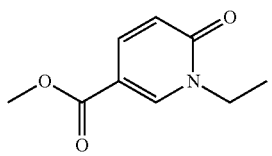

A solution of methyl 2-oxo-2H-pyran-5-carboxylate (0.500 g, 3.24 mmol) in methanol (10.8 mL) at room temperature was treated with ethanamine (2.02 mL, 4.05 mmol) and triethylamine (0.796 mL, 5.67 mmol). Reaction mixture was stirred for 1 h before it was concentrated, and purified by silica gel chromatography (ISCO, ethyl acetate/hexanes, 3/1, over 20 minutes) to give methyl 1-ethyl-6-oxo-1,6-dihydropyridine-3-carboxylate (0.380 g, 2.09 mmol, 64%) as a brown oil. $^1$H NMR (300 MHz, Chloroform-d) δ 8.20 (dd, J=2.5, 0.6 Hz, 1H), 7.84 (dd, J=9.5, 2.5 Hz, 1H), 6.58-6.46 (m, 1H), 4.05 (q, J=7.2 Hz, 2H), 3.87 (s, 3H), 1.40 (t, J=7.2 Hz, 3H); LCMS (ESI) m/z: 182.2 [M+H]$^+$.

Step 4: Preparation of 1-ethyl-6-oxo-1,6-dihydropyridine-3-carboxylic acid

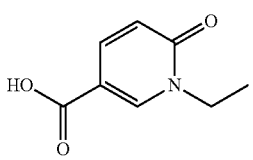

To a solution of methyl 1-ethyl-6-oxo-1,6-dihydropyridine-3-carboxylate (0.180 g, 0.993 mmol) in tetrahydrofuran (3.31 mL) and water (0.83 mL) at 25° C. was added lithium hydroxide hydrate (0.0625 g, 1.49 mmol) in one portion. The reaction mixture was stirred at room temperature 3 h before it was evaporated to dryness, diluted with water (15 mL) and adjusted to pH=2 with 1N hydrogen chloride solution. The reaction mixture was extracted with ethyl acetate (3×20 mL). The combined organic layers were dried over magnesium sulfate, filtered and concentrated in vacou to give 1-ethyl-6-oxo-1,6-dihydropyridine-3-carboxylic acid (0.066 g, 0.407 mmol, 40.9%) as a yellow solid. $^1$H NMR (300 MHz, Dimethylsulfoxide-d$_6$) δ 12.80 (s, 1H), 8.46 (d, J=2.6 Hz, 1H), 7.77 (dt, J=9.5, 1.8 Hz, 1H), 6.39 (d, J=9.5 Hz, 1H), 3.98 (q, J=7.1 Hz, 2H), 1.20 (q, J=6.7 Hz, 4H); LCMS (ESI) m/z: 168.2 [M+H]$^+$. Used in the next step without further purification.

Step 5: Preparation of N-[5-(3-chloro-4-fluorophenoxy)pyridin-2-yl]-1-ethyl-6-oxo-1,6-dihydropyridine-3-carboxamide

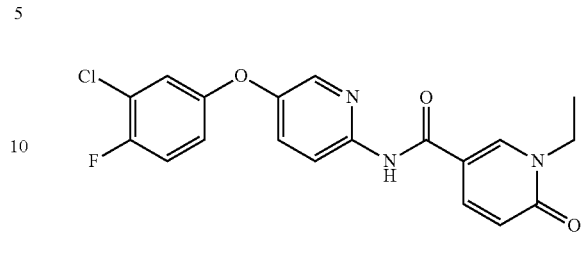

To a solution of 1-ethyl-6-oxo-1,6-dihydropyridine-3-carboxylic acid (0.060 g, 0.359 mmol), 5-(3-chloro-4-fluorophenoxy)pyridin-2-amine (0.0856 g, 0.359 mmol) and [bis(dimethylamino)methylidene]({3H-[1,2,3]triazolo[4,5-b]pyridin-3-yl})oxidanium; hexafluoro-λ$^5$-phosphanuide (0.136 g, 0.3589 mmol) in tetrahydrofuran (1.2 mL) at room temperature was added N,N-diisopropylethylamine (0.124 mL, 0.718 mmol) dropwise. Reaction was stir at room temperature for 16 h. Reaction solution was quenched with water (1 mL). The aqueous layer was extracted with ethyl acetate (5 mL×3). The combined organic layers were washed with brine, dried over magnesium sulfate, filtered and concentrated. The crude residue was purified over silica gel chromatography (ISCO, 12 g, eluting with 0-80% ethyl acetate/hexanes for 20 minutes) to afford N-[5-(3-chloro-4-fluorophenoxy)pyridin-2-yl]-1-ethyl-6-oxo-1,6-di hydropyridine-3-carboxamide (45.0 mg, 0.116 mmol, 32.2%). $^1$H NMR (300 MHz, Dimethylsulfoxide-d$_6$) δ 10.73 (s, 1H), 8.65 (d, J=2.7 Hz, 1H), 8.31-8.10 (m, 2H), 8.00-7.91 (m, 1H), 7.61 (dd, J=9.1, 3.0 Hz, 1H), 7.46 (t, J=9.1 Hz, 1H), 7.36 (dd, J=6.2, 3.0 Hz, 1H), 7.17-6.95 (m, 1H), 6.43 (d, J=9.5 Hz, 1H), 3.97 (q, J=7.2 Hz, 2H), 1.28 (t, J=7.1 Hz, 3H); LCMS (ESI) m/z 388.1 [M+H]$^+$.

Example 170. Preparation of N-(5-(3-chlorobenzyloxy)pyridin-2-yl)-1-methyl-6-oxo-1,4,5,6-tetrahydropyridazine-3-carboxamide (170)

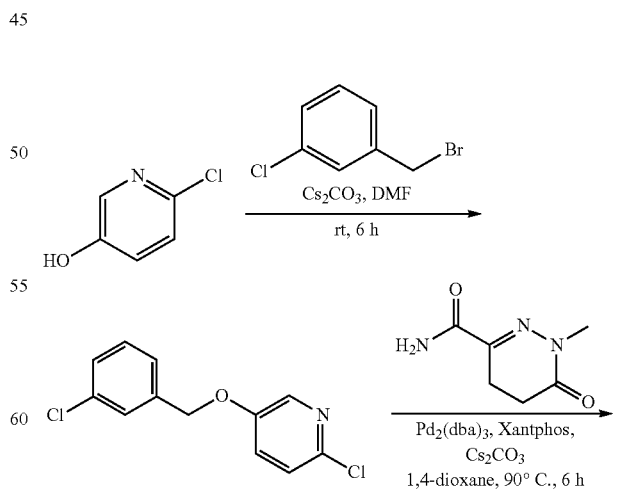

-continued

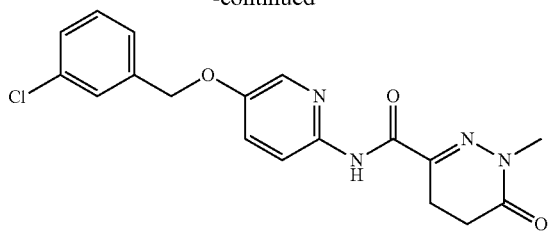

Step 1: Preparation of
2-chloro-5-(3-chlorobenzyloxy)pyridine

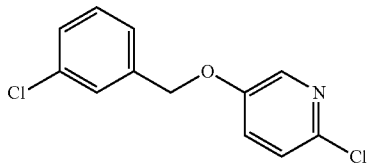 [SMILES: Clc1cccc(COc2ccc(Cl)nc2)c1]

A suspension of 6-chloropyridin-3-ol (1.8 g, 14 mmol), 1-(bromomethyl)-3-chlorobenzene (3.18 g, 15.4 mmol) and cesium carbonate (5.02 g, 15.4 mmol) in N,N-dimethylformamide (10 mL) was stirred at room temperature for 6 h. The solid was filtered and the filtrate was extracted with dichloromethane (50 mL×2). The combined organic layers were washed with brine (50 mL), dried over sodium sulfate, filtered and concentrated. The crude residue was purified by column chromatography (silica gel, petroleum ether/ethyl acetate=10/1) to give 2-chloro-5-(3-chlorobenzyloxy)pyridine (2.6 g, 10.3 mmol, 73.4%) as a white solid. LCMS (ESI) m/z: 254.1 [M+H]$^+$.

Step 2: Preparation of N-(5-(3-chlorobenzyloxy)pyridin-2-yl)-1-methyl-6-oxo-1,4,5,6-tetrahydropyridazine-3-carboxamide

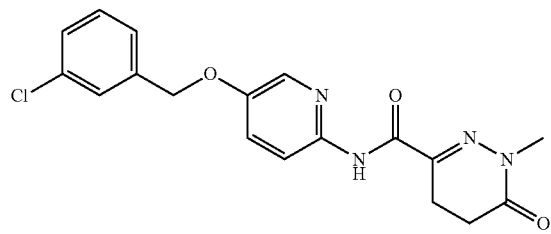 [SMILES: CN1N=C(C(=O)Nc2ccc(OCc3cccc(Cl)c3)cn2)CCC1=O]

A suspension of 1-methyl-6-oxo-1,4,5,6-tetrahydropyridazine-3-carboxamide (0.248 g, 1.6 mmol), 2-chloro-5-(3-chlorobenzyloxy)pyridine (0.202 g, 0.8 mmol), tris(dibenzylideneacetone)dipalladium(0) (0.073 g, 0.08 mmol), 4,5-bis(diphenylphosphino)-9,9-dimethylxanthene (0.046 g, 0.08 mmol) and cesium carbonate (0.522 g, 1.6 mmol) in 1,4-dioxane (6 mL) was stirred at 90° C. for 3 h under argon. The reaction mixture was cooled and extracted with ethyl acetate (50 mL×2). The combined organic layers were washed with brine (50 mL) dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/0.01% aqueous trifluoroacetic acid) to give N-(5-(3-chlorobenzyloxy)pyridin-2-yl)-1-methyl-6-oxo-1,4,5,6-tetrahydropyridazine-3-carboxamide (0.0686 g, 0.18 mmol, 23.1%) as a white solid. $^1$H NMR (500 MHz, Dimethylsulfoxide-d$_6$) δ 9.70 (s, 1H), 8.16 (d, J=3.5 Hz, 1H), 8.04 (d, J=8.5 Hz, 1H), 7.58 (dd, J=8.5, 3.0 Hz, 1H), 7.55 (s, 1H), 7.45-7.41 (m, 3H), 5.19 (s, 2H), 3.56 (s, 3H), 2.85 (t, J=8.3 Hz, 2H), 2.52 (t, J=7.0 Hz, 2H); LCMS (ESI) m/z: 373.0 [M+H]$^+$.

Example 171. Preparation of N-(5-(3-chlorobenzyloxy)pyridin-2-yl)-1-methyl-6-oxo-1,6-dihydropyridazine-3-carboxamide (171)

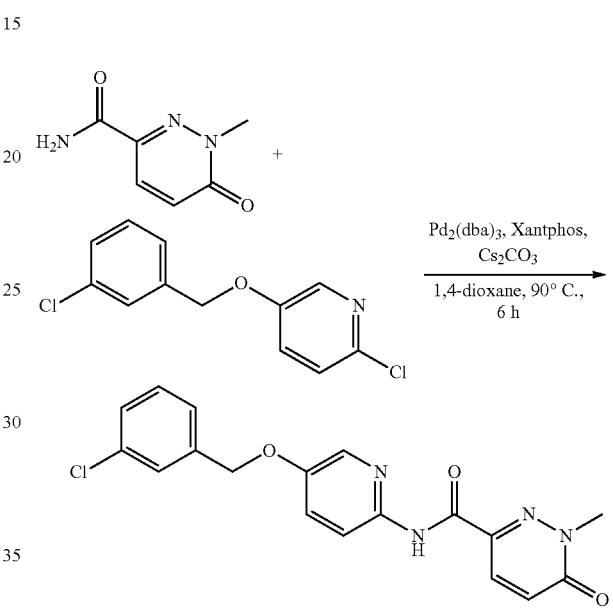

Step 1: Preparation of N-(5-(3-chlorobenzyloxy)pyridin-2-yl)-1-methyl-6-oxo-1,6-dihydropyridazine-3-carboxamide

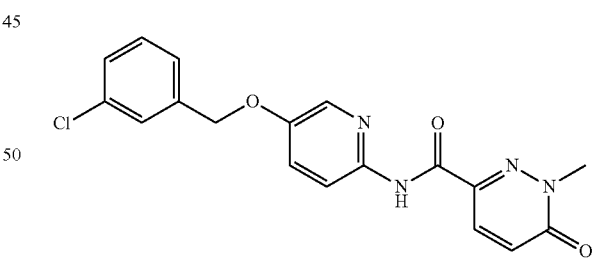

A suspension of 1-methyl-6-oxo-1,6-dihydropyridazine-3-carboxamide (0.245 g, 1.6 mmol), 2-chloro-5-(3-chlorobenzyloxy) pyridine (0.202 g, 0.8 mmol), tris(dibenzylideneacetone)dipalladium(0) (0.073 g, 0.08 mmol), 4,5-bis(diphenylphosphino)-9,9-dimethylxanthene (0.046 g, 0.08 mmol) and cesium carbonate (0.522 g, 1.6 mmol) in 1,4-dioxane (6 mL) was stirred at 90° C. for 6 h under argon. The reaction mixture was extracted with ethyl acetate (50 mL×2). The combined organic layers were washed with brine (50 mL), dried over sodium sulfate, filtered and concentrated. The crude residue was washed with methanol/acetonitrile=½ (4.5 mL) to give N-(5-(3-chlorobenzyloxy)

pyridin-2-yl)-1-methyl-6-oxo-1,6-dihydropyridazine-3-carboxamide (0.0574 g, 0.16 mmol, 19.4%) as a white solid. ¹H NMR (400 MHz, Dimethylsulfoxide-d₆) δ 10.10 (s, 1H), 8.19 (d, J=1.6 Hz, 1H), 8.07 (d, J=9.2 Hz, 1H), 7.94 (d, J=9.6 Hz, 1H), 7.60 (dd, J=8.8, 3.2 Hz, 1H), 7.55 (s, 1H), 7.45-7.41 (m, 3H), 7.07 (d, J=9.2 Hz, 1H), 5.20 (s, 2H), 3.79 (s, 3H)); LCMS (ESI) m/z: 371.0 [M+H]⁺.

Example 172. Preparation of N-(5-(3-chlorobenzyloxy)pyridin-2-yl)-1-methyl-6-oxo-1,6-dihydropyridazine-3-carboxamide (172)

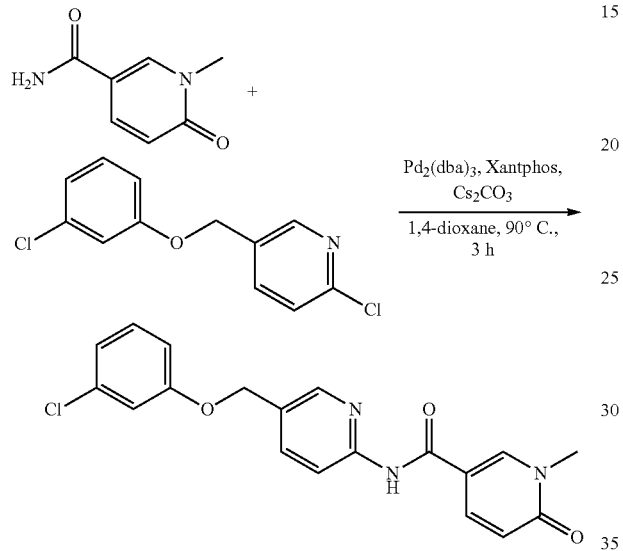

Step 1: Preparation of N-(5-((3-chlorophenoxy)methyl)pyridin-2-yl)-1-methyl-6-oxo-1,6-dihydropyridine-3-carboxamide

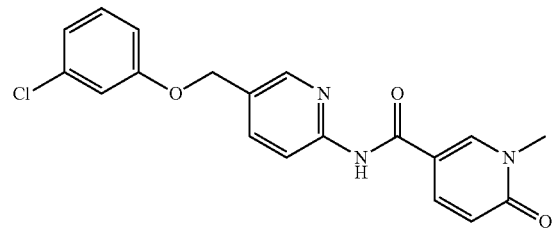 [SMILES: Cn1cc(C(=O)Nc2ccc(COc3cccc(Cl)c3)cn2)ccc1=O]

A suspension of 1-methyl-6-oxo-1,6-dihydropyridine-3-carboxamide (0.243 g, 1.6 mmol), 2-chloro-5-((3-chlorophenoxy)methyl) pyridine (0.202 g, 0.8 mmol), tris(dibenzylideneacetone)dipalladium(0) (0.073 g, 0.08 mmol), 4,5-bis(diphenylphosphino)-9,9-dimethylxanthene (0.046 g, 0.08 mmol) and cesium carbonate (0.522 g, 1.6 mmol) in 1,4-dioxane (6 mL) was stirred at 90° C. for 3 h under argon. The reaction mixture was extracted with ethyl acetate (100 mL×2). The combined organic layers were washed with brine (100 mL), dried over sodium sulfate, filtered and concentrated. The crude residue was purified by column chromatography (silica gel, dichloromethane/methanol=50/1) to give N-(5-((3-chlorophenoxy)methyl)pyridin-2-yl)-1-methyl-6-oxo-1,6-dihydropyridine-3-carboxamide (0.0565 g, 0.15 mmol, 19.2%) as a pink solid. ¹H NMR (500 MHz, Dimethylsulfoxide-d₆) δ 10.65 (s, 1H), 8.69 (d, J=2.5 Hz, 1H), 8.47 (d, J=1.5 Hz, 1H), 8.17 (d, J=8.0 Hz, 1H), 7.99 (dd, J=9.5, 2.5 Hz, 1H), 7.91 (dd, J=8.5, 2.0 Hz, 1H), 7.33 (t, J=8.0 Hz, 1H), 7.14 (t, J=1.8 Hz, 1H), 7.03-7.00 (m, 2H), 6.44 (d, J=9.5 Hz, 1H), 5.14 (s, 2H), 3.51 (s, 3H); LCMS (ESI) m/z: 370.1 [M+H]⁺.

Example 173. Preparation of N-(5-((3-Chlorophenylamino)methyl)pyridin-2-yl)-1-methyl-6-oxo-1,6-dihydropyridine-3-carboxamide (173)

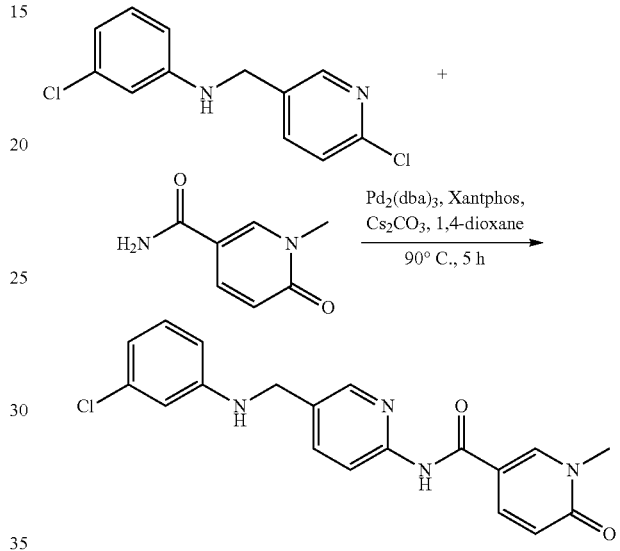

Step 1: Preparation of N-(5-((3-chlorophenylamino)methyl)pyridin-2-yl)-1-methyl-6-oxo-1,6-dihydropyridine-3-carboxamide

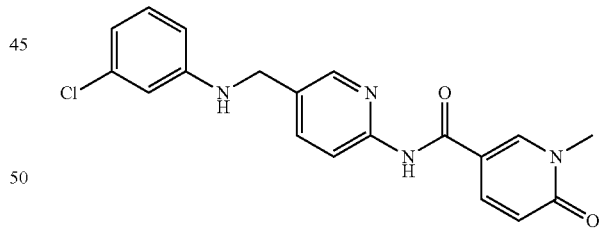

To a solution of 3-chloro-N-((6-chloropyridin-3-yl)methyl)aniline (0.130 g, 0.51 mmol) in anhydrous 1,4-dioxane (15 mL) at room temperature was added 1-methyl-6-oxo-1,6-dihydropyridine-3-carboxamide (0.078 g, 0.51 mmol), tris(dibenzylideneacetone)dipalladium(0) (24 mg, 0.03 mmol), 4,5-bis(diphenylphosphino)-9,9-dimethylxanthene (0.030 g, 0.05 mmol) and cesium carbonate (0.251 g, 0.77 mmol) under nitrogen. The reaction mixture was stirred at 90° C. for 5 h, cooled to room temperature and diluted with water (100 mL). The aqueous layer was extracted with ethyl acetate (80 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-((3-chlorophenylamino)methyl)pyridin-2-yl)-1-methyl-6-oxo-1,6-dihydropyridine-3-carboxamide (0.127 g, 0.34 mmol, 67%) as a white solid. $^1$H NMR (400 MHz, Dimethylsulfoxide-$d_6$) δ 10.54 (s, 1H), 8.67 (d, J=2.4 Hz, 1H), 8.36 (d, J=1.6 Hz, 1H), 8.09 (d, J=8.8 Hz, 1H), 7.98 (dd, $J_1$=2.8 Hz, $J_2$=9.6 Hz, 1H), 7.78 (dd, J>=2.0 Hz, $J_2$=8.4 Hz, 1H), 7.06 (t, J=8.0 Hz, 1H), 6.61 (t, J=2.0 Hz, 1H), 6.57-6.52 (m, 3H), 6.43 (d, J=9.6 Hz, 1H), 4.27 (d, J=5.6 Hz, 2H), 3.50 (s, 3H); LCMS (ESI) m/z: 369.1 [M+H]$^+$.

Example 174. Preparation of N-(5-((3-Chlorophenylamino)methyl)pyridin-2-yl)-1-methyl-6-oxo-1,6-dihydropyridazine-3-carboxamide (174)

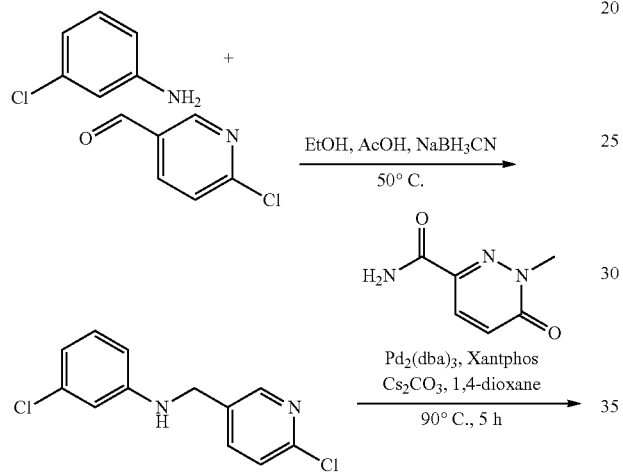

Step 1: Preparation of 3-chloro-N-((6-chloropyridin-3-yl)methyl)aniline

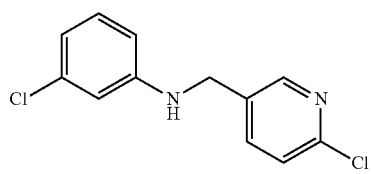 [SMILES: Clc1cccc(NCc2ccc(Cl)nc2)c1]

To a solution of 3-chloroaniline (3.0 g, 23.5 mmol) in ethanol (60 mL) at room temperature was added 6-chloronicotinaldehyde (3.33 g, 23.5 mmol), acetic acid (0.141 g, 2.35 mmol) and sodium cyanoborohydride (4.43 g, 70.55 mmol). The reaction mixture was stirred at 50° C. for 5 h before it was cooled to room temperature and diluted with water (200 mL). The aqueous layer was extracted with ethyl acetate (100 mL×3). The combined organic layers were washed with brine (200 mL), dried over anhydrous sodium sulfate, filtered and concentrated. The cruse product was purified by column chromatography (silica gel, petroleum ether/ethyl acetate=1/1) to afford 3-chloro-N-((6-chloropyridin-3-yl)methyl)aniline (4.5 g, 17.8 mmol, 75%) as a white solid. LCMS (ESI) m/z: 254.1 [M+H]$^+$.

Step 2: Preparation of N-(5-((3-chlorophenylamino)methyl)pyridin-2-yl)-1-methyl-6-oxo-1,6-dihydropyridazine-3-carboxamide

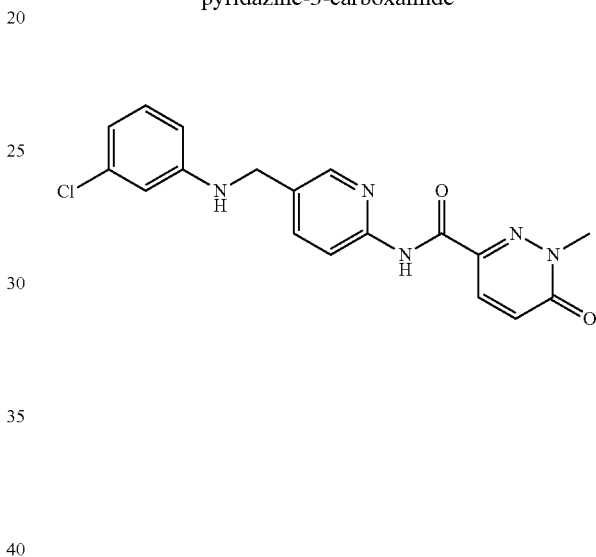

To a solution of 3-chloro-N-((6-chloropyridin-3-yl)methyl)aniline (0.100 g, 0.40 mmol) in anhydrous 1,4-dioxane (12 mL) at room temperature was added 1-methyl-6-oxo-1,6-dihydropyridazine-3-carboxamide (0.061 g, 0.40 mmol), tris(dibenzylideneacetone)dipalladium(0) (0.018 g, 0.02 mmol), 4,5-bis(diphenylphosphino)-9,9-dimethylxanthene (0.024.0 g, 0.04 mmol) and cesium carbonate (0.194 g, 0.60 mmol) under nitrogen. The reaction mixture was stirred at 90° C. for 5 h before it was cooled to room temperature and diluted with water (100 mL). The aqueous layer was extracted with ethyl acetate (80 mL×3). The combined organic layers were washed with brine (100 mL), dried over anhydrous sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(5-((3-chlorophenylamino)methyl)pyridin-2-yl)-1-methyl-6-oxo-1,6-dihydropyridazine-3-carboxamide (0.105 g, 0.28 mmol, 71%) as a white solid. $^1$H NMR (500 MHz, Dimethylsulfoxide-$d_6$) δ 8.38 (d, J=1.5 Hz, 1H), 8.12 (d, J=8.5 Hz, 1H), 7.95 (d, J=9.5 Hz, 1H), 7.84 (dd, $J_1$=2.5 Hz, $J_2$=8.5 Hz, 1H), 7.09-7.04 (m, 2H), 6.61-6.53 (m, 4H), 4.29 (d, J=5.5 Hz, 2H), 3.79 (s, 3H); LCMS (ESI) m/z: 370.0 [M+H]$^+$.

Example 175. Preparation of N-(5-(3-chlorobenzyl) pyrimidin-2-yl)-1-methyl-6-oxo-1,4,5,6-tetrahydro-pyridazine-3-carboxamide (175)

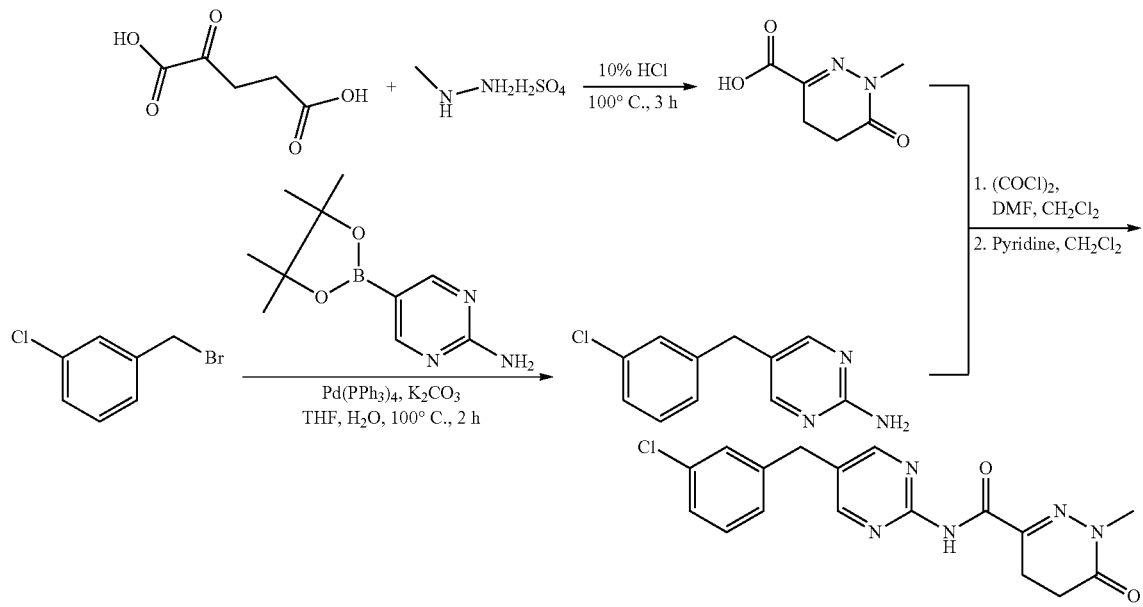

Step 1: Preparation of 1-methyl-6-oxo-1,4,5,6-tetra-hydropyridazine-3-carboxylic acid

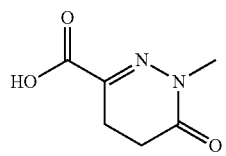

To a solution of 2-oxopentanedioic acid (10 g, 68 mmol) in 10% hydrogen chloride (40 mL) was added methylhydrazine sulfate (9.8 g, 68 mmol) in three portions. Reaction was stirred at 100° C. for 3 h before it was cooled to room temperature and extracted with tetrahydrofuran (100 mL×3). The combined organic layers were washed with brine (50 mL×2), dried over sodium sulfate, filtered and concentrated. The crude solid was washed with petroleum ether (20 mL) to offer 1-methyl-6-oxo-1,4,5,6-tetrahydropyridazine-3-carboxylic acid as a white solid (5.6 g, 52.8%); LCMS (ESI) m/z: 157.1 [M+H]+.

Step 2: Preparation of 5-(3-chlorobenzyl)pyrimidin-2-amine

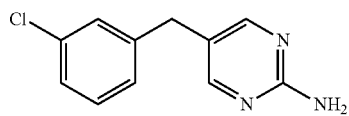

A suspension of potassium carbonate (1.66 g, 12 mmol), tetrakis(triphenylphosphine)palladium(0) (0.277 g, 0.24 mmol) in tetrahydrofuran (6 mL) and water (6 mL) was stirred at room temperature for 0.5 h. Then a solution of 1-(bromomethyl)-3-chlorobenzene (0.812 g, 4 mmol) and 5-(4,4,5,5-tetramethyl-1,3,2-dioxaborolan-2-yl)pyrimidin-2-amine (0.972 g, 4.4 mmol) in tetrahydrofuran (16 mL) was added. The reaction mixture was stirred at 100° C. for 2 h before it was cooled and filtered. The filtrate was extracted with ethyl acetate (50 mL×2), washed with aqueous 1 N hydrogen chloride (30 mL×2) and neutralized with aqueous sodium bicarbonate. The resulting precipitate was filtered and dissolved in ethyl acetate (50 mL). The organic layer was washed with brine, dried over sodium sulfate, filtered and concentrated to give 5-(3-chlorobenzyl)pyrimidin-2-amine (6.00 g, 3.01 mmol, 68.5%) as a white solid. LCMS (ESI) m/z: 220.1 [M+H]+.

Step 3: Preparation of N-(5-(3-chlorobenzyl)pyrimidin-2-yl)-1-methyl-6-oxo-1,4,5,6-tetrahydro-pyridazine-3-carboxamide

To a solution of 1-methyl-6-oxo-1,4,5,6-tetrahydro-pyridazine-3-carboxylic acid (0.120 g, 0.75 mmol) in dichloromethane (20 mL) at 0° C. was added N,N-dimethylformamide (1 drop) and oxalyl chloride (0.476 g, 3.75 mmol) dropwise. Reaction was warmed to room temperature over 2 h before it was concentrated. The crude solid was re-dissolved in dichloromethane (5 mL) and added to a solution of 5-(3-chlorobenzyl)pyrimidin-2-amine (0.197 g, 0.9 mmol) in pyridine (3 mL) at 0° C. Reaction mixture was warmed to room temperature over 2 h. Reaction was poured into ice water and extracted with ethyl acetate (50 mL×2). The combined organic layers were washed with brine (60 mL), dried over sodium sulfate, filtered and concentrated. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to yield N-(5-(3-chlorobenzyl)pyrimidin-2-yl)-1-methyl-6-oxo-1,4,5,6-tetrahydropyridazine-3-carboxamide as a white solid (0.0656 g, 0.191 mmol, 25.4%). $^1$H NMR (500 MHz, Dimethylsulfoxide-$d_6$) δ 10.08 (s, 1H), 8.66 (s, 2H), 7.41 (s, 1H), 7.35 (t, J=7.5 Hz, 1H), 7.30-7.26 (m, 2H), 3.97 (s, 2H), 3.33 (s, 3H), 2.82 (t, J=8.5 Hz, 2H), 2.51 (t, J=6.5 Hz, 2H); LCMS (ESI) m/z: 358.1 [M+H]$^+$.

Example 176. Preparation of N-(6-(3-fluorobenzyl)pyridazin-3-yl)-1-methyl-6-oxo-1,6-dihydropyridine-3-carboxamide (176)

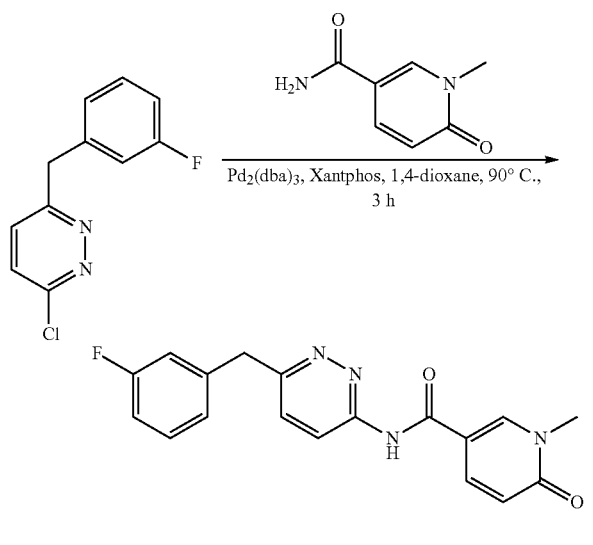

Step 1: Preparation of N-(6-(3-fluorobenzyl)pyridazin-3-yl)-1-methyl-6-oxo-1,6-dihydropyridine-3-carboxamide

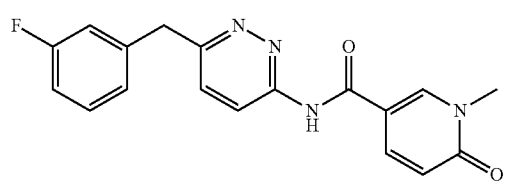 [SMILES: Cn1cc(C(=O)Nc2ccc(Cc3cccc(F)c3)nn2)ccc1=O]

A mixture of 3-chloro-6-(3-fluorobenzyl)pyridazine (0.25 g, 1.13 mmol), 1-methyl-6-oxo-1,6-dihydropyridine-3-carboxamide (0.34 g, 2.25 mmol), tris(dibenzylideneacetone)dipalladium(0) (0.10 g, 0.11 mmol), XantPhos (0.10 g, 0.17 mmol) and cesium carbonate (0.73 g, 2.25 mmol) in 1,4-dioxane (10.0 mL) was stirred under nitrogen atmosphere at 90° C. for 3 h. The reaction mixture was cooled down to room temperature and filtered. The filtrate was concentrated, under reduced pressure and the crude sample was dissolved in minimal N,N-dimethylformamide and purified via prep-HPLC (Boston C18 21*250 mm 10 μm column; acetonitrile/0.01% aqueous trifluoroacetic acid) to give N-(6-(3-fluorobenzyl)pyridazin-3-yl)-1-methyl-6-oxo-1,6-dihydropyridine-3-carboxamide (0.0686 g, 0.20 mmol, 17.7%) as a white solid. $^1$H NMR (500 MHz, Dimethylsulfoxide-$d_6$) δ 11.15 (s, 1H), 8.71 (d, J=2.5 Hz, 1H), 8.25 (d, J=9.1 Hz, 1H), 8.00 (dd, J=9.5, 2.5 Hz, 1H), 7.61 (d, J=9.5 Hz, 1H), 7.36 (dd, J=14.3, 8.0 Hz, 1H), 7.16-7.04 (m, 3H), 6.44 (d, J=9.5 Hz, 1H), 4.29 (s, 2H), 3.51 (s, 3H); LCMS (ESI) for m/z: 339.1 [M+H]$^+$.

Example 177. Preparation of N-(6-(5-chloro-2-fluorobenzyl)pyridazin-3-yl)-1-methyl-6-oxo-1,4,5,6-tetrahydropyridazine-3-carboxamide (177)

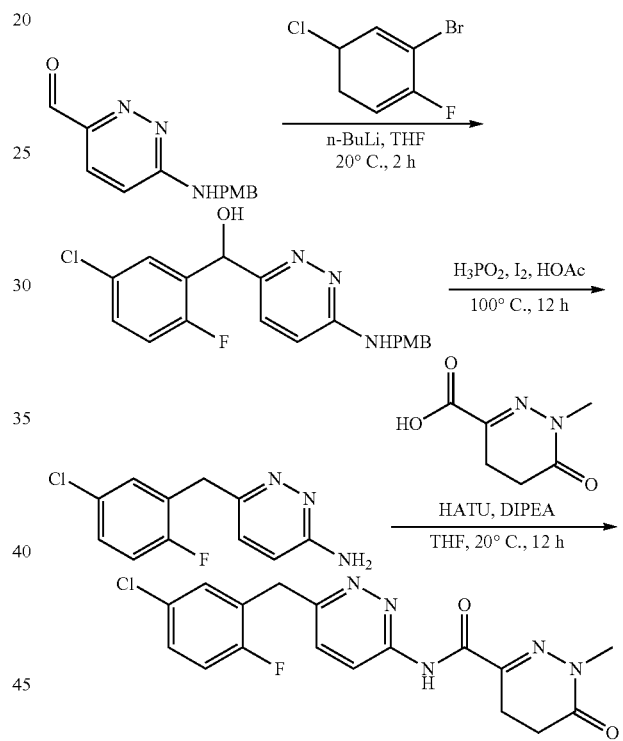

Step 1: Preparation of (5-chloro-2-fluorophenyl)(6-(4-methoxybenzylamino)pyridazin-3-yl)methanol

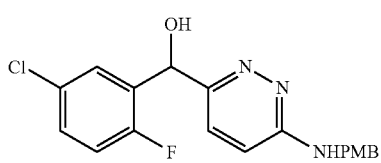

To a solution of 2-bromo-4-chloro-1-fluorobenzene (1.03 g, 4.94 mmol) in tetrahydrofuran (20 mL) at −78° C. was added n-butyllithium (4.0 mL, 9.88 mmol) under nitrogen. The reaction mixture was stirred at −78° C. for 2 h before a solution of 6-(4-methoxybenzylamino)pyridazine-3-carbaldehyde (0.800 g, 3.29 mmol) in tetrahydrofuran (3 mL) was added dropwise. The reaction mixture was stirred for another 2 h and was warmed to 20° C. Aqueous ammonium chloride was added to quench the reaction and the volatiles were removed under reduced pressure. The aqueous layer was extracted with dichloromethane (50 mL×2). The combined organic layers were dried over sodium sulfate, filtered and concentrated. The crude sample was purified by column chromatography (silica gel, petroleum ether/ethyl acetate=4/1 to 1/1) to give (5-chloro-2-fluorophenyl)(6-(4-methoxybenzylamino)pyridazin-3-yl)methanol (0.330 g, 0.888 mmol, 27%) as a yellow solid. LCMS (ESI) m/z: 374.0 [M+H]$^+$.

Step 2: Preparation of 6-(5-chloro-2-fluorobenzyl)pyridazin-3-amine

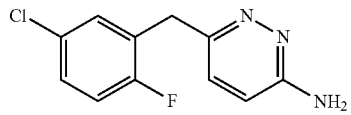 [SMILES: Nc1ccc(Cc2cc(Cl)ccc2F)nn1]

To a solution of (5-chloro-2-fluorophenyl)(6-(4-methoxybenzylamino)pyridazin-3-yl)methanol (0.330 g, 0.885 mmol) and hypophosphorous acid (0.973 g, 7.08 mmol) in acetic acid (4.0 mL) was added iodide (0.337 g, 1.33 mmol). The reaction was heated to 100° C. and stirred for 20 h. The reaction solution was slowly added to aqueous sodium bicarbonate and was extracted with dichloromethane (50 mL×2). The combined organic layers were collected, dried over sodium sulfate, filtered and concentrated to give 6-(5-chloro-2-fluorobenzyl)pyridazin-3-amine (0.160 g, crude) as a white solid; LCMS (ESI) m/z: 238.1 [M+H]$^+$.

Step 3: Preparation of N-(6-(5-chloro-2-fluorobenzyl)pyridazin-3-yl)-1-methyl-6-oxo-1,4,5,6-tetrahydropyridazine-3-carboxamide

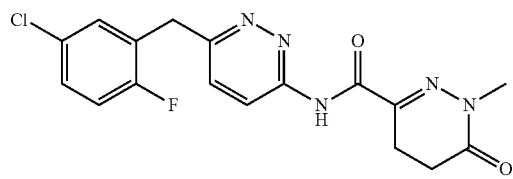 [SMILES: CN1N=C(C(=O)Nc2ccc(Cc3cc(Cl)ccc3F)nn2)CCC1=O]

To a solution of 1-methyl-6-oxo-1,4,5,6-tetrahydropyridazine-3-carboxylic acid (0.100 g, 0.641 mmol), N,N-diisopropylethylamine (0.249 g, 1.92 mmol) in tetrahydrofuran (5 mL) at 20° C. was added 1-[bis(dimethylamino)methylene]-1H-1,2,3-triazolo[4,5-b]pyridinium 3-oxid hexafluorophosphate (0.366 g, 0.962 mmol). The reaction was stirred for 20 minutes before a solution of 6-(5-chloro-2-fluorobenzyl)pyridazin-3-amine (0.152 g, 0.641 mmol) in tetrahydrofuran (1.0 mL) was added. Then reaction mixture was stirred at 20° C. for 16 h. The volatiles were removed under reduced pressure and the slurry was added to a mixture of dichloromethane (50 mL) and water (50 mL). The organic layer was collected, dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(6-(5-chloro-2-fluorobenzyl)pyridazin-3-yl)-1-methyl-6-oxo-1,4,5,6-tetrahydropyridazine-3-carboxamide (0.0233 g, 0.0641 mmol, 10%) as a white solid. $^1$H NMR (400 MHz, Dimethylsulfoxide-d$_6$) δ 10.42 (s, 1H), 8.25 (d, J=9.0 Hz, 1H), 7.64 (d, J=9.0 Hz, 1H), 7.47-7.49 (m, 1H), 7.37-7.40 (m, 1H), 7.24-7.28 (m, 1H), 4.30 (s, 2H), 3.38 (s, 3H), 2.86 (t, J=8.5 Hz, 1H), 2.52-2.55 (m, 2H); LCMS (ESI) m/z: 376.0 [M+H]$^+$.

Example 178. Preparation of 1-cyclopropyl-N-{6-[(3-fluorophenyl)methyl]pyridazin-3-yl}-6-oxo-1,6-dihydropyridazine-3-carboxamide (178)

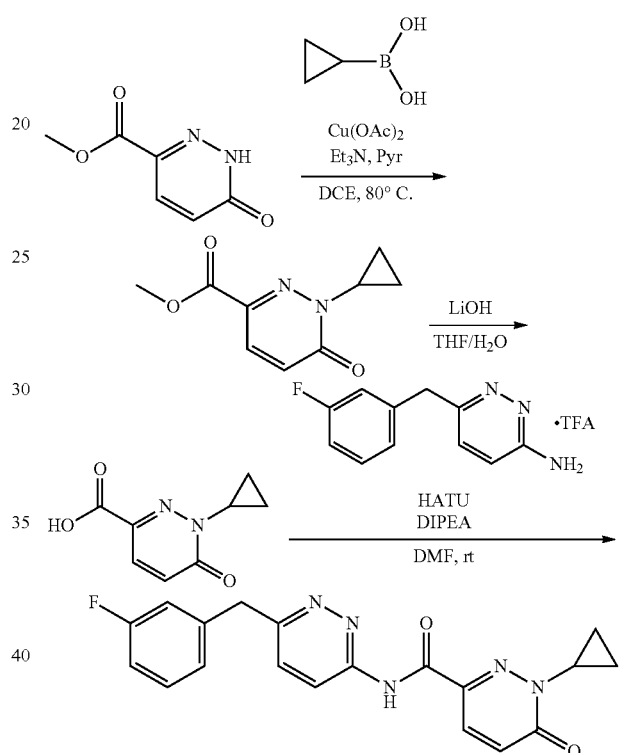

Step 1: Preparation of methyl 1-cyclopropyl-6-oxo-1,6-dihydropyridazine-3-carboxylate

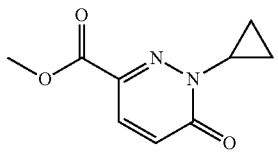

Combined methyl 6-oxo-1,6-dihydropyridazine-3-carboxylate (0.400 g, 2.59 mmol) with cyclopropylboronic acid (0.444 g, 5.18 mmol) and copper(II) acetate (0.940 g, 5.18 mmol) and suspended in 1,2-dichloroethane (8.63 mL). Added triethylamine (1.43 mL, 10.3 mmol) and pyridine (1.04 mL, 12.9 mmol). The reaction was degassed by cycling with vacuum and nitrogen for 3 cycles. Stirred 16 h at 80° C. Cooled to room temperature and quenched with saturated aqueous ammonium chloride (15 mL). Extracted mixture with ethyl acetate (3×15 mL). The combined organic layers were dried over sodium sulfate, filtered, and concentrated. Purified reaction by column chromatography (eluting with 0-100% ethyl acetate/hexanes through 24 g of silica gel) to give methyl 1-cyclopropyl-6-oxo-1,6-dihydropyridazine-3-carboxylate as a yellow solid (160 mg, 0.824 mmol, 32%). ¹H NMR (300 MHz, Chloroform-d) δ 8.01 (d, J=9.7 Hz, 1H), 7.13 (d, J=9.7 Hz, 1H), 4.36 (td, J=7.5, 3.7 Hz, 1H), 4.14 (s, 3H), 1.48-1.36 (m, 2H), 1.36-1.22 (m, 2H)

Step 2: Preparation of 1-cyclopropyl-6-oxo-1,6-dihydropyridazine-3-carboxylic acid

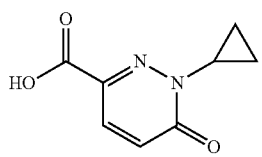 [SMILES: O=C(O)c1ccc(=O)n(C2CC2)n1]

Dissolved methyl 1-cyclopropyl-6-oxo-1,6-dihydropyridazine-3-carboxylate (0.160 g, 0.8239 mmol) in tetrahydrofuran (2.0 mL) and added lithium hydrate hydroxide (0.103 g, 2.47 mmol) and water (1.0 mL). Stirred 16 h at rt. Acidified with 10% hydrochloric acid solution (5 mL) and extracted with ethyl acetate (15 mL), then washed with brine (10 mL). The combined organic layers were dried over sodium sulfate, filtered, and concentrated to give 1-cyclopropyl-6-oxo-1,6-dihydropyridazine-3-carboxylic acid (83 mg, 0.461 mmol, 56%) as a yellow solid ¹H NMR (300 MHz, Chloroform-d) δ 7.90 (d, J=9.6 Hz, 1H), 7.03 (d, J=9.7 Hz, 1H), 4.30-4.14 (m, 1H), 1.27-1.00 (m, 4H).

Step 3: Preparation of 1-cyclopropyl-N-{6-[(3-fluorophenyl)methyl]pyridazin-3-yl}-6-oxo-1,6-dihydropyridazine-3-carboxamide

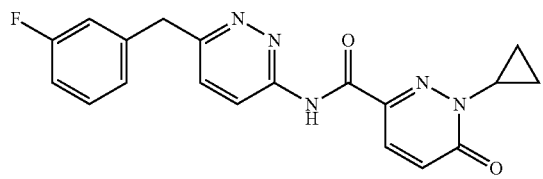 [SMILES: O=C(Nc1ccc(Cc2cccc(F)c2)nn1)c1ccc(=O)n(C2CC2)n1]

Dissolved 6-[(3-fluorophenyl)methyl]pyridazin-3-amine; trifluoroacetic acid (0.146 g, 0.4606 mmol) in N,N'-dimethylformamide (1.53 mL) and added 1-cyclopropyl-6-oxo-1,6-dihydropyridazine-3-carboxylic acid (0.083 g, 0.4606 mmol) and [bis(dimethylamino)methylidene]({3H-[1,2,3]triazolo[4,5-b]pyridin-3-yl})oxidanium; tetrafluoroboranuide (0.148 g, 0.4606 mmol). Carefully added ethylbis(propan-2-yl)amine (239 µL, 1.38 mmol) and stirred at room temperature 16 h. Diluted with ethyl acetate (15 mL) and washed 3 times with water (10 mL), then once with brine (15 mL). The combined organic layers were dried over sodium sulfate, filtered, and concentrated. Purified reaction by column chromatography (eluting with 0-100% ethyl acetate/hexanes through 24 g of silica gel) to give 1-cyclopropyl-N-{6-[(3-fluorophenyl)methyl]pyridazin-3-yl}-6-oxo-1,6-dihydropyridazine-3-carboxamide as a beige, waxy solid (40 mg, 0.109 mmol, 24%). ¹H NMR (300 MHz, Chloroform-d) δ 9.73 (s, 1H), 8.47 (d, J=9.1 Hz, 1H), 8.01 (d, J=9.7 Hz, 1H), 7.36 (d, J=9.2 Hz, 1H), 7.34-7.26 (m, 2H), 7.16-6.90 (m, 4H), 4.34 (s, 2H), 4.16 (d, J=7.2 Hz, 1H), 1.31-1.08 (m, 4H); LCMS (ESI) m/z: 366.3 [M+H]⁺.

Example 179. Preparation of N-(6-(3-chloro-4-fluorobenzyl)pyridazin-3-yl)-1-methyl-6-oxo-1,4,5,6-tetrahydropyridazine-3-carboxamide (179)

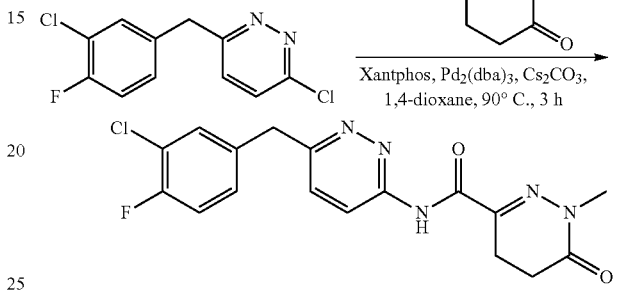

Step 1: Preparation of N-(6-(3-chloro-4-fluorobenzyl)pyridazin-3-yl)-1-methyl-6-oxo-1,4,5,6-tetrahydropyridazine-3-carboxamide

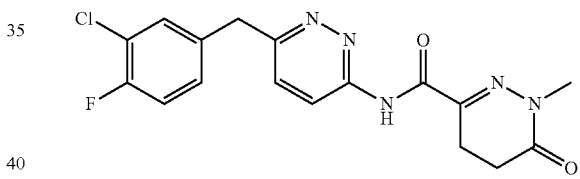

A mixture of 3-chloro-6-(3-chloro-4-fluorobenzyl)pyridazine (103 mg, 0.40 mmol), 1-methyl-6-oxo-1,6-dihydropyridazine-3-carboxamide (122 mg, 0.80 mmol), tris(dibenzylideneacetone)dipalladium(0) (35 mg, 0.04 mmol), 4,5-bis(diphenylphosphino)-9,9-dimethylxanthene (35 mg, 0.06 mmol) and cesium carbonate (261 mg, 0.80 mmol) in dry 1,4-dioxane (4 mL) was stirred at 90° C. for 3 h under argon. The reaction mixture was cooled to room temperature and the mixture was diluted with ethyl acetate (50 mL). The combined organic layers were washed with water (25 mL) and brine (25 mL), dried over sodium sulfate, filtered and concentrated. The residue was first purified by column chromatography (silica gel, ethyl acetate/petroleum ether=2/1) and by prep-HPLC (Sunfire prep C18 10 µm OBD 19*250 mm; mobile phase: [water (0.05% trifluoroacetic acid)-acetonitrile]; B %: 60%-88%, 15 minutes) to offer N-(6-(3-chloro-4-fluorobenzyl)pyridazin-3-yl)-1-methyl-6-oxo-1,4,5,6-tetrahydropyridazine-3-carboxamide (36 mg, 0.096 mmol, 24.0%) as a white solid. ¹H NMR (500 MHz, Dimethylsulfoxide-d₆) δ 10.43 (s, 1H), 8.25 (d, J=9.1 Hz, 1H), 7.67 (d, J=9.1 Hz, 1H), 7.56 (dd, J=7.2, 2.0 Hz, 1H), 7.33 (dd, J=21.6, 5.7 Hz, 2H), 4.27 (s, 2H), 3.38 (s, 3H), 2.85 (t, J=8.5 Hz, 2H), 2.54 (d, J=8.5 Hz, 2H); LCMS (ESI) m/z: 376.0 [M+H]⁺.

Example 180. Preparation of N-(6-(3-chloro-4-fluorobenzyl)pyridazin-3-yl)-1-methyl-6-oxo-1,6-dihydropyridazine-3-carboxamide (180)

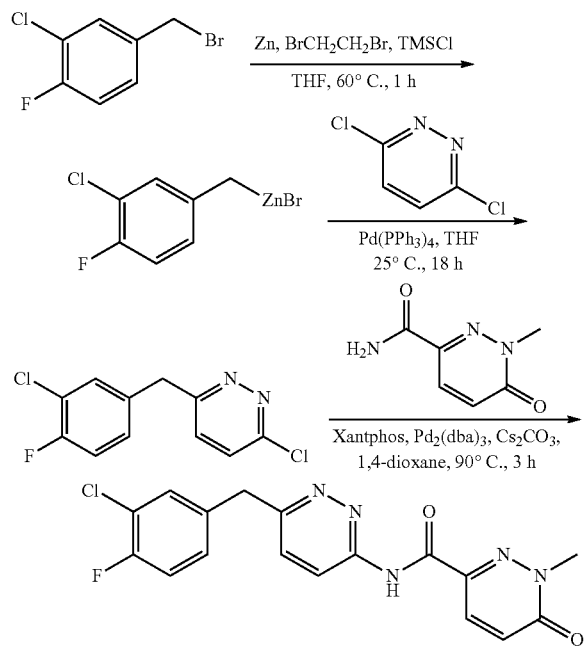

Step 1: Preparation of 3-chloro-6-(3-chloro-4-fluorobenzyl)pyridazine

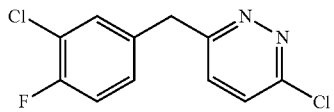 [SMILES: Fc1ccc(Cc2ccc(Cl)nn2)cc1Cl]

A 2-neck flask equipped with a magnetic stirring bar and a condenser was charged with lithium chloride (535 mg, 12.75 mmol). The flask was heated with a heat gun (400° C.) for 10 minutes under high vacuum. After cooling to 25° C., the flask was flushed with argon (3×) before activated zinc dust (1815 mg, 12.75 mmol) was added followed by tetrahydrofuran (10 mL). A solution of 1,2-dibromethane (0.14 mL, 1.57 mmol) in tetrahydrofuran (1 mL) was added dropwise over 5 minutes. The reaction mixture was heated to 60° C. for 5 minutes. After cooling to 25° C., a solution of trimethylsilyl chloride (0.2 mL, 2.32 mmol) in tetrahydrofuran (1 mL) was added dropwise over 5 minutes. The reaction solution was heated to 60° C. for 30 minutes before a solution of 4-(bromomethyl)-2-chloro-1-fluorobenzene (2.17 g, 9.80 mmol) in tetrahydrofuran (3 mL) was added dropwise over 20 minutes. The resulting solution was stirred at 60° C. for 1 h before it was cooled to room temperature and added dropwise to a solution of 3,6-dichloropyridazine (906 mg, 6.13 mmol) and tetraphenyl palladium (304 mg, 0.29 mmol) in tetrahydrofuran (10 mL) over 5 minutes. The reaction mixture was stirred at 23° C. for 18 h. The reaction mixture was quenched with aqueous saturated ammonium chloride (25 mL). The aqueous layer was extracted with ethyl acetate (25 mL×3). The combined organic layers were washed brine (25 mL), dried over sodium sulfate, filtered and concentrated. The residue was purified by column chromatography (silica gel, ethyl acetate/petroleum ether=1/1) to offer 3-chloro-6-(3-chloro-4-fluorobenzyl)pyridazine (650 mg, 2.54 mmol, 41.4%) as a yellow solid. LCMS (ESI) m/z: 257.0 [M+H]$^+$.

Step 2: Preparation of N-(6-(3-chloro-4-fluorobenzyl)pyridazin-3-yl)-1-methyl-6-oxo-1,6-dihydropyridazine-3-carboxamide

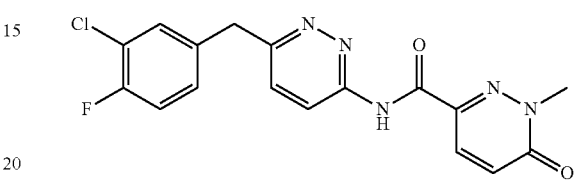

A mixture of 3-chloro-6-(3-chloro-4-fluorobenzyl)pyridazine (103 mg, 0.40 mmol), 1-methyl-6-oxo-1,6-dihydropyridazine-3-carboxamide (122 mg, 0.80 mmol), tris(dibenzylideneacetone)dipalladium(0) (35 mg, 0.04 mmol), 4,5-bis(diphenylphosphino)-9,9-dimethylxanthene (35 mg, 0.06 mmol) and cesium carbonate (261 mg, 0.80 mmol) in dry 1,4-dioxane (4 mL) was stirred at 90° C. for 3 h under argon. The reaction mixture was cooled to room temperature and diluted with ethyl acetate (50 mL). The combined organic layers were washed with water (25 mL) and brine (25 mL), dried over sodium sulfate, filtered and concentrated. The residue was first purified by column chromatography (silica gel, ethyl acetate/petroleum ether=2/1) and by prep-HPLC (Sunfire prep C18 10 μm OBD 19*250 mm; mobile phase: [water (0.05% trifluoroacetic acid)-acetonitrile]; B %: 60%-88%, 15 minutes) to offer N-(6-(3-chloro-4-fluorobenzyl)pyridazin-3-yl)-1-methyl-6-oxo-1,6-dihydropyridazine-3-carboxamide (35 mg, 0.094 mmol, 23.5%) as a white solid. $^1$H NMR (500 MHz, Dimethylsulfoxide-d$_6$) δ 10.89 (s, 1H), 8.30 (d, J=9.1 Hz, 1H), 7.95 (d, J=9.7 Hz, 1H), 7.70 (d, J=9.1 Hz, 1H), 7.57 (dd, J=7.2, 1.8 Hz, 1H), 7.44-7.25 (m, 2H), 7.09 (d, J=9.7 Hz, 1H), 4.29 (s, 2H), 3.81 (s, 3H); LCMS (ESI) m/z: 374.1 [M+H]$^+$.

Example 181. Preparation of N-(6-((3-chlorophenoxy)methyl)pyridazin-3-yl)-1-methyl-6-oxo-1,4,5,6-tetrahydropyridazine-3-carboxamide (181)

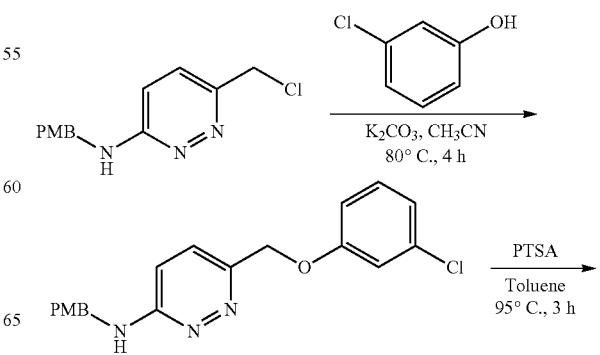

-continued

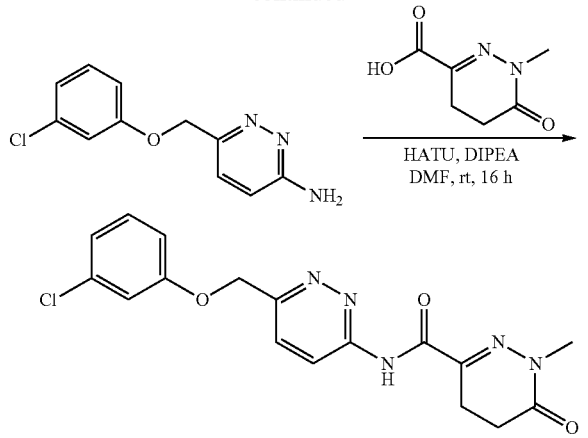

Step 1: Preparation of 6-((3-chlorophenoxy)methyl)-N-(4-methoxybenzyl)pyridazin-3-amine

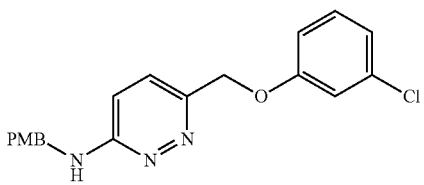

A mixture of 6-(chloromethyl)-N-(4-methoxybenzyl)pyridazin-3-amine (0.58 g, 2.2 mmol), 3-chlorophenol (0.28 g, 2.2 mmol) and potassium carbonate (0.6 g, 4.4 mmol) in acetonitrile (45 mL) was stirred at 80° C. for 4 h. The reaction mixture was concentrated, and the residue was diluted with ethyl acetate/water (20 mL/20 mL) mixture and extracted with ethyl acetate (25 mL×2). The combined organic layers were washed with brine (25 mL), dried over sodium sulfate, filtered and concentrated. The crude material was purified by Combi-Flash (Biotage, 40 g silica gel, eluted with methanol/ethyl acetate=1/20 in petroleum ether from 40% to 50%) to give 6-((3-chlorophenoxy)methyl)-N-(4-methoxybenzyl)pyridazin-3-amine (0.33 g, 0.93 mmol, 42.3%) as a white solid. LCMS (ESI) m/z: 356.1 [M+H]$^+$.

Step 2: Preparation of 6-((3-chlorophenoxy)methyl)pyridazin-3-amine

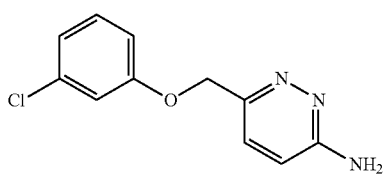 [SMILES: Nc1ccc(COc2cccc(Cl)c2)nn1]

To a solution of 6-((3-chlorophenoxy)methyl)-N-(4-methoxybenzyl)pyridazin-3-amine (0.3 g, 0.84 mmol) in dry toluene (20 mL) was added p-toluenesulfonic acid (0.58 g, 3.38 mmol) and the reaction was stirred at 95° C. for 3 h. The reaction mixture was concentrated. The residue was diluted with ethyl acetate/water (20 mL/20 mL), neutralized with sodium bicarbonate aqueous solution and extracted with ethyl acetate (25 mL) twice. The combined organic layers were washed with brine (25 mL), dried over sodium sulfate, filtered and concentrated. The crude material was purified by Combi-Flash (Biotage, 25 g silica gel, eluted with methanol/dichloromethane (1:10, containing 0.5% 7N ammonia methanol) in dichloromethane from 40% to 50%) to yield 6-((3-chlorophenoxy)methyl)pyridazin-3-amine (0.15 g, 0.64 mmol, 75.7%) as a white solid. LCMS (ESI) m/z: 236.1 [M+H]$^+$.

Step 3: Preparation of N-(6-((3-chlorophenoxy)methyl)pyridazin-3-yl)-1-methyl-6-oxo-1,4,5,6-tetrahydropyridazine-3-carboxamide

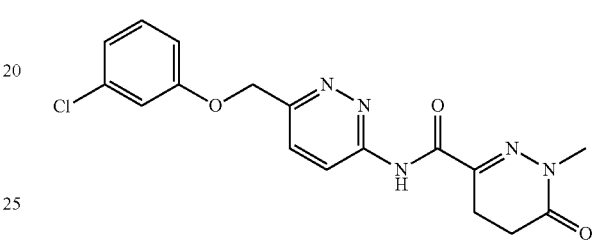

To a solution of 1-methyl-6-oxo-1,4,5,6-tetrahydropyridazine-3-carboxylic acid (0.044 g, 0.28 mmol), 1-[bis(dimethylamino)methylene]-1H-1,2,3-triazolo[4,5-b]pyridinium 3-oxid hexafluorophosphate (0.117 g, 0.31 mmol) in N,N-dimethylformamide (8 mL) at room temperature was added N,N-diisopropylethylamine (0.067 g, 0.52 mmol) dropwise. The reaction was stirred for 20 min and 6-((3-chlorophenoxy)methyl)pyridazin-3-amine (0.060 g, 0.26 mmol) was added in one portion. The reaction mixture was stirred at room temperature for 16 h. The reaction was diluted with ethyl acetate/water (20 mL/20 mL), separated and the aqueous layer was extracted with ethyl acetate (20 mL×2). The combined organic layers were washed with brine (30 mL), dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(6-((3-chlorophenoxy)methyl)pyridazin-3-yl)-1-methyl-6-oxo-1,4,5,6-tetrahydropyridazine-3-carboxamide (0.030 g, 0.08 mmol, 31.5%) as a white solid. $^1$H NMR (500 MHz, Dimethylsulfoxide-d$_6$) δ 10.58 (s, 1H), 8.38 (d, 1H, J=9 Hz), 7.90 (d, 1H, J=9.5 Hz), 7.35 (t, 1H, J=8 Hz), 7.17-7.21 (m, 1H), 7.01-7.08 (m, 2H), 5.40 (s, 2H), 3.39 (s, 3H), 2.87 (t, 2H, J=8.5 Hz), 2.55 (t, 2H, J=8.5 Hz); LCMS (ESI) m/z: 374.1 [M+H]$^+$.

Example 182. Preparation of N-(6-(3-methoxybenzyl)pyridazin-3-yl)-1-methyl-6-oxo-1,4,5,6-tetrahydropyridazine-3-carboxamide (1821

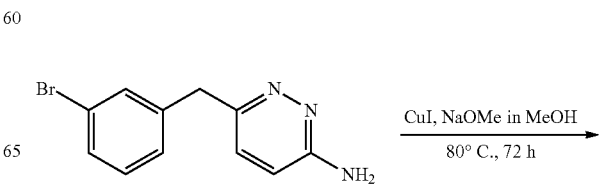

Step 1: Preparation of 6-(3-methoxybenzyl)pyridazin-3-amine

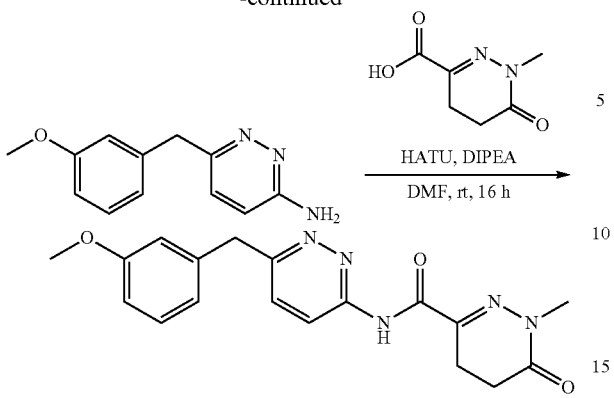

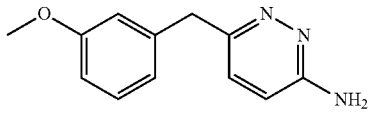 [SMILES: COc1cccc(Cc2ccc(N)nn2)c1]

A mixture of 6-(3-bromobenzyl)pyridazin-3-amine (0.264 g, 1.0 mmol) and copper(I) iodide (0.095 g, 0.5 mmol) in sodium methoxide (5 mL, methanol) was stirred at 80° C. for 72 h in a sealed tube.

Water (30 mL) was added to quench the reaction. The aqueous layer was extracted with ethyl acetate (50 mL×3). The combined organic layers were dried with sodium sulfate, filtered and concentrated. The crude material was purified by Prep-TLC (dichloromethane/ammonia in methanol (7N)=15/1) to give 6-(3-methoxybenzyl)pyridazin-3-amine (0.086 g, 0.60 mmol, 40%) as a white solid. LCMS (ESI) m/z: 216.1 [M+H]+.

Step 2: Preparation of N-(6-(3-methoxybenzyl)pyridazin-3-yl)-1-methyl-6-oxo-1,4,5,6-tetrahydropyridazine-3-carboxamide

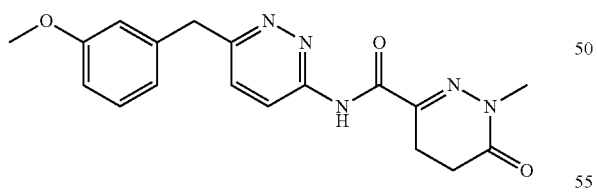

To a solution of 1-methyl-6-oxo-1,4,5,6-tetrahydropyridazine-3-carboxylic acid (0.071 g, 0.45 mmol) and 1-[bis(dimethylamino)methylene]-1H-1,2,3-triazolo[4,5-b]pyridinium 3-oxid hexafluorophosphate (0.171 g, 0.45 mmol) in N,N-dimethylformamide (3 mL) was added N,N-diisopropylethylamine (0.116 g, 0.9 mmol) at room temperature under nitrogen. The mixture was stirred at room temperature for 30 minutes before 6-(3-methoxybenzyl)pyridazin-3-amine (0.064 g, 0.3 mmol) was added. Reaction mixture was stirred at room temperature for 16 h before it was diluted with ethyl acetate (80 mL). The organic layer was washed with brine (40 mL×3). The combined organic layers were dried with sodium sulfate, filtered and concentrated. The crude product was purified by Prep-TLC (dichloromethane/ammonia in methanol (7N)=35/1) to give N-(6-(3-methoxybenzyl)pyridazin-3-yl)-1-methyl-6-oxo-1,4,5,6-tetrahydropyridazine-3-carboxamide (0.0573 g, mmol, 41%) as a white solid. $^1$H NMR (400 MHz, Dimethylsulfoxide-$d_6$) δ 10.42 (s, 1H), 8.23 (d, J=9.0 Hz, 1H), 7.63 (d, J=9.0 Hz, 1H), 7.23 (t, J=8.0 Hz, 1H), 6.88-6.89 (m, 1H), 6.85 (d, J=7.5 Hz, 1H), 6.80 (dd, $J_1$=2.0 Hz, $J_2$=8.0 Hz, 1H), 4.23 (s, 2H), 3.73 (s, 3H), 3.39 (s, 3H), 2.86 (t, J=7.5 Hz, 2H), 2.51-2.56 (m, 2H); LCMS (ESI) m/z: 354.2 [M+H]+.

Example 183. Preparation of N-(6-(3-chlorobenzyl)pyridazin-3-yl)-1-methyl-6-oxo-1,6-dihydropyridine-3-carboxamide (183)

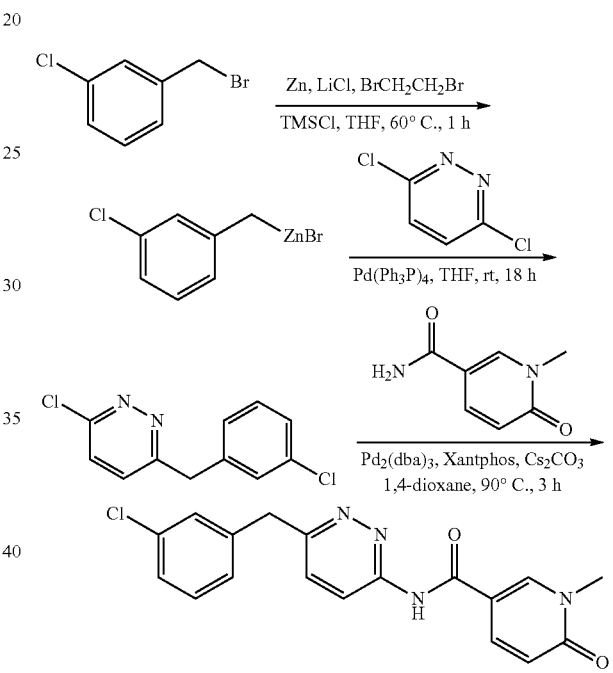

Step 1: Preparation of 3-chloro-6-(3-chlorobenzyl)pyridazine

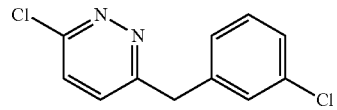 [SMILES: Clc1cccc(Cc2ccc(Cl)nn2)c1]

A 2-neck flask equipped with a magnetic stirring bar and a condenser was charged with lithium chloride (1.07 g, 25.5 mmol). The flask was heated with a heat gun (400° C.) for 10 min under high vacuum. Reaction vessel was cooled to 25° C. and flushed with argon (3×) and activated zinc dust (1.63 g, 25.5 mmol) followed by tetrahydrofuran (20 mL). A solution of 1,2-dibromoethane (0.27 mL, 3.13 mmol) in tetrahydrofuran (2 mL) was added dropwise over 5 min and the reaction mixture was heated to 60° C. Reaction mixture was cooled to room temperature before a solution of trimethylsilyl chloride (0.40 mL, 4.63 mmol) in tetrahydrofuran (2 mL) was added dropwise over 5 min was added and the mixture was heated to 60° C. for 30 minutes before a solution of 1-(bromomethyl)-3-chlorobenzene (4.00 g, 19.6 mmol) in tetrahydrofuran (6 mL) was added over 20 min. The resulting mixture was stirred at 60° C. for 1 h. The mixture was cooled to room temperature, before a solution of 3,6-dichloropyridazine (1.82 g, 12.3 mmol) and tetraphenyl palladium (0.710 g, 0.62 mmol) in tetrahydrofuran (20 mL) was added and stirred at room temperature for 18 h. Reaction mixture was quenched with aqueous saturated solution of ammonium chloride (50 mL) and extracted with ethyl acetate (50 mL×3). The combined organic layers were washed with brine (50 mL), dried over sodium sulfate, filtered and concentrated. The crude residue was purified by column chromatography (silica gel, ethyl acetate/petroleum ether=1/1) to afford 3-chloro-6-(3-chlorobenzyl)pyridazine (1.77 g, 7.44 mmol, 60.5%) as a pale yellow solid. LCMS (ESI) m/z: 239.1 [M+H]$^+$.

Step 2: Preparation of N-(6-(3-chlorobenzyl)pyridazin-3-yl)-1-methyl-6-oxo-1,6-dihydropyridine-3-carboxamide

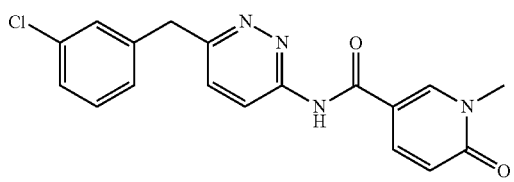

A mixture of 3-chloro-6-(3-chlorobenzyl)pyridazine (0.050 g, 0.21 mmol), 1-methyl-6-oxo-1,6-dihydropyridine-3-carboxamide (0.064 g, 0.42 mmol), tris(dibenzylideneacetone)dipalladium(0) (0.019 g, 0.021 mmol), XantPhos (0.018 g, 0.0315 mmol) and cesium carbonate (0.137 g, 0.42 mmol) in dry 1,4-dioxane (2 mL) was stirred at 90° C. for 3 h under argon. Reaction vessel was cooled to room temperature and diluted with ethyl acetate (50 mL). The organic layer washed with water (25 mL) and brine (25 mL), dried over sodium sulfate, filtered and concentrated. The residue was purified by column chromatography (silica gel, 100% ethyl acetate) to yield N-(6-(3-chlorobenzyl)pyridazin-3-yl)-1-methyl-6-oxo-1,6-dihydropyridine-3-carboxamide (0.020 g, 0.056 mmol, 26.9%) as a white solid. $^1$H NMR (500 MHz, Dimethylsulfoxide-d$_5$) δ 11.16 (s, 1H), 8.72 (s, 1H), 8.26 (d, J=9.1 Hz, 1H), 8.00 (dd, J=9.5, 1.4 Hz, 1H), 7.64 (d, J=9.1 Hz, 1H), 7.43-7.19 (m, 4H), 6.45 (d, J=9.5 Hz, 1H), 4.28 (s, 2H), 3.51 (s, 3H); LCMS (ESI) m/z: 355.1 [M+H]$^+$.

Example 184. Preparation of N-(6-(3-chlorobenzyl)pyridazin-3-yl)-1-ethyl-6-oxo-1,6-dihydropyridine-3-carboxamide (184)

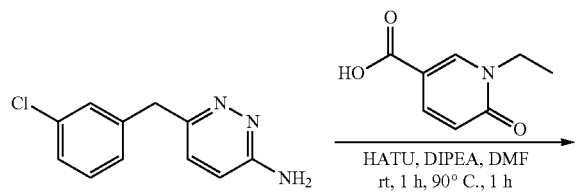

-continued

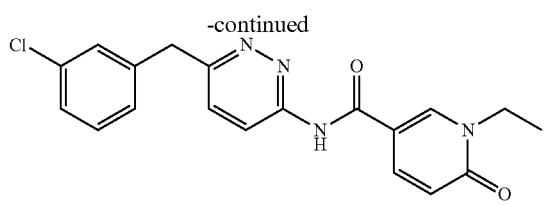

Step 1: Preparation of N-(6-(3-chlorobenzyl)pyridazin-3-yl)-1-ethyl-6-oxo-1,6-dihydropyridine-3-carboxamide

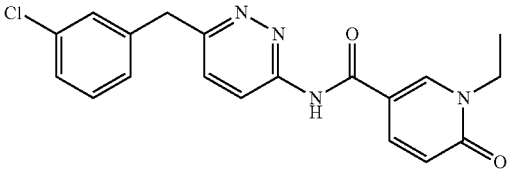 [SMILES: CCn1cc(C(=O)Nc2ccc(Cc3cccc(Cl)c3)nn2)ccc1=O]

A mixture of 6-(3-chlorobenzyl)pyridazin-3-amine (0.066 g, 0.30 mmol), 1-ethyl-6-oxo-1,6-dihydropyridine-3-carboxylic acid (0.066 g, 0.39 mmol), 1-[bis(dimethylamino)methylene]-1H-1,2,3-triazolo[4,5-b]pyridinium 3-oxid hexafluorophosphate (0.150 g, 0.39 mmol) and N,N-diisopropylethylamine (0.120 g, 0.90 mmol) in N,N-dimethylformamide (3 mL) was stirred at room temperature for 1 h and then at 90° C. for 1 h. Reaction mixture was cooled to room temperature and purified directly by prep-HPLC (column: Sunfire prep C18 10 μm OBD 19*250 mm; mobile phase: [water (0.05% trifluoroacetic acid)-acetonitrile]; B %: 60%-88%, 15 minutes) to yield N-(6-(3-chlorobenzyl)pyridazin-3-yl)-1-ethyl-6-oxo-1,6-dihydropyridine-3-carboxamide (0.040 g, 0.11 mmol, 36.2%) as a white solid. $^1$H NMR (500 MHz, Dimethylsulfoxide-d$_6$) 611.23 (s, 1H), 8.70 (d, J=2.5 Hz, 1H), 8.27 (d, J=9.2 Hz, 1H), 7.96 (dd, J=9.5, 2.6 Hz, 1H), 7.64 (d, J=9.2 Hz, 1H), 7.32 (ddd, J=42.1, 18.9, 8.9 Hz, 4H), 6.45 (d, J=9.5 Hz, 1H), 4.28 (s, 2H), 3.99 (q, J=7.1 Hz, 2H), 1.29 (t, J=7.1 Hz, 3H); LCMS (ESI) m/z: 369.1 [M+H]$^+$.

Example 185. Preparation of N-(6-(3-chlorobenzyl)pyridazin-3-yl)-1-ethyl-6-oxo-1,6-dihydropyridazine-3-carboxamide (185)

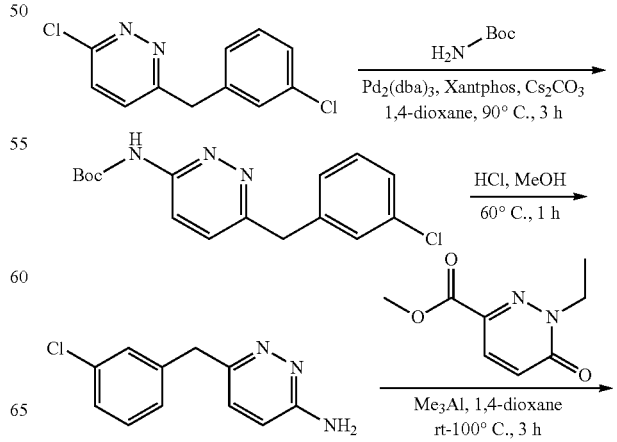

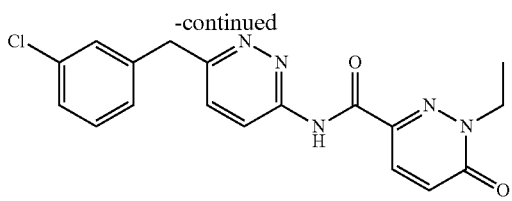

Step 1: Preparation of 6-(3-chlorobenzyl)pyridazin-3-amine

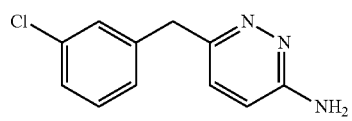 [SMILES: Nc1ccc(Cc2cccc(Cl)c2)nn1]

A mixture of 3-chloro-6-(3-chlorobenzyl)pyridazine (1.50 g, 6.30 mmol), tert-butyl carbamate (1.48 g, 12.6 mmol), tris(dibenzylideneacetone)dipalladium(0) (0.577 g, 0.63 mmol), XantPhos (0.547 g, 0.95 mmol) and cesium carbonate (4.46 g, 12.61 mmol) in dry 1,4-dioxane (50 mL) was stirred at 90° C. for 3 h under argon. Reaction mixture was cooled to room temperature and the mixture was diluted with ethyl acetate (300 mL). The organic layer was washed with water (100 mL) and brine (100 mL), dried over sodium sulfate, filtered and concentrated. The crude residue was taken up in methanol (30 mL) and hydrochloric acid (3 M in methanol, 30 mL) was added. The mixture was stirred at 60° C. for 1 h, then cooled to room temperature and concentrated in vacuo. The crude residue was diluted with ethyl acetate (200 mL) and washed with 0.5 N hydrochloric acid (50 mL×3). The combined aqueous layers were adjusted to pH=8 with solid potassium carbonate and extracted with ethyl acetate (50 mL×3). The combined organics were washed with brine (50 mL), dried over sodium sulfate, filtered and concentrated to afford 6-(3-chlorobenzyl) pyridazin-3-amine (0.750 g, 3.42 mmol, 54.4%) as an off-white solid. LCMS (ESI) m/z: 220.1 [M+H]$^+$.

Step 2: Preparation of N-(6-(3-chlorobenzyl) pyridazin-3-yl)-1-ethyl-6-oxo-1,6-dihydro-pyridazine-3-carboxamide

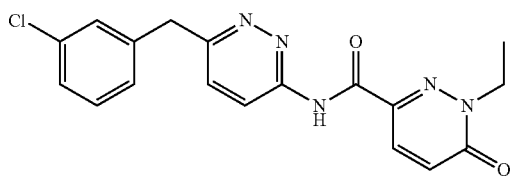 [SMILES: CCn1nc(C(=O)Nc2ccc(Cc3cccc(Cl)c3)nn2)ccc1=O]

To a solution of 6-(3-chlorobenzyl)pyridazin-3-amine (0.180 g, 0.82 mmol) in dry 1,4-dioxane (2 mL) was added trimethylaluminum (0.40 mL, 0.80 mmol, 2 M in toluene) dropwise under argon. The mixture was stirred at room temperature for 1 h before a solution of methyl 1-ethyl-6-oxo-1,6-dihydropyridazine-3-carboxylate (0.036 g, 0.2 mmol) in dry 1,4-dioxane (1 mL) was added dropwise to the above solution. The mixture was stirred at 100° C. for 3 h. After being cooled down to room temperature, the mixture was quenched with 0.5 N hydrochloric acid (25 mL) and ethyl acetate (50 mL). The organic layer was washed with 0.5 N hydrochloric acid (25 mL×2), and brine (25 mL), dried over sodium sulfate, filtered and concentrated. The residue was purified by column chromatography (silica gel, ethyl acetate/petroleum ether=2/1) to give N-(6-(3-chlorobenzyl) pyridazin-3-yl)-1-ethyl-6-oxo-1,6-dihydropyridazine-3-carboxamide (30 mg, 0.081 mmol, 40.7%) as a white solid. $^1$H NMR (500 MHz, Dimethylsulfoxide-d$_6$) δ 10.93 (s, 1H), 8.30 (d, J=9.1 Hz, 1H), 7.93 (d, J=9.7 Hz, 1H), 7.70 (d, J=9.1 Hz, 1H), 7.45-7.20 (m, 4H), 7.08 (d, J=9.7 Hz, 1H), 4.30 (s, 2H), 4.25-4.16 (m, 2H), 1.37 (t, J=7.1 Hz, 3H). LCMS (ESI) m/z: 370.0 [M+H]$^+$.

Example 186. Preparation of N-(6-benzylpyridazin-3-yl)-1-methyl-6-oxo-1,4,5,6-tetrahydropyridazine-3-carboxamide (186)

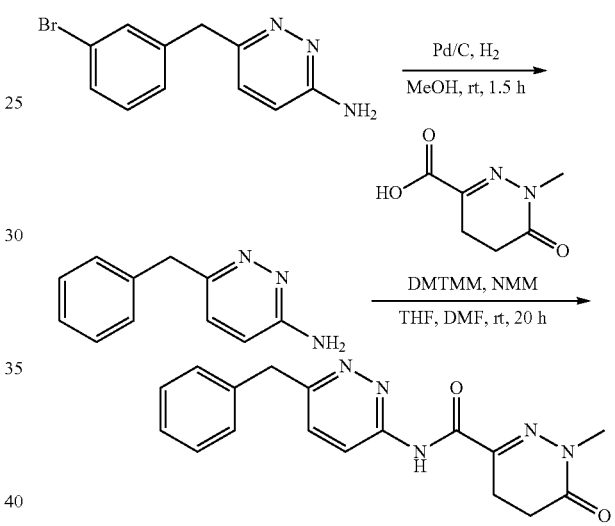

Step 1: Preparation of 6-benzylpyridazin-3-amine

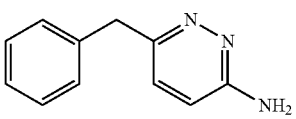 [SMILES: Nc1ccc(Cc2ccccc2)nn1]

To a solution of 6-(3-bromobenzyl)pyridazin-3-amine (0.264 g, 1 mmol) in methanol (30 mL) was added palladium on carbon (0.106 mg, 0.5 mmol) under hydrogen balloon at room temperature. The mixture was stirred at room temperature for 1.5 h before it was filtered through Celite® and washed with methanol (30 mL). The filtrate was concentrated, to give 6-benzylpyridazin-3-amine (0.260 g, crude) as a yellow solid. LCMS (ESI) m/z: 186.2 [M+H]$^+$.

Step 2: Preparation of N-(6-benzylpyridazin-3-yl)-1-methyl-6-oxo-1,4,5,6-tetrahydropyridazine-3-carboxamide

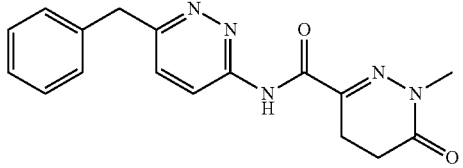 [SMILES: CN1N=C(C(=O)Nc2ccc(Cc3ccccc3)nn2)CCC1=O]

To a solution of 6-benzylpyridazin-3-amine (0.130 g crude, 0.5 mmol), 1-methyl-6-oxo-1,4,5,6-tetrahydropyridazine-3-carboxylic acid (0.094 g, 0.6 mmol) and N-methylmorpholine (0.152 g, 1.5 mmol) in tetrahydrofuran (15 mL) and N,N-dimethylformamide (15 mL) was added 4-(4,6-dimethoxy-1,3,5-triazin-2-yl)-4-methylmorpholinium chloride (0.147 g, 0.5 mmol) at room temperature under argon. The mixture was stirred at room temperature for 20 h before it was diluted with ethyl acetate (100 mL) and washed with brine (50 mL×3). The organic layers were dried with sodium sulfate, filtered and concentrated. The crude product was purified by Prep-TLC (dichloromethane:ammonia in methanol (7 N)=35/1) to give N-(6-benzylpyridazin-3-yl)-1-methyl-6-oxo-1,4,5,6-tetrahydropyridazine-3-carboxamide as a white solid (0.080 g, 0.245 mmol, 49%). $^1$H NMR (500 MHz, Dimethylsulfoxide-$d_6$) δ 10.42 (s, 1H), 8.24 (d, J=9.5 Hz, 1H), 7.63 (d, J=9.5 Hz, 1H), 7.29-7.34 (m, 4H), 7.23 (t, J=7 Hz, 1H), 4.27 (s, 2H), 3.39 (s, 3H), 2.85 (t, J=8.5 Hz, 2H), 2.46-2.56 (m, 2H). LCMS (ESI) m/z: 324.2 [M+H]$^+$.

Example 187. Preparation of N-(6-(3-cyclopropylbenzyl)pyridazin-3-yl)-1-methyl-6-oxo-1,4,5,6-tetrahydropyridazine-3-carboxamide (187)

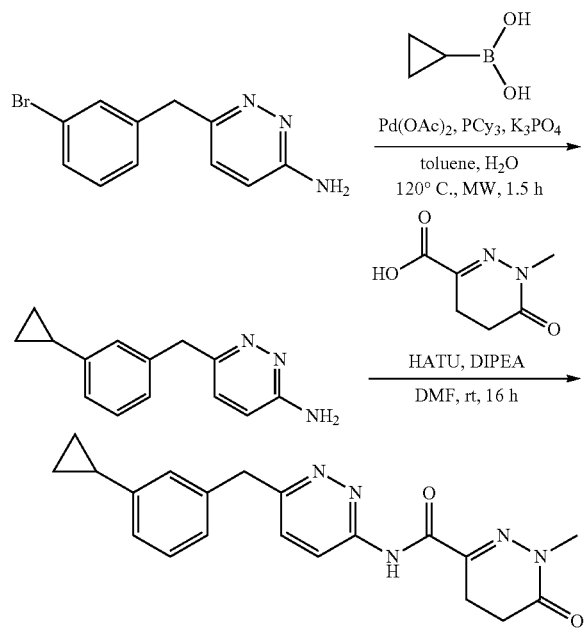

Step 1: Preparation of 6-(3-cyclopropylbenzyl)pyridazin-3-amine

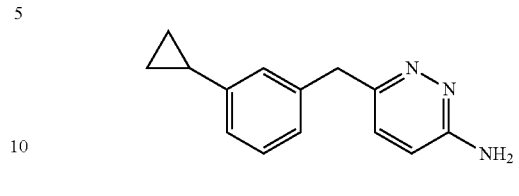

To a solution of 6-(3-bromobenzyl)pyridazin-3-amine (0.264 g, 1 mmol), cyclopropylboronic acid (0.258 g, 3 mmol), tricyclohexylphosphine tetrafluoroborate (0.037 g, 0.1 mmol) and potassium phosphate (0.424 g, 2 mmol) in toluene (8 mL) and water (2 mL) was added palladium(II) acetate (0.023 g, 0.1 mmol) under argon. The mixture was stirred at 120° C. for 1.5 h in the microwave. Reaction was cooled to room temperature and diluted with ethyl acetate (100 mL). The organic layer was washed with water (30 mL×2), dried with sodium sulfate, filtered and concentrated. The crude sample was purified by column chromatography (dichloromethane/ammonia in methanol (7 N)=20/1) to give N-(6-(3-cyclopropylbenzyl)pyridazin-3-yl)-1-methyl-6-oxo-1,4,5,6-tetrahydropyridazine-3-carboxamide as a light-yellow solid (0.110 g, 0.49 mmol, 49%); LCMS (ESI) 226.2 [M+H]$^+$.

Step 2: Preparation of N-(6-(3-cyclopropylbenzyl)pyridazin-3-yl)-1-methyl-6-oxo-1,4,5,6-tetrahydropyridazine-3-carboxamide

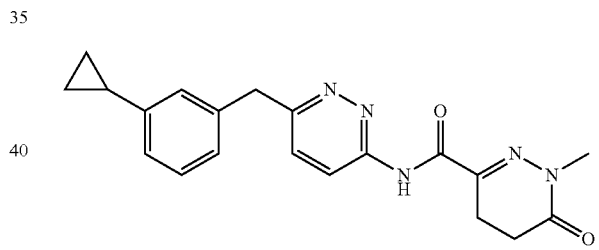

To a solution of 1-methyl-6-oxo-1,4,5,6-tetrahydropyridazine-3-carboxylic acid (0.059 g, 0.375 mmol) and 1-[bis(dimethylamino)methylene]-1H-1,2,3-triazolo[4,5-b]pyridinium 3-oxid hexafluorophosphate (0.143 g, 0.375 mmol) in N,N-dimethylformamide (3 mL) was added N,N-diisopropylethylamine (0.097 g, 0.75 mmol) at room temperature under nitrogen. The mixture was stirred at room temperature for 30 minutes before 6-(3-cyclopropylbenzyl)pyridazin-3-amine (0.057 g, 0.25 mmol) was added. The reaction mixture was stirred at room temperature for 20 h and diluted with ethyl acetate (80 mL). The organic layer was washed with brine (30 mL×3), dried with sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(6-(3-cyclopropylbenzyl)pyridazin-3-yl)-1-methyl-6-oxo-1,4,5,6-tetrahydropyridazine-3-carboxamide (67.1 mg, 0.132 mmol, 53%) as a colorless oil. $^1$H NMR (500 MHz, Dimethylsulfoxide-$d_6$) δ 10.42 (s, 1H), 8.23 (d, J=9 Hz, 1H), 7.61 (d, J=9 Hz, 1H), 7.18 (t, J=7.5 Hz, 1H), 7.02-7.04 (m, 2H), 6.91 (d, J=8.0 Hz, 1H), 4.21 (s, 2H), 3.39 (s, 3H), 2.85

(t, J=8.5 Hz, 2H), 2.51-2.56 (m, 2H), 1.85-1.90 (m, 1H), 0.91-0.94 (m, 2H), 0.62-0.65 (m, 2H). LCMS (ESI) m/z: 364.2 [M+H]⁺.

Example 188. Preparation of N-(6-(3,4-dichlorobenzyl)pyridazin-3-yl)-1-methyl-6-oxo-1,4,5,6-tetrahydropyridazine-3-carboxamide (188)

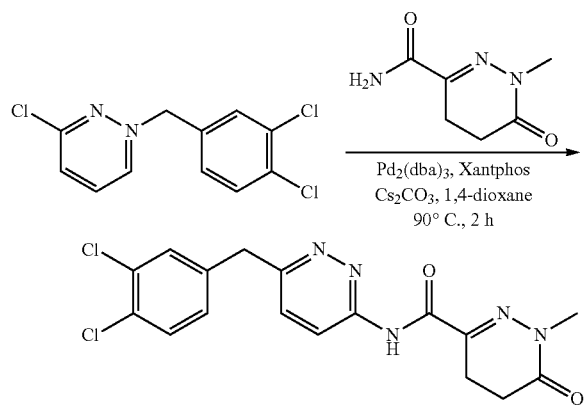

Step 1: Preparation of N-(6-(3,4-dichlorobenzyl)pyridazin-3-yl)-1-methyl-6-oxo-1,4,5,6-tetrahydropyridazine-3-carboxamide

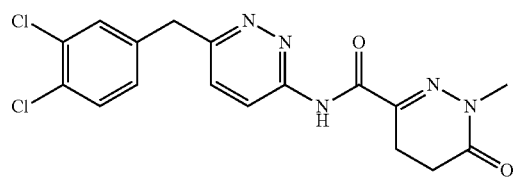 [SMILES: CN1N=C(C(=O)Nc2ccc(Cc3ccc(Cl)c(Cl)c3)nn2)CCC1=O]

A mixture of 3-chloro-6-(3,4-dichlorobenzyl)pyridazine (0.150 g, 0.55 mmol), 1-methyl-6-oxo-1,4,5,6-tetrahydropyridazine-3-carboxamide (0.171 g, 1.10 mmol), tris(dibenzylideneacetone)dipalladium(0) (50 mg, 0.055 mmol), XantPhos (48 mg, 0.083 mmol) and cesium carbonate (0.358 g, 1.10 mmol) in dry 1,4-dioxane (5 mL) was stirred at 90° C. for 2 h under argon. After being cooled to room temperature, the mixture was diluted with ethyl acetate (50 mL) and washed with water (25 mL) and brine (25 mL). The organic layer was dried over sodium sulfate, filtered and concentrated. The residue was purified by column chromatography (ethyl acetate/petroleum ether=2/1) followed by prep-HPLC (column: Sunfire prep C18 10 μm OBD 19*250 mm; mobile phase: [water (0.05% trifluoroacetic acid)-acetonitrile]; B %: 60%-88%, 15 minutes) to give N-(6-(3,4-dichlorobenzyl)pyridazin-3-yl)-1-methyl-6-oxo-1,4,5,6-tetrahydropyridazine-3-carboxamide (45 mg, 0.12 mmol, 21.8%) as a white solid. ¹H NMR (500 MHz, Dimethylsulfoxide-d₆) δ 10.44 (s, 1H), 8.25 (d, J=9.1 Hz, 1H), 7.68 (d, J=9.1 Hz, 1H), 7.60 (dd, J=16.9, 5.1 Hz, 2H), 7.29 (dd, J=8.3, 2.0 Hz, 1H), 4.28 (s, 2H), 3.38 (s, 3H), 2.85 (t, J=8.5 Hz, 2H), 2.54 (t, J=8.5 Hz, 2H); LCMS (ESI) m/z: 392.0 [M+H]⁺.

Example 189. Preparation of 6-(3-chlorobenzyl)-N-(1-methyl-6-oxo-1,6-dihydropyridin-3-yl)pyridazine-3-carboxamide (189)

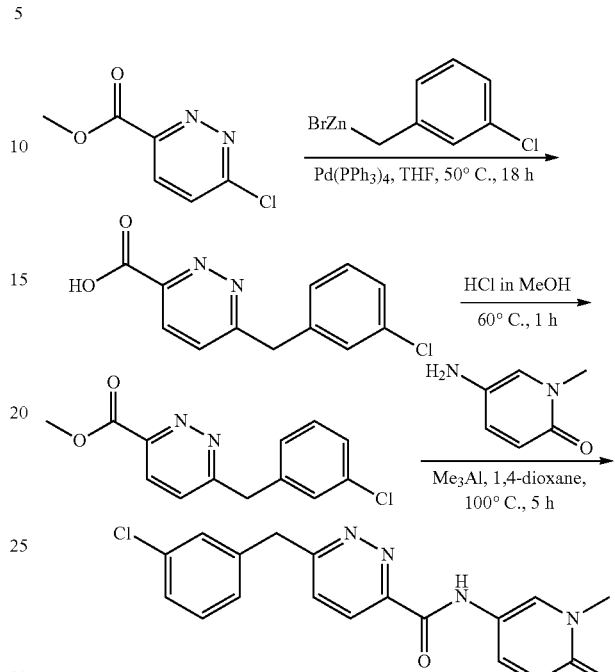

Step 1: Preparation of methyl 6-(3-chlorobenzyl)pyridazine-3-carboxylate

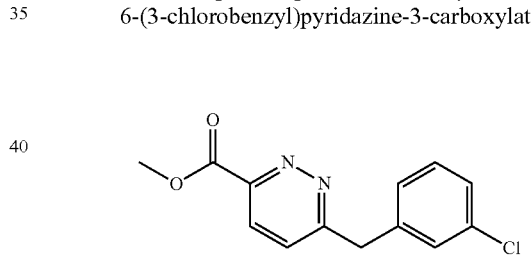

A solution of (3-chlorobenzyl)zinc(II) bromide (60 mL, 39.2 mmol) was added dropwise to a solution of methyl 6-chloropyridazine-3-carboxylate (4.23 g, 24.60 mmol) and tetrakis(triphenylphosphine)palladium(0) (1.42 g, 1.23 mmol) in tetrahydrofuran (40 mL). The reaction mixture was stirred at 50° C. for 18 h before it was quenched with aqueous saturated solution of ammonium chloride (50 mL). The aqueous layer was extracted with ethyl acetate (50 mL×3). The combined organic layers were washed with brine (50 mL), dried over sodium sulfate, filtered and concentrated. The crude residue was taken up in methanol (100 mL) and hydrochloric acid (3.0 M, 10 mL) was added. The mixture was stirred at 60° C. for 1 h. Concentration followed by purification via column chromatography (silica gel, ethyl acetate/petroleum ether=1/1) gives 6-(3-chlorobenzyl)pyridazine-3-carboxylate (1.78 g, 6.79 mmol, 27.6%) as a yellow solid. LCMS (ESI) m/z: 263.0 [M+H]⁺.

Step 2: Preparation of 6-(3-chlorobenzyl)-N-(1-methyl-6-oxo-1,6-di hydropyridin-3-yl)pyridazine-3-carboxamide

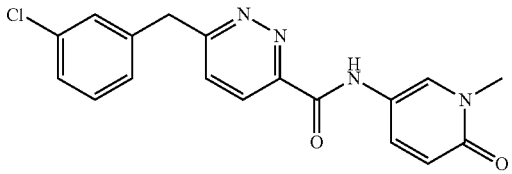 [SMILES: Cn1cc(NC(=O)c2ccc(Cc3cccc(Cl)c3)nn2)ccc1=O]

To a solution of 5-amino-1-methylpyridin-2(1H)-one (0.194 g, 1.56 mmol) in dry 1,4-dioxane (5 mL) was added dropwise trimethylaluminum (0.76 mL, 1.52 mmol, 2 M in toluene) under argon. The mixture was stirred at room temperature for 1 h before a solution of 6-(3-chlorobenzyl)pyridazine-3-carboxylate (0.100 g, 0.38 mmol) in dry 1,4-dioxane (3 mL) was added dropwise. The mixture was stirred at 100° C. for 5 h. Reaction mixture was cooled to room temperature and quenched with 0.5 N hydrochloric acid (25 mL). The aqueous layer was extracted with ethyl acetate (100 mL). The organic layer was washed with 0.5 N hydrochloric acid (25 mL×2), brine (50 mL), dried over sodium sulfate, filtered and concentrated. The residue was purified by column chromatography (silica gel, ethyl acetate/methanol=20/1) and prep-HPLC (column: Sunfire prep C18 10 μm OBD 19*250 mm; mobile phase: [water (0.05% trifluoroacetic acid)-acetonitrile]; B %: 60%-88%, 15 minutes) to give 6-(3-chlorobenzyl)-N-(1-methyl-6-oxo-1,6-dihydropyridin-3-yl)pyridazine-3-carboxamide (75 mg, 0.21 mmol, 55.8%) as a yellow solid. $^1$H NMR (500 MHz, Dimethylsulfoxide-d$_6$) δ 10.92 (s, 1H), 8.36 (d, J=2.7 Hz, 1H), 8.20 (d, J=8.6 Hz, 1H), 7.87 (d, J=8.6 Hz, 1H), 7.80 (dd, J=9.7, 2.8 Hz, 1H), 7.46 (s, 1H), 7.40-7.24 (m, 3H), 6.44 (d, J=9.7 Hz, 1H), 4.44 (s, 2H), 3.46 (s, 3H); LCMS (ESI) m/z: 355.1 [M+H]$^+$.

Example 190. Preparation of 6-(3-chlorobenzyl)-N-(1-methyl-6-oxo-1,4,5,6-tetrahydropyridazin-3-yl)pyridazine-3-carboxamide (190)

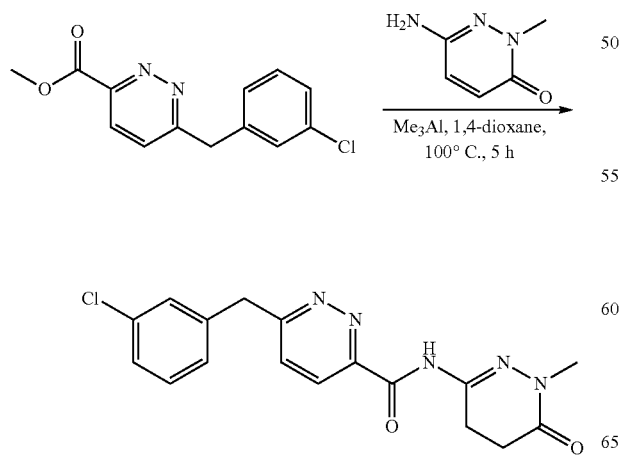

Step 1: Preparation of 6-(3-chlorobenzyl)-N-(1-methyl-6-oxo-1,4,5,6-tetrahydropyridazin-3-yl)pyridazine-3-carboxamide

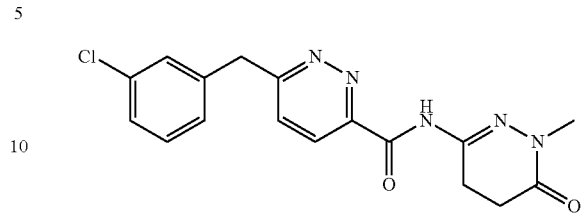

To a solution of 6-amino-2-methyl-4,5-dihydropyridazin-3(2H)-one (0.100 g, 0.78 mmol) in dry 1,4-dioxane (3 mL) was added trimethylaluminum (0.38 mL, 0.76 mmol, 2.0 M in toluene) dropwise under argon. The mixture was stirred at room temperature for 1 h before a solution of 6-(3-chlorobenzyl)pyridazine-3-carboxylate (0.050 g, 0.19 mmol) in dry 1,4-dioxane (1 mL) was added dropwise. The reaction mixture was stirred at 100° C. for 5 h. Reaction vessel was cooled to room temperature and quenched with 0.5 N hydrochloric acid (25 mL). The aqueous layer was extracted with ethyl acetate (100 mL). The organic layer was washed with 0.5 N hydrochloric acid (25 mL×2), brine (50 mL), dried over sodium sulfate, filtered and concentrated. The residue was purified by column chromatography (ethyl acetate/methanol=20/1) and prep-HPLC (column: Sunfire prep C18 10 μm OBD 19*250 mm; mobile phase: [water (0.05% trifluoroacetic acid)-acetonitrile]; B %: 60%-88%, 15 minutes) to give 6-(3-chlorobenzyl)-N-(1-methyl-6-oxo-1,4,5,6-tetrahydropyridazin-3-yl)pyridazine-3-carboxamide (13 mg, 0.036 mmol, 19.2%) as a white solid. $^1$H NMR (500 MHz, Dimethylsulfoxide-d$_6$) δ 10.59 (s, 1H), 8.19 (d, J=8.6 Hz, 1H), 7.88 (d, J=8.7 Hz, 1H), 7.45 (s, 1H), 7.40-7.22 (m, 3H), 4.44 (s, 2H), 3.25-3.03 (m, 5H), 2.49 (d, J=8.7 Hz, 2H); LCMS (ESI) m/z: 358.1 [M+H]$^+$.

Example 191. Preparation of N-(6-(3-bromobenzyl)pyridazin-3-yl)-1-methyl-6-oxo-1,4,5,6-tetrahydropyridazine-3-carboxamide (191)

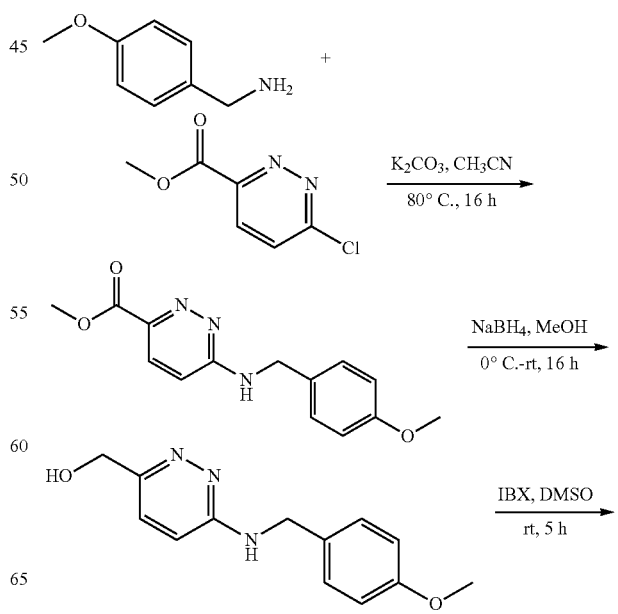

-continued

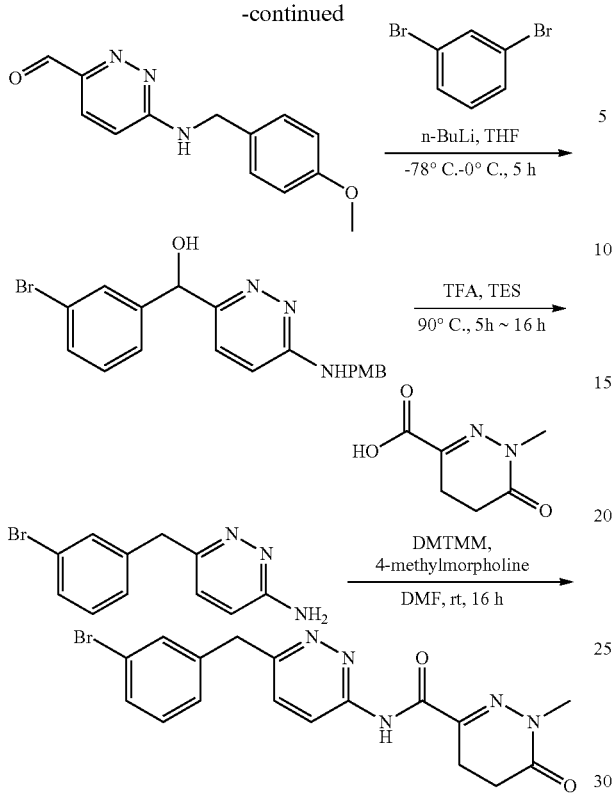

Step 1: Preparation of methyl 6-(4-methoxybenzylamino)pyridazine-3-carboxylate

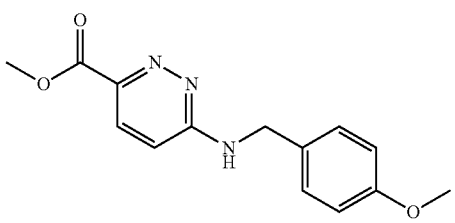

To a solution of (4-methoxyphenyl)methanamine (19.9 g, 145 mmol) in acetonitrile (150 mL) at room temperature was added potassium carbonate (20.0 g, 145 mmol) and methyl 6-chloropyridazine-3-carboxylate (12.5 g, 72.4 mmol). The reaction mixture was stirred at 80° C. for 16 h before it was cooled to room temperature and diluted with water (300 mL). The aqueous layer was extracted with ethyl acetate (200 mL×3). The combined organic layers were washed with brine, dried over sodium sulfate, filtered and concentrated. The crude residue was purified by column chromatography (silica gel, ethyl acetate/petroleum ether=1/3) to afford methyl 6-(4-methoxybenzylamino)pyridazine-3-carboxylate (28.0 g, crude) as a light yellow oil. (LCMS (ESI) m/z: 274.1 [M+H]$^+$. Used in the next step directly without additional purification.

Step 2: Preparation of (6-(4-Methoxybenzylamino)pyridazin-3-yl)methanol

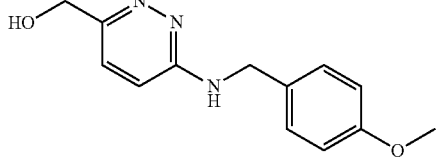

To a solution of methyl 6-(4-methoxybenzylamino) pyridazine-3-carboxylate (9.2 g, 33.7 mmol) in methanol (336 mL) at 0° C. was added sodium borohydride (2.56 g, 67.3 mmol). The mixture was stirred at room temperature for 16 h before it was quenched with ice water (200 mL). The aqueous layer was extracted with dichloromethane (200 mL×4). The combined organic layers were dried over sodium sulfate, filtered and concentrated. The crude sample was purified by column chromatography (silica gel, ethyl acetate/petroleum ether=3/1) to afford (6-(4-methoxybenzylamino)pyridazin-3-yl)methanol (4.3 g, 17.5 mmol, 52.1%) as a white solid. (LCMS (ESI) m/z: 246.1 [M+H]$^+$.

Step 3: Preparation of 6-(4-Methoxybenzylamino)pyridazine-3-carbaldehyde

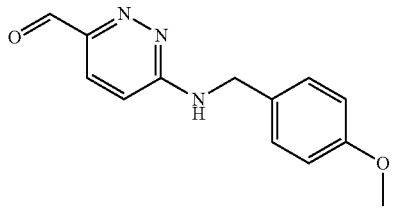 [SMILES: COc1ccc(CNc2ccc(C=O)nn2)cc1]

To a solution of (6-(4-methoxybenzylamino)pyridazin-3-yl)methanol (4.3 g, 17.5 mmol) in dimethylsulfoxide (175 mL) at 0° C. was added 2-iodoxybenzoic acid (7.36 g, 26.3 mmol). The reaction mixture was stirred at room temperature for 5 h before it was quenched with water (300 mL). The aqueous layer was extracted with ethyl acetate (150 mL×3). The combined organic layers were washed with aqueous solution of sodium bicarbonate (100 mL), dried over sodium sulfate, filtered and concentrated. The crude sample was purified by column chromatography (silica gel, ethyl acetate/petroleum ether=2/1) to afford 6-(4-methoxybenzylamino)pyridazine-3-carbaldehyde (4.0 g, 16.4 mmol, 93.8%) as a white solid. LCMS (ESI) m/z: 244.1 [M+H]$^+$.

Step 4: Preparation of (3-bromophenyl)(6-(4-methoxybenzylamino)pyridazin-3-yl)methanol

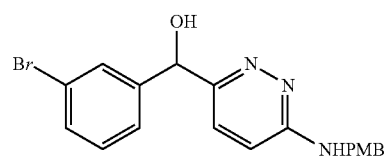

To a solution of 1,3-dibromobenzene (6.11 g, 25.9 mmol) in anhydrous tetrahydrofuran (86 mL) at −78° C., was added n-butyllithium (10.4 mL, 25.9 mmol, 2.5 M in hexanes) under nitrogen. The reaction mixture was stirred at −78° C. for 1 h before 6-(4-methoxybenzylamino)pyridazine-3-carbaldehyde (2.1 g, 8.63 mmol) was added. Reaction was warmed to 0° C. over 5 h before it was quenched with ice water (300 mL). The aqueous layer was extracted with ethyl acetate (100 mL×3). The combined organic layers were washed with brine, dried over sodium sulfate, filtered, and concentrated. The crude sample was purified by column chromatography (silica gel, dichloromethane/methanol=10/1) to afford (3-bromophenyl)(6-(4-methoxybenzylamino)pyridazin-3-yl)methanol (3.8 g, crude) as a white solid. (LCMS (ESI) m/z: 400.0 [M+H]⁺.

Step 5: Preparation of 6-(3-Bromobenzyl)pyridazin-3-amine

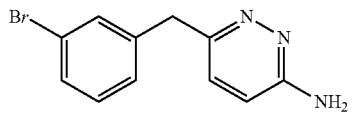

To a solution of (3-bromophenyl)(6-(4-methoxybenzylamino)pyridazin-3-yl)methanol (3.3 g, 8.27 mmol) in acetic acid (82 mL) was added hypophosphorous acid (48%, 9.10 g, 66.2 mmol) and iodine (3.15 g, 12.41 mmol). The mixture was stirred at 100° C. for 32 h before it was cooled to room temperature and concentrated. The residue was diluted with water (200 mL) and aqueous solution of sodium bicarbonate (100 mL). The aqueous layer was extracted with dichloromethane (100 mL×4). The combined organic layers were dried over sodium sulfate, filtered and concentrated. Purification by column chromatography (silica gel, dichloromethane/methanol=10/1) affords 6-(3-bromobenzyl)pyridazin-3-amine (2.6 g, crude) as a white solid. LCMS (ESI) m/z: 264.1 [M+H]⁺.

Step 6: Preparation of N-(6-(3-bromobenzyl)pyridazin-3-yl)-1-methyl-6-oxo-1,4,5,6-tetrahydropyridazine-3-carboxamide

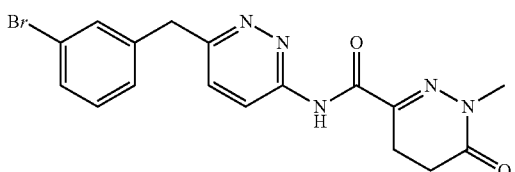

To a solution of 6-(3-bromobenzyl)pyridazin-3-amine (0.100 g, 0.378 mmol) in N,N-dimethylformamide (4 mL) at room temperature was added 1-methyl-6-oxo-1,4,5,6-tetrahydropyridazine-3-carboxylic acid (0.060 g, 0.454 mmol), 4-(4,6-dimethoxy-1,3,5-triazin-2-yl)-4-methylmorpholinium chloride (0.134 g, 0.454 mmol) and 4-methylmorpholine (0.192 g, 1.89 mmol). The reaction mixture was stirred at room temperature for 16 h before it was diluted with water (100 mL). The aqueous layer was extracted with ethyl acetate (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(6-(3-bromobenzyl)pyridazin-3-yl)-1-methyl-6-oxo-1,4,5,6-tetrahydropyridazine-3-carboxamide (30.0 mg, 0.074 mmol, 19.6%) as a white solid. ¹H NMR (400 MHz, Dimethylsulfoxide-d₆) δ 10.44 (s, 1H), 8.25 (d, J=9.2 Hz, 1H), 7.67 (d, J=9.2 Hz, 1H), 7.53 (s, 1H), 7.45-7.42 (m, 1H), 7.31-7.26 (m, 2H), 4.27 (s, 2H), 3.38 (s, 3H), 2.85 (t, J=20.0 Hz, 2H), 2.54 (t, J=20.0 Hz, 2H); LCMS (ESI) m/z: 402.1 [M+H]⁺.

Example 192. Preparation of N-(6-(3-chloro-4-fluorobenzyl)pyridazin-3-yl)-1-methyl-6-oxo-1,4,5,6-tetrahydropyridazine-3-carboxamide (192)

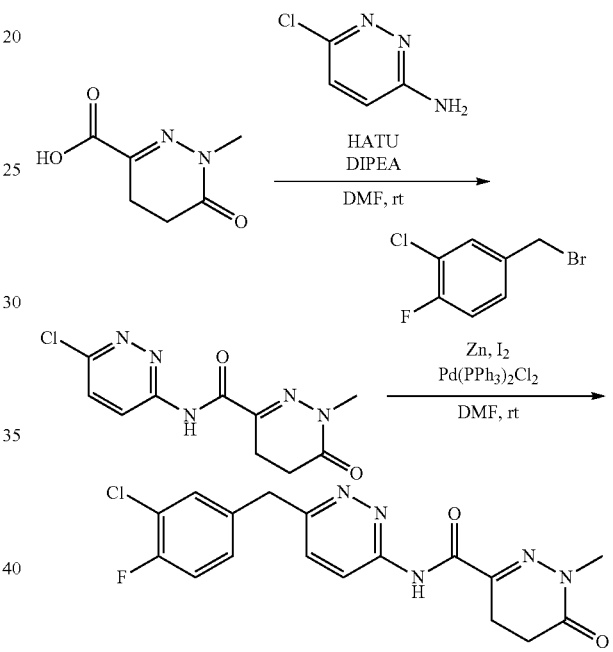

Step 1: Preparation of N-(6-chloropyridazin-3-yl)-1-methyl-6-oxo-1,4,5,6-tetrahydropyridazine-3-carboxamide

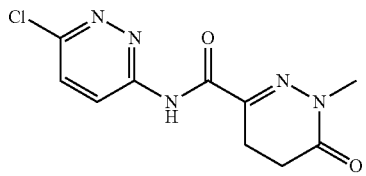 [SMILES: CN1N=C(C(=O)Nc2ccc(Cl)nn2)CCC1=O]

In a 40 mL reaction vial, 1-methyl-6-oxo-1,4,5,6-tetrahydropyridazine-3-carboxylic acid (0.5 g, 3.20 mmol) was combined with 6-chloropyridazin-3-amine (0.414 g, 3.20 mmol) and 2-(3H-[1,2,3]triazolo[4,5-b]pyridin-3-yl)-1,1,3,3-tetramethyluronium tetrafluoroborate (1.03 g, 3.20 mmol). To the vial N,N′-dimethylformamide (16.0 mL) was added followed by N-N-N,N-diisopropylethyl amine (0.835 mL, 4.80 mmol). The reaction is stirred 16 h at room temperature.

The reaction is diluted with ethyl acetate (25 mL) and washed 3 times with water (10 mL), then once with brine (15 mL). The mixture is dried over sodium sulfate, filtered, and concentrated. Purified reaction by column chromatography (eluting with 0-100% ethyl acetate/hexanes through 24 g of silica gel) to give N-(6-chloropyridazin-3-yl)-1-methyl-6-oxo-1,4,5,6-tetrahydropyridazine-3-carboxamide (381 mg, 1.42 mmol, 44%) as a yellow solid. ¹H NMR (300 MHz, Chloroform-d) δ 9.84 (s, 1H), 8.55 (d, J=9.3 Hz, 1H), 7.56 (dd, J=9.3, 0.7 Hz, 1H), 3.51 (s, 3H), 3.09-2.93 (m, 2H), 2.63 (t, J=8.6 Hz, 2H).

Step 2: Preparation of N-(6-(3-chloro-4-fluorobenzyl)pyridazin-3-yl)-1-methyl-6-oxo-1,4,5,6-tetrahydropyridazine-3-carboxamide

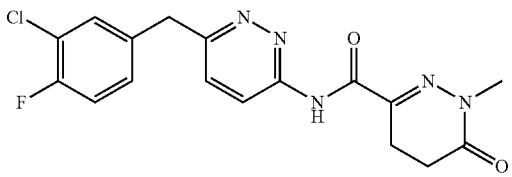

In a 40 mL reaction vial, suspended bis(triphenylphosphine)palladium(II) dichloride (0.050 mg, 0.071 mmol) in N,N'-dimethylformamide (5.0 mL). The reaction was degassed by cycling with vacuum and nitrogen gas for 3 cycles. Added iodine (0.018 g, 0.071 mmol) and stirred at room temperature for 5 min. Added 4-(bromomethyl)-2-chloro-1-fluorobenzene (191 µL, 1.42 mmol) and stirred at 80° C. for 3 h. Cooled to room temperature and added zinc dust (0.185 g, 2.84 mmol) and N-(6-chloropyridazin-3-yl)-1-methyl-6-oxo-1,4,5,6-tetrahydropyridazine-3-carboxamide (0.381 g, 1.42 mmol) then stirred 16 h at room temperature. Diluted with ethyl acetate (15 mL) and washed with water (10 mL×3), then with brine (10 mL). The combined organic layers were dried over sodium sulfate, filtered, and concentrated. Purified by column chromatography (eluting with 0-100% ethyl acetate/hexanes through 24 g of silica gel) to give N-(6-(3-chloro-4-fluorobenzyl)pyridazin-3-yl)-1-methyl-6-oxo-1,4,5,6-tetrahydropyridazine-3-carboxamide as a white solid (59 mg, 0.157 mmol, 11%). ¹H NMR (300 MHz, Chloroform-d) δ 9.79 (s, 1H), 8.44 (d, J=9.2 Hz, 1H), 7.40-7.25 (m, 3H), 7.25-7.04 (m, 2H), 4.28 (s, 2H), 3.51 (s, 3H), 2.98 (t, J=8.6 Hz, 2H), 2.62 (t, J=8.5 Hz, 2H); LCMS (ESI) m/z: 376.206 [M+H]⁺.

Example 193. Preparation of N-(6-(3-fluorobenzyl)pyridazin-3-yl)-1-methyl-6-oxo-1,4,5,6-tetrahydropyridazine-3-carboxamide (193)

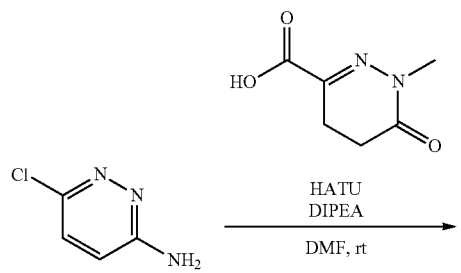

Step 1: Preparation of N-(6-chloropyridazin-3-yl)-1-methyl-6-oxo-1,4,5,6-tetrahydropyridazine-3-carboxamide

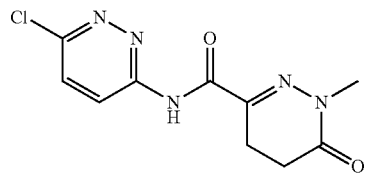 [SMILES: CN1N=C(C(=O)Nc2ccc(Cl)nn2)CCC1=O]

In a 40 mL reaction vial, 1-methyl-6-oxo-1,4,5,6-tetrahydropyridazine-3-carboxylic acid (0.5 g, 3.20 mmol) was combined with 6-chloropyridazin-3-amine (0.414 g, 3.20 mmol) and 2-(3H-[1,2,3]triazolo[4,5-b]pyridin-3-yl)-1,1,3,3-tetramethyluronium tetrafluoroborate (1.03 g, 3.20 mmol). To the vial N,N'-dimethylformamide (16.0 mL) was added followed by N-N-N,N-diisopropylethyl amine (835 µL, 4.80 mmol). The reaction is stirred 16 h at room temperature. The reaction is diluted with ethyl acetate (20 mL) and washed with water (10 mL×3), then once with brine (10 mL). The mixture is dried over sodium sulfate, filtered, and concentrated. Purified reaction by column chromatography (eluting with 0-100% ethyl acetate/hexanes through 24 g of silica gel) to give of N-(6-chloropyridazin-3-yl)-1-methyl-6-oxo-1,4,5,6-tetrahydropyridazine-3-carboxamide as a yellow solid (381 mg, 1.42 mmol, 44%). ¹H NMR (300 MHz, Chloroform-d) δ 9.84 (s, 1H), 8.55 (d, J=9.3 Hz, 1H), 7.56 (dd, J=9.3, 0.7 Hz, 1H), 3.51 (s, 3H), 3.09-2.93 (m, 2H), 2.63 (t, J=8.6 Hz, 2H).

Step 2: Preparation of N-(6-(3-fluorobenzyl)pyridazin-3-yl)-1-methyl-6-oxo-1,4,5,6-tetrahydropyridazine-3-carboxamide

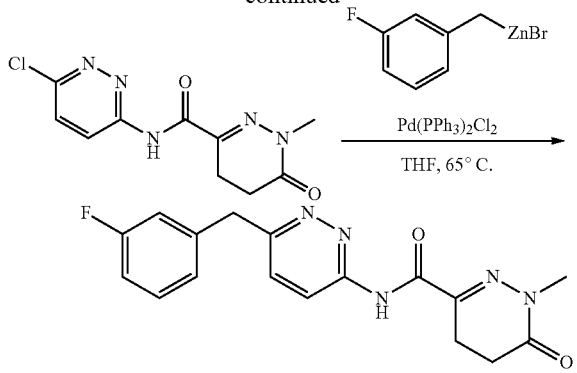

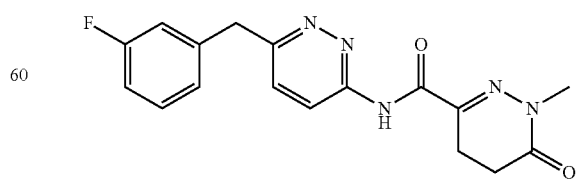

Suspended N-(6-chloropyridazin-3-yl)-1-methyl-6-oxo-1,4,5,6-tetrahydropyridazine-3-carboxamide (0.381 g, 1.42 mmol) in tetrahydrofuran (8.0 mL) and added bis(triphenylphosphine)palladium(II) dichloride (0.050 mg, 0.07100 mmol). The reaction was degassed by cycling with vacuum and nitrogen gas for 3 cycles. Slowly added 3-Fluorobenzylzinc chloride (0.5M in tetrahydrofuran, 8.52 mL, 4.26 mmol) and stirred 16 h at 65° C. Cooled to room temperature and quenched with saturated aqueous ammonium chloride (20 mL). Diluted with ethyl acetate (20 mL), then washed with water (10 mL), then brine (10 mL). The combined organic layers were dried over sodium sulfate, filtered, and concentrated. Purified reaction by column chromatography (eluting with 0-100% ethyl acetate/hexanes through 24 g of silica gel. Purification was repeated twice to obtain clean product. Isolated N-(6-(3-fluorobenzyl)pyridazin-3-yl)-1-methyl-6-oxo-1,4,5,6-tetrahydropyridazine-3-carboxamide as a white solid (85 mg, 0.249 mmol, 18%). $^1$H NMR (300 MHz, Chloroform-d) δ 9.79 (s, 1H), 8.42 (d, J=9.2 Hz, 1H), 7.39-7.27 (m, 3H), 7.07 (d, J=7.6 Hz, 1H), 6.98 (d, J=10.0 Hz, 2H), 4.33 (s, 2H), 3.51 (s, 3H), 2.98 (t, J=8.6 Hz, 2H), 2.62 (t, J=8.5 Hz, 2H); LCMS (ESI) m/z: 342.2 [M+H]$^+$.

Example 194. Preparation of 1-methyl-6-oxo-N-(6-(3-(trifluoromethyl)benzyl)pyridazin-3-yl)-1,4,5,6-tetrahydropyridazine-3-carboxamide (194)

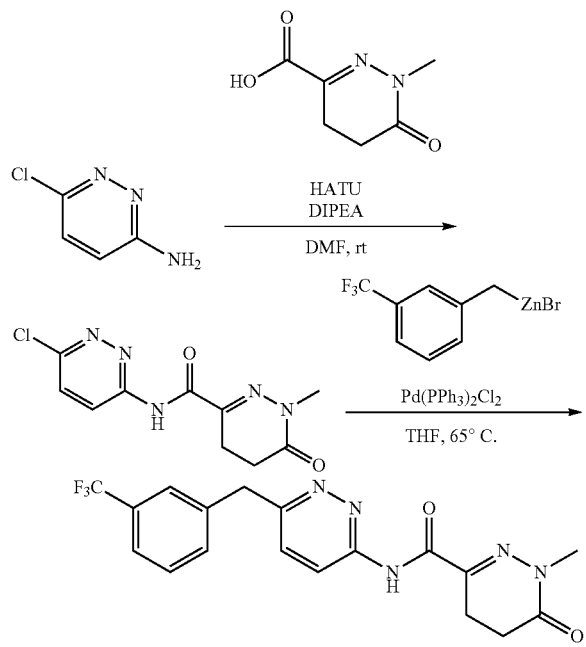

Step 1: Preparation of N-(6-chloropyridazin-3-yl)-1-methyl-6-oxo-1,4,5,6-tetrahydropyridazine-3-carboxamide

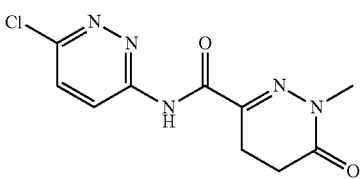 [SMILES: CN1N=C(C(=O)Nc2ccc(Cl)nn2)CCC1=O]

In a 40 mL reaction vial, 1-methyl-6-oxo-1,4,5,6-tetrahydropyridazine-3-carboxylic acid (0.500 g, 3.20 mmol) was combined with 6-chloropyridazin-3-amine (0.414 g, 3.20 mmol) and 2-(3H-[1,2,3]triazolo[4,5-b]pyridin-3-yl)-1,1,3,3-tetramethyluronium tetrafluoroborate (1.03 g, 3.20 mmol). To the vial N,N'-dimethylformamide (16.0 mL) was added followed by N-N-N,N-diisopropylethyl amine (835 µL, 4.80 mmol). The reaction is stirred 16 h at room temperature. The reaction is diluted with ethyl acetate (15 mL×3) with water (10 mL), then with brine (10 mL). The mixture is dried over sodium sulfate, filtered, and concentrated. Purified reaction by column chromatography (eluting with 0-100% ethyl acetate/hexanes through 24 g of silica gel) to give N-(6-chloropyridazin-3-yl)-1-methyl-6-oxo-1,4,5,6-tetrahydropyridazine-3-carboxamide as a yellow solid (156 mg, 0.583 mmol, 18%). $^1$H NMR (300 MHz, Chloroform-d) δ 9.84 (s, 1H), 8.55 (d, J=9.3 Hz, 1H), 7.56 (dd, J=9.3, 0.7 Hz, 1H), 3.51 (s, 3H), 3.09-2.93 (m, 2H), 2.63 (t, J=8.6 Hz, 2H).

Step 2: Preparation of 1-methyl-6-oxo-N-(6-(3-(trifluoromethyl)benzyl)pyridazin-3-yl)-1,4,5,6-tetrahydropyridazine-3-carboxamide

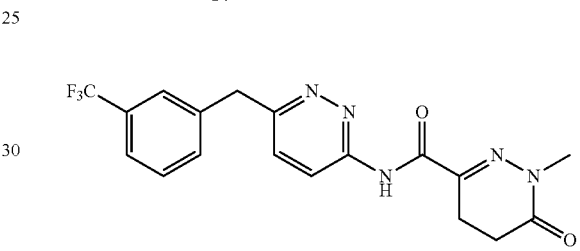

In a 40 mL reaction vial, suspended dust zinc dust (0.121 g, 1.86 mmol) in N,N'-dimethylformamide (3.0 mL) and carefully added iodine (0.008 g, 0.029 mmol). Stirred at room temperature for 5 min. Slowly added 1-(bromomethyl)-3-(trifluoromethyl)benzene (269 µL, 1.74 mmol) and stirred at 85° C. for 4 h. Cooled to room temperature and added bis(triphenylphosphine)palladium(II) dichloride (0.020 g, 0.02914 mmol) and N-(6-chloropyridazin-3-yl)-1-methyl-6-oxo-1,4,5,6-tetrahydropyridazine-3-carboxamide (0.156 g, 0.5828 mmol). The reaction was degassed by cycling with vacuum and nitrogen for 3 cycles. Stirred reaction at room temperature 16 h. Diluted with ethyl acetate (15 mL) and washed with water (10 mL×3) and then with brine (15 mL). The combined organic layers were dried over sodium sulfate, filtered, and concentrated. Purified reaction by column chromatography (eluting with 0-100% ethyl acetate/hexanes through 24 g of silica gel) to give 1-methyl-6-oxo-N-(6-(3-(trifluoromethyl)benzyl)pyridazin-3-yl)-1,4,5,6-tetrahydropyridazine-3-carboxamide as a pale yellow solid (25 mg, 0.064 mmol, 11%). $^1$H NMR (300 MHz, Chloroform-d) δ 9.79 (s, 1H), 8.43 (d, J=9.2 Hz, 1H), 7.63-7.43 (m, 4H), 7.33 (d, J=9.2 Hz, 1H), 4.39 (s, 2H), 3.51 (s, 3H), 3.04-2.92 (m, 2H), 2.62 (t, J=8.5 Hz, 2H); LCMS (ESI) m/z: 392.2 [M+H]$^+$.

Example 195. Preparation of N-(6-(3-fluorobenzyl)pyridazin-3-yl)-1-methyl-6-oxo-1,6-dihydropyridazine-3-carboxamide (195)

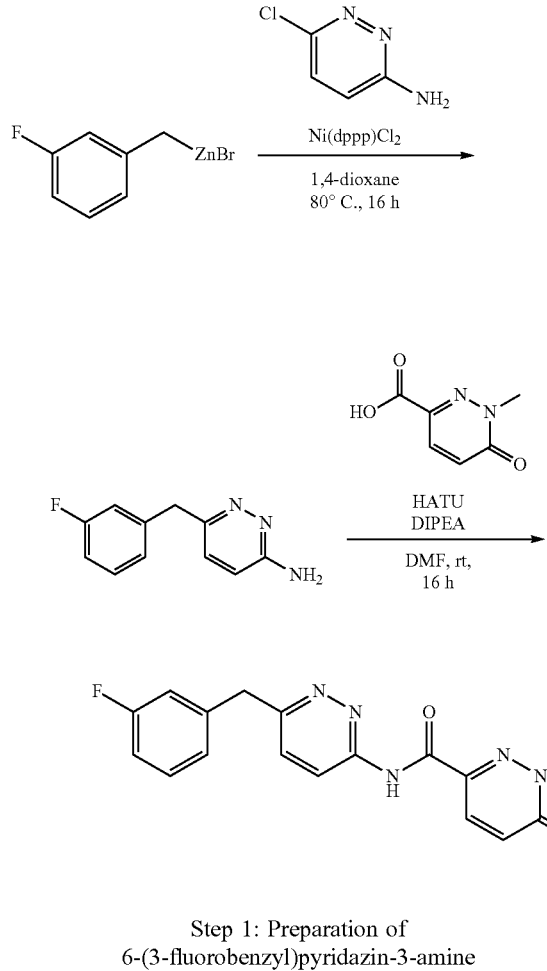

Step 1: Preparation of 6-(3-fluorobenzyl)pyridazin-3-amine

In a 40 mL reaction vial, suspended 6-chloropyridazin-3-amine (0.200 g, 1.54 mmol) and [1,3-bis(diphenylphosphino)propane]dichloronickel(II) (0.166 g, 0.308 mmol) in 1,4-dioxane (7.70 mL). The reaction was degassed by cycling with vacuum and nitrogen gas for 3 cycles. Carefully added (3-fluorobenzyl)zinc(II) chloride (9.24 mL, 4.62 mmol), then stirred at 80° C. for 16 h. Cooled to room temperature and diluted with saturated aqueous ammonium chloride (15 mL). Extracted with ethyl acetate (20 mL), then washed with water (10 mL) then brine (15 mL). The combined organic layers were dried over sodium sulfate, filtered, and concentrated. Purified reaction by column chromatography (eluting with 0-100% ethyl acetate/hexanes through 12 g of silica gel) to give 6-(3-fluorobenzyl)pyridazin-3-amine as a yellow oil (249 mg, 1.22 mmol, 80%). (LCMS (ESI) m/z: 204.1 [M+H]$^+$.

Step 2: Preparation of N-(6-(3-fluorobenzyl)pyridazin-3-yl)-1-methyl-6-oxo-1,6-dihydropyridazine-3-carboxamide

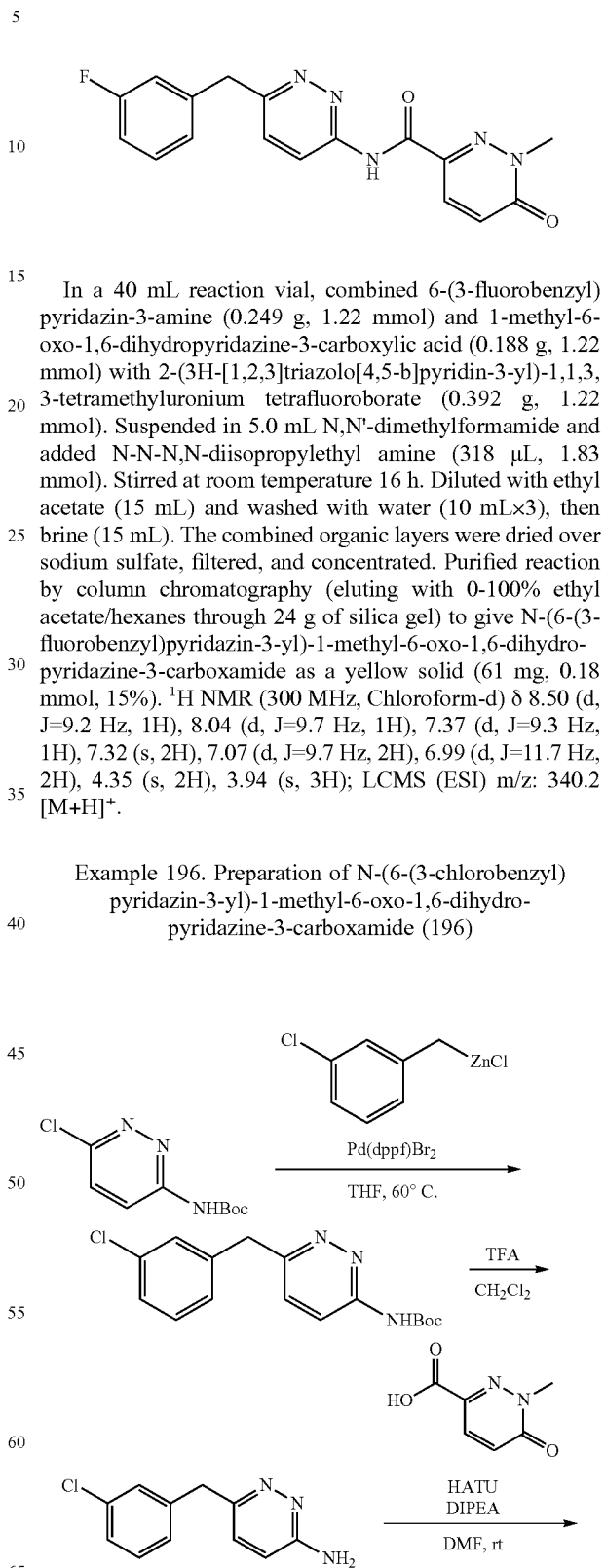

In a 40 mL reaction vial, combined 6-(3-fluorobenzyl)pyridazin-3-amine (0.249 g, 1.22 mmol) and 1-methyl-6-oxo-1,6-dihydropyridazine-3-carboxylic acid (0.188 g, 1.22 mmol) with 2-(3H-[1,2,3]triazolo[4,5-b]pyridin-3-yl)-1,1,3,3-tetramethyluronium tetrafluoroborate (0.392 g, 1.22 mmol). Suspended in 5.0 mL N,N'-dimethylformamide and added N-N-N,N-diisopropylethyl amine (318 µL, 1.83 mmol). Stirred at room temperature 16 h. Diluted with ethyl acetate (15 mL) and washed with water (10 mL×3), then brine (15 mL). The combined organic layers were dried over sodium sulfate, filtered, and concentrated. Purified reaction by column chromatography (eluting with 0-100% ethyl acetate/hexanes through 24 g of silica gel) to give N-(6-(3-fluorobenzyl)pyridazin-3-yl)-1-methyl-6-oxo-1,6-dihydropyridazine-3-carboxamide as a yellow solid (61 mg, 0.18 mmol, 15%). $^1$H NMR (300 MHz, Chloroform-d) δ 8.50 (d, J=9.2 Hz, 1H), 8.04 (d, J=9.7 Hz, 1H), 7.37 (d, J=9.3 Hz, 1H), 7.32 (s, 2H), 7.07 (d, J=9.7 Hz, 2H), 6.99 (d, J=11.7 Hz, 2H), 4.35 (s, 2H), 3.94 (s, 3H); LCMS (ESI) m/z: 340.2 [M+H]$^+$.

Example 196. Preparation of N-(6-(3-chlorobenzyl)pyridazin-3-yl)-1-methyl-6-oxo-1,6-dihydropyridazine-3-carboxamide (196)

-continued

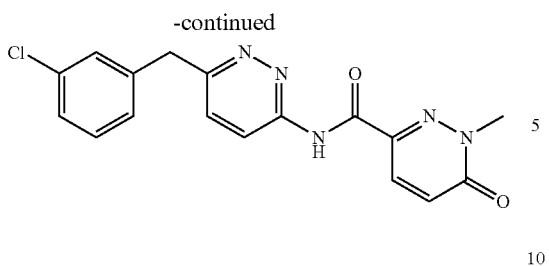

Step 1: Preparation of tert-butyl N-{6-[(3-chloro-phenyl)methyl]pyridazin-3-yl}carbamate)

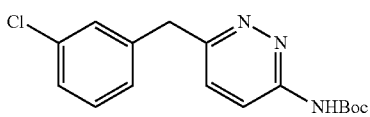 [SMILES: CC(C)(C)OC(=O)Nc1ccc(Cc2cccc(Cl)c2)nn1]

In a 40 mL vial, combined tert-butyl N-(6-chloro-pyridazin-3-yl)carbamate (0.400 g, 1.74 mmol) with [(2-di-tert-butylphosphino-2',4',6'-triisopropyl-1,1'-biphenyl)-2-(2'-amino-1,1'-biphenyl)]palladium(II) methanesulfonate (0.027 g, 0.0348 mmol), then suspended in tetrahydrofuran (3.48 mL). The reaction was degassed by cycling with vacuum and nitrogen gas for 3 cycles. Slowly added 3-chlorobenzylzinc chloride (0.5 M in tetrahydrofuran, 6.96 mL, 3.48 mmol) and stirred 16 h at 60° C. Dibromo[1,1-bis(diphenylphosphino)ferrocene]palladium(II) (0.025 g, 0.030 mmol) was added and stirred at 70° C. for 16 h. Cooled to room temperature and diluted with ethyl acetate (20 mL). Washed with saturated aqueous ammonium chloride (15 mL), water (10 mL), then brine (15 mL). The combined organic layers were dried over sodium sulfate, filtered, and concentrated. Purified reaction by column chromatography (eluting with 0-100% ethyl acetate/hexanes through 24 g of silica gel) to give tert-butyl N-{6-[(3-chlorophenyl)methyl]pyridazin-3-yl}carbamate) as a white solid (162 mg, 0.506 mmol, 29%). ¹H NMR (300 MHz, Chloroform-d) δ 8.16 (d, J=9.2 Hz, 1H), 7.32-7.20 (m, 3H), 4.26 (s, 2H), 1.54 (s, 9H).

Step 2: Preparation of 6-[(3-chlorophenyl)methyl]pyridazin-3-amine

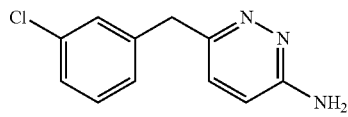 [SMILES: Nc1ccc(Cc2cccc(Cl)c2)nn1]

Dissolved tert-butyl N-{6-[(3-chlorophenyl)methyl]pyridazin-3-yl}carbamate (162 mg, 0.5065 mmol) in dichloromethane and added 2,2,2-trifluoroacetic acid (0.25 mL, 0.507 mmol). Stirred at room temperature 16 h. Reaction is concentrated in vacuo and is taken crude to next reaction.

Step 3: Preparation of N-{6-[(3-chlorophenyl)methyl]pyridazin-3-yl}-1-methyl-6-oxo-1,6-dihydro-pyridazine-3-carboxamide

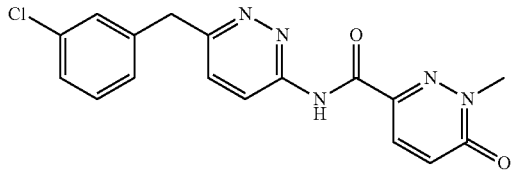

Combined 6-[(3-chlorophenyl)methyl]pyridazin-3-amine (0.111 g, 0.5053 mmol), 1-methyl-6-oxo-1,6-dihydro-pyridazine-3-carboxylic acid (0.078 g, 0.5053 mmol), and [bis(dimethylamino)methylidene]({3H-[1,2,3]triazolo[4,5-b]pyridin-3-yl})oxidanium; tetrafluoroboranuide (0.162 g, 0.5053 mmol) in a 25 mL round bottom flask and dissolved in 2.0 mL N,N'-dimethylformamide. Added ethylbis(propan-2-yl)amine (131 µL, 0.7579 mmol) and stirred at room temperature 16 h. Diluted with ethyl acetate (15 mL), then washed with water (10 mL×3) and brine (10 mL). The combined organic layers were dried over sodium sulfate, filtered, and concentrated. Purified reaction by column chromatography (eluting with 0-100% ethyl acetate/hexanes through 24 g of silica gel) to give N-{6-[(3-chlorophenyl)methyl]pyridazin-3-yl}-1-methyl-6-oxo-1,6-dihydro-pyridazine-3-carboxamide as a white solid (57 mg, 0.16 mmol, 32%). ¹H NMR (300 MHz, Chloroform-d) δ 8.56 (d, J=9.2 Hz, 1H), 8.03 (d, J=9.7 Hz, 1H), 7.41 (d, J=9.3 Hz, 1H), 7.19 (s, 4H), 7.07 (d, J=9.8 Hz, 1H), 4.33 (s, 2H), 3.95 (d, J=0.8 Hz, 3H); LCMS (ESI) m/z: 356.2 [M+H]⁺.

Example 197. Preparation of N-(6-(3-chlorobenzyl)pyridazin-3-yl)-1-methyl-6-oxo-1,4,5,6-tetrahydro-pyridazine-3-carboxamide (197)

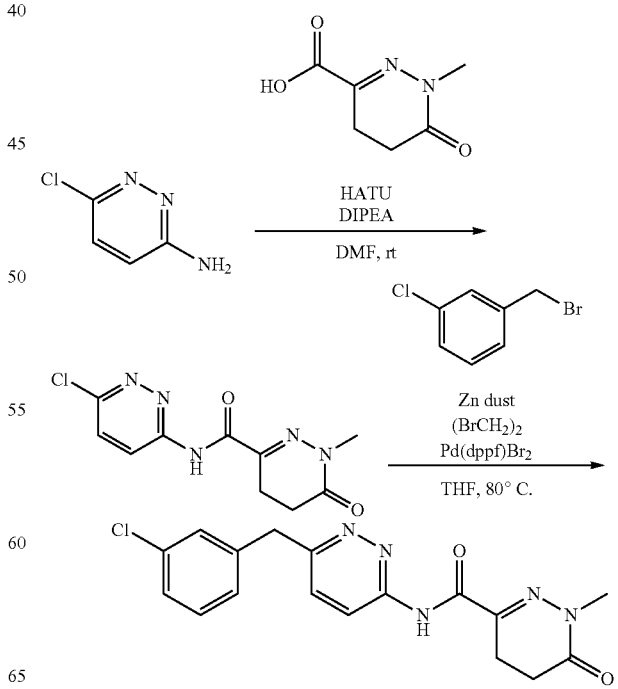

Step 1: Preparation of N-(6-chloropyridazin-3-yl)-1-methyl-6-oxo-1,4,5,6-tetrahydropyridazine-3-carboxamide

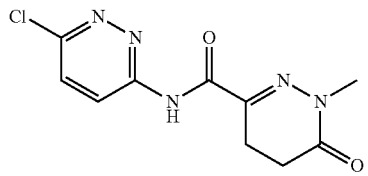 [SMILES: CN1N=C(C(=O)Nc2ccc(Cl)nn2)CCC1=O]

In a 40 mL reaction vial, 1-methyl-6-oxo-1,4,5,6-tetrahydropyridazine-3-carboxylic acid (0.5 g, 3.20 mmol) was combined with 6-chloropyridazin-3-amine (0.414 g, 3.20 mmol) and 2-(3H-[1,2,3]triazolo[4,5-b]pyridin-3-yl)-1,1,3,3-tetramethyluronium tetrafluoroborate (1.03 g, 3.20 mmol). To the vial N,N'-dimethylformamide (16.0 mL) was added followed by N-N-N,N-diisopropylethyl amine (835 µL, 4.80 mmol). The reaction is stirred 16 h at room temperature. The reaction is diluted with ethyl acetate (20 mL) and washed with water (10 mL×3), then with brine (15 mL). The mixture is dried over sodium sulfate, filtered, and concentrated. Purified reaction by column chromatography (eluting with 0-100% ethyl acetate/hexanes through 24 g of silica gel) to give N-(6-chloropyridazin-3-yl)-1-methyl-6-oxo-1,4,5,6-tetrahydropyridazine-3-carboxamide as a white solid (140 mg, 0.523 mmol, 16%). $^1$H NMR (300 MHz, Chloroform-d) δ 8.55 (d, J=9.3 Hz, 1H), 7.56 (dd, J=9.3, 0.7 Hz, 1H), 3.51 (s, 3H), 2.99 (m, 2H), 2.63 (t, J=8.5 Hz, 2H).

Step 2: Preparation of N-(6-(3-chlorobenzyl)pyridazin-3-yl)-1-methyl-6-oxo-1,4,5,6-tetrahydropyridazine-3-carboxamide

Suspend zinc dust (0.048 g, 0.7322 mmol) in tetrahydrofuran (2.61 mL) and added 1,2-dibromoethane (18.0 µL, 0.2092 mmol). Heated to 65° C. for 5 minutes. Cooled to 0° C. and added 1-(bromomethyl)-3-chlorobenzene (81.7 µL, 0.6275 mmol). Stirred at 0° C. for 1 hour. Add [1,1'-bis(diphenylphosphino)ferrocene]dibromopalladium(II) (0.021 mg, 0.02615 mmol) and stirred at room temperature for 30 minutes. Add N-(6-chloropyridazin-3-yl)-1-methyl-6-oxo-1,4,5,6-tetrahydropyridazine-3-carboxamide (0.140 g, 0.523 mmol) and stirred at 80° C. for 16 h. Cooled to room temperature and diluted with ethyl acetate (15 mL). Washed with 1 N aqueous sodium hydroxide (10 mL), water (10 mL), then brine (10 mL). The combined organic layers were dried over sodium sulfate, filtered, and concentrated. Purified reaction by column chromatography (eluting with 0-100% ethyl acetate/hexanes through 24 g of silica gel) to give N-(6-(3-chlorobenzyl)pyridazin-3-yl)-1-methyl-6-oxo-1,4,5,6-tetrahydropyridazine-3-carboxamide as a white solid (17 mg, 0.047 mmol, 9%). $^1$H NMR (300 MHz, Chloroform-d) δ 9.80 (s, 1H), 8.43 (d, J=9.1 Hz, 1H), 7.37-7.27 (m, 3H), 4.31 (s, 2H), 3.51 (s, 3H), 2.98 (t, J=8.5 Hz, 2H), 2.62 (t, J=8.6 Hz, 2H); LCMS (ESI) m/z 358.4 [M+H]$^+$.

Example 198. Preparation of N-(6-(cyclohexylmethyl)pyridazin-3-yl)-1-methyl-6-oxo-1,4,5,6-tetrahydropyridazine-3-carboxamide (198)

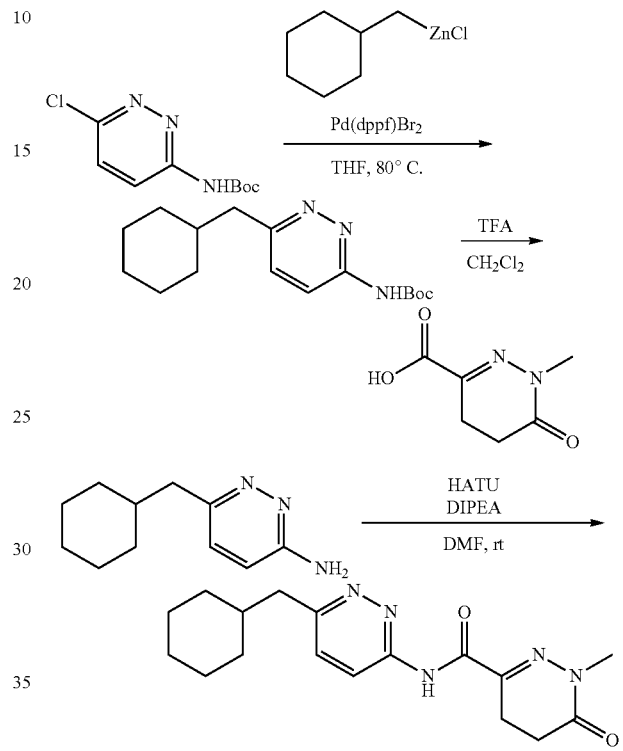

Step 1: Preparation of tert-butyl N-[6-(cyclohexylmethyl)pyridazin-3-yl]carbamate

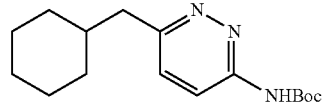 [SMILES: CC(C)(C)OC(=O)Nc1ccc(CC2CCCCC2)nn1]

Combined tert-butyl N-(6-chloropyridazin-3-yl)carbamate (0.200 g, 0.8708 mmol) and [1,1'-bis(diphenylphosphino)ferrocene]dibromopalladium(II) (0.036 g, 0.04354 mmol) in a 40 mL reaction vial and suspended in tetrahydrofuran (2.0 mL). The reaction was degassed by cycling with vacuum and nitrogen gas for 3 cycles. Carefully added chloro(cyclohexylmethyl)zinc dust (0.5M in tetrahydrofuran, 5.22 mL, 2.61 mmol) by syringe, then stirred 16 h at 80° C. The reaction was cooled to room temperature and quenched with saturated aqueous ammonium chloride (15 mL). The mixture was extracted with ethyl acetate (20 mL), then washed with water (10 mL), then brine (10 mL). The reaction was dried over sodium sulfate, filtered, and concentrated. Purified reaction by column chromatography (eluting with 0-100% ethyl acetate/hexanes through 24 g of silica gel) to give tert-butyl N-[6-(cyclohexylmethyl)pyridazin-3-yl]carbamate as a white solid (170 mg, 0.583 mmol, 67%). ¹H NMR (300 MHz, Chloroform-d) δ 8.12 (d, J=9.1 Hz, 1H), 7.25 (s, 1H), 2.79 (d, J=7.0 Hz, 2H), 1.92-1.58 (m, 6H), 1.55 (s, 9H), 1.19 (m, 3H), 1.02 (m, 3H).

Step 2: Preparation of 6-(cyclohexylmethyl)pyridazin-3-amine

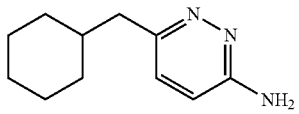

Reaction was dissolved in dichloromethane (5.0 mL) and cooled to 0° C. Slowly added 2,2,2-trifluoroacetic acid (0.4 mL, 0.5834 mmol) and stirred at 0° C. to room temperature over 3 h. Concentrated in vacuo, and reaction was taken crude to next step. ¹H NMR (300 MHz, Chloroform-d) δ7.49 (d, J=9.4 Hz, 1H), 7.28 (d, J=5.2 Hz, 2H), 2.65 (d, J=6.9 Hz, 2H), 1.70 (d, J=10.8 Hz, 8H), 1.21 (d, J=9.7 Hz, 4H), 1.01 (d, J=12.0 Hz, 3H).

Step 3: Preparation of N-[6-(cyclohexylmethyl)pyridazin-3-yl]-1-methyl-6-oxo-1,4,5,6-tetrahydropyridazine-3-carboxamide

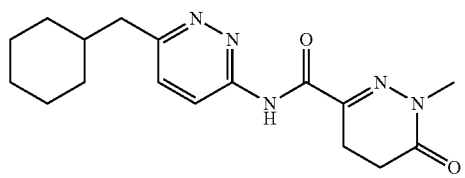 [SMILES: CN1N=C(C(=O)Nc2ccc(CC3CCCCC3)nn2)CCC1=O]

Combined 6-(cyclohexylmethyl)pyridazin-3-amine (0.111 g, 0.5803 mmol), 1-methyl-6-oxo-1,4,5,6-tetrahydropyridazine-3-carboxylic acid (0.091 g, 0.5803 mmol) and 1-[Bis(dimethylamino)methylene]-1H-1,2,3-triazolo[4,5-b]pyridinium 3-oxid hexafluorophosphate (0.186 g, 0.5803 mmol) in a 25 mL round bottom flask and dissolved in N,N'-dimethylformamide (3.0 mL). Added ethylbis(propan-2-yl)amine (150 µL, 0.8704 mmol) and stirred 16 h at room temperature. Diluted with ethyl acetate (15 mL) and washed 3 times with water (10 mL), then once with brine (10 mL). The combined organic layers were dried over sodium sulfate, filtered, and concentrated. Purified reaction by column chromatography (eluting with 0-100% ethyl acetate/hexanes through 24 g of silica gel) to give N-[6-(cyclohexylmethyl)pyridazin-3-yl]-1-methyl-6-oxo-1,4,5,6-tetrahydropyridazine-3-carboxamide as a white solid (27 mg, 0.082 mmol, 14%). ¹H NMR (300 MHz, Chloroform-d) δ 8.58 (d, J=8.9 Hz, 1H), 7.48 (d, J=9.2 Hz, 1H), 3.53 (s, 3H), 2.99 (t, J=8.5 Hz, 2H), 2.89 (d, J=7.1 Hz, 2H), 2.63 (t, J=8.5 Hz, 2H), 1.69 (d, J=13.5 Hz, 8H), 1.21 (d, J=9.4 Hz, 3H); LCMS (ESI) m/z: 330.2 [M+H]⁺

Example 199. Preparation of 1-ethyl-N-(6-(3-fluorobenzyl)pyridazin-3-yl)-6-oxo-1,6-dihydropyridazine-3-carboxamide (199)

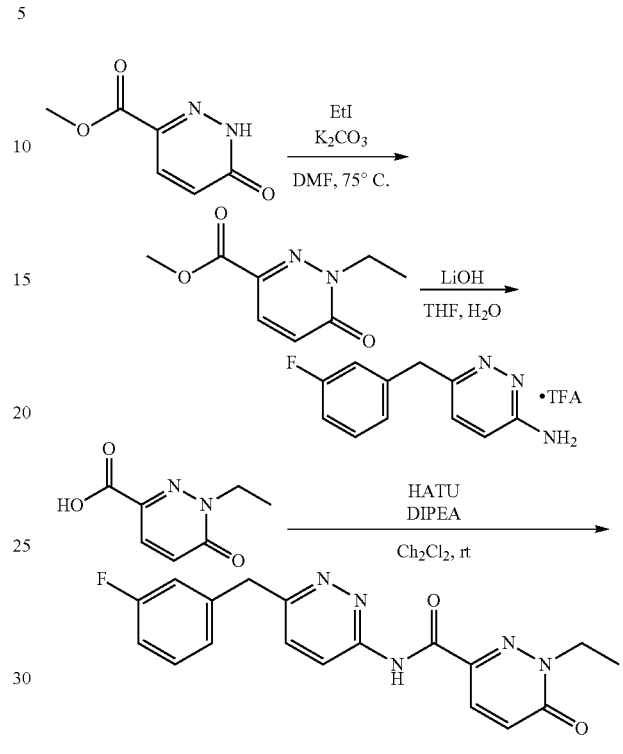

Step 1: Preparation of methyl 1-ethyl-6-oxo-1,6-dihydropyridazine-3-carboxylate

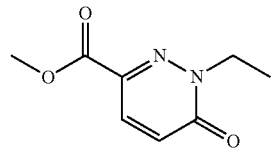

Dissolved methyl 6-oxo-1,6-dihydropyridazine-3-carboxylate (0.500 g, 3.24 mmol) in N,N'-dimethylformamide (5.0 mL) and added potassium carbonate (0.671 g, 4.86 mmol) and iodoethane (3904, 4.86 mmol). Stirred at 75° C. for 16 h. Cooled to room temperature and diluted with ethyl acetate (20 mL). Washed with water (10 mL×3), then with brine (15 mL). The combined organic layers were dried over sodium sulfate, filtered, and concentrated. Purified reaction by column chromatography (eluting with 0-50% ethyl acetate/hexanes through 24 g of silica gel) to give methyl 1-ethyl-6-oxo-1,6-dihydropyridazine-3-carboxylate (211 mg, 1.15 mmol, 36%) as a pale yellow solid. ¹H NMR (300 MHz, Chloroform-d) δ 7.86 (d, J=9.7 Hz, 1H), 6.96 (d, J=9.7 Hz, 1H), 4.33 (q, J=7.2 Hz, 2H), 3.98 (s, 3H), 1.43 (t, J=7.2 Hz, 3H).

Step 2: Preparation of 1-ethyl-6-oxo-1,6-dihydropyridazine-3-carboxylic acid

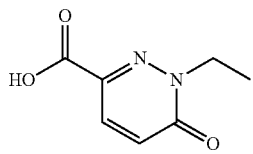

Dissolved methyl 1-ethyl-6-oxo-1,6-dihydropyridazine-3-carboxylate (0.211 g, 1.15 mmol) in tetrahydrofuran (2.0 mL) and water (1.0 mL). Added lithium hydroxide hydrate (0.144 g, 3.44 mmol) and stirred at room temperature 16 h. Acidified with 10% hydrochloric acid solution (6 mL), then extracted with ethyl acetate (15 mL). Washed organic layer with brine (10 mL), then dried over sodium sulfate. Filtered and concentrated to yield 1-ethyl-6-oxo-1,6-dihydropyridazine-3-carboxylic acid (106 mg, 0.630 mmol, 55%) as a white solid. $^1$H NMR (300 MHz, Chloroform-d) δ 7.93 (d, J=9.7 Hz, 1H), 7.04 (d, J=9.6 Hz, 1H), 4.32 (q, J=7.2 Hz, 2H), 1.46 (t, J=7.2 Hz, 3H).

Step 3: Preparation of 1-ethyl-N-{6-[(3-fluorophenyl)methyl]pyridazin-3-yl}-6-oxo-1,6-dihydropyridazine-3-carboxamide

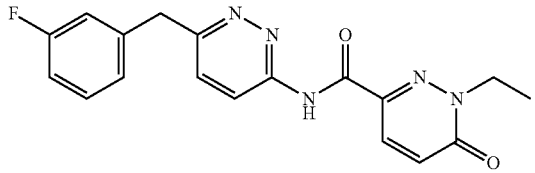 [SMILES: CCn1nc(C(=O)Nc2ccc(Cc3cccc(F)c3)nn2)ccc1=O]

Combined 6-[(3-fluorophenyl)methyl]pyridazin-3-amine; trifluoroacetic acid (0.100 g, 0.3152 mmol) and 1-ethyl-6-oxo-1,6-dihydropyridazine-3-carboxylic acid (0.053 g, 0.3152 mmol) with [bis(dimethylamino)methylidene]({3H-[1,2,3]triazolo[4,5-b]pyridin-3-yl})oxidanium; tetrafluoroboranuide (0.101 g, 0.3152 mmol). Dissolved in methylene chloride (2.0 mL) and added ethylbis(propan-2-yl)amine (136 µL, 0.7879 mmol). Stirred at room temperature 16 h. Directly purified reaction by column chromatography (eluting with 0-100% ethyl acetate/hexanes through 12 g of silica gel) to give 1-ethyl-N-{6-[(3-fluorophenyl)methyl]pyridazin-3-yl}-6-oxo-1,6-dihydropyridazine-3-carboxamide (18 mg, 0.051 mmol, 16%) as a yellow solid. $^1$H NMR (300 MHz, Chloroform-d) δ 8.57 (d, J=9.7 Hz, 1H), 8.01 (dd, J=9.7, 0.6 Hz, 1H), 7.42 (d, J=9.2 Hz, 1H), 7.39-7.28 (m, 1H), 7.14-6.92 (m, 4H), 4.37 (d, J=5.1 Hz, 4H), 1.49 (t, J=7.2 Hz, 3H); LCMS (ESI) m/z: 354.2 [M+H]$^+$.

Example 200. Preparation of N-(6-(3-fluorobenzyl)pyridazin-3-yl)-1-methyl-6-oxo-1,4,5,6-tetrahydropyridazine-3-carboxamide (200)

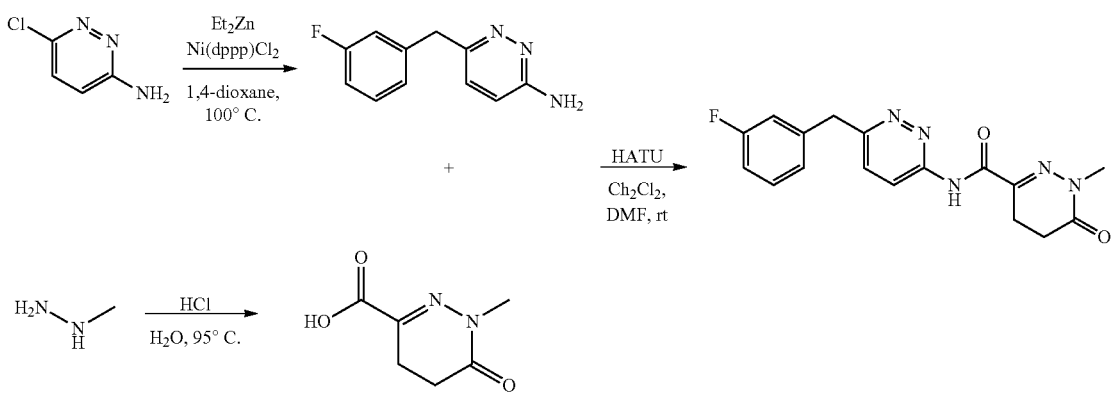

Step 1: Preparation of 1-methyl-6-oxo-1,4,5,6-tetrahydropyridazine-3-carboxylic acid

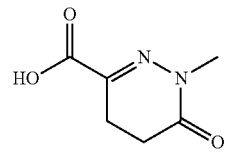

In a 40 mL reaction vial, dissolved 2-oxopentanedioic acid (3.0 g, 20.5 mmol) in 15.0 mL of 10% hydrochloric acid. Stirred until completely dissolved. Carefully added methylhydrazine (1.07 mL, 20.5 mmol) to the reaction, then stirred at 95° C. for 3 h. Cooled to room temperature and diluted with water (15 mL). Extracted twice with dichloromethane (30 mL). The combined organic layers were dried over sodium sulfate, filtered, and concentrated to give 1-methyl-6-oxo-1,4,5,6-tetrahydropyridazine-3-carboxylic acid as a white solid (1.47 g, 9.41 mmol, 46%). $^1$H NMR (300 MHz, Chloroform-d) δ 3.48 (s, 3H), 2.95 (d, J=8.6, 2H), 2.62 (t, J=8.6 Hz, 2H).

Step 2: Preparation of 6-(3-fluorobenzyl)pyridazin-3-amine

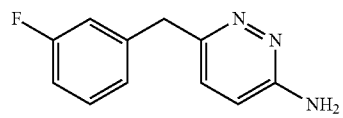

Dissolved [1,3-bis(diphenylphosphino)propane]dichloronickel(II) (0.166 g, 0.3080 mmol) in 1,4-dioxane (8.0 mL) in a 40 mL reaction vial and introduced an atmosphere of nitrogen. Carefully added diethylzinc dust (1.0M in tetrahydrofuran, 7.70 mL, 7.70 mmol) and stirred at room temperature for 10 min. Slowly added 1-(bromomethyl)-3-fluorobenzene (1.12 mL, 9.24 mmol) and stirred at 100° C. for 4 h. Added a solution of 6-chloropyridazin-3-amine (0.2 g, 1.54 mmol) in 2.0 mL of tetrahydrofuran via syringe and stirred at 100° C. for 2 h. Cooled to room temperature and quenched with methanol (5 mL) and concentrated hydrochloric acid (2 mL). Basified (pH ~10) with 1M aqueous sodium hydroxide (15 mL), then extracted with ethyl acetate (20 mL), then washed with brine (10 mL×2). The combined organic layers were dried over sodium sulfate, filtered, and concentrated. Purified reaction by column chromatography (eluting with 0-100% ethyl acetate/hexanes through 12 g of silica gel) to give 6-(3-fluorobenzyl)pyridazin-3-amine as a white solid (86 mg, 0.423 mmol, 27%). $^1$H NMR (300 MHz, Chloroform-d) δ 7.24 (d, J=6.2 Hz, 1H), 7.18-6.85 (m, 4H), 6.69 (d, J=9.0 Hz, 1H), 4.64 (s, 2H), 4.20 (s, 2H).

Step 3: Preparation of N-(6-(3-fluorobenzyl)pyridazin-3-yl)-1-methyl-6-oxo-1,4,5,6-tetrahydropyridazine-3-carboxamide

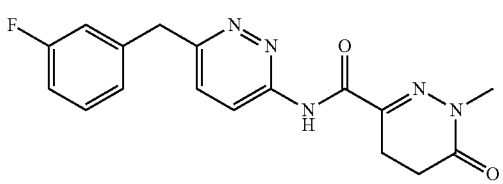 [SMILES: CN1N=C(C(=O)Nc2ccc(Cc3cccc(F)c3)nn2)CCC1=O]

Combined 6-(3-fluorobenzyl)pyridazin-3-amine (0.086 g, 0.4231 mmol) and 1-methyl-6-oxo-1,4,5,6-tetrahydropyridazine-3-carboxylic acid (0.066 g, 0.4231 mmol) and added 2-(1H-benzo[d][1,2,3]triazol-1-yl)-1,1,3,3-tetramethyluronium tetrafluoroborate (0.135 g, 0.4231 mmol). Added 1.0 mL dichloromethane, followed by 0.50 mL N,N'-dimethylformamide. Stirred reaction at room temperature 16 h. Diluted with ethyl acetate (15 mL) and washed 3 times with water (10 mL) and once with brine (10 mL). The combined organic layers were dried over sodium sulfate, filtered, and concentrated. Purified reaction by column chromatography (eluting with 0-50% ethyl acetate/dichloromethane through 12 g of silica gel) to give N-(6-(3-fluorobenzyl)pyridazin-3-yl)-1-methyl-6-oxo-1,4,5,6-tetrahydropyridazine-3-carboxamide as a white solid (22 mg, 0.064 mmol, 15%). $^1$H NMR (300 MHz, Chloroform-d) δ 8.43 (d, J=9.1 Hz, 1H), 7.33 (d, J=9.1 Hz, 2H), 7.14-6.87 (m, 2H), 4.33 (s, 2H), 3.51 (s, 3H), 2.98 (t, J=8.5 Hz, 2H), 2.62 (t, J=8.5 Hz, 2H); LCMS (ESI) m/z: 342.3 [M+H]$^+$.

Example 201. Preparation of N-(5-benzylthiazol-2-yl)-1-methyl-6-oxo-1,4,5,6-tetrahydropyridazine-3-carboxamide (201)

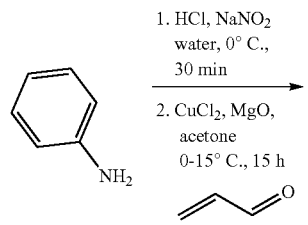

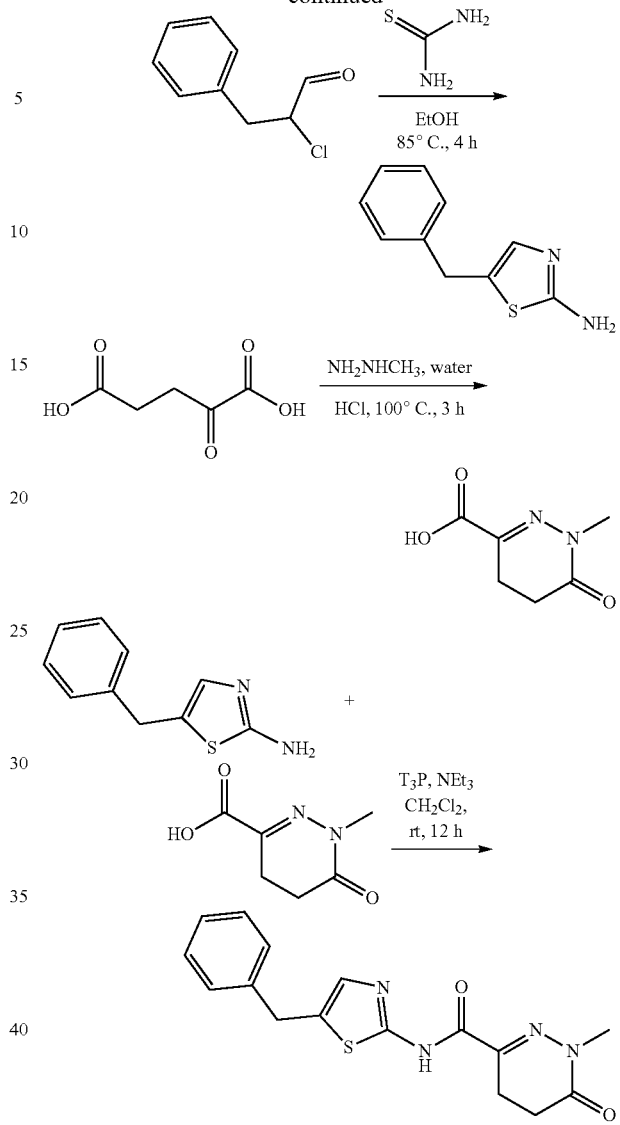

Step 1: Preparation of 1-methyl-6-oxo-1,4,5,6-tetrahydropyridazine-3-carboxylic acid

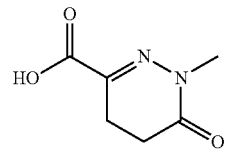

To a solution of 2-oxopentanedioic acid (4.99 g, 34.1 mmol) in aqueous hydrogen chloride solution (50 mL, 10%) was added methylhydrazine (3.93 g, 34.1 mmol, 50% in water) dropwise. The mixture was stirred at 100° C. for 3 h. The mixture was extracted with dichloromethane (10×30 mL). The combined organic layers were dried and concentrated in vacuo to give a residue. The residue was recrystallized from ethanol (20 mL) and filtered to give 1-methyl-6-oxo-1,4,5,6-tetrahydropyridazine-3-carboxylic acid (2.5 g, 16.0 mmol, 47%) as white solid. ¹H NMR (400 MHz, Chloroform-d) δ 9.63 (br. s, 1H), 3.46 (s, 3H), 2.98-2.83 (m, 2H), 2.67-2.54 (m, 2H).

Step 2: Preparation of 2-chloro-3-phenyl-propanal

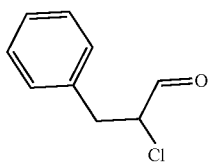 [SMILES: O=CC(Cl)Cc1ccccc1]

To a mixture of aniline (2.61 g, 28 mmol) in water (15 mL) at 0° C. was added hydrogen chloride (4 mL, 12M) followed by a solution of sodium nitrate (2.13 g, 30.8 mmol) in water (4 mL) drop wise. After addition, the mixture was stirred for 30 minutes at 0-15° C. and the mixture was treated with solid sodium bicarbonate to adjust pH=6 at 0° C. In another three-neck bottom, copper(II) chloride (1.51 g, 11.2 mmol), magnesium oxide (0.282 g, 7.00 mmol) and prop-2-enal (1.57 g, 28.0 mmol) in acetone (10 mL) were stirred. To the above solution was added dropwise the former solution at 0° C. After addition, the mixture was warmed slowly to 15° C. and stirred for 15 h. The mixture was concentrated, in vacuo to give 2-chloro-3-phenyl-propanal (5.0 g, crude) as a yellow oil. Used directly in the next step without additional purification.

Step 3: Preparation of 5-benzylthiazol-2-amine

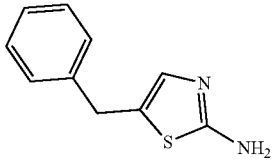 [SMILES: Nc1ncc(Cc2ccccc2)s1]

To a mixture of 2-chloro-3-phenyl-propanal (4 g, 7.12 mmol) in ethanol (100 mL) at 85° C. was added isothiourea (2 g, 26.3 mmol). The reaction mixture was stirred at 85° C. for 4 h. The mixture was concentrated in vacuo to give a residue. The crude product was purified by column chromatography (ISCO, 40 g silica, 0-20% ethyl acetate in petroleum ether, gradient over 30 minutes) to give 5-benzylthiazol-2-amine (0.4 g, 2.10 mmol, 30%) as a thick red solid.

Step 4: Preparation of N-(5-benzylthiazol-2-yl)-1-methyl-6-oxo-1,4,5,6-tetrahydropyridazine-3-carboxamide

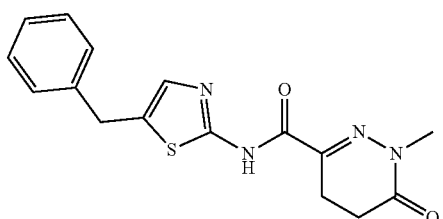

To a solution of 1-methyl-6-oxo-1,4,5,6-tetrahydropyridazine-3-carboxylic acid (0.150 g, 0.961 mmol) and 5-benzylthiazol-2-amine (0.365 g, 1.92 mmol) in dichloromethane (15 mL) was added triethylamine (0.291 g, 2.88 mmol) and propylphosphonic anhydride solution in ethyl acetate (1.22 g, 1.92 mmol, 50% purity). The mixture was stirred at 25° ° C. for 12 h. The mixture was poured into ice-water (10 mL) and extracted with dichloromethane (10 mL×2). The combined organic layers were dried over sodium sulfate, filtered and concentrated in vacuo to give a residue. The crude material was purified by prep-HPLC ((Waters X bridge 150*25 5 uM column; 45-65% acetonitrile in a 10 mM ammonium acetate solution in water, 12 min gradient) to give N-(5-benzylthiazol-2-yl)-1-methyl-6-oxo-1,4,5,6-tetrahydropyridazine-3-carboxamide (0.190 g, 0.558 mmol, 58%) as a yellow solid. ¹H NMR (400 MHz, Dimethylsulfoxide-d₆) δ 11.80 (br. s, 1H), 7.37-7.13 (m, 6H), 4.09 (s, 2H), 3.31 (s, 3H), 2.85-2.74 (m, 2H), 2.52-2.49 (m, 2H). ¹H NMR (400 MHz, Chloroform-d)=9.97 (br. s, 1H), 7.34-7.28 (m, 2H), 7.27-7.21 (m, 3H), 7.18 (s, 1H), 4.10 (s, 2H), 3.44 (s, 3H), 3.00-2.89 (m, 2H), 2.63-2.51 (m, 2H); LCMS (ESI) m/z: 329.1 [M+H]⁺.

Example 202. Preparation of N-(5-(3-fluorobenzyl)thiazol-2-yl)-1-methyl-6-oxo-1,6-dihydropyridazine-3-carboxamide (202)

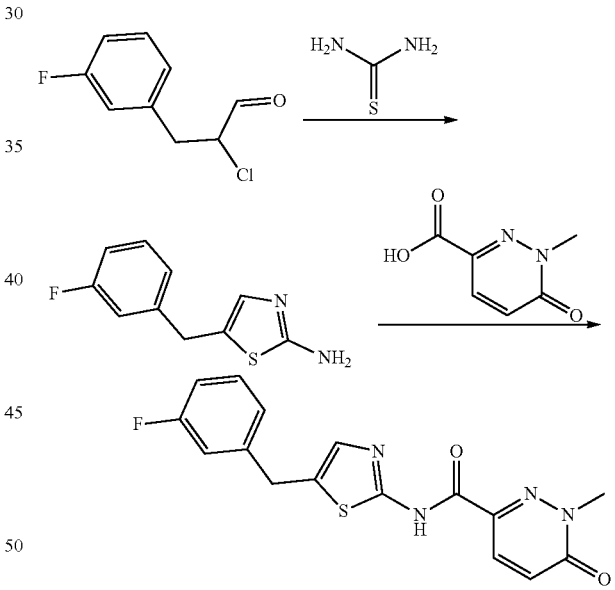

Compound 202 was synthesized according to the synthetic procedure reported for the preparation of compound 201.

N-(5-(3-fluorobenzyl)thiazol-2-yl)-1-methyl-6-oxo-1,6-dihydropyridazine-3-carboxamide (0.033 g, 0.094 mmol, 10%) was obtained as a yellow solid. ¹H NMR (400 MHz, Dimethylsulfoxide-d₆) δ 11.19 (br. s, 1H), 7.90 (d, J=9.7 Hz, 1H), 7.43-7.33 (m, 2H), 7.17-7.11 (m, 2H), 7.10-7.02 (m, 2H), 4.15 (s, 2H), 3.77 (s, 3H); LCMS (ESI) m/z: 345.0 [M+H]⁺.

Example 203. Preparation of N-(5-(3-fluorophenoxy)thiazol-2-yl)-1-methyl-6-oxo-1,4,5,6-tetrahydropyridazine-3-carboxamide (203)

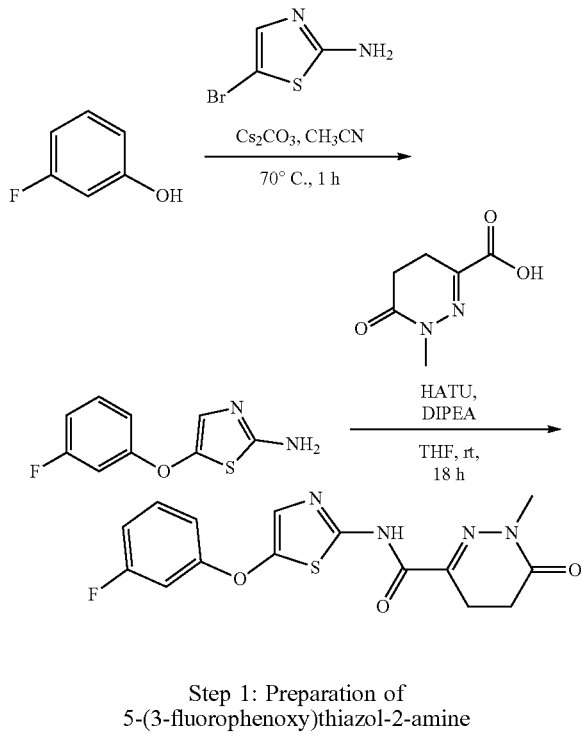

Step 1: Preparation of 5-(3-fluorophenoxy)thiazol-2-amine

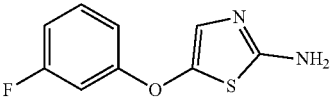 [SMILES: Nc1ncc(Oc2cccc(F)c2)s1]

To a mixture of 5-bromothiazol-2-amine (0.100 g, 0.562 mmol) and cesium carbonate (0.275 g, 0.843 mmol) in acetonitrile (2 mL) at 70° C. was added a solution of 3-fluorophenol (0.082 g, 0.731 mmol) in acetonitrile (1 mL) dropwise. Then the reaction was stirred at 70° C. for 1 h. The reaction was cooled to room temperature and diluted with water (30 mL). The aqueous layer was extracted with ethyl acetate (20 mL×3). The combined organic layers were washed with brine (30 mL), dried over sodium sulfate, filtered and concentrated in vacuo to give 5-(3-fluorophenoxy)thiazol-2-amine (0.100 g, crude) as a brown oil which was used directly in the next step. LCMS (ESI) m/z: 211.1 [M+H]$^+$.

Step 2: Preparation of N-(5-(3-fluorophenoxy)thiazol-2-yl)-1-methyl-6-oxo-1,4,5,6-tetrahydropyridazine-3-carboxamide

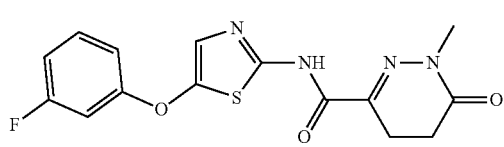 [SMILES: CN1N=C(C(=O)Nc2ncc(Oc3cccc(F)c3)s2)CCC1=O]

To a mixture of 5-(3-fluorophenoxy)thiazol-2-amine (0.090 g, 0.428 mmol) and 1-methyl-6-oxo-1,4,5,6-tetrahydropyridazine-3-carboxylic acid (0.067 g, 0.428 mmol) in tetrahydrofuran (1 mL) at room temperature was added 1-[bis(dimethylamino)methylene]-1H-1,2,3-triazolo[4,5-b]pyridinium 3-oxid hexafluorophosphate (0.195 g, 0.514 mmol) and diisopropylethylamine (0.110 g, 0.856 mmol). The reaction was stirred at room temperature 16 h and was combined with another batch (90 mg). Reaction mixture was diluted with water (20 mL) and the aqueous layer was extracted with ethyl acetate (10 mL×3). The combined organic layers were washed with brine (10 mL), dried over sodium sulfate, filtered and concentrated in vacuo. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-fluorophenoxy)thiazol-2-yl)-1-methyl-6-oxo-1,4,5,6-tetrahydropyridazine-3 carboxamide (20.1 mg, 0.058 mmol, 12%,) as a light-yellow solid. $^1$H NMR (500 MHz, Dimethylsulfoxide-d$_6$) δ 12.10 (s, 1H), 7.45 (dd, J=15.0, 8.0 Hz, 1H), 7.39 (s, 1H), 7.09-6.93 (m, 3H), 3.37 (s, 3H), 2.84 (t, J=8.5 Hz, 2H), 2.59-2.57 (m, 2H); LCMS (ESI) m/z: 349.0 [M+H]$^+$.

Example 204. Preparation of N-(5-((3-fluorophenyl)(methoxy)methyl)thiazol-2-yl)-1-methyl-6-oxo-1,4,5,6-tetrahydropyridazine-3-carboxamide (204)

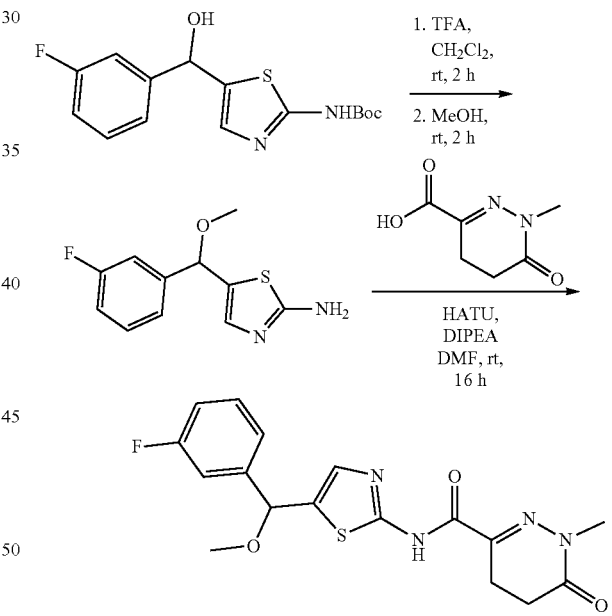

Step 1: Preparation of 5-((3-fluorophenyl)(methoxy)methyl)thiazol-2-amine

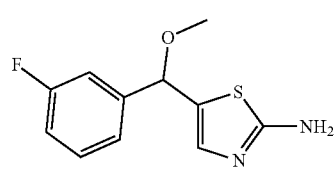 [SMILES: COC(c1cccc(F)c1)c1cnc(N)s1]

A mixture of tert-butyl 5-((3-fluorophenyl)(hydroxy)methyl)thiazol-2-ylcarbamate (0.200 g, 0.62 mmol) and trifluoroacetic acid (2 mL) in dichloromethane (2 mL) was stirred at room temperature for 1 h. Methanol (2 mL) was added and the reaction continued to stir for an additional 1 h at room temperature. The reaction mixture was concentrated, and the residue was dissolved in ethyl acetate (60 mL). The organic layer was washed with saturated sodium bicarbonate aqueous solution (60 mL) and brine (60 mL), dried over sodium sulfate, filtered and concentrated under reduced pressure. The crude residue was purified by column chromatography (silica gel, petroleum ether/ethyl acetate=1/1) to afford 5-((3-fluorophenyl)(methoxy)methyl)thiazol-2-amine (0.120 g, 0.50 mmol, 81%,) as a yellow solid. LCMS (ESI) m/z: 239.1 [M+H]+.

Step 2: Preparation of N-(5-((3-fluorophenyl)(methoxy)methyl)thiazol-2-yl)-1-methyl-6-oxo-1,4,5,6-tetrahydropyridazine-3-carboxamide

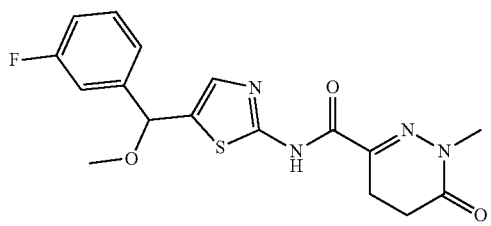 [SMILES: COC(c1cccc(F)c1)c1cnc(NC(=O)C2=NN(C)C(=O)CC2)s1]

To a stirred solution of 5-((3-fluorophenyl)(methoxy)methyl)thiazol-2-amine (0.110 g, 0.46 mmol), 1-methyl-6-oxo-1,4,5,6-tetrahydropyridazine-3-carboxylic acid (0.108 g, 0.69 mmol) and N,N-diisopropylethylamine (0.297 g, 2.30 mmol) in N,N-dimethylformamide (5 mL) was added 1-[bis(dimethylamino)methylene]-1H-1,2,3-triazolo[4,5-b]pyridinium 3-oxid hexafluorophosphate (0.262 g, 0.69 mmol). The mixture was stirred for 16 h at room temperature and heated to 50° C. for another 16 h. The reaction mixture was poured into water (60 mL) and extracted with ethyl acetate (40 mL×2). The combined organics were washed with brine (80 mL), dried over sodium sulfate, filtered and concentrated under reduced pressure. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to give N-(5-((3-fluorophenyl)(methoxy)methyl)thiazol-2-yl)-1-methyl-6-oxo-1,4,5,6-tetrahydropyridazine-3-carboxamide (0.085 g, 0.23 mmol, 49%,) as a white solid. $^1$H NMR (400 MHz, Dimethylsulfoxide-d$_6$) δ 12.01 (s, 1H), 7.50-7.38 (m, 2H), 7.28-7.10 (m, 3H), 5.67 (s, 1H), 3.32 (s, 3H), 3.29 (s, 3H), 2.89-2.77 (m, 2H), 2.53-2.47 (m, 2H); LCMS (ESI) m/z: 377.0 [M+H]+.

Example 205. Preparation of N-(5-((3-fluorophenyl)(hydroxy)methyl)thiazol-2-yl)-1-methyl-6-oxo-1,4,5,6-tetrahydropyridazine-3-carboxamide (205)

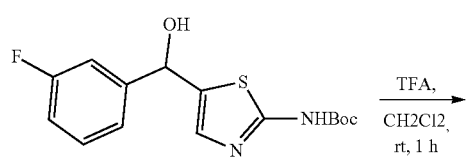

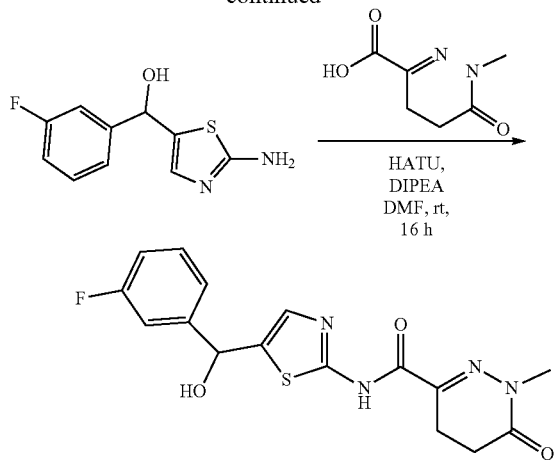

Step 1: Preparation of (2-aminothiazol-5-yl)(3-fluorophenyl)methanol

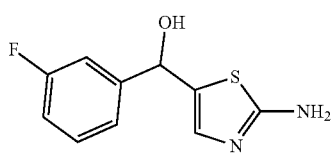 [SMILES: Nc1ncc(C(O)c2cccc(F)c2)s1]

The mixture of tert-butyl 5-((3-fluorophenyl)(hydroxy)methyl)thiazol-2-ylcarbamate (0.300 g, 0.93 mmol) and trifluoroacetic acid (1 mL) in dichloromethane (3 mL) was stirred at room temperature for 1 h. The reaction mixture was concentrated, and the residue was dissolved in ethyl acetate (100 mL), washed with saturated sodium bicarbonate aqueous solution (60 mL) and brine (100 mL), dried over sodium sulfate, filtered and concentrated under reduced pressure to yield (2-aminothiazol-5-yl)(3-fluorophenyl)methanol (0.207 g, 0.93 mmol, 100%) as a yellow solid. LCMS (ESI) m/z: 225.1 [M+H]+.

Step 2: Preparation of N-(5-((3-fluorophenyl)(hydroxy)methyl)thiazol-2-yl)-1-methyl-6-oxo-1,4,5,6-tetrahydropyridazine-3-carboxamide

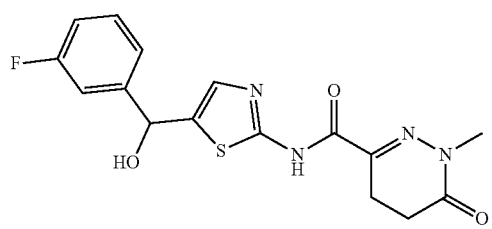 [SMILES: CN1N=C(C(=O)Nc2ncc(C(O)c3cccc(F)c3)s2)CCC1=O]

To a stirred solution of (2-aminothiazol-5-yl)(3-fluorophenyl)methanol (0.207 g, 0.93 mmol), 1-methyl-6-oxo-1,4,5,6-tetrahydropyridazine-3-carboxylic acid (145 mg, 0.93 mmol) and N,N-diisopropylethylamine (0.361 g, 2.79 mmol) in N,N-dimethylformamide (5 mL) was added 1-[bis(dimethylamino)methylene]-1H-1,2,3-triazolo[4,5-b]pyridinium 3-oxid hexafluorophosphate (0.389 g, 1.02 mmol).

The mixture was stirred at room temperature for 16 h. The reaction mixture was poured into water (60 mL) and extracted with ethyl acetate (40 mL×2). The combined organics were washed with brine (80 mL), dried over sodium sulfate, filtered and concentrated under reduced pressure. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-((3-fluorophenyl)(hydroxy)methyl)thiazol-2-yl)-1-methyl-6-oxo-1,4,5,6-tetrahydropyridazine-3-carboxamide (40 mg, 0.11 mmol, 12%) as a white solid. $^1$H NMR (400 MHz, Dimethylsulfoxide-d$_6$) δ 11.93 (s, 1H), 7.40 (td, J=8.1, 6.2 Hz, 1H), 7.32-7.19 (m, 3H), 7.15-7.05 (m, 1H), 6.39 (d, J=4.4 Hz, 1H), 5.99 (d, J=3.6 Hz, 1H), 3.34 (s, 3H), 2.89-2.78 (m, 2H), 2.53-2.48 (m, 2H); LCMS (ESI) m/z: 363.1 [M+H]$^+$.

Example 206. Preparation of N-(5-(2-fluorobenzyl)thiazol-2-yl)-1-methyl-6-oxo-1,4,5,6-tetrahydropyridazine-3-carboxamide (206)

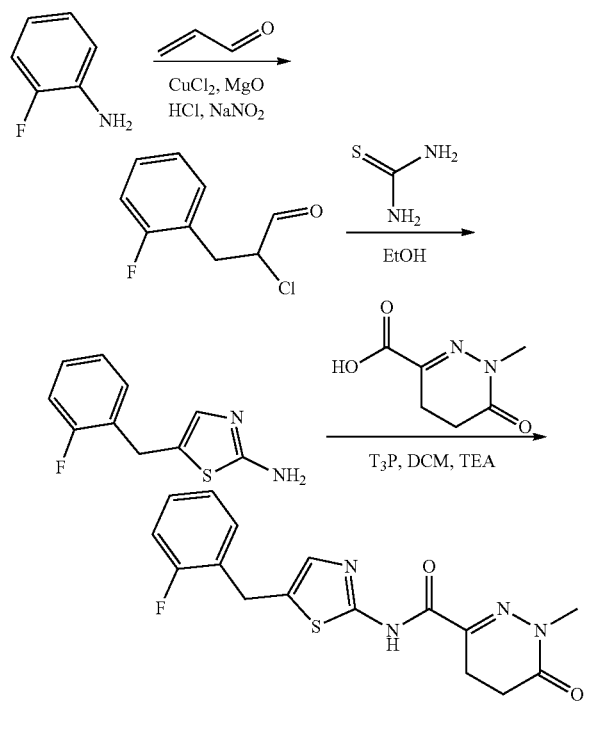

Step 1: Preparation of N-(5-(2-fluorobenzyl)thiazol-2-yl)-1-methyl-6-oxo-1,4,5,6-tetrahydropyridazine-3-carboxamide

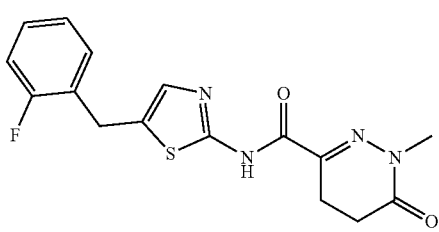 [SMILES: CN1N=C(C(=O)Nc2ncc(Cc3ccccc3F)s2)CCC1=O]

N-(5-(2-fluorobenzyl)thiazol-2-yl)-1-methyl-6-oxo-1,4,5,6-tetrahydropyridazine-3-carboxamide was synthesized according to the synthetic procedure reported for the preparation of compound 201. Compound N-(5-(2-fluorobenzyl)thiazol-2-yl)-1-methyl-6-oxo-1,4,5,6-tetrahydropyridazine-3-carboxamide (0.177 g, 0.505 mmol, 61%) was obtained as a pale yellow solid. $^1$H NMR (400 MHz, Chloroform-d) δ10.12 (br. s, 1H), 7.27-7.19 (m, 3H), 7.12-7.02 (m, 2H), 4.13 (s, 2H), 3.43 (s, 3H), 2.97 (t, J=8.6 Hz, 2H), 2.59 (t, J=8.8 Hz, 2H); LCMS (ESI) m/z: 347.0 [M+H]$^+$.

Example 207. Preparation of N-(5-(3-chlorobenzyl)thiazol-2-yl)-1-methyl-6-oxo-1,4,5,6-tetrahydropyridazine-3-carboxamide (207)

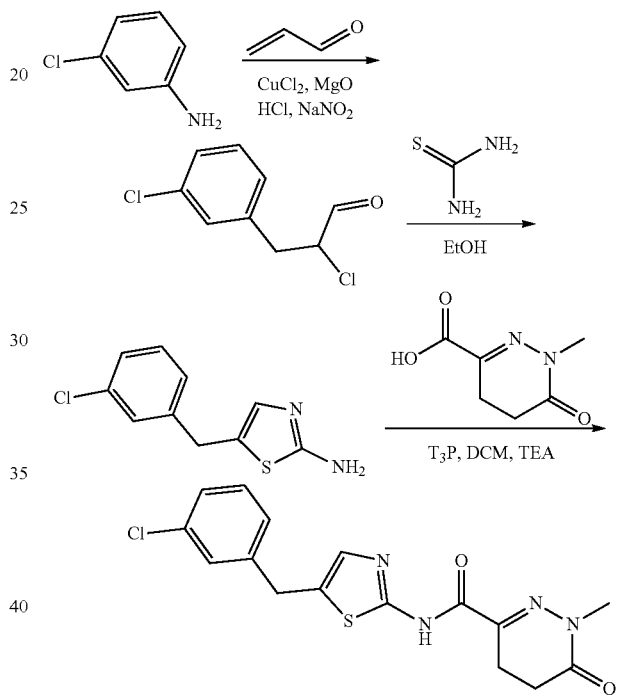

Step 1: Preparation of N-(5-(3-chlorobenzyl)thiazol-2-yl)-1-methyl-6-oxo-1,4,5,6-tetrahydropyridazine-3-carboxamide

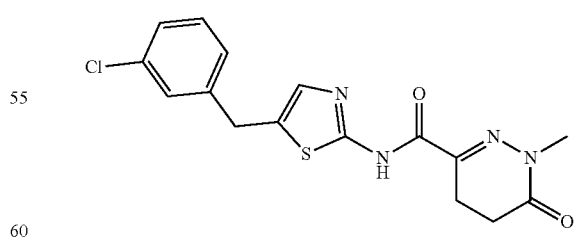

N-(5-(3-chlorobenzyl)thiazol-2-yl)-1-methyl-6-oxo-1,4,5,6-tetrahydropyridazine-3-carboxamide was synthesized according to the synthetic procedure reported for the preparation of compound 201. Compound N-(5-(3-chlorobenzyl)thiazol-2-yl)-1-methyl-6-oxo-1,4,5,6-tetrahydropyridazine-3-carboxamide (0.231 g, 0.631 mmol, 66%) was obtained as a yellow solid. $^1$H NMR (400 MHz, Dimethylsulfoxide-$d_6$) δ 11.87 (br. s, 1H), 7.37-7.31 (m, 3H), 7.30-7.21 (m, 2H), 4.12 (s, 2H), 3.33 (s, 3H), 2.85-2.75 (m, 2H), 2.51 (s, 2H); LCMS (ESI) m/z: 363.0 [M+H]$^+$.

Example 208. Preparation of N-(5-(4-fluorobenzyl)thiazol-2-yl)-1-methyl-6-oxo-1,4,5,6-tetrahydropyridazine-3-carboxamide (208)

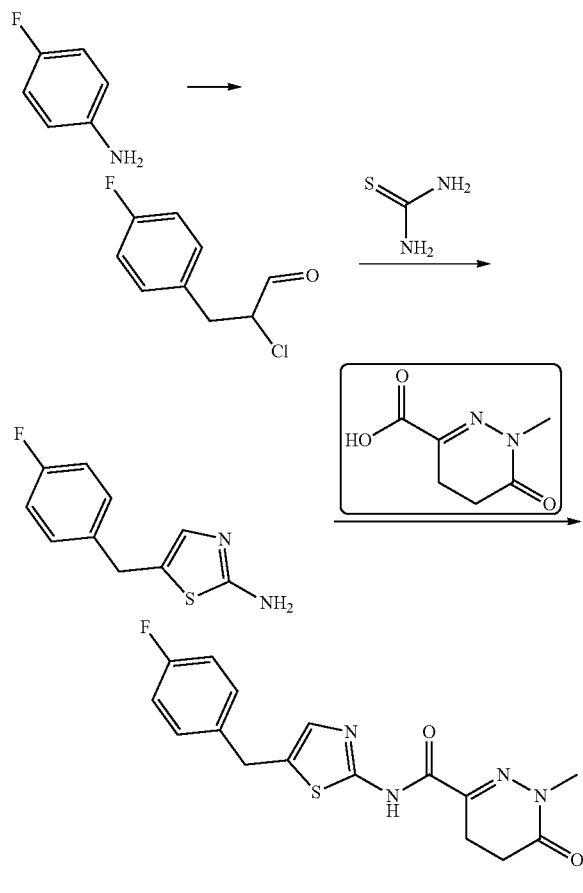

Step 1: Preparation of N-(5-(4-fluorobenzyl)thiazol-2-yl)-1-methyl-6-oxo-1,4,5,6-tetrahydropyridazine-3-carboxamide N-(5-(4-fluorobenzyl)thiazol-2-yl)-1-methyl-6-oxo-1,4,5,6-tetrahydropyridazine-3-carboxamide was synthesized according to the synthetic procedure reported for the preparation of compound 201. Compound N-(5-(4-fluorobenzyl)thiazol-2-yl)-1-methyl-6-oxo-1,4,5,6-tetrahydropyridazine-3-carboxamide (0.113 g, 0.322 mmol, 33%) was obtained as a yellow solid. $^1$H NMR (400 MHz, Chloroform-d) δ 10.10 (br. s, 1H), 7.23-7.17 (m, 3H), 7.02-6.98 (m, 2H), 4.07 (s, 2H), 3.43 (s, 3H), 3.01-2.92 (m, 2H), 2.66-2.54 (m, 2H); LCMS (ESI) m/z: 347.0 [M+H]$^+$.

Example 209. Preparation of N-(5-(3-cyanobenzyl)thiazol-2-yl)-1-methyl-6-oxo-1,4,5,6-tetrahydropyridazine-3-carboxamide (209)

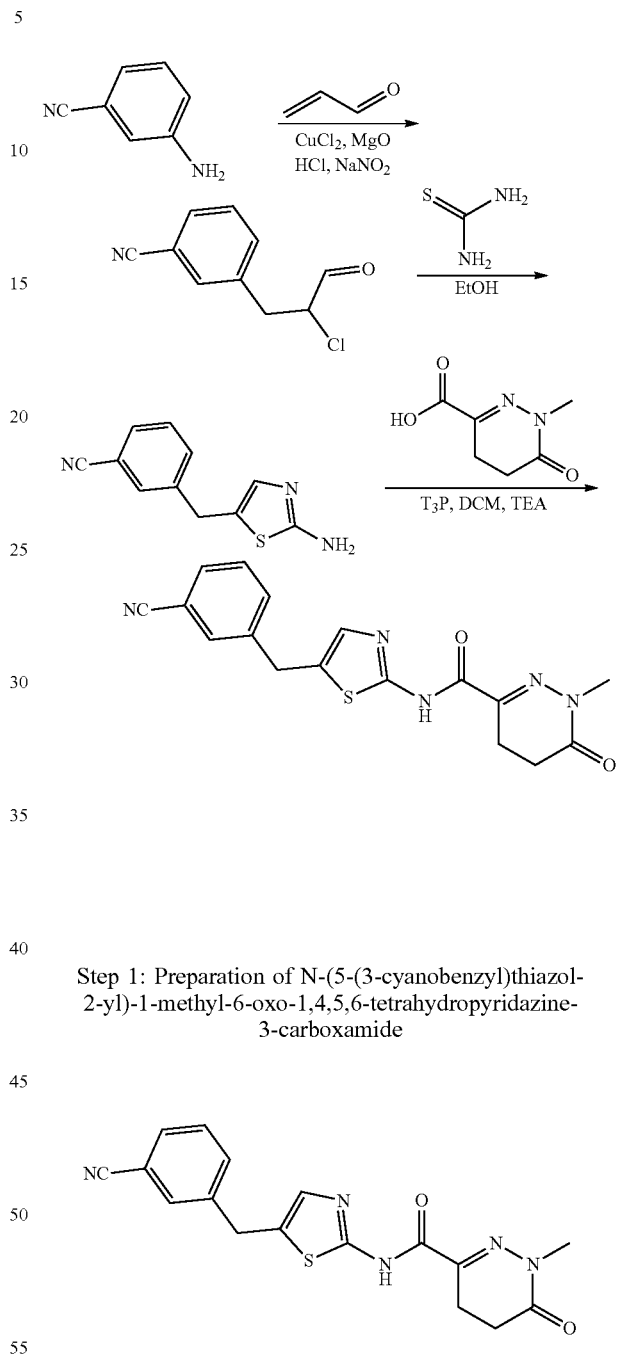

Step 1: Preparation of N-(5-(3-cyanobenzyl)thiazol-2-yl)-1-methyl-6-oxo-1,4,5,6-tetrahydropyridazine-3-carboxamide N-(5-(3-cyanobenzyl)thiazol-2-yl)-1-methyl-6-oxo-1,4,5,6-tetrahydropyridazine-3-carboxamide was synthesized according to the synthetic procedure reported for the preparation of compound 201. Compound N-(5-(3-cyanobenzyl)thiazol-2-yl)-1-methyl-6-oxo-1,4,5,6-tetrahydropyridazine-3-carboxamide (0.206 g, 0.563 mmol, 73%) was obtained as a white solid. $^1$H NMR (400 MHz, Chloroform-d) δ 10.05 (br. s, 1H), 7.57-7.52 (m, 2H), 7.52-7.48 (m, 1H), 7.46-7.40 (m, 1H), 7.22 (s, 1H), 4.15 (s, 2H), 3.45 (s, 3H), 2.97 (t, J=8.6 Hz, 2H), 2.60 (t, J=8.8 Hz, 2H); LCMS (ESI) m/z: 354.1 [M+H]$^+$.

Example 210. Preparation of N-(5-(3-methoxybenzyl)thiazol-2-yl)-1-methyl-6-oxo-1,4,5,6-tetrahydropyridazine-3-carboxamide (210)

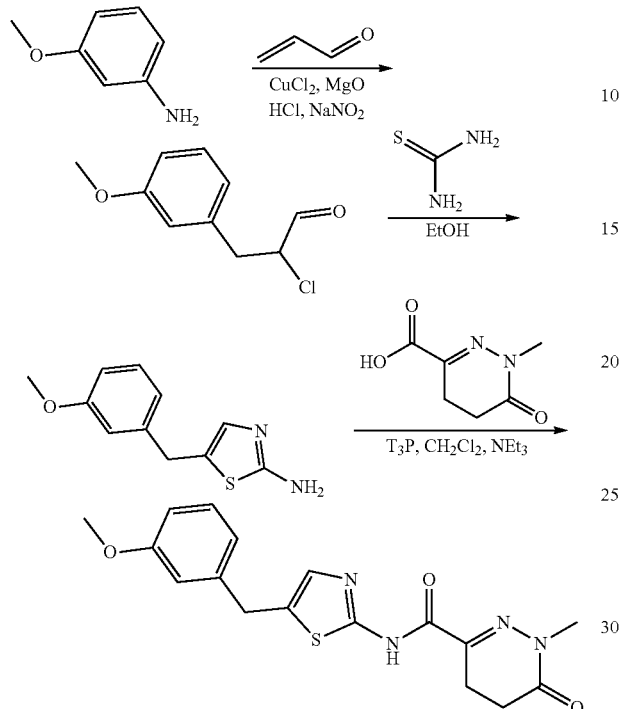

Step 1: Preparation of N-(5-(3-methoxybenzyl)thiazol-2-yl)-1-methyl-6-oxo-1,4,5,6-tetrahydropyridazine-3-carboxamide

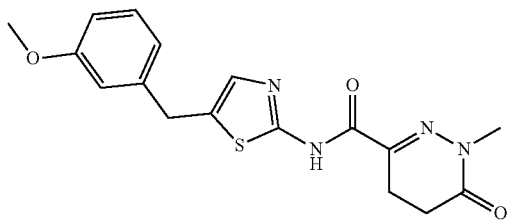 [SMILES: COc1cccc(Cc2cnc(NC(=O)C3=NN(C)C(=O)CC3)s2)c1]

Compound N-(5-(3-methoxybenzyl)thiazol-2-yl)-1-methyl-6-oxo-1,4,5,6-tetrahydropyridazine-3-carboxamide was synthesized according to the synthetic procedure reported for the preparation of compound 201. N-(5-(3-methoxybenzyl)thiazol-2-yl)-1-methyl-6-oxo-1,4,5,6-tetrahydropyridazine-3-carboxamide (0.162 g, 0.452 mmol, 54%) was obtained as a yellow solid. $^1$H NMR (400 MHz, Chloroform-d) δ 10.06 (br. s, 1H), 7.26-7.18 (m, 2H), 6.85 (d, J=7.5 Hz, 1H), 6.82-6.75 (m, 2H), 4.08 (s, 2H), 3.79 (s, 3H), 3.44 (s, 3H), 2.97 (t, J=8.6 Hz, 2H), 2.59 (t, J=8.4 Hz, 2H); LCMS (ESI) m/z: 359.0 [M+H]$^+$.

Example 211. Preparation of N-(5-(3-fluorobenzyl)-1,3,4-thiadiazol-2-yl)-1-methyl-6-oxo-1,4,5,6-tetrahydropyridazine-3-carboxamide (211)

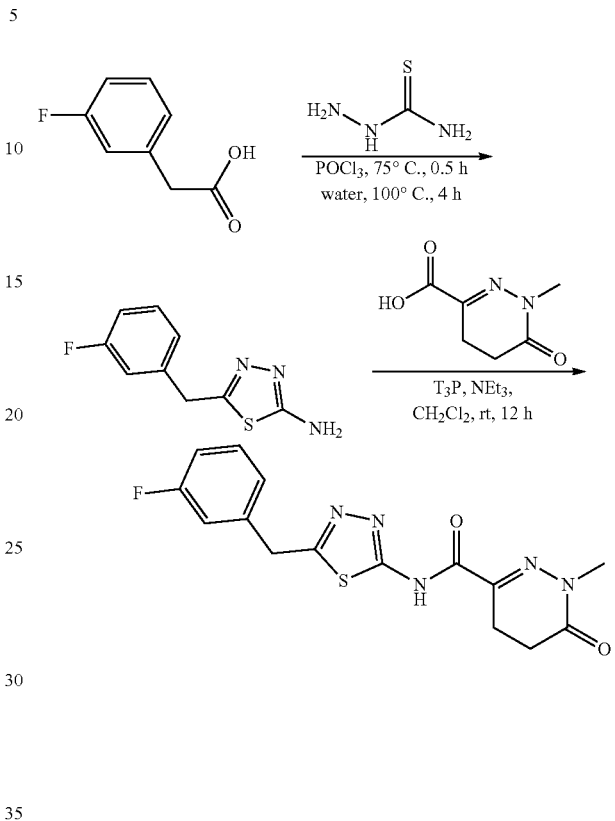

Step 1: Preparation of 5-[(3-fluorophenyl)methyl]-1,3,4-thiadiazol-2-amine

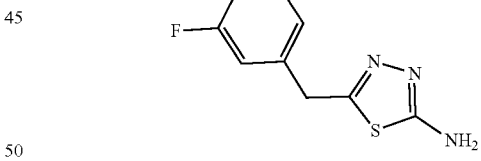

A mixture of 2-(3-fluorophenyl)acetic acid (2.00 g, 13.0 mmol) and aminothiourea (1.18 g, 13.0 mmol) in phosphorus(V) oxychloride (3 mL) was stirred and heated to 75° C. for 0.5 h. The mixture was cooled to 15° C. and water (10 mL) was added dropwise. The mixture was then stirred at 100° C. for 4 h. The reaction was then cooled to 15° C. and basified to pH=8 with 50% sodium hydroxide aqueous solution. The precipitate was filtered and the cake was dried in vacuo to give 5-[(3-fluorophenyl)methyl]-1,3,4-thiadiazol-2-amine (2.0 g, 7.46 mmol, 57%) as a white solid. The solid was used directly in the next step. $^1$H NMR (400 MHz, Dimethylsulfoxide-d$_6$) δ 7.43-7.32 (m, 1H), 7.21-7.02 (m, 5H), 4.19 (s, 2H).

Step 2: Preparation of N-(5-(3-fluorobenzyl)-1,3,4-thiadiazol-2-yl)-1-methyl-6-oxo-1,4,5,6-tetrahydropyridazine-3-carboxamide

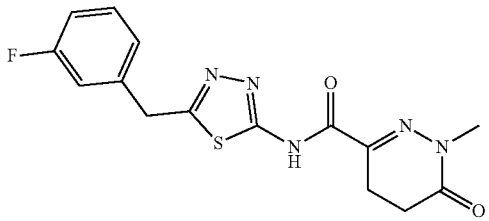 [SMILES: CN1N=C(C(=O)Nc2nnc(Cc3cccc(F)c3)s2)CCC1=O]

To a solution of 1-methyl-6-oxo-1,4,5,6-tetrahydropyridazine-3-carboxylic acid (0.15 g, 0.961 mmol) and 5-[(3-fluorophenyl)methyl]-1,3,4-thiadiazol-2-amine (0.201 g, 0.961 mmol) in dichloromethane (15 mL) at 25° C. was added sequentially triethylamine (0.194 g, 1.92 mmol) and propylphosphonic anhydride in ethyl acetate (0.917 g, 1.44 mmol, 50% purity). The mixture was stirred at 25° C. for 12 h. The reaction was poured into ice-water (10 mL) and extracted with dichloromethane (10 mL×2). The combined organic layers were dried over sodium sulfate, filtered and concentrated in vacuo. The residue was purified via prep-HPLC (Waters X bridge 150*25 5 uM column; 15-45% acetonitrile in a 10 mM ammonium bicarbonate solution in water, 12 minutes gradient) to give N-(5-(3-fluorobenzyl)-1,3,4-thiadiazol-2-yl)-1-methyl-6-oxo-1,4,5,6-tetrahydropyridazine-3-carboxamide (0.240 g, 0.676 mmol, 70%) as a white solid. $^{1}$H NMR (400 MHz, Chloroform-d) δ 10.55 (br. s, 1H), 7.31 (dt, J=6.1, 7.9 Hz, 1H), 7.09 (d, J=7.7 Hz, 1H), 7.05-6.95 (m, 2H), 4.36 (s, 2H), 3.43 (s, 3H), 2.96 (t, J=8.6 Hz, 2H), 2.66-2.57 (m, 2H); LCMS (ESI) m/z: 348.0 $[M+H]^{+}$.

Example 212. Preparation of N-(5-(3-methoxybenzyl)thiazol-2-yl)-1-methyl-6-oxo-1,6-dihydropyridazine-3-carboxamide (212)

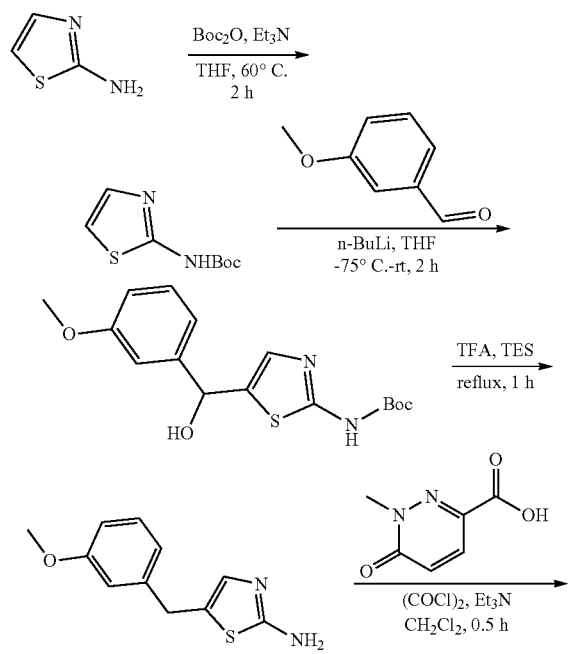

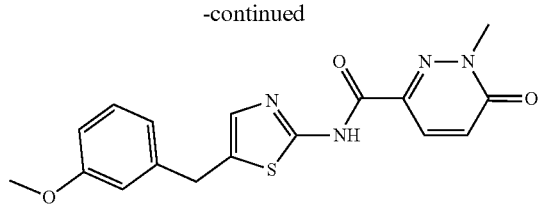

Step 1: Preparation of tert-butyl thiazol-2-ylcarbamate

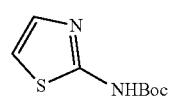 [SMILES: CC(C)(C)OC(=O)Nc1nccs1]

Di-tert-butyl dicarbonate (6.54 g, 30.0 mmol) was slowly added to a mixture of thiazol-2-amine (3.0 g, 30.0 mmol) and triethylamine (6.07 g, 60.0 mmol) in tetrahydrofuran (20 mL). The mixture was heated to 60° C. and stirred for 2 h. The volatiles were removed under reduced pressure. The crude residue was added to a mixture of petroleum ether/ethyl acetate=50:1 and the mixture was stirred for 2 h. Filtration afforded crude tert-butyl thiazol-2-ylcarbamate (4.4 g, crude) as a yellow solid. LCMS (ESI) m/z: 201.1 $[M+H]^{+}$.

Step 2: Preparation of tert-butyl 5-(hydroxy(3-methoxyphenyl)methyl)thiazol-2-ylcarbamate

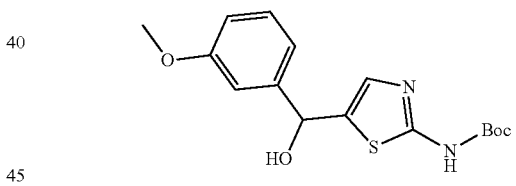

A solution of tert-butyl thiazol-2-ylcarbamate (1.2 g, 6.0 mmol) in tetrahydrofuran (20 mL) at −70° C., was treated slowly with n-butyllithium (5.3 mL, 13.2 mmol). The reaction was stirred at −70° C. for 2 h before a solution of 3-methoxybenzaldehyde (1.22 g, 9.0 mmol) in tetrahydrofuran (5 mL) was slowly added to the reaction mixture. Water was added to quench the reaction. The volatiles were removed under reduced pressure. The aqueous layer was extracted with dichloromethane (100 mL) and the organic phase was then washed with brine (50 mL), dried over sodium sulfate, filtered, concentrated. The crude residue was purified by column chromatography (silica gel, petroleum ether/ethyl acetate=1/1) to yield tert-butyl 5-(hydroxy(3-methoxyphenyl)methyl)thiazol-2-ylcarbamate (1.22 g, 61%) as a yellow solid. LCMS (ESI) m/z: 337.1 $[M+H]^{+}$.

Step 3: Preparation of 5-(3-methoxybenzyl)thiazol-2-amine

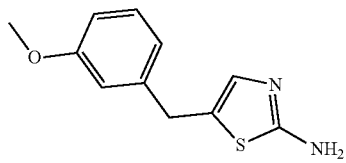

A solution of tert-butyl 5-(hydroxy(3-methoxyphenyl)methyl)thiazol-2-ylcarbamate (1.2 g, 3.57 mmol) in trifluoroacetic acid (10.0 mL) was treated with triethylsilane (1.66 g, 14.28 mmol) and was heated to 90° C. for 1 h. Trifluoroacetic acid was removed under reduced pressure and the crude residue was dissolved in dichloromethane (50 mL). The organic layer was washed with sodium bicarbonate (50 mL), brine (50 mL×1), dried over sodium sulfate, filtered and concentrated in vacuo. The crude sample was purified by column chromatography (silica gel, petroleum ether/ethyl acetate=1/1) to afford 5-(3-methoxybenzyl)thiazol-2-amine (0.700 g, 3.18 mmol, 89%) as a yellow solid. LCMS (ESI) m/z: 221.1 [M+H]$^+$.

Step 4: Preparation of 1-methyl-6-oxo-1,6-dihydropyridazine-3-carboxylic acid

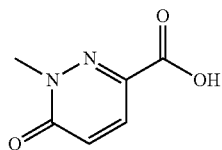

To a solution of methyl 1-methyl-6-oxo-1,6-dihydropyridazine-3-carboxylate (0.15 g, 0.892 mmol) in water (1.5 mL) was added sodium hydroxide (0.071 g, 1.79 mmol). The mixture was heated to 60° C. and stirred for 1 h. Solution was acidified to pH value to 1-3 with 1N hydrogen chloride and then all volatiles were removed to afford 1-methyl-6-oxo-1,6-dihydropyridazine-3-carboxylic acid (0.100 g, crude) as a white solid. LCMS (ESI) m/z: 155.1 [M+H]$^+$.

Step 5: Preparation of N-(5-(3-methoxybenzyl)thiazol-2-yl)-1-methyl-6-oxo-1,6-dihydropyridazine-3-carboxamide

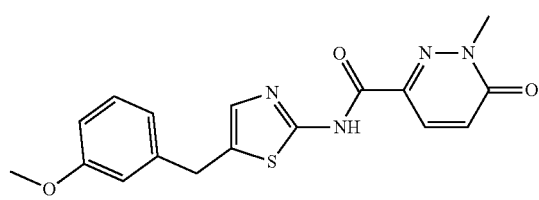 [SMILES: COc1cccc(Cc2cnc(NC(=O)c3ccc(=O)n(C)n3)s2)c1]

To a solution of 1-methyl-6-oxo-1,6-dihydropyridazine-3-carboxylic acid (0.100 g, 0.649 mmol) in dichloromethane (2 mL) at 20° C. was added oxalyl chloride (1 mL). Reaction mixture was stirred at 20° C. for 0.5 h and concentrated in vacuo. The crude solid was dissolved in dichloromethane (4.0 mL) and added to a mixture of 5-(3-methoxybenzyl)thiazol-2-amine (0.186 g, 0.844 mmol) and triethylamine (0.256 g, 2.53 mmol) in dichloromethane (5.0 mL) dropwise. The reaction was stirred at 0° C. for 20 minutes and was concentrated, in vacuo. The residue was added to a mixture of dichloromethane (50 mL) and water (50 mL). The organic layer was collected, dried over sodium sulfate, filtered and concentrated under reduced pressure. The crude sample was dissolved in minimal N,N-dimethylformamide and purified via prep-HPLC (Boston C18 21*250 mm 10 μm column; the mobile phase acetonitrile/0.01% aqueous trifluoroacetic acid) to give N-(5-(3-methoxybenzyl)thiazol-2-yl)-1-methyl-6-oxo-1,6-dihydropyridazine-3-carboxamide as a white solid (0.0692 g, 0.195 mmol, 30%). $^1$H NMR (400 MHz, Dimethylsulfoxide-d$_6$) δ 12.28 (s, 1H), 7.89-7.91 (d, J=7.6 Hz, 1H), 7.35 (s, 1H), 7.24-7.26 (t, J=6.2 Hz, 1H), 7.04-7.06 (d, J=7.6 Hz, 1H), 6.80-6.86 (m, 3H), 4.09 (s, 2H), 3.77 (s, 3H), 3.745 (s, 3H); LCMS (ESI) m/z: 357.1 [M+H]$^+$.

Example 213. Preparation of N-(5-(4-chlorobenzyl)thiazol-2-yl)-1-methyl-6-oxo-1,4,5,6-tetrahydropyridazine-3-carboxamide (213)

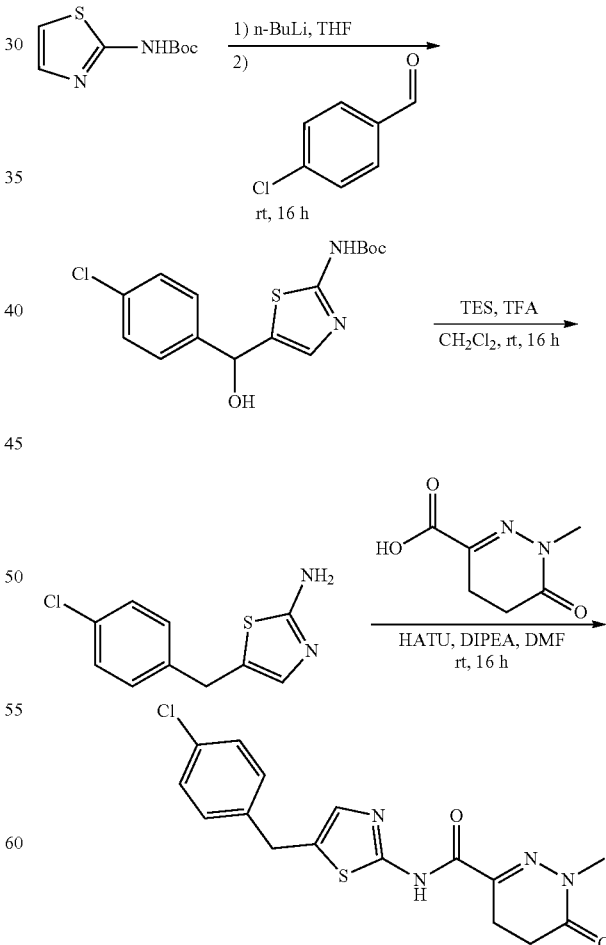

Step 1: Preparation of tert-butyl 5-((4-chlorophenyl)(hydroxy)methyl)thiazol-2-ylcarbamate

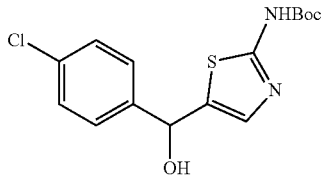 [SMILES: CC(C)(C)OC(=O)Nc1ncc(C(O)c2ccc(Cl)cc2)s1]

To a solution of tert-butyl thiazol-2-ylcarbamate (1.00 g, 5.00 mmol) in tetrahydrofuran (40 mL) at −78° C. was added n-butyllithium (4.4 mL, 11 mmol, 2.5 M in hexanes) dropwise under nitrogen. The reaction was stirred at −78° C. for 1 h and a solution of 4-chlorobenzaldehyde (0.66 g, 4.75 mmol) in tetrahydrofuran (10 mL) was added dropwise at −78° C. The reaction mixture was then stirred at −78° C. for 30 minutes and warmed to room temperature 16 h. The reaction was quenched with aqueous ammonium chloride solution, extracted with ethyl acetate (40 mL×2). The combined organic phases were washed with brine (40 mL), dried over sodium sulfate, filtered and concentrated. The residue was purified by column chromatography (Biotage, 40 g silica gel, eluted with ethyl acetate in petroleum ether from 40% to 50%) to yield tert-butyl 5-((4-chlorophenyl)(hydroxy)methyl)thiazol-2-ylcarbamate (0.6 g, 1.76 mmol, 35%) as an off-white solid. LCMS (ESI) m/z: 341.1 [M+H]$^+$.

Step 2: Preparation of 5-(4-chlorobenzyl)thiazol-2-amine

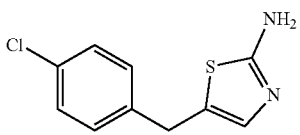 [SMILES: Nc1ncc(Cc2ccc(Cl)cc2)s1]

To a solution of tert-butyl 5-((4-chlorophenyl)(hydroxy)methyl)thiazol-2-ylcarbamate (0.55 g, 1.62 mmol) in dichloromethane (20 mL) at room temperature was added triethylsilane (2 mL, 12.9 mmol). Reaction mixture was cooled to 0° C. and then trifluoroacetic acid (1.65 mL, 21.8 mmol) was added dropwise. After the addition, the reaction was stirred at room temperature 16 h. The volatiles were removed under reduced pressure and the residue was diluted with dichloromethane (10 mL), neutralized with aqueous sodium bicarbonate solution and extracted with dichloromethane (20 mL×2). The combined organic layers were washed with brine (20 mL), dried over sodium sulfate, filtered and concentrated. The crude sample was purified by CombiFlash (Biotage, 40 g silica gel, eluted with methanol:dichloromethane=1:15) to afford 5-(4-chlorobenzyl)thiazol-2-amine (0.17 g, 0.76 mmol, 47%) as a white solid. LCMS (ESI) m/z: 225.1 [M+H]$^+$.

Step 3: Preparation of N-(5-(4-chlorobenzyl)thiazol-2-yl)-1-methyl-6-oxo-1,4,5,6-tetrahydropyridazine-3-carboxamide A solution of 1-methyl-6-oxo-1,4,5,6-tetrahydropyridazine-3-carboxylic acid (0.110 g, 0.72 mmol), 1-[bis(dimethylamino)methylene]-1H-1,2,3-triazolo[4,5-b]pyridinium 3-oxid hexafluorophosphate (0.3 g, 0.08 mmol) and N,N-diisopropylethylamine (0.22 mL, 1.33 mmol) in N,N-dimethylformamide (10 mL) was stirred at room temperature for 30 minutes. Then the 5-(4-chlorobenzyl)thiazol-2-amine (0.15 g, 0.67 mmol) was added and the reaction mixture was stirred at room temperature 16 h. The reaction solution was diluted with ethyl acetate/water (20 mL/20 mL) and extracted with ethyl acetate (20 mL×2). The combined organic phases were washed with brine (20 mL), dried over sodium sulfate, filtered and concentrated. The crude sample was dissolved in minimal N,N-dimethylformamide and purified by prep-HPLC (Boston C18 21*250 mm 10 μm column. The mobile phase was acetonitrile/10 mM ammonium acetate aqueous solution) to yield N-(5-(4-chlorobenzyl)thiazol-2-yl)-1-methyl-6-oxo-1,4,5,6-tetrahydropyridazine-3-carboxamide (0.140 g, 0.38 mmol, 57.8%) as a white solid. $^1$H NMR (500 MHz, Methanol-d$_4$) δ 7.25-7.35 (m, 4H), 7.24 (s, 1H), 4.13 (s, 2H), 3.46 (s, 3H), 2.94 (t, J=8.5 Hz, 2H), 2.60 (t, J=8.5 Hz, 2H); LCMS (ESI) m/z: 363.0 [M+H]$^+$.

Example 214. Preparation of N-(5-(1-(3-fluorophenyl)ethyl)thiazol-2-yl)-1-methyl-6-oxo-1,4,5,6-tetrahydropyridazine-3-carboxamide (214)

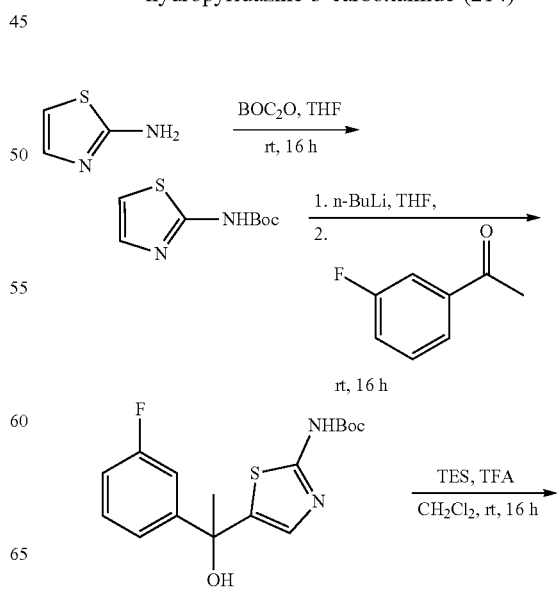

Step 1: Preparation of tert-butyl thiazol-2-ylcarbamate

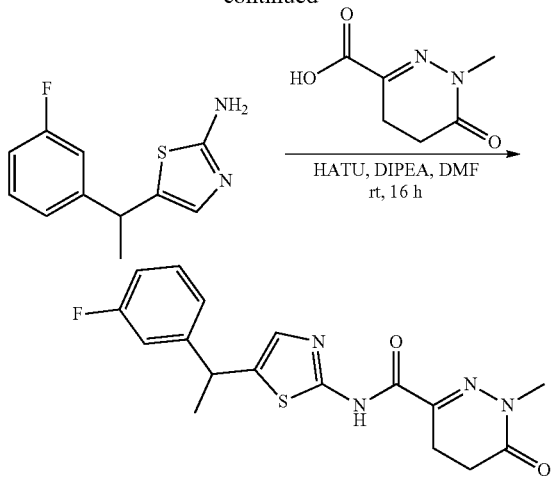

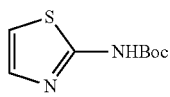

To a solution of thiazol-2-amine (10.0 g, 100 mmol) in tetrahydrofuran (30 mL) at room temperature was added a solution of di-tert-butyl dicarbonate (26.2 g, 120 mmol) in tetrahydrofuran (10 mL) slowly. After the addition, the reaction was stirred at room temperature 16 h. The reaction was concentrated, and the resulting residue was dispersed in a solution mixture of petroleum ether/ethyl acetate=100 mL/2 mL, filtered and dried in vacuo to give tert-butyl thiazol-2-ylcarbamate (18 g, 90 mmol, 90%) as a yellow solid. $^1$H NMR (500 MHz, Dimethylsulfoxide-$d_6$): δ 11.41 (s, 1H), 7.35 (d, J=3.5 Hz, 1H), 7.14 (d, J=4 Hz, 1H), 1.48 (s, 9H); LCMS (ESI) m/z: 145.0 [M-55]+. Used in the next step directly without additional purification.

Step 2: Preparation of tert-butyl 5-(1-(3-fluorophenyl)-1-hydroxyethyl)thiazol-2-ylcarbamate

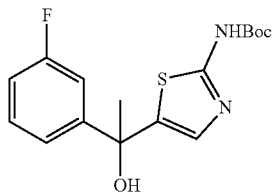 [SMILES: CC(C)(C)OC(=O)Nc1ncc(C(C)(O)c2cccc(F)c2)s1]

Used the same procedure as for synthesis of compound 213. Compound tert-butyl 5-(1-(3-fluorophenyl)-1-hydroxyethyl)thiazol-2-ylcarbamate (0.9 g, 2.66 mmol, 53%) was obtained as a yellow solid. LCMS (ESI) m/z: 339.1 [M+H]+. Used in the next step directly without additional purification.

Step 3: Preparation of 5-(1-(3-fluorophenyl)ethyl)thiazol-2-amine

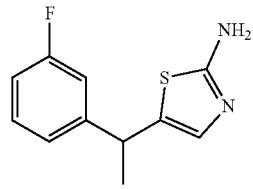

Used the same procedure as for synthesis of compound 213 5-(4-chlorobenzyl)thiazol-2-amine using tert-butyl 5-(1-(3-fluorophenyl)-1-hydroxyethyl)thiazol-2-ylcarbamate (0.4 g, 1.18 mmol). Compound 5-(1-(3-fluorophenyl)ethyl)thiazol-2-amine (0.15 g, 0.67 mmol, 57%) was obtained as a white solid. LCMS (ESI) m/z: 223.1 [M+H]+. Used in the next step directly without additional purification.

Step 4: Preparation of N-(5-(1-(3-fluorophenyl)ethyl)thiazol-2-yl)-1-methyl-6-oxo-1,4,5,6-tetrahydropyridazine-3-carboxamide

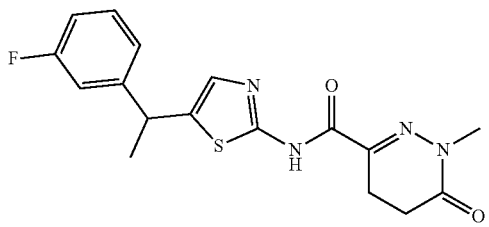 [SMILES: CC(c1cccc(F)c1)c1cnc(NC(=O)C2=NN(C)C(=O)CC2)s1]

Used the same procedure as for synthesis of compound 213 N-(5-(4-chlorobenzyl)thiazol-2-yl)-1-methyl-6-oxo-1,4,5,6-tetrahydropyridazine-3-carboxamide using 5-(1-(3-fluorophenyl)ethyl)thiazol-2-amine (0.13 g, 0.58 mmol). Compound N-(5-(1-(3-fluorophenyl)ethyl)thiazol-2-yl)-1-methyl-6-oxo-1,4,5,6-tetrahydropyridazine-3-carboxamide (0.131 g, 0.36 mmol, 62%) was obtained as a white solid. $^1$H NMR (500 MHz, Methanol-$d_4$) δ 7.36 (m, 1H), 7.25 (s, 1H), 7.14 (d, J=8 Hz, 1H), 7.04 (m, 1H), 6.98 (m, 1H), 4.40 (m, 1H), 3.46 (s, 3H), 2.94 (t, J=9 Hz, 2H), 2.60 (t, J=9 Hz, 2H), 1.71 (d, J=7.5 Hz, 3H); LCMS (ESI) m/z: 361.1 [M+H]+.

Example 215. Preparation of N-(1-(3-chlorobenzyl)-1H-pyrazol-4-yl)-1-methyl-6-oxo-1,6-dihydropyridazine-3-carboxamide (215)

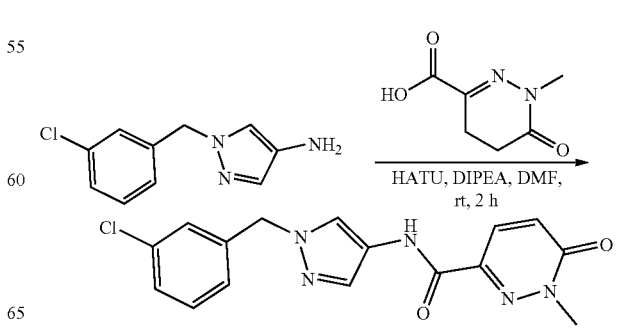

Step 1: Preparation of N-(1-(3-chlorobenzyl)-1H-pyrazol-4-yl)-1-methyl-6-oxo-1,6-dihydropyridazine-3-carboxamide

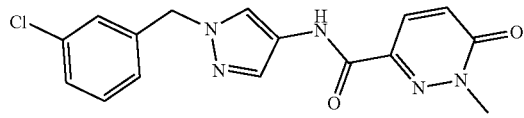 [SMILES: Cn1nc(C(=O)Nc2cnn(Cc3cccc(Cl)c3)c2)ccc1=O]

To a stirred solution of 1-(3-chlorobenzyl)-1H-pyrazol-4-amine (0.090 g, 0.44 mmol), 1-methyl-6-oxo-1,6-dihydropyridazine-3-carboxylic acid (0.080 g, 0.52 mmol) and 1-[bis(dimethylamino)methylene]-1H-1,2,3-triazolo[4,5-b]pyridinium 3-oxid hexafluorophosphate (0.198 g, 0.52 mmol) in N,N-dimethylformamide (5.00 mL) was added N,N-diisopropylethylamine (0.168 g, 1.31 mmol). After addition, the reaction mixture was stirred at room temperature for 2 h. The crude sample was dissolved in minimal N,N-dimethylformamide and purified via prep-HPLC Sunfire prep C18 10 μm OBD 19*250 mm; mobile phase: [water (0.05% trifluoroacetic acid)-acetonitrile]; B %: 60%-88%, 15 minutes) to give N-(1-(3-chlorobenzyl)-1H-pyrazol-4-yl)-1-methyl-6-oxo-1,6-dihydropyridazine-3-carboxamide (0.040 g, 0.12 mmol, 26.8%) as a white solid. $^1$H NMR (500 MHz, Dimethylsulfoxide-$d_5$) δ 10.60 (s, 1H), 8.19 (s, 1H), 7.91 (d, J=9.7 Hz, 1H), 7.72 (s, 1H), 7.38 (d, J=7.4 Hz, 2H), 7.28 (s, 1H), 7.20 (d, J=6.7 Hz, 1H), 7.05 (d, J=9.7 Hz, 1H), 5.34 (s, 2H), 3.78 (s, 3H); LCMS (ESI) m/z: 344.0 [M+H]$^+$.

Example 216. Preparation of N-(5-(3-chloro-5-fluorobenzyl)thiazol-2-yl)-1-methyl-6-oxo-1,4,5,6-tetrahydropyridazine-3-carboxamide (216)

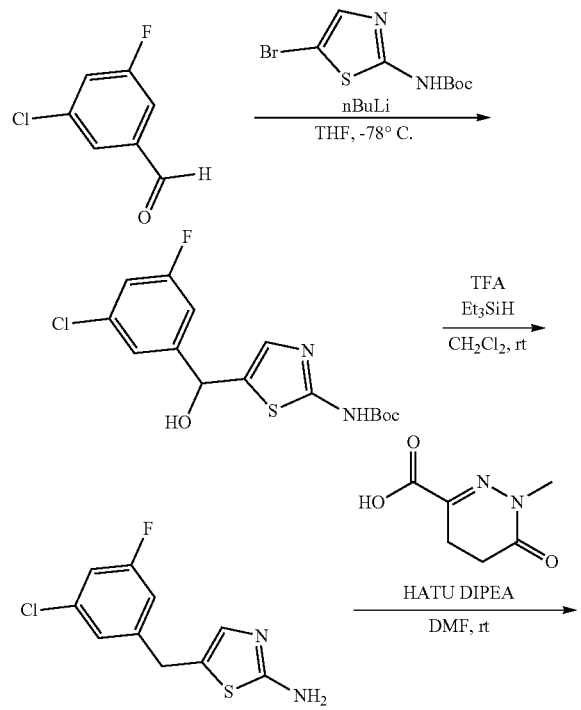

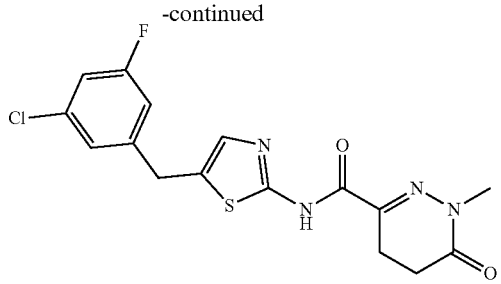

Step 1: Preparation of tert-butyl (5-((3-chloro-5-fluorophenyl)(hydroxy)methyl)thiazol-2-yl)carbamate

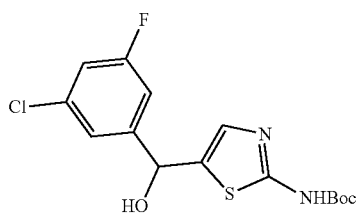 [SMILES: CC(C)(C)OC(=O)Nc1ncc(C(O)c2cc(F)cc(Cl)c2)s1]

Dissolved tert-butyl (5-bromothiazol-2-yl)carbamate (0.5 g, 2.49 mmol) in tetrahydrofuran (12.4 mL) and cooled to −78° C. Carefully added n-butyllithium (1.6M in hexanes, 1.59 mL, 3.98 mmol) and stirred for 10 minutes, followed by 3-chloro-5-fluorobenzaldehyde (424 μL, 3.48 mmol). Quenched with saturated aqueous ammonium chloride (15 mL) and extracted with ethyl acetate (20 mL). Washed with brine (15 mL), then dried over sodium sulfate. Filtered, then concentrated in vacuo. Purified reaction by column chromatography (eluting with 0-50% ethyl acetate/hexanes through 40 g of silica gel) to give tert-butyl (5-((3-chloro-5-fluorophenyl)(hydroxy)methyl)thiazol-2-yl)carbamate as an orange oil (138 mg, 0.384 mmol, 15%). $^1$H NMR (300 MHz, Chloroform-d) δ 7.25-6.95 (m, 4H), 5.99 (s, 1H), 1.54 (s, 9H).

Step 2: Preparation of 5-(3-chloro-5-fluorobenzyl)thiazol-2-amine

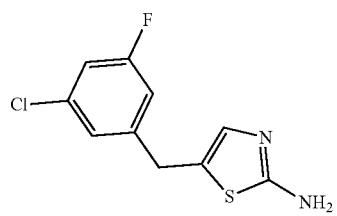 [SMILES: Nc1ncc(Cc2cc(F)cc(Cl)c2)s1]

Dissolved tert-butyl (5-((3-chloro-5-fluorophenyl)(hydroxy)methyl)thiazol-2-yl)carbamate (0.138 g, 0.3845 mmol) in methylene chloride (1.92 mL) and added triethylsilane (306 μL, 1.92 mmol) and 2,2,2-trifluoroacetic acid (235 μL, 3.07 mmol). Stirred 16 h at room temperature. Concentrated to remove solvent. Diluted with ethyl acetate (15 mL), then washed with saturated aqueous sodium bicarbonate (10 mL), and then brine (10 mL). The combined organic layers were dried over sodium sulfate, filtered, and concentrated. Material is taken crude to next step.

Step 3: Preparation of N-(5-(3-chloro-5-fluorobenzyl)thiazol-2-yl)-1-methyl-6-oxo-1,4,5,6-tetrahydropyridazine-3-carboxamidecarboxamide

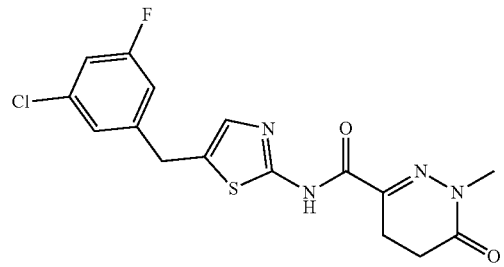 [SMILES: CN1N=C(C(=O)Nc2ncc(Cc3cc(F)cc(Cl)c3)s2)CCC1=O]

Combined 5-(3-chloro-5-fluorobenzyl)thiazol-2-amine (0.093 g, 0.383 mmol) and 1-methyl-6-oxo-1,4,5,6-tetrahydropyridazine-3-carboxylic acid (0.060 g, 0.383 mmol) in a 25 mL round bottom flask and added 2-(3H-[1,2,3]triazolo[4,5-b]pyridin-3-yl)-1,1,3,3-tetramethyluronium tetrafluoroborate (0.123 g, 0.3831 mmol). Dissolved in N,N'-dimethylformamide (1.91 mL) and added N-N-N,N-diisopropylethyl amine (100 μL, 0.5746 mmol). Stirred at room temperature 16 h. Diluted with ethyl acetate (15 mL) and washed 3 times with water (10 mL), then brine (10 mL). The combined organic layers were dried over sodium sulfate, filtered, and concentrated. Purified reaction by column chromatography (eluting with 0-100% ethyl acetate/hexanes through 24 g of silica gel) to give N-(5-(3-chloro-5-fluorobenzyl)thiazol-2-yl)-1-methyl-6-oxo-1,4,5,6-tetrahydropyridazine-3-carboxamidecarboxamide as a pale yellow solid (29 mg, 0.076 mmol, 20%). $^1$H NMR (300 MHz, Chloroform-d) δ 7.24 (s, 1H), 7.05 (s, 1H), 7.00 (d, J=8.3 Hz, 1H), 6.87 (d, J=9.0 Hz, 1H), 4.09 (s, 2H), 3.47 (s, 3H), 2.99 (t, J=8.6 Hz, 2H), 2.61 (t, J=8.6 Hz, 2H); LCMS (ESI) m/z 381.4 [M+H]$^+$.

Example 217. Preparation of N-(5-(3-fluorobenzyl)thiazol-2-yl)-1-methyl-1,4,5,6-tetrahydropyridazine-3-carboxamide (217)

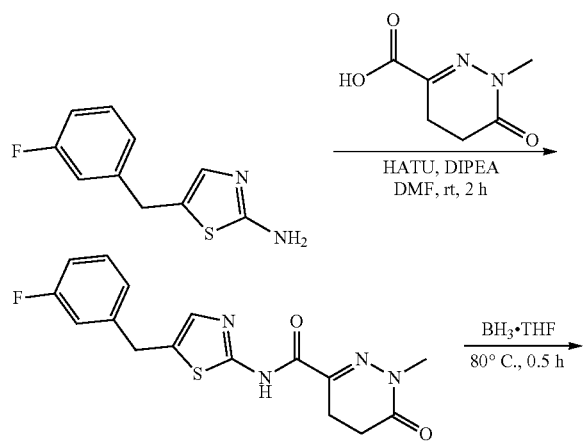

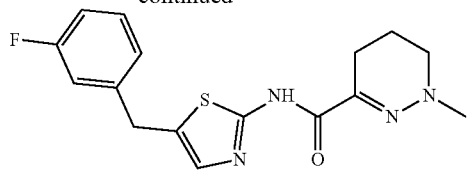

Step 1: Preparation of N-(5-(3-fluorobenzyl)thiazol-2-yl)-1-methyl-6-oxo-1,4,5,6-tetrahydropyridazine-3-carboxamide

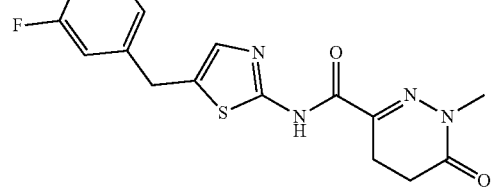

To a stirred solution of 5-(3-fluorobenzyl)thiazol-2-amine (0.208 g, 1.00 mmol), 1-methyl-6-oxo-1,4,5,6-tetrahydropyridazine-3-carboxylic acid (0.172 g, 1.10 mmol) and 1-[bis(dimethylamino)methylene]-1H-1,2,3-triazolo[4,5-b]pyridinium 3-oxid hexafluorophosphate (0.418 g, 1.10 mmol) in N,N-dimethylformamide (5.00 mL) was added N,N-diisopropylethylamine (0.387 g, 3.00 mmol). After addition, the reaction mixture was stirred at room temperature for 2 h. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give (5-(3-fluorobenzyl)thiazol-2-yl)-1-methyl-6-oxo-1,4,5,6-tetrahydropyridazine-3-carboxamide (0.240 g, 0.69 mmol, 69.4%) as an off-white solid. LCMS (ESI) m/z: 347.0 [M+H]$^+$.

Step 2: Preparation of N-(5-(3-fluorobenzyl)thiazol-2-yl)-1-methyl-1,4,5,6-tetrahydropyridazine-3-carboxamide

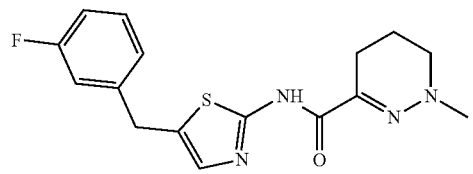 [SMILES: CN1CCCC(C(=O)Nc2ncc(Cc3cccc(F)c3)s2)=N1]

To a solution of (5-(3-fluorobenzyl)thiazol-2-yl)-1-methyl-6-oxo-1,4,5,6-tetrahydropyridazine-3-carboxamide (0.140 g, 0.40 mmol) in tetrahydrofuran (10.0 mL) was added borane-tetrahydrofuran (4.00 mL, 4.00 mmol, 1 M). The mixture was stirred at 80° C. for 0.5 h. After being cooled to 0° C., the mixture was quenched with methanol (10.0 mL) and adjusted to pH 2 with aqueous 1 N hydrogen chloride solution. The resulting mixture was stirred at 80° C. for 30 minutes. After being concentrated, the residue was dissolved in ethyl acetate (50 mL), washed with aqueous saturated sodium bicarbonate solution (25 mL) and brine (25 mL), dried over sodium sulfate, filtered and concentrated. The crude sample was dissolved in minimal N,N-dimethylformamide and purified via prep-HPLC (Sunfire prep C18 10 μm OBD 19*250 mm; mobile phase: [water (0.05% trifluoroacetic acid)-acetonitrile]; B %: 60%-88%, 15 minutes) to give N-(5-(3-fluorobenzyl)thiazol-2-yl)-1-methyl-1,4,5,6-tetrahydropyridazine-3-carboxamide (0.070 g, 0.21 mmol, 52.7%) as a white solid. $^1$H NMR (500 MHz, Dimethylsulfoxide-d$_6$) δ 10.79 (s, 1H), 7.36 (td, J=8.0, 6.4 Hz, 1H), 7.23 (s, 1H), 7.17-6.99 (m, 3H), 4.10 (s, 2H), 3.18-2.96 (m, 5H), 2.26 (t, J=6.6 Hz, 2H), 1.86-1.70 (m, 2H); LCMS (ESI) m/z: 333.1 [M+H]$^+$.

Example 218. Preparation of N-(4-chloro-5-(3-fluorobenzyl)thiazol-2-yl)-1-methyl-6-oxo-1,4,5,6-tetrahydropyridazine-3-carboxamide (218)

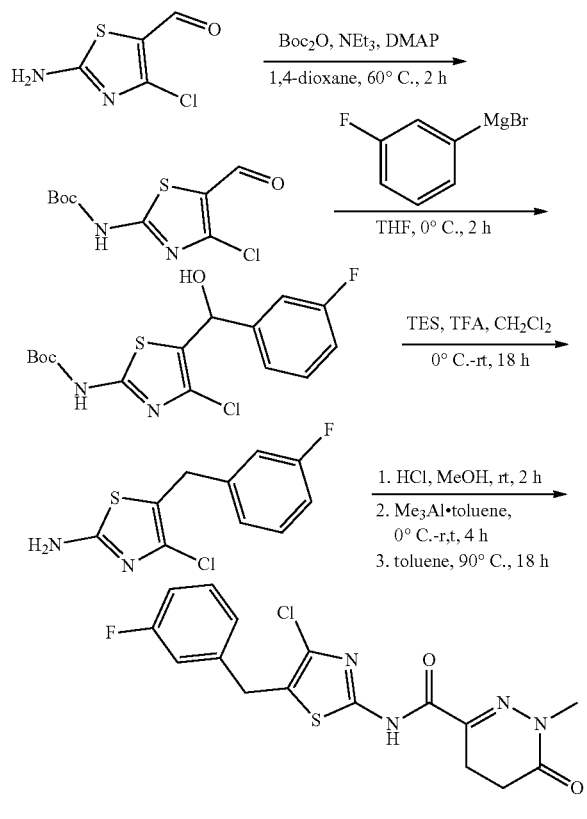

Step 1: Preparation of tert-butyl 4-chloro-5-formylthiazol-2-ylcarbamate

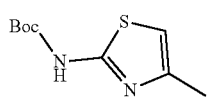

A solution of 2-amino-4-chlorothiazole-5-carbaldehyde (1.00 g, 6.17 mmol), di-tert-butyl dicarbonate (1.6 g, 7.40 mmol) and 4-(dimethylamino)pyridine (0.076 g, 0.62 mmol) in dry 1,4-dioxane (15 mL) was stirred at 60° C. for 2 h. After being concentrated, the residue was purified by column chromatography (silica gel, petroleum ether/ethyl acetate=4/1). Compound tert-butyl 4-chloro-5-formylthiazol-2-ylcarbamate (1.30 g, 4.96 mmol, 80.4%) was obtained as a brown solid. LCMS (ESI) m/z: 263.0 [M+H]$^+$.

Step 2: Preparation of tert-butyl 4-chloro-5-((3-fluorophenyl)(hydroxy)methyl)thiazol-2-ylcarbamate

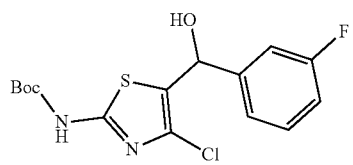 [SMILES: CC(C)(C)OC(=O)Nc1nc(Cl)c(C(O)c2cccc(F)c2)s1]

To an ice-cooled solution of tert-butyl 4-chloro-5-formylthiazol-2-ylcarbamate (1.12 g, 4.27 mmol) in tetrahydrofuran (20 mL) was added a solution of 3-fluorophenyl) magnesium bromide (8.55 mL, 8.55 mmol, 1 M in tetrahydrofuran) dropwise. The mixture was stirred at 0° C. for 1 h. The reaction was quenched with aqueous saturated ammonium chloride solution (10 mL) and extracted with ethyl acetate (50 mL×3). The combined organic layers were washed with brine (50 mL), dried with sodium sulfate, filtered and concentrated. The residue was purified by column chromatography (silica gel, petroleum ether/ethyl acetate=4/1) to afford tert-butyl 4-chloro-5-((3-fluorophenyl)(hydroxy)methyl)thiazol-2-ylcarbamate (1.01 g, 2.82 mmol, 66.1%) as a yellow solid. LCMS (ESI) m/z: 359.0 [M+H]$^+$.

Step 3: Preparation of 4-chloro-5-(3-fluorobenzyl)thiazol-2-amine

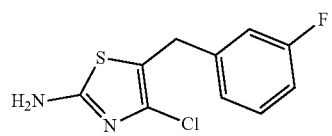 [SMILES: Nc1nc(Cl)c(Cc2cccc(F)c2)s1]

To an ice-cooled solution of tert-butyl 4-chloro-5-((3-fluorophenyl)(hydroxy)methyl)thiazol-2-ylcarbamate (1.00 g, 2.79 mmol) and triethylsilane (3.60 mL, 22.32 mmol) in dichloromethane (10.0 mL) was added trifluoroacetic acid (2.90 mL, 39.1 mmol) dropwise. The mixture was warmed to room temperature and stirred for 18 h. The volatiles were removed under reduced pressure and the resulting residue was purified by column chromatography (silica gel, petroleum ether/ethyl acetate=3/1) to yield 4-chloro-5-(3-fluorobenzyl)thiazol-2-amine (0.650 g, 2.69 mmol, 96.3%) as a yellow solid. LCMS (ESI) m/z: 243.1 [M+H]$^+$.

Step 4: Preparation of N-(4-chloro-5-(3-fluorobenzyl)thiazol-2-yl)-1-methyl-6-oxo-1,4,5,6-tetrahydropyridazine-3-carboxamide

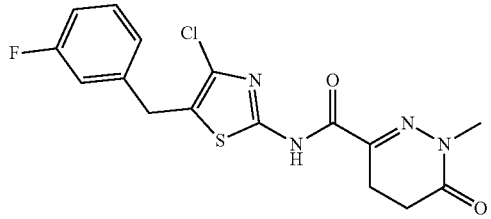

To a solution of 4-chloro-5-(3-fluorobenzyl)thiazol-2-amine (0.557 g, 2.30 mmol) in methanol (5.00 mL) was added hydrogen chloride (1.15 ml, 3.45 mmol, 3.0 M in methanol). The mixture was stirred at room temperature for 2 h. The volatiles were removed under reduced pressure and the resulting residue was dissolved in dry toluene (5.00 mL). Trimethylaluminum (1.15 mL, 2.30 mmol, 2.0 M in toluene) was added dropwise at 0° C. The reaction mixture was warmed to room temperature and stirred for 4 h. This solution was added dropwise to a solution of methyl 1-methyl-6-oxo-1,4,5,6-tetrahydropyridazine-3-carboxylate (0.326 g, 1.92 mmol) in toluene (1.00 mL). The mixture was stirred at 90° C. for 18 h in a sealed tube. After being cooled to room temperature, the mixture was quenched with water (25 mL) and extracted with ethyl acetate (50 mL×3). The combined organic layers were washed with aqueous 1 N hydrogen chloride (50 mL) and brine (50 mL), dried over sodium sulfate, filtered and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(4-chloro-5-(3-fluorobenzyl)thiazol-2-yl)-1-methyl-6-oxo-1,4,5,6-tetrahydropyridazine-3-carboxamide (0.100 g, 0.26 mmol, 31.3%) was obtained as a white solid. $^1$H NMR (500 MHz, Dimethylsulfoxide-$d_5$) δ 12.38 (s, 1H), 7.39 (d, J=6.3 Hz, 1H), 7.20-6.95 (m, 3H), 4.11 (s, 2H), 3.35 (s, 3H), 2.81 (t, J=8.5 Hz, 2H), 2.53 (d, J=8.5 Hz, 2H); LCMS (ESI) m/z: 381.0 [M+H]$^+$.

Example 219. Preparation of N-(5-(3-fluorobenzyl)-4-methylthiazol-2-yl)-1-methyl-6-oxo-1,4,5,6-tetrahydropyridazine-3-carboxamide (219)

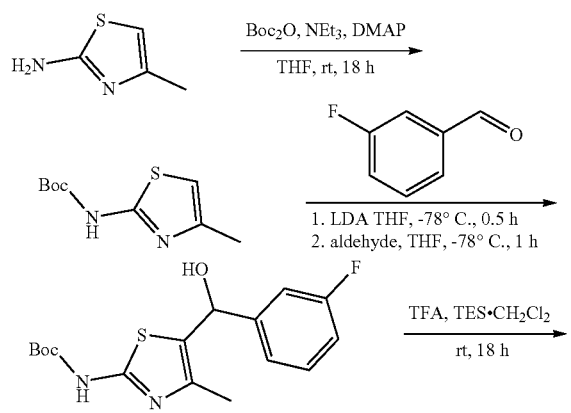

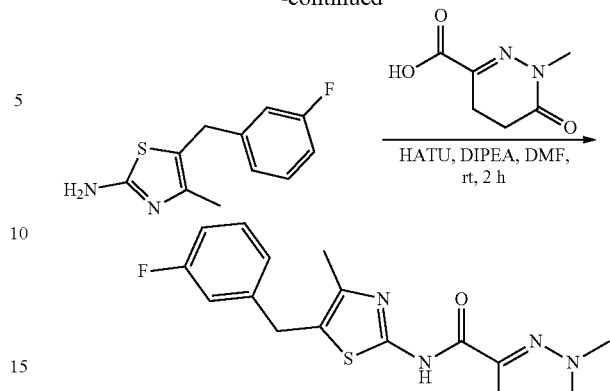

Step 1: Preparation of tert-butyl 4-methylthiazol-2-ylcarbamate

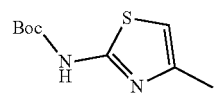

A solution of 4-methylthiazol-2-amine (2.50 g, 21.9 mmol), di-tert-butyl dicarbonate (5.26 g, 24.1 mmol), 4-(dimethylamino)pyridine (0.025 g, 10 wt. %) and triethylamine (3.95 mL, 28.5 mmol) in dry tetrahydrofuran (50 mL) was stirred at room temperature for 18 h. After being filtered, the filtrate was concentrated, and purified by column chromatography (silica gel, petroleum ether/ethyl acetate=10/1) to give tert-butyl 4-methylthiazol-2-ylcarbamate (2.70 g, 12.6 mmol, 57.6%) as a white solid. LCMS (ESI) m/z: 215.1 [M+H]$^+$.

Step 2: Preparation of tert-butyl 5-((3-fluorophenyl)(hydroxy)methyl)-4-methylthiazol-2-ylcarbamate

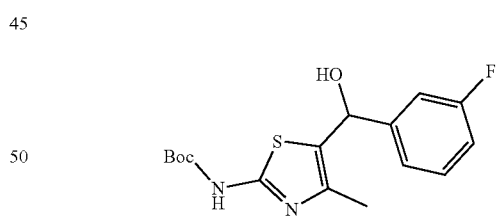

To a solution of tert-butyl 4-methylthiazol-2-ylcarbamate (1.07 g, 5.00 mmol) in tetrahydrofuran (15 mL) was added lithium diisopropylamide (6.25 mL, 12.5 mmol, 2.0 M) dropwise at −78° C. The mixture was stirred at −78° C. for 30 minutes before a solution of 3-fluorobenzaldehyde (0.744 g, 6.00 mmol) was added dropwise. The mixture was stirred for another 1 h at −78° C. and it was quenched with aqueous saturated ammonium chloride (50 mL). The mixture was extracted with ethyl acetate (50 mL×3). The combined organic layers were washed with brine (50 mL), dried with sodium sulfate, filtered and concentrated. The residue was purified by column chromatography (silica gel, petroleum ether/ethyl acetate=1/1) to give tert-butyl 5-((3-fluorophenyl)(hydroxy)methyl)-4-methylthiazol-2-ylcarbamate (1.30 g, 3.85 mmol, 76.9%) as a colorless oil. LCMS (ESI) m/z: 339.1 [M+H]⁺.

Step 3: Preparation of
5-(3-fluorobenzyl)-4-methylthiazol-2-amine

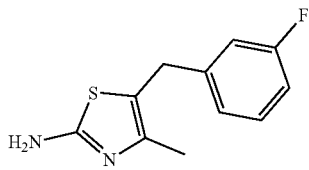

To an ice-cooled solution of tert-butyl 5-((3-fluorophenyl)(hydroxy)methyl)-4-methylthiazol-2-ylcarbamate (0.338 g, 1.00 mmol) and triethylsilane (0.930 g, 8.00 mmol) in dichloromethane (5.00 mL) was added trifluoroacetic acid (1.60 g, 14.0 mmol) dropwise. The mixture was warmed to room temperature and stirred for 18 h. The volatiles were removed under reduced pressure and the residue was purified by column chromatography (silica gel, petroleum ether/ ethyl acetate=1/1) to give 5-(3-fluorobenzyl)-4-methylthiazol-2-amine (0.206 g, 0.93 mmol, 92.8%) as a white solid. LCMS (ESI) m/z: 223/1 [M+H]⁺.

Step 4: Preparation of N-(5-(3-fluorobenzyl)-4-methylthiazol-2-yl)-1-methyl-6-oxo-1,4,5,6-tetrahydropyridazine-3-carboxamide

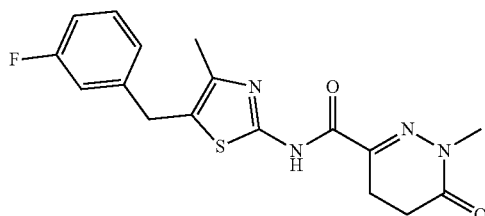

To a stirred solution of 5-(3-fluorobenzyl)-4-methylthiazol-2-amine (0.180 g, 0.81 mmol), 1-methyl-6-oxo-1,4,5,6-tetrahydropyridazine-3-carboxylic acid (0.151 g, 0.97 mmol) and 1-[bis(dimethylamino)methylene]-1H-1,2,3-triazolo[4,5-b]pyridinium 3-oxid hexafluorophosphate (0.369 g, 0.97 mmol) in N,N-dimethylformamide (5.00 mL) was added N,N-diisopropylethylamine (0.313 g, 2.43 mmol). After addition, the reaction mixture was stirred at room temperature for 2 h. The crude sample was dissolved in minimal N,N-dimethylformamide and purified via prep-HPLC (Boston C18 21*250 mm 10 μm column; acetonitrile/ 0.01% aqueous trifluoroacetic acid) to give N-(5-(3-fluorobenzyl)-4-methylthiazol-2-yl)-1-methyl-6-oxo-1,4,5,6-tetrahydropyridazine-3-carboxamide (0.066 mg, 0.18 mmol, 22.6%) as a white solid. ¹H NMR (500 MHz, Dimethylsulfoxide-d₆) δ 11.83 (s, 1H), 7.36 (dd, J=14.9, 7.4 Hz, 1H), 7.06 (dd, J=18.6, 8.6 Hz, 3H), 4.07 (s, 2H), 2.81 (t, J=8.5 Hz, 2H), 2.59-2.41 (m, 6H), 2.27 (s, 3H); LCMS (ESI) m/z: 361.1 [M+H]⁺.

Example 220. Preparation of N-(5-(3-fluorobenzyl)thiazol-2-yl)-N,1-dimethyl-6-oxo-1,4,5,6-tetrahydropyridazine-3-carboxamide (220)

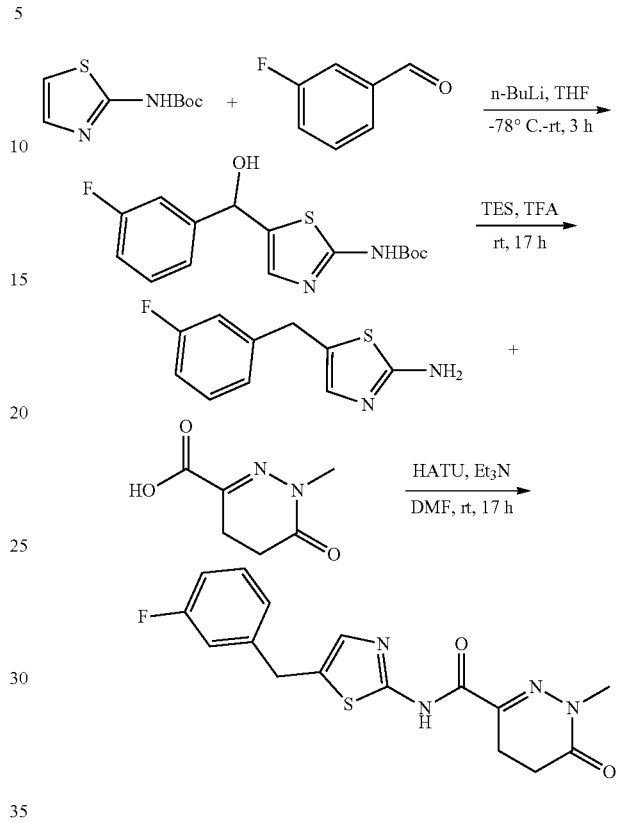

Step 1: Preparation of tert-butyl 5-((3-fluorophenyl)(hydroxy)methyl)thiazol-2-ylcarbamate

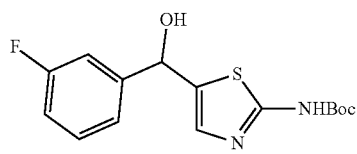 [SMILES: CC(C)(C)OC(=O)Nc1ncc(C(O)c2cccc(F)c2)s1]

To a stirred solution of tert-butyl thiazol-2-ylcarbamate (5.0 g, 25.0 mmol) in tetrahydrofuran (100 mL) at −78° C. was added n-butyllithium (22 mL, 55 mmol, 2.5 M) dropwise over 5 minutes under nitrogen. After stirring for 30 minutes, 3-fluorobenzaldehyde (4.65 g, 37.5 mmol) was added. The solution was warmed to room temperature over 2 h, and then poured into ice-water (100 mL). The solution was adjusted to pH=6-7 with 1 M hydrogen chloride (20 mL), extracted with ethyl acetate (100 mL×2), washed with brine (100 mL), dried over sodium sulfate, filtered and concentrated in vacuo. The crude sample was treated with tert-butyl methyl ether (50 mL to afford tert-butyl 5-((3-fluorophenyl)(hydroxy)methyl)thiazol-2-ylcarbamate (6.5 g, 20.0 mmol, 80%) as a brown solid. LCMS (ESI) m/z: 325.1 [M+H]⁺.

Step 2: Preparation of 5-(3-fluorobenzyl)thiazol-2-amine

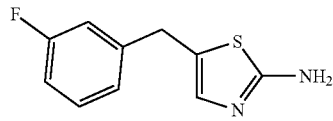 [SMILES: Nc1ncc(Cc2cccc(F)c2)s1]

To a stirred solution of tert-butyl 5-((3-fluorophenyl)(hydroxy)methyl)thiazol-2-ylcarbamate (1.0 g, 3.1 mmol) in trifluoroacetic acid (15.0 mL) at 0° C. was added triethylsilane (1.39 g, 12.4 mmol). The solution was stirred at room temperature for 17 h. The volatiles were removed under reduced pressure and the crude sample was diluted with aqueous saturated sodium bicarbonate (100 mL) and extracted with ethyl acetate (50 mL×2). The combined organic layers were washed with brine (50 mL), dried over sodium sulfate, filtered and concentrated in vacuo. The crude sample was treated with tert-butyl methyl ether (10 mL) to afford 5-(3-fluorobenzyl)thiazol-2-amine (0.6 g, 2.88 mmol, 93%) as a brown solid. LCMS (ESI) m/z: 209.1 [M+H]⁺.

Step 3: Preparation of N-(5-(3-fluorobenzyl)thiazol-2-yl)-1-methyl-6-oxo-1,4,5,6-tetrahydropyridazine-3-carboxamide

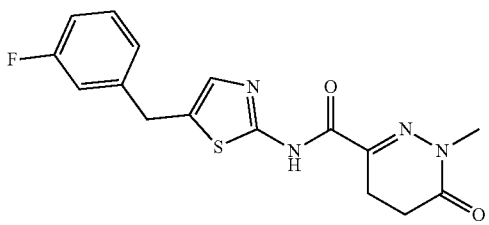 [SMILES: CN1N=C(C(=O)Nc2ncc(Cc3cccc(F)c3)s2)CCC1=O]

A solution of 5-(3-fluorobenzyl)thiazol-2-amine (0.3 g, 1.44 mmol), 1-methyl-6-oxo-1,4,5,6-tetrahydropyridazine-3-carboxylic acid (0.270 g, 1.73 mmol), 1-[bis(dimethylamino)methylene]-1H-1,2,3-triazolo[4,5-b]pyridinium 3-oxid hexafluorophosphate (0.657 g, 1.73 mmol) and triethylamine (0.727 g, 7.2 mmol) in N,N-dimethylformamide (5.00 mL) was stirred at room temperature for 17 h. The crude sample was dissolved in minimal N,N-dimethylformamide and purified via prep-HPLC (Sunfire prep C18 10 µm OBD 19*250 mm; mobile phase: [water (0.05% sodium bicarbonate)-acetonitrile]; B %: 40%-50%, 7 minutes) to give N-(5-(3-fluorobenzyl)thiazol-2-yl)-1-methyl-6-oxo-1,4,5,6-tetrahydropyridazine-3-carboxamide (0.300 g, 0.87 mmol, 60%) as a white solid. ¹H NMR (400 MHz, Chloroform-d) δ 9.98 (s, 1H), 7.25-7.31 (m, 1H), 7.21 (s, 1H), 7.04 (d, J=8.0 Hz, 1H), 6.94 (t, J=6.0 Hz, 2H), 4.10 (s, 2H), 3.45 (s, 3H), 2.97 (t, J=8.8 Hz, 2H), 2.59 (t, J=8.8 Hz, 2H); LCMS (ESI) m/z: 347.0 [M+H]⁺.

Example 221. Preparation of N-(5-(3-fluorobenzyl)thiazol-2-yl)-1-methyl-6-oxo-1,4,5,6-tetrahydropyridazine-3-carboxamide (221)

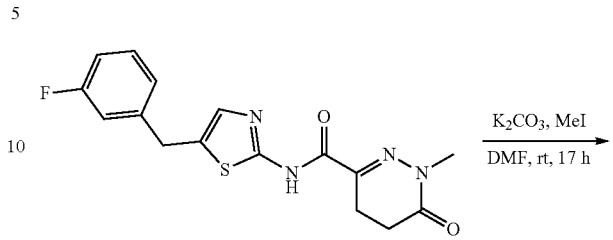

Step 1: Preparation of N-(5-(3-fluorobenzyl)thiazol-2-yl)-N,1-dimethyl-6-oxo-1,4,5,6-tetrahydropyridazine-3-carboxamide

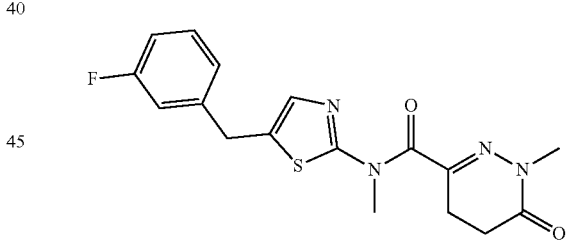

To a stirred solution of N-(5-(3-fluorobenzyl)thiazol-2-yl)-1-methyl-6-oxo-1,4,5,6-tetrahydropyridazine-3-carboxamide (0.200 g, 0.58 mmol) and potassium carbonate (0.120 g, 0.87 mmol) in N,N-dimethylformamide (5.0 mL) was added iodomethane (0.246 g, 1.73 mmol) at room temperature for 17 h. The reaction mixture was filtered, and the filtrate was concentrated. The crude sample was dissolved in minimal N,N-dimethylformamide and purified via prep-HPLC (Sunfire prep C18 10 µm OBD 19*250 mm; mobile phase: [water (0.05% sodium bicarbonate)-acetonitrile]; B %: 40%-50%, 7 minutes) to afford N-(5-(3-fluorobenzyl)thiazol-2-yl)-N,1-dimethyl-6-oxo-1,4,5,6-tetrahydropyridazine-3-carboxamide (0.0625 g, 0.17 mmol, 30%) as a white solid. LCMS (ESI) m/z: 361.1 [M+H]⁺. ¹H NMR (500 MHz, Chloroform-d) δ 7.32 (s, 1H), 7.24-7.28 (m, 2H), 7.02 (d, J=8.0 Hz, 1H), 6.93 (dd, J=9.0 Hz, J=2.0 Hz, 2H), 4.10 (s, 2H), 3.82 (s, 3H), 3.40 (s, 3H), 2.92 (t, J=8.5 Hz, 2H), 2.61 (t, J=8.5 Hz, 2H).

Example 222. Preparation of N-(5-(3-Chlorobenzyl)thiazol-2-yl)-1-isopropyl-6-oxo-1,4,5,6-tetrahydropyridazine-3-carboxamide (222)

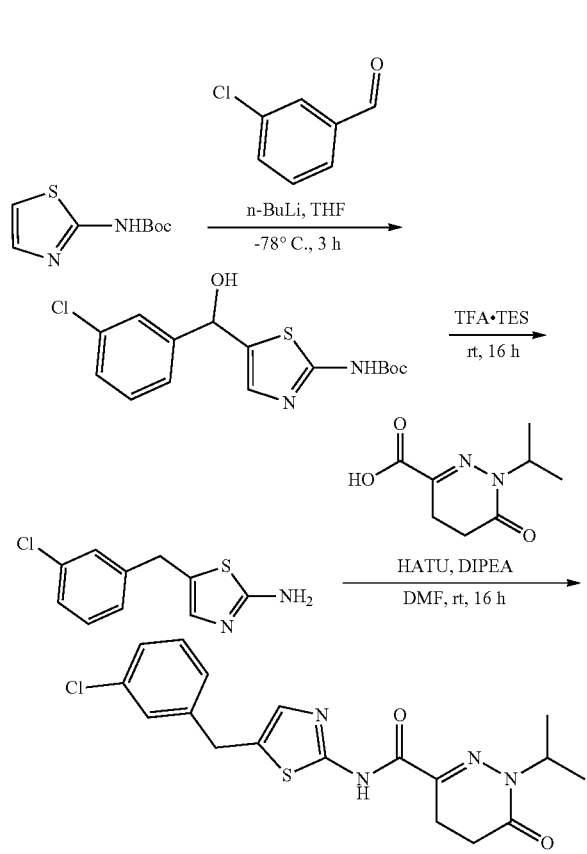

Step 1: Preparation of tert-butyl (5-((3-chlorophenyl)(hydroxy)methyl)thiazol-2-yl)carbamate

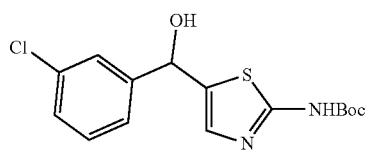 [SMILES: CC(C)(C)OC(=O)Nc1ncc(C(O)c2cccc(Cl)c2)s1]

To a solution of tert-butyl thiazol-2-ylcarbamate (2.8 g, 14.0 mmol) in anhydrous tetrahydrofuran (80 mL) was added n-butyllithium (8.4 mL, 21.0 mmol, 2.5 M in tetrahydrofuran) at −78° C. under nitrogen. The reaction mixture was stirred at −78° C. for 1 h before 3-chlorobenzaldehyde (2.95 g, 21.0 mmol) was added. Reaction was warmed to 0° C. for 3 h, quenched with aqueous solution of ammonium chloride (20 mL) and extracted with ethyl acetate (80 mL×3). The combined organic layers were washed with brine, dried over sodium sulfate, filtered and concentrated in vacuo. The residue was purified by column chromatography (silica gel, petroleum ether/ethyl acetate=2:1) to afford tert-butyl (5-((3-chlorophenyl)(hydroxy)methyl)thiazol-2-yl)carbamate (2.8 g, 8.2 mmol, 58.6%) as a brown solid. LCMS (ESI) m/z: 341.1 [M+H]$^+$.

Step 2: Preparation of 5-(3-chlorobenzyl)thiazol-2-amine

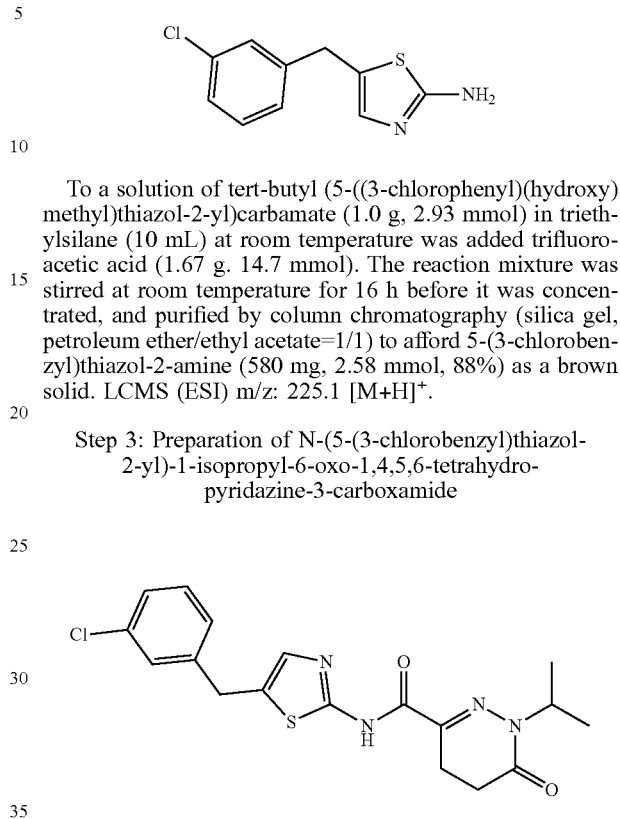

To a solution of tert-butyl (5-((3-chlorophenyl)(hydroxy)methyl)thiazol-2-yl)carbamate (1.0 g, 2.93 mmol) in triethylsilane (10 mL) at room temperature was added trifluoroacetic acid (1.67 g, 14.7 mmol). The reaction mixture was stirred at room temperature for 16 h before it was concentrated, and purified by column chromatography (silica gel, petroleum ether/ethyl acetate=1/1) to afford 5-(3-chlorobenzyl)thiazol-2-amine (580 mg, 2.58 mmol, 88%) as a brown solid. LCMS (ESI) m/z: 225.1 [M+H]$^+$.

Step 3: Preparation of N-(5-(3-chlorobenzyl)thiazol-2-yl)-1-isopropyl-6-oxo-1,4,5,6-tetrahydropyridazine-3-carboxamide To a solution of 5-(3-chlorobenzyl)thiazol-2-amine (0.098 g, 0.53 mmol), 1-isopropyl-6-oxo-1,4,5,6-tetrahydropyridazine-3-carboxylic acid (0.120 g, 0.53 mmol) and 1-[bis(dimethylamino)methylene]-1H-1,2,3-triazolo[4,5-b]pyridinium 3-oxid hexafluorophosphate (0.263 g, 0.69 mmol) in N,N-dimethylformamide (6 mL) was added N,N-diisopropylethylamine (0.276 g, 2.14 mmol). The mixture was stirred at room temperature for 16 h and concentrated. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-chlorobenzyl)thiazol-2-yl)-1-isopropyl-6-oxo-1,4,5,6-tetrahydropyridazine-3-carboxamide (0.098 g, 0.25 mmol, 47.2%) as a white solid. $^1$H NMR (500 MHz, Dimethylsulfoxide-d$_6$) δ 12.07 (s, 1H), 7.44-7.16 (m, 5H), 4.84 (dt, J=13.3, 6.6 Hz, 1H), 4.15 (s, 2H), 2.86-2.70 (m, 2H), 2.48 (d, J=8.5 Hz, 2H), 1.24 (d, J=6.6 Hz, 6H); LCMS (ESI) m/z: 391.1 [M+H]$^+$.

Example 223. Preparation of N-(5-(3-fluorobenzyl)thiazol-2-yl)-1-methyl-6-oxopiperidine-3-carboxamide (223)

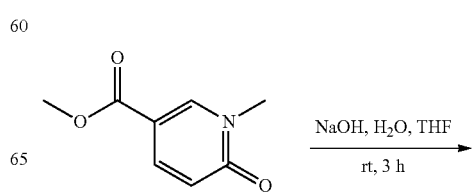

-continued

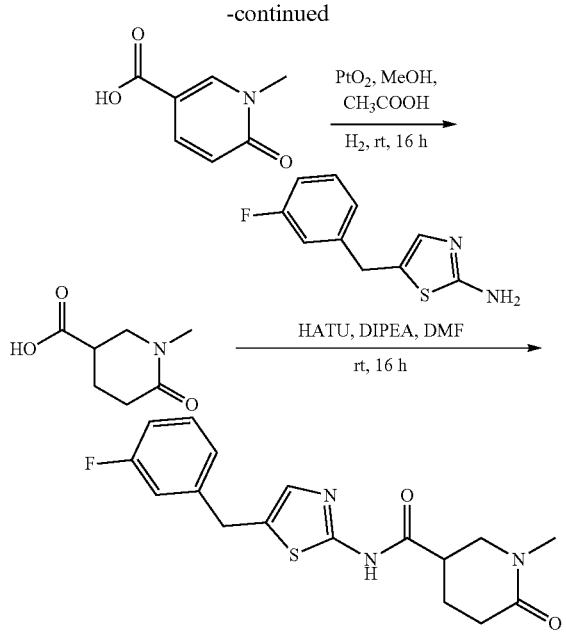

Step 1: Preparation of 1-methyl-6-oxo-1,6-dihydropyridine-3-carboxylic acid

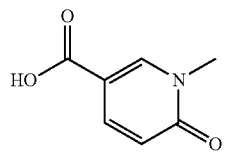

To a solution of methyl 1-methyl-6-oxo-1,6-dihydropyridine-3-carboxylate (1.5 g, 8.97 mmol) in tetrahydrofuran (10.0 mL) at room temperature was added sodium hydroxide (1.44 g, 35.9 mmol) and water (10.0 mL). The reaction mixture was stirred at room temperature for 16 h, diluted with water (100 mL), adjusted to pH=3-4 with aqueous 2 M hydrogen chloride and extracted with ethyl acetate (80 mL×3). The combined organic layers were washed with brine, dried over sodium sulfate, filtered and concentrated to afford 1-methyl-6-oxo-1,6-dihydropyridine-3-carboxylic acid (1.1 g, 7.18 mmol, 80.0%) as a white solid. LCMS (ESI) m/z: 154.1 [M+H]⁺.

Step 2: Preparation of 1-methyl-6-oxopiperidine-3-carboxylic acid

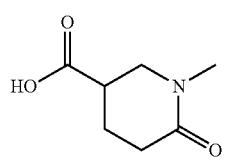

To a solution of 1-methyl-6-oxopiperidine-3-carboxylic acid (0.130 g, 0.85 mmol) in methanol (8 mL) and acetic acid (2.0 mL) at room temperature was added platinum(IV) oxide (0.100 g). The reaction mixture was stirred at room temperature for 16 h under hydrogen atmosphere. The reaction solution was filtered and concentrated to afford 1-methyl-6-oxopiperidine-3-carboxylic acid (0.135 g, crude) as a white solid. LCMS (ESI) m/z: 158.2 [M+H]⁺.

Step 3: Preparation of N-(5-(3-Fluorobenzyl)thiazol-2-yl)-1-methyl-6-oxopiperidine-3-carboxamide

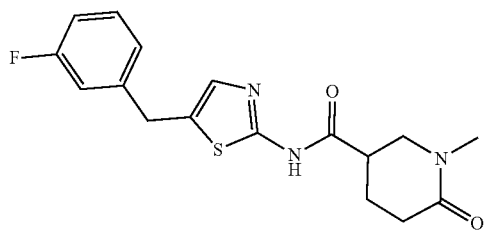 [SMILES: CN1CC(C(=O)Nc2ncc(Cc3cccc(F)c3)s2)CCC1=O]

To a solution of 1-methyl-6-oxopiperidine-3-carboxylic acid (0.135 g, 0.85 mmol), 5-(3-fluorobenzyl)thiazol-2-amine (0.177 g, 0.85 mmol) and 1-[bis(dimethylamino)methylene]-1H-1,2,3-triazolo[4,5-b]pyridinium 3-oxid hexafluorophosphate (0.422.0 g, 1.11 mmol) in N,N-dimethylformamide (6 mL) at room temperature was added N,N-diisopropylethylamine (0.440 g, 3.4 mmol). The mixture was stirred at room temperature for 16 h.

The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-fluorobenzyl)thiazol-2-yl)-1-methyl-6-oxopiperidine-3-carboxamide (0.135 g, 0.388 mmol, 45.6%) as a white solid. ¹H NMR (500 MHz, Dimethylsulfoxide-d₆) δ 12.15 (s, 1H), 7.39-7.32 (m, 1H), 7.28 (s, 1H), 7.11-7.03 (m, 3H), 4.11 (s, 3H), 3.43 (dd, J=11.9, 9.0 Hz, 2H), 3.07-2.96 (m, 1H), 2.82 (d, J=16.3 Hz, 3H), 2.31-2.17 (m, 2H), 2.05-1.94 (m, 1H), 1.93-1.81 (m, 1H); LCMS (ESI) m/z: 348.1 [M+H]⁺.

Example 224. Preparation of N-(5-(3-fluorobenzyl)thiazol-2-yl)-1-methyl-6-oxo-1,6-dihydropyridine-3-carboxamide (214)

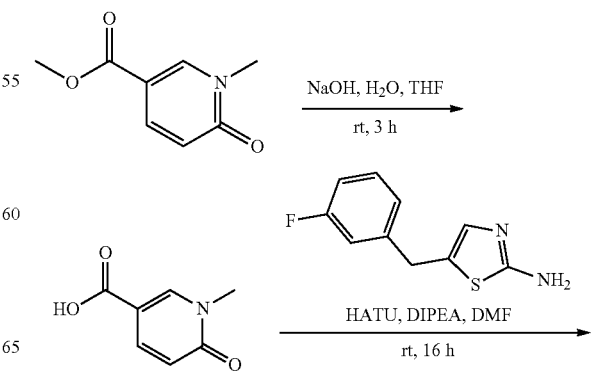

-continued

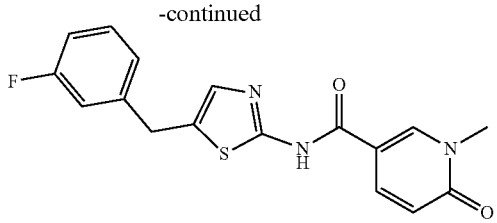

Step 1: Preparation of 1-methyl-6-oxo-1,6-dihydropyridine-3-carboxylic acid

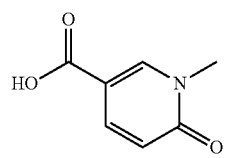

To a solution of methyl 1-methyl-6-oxo-1,6-dihydropyridine-3-carboxylate (1.5 g, 8.97 mmol) in tetrahydrofuran (10 mL) and water (10 mL) at room temperature was added sodium hydroxide (1.44 g, 35.9 mmol). The reaction mixture was stirred at room temperature for 3 h. The mixture was diluted with water (100 mL), pH was adjusted to ~3-4 with aqueous 2 M hydrogen chloride and extracted with ethyl acetate (80 mL×3). The combined organic layers were dried over sodium sulfate, filtered and concentrated to afford 1-methyl-6-oxo-1,6-dihydropyridine-3-carboxylic acid (1.1 g, 7.18 mmol, 80.0%) as a white solid. LCMS (ESI) m/z: 154.1 [M+H]$^+$.

Step 2: Preparation of N-(5-(3-fluorobenzyl)thiazol-2-yl)-1-methyl-6-oxo-1,6-dihydropyridine-3-carboxamide

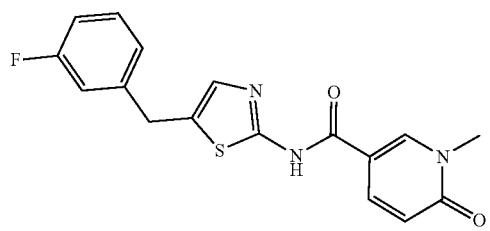 [SMILES: Cn1cc(C(=O)Nc2ncc(Cc3cccc(F)c3)s2)ccc1=O]

To a solution of 1-methyl-6-oxo-1,6-dihydropyridine-3-carboxylic acid (0.367 g, 2.4 mmol), 5-(3-fluorobenzyl)thiazol-2-amine (0.500 mg, 2.4 mmol) and 1-[bis(dimethylamino)methylene]-1H-1,2,3-triazolo[4,5-b]pyridinium 3-oxid hexafluorophosphate (1.19 g, 3.12 mmol) in N,N-dimethylformamide (6 mL) was added N,N-diisopropylethylamine (1.24 g, 9.6 mmol). The mixture was stirred at room temperature for 16 h. The crude sample was dissolved in minimal N,N-dimethylformamide and purified via prep-HPLC (Boston C18 21*250 mm 10 μm column; acetonitrile/ 0.01% aqueous trifluoroacetic acid) to give N-(5-(3-fluorobenzyl)thiazol-2-yl)-1-methyl-6-oxo-1,6-dihydropyridine-3-carboxamide (0.450 g, 1.31 mmol, 54.6%) as a white solid. $^1$H NMR (500 MHz, Dimethyl-sulfoxide-$d_6$) δ 12.22 (s, 1H), 8.68 (d, J=2.4 Hz, 1H), 7.99 (dd, J=9.5, 2.7 Hz, 1H), 7.40-7.32 (m, 2H), 7.14-7.04 (m, 3H), 6.44 (d, J=9.6 Hz, 1H), 4.13 (s, 2H), 3.50 (s, 3H); LCMS (ESI) m/z: 334.0 [M+H]$^+$.

Example 225. Preparation of N-(5-(3-chlorobenzyl)thiazol-2-yl)-1-(oxetan-3-yl)-6-oxo-1,6-dihydropyridazine-3-carboxamide (225)

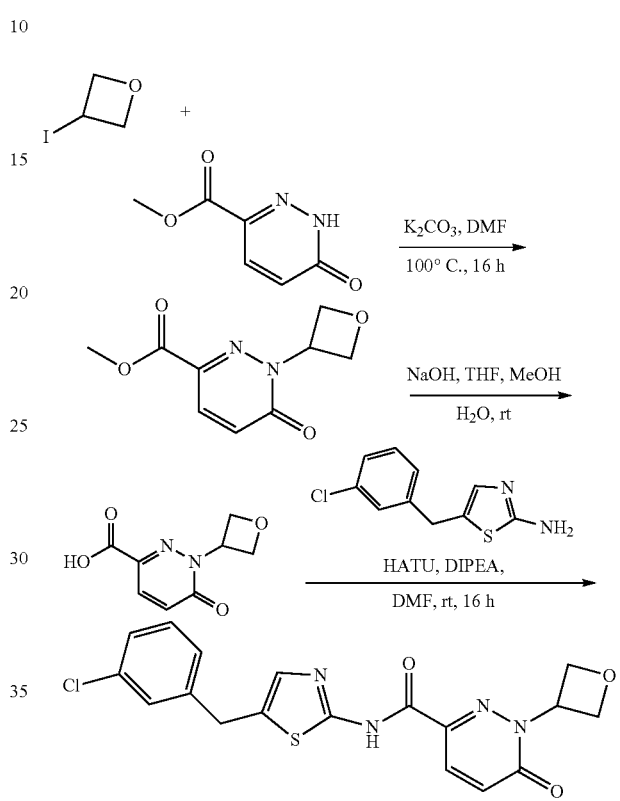

Step 1: Preparation of methyl 1-(oxetan-3-yl)-6-oxo-1,6-dihydropyridazine-3-carboxylate

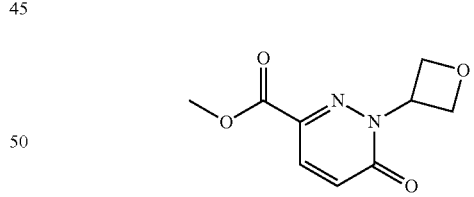

To a solution of methyl 6-oxo-1,6-dihydropyridazine-3-carboxylate (2.0 g, 13.0 mmol) in N,N-dimethylformamide (60 mL) at room temperature was added 3-iodooxetane (4.77 g, 26.0 mmol) and potassium carbonate (3.58 g, 26.0 mmol). The reaction mixture was stirred at 100° C. for 16 h, cooled to room temperature, diluted with water (300 mL) and extracted with ethyl acetate (80 mL×3). The combined organic layers were washed with brine, dried over sodium sulfate, filtered, and concentrated in vacuo. The residue was purified by column chromatography (silica gel, petroleum ether/ethyl acetate=3:1) to afford methyl 1-(oxetan-3-yl)-6-oxo-1,6-dihydropyridazine-3-carboxylate (1.5 g, 7.14 mmol, 55%) as a white solid. LCMS (ESI) m/z: 211.1 [M+H]$^+$.

Step 2: Preparation of 1-(oxetan-3-yl)-6-oxo-1,6-dihydropyridazine-3-carboxylic acid

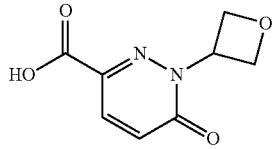 [SMILES: O=C(O)c1ccc(=O)n(C2COC2)n1]

To a solution of methyl 1-(oxetan-3-yl)-6-oxo-1,6-dihydropyridazine-3-carboxylate (0.200 g, 0.95 mmol) in tetrahydrofuran (8 mL) and water (8 mL) was added sodium hydroxide (0.152 g, 3.80 mmol) at room temperature. The reaction mixture was stirred at room temperature for 3 h. Concentration affords 1-(oxetan-3-yl)-6-oxo-1,6-dihydropyridazine-3-carboxylic acid (0.370 g, crude) as a white solid. LCMS (ESI) m/z: 197.1 [M+H]$^+$.

Step 3: Preparation of N-(5-(3-chlorobenzyl)thiazol-2-yl)-1-(oxetan-3-yl)-6-oxo-1,6-dihydropyridazine-3-carboxamide

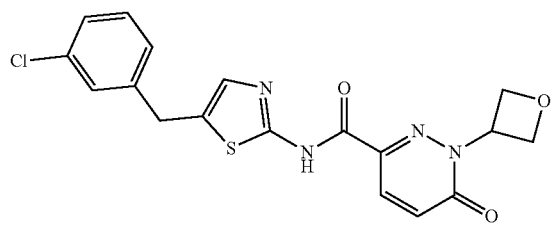 [SMILES: O=C(Nc1ncc(Cc2cccc(Cl)c2)s1)c1ccc(=O)n(C2COC2)n1]

To a solution of 1-(oxetan-3-yl)-6-oxo-1,6-dihydropyridazine-3-carboxylic acid (0.370 g, 0.95 mmol), 5-(3-chlorobenzyl)thiazol-2-amine (0.213 g, 0.95 mmol) and 1-[bis(dimethylamino)methylene]-1H-1,2,3-triazolo[4,5-b]pyridinium 3-oxid hexafluorophosphate (0.471 g, 1.24 mmol) in N,N-dimethylformamide (8 mL) at room temperature was added N,N-diisopropylethylamine (0.491 g, 3.80 mmol). The mixture was stirred at room temperature for 3 h. The crude sample was dissolved in minimal N,N-dimethylformamide and purified via prep-HPLC (Boston C18 21*250 mm 10 μm column; acetonitrile/0.01% aqueous trifluoroacetic acid) to afford N-(5-(3-chlorobenzyl)thiazol-2-yl)-1-(oxetan-3-yl)-6-oxo-1,6-dihydropyridazine-3-carboxamide (0.042 g, 0.10 mmol, 10.5%) as a white solid. $^1$H NMR (500 MHz, Dimethylsulfoxide-d$_6$) δ 12.61 (s, 1H), 7.93 (d, J=9.7 Hz, 1H), 7.40-7.35 (m, 3H), 7.29 (dd, J=15.5, 7.9 Hz, 2H), 7.08 (d, J=9.7 Hz, 1H), 5.85-5.79 (m, 1H), 5.10 (t, J=6.7 Hz, 2H), 4.83 (t, J=7.3 Hz, 2H), 4.17 (s, 2H); LCMS (ESI) m/z: 403.0 [M+H]$^+$.

Example 226. Preparation of N-(5-(3-fluorobenzyl)thiazol-2-yl)-1-(2-fluoroethyl)-6-oxo-1,6-dihydropyridazine-3-carboxamide (226)

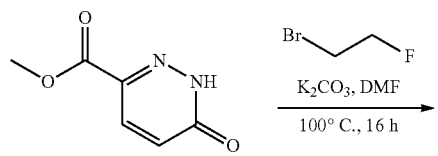

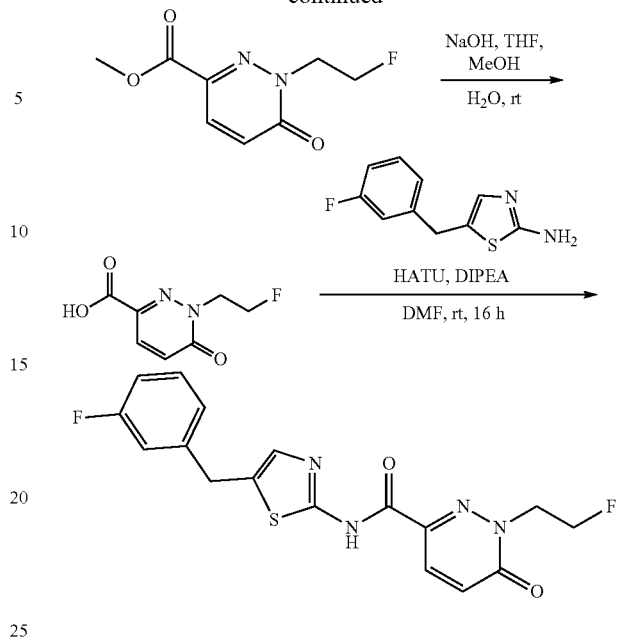

Step 1: Preparation of methyl 1-(2-fluoroethyl)-6-oxo-1,6-dihydropyridazine-3-carboxylate

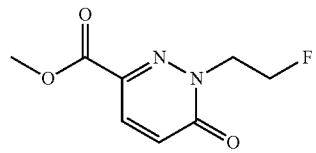

To a solution of methyl 6-oxo-1,6-dihydropyridazine-3-carboxylate (2.5 g, 16.2 mmol) in N,N-dimethylformamide (60.0 mL) was added 1-bromo-2-fluoroethane (4.12 g, 32.4 mmol) and potassium carbonate (4.48 g, 32.4 mmol). The reaction mixture was stirred at 100° C. for 16 h, cooled to room temperature, diluted with water (300 mL) and extracted with ethyl acetate (80 mL×3). The combined organic layers were washed with brine, dried over sodium sulfate, filtered, and concentrated in vacuo. The residue was purified by column chromatography (silica gel, petroleum ether/ethyl acetate=2/1) to afford methyl 1-(2-fluoroethyl)-6-oxo-1,6-dihydropyridazine-3-carboxylate (2.2 g, 11.0 mmol, 67.8%) as a white solid. LCMS (ESI) m/z: 201.1 [M+H]$^+$.

Step 2: Preparation of 1-(2-Fluoroethyl)-6-oxo-1,6-dihydropyridazine-3-carboxylic acid

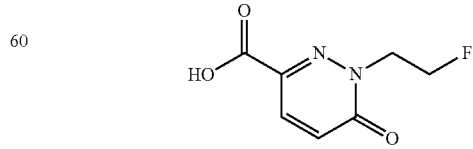

To a solution of methyl 1-(2-fluoroethyl)-6-oxo-1,6-dihydropyridazine-3-carbox0ylate (0.200 g, 1.0 mmol) in tetrahydrofuran (8 mL) and water (8 mL) was added sodium hydroxide (0.016 g, 4.0 mmol). The reaction mixture was stirred at room temperature for 3 h. Concentration affords 1-(2-fluoroethyl)-6-oxo-1,6-dihydropyridazine-3-carboxylic acid (0.400 g, crude) as a white solid. LCMS (ESI) m/z: 187.1 [M+H]⁺.

Step 3: Preparation of N-(5-(3-fluorobenzyl)thiazol-2-yl)-1-(2-fluoroethyl)-6-oxo-1,6-dihydropyridazine-3-carboxamide

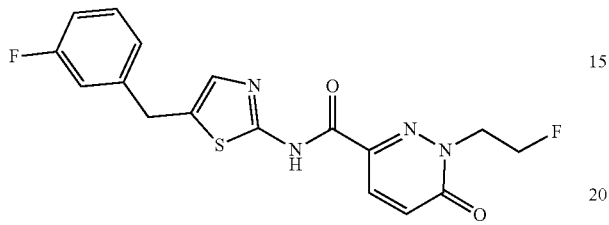

To a solution of 1-(2-fluoroethyl)-6-oxo-1,6-dihydropyridazine-3-carboxylic acid (0.400 g, crude) in N,N-dimethylformamide (6 mL) at room temperature was added 5-(3-fluorobenzyl)thiazol-2-amine (0.208 g, 1.0 mmol), 1-[bis(dimethylamino)methylene]-1H-1,2,3-triazolo[4,5-b]pyridinium 3-oxid hexafluorophosphate (0.494 g, 1.3 mmol) and N,N-diisopropylethylamine (0.517 g, 4.0 mmol). The mixture was stirred at room temperature for 16 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3-fluorobenzyl)thiazol-2-yl)-1-(2-fluoroethyl)-6-oxo-1,6-dihydropyridazine-3-carboxamide (0.230 g, 0.227 mmol, 22.7%) as a white solid. ¹H NMR (500 MHz, Dimethylsulfoxide-d₆) δ 12.42 (s, 1H), 7.91 (d, J=9.7 Hz, 1H), 7.40-7.35 (m, 2H), 7.15-7.12 (m, 2H), 7.10-7.04 (m, 2H), 4.99 (t, J=4.9 Hz, 1H), 4.90 (t, J=4.9 Hz, 1H), 4.51 (t, J=4.9 Hz, 1H), 4.46 (t, J=4.9 Hz, 1H), 4.16 (s, 2H); LCMS (ESI) m/z: 377.0 [M+H]⁺.

Example 227. Preparation of 1-ethyl-N-(5-(3-fluorobenzyl)thiazol-2-yl)-6-oxo-1,6-dihydropyridazine-3-carboxamide (227)

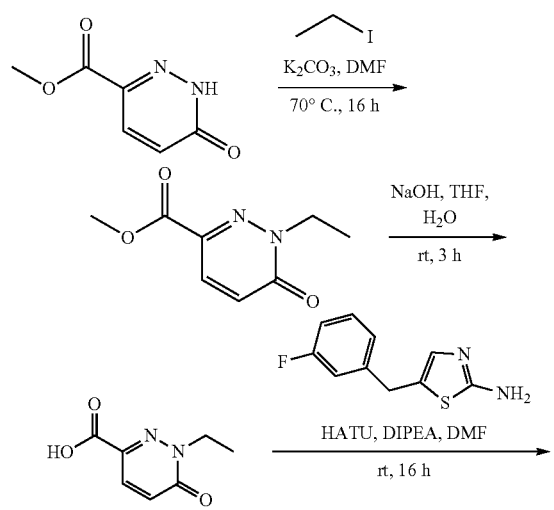

-continued

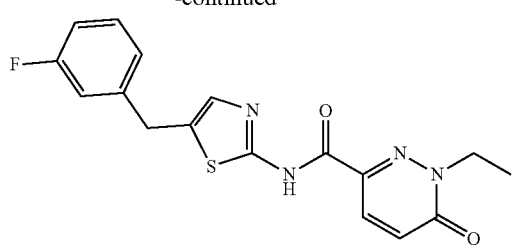

Step 1: Preparation of methyl 1-ethyl-6-oxo-1,6-dihydropyridazine-3-carboxylate

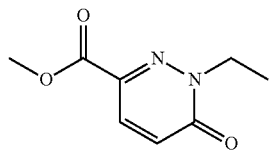

To a solution of methyl 6-oxo-1,6-dihydropyridazine-3-carboxylate (1.1 g, 7.14 mmol) in N,N-dimethylformamide (20 mL) at room temperature was added potassium carbonate (1.97 g, 14.3 mmol) and iodoethane (2.23 g, 14.3 mmol). The reaction mixture was stirred at 70° C. for 16 h, cooled to room temperature, diluted with water (300 mL) and extracted with ethyl acetate (80 mL×3). The combined organic layers were washed with brine, dried over sodium sulfate, filtered and concentrated to afford methyl 1-ethyl-6-oxo-1,6-dihydropyridazine-3-carboxylate (1.0 g, 5.49 mmol, 76.9%) as a white solid. LCMS (ESI) m/z: 183.1 [M+H]⁺.

Step 2: Preparation of 1-ethyl-6-oxo-1,6-dihydropyridazine-3-carboxylic acid

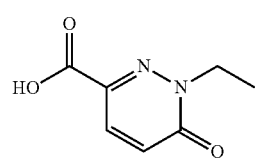

To a solution of methyl 1-ethyl-6-oxo-1,6-dihydropyridazine-3-carboxylate (0.410 g, 2.25 mmol) in tetrahydrofuran (15 mL) and water (2 mL) at room temperature was added sodium hydroxide (0.180 g. 4.5 mmol). The reaction mixture was stirred at room temperature for 3 h and adjusted to pH=6-7 with aqueous 2 M hydrogen chloride. The mixture was concentrated, to afford 1-ethyl-6-oxo-1,6-dihydropyridazine-3-carboxylic acid (0.660 g, crude) as a white solid. LCMS (ESI) m/z: 169.1 [M+H]⁺.

Step 3: Preparation of 1-ethyl-N-(5-(3-fluorobenzyl)thiazol-2-yl)-6-oxo-1,6-dihydropyridazine-3-carboxamide

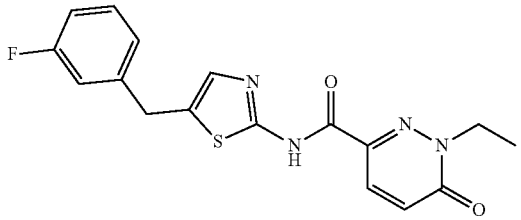 [SMILES: CCn1nc(C(=O)Nc2ncc(Cc3cccc(F)c3)s2)ccc1=O]

To a solution of 1-ethyl-6-oxo-1,6-dihydropyridazine-3-carboxylic acid (0.660 mg, 2.25 mmol), 5-(3-fluorobenzyl)thiazol-2-amine (0.360 g, 1.73 mmol) and 1-[bis(dimethylamino)methylene]-1H-1,2,3-triazolo[4,5-b]pyridinium 3-oxid hexafluorophosphate (0.921 g, 2.42 mmol) in N,N-dimethylformamide (8 mL) was added N,N-diisopropylethylamine (0.894 g, 6.92 mmol). The reaction mixture was stirred at room temperature for 16 h. The crude sample was dissolved in minimal N,N-dimethylformamide and purified via prep-HPLC (Boston C18 21*250 mm 10 μm column; acetonitrile/0.01% aqueous trifluoroacetic acid) to give 1-ethyl-N-(5-(3-fluorobenzyl)thiazol-2-yl)-6-oxo-1,6-dihydropyridazine-3-carboxamide (0.201 g, 0.56 mmol, 32.4%) as a white solid. $^1$H NMR (500 MHz, Dimethylsulfoxide-d$_6$) δ 12.37 (s, 1H), 7.88 (d, J=9.7 Hz, 1H), 7.44-7.32 (m, 2H), 7.18-7.11 (m, 2H), 7.10-7.00 (m, 2H), 4.22-4.13 (m, 4H), 1.35 (t, J=7.2 Hz, 3H); LCMS (ESI) m/z: 359.0 [M+H]$^+$.

Example 228. Preparation of N-(5-(3,4-difluorobenzyl)thiazol-2-yl)-1-methyl-6-oxo-1,4,5,6-tetrahydropyridazine-3-carboxamide (22111

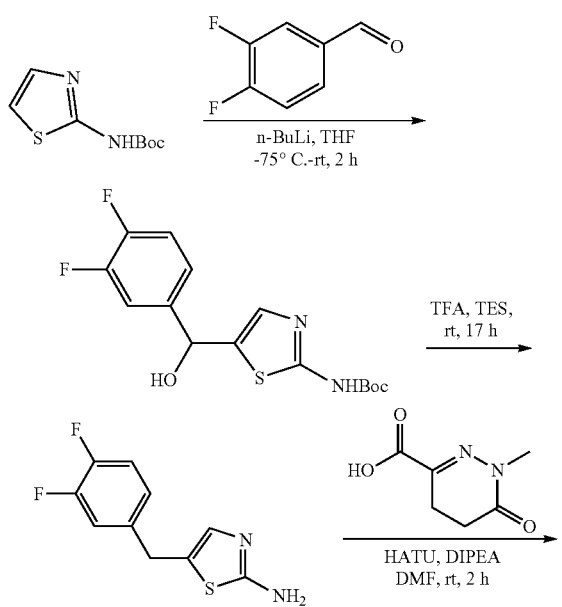

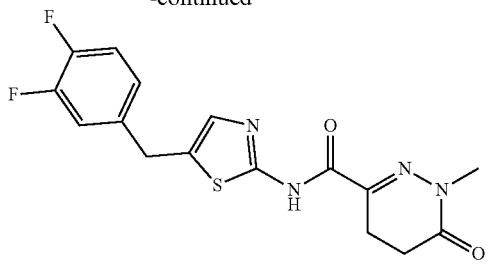

Step 1: Preparation of tert-butyl 5-((3,4-difluorophenyl)(hydroxy)methyl)thiazol-2-ylcarbamate

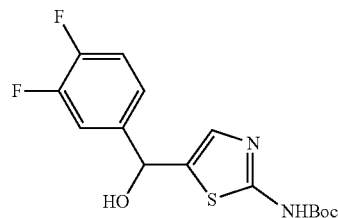 [SMILES: CC(C)(C)OC(=O)Nc1ncc(C(O)c2ccc(F)c(F)c2)s1]

To a solution of tert-butyl thiazol-2-ylcarbamate (1.5 g, 7.5 mmol) in tetrahydrofuran (30 mL) at −75° C. was added n-butyllithium (6.6 mL, 16.5 mmol) dropwise. Reaction mixture was stirred for 30 minutes before 3,4-difluorobenzaldehyde (1.6 g, 11.3 mmol) was added slowly. Reaction was warmed to room temperature over 2 h. The reaction solution was poured into ice water (50 mL) and pH was adjusted to 6-7 with aqueous 1 N hydrogen chloride. The aqueous layer was extracted with ethyl acetate (50 mL×2). The combined organic layers were washed with brine (50 mL), dried over sodium sulfate, filtered and concentrated. Treatment of crude residue with tert-butyl methyl ether (5 mL) provides tert-butyl 5-((3,4-difluorophenyl)(hydroxy)methyl)thiazol-2-ylcarbamate (0.930 g, 2.72 mmol, 36.3%) as a white solid. LCMS (ESI) m/z: 343.1 [M+H]$^+$. Used in the next step directly without additional purification.

Step 2: Preparation of 5-(3,4-difluorobenzyl)thiazol-2-amine

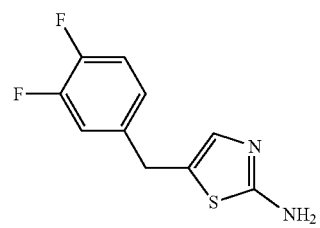 [SMILES: Nc1ncc(Cc2ccc(F)c(F)c2)s1]

To a solution of tert-butyl 5-((3,4-difluorophenyl)(hydroxy)methyl)thiazol-2-ylcarbamate (0.830 g, 2.43 mmol) in trifluoroacetic acid (12 mL) at 0° C. was added triethylsilane (1.13 g, 9.7 mmol). Reaction was warmed to room temperature and stirred for 5 h. The reaction mixture was concentrated and diluted with aqueous saturated sodium bicarbonate solution (50 mL). The aqueous phase was extracted with ethyl acetate (30 mL×2). Combined organic layers were washed with brine (30 mL), dried over sodium sulfate, filtered and concentrated. Treatment of the crude reside with tert-butyl methyl ether (2 mL) gives 5-(3,4-difluorobenzyl)thiazol-2-amine (0.250 g, 1.11 mmol, 45.5%) as a white solid. LCMS (ESI) m/z: 227.1 [M+H]$^+$.

Step 3: Preparation of N-(5-(3,4-difluorobenzyl)thiazol-2-yl)-1-methyl-6-oxo-1,4,5,6-tetrahydropyridazine-3-carboxamide

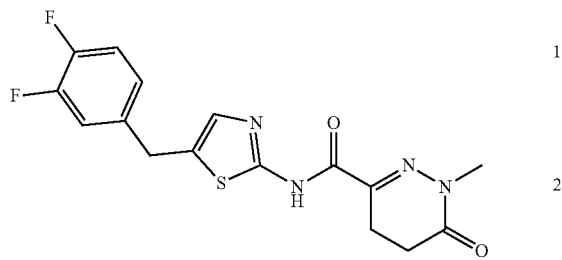

A solution of 1-methyl-6-oxo-1,4,5,6-tetrahydropyridazine-3-carboxylic acid (0.070 g, 0.448 mmol), 5-(3,4-difluorobenzyl)thiazol-2-amine (0.121 g, 0.54 mmol), 1-[bis(dimethylamino)methylene]-1H-1,2,3-triazolo[4,5-b]pyridinium 3-oxid hexafluorophosphate (0.255 g, 0.67 mmol) and N,N-diisopropylethylamine (0.173 g, 1.34 mmol) in N,N-dimethylformamide (3 mL) was stirred at room temperature for 2 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-(3,4-difluorobenzyl)thiazol-2-yl)-1-methyl-6-oxo-1,4,5,6-tetrahydropyridazine-3-carboxamide (0.119 g, 0.327 mmol, 73%) as a white solid. $^1$H NMR (500 MHz, Dimethylsulfoxide-d$_6$) δ 11.90 (s, 1H), 7.45-7.35 (m, 2H), 7.33 (s, 1H), 7.14-7.12 (m, 1H), 4.24 (s, 2H), 3.35 (s, 3H), 2.82 (t, J=8.5 Hz, 2H), 2.51 (t, J=5.75 Hz, 2H); LCMS (ESI) m/z: 364.37 [M+H]$^+$.

Example 229. Preparation of N-(5-(3,5-difluorobenzyl)thiazol-2-yl)-1-methyl-6-oxo-1,4,5,6-tetrahydropyridazine-3-carboxamide (229)

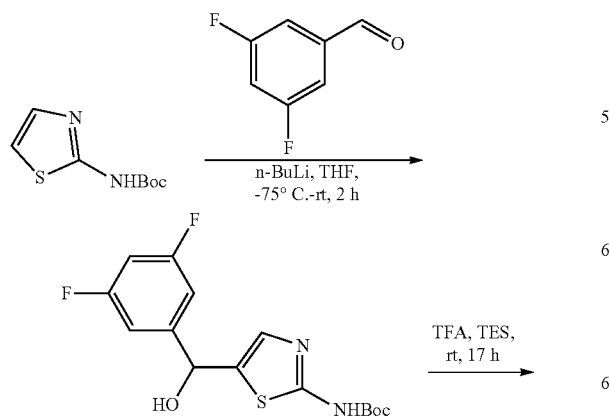

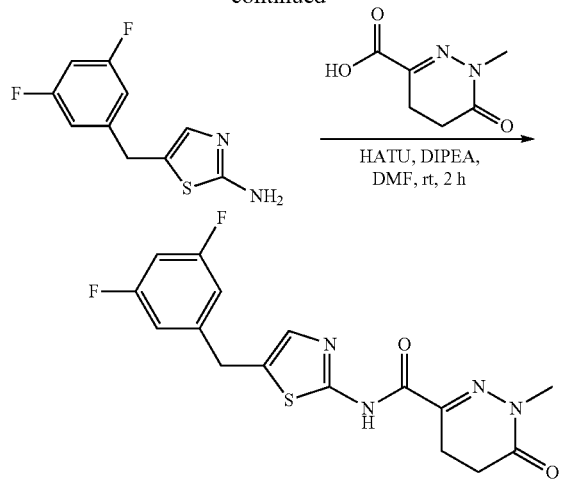

Step 1: Preparation of tert-butyl 5-((3,5-difluorophenyl)(hydroxy)methyl)thiazol-2-ylcarbamate

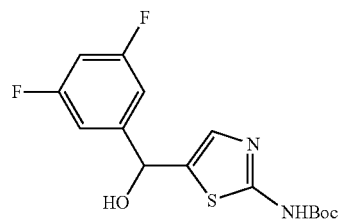 [SMILES: CC(C)(C)OC(=O)Nc1ncc(C(O)c2cc(F)cc(F)c2)s1]

To a solution of tert-butyl thiazol-2-ylcarbamate (1.5 g, 7.5 mmol) in tetrahydrofuran (30 mL) at −78° C. was added n-butyllithium (6.6 mL, 16.5 mmol) dropwise. Reaction was stirred at this temperature for 30 minutes before 3,4-difluorobenzaldehyde (1.6 g, 11.3 mmol) was added. Reaction was warmed to room temperature over 2 h. Reaction solution was poured into ice water (50 mL) and pH was adjusted to 6-7 with aqueous 1 N hydrogen chloride. The aqueous layer was extracted with ethyl acetate (50 mL×2). Combined organic phases were washed with brine (50 mL), dried over sodium sulfate, filtered and concentrated. Treatment of crude residue with tert-butyl methyl ether (5 mL) affords tert-butyl 5-((3,5-difluorophenyl)(hydroxy)methyl)thiazol-2-ylcarbamate (0.650 g, 1.90 mmol, 25.3%) as a brown solid. LCMS (ESI) m/z: 343.1 [M+H]$^+$. Used in the next step directly without additional purification.

Step 2: Preparation of 5-(3,5-difluorobenzyl)thiazol-2-amine

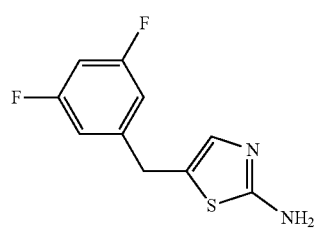

To a solution of tert-butyl 5-((3,5-difluorophenyl)(hydroxy)methyl)thiazol-2-ylcarbamate (0.590 g, 1.73 mmol) in trifluoroacetic acid (8 mL) at 0° C. was added triethylsilane (0.8 g, 6.9 mmol). Reaction was warmed to room temperature and stirred for 5 h. Volatiles were removed and the crude residue was diluted with aqueous saturated sodium bicarbonate solution (50 mL) and extracted with ethyl acetate (30 mL×2). Combined organic layers were washed with brine (30 mL), dried over sodium sulfate, filtered and concentrated. Treatment of the crude material with tert-butyl methyl ether (2 mL) gives 5-(3,5-difluorobenzyl)thiazol-2-amine (0.340 g, 0.513 mmol, 87%) as a yellow solid. LCMS (ESI) 227.1 [M+H]⁺.

Step 3: Preparation of N-(5-(3,5-difluorobenzyl)thiazol-2-yl)-1-methyl-6-oxo-1,4,5,6-tetrahydropyridazine-3-carboxamide

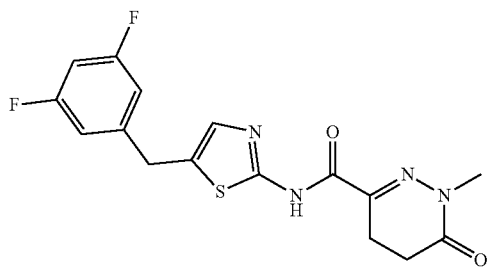 [SMILES: CN1N=C(C(=O)Nc2ncc(Cc3cc(F)cc(F)c3)s2)CCC1=O]

A solution of 1-methyl-6-oxo-1,4,5,6-tetrahydropyridazine-3-carboxylic acid (0.100 g, 0.464 mmol), 5-(3,5-difluorobenzyl)thiazol-2-amine (0.174 g, 0.77 mmol), 1-[bis(dimethylamino)methylene]-1H-1,2,3-triazolo[4,5-b]pyridinium 3-oxid hexafluorophosphate (0.365 g, 0.96 mmol) and N,N-diisopropylethylamine (0.248 g, 1.92 mmol) in N,N-dimethylformamide (5 mL) was stirred at room temperature for 2 h. The crude sample was dissolved in minimal N,N-dimethylformamide and purified via prep-HPLC (Boston C18 21*250 mm 10 µm column; acetonitrile/0.01% aqueous trifluoroacetic acid) to give N-(5-(3,5-difluorobenzyl)thiazol-2-yl)-1-methyl-6-oxo-1,4,5,6-tetrahydropyridazine-3-carboxamide (0.132 g, 0.263 mmol, 56.6%) as a white solid. $^1$H NMR (500 MHz, Dimethylsulfoxide-d$_6$) δ 11.92 (s, 1H), 7.36 (s, 1H), 7.12-7.08 (m, 1H), 7.04 (d, J=6.5 Hz, 2H), 4.15 (s, 2H), 3.35 (s, 3H), 2.82 (t, J=8.5 Hz, 2H), 2.51 (t, J=6.5 Hz, 2H); LCMS (ESI) m/z: 364.4 [M+H]⁺.

Example 230. Preparation of N-(5-(2-chlorobenzyl)thiazol-2-yl)-1-methyl-6-oxo-1,4,5,6-tetrahydropyridazine-3-carboxamide (230)

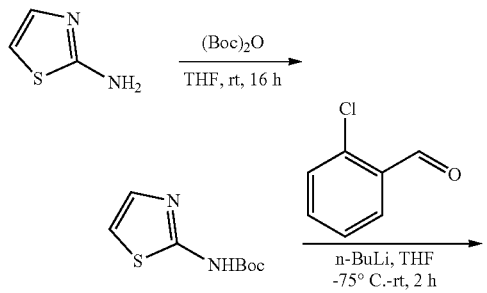

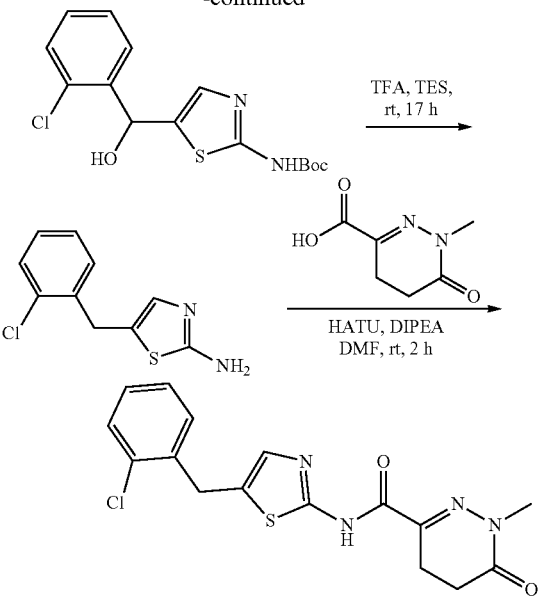

Step 1: Preparation of tert-butyl thiazol-2-ylcarbamate

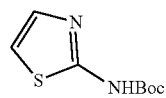

To a solution of thiazol-2-amine (11 g, 100 mmol) in tetrahydrofuran (5 mL) at 0° C. was added di-tert-butyl dicarbonate (26.2 g, 120 mmol). Reaction was stirred at room temperature for 17 h. Concentration followed by treatment of the resulting solid with petroleum ether/ethyl acetate=100:2 (100 mL) affords tert-butyl thiazol-2-ylcarbamate as a faint yellow solid (16.9 g, 84.5 mmol, 84.5%). LCMS (ESI) m/z: 145.1 [M-56]±. Used in the next step directly without additional purification.

Step 2: Preparation of tert-butyl 5-((2-chlorophenyl)(hydroxy)methyl)thiazol-2-ylcarbamate

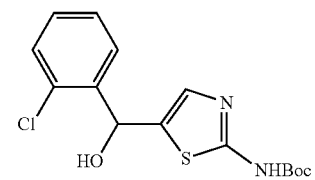 [SMILES: CC(C)(C)OC(=O)Nc1ncc(C(O)c2ccccc2Cl)s1]

To a solution of tert-butyl thiazol-2-ylcarbamate (1 g, 5.00 mmol) in tetrahydrofuran (20 mL) at −78° C. was added n-butyllithium (4.4 mL, 11.0 mmol) dropwise. Reaction was stirred for 30 minutes, before 2-chlorobenzaldehyde (1.05 g, 7.50 mmol) was added at −78° C. Reaction mixture was warmed to room temperature over 2 h. The solution was poured into ice water (50 mL) and neutralized with aqueous 1 N hydrogen chloride and extracted with ethyl acetate (50 mL×2). The combined organic layers were washed with brine (50 mL), dried over sodium sulfate, filtered and concentrated. Treatment of the crude sample with tert-butyl methyl ether (5 mL) gives tert-butyl 5-((2-chlorophenyl)(hydroxy)methyl)thiazol-2-ylcarbamate as a white solid (0.340 g, 1.00 mmol, 20%); LCMS (ESI) m/z: 341.1 [M+H]⁺.

Step 3: Preparation of 5-(2-chlorobenzyl)thiazol-2-amine

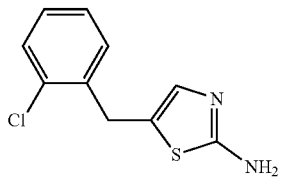 [SMILES: Nc1ncc(Cc2ccccc2Cl)s1]

To a solution of tert-butyl 5-((2-chlorophenyl)(hydroxy)methyl)thiazol-2-ylcarbamate (0.300 g, 0.88 mmol) in tetrahydrofuran (6 mL) at 0° C. was added triethylsilane (0.409 g, 3.56 mmol). Reaction mixture was warmed to room temperature and stirred for 17 h. Then the reaction mixture was concentrated, diluted with saturated sodium bicarbonate solution (20 mL), and extracted with ethyl acetate (30 mL×2). The combined organic layers were washed with brine (30 mL), dried over sodium sulfate, concentrated and triturated with tert-butyl methyl ether (1 mL) to offer 5-(2-chlorobenzyl)thiazol-2-amine (0.140 g, 0.412 mmol, 46.8%) as a white solid. LCMS (ESI) m/z: 225.1 [M+H]⁺.

Step 4: Preparation of N-(5-(2-chlorobenzyl)thiazol-2-yl)-1-methyl-6-oxo-1,4,5,6-tetrahydropyridazine-3-carboxamide

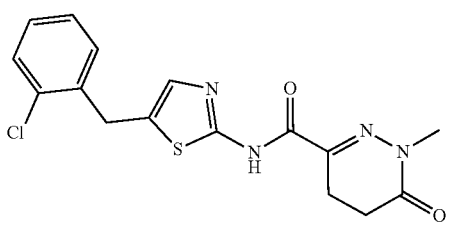 [SMILES: CN1N=C(C(=O)Nc2ncc(Cc3ccccc3Cl)s2)CCC1=O]

A solution of 1-methyl-6-oxo-1,4,5,6-tetrahydropyridazine-3-carboxylic acid (0.070 g, 0.35 mmol), 5-(2-chlorobenzyl)thiazol-2-amine (0.120 g, 0.54 mmol), 1-[bis(dimethylamino)methylene]-1H-1,2,3-triazolo[4,5-b]pyridinium 3-oxid hexafluorophosphate (0.257 g, 0.675 mmol) and N,N-diisopropylethylamine (0.174 g, 1.35 mmol) in N,N-dimethylformamide (3 mL) was stirred at room temperature for 2 h. The crude sample was dissolved in minimal N,N-dimethylformamide and purified via prep-HPLC (Boston C18 21*250 mm 10 μm column; acetonitrile/ 0.01% aqueous trifluoroacetic acid) to give N-(5-(2-chlorobenzyl)thiazol-2-yl)-1-methyl-6-oxo-1,4,5,6-tetrahydropyridazine-3-carboxamide (0.160 g, 0.343 mmol, 98%) as a white solid. ¹H NMR (500 MHz, Dimethylsulfoxide-d₆) δ 11.89 (s, 1H), 7.47-7.42 (m, 2H), 7.34-7.27 (m, 3H), 4.22 (s, 2H), 3.34 (s, 3H), 2.82 (t, J=8.5 Hz, 2H), 2.51-2.49 (m, 2H); LCMS (ESI) m/z: 363.0 [M+H]⁺.

Example 231. Preparation of N-(5-((5-chloropyridin-3-yl)methyl)thiazol-2-yl)-1-methyl-6-oxo-1,4,5,6-tetrahydropyridazine-3-carboxamide (231)

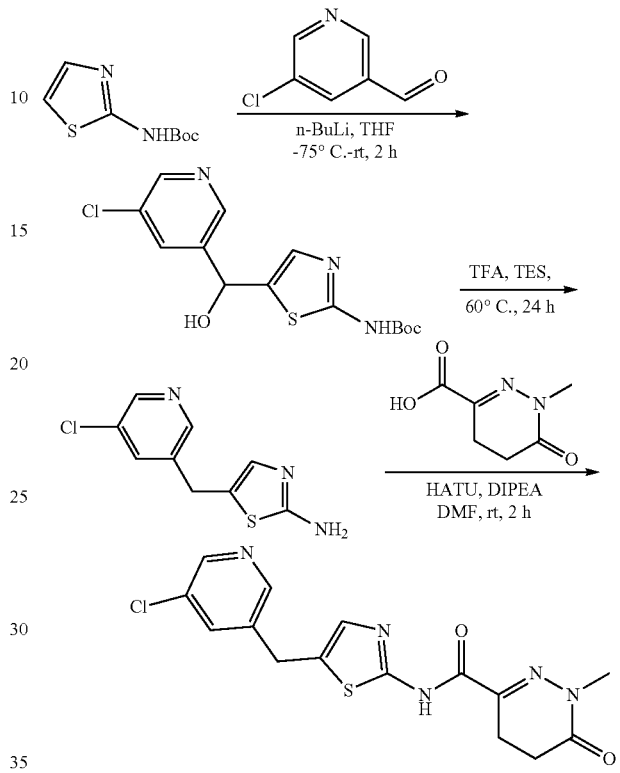

Step 1: Preparation of tert-butyl 5-((5-chloropyridin-3-yl)(hydroxy)methyl)thiazol-2-ylcarbamate

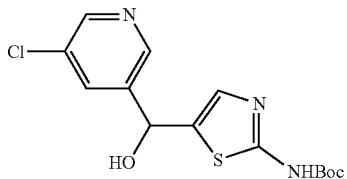 [SMILES: CC(C)(C)OC(=O)Nc1ncc(C(O)c2cncc(Cl)c2)s1]

To a solution of tert-butyl thiazol-2-ylcarbamate (1.8 g, 9 mmol) in tetrahydrofuran (54 mL) at −78° C. was added n-butyllithium (7.9 mL, 19.8 mmol) dropwise. Reaction was stirred for 1 h at −78° C. for 1 h before a solution of 5-chloronicotinaldehyde (1.9 g, 13.5 mmol) in tetrahydrofuran (5 mL) was added. Reaction mixture was warmed to room temperature over 2 h. The mixture was poured into ice water (50 mL), pH was adjusted to 6-7 with aqueous 1 N hydrogen chloride and extracted with ethyl acetate (100 mL×2). Combined organic layers were washed with brine (100 mL), dried over sodium sulfate, filtered and concentrated. Purification by column chromatography (silica gel, petroleum ether/ethyl acetate=1:10~½) affords tert-butyl 5-((5-chloropyridin-3-yl)(hydroxy)methyl)thiazol-2-ylcarbamate (1.7 g, 55.4%) as a white solid. LCMS (ESI) m/z: 342.1 [M+H]⁺.

Step 2: Preparation of 5-((5-chloropyridin-3-yl)methyl)thiazol-2-amine

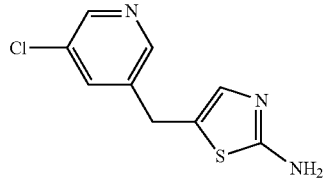 [SMILES: Nc1ncc(Cc2cncc(Cl)c2)s1]

To a solution of tert-butyl 5-((5-chloropyridin-3-yl)(hydroxy)methyl)thiazol-2-ylcarbamate (1.5 g, 4.4 mmol) in trifluoroacetic acid (22 mL) at 0° C. was added triethylsilane (2.04 g, 17.6 mmol). Reaction was stirred at 60° C. for 24 h. The reaction mixture was concentrated, and diluted with saturated aqueous sodium bicarbonate solution to form a precipitate. The precipitate was filtered and washed with petroleum ether to give 5-((5-chloropyridin-3-yl)methyl)thiazol-2-amine (0.900 g, 3.54 mmol, 80.4%) as a yellow solid. LCMS (ESI) m/z: 226.0 [M+H]$^+$.

Step 3: Preparation of N-(5-((5-chloropyridin-3-yl)methyl)thiazol-2-yl)-1-methyl-6-oxo-1,4,5,6-tetrahydropyridazine-3-carboxamide

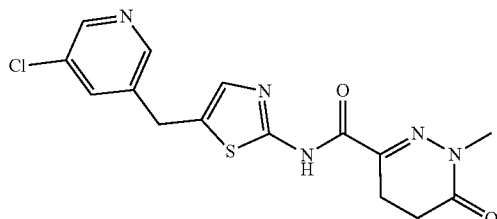

A solution of 1-methyl-6-oxo-1,4,5,6-tetrahydropyridazine-3-carboxylic acid (0.080 g, 0.51 mmol), 5-((5-chloropyridin-3-yl)methyl)thiazol-2-amine (0.138 g, 0.62 mmol), 1-[bis(dimethylamino)methylene]-1H-1,2,3-triazolo[4,5-b]pyridinium 3-oxid hexafluorophosphate (0.291 g, 0.765 mmol) and N,N-diisopropylethylamine (0.197 g, 1.53 mmol) in N,N-dimethylformamide (3 mL) was stirred at room temperature for 8 h. The crude sample was dissolved in minimal N,N-dimethylformamide and purified via prep-HPLC (Boston C18 21*250 mm 10 μm column; acetonitrile/ 0.01% aqueous trifluoroacetic acid) to give N-(5-((5-chloropyridin-3-yl) methylthiazol-2-yl)-1-methyl-6-oxo-1,4,5,6-tetrahydropyridazine-3-carboxamide as a yellow solid (0.0697 g, 0.158 mmol, 31%). $^1$H NMR (500 MHz, Dimethylsulfoxide-d$_6$) δ 11.94 (s, 1H), 8.52 (t, J=2.3 Hz, 2H), 7.88 (t, J=2.1 Hz, 1H), 7.37 (s, 1H), 4.19 (s, 2H), 3.35 (s, 3H), 2.82 (t, J=8.5 Hz, 2H), 2.51 (t, J=5.3 Hz, 2H); LCMS (ESI) m/z: 363.8 [M+H]$^+$.

Example 232. Preparation of N-(4-chloro-5-(3-fluorobenzyl)thiazol-2-yl)-1-methyl-6-oxo-1,6-dihydropyridazine-3-carboxamide (232)

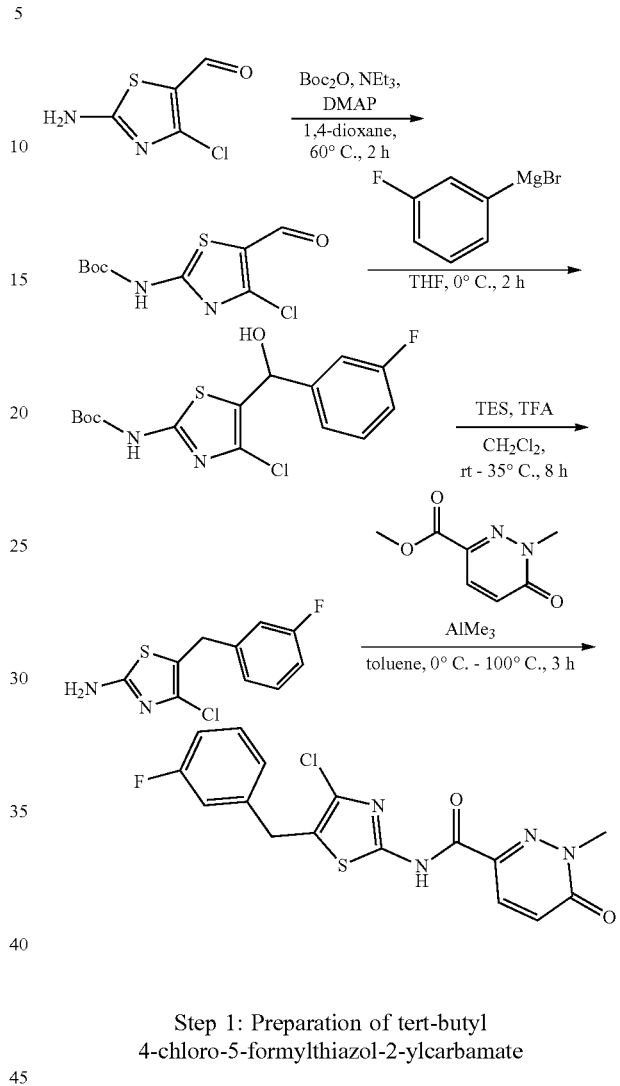

Step 1: Preparation of tert-butyl 4-chloro-5-formylthiazol-2-ylcarbamate

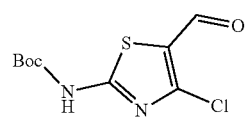 [SMILES: CC(C)(C)OC(=O)Nc1nc(Cl)c(C=O)s1]

To a solution of 2-amino-4-chlorothiazole-5-carbaldehyde (0.838 g, 5.15 mmol) and di-tert-butyl dicarbonate (1.35 g, 6.18 mmol) in 1,4-dioxane (25 mL) at room temperature was added 4-dimethylaminopyridine (0.063 g, 0.52 mmol) under nitrogen. The reaction mixture was stirred at 60° C. for 2 h. The reaction mixture was diluted with ethyl acetate (150 mL) and washed with aqueous 1 N hydrochloric acid solution (30 mL×2). The combined organic layers were dried over sodium sulfate, filtered and concentrated. The crude product was purified by column chromatography (silica gel, petroleum ether/ethyl acetate 4/1) to give tert-butyl 4-chloro-5-formylthiazol-2-ylcarbamate (1.17 g, 4.45 mmol, 87%) as a yellow solid. (LCMS (ESI) m/z: 207.1 [M-56+H]+.

Step 2: Preparation of tert-butyl 4-chloro-5-((3-fluorophenyl)(hydroxy)methyl)thiazol-2-ylcarbamate

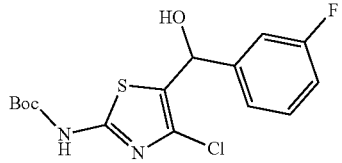 [SMILES: CC(C)(C)OC(=O)Nc1nc(Cl)c(C(O)c2cccc(F)c2)s1]

To a solution of tert-butyl 4-chloro-5-formylthiazol-2-ylcarbamate (1.14 g, 4.3 mmol) in tetrahydrofuran (40 mL) at 0° C. was added (3-fluorophenyl)magnesium bromide (5.4 mL, 10.8 mmol) dropwise under argon. The reaction mixture was stirred at 0° C. for 2 h. Reaction was quenched with aqueous ammonium chloride solution (20 mL) and extracted with ethyl acetate (100 mL×3). The combined organic layers were dried over sodium sulfate, filtered and concentrated. The crude product was purified by column chromatography (silica gel, petroleum ether/ethyl acetate 3/1) to give tert-butyl 4-chloro-5-((3-fluorophenyl)(hydroxy)methyl)thiazol-2-ylcarbamate (1.51 g, 4.2 mmol, 97%) as a yellow solid. LCMS (ESI) m/z: 303.0 [M-56+H]+.

Step 3: Preparation of 4-chloro-5-(3-fluorobenzyl)thiazol-2-amine

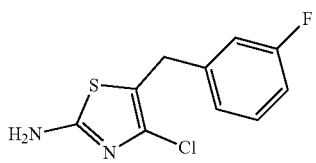 [SMILES: Nc1nc(Cl)c(Cc2cccc(F)c2)s1]

To a solution of tert-butyl 4-chloro-5-((3-fluorophenyl)(hydroxy)methyl)thiazol-2-ylcarbamate (1.49 g, 4.16 mmol) and triethoxysilane (5.46 g, 58.24 mmol) in dichloromethane (50 mL) was added trifluoroacetic acid (6.64 g, 58.2 mmol) at room temperature under nitrogen. The reaction mixture was stirred at 35° C. for 8 h. The volatiles were concentrated and the slurry was adjusted to pH 9 with saturated sodium bicarbonate aqueous. The aqueous layer was extracted with dichloromethane (80 mL×3). The combined organic layers were dried over sodium sulfate, filtered and concentrated. The crude product was purified by column chromatography (silica gel, petroleum ether/ethyl acetate=3/1) to give 4-chloro-5-(3-fluorobenzyl)thiazol-2-amine (800 mg, 3.3 mmol, 80%) as a light-yellow solid. LCMS (ESI) m/z: 243.1 [M+H]+.

Step 4: Preparation of N-(4-chloro-5-(3-fluorobenzyl)thiazol-2-yl)-1-methyl-6-oxo-1,6-dihydropyridazine-3-carboxamide

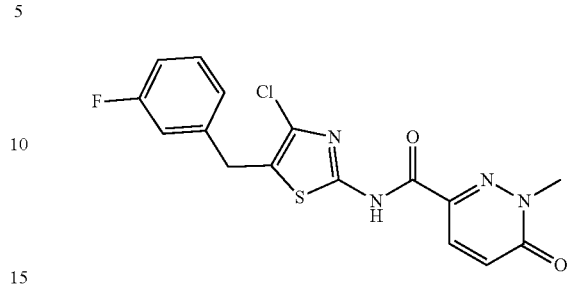

To a solution of 4-chloro-5-(3-fluorobenzyl)thiazol-2-amine (0.291 g, 1.2 mmol) in toluene (5 mL) at room temperature was added trimethylaluminum (0.6 mL, 1.2 mmol, 2 M in toluene) slowly under argon. The reaction mixture was stirred at room temperature for 1 h before methyl 1-methyl-6-oxo-1,6-dihydropyridazine-3-carboxylate (0.168 g, 1.0 mmol) in toluene (5 mL) was added. The resulting solution was heated to 100° C. and stirred for 3 h. Reaction mixture was cooled to room temperature and quenched with methanol and aqueous 2 N hydrochloric acid. The volatiles were removed in vacuo and water (20 mL) was added. The aqueous layer was extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(4-chloro-5-(3-fluorobenzyl)thiazol-2-yl)-1-methyl-6-oxo-1,6-dihydropyridazine-3-carboxamide (0.200 g, 0.53 mmol, 53%) as a white solid. ¹H NMR (500 MHz, Dimethylsulfoxide-d₆) δ 12.75 (s, 1H), 7.89 (d, J=9.5 Hz, 1H), 7.37-7.42 (m, 1H), 7.10-7.14 (m, 3H), 7.05-7.08 (m, 1H), 4.13 (s, 2H), 3.78 (s, 3H); LCMS (ESI) m/z: 379.0 [M+H]+.

Example 233. Preparation of N-(4-cyano-5-(3-fluorobenzyl)thiazol-2-yl)-1-methyl-6-oxo-1,6-dihydropyridazine-3-carboxamide (233)

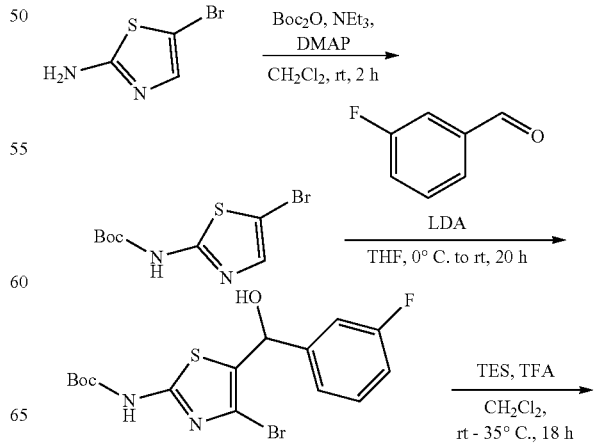

-continued

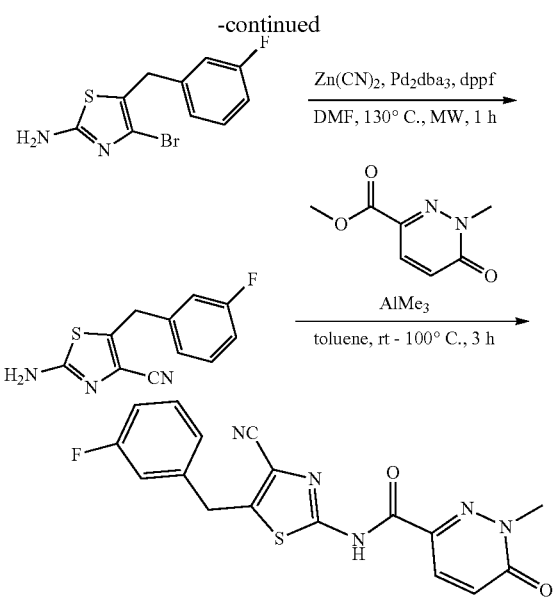

Step 1: Preparation of tert-butyl 5-bromothiazol-2-ylcarbamate

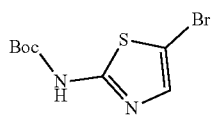

To a solution of 5-bromothiazol-2-amine (4.46 g, 24.9 mmol), di-tert-butyl dicarbonate (6.52 g, 30 mmol) and 4-dimethylaminopyridine (0.304 g, 2.5 mmol) in dichloromethane (120 mL) at room temperature was added triethylamine (6.3 g, 62.3 mmol) dropwise under nitrogen. The reaction mixture was stirred at room temperature for 2 h. The reaction mixture was diluted with dichloromethane (200 mL) and washed with 1N hydrochloric acid solution (50 mL×2). The combined organic layers were dried over sodium sulfate, filtered and concentrated. The crude product was purified by column chromatography (silica gel, petroleum ether/ethyl acetate=10/1) to give tert-butyl 5-bromothiazol-2-ylcarbamate as a white solid (4.04 g, 18.1 mmol, 73%); LCMS (ESI) m/z: 223.0 [M+H]+.

Step 2: Preparation of methyl tert-butyl 4-bromo-5-((3-fluorophenyl)(hydroxy)methyl)thiazol-2-ylcarbamate

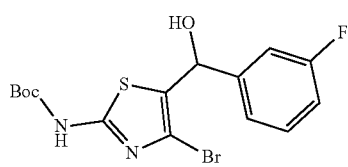 [SMILES: CC(C)(C)OC(=O)Nc1nc(Br)c(C(O)c2cccc(F)c2)s1]

To a solution of lithium diisopropylamide (16.5 mL, 33 mmol) in tetrahydrofuran (20 mL) at 0° C. was added tert-butyl 5-bromothiazol-2-ylcarbamate (2.8 g, 10.0 mmol) slowly under argon. The reaction mixture was stirred at 0° C. for 30 minutes before a solution of 3-fluorobenzaldehyde (4.1 g, 33.0 mmol) in tetrahydrofuran (10 mL) was added. The reaction solution was warmed to room temperature and stirred for 20 h. The reaction mixture was diluted with water (30 mL) and extracted with ethyl acetate (150 mL×3). The combined organic layers were dried over sodium sulfate, filtered and concentrated. The crude product was purified by column chromatography (silica gel, petroleum ether/ethyl acetate=4/1) to give tert-butyl 4-bromo-5-((3-fluorophenyl)(hydroxy)methyl)thiazol-2-ylcarbamate as a yellow solid (2.5 g, 6.2 mmol, 62%). LCMS (ESI) m/z: 346.9 [M-56+H]+.

Step 3: Preparation of 4-bromo-5-(3-fluorobenzyl)thiazol-2-amine

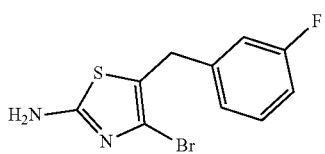 [SMILES: Nc1nc(Br)c(Cc2cccc(F)c2)s1]

To a solution of tert-butyl 4-bromo-5-((3-fluorophenyl)(hydroxy)methyl)thiazol-2-ylcarbamate (2.0 g, 5 mmol) and triethylsilane (6.57 g, 40 mmol) in dichloromethane (20 mL) at room temperature was added trifluoroacetic acid (8 g, 70 mmol) under nitrogen. The reaction mixture was stirred at 35° C. for 18 h. The volatiles were concentrated and the slurry was adjusted to pH 9 with aqueous saturated sodium bicarbonate. The aqueous layer was extracted with dichloromethane (100 mL×3). The combined organic layers were dried over sodium sulfate, filtered and concentrated. The crude product was purified by column chromatography (silica gel, petroleum ether/ethyl acetate=3/1) to give 4-bromo-5-(3-fluorobenzyl)thiazol-2-amine (1.09 g, 3.8 mmol, 76%) as a light-yellow solid. LCMS (ESI) m/z: 287.0 [M+H]+.

Step 4: Preparation of 2-amino-5-(3-fluorobenzyl)thiazole-4-carbonitrile

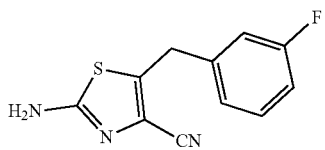 [SMILES: N#Cc1nc(N)sc1Cc1cccc(F)c1]

To a solution of 4-bromo-5-(3-fluorobenzyl)thiazol-2-amine (0.824 g, 2.87 mmol) and zinc cyanide (0.253 g, 2.15 mmol) and 1,1'-bis(diphenylphosphino)ferrocene (0.078 g, 0.14 mmol) in N,N-dimethylformamide (10 mL) at room temperature was added tris(dibenzylideneacetone) dipalladium(0) (0.082 g, 0.14 mmol) under nitrogen. The reaction mixture was stirred at 130° C. in the microwave for 1 h. The reaction mixture was cooled to room temperature and diluted with ethyl acetate (150 mL). The combined organic layers were washed with brine (50 mL×3), dried over sodium sulfate, filtered and concentrated. The crude product was purified by column chromatography (silica gel, petroleum ether/ethyl acetate=3/1) to give 2-amino-5-(3-fluorobenzyl)thiazole-4-carbonitrile as a brown solid (0.210 g, 0.9 mmol, 30%); LCMS (ESI) m/z: 234.1 [M+H]+.

Step 5: Preparation of N-(4-cyano-5-(3-fluorobenzyl)thiazol-2-yl)-1-methyl-6-oxo-1,6-dihydropyridazine-3-carboxamide

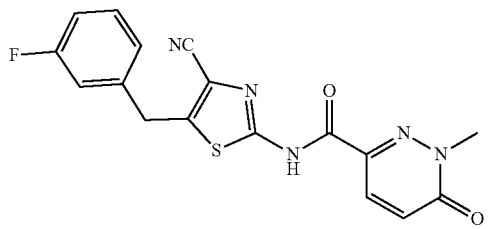 [SMILES: Cn1nc(C(=O)Nc2nc(C#N)c(Cc3cccc(F)c3)s2)ccc1=O]

To a solution of 2-amino-5-(3-fluorobenzyl)thiazole-4-carbonitrile (0.100 g, 0.43 mmol) in toluene (5 mL) at room temperature was added trimethylaluminum (0.25 mL, 0.5 mmol, 2 M in toluene) slowly under argon. The reaction mixture was stirred at room temperature for 1 h before methyl 1-methyl-6-oxo-1,6-dihydropyridazine-3-carboxylate (0.072 mg, 0.43 mmol) in toluene (5 mL) was added. The reaction mixture was heated to 100° C. and stirred for 3 h before it was cooled to room temperature and quenched with methanol and aqueous 2 N hydrochloric acid. The volatiles were removed and water (20 mL) was added. The aqueous layer was extracted with dichloromethane (50 mL×3). The combined organic layers were dried over sodium sulfate, filtered and concentrated. The crude sample was dissolved in minimal N,N-dimethylformamide and purified via prep-HPLC (Boston C18 21*250 mm 10 μm column. The mobile phase was acetonitrile/10 mM ammonium acetate aqueous solution) to give N-(4-cyano-5-(3-fluorobenzyl)thiazol-2-yl)-1-methyl-6-oxo-1,6-dihydropyridazine-3-carboxamide (3.1 mg, 0.01 mmol, 2%) as a white solid. $^1$H NMR (400 MHz, Dimethylsulfoxide-$d_6$) δ 12.93 (s, 1H), 7.90 (d, J=9.6 Hz, 1H), 7.42 (dd, $J_1$=6.4 Hz, $J_2$=7.6 Hz, 1H), 7.14-7.23 (m, 3H), 7.07 (d, J=9.6 Hz, 1H), 4.37 (s, 2H), 3.78 (s, 3H); LCMS (ESI) m/z: 370.0 [M+H]+.

Example 234. Preparation of N-(5-(2,4-difluorobenzyl)thiazol-2-yl)-1-methyl-6-oxo-1,4,5,6-tetrahydropyridazine-3-carboxamide (234)

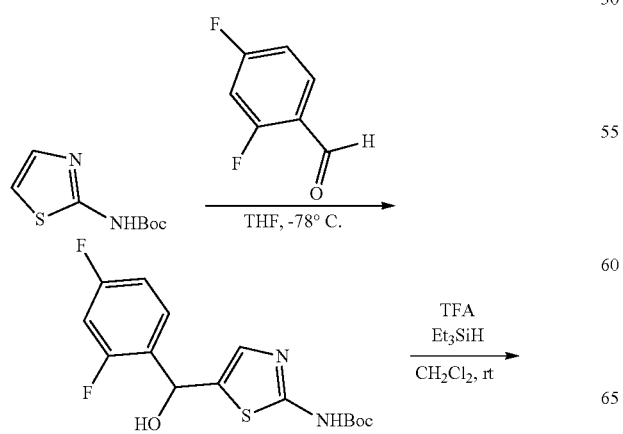

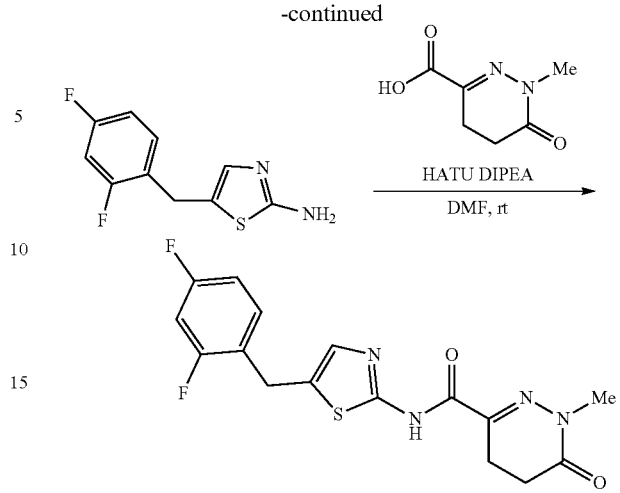

Step 1: Preparation of tert-butyl (5-((2,4-difluorophenyl)(hydroxy)methyl)thiazol-2-yl)carbamate

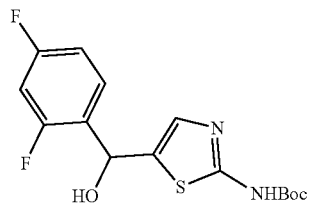

Dissolved tert-butyl thiazol-2-ylcarbamate (0.5 g, 2.49 mmol) in tetrahydrofuran (12.4 mL) and cooled to −78° C. Carefully added n-butyllithium (1.6 M in hexanes, 1.39 mL, 3.48 mmol) and stirred for 10 minutes, followed by 2,4-difluorobenzaldehyde (325 μL, 2.98 mmol). Quenched with saturated aqueous ammonium chloride (15 mL) and extracted with ethyl acetate (20 mL). Washed with brine (10 mL), then dried over sodium sulfate. Filtered and concentrated in vacuo. Purified reaction by column chromatography (eluting with 0-50% ethyl acetate/hexanes through 24 g of silica gel) to give tert-butyl (5-((2,4-difluorophenyl)(hydroxy)methyl)thiazol-2-yl)carbamate as an orange solid (165 mg, 0.482 mmol, 19%). $^1$H NMR (300 MHz, Chloroform-d) δ 7.62 (d, J=6.4 Hz, 1H), 7.15 (s, 1H), 6.96 (d, J=10.0 Hz, 2H), 6.88-6.75 (m, 1H), 6.26 (s, 1H), 1.53 (s, 9H).

Step 2: Preparation of 5-(2,4-difluorobenzyl)thiazol-2-amine

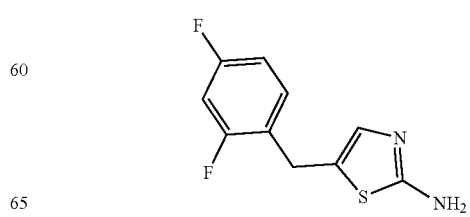

Dissolved tert-butyl (5-((2,4-difluorophenyl)(hydroxy) methyl)thiazol-2-yl)carbamate (0.165 g, 0.4819 mmol) in methylene chloride (2.40 mL) and added triethylsilane (383 µL, 2.40 mmol) and 2,2,2-trifluoroacetic acid (294 µL, 3.85 mmol) in a 50 mL round bottom flask. Stirred 16 h at room temperature. After 9 h, added 0.1 mL more of 2,2,2-trifluoroacetic acid and stirred 16 h again. Concentrated to remove solvent, then diluted with ethyl acetate (15 mL) and washed with saturated aqueous sodium bicarbonate (10 mL), then brine (15 mL). The combined organic layers were dried over sodium sulfate, filtered, and concentrated. 5-(2,4-Difluorobenzyl)thiazol-2-amine is taken crude to next step. $^1$H NMR (300 MHz, Chloroform-d) δ 7.18 (d, J=6.4 Hz, 1H), 6.91-6.82 (m, 2H), 6.80 (d, J=1.1 Hz, 1H), 3.95 (s, 2H).

Step 3: Preparation of N-(5-(2,4-difluorobenzyl) thiazol-2-yl)-1-methyl-6-oxo-1,4,5,6-tetrahydro-pyridazine-3-carboxamide

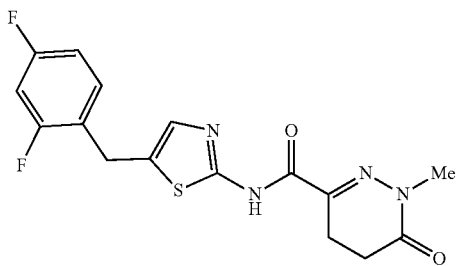 [SMILES: CN1N=C(C(=O)Nc2ncc(Cc3ccc(F)cc3F)s2)CCC1=O]

Combined 5-(2,4-difluorobenzyl)thiazol-2-amine (0.158 g, 0.6983 mmol) and 1-methyl-6-oxo-1,4,5,6-tetrahydropyridazine-3-carboxylic acid (0.109 g, 0.6983 mmol) in a 25 mL round bottom flask and added 2-(3H-[1,2,3]triazolo[4,5-b]pyridin-3-yl)-1,1,3,3-tetramethyluronium tetrafluoroborate (0.224 g, 0.6983 mmol). Dissolved in N,N'-dimethylformamide (3.49 mL) and added N-N-N,N-diisopropylethyl amine (180 µL, 1.04 mmol). Stirred at room temperature 16 h. Diluted with ethyl acetate (15 mL) and washed 3 times with water (10 mL), then brine (15 mL). The combined organic layers were dried over sodium sulfate, filtered, and concentrated. Purified reaction by column chromatography (eluting with 0-100% ethyl acetate/hexanes through 24 g of silica gel) to give N-(5-(2,4-difluorobenzyl)thiazol-2-yl)-1-methyl-6-oxo-1,4,5,6-tetrahydropyridazine-3-carboxamide as a pale yellow solid (93 mg, 0.255 mmol, 37%). $^1$H NMR (300 MHz, Chloroform-d) δ 7.26-7.15 (m, 2H), 6.84 (t, J=9.3 Hz, 2H), 4.10 (s, 2H), 3.46 (s, 3H), 2.98 (t, J=8.6 Hz, 2H), 2.61 (t, J=8.6 Hz, 2H); LCMS (ESI) m/z 365.4 [M+H]$^+$.

Example 235. Preparation of N-(5-(2,5-difluorobenzyl)thiazol-2-yl)-1-methyl-6-oxo-1,4,5,6-tetrahydropyridazine-3-carboxamide (235)

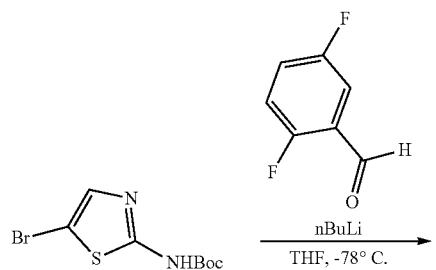

Step 1: Preparation of tert-butyl (5-((2,5-difluorophenyl)(hydroxy)methyl)thiazol-2-yl)carbamate

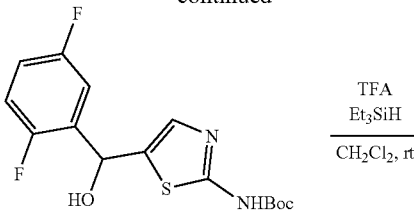

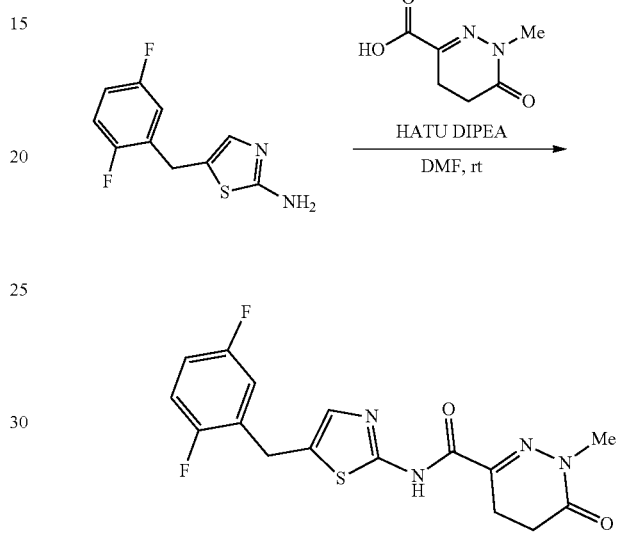

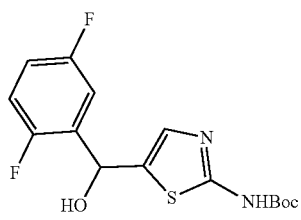 [SMILES: CC(C)(C)OC(=O)Nc1ncc(C(O)c2cc(F)ccc2F)s1]

Dissolved tert-butyl (5-bromothiazol-2-yl)carbamate (0.5 g, 1.79 mmol) in tetrahydrofuran (8.95 mL) and cooled to −78° C. Carefully added n-butyllithium (1.6M in hexanes, 1.14 mL, 2.86 mmol) and stirred for 10 minutes, followed by 2,5-difluorobenzaldehyde (271 uL, 2.50 mmol). Stirred at −78° C. for 3 h. Warmed to room temperature and quenched with saturated aqueous ammonium chloride (15 mL). Extracted with ethyl acetate (20 mL) and washed with brine (15 mL). The combined organic layers were dried over sodium sulfate, filtered, and concentrated. Purified reaction by column chromatography (eluting with 0-50% ethyl acetate/hexanes through 24 g of silica gel) to give tert-butyl (5-((2,5-difluorophenyl)(hydroxy)methyl)thiazol-2-yl)carbamate as a yellow solid (150 mg, 0.438 mmol, 24%). $^1$H NMR (300 MHz, Chloroform-d) δ 7.37 (d, J=3.0 Hz, 1H), 7.17 (s, 1H), 7.10-6.92 (m, 2H), 6.27 (s, 1H), 1.53 (s, 9H).

Step 2: Preparation of 5-(2,5-difluorobenzyl)thiazol-2-amine

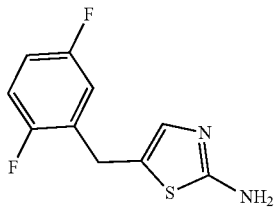 [SMILES: Nc1ncc(Cc2cc(F)ccc2F)s1]

Dissolved tert-butyl (5-((2,5-difluorophenyl)(hydroxy)methyl)thiazol-2-yl)carbamate (0.150 g, 0.4381 mmol) in 5 mL dichloromethane and added 2,2,2-trifluoroacetic acid (267 µL, 3.50 mmol) and triethylsilane (348 µL, 2.19 mmol). Stirred 16 h at room temperature. A second load of 2,2,2-trifluoroacetic acid (267 µL, 3.50 mmol) and triethylsilane (348 µL, 2.19 mmol) was added. Reaction was stirred for another night at room temperature. Concentrated to remove solvent and 2,2,2-trifluoroacetic acid, then diluted in dichloromethane (20 mL) and washed with saturated aqueous sodium bicarbonate (15 mL). The combined organic layers were dried over sodium sulfate, filtered, and concentrated. Crude product is taken to the next step. $^1$H NMR (300 MHz, Chloroform-d) δ 6.99-6.84 (m, 2H), 6.84-6.74 (m, 1H), 6.70 (s, 1H), 3.83 (s, 2H).

Step 3: Preparation of N-(5-(2,5-difluorobenzyl)thiazol-2-yl)-1-methyl-6-oxo-1,4,5,6-tetrahydropyridazine-3-carboxamide

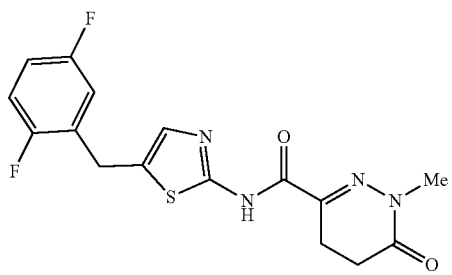 [SMILES: CN1N=C(C(=O)Nc2ncc(Cc3cc(F)ccc3F)s2)CCC1=O]

Combined 5-(2,5-difluorobenzyl)thiazol-2-amine (0.088 g, 0.3889 mmol) and 1-methyl-6-oxo-1,4,5,6-tetrahydropyridazine-3-carboxylic acid (60.7 mg, 0.3889 mmol) with 2-(3H-[1,2,3]triazolo[4,5-b]pyridin-3-yl)-1,1,3,3-tetramethyluronium tetrafluoroborate (0.137 g, 0.4277 mmol) in a 25 mL round bottom flask and dissolved in N,N'-dimethylformamide (2.0 mL). Added N-N-N,N-diisopropylethylamine (101 µL, 0.5833 mmol) and stirred 16 h at room temperature. Diluted with ethyl acetate (15 mL) and washed 3 times with water (10 mL) and once with brine (10 mL). The combined organic layers were dried over sodium sulfate, filtered, and concentrated. Purified reaction by column chromatography (eluting with 0-100% ethyl acetate/hexanes through 24 g of silica gel) to give N-(5-(2,5-difluorobenzyl)thiazol-2-yl)-1-methyl-6-oxo-1,4,5,6-tetrahydropyridazine-3-carboxamide as a slightly yellow solid (32 mg, 0.088 mmol, 23%). $^1$H NMR (300 MHz, Chloroform-d) δ 7.28 (s, 1H), 7.04 (s, 1H), 6.94 (d, J=7.7 Hz, 2H), 4.12 (s, 2H), 3.46 (d, J=0.9 Hz, 3H), 2.99 (t, J=8.6 Hz, 2H), 2.61 (t, J=8.6 Hz, 2H); LCMS (ESI) m/z 365.5 [M+H]$^+$.

Example 236. Preparation of N-(5-(3-chlorobenzyl)thiazol-2-yl)-1-methyl-6-oxo-1,6-dihydropyridazine-3-carboxamide (236)

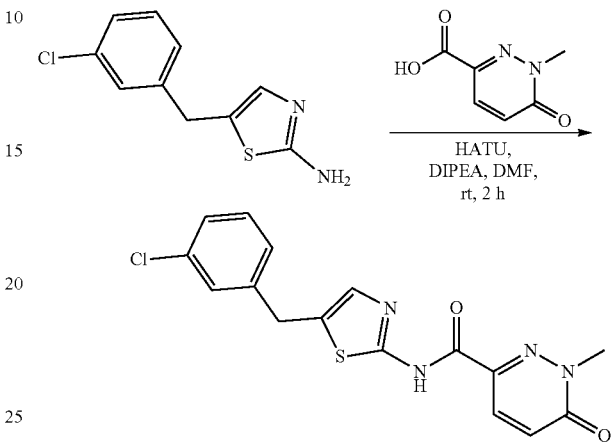

Step 1: Preparation of N-(5-(3-chlorobenzyl)thiazol-2-yl)-1-methyl-6-oxo-1,6-dihydropyridazine-3-carboxamide

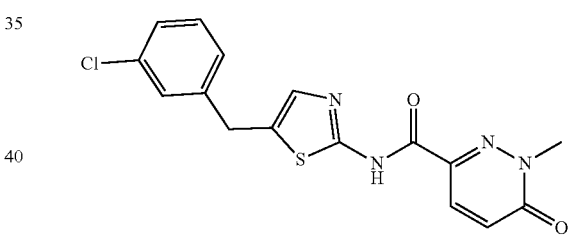

To a stirred solution of 5-(3-chlorobenzyl)thiazol-2-amine (0.100 g, 0.45 mmol), 1-methyl-6-oxo-1,6-dihydropyridazine-3-carboxylic acid (0.083 g, 0.54 mmol) and 1-[bis(dimethylamino)methylene]-1H-1,2,3-triazolo[4,5-b]pyridinium 3-oxid hexafluorophosphate (0.200 g, 0.54 mmol) in N,N-dimethylformamide (5.00 mL) was added N,N-diisopropylethylamine (0.170 g, 1.34 mmol). After addition, the reaction mixture was stirred at room temperature for 2 h. The crude sample was dissolved in minimal N,N-dimethylformamide and purified via prep-HPLC (Sunfire prep C18 10 µm OBD 19*250 mm; mobile phase: [water (0.05% trifluoroacetic acid)-acetonitrile]; B %: 60%-88%, 15 minutes) to give N-(5-(3-chlorobenzyl)thiazol-2-yl)-1-methyl-6-oxo-1,6-dihydropyridazine-3-carboxamide (0.070 g, 0.19 mmol, 43.2%) as a white solid. $^1$H NMR (500 MHz, Dimethylsulfoxide-d$_6$) δ 12.30 (s, 1H), 7.90 (d, J=9.7 Hz, 1H), 7.45-7.33 (m, 3H), 7.29 (dd, J=16.6, 7.9 Hz, 2H), 7.05 (d, J=9.7 Hz, 1H), 4.15 (s, 2H), 3.77 (s, 3H); LCMS (ESI) m/z: 361.0 [M+H]$^+$.

Example 237. Preparation of N-(5-((3-fluorophenyl)(methyl)amino)thiazol-2-yl)-1-methyl-6-oxo-1,4,5,6-tetrahydropyridazine-3-carboxamide (237)

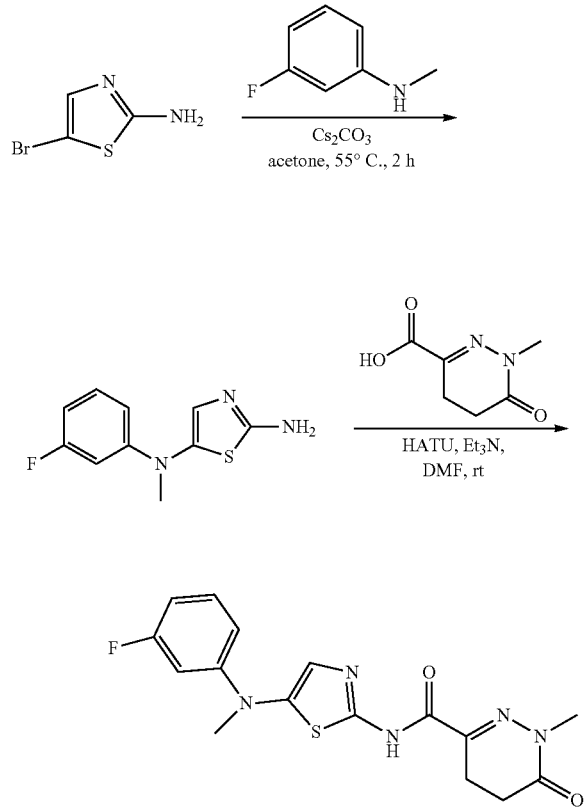

Step 1: Preparation of N-(3-fluorophenyl)-N-methylthiazole-2,5-diamine

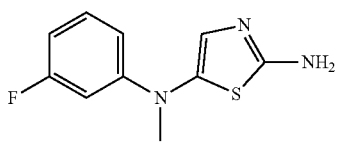

To a stirred solution of 5-bromothiazol-2-amine (0.30 g, 1.68 mmol) in acetone (10.0 mL) at room temperature was added 3-fluoro-N-methylbenzenamine (0.31 g, 2.51 mmol) and cesium carbonate (0.66 g, 2.01 mmol). The reaction mixture was heated to 55° C. and stirred at this temperature for 2 h. The reaction mixture was cooled to room temperature and filtered. The filtrate was concentrated. The residue was diluted with water (20 mL) and extracted with ethyl acetate (30 mL×2). The combined organic layers were washed with brine (20 mL×2), dried over anhydrous sodium sulfate, filtered and concentrated under reduced pressure. The residue was purified by column chromatography (silica gel, petroleum ether/ethyl acetate=4/1) to give N-(3-fluorophenyl)-N-methylthiazole-2,5-diamine (0.26 g, 1.17 mmol, 69.6%) as a yellow solid. LCMS (ESI) m/z: 224.1 [M+H]$^+$.

Step 2: Preparation of N-(5-((3-fluorophenyl)(methyl)amino)thiazol-2-yl)-1-methyl-6-oxo-1,4,5,6-tetrahydropyridazine-3-carboxamide

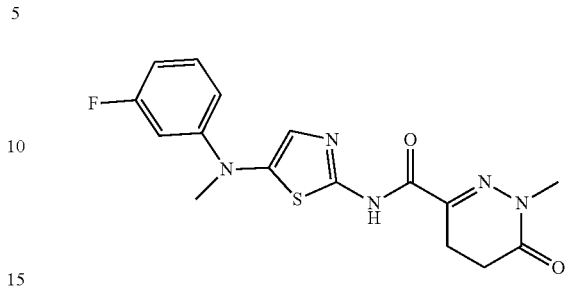

To a solution of N-(3-fluorophenyl)-N-methylthiazole-2,5-diamine (0.25 g, 1.12 mmol), 1-methyl-6-oxo-1,4,5,6-tetrahydropyridazine-3-carboxylic acid (0.21 g, 1.35 mmol) and 1-[bis(dimethylamino)methylene]-1H-1,2,3-triazolo[4,5-b]pyridinium 3-oxid hexafluorophosphate (0.51 g, 1.35 mmol) in N,N-dimethylformamide (5 mL) was added triethylamine (0.34 g, 3.36 mmol). The mixture was stirred at room temperature for 2 h. The crude sample was dissolved in minimal N,N-dimethylformamide and purified via prep-HPLC (Boston C18 21*250 mm 10 μm column; acetonitrile/0.01% aqueous trifluoroacetic acid) to give N-(5-((3-fluorophenyl)(methyl)amino)thiazol-2-yl)-1-methyl-6-oxo-1,4,5,6-tetrahydropyridazine-3-carboxamide (0.228 g, 0.63 mmol, 56.2%) as a white solid. $^1$H NMR (500 MHz, Dimethylsulfoxide-d$_6$) δ 11.99 (s, 1H), 7.38 (s, 1H), 7.24 (dd, J=15.2, 9.0 Hz, 1H), 6.66-6.60 (m, 3H), 3.37 (s, 3H), 3.27 (s, 3H), 2.83 (t, J=8.5 Hz, 2H), 2.53 (t, J=8.5 Hz, 2H); LCMS (ESI) m/z: 362.0 [M+H]$^+$.

Example 238. Characterization Data of Compounds of the Invention

The following compounds were synthesized by methods similar to those described above.

Compound 238: $^1$H NMR (300 MHz, Chloroform-d) δ 8.57 (d, J=9.1 Hz, 1H), 8.17 (d, J=3.7 Hz, 2H), 8.09-7.93 (m, 2H), 7.41 (s, 1H), 7.09 (d, J=7.6 Hz, 1H), 6.99 (d, J=5.3 Hz, 2H), 4.37 (s, 2H); LCMS (ESI) m/z: 349.2 [M+H]+.

Compound 239: $^1$H NMR (300 MHz, Chloroform-d) δ 10.45 (s, 1H), 8.36 (d, J=8.4 Hz, 1H), 8.33-8.20 (m, 1H), 7.87 (s, 1H), 7.59 (dd, J=8.5, 2.4 Hz, 1H), 7.30 (s, 1H), 7.10-6.84 (m, 3H), 3.99 (s, 2H), 2.80 (s, 3H), 2.64 (s, 3H); LCMS (ESI) m/z: 337.4 [M+H]+.

Compound 240: $^1$H NMR (300 MHz, DMSO-d6) δ 10.93 (s, 1H), 8.33 (dd, J=2.5, 0.8 Hz, 1H), 8.04 (dd, J=8.5, 0.8 Hz, 1H), 7.81 (d, J=7.0 Hz, 1H), 7.72 (dd, J=8.5, 2.4 Hz, 1H), 7.34 (td, J=8.0, 6.3 Hz, 1H), 7.27-6.96 (m, 4H), 6.93 (dd, J=2.0, 0.6 Hz, 1H), 6.60 (dd, J=7.0, 2.0 Hz, 1H), 3.98 (s, 2H), 3.45 (s, 3H); LCMS (ESI) m/z: 338.4 [M+H]+.

Compound 241: $^1$H NMR (300 MHz, Chloroform-d) δ 10.54 (s, 1H), 8.43-8.17 (m, 3H), 7.65-7.45 (m, 2H), 7.11 (dt, J=10.2, 8.3 Hz, 1H), 7.03-6.82 (m, 2H), 3.95 (s, 2H), 2.85 (s, 3H); LCMS (ESI) m/z: 341.4 [M+H]+.

Compound 242: $^1$H NMR (300 MHz, DMSO-d6) δ 10.39 (s, 1H), 9.04 (d, J=5.0 Hz, 1H), 8.38 (d, J=2.3 Hz, 1H), 8.19 (d, J=8.5 Hz, 1H), 7.96 (d, J=5.0 Hz, 1H), 7.82 (dd, J=8.5, 2.4 Hz, 1H), 7.25-6.88 (m, 3H), 4.01 (s, 2H), 2.78 (s, 3H); LCMS (ESI) m/z: 341.4 [M+H]+.

Compound 243: $^1$H NMR (300 MHz, Chloroform-d) δ 10.54 (s, 1H), 8.43-8.20 (m, 3H), 7.57 (d, J=8.6 Hz, 2H), 7.33-7.13 (m, 3H), 7.13-7.00 (m, 1H), 3.97 (s, 2H), 2.86 (s, 3H); LCMS (ESI) m/z: 339.3 [M+H]+.

Compound 244: $^1$H NMR (300 MHz, Chloroform-d) δ 10.44 (s, 1H), 8.95 (d, J=5.0 Hz, 1H), 8.38 (d, J=8.5 Hz, 1H), 8.26 (d, J=2.4 Hz, 1H), 8.09-7.92 (m, 1H), 7.60 (d, J=2.3 Hz, 1H), 7.23 (dd, J=7.0, 2.1 Hz, 1H), 7.09 (d, J=8.5 Hz, 2H), 3.96 (s, 2H), 2.86 (s, 3H); LCMS (ESI) m/z: 357.4 [M+H]+.

Compound 245: $^1$H NMR (500 MHz, MeOD) δ 8.62 (s, 1H), 7.37-7.34 (m, 1H), 7.17-7.15 (d, J 7.7 Hz, 1H), 7.13-7.11 (d, J=9.7 Hz, 1H), 7.02-7.00 (m, 1H), 4.37 (s, 2H), 3.53-3.42 (m, 3H), 3.04-2.93 (m, 2H), 2.62-2.60 (m, 2H); LCMS (ESI) m/z: 343.1 [M+H]+.

Compound 246: $^1$H NMR (500 MHz, DMSO-d6) δ 10.43 (s, 1H), 8.24 (d, J=9.1 Hz, 1H), 7.68 (d, J=9.1 Hz, 1H), 7.27 (ddd, J=29.5, 23.6, 12.8 Hz, 4H), 3.38 (s, 3H), 3.21 (t, J=7.8 Hz, 2H), 3.05 (t, J 7.8 Hz, 2H), 2.86 (t, J=8.5 Hz, 2H), 2.54 (t, J=8.5 Hz, 2H); LCMS (ESI) m/z: 372.1 [M+H]+.

Compound 247: $^1$H NMR (500 MHz, DMSO-d6) δ 10.41 (s, 1H), 8.28 (d, J=9.0 Hz, 1H), 7.70 (d, J=9.0 Hz, 1H), 6.97 (d, J=4.0 Hz, 1H), 6.87 (d, J=3.5 Hz, 1H), 4.42 (s, 2H), 3.38 (s, 2H), 2.85 (t, J=8.5 Hz, 2H), 2.54 (t, J=8.5 Hz, 2H); LCMS (ESI) m/z: 364.0 [M+H]+.

Compound 248: $^1$H NMR (400 MHz, Dimethylsulfoxide-d6) δ 10.62 (s, 1H), 8.67 (s, 1H), 8.29 (s, 1H), 8.02 (d, J=8 Hz, 1H), 7.98 (d, J=9.5 Hz, 1H), 7.71 (d, J=8.5 Hz, 1H), 7.30 (t, J=6 Hz, 2H), 7.12 (t, J=8.3 Hz, 2H), 6.44 (t, J=9.5 Hz, 2H), 3.95 (s, 2H), 3.50 (s, 3H); LCMS (ESI) m/z: 338.1 [M+H]+.

Compound 249: $^1$H NMR (500 MHz, DMSO-d6) δ 9.52 (s, 1H), 8.20 (d, J=1.5 Hz, 1H), 7.71 (d, J=8.6 Hz, 1H), 7.58 (dd, J=8.6, 2.1 Hz, 1H), 7.43 (d, J=1.5 Hz, 1H), 7.37-7.19 (m, 4H), 6.11 (s, 1H), 4.74 (s, 2H), 4.14 (t, J=5.3 Hz, 2H), 4.01-3.87 (m, 4H); LCMS (ESI) m/z: 368.0 [M+H]+.

Compound 250: $^1$H NMR (500 MHz, CDCl3) δ 8.00 (dd, J=29.7, 5.2 Hz, 2H), 7.45 (dd, J=8.6, 2.3 Hz, 1H), 7.24-7.10 (m, 3H), 7.04 (d, J=7.1 Hz, 1H), 6.94 (s, 1H), 4.81 (s, 4H), 4.23 (s, 4H), 3.88 (s, 2H); LCMS (ESI) m/z: 344.0 [M+H]+.

Compound 251: $^1$H NMR (500 MHz, DMSO-d6) δ 10.05 (s, 1H), 8.33 (s, 1H), 8.08-8.06 (d, J=8.4 Hz, 1H), 7.88 (s, 1H), 7.75-7.72 (d, J=8.6 Hz, 1H), 7.43-7.26 (m, 1H), 7.12-7.10 (t, J=7.2 Hz, 2H), 7.04-7.01 (t, J=8.6 Hz, 1H), 3.99 (s, 2H), 3.79 (s, 3H), 2.17 (s, 3H); LCMS (ESI) m/z: 353.0 [M+H]+.

Compound 252: $^1$H NMR (500 MHz, DMSO-d6) δ 10.23 (s, 1H), 9.19 (s, 1H), 8.71 (s, 1H), 8.34 (d, J=2.0 Hz, 1H), 8.17 (d, J=8.5 Hz, 1H), 7.79 (dd, J=8.5, 2.0 Hz, 1H), 7.35 (dd, J=14.5, 8.0 Hz, 1H), 7.12 (t, J=7.5 Hz, 2H), 7.04 (dd, J=12.0, 5.5 Hz, 1H), 3.99 (s, 2H), 2.64 (s, 3H); LCMS (ESI) m/z: 323.1 [M+H]+.

Compound 253: $^1$H NMR (500 MHz, DMSO-d6) δ 10.42 (s, 1H), 8.23 (d, J=9.0 Hz, 1H), 7.62 (d, J=9.0 Hz, 1H), 7.33-7.21 (m, 5H), 4.26 (s, 2H), 3.38 (s, 3H), 2.85 (t, J=8.5 Hz, 2H), 2.54 (t, J=8.5 Hz, 2H); LCMS (ESI) m/z: 324.1 [M+H]+.

Compound 254: $^1$H NMR (500 MHz, DMSO-d6) δ 11.06 (s, 1H), 8.22 (d, J=8.5 Hz, 1H), 7.96 (d, J=10.0 Hz, 1H), 7.89 (d, J=9.0 Hz, 1H), 7.45 (s, 1H), 7.38-7.35 (m, 1H), 7.32-7.30 (m, 2H), 7.06 (d, J=10.0 Hz, 1H), 4.45 (s, 2H), 3.62 (s, 3H); LCMS (ESI) m/z: 356.0 [M+H]+.

Compound 255: $^1$H NMR (400 MHz, DMSO-d6) δ 8.37 (d, J=1.6 Hz, 1H), 7.85 (s, 1H), 7.39 (s, 1H), 7.34 (t, J=7.8 Hz, 1H), 7.28-7.25 (m, 2H), 4.12 (s, 2H), 3.39 (s, 3H), 3.16 (t, J=8.4 Hz, 2H), 2.60 (t, J=8.4 Hz, 2H);

Compound 256: $^1$H NMR (500 MHz, DMSO-d6) δ 10.10 (s, 1H), 8.34-8.35 (d, J=2.0 Hz, 1H), 8.04-8.06 (d, J=8.5 Hz, 1H), 7.89-7.91 (d, J=10.0 Hz, 1H), 7.73-7.75 (m, 1H), 7.32-7.34 (m, 2H), 7.22-7.28 (m, 2H), 7.05-7.07 (m, 1H), 4.08-4.09 (t, J=3.5 Hz, 1H), 3.98 (s, 2H); LCMS (ESI) m/z: 381.1 [M+H]+.

Compound 257: $^1$H NMR (400 MHz, DMSO-d6) δ 10.90 (s, 1H), 8.30 (d, J=9.2 Hz, 1H), 7.93 (d, J=10.0 Hz, 1H), 7.70 (d, J=9.2 Hz, 1H), 7.40-7.26 (m, 3H), 7.08 (d, J=10.0 Hz, 1H), 4.30 (s, 2H), 4.16 (t, J=7.2 Hz, 2H), 1.88-1.79 (m, 2H), 0.93 (t, J=7.4 Hz, 3H); LCMS (ESI) m/z: 384.1 [M+H]+.

Compound 258: $^1$H NMR (500 MHz, DMSO-d6) δ 10.84 (s, 1H), 8.40-8.41 (d, J=2.5 Hz, 1H), 8.31 (d, J=1.5 Hz, 1H), 8.02-8.03 (d, J=8.5 Hz, 1H), 7.89-7.91 (m, 1H), 7.71-7.73 (m, 1H), 7.32-7.36 (m, 2H), 7.10-7.12 (m, 2H), 7.03 (m, 1H), 6.42-6.46 (d, J=10.0 Hz, 1H), 3.97 (s, 2H), 3.39 (m, 1H); LCMS (ESI) m/z: 364.1 [M+H]+.

Compound 259: $^1$H NMR (500 MHz, DMSO-d6) δ 11.28 (s, 1H), 8.75 (d, J=2.7 Hz, 1H), 8.40 (d, J=9.2 Hz, 1H), 8.02 (dd, J=9.5, 2.7 Hz, 1H), 7.87 (d, J=9.3 Hz, 1H), 7.34 (t, J=8.1 Hz, 1H), 7.19 (t, J=2.2 Hz, 1H), 7.10-6.99 (m, 2H), 6.46 (d, J=9.5 Hz, 1H), 5.39 (s, 2H), 3.52 (s, 3H); LCMS (ESI) m/z: 371.1 [M+H]+.

Compound 260: $^1$H NMR (500 MHz, DMSO-d6) δ 9.83 (s, 1H), 8.46 (s, 1H), 8.14 (d, J=8.5 Hz, 1H), 7.96 (d, J=8.0 Hz, 1H), 7.34 (dd, J=15.6, 8.1 Hz, 1H), 6.91 (dd, J=24.8, 9.7 Hz, 2H), 6.80 (t, J=8.4 Hz, 1H), 5.13 (s, 2H), 3.37 (s, 3H), 2.86 (t, J=8.4 Hz, 2H), 2.61-2.52 (m, 2H).

Compound 261: $^1$H NMR (500 MHz, DMSO-d6) δ 9.84 (s, 1H), 8.46 (d, J=1.9 Hz, 1H), 8.14 (d, J=8.5 Hz, 1H), 7.95 (dd, J=8.5, 2.2 Hz, 1H), 7.33 (t, J=8.2 Hz, 1H), 7.14 (t, J=2.1 Hz, 1H), 7.06-6.96 (m, 2H), 5.14 (s, 2H), 3.37 (s, 3H), 2.86 (t, J=8.5 Hz, 2H), 2.53 (t, J=8.5 Hz, 2H); LCMS (ESI) m/z: 373.0 [M+H]+.

Compound 262: $^1$H NMR (500 MHz, DMSO-d6) δ 10.24 (s, 1H), 8.49 (d, J=1.8 Hz, 1H), 8.20 (d, J=8.5 Hz, 1H), 8.03-7.90 (m, 2H), 7.33 (t, J=8.2 Hz, 1H), 7.17-6.98 (m, 4H), 5.16 (s, 2H), 3.80 (s, 3H); LCMS (ESI) m/z: 371.1 [M+H]+.

Compound 263: $^1$H NMR (500 MHz, DMSO-d6) δ 10.63 (s, 1H), 8.69 (d, J=2.6 Hz, 1H), 8.47 (d, J=1.9 Hz, 1H), 8.17 (d, J=8.5 Hz, 1H), 7.95 (ddd, J=10.9, 9.0, 2.5 Hz, 2H), 7.33 (t, J=8.2 Hz, 1H), 7.14 (t, J=2.1 Hz, 1H), 7.06-6.97 (m, 2H), 6.44 (d, J=9.5 Hz, 1H), 5.14 (s, 2H), 3.51 (s, 3H); LCMS (ESI) m/z: 370.0 [M+H]+.

Compound 264: $^1$H NMR (400 MHz, DMSO-d6) δ 10.72 (s, 1H), 8.67 (d, J=2.4 Hz, 1H), 8.47 (d, J=1.6 Hz, 1H), 8.17 (d, J=8.4 Hz, 1H), 7.95 (dd, J=9.6, 2.8 Hz, 1H), 7.91 (dd, J=8.8, 2.4 Hz, 1H), 7.33 (t, J=8.2 Hz, 1H), 7.14 (t, J=4.0 Hz, 1H), 7.04-7.00 (m, 2H), 6.43 (d, J=9.6 Hz, 1H), 5.14 (s, 2H), 4.01-3.95 (m, 2H), 1.28 (t, J=7.2 Hz, 3H); LCMS (ESI) m/z: 384.1 [M+H]+.

Compound 265: $^1$H NMR (500 MHz, DMSO-d6) δ 9.83 (s, 1H), 8.45 (d, J=2.3 Hz, 1H), 8.17-8.09 (m, 1H), 7.95 (dd, J=8.6, 2.3 Hz, 1H), 7.36 (t, J=9.1 Hz, 1H), 7.30 (dd, J=6.1, 3.1 Hz, 1H), 7.08-6.98 (m, 1H), 5.12 (s, 2H), 3.37 (s, 3H), 2.86 (t, J=8.5 Hz, 2H), 2.53 (t, J=8.5 Hz, 2H); LCMS (ESI) m/z: 391.1 [M+H]+.

Compound 266: $^1$H NMR (500 MHz, DMSO-d6) δ 10.64 (s, 1H), 8.69 (d, J=2.7 Hz, 1H), 8.46 (d, J=2.3 Hz, 1H), 8.16 (d, J=8.6 Hz, 1H), 7.99 (dd, J=9.5, 2.7 Hz, 1H), 7.91 (dd, J=8.6, 2.4 Hz, 1H), 7.36 (t, J=9.1 Hz, 1H), 7.30 (dd, J=6.1, 3.1 Hz, 1H), 7.09-7.01 (m, 1H), 6.44 (d, J=9.5 Hz, 1H), 5.12 (s, 2H), 3.51 (s, 3H); LCMS (ESI) m/z: 388.0 [M+H]+.

Compound 267: $^1$H NMR (400 MHz, DMSO-d6) δ 11.17 (s, 1H), 8.72 (d, J=2.4 Hz, 1H), 8.27 (d, J=9.6 Hz, 1H), 8.00 (dd, J=9.6, 2.4 Hz, 1H), 7.62 (d, J=9.2 Hz, 1H), 7.34-7.21 (m, 2H), 6.45 (d, J=9.6 Hz, 1H), 4.34 (s, 2H), 3.51 (s, 3H); LCMS (ESI) m/z: 375.1 [M+H]+.

Compound 268: ¹H NMR (500 MHz, DMSO-d6) δ 9.70 (s, 1H), 8.16 (d, J=2.5 Hz, 1H), 8.03 (d, J=9.0 Hz, 1H), 7.69 (s, 1H), 7.59 (dd, J=9.0, 3.0 Hz, 1H), 7.55 (d, J=8.0 Hz, 1H), 7.48 (d, J=8.0 Hz, 1H), 7.38 (t, J=8.0 Hz, 1H), 5.19 (s, 2H), 3.36 (s, 3H), 2.85 (t, J=8.5 Hz, 2H), 2.52 (t, J=8.5 Hz, 2H); LCMS (ESI) m/z: 417.0/419.0 [M+H]+.

Compound 269: ¹H NMR (500 MHz, DMSO-d6) δ 9.72 (s, 1H), 8.18 (d, J=3.0 Hz, 1H), 8.05 (d, J=9.0 Hz, 1H), 7.87-7.85 (m, 1H), 7.84 (s, 1H), 7.73 (d, J=9.0 Hz, 1H), 7.60 (dd, J=9.0, 3.0 Hz, 1H), 5.25 (s, 2H), 3.36 (s, 3H), 2.85 (t, J=8.5 Hz, 2H), 2.52 (t, J=8.5 Hz, 2H); LCMS (ESI) m/z: 382.1 [M+H]+.

Compound 270: ¹H NMR (400 MHz, DMSO-d6) δ 9.73 (s, 1H), 8.18 (d, J=3.2 Hz, 1H), 8.05 (d, J=9.0 Hz, 1H), 7.87 (dd, J=8.4, 2.4 Hz, 1H), 7.83 (s, 1H), 7.73 (d, J=9.6 Hz, 1H), 7.60 (dd, J=9.2, 3.2 Hz, 1H), 5.24 (s, 2H), 3.35 (s, 3H), 2.85 (t, J=8.6 Hz, 2H), 2.52 (d, J=7.0 Hz, 2H); LCMS (ESI) m/z: 382.0 [M+H]+.

Compound 271: ¹H NMR (500 MHz, DMSO-d6) δ 10.46 (s, 1H), 8.27 (d, J=9.0 Hz, 1H), 7.67 (d, J=9.0 Hz, 1H), 7.39 (t, J=3.5 Hz, 1H), 6.97 (t, J=3.5 Hz, 2H), 4.47 (s, 2H), 3.53 (s, 3H), 2.85 (t, J=8.5 Hz, 2H), 2.54 (t, J=9.0 Hz, 2H); LCMS (ESI) m/z: 330.1 [M+H]+.

Compound 272: ¹H NMR (400 MHz, DMSO-d6) δ 10.90 (s, 1H), 8.64 (d, J=2.4 Hz, 1H), 8.32 (d, J=1.9 Hz, 1H), 8.08 (d, J=8.6 Hz, 1H), 7.96 (dd, J=9.6, 2.5 Hz, 1H), 7.70 (dd, J=8.6, 2.1 Hz, 1H), 7.35 (d, J=6.4 Hz, 1H), 7.10 (dd, J=21.8, 15.3 Hz, 3H), 6.46 (d, J=9.5 Hz, 1H), 5.55 (d, J=7.4 Hz, 1H), 4.89 (d, J=7.2 Hz, 4H), 3.98 (s, 2H); LCMS (ESI) m/z: 380.0 [M+H]+.

Compound 273: ¹H NMR (400 MHz, DMSO-d6) δ 10.90 (s, 1H), 8.64 (d, J=2.4 Hz, 1H), 8.32 (d, J=1.9 Hz, 1H), 8.08 (d, J=8.5 Hz, 1H), 7.96 (dd, J=9.6, 2.5 Hz, 1H), 7.70 (dd, J=8.6, 2.3 Hz, 1H), 7.30 (ddd, J=22.2, 10.8, 5.7 Hz, 4H), 6.46 (d, J=9.6 Hz, 1H), 5.67-5.46 (m, 1H), 4.89 (d, J=7.2 Hz, 4H), 3.97 (s, 2H); LCMS (ESI) m/z: 396.1 [M+H]+.

Compound 274: ¹H NMR (500 MHz, DMSO-d6) δ 9.80 (s, 1H), 8.59-8.45 (m, 2H), 8.35 (s, 1H), 8.04 (d, J=8.4 Hz, 1H), 7.88 (s, 1H), 7.79 (d, J=6.5 Hz, 1H), 4.02 (s, 2H), 3.36 (s, 3H), 2.85 (t, J=8.5 Hz, 2H), 2.53 (t, J=8.5 Hz, 2H); LCMS (ESI) m/z: 358.0 [M+H]+.

Compound 275: ¹H NMR (400 MHz, DMSO-d6) δ 10.16 (s, 1H), 8.50 (dd, J=10.9, 2.0 Hz, 2H), 8.36 (d, J=1.9 Hz, 1H), 8.08 (d, J=8.5 Hz, 1H), 7.93 (d, J=9.7 Hz, 1H), 7.86 (t, J=2.1 Hz, 1H), 7.79 (dd, J=8.5, 2.3 Hz, 1H), 7.06 (d, J=9.7 Hz, 1H), 4.01 (s, 2H), 3.77 (s, 3H); LCMS (ESI) m/z: 356.1 [M+H]+.

Compound 276: ¹H NMR (500 MHz, DMSO-d6) δ 10.66 (s, 1H), 8.68 (d, J=2.6 Hz, 1H), 8.52 (dd, J=11.3, 2.0 Hz, 2H), 8.36 (d, J=2.1 Hz, 1H), 8.05 (d, J=8.6 Hz, 1H), 7.98 (dd, J=9.5, 2.7 Hz, 1H), 7.89 (t, J=2.0 Hz, 1H), 7.78 (dd, J=8.6, 2.3 Hz, 1H), 6.44 (d, J=9.5 Hz, 1H), 4.02 (s, 2H), 3.50 (s, 3H); LCMS (ESI) m/z: 355.0 [M+H]+.

Compound 277: ¹H NMR (400 MHz, DMSO-d6) δ 9.73 (s, 1H), 8.85 (d, J=8.0 Hz, 2H), 8.37 (d, J=1.6 Hz, 1H), 8.14 (s, 1H), 8.04 (d, J=8.4 Hz, 1H), 7.79 (dd, J=8.4, 2.4 Hz, 1H), 4.11 (s, 2H), 3.36 (s, 3H), 2.85 (t, J=8.4 Hz, 2H), 2.53 (d, J=8.4 Hz, 2H); LCMS (ESI) m/z: 392.0 [M+H]+.

Compound 278: ¹H NMR (400 MHz, DMSO-d6) δ 10.11 (s, 1H), 8.77 (d, J=5.2 Hz, 1H), 8.36 (d, J=2 Hz, 1H), 8.07 (d, J=8.4 Hz, 1H), 7.93 (d, J=9.6 Hz, 1H), 7.77-7.82 (m, 2H), 7.60-7.63 (m, 1H), 7.06 (d, J=9.2 Hz, 1H), 4.24 (s, 2H), 3.78 (s, 3H); LCMS (ESI) m/z: 390.1 [M+H]+.

Compound 279: ¹H NMR (400 MHz, DMSO-d6) δ 8.77 (d, J=5.2 Hz, 1H), 8.65 (d, J=2 Hz, 1H), 8.34 (s, 1H), 8.04 (d, J=8.8 Hz, 1H), 7.93-7.99 (m, 1H), 7.71-7.78 (m, 2H), 7.60-7.63 (m, 1H), 6.41 (d, J=9.6 Hz, 1H), 4.22 (s, 2H), 3.48 (s, 3H); LCMS (ESI) m/z: 389.1 [M+H]+.

Compound 280: ¹H NMR (500 MHz, DMSO-d6) δ 10.22 (s, 1H), 8.36 (s, 1H), 8.34-8.31 (d, J 1.9 Hz, 1H), 8.07-8.06 (d, J=8.5 Hz, 1H), 7.76-7.74 (m, 1H), 7.35-7.33 (m, 1H), 7.12-7.10 (t, J=7.9 Hz, 2H), 7.04-7.01 (m, 5.2 Hz, 1H), 3.99 (s, 2H), 3.85 (s, 3H); LCMS (ESI) m/z: 416.9 [M+H]+.

Compound 281: ¹H NMR (400 MHz, DMSO-d6) δ 9.87 (d, J=13.2 Hz, 1H), 7.79 (d, J=8.8 Hz, 1H), 7.71 (d, J=2.4 Hz, 1H), 7.40-7.34 (m, 1H), 7.22-7.16 (m, 3H), 7.08-7.04 (m, 1H), 4.33 (s, 2H), 2.81 (t, J=8.8 Hz, 2H), 2.52-2.49 (m, 5H); LCMS (ESI) m/z: 356.2 [M+H]+.

Compound 282: ¹H NMR (500 MHz, DMSO-d6) δ 10.13 (s, 1H), 8.34 (d, J=2.0 Hz, 1H), 8.08 (d, J=8.5 Hz, 1H), 7.95 (d, J=10.0 Hz, 1H), 7.76 (dd, J=8.5, 2.5 Hz, 1H), 7.08 (d, J=9.5 Hz, 1H), 6.91 (s, 1H), 6.87-6.85 (m, 2H), 3.93 (s, 2H), 3.79 (s, 3H), 3.75 (s, 3H); LCMS (ESI) m/z: 385.1 [M+H]+.

Compound 283: ¹H NMR (400 MHz, DMSO-d6) δ 10.91 (s, 1H), 8.33 (d, J=2.3 Hz, 1H), 8.15 (s, 1H), 8.00 (d, J=8.5 Hz, 1H), 7.72 (dd, J=8.6, 2.4 Hz, 1H), 7.39-7.26 (m, 1H), 7.16-7.07 (m, 2H), 7.08-6.99 (m, 1H), 3.98 (s, 2H), 3.35 (s, 3H); LCMS (ESI) m/z: 328.1 [M+H]+.

Compound 284: ¹H NMR (500 MHz, DMSO-d6) δ 10.75 (s, 1H), 8.71 (d, J=1.5 Hz, 1H), 8.10 (d, J=8.0 Hz, 1H), 7.97-7.93 (m, 2H), 7.93-7.91 (m, 1H), 7.42-7.41 (m, 3H), 7.37-7.34 (m, 1H), 7.30-7.27 (m, 2H), 4.13 (s, 2H), 2.96 (s, 6H); LCMS (ESI) m/z: 394.2 [M+H]+.

Compound 285: ¹H NMR (500 MHz, DMSO-d6) δ 9.76 (s, 1H), 8.30 (d, J=1.5 Hz, 1H), 8.07-8.09 (d, J=13.5 Hz, 1H), 7.98 (d, J=2.0 Hz, 1H), 7.76-7.78 (m, 1H), 7.32-7.37 (m, 1H), 7.10-7.13 (m, 2H), 7.01-7.05 (m, 1H), 6.83 (d, J=2.0 Hz, 1H), 3.98 (s, 2H), 3.86-3.89 (m, 1H), 1.15-1.18 (m, 2H), 1.01-1.05 (m, 2H); LCMS (ESI) m/z: 337.1 [M+H]+.

Compound 286: ¹H NMR (500 MHz, DMSO-d6) δ 10.14 (s, 1H), 7.93 (d, J=9.7 Hz, 1H), 7.80 (dd, J=38.0, 5.9 Hz, 2H), 7.44 (s, 1H), 7.35 (ddd, J=22.5, 15.0, 7.5 Hz, 3H), 7.20 (dd, J=8.8, 2.0 Hz, 1H), 7.07 (d, J=9.7 Hz, 1H), 4.35 (s, 2H), 3.77 (s, 3H); LCMS (ESI) m/z: 370.0 [M+H]+.

Compound 287: ¹H NMR (500 MHz, DMSO-d6) δ 10.98 (s, 1H), 8.71 (d, J=2.5 Hz, 1H), 8.33 (d, J=2.3 Hz, 1H), 8.10-8.02 (m, 2H), 7.89 (t, J=59.4 Hz, 1H), 7.71 (dd, J=8.5, 2.4 Hz, 1H), 7.40-7.29 (m, 1H), 7.15-7.08 (m, 2H), 7.06-6.99 (m, 1H), 6.61 (d, J=9.8 Hz, 1H), 3.98 (s, 2H); LCMS (ESI) m/z: 374.1 [M+H]+.

Compound 288: ¹H NMR (500 MHz, DMSO-d6) δ 10.87 (s, 1H), 8.28 (d, J=9.1 Hz, 1H), 7.95 (d, J=9.6 Hz, 1H), 7.70 (d, J=9.1 Hz, 1H), 7.36 (s, 1H), 7.29 (d, J=7.7 Hz, 1H), 7.23 (dd, J=21.1, 4.6 Hz, 2H), 7.09 (d, J=9.7 Hz, 1H), 3.81 (s, 3H), 3.22 (dd, J=8.9, 6.7 Hz, 2H), 3.06 (t, J=7.9 Hz, 2H); LCMS (ESI) m/z: 370.1 [M+H]+.

Compound 289: ¹H NMR (400 MHz, DMSO-d6) δ 11.19 (s, 1H), 9.19 (d, J=2.0 Hz, 1H), 9.12 (s, 2H), 8.43 (dd, J=8.4, 2.4 Hz, 1H), 8.36 (d, J=2.0 Hz, 1H), 8.13 (d, J=8.4 Hz, 1H), 7.75 (dd, J=8.4, 2.4 Hz, 1H), 7.61 (d, J=8.0 Hz, 1H), 7.37-7.33 (m, 2H), 7.29-7.24 (m, 2H), 4.42 (t, J=5.8 Hz, 2H), 3.99 (s, 2H), 2.67 (t, J=5.2 Hz, 3H); LCMS (ESI) m/z: 367.0 [M+H]+.

Compound 290: ¹H NMR (500 MHz, DMSO-d6) δ 11.14-11.15 (d, J=7.0 Hz, 1H), 8.95 (s, 1H), 8.35 (d, J=2.0 Hz, 1H), 8.20-8.23 (dd, J=12.0, 1.5 Hz, 1H), 8.11-8.12 (d, J=8.5 Hz, 1H), 7.73-7.75 (dd, J=8.5, 2.0 Hz, 1H), 7.28-7.36 (m, 2H), 7.23-7.27 (m, 2H), 5.46-5.48 (t, J=6.0 Hz, 1H), 4.64-4.65 (dd, J=6.0, 1.5 Hz, 2H), 3.98 (s, 2H); LCMS (ESI) m/z: 372.0 [M+H]+.

Compound 291: ¹H NMR (500 MHz, DMSO-d6) δ 10.89 (s, 1H), 8.42-8.46 (m, 2H), 8.14-8.16 (d, J=10.5 Hz, 1H), 7.88-7.92 (m, 2H), 7.34-7.38 (m, 1H), 7.30-7.34 (m, 1H), 7.13 (m, 1H), 6.99-7.02 (m, 2H), 6.41-6.43 (d, J=12.0 Hz, 1H), 5.12 (s, 2H), 3.35-3.39 (m, 1H), 1.00-1.02 (d, J=7.5 Hz, 4H); LCMS (ESI) m/z: 396.1 [M+H]+.

Compound 292: $^1$H NMR (400 MHz, DMSO-d6) δ 11.11 (s, 1H), 9.06 (d, J=2.0 Hz, 1H), 8.49 (d, J=1.6 Hz, 1H), 8.36 (dd, J=8.0, 2.4 Hz, 1H), 8.22 (d, J=8.8 Hz, 1H), 7.94 (dd, J=8.8, 2.0 Hz, 1H), 7.58 (d, J=8.0 Hz, 1H), 7.32 (t, J=8.0 Hz, 1H), 7.14 (t, J=2.0 Hz, 1H), 7.02 (dd, J=8.0, 2.0 Hz, 2H), 5.57 (t, J=6.0 Hz, 1H), 5.15 (s, 2H), 4.63 (d, J=6.4 Hz, 2H); LCMS (ESI) m/z: 370.1 [M+H]+.

Compound 293: $^1$H NMR (500 MHz, DMSO-d6) δ 11.11 (s, 1H), 9.07 (d, J=2.5 Hz, 1H), 8.49 (d, J=2.0 Hz, 1H), 8.37 (dd, J=8.0, 2.5 Hz, 1H), 8.23 (d, J=8.5 Hz, 1H), 7.94 (dd, J=8.5, 2.0 Hz, 1H), 7.60 (d, J=8.0 Hz, 1H), 7.36 (t, J=9.0 Hz, 1H), 7.32-7.30 (m, 1H), 7.07-7.04 (m, 1H), 5.58 (t, J=6.0 Hz, 1H), 5.14 (s, 2H), 4.65 (d, J=6.0 Hz, 2H); LCMS (ESI) m/z: 388.1 [M+H]+.

Compound 294: $^1$H NMR (500 MHz, DMSO-d6) δ 8.67 (s, 1H), 8.05 (d, J=7.5 Hz, 1H), 7.92 (d, J=7.5 Hz, 1H), 7.50-7.44 (m, 4H), 7.00 (t, J=56 Hz, 1H), 4.18 (s, 2H), 3.27-3.19 (m, 2H), 3.17 (s, 3H), 2.48 (t, J=8.0 Hz, 2H); LCMS (ESI) m/z: 373.1 [M+H]+.

Compound 295: $^1$H NMR (400 MHz, DMSO-d6) δ 11.26 (s, 1H), 9.20 (d, J=1.6 Hz, 1H), 8.51 (dd, J=8.0, 2.0 Hz, 1H), 8.36 (d, J=2.0 Hz, 1H), 8.13 (d, J=8.4 Hz, 1H), 7.84 (d, J=8.4 Hz, 1H), 7.76 (dd, J=8.1, 2.0 Hz, 1H), 7.36-7.33 (m, 2H), 7.29-7.24 (m, 2H), 7.06 (t, J=54.8 Hz, 1H), 3.99 (s, 2H); LCMS (ESI) m/z: 374.0 [M+H]+.

Compound 296: $^1$H NMR (400 MHz, TFA) δ 8.71 (d, J=8.9 Hz, 1H), 8.58 (s, 1H), 8.18 (d, J=8.9 Hz, 1H), 7.80-7.64 (m, 2H), 7.64-7.41 (m, 2H), 4.09 (d, J=18.2 Hz, 3H), 3.59 (ddd, J=20.6, 13.1, 7.0 Hz, 6H), 3.34 (t, J=8.7 Hz, 2H); LCMS (ESI) m/z: 371.1 [M+H]+.

Compound 297: $^1$H NMR (500 MHz, DMSO-d6) δ 10.10 (s, 1H), 8.21 (d, J=1.9 Hz, 1H), 8.07 (d, J=8.5 Hz, 1H), 7.95 (d, J=9.6 Hz, 1H), 7.75 (dd, J=8.5, 2.3 Hz, 1H), 7.36-7.27 (m, 2H), 7.25 (d, J=1.8 Hz, 1H), 7.19 (d, J=7.5 Hz, 1H), 7.08 (d, J=9.6 Hz, 1H), 3.79 (s, 3H), 2.91 (s, 4H); LCMS (ESI) m/z: 369.1 [M+H]+.

Compound 298: $^1$H NMR (500 MHz, MeOD) δ 8.61 (s, 1H), 8.28 (s, 1H), 8.10 (dd, J=9.5, 2.6 Hz, 1H), 8.04 (s, 1H), 7.85 (d, J=8.1 Hz, 1H), 7.31 (t, J=7.6 Hz, 2H), 7.25-7.15 (m, 3H), 6.63 (d, J=9.5 Hz, 1H), 3.68 (s, 3H), 2.35 (t, J=7.3 Hz, 2H), 1.70-1.51 (m, 2H); LCMS (ESI) m/z: 346.1 [M+H]+.

Compound 299: $^1$H NMR (500 MHz, DMSO-d6) δ 11.15 (s, 1H), 8.93 (d, J=2.5 Hz, 1H), 8.35 (d, J=1.5 Hz, 1H), 8.26 (dd, J=2.5 Hz, 8.5 Hz, 1H), 8.11 (d, J=8.5 Hz, 1H), 7.81 (d, J=8.5 Hz, 1H), 7.74 (dd, J=2.5 Hz, 8.5 Hz, 1H), 7.21-7.38 (m, 4H), 3.99 (s, 2H); LCMS (ESI) m/z: 402.0, 404.0 [M+H]+.

Compound 300: $^1$H NMR (500 MHz, DMSO-d6) δ 10.12 (s, 1H), 8.58 (s, 1H), 8.19 (d, J=2.5 Hz, 1H), 8.04 (d, J=9.2 Hz, 1H), 7.95 (d, J=10.0 Hz, 1H), 7.70 (dd, J=8.5, 3.0 Hz, 1H), 7.28-7.23 (m, 1H), 7.08 (d, J=10.0 Hz, 1H), 6.85 (dd, J=8.1, 1.6 Hz, 1H), 6.80-6.77 (m, 1H), 6.63-6.60 (m, 1H), 3.79 (s, 3H); LCMS (ESI) m/z: 340.1 [M+H]+.

Compound 301: $^1$H NMR (500 MHz, DMSO-d6) δ 10.20 (s, 1H), 8.25 (d, J=2.0 Hz, 1H), 8.15 (d, J=9.0 Hz, 1H), 7.96 (d, J=9.5 Hz, 1H), 7.72 (dd, J=9.0, 2.5 Hz, 1H), 7.25-7.23 (m, 1H), 7.08 (d, J=10.0 Hz, 1H), 6.70-6.65 (m, 3H), 3.80 (s, 3H), 3.30 (s, 3H); LCMS (ESI) m/z: 354.1 [M+H]+.

Compound 302: $^1$H NMR (500 MHz, DMSO-d6) δ 10.66 (s, 1H), 8.68 (d, J=3.0 Hz, 1H), 8.23 (d, J=2.5 Hz, 1H), 8.12 (d, J=8.5 Hz, 1H), 8.00 (dd, J=9.5, 2.5 Hz, 1H), 7.70 (dd, J=9.5, 3.0 Hz, 1H), 7.26-7.21 (m, 1H), 6.68-6.61 (m, 3H), 6.44 (d, J=9.5 Hz, 1H), 3.51 (s, 3H), 3.29 (s, 3H); LCMS (ESI) m/z: 353.0 [M+H]+.

Compound 303: $^1$H NMR (500 MHz, DMSO-d6) δ 10.05 (s, 1H), 8.54 (s, 1H), 8.20 (d, J=2.5 Hz, 1H), 8.04-8.06 (d, J=9.0 Hz, 1H), 7.90-7.92 (d, J=10.0 Hz, 1H), 7.65-7.68 (m, 1H), 7.22-7.26 (m, 1H), 7.05-7.07 (d, J=9.0 Hz, 1H), 6.97-6.99 (m, 2H), 6.83-6.85 (m, 1H), 4.09-4.10 (m, 1H), 1.27-1.28 (m, 2H), 1.01-1.03 (m, 2H); LCMS (ESI) m/z: 382.0 [M+H]+.

Compound 304: $^1$H NMR (500 MHz, DMSO-d6) δ 10.04 (s, 1H), 8.57 (s, 1H), 8.20-8.21 (d, J=2.5 Hz, 1H), 8.04-8.06 (d, J=8.5 Hz, 1H), 7.90-7.92 (d, J=9.0 Hz, 1H), 7.66-7.69 (m, 1H), 7.24-7.26 (m, 1H), 7.05-7.07 (d, J=9.5 Hz, 1H), 6.83-6.85 (d, J=8.0 Hz, 1H), 6.76-6.78 (d, J=11.5 Hz, 1H), 6.59-6.62 (m, 1H), 4.08-4.11 (m, 1H), 1.27-1.28 (m, 2H), 1.00-1.04 (m, 2H); LCMS (ESI) m/z: 366.1 [M+H]+.

Compound 305: $^1$H NMR (400 MHz, DMSO-d6) δ 8.29 (s, 1H), 7.78 (d, J=2.7 Hz, 1H), 7.42 (dd, J=9.6, 2.8 Hz, 1H), 7.31 (t, J=8.1 Hz, 1H), 7.01 (ddd, J=22.5, 10.2, 2.0 Hz, 3H), 6.36 (d, J=9.6 Hz, 1H), 4.70-4.60 (m, 1H), 3.78 (dd, J=8.7, 5.2 Hz, 2H), 3.41 (s, 3H), 3.30-3.13 (m, 2H), 1.95 (d, J=12.0 Hz, 2H), 1.64-1.40 (m, 2H); LCMS (ESI) m/z: 362.0 [M+H]+.

Compound 306: $^1$H NMR (500 MHz, DMSO-d6) δ 7.75 (d, J=3.1 Hz, 1H), 7.38 (dd, J=9.8, 3.1 Hz, 1H), 7.32 (t, J=8.2 Hz, 1H), 7.11-7.10 (t, J=2.1 Hz, 1H), 7.03-6.94 (m, 2H), 6.36-6.34 (d, J=9.8 Hz, 1H), 4.77-4.64 (m, 1H), 3.77-3.75 (d, J=55.8 Hz, 2H), 3.43 (s, 1H), 3.39 (s, 3H), 3.36-3.19 (m, 1H), 1.99 (s, 2H), 1.64-1.62 (d, J=10.2 Hz, 2H); LCMS (ESI) m/z: 363.1 [M+H]+.

Compound 307: $^1$H NMR (500 MHz, DMSO-d6) δ 7.47 (d, J=9.8 Hz, 1H), 7.32 (t, J=8.2 Hz, 1H), 7.11 (d, J=2.0 Hz, 1H), 7.04 (d, J=9.8 Hz, 1H), 7.02-6.95 (m, 2H), 4.78-4.56 (m, 1H), 3.76 (d, J=48.0 Hz, 2H), 3.57 (s, 3H), 3.50-3.31 (m, 2H), 1.99 (s, 2H), 1.67 (s, 2H); LCMS (ESI) m/z: 364.0 [M+H]+.

Compound 308: $^1$H NMR (500 MHz, DMSO-d6) δ 8.14 (s, 1H), 7.75 (d, J=2.5 Hz, 1H), 7.39 (dd, J1=2.5 Hz, J2=9.0 Hz, 1H), 7.31-7.34 (m, 1H), 7.25-7.27 (m, 2H), 7.16 (d, J=8.0 Hz, 1H), 6.33 (d, J=9.5 Hz, 1H), 4.01-4.04 (m, 2H), 3.39 (s, 3H), 2.70 (t, J=12 Hz, 2H), 2.50-2.55 (m, 2H), 1.70-1.75 (m, 1H), 1.54-1.56 (m, 2H), 1.04-1.12 (m, 2H); LCMS (ESI) m/z: 360.1 [M+H]+.

Compound 309: $^1$H NMR (400 MHz, DMSO-d6) δ 9.22 (s, 1H), 7.61 (d, J=9.6 Hz, 1H), 7.31-7.34 (m, 1H), 7.25-7.27 (m, 2H), 7.16 (d, J=7.6 Hz, 1H), 6.87 (d, J=9.6 Hz, 1H), 4.04-4.07 (m, 2H), 3.55 (s, 3H), 2.72 (t, J=12.4 Hz, 2H), 2.50-2.55 (m, 2H), 1.70-1.76 (m, 1H), 1.52-1.55 (m, 2H), 1.03-1.14 (m, 2H); LCMS (ESI) m/z: 361.1 [M+H]+.

Compound 310: $^1$H NMR (400 MHz, DMSO-d6) δ 8.70 (d, J=1.2 Hz, 1H), 8.09-8.05 (m, 2H), 7.97-7.95 (m, 1H), 7.12-7.04 (m, 4H), 4.14 (s, 2H), 3.61 (s, 3H); LCMS (ESI) m/z: 357.1 [M+H]+.

Compound 311: $^1$H NMR (400 MHz, DMSO-d6) δ 10.49 (s, 1H), 8.69 (d, J=1.6 Hz, 1H), 8.34 (d, J=2.8 Hz, 1H), 8.04 (d, J=8.0 Hz, 1H), 7.93-7.91 (m, 1H), 7.79-7.76 (m, 1H), 7.12-7.07 (m, 3H), 6.42 (d, J=9.6 Hz, 1H), 4.13 (s, 2H), 3.44 (s, 3H); LCMS (ESI) m/z: 356.0 [M+H]+.

Compound 312: $^1$H NMR (400 MHz, DMSO-d6) δ 9.91 (s, 1H), 8.67 (s, 1H), 8.07 (d, J=9.6 Hz, 2H), 7.92 (d, J=7.2 Hz, 1H), 7.45-7.34 (m, 2H), 7.16 (s, 1H), 7.05 (s, 1H), 4.10 (s, 2H), 3.60 (s, 3H); LCMS (ESI) m/z: 357.1 [M+H]+.

Compound 313: $^1$H NMR (400 MHz, DMSO-d6) δ 10.49 (s, 1H), 8.67 (d, J=1.6 Hz, 1H), 8.34 (d, J=2.8 Hz, 1H), 8.04 (d, J=8.0 Hz, 1H), 7.90-7.88 (m, 1H), 7.79-7.76 (m, 1H), 7.45-7.35 (m, 2H), 7.16-7.13 (m, 1H), 6.42 (d, J=9.6 Hz, 1H), 4.10 (s, 2H), 3.44 (s, 3H); LCMS (ESI) m/z: 356.0 [M+H]+.

Compound 314: ¹H NMR (400 MHz, DMSO-d6) δ 10.59 (t, J=7.8 Hz, 1H), 8.42 (s, 1H), 8.28 (s, 1H), 8.11 (s, 1H), 8.06-8.03 (m, 1H), 7.71 (d, J=6.8 Hz, 1H), 7.38-7.34 (m, 2H), 7.11 (s, 1H), 3.94 (s, 2H), 3.87 (s, 3H); LCMS (ESI) m/z: 329.0 [M+H]+.

Compound 315: ¹H NMR (400 MHz, DMSO-d6) δ 10.61 (s, 1H), 8.43 (s, 1H), 8.32 (d, J=1.6 Hz, 1H), 8.13 (s, 1H), 8.07 (d, J=8.8 Hz, 1H), 7.76 (d, J=8.6 Hz, 1H), 7.10-7.03 (m, 3H), 3.98 (s, 2H), 3.88 (s, 3H); LCMS (ESI) m/z: 329.0 [M+H]+.

Compound 316: ¹H NMR (400 MHz, DMSO-d6) δ 10.47 (s, 1H), 8.41 (s, 1H), 8.30 (d, J=1.6 Hz, 1H), 8.10 (d, J=10.4 Hz, 2H), 7.69 (dd, J=8.4, 2.0 Hz, 1H), 7.27-7.23 (m, 2H), 7.15 (d, J=9.6 Hz, 1H), 3.95 (s, 2H), 3.86 (s, 3H); LCMS (ESI) m/z: 345.1 [M+H]+.

Compound 317: ¹H NMR (400 MHz, DMSO-d6) δ 12.77 (s, 1H), 7.89 (d, J=9.6 Hz, 1H), 7.37-7.43 (m, 1H), 7.05-7.15 (m, 4H), 4.11 (s, 2H), 3.78 (s, 3H); LCMS (ESI) m/z: 423.0 [M+H]+.

Compound 319: ¹H NMR (400 MHz, DMSO-d6) δ 11.21 (s, 1H), 8.85 (d, J=1.2 Hz, 1H), 8.45-8.48 (m, 1H), 8.36 (d, J=1.2 Hz, 1H), 8.09-8.11 (d, J=8.4 Hz, 1H), 7.74-7.76 (m, 1H), 7.29-7.36 (m, 2H), 7.23-7.29 (m, 2H), 3.98 (s, 2H); LCMS (ESI) m/z: 376.0 [M+H]+.

Compound 320: ¹H NMR (400 MHz, DMSO-d6) δ 11.06 (s, 1H), 9.09 (d, J=2 Hz, 1H), 8.31-8.43 (m, 2H), 8.13 (d, J=8.8 Hz, 1H), 7.74 (d, J=8 Hz, 2H), 7.19-7.39 (m, 4H), 5.51 (d, J=1.6 Hz, 1H), 4.56 (d, J=1.2 Hz, 1H), 3.92-4.03 (m, 4H), 1.40 (t, J=6.8 Hz, 3H); LCMS (ESI) m/z: 394.1 [M+H]+.

Compound 321: ¹H NMR (400 MHz, DMSO-d6) δ 10.35 (s, 1H), 8.68 (s, 1H), 8.20-8.17 (m, 3H), 8.03-8.01 (m, 1H), 7.70 (dd, J=8.4, 2.0 Hz, 1H), 5.54 (t, J=5.8 Hz, 1H), 4.67 (d, J=5.6 Hz, 2H), 2.47 (d, J=6.8 Hz, 2H), 1.66-1.60 (m, 5H), 1.55-1.48 (m, 1H), 1.23-1.10 (m, 3H), 0.97-0.88 (m, 2H); LCMS (ESI) m/z: 326.2 [M+H]+.

Compound 322: ¹H NMR (400 MHz, DMSO-d6) δ 9.13 (s, 1H), 7.65 (d, J=10.0 Hz, 1H), 7.30-7.34 (m, 2H), 7.24-7.26 (m, 2H), 7.15 (d, J=9.0 Hz, 1H), 6.95 (d, J=10.0 Hz, 1H), 3.84 (s, 1H), 3.56 (s, 3H), 2.50-2.54 (m, 2H), 1.62-1.65 (m, 3H), 1.47-1.52 (m, 4H), 1.15-1.20 (m, 2H); LCMS (ESI) m/z: 375.2 [M+H]+.

Compound 323: ¹H NMR (500 MHz, DMSO-d6) δ 11.58 (bs, 1H), 9.49 (s, 1H), 8.28 (d, J=2.0 Hz, 1H), 8.07 (d, J=8.5 Hz, 1H), 7.75 (d, J=8.5 Hz, 1H), 7.52 (dd, J=7.0, 2.0 Hz, 1H), 7.35 (t, J=9.0 Hz, 1H), 7.30-7.26 (m, 1H), 5.90 (s, 1H), 3.95 (s, 2H), 3.64 (s, 3H); LCMS (ESI) m/z: 361.0 [M+H]+.

Compound 324: ¹H NMR (500 MHz, DMSO-d6) δ 11.61 (bs, 1H), 9.56 (s, 1H), 8.28 (d, J=2.0 Hz, 1H), 8.06 (d, J=8.5 Hz, 1H), 7.76 (dd, J=8.5, 1.5 Hz, 1H), 7.39-7.35 (m, 2H), 7.12-7.10 (m, 1H), 5.90 (s, 1H), 3.95 (s, 2H), 3.64 (s, 3H); LCMS (ESI) m/z: 345.1 [M+H]+.

Compound 325: ¹H NMR (500 MHz, DMSO-d6) δ 11.67 (bs, 1H), 9.95 (s, 1H), 8.33 (d, J=1.5 Hz, 1H), 8.07 (d, J=9.0 Hz, 1H), 7.89 (dd, J=8.5, 1.5 Hz, 1H), 7.10-7.04 (m, 3H), 5.93 (s, 1H), 4.00 (s, 2H), 3.65 (s, 3H); LCMS (ESI) m/z: 345.1 [M+H]+.

Compound 326: ¹H NMR (500 MHz, DMSO-d6) δ 10.70 (s, 1H), 8.65 (d, J=2.0 Hz, 1H), 8.17 (d, J=2.0 Hz, 1H), 8.02 (d, J=8.5 Hz, 1H), 7.95 (dd, J=9.5, 2.5 Hz, 1H), 7.69 (dd, J=8.5, 2.0 Hz, 1H), 6.44 (d, J=10.0 Hz, 1H), 3.98 (q, J=7.0 Hz, 2H), 2.47 (d, J=7.0 Hz, 2H), 1.67-1.60 (m, 5H), 1.51-1.47 (m, 1H), 1.28 (t, J=7.0 Hz, 3H), 1.21-1.07 (m, 3H), 0.96-0.89 (m, 2H); LCMS (ESI) m/z: 340.1 [M+H]+.

Compound 327: ¹H NMR (500 MHz, DMSO-d6) δ 11.28 (s, 1H), 9.23 (d, J=1.5 Hz, 1H), 8.54 (dd, J=8.0, 2.0 Hz, 1H), 8.22-8.20 (m, 2H), 8.11 (d, J=9.0 Hz, 1H), 7.68 (dd, J=8.5, 2.0 Hz, 1H), 2.48 (d, J=7.5 Hz, 2H), 1.67-1.60 (m, 5H), 1.52-1.47 (m, 1H), 1.21-1.10 (m, 3H), 0.96-0.89 (m, 2H); LCMS (ESI) m/z: 321.1 [M+H]+.

Compound 328: ¹H NMR (500 MHz, DMSO-d6) δ 12.49 (s, 1H), 8.47 (d, J=6.0 Hz, 1H), 8.29 (s, 1H), 8.20 (dd, J=13.0, 7.5 Hz, 2H), 7.70 (d, J=8.0 Hz, 1H), 7.36 ((dd, J=19.0, 9.0 Hz, 2H), 7.12 (s, 1H), 6.60 (t, J=7.0 Hz, 1H), 3.94 (s, 2H), 3.63 (s, 3H); LCMS (ESI) m/z: 356.0 [M+H]+.

Compound 329: ¹H NMR (500 MHz, DMSO-d6) δ 12.49 (s, 1H), 8.47 (dd, J=7.0, 2.0 Hz, 1H), 8.31 (d, J=2.0 Hz, 1H), 8.22-8.17 (m, 2H), 7.73 (dd, J=8.5, 2.0 Hz, 1H), 7.08-7.03 (m, 3H), 6.60 (t, J 7.0 Hz, 1H), 3.97 (s, 2H), 3.63 (s, 3H); LCMS (ESI) m/z: 327.1 [M+H]+.

Compound 330: ¹H NMR (500 MHz, DMSO-d6) δ 12.48 (s, 1H), 8.46 (dd, J=7.0, 2.0 Hz, 1H), 8.30 (d, J=1.5 Hz, 1H), 8.22-8.17 (m, 2H), 7.71 (dd, J=8.5, 2.0 Hz, 1H), 7.39-7.31 (m, 2H), 7.25 (dd, J=16.0, 8.0 Hz, 2H), 6.60 (t, J=7.0 Hz, 1H), 3.96 (s, 2H), 3.63 (s, 3H); LCMS (ESI) m/z: 354.1 [M+H]+.

Compound 331: ¹H NMR (400 MHz, DMSO-d6) δ 12.49 (s, 1H), 8.46 (d, J=6.4 Hz, 1H), 8.30 (s, 1H), 8.20 (t, J=8.2 Hz, 2H), 7.71 (d, J=8.4 Hz, 1H), 7.52 (d, J=6.8 Hz, 1H), 7.35 (t, J=9.0 Hz, 1H), 7.30-7.27 (m, 1H), 6.60 (t, J=6.8 Hz, 1H), 3.95 (s, 2H), 3.63 (s, 3H); LCMS (ESI) m/z: 372.0 [M+H]+.

Compound 332: ¹H NMR (500 MHz, DMSO) δ 12.51 (s, 1H), 8.48-8.46 (m, 1H), 8.29 (s, 1H), 8.21 (d, J=8.5 Hz, 2H), 7.72-7.70 (m, 1H), 7.35 (dd, J=14.5, 7.5 Hz, 1H), 7.12 (t, J=7.5 Hz, 2H), 7.04 (t, J=8.5 Hz, 1H), 6.63 (t, J=7.0 Hz, 1H), 4.12 (q, J=7.0 Hz, 2H), 3.97 (s, 2H), 1.31 (t, J=7.0 Hz, 3H); LCMS (ESI) m/z: 352.1 [M+H]+.

Compound 333: ¹H NMR (500 MHz, DMSO-d6) δ 11.12 (s, 1H), 8.98 (s, 1H), 8.35 (s, 1H), 8.27-8.29 (d, J=10 Hz, 1H), 8.11-8.12 (d, J=8.5 Hz, 1H), 7.73-7.75 (d, J=8.5 Hz, 1H), 7.33-7.36 (m, 2H), 7.23-7.28 (m, 2H), 7.01-7.07 (m, 1H), 6.47-6.50 (d, J=17.5 Hz, 1H), 5.74-5.76 (d, J=11.0 Hz, 1H), 3.98 (s, 2H); LCMS (ESI) m/z: 368.0 [M+H]+.

Compound 334: ¹H NMR (500 MHz, DMSO-d6) δ 10.24 (s, 1H), 8.34 (d, J=1.9 Hz, 1H), 8.19-7.96 (m, 2H), 7.76 (dd, J=8.5, 2.2 Hz, 1H), 7.34 (dd, J=7.9, 6.6 Hz, 1H), 7.12 (t, J=8.3 Hz, 2H), 7.04 (d, J=1.8 Hz, 1H), 3.99 (s, 2H); LCMS (ESI) m/z: 391.9, 393.9 [M+H]+.

Compound 335: ¹H NMR (400 MHz, DMSO-d6) δ 10.16 (s, 1H), 8.54 (d, J=6.4 Hz, 1H), 8.36 (s, 1H), 8.11 (d, J=8.4 Hz, 1H), 7.72-7.84 (m, 1H), 7.28-7.42 (m, 1H), 6.92-7.18 (m, 4H), 3.99 (s, 2H), 3.54 (s, 3H); LCMS (ESI) m/z: 339.1 [M+H]+.

Compound 336: ¹H NMR (500 MHz, DMSO-d6) δ 8.31 (d, J=2.5 Hz, 1H), 7.92 (d, J=8.0 Hz, 1H), 7.85 (dd, J1=2.5 Hz, J2=9.5 Hz, 1H), 7.30-7.33 (m, 1H), 7.24-7.25 (m, 2H), 7.15 (d, J=7.5 Hz, 1H), 6.38 (d, J=9.0 Hz, 1H), 3.64-3.68 (m, 1H), 3.47 (s, 3H), 2.49-2.51 (m, 2H), 1.82 (d, J=11.0 Hz, 2H), 1.65 (d, J=12.5 Hz, 2H), 1.46-1.50 (m, 1H), 1.24 (dd, J1=10.5 Hz, J2=23.0 Hz, 2H), 1.06 (dd, J1=11.0 Hz, J2=24.5 Hz, 2H); LCMS (ESI) m/z: 359.1 [M+H]+.

Compound 337: ¹H NMR (500 MHz, DMSO-d6) δ 10.69 (s, 1H), 8.68 (d, J=2.7 Hz, 1H), 8.37 (dd, J=2.4, 0.9 Hz, 1H), 8.11 (dd, J=8.7, 0.9 Hz, 1H), 7.97 (dd, J=9.5, 2.7 Hz, 1H), 7.80 (dd, J=8.7, 2.3 Hz, 1H), 6.43 (d, J=9.5 Hz, 1H), 3.50 (s, 3H), 1.62-1.50 (m, 1H), 0.95-0.85 (m, 2H), 0.79-0.71 (m, 2H); LCMS (ESI) m/z: 294.2 [M+H]+.

Compound 338: ¹H NMR (500 MHz, DMSO-d6) δ 10.08 (s, 1H), 8.28 (d, J=5.1 Hz, 1H), 8.03 (s, 1H), 7.94 (d, J=9.7

Hz, 1H), 7.45-7.35 (m, 2H), 7.33-7.27 (m, 2H), 7.12-7.03 (m, 2H), 4.03 (s, 2H), 3.78 (s, 3H); LCMS (ESI) m/z: 355.1 [M+H]+.

Compound 339: ¹H NMR (500 MHz, DMSO-d6) δ 8.53 (d, J=10.0 Hz, 1H), 7.80-7.77 (m, 1H), 7.56-7.52 (m, 1H), 7.38-7.33 (m, 1H), 7.17-7.13 (m, 2H), 7.07-7.03 (m, 1H), 4.04 (s, 2H), 3.69-3.67 (m, 1H), 3.60-3.58 (m, 2H), 3.46 (s, 1H), 3.39-3.37 (m, 1H), 3.28 (s, 1H), 1.18 (s, 3H), 1.05 (s, 3H); LCMS (ESI) m/z: 329.1 [M+H]+.

Compound 340: ¹H NMR (500 MHz, DMSO-d6) δ 11.93 (s, 1H), 7.66 (s, 1H), 7.64-7.52 (m, 3H), 7.36 (s, 1H), 4.24 (s, 2H), 3.35 (s, 3H), 2.82 (t, J=8.5 Hz, 2H), 2.53 (s, 2H); LCMS (ESI) m/z: 397.0 [M+H]+.

Compound 341: ¹H NMR (500 MHz, DMSO-d6) δ 12.49-11.25 (m, 1H), 7.80 (d, J=8.0 Hz, 2H), 7.50 (d, J=7.5 Hz, 2H), 7.36 (s, 1H), 4.23 (s, 2H), 3.35 (s, 3H), 2.82 (t, J=8.5 Hz, 2H), 2.52 (t, J=5.3 Hz, 2H); LCMS (ESI) m/z: 354.1 [M+H]+.

Compound 342: ¹H NMR (400 MHz, DMSO-d6) δ 10.52 (s, 1H), 8.66 (d, J=2.3 Hz, 1H), 8.50 (s, 1H), 8.17 (d, J=2.6 Hz, 1H), 8.10-7.95 (m, 2H), 7.65 (dd, J=9.0, 2.7 Hz, 1H), 7.24 (t, J=7.9 Hz, 1H), 6.96 (d, J=8.1 Hz, 2H), 6.84 (d, J=7.4 Hz, 1H), 6.44 (d, J=9.5 Hz, 1H), 3.51 (s, 3H); LCMS (ESI) m/z: 355.0 [M+H]+.

Compound 343: ¹H NMR (500 MHz, DMSO-d6) δ 11.21 (s, 1H), 7.37-7.33 (m, 1H), 7.11-7.03 (m, 3H), 6.82 (d, J=4.0 Hz, 1H), 6.67 (d, J=4.0 Hz, 1H), 4.07 (s, 2H), 3.36 (s, 3H), 2.81 (t, J=8.5 Hz, 2H), 2.51 (t, J=3.5 Hz, 2H); LCMS (ESI) m/z: 346.1 [M+H]+.

Compound 344: ¹H NMR (400 MHz, DMSO-d6) δ 11.48 (s, 1H), 9.50 (s, 1H), 8.75 (d, J=7.2 Hz, 1H), 8.61 (s, 1H), 8.40 (d, J=1.6 Hz, 1H), 8.13 (d, J=8.4 Hz, 1H), 7.85 (dd, J=8.4, 2.0 Hz, 1H), 7.54 (d, J=7.2 Hz, 1H), 7.37 (dd, J=14.4, 8.0 Hz, 1H), 7.14 (t, J=7.6 Hz, 2H), 7.08-7.03 (m, 1H), 4.03 (s, 2H); LCMS (ESI) m/z: 348.1 [M+H]+.

Compound 345: ¹H NMR (500 MHz, DMSO-d6) δ 12.83 (s, 1H), 7.91 (d, J=9.5 Hz, 1H), 7.43-7.39 (m, 1H), 7.24-7.21 (m, 2H), 7.14-7.11 (m, 1H), 7.06 (d, J=10.0 Hz, 1H), 4.43 (s, 2H), 3.79 (s, 3H); LCMS (ESI) m/z: 346.1 [M+H]+.

Compound 346: ¹H NMR (500 MHz, DMSO-d6) δ 12.88 (s, 1H), 7.92 (d, J=10.0 Hz, 1H), 7.38-7.35 (m, 2H), 7.27 (d, J=9.5 Hz, 1H), 7.07 (d, J=9.5 Hz, 1H), 4.45 (s, 2H), 3.79 (s, 3H); LCMS (ESI) m/z: 380.1 [M+H]+.

Compound 347: ¹H NMR (500 MHz, DMSO-d6) δ 12.85 (bs, 1H), 7.91 (d, J=9.5 Hz, 1H), 7.64 (d, J=6.5 Hz, 2H), 7.41-7.39 (m, 2H), 7.06 (d, J=9.5 Hz, 1H), 4.42 (s, 2H), 3.78 (s, 3H); LCMS (ESI) m/z: 380.0 [M+H]+.

Compound 348: ¹H NMR (500 MHz, DMSO-d6) δ 11.05 (s, 1H), 9.07 (s, 1H), 8.34-8.33 (m, 2H), 8.12 (d, J=8.5 Hz, 1H), 7.73 (dd, J=9.0, 2.0 Hz, 1H), 7.36-7.23 (m, 5H), 4.52 (d, J=9.0 Hz, 2H), 3.98 (s, 2H), 2.90 (s, 3H), 1.44 (s, 4.2H), 1.29 (s, 4.8H); LCMS (ESI) m/z: 467.0 [M+H]+.

Compound 349: ¹H NMR (400 MHz, DMSO-d6) δ 10.53 (s, 1H), 8.66 (d, J=2.4 Hz, 1H), 8.53 (s, 1H), 8.18 (d, J=2.8 Hz, 1H), 8.04 (d, J=8.8 Hz, 1H), 8.00 (dd, J=9.6, 2.8 Hz, 1H), 7.67 (dd, J=9.2, 2.8 Hz, 1H), 7.28-7.22 (m, 1H), 6.83 (dd, J=8.0, 1.2 Hz, 1H), 6.78-6.74 (m, 1H), 6.74-6.58 (m, 1H), 6.44 (d, J=9.2 Hz, 1H), 3.51 (s, 3H); LCMS (ESI) m/z: 339.1 [M+H]+.

Compound 350: ¹H NMR (500 MHz, DMSO-d6) δ 12.71 (bs, 1H), 8.72 (d, J=2.5 Hz, 1H), 8.02 (dd, J=10.0, 2.5 Hz, 1H), 7.62 (dd, J=7.0, 2.0 Hz, 1H), 7.42-7.36 (m, 2H), 6.46 (d, J=9.5 Hz, 1H), 4.39 (s, 2H), 3.51 (s, 3H); LCMS (ESI) m/z: 379.1 [M+H]+.

Compound 351: ¹H NMR (500 MHz, DMSO-d6) δ 10.69 (s, 1H), 9.11 (s, 2H), 7.95 (d, J=9.7 Hz, 1H), 7.51-7.16 (m, 4H), 7.09 (d, J=9.7 Hz, 1H), 4.22 (s, 2H), 3.81 (s, 3H); LCMS (ESI) m/z: 356.0 [M+H]+.

Compound 352: ¹H NMR (400 MHz, DMSO-d6) δ 8.48 (s, 1H), 7.63 (d, J=8.0 Hz, 1H), 7.36-7.31 (m, 2H), 7.19 (dd, J=9.6, 2.8 Hz, 1H), 7.12-7.01 (m, 3H), 6.72 (d, J=2.8 Hz, 1H), 6.29 (d, J=9.6 Hz, 1H), 5.45 (t, J=5.8 Hz, 1H), 4.12 (d, J=5.6 Hz, 2H), 3.98 (s, 2H), 3.29 (s, 3H); LCMS (ESI) m/z: 324.1 [M+H]+.

Compound 353: ¹H NMR (400 MHz, DMSO-d6) δ 12.72 (s, 1H), 8.72 (d, J=2.4 Hz, 1H), 8.00 (dd, J1=2.8, J2=9.6 Hz, 1H), 7.42 (dd, J1=8.0 Hz, J2=14.4 Hz, 1H), 7.11-7.21 (m, 3H), 6.47 (d, J=9.6 Hz, 1H), 4.35 (s, 2H), 3.51 (s, 3H); LCMS (ESI) m/z: 369.0 [M+H]+.

Compound 354: ¹H NMR (400 MHz, DMSO-d6) δ 11.26 (s, 1H), 9.22 (d, J=1.6 Hz, 1H), 8.49 (dd, J=2.4, 8 Hz, 1H), 8.37 (d, J=2 Hz, 1H), 8.14 (d, J=8.4 Hz, 1H), 8.05 (d, J=8 Hz, 1H), 7.75 (dd, J=2.4, 8.4 Hz, 1H), 7.21-7.40 (m, 4H), 3.99 (s, 2H), 2.68 (s, 3H); LCMS (ESI) m/z: 366.1 [M+H]+.

Compound 355: ¹H NMR (400 MHz, DMSO-d6) δ 10.46 (s, 1H), 8.49 (s, 1H), 8.29 (d, J=1.6 Hz, 1H), 8.13-8.10 (m, 2H), 7.67 (dd, J=8.4, 1.6 Hz, 1H), 7.35 (dd, J=14.4, 7.6 Hz, 1H), 7.13-7.10 (m, 2H), 7.04 (t, J=8.6 Hz, 1H), 4.17 (q, J=7.2 Hz, 2H), 3.96 (s, 2H), 1.39 (t, J=7.2 Hz, 3H); LCMS (ESI) m/z: 325.1 [M+H]+.

Compound 356: ¹H NMR (400 MHz, DMSO-d6) δ 10.51 (s, 1H), 8.41 (s, 1H), 8.28 (d, J=1.6 Hz, 1H), 8.11 (s, 1H), 8.07 (d, J=8.4 Hz, 1H), 7.68 (dd, J=8.6, 2.0 Hz, 1H), 7.34 (dd, J=14.4, 8.0 Hz, 1H), 7.12-7.09 (m, 2H), 7.05-7.00 (m, 1H), 3.95 (s, 2H), 3.86 (s, 3H); LCMS (ESI) m/z: 311.0 [M+H]+.

Compound 357: ¹H NMR (500 MHz, DMSO-d6) δ 10.48 (s, 1H), 8.67 (d, J=2.0 Hz, 1H), 8.34 (d, J=2.5 Hz, 1H), 8.03 (d, J=7.5 Hz, 1H), 7.90-7.88 (m, 1H), 7.78-7.76 (m, 1H), 7.38-7.34 (m, 1H), 7.17-7.12 (m, 2H), 7.07-7.03 (m, 1H), 6.41 (d, J=9.5 Hz, 1H), 4.12 (s, 2H), 3.44 (s, 3H); LCMS (ESI) m/z: 338.0 [M+H]+.

Compound 358: ¹H NMR (500 MHz, DMSO-d6) δ 9.52 (d, J=2.5 Hz, 1H), 9.17 (d, J=2.0 Hz, 1H), 8.38 (d, J=2.0 Hz, 1H), 8.17 (d, J=8.5 Hz, 1H), 7.78 (dd, J=8.5 Hz, J=2.0 Hz, 1H), 7.34-7.39 (m, 1H), 7.12-7.15 (m, 2H), 7.05 (td, J=8.5 Hz, J=2.5 Hz, 1H), 6.08 (s, 1H), 4.01 (m, 2H); LCMS (ESI) m/z: 366.0 [M+H]+.

Compound 359: ¹H NMR (400 MHz, DMSO-d6) δ 11.10 (s, 1H), 9.27 (s, 1H), 8.87 (s, 1H), 8.57 (d, J=2.4 Hz, 1H), 8.14 (dd, J=9.5, 2.4 Hz, 1H), 7.38 (dd, J=14.4, 7.9 Hz, 1H), 7.19 (d, J=7.3 Hz, 2H), 7.10 (t, J=8.5 Hz, 1H), 6.52 (d, J=9.5 Hz, 1H), 3.82 (s, 2H), 3.53 (s, 3H); LCMS (ESI) m/z: 339.1 [M+H]+.

Compound 360: ¹H NMR (400 MHz, DMSO-d6) δ 10.17 (s, 1H), 8.35 (d, J=1.9 Hz, 1H), 8.10 (d, J=8.4 Hz, 1H), 7.96 (d, J=9.7 Hz, 1H), 7.87 (dd, J=8.5, 2.2 Hz, 1H), 7.28 (dt, J=24.9, 12.5 Hz, 1H), 7.08 (d, J=9.7 Hz, 1H), 6.90-6.65 (m, 3H), 4.23 (t, J=6.6 Hz, 2H), 3.80 (s, 3H), 3.06 (t, J=6.6 Hz, 2H); LCMS (ESI) m/z: 369.1 [M+H]+.

Compound 361: ¹H NMR (400 MHz, DMSO-d6) δ 10.45 (s, 1H), 8.64 (d, J=2.4 Hz, 1H), 8.17 (d, J=2.8 Hz, 1H), 8.05 (d, J=9.2 Hz, 1H), 7.98 (dd, J=9.6, 2.4 Hz, 1H), 7.57-7.54 (m, 2H), 7.45-7.42 (m, 3H), 6.43 (d, J=9.6 Hz, 1H), 5.20 (s, 2H), 3.50 (s, 3H); LCMS (ESI) m/z: 370.1 [M+H]+.

Compound 362: ¹H NMR (400 MHz, DMSO-d6) δ 10.20 (s, 1H), 8.36 (d, J=1.9 Hz, 1H), 8.11 (d, J=8.5 Hz, 1H), 8.00-7.81 (m, 2H), 7.36-7.19 (m, 2H), 7.08 (d, J=9.7 Hz, 1H), 6.93 (dd, J=12.1, 5.1 Hz, 3H), 4.21 (t, J=6.6 Hz, 2H), 3.80 (s, 3H), 3.06 (t, J=6.6 Hz, 2H); LCMS (ESI) m/z: 351.1 [M+H]+.

Compound 363: ¹H NMR (400 MHz, DMSO-d6) δ 10.87 (s, 1H), 8.73 (d, J=1.6 Hz, 1H), 8.10-8.13 (m, 2H), 7.91-7.97 (m, 2H), 7.41 (s, 1H), 7.23-7.36 (m, 3H), 4.12 (s, 2H), 3.73 (s, 3H); LCMS (ESI) m/z: 355.1 [M+H]+.

Compound 364: ¹H NMR (400 MHz, DMSO-d6) δ 10.32 (s, 1H), 8.94 (d, J=4.8 Hz, 1H), 8.37 (d, J=2.4 Hz, 1H), 8.16 (d, J=8.8 Hz, 1H), 7.72-7.84 (m, 2H), 7.30-7.40 (m, 1H), 6.98-7.17 (m, 3H), 4.07 (s, 3H), 4.00 (s, 2H); LCMS (ESI) m/z: 339.1 [M+H]+.

Compound 365: ¹H NMR (500 MHz, DMSO-d6) δ 8.43-8.46 (m, 2H), 8.15-8.17 (d, J=9.0 Hz, 1H), 7.89-7.92 (m, 2H), 7.34-7.38 (m, 1H), 7.30-7.31 (m, 1H), 7.03-7.06 (m, 1H), 5.12 (s, 2H), 3.37-3.41 (m, 1H), 1.02-1.03 (d, J=5.5 Hz, 4H); LCMS (ESI) m/z: 414.0 [M+H]+.

Compound 366: ¹H NMR (400 MHz, DMSO-d6) δ 9.05 (d, J=2 Hz, 1H), 8.34 (d, J=2 Hz, 1H), 8.26 (dd, J=2 Hz, 8.4 Hz, 1H), 8.13 (d, J=8.8 Hz, 1H), 7.73 (dd, J=2 Hz, 8.4 Hz, 1H), 7.41 (d, J=8.4 H, 1H), 7.19-7.38 (m, 4H), 4.71 (brs, 1H), 3.98 (s, 2H), 3.78 (t, J=6.4 Hz, 2H), 2.95 (t, J=6.4 Hz, 2H); LCMS (ESI) m/z: 368.1 [M+H]+.

Compound 367: ¹H NMR (400 MHz, DMSO-d6) δ 10.12 (s, 1H), 8.56 (s, 1H), 8.19 (d, J=2.6 Hz, 1H), 8.09 (d, J=8.9 Hz, 1H), 7.96 (d, J=9.7 Hz, 1H), 7.69 (dd, J=8.9, 2.8 Hz, 1H), 7.25 (t, J=7.9 Hz, 1H), 7.09 (d, J=9.7 Hz, 1H), 6.99 (d, J=7.9 Hz, 2H), 6.85 (d, J=7.1 Hz, 1H), 3.80 (s, 3H); LCMS (ESI) m/z: 356.0 [M+H]+.

Compound 369: ¹H NMR (500 MHz, DMSO-d6) δ 8.31 (d, J=8.0 Hz, 1H), 7.84 (d, J=10.0 Hz, 1H), 7.31 (t, J=8.0 Hz, 1H), 7.05-6.95 (m, 4H), 4.63 (s, 1H), 3.90-3.84 (m, 1H), 3.74 (s, 3H), 1.95-1.93 (m, 2H), 1.80-1.73 (m, 2H), 1.69-1.60 (m, 4H); LCMS (ESI) m/z: 362.0 [M+H]+.

Compound 370: ¹H NMR (400 MHz, DMSO-d6) δ 9.67 (s, 1H), 8.14 (d, J=2.0 Hz, 1H), 8.01 (d, J=8.4 Hz, 1H), 7.65 (dd, J=8.4, 2.4 Hz, 1H), 3.36 (s, 2H), 2.85 (t, J=8.6 Hz, 2H), 2.53 (d, J=8.8 Hz, 2H), 2.45 (d, J=6.8 Hz, 2H), 1.66-1.58 (m, 5H), 1.54-1.43 (m, 1H), 1.24-1.08 (m, 3H), 0.96-0.87 (m, 2H); LCMS (ESI) m/z: 329.2 [M+H]+.

Compound 371: ¹H NMR (400 MHz, DMSO-d6) δ 10.03 (s, 1H), 8.32 (d, J=1.5 Hz, 1H), 8.09 (d, J=8.6 Hz, 1H), 7.91 (d, J=2.2 Hz, 1H), 7.85 (d, J=8.6 Hz, 1H), 7.38 (ddd, J=17.0, 9.3, 5.3 Hz, 2H), 7.19-7.08 (m, 1H), 6.87 (d, J=2.3 Hz, 1H), 3.98 (s, 5H); LCMS (ESI) m/z: 329.1 [M+H]+.

Compound 372: ¹H NMR (400 MHz, DMSO-d6) δ 10.33 (s, 1H), 8.70 (d, J=2.8 Hz, 1H), 8.34 (d, J=1.9 Hz, 1H), 8.07 (d, J=8.5 Hz, 1H), 7.75 (dd, J=8.5, 2.3 Hz, 1H), 7.40-7.30 (m, 1H), 7.25 (d, J=2.4 Hz, 1H), 7.13 (dd, J=10.8, 4.5 Hz, 2H), 7.04 (d, J=2.3 Hz, 1H), 3.99 (s, 2H); LCMS (ESI) m/z: 365.0 [M+H]+.

Compound 373: ¹H NMR (400 MHz, DMSO-d6) δ 10.61 (s, 1H), 8.43 (s, 1H), 8.32 (d, J=1.6 Hz, 1H), 8.13 (s, 1H), 8.07 (d, J=8.8 Hz, 1H), 7.76 (d, J=8.6 Hz, 1H), 7.10-7.03 (m, 3H), 3.98 (s, 2H), 3.88 (s, 3H); LCMS (ESI) m/z: 341.0 [M+H]+.

Compound 374: ¹H NMR (400 MHz, DMSO-d6) δ 10.99 (brs, 1H), 9.04 (d, J=2 Hz, 1H), 8.28-8.38 (m, 2H), 8.13 (d, J=8.4 Hz, 1H), 7.68-7.80 (m, 2H), 7.19-7.40 (m, 4H), 5.38 (s, 1H), 3.98 (s, 2H), 1.46 (s, 6H); LCMS (ESI) m/z: 382.1 [M+H]+.

Compound 375: ¹H NMR (400 MHz, DMSO-d6) δ 11.08 (s, 1H), 9.08 (s, 1H), 8.42 (dd, J=8.0, 2.0 Hz, 1H), 8.20 (d, J=1.6 Hz, 1H), 8.10 (d, J=8.4 Hz, 1H), 7.71-7.64 (m, 1H), 4.67 (s, 2H), 2.48 (m, 2H), 1.68-1.61 (m, 5H), 1.53-1.48 (m, 1H), 1.24-1.10 (m, 3H), 0.98-0.89 (m, 2H); LCMS (ESI) m/z: 326.2 [M+H]+.

Compound 376: ¹H NMR (300 MHz, Chloroform-d) δ 8.55 (d, J=9.1 Hz, 1H), 8.02 (d, J=9.7 Hz, 1H), 7.43 (d, J=9.0 Hz, 1H), 7.31 (d, J=6.3 Hz, 2H), 7.06 (d, J=9.7 Hz, 2H), 6.98 (d, J=2.1 Hz, 2H), 4.36 (s, 2H), 4.16 (d, J=7.5 Hz, 2H), 1.54-1.36 (m, 1H), 0.68-0.57 (m, 2H), 0.52 (d, J=4.9 Hz, 2H); LCMS (ESI) m/z: 380.3 [M+H]+.

Compound 377: ¹H NMR (500 MHz, DMSO-d6) δ 12.17 (s, 1H), 7.37-7.33 (m, 1H), 7.28 (s, 1H), 7.11-7.03 (m, 3H), 4.11 (s, 2H), 3.57 (t, J=8.7 Hz, 1H), 3.44-3.36 (m, 2H), 2.70 (s, 3H), 2.54-2.48 (m, 1H), 2.46-2.41 (m, 1H); LCMS (ESI) m/z: 334.1 [M+H]+.

Compound 378: ¹H NMR (400 MHz, DMSO-d6) δ 11.81 (s, 1H), 7.32-7.22 (m, 2H), 7.17-7.06 (m, 2H), 6.88 (s, 1H), 3.97 (s, 2H), 3.34 (s, 3H), 2.83 (t, J=8.5 Hz, 2H), 2.53 (t, J=8.4 Hz, 2H); LCMS (ESI) m/z: 347.1 [M+H]+.

Compound 379: ¹H NMR (500 MHz, DMSO-d6) δ 11.23 (s, 1H), 8.70 (d, J=2.6 Hz, 1H), 8.27 (d, J=9.2 Hz, 1H), 7.96 (dd, J=9.5, 2.6 Hz, 1H), 7.61 (d, J=9.5 Hz, 1H), 7.36-7.32 (m, 2H), 7.20-7.07 (m, 2H), 6.45 (d, J=9.5 Hz, 1H), 4.26 (s, 2H), 3.99 (q, J=7.1 Hz, 2H), 1.29 (t, J=7.1 Hz, 3H); LCMS (ESI) m/z: 353.1 [M+H]+.

Compound 380: ¹H NMR (400 MHz, Dimethylsulfoxide-d6) δ 11.96 (s, 1H), 7.84 (d, 1H, J=7.6 Hz), 7.68 (t, 1H, J=7.6 Hz), 7.57 (d, 1H, J=7.6 Hz), 7.47 (d, 1H, J=7.6 Hz), 7.32 (s, 1H), 4.33 (s, 2H), 3.35 (s, 3H), 2.82 (t, 2H, J=8.4 Hz), 2.51 (t, 2H, J=8.4 Hz); LCMS (ESI) m/z: 354.1 [M+H]+.

Compound 381: ¹H NMR (300 MHz, Chloroform-d) δ 8.56-8.40 (m, 1H), 7.91 (s, 1H), 7.48 (dd, J=8.0, 2.3 Hz, 1H), 7.36-7.23 (m, 2H), 7.04-6.80 (m, 3H), 4.64 (d, J=5.6 Hz, 2H), 3.98 (s, 2H), 3.43 (s, 3H), 3.00-2.85 (m, 2H), 2.53 (t, J=8.5 Hz, 2H); LCMS (ESI) m/z: 355.4 [M+H]+.

Compound 382: ¹H NMR (500 MHz, MeOD) δ 8.36 (d, J=5.8 Hz, 1H), 7.73 (dd, J=5.8, 2.1 Hz, 1H), 7.67 (d, J=1.9 Hz, 1H), 7.34-7.25 (m, 2H), 7.25-7.15 (m, 2H), 4.09 (s, 2H), 3.45 (s, 3H), 2.91 (t, J=8.6 Hz, 2H), 2.57 (t, J=8.6 Hz, 2H); LCMS (ESI) m/z: 357.1 [M+H]+.

Compound 383: ¹H NMR (400 MHz, DMSO-d6) δ 9.69 (s, 1H), 8.27 (d, J=2.0 Hz, 1H), 8.01 (d, J=6.8 Hz, 1H), 7.68-7.70 (m, 1H), 7.16 (s, 4H), 3.90 (s, 4H), 3.36 (s, 3H), 2.82-2.86 (m, 2H), 2.52-2.54 (m, 2H), 1.17 (d, J=5.6 Hz, 6H); LCMS (ESI) m/z: 365.2 [M+H]+.

Compound 384: ¹H NMR (400 MHz, DMSO-d6) δ 10.89 (s, 1H), 8.31 (d, J=9.0 Hz, 1H), 7.95 (d, J=9.5 Hz, 1H), 7.72 (d, J=9.5 Hz, 1H), 7.32 (d, J=2 Hz, 1H), 7.28 (s, 1H), 7.19 (d, J=9 Hz, 1H), 7.08 (d, J=10 Hz, 1H), 4.32 (s, 2H), 3.81 (s, 3H); LCMS (ESI) m/z: 374.1 [M+H]+.

Compound 385: ¹H NMR (500 MHz, DMSO-d6) δ 11.73 (s, 1H), 9.82 (s, 1H), 7.28-7.15 (m, 2H), 6.83 (d, J=2.4 Hz, 1H), 6.72 (dd, J=8.4, 2.4 Hz, 1H), 4.08 (s, 2H), 3.34 (s, 3H), 2.82 (t, J=8.5 Hz, 2H), 2.52 (t, J=8.5 Hz, 2H); LCMS (ESI) m/z: 379.0 [M+H]+.

Compound 386: ¹H NMR (500 MHz, DMSO-d6) δ 12.06 (s, 1H), 7.40-7.33 (m, 2H), 7.16-7.10 (m, 2H), 7.07 (td, J=8.5, 2.0 Hz, 1H), 4.80 (t, J=5.0 Hz, 1H), 4.71 (t, J=5.0 Hz, 1H), 4.15 (s, 2H), 4.09 (t, J=5.0 Hz, 1H), 4.06-3.99 (m, 1H), 2.84 (q, J=8.4 Hz, 2H), 2.56 (t, J=8.5 Hz, 2H); LCMS (ESI) m/z: 379.0 [M+H]+.

Compound 387: ¹H NMR (400 MHz, DMSO-d6) δ 9.77 (s, 1H), 7.94-7.94 (d, J=2.8 Hz, 1H), 7.54 (d, J=1.2 Hz, 1H), 7.28-7.40 (m, 4H), 4.00 (s, 2H), 3.84 (s, 3H), 3.33 (s, 3H), 2.80-2.84 (t, J=6.8 Hz, 2H), 2.51-2.53 (m, 2H); LCMS (ESI) m/z: 387.1 [M+H]+.

Compound 388: ¹H NMR (400 MHz, CDCl3) δ=9.23 (s, 1H), 7.55 (s, 1H), 7.36-7.29 (m, 1H), 7.12 (d, J=7.7 Hz, 1H), 7.07-6.93 (m, 2H), 4.28 (s, 2H), 3.49 (s, 3H), 3.03-2.92 (m, 2H), 2.60 (t, J=8.6 Hz, 2H); LCMS (ESI) 347.1 [M+H]+.

Compound 389: ¹H NMR (500 MHz, Dimethylsulfoxide-d6) δ 12.34 (s, 1H), 7.90 (d, J=9.7 Hz, 1H), 7.80 (s, 1H), 7.72 (d, J=8.0 Hz, 1H), 7.65 (d, J=7.5 Hz, 1H), 7.55 (t, J=7.5 Hz, 1H), 7.38 (s, 1H), 7.06 (d, J=9.7 Hz, 1H), 4.21 (s, 2H), 3.77 (s, 3H); LCMS (ESI) 352.0 [M+H]+.

Compound 390: ¹H NMR (500 MHz, DMSO-d6) δ 8.38 (d, J=8.5 Hz, 1H), 7.98 (d, J=7.9 Hz, 1H), 7.90 (d, J=8.4 Hz, 1H), 7.78-7.71 (m, 1H), 7.60 (t, J=7.5 Hz, 1H), 7.51-7.49 (m, 2H), 7.41 (d, J=3.5 Hz, 1H), 6.01 (s, 2H), 2.89 (t, J=8.25 Hz, 5H), 2.31 (t, J=8.4 Hz, 2H); LCMS (ESI) 380.0 [M+H]+.

Compound 391: ¹H NMR (500 MHz, DMSO-d6) δ 11.18 (s, 1H), 8.53 (s, 1H), 8.36-8.29 (m, 2H), 8.15-8.11 (m, 2H), 7.84-7.73 (m, 2H), 7.36 (dd, J=14.4, 8.0 Hz, 1H), 7.17-6.99 (m, 3H), 4.00 (s, 2H), 3.30 (s, 3H); LCMS (ESI) 385.0 [M+H]+.

Compound 392: ¹H NMR (500 MHz, DMSO-d6) δ 9.71 (s, 1H), 8.33 (d, J=1.7 Hz, 1H), 8.28 (d, J=1.9 Hz, 1H), 8.02 (d, J=8.5 Hz, 1H), 7.70 (dd, J=8.5, 2.2 Hz, 1H), 7.49 (dd, J=8.0, 2.1 Hz, 1H), 7.20 (d, J=8.0 Hz, 1H), 3.90 (s, 2H), 3.35 (s, 3H), 2.85 (t, J=8.5 Hz, 2H), 2.52 (t, J=8.3 Hz, 2H), 2.05-2.02 (m, 1H), 0.92-0.84 (m, 4H); LCMS (ESI) m/z 364.1 [M+H]+.

Compound 393: ¹H NMR (500 MHz, CH₃OD) δ 8.14 (d, J=11.9 Hz, 2H), 7.54 (d, J=8.8 Hz, 1H), 7.30 (ddd, J=40.7, 24.1, 7.6 Hz, 4H), 4.51 (d, J=8.5 Hz, 4H), 4.08 (s, 2H), 3.70-3.49 (m, 4H), 2.04-1.88 (m, 4H); LCMS (ESI) m/z: 372.1 [M+H]+.

Compound 394: ¹H NMR (500 MHz, Dimethylsulfoxide-d6) δ 11.20 (s, 1H), 8.33 (d, 1H, J=9.5 Hz), 7.97 (d, 1H, J=9 Hz), 7.79 (s, 1H), 7.62-7.70 (m, 2H), 7.37-7.56 (m, 3H), 2.17 (s, 3H); LCMS (ESI) m/z: 274.0 [M+H]+.

Compound 395: ¹H NMR (300 MHz, Chloroform-d) δ 8.62 (d, J=9.1 Hz, 1H), 8.04 (d, J=9.7 Hz, 1H), 7.49 (d, J=9.1 Hz, 1H), 7.07 (d, J=9.7 Hz, 1H), 3.95 (s, 3H), 2.89 (d, J=7.3 Hz, 2H), 2.15 (m, 1H), 1.00 (d, J=6.6 Hz, 6H); LCMS (ESI) m/z: 288.2 [M+H]+

Compound 396: ¹H NMR (500 MHz, Dimethylsulfoxide-d6) δ 9.83 (s, 1H), 8.28 (d, J=1.7 Hz, 1H), 8.07 (d, J=8.5 Hz, 1H), 7.79 (dd, J=8.5, 2.0 Hz, 1H), 4.48 (s, 2H), 3.36 (s, 3H), 2.86 (t, J=8.5 Hz, 2H), 2.60-2.51 (m, 2H), 1.42 (s, 3H), 0.78 (t, J=5.5 Hz, 2H), 0.45 (q, J=4.9 Hz, 2H); LCMS (ESI) m/z: 317.2 [M+H]+.

Compound 397: ¹H NMR (500 MHz, DMSO-d6) δ 7.91 (d, J=2 Hz, 1H), 7.26-7.34 (m, 2H), 6.95-7.09 (m, 3H), 6.71 (t, J=5.5 Hz, 1H), 6.48 (d, J=8.5 Hz, 1H), 4.07 (d, J=6 Hz, 2H), 3.77 (s, 2H), 3.18 (s, 3H), 2.45 (t, J=8 Hz, 2H), 2.31 (t, J=8 Hz, 2H); LCMS (ESI) m/z: 327.1 [M+H]+.

Compound 398: ¹H NMR (400 MHz, CDCl3) δ 8.57 (br s, 1H), 8.46 (br d, J=4.0 Hz, 1H), 7.74 (br d, J=7.8 Hz, 1H), 7.34 (br dd, J=4.8, 7.6 Hz, 1H), 6.60 (br s, 1H), 4.99 (d, J=1.7 Hz, 2H), 3.46 (s, 3H), 2.99-2.92 (m, 2H), 2.61 (br t, J=8.6 Hz, 2H); LCMS (ESI) m/z: 330.0 [M+H]+.

Compound 399: ¹H NMR (500 MHz, CDCl3) δ 7.33 (dd, J=14.5, 7.5 Hz, 1H), 7.07 (d, J=7.5 Hz, 1H), 7.00 (t, J=7.5 Hz, 2H), 6.74 (s, 1H), 4.03 (s, 2H), 3.49 (s, 3H), 2.97 (t, J=8.5 Hz, 2H), 2.61 (t, J=8.5 Hz, 2H); LCMS (ESI) m/z: 331.1 [M+H]+.

Compound 400: ¹H NMR (500 MHz, DMSO-d6) δ 12.36 (s, 1H), 7.38-7.31 (m, 2H), 7.12-7.03 (m, 3H), 4.34-4.32 (m, 1H), 4.12 (s, 2H), 2.64 (s, 3H), 2.30-2.18 (m, 3H), 1.92-1.87 (m, 1H); LCMS (ESI) m/z: 334.1 [M+H]+.

Compound 401: ¹H NMR (500 MHz, DMSO-d6) δ 10.21 (s, 1H), 8.82 (d, J=2.4 Hz, 1H), 8.07 (dd, J=8.4, 2.5 Hz, 1H), 7.40-7.22 (m, 2H), 7.17-7.06 (m, 2H), 7.03 (s, 1H), 4.07 (s, 2H), 3.37 (s, 3H), 2.83 (t, J=8.5 Hz, 2H), 2.52 (d, J=9.8 Hz, 2H); LCMS (ESI) m/z: 341.1 [M+H]+.

Compound 402: ¹H NMR (400 MHz, DMSO-d6) δ 9.76 (s, 1H), 8.33 (d, J=2.0 Hz, 1H), 8.06 (d, J=8.5 Hz, 1H), 7.79 (dd, J=8.5, 2.3 Hz, 1H), 7.38 (d, J=1.2 Hz, 1H), 4.27 (s, 2H), 3.36 (s, 3H), 2.85 (t, J=8.5 Hz, 2H), 2.85 (t, J=6.8 Hz, 2H), 2.37 (s, 3H); LCMS (ESI) m/z: 344.0 [M+H]+.

Compound 403: ¹H NMR (500 MHz, CH₃OD) δ 8.11 (d, J=11.3 Hz, 2H), 7.50 (d, J=8.8 Hz, 1H), 7.30 (ddd, J=41.7, 24.7, 7.7 Hz, 4H), 4.31 (dd, J=22.0, 13.1 Hz, 4H), 4.07 (s, 2H), 3.73 (dq, J=9.1, 5.9 Hz, 2H), 2.23 (s, 3H); LCMS (ESI) m/z: 344.0[M+H]+.

Compound 404: ¹H NMR (400 MHz, DMSO-d6) δ 12.37 (s, 1H), 8.17-8.19 (d, J=7.2 Hz, 1H), 7.43-7.45 (d, J=7.2 Hz, 1H), 7.37-7.39 (m, 2H), 7.13-7.16 (m, 2H), 7.07 (m, 1H), 4.17 (s, 2H), 4.15 (s, 3H); LCMS (ESI) m/z: 345.1 [M+H]+.

Compound 405: ¹H NMR (500 MHz, DMSO-d6) δ 10.31 (s, 1H), 8.14 (s, 1H), 7.68 (s, 1H), 7.44-7.31 (m, 2H), 7.26 (s, 1H), 7.19 (d, J=6.5 Hz, 1H), 5.33 (s, 2H), 3.34 (s, 3H), 2.82 (t, J=8.5 Hz, 2H), 2.48 (d, J=8.5 Hz, 2H); LCMS (ESI) m/z: 346.1 [M+H]+.

Compound 406: ¹H NMR (400 MHz, DMSO-d6) δ 11.61 (s, 1H), 7.34 (td, J=7.9, 6.1 Hz, 1H), 7.12-6.99 (m, 3H), 6.93 (s, 1H), 4.00 (s, 2H), 3.34 (s, 3H), 2.84 (t, J=8.5 Hz, 2H), 2.51 (t, J=8.5 Hz, 2H); LCMS (ESI) m/z: 347.0 [M+H]+.

Compound 407: ¹H NMR (500 MHz, Dimethylsulfoxide-d6) δ 11.03 (s, 1H), 7.36-7.20 (m, 4H), 3.98 (s, 3H), 3.33 (s, 3H), 2.81 (q, J=8.9 Hz, 2H), 2.53 (s, 2H); LCMS (ESI) m/z: 347.0 [M+H]+.

Compound 408: ¹H NMR (400 MHz, CDCl3) δ 10.30 (br s, 1H), 7.33-7.27 (m, 1H), 7.10 (d, J=7.6 Hz, 1H), 7.03 (br d, J=9.7 Hz, 1H), 6.95 (dt, J=2.5, 8.5 Hz, 1H), 4.21 (s, 2H), 3.46 (s, 3H), 3.01 (t, J=8.6 Hz, 2H), 2.71-2.57 (m, 2H); LCMS (ESI) m/z: 348.0 [M+H]+.

Compound 409: ¹H NMR (400 MHz, DMSO-d6) δ 11.48 (s, 1H), 7.38-7.44 (m, 3H), 7.31 (s, 1H), 4.30 (s, 2H), 3.39 (s, 3H), 2.79 (t, J=6.8 Hz, 2H), 2.50-2.53 (m, 2H); LCMS (ESI) m/z: 348.1 [M+H]+.

Compound 410: ¹H NMR (500 MHz, DMSO-d6) δ 11.25 (s, 1H), 8.71 (d, J=2.6 Hz, 1H), 8.27 (d, J=9.2 Hz, 1H), 7.96 (dd, J=9.5, 2.6 Hz, 1H), 7.64 (d, J=9.2 Hz, 1H), 7.37 (dd, J=14.2, 7.8 Hz, 1H), 7.19-7.02 (m, 3H), 6.45 (d, J=9.5 Hz, 1H), 4.27 (s, 2H), 3.99 (q, J=7.1 Hz, 2H), 1.29 (t, J=7.1 Hz, 3H); LCMS (ESI) m/z: 353.1 [M+H]+.

Compound 411: ¹H NMR (300 MHz, Chloroform-d) δ 8.46 (s, 1H), 8.39 (s, 1H), 7.96 (d, J=9.6 Hz, 1H), 7.67 (s, 1H), 7.46 (s, 1H), 7.31 (s, 5H), 7.04-6.90 (m, 3H), 6.87 (d, J=9.6 Hz, 1H), 4.79 (d, J=5.8 Hz, 2H), 4.03 (s, 2H), 3.87 (s, 3H); LCMS (ESI) m/z: 353.5 [M+H]+.

Compound 412: ¹H NMR (500 MHz, Dimethylsulfoxide-d6) δ 9.72 (s, 1H), 8.23 (d, J=1.8 Hz, 1H), 8.06 (d, J=8.4 Hz, 1H), 7.76 (d, J=2.2 Hz, 1H), 3.45 (s, 2H), 3.36 (s, 3H), 2.86 (t, J=8.5 Hz, 2H), 2.54 (d, J=8.5 Hz, 2H), 2.32 (s, 4H), 1.31 (t, J=5.5 Hz, 4H), 0.88 (s, 6H); LCMS (ESI) m/z: 358.3 [M+H]+.

Compound 413: ¹H NMR (400 MHz, DMSO-d6) δ 12.75 (s, 1H), 8.23 (s, 1H), 7.72 (dt, J=7.6, 1.4 Hz, 1H), 7.71-7.59 (m, 2H), 7.54 (tdd, J=8.4, 2.7, 1.1 Hz, 1H), 3.38 (s, 3H), 2.89 (t, J=8.5 Hz, 2H), 2.56 (t, J=8.5 Hz, 2H); LCMS (ESI) m/z: 361.0 [M+H]+.

Compound 414: ¹H NMR (400 MHz, CDCl3) δ 9.99 (br s, 1H), 7.33-7.22 (m, 1H), 7.20 (s, 1H), 7.03 (br d, J=7.5 Hz, 1H), 6.97-6.89 (m, 2H), 4.10 (s, 2H), 3.93-3.80 (m, 2H), 2.95 (dt, J=2.2, 8.6 Hz, 2H), 2.58 (dt, J=2.2, 8.5 Hz, 2H), 1.25 (dt, J=2.3, 7.0 Hz, 3H); LCMS (ESI) m/z: 361.1 [M+H]+.

Compound 415: ¹H NMR (400 MHz, DMSO-d6) δ 10.45 (s, 1H), 8.55 (s, 1H), 8.37-8.38 (m, 1H), 8.15 (d, J=8.5 Hz, 1H), 8.05 (d, J=0.5 Hz, 1H), 7.80-7.86 (m, 1H), 7.25-7.38 (m, 4H), 4.00 (s, 2H); LCMS (ESI) m/z: 364.0 [M+H]+.

Compound 416: ¹H NMR (500 MHz, CDCl3) δ 7.48 (dd, J=8.0, 1.5 Hz, 1H), 7.26 (dd, J=8.5, 1.5 Hz, 1H), 7.18-7.10

(m, 3H), 3.50 (s, 3H), 2.99 (t, J=8.5 Hz, 2H), 2.63 (t, J=8.5 Hz, 2H); LCMS (ESI) m/z: 365.0 [M+H]+.

Compound 417: $^1$H NMR (400 MHz, DMSO-d6) δ 10.11 (s, 1H), 8.35 (s, 1H), 8.14-8.35 (m, 3H), 7.77-7.79 (m, 1H), 7.33-7.37 (m, 1H), 7.02-7.14 (m, 3H), 3.80 (s, 2H); LCMS (ESI) m/z: 366.1 [M+H]+.

Compound 418: $^1$H NMR (500 MHz, Dimethylsulfoxide-d6) δ 10.51 (brs, 1H), 8.35 (d, 1H, J=9 Hz), 8.06 (d, 1H, J=9 Hz), 7.82 (s, 1H), 7.65-7.74 (m, 2H), 7.56 (d, 1H, J=16.5 Hz), 7.40-7.49 (m, 2H), 3.40 (s, 3H), 2.88 (t, 2H, J=8.5 Hz), 2.56 (t, 2H, J=8.5 Hz); LCMS (ESI) m/z: 370.1 [M+H]+.

Compound 419: $^1$H NMR (500 MHz, DMSO-d6) δ 11.84 (s, 1H), 7.25-7.41 (m, 4H), 7.02-7.09 (m, 1H), 6.35 (s, 1H), 3.34 (s, 3H), 2.77-2.86 (m, 2H), 2.50-2.56 (m, 2H), 1.89 (s, 3H); LCMS (ESI) m/z: 377.1 [M+H]+.

Compound 420: $^1$H NMR (500 MHz, CDCl3) δ 10.23 (s, 1H), 7.27-7.30 (m, 1H), 7.18 (s, 1H), 7.03 (d, J=7.5 Hz, 1H), 6.92-6.95 (m, 2H), 4.09 (s, 2H), 4.04 (t, J=5.5 Hz, 2H), 3.92 (t, J=5.5 Hz, 2H), 2.93 (t, J=8.5 Hz, 2H), 2.73 (s, 1H), 2.59 (t, J=8.5 Hz, 2H); LCMS (ESI) m/z: 377.1 [M+H]+.

Compound 421: $^1$H NMR (500 MHz, Dimethylsulfoxide-d6) δ 10.20 (s, 1H), 8.35 (s, 1H), 8.08 (d, J=8.5 Hz, 1H), 7.92 (d, J=9.5 Hz, 1H), 7.76 (dd, J=8.5, 2.0 Hz, 1H), 7.37-7.33 (m, 1H), 7.12-7.10 (m, 2H), 7.05-7.02 (m, 2H), 5.33-5.30 (m, 1H), 4.00 (s, 2H), 2.63-2.55 (m, 2H), 2.33-2.28 (m, 2H), 1.87-1.80 (m, 2H); LCMS (ESI) m/z: 379.1 [M+H]+.

Compound 422: $^1$H NMR (500 MHz, DMSO-d6) δ 8.38 (d, J=8.5 Hz, 1H), 7.97 (d, J=7.7 Hz, 1H), 7.90 (d, J=8.5 Hz, 1H), 7.78 (d, J=4.7 Hz, 1H), 7.77-7.73 (m, 1H), 7.61-7.58 (m, 1H), 7.52 (d, J=8.5 Hz, 1H), 7.18 (d, J=4.7 Hz, 1H), 5.74 (s, 2H), 3.26 (s, 3H), 2.81 (t, J=8.4 Hz, 2H), 2.36 (t, J=8.4 Hz, 2H); LCMS (ESI) m/z: 379.4 [M+H]+.

Compound 423: $^1$H NMR (500 MHz, DMSO-d6) δ 11.12 (s, 1H), 8.36 (d, J=2.0 Hz, 1H), 8.25-8.19 (m, 2H), 8.12 (d, J=8.5 Hz, 1H), 8.06 (d, J=8.5 Hz, 2H), 7.76 (dd, J=8.5, 2.4 Hz, 1H), 7.39-7.32 (m, 1H), 7.16-7.00 (m, 3H), 4.00 (s, 2H), 3.30 (s, 3H); LCMS (ESI) m/z: 385.0 [M+H]+.

Compound 424: $^1$H NMR (500 MHz, DMSO-d6) δ 11.98 (s, 1H), 7.48 (s, 1H), 7.32-7.44 (m, 2H), 7.08-7.25 (m, 3H), 3.35 (s, 3H), 3.18 (s, 3H), 2.78-2.84 (m, 2H), 2.48-2.54 (m, 2H), 1.89 (s, 3H); LCMS (ESI) m/z: 391.1 [M+H]+.

Compound 425: $^1$H NMR (400 MHz, DMSO-d6) δ 9.48 (brs, 1H), 8.35 (s, 1H), 8.29 (d, J=6 Hz, 1H), 8.11 (d, J=8.4 Hz, 1H), 7.78 (dd, J=2 Hz, 8.4 Hz, 1H), 7.29-7.39 (m, 1H), 7.08-7.18 (m, 2H), 6.98-7.07 (m, 1H), 6.95 (d, J=6 Hz, 1H), 3.99 (s, 2H); LCMS (ESI) m/z: 325.1 [M+H]+.

Compound 426: $^1$H NMR (400 MHz, DMSO-d6) δ 10.29 (bs, 1H), 8.85 (d, J=2.4 Hz, 1H), 8.32 (d, J=1.9 Hz, 1H), 8.02 (t, J=2.2 Hz, 1H), 7.92 (d, J=9.7 Hz, 1H), 7.39-7.32 (m, 2H), 7.31-7.27 (m, 1H), 7.27-7.21 (m, 1H), 7.07 (d, J=9.7 Hz, 1H), 4.01 (s, 2H), 3.79 (s, 3H); LCMS (ESI) m/z: 355.0 [M+H]+.

Compound 427: $^1$H NMR (400 MHz, DMSO-d6) δ 10.48 (s, 1H), 8.65 (d, J=2.4 Hz, 1H), 8.19 (d, J=3.2 Hz, 1H), 8.07 (d, J=8.8 Hz, 1H), 7.98 (dd, J=9.2, 2.4 Hz, 1H), 7.86 (dd, J=8.8, 2.4 Hz, 1H), 7.83 (s, 1H), 7.73 (d, J=10.0 Hz, 1H), 7.57 (dd, J=8.8, 2.8 Hz, 1H), 6.43 (d, J=9.6 Hz, 1H), 5.25 (s, 2H), 3.50 (s, 3H); LCMS (ESI) m/z: 379.0 [M+H]+.

Compound 428: $^1$H NMR (400 MHz, DMSO-d6) δ 10.53 (s, 1H), 9.23 (d, J=1.2 Hz, 1H), 8.58 (dd, J=8.4, 2.0 Hz, 1H), 8.51 (s, 1H), 8.32 (dd, J=14.0, 8.0 Hz, 2H), 8.02 (dd, J=8.4, 2.0 Hz, 1H), 7.37 (t, J=9.2 Hz, 1H), 7.32 (dd, J=6.0, 2.8 Hz, 1H), 7.08-7.04 (m, 1H), 5.15 (s, 2H), 3.95 (s, 3H); LCMS (ESI) m/z: 416.0 [M+H]+.

Compound 429: $^1$H NMR (400 MHz, DMSO-d6) δ 11.17 (s, 1H), 9.39 (s, 1H), 8.65 (d, J=7.2 Hz, 1H), 8.53 (s, 1H), 8.37 (d, J=2.0 Hz, 1H), 8.12 (d, J=8.4 Hz, 1H), 7.76 (dd, J=8.4, 2.0 Hz, 1H), 7.45-7.25 (m, 5H), 4.00 (s, 2H); LCMS (ESI) m/z: 364.0 [M+H]+.

Compound 430: $^1$H NMR (400 MHz, DMSO-d6) δ 12.33 (s, 1H), 7.89 (dd, J1=4.0 Hz, J2=9.6 Hz, 1H), 7.69 (s, 1H), 7.31-7.39 (m, 2H), 7.17-7.19 (m, 2H), 7.05-7.09 (m, 2H), 4.62 (s, 2H), 3.78 (s, 3H); LCMS (ESI) m/z: 388.0 [M+H]+.

Compound 431: $^1$H NMR (400 MHz, DMSO-d6) δ 12.66 (bs, 1H), 8.73 (d, J=1.2 Hz, 1H), 8.00 (dd, J=9.6, 2.4 Hz, 1H), 7.36 (dt, J=8.8, 2.4 Hz, 1H), 7.32 (s, 1H), 7.25-7.22 (m, 1H), 6.45 (d, J=9.2 Hz, 1H), 4.41 (s, 2H), 3.49 (s, 3H); LCMS (ESI) m/z: 379.0 [M+H]+.

Compound 432: $^1$H NMR (400 MHz, DMSO-d6) δ 7.59 (d, J=9.6 Hz, 1H), 7.30-7.28 (t, J=8.2 Hz, 1H), 7.10-7.08 (t, J=2.1 Hz, 1H), 7.03-6.93 (m, 3H), 4.79-4.68 (m, 1H), 4.01-3.89 (m, 1H), 3.80 (d, J=14.3 Hz, 1H), 3.65 (s, 3H), 3.46-3.44 (m, 2H), 1.98 (s, 2H), 1.63 (s, 2H); LCMS (ESI) m/z: 348.1 [M+H]+.

Compound 433: $^1$H NMR (400 MHz, DMSO-d6) δ 7.83 (d, J=2.6 Hz, 1H), 7.31 (tdd, J=20.0, 13.0, 6.9 Hz, 3H), 7.15 (dd, J=17.6, 8.9 Hz, 2H), 7.05 (t, J=8.6 Hz, 1H), 6.59 (d, J=9.0 Hz, 1H), 4.49 (d, J=5.8 Hz, 2H), 3.34 (s, 3H), 2.87 (t, J=8.5 Hz, 2H), 2.55 (t, J=7.5 Hz, 2H); LCMS (ESI) m/z: 357.1 [M+H]+.

Compound 434: $^1$H NMR (400 MHz, DMSO-d6) δ 8.96 (s, 1H), 7.72 (d, J=10.0 Hz, 1H), 7.29-7.33 (m, 1H), 7.24-7.25 (m, 2H), 7.13 (d, J=7.6 Hz, 1H), 6.92 (d, J=10.0 Hz, 1H), 6.82 (d, J=8.0 Hz, 1H), 3.51 (s, 3H), 3.38-3.42 (m, 1H), 2.48-2.51 (m, 2H), 1.86-1.89 (m, 2H), 1.62-1.65 (m, 2H), 1.48-1.53 (m, 1H), 1.02-1.14 (m, 4H); LCMS (ESI) m/z: 375.1 [M+H]+.

Compound 435: $^1$H NMR (400 MHz, DMSO-d6) δ 9.66-9.75 (m, 1H), 8.37 (d, J=1.2 Hz, 1H), 8.28 (d, J=1.6 Hz, 1H), 8.01 (d, J=8.4 Hz, 1H), 7.69 (dd, J1=2.0 Hz, J2=8.4 Hz, 1H), 7.52 (dd, J1=2.0 Hz, J2=8.4 Hz, 1H), 7.16 (d, J=8.4 Hz, 1H), 3.92 (s, 2H), 3.34 (s, 3H), 2.83 (t, J=8.4 Hz, 2H), 2.45-2.56 (m, 2H), 2.40 (s, 3H); LCMS (ESI) m/z: 338.1 [M+H]+.

Compound 436: $^1$H NMR (400 MHz, DMSO-d6) δ 9.69 (s, 1H), 8.27 (d, J=2.0 Hz, 1H), 8.00 (d, J=8.4 Hz, 1H), 7.68 (dd, J1=2.4 Hz, J2=8.4 Hz, 1H), 7.23-7.26 (m, 1H), 7.18 (s, 1H), 7.10-7.14 (m, 2H), 5.13 (t, J=5.6 Hz, 1H), 4.34 (d, J=5.2 Hz, 2H), 3.93 (s, 2H), 3.35 (s, 3H), 2.84 (t, J=8.4 Hz, 2H), 2.50-2.53 (m, 2H); LCMS (ESI) m/z: 353.2 [M+H]+.

Compound 437: $^1$H NMR (400 MHz, DMSO-d6) δ 9.71 (s, 1H), 8.29-8.32 (m, 2H), 8.25 (d, J=1.2 Hz, 1H), 8.02 (d, J=8.4 Hz, 1H), 7.71 (dd, J1=2.4 Hz, J2=8.4 Hz, 1H), 7.46 (s, 1H), 3.93 (s, 2H), 3.48 (s, 3H), 2.84 (t, J=8.4 Hz, 2H), 2.48-2.53 (m, 2H), 2.24 (s, 3H); LCMS (ESI) m/z: 338.1 [M+H]+.

Compound 438: $^1$H NMR (400 MHz, DMSO-d6) δ 9.72 (s, 1H), 8.22 (d, J=2.0 Hz, 1H), 8.02 (d, J=8.4 Hz, 1H), 7.67 (dd, J1=2.4 Hz, J2=8.8 Hz, 1H), 7.30-7.35 (m, 1H), 7.06-7.10 (m, 2H), 6.99-7.04 (m, 1H), 3.93 (s, 2H), 3.85 (t, J=4.4 Hz, 1H), 3.19-3.23 (m, 1H), 3.14 (s, 3H), 3.00 (dd, J1=4.8 Hz, J2=10.0 Hz, 1H), 2.40-2.43 (m, 2H), 2.35 (s, 3H), 1.84 (dd, J1=4.4 Hz, J2=13.6 Hz, 1H); LCMS (ESI) m/z: 344.2 [M+H]+.

Compound 439: $^1$H NMR (400 MHz, DMSO-d6) δ 9.83 (s, 1H), 8.23 (d, J=1.6 Hz, 1H), 7.68-7.72 (m, 2H), 7.63 (s, 1H), 7.50-7.53 (d, J=10.0 Hz, 1H), 7.12-7.15 (m, 1H), 6.54-6.57 (d, J=9.2 Hz, 1H), 4.51-4.52 (d, J=6.4 Hz, 2H), 3.32-3.34 (d, J=6.0 Hz, 3H), 2.78-2.82 (m, 2H), 2.46-2.48 (m, 2H); LCMS (ESI) m/z: 381.1 [M+H]+.

Compound 440: $^1$H NMR (400 MHz, DMSO-d6) δ 9.97 (s, 1H), 9.71 (s, 1H), 8.32 (d, J=2.4 Hz, 1H), 8.02 (d, J=8.4 Hz, 1H), 7.72-7.77 (m, 3H), 7.62 (d, J=7.6 Hz, 1H), 7.53-

7.56 (m, 1H), 4.06 (s, 2H), 3.35 (s, 3H), 2.84 (t, J=8.4 Hz, 2H), 2.49-2.53 (m, 2H); LCMS (ESI) m/z: 351.1 [M+H]+.

Compound 441: ¹H NMR (400 MHz, TFA) δ 8.80 (d, J=4.4 Hz, 1H), 8.78 (d, J=4.8 Hz, 1H), 8.74 (d, J=2.8 Hz, 1H), 8.42 (d, J=9.6 Hz, 1H), 8.22 (s, 1H), 8.07 (d, J=8.0 Hz, 1H), 8.00 (t, J=9.2 Hz, 2H), 5.85 (s, 2H), 4.58 (s, 3H); LCMS (ESI) m/z: 380.0 [M+H]+.

Compound 442: ¹H NMR (500 MHz, CDCl3) δ 10.71 (s, 1H), 8.60-8.38 (m, 3H), 8.22 (s, 1H), 7.83 (dd, J=8.8, 1.8 Hz, 1H), 7.48 (d, J=8.3 Hz, 1H), 4.14 (s, 2H), 3.50 (s, 3H), 2.96 (t, J=8.6 Hz, 2H), 2.62 (t, J=8.6 Hz, 2H); LCMS (ESI) m/z: 342.1 [M+H]+.

Compound 443: ¹H NMR (500 MHz, DMSO) δ 10.41 (s, 1H), 9.07 (s, 2H), 7.42-7.20 (m, 4H), 4.21 (s, 2H), 3.38 (s, 3H), 2.84 (t, J=8.5 Hz, 2H), 2.53 (d, J=8.5 Hz, 2H); LCMS (ESI) m/z: 358.1 [M+H]+.

Compound 444: ¹H NMR (500 MHz, DMSO-d6) δ 9.68 (s, 1H), 8.21 (d, J=1.5 Hz, 1H), 8.02 (d, J=8 Hz, 1H), 7.68-7.74 (m, 1H), 5.77-5.88 (m, 1H), 4.93-5.06 (m, 2H), 3.36 (s, 3H), 2.86 (t, J=8.5 Hz, 2H), 2.68 (t, J=7.5 Hz, 2H), 2.51-2.56 (m, 2H), 2.30-2.38 (m, 2H); LCMS (ESI) m/z: 287.1 [M+H]+.

Compound 445: ¹H NMR (500 MHz, DMSO-d6) δ 9.75 (s, 1H), 8.34 (d, J=1.5 Hz, 1H), 8.00-8.10 (m, 2H), 7.70-7.81 (m, 2H), 7.65 (d, J=7.5 Hz, 1H), 4.21 (s, 2H), 3.36 (s, 3H), 2.85 (t, J=8.5 Hz, 2H), 2.52 (t, J=8.5 Hz, 2H); LCMS (ESI) m/z: 392.2 [M+H]+.

Compound 446: ¹H NMR (500 MHz, DMSO-d6) δ 10.08-10.20 (m, 1H), 8.24 (d, J=2.0 Hz, 1H), 7.98-8.01 (m, 1H), 7.65-7.68 (m, 1H), 7.33 (dd, J1=7.5 Hz, J2=15.0 Hz, 1H), 7.09-7.11 (m, 2H), 7.02-7.05 (m, 1H), 4.29-4.34 (m, 1H), 3.97-3.97 (m, 3H), 3.62 (dd, J1=5.5 Hz, J2=10.5 Hz, 1H), 3.26-3.35 (m, 1H), 3.18-3.24 (m, 3H), 2.45-2.51 (m, 1H), 1.87-1.89 (m, 1H), 1.40 (s, 3H), 1.25-1.28 (m, 6H); LCMS (ESI) m/z: 430.2 [M+H]+.

Compound 447: ¹H NMR (500 MHz, DMSO-d6) δ 10.20 (s, 1H), 8.23 (d, J=2.0 Hz, 1H), 8.03 (d, J=8.5 Hz, 1H), 7.66 (dd, J1=2.0 Hz, J2=9.0 Hz, 1H), 7.32-7.36 (m, 1H), 7.08-7.11 (m, 2H), 7.01-7.05 (m, 1H), 3.94 (s, 2H), 3.85-3.87 (m, 1H), 3.73-3.75 (m, 1H), 3.11 (s, 3H), 3.00-3.03 (m, 1H), 2.90-2.92 (m, 1H), 2.10-2.15 (m, 1H), 2.02-2.05 (s, 1H); LCMS (ESI) m/z: 330.2 [M+H]+.

Compound 448: ¹H NMR (500 MHz, DMSO-d6) δ 10.27 (s, 1H), 8.34 (d, J=2.0 Hz, 1H), 8.19 (d, J=8.5 Hz, 1H), 8.10 (dd, J=8.5, 4.0 Hz, 1H), 7.91 (t, J=9.0 Hz, 1H), 7.78 (dd, J=8.5, 2.0 Hz, 1H), 7.35 (dd, J=14.5, 8.0 Hz, 1H), 7.14-7.02 (m, 3H), 3.99 (s, 2H), 2.59 (d, J=3.0 Hz, 3H); LCMS (ESI) m/z: 340.1 [M+H]+.

Compound 449: ¹H NMR (500 MHz, DMSO-d6) δ 10.51-10.52 (m, 1H), 8.67 (d, J=2.0 Hz, 1H), 8.39 (d, J=1.5 Hz, 1H), 8.29 (d, J=2.0 Hz, 1H), 8.05 (d, J=8.5 Hz, 1H), 7.98 (dd, J1=2.0 Hz, J2=9.5 Hz, 1H), 7.67 (dd, J1=2.0 Hz, J2=8.5 Hz, 1H), 7.53 (dd, J1=2.0 Hz, J2=8.5 Hz, 1H), 7.18 (d, J=8.0 Hz, 1H), 6.43 (d, J=9.0 Hz, 1H), 3.93 (s, 2H), 3.49 (s, 3H), 2.42 (s, 3H); LCMS (ESI) m/z: 335.1 [M+H]+.

Compound 450: ¹H NMR (500 MHz, DMSO-d6) δ 10.54 (s, 1H), 8.67 (d, J=2.5 Hz, 1H), 8.31-8.34 (m, 2H), 8.27 (d, J=1.5 Hz, 1H), 8.06 (d, J=8.5 Hz, 1H), 7.98 (dd, J1=3.0 Hz, J2=9.5 Hz, 1H), 7.69 (dd, J1=2.0 Hz, J2=8.5 Hz, 1H), 7.47 (s, 1H), 6.43 (d, J=9.5 Hz, 1H), 3.94 (s, 2H), 3.50 (s, 3H), 2.26 (s, 3H); LCMS (ESI) m/z: 335.1 [M+H]+.

Compound 451: ¹H NMR (500 MHz, DMSO-d6) δ 10.56 (s, 1H), 8.38 (d, J=8.5 Hz, 1H), 8.26 (d, J=1.5 Hz, 1H), 8.19 (d, J=8.5 Hz, 1H), 8.11 (d, J=9.0 Hz, 1H), 7.80 (d, J=8.0 Hz, 1H), 7.33-7.38 (m, 2H), 7.25-7.29 (m, 2H), 4.00 (s, 2H); LCMS (ESI) m/z: 369.2 [M+H]+.

Compound 452: ¹H NMR (500 MHz, DMSO-d6) δ 10.63 (s, 1H), 8.69 (d, J=2.7 Hz, 1H), 8.45 (d, J=2.3 Hz, 1H), 8.16 (d, J=8.6 Hz, 1H), 7.99 (dd, J=9.5, 2.7 Hz, 1H), 7.90 (dd, J=8.6, 2.4 Hz, 1H), 7.20-7.10 (m, 2H), 7.08-7.00 (m, 2H), 6.44 (d, J=9.5 Hz, 1H), 5.08 (s, 2H), 3.51 (s, 3H); LCMS (ESI) m/z: 354.1 [M+H]+.

Compound 453: ¹H NMR (500 MHz, DMSO-d6) δ 10.70 (s, 1H), 8.68 (d, J=2.6 Hz, 1H), 8.52-8.43 (m, 2H), 8.36 (d, J=2.0 Hz, 1H), 8.06-7.96 (m, 2H), 7.80 (dd, J=8.6, 2.3 Hz, 1H), 7.71 (d, J=9.8 Hz, 1H), 6.44 (d, J=9.5 Hz, 1H), 4.06 (s, 2H), 3.51 (s, 3H); LCMS (ESI) m/z: 339.1 [M+H]+.

Compound 454: ¹H NMR (500 MHz, DMSO-d6) δ 10.73 (s, 1H), 8.49 (dd, J1=9.0 Hz, J2=19.0 Hz, 2H), 8.40 (d, J=2.0 Hz, 1H), 8.18 (d, J=8.5 Hz, 1H), 7.82 (dd, J1=2.0 Hz, J2=8.5 Hz, 1H), 7.34-7.38 (m, 2H), 7.26-7.30 (m, 2H), 4.02 (s, 3H), 4.01 (s, 2H); LCMS (ESI) m/z: 383.2 [M+H]+.

Compound 455: ¹H NMR (500 MHz, DMSO-d6) δ 10.76 (s, 1H), 8.32 (s, 1H), 8.02 (d, J=8.4 Hz, 1H), 7.72-7.70 (m, 1H), 7.35-7.33 (m, 1H), 7.12-7.10 (m, 3H), 7.04-7.01 (t, J=8.9 Hz, 1H), 5.52 (s, 2H), 3.98 (s, 2H), 3.79 (s, 3H), 3.69 (s, 3H); LCMS (ESI) m/z: 447.2 [M+H]+.

Compound 456: ¹H NMR (500 MHz, DMSO-d6) δ 10.76 (s, 1H), 8.33 (s, 1H), 8.02 (d, J=8.6 Hz, 1H), 7.72-7.70 (d, J=9.1 Hz, 1H), 7.39-7.30 (m, 2H), 7.28-7.26 (d, J=8.1 Hz, 1H), 7.23-7.20 (d, J=7.4 Hz, 1H), 7.13 (d, J=8.5 Hz, 2H), 6.85-6.83 (d, J=8.6 Hz, 2H), 6.77 (s, 1H), 5.52 (s, 2H), 3.97 (s, 2H), 3.79 (s, 3H), 3.69 (s, 3H); LCMS (ESI) m/z: 463.1 [M+H]+.

Compound 457: ¹H NMR (500 MHz, DMSO-d6) δ 10.87 (s, 1H), 8.58 (s, 1H), 8.21 (d, J=2.1 Hz, 1H), 8.12-7.92 (m, 2H), 7.86 (dd, J=9.3, 2.4 Hz, 1H), 7.37 (dd, J=14.4, 7.8 Hz, 1H), 7.25-7.02 (m, 3H), 6.49 (d, J=9.4 Hz, 1H), 3.77 (s, 2H), 3.50 (s, 3H); LCMS (ESI) m/z: 338.1 [M+H]+.

Compound 458: ¹H NMR (500 MHz, DMSO-d6) δ 10.91 (s, 1H), 8.29 (d, J=2.3 Hz, 1H), 8.03 (d, J=8.5 Hz, 1H), 7.71 (dd, J=8.5, 2.4 Hz, 1H), 7.39-7.28 (m, 1H), 7.16-7.06 (m, 2H), 7.06-6.99 (m, 1H), 4.63-4.53 (m, 1H), 4.44 (t, J=9.0 Hz, 1H), 4.27-4.18 (m, 1H), 3.96 (s, 2H), 2.75 (s, 3H); LCMS (ESI) m/z: 330.1 [M+H]+.

Compound 459: ¹H NMR (500 MHz, DMSO-d6) δ 11.09 (s, 1H), 8.36 (d, J=1.8 Hz, 1H), 8.01 (d, J=8.5 Hz, 1H), 7.75 (dd, J=8.5, 2.2 Hz, 1H), 7.35 (d, J=6.4 Hz, 1H), 7.11 (t, J=7.3 Hz, 2H), 7.04 (s, 1H), 6.27 (s, 1H), 3.99 (s, 2H), 3.71 (s, 3H), 3.44 (s, 3H); LCMS (ESI) m/z: 341.0 [M+H]+.

Compound 460: ¹H NMR (500 MHz, DMSO-d6) δ 11.13 (s, 1H), 8.37 (d, J=2.0 Hz, 1H), 8.02 (d, J=8.5 Hz, 1H), 7.76 (dd, J=8.5, 2.3 Hz, 1H), 7.35 (dd, J=9.6, 5.6 Hz, 2H), 7.28 (d, J=8.3 Hz, 1H), 7.24 (d, J=7.6 Hz, 1H), 6.32 (s, 1H), 3.99 (s, 2H), 3.74 (s, 3H), 3.48 (s, 3H); LCMS (ESI) m/z: 357.1 [M+H]+.

Compound 461: ¹H NMR (500 MHz, DMSO-d6) δ 12.65 (bs, 1H), 8.73 (s, 1H), 8.01 (dd, J=9.5, 3.0 Hz, 1H), 7.41 (dd, J=14.0, 3.0 Hz, 1H), 7.22-7.19 (m, 2H), 7.12 (td, J=9.5, 2.0 Hz, 1H), 6.46 (d, J=9.5 Hz, 1H), 4.40 (s, 2H), 3.51 (s, 3H); LCMS (ESI) m/z: 345.1 [M+H]+.

Compound 462: ¹H NMR (500 MHz, DMSO-d6) δ 12.65 (bs, 1H), 8.74 (s, 1H), 8.01 (dd, J=9.5, 3.0 Hz, 1H), 7.45 (s, 1H), 7.41-7.32 (m, 3H), 6.46 (d, J=9.5 Hz, 1H), 4.40 (s, 2H), 3.51 (s, 3H); LCMS (ESI) m/z: 361.1 [M+H]+.

Compound 463: ¹H NMR (500 MHz, DMSO-d6) δ 12.78 (s, 1H), 10.92 (s, 1H), 8.73 (d, J=1.5 Hz, 1H), 8.33 (d, J=2.5 Hz, 1H), 8.18 (d, J=2.0 Hz, 1H), 8.10 (d, J=8.5 Hz, 1H), 7.72 (dd, J=8.5 Hz, J=2.5 Hz, 1H), 7.33-7.37 (m, 1H), 7.11-7.13 (m, 2H), 7.03 (td, J=8.5 Hz, 2.0 Hz, 1H), 3.99 (s, 2H); LCMS (ESI) m/z: 365.0 [M+H]+.

Compound 464: ¹H NMR (500 MHz, DMSO-d6) δ 8.01 (d, J=2.4 Hz, 1H), 7.50-7.48 (m, 1H), 7.31-7.30 (t, J=8.2 Hz, 1H), 7.10-7.08 (t, J=2.1 Hz, 1H), 7.04-6.91 (m, 2H), 6.40 (d, J=9.3 Hz, 1H), 4.86-4.60 (m, 1H), 3.79 (s, 2H), 3.46 (s, 3H), 3.40-3.25 (m, 2H), 1.97-1.95 (m, 2H), 1.69-1.48 (m, 2H); LCMS (ESI) m/z: 347.0 [M+H]+.

Compound 465: $^1$H NMR (500 MHz, DMSO-d6) δ 8.35 (d, J=7.5 Hz, 1H), 7.89 (dd, J1=2.5 Hz, J2=9.5 Hz, 1H), 7.81 (d, J=7.0 Hz, 1H), 7.31-7.34 (m, 1H), 7.25-7.26 (m, 2H), 7.15 (d, J=7.0 Hz, 1H), 6.40 (d, J=9.5 Hz, 1H), 3.89 (dd, J1=3.5 Hz, J2=7.5 Hz, 1H), 3.50 (s, 3H), 2.51-2.61 (m, 2H), 1.72-1.75 (m, 1H), 1.65-1.70 (m, 2H), 1.51-1.55 (m, 2H), 1.41-1.48 (m, 4H); LCMS (ESI) m/z: 359.1 [M+H]+.

Compound 466: $^1$H NMR (500 MHz, DMSO-d6) δ 8.36 (d, J=2.0 Hz, 1H), 8.00 (d, J=7.5 Hz, 1H), 7.88 (dd, J=9.5, 2.5 Hz, 1H), 7.31 (t, J=8.0 Hz, 1H), 7.03-6.93 (m, 3H), 6.39 (d, J=9.5 Hz, 1H), 4.62 (s, 1H), 3.87 (s, 1H), 3.48 (s, 3H), 1.94 (d, J=5.0 Hz, 2H), 1.66 (t, J=11.0 Hz, 6H); LCMS (ESI) m/z: 361.1 [M+H]+.

Compound 467: $^1$H NMR (500 MHz, DMSO-d6) δ 9.43 (t, J=6.5 Hz, 1H), 8.90 (d, J=2.0 Hz, 1H), 8.39 (d, J=3.0 Hz, 1H), 8.19 (dd, J=8.5, 2.0 Hz, 1H), 8.07 (d, J=8.0 Hz, 1H), 7.97 (dd, J=9.5, 3.0 Hz, 1H), 7.38-7.34 (m, 1H), 7.17 (d, J=7.5 Hz, 1H), 7.14 (d, J=10.0 Hz, 1H), 7.08-7.04 (m, 1H), 6.54 (d, J=9.0 Hz, 1H), 4.52 (d, J=6.5 Hz, 2H), 3.54 (s, 3H); LCMS (ESI) m/z: 338.0 [M+H]+.

Compound 468: $^1$H NMR (500 MHz, DMSO-d6) δ 9.65 (s, 1H), 8.24 (s, 1H), 8.03 (d, J=8.4 Hz, 1H), 7.76 (d, J=8.4 Hz, 1H), 3.36 (s, 3H), 2.86 (t, J=8.5 Hz, 2H), 2.62-2.38 (m, 5H), 1.07-0.87 (m, 1H), 0.58-0.39 (m, 2H), 0.21 (q, J=4.7 Hz, 2H); LCMS (ESI) m/z: 287.2[M+H]+.

Compound 469: $^1$H NMR (500 MHz, DMSO-d6) δ 9.70 (s, 1H), 8.33 (d, J=5.0 Hz, 1H), 8.29 (d, J=2.0 Hz, 1H), 8.01 (d, J=8.5 Hz, 1H), 7.75 (dd, J=8.5, 2.0 Hz, 1H), 7.15 (s, 1H), 7.05 (d, J=4.5 Hz, 1H), 4.03 (s, 2H), 3.36 (s, 3H), 2.84 (t, J=8.3 Hz, 2H), 2.52 (t, J=7.8 Hz, 2H), 2.27 (s, 3H); LCMS (ESI) m/z: 338.2 [M+H]+.

Compound 470: $^1$H NMR (500 MHz, DMSO-d6) δ 9.74 (s, 1H), 8.33 (d, J=2.0 Hz, 1H), 8.03 (d, J=8.5 Hz, 1H), 7.86 (t, J=7.5 Hz, 1H), 7.75 (dd, J=8.5, 2.0 Hz, 1H), 7.49 (d, J=10.5 Hz, 1H), 7.33 (d, J=8.0 Hz, 1H), 4.07 (s, 2H), 3.36 (s, 3H), 2.85 (t, J=8.5 Hz, 2H), 2.53 (d, J=8.5 Hz, 2H); LCMS (ESI) m/z: 366.1 [M+H]+.

Compound 471: $^1$H NMR (500 MHz, DMSO-d6) δ 9.88 (s, 1H), 7.92-7.78 (m, 4H), 7.40-7.26 (m, 4H), 3.88 (s, 2H), 2.78 (t, J=8.5 Hz, 2H), 2.48 (d, J=8.5 Hz, 2H); (ESI) m/z: 372.1 [M+H]+.

Compound 472: $^1$H NMR (500 MHz, DMSO-d6) δ 9.95 (s, 1H), 8.20 (d, J=1.9 Hz, 1H), 7.89 (dd, J=8.8, 2.0 Hz, 1H), 7.66 (d, J=8.8 Hz, 1H), 7.40-7.18 (m, 4H), 4.07-3.82 (m, 5H), 3.83-3.65 (m, 2H), 2.49-2.43 (m, 1H), 1.00 (d, J=6.2 Hz, 3H); LCMS (ESI) m/z: 346.1 [M+H]+.

Compound 474: $^1$H NMR (400 MHz, DMSO-d6) δ 9.76 (s, 1H), 8.67 (d, J=4 Hz, 1H), 8.36 (s, 1H), 8.05 (d, J=6.8 Hz, 1H), 7.85 (s, 1H), 7.78-7.80 (m, 2H), 7.60 (d, J=3.6 Hz, 1H), 4.13 (s, 2H), 3.36 (s, 3H), 2.83-2.86 (m, 2H), 2.52-2.54 (m, 2H); LCMS (ESI) m/z: 392.1 [M+H]+

Compound 475: $^1$H NMR (500 MHz, Dimethylsulfoxide-d6) δ 10.17 (s, 1H), 9.23 (s, 1H), 8.46 (s, 1H), 7.46-7.16 (m, 4H), 4.14 (s, 2H), 3.36 (s, 3H), 2.86 (t, J=8.4 Hz, 2H), 2.53 (t, J=8.4 Hz, 2H); LCMS (ESI) m/z: 358.1 [M+H]+.

Example 239. Characterization Data of Compounds of the Invention

The following compounds were synthesized by methods similar to those described above.

| CMPD No. | | Characterization Data |
|---|---|---|
| 476 | LCMS (ESI) m/z: 315.1 [M + H]+. | $^1$H NMR (500 MHz, DMSO-d$_6$) δ 11.63 (s, 1H), 9.63 (s, 1H), 8.14 (d, J = 1.8 Hz, 1H), 8.05 (d, J = 8.5 Hz, 1H), 7.73 (dd, J = 8.5, 2.1 Hz, 1H), 5.91 (s, 1H), 3.65 (s, 3H), 2.47 (d, J = 7.1 Hz, 2H), 1.63 (dd, J = 25.7, 11.7 Hz, 5H), 1.54-1.44 (m, 1H), 1.22-1.08 (m, 3H), 0.92 (q, J = 12.0 Hz, 2H). |
| 477 | LCMS (ESI) m/z: 327.1 [M + H]+. | $^1$H NMR (500 MHz, DMSO-d$_6$) δ 9.76 (s, 1H), 8.19 (s, 1H), 8.06 (d, J = 8.5 Hz, 1H), 7.70 (dd, J = 8.6, 2.0 Hz, 1H), 6.19 (s, 1H), 2.86 (t, J = 8.5 Hz, 2H), 2.54 (d, J = 8.5 Hz, 2H), 2.34-2.29 (m, 2H), 2.26-2.25 (m, 2H), 1.66-1.44 (m, 6H). |
| 478 | LCMS (ESI) m/z: 351.1 [M + H]+. | $^1$H NMR (400 MHz, DMSO-d$_6$) δ 11.36 (s, 1H), 9.23 (s, 1H), 8.54 (dd, J = 8.1, 1.7 Hz, 1H), 8.39 (s, 1H), 8.21 (d, J = 8.1 Hz, 1H), 8.13 (d, J = 8.5 Hz, 1H), 7.79 (dd, J = 8.5, 1.7 Hz, 1H), 7.17-7.00 (m, 3H), 4.01 (s, 2H). |
| 479 | LCMS (ESI) for C$_{19}$H$_{17}$ClN$_4$O$_2$ [M + H]+: 369.1 | $^1$H NMR (400 MHz, DMSO-d$_6$) δ 11.29 (s, 1H), 9.27 (s, 2H), 8.36 (s, 1H), 8.13 (d, J = 8.5 Hz, 1H), 7.76 (d, J = 8.6 Hz, 1H), 7.45-7.15 (m, 4H), 4.66 (s, 2H), 4.01 (s, 2H), 3.40 (s, 3H). |
| 480 | LCMS (ESI) m/z: 341.2 [M + H]+. | $^1$H NMR (500 MHz, CDCl$_3$) δ 8.40 (s, 1H), 8.21-8.11 (m, 2H), 7.54 (dd, J = 8.5, 2.2 Hz, 1H), 7.05-6.83 (m, 4H), 5.57-5.52 (m, 1H), 4.14 (d, J = 4 Hz, 2H), 3.97 (s, 2H), 2.97 (s, 3H). |
| 481 | LCMS (ESI) m/z: 338.0 [M + H]+. | $^1$H NMR (500 MHz, DMSO-d$_6$) δ 11.20 (s, 1H), 9.08 (d, J = 2.0 Hz, 1H), 8.75 (d, J = 1.7 Hz, 1H), 8.53-8.31 (m, 2H), 8.11 (d, J = 8.5 Hz, 1H), 7.77 (dd, J = 8.6, 2.3 Hz, 1H), 7.36 (dd, J = 14.4, 8.0 Hz, 1H), 7.13 (t, J = 7.9 Hz, 2H), 7.05 (d, J = 2.5 Hz, 1H), 4.65 (s, 2H), 4.00 (s, 2H). |
| 482 | LCMS (ESI) m/z: 364.0 [M + H]+. | $^1$H NMR (500 MHz, DMSO-d$_6$) δ 11.36 (s, 1H), 9.23 (d, J = 1.9 Hz, 1H), 8.54 (dd, J = 8.1, 2.2 Hz, 1H), 8.41 (d, J = 2.0 Hz, 1H), 8.21 (d, J = 8.1 Hz, 1H), 8.15 (d, J = 8.5 Hz, 1H), 7.85 (dd, J = 8.6, 2.2 Hz, 1H), 7.06 (t, J = 8.0 Hz, 1H), 6.61 (t, J = 2.0 Hz, 1H), 6.57-6.53 (m, 2H), 4.31 (s, 2H). |
| 483 | LCMS (ESI) m/z: 354.1 [M + H]+. | $^1$H NMR (500 MHz, DMSO-d$_6$) δ 11.28 (s, 1H), 9.13 (d, J = 1.8 Hz, 1H), 8.80 (d, J = 1.5 Hz, 1H), 8.48 (d, J = 16.8 Hz, 1H), 8.37 (d, J = 2.0 Hz, 1H), 8.12 (d, J = 8.5 Hz, 1H), 7.80 (dd, J = 8.5, 2.3 Hz, 1H), 7.36 (dd, J = 12.7, 4.7 Hz, 2H), 7.31-7.20 (m, 2H), 4.67 (s, 2H), 3.99 (s, 2H). |

-continued

| CMPD No. | Characterization Data |
|---|---|
| 484 | LCMS (ESI) m/z: 341.5 [M + H]+. ¹H NMR (300 MHz, Chloroform-d) δ 10.55 (s, 1H), 8.41-8.20 (m, 3H), 7.58 (ddd, J = 8.6, 3.0, 0.6 Hz, 2H), 6.81-6.57 (m, 3H), 3.97 (s, 2H), 2.86 (s, 3H). |
| 485 | LCMS (ESI) m/z: 341.5 [M + H]+. ¹H NMR (300 MHz, Chloroform-d) δ 10.42 (s, 1H), 8.95 (d, J = 5.0 Hz, 1H), 8.37 (dd, J = 8.5, 0.8 Hz, 1H), 8.25 (dt, J = 2.5, 0.7 Hz, 1H), 8.01 (dd, J = 5.0, 0.7 Hz, 1H), 7.57 (ddd, J = 8.5, 2.4, 0.6 Hz, 1H), 7.20-6.84 (m, 3H), 3.96 (s, 2H), 2.85 (d, J = 0.6 Hz, 3H). |
| 486 | LCMS (ESI) m/z: 357.5 [M + H]+. ¹H NMR (300 MHz, Chloroform-d) δ 10.17 (s, 1H), 8.83 (d, J = 4.8 Hz, 1H), 8.35 (d, J = 8.5 Hz, 1H), 8.23 (d, J = 2.3 Hz, 1H), 7.85 (dd, J = 4.8, 1.4 Hz, 1H), 7.57 (dd, J = 8.5, 2.4 Hz, 1H), 7.20-6.83 (m, 2H), 4.16 (s, 3H), 3.95 (s, 2H). |
| 487 | LCMS (ESI) m/z: 370.0 [M + H]⁺. ¹H NMR (500 MHz, DMSO-d₆) δ 10.57 (s, 1H), 8.80 (s, 1H), 8.37 (d, J = 2.8 Hz, 1H), 8.20-7.97 (m, 2H), 7.80 (dd, J = 9.7, 2.9 Hz, 1H), 7.35 (t, J = 8.2 Hz, 1H), 7.18 (t, J = 2.2 Hz, 1H), 7.05 (dd, J = 8.1, 2.1 Hz, 2H), 6.43 (d, J = 9.7 Hz, 1H), 5.33 (s, 2H), 3.45 (s, 3H). |
| 488 | LCMS (ESI) m/z: 388.0 [M + H]⁺. ¹H NMR (500 MHz, DMSO-d₆) δ 10.57 (s, 1H), 8.80 (s, 1H), 8.37 (d, J = 2.8 Hz, 1H), 8.13 (dt, J = 8.1, 4.9 Hz, 2H), 7.79 (dd, J = 9.7, 2.8 Hz, 1H), 7.51-7.29 (m, 2H), 7.08 (dt, J = 9.1, 3.5 Hz, 1H), 6.43 (d, J = 9.7 Hz, 1H), 5.31 (s, 2H), 3.45 (s, 3H). |
| 489 | LCMS (ESI) m/z: 357.1/359.0 [M + H]+. ¹H NMR (500 MHz, DMSO-d₆) δ 11.60 (bs, 1H), 9.58 (s, 1H), 8.29 (d, J = 2.0 Hz, 1H), 8.07 (d, J = 8.5 Hz, 1H), 7.78 (d, J = 8.5 Hz, 1H), 7.36-7.32 (m, 2H), 7.28-7.23 (m, 2H), 5.90 (s, 1H), 4.02-3.97 (m, 4H), 1.32 (t, J = 7.0 Hz, 3H); |
| 490 | LCMS (ESI) m/z: 389.0 [M + H]⁺. ¹H NMR (500 MHz, DMSO-d₆) δ 10.47 (s, 1H), 9.25 (s, 2H), 8.34 (s, 1H), 8.17 (d, J = 8.4 Hz, 1H), 7.79 (dd, J = 8.5, 2.2 Hz, 1H), 7.44-7.26 (m, 1H), 7.13 (dd, J = 12.0, 5.0 Hz, 2H), 7.04 (td, J = 8.7, 2.3 Hz, 1H), 4.00 (s, 2H). |
| 491 | LCMS (ESI) m/z: 391.1 [M + H]⁺. ¹H NMR (500 MHz, DMSO-d₆) δ 11.14 (s, 1H), 9.13 (d, J = 1.5 Hz, 1H), 8.43 (dd, J = 8.0, 2.0 Hz, 1H), 8.36 (d, J = 2 Hz, 1H), 8.13 (d, J = 8.5 Hz, 1H), 7.73-7.78 (m, 2H), 7.22-7.38 (m, 4H), 3.99 (s, 2H), 1.74 (s, 6H). |
| 492 | LCMS (ESI) m/z: 365.0 [M + H]⁺. ¹H NMR (500 MHz, DMSO-d₆) δ 11.43 (s, 1H), 9.24 (d, J = 1.9 Hz, 1H), 8.66-8.45 (m, 2H), 8.23 (t, J = 7.5 Hz, 2H), 7.98 (dd, J = 8.6, 2.2 Hz, 1H), 7.34 (t, J = 8.2 Hz, 1H), 7.20-6.93 (m, 3H), 5.17 (s, 2H). |
| 493 | LCMS (ESI) m/z: 351.1 [M + H]⁺. ¹H NMR (500 MHz, DMSO-d₆) δ 10.40 (s, 1H), 9.22 (d, J = 1.2 Hz, 1H), 8.62 (dd, J = 8.1, 2.0 Hz, 1H), 8.38 (d, J = 1.9 Hz, 1H), 8.32 (d, J = 8.1 Hz, 1H), 8.19 (d, J = 8.5 Hz, 1H), 7.82 (dd, J = 8.5, 2.2 Hz, 1H), 7.11-6.99 (m, 3H), 4.00 (s, 2H). |
| 494 | LCMS (ESI) m/z: 355.0/357.0 [M + H]⁺. ¹H NMR (500 MHz, DMSO-d₆) δ 9.25 (s, 2H), 8.35 (d, J = 2.5 Hz, 1H), 8.13 (d, J = 8.5 Hz, 1H), 7.75 (dd, J₁ = 2.0 Hz, J₂ = 8.5 Hz, 1H), 7.36-7.33 (m, 2H), 7.28-7.23 (m, 2H), 5.47 (bs, 1H), 4.68 (s, 2H), 3.99 (s, 2H); |
| 495 | LCMS (ESI) m/z: 339.1 [M + H]+. ¹H NMR (400 MHz, DMSO-d₆) δ 10.53 (s, 1H), 8.65 (s, 1H), 8.12-8.02 (m, 2H), 7.93-7.82 (m, 1H), 7.33-7.30 (dd, J = 8.3, 5.7 Hz, 2H), 7.14-7.10 (t, J = 8.8 Hz, 2H), 7.04-7.01 (d, J = 9.9 Hz, 1H), 4.10 (s, 2H), 3.60 (s, 3H). |
| 496 | LCMS (ESI) m/z: 338.0 [M + H]+. ¹H NMR (400 MHz, DMSO-d₆) δ 10.47 (s, 1H), 8.64 (s, 1H), 8.33 (d, J = 2.6 Hz, 1H), 8.02 (d, J = 8.0 Hz, 1H), 7.92-7.82 (m, 1H), 7.76-7.73 (dd, J = 9.7, 2.7 Hz, 1H), 7.32-7.30 (dd, J = 8.3, 5.7 Hz, 2H), 7.14-7.10 (t, J = 8.8 Hz, 2H), 6.41 (d, J = 9.7 Hz, 1H), 4.06-4.03 (d, J = 24.4 Hz, 2H), 3.43 (s, 3H). |
| 497 | LCMS (ESI) m/z: 338.0 [M + H]⁺. ¹H NMR (500 MHz, DMSO-d₆) δ 10.50 (s, 1H), 8.68 (d, J = 5.0 Hz, 1H), 8.35 (d, J = 2.0 Hz, 1H), 8.22 (d, J = 8.5 Hz, 1H), 8.18 (d, J = 0.7 Hz, 1H), 7.81 (dd, J = 8.5, 2.3 Hz, 1H), 7.68-7.60 (m, 1H), 7.41-7.31 (m, 1H), 7.13 (dd, J = 11.4, 4.8 Hz, 2H), 7.06-7.03 (m, 1H), 4.68 (s, 2H), 4.00 (m, 2H). |
| 498 | LCMS (ESI) m/z: 364.0 [M + H]⁺. ¹H NMR (500 MHz, DMSO-d₆) δ 10.43 (s, 1H), 9.22 (d, J = 1.2 Hz, 1H), 8.62 (dd, J = 8.1, 1.9 Hz, 1H), 8.41 (d, J = 1.6 Hz, 1H), 8.33 (d, J = 8.1 Hz, 1H), 8.21 (d, J = 8.5 Hz, 1H), 7.89 (dd, J = 8.5, 2.0 Hz, 1H), 7.06 (t, J = 8.0 Hz, 1H), 6.70-6.46 (m, 4H), 4.31 (s, 2H). |
| 499 | LCMS (ESI) m/z: 418.0 [M + H]⁺. ¹H NMR (500 MHz, DMSO-d₆) δ 11.15 (s, 1H), 9.16 (d, J = 1.8 Hz, 1H), 8.44 (dd, J = 8.4, 2.3 Hz, 1H), 8.36 (d, J = 2.0 Hz, 1H), 8.14 (d, J = 8.5 Hz, 1H), 7.84 (d, J = 8.3 Hz, 1H), 7.75 (dd, J = 8.5, 2.3 Hz, 1H), 7.40-7.32 (m, 2H), 7.22-7.28 (m, 2H), 6.76 (s, 1H), 6.39 (s, 1H), 3.99 (s, 2H). |
| 500 | LCMS (ESI) m/z: 334.0 [M + H]⁺. ¹H NMR (500 MHz, DMSO-d₆) δ 10.63 (s, 1H), 9.54 (s, 2H), 8.36 (s, 1H), 8.16 (d, J = 8.4 Hz, 1H), 7.80 (d, J = 8.1 Hz, 1H), 7.35 (dd, J = 14.5, 7.8 Hz, 2H), 7.13 (t, J = 8.6 Hz, 2H), 7.05 (dd, J = 12.7, 4.6 Hz, 1H), 4.00 (s, 2H). |
| 501 | LCMS (ESI) m/z: 379.1 [M + H]⁺. ¹H NMR (500 MHz, DMSO-d₆) δ 9.74 (s, 1H), 8.34 (d, J = 1.9 Hz, 1H), 8.09 (d, J = 8.4 Hz, 1H), 7.94 (d, J = 9.7 Hz, 1H), 7.82-7.63 (m, 2H), 7.40-7.31 (m, 2H), 7.30-7.20 (m, 2H), 7.14 (d, J = 9.7 Hz, 1H), 5.92-5.68 (m, 2H), 3.98 (s, 2H). |

-continued

| CMPD No. | Characterization Data |
|---|---|
| 502 | LCMS (ESI) m/z: 366.1/368.0 [M + H]+. ¹H NMR (500 MHz, DMSO-d₆) δ 10.42 (s, 1H), 9.22 (d, J = 1.5 Hz, 1H), 8.55 (dd, J = 8.0, 1.5 Hz, 1H), 8.35 (d, J = 1.0 Hz, 1H), 8.30 (d, J = 8.0 Hz, 1H), 8.20 (d, J = 8.5 Hz, 1H), 7.79 (dd, J = 8.0, 1.5 Hz, 1H), 7.36-7.32 (m, 2H), 7.28-7.24 (m, 2H), 3.98 (s, 2H), 2.7 (s, 3H); |
| 503 | LCMS (ESI) m/z: 356.0 [M + H]⁺. ¹H NMR (500 MHz, DMSO-d₆) δ 11.25 (s, 1H), 9.13 (s, 1H), 8.79 (s, 1H), 8.48 (s, 1H), 8.37 (d, J = 1.9 Hz, 1H), 8.12 (d, J = 8.5 Hz, 1H), 7.85-7.72 (m, 1H), 7.47-7.32 (m, 3H), 7.13 (d, J = 1.9 Hz, 1H), 4.68 (s, 2H), 3.98 (s, 2H). |
| 504 | LCMS (ESI) m/z: 327.1 [M + H]⁺. ¹H NMR (500 MHz, DMSO-d₆) δ 10.46 (s, 1H), 9.14 (s, 2H), 8.35 (s, 1H), 8.17 (d, J = 8.3 Hz, 1H), 7.79 (dd, J = 8.5, 2.2 Hz, 1H), 7.46-7.30 (m, 1H), 7.13 (dd, J = 12.0, 4.9 Hz, 2H), 7.04 (td, J = 8.7, 2.3 Hz, 1H), 4.00 (s, 2H). |
| 505 | LCMS (ESI) m/z: 308.3 [M + H]+. ¹H NMR (300 MHz, DMSO-d6) δ 11.11 (s, 1H), 8.84-8.63 (m, 2H), 8.35 (dd, J = 2.5, 0.8 Hz, 1H), 8.11 (dd, J = 8.4, 0.8 Hz, 1H), 8.01-7.82 (m, 2H), 7.83-7.48 (m, 4H), 7.35 (td, J = 8.0, 6.3 Hz, 1H), 7.21-6.97 (m, 3H), 3.99 (s, 2H). |
| 506 | LCMS (ESI) m/z: 349.3 [M + H]+. ¹H NMR (300 MHz, Chloroform-d) δ 10.32 (s, 1H), 8.85 (d, J = 4.9 Hz, 1H), 8.42-8.31 (m, 1H), 8.27 (dd, J = 2.4, 0.8 Hz, 1H), 7.93 (d, J = 4.9 Hz, 1H), 7.59 (dd, J = 8.5, 2.4 Hz, 1H), 7.39-7.21 (m, 2H), 7.09-6.80 (m, 3H), 2.46-2.28 (m, 1H), 1.33-1.11 (m, 4H). |
| 507 | LCMS (ESI) m/z: 368.1 [M + H]+. ¹H NMR (500 MHz, DMSO-d₆) δ 10.41 (s, 1H), 9.22 (s, 1H), 8.55 (d, J = 8.0 Hz, 1H), 8.34 (s, 1H), 8.31 (d, J = 8.0 Hz, 1H), 8.20 (d, J = 8.5 Hz, 1H), 7.79 (d, J = 8.5 Hz, 1H), 7.39-7.33 (m, 2H), 7.12 (s, 1H), 3.97 (s, 2H), 2.70 (s, 3H); . |
| 508 | LCMS (ESI) m/z: 346.1 [M + H]⁺. ¹H NMR (500 MHz, DMSO-d₆) δ 10.90 (s, 1H), 8.32 (d, J = 2.1 Hz, 1H), 8.15 (s, 1H), 7.99 (d, J = 8.5 Hz, 1H), 7.71 (dd, J = 8.6, 2.3 Hz, 1H), 7.42-7.30 (m, 2H), 7.11 (s, 1H), 3.95 (s, 2H), 3.35 (s, 3H). |
| 509 | LCMS (ESI) m/z: 346.1 [M + H]⁺. ¹H NMR (500 MHz, DMSO-d₆) 6 10.91 (s, 1H), 8.35 (d, J = 1.5 Hz, 1H), 8.15 (s, 1H), 8.00 (d, J = 8.5 Hz, 1H), 7.75 (dd, J = 8.5, 2.0 Hz, 1H), 7.06 (m, 3H), 3.98 (s, 2H), 3.35 (s, 3H). |
| 510 | LCMS (ESI) m/z: 368.1/370.1 [M + H]+. ¹H NMR (400 MHz, DMSO-d₆) δ 10.37 (s, 1H), 8.71 (d, J = 1.6 Hz, 1H), 8.34 (d, J = 2.0 Hz, 1H), 8.21 (d, J = 8.4 Hz, 1H), 8.16 (d, J = 8.0 Hz, 1H), 8.05 (dd, J = 8.0, 2.0 Hz, 1H), 7.78 (dd, J = 8.4, 2.4 Hz, 1H), 7.36 (d, J = 1.6 Hz, 1H), 7.33 (d, J = 7.6 Hz, 1H), 7.28-7.24 (m, 2H), 5.55 (d, J = 4.4 Hz, 1H), 4.93-4.91 (m, 1H), 3.98 (s, 2H), 1.40 (d, J = 6.8 Hz, 3H); |
| 511 | LCMS (ESI) m/z: 370.2 [M + H]+. ¹H NMR (400 MHz, DMSO-d₆) δ 10.38 (s, 1H), 8.71 (d, J = 1.6 Hz, 1H), 8.33 (d, J = 2.0 Hz, 1H), 8.21 (d, J = 8.4 Hz, 1H), 8.16 (d, J = 8.0 Hz, 1H), 8.05 (dd, J = 8.0, 2.0 Hz, 1H), 7.78 (dd, J = 8.4, 2.4 Hz, 1H), 7.41-7.33 (m, 2H), 7.14-7.11 (m, 1H), 5.55 (d, J = 4.0 Hz, 1H), 4.95-4.89 (m, 1H), 3.97 (s, 2H), 1.40 (d, J = 6.4 Hz, 3H); |
| 512 | LCMS (ESI) m/z: 369.1/371.1 [M + H]+. ¹H NMR (400 MHz, DMSO-d₆) δ 8.38-8.35 (m, 2H), 8.18 (d, J = 8.4 Hz, 1H), 8.05 (d, J = 8.4 Hz, 1H), 7.80 (dd, J = 8.4, 2.4 Hz, 1H), 7.37-7.33 (m, 2H), 7.29-7.25 (m, 2H), 5.85 (d, J = 4.0 Hz, 1H), 5.14-5.11 (m, 1H), 4.00 (s, 2H), 1.50 (d, J = 6.4 Hz, 3H); LCMS (ESI) m/z: 369.1/371.1 [M + H]. |
| 513 | LCMS (ESI) m/z: 370.0 [M + H]⁺. ¹H NMR (400 MHz, DMSO-d₆) δ 11.02 (s, 1H), 9.05 (d, J = 2.0 Hz, 1H), 8.34 (t, J = 5.2, 2H), 8.13 (d, J = 8.4 Hz, 1H), 7.74-7.67 (m, 1H), 7.63 (d, J = 4.0 Hz, 1H), 7.10-7.04 (m, 3H), 5.54 (s, 1H), 4.82-4.77 (m, 1H), 3.99 (s, 2H), 1.39 (d, J = 6.0 Hz, 3H). |
| 514 | LCMS (ESI) m/z: 370.0 [M + H]⁺. ¹H NMR (400 MHz, DMSO-d₆) δ 11.01 (s, 1H), 9.05 (d, J = 1.8 Hz, 1H), 8.47-8.29 (m, 2H), 8.13 (d, J = 8.5 Hz, 1H), 7.73 (dd, J = 8.6, 2.4 Hz, 1H), 7.63 (d, J = 8.2 Hz, 1H), 7.47-7.29 (m, 2H), 7.17-7.06 (m, 1H), 5.54 (d, J = 4.7 Hz, 1H), 4.88-4.65 (m, 1H), 3.97 (s, 2H), 1.39 (d, J = 6.6 Hz, 3H). |
| 515 | LCMS (ESI) m/z: 356.1 [M + H]⁺. ¹H NMR (400 MHz, DMSO-d₆) δ 10.94 (s, 1H), 8.33 (s, 1H), 8.04 (s, 1H), 7.77 (d, J = 40.6 Hz, 2H), 7.37 (s, 2H), 7.03 (d, J = 68.1 Hz, 2H), 6.61 (s, 1H), 3.96 (s, 2H), 3.40 (s, 3H). |
| 516 | LCMS (ESI) m/z: 369.1 [M + H]+. ¹H NMR (400 MHz, DMSO-d₆) δ 10.66 (bs, 1H), 8.50 (d, J = 8.4 Hz, 1H), 8.40 (d, J = 2.0 Hz, 1H), 8.36 (d, J = 8.8 Hz, 1H), 8.18 (d, J = 8.8 Hz, 1H), 7.82 (dd, J = 8.4, 2.4 Hz, 1H), 7.42-7.34 (m, 2H), 7.15-7.13 (m, 1H), 3.99 (s, 2H), 2.85 (s, 3H); |
| 517 | LCMS (ESI) m/z: 367.0/369.1 [M + H]+. ¹H NMR (400 MHz, DMSO-d₆) δ 10.75 (s, 1H), 8.50 (d, J = 8.8 Hz, 1H), 8.40 (d, J = 2.0 Hz, 1H), 8.36 (d, J = 8.8 Hz, 1H), 8.18 (d, J = 8.4 Hz, 1H), 7.82 (dd, J = 8.4, 2.4 Hz, 1H), 7.38-7.33 (m, 2H), 7.29-7.25 (m, 2H), 4.01 (s, 2H), 2.85 (s, 3H);. |
| 518 | LCMS (ESI) m/z: 405.0 [M + H]⁺. ¹H NMR (400 MHz, DMSO-d₆) δ 10.47 (s, 1H), 9.25 (s, 2H), 8.34 (s, 1H), 8.17 (d, J = 8.3 Hz, 1H), 7.79 (dd, J = 8.5, 2.1 Hz, 1H), 7.38 (ddd, J = 19.4, 7.6, 5.3 Hz, 2H), 7.13 (d, J = 2.0 Hz, 1H), 3.97 (s, 2H). |
| 519 | LCMS (ESI) m/z: 368.0 [M + H]⁺. ¹H NMR (400 MHz, DMSO-d₆) δ 11.02 (s, 1H), 9.05 (d, J = 1.6 Hz, 1H), 8.36-8.40 (m, 2H), 8.13 (d, J = 8.4 Hz, 1H), 7.75-7.72 (m, 1H), 7.63 (d, J = 8.0 Hz, 1H), 7.37-7.33 (m, 2H), 7.29-7.24 (m, 2H), 5.54 (d, J = 4.4 Hz, 1H), 4.81-4.78 (m, 1H), 3.98 (s, 2H), 1.39 (d, J = 6.8 Hz, 3H). |
| 520 | LCMS (ESI) m/z: 368.0 [M + H]⁺. ¹H NMR (400 MHz, DMSO-d₆) δ 11.02 (s, 1H), 9.05 (d, J = 1.6 Hz, 1H), 8.36-8.40 (m, 2H), 8.13 (d, J = 8.4 Hz, 1H), 7.75-7.72 (m, 1H), |

-continued

| CMPD No. | Characterization Data |
|---|---|
| | 7.63 (d, J = 8.0 Hz, 1H), 7.37-7.33 (m, 2H), 7.29-7.24 (m, 2H), 5.54 (d, J = 4.4 Hz, 1H), 4.81-4.78 (m, 1H), 3.98 (s, 2H), 1.40 (d, J = 6.8 Hz, 3H). |
| 521 | LCMS (ESI) m/z: 364.9 [M + H]+. $^1$H NMR (400 MHz, DMSO-d$_6$) δ 11.27 (s, 1H), 9.47 (s, 2H), 9.28 (d, J = 9.2 Hz, 1H), 8.95 (d, J = 9.6 Hz, 1H), 8.40 (s, 1H), 8.09 (d, J = 8.0 Hz, 1H), 7.83 (dd, J = 8.5, 2.3 Hz, 1H), 7.38-7.33 (m, 2H), 7.30-7.28 (m, 2H), 4.01 (s, 2H). |
| 522 | LCMS (ESI) m/z: 385.9 [M + H]+. $^1$H NMR (400 MHz, DMSO-d$_6$) δ 11.02 (s, 1H), 9.05 (s, 1H), 8.35 (s, 2H), 8.13 (d, J = 8.3 Hz, 1H), 7.73 (d, J = 8.5 Hz, 1H), 7.63 (d, J = 8.0 Hz, 1H), 7.53 (d, J = 7.2 Hz, 1H), 7.42-7.20 (m, 2H), 5.55 (s, 1H), 4.80 (d, J = 6.0 Hz, 1H), 3.97 (s, 2H), 1.39 (d, J = 6.4 Hz, 3H). |
| 523 | LCMS (ESI) m/z: 371.0 [M + H]+. $^1$H NMR (400 MHz, DMSO-d$_6$) δ 10.02 (s, 1H), 8.33 (d, J = 1.8 Hz, 1H), 8.08 (d, J = 8.4 Hz, 1H), 7.88 (d, J = 1.2 Hz, 1H), 7.75 (dd, J = 8.5, 2.4 Hz, 1H), 7.36-7.33 (m, 2H), 7.12 (s, 1H), 3.96 (s, 2H), 3.79 (s, 3H), 2.17 (d, J = 1.1 Hz, 3H). |
| 524 | LCMS (ESI) m/z: 371.0 [M + H]+. $^1$H NMR (400 MHz, DMSO-d$_6$) δ 10.07 (s, 1H), 8.35 (d, J = 4.0 Hz, 1H), 8.09 (d, J = 8.5 Hz, 1H), 7.89 (d, J = 1.2 Hz, 1H), 7.78 (dd, J = 8.5, 2.4 Hz, 1H), 7.14-6.96 (m, 3H), 3.99 (s, 2H), 3.80 (s, 3H), 2.17 (d, J = 1.1 Hz, 3H). |
| 525 | LCMS (ESI) m/z: 352.0 [M + H]+. $^1$H NMR (400 MHz, DMSO-d$_6$) δ 9.43 (s, 2H), 8.36 (d, J = 2.0 Hz, 1H), 8.12 (d, J = 8.4 Hz, 1H), 7.77 (dd, J$_1$ = 2.0 Hz, J$_2$ = 8.4 Hz, 1H), 7.40-7.33 (m, 2H), 7.13-7.12 (m, 1H), 3.97 (s, 2H); |
| 526 | LCMS (ESI) m/z: 351.1 [M + H]+. $^1$H NMR (400 MHz, DMSO-d$_6$) δ 11.30 (s, 1H), 9.26 (d, J = 2.0 Hz, 1H), 8.76 (d, J = 1.6 Hz, 1H), 8.56-8.59 (q, J = 3.6 Hz, 1H), 7.96-8.14 (m, 3H), 7.08-7.12 (m, 3H), 4.16 (s, 2H). |
| 527 | LCMS (ESI) m/z: 399.0 [M + H]+. $^1$H NMR (400 MHz, DMSO-d$_6$) δ 11.64 (s, 1H), 9.14 (s, 1H), 8.83 (s, 1H), 8.40 (d, J = 1.9 Hz, 1H), 8.12 (d, J = 8.5 Hz, 1H), 7.78 (dd, J = 8.5, 2.3 Hz, 1H), 7.40-7.31 (m, 1H), 7.14 (t, J = 8.0 Hz, 2H), 7.06 (d, J = 8.4 Hz, 1H), 4.01 (s, 2H). |
| 528 | LCMS (ESI) m/z: 391.0 [M + H]+. $^1$H NMR (400 MHz, DMSO-d$_6$) δ 10.15 (s, 1H), 8.36 (d, J = 1.9 Hz, 1H), 8.09 (d, J = 8.4 Hz, 1H), 7.95 (d, J = 9.7 Hz, 1H), 7.78 (dd, J = 8.5, 2.3 Hz, 1H), 7.50-7.38 (m, 2H), 7.08 (d, J = 9.7 Hz, 1H), 3.97 (s, 2H), 3.79 (s, 3H). |
| 529 | LCMS (ESI) m/z: 352.0 [M + H]+. $^1$H NMR (400 MHz, DMSO-d$_6$) δ 11.02 (s, 1H), 9.06 (t, J = 8.4 Hz, 1H), 8.40-8.33 (m, 2H), 8.13 (d, J = 8.5 Hz, 1H), 7.73 (dd, J = 8.5, 2.3 Hz, 1H), 7.63 (d, J = 8.2 Hz, 1H), 7.41-7.27 (m, 1H), 7.20-7.09 (m, 2H), 7.06-7.02 (m, 1H), 5.55 (s, 1H), 4.80 (q, J = 6.5 Hz, 1H), 3.99 (s, 2H), 1.40 (d, J = 6.6 Hz, 3H). |
| 530 | LCMS (ESI) m/z: 371.1 [M + H]+. $^1$H NMR (400 MHz, DMSO-d$_6$) δ 10.58 (s, 1H), 8.38-8.35 (m, 2H), 8.18 (d, J = 8.8 Hz, 1H), 8.05 (d, J = 8.8 Hz, 1H), 7.80 (dd, J = 8.4, 2.4 Hz, 1H), 7.42-7.34 (m, 2H), 7.15-7.12 (m, 1H), 5.86 (d, J = 4.8 Hz, 1H), 5.13-5.11 (m, 1H), 3.98 (s, 2H), 1.50 (d, J = 6.8 Hz, 3H); |
| 531 | LCMS (ESI) m/z: 367.1 [M + H]+. $^1$H NMR (400 MHz, DMSO-d$_6$) δ 10.07 (s, 1H), 8.33 (d, J = 1.9 Hz, 1H), 8.09 (d, J = 8.5 Hz, 1H), 7.79 (s, 1H), 7.76 (dd, J = 8.5, 2.3 Hz, 1H), 7.38-7.35 (m, 1H), 7.21-7.09 (m, 2H), 7.08-7.03 (m, 1H), 3.99 (s, 2H), 3.80 (s, 3H), 2.57-2.53 (m, 2H), 1.16 (t, J = 7.4 Hz, 3H). |
| 532 | LCMS (ESI) m/z: 357.1 [M + H]+. $^1$H NMR (400 MHz, DMSO-d$_6$) δ 12.15 (s, 1H), 8.36 (d, J = 2.0 Hz, 1H), 8.22 (dt, J = 14.0, 6.4 Hz, 3H), 7.78 (dd, J = 8.5, 2.3 Hz, 1H), 7.13-7.00 (m, 3H), 3.99 (s, 2H), 3.84 (s, 3H). |
| 533 | LCMS (ESI) m/z: 356.1 [M + H]+. $^1$H NMR (400 MHz, DMSO-d$_6$) δ 10.94 (s, 1H), 8.36 (d, J = 2.0 Hz, 1H), 8.06 (d, J = 8.5 Hz, 1H), 7.81 (d, J = 7.0 Hz, 1H), 7.75 (dd, J = 8.5, 2.3 Hz, 1H), 7.14-7.00 (m, 3H), 6.95 (d, J = 1.7 Hz, 1H), 6.61 (dd, J = 7.0, 1.9 Hz, 1H), 3.99 (s, 2H), 3.47 (s, 3H). |
| 534 | LCMS (ESI) m/z: 358.1 [M + H]+. $^1$H NMR (400 MHz, DMSO-d$_6$) δ 10.40 (s, 1H), 9.21 (d, J = 1.0 Hz, 1H), 8.62 (dd, J = 8.0, 1.9 Hz, 1H), 8.37 (d, J = 1.8 Hz, 1H), 8.32 (d, J = 8.2 Hz, 1H), 8.18 (d, J = 8.5 Hz, 1H), 7.90 (dd, J = 6.2, 2.0 Hz, 1H), 7.81 (dd, J = 8.5, 2.0 Hz, 1H), 7.77-7.64 (m, 1H), 7.47 (t, J = 8.0 Hz, 1H), 4.03 (s, 2H). |
| 535 | LCMS (ESI) m/z: 358.0 [M + H]+. $^1$H NMR (400 MHz, DMSO-d$_6$) δ 11.34 (s, 1H), 9.22 (s, 1H), 8.53 (dd, J = 8.0, 2.0 Hz, 1H), 8.40 (d, J = 2.0 Hz, 1H), 8.20 (d, J = 8.4 Hz, 1H), 8.13 (d, J = 8.8 Hz, 1H), 7.80 (dd, J = 8.8, 2.4 Hz, 1H), 7.73-7.69 (m, 2H), 7.59 (d, J = 9.6 Hz, 1H), 4.06 (s, 2H); |
| 536 | LCMS (ESI) m/z: 358.0 [M + H]+. $^1$H NMR (400 MHz, DMSO-d$_6$) δ 10.41 (s, 1H), 9.22 ( dd, J = 2.0, 0.8 Hz, 1H), 8.62 (dd, J = 8.0, 2.0 Hz, 1H), 8.40 (d, J = 2.0 Hz, 1H), 8.32 (dd, J = 8.4, 0.8 Hz, 1H), 8.19 (d, J = 8.4 Hz, 1H), 7.84 (dd, J = 8.8, 2.4 Hz, 1H), 7.72-7.70 (m, 2H), 7.61-7.58 (m, 1H), 4.06 (s, 2H); |
| 537 | LCMS (ESI) m/z: 357.0 [M + H]+. $^1$H NMR (400 MHz, DMSO-d$_6$) δ 10.15 (s, 1H), 8.29 (d, J = 2.1 Hz, 1H), 8.08 (d, J = 8.5 Hz, 1H), 7.95 (d, J = 9.7 Hz, 1H), 7.70 (dd, J = 8.5, 2.2 Hz, 1H), 7.41 (dd, J = 15.4, 8.7 Hz, 1H), 7.29-7.19 (m, 1H), 7.06 (dd, J = 13.5, 6.1 Hz, 2H), 3.98 (s, 2H), 3.79 (s, 3H). |
| 538 | LCMS (ESI) m/z: 356.0 [M + H]+. $^1$H NMR (400 MHz, DMSO-d$_6$) δ 10.58 (s, 1H), 8.67 (d, J = 2.5 Hz, 1H), 8.27 (s, 1H), 8.11-7.89 (m, 2H), 7.73-7.58 (m, 1H), 7.41 (dd, J = 15.5, 8.6 Hz, 1H), 7.29-7.18 (m, 1H), 7.07 (t, J = 8.3 Hz, 1H), 6.43 (d, J = 9.5 Hz, 1H), 3.96 (s, 2H), 3.50 (s, 3H). |
| 539 | LCMS (ESI) m/z: 357.1 [M + H]+. $^1$H NMR (400 MHz, DMSO-d$_6$) δ 10.14 (s, 1H), 8.31 (s, 1H), 8.09 (d, J = 8.5 Hz, 1H), 7.95 (d, J = 9.7 Hz, 1H), 7.73 (d, J = 8.4 Hz, 1H), |

-continued

| CMPD No. | Characterization Data |
|---|---|
| | 7.24 (td, J = 8.9, 4.8 Hz, 2H), 7.19-7.00 (m, 2H), 3.99 (s, 2H), 3.79 (s, 3H). |
| 540 | LCMS (ESI) m/z: 341.0 [M + H]$^+$. $^1$H NMR (400 MHz, DMSO-$d_6$) δ 10.74 (s, 1H), 8.33 (d, J = 2.0 Hz, 1H), 8.03 (d, J = 8.5 Hz, 1H), 7.71 (dd, J = 8.6, 2.3 Hz, 1H), 7.35 (dd, J = 14.3, 8.0 Hz, 1H), 7.19 (s, 1H), 7.15-7.08 (m, 2H), 7.04 (dd, J = 12.0, 5.5 Hz, 1H), 4.41 (s, 2H), 4.04 (s, 3H), 3.98 (s, 2H). |
| 541 | LCMS (ESI) m/z: 351.1 [M + H]$^+$. $^1$H NMR (400 MHz, DMSO-$d_6$) δ 11.32 (s, 1H), 9.22 (d, J = 1.6 Hz, 1H), 8.53 (dd, $J_1$ = 2.0 Hz, $J_2$ = 8.4 Hz, 1H), 8.36 (d, J = 2.4 Hz, 1H), 8.20 (dd, $J_1$ = 0.4 Hz, $J_2$ = 8.0 Hz, 1H), 8.12 (d, J = 8.8 Hz, 1H), 7.75 (dd, $J_1$ = 2.4 Hz, $J_2$ = 8.8 Hz, 1H), 7.40-7.33 (m, 2H), 7.13-7.10 (m, 1H), 3.97 (s, 2H); |
| 542 | LCMS (ESI) m/z: 351.0 [M + H]$^+$. $^1$H NMR (400 MHz, DMSO-$d_6$) δ 11.29 (s, 1H), 8.94 (d, J = 5.0 Hz, 1H), 8.53 (s, 1H), 8.37 (d, J = 2.1 Hz, 1H), 8.20 (dd, J = 5.1, 1.7 Hz, 1H), 8.11 (d, J = 8.5 Hz, 1H), 7.76 (dd, J = 8.5, 2.4 Hz, 1H), 7.47-7.28 (m, 2H), 7.13 (s, 1H), 3.98 (s, 2H). |
| 543 | LCMS (ESI) m/z: 390.0 [M + H]$^+$. $^1$H NMR (400 MHz, DMSO-$d_6$) δ 10.54 (s, 1H), 8.67 (d, J = 2.6 Hz, 1H), 8.33 (d, J = 2.1 Hz, 1H), 8.06 (d, J = 8.5 Hz, 1H), 7.98 (dd, J = 9.5, 2.7 Hz, 1H), 7.72 (dd, J = 8.6, 2.3 Hz, 1H), 7.42 (ddd, J = 12.9, 6.5, 1.8 Hz, 2H), 6.43 (d, J = 9.5 Hz, 1H), 3.95 (s, 2H), 3.50 (s, 3H). |
| 544 | LCMS (ESI) m/z: 339.1 [M + H]$^+$. $^1$H NMR (400 MHz, DMSO-$d_6$) δ 10.53 (s, 1H), 8.97 (s, 2H), 8.34 (d, J = 1.6 Hz, 1H), 8.19 (d, J = 8.4 Hz, 1H), 7.80 (dd, $J_1$ = 2.0 Hz, $J_2$ = 8.4 Hz, 1H), 7.38-7.32 (m, 1H), 7.14-7.11 (m, 2H), 7.04 (td, $J_1$ = 2.4 Hz, $J_2$ = 8.8 Hz, 1H), 4.68 (s, 2H), 4.00 (s, 2H); |
| 545 | LCMS (ESI) m/z: 370.2 [M + H]$^+$. $^1$H NMR (400 MHz, DMSO-$d_6$) δ 10.53 (s, 1H), 10.53 (s, 1H), 8.66 (d, J = 2.6 Hz, 1H), 8.66 (d, J = 2.6 Hz, 1H), 8.31 (d, J = 2.1 Hz, 1H), 8.31 (d, J = 2.1 Hz, 1H), 8.06 (d, J = 8.5 Hz, 1H), 7.98 (dd, J = 9.5, 2.7 Hz, 1H), 7.69 (dd, J = 8.6, 2.4 Hz, 1H), 7.50-7.37 (m, 4H), 7.00 (t, J = 56.0 Hz, 1H), 6.43 (d, J = 9.5 Hz, 1H), 4.03 (s, 2H), 4.03 (s, 2H), 3.50 (s, 3H), 3.50 (s, 3H). |
| 546 | LCMS (ESI) m/z: 339.0 [M + H]$^+$. $^1$H NMR (400 MHz, DMSO-$d_6$) δ 12.12 (s, 1H), 8.33 (d, J = 1.9 Hz, 1H), 8.25-8.20 (m, 2H), 8.18 (d, J = 8.5 Hz, 1H), 7.75 (dd, J = 8.5, 2.2 Hz, 1H), 7.35 (dd, J = 14.3, 8.0 Hz, 1H), 7.16-7.08 (m, 2H), 7.04 (td, J = 8.6, 2.3 Hz, 1H), 3.98 (s, 2H), 3.83 (s, 3H). |
| 547 | LCMS (ESI) m/z: 357.0 [M + H]$^+$. $^1$H NMR (400 MHz, DMSO-$d_6$) δ 12.13 (s, 1H), 8.33 (d, J = 2.0 Hz, 1H), 8.22 (q, J = 4.3 Hz, 2H), 8.18 (d, J = 8.5 Hz, 1H), 7.75 (dd, J = 8.5, 2.2 Hz, 1H), 7.42-7.29 (m, 2H), 7.15-7.07 (m, 1H), 3.96 (s, 2H), 3.84 (s, 3H). |
| 548 | LCMS (ESI) m/z: 357.1 [M + H]$^+$. $^1$H NMR (400 MHz, DMSO-$d_6$) δ 10.15 (s, 1H), 8.54 (d, J = 6.5 Hz, 1H), 8.36 (d, J = 1.9 Hz, 1H), 8.11 (d, J = 8.4 Hz, 1H), 7.78 (dd, J = 8.5, 2.3 Hz, 1H), 7.46-7.29 (m, 2H), 7.17-7.08 (m, 1H), 7.04 (d, J = 6.5 Hz, 1H), 3.97 (s, 2H), 3.54 (s, 3H). |
| 549 | LCMS (ESI) m/z: 352.0 [M + H]$^+$. $^1$H NMR (400 MHz, DMSO-$d_6$) δ 10.62 (s, 1H), 9.54 (s, 2H), 8.36 (s, 1H), 8.16 (d, J = 8.0 Hz, 1H), 7.79 (dd, J = 8.5, 2.0 Hz, 1H), 7.37 (dt, J = 19.4, 5.6 Hz, 2H), 7.13 (s, 1H), 3.98 (s, 2H). |
| 550 | LCMS (ESI) m/z: 363.1 [M + H]$^+$. $^1$H NMR (400 MHz, DMSO-$d_6$) δ 10.54 (s, 1H), 8.66 (d, J = 2.6 Hz, 1H), 8.32 (d, J = 2.0 Hz, 1H), 8.06 (d, J = 8.5 Hz, 1H), 7.98 (dd, J = 9.5, 2.7 Hz, 1H), 7.88 (dd, J = 6.3, 2.2 Hz, 1H), 7.70 (dd, J = 8.0, 2.2 Hz, 2H), 7.47 (t, J = 8.0 Hz, 1H), 6.43 (d, J = 9.0 Hz, 1H), 4.00 (s, 2H), 3.50 (s, 3H). |
| 551 | LCMS (ESI) m/z: 357.2 [M + H]$^+$. $^1$H NMR (400 MHz, DMSO-$d_6$) δ 10.14 (s, 1H), 8.30 (t, J = 10.6 Hz, 1H), 8.09 (d, J = 8.5 Hz, 1H), 7.95 (d, J = 9.7 Hz, 1H), 7.72 (dd, J = 8.5, 2.1 Hz, 1H), 7.31 (dt, J = 7.7, 6.8 Hz, 1H), 7.25-7.13 (m, 2H), 7.08 (d, J = 9.7 Hz, 1H), 4.06 (s, 2H), 3.79 (s, 3H). |
| 552 | LCMS (ESI) m/z: 356.2 [M + H]$^+$. $^1$H NMR (400 MHz, DMSO-$d_6$) δ 10.55 (s, 1H), 8.67 (d, J = 2.5 Hz, 1H), 8.29 (d, J = 1.9 Hz, 1H), 8.07 (d, J = 8.5 Hz, 1H), 7.98 (dd, J = 9.5, 2.6 Hz, 1H), 7.66 (dd, J = 8.6, 2.2 Hz, 1H), 7.42-7.25 (m, 1H), 7.24-7.08 (m, 2H), 6.43 (d, J = 9.5 Hz, 1H), 4.04 (s, 2H), 3.50 (s, 3H). |
| 553 | LCMS (ESI) m/z: 353.1 [M + H]$^+$. $^1$H NMR (400 MHz, DMSO-$d_6$) δ 10.46 (s, 1H), 9.17 (s, 2H), 8.36 (d, J = 2.0 Hz, 1H), 8.20 (d, J = 8.4 Hz, 1H), 7.81 (dd, $J_1$ = 2.0 Hz, $J_2$ = 8.4 Hz, 1H), 7.09-7.04 (m, 3H), 6.87 (dd, $J_1$ = 11.6 Hz, $J_2$ = 18.0 Hz, 1H), 6.31 (d, J = 18.0 Hz, 1H), 5.68 (d, J = 10.8 Hz, 1H), 4.00 (s, 2H); |
| 554 | LCMS (ESI) m/z: 371.0 [M + H]$^+$. $^1$H NMR (400 MHz, DMSO-$d_6$) δ 10.41 (s, 1H), 9.54-9.07 (m, 3H), 8.36 (d, J = 1.9 Hz, 1H), 8.17 (d, J = 8.5 Hz, 1H), 7.80 (dd, J = 8.5, 2.2 Hz, 1H), 7.43-7.30 (m, 2H), 7.13 (brs, 1H), 3.98 (s, 2H). |
| 555 | LCMS (ESI) m/z: 365.1 [M + H]$^+$. $^1$H NMR (400 MHz, DMSO-$d_6$) δ 11.54 (s, 1H), 9.65 (s, 1H), 9.26 (s, 1H), 8.73 (s, 1H), 8.40 (s, 1H), 8.12 (d, J = 8.5 Hz, 1H), 7.77 (dd, J = 8.5, 2.3 Hz, 1H), 7.36 (td, J = 8.0, 6.4 Hz, 1H), 7.14 (dd, J = 10.4, 4.3 Hz, 2H), 7.05 (td, J = 8.6, 2.3 Hz, 1H), 4.01 (s, 2H). |
| 556 | LCMS (ESI) m/z: 381.0 [M + H]$^+$. $^1$H NMR (400 MHz, DMSO-$d_6$) δ 11.53 (s, 1H), 9.64 (s, 1H), 9.26 (s, 1H), 8.73 (s, 1H), 8.40 (d, J = 1.7 Hz, 1H), 8.12 (d, J = 8.5 Hz, 1H), 7.77 (dd, J = 8.5, 2.1 Hz, 1H), 7.42-7.32 (m, 2H), 7.31-7.22 (m, 2H), 4.01 (s, 2H). |
| 557 | LCMS (ESI) m/z: 380.0 [M + H]$^+$. $^1$H NMR (400 MHz, MeOD-$d_4$) δ 8.98 (d, J = 2.0 Hz, 1H), 8.38-8.22 (m, 2H), 8.15 (d, J = 8.5 Hz, 1H), 7.90 (d, J = 8.4 Hz, 1H), |

-continued

| CMPD No. | Characterization Data |
|---|---|
| | 7.69 (dd, J = 8.5, 2.3 Hz, 1H), 7.10-7.25 (m, 4H), 4.01 (s, 2H), 1.45 (dd, J = 7.5, 4.4 Hz, 2H), 1.28 (dd, J = 7.5, 4.4 Hz, 2H). |
| 558 | LCMS (ESI) m/z: 382.0 [M + H]⁺. ¹H NMR (400 MHz, DMSO-d₆) δ 10.14 (s, 1H), 8.36 (d, J = 1.7 Hz, 1H), 8.09 (d, J = 8.5 Hz, 1H), 7.95 (d, J = 9.7 Hz, 1H), 7.90-7.81 (m, 1H), 7.81-7.73 (m, 2H), 7.08 (d, J = 9.7 Hz, 1H), 4.01 (s, 2H), 3.79 (s, 3H). |
| 559 | LCMS (ESI) m/z: 357.1 [M + H]⁺. ¹H NMR (400 MHz, DMSO-d₆) δ 10.49 (s, 1H), 8.97 (s, 2H), 8.36 (d, J = 2.0 Hz, 1H), 8.19 (d, J = 8.4 Hz, 1H), 7.81 (dd, J₁ = 2.0 Hz, J₂ = 8.4 Hz, 1H), 7.06-7.04 (m, 3H), 5.63 (t, J = 5.7 Hz, 1H), 4.68 (d, J = 6.0 Hz, 2H), 4.00 (s, 2H); |
| 560 | LCMS (ESI) m/z: 341.0 [M + H]⁺. ¹H NMR (400 MHz, DMSO-d₆) δ 9.46 (s, 1H), 8.28 (d, J = 2.1 Hz, 1H), 8.09 (d, J = 8.5 Hz, 1H), 7.72 (dd, J = 8.5, 2.2 Hz, 1H), 7.34 (dd, J = 14.3, 8.0 Hz, 1H), 7.18-7.09 (m, 2H), 7.06-7.02 (m, 1H), 6.75 (s, 1H), 5.43 (d, J = 5.1 Hz, 1H), 4.55 (d, J = 4.7 Hz, 2H), 3.97 (d, J = 5.8 Hz, 2H), 3.91 (s, 3H). |
| 561 | LCMS (ESI) m/z: 371.0 [M + H]⁺. ¹H NMR (400 MHz, DMSO-d₆) δ 10.12 (s, 1H), 8.34 (d, J = 1.9 Hz, 1H), 8.09 (d, J = 8.5 Hz, 1H), 7.95 (d, J = 9.7 Hz, 1H), 7.75 (dd, J = 8.5, 2.3 Hz, 1H), 7.44-7.25 (m, 4H), 7.15-6.82 (t, J = 56.0 Hz, 1H), 7.10 (d, J-9.6 Hz, 1H), 4.05 (s, 2H), 3.79 (s, 3H). |
| 562 | LCMS (ESI) m/z: 388.9 [M + H]⁺. ¹H NMR (400 MHz, DMSO-d₆) δ 10.15 (s, 1H), 8.37 (d, J = 1.9 Hz, 1H), 8.10 (d, J = 8.5 Hz, 1H), 7.95 (d, J = 9.7 Hz, 1H), 7.83-7.75 (m, 1H), 7.36 (d, J-12.8 Hz, 2H), 7.28 (d, J = 8.8 Hz, 1H), 7.16-6.88 (m, 2H), 4.06 (s, 2H), 3.79 (s, 3H). |
| 563 | LCMS (ESI) m/z: 351.0 [M + H]⁺. ¹H NMR (400 MHz, DMSO-d₆) δ 11.29 (s, 1H), 8.94 (d, J = 5.0 Hz, 1H), 8.53 (s, 1H), 8.37 (d, J = 2.1 Hz, 1H), 8.20 (dd, J = 5.1, 1.7 Hz, 1H), 8.11 (d, J = 8.5 Hz, 1H), 7.76 (dd, J = 8.5, 2.4 Hz, 1H), 7.47-7.28 (m, 2H), 7.13 (s, 1H), 3.98 (s, 2H). |
| 564 | LCMS (ESI) m/z: 364.1 [M + H]⁺. ¹H NMR (400 MHz, DMSO-d₆) δ 10.13 (s, 1H), 8.35 (s, 1H), 8.08 (d, J = 8.5 Hz, 1H), 7.95 (d, J = 9.6 Hz, 1H), 7.89 (d, J = 4.7 Hz, 1H), 7.76 (d, J = 8.2 Hz, 1H), 7.70 (s, 1H), 7.47 (t, J = 9.0 Hz, 1H), 7.08 (d, J = 9.6 Hz, 1H), 4.02 (s, 2H), 3.79 (s, 3H). |
| 565 | LCMS (ESI) m/z: 356.1 [M + H]⁺. ¹H NMR (400 MHz, DMSO-d₆) δ 10.54 (s, 1H), 8.67 (d, J = 2.6 Hz, 1H), 8.29 (d, J = 2.0 Hz, 1H), 8.06 (d, J = 8.5 Hz, 1H), 7.98 (dd, J = 9.5, 2.7 Hz, 1H), 7.67 (dd, J = 8.6, 2.2 Hz, 1H), 7.25 (ddd, J = 14.1, 7.1, 3.9 Hz, 2H), 7.14 (td, J = 8.2, 4.5 Hz, 1H), 6.43 (d, J = 9.5 Hz, 1H), 3.97 (s, 2H), 3.50 (s, 3H). |
| 566 | LCMS (ESI) m/z: 356.1 [M + H]⁺. ¹H NMR (400 MHz, DMSO-d₆) δ 10.55 (s, 1H), 8.66 (d, J = 2.6 Hz, 1H), 8.24 (d, J = 1.9 Hz, 1H), 8.05 (d, J = 8.6 Hz, 1H), 7.97 (dd, J = 9.5, 2.7 Hz, 1H), 7.60 (dd, J = 8.5, 2.2 Hz, 1H), 7.38 (t, J = 8.3 Hz, 1H), 7.13 (t, J = 7.9 Hz, 2H), 6.42 (d, J = 9.5 Hz, 1H), 3.99 (s, 2H), 3.49 (s, 3H). |
| 567 | LCMS (ESI) m/z: 365.1 [M + H]+. ¹H NMR (400 MHz, DMSO-d₆) δ 10.48 (s, 1H), 8.77-8.78 (d, J = 4.4 Hz, 1H), 8.72 (s, 1H), 8.62 (s, 1H), 8.50-8.51 (d, J = 5.2 Hz, 1H), 8.15-8.17 (d, J = 8.0 Hz, 1H), 7.96-7.99 (m, 1H), 7.52-7.54 (m, 1H), 7.34-7.40 (d, J = 7.2 Hz, 1H), 7.15-7.21 (m, 2H), 7.06-7.09 (m, 2H), 4.15 (s, 2H), 2.81-2.82 (d, J = 4.8 Hz, 3H). |
| 568 | LCMS (ESI) m/z: 353.1 [M + H]⁺. ¹H NMR (400 MHz, DMSO-d₆) δ 10.45 (s, 1H), 9.17 (s, 2H), 8.34 (d, J = 1.6 Hz, 1H), 8.19 (d, J = 8.4 Hz, 1H), 7.78 (dd, J₁ = 2.0 Hz, J₂ = 8.4 Hz, 1H), 7.40-7.33 (m, 2H), 7.14-7.11 (m, 1H), 6.87 (dd, J₁ = 11.2 Hz, J₂ = 17.6 Hz, 1H), 6.31 (d, J = 18.0 Hz, 1H), 5.68 (d, J = 11.2 Hz, 1H), 3.97 (s, 2H); |
| 569 | LCMS (ESI) m/z: 336.2 [M + H]⁺. ¹H NMR (400 MHz, DMSO-d₆) δ 10.56 (s, 1H), 8.80 (s, 1H), 8.37 (d, J = 2.8 Hz, 1H), 8.23-8.03 (m, 2H), 7.80 (dd, J = 9.7, 2.8 Hz, 1H), 7.32 (dd, J = 8.6, 7.4 Hz, 2H), 7.19-6.90 (m, 3H), 6.43 (d, J = 9.7 Hz, 1H), 5.27 (d, J = 17.1 Hz, 2H), 3.45 (s, 3H). |
| 570 | LCMS (ESI) m/z: 366.0 [M + H]⁺. ¹H NMR (400 MHz, DMSO-d₆) δ 11.33 (s, 1H), 8.90 (d, J = 5.0 Hz, 1H), 8.54 (d, J = 0.8 Hz, 1H), 8.37 (d, J = 2.1 Hz, 1H), 8.16 (dd, J = 5.0, 1.7 Hz, 1H), 8.12 (d, J = 8.5 Hz, 1H), 7.76 (dd, J = 8.5, 2.3 Hz, 1H), 7.36 (td, J = 8.0, 6.4 Hz, 1H), 7.18-7.09 (m, 2H), 7.04 (td, J = 8.4, 2.1 Hz, 1H), 4.00 (s, 2H), 3.93 (s, 3H). |
| 571 | LCMS (ESI) m/z: 391.0 [M + H]⁺. ¹H NMR (400 MHz, DMSO-d₆) δ 10.15 (s, 1H), 8.30 (s, 1H), 8.08 (d, J = 8.5 Hz, 1H), 7.95 (d, J = 9.7 Hz, 1H), 7.69 (d, J = 8.4 Hz, 1H), 7.47 (d, J = 17.8, 8.8 Hz, 1H), 7.30 (dd, J = 8.5, 4.2 Hz, 1H), 7.08 (d, J = 9.7 Hz, 1H), 4.11 (s, 2H), 3.79 (s, 3H). |
| 572 | LCMS (ESI) m/z: 390.0 [M + H]⁺. ¹H NMR (400 MHz, DMSO-d₆) δ 10.55 (s, 1H), 8.67 (d, J = 2.6 Hz, 1H), 8.27 (d, J = 2.0 Hz, 1H), 8.06 (d, J = 8.5 Hz, 1H), 7.98 (dd, J = 9.5, 2.7 Hz, 1H), 7.63 (dd, J = 8.6, 2.4 Hz, 1H), 7.47 (d, J = 18.3, 8.5 Hz, 1H), 7.33-7.23 (m, 1H), 6.43 (d, J = 9.5 Hz, 1H), 4.09 (s, 2H), 3.50 (s, 3H). |
| 573 | LCMS (ESI) m/z: 359.2 [M + H]+. ¹H NMR (300 MHz, DMSO-d₆) δ 10.34 (s, 1H), 8.31 (d, J = 2.9 Hz, 1H), 8.22 (dd, J = 9.1, 1.6 Hz, 1H), 7.97 (dd, J = 9.7, 1.5 Hz, 1H), 7.75 (dt, J = 9.0, 2.2 Hz, 1H), 7.17-6.93 (m, 2H), 6.83 (dt, J = 8.6, 2.0 Hz, 2H), 3.80 (s, 3H); |

| CMPD No. | Characterization Data |
|---|---|
| 574 | LCMS (ESI) m/z: 381.1 [M + H]⁺. ¹H NMR (400 MHz, DMSO-d₆) δ 10.56 (s, 1H), 8.68 (s, 1H), 8.34 (s, 1H), 8.06 (d, J = 8.5 Hz, 1H), 7.98 (dd, J = 9.5, 2.4 Hz, 1H), 7.90-7.80 (m, 1H), 7.73 (m, 2H), 6.43 (d, J = 9.5 Hz, 1H), 3.99 (s, 2H), 3.50 (s, 3H). |
| 575 | LCMS (ESI) m/z: 389.0 [M + H]⁺. ¹H NMR (400 MHz, DMSO-d₆) δ 8.34 (d, J = 2.0 Hz, 1H), 8.09 (d, J = 8.5 Hz, 1H), 7.95 (d, J = 9.7 Hz, 1H), 7.75 (dd, J = 8.5, 2.4 Hz, 1H), 7.52 (dd, J = 11.6, 6.0 Hz, 2H), 7.33 (d, J = 11.9 Hz, 1H), 7.18 (t, J = 56.0 Hz, 1H), 7.08 (d, J = 9.7 Hz, 1H), 4.03 (s, 2H), 3.79 (s, 3H). |
| 576 | LCMS (ESI) m/z: 351.9 [M + H]⁺. ¹H NMR (400 MHz, DMSO-d₆) δ 10.79 (s, 1H), 8.63 (d, J = 8.7 Hz, 1H), 8.56 (d, J = 8.7 Hz, 1H), 8.39 (s, 1H), 8.14 (d, J = 8.5 Hz, 1H), 7.81 (dd, J = 8.5, 2.3 Hz, 1H), 7.37 (m, 2H), 7.14 (s, 1H), 3.99 (s, 2H). |
| 577 | LCMS (ESI) m/z: 374.9 [M + H]⁺. ¹H NMR (400 MHz, DMSO-d₆) δ 10.66 (s, 1H), 8.29 (d, J = 14.3 Hz, 1H), 7.90 (d, J = 9.7 Hz, 1H), 7.79 (dd, J = 10.6, 1.6 Hz, 1H), 7.51-7.30 (m, 2H), 7.27-7.12 (m, 1H), 7.06 (d, J = 9.7 Hz, 1H), 4.04 (s, 2H), 3.78 (s, 3H). |
| 578 | LCMS (ESI) m/z: 365.0 [M + H]⁺. ¹H NMR (400 MHz, DMSO-d₆) δ 11.30 (s, 1H), 8.88 (d, J = 4.9 Hz, 1H), 8.81 (d, J = 5.0 Hz, 1H), 8.48 (d, J = 1.0 Hz, 1H), 8.36 (d, J = 2.0 Hz, 1H), 8.14-8.06 (m, 2H), 7.75 (dd, J = 8.6, 2.4 Hz, 1H), 7.41-7.31 (m, 1H), 7.13 (t, J = 7.0 Hz, 2H), 7.05 (t, J = 8.6 Hz, 1H), 4.00 (s, 2H), 2.85 (d, J = 4.8 Hz, 3H). |
| 579 | LCMS (ESI) m/z: 333.1 [M + H]⁺. ¹H NMR (400 MHz, DMSO-d₆) δ 11.24 (s, 1H), 9.31 (s, 1H), 9.20 (s, 1H), 8.83 (d, J = 1.9 Hz, 1H), 8.36 (s, 1H), 8.12 (d, J = 8.5 Hz, 1H), 7.76 (d, J = 8.6 Hz, 1H), 7.36 (dd, J = 14.3, 6.5 Hz, 1H), 7.20-7.09 (m, 2H), 7.04 (t, J = 8.6 Hz, 1H), 4.0 (s, 2H). |
| 580 | LCMS (ESI) m/z: 356.0 [M + H]⁺. ¹H NMR (400 MHz, DMSO-d₆) δ 11.18 (s, 1H), 9.08 (d, J = 11.2 Hz, 1H), 8.75 (d, J = 11.4 Hz, 1H), 8.39 (dd, J = 25.3, 11.2 Hz, 2H), 8.10 (dd, J = 12.6, 8.5 Hz, 1H), 7.80 (d, J = 9.2 Hz, 1H), 7.04 (s, 3H), 4.65 (d, J = 12.6 Hz, 2H), 3.99 (d, J = 12.4 Hz, 2H). |
| 581 | LCMS (ESI) m/z: 341.1 [M + H]⁺. ¹H NMR (400 MHz, DMSO-d₆) δ 11.21 (s, 1H), 9.18 (s, 2H), 8.37 (d, J = 1.9 Hz, 1H), 8.13 (d, J = 8.5 Hz, 1H), 7.77 (dd, J = 8.5, 2.3 Hz, 1H), 7.06 (dd, J = 11.5, 4.5 Hz, 3H), 4.00 (s, 2H), 2.70 (s, 3H). |
| 582 | LCMS (ESI) m/z: 370.0 [M + H]⁺. ¹H NMR (400 MHz, DMSO-d₆) δ 10.63 (s, 1H), 8.64 (d, J = 2.6 Hz, 1H), 8.31 (d, J = 1.9 Hz, 1H), 8.06 (d, J = 8.5 Hz, 1H), 7.94 (dd, J = 9.5, 2.7 Hz, 1H), 7.69 (dd, J = 8.6, 2.4 Hz, 1H), 7.44-7.30 (m, 2H), 7.19-7.00 (m, 1H), 6.43 (d, J = 9.5 Hz, 1H), 3.97 (dd, J = 13.4, 6.2 Hz, 4H), 1.27 (t, J = 7.1 Hz, 3H). |
| 583 | LCMS (ESI) m/z: 370.0 [M + H]⁺. ¹H NMR (400 MHz, DMSO-d₆) δ 10.64 (s, 1H), 8.65 (d, J = 2.6 Hz, 1H), 8.33 (d, J = 2.0 Hz, 1H), 8.07 (d, J = 8.6 Hz, 1H), 7.94 (dd, J = 9.5, 2.7 Hz, 1H), 7.72 (dd, J = 8.6, 2.4 Hz, 1H), 7.06 (d, J = 12.9, 4.5 Hz, 3H), 6.43 (d, J = 9.5 Hz, 1H), 4.05-3.91 (m, 4H), 1.28 (t, J = 7.1 Hz, 3H). |
| 584 | LCMS (ESI) m/z: 337.3 [M + H]⁺. ¹H NMR (400 MHz, DMSO-d₆) δ 10.23 (s, 1H), 8.48 (t, J = 9.8 Hz, 1H), 8.19 (d, J = 8.6 Hz, 1H), 8.08-7.85 (m, 2H), 7.45-7.20 (m, 2H), 7.14-6.88 (m, 4H), 5.12 (s, 2H), 3.80 (s, 3H). |
| 585 | LCMS (ESI) m/z: 361.0 [M + H]⁺. ¹H NMR (400 MHz, DMSO-d₆) δ 10.61 (s, 1H), 8.37 (dd, J = 5.5, 3.3 Hz, 2H), 8.20 (d, J = 8.9 Hz, 1H), 8.14 (d, J = 8.5 Hz, 1H), 7.79 (dd, J = 8.5, 2.3 Hz, 1H), 7.38 (ddt, J = 14.0, 11.0, 5.3 Hz, 2H), 7.17-7.08 (m, 1H), 3.98 (s, 2H). |
| 586 | LCMS (ESI) m/z: 359.2 [M + H]+. ¹H NMR (300 MHz, DMSO-d₆) δ 10.34 (s, 1H), 8.37-8.30 (m, 1H), 8.30-8.16 (m, 1H), 7.96 (d, J = 9.7 Hz, 1H), 7.74 (dd, J = 9.0, 3.0 Hz, 1H), 7.24 (dt, J = 8.7, 2.1 Hz, 1H), 7.09 (d, J = 9.7 Hz, 1H), 6.99 (dt, J = 8.5, 2.3 Hz, 2H), 3.80 (s, 3H); |
| 587 | LCMS (ESI) m/z: 358.2 [M + H]+. ¹H NMR (300 MHz, DMSO-d₆) δ 10.66 (s, 1H), 8.67 (d, J = 2.7 Hz, 1H), 8.27-8.11 (m, 2H), 7.99 (dd, J = 9.6, 2.7 Hz, 1H), 7.60 (dd, J = 9.0, 3.0 Hz, 1H), 7.47 (dt, J = 10.5, 9.2 Hz, 1H), 7.28 (ddd, J = 11.8, 6.8, 3.0 Hz, 1H), 6.90 (dtd, J = 9.2, 3.3, 1.8 Hz, 1H), 6.44 (d, J = 9.5 Hz, 1H), 3.50 (s, 3H); |
| 588 | LCMS (ESI) m/z: 358.3 [M + H]+. ¹H NMR (300 MHz, DMSO-d₆) δ 10.71 (s, 1H), 8.68 (d, J = 2.7 Hz, 1H), 8.28 (dd, J = 3.0, 0.6 Hz, 1H), 8.21 (dd, J = 9.0, 0.7 Hz, 1H), 8.00 (dd, J = 9.6, 2.7 Hz, 1H), 7.69 (dd, J = 9.0, 3.0 Hz, 1H), 7.03 (tt, J = 9.4, 2.3 Hz, 1H), 6.87-6.75 (m, 2H), 6.44 (d, J = 9.5 Hz, 1H), 3.57 (s, 3H), 3.50 (s, 3H). |
| 589 | LCMS (ESI) m/z: 374.1 [M + H]+. ¹H NMR (300 MHz, DMSO-d₆) δ 10.71 (s, 1H), 8.68 (d, J = 2.6 Hz, 1H), 8.28 (dd, J = 3.0, 0.7 Hz, 1H), 8.21 (dd, J = 9.1, 0.7 Hz, 1H), 8.00 (dd, J = 9.5, 2.7 Hz, 1H), 7.69 (dd, J = 9.1, 3.0 Hz, 1H), 7.22 (dt, J = 8.7, 2.1 Hz, 1H), 7.04-6.90 (m, 2H), 6.44 (d, J = 9.5 Hz, 1H), 3.50 (s, 3H); |
| 590 | LCMS (ESI) m/z: 357.1 [M + H]⁺. ¹H NMR (400 MHz, DMSO-d₆) δ 10.16 (s, 1H), 8.55 (d, J = 6.5 Hz, 1H), 8.38 (d, J = 1.9 Hz, 1H), 8.12 (d, J = 8.5 Hz, 1H), 7.81 (dd, J = 8.5, 2.3 Hz, 1H), 7.16-6.93 (m, 4H), 4.00 (s, 2H), 3.54 (s, 3H). |
| 591 | LCMS (ESI) m/z: 352.1 [M + H]⁺. ¹H NMR (400 MHz, DMSO-d₆) δ 10.49 (s, 1H), 9.43 (s, 1H), 9.39 (d, J = 1.6 Hz, 1H), 8.36 (d, J = 2.0 Hz, 1H), 8.13 (d, J = 8.8 Hz, 1H), 7.80 (dd, J₁ = 2.4 Hz, J₂ = 8.4 Hz, 1H), 7.41-7.33 (m, 2H), 7.14-7.11 (m, 1H), 3.98 (s, 2H); |
| 592 | LCMS (ESI) m/z: 361.1 [M + H]⁺. ¹H NMR (400 MHz, DMSO-d₆) δ 11.20 (s, 1H), 9.15 (d, J = 1.8 Hz, 1H), 8.92 (d, J = 4.8 Hz, 1H), 8.50 (dd, J = 8.1, 2.1 Hz, 1H), 8.36 |

-continued

| CMPD No. | Characterization Data |
|---|---|
| | (d, J = 1.9 Hz, 1H), 8.13 (dd, J = 8.3, 2.0 Hz, 2H), 7.75 (dd, J = 8.5, 2.3 Hz, 1H), 7.43-7.14 (m, 4H), 3.99 (s, 2H), 2.85 (d, J = 4.8 Hz, 3H). |
| 593 | LCMS (ESI) m/z: 383.1 [M + H]⁺. ¹H NMR (400 MHz, DMSO-d₆) δ 11.22 (s, 1H), 9.15 (s, 1H), 8.94 (d, J = 4.7 Hz, 1H), 8.50 (d, J = 8.1 Hz, 1H), 8.35 (s, 1H), 8.13 (d, J = 8.0 Hz, 2H), 7.75 (d, J = 8.5 Hz, 1H), 7.37 (dd, J = 18.9, 8.5 Hz, 2H), 7.13 (s, 1H), 3.98 (s, 2H), 2.85 (d, J = 4.5 Hz, 3H). |
| 594 | LCMS (ESI) m/z: 350.1 [M + H]+. ¹H NMR (400 MHz, CF₃COOD)δ9.01 (s, 1H), 8.81 (s, 1H), 8.46-8.42 (m, 2H), 7.89 (d, J = 8.8 Hz, 1H), 7.55-7.50 (m, 2H), 7.42 (d, J = 8.8 Hz, 1H), 4.67 (q, J = 7.6 Hz, 2H), 4.36 (s, 2H), 1.78 (t, J = 7.2 Hz, 3H); |
| 595 | LCMS (ESI) m/z: 348.1 [M + H]+. ¹H NMR (400 MHz, DMSO-d₆) δ 11.20 (s, 1H), 9.18 (s, 2H), 8.39 (d, J = 2.4 Hz, 1H), 8.13 (d, J = 8.4 Hz, 1H), 7.79 (dd, J = 8.4, 2.4 Hz, 1H), 7.72-7.69 (m, 2H), 7.60-7.57 (m, 1H), 4.05 (s, 2H), 2.70 (s, 3H); |
| 596 | LCMS (ESI) m/z: 387.1 [M + H]⁺. ¹H NMR (400 MHz, DMSO-d₆) δ 10.06 (s, 1H), 8.36 (s, 1H), 8.10 (d, J = 8.5 Hz, 1H), 7.79 (dd, J = 8.0, 2.1 Hz, 1H), 7.26 (s, 1H), 7.06-7.03 (m, 3H), 3.99 (s, 2H), 3.93 (s, 3H), 3.78 (s, 3H). |
| 597 | LCMS (ESI) m/z: 369.1 [M + H]⁺. ¹H NMR (400 MHz, DMSO-v δ 10.11 (s, 1H), 8.32 (d, J = 2.1 Hz, 1H), 8.08 (d, J = 8.5 Hz, 1H), 7.95 (d, J = 9.7 Hz, 1H), 7.74 (dd, J = 8.5, 2.3 Hz, 1H), 7.23-7.00 (m, 3H), 6.83-6.77 (m, 1H), 3.95 (d, J = 10.9 Hz, 2H), 3.81 (s, 3H), 3.79 (s, 3H). |
| 598 | LCMS (ESI) m/z: 375.2 [M + H]⁺. ¹H NMR (400 MHz, DMSO-d₆) δ 9.82 (s, 1H), 8.45 (s, 1H), 8.14 (d, J = 8.5 Hz, 1H), 8.02-7.77 (m, 1H), 7.37 (dd, J = 19.7, 9.6 Hz, 1H), 7.20 (ddd, J = 12.5, 6.9, 3.0 Hz, 1H), 6.88 (d, J = 9.0 Hz, 1H), 5.10 (s, 2H), 3.37 (s, 3H), 2.86 (t, J = 8.4 Hz, 2H), 2.54 (d, J = 8.5 Hz, 2H). |
| 599 | LCMS (ESI) m/z: 355.3 [M + H]⁺. ¹H NMR (400 MHz, DMSO-d₆)) δ 10.23 (s, 1H), 8.48 (d, J = 1.9 Hz, 1H), 8.19 (d, J = 8.4 Hz, 1H), 7.97 (dd, J = 9.1, 3.3 Hz, 2H), 7.35-6.85 (m, 5H), 5.10 (s, 2H), 3.80 (s, 3H). |
| 600 | LCMS (ESI) m/z: 336.2 [M + H]⁺. ¹H NMR (400 MHz, DMSO-d₆) δ 10.64 (s, 1H), 8.69 (d, J = 2.1 Hz, 1H), 8.47 (s, 1H), 8.16 (d, J = 8.6 Hz, 1H), 8.06-7.79 (m, 2H), 7.31 (t, J = 7.8 Hz, 2H), 7.16-6.89 (m, 3H), 6.44 (d, J = 9.5 Hz, 1H), 5.11 (s, 2H), 3.51 (s, 3H). |
| 601 | LCMS (ESI) m/z: 394.0 [M + H]⁺. ¹H NMR (400 MHz, DMSO-d₆) δ 11.23 (s, 1H), 8.92 (d, J = 2.1 Hz, 1H), 8.66 (d, J = 2.1 Hz, 1H), 8.38 (d, J = 1.9 Hz, 1H), 8.11 (d, J = 8.5 Hz, 1H), 7.77 (dd, J = 8.5, 2.3 Hz, 1H), 7.22-6.86 (m, 3H), 4.00 (s, 2H). |
| 602 | LCMS (ESI) m/z: 361.0/363.0 [M + H]⁺. ¹H NMR (400 MHz, DMSO-d₆) δ 10.28 (s, 1H), 9.14 (s, 1H), 8.97 (s, 1H), 8.35 (s, 1H), 8.14 (d, J = 8.4 Hz, 1H), 7.79 (d, J = 8.4 Hz, 1H), 7.40-7.32 (m, 2H), 7.13 (bs, 1H), 3.97 (s, 2H); |
| 603 | LCMS (ESI) m/z: 357.1 [M + H]⁺. ¹H NMR (400 MHz, DMSO-d₆) δ 10.48 (s, 1H), 8.96 (s, 2H), 8.33 (d, J = 1.6 Hz, 1H), 8.18 (d, J = 8.4 Hz, 1H), 7.78 (dd, J₁ = 2.0 Hz, J₂ = 8.4 Hz, 1H), 7.40-7.32 (m, 2H), 7.13-7.10 (m, 1H), 5.63 (bs, 1H), 4.68 (s, 2H), 3.97 (s, 2H); |
| 604 | LCMS (ESI) m/z: 371.1 [M + H]⁺. ¹H NMR (400 MHz, DMSO-d₆) δ 10.47 (s, 1H), 9.00 (s, 2H), 8.33 (d, J = 2.0 Hz, 1H), 8.18 (d, J = 8.8 Hz, 1H), 7.78 (dd, J₁ = 2.0 Hz, J₂ = 8.4 Hz, 1H), 7.40-7.32 (m, 2H), 7.13-7.10 (m, 1H), 5.66 (d, J = 4.4 Hz, 1H), 4.96-4.93 (m, 1H), 1.44 (d, J = 6.4 Hz, 3H), 3.97 (s, 2H); |
| 605 | LCMS (ESI) m/z: 384.0/386.0 [M + H]⁺. ¹H NMR (400 MHz, DMSO-d₆) δ 10.99 (s, 1H), 9.05 (d, J = 2.0 Hz, 1H), 8.33 (dd, J₁ = 2.0 Hz, J₂ = 8.4 Hz, 2H), 8.12 (d, J = 8.4 Hz, 1H), 7.73 (dd, J₁ = 2.4 Hz, J₂ = 8.4 Hz, 1H), 7.60 (d, J = 8.0 Hz, 1H), 7.36-7.32 (m, 2H), 7.28-7.23 (m, 2H), 5.57 (d, J = 4.4 Hz, 1H), 4.77 (m, 1H), 4.66-4.64 (m, 1H), 3.98 (s, 2H), 3.73-3.70 (m, 1H), 3.54-3.50 (m, 1H); |
| 606 | LCMS (ESI) m/z: 362.1 [M + H]⁺. ¹H NMR (500 MHz, TFA) 69.15 (s, 1H), 9.04 (s, 1H), 8.99 (d, J = 9.0 Hz, 1H), 8.62 (d, J = 8.9 Hz, 1H), 8.04 (d, J = 7.2 Hz, 1H), 7.90 (d, J = 8.7 Hz, 1H), 4.87 (s, 2H), 3.68 (s, 3H), 3.61 (s, 3H). |
| 607 | LCMS (ESI) m/z: 375.2 [M + H]⁺. ¹H NMR (400 MHz, DMSO-d₆) δ 9.83 (s, 1H), 8.45 (s, 1H), 8.14 (d, J = 8.5 Hz, 1H), 7.95 (d, J = 8.4 Hz, 1H), 7.31 (dt, J = 8.8, 7.4 Hz, 2H), 7.04 (s, 1H), 5.16 (s, 2H), 3.37 (s, 3H), 2.86 (t, J = 8.5 Hz, 2H), 2.54 (d, J = 8.5 Hz, 2H). |
| 608 | LCMS (ESI) m/z: 385.0 [M + H]⁺. ¹H NMR (400 MHz, DMSO-d₆) δ 11.37 (s, 1H), 9.15 (d, J = 1.7 Hz, 1H), 8.76 (d, J = 1.8 Hz, 1H), 8.39 (d, J = 2.1 Hz, 1H), 8.12 (d, J = 8.5 Hz, 1H), 7.79 (dd, J = 8.5, 2.3 Hz, 1H), 7.20-6.98 (m, 3H), 4.01 (s, 2H). |
| 609 | LCMS (ESI) m/z: 378.1 [M + H]⁺. ¹H NMR (400 MHz, DMSO-d₆) δ 10.05 (s, 1H), 8.36 (d, J = 2.0 Hz, 1H), 8.09 (d, J = 8.5 Hz, 1H), 7.88 (s, 1H), 7.79 (dd, J = 8.0, 2.3 Hz, 1H), 7.70-7.68 (m, 2H), 7.58 (d, J = 9.9 Hz, 1H), 4.05 (s, 2H), 3.79 (s, 3H), 2.17 (s, 3H). |
| 610 | LCMS (ESI) m/z: 378.1 [M + H]⁺. ¹H NMR (400 MHz, DMSO-d₆) δ 10.04 (s, 1H), 8.34 (s, 1H), 8.08 (d, J = 8.5 Hz, 1H), 7.88-7.85 (m, 2H), 7.76 (d, J = 8.4 Hz, 1H), 7.69 (d, J = 8.0 Hz, 1H), 7.47 (t, J = 8.0 Hz, 1H), 4.02 (s, 2H), 3.79 (s, 3H), 2.17 (s, 3H). |
| 611 | LCMS (ESI) m/z: 359.9 [M + H]⁺. ¹H NMR (400 MHz, DMSO-d₆) δ 10.56 (s, 1H), 8.66 (s, 1H), 8.30-8.40 (m, 2H), 8.09-8.16 (m, 1H), 7.70-7.81 (m, 1H), 7.30-7.41 (m, 1H), 7.00-7.18 (m, 3H), 3.99 (s, 2H). |

-continued

| CMPD No. | Characterization Data |
|---|---|
| 612 | LCMS (ESI) m/z: 376.0 [M + H]+. ¹H NMR (400 MHz, DMSO-d₆) δ 11.44 (s, 1H), 9.41 (d, J = 2.0 Hz, 1H), 9.08 (d, J = 2.0 Hz, 1H), 8.41 (t, J = 14.1 Hz, 1H), 8.13 (d, J = 8.5 Hz, 1H), 7.80 (dd, J = 8.6, 2.3 Hz, 1H), 7.20-7.00 (m, 3H), 4.01 (s, 2H). |
| 613 | LCMS (ESI) m/z: 351.1 [M + H]+. ¹H NMR (400 MHz, DMSO-d₆) δ 10.54 (s, 1H), 8.67 (d, J = 2.6 Hz, 1H), 8.31 (d, J = 2.0 Hz, 1H), 8.14-8.03 (m, 2H), 7.98 (dd, J = 9.5, 2.6 Hz, 1H), 7.69 (dd, J = 8.5, 2.3 Hz, 1H), 6.96-6.84 (m, 1H), 6.71 (s, 1H), 6.43 (d, J = 9.5 Hz, 1H), 3.92 (s, 2H), 3.82 (s, 3H), 3.50 (s, 3H). |
| 614 | LCMS (ESI) m/z: 364.0 [M + H]+. ¹H NMR (400 MHz, DMSO-d₆) δ 10.16 (s, 1H), 8.33 (d, J = 1.9 Hz, 1H), 8.10 (d, J = 8.5 Hz, 1H), 7.95 (d, J = 9.7 Hz, 1H), 7.89-7.80 (m, 1H), 7.74 (dd, J = 11.2, 4.2 Hz, 2H), 7.39 (t, J = 7.7 Hz, 1H), 7.08 (d, J = 9.7 Hz, 1H), 4.08 (s, 2H), 3.79 (s, 3H). |
| 615 | LCMS (ESI) m/z: 371.2 [M + H]+. ¹H NMR (400 MHz, DMSO-d₆) δ 10.24 (s, 1H), 8.51 (s, 1H), 8.20 (d, J = 8.4 Hz, 1H), 7.98 (dd, J = 12.4, 5.9 Hz, 2H), 7.45 (d, J = 7.9 Hz, 1H), 7.39-7.25 (m, 2H), 7.09 (d, J = 9.7 Hz, 1H), 6.99 (dd, J = 10.6, 4.3 Hz, 1H), 5.23 (s, 2H), 3.80 (s, 3H). |
| 616 | LCMS (ESI) m/z: 365.1 [M + H]+. ¹H NMR (400 MHz, DMSO-d₆) δ 11.25 (s, 1H), 9.05 (s, 1H), 8.47 (s, 1H), 8.37 (S, 1H), 8.24-8.03 (m, 2H), 7.78 (d, J = 8.5 Hz, 1H), 7.06 (dd, J = 14.7, 8.8 Hz, 3H), 4.27-3.81 (m, 2H), 2.57 (s, 3H). |
| 617 | LCMS (ESI) m/z: 379.0/381.0 [M + H]+. ¹H NMR (400 MHz, DMSO-d₆) δ 10.55 (s, 1H), 8.67 (d, J = 2.8 Hz, 1H), 8.32 (d, J = 2.0 Hz, 1H), 8.06 (d, J = 8.4 Hz, 1H), 7.97 (dd, J₁ = 2.8 Hz, J₂ = 9.6 Hz, 1H), 7.94 (d, J = 2.0 Hz, 1H), 7.72-7.62 (m, 3H), 8.42 (d, J = 9.6 Hz, 1H), 4.00 (s, 2H), 3.49 (s, 3H), ; |
| 618 | LCMS (ESI) m/z: 379.0/381.0 [M + H]+. ¹H NMR (400 MHz, DMSO-d₆) δ 10.56 (s, 1H), 8.67 (d, J = 2.4 Hz, 1H), 8.35 (d, J = 2.0 Hz, 1H), 8.06 (d, J = 8.4 Hz, 1H), 7.97 (dd, J₁ = 2.4 Hz, J₂ = 9.6 Hz, 1H), 7.90 (t, J = 1.6 Hz, 1H), 7.80 (t, J = 1.6 Hz, 1H), 7.77-7.72 (m, 2H), 6.43 (d, J = 9.6 Hz, 1H), 4.01 (s, 2H), 3.49 (s, 3H); |
| 619 | LCMS (ESI) m/z: 374.1 [M + H]+. ¹H NMR (400 MHz, DMSO-d₆) δ 11.07 (s, 1H), 8.80 (d, J = 1.9 Hz, 1H), 8.36 (s, 2H), 8.12 (d, J = 8.5 Hz, 1H), 7.76 (dd, J = 8.5, 2.2 Hz, 1H), 7.22-6.96 (m, 3H), 4.00 ( s, 2H), 2.41 (s, 3H). |
| 620 | LCMS (ESI) m/z: 363.0 [M + H]+. ¹H NMR (400 MHz, DMSO-d₆) δ 10.94 (s, 1H), 8.38 (d, J = 2.0 Hz, 1H), 8.06 (d, J = 8.5 Hz, 1H), 7.81 (d, J = 7.0 Hz, 1H), 7.77 (dd, J = 8.5, 2.3 Hz, 1H), 7.74-7.64 (m, 2H), 7.58 (d, J = 9.8 Hz, 1H), 6.94 (d, J = 1.8 Hz, 1H), 6.61 (dd, J = 7.0, 2.0 Hz, 1H), 4.05 (s, 2H), 3.46 (s, 3H). |
| 621 | LCMS (ESI) m/z: 327.2 [M + H]+. ¹H NMR (300 MHz, Chloroform-d) δ 59.68 (dd, J = 2.4, 1.2 Hz, 1H), 9.48 (dd, J = 5.3, 1.3 Hz, 1H), 8.70 (s, 1H), 8.30 (d, J = 8.5 Hz, 1H), 8.19 (d, J = 2.3 Hz, 1H), 7.93 (dd, J = 5.3, 2.4 Hz, 1H), 7.61 (dd, J = 8.5, 2.4 Hz, 1H), 7.24-6.80 (m, 2H), 3.96 (s, 2H). |
| 622 | LCMS (ESI) m/z: 327.2 [M + H]+. ¹H NMR (300 MHz, Chloroform-d) δ 9.68 (dd, J = 2.4, 1.2 Hz, 1H), 9.48 (dd, J = 5.3, 1.2 Hz, 1H), 8.66 (s, 1H), 8.31 (d, J = 8.5 Hz, 1H), 8.24-8.14 (m, 1H), 7.93 (dd, J = 5.3, 2.4 Hz, 1H), 7.62 (dd, J = 8.6, 2.4 Hz, 1H), 6.70 (ddt, J = 10.1, 4.5, 2.3 Hz, 3H), 3.98 (s, 2H). |
| 623 | LCMS (ESI) m/z: 352.1 [M + H]+. ¹H NMR (400 MHz, DMSO-d₆) δ 10.46 (s, 1H), 8.55 (d, J = 2.5 Hz, 1H), 8.30 (d, J = 2.1 Hz, 1H), 8.06 (d, J = 8.5 Hz, 1H), 7.93-7.88 (m, 1H), 7.69 (dd, J = 8.6, 2.4 Hz, 1H), 7.30-7.36 (m, 1H), 7.10-7.16 (m, 2H), 6.95-7.08 (m, 1H), 3.97 (s, 2H), 3.51 (s, 3H), 2.05 (s, 3H). |
| 624 | LCMS (ESI) m/z: 353.1 [M + H]+. ¹H NMR (400 MHz, DMSO-d₆) δ 8.33 (d, J = 2.0 Hz, 1H), 8.21-8.14 (m, 2H), 7.75 (dd, J = 8.5, 2.3 Hz, 1H), 7.35 (td, J = 8.0, 6.3 Hz, 1H), 7.15-7.08 (m, 2H), 7.03 (td, J = 8.4, 2.3 Hz, 1H), 3.98 (s, 2H), 3.78 (s, 3H), 2.40 (s, 3H). |
| 625 | LCMS (ESI) m/z: 357.0 [M + H]+. ¹H NMR (400 MHz, DMSO-d₆) δ 10.15 (s, 1H), 8.29 (d, J = 2.1 Hz, 1H), 8.08 (d, J = 8.5 Hz, 1H), 7.95 (d, J = 9.7 Hz, 1H), 7.70 (dd, J = 8.5, 2.2 Hz, 1H), 7.41 (dd, J = 15.4, 8.7 Hz, 1H), 7.29-7.19 (m, 1H), 7.06 (dd, J = 13.5, 6.1 Hz, 2H), 3.98 (s, 2H), 3.79 (s, 3H). |
| 626 | LCMS (ESI) m/z: 380.0/382.0 [M + H]+. ¹H NMR (400 MHz, CDCl₃) δ 9.47 (s, 1H), 8.30 (d, J = 8.8 Hz, 1H), 8.20 (s, 1H), 8.05 (d, J = 9.6 Hz, 1H), 7.55-7.52 (m, 2H), 7.40 (s, 1H), 7.36 (s, 1H), 7.04 (d, J = 10.0 Hz, 1H), 3.99 (s, 2H), 3.89 (s, 3H); |
| 627 | LCMS (ESI) m/z: 334.0 [M + H]+. ¹H NMR (400 MHz, DMSO-d₆) δ 10.95 (s, 1H), 9.29-9.16 (m, 2H), 8.72 (d, J = 1.7 Hz, 1H), 8.14 (d, J = 8.0 Hz, 1H), 7.97 (dd, J = 8.0, 2.1 Hz, 1H), 7.45-7.32 (m, 1H), 7.25-7.13 (m, 2H), 7.09-7.04 (m, 1H), 4.15 (s, 2H). |
| 628 | LCMS (ESI) m/z: 363.1 [M + H]+. ¹H NMR (400 MHz, DMSO-d₆) δ 11.08 (s, 1H), 9.01 (d, J = 2.1 Hz, 1H), 8.69 (d, J = 1.9 Hz, 1H), 8.38 (d, J = 2.0 Hz, 1H), 8.26 (d, J = 2.0 Hz, 1H), 8.13 (d, J = 8.5 Hz, 1H), 7.78 (dd, J = 8.6, 2.4 Hz, 1H), 7.74-7.66 (m, 2H), 7.62-7.55 (m, 1H), 5.49 (s, 1H), 4.62 (s, 2H), 4.05 (s, 2H). |
| 629 | LCMS (ESI) m/z: 351.1 [M + H]+. ¹H NMR (400 MHz, DMSO-d₆) δ 11.32 (s, 1H), 9.22 (d, J = 1.6 Hz, 1H), 8.53 (dd, J₁ = 2.4 Hz, J₂ = 8.4 Hz, 1H), 8.34 (d, J = 1.6 Hz, 1H), 8.20 (d, J = 8.0 Hz, 1H), 8.12 (d, J = 8.4 Hz, 1H), 7.73 (dd, J₁ = 2.4 Hz, J₂ = 8.4 Hz, 1H), 7.28-7.21 (m, 2H), 7.15-7.12 (m, 1H), 3.99 (s, 2H); |
| 630 | LCMS (ESI) m/z: 356.1 [M + H]+. ¹H NMR (400 MHz, DMSO-d₆) δ 10.95 (s, 1H), 8.32 (d, J = 1.5 Hz, 1H), 8.05 (d, J-8.5 Hz, 1H), 7.81 (d, J-7.0 Hz, 1H), 7.70 (dd, J = 8.5, 2.0 Hz, 1H), 7.35-7.19 (m, 2H), 7.14 (dd, J = 7.8, |

| CMPD No. | Characterization Data |
|---|---|
| | 3.8 Hz, 1H), 6.94 (d, J = 1.5 Hz, 1H), 6.61 (dd, J = 7.0, 1.8 Hz, 1H), 3.99 (s, 2H), 3.46 (s, 3H). |
| 631 | LCMS (ESI) m/z: 389.0 [M + H]+. $^1$H NMR (400 MHz, DMSO-d$_6$) δ 10.72 (s, 1H), 8.91 (d, J = 6.0 Hz, 2H), 8.70 (d, J = 1.6 Hz, 1H), 8.12 (d, J = 8.0 Hz, 1H), 7.96 (dd, J = 80, 2.1 Hz, 1H), 7.46-7.34 (m, 1H), 7.25-7.12 (m, 2H), 7.09-7.04 (m, 1H), 4.14 (s, 2H). |
| 632 | LCMS (ESI) m/z: 393.9 [M + H]+. $^1$H NMR (400 MHz, DMSO-d$_6$) δ 9.90 (s, 1H), 8.56 (s, 1H), 8.33 (d, J = 1.5 Hz, 1H), 8.09 (d, J = 8.5 Hz, 1H), 7.75 (dd, J = 8.5, 1.9 Hz, 1H), 7.35 (dd, J = 14.4, 7.9 Hz, 1H), 7.12 (t, J = 7.4 Hz, 2H), 7.04 (dd, J = 11.9, 5.3 Hz, 1H), 3.98 (s, 2H). |
| 633 | LCMS (ESI) m/z: 314.1 [M + H]+. $^1$H NMR (400 MHz, DMSO-d$_6$) δ 9.90 (s, 1H), 9.28 (d, J = 1.7 Hz, 1H), 8.61 (d, J = 1.7 Hz, 1H), 8.32 (s, 1H), 8.14 (d, J = 8.5 Hz, 1H), 7.76 (dd, J = 8.4, 1.9 Hz, 1H), 7.35 (dd, J = 14.3, 7.9 Hz, 1H), 7.23-7.08 (m, 2H), 7.04 (t, J = 7.6 Hz, 1H), 3.98 (s, 2H). |
| 634 | LCMS (ESI) m/z: 373.0 [M + H]+. $^1$H NMR (400 MHz, DMSO-d$_6$) δ 10.28 (s, 1H), 9.14 (d, J = 1.2 Hz, 1H), 8.97 (d, J = 1.2 Hz, 1H), 8.35 (d, J = 2.0 Hz, 1H), 8.14 (d, J = 8.4 Hz, 1H), 7.79 (dd, J = 8.4, 2.2 Hz, 1H), 7.20-7.03 (m, 2H), 6.86-6.71 (m, 1H), 3.95 (s, 2H), 3.82 (s, 3H). |
| 635 | LCMS (ESI) m/z: 361.0 [M + H]+. $^1$H NMR (400 MHz, DMSO-d$_6$) δ 10.30 (s, 1H), 9.15 (d, J = 1.2 Hz, 1H), 8.97 (d, J = 1.2 Hz, 1H), 8.38 (d, J = 2.0 Hz, 1H), 8.16 (d, J = 8.4 Hz, 1H), 7.82 (dd, J = 8.4, 2.4 Hz, 1H), 7.16-6.97 (m, 3H), 4.00 (s, 2H). |
| 636 | LCMS (ESI) m/z: 351.1 [M + H]+. $^1$H NMR (400 MHz, DMSO-d$_6$) δ 10.87 (s, 1H), 9.03 (s, 1H), 8.67 (d, J = 10.1 Hz, 1H), 8.34 (s, 1H), 8.12 (d, J = 7.8 Hz, 1H), 7.78 (d, J = 8.4 Hz, 1H), 7.35 (dd, J = 14.4, 7.9 Hz, 1H), 7.19-6.96 (m, 3H), 3.99 (s, 2H). |
| 637 | LCMS (ESI) m/z: 326.1 [M + H]+. $^1$H NMR (400 MHz, DMSO-d$_6$) δ 11.05 (s, 1H), 9.06 (d, J = 1.9 Hz, 1H), 8.36 (dd, J = 8.2, 2.3 Hz, 1H), 8.27 (d, J = 2.2 Hz, 1H), 8.17 (d, J = 8.6 Hz, 1H), 7.74 (dd, J = 8.6, 2.3 Hz, 1H), 7.59 (d, J = 8.2 Hz, 1H), 6.32 (s, 1H), 5.61 (s, 1H), 4.64 (s, 2H), 3.69 (t, J = 5.4 Hz, 2H), 3.60 (t, J = 5.5 Hz, 2H), 2.47 (t, J = 5.4 Hz, 2H), 2.36 (t, J = 5.0 Hz, 2H). |
| 638 | LCMS (ESI) m/z: 364.1 [M + H]+. $^1$H NMR (400 MHz, DMSO-d$_6$) δ 10.48 (s, 1H), 9.44 (d, J = 1.2 Hz, 1H), 9.39 (d, J = 1.2 Hz, 1H), 8.37 (d, J = 1.8 Hz, 1H), 8.14 (d, J = 8.4 Hz, 1H), 7.80 (dd, J = 8.5, 2.2 Hz, 1H), 7.12 (m, 2H), 6.80 (m, 1H), 3.95 (s, 2H), 3.82 (s, 3H). |
| 639 | LCMS (ESI) m/z: 352.0 [M + H]+. $^1$H NMR (400 MHz, DMSO-d$_6$) δ 10.50 (s, 1H), 9.44 (s, 1H), 9.39 (s, 1H), 8.39 (s, 1H), 8.15 (d, J = 8.4 Hz, 1H), 7.83 (d, J = 8.4 Hz, 1H), 7.05 (d, J = 8.6 Hz, 3H), 4.01 (s, 2H). |
| 640 | LCMS (ESI) m/z: 339.0 [M + H]+. $^1$H NMR (400 MHz, DMSO-d$_6$) δ 10.27 (s, 1H), 8.98 (s, 1H), 8.35 (d, J = 1.9 Hz, 1H), 8.07 (d, J = 8.5 Hz, 1H), 7.76 (dd, J = 8.5, 2.2 Hz, 1H), 7.35 (dd, J = 14.3, 8.0 Hz, 1H), 7.13 (t, J = 7.4 Hz, 2H), 7.04 (t, J = 8.6 Hz, 3H), 3.99 (s, 2H). |
| 641 | LCMS (ESI) m/z: 364.0 [M + H]+. $^1$H NMR (400 MHz, DMSO-d$_6$) δ 10.16 (s, 1H), 8.33 (d, J = 2.0 Hz, 1H), 8.09 (d, J = 8.5 Hz, 1H), 7.99-7.96 (m, 1H), 7.95 (d, J = 9.8 Hz, 1H), 7.89-7.81 (m, 1H), 7.74 (dd, J = 8.5, 2.2 Hz, 1H), 7.50-7.39 (m, 1H), 7.08 (d, J = 9.7 Hz, 1H), 4.05 (s, 2H), 3.79 (s, 3H). |
| 642 | LCMS (ESI) m/z: 341.1 [M + H]+ $^1$H NMR (400 MHz, DMSO-d6) δ 10.41 (S, 1H), 8.28 (d, J = 1.6 Hz, 1H), 7.99 (d, J = 8.8 Hz, 1H), 7.77 (S, 1H), 7.66 (dd, J$_1$ = 2.4 Hz, J$_2$ = 8.8 Hz, 1H), 7.35 (dd, J$_1$ = 7.6 Hz, J$_2$ = 14.0 Hz, 1H), 7.10-7.13 (m, 2H), 7.01-7.06 (m, 1H), 3.96 (s, 2H), 3.38 (s, 3H), 3.22 (s, 3H);. |
| 643 | LCMS (ESI) m/z: 359.0 [M + H]+. $^1$H NMR (400 MHz, DMSO-d6) δ 10.41 (S, 1H), 8.27 (d, J = 2.0 Hz, 1H), 7.99 (d, J = 8.4 Hz, 1H), 7.77 (S, 1H), 7.65 (dd, J$_1$ = 2.0 Hz, J$_2$ = 8.4 Hz, 1H), 7.33-7.39 (m, 2H), 7.09-7.12 (m, 1H), 3.93 (s, 2H), 3.38 (s, 3H), 3.22 (s, 3H); |
| 644 | LCMS (ESI) m/z: 359.1 [M + H]+. $^1$H NMR (400 MHz, DMSO-d6) δ 10.42 (S, 1H), 8.30 (d, J = 2.0 Hz, 1H), 8.00 (d, J = 8.4 Hz, 1H), 7.78 (S, 1H), 7.69 (dd, J$_1$ = 2.0 Hz, J$_2$ = 8.4 Hz, 1H), 7.03-7.10 (m, 3H), 3.96 (s, 2H), 3.38 (s, 3H), 3.22 (s, 3H); |
| 645 | LCMS (ESI) m/z: 332.1 [M + H]+. $^1$H NMR (400 MHz, DMSO-d$_6$) δ 10.08 (s, 1H), 9.00 (s, 1H), 8.33 (d, J = 1.9 Hz, 1H), 8.04 (d, J = 8.5 Hz, 1H), 7.74 (dd, J = 8.5, 2.3 Hz, 1H), 7.35 (td, J = 8.0, 6.4 Hz, 1H), 7.12 (dd, J = 10.5, 4.4 Hz, 2H), 7.04 (td, J = 8.7, 2.4 Hz, 1H), 3.98 (s, 2H). |
| 646 | LCMS (ESI) m/z: 368.1 [M + H]+. $^1$H NMR (400 MHz, DMSO-d$_6$) δ 510.30 (s, 1H), 9.14 (d, J = 1.6 Hz, 1H), 8.97 (d, J = 1.6 Hz, 1H), 8.40 (d, J = 2.0 Hz, 1H), 8.15 (d, J = 8.4 Hz, 1H), 7.84 (dd, J = 8.4, 2.4 Hz, 1H), 7.70-7.72 (m, 2H), 7.58-7.61 (m, 1H), 4.01 (s, 2H). |
| 647 | LCMS (ESI) m/z: 382.0 [M + H]+. $^1$H NMR (400 MHz, DMSO-d$_6$) δ 10.56 (s, 1H), 8.67 (d, J = 2.5 Hz, 1H), 8.26 (d, J = 2.0 Hz, 1H), 8.06 (d, J = 8.6 Hz, 1H), 7.98 (dd, J = 9.5, 2.5 Hz, 1H), 7.73 (dd, J = 8.7, 2.4 Hz, 1H), 7.44-7.24 (m, 2H), 7.09 (brs, 1H), 6.43 (d, J = 9.5 Hz, 1H), 3.50 (s, 3H), 1.31 (s, 4H). |
| 648 | LCMS (ESI) m/z: 363.1 [M + H]+. $^1$H NMR (400 MHz, DMSO-d$_6$) δ 10.56 (s, 1H), 8.67 (d, J = 2.6 Hz, 1H), 8.30 (d, J = 2.1 Hz, 1H), 8.07 (d, J = 8.6 Hz, 1H), 8.01-7.92 (m, 2H), 7.85-7.72 (m, 1H), 7.68 (dd, J = 8.6, 2.3 Hz, 1H), 7.48-7.40 (m, 1H), 6.43 (d, J = 9.5 Hz, 1H), 4.03 (s, 2H), 3.50 (s, 3H). |

-continued

| CMPD No. | Characterization Data |
|---|---|
| 649 | LCMS (ESI) m/z: 355.0 [M + H]+. ¹H NMR (400 MHz, DMSO-d$_6$) δ 11.06 (s, 1H), 9.14 (s, 2H), 8.34 (d, J = 2.2 Hz, 1H), 8.11 (d, J = 8.5 Hz, 1H), 7.73 (dd, J = 8.5, 2.3 Hz, 1H), 7.35 (dd, J = 9.4, 6.0 Hz, 2H), 7.30-7.20 (m, 2H), 4.00 (s, 3H), 3.98 (s, 2H). |
| 650 | LCMS (ESI) m/z: 326.2 [M + H]+. ¹H NMR (500 MHz, DMSO-d6) δ 11.60 (bs, 1H), 9.58 (s, 1H), 8.29 (d, J = 2.0 Hz, 1H), 8.07 (d, J = 8.5 Hz, 1H), 7.78 (d, J = 8.5 Hz, 1H), 7.36-7.32 (m, 2H), 7.28-7.23 (m, 2H), 5.90 (s, 1H), 4.02-3.97 (m, 4H), 1.32 (t, J = 7.0 Hz, 3H); |
| 651 | LCMS (ESI) m/z: 326.2 [M + H]+. ¹H NMR (300 MHz, Chloroform-d) δ 9.08-8.77 (m, 2H), 8.74 (s, 1H), 8.34 (dd, J = 8.6, 0.8 Hz, 1H), 8.15 (dd, J = 2.3, 0.8 Hz, 1H), 7.88-7.68 (m, 2H), 7.60 (dd, J = 8.5, 2.4 Hz, 1H), 6.70 (dq, J = 7.2, 3.1, 2.4 Hz, 3H), 3.96 (s, 2H). |
| 652 | LCMS (ESI) m/z: 355.0 [M + H]+. ¹H NMR (400 MHz, DMSO-d$_6$) δ 10.73 (s, 1H), 9.06 (d, J = 3.3 Hz, 1H), 8.99 (d, J = 3.3 Hz, 1H), 8.32 (d, J = 2.0 Hz, 1H), 8.06 (d, J = 8.5 Hz, 1H), 7.71 (dd, J = 8.6, 2.4 Hz, 1H), 7.39-7.31 (m, 2H), 7.27 (ddd, J = 13.7, 7.8, 4.3 Hz, 2H), 3.97 (s, 2H), 3.51 (s, 3H). |
| 653 | LCMS (ESI) m/z: 383.1 [M + H]+. ¹H NMR (400 MHz, DMSO-d$_6$) δ 10.15 (s, 1H), 8.29 (d, J = 2.1 Hz, 1H), 8.08 (d, J = 8.6 Hz, 1H), 7.95 (d, J = 9.7 Hz, 1H), 7.79 (dd, J = 8.6, 2.4 Hz, 1H), 7.39-7.28 (m, 2H), 7.05-7.12 (m, 2H), 3.79 (s, 3H), 1.32 (s, 4H). |
| 654 | LCMS (ESI) m/z: 359.1 [M + H]+. ¹H NMR (400 MHz, DMSO-d$_6$) δ 10.50 (s, 1H), 9.42 (s, 1H), 9.40 (s, 1H), 8.39 (s, 1H), 8.14 (d, J = 8.4 Hz, 1H), 7.90 (d, J = 5.8 Hz, 1H), 7.82 (d, J = 8.2 Hz, 1H), 7.71 (s, 1H), 7.48 (t, J = 8.8 Hz, 1H), 4.04 (s, 2H). |
| 655 | LCMS (ESI) m/z: 359.1 [M + H]+. ¹H NMR (400 MHz, DMSO-d$_6$) δ 510.51 (s, 1H), 9.44 (d, J = 1.4 Hz, 1H), 9.40 (d, J = 1.4 Hz, 1H), 8.41 (d, J = 2.0 Hz, 1H), 8.15 (d, J = 8.4 Hz, 1H), 7.85 (dd, J = 8.4, 2.4 Hz, 1H), 7.71 (dd, J = 8.0, 2.0 Hz, 2H), 7.66-7.53 (m, 1H), 4.06 (s, 2H). |
| 656 | LCMS (ESI) m/z: 334.0 [M + H]+. ¹H NMR (400 MHz, DMSO-d$_6$) δ 11.41 (s, 1H), 9.64 (s, 1H), 9.47 (d, J = 5.2 Hz, 1H), 8.41 (s, 1H), 8.14-8.12 (m, 2H), 7.81 (d, J = 8.4 Hz, 1H), 7.73-7.70 (m, 2H), 7.59 (d, J = 9.2 Hz, 1H), 4.06 (s, 2H). |
| 657 | LCMS (ESI) m/z: 361.0 [M + H]+. ¹H NMR (400 MHz, DMSO-d$_6$) δ 11.43 (s, 1H), 9.61 (s, 1H), 8.39 (s, 2H), 8.11 (d, J = 8.4 Hz, 1H), 7.80 (d, J = 6.4 Hz, 1H), 7.10-7.04 (m, 3H), 4.01 (s, 2H). |
| 658 | LCMS (ESI) m/z: 373.0 [M + H]+. ¹H NMR (400 MHz, DMSO-d$_6$) δ 10.26 (s, 1H), 8.50 (d, J = 2.1 Hz, 1H), 8.20 (d, J = 8.5 Hz, 1H), 8.05-7.87 (m, 2H), 7.09 (d, J = 9.7 Hz, 1H), 6.98-6.69 (m, 3H), 5.16 (s, 2H), 3.80 (s, 3H). |
| 659 | LCMS (ESI) m/z: 377.0 [M + H]+. ¹H NMR (400 MHz, DMSO-d$_6$) δ 10.30 (s, 1H), 9.15 (s, 1H), 8.97 (s, 1H), 8.38 (d, J = 1.6 Hz, 1H), 8.16 (d, J = 8.4 Hz, 1H), 7.83 (dd, J = 8.8, 2.0 Hz, 1H), 7.26-7.29 (m, 2H), 7.18 (d, J = 10.0, 1H), 4.00 (s, 2H). |
| 660 | LCMS (ESI) m/z: 411.1 [M + H]+. ¹H NMR (400 MHz, DMSO-d$_6$) δ 10.29 (s, 1H), 8.62 (d, J = 2.5 Hz, 1H), 7.98 (dd, J = 9.5, 2.6 Hz, 1H), 7.94 (d, J = 8.8 Hz, 1H), 7.68 (d, J = 2.8 Hz, 1H), 7.35 (t, J = 8.2 Hz, 1H), 7.08-7.04 (m, 1H), 7.02 (dd, J = 8.9, 2.9 Hz, 1H), 6.98 (t, J = 2.1 Hz, 1H), 6.89 (dd, J = 8.3, 1.9 Hz, 1H), 6.42 (d, J = 9.5 Hz, 1H), 5.25-5.19 (m, 1H), 4.39-4.35 (m, 2H), 3.83 (dd, J = 8.6, 3.9 Hz, 2H), 3.49 (s, 3H). |
| 661 | LCMS (ESI) m/z: 368.1 [M + H]+. ¹H NMR (400 MHz, DMSO-d$_6$) δ 10.51 (s, 1H), 9.44 (d, J = 1.4 Hz, 1H), 9.40 (d, J = 1.4 Hz, 1H), 8.40 (d, J = 2.0 Hz, 1H), 8.15 (d, J = 8.4 Hz, 1H), 7.84 (dd, J = 8.4, 2.4 Hz, 1H), 7.35-7.22 (m, 2H), 7.23-7.13 (m, 1H), 4.01 (s, 2H). |
| 662 | LCMS (ESI) m/z: 352.0 [M + H]+. ¹H NMR (400 MHz, DMSO-d$_6$) δ 11.50 (s, 1H), 9.88 (d, J = 2.1 Hz, 1H), 8.82 (d, J = 2.1 Hz, 1H), 8.40 (d, J = 2.0 Hz, 1H), 8.13 (d, J = 8.5 Hz, 1H), 7.81 (dd, J = 8.5, 2.4 Hz, 1H), 7.22-6.90 (m, 3H), 4.01 (s, 2H). |
| 663 | LCMS (ESI) m/z: 372.1 [M + H]+. ¹H NMR (400 MHz, DMSO-d$_6$) δ 11.26 (s, 1H), 9.04 (d, J = 1.5 Hz, 1H), 8.47 (d, J = 1.3 Hz, 1H), 8.40 (d, J = 1.8 Hz, 1H), 8.13 (d, J = 8.5 Hz, 1H), 7.80 (dd, J = 8.5, 2.3 Hz, 1H), 7.72-7.69 (m, 2H), 7.59 (d, J = 9.8 Hz, 1H), 4.06 (s, 2H), 2.57 (s, 3H). |
| 664 | LCMS (ESI) m/z: 372.9 [M + H]+. ¹H NMR (400 MHz, DMSO-d$_6$) δ 10.25 (s, 1H), 8.49 (d, J = 2.1 Hz, 1H), 8.19 (d, J = 8.5 Hz, 1H), 8.08-7.84 (m, 2H), 7.38 (dd, J = 19.8, 9.4 Hz, 1H), 7.21 (ddd, J = 12.3, 6.6, 2.8 Hz, 1H), 7.09 (d, J = 9.7 Hz, 1H), 6.94-6.82 (m, 1H), 5.12 (s, 2H), 3.80 (s, 3H). |
| 665 | LCMS (ESI) m/z: 381.1 [M + H]+. ¹H NMR (400 MHz, DMSO-d$_6$) δ 11.09 (s, 1H), 8.80 (d, J = 2.2 Hz, 1H), 8.37 (dd, J = 9.5, 1.9 Hz, 2H), 8.12 (d, J = 8.5 Hz, 1H), 7.78 (dd, J = 8.5, 2.4 Hz, 1H), 7.70 (d, J = 5.3 Hz, 2H), 7.59 (d, J = 9.9 Hz, 1H), 4.05 (s, 2H), 2.41 (s, 3H). |
| 666 | LCMS (ESI) m/z: 368.1/370.0 [M + H]+. ¹H NMR (400 MHz, DMSO-d$_6$) δ 10.36 (s, 1H), 9.10 (d, J = 4.8 Hz, 1H), 8.41 (d, J = 2.0 Hz, 1H), 8.15-8.13 (m, 2H), 7.84 (dd, J = 8.4, 2.4 Hz, 1H), 7.72-7.70 (m, 2H), 7.61-7.58 (m, 1H), 4.07 (s, 2H); |
| 667 | LCMS (ESI) m/z: 388.9 [M + H]+. ¹H NMR (400 MHz, DMSO-d$_6$) δ 10.24 (s, 1H), 8.50 (s, 1H), 8.20 (d, J = 8.6 Hz, 1H), 8.06-7.88 (m, 2H), 7.50 (t, J = 8.9 Hz, 1H), 7.20 (dd, J = 11.4, 2.7 Hz, 1H), 7.09 (d, J = 9.7 Hz, 1H), 6.94 (d, J = 11.4 Hz, 1H), 5.15 (s, 2H), 3.80 (s, 3H). |
| 668 | LCMS (ESI) m/z: 375.0/377.0 ¹H NMR (400 MHz, DMSO-d$_6$) δ 10.42 (s, 1H), 8.30 (d, J = 2.4 Hz, 1H), 8.00 (d, J = 8.4 Hz, 1H), 7.77 (s, 1 H), 7.69 (dd, J$_1$ = 2.4 Hz, |

| CMPD No. | | Characterization Data |
|---|---|---|
| | [M + H]⁺. | $J_2$ = 8.4 Hz, 1H), 7.28 (dt, $J_1$ = 2.4 Hz, $J_2$ = 8.8 Hz, 1H), 7.24-(s, 1H), 7.18-7.15 (m, 1H), 3.96 (s, 2H), 3.38 (s, 3H), 3.22 (s, 3H); |
| 669 | LCMS (ESI) m/z: 350.1 [M + H]⁺. | ¹H NMR (400 MHz, DMSO-d₆) δ 11.40 (s, 1H), 9.64 (s, 1H), 9.47 (d, J = 5.3 Hz, 1H), 8.41 (d, J = 1.7 Hz, 1H), 8.14 (dd, J = 8.3, 3.6 Hz, 2H), 7.90 (s, 1H), 7.80 (t, J = 10.2 Hz, 3H), 4.05 (s, 2H). |
| 670 | LCMS (ESI) m/z: 371.2 [M + H]⁺. | ¹H NMR (400 MHz, DMSO-d₆) δ 10.23 (s, 1H), 8.48 (d, J = 1.8 Hz, 1H), 8.19 (d, J = 8.5 Hz, 1H), 7.97 (dd, J = 9.1, 3.4 Hz, 2H), 7.43-7.28 (m, 2H), 7.18-6.92 (m, 3H), 5.12 (s, 2H), 3.80 (s, 3H). |
| 671 | LCMS (ESI) m/z: 396.0 [M + H]⁺. | ¹H NMR (400 MHz, DMSO-d₆) δ 10.27 (s, 1H), 8.51 (s, 1H), 8.21 (d, J = 8.5 Hz, 1H), 7.98 (t, J = 8.4 Hz, 2H), 7.68-7.53 (m, 3H), 7.09 (d, J = 9.6 Hz, 1H), 5.23 (s, 2H), 3.80 (s, 3H). |
| 672 | LCMS (ESI) m/z: 357.1 [M + H]⁺. | ¹H NMR (400 MHz, DMSO-d₆) δ 9.79 (s, 1H), 8.61 (s, 1H), 8.32 (s, 1H), 8.14 (d, J = 8.4 Hz, 1H), 8.05 (s, 1H), 7.78 (d, J = 8.4 Hz, 1H), 7.05 (dd, J = 14.7, 8.8 Hz, 3H), 3.98 (s, 2H), 3.55 (s, 3H). |
| 673 | LCMS (ESI) m/z: 357.1 [M + H]⁺. | ¹H NMR (400 MHz, DMSO-d₆) δ 9.78 (s, 1H), 8.62 (s, 1H), 8.30 (s, 1H), 8.13 (d, J-8.5 Hz, 1H), 8.05 (s, 1H), 7.80-7.71 (m, 1H), 7.36 (dd, J = 19.3, 8.6 Hz, 2H), 7.12-7.04 (m, 1H), 3.95 (s, 2H), 3.55 (s, 3H). |
| 674 | LCMS (ESI) m/z: 384.0 [M + H]⁺. | ¹H NMR (400 MHz, DMSO-d₆) δ 10.31 (s, 1H), 9.15 (s, 1H), 8.98 (d, J = 1.2 Hz, 1H), 8.40 (d, J = 1.6 Hz, 1H), 8.16 (d, J = 8.4 Hz, 1H), 7.79-7.91 (m, 4H), 4.05 (s, 2H). |
| 675 | LCMS (ESI) m/z: 383.1 [M + H]⁺. | ¹H NMR (400 MHz, DMSO-d₆) δ 8.87 (d, J = 4.8 Hz, 1H), 8.82 (d, J = 5.0 Hz, 1H), 8.50 (s, 1H), 8.21 (t, J = 5.6 Hz, 2H), 8.10 (dd, J = 5.0, 1.5 Hz, 1H), 7.63 (d, J = 6.8 Hz, 1H), 7.54 (dd, J = 9.0, 3.0 Hz, 1H), 7.39 (d, J = 7.7 Hz, 1H), 7.27 (d, J = 7.6 Hz, 1H), 7.18 (d, J = 8.1 Hz, 1H), 2.86 (d, J = 4.8 Hz, 3H). |
| 676 | LCMS (ESI) m/z: 370.1 [M + H]⁺. | ¹H NMR (400 MHz, DMSO-d₆) δ 10.48 (s, 1H), 8.55 (d, J = 1.9 Hz, 1H), 8.32 (s, 1H), 8.07 (d, J = 8.5 Hz, 1H), 7.91 (s, 1H), 7.72 (dd, J = 8.5, 1.9 Hz, 1H), 7.05 (dd, J = 12.5, 4.6 Hz, 3H), 3.97 (s, 2H), 3.51 (s, 3H), 2.05 (s, 3H). |
| 677 | LCMS (ESI) m/z: 374.9 [M + H]⁺. | ¹H NMR (400 MHz, DMSO-d₆) δ 10.50 (s, 1H), 9.44 (s, 1H), 9.40 (s, 1H), 8.42 (s, 1H), 8.15 (s, 1H), 7.94-7.74 (m, 4H), 4.06 (s, 2H). |
| 678 | LCMS (ESI) m/z: 383.1 [M + H]⁺. | ¹H NMR (400 MHz, DMSO-d₆) δ 10.39 (s, 1H), 8.78 (d, J = 4.4 Hz, 1H), 8.62 (s, 1H), 8.54 (d, J = 2.5 Hz, 1H), 8.51 (d, J = 5.1 Hz, 1H), 8.23 (d, J = 8.7 Hz, 1H), 7.71 (d, J = 7.7 Hz, 1H), 7.57-7.46 (m, 3H), 7.39 (dd, J = 14.9, 7.2 Hz, 2H), 2.82 (d, J = 4.4 Hz, 3H). |
| 679 | LCMS (ESI) m/z: 370.1 [M + H]⁺. | ¹H NMR (400 MHz, DMSO-d₆) δ 10.46 (s, 1H), 8.55 (d, J = 2.2 Hz, 1H), 8.30 (s, 1H), 8.06 (d, J = 8.5 Hz, 1H), 7.90 (s, 1H), 7.69 (dd, J = 8.6, 2.1 Hz, 1H), 7.37 (dd, J = 10.6, 8.5 Hz, 2H), 7.12 (s, 1H), 3.94 (s, 2H), 3.51 (s, 3H), 2.05 (s, 3H). |
| 680 | LCMS (ESI) m/z: 391.0 [M + H]⁺. | ¹H NMR (400 MHz, DMSO-d₆) δ 10.17 (s, 1H), 8.33 (s, 1H), 8.09 (d, J = 8.5 Hz, 1H), 7.95 (d, J = 9.7 Hz, 1H), 7.73 (dd, J = 8.0, 2.0 Hz, 1H), 7.47-7.42 (m, 1H), 7.26 (d, J = 8.9 Hz, 1H), 7.08 (d, J = 9.7 Hz, 1H), 4.14 (s, 2H), 3.79 (s, 3H). |
| 681 | LCMS (ESI) m/z: 383.0 [M + H]⁺. | ¹H NMR (400 MHz, DMSO-d₆) δ 11.58 (s, 1H), 8.41 (s, 1H), 7.93 (d, J = 8.3 Hz, 1H), 7.80 (dd, J = 8.5, 2.4 Hz, 1H), 7.47-7.32 (m, 2H), 7.32-7.16 (m, 2H), 4.00 (s, 2H). |
| 682 | LCMS (ESI) m/z: 401.0 [M + H]⁺. | ¹H NMR (400 MHz, DMSO-d₆) δ 11.82 (s, 1H), 11.36 (s, 1H), 10.35 (s, 1H), 8.36 (d, J = 2.0 Hz, 1H), 7.94 (d, J = 8.0 Hz, 1H), 7.77 (dd, J = 8.0, 2.3 Hz, 1H), 7.35-7.30 (m, 2H), 7.28-7.23 (m, 2H), 3.99 (s, 2H). |
| 683 | LCMS (ESI) m/z: 341.1 [M + H]⁺. | ¹H NMR (400 MHz, DMSO-d₆) δ 10.50 (s, 1H), 9.28 (s, 1H), 8.36 (d, J = 2.0 Hz, 1H), 8.04 (d, J = 8.5 Hz, 1H), 7.77 (dd, J = 8.5, 2.3 Hz, 1H), 7.05 (dd, J = 9.6, 4.4 Hz, 3H), 3.99 (s, 2H). |

Example 240. Stearoyl-CoA desaturase (SCD) is the target of the Compounds of the Invention A. Materials and Methods: Compound Profiling Methods Strains expressing SCD1 or SCD5 as the sole desaturase, the human SCD1 and SCD5 genes were used to evaluate inhibition of SCD1/SCD5 using reduced growth as a surrogate for SCD inhibition. These yeast strains express human SCD1 or SCD5 from a plasmid harbored in a strain in which the yeast OLE1 gene is deleted.

All compound profiling experiments were performed using the same basic protocol. Yeast were cultured using standard techniques in complete synthetic media lacking uracil and containing yeast nitrogen base supplemented with 2% (w/v) glucose (SD-Ura) Starter cultures were inoculated in 3 mL SD-Ura media containing 0.01% tween and 0.2 mM palmitoleic and oleic acid. Cultures were incubated overnight in a 30° C. shaker incubator (225 rpm). Saturated morning cultures were centrifuged, washed in SD-Ura media lacking TWEEN-20 and fatty acids, and then diluted 1:20 in fresh SD-Ura media also lacking TWEEN-20 and fatty acids. Cells were grown for 6 h to an $OD_{600}$ (optical density) of ~0.4-0.8 at 30° C. with shaking.

Compound stocks (10 mM in 100% DMSO) were arrayed into 384-round well, v-bottom polypropylene plates and diluted according to indicated dilution factors. Compound administration was performed in two separate steps. First, 15 μL of SD-Ura was dispensed into clear 384-well assay plates using a MULTIDROP™ Combi reagent dispenser. The diluted compound stock plates were then applied to the assay plates using an automated workstation (Perkin Elmer JANUS™) outfitted with a 384-pin tool containing slotted pins that deliver 100 nL of compound. The cultures described above were centrifuged and washed with media lacking TWEEN-20 or oleic and palmitoleic acids. Cultures were then resuspended at a 2-fold concentrated OD600 of 0.02 (final $OD_{600}$ of 0.0.01) in SD-Ura. 15 μL of diluted culture was then dispensed into the pinned assay plate to achieve 30 μL of the 1×$OD_{600}$ culture (0.01) and a top drug concentration of 33.3 μM.

After yeast delivery, assay plates were incubated under humidified conditions at 30° C. for 40 h. Yeast growth was monitored by reading the $OD_{600}$ of each well using a microplate reader (Perkin Elmer EnVision™). Data were analyzed as follows. Raw data were processed by background subtracting and converting values to a percent of the nontreated condition for that strain [(EXP-0.035)/(DMSO-0.035)×100%].

B. Results

Using the methods described above, the inhibition of SCD1 and SCD5 was tested for compounds of the invention. The results are shown in Table 3.

TABLE 3

Inhibition of SCD1 and SCD5 by Compounds of the Invention

| Compound No. | SCD1 IC50 (μM) | SCD5 IC50 (μM) |
|---|---|---|
| 1 | >45.00 | 5.16 |
| 2 | >45.00 | 2.65 |
| 3 | 0.99 | 0.45 |
| 4 | 1.73 | 0.58 |
| 5 | 3.34 | 1.87 |
| 6 | >45.00 | 1.02 |
| 7 | 2.07 | 0.02 |
| 8 | >45.00 | 4.20 |
| 9 | 3.04 | 0.56 |
| 10 | 9.54 | 0.50 |
| 11 | 2.74 | 0.08 |
| 12 | 1.60 | 0.21 |
| 13 | >45.00 | 1.54 |
| 14 | 17.28 | 3.74 |
| 15 | >45.00 | 0.45 |
| 16 | >45.00 | 13.28 |
| 17 | >45.00 | 0.77 |
| 18 | 8.57 | 1.60 |
| 19 | >45.00 | 4.69 |
| 20 | 0.22 | 0.03 |
| 21 | >45.00 | 1.78 |
| 22 | >45.00 | 0.46 |
| 23 | >45.00 | 2.49 |
| 24 | 10.80 | 0.29 |
| 25 | 4.03 | 0.53 |
| 26 | >45.00 | 1.95 |
| 27 | >45.00 | 0.39 |
| 28 | 1.95 | 0.02 |
| 29 | 11.86 | 0.05 |
| 30 | >45.00 | 3.53 |
| 31 | 6.28 | 0.05 |
| 32 | 26.43 | 0.31 |
| 33 | >45.00 | 17.98 |
| 34 | >45.00 | 0.71 |
| 35 | >45.00 | 0.30 |
| 36 | 16.89 | 0.38 |
| 37 | 10.25 | 0.05 |
| 38 | 15.66 | 0.89 |
| 39 | >45.00 | 0.92 |
| 40 | 0.11 | 0.01 |
| 41 | 0.19 | 0.01 |
| 42 | 2.41 | 0.08 |
| 43 | 4.06 | 0.21 |
| 44 | 14.12 | 0.78 |
| 45 | 15.39 | 0.43 |
| 46 | 0.06 | 0.01 |
| 47 | 1.10 | 0.13 |
| 48 | 0.15 | 0.01 |
| 49 | >45.00 | 21.22 |
| 50 | 1.53 | 0.02 |
| 51 | >45.00 | 1.56 |
| 52 | 8.21 | 0.13 |
| 53 | 0.28 | 0.01 |
| 54 | 12.02 | 0.58 |
| 55 | 1.21 | 0.16 |
| 56 | 0.02 | 0.01 |
| 57 | 0.56 | 0.01 |
| 58 | >45.00 | 35.65 |
| 59 | 0.31 | 0.01 |
| 60 | 4.38 | 0.65 |
| 61 | 7.52 | 0.60 |
| 62 | 2.34 | 2.06 |
| 63 | 0.38 | 0.32 |
| 64 | 0.56 | 0.06 |
| 65 | 1.21 | 0.14 |
| 66 | 1.44 | 0.01 |
| 67 | 0.44 | 0.12 |
| 68 | 1.65 | 0.26 |
| 69 | >45.00 | 0.27 |
| 70 | 2.90 | 0.49 |
| 71 | >45.00 | 3.91 |
| 72 | 4.70 | 0.39 |
| 73 | 8.08 | 0.17 |
| 74 | 0.25 | 0.01 |
| 75 | 1.49 | 0.01 |
| 76 | 0.01 | 0.01 |
| 77 | >45.00 | 6.73 |
| 78 | >45.00 | 0.64 |
| 79 | 5.19 | 0.01 |
| 80 | 27.88 | 1.57 |
| 81 | >45.00 | 2.42 |
| 82 | >45.00 | 0.03 |
| 83 | >45.00 | 0.42 |
| 84 | 6.66 | 0.37 |
| 85 | 3.21 | 0.30 |
| 86 | 9.69 | 0.07 |
| 87 | >45.00 | 0.28 |
| 88 | 0.65 | 0.02 |
| 89 | 0.11 | 0.01 |
| 90 | 18.02 | 0.62 |
| 91 | 0.01 | 0.01 |
| 92 | 0.11 | 0.02 |
| 93 | 0.55 | 0.02 |
| 94 | 0.03 | 0.01 |
| 95 | >45.00 | 0.01 |
| 96 | 1.08 | 0.13 |
| 97 | 1.10 | 0.02 |
| 98 | 2.96 | 0.04 |
| 99 | 0.14 | 0.01 |
| 100 | 1.74 | 0.02 |
| 101 | 1.08 | 0.02 |
| 102 | 10.35 | 0.08 |
| 103 | 0.16 | 0.08 |
| 104 | 0.04 | 0.04 |
| 105 | >45.00 | 0.83 |
| 106 | >45.00 | 1.24 |
| 107 | >45.00 | 1.06 |
| 108 | 7.61 | 1.40 |
| 109 | 0.37 | 0.28 |
| 110 | 3.94 | 0.22 |
| 111 | 0.01 | 0.01 |
| 112 | 0.01 | 0.01 |
| 113 | 0.08 | 0.01 |
| 114 | 0.05 | 0.01 |
| 115 | >45.00 | 0.05 |
| 116 | 0.01 | 0.01 |
| 117 | 0.63 | 0.07 |
| 118 | >45.00 | 0.44 |
| 119 | 0.01 | 0.01 |
| 120 | >45.00 | 0.03 |
| 121 | 0.02 | 0.02 |
| 122 | 0.01 | 0.01 |
| 123 | >45.00 | 8.94 |
| 124 | >45.00 | 10.05 |
| 125 | 0.01 | 0.01 |
| 126 | 0.83 | 0.23 |

TABLE 3-continued

Inhibition of SCD1 and SCD5 by Compounds of the Invention

| Compound No. | SCD1 IC50 (μM) | SCD5 IC50 (μM) |
|---|---|---|
| 127 | 3.12 | 0.22 |
| 128 | 0.18 | 0.01 |
| 129 | >45.00 | 0.05 |
| 130 | >45.00 | 0.04 |
| 131 | 0.01 | 0.01 |
| 132 | 0.01 | 0.01 |
| 133 | >45.00 | 0.23 |
| 134 | 0.09 | 0.01 |
| 135 | 14.14 | 0.15 |
| 136 | 1.26 | 0.49 |
| 137 | 0.01 | 0.01 |
| 138 | 0.55 | 0.08 |
| 139 | 4.93 | 0.06 |
| 140 | 0.29 | 0.01 |
| 141 | >45.00 | 0.16 |
| 142 | >45.00 | 0.01 |
| 143 | 0.51 | 0.37 |
| 144 | 0.01 | 0.01 |
| 145 | 1.71 | 0.10 |
| 146 | 0.19 | 0.01 |
| 147 | 0.31 | 0.04 |
| 148 | 0.01 | 0.01 |
| 149 | 0.23 | 0.01 |
| 150 | 0.02 | 0.01 |
| 151 | 1.34 | 0.08 |
| 152 | >45.00 | 1.99 |
| 153 | 5.30 | 7.60 |
| 154 | >45.00 | 14.64 |
| 155 | 24.70 | 7.80 |
| 156 | >45.00 | 28.15 |
| 157 | >45.00 | 6.65 |
| 158 | 10.48 | 6.19 |
| 159 | >45.00 | 8.04 |
| 160 | >45.00 | 3.07 |
| 161 | >45.00 | 1.64 |
| 162 | >45.00 | 1.79 |
| 163 | >45.00 | 0.24 |
| 164 | >45.00 | 6.22 |
| 165 | 14.15 | 3.31 |
| 166 | 14.73 | 9.36 |
| 167 | 25.90 | 0.93 |
| 168 | >45.00 | 1.72 |
| 169 | >45.00 | 2.48 |
| 170 | >45.00 | 1.07 |
| 171 | >45.00 | 0.86 |
| 172 | 2.29 | 0.37 |
| 173 | 1.72 | 0.15 |
| 174 | 7.56 | 0.08 |
| 175 | >45.00 | 20.08 |
| 176 | >45.00 | 2.66 |
| 177 | >45.00 | 5.49 |
| 178 | 6.67 | 0.77 |
| 179 | >45.00 | 1.03 |
| 180 | 6.02 | 0.91 |
| 181 | >45.00 | 1.22 |
| 182 | >45.00 | 13.26 |
| 183 | 10.67 | 1.41 |
| 184 | >45.00 | 28.93 |
| 185 | >45.00 | 8.59 |
| 186 | >45.00 | 12.59 |
| 187 | >45.00 | 6.51 |
| 188 | 4.40 | 0.19 |
| 189 | >45.00 | 5.07 |
| 190 | >45.00 | 33.00 |
| 191 | >45.00 | 2.68 |
| 192 | 11.87 | 1.31 |
| 193 | >45.00 | 2.29 |
| 194 | >45.00 | 1.54 |
| 195 | 15.91 | 2.31 |
| 196 | 5.58 | 1.56 |
| 197 | 2.75 | 0.37 |
| 198 | >45.00 | 7.18 |
| 199 | >45.00 | 5.80 |
| 200 | >45.00 | 0.44 |
| 201 | 0.59 | 0.19 |
| 202 | 0.02 | 0.02 |
| 203 | 4.24 | 3.72 |
| 204 | >45.00 | 27.91 |
| 205 | >45.00 | 29.42 |
| 206 | 3.36 | 2.51 |
| 207 | 0.09 | 0.01 |
| 208 | 0.13 | 0.05 |
| 209 | 1.69 | 2.45 |
| 210 | 0.38 | 1.31 |
| 211 | 14.56 | 2.94 |
| 212 | 0.15 | 0.04 |
| 213 | 0.39 | 0.38 |
| 214 | 14.54 | 1.75 |
| 215 | 1.28 | 4.02 |
| 216 | 0.01 | 0.02 |
| 217 | 3.69 | 2.38 |
| 218 | 2.73 | 0.36 |
| 219 | 1.58 | 1.35 |
| 220 | 0.66 | 0.52 |
| 221 | >45.00 | >45.00 |
| 222 | 7.45 | 2.51 |
| 223 | >45.00 | 11.28 |
| 224 | 0.31 | 0.22 |
| 225 | 2.07 | 1.96 |
| 226 | 7.27 | 5.71 |
| 227 | 0.44 | 0.36 |
| 228 | 0.34 | 0.32 |
| 229 | 0.14 | 0.11 |
| 230 | 2.88 | 3.80 |
| 231 | 8.93 | 3.17 |
| 232 | 0.14 | 0.07 |
| 233 | 1.63 | 0.87 |
| 234 | 6.30 | 1.44 |
| 235 | 1.88 | 1.77 |
| 236 | 0.01 | 0.01 |
| 237 | 7.21 | 3.20 |
| 238 | 4.06 | 3.96 |
| 239 | 0.25 | 0.01 |
| 240 | 4.39 | 0.31 |
| 241 | 2.03 | 0.07 |
| 242 | 0.05 | 0.01 |
| 243 | 0.06 | 0.01 |
| 244 | 0.01 | 0.01 |
| 245 | >45.00 | >45.00 |
| 246 | 6.45 | 1.59 |
| 247 | >45.00 | 2.02 |
| 248 | 0.20 | 0.01 |
| 249 | >45.00 | 6.75 |
| 250 | >45.00 | 9.75 |
| 251 | >45.00 | 0.15 |
| 252 | 0.69 | 0.13 |
| 253 | >45.00 | 4.75 |
| 254 | >45.00 | 3.53 |
| 255 | >45.00 | 4.74 |
| 256 | 0.75 | 0.04 |
| 257 | >45.00 | 4.36 |
| 258 | 3.86 | 0.18 |
| 259 | 5.37 | 0.57 |
| 260 | 4.58 | 0.17 |
| 261 | 1.42 | 0.05 |
| 262 | 3.98 | 0.26 |
| 263 | >45.00 | 0.17 |
| 264 | >45.00 | 8.84 |
| 265 | 23.25 | 0.35 |
| 266 | 1.85 | 0.40 |
| 267 | >45.00 | 10.56 |
| 268 | >45.00 | 3.04 |
| 269 | >45.00 | 0.03 |
| 270 | >45.00 | 6.88 |
| 271 | >45.00 | 14.78 |
| 272 | >45.00 | 12.96 |
| 273 | >45.00 | 3.25 |
| 274 | >45.00 | 0.76 |
| 275 | >45.00 | 3.02 |
| 276 | >45.00 | 0.95 |

TABLE 3-continued

Inhibition of SCD1 and SCD5 by Compounds of the Invention

| Compound No. | SCD1 IC50 (µM) | SCD5 IC50 (µM) |
|---|---|---|
| 277 | >45.00 | 13.40 |
| 278 | 39.92 | 2.03 |
| 279 | 21.48 | 1.96 |
| 280 | 0.13 | 0.02 |
| 281 | >45.00 | 2.75 |
| 282 | 0.21 | 0.02 |
| 283 | 2.96 | 0.27 |
| 284 | >45.00 | 4.52 |
| 285 | 9.41 | 1.43 |
| 286 | 4.00 | 0.24 |
| 287 | 0.86 | 0.14 |
| 288 | >45.00 | 2.52 |
| 289 | >45.00 | 9.20 |
| 290 | 0.01 | 0.01 |
| 291 | 22.53 | 4.91 |
| 292 | 2.07 | 0.01 |
| 293 | 0.08 | 0.04 |
| 294 | >45.00 | 0.30 |
| 295 | 22.49 | 0.34 |
| 296 | >45.00 | 0.86 |
| 297 | >45.00 | 1.20 |
| 298 | 2.75 | 0.34 |
| 299 | >45.00 | 3.79 |
| 300 | >45.00 | 5.60 |
| 301 | >45.00 | 5.22 |
| 302 | >45.00 | 3.34 |
| 303 | 4.18 | 0.97 |
| 304 | >45.00 | 2.70 |
| 305 | 27.05 | 6.94 |
| 306 | 3.86 | 2.11 |
| 307 | 1.17 | 0.57 |
| 308 | 22.84 | 3.12 |
| 309 | 0.54 | 0.05 |
| 310 | 0.14 | 0.01 |
| 311 | 1.02 | 0.01 |
| 312 | 1.82 | 0.03 |
| 313 | 1.86 | 0.02 |
| 314 | 0.10 | 0.02 |
| 315 | 0.01 | 0.01 |
| 316 | 0.01 | 0.01 |
| 317 | 0.98 | 0.10 |
| 318 | 0.13 | 0.05 |
| 319 | >45.00 | 0.46 |
| 320 | >45.00 | 1.58 |
| 321 | 0.01 | 0.01 |
| 322 | 12.65 | 6.07 |
| 323 | 10.68 | 0.81 |
| 324 | >45.00 | 1.13 |
| 325 | 16.45 | 0.66 |
| 326 | >45.00 | 4.71 |
| 327 | >45.00 | 1.32 |
| 328 | 1.76 | 0.01 |
| 329 | 0.10 | 0.01 |
| 330 | 0.57 | 0.01 |
| 331 | 0.13 | 0.01 |
| 332 | 1.68 | 0.48 |
| 333 | 0.11 | 0.18 |
| 334 | >45.00 | 9.39 |
| 335 | 15.40 | 0.69 |
| 336 | >45.00 | 4.27 |
| 337 | >45.00 | 9.87 |
| 338 | >45.00 | 16.30 |
| 339 | >45.00 | 17.74 |
| 340 | 0.09 | 0.12 |
| 341 | >45.00 | 2.70 |
| 342 | >45.00 | 20.94 |
| 343 | 3.14 | 3.42 |
| 344 | >45.00 | 26.31 |
| 345 | 3.95 | 2.52 |
| 346 | 0.34 | 0.55 |
| 347 | 0.68 | 0.71 |
| 348 | 7.37 | 4.96 |
| 349 | >45.00 | 32.30 |
| 350 | 2.60 | 5.42 |
| 351 | >45.00 | 35.45 |
| 352 | >45.00 | 35.46 |
| 353 | 1.94 | 1.36 |
| 354 | 6.78 | 0.28 |
| 355 | 0.54 | 0.16 |
| 356 | 0.12 | 0.04 |
| 357 | 4.06 | 0.05 |
| 358 | 6.05 | 0.17 |
| 359 | 18.66 | 3.27 |
| 360 | 32.56 | 6.59 |
| 361 | >45.00 | 2.63 |
| 362 | >45.00 | 14.53 |
| 363 | 3.16 | 0.13 |
| 364 | 0.71 | 0.02 |
| 365 | 25.81 | 4.00 |
| 366 | 0.02 | 0.02 |
| 367 | 25.84 | 2.98 |
| 368 | 1.37 | 0.24 |
| 369 | >45.00 | 14.02 |
| 370 | >45.00 | 6.65 |
| 371 | 0.12 | 0.01 |
| 372 | >45.00 | 0.77 |
| 373 | 0.30 | 0.03 |
| 374 | 38.46 | 7.04 |
| 375 | 0.01 | 0.01 |
| 376 | >45.00 | >45.00 |
| 377 | >45.00 | >45.00 |
| 378 | >45.00 | >45.00 |
| 379 | >45.00 | >45.00 |
| 380 | >45.00 | >45.00 |
| 381 | >45.00 | >45.00 |
| 382 | >45.00 | >45.00 |
| 383 | >45.00 | >45.00 |
| 384 | >45.00 | >45.00 |
| 385 | >45.00 | >45.00 |
| 386 | >45.00 | >45.00 |
| 387 | >45.00 | >45.00 |
| 388 | 17.63 | >45.00 |
| 389 | >45.00 | >45.00 |
| 390 | >45.00 | >45.00 |
| 391 | 1.24 | >45.00 |
| 392 | >45.00 | >45.00 |
| 393 | >45.00 | >45.00 |
| 394 | >45.00 | >45.00 |
| 395 | >45.00 | >45.00 |
| 396 | >45.00 | >45.00 |
| 397 | >45.00 | >45.00 |
| 398 | >45.00 | >45.00 |
| 399 | >45.00 | >45.00 |
| 400 | >45.00 | >45.00 |
| 401 | >45.00 | >45.00 |
| 402 | >45.00 | >45.00 |
| 403 | >45.00 | >45.00 |
| 404 | >45.00 | >45.00 |
| 405 | >45.00 | >45.00 |
| 406 | >45.00 | >45.00 |
| 407 | >45.00 | >45.00 |
| 408 | >45.00 | >45.00 |
| 409 | >45.00 | >45.00 |
| 410 | >45.00 | >45.00 |
| 411 | >45.00 | >45.00 |
| 412 | >45.00 | >45.00 |
| 413 | >45.00 | >45.00 |
| 414 | 25.02 | >45.00 |
| 415 | >45.00 | >45.00 |
| 416 | >45.00 | >45.00 |
| 417 | >45.00 | >45.00 |
| 418 | >45.00 | >45.00 |
| 419 | >45.00 | >45.00 |
| 420 | >45.00 | >45.00 |
| 421 | >45.00 | >45.00 |
| 422 | >45.00 | >45.00 |
| 423 | >45.00 | >45.00 |
| 424 | >45.00 | >45.00 |
| 425 | >45.00 | >45.00 |
| 426 | >45.00 | >45.00 |

TABLE 3-continued

Inhibition of SCD1 and SCD5 by Compounds of the Invention

| Compound No. | SCD1 IC50 (μM) | SCD5 IC50 (μM) |
|---|---|---|
| 427 | >45.00 | >45.00 |
| 428 | >45.00 | >45.00 |
| 429 | >45.00 | >45.00 |
| 430 | >45.00 | >45.00 |
| 431 | 1.07 | >45.00 |
| 432 | >45.00 | >45.00 |
| 433 | >45.00 | >45.00 |
| 434 | >45.00 | >45.00 |
| 435 | >45.00 | >45.00 |
| 436 | 6.24 | >45.00 |
| 437 | >45.00 | >45.00 |
| 438 | >45.00 | >45.00 |
| 439 | >45.00 | >45.00 |
| 440 | >45.00 | >45.00 |
| 441 | >45.00 | >45.00 |
| 442 | >45.00 | >45.00 |
| 443 | >45.00 | >45.00 |
| 444 | >45.00 | >45.00 |
| 445 | >45.00 | >45.00 |
| 446 | >45.00 | >45.00 |
| 447 | >45.00 | >45.00 |
| 448 | >45.00 | >45.00 |
| 449 | >45.00 | >45.00 |
| 450 | >45.00 | >45.00 |
| 451 | 1.40 | >45.00 |
| 452 | >45.00 | >45.00 |
| 453 | 0.18 | >45.00 |
| 454 | 1.93 | >45.00 |
| 455 | >45.00 | >45.00 |
| 456 | >45.00 | >45.00 |
| 457 | >45.00 | >45.00 |
| 458 | >45.00 | >45.00 |
| 459 | >45.00 | >45.00 |
| 460 | >45.00 | >45.00 |
| 461 | >45.00 | >45.00 |
| 462 | >45.00 | >45.00 |
| 463 | >45.00 | >45.00 |
| 464 | >45.00 | >45.00 |
| 465 | >45.00 | >45.00 |
| 466 | >45.00 | >45.00 |
| 467 | >45.00 | >45.00 |
| 468 | >45.00 | >45.00 |
| 469 | >45.00 | >45.00 |
| 470 | >45.00 | >45.00 |
| 471 | >45.00 | >45.00 |
| 472 | >45.00 | >45.00 |
| 473 | >45.00 | >45.00 |
| 474 | NT | NT |
| 475 | NT | NT |
| 476 | >45.00 | 7.6 |
| 477 | >45.00 | 18 |
| 478 | 2.1 | 0.019 |
| 479 | 12 | 0.68 |
| 480 | 3.5 | 0.23 |
| 481 | 0.12 | 0.027 |
| 482 | 4.8 | 0.62 |
| 483 | 0.075 | 0.017 |
| 484 | 0.53 | 0.014 |
| 485 | 0.21 | 0.021 |
| 486 | 7.8 | 0.11 |
| 487 | 4.6 | 0.31 |
| 488 | 5.8 | 0.109 |
| 489 | >45.00 | 0.544 |
| 490 | >45.00 | 2.2 |
| 491 | 25 | 6.5 |
| 492 | >45.00 | 5.8 |
| 493 | 32 | 0.043 |
| 494 | 0.01 | 0.01 |
| 495 | 0.56 | 0.015 |
| 496 | 0.222 | 0.01 |
| 497 | 0.01 | 0.01 |
| 498 | 2.7 | 5.2 |
| 499 | 10 | 0.82 |
| 500 | >45.00 | 0.01 |
| 501 | 0.01 | 0.01 |
| 502 | >45.00 | 0.01 |
| 503 | 0.012 | 0.01 |
| 504 | 2.8 | 0.26 |
| 505 | NT | NT |
| 506 | 1.5 | 0.014 |
| 507 | 0.98 | 1.2 |
| 508 | 2.6 | 0.45 |
| 509 | 0.43 | 0.12 |
| 510 | 0.1 | 0.077 |
| 511 | 0.143 | 0.19 |
| 512 | 0.049 | 0.06 |
| 513 | 0.77 | 0.17 |
| 514 | 2.6 | 0.32 |
| 515 | 5.9 | 0.32 |
| 516 | 0.96 | 0.77 |
| 517 | 0.18 | 0.14 |
| 518 | >45.00 | 1.7 |
| 519 | 0.88 | 0.22 |
| 520 | 0.36 | 0.09 |
| 521 | 2.5 | 5.3 |
| 522 | 0.36 | 0.06 |
| 523 | >45.00 | 0.11 |
| 524 | >45.00 | 0.029 |
| 525 | >45.00 | 0.55 |
| 526 | 0.099 | 0.01 |
| 527 | >45.00 | 1.3 |
| 528 | 0.06 | 0.01 |
| 529 | 1.1 | 0.67 |
| 530 | 0.16 | 0.19 |
| 531 | 1.3 | 0.34 |
| 532 | 0.01 | 0.01 |
| 533 | 0.22 | 0.01 |
| 534 | 6 | 0.2 |
| 535 | >45.00 | 0.48 |
| 536 | 1 | 0.11 |
| 537 | 17 | 0.49 |
| 538 | 1.6 | 0.18 |
| 539 | 3.5 | 0.17 |
| 540 | 0.06 | 0.01 |
| 541 | 6.6 | 0.22 |
| 542 | 18 | 0.01 |
| 543 | 0.037 | 0.01 |
| 544 | 0.01 | 0.96 |
| 545 | 0.71 | 0.1 |
| 546 | 0.32 | 0.027 |
| 547 | 0.24 | 0.01 |
| 548 | >45.00 | 3 |
| 549 | >45.00 | 0.89 |
| 550 | 2.4 | 0.37 |
| 551 | >45.00 | 1.2 |
| 552 | 1.9 | 0.36 |
| 553 | NT | NT |
| 554 | 3.2 | 8.8 |
| 555 | 0.74 | 0.01 |
| 556 | 2.3 | 0.01 |
| 557 | >45.00 | 1.9 |
| 558 | 43 | 0.064 |
| 559 | 0.01 | 0.01 |
| 560 | 0.25 | 0.022 |
| 561 | 6.7 | 0.2 |
| 562 | 1 | 0.01 |
| 563 | 1.1 | 0.57 |
| 564 | 1.4 | 0.062 |
| 565 | 2.7 | 0.02 |
| 566 | >45.00 | 5.6 |
| 567 | 0.01 | 0.01 |
| 568 | 3.9 | 0.88 |
| 569 | >45.00 | 1.2 |
| 570 | 10 | 0.43 |
| 571 | 0.52 | 0.01 |
| 572 | 0.017 | 0.01 |
| 573 | >45.00 | 2.3 |
| 574 | NT | NT |
| 575 | 0.37 | 0.01 |
| 576 | >45.00 | 0.4 |

TABLE 3-continued

Inhibition of SCD1 and SCD5 by Compounds of the Invention

| Compound No. | SCD1 IC50 (µM) | SCD5 IC50 (µM) |
|---|---|---|
| 577 | 23 | 6.4 |
| 578 | >45.00 | 0.37 |
| 579 | >45.00 | 0.74 |
| 580 | 0.019 | 0.01 |
| 581 | 0.68 | 0.062 |
| 582 | 4.3 | 0.28 |
| 583 | NT | NT |
| 584 | >45.00 | 1.2 |
| 585 | >45.00 | 0.38 |
| 586 | >45.00 | 1.3 |
| 587 | 17 | 1.1 |
| 588 | 6.2 | 0.53 |
| 589 | 2.3 | 0.15 |
| 590 | 30 | 0.47 |
| 591 | 2.2 | 0.018 |
| 592 | >45.00 | 0.276 |
| 593 | >45.00 | 0.43 |
| 594 | 3.1 | 0.12 |
| 595 | 35 | 0.42 |
| 596 | 1.08 | 0.026 |
| 597 | 2.6 | 0.07 |
| 598 | 39 | 0.15 |
| 599 | >45.00 | 0.94 |
| 600 | 28 | 1.6 |
| 601 | >45.00 | 0.034 |
| 602 | >45.00 | 0.066 |
| 603 | 0.01 | 0.01 |
| 604 | 0.037 | 0.042 |
| 605 | 0.28 | 0.32 |
| 606 | 0.61 | 0.17 |
| 607 | >45.00 | 0.58 |
| 608 | 0.91 | 0.027 |
| 609 | >45.00 | 0.284 |
| 610 | 3.4 | 0.6 |
| 611 | >45.00 | 0.371 |
| 612 | 4.4 | 1.2 |
| 613 | 3.4 | 0.6 |
| 614 | >45.00 | 2.5 |
| 615 | >45.00 | 0.079 |
| 616 | 0.522 | 0.01 |
| 617 | 0.22 | 0.039 |
| 618 | 0.51 | 0.022 |
| 619 | 28 | 0.15 |
| 620 | 0.2 | 0.2 |
| 621 | 0.035 | 0.025 |
| 622 | 0.023 | 0.016 |
| 623 | 0.232 | 0.019 |
| 624 | >45.00 | 0.054 |
| 625 | 4.8 | 0.31 |
| 626 | >45.00 | 0.014 |
| 627 | 0.327 | 0.01 |
| 628 | 0.19 | 0.03 |
| 629 | 3.3 | 0.25 |
| 630 | 1.1 | 0.32 |
| 631 | 0.65 | 2.2 |
| 632 | >45.00 | 0.07 |
| 633 | 1.8 | 0.27 |
| 634 | >45.00 | 0.28 |
| 635 | >45.00 | 0.062 |
| 636 | >45.00 | 0.142 |
| 637 | 12 | 8.1 |
| 638 | 3.2 | 0.098 |
| 639 | 0.49 | 0.039 |
| 640 | 3.2 | 1.3 |
| 641 | >45.00 | 0.54 |
| 642 | 0.092 | 0.01 |
| 643 | 0.072 | 0.01 |
| 644 | 0.042 | 0.01 |
| 645 | 1.3 | 0.21 |
| 646 | >45.00 | 0.14 |
| 647 | 9.3 | 2.4 |
| 648 | >45.00 | 0.99 |
| 649 | 1.4 | 0.48 |
| 650 | 0.17 | 0.056 |
| 651 | 0.09 | 0.024 |
| 652 | 1.9 | 0.086 |
| 653 | >45.00 | 1.4 |
| 654 | 1.9 | 0.056 |
| 655 | 0.36 | 0.035 |
| 656 | 0.22 | 0.11 |
| 657 | 0.01 | 0.01 |
| 658 | 1.6 | 0.18 |
| 659 | 0.35 | 0.055 |
| 660 | >45.00 | 8.9 |
| 661 | 0.18 | 0.01 |
| 662 | 0.3 | 0.18 |
| 663 | >45.00 | 0.039 |
| 664 | 31 | 0.9 |
| 665 | >45.00 | 0.49 |
| 666 | 3.6 | 0.29 |
| 667 | >45.00 | 0.31 |
| 668 | 0.01 | 0.01 |
| 669 | 0.22 | 0.073 |
| 670 | >45.00 | 1.8 |
| 671 | >45.00 | 2 |
| 672 | 0.5 | 0.42 |
| 673 | 3.1 | 0.36 |
| 675 | >45.00 | 12 |
| 676 | 0.083 | 0.01 |
| 677 | >45.00 | 0.079 |
| 678 | 0.32 | 0.38 |
| 679 | 0.57 | 0.01 |
| 680 | 2.7 | 0.025 |
| 681 | >45.00 | 2.1 |
| 682 | 0.1 | 0.2 |
| 683 | 8.1 | 3.9 |

"NT" indicates not tested

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A compound having the structure of Formula Ic:

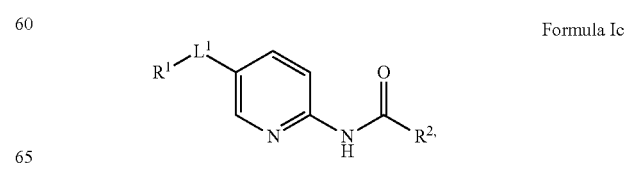

Formula Ic wherein
R[1] is
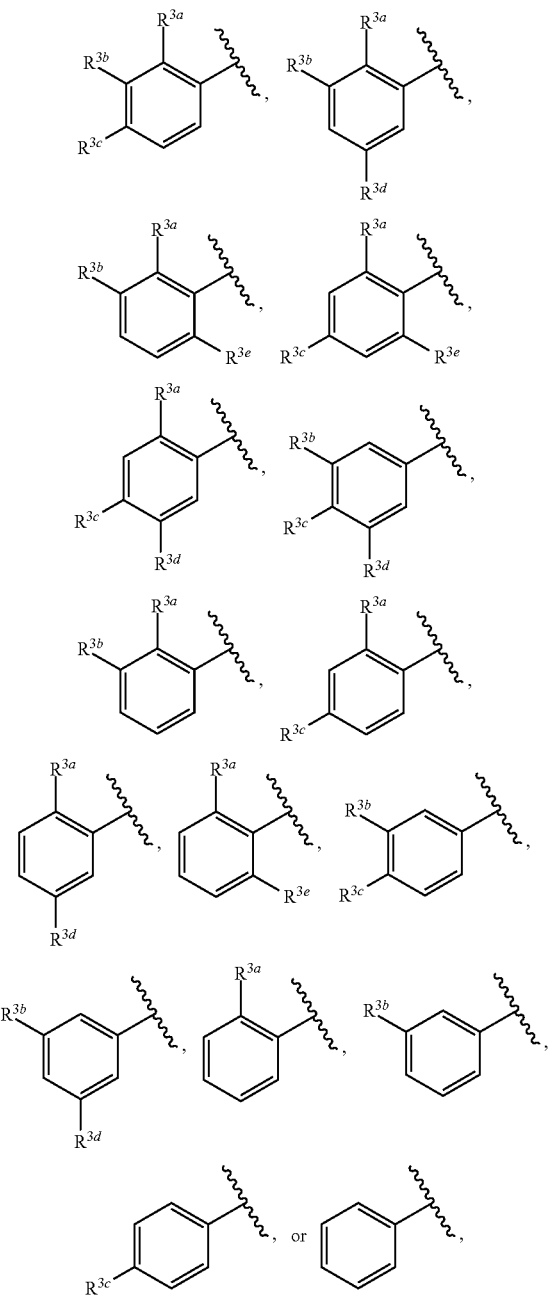
wherein
each of R[3a], R[3b], R[3c], R[3d], and R[3e] is, independently, H, F, Cl, Br, I, CN,
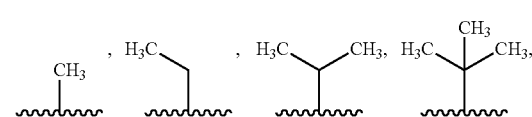
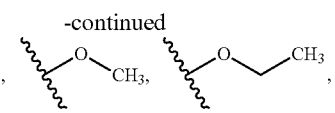
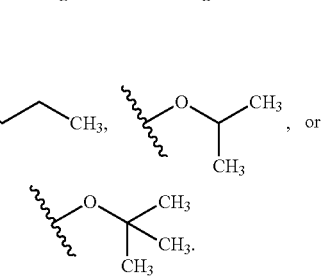
L[1] is optionally substituted C1-C6 alkylene; and
R[2] is
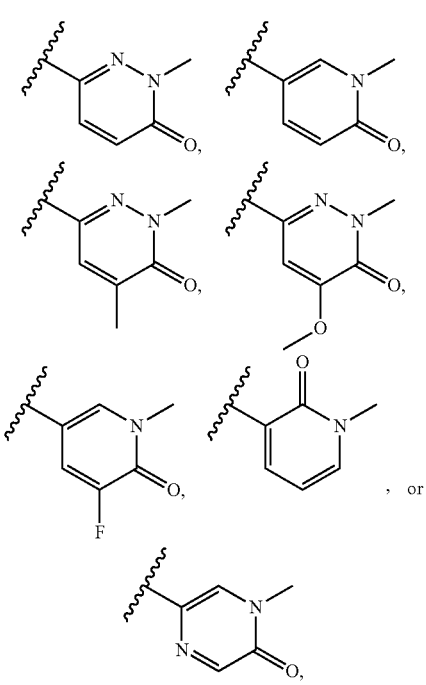
or a pharmaceutically acceptable salt thereof.
2. The compound of claim 1, wherein L[1] is
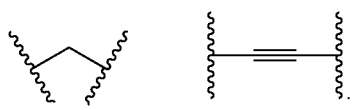
3. The compound of claim 1, wherein R[1] is
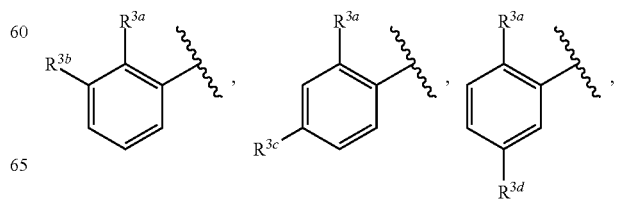

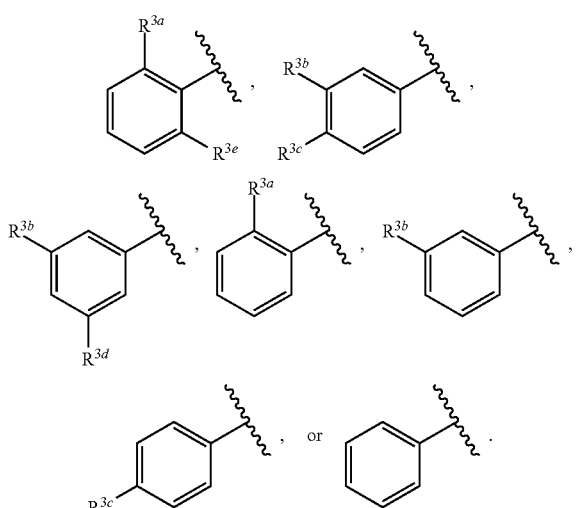

4. The compound of claim 1, wherein R¹ is phenyl, 3-fluoro-phenyl, 4-fluoro-phenyl, 3-chloro-phenyl, 4-chloro-phenyl, 2-methoxy-phenyl, 3-methoxy-phenyl, 4-methoxy-phenyl, 3,4-di-fluoro-phenyl, 3,4-dichloro-phenyl, 3,5-di-fluoro-phenyl, 3,5-dichloro-phenyl, 3-chloro-4-fluoro-phenyl, 4-chloro-3-fluoro-phenyl, 3-chloro-4-nitrile-phenyl, 3-nitrile-4-fluoro-phenyl, 3 bromo-phenyl, 3 cyano-5-fluoro-phenyl, 3-chloro-5-fluoro-phenyl, 3-chloro-5-cyano-phenyl, or 3-chloro-5-methoxy-phenyl.

5. The compound of claim 1, wherein the compound is selected from the group consisting of:

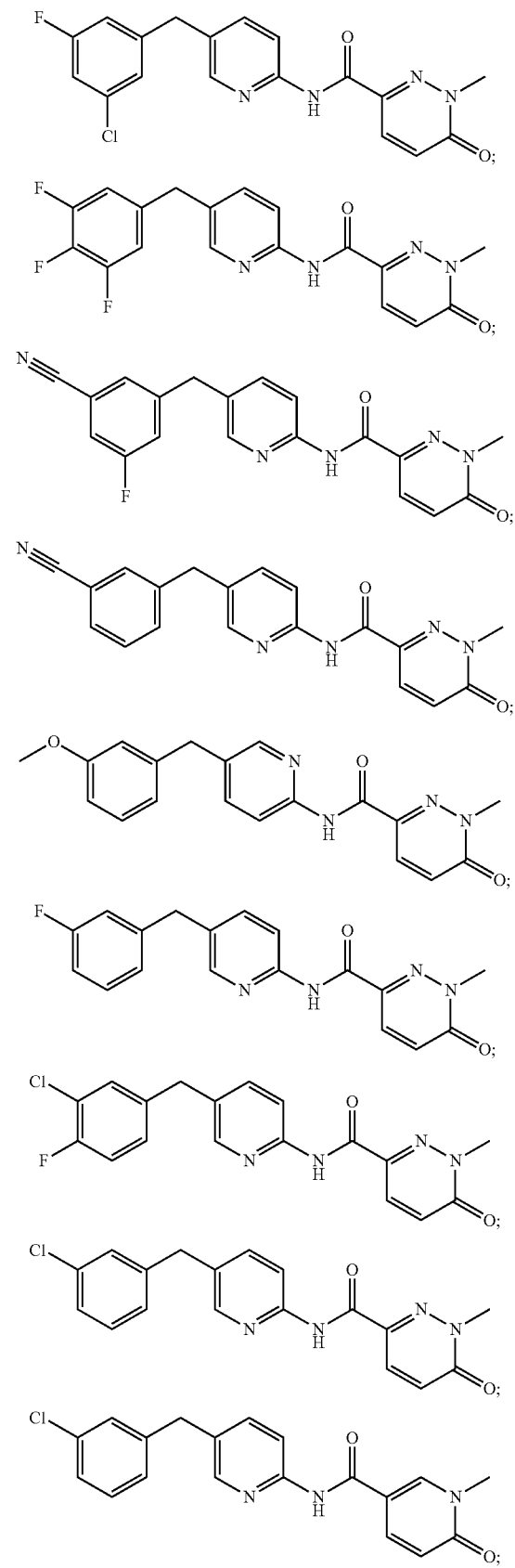

-continued

709
-continued
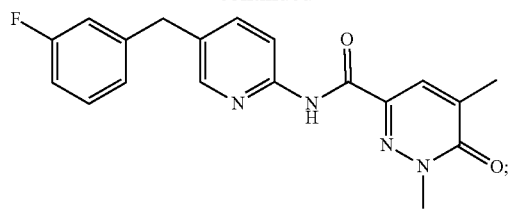
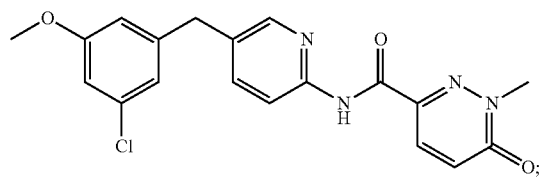
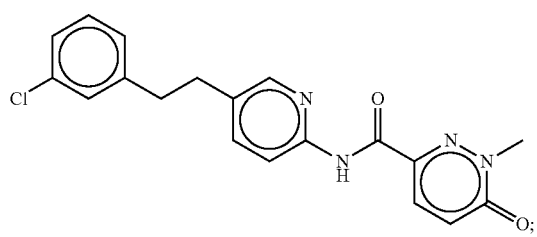
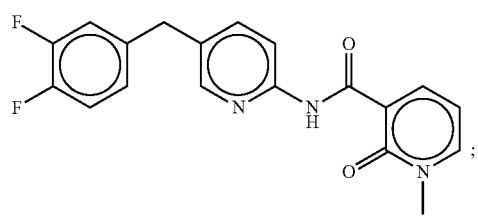
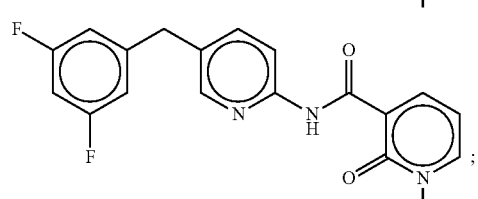
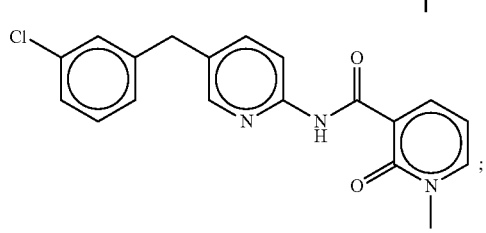
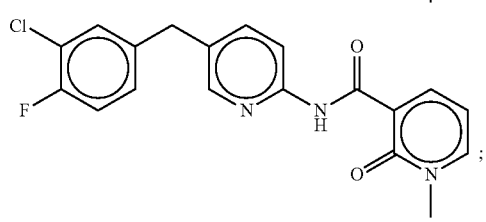
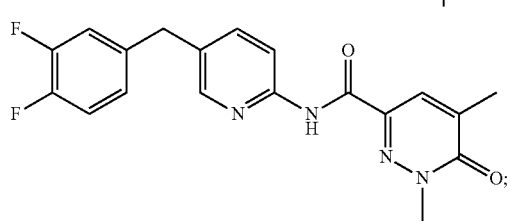
710
-continued
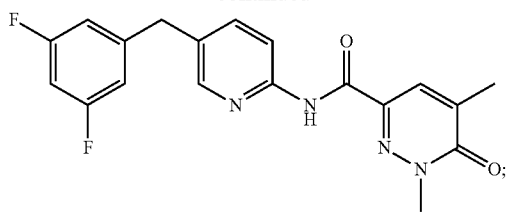
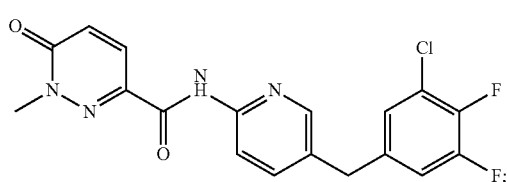
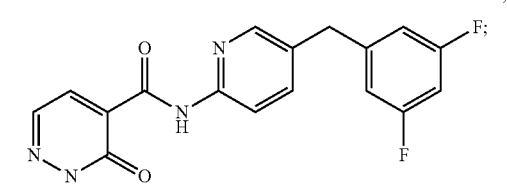
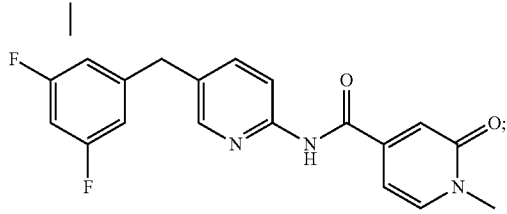
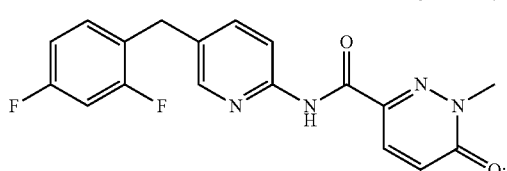
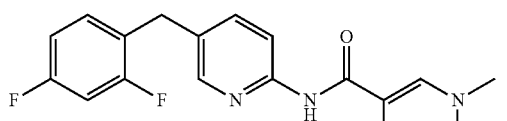
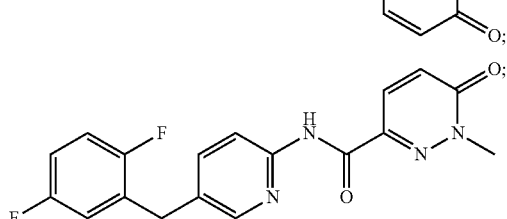
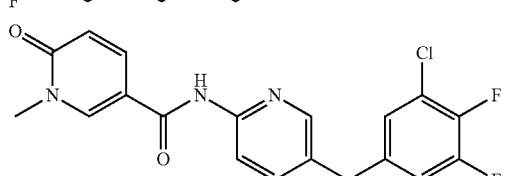
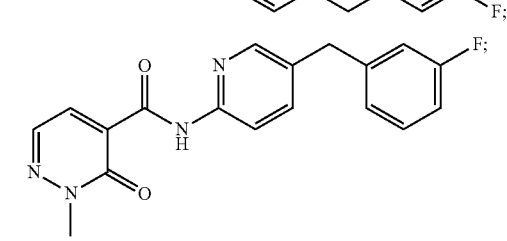

-continued
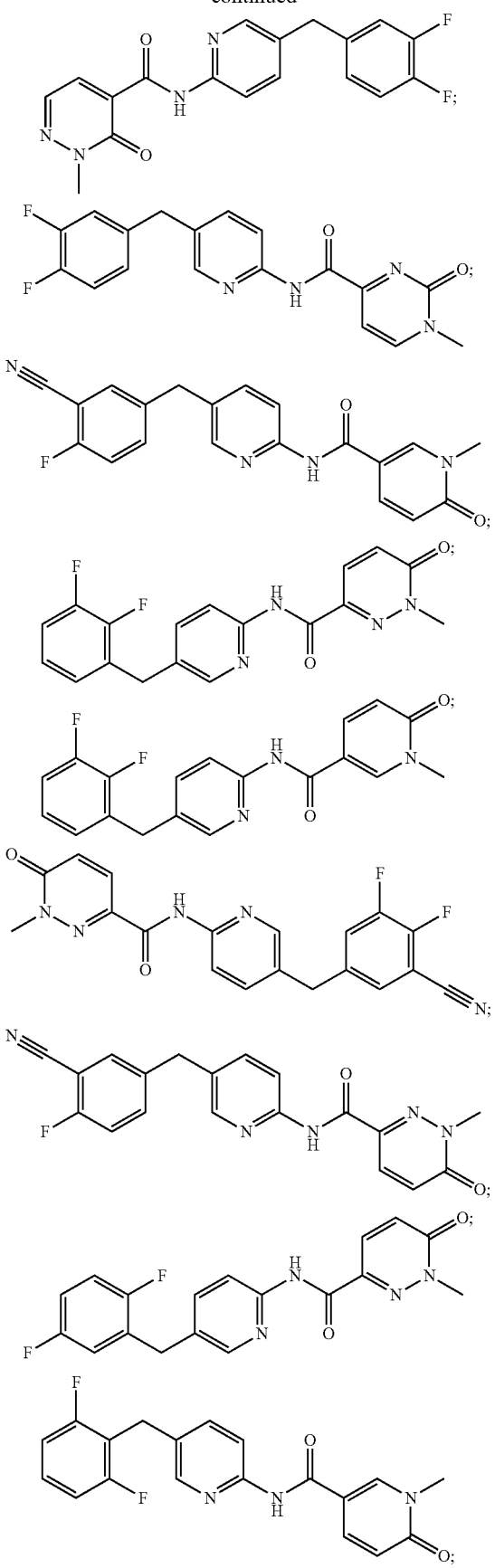
-continued
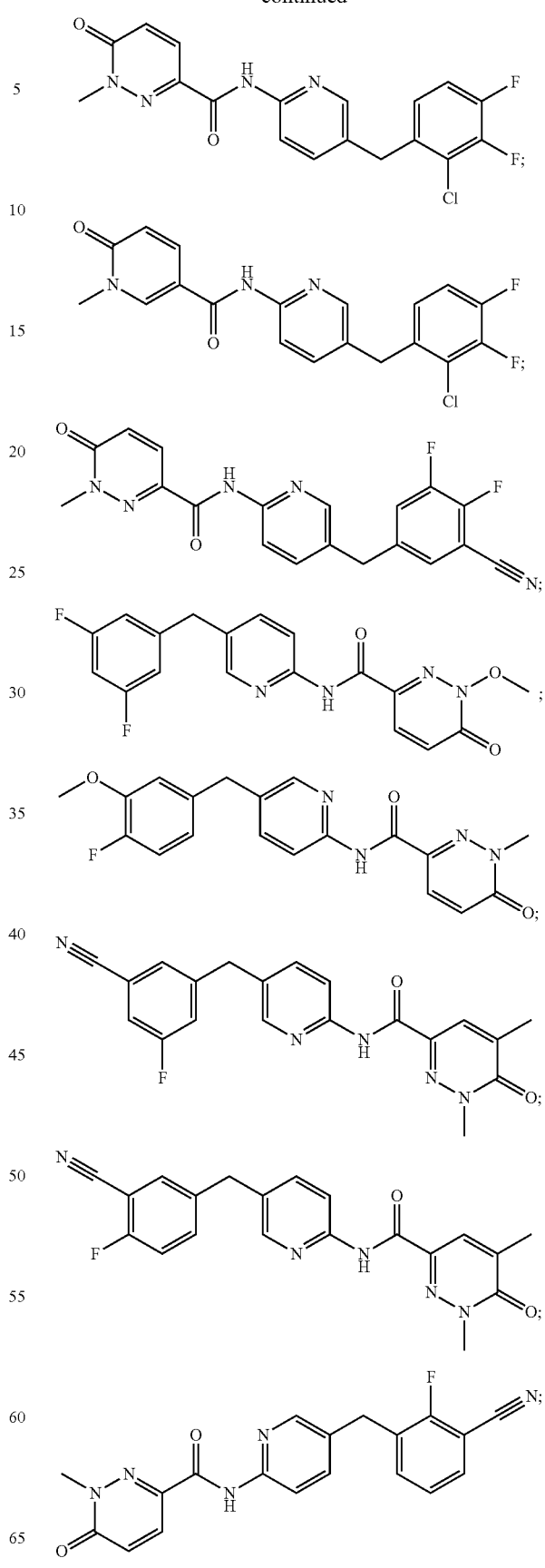

6. A pharmaceutical composition comprising a compound, or pharmaceutically acceptable salt thereof, of claim 1, and a pharmaceutically acceptable excipient.

7. The compound of claim 1, wherein the compound has the following structure:

or a pharmaceutically acceptable salt thereof.

8. The compound of claim 2, wherein the compound is selected from the group consisting of:

715
-continued
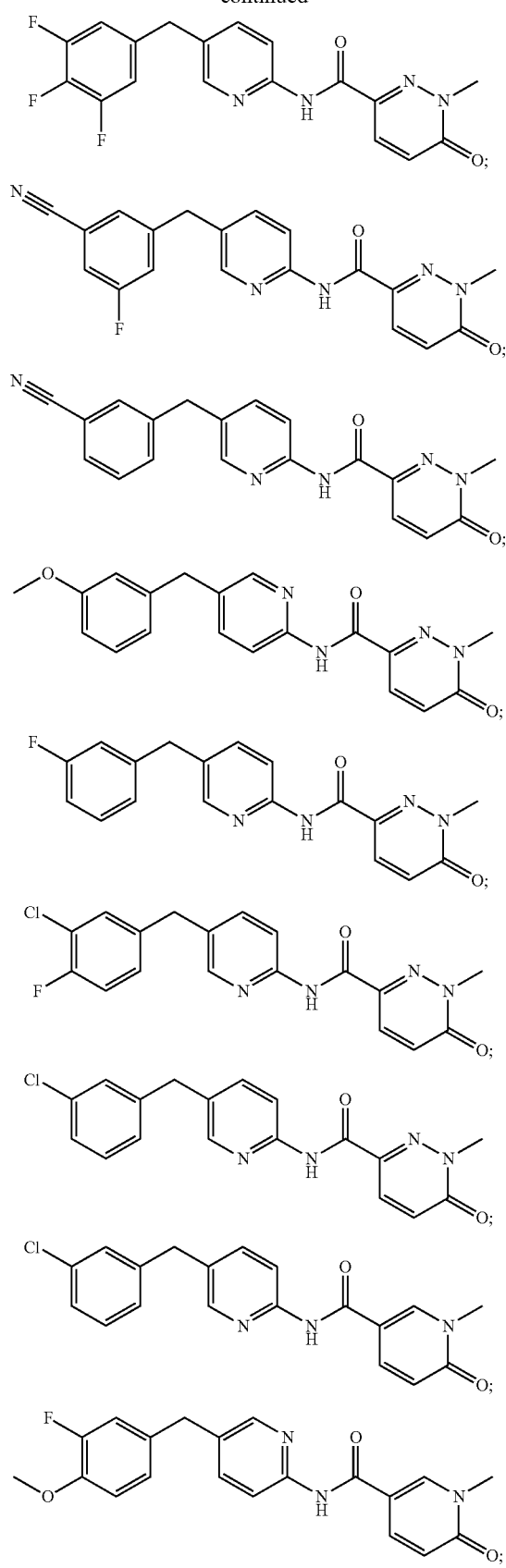
716
-continued
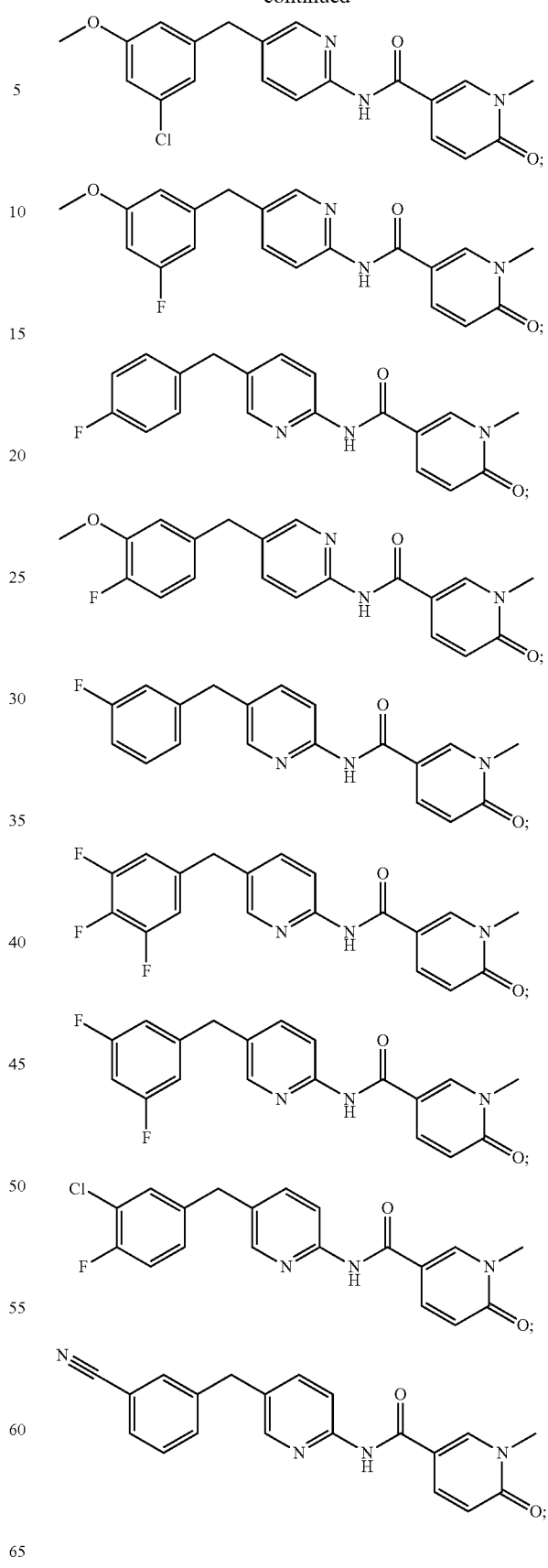

717
-continued
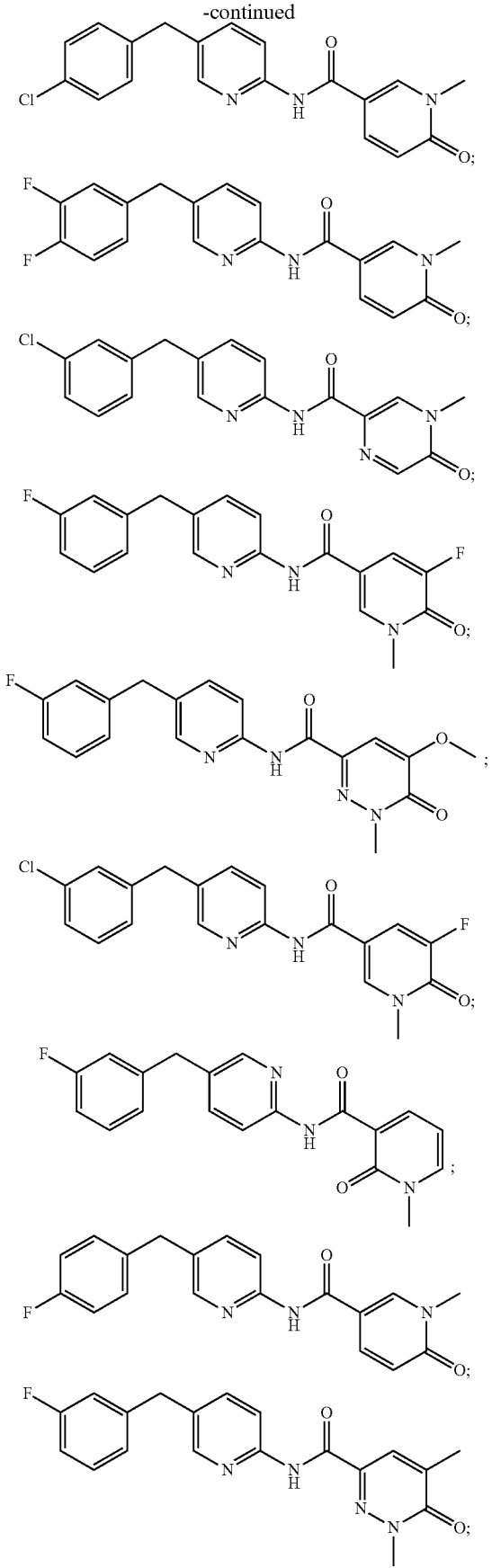
718
-continued
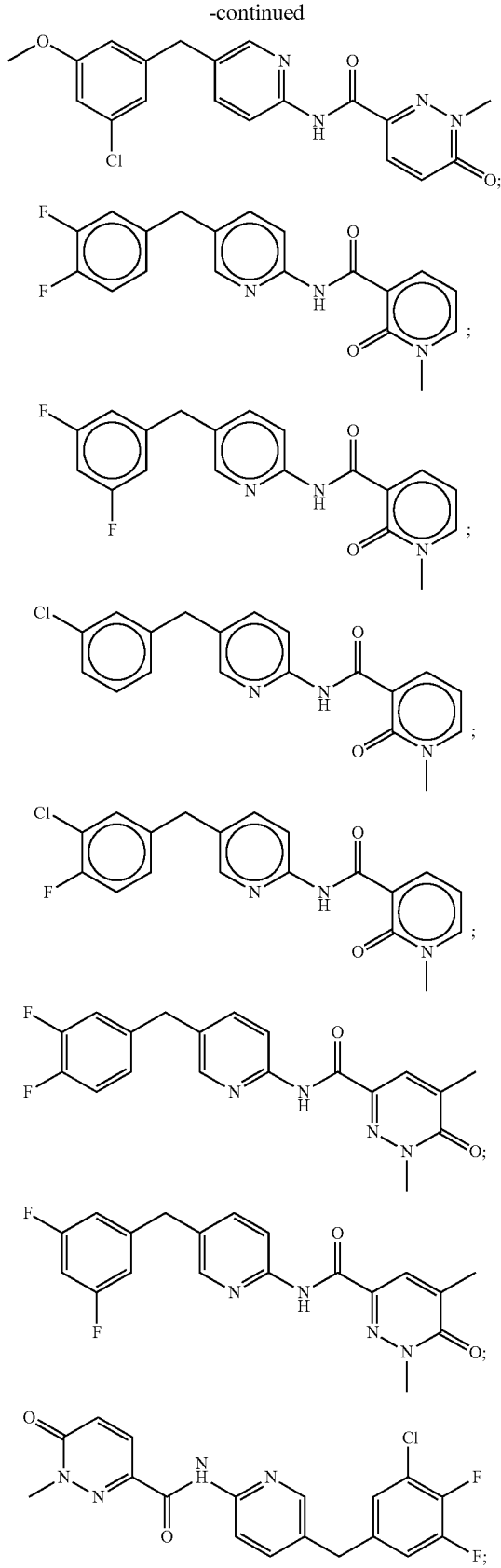

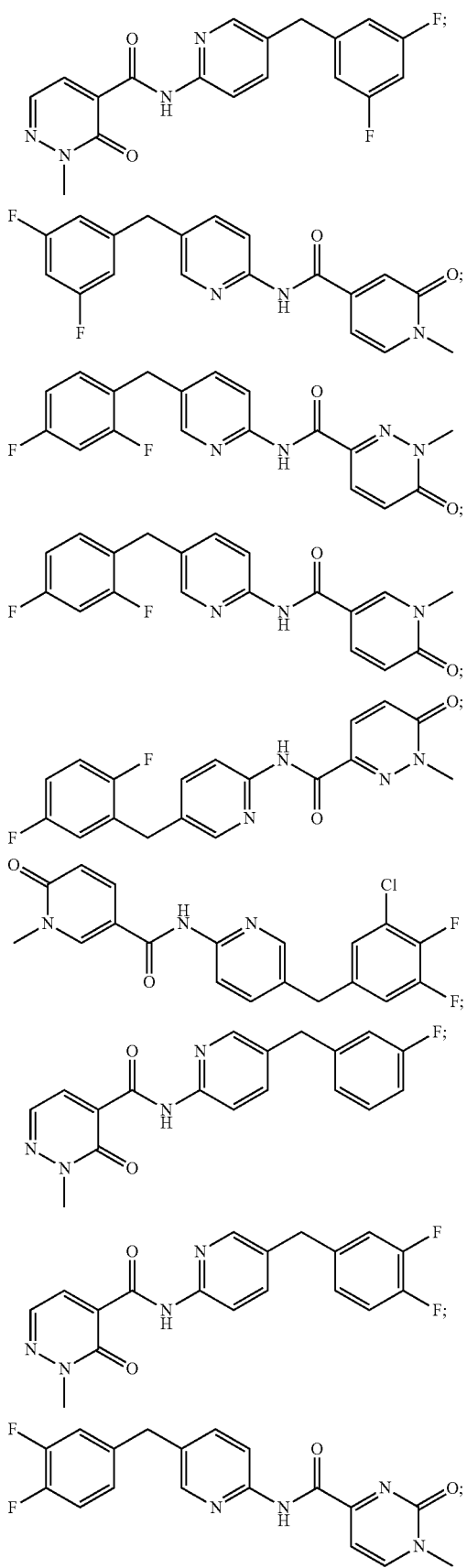
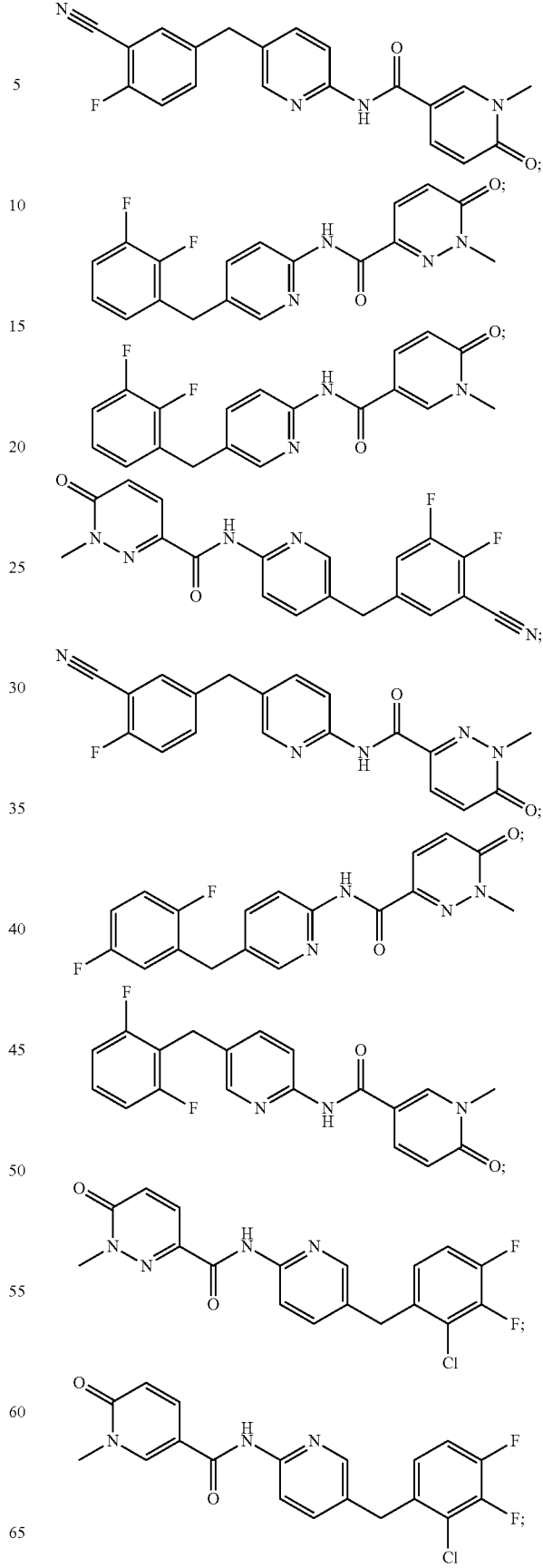

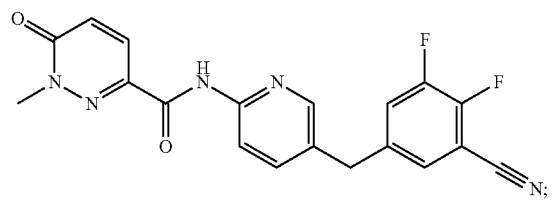
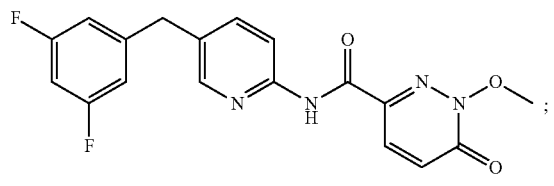
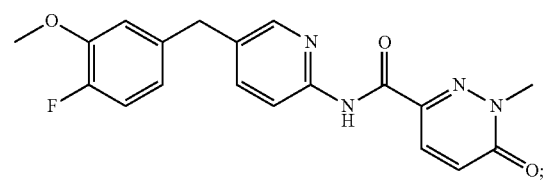
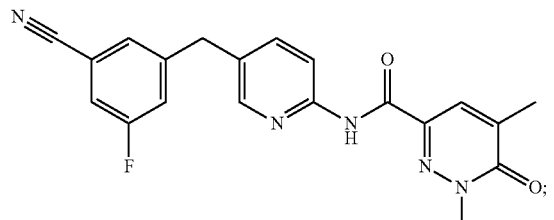
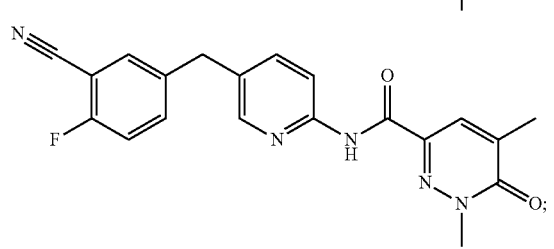
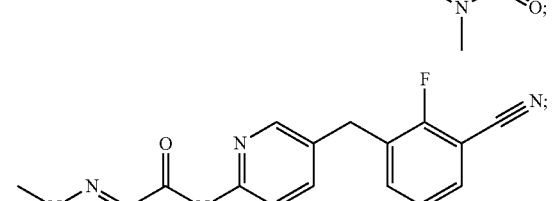
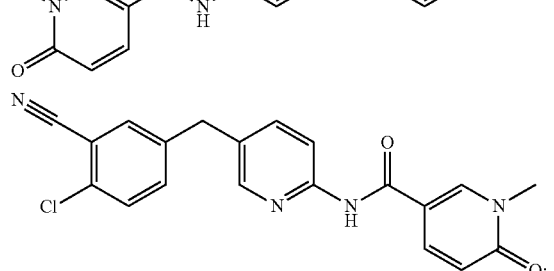
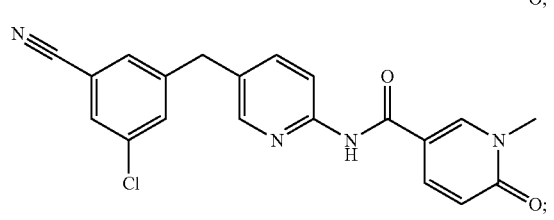
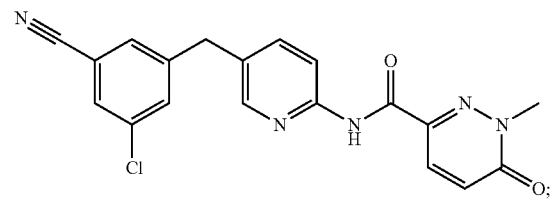
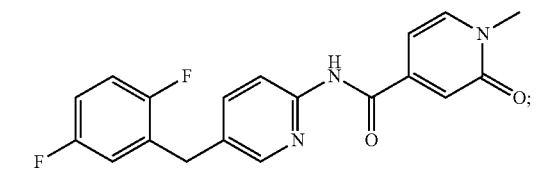
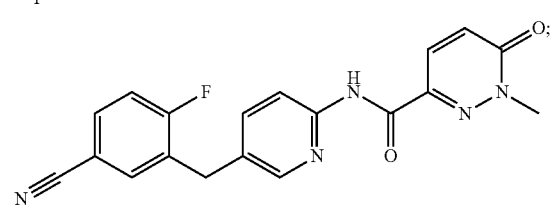
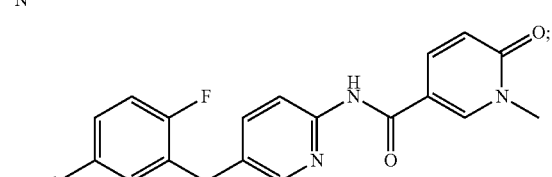
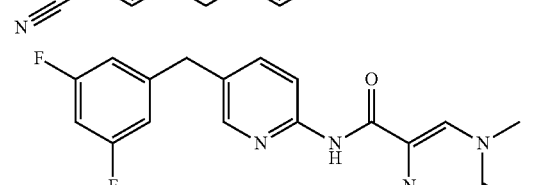
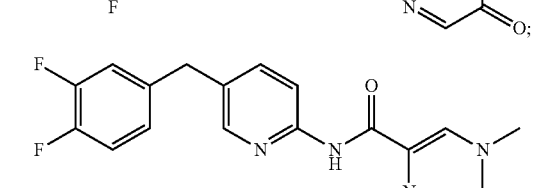
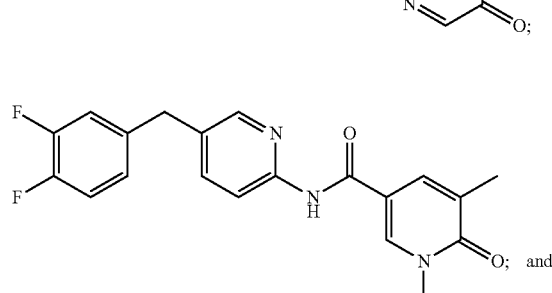
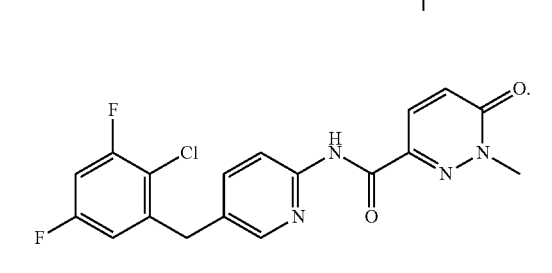

9. The compound of claim 3, wherein the compound is selected from the group consisting of:
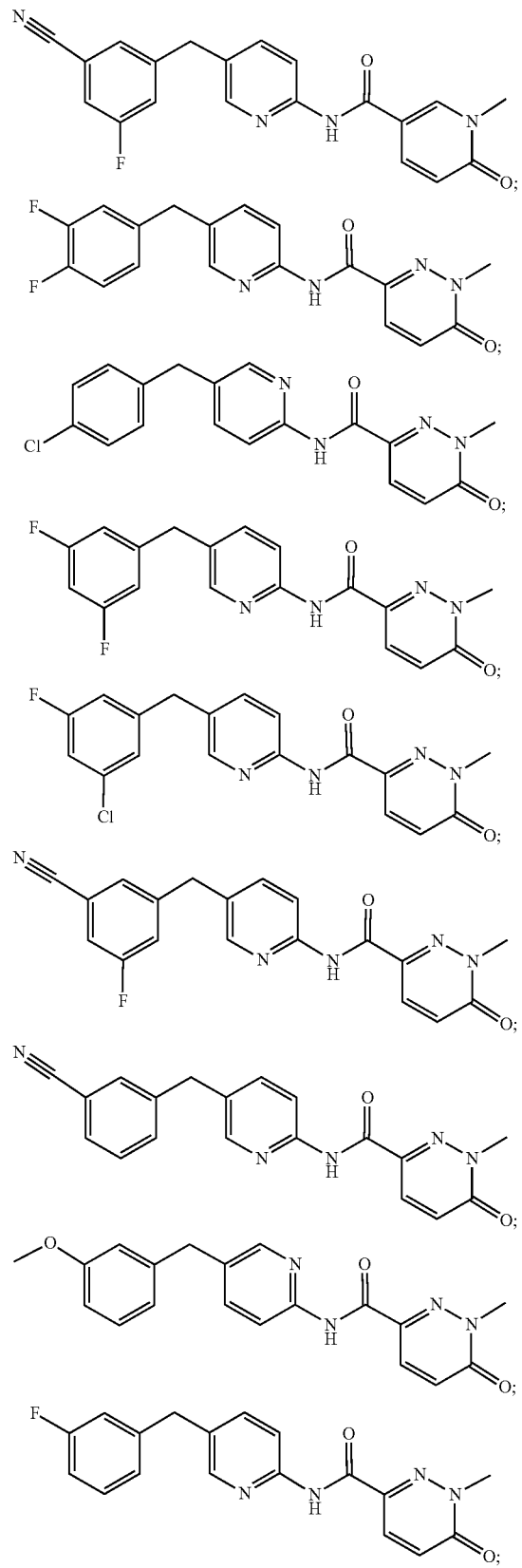
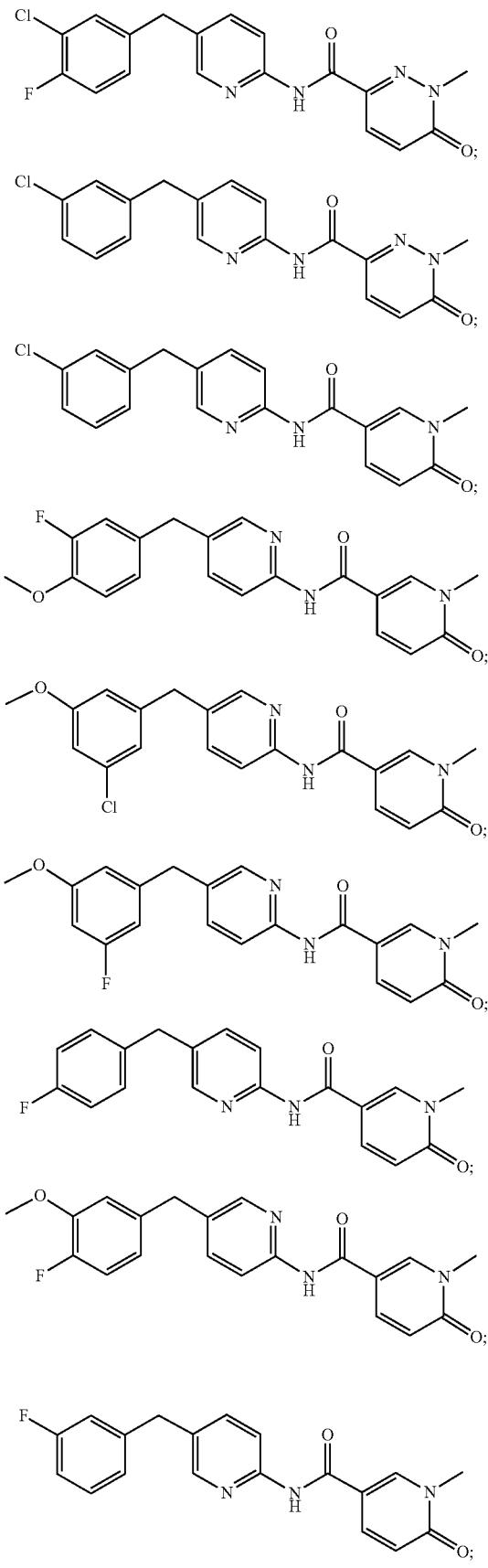

725
-continued

726
-continued

727 -continued
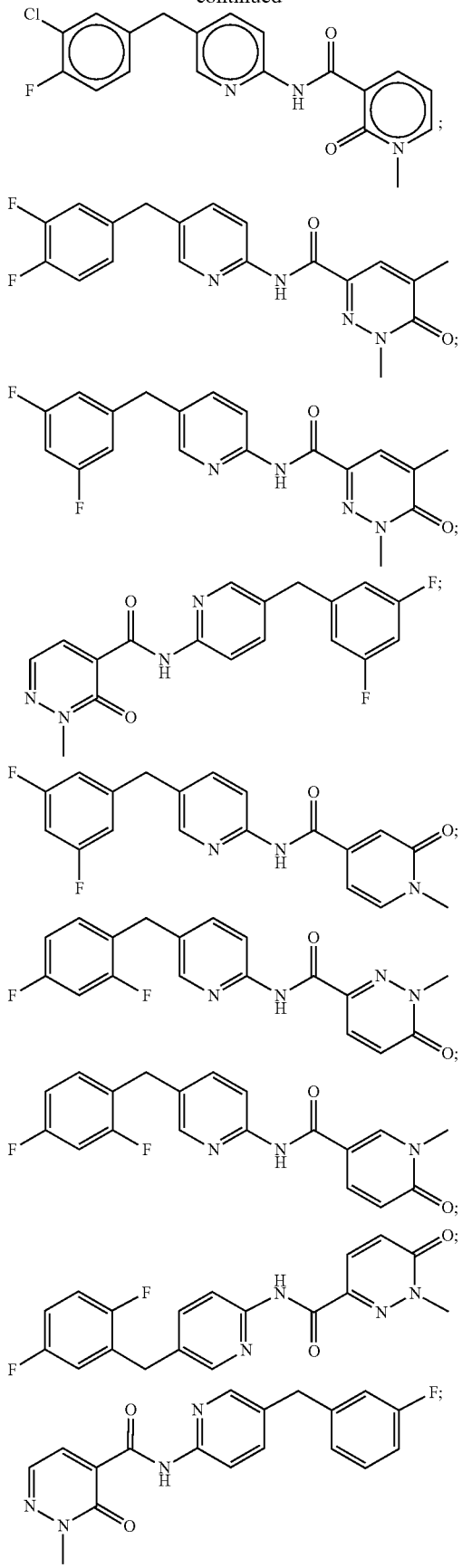
728 -continued
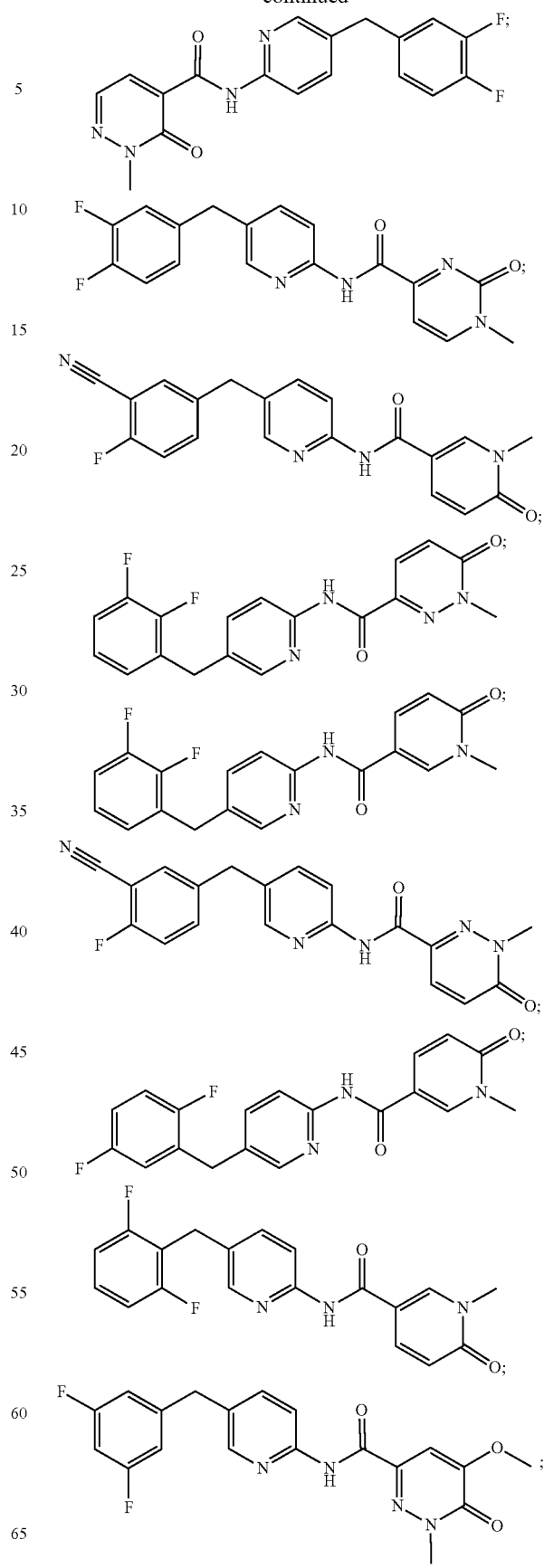

-continued
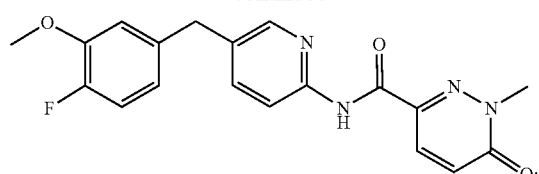
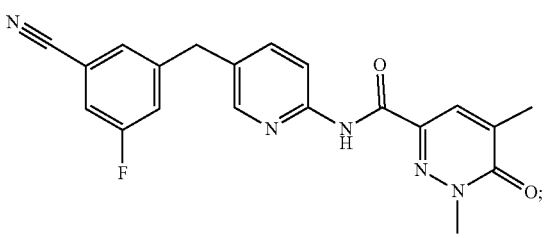
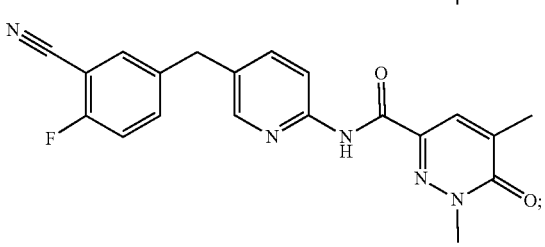
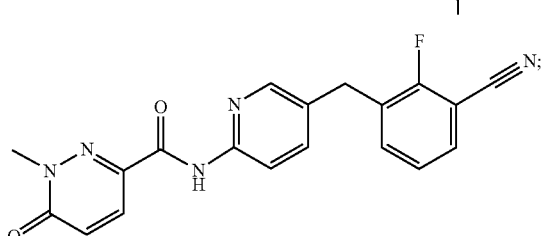
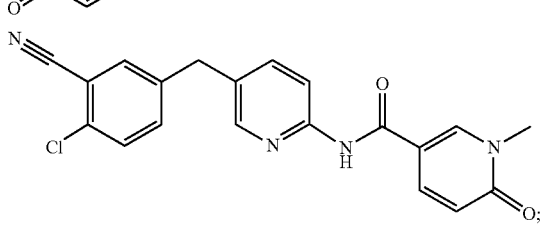
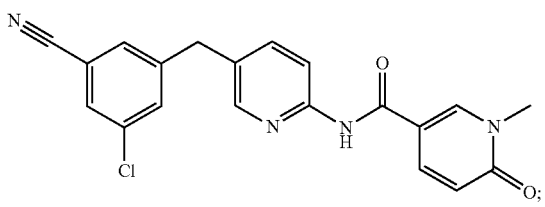
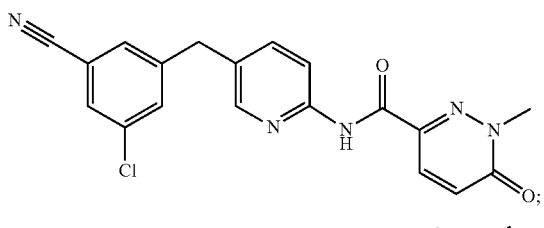
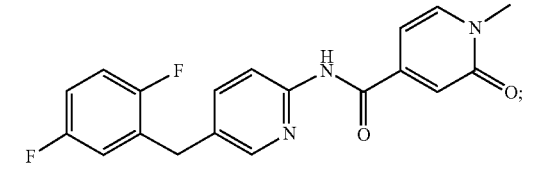
-continued
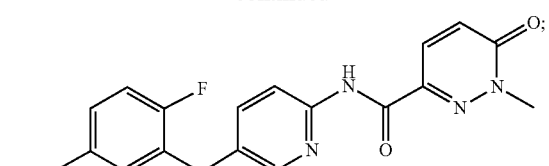
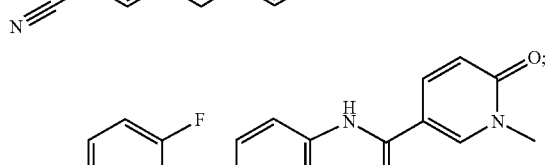
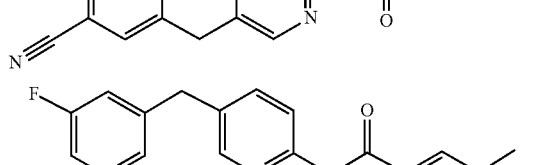
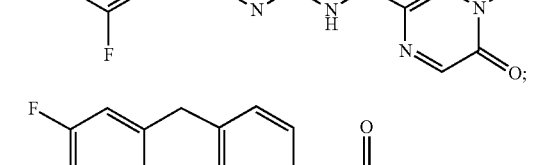
and
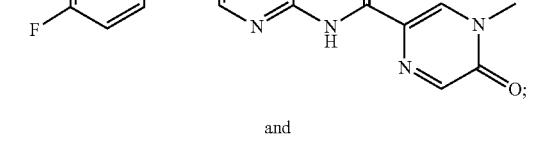
10. The compound of claim 1, wherein the compound is
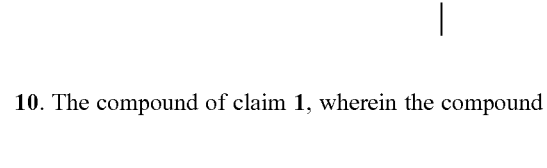
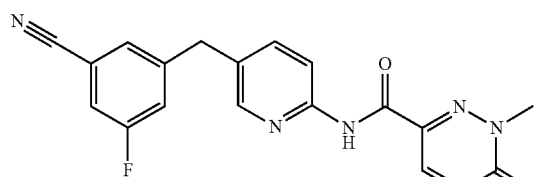

-continued
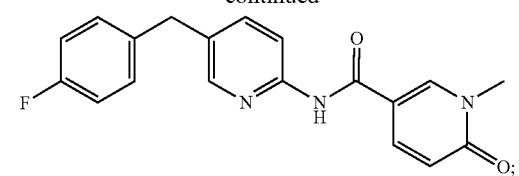
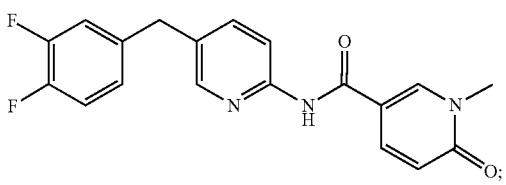 [SMILES: Cn1cc(C(=O)Nc2ccc(Cc3ccc(F)c(F)c3)cn2)ccc1=O]
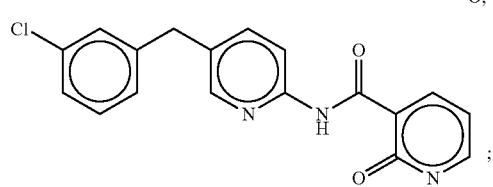
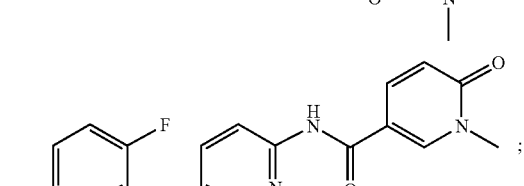
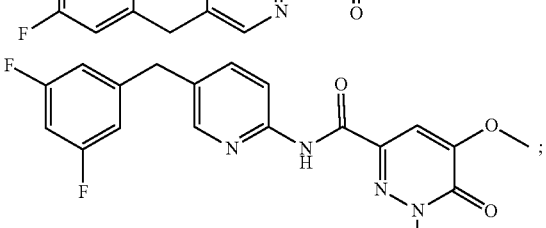
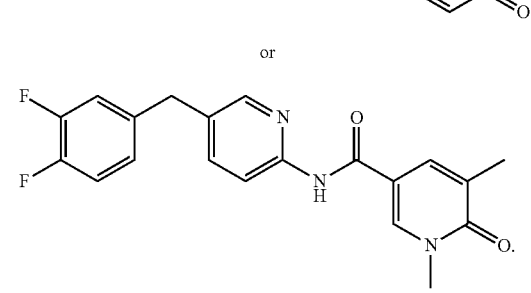
or
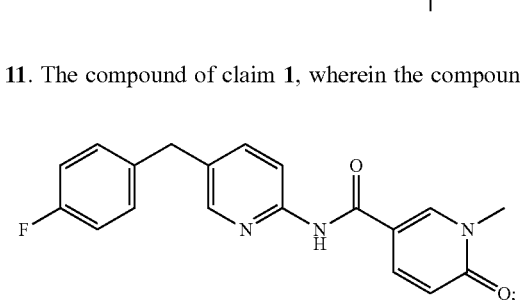
11. The compound of claim 1, wherein the compound is
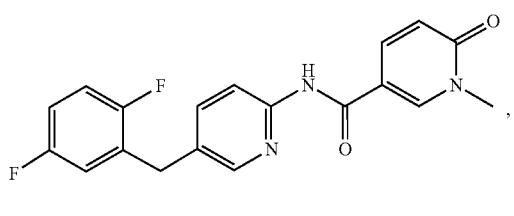 [SMILES: Cn1cc(C(=O)Nc2ccc(Cc3cc(F)ccc3F)cn2)ccc1=O]
-continued
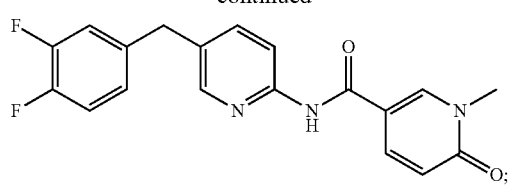
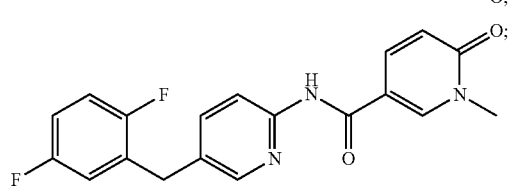
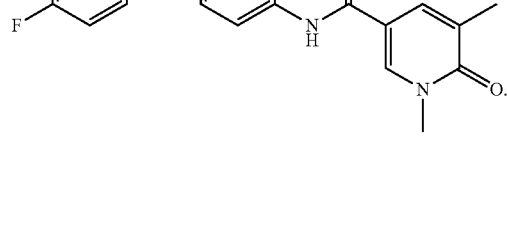
or
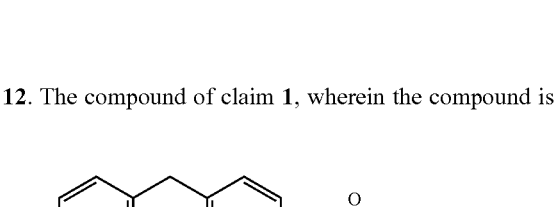
12. The compound of claim 1, wherein the compound is
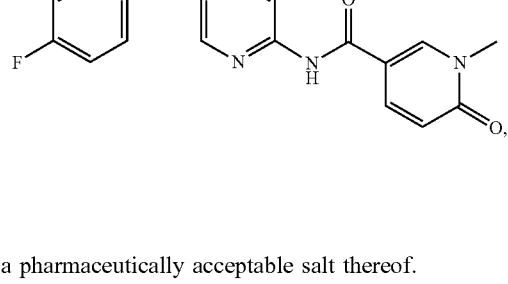
or a pharmaceutically acceptable salt thereof.
13. The compound of claim 1, wherein the compound is
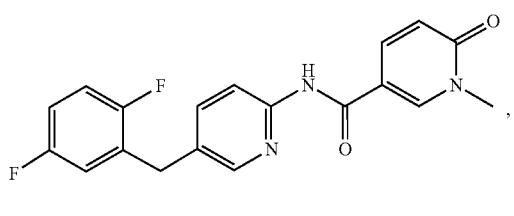 [SMILES: Cn1cc(C(=O)Nc2ccc(Cc3cc(F)ccc3F)cn2)ccc1=O]
or a pharmaceutically acceptable salt thereof.

14. The compound of claim 1, wherein the compound is

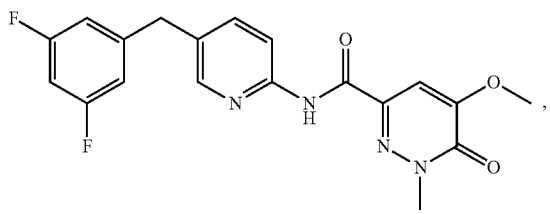 [SMILES: COc1cc(C(=O)Nc2ccc(Cc3cc(F)cc(F)c3)cn2)nn(C)c1=O]

or a pharmaceutically acceptable salt thereof.

15. The compound of claim 1, wherein the compound is

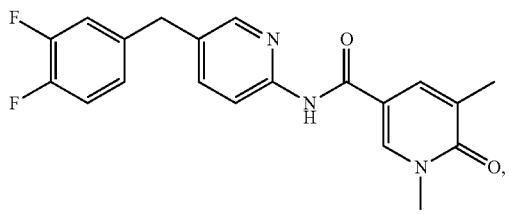 [SMILES: Cc1cc(C(=O)Nc2ccc(Cc3ccc(F)c(F)c3)cn2)cn(C)c1=O]

or a pharmaceutically acceptable salt thereof.

16. The compound of claim 1, wherein the compound is

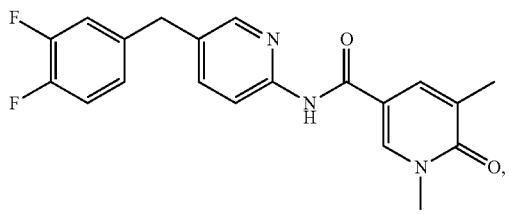 [SMILES: Cc1cc(C(=O)Nc2ccc(Cc3ccc(F)c(F)c3)cn2)cn(C)c1=O]

17. The compound of claim 1, wherein the compound is

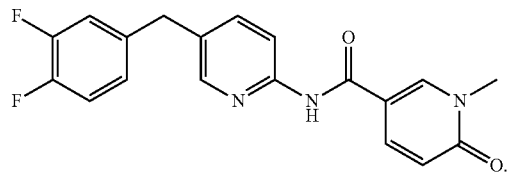 [SMILES: Cn1cc(C(=O)Nc2ccc(Cc3ccc(F)c(F)c3)cn2)ccc1=O]

18. The compound of claim 1, wherein the compound is

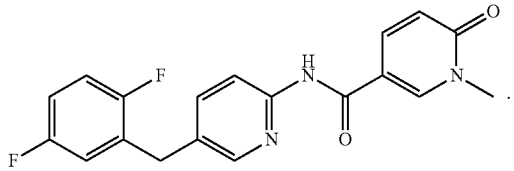 [SMILES: Cn1cc(C(=O)Nc2ccc(Cc3cc(F)ccc3F)cn2)ccc1=O]

19. The compound of claim 1, wherein the compound is

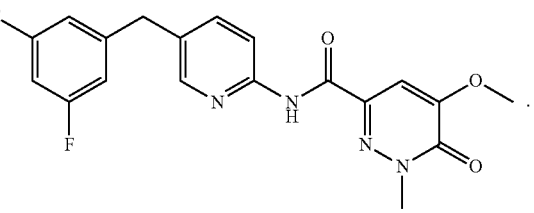

20. The compound of claim 1, wherein the compound is

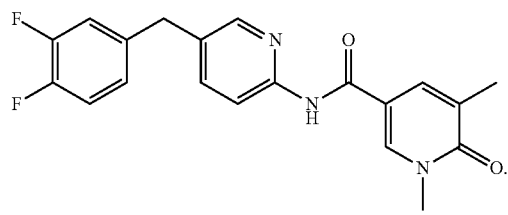 [SMILES: Cc1cc(C(=O)Nc2ccc(Cc3ccc(F)c(F)c3)cn2)cn(C)c1=O]

* * * * *